(12) United States Patent
Cutshall et al.

(10) Patent No.: US 12,195,427 B2
(45) Date of Patent: *Jan. 14, 2025

(54) MASP-2 INHIBITORS AND METHODS OF USE

(71) Applicant: Omeros Corporation, Seattle, WA (US)

(72) Inventors: Neil S. Cutshall, Snohomish, WA (US); Jennifer Lynn Gage, Kenmore, WA (US); Franz A. Gruswitz, Bellevue, WA (US); Juhienah Khalaf, Hamilton, MT (US); Thomas L. Little, Seattle, WA (US); Markus Metz, Bellevue, WA (US); Jeremiah H. Nguyen, Kent, WA (US); Peter Kurt Nollert von Specht, Bainbridge Island, WA (US); Jennifer Tsoung, Seattle, WA (US); Michael Cicirelli, Kirkland, WA (US); Sara Rebecca Goldstein, Seattle, WA (US); Santosh Kumar Keshipeddy, Bellevue, WA (US); Do Yeon Kwon, Seattle, WA (US); Robert Huerta Lemus, Seattle, WA (US); Sudheer Babu Vaddela, Bellevue, WA (US)

(73) Assignee: Omeros Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/060,456

(22) Filed: Nov. 30, 2022

(65) Prior Publication Data

US 2023/0145071 A1 May 11, 2023

Related U.S. Application Data

(63) Continuation of application No. 16/425,791, filed on May 29, 2019, now Pat. No. 11,584,714, which is a
(Continued)

(51) Int. Cl.
| | | |
|---|---|---|
| C07D 401/12 | (2006.01) |
| A61K 31/4439 | (2006.01) |
| C07C 235/88 | (2006.01) |
| C07C 251/24 | (2006.01) |
| C07D 205/04 | (2006.01) |
| C07D 207/16 | (2006.01) |
| C07D 207/24 | (2006.01) |
| C07D 207/36 | (2006.01) |
| C07D 211/60 | (2006.01) |
| C07D 213/73 | (2006.01) |
| C07D 213/81 | (2006.01) |
| C07D 217/14 | (2006.01) |
| C07D 231/44 | (2006.01) |
| C07D 233/64 | (2006.01) |
| C07D 235/30 | (2006.01) |

(Continued)

(52) U.S. Cl.
CPC .......... *C07D 205/04* (2013.01); *C07C 235/88* (2013.01); *C07C 251/24* (2013.01); *C07D 207/16* (2013.01); *C07D 207/24* (2013.01); *C07D 207/36* (2013.01); *C07D 211/60* (2013.01); *C07D 213/73* (2013.01); *C07D 213/81* (2013.01); *C07D 217/14* (2013.01); *C07D 231/44* (2013.01); *C07D 233/64* (2013.01); *C07D 235/30* (2013.01); *C07D 239/94* (2013.01); *C07D 239/96* (2013.01); *C07D 249/08* (2013.01); *C07D 257/04* (2013.01); *C07D 277/56* (2013.01); *C07D 295/033* (2013.01); *C07D 295/135* (2013.01); *C07D 295/26* (2013.01); *C07D 401/06* (2013.01); *C07D 401/12* (2013.01); *C07D 401/14* (2013.01); *C07D 403/06* (2013.01); *C07D 403/12* (2013.01); *C07D 409/10* (2013.01); *C07D 409/14* (2013.01); *C07D 413/12* (2013.01); *C07D 413/14* (2013.01); *C07D 417/12* (2013.01); *C07D 417/14* (2013.01); *C07D 471/04* (2013.01); *C07D 471/06* (2013.01); *C07D 495/04* (2013.01)

(58) Field of Classification Search
CPC ... C07D 401/12; A61K 31/4439; A61P 13/12; A61P 29/00; C12Q 1/00
USPC ........................................ 546/279.1; 514/343
See application file for complete search history.

(56) References Cited

U.S. PATENT DOCUMENTS

| | | | |
|---|---|---|---|
| 4,331,647 A | 5/1982 | Goldenberg et al. |
| 4,816,567 A | 3/1989 | Cabilly et al. |

(Continued)

FOREIGN PATENT DOCUMENTS

| | | | |
|---|---|---|---|
| AU | 2013201779 A1 | 4/2013 |
| CL | 202003083 | 5/2019 |

(Continued)

OTHER PUBLICATIONS

Clark J,E, Dudler T, Marber M,S, et al. Cardioprotection by an anti-MASP-2 antibody in a murine model of myocardial infarction. Open Heart 2018;5:e000652. doi:10.1136/ openhrt-2017-000652.
(Continued)

*Primary Examiner* — Charanjit Aulakh
(74) *Attorney, Agent, or Firm* — Christensen O'Connor Johnson Kindness PLLC

(57) ABSTRACT

The present disclosure provides, inter alia, compounds with MASP-2 inhibitory activity, compositions of such compounds and methods of making and using such compounds.

18 Claims, 76 Drawing Sheets

Specification includes a Sequence Listing.

Related U.S. Application Data continuation of application No. PCT/US2019/034220, filed on May 28, 2019.

(60) Provisional application No. 62/677,472, filed on May 29, 2018, provisional application No. 62/677,538, filed on May 29, 2018, provisional application No. 62/677,495, filed on May 29, 2018, provisional application No. 62/677,514, filed on May 29, 2018.

(51) Int. Cl.

| | |
|---|---|
| *C07D 239/94* | (2006.01) |
| *C07D 239/96* | (2006.01) |
| *C07D 249/08* | (2006.01) |
| *C07D 257/04* | (2006.01) |
| *C07D 277/56* | (2006.01) |
| *C07D 295/033* | (2006.01) |
| *C07D 295/135* | (2006.01) |
| *C07D 295/26* | (2006.01) |
| *C07D 401/06* | (2006.01) |
| *C07D 401/14* | (2006.01) |
| *C07D 403/06* | (2006.01) |
| *C07D 403/12* | (2006.01) |
| *C07D 409/10* | (2006.01) |
| *C07D 409/14* | (2006.01) |
| *C07D 413/12* | (2006.01) |
| *C07D 413/14* | (2006.01) |
| *C07D 417/12* | (2006.01) |
| *C07D 417/14* | (2006.01) |
| *C07D 471/04* | (2006.01) |
| *C07D 471/06* | (2006.01) |
| *C07D 495/04* | (2006.01) |

(56) References Cited

U.S. PATENT DOCUMENTS

| | | |
|---|---|---|
| 4,946,778 A | 8/1990 | Ladner et al. |
| 5,211,657 A | 5/1993 | Yamada et al. |
| 5,223,409 A | 6/1993 | Ladner et al. |
| 5,403,484 A | 4/1995 | Ladner et al. |
| 5,552,157 A | 9/1996 | Yagi et al. |
| 5,565,213 A | 10/1996 | Nakamori et al. |
| 5,567,434 A | 10/1996 | Szoka |
| 5,571,698 A | 11/1996 | Ladner et al. |
| 5,610,288 A | 3/1997 | Rubenstein |
| 5,693,762 A | 12/1997 | Queen et al. |
| 5,718,709 A | 2/1998 | Considine et al. |
| 5,738,868 A | 4/1998 | Shinkarenko |
| 5,739,119 A | 4/1998 | Galli et al. |
| 5,741,516 A | 4/1998 | Webb et al. |
| 5,759,829 A | 6/1998 | Shewmaker et al. |
| 5,789,573 A | 8/1998 | Baker et al. |
| 5,795,587 A | 8/1998 | Gao et al. |
| 5,801,154 A | 9/1998 | Baracchini et al. |
| 5,866,573 A | 2/1999 | Sanderson et al. |
| 6,649,592 B1 | 11/2003 | Larson |
| 6,653,316 B1 | 11/2003 | South et al. |
| 7,015,230 B1 | 3/2006 | South et al. |
| 7,919,094 B2 | 4/2011 | Schwaeble |
| 8,652,477 B2 | 2/2014 | Schwaeble |
| 8,840,893 B2 | 9/2014 | Schwaeble |
| 8,889,712 B2 | 11/2014 | Borzilleri et al. |
| 8,937,065 B2 | 1/2015 | Becker et al. |
| 8,951,522 B2 | 2/2015 | Demopulos |
| 9,011,860 B2 | 4/2015 | Dudler et al. |
| 9,469,608 B2 | 10/2016 | Chobanian et al. |
| 9,475,885 B2 | 10/2016 | Dudler |
| 9,644,035 B2 | 5/2017 | Demopulos |
| 11,299,479 B1 | 4/2022 | Ashcraft et al. |
| 11,584,714 B2 | 2/2023 | Cutshall |
| 11,661,418 B2 | 5/2023 | Cutshall |
| 11,807,641 B2 * | 11/2023 | Cicirelli .................... A61P 7/02 |
| 12,030,853 B2 | 7/2024 | Cutshall et al. |
| 2002/0019369 A1 | 2/2002 | Li et al. |
| 2002/0119992 A1 | 8/2002 | Selnick et al. |
| 2004/0072862 A1 | 4/2004 | Bitler et al. |
| 2005/0004031 A1 | 1/2005 | Subasinghe |
| 2006/0002937 A1 | 1/2006 | Schwaeble et al. |
| 2007/0172483 A1 | 7/2007 | Schwaeble et al. |
| 2013/0266560 A1 | 10/2013 | Demopulos |
| 2013/0344073 A1 | 12/2013 | Schwaeble |
| 2015/0166675 A1 | 6/2015 | Demopulos |
| 2015/0315141 A1 | 11/2015 | Chobanian et al. |
| 2017/0137537 A1 | 5/2017 | Demopulos |
| 2017/0166660 A1 | 6/2017 | Schwaeble |
| 2017/0189525 A1 | 7/2017 | Brunskill |
| 2017/0253667 A1 | 9/2017 | Brunskill |
| 2017/0267781 A1 | 9/2017 | Demopulos |
| 2017/0283508 A1 | 10/2017 | Demopulos |
| 2018/0105604 A1 | 4/2018 | Brunskill |
| 2019/0367452 A1 | 12/2019 | Cutshall |
| 2021/0171461 A1 | 6/2021 | Cutshall |
| 2021/0171512 A1 | 6/2021 | Cutshall |
| 2021/0171531 A1 | 6/2021 | Cicirelli |
| 2021/0179612 A1 | 6/2021 | Cutshall |
| 2024/0092788 A1 | 3/2024 | Cutshall et al. |

FOREIGN PATENT DOCUMENTS

| | | |
|---|---|---|
| CL | 202103105 | 5/2019 |
| CL | 202000610 | 4/2022 |
| CN | 1127509 A | 7/1996 |
| CN | 104661676 A | 5/2015 |
| CO | 5160330 | 5/2002 |
| EP | 0321201 | 6/1989 |
| EP | 0 321 201 B1 | 12/1994 |
| JP | 20014515922 A | 9/2001 |
| JP | 2004516286 A | 6/2004 |
| JP | 2005514332 | 5/2005 |
| JP | 2007-535474 A | 12/2007 |
| JP | 2010-515729 A | 5/2010 |
| JP | 2014-506877 A | 3/2014 |
| JP | 2014-520108 A | 8/2014 |
| JP | 2017-508789 A | 3/2017 |
| JP | 2022-552048 A | 12/2022 |
| RU | 2014133019 A | 2/2016 |
| WO | WO 1988/004300 A1 | 6/1988 |
| WO | WO 1991/011465 A1 | 8/1991 |
| WO | 1994029336 A1 | 12/1994 |
| WO | WO 1994/029335 | 12/1994 |
| WO | WO 1994/29336 A1 | 12/1994 |
| WO | WO 1995/023609 A1 | 9/1995 |
| WO | WO 1999/61442 | 12/1999 |
| WO | 2000/039124 A1 | 7/2000 |
| WO | 200039124 A1 | 7/2000 |
| WO | WO 2000/55188 A1 | 9/2000 |
| WO | WO 2000/69834 | 11/2000 |
| WO | WO 2001/079195 A2 | 10/2001 |
| WO | 01/87851 | 11/2001 |
| WO | WO 2001/087854 A1 | 11/2001 |
| WO | WO 2002/50056 A1 | 6/2002 |
| WO | WO 2003/028729 A2 | 4/2003 |
| WO | WO 2003/029224 | 4/2003 |
| WO | WO 2004/009664 A2 | 1/2004 |
| WO | 2004032834 A1 | 4/2004 |
| WO | 2005002627 A2 | 1/2005 |
| WO | WO 2006/101860 | 9/2006 |
| WO | 2008/085608 A1 | 7/2008 |
| WO | WO 2008/085608 | 7/2008 |
| WO | WO 2010/141406 A2 | 12/2010 |
| WO | 2012007777 A1 | 1/2012 |
| WO | 2012/093101 A1 | 7/2012 |
| WO | 2012/139081 A2 | 10/2012 |
| WO | WO 2012/151481 A1 | 11/2012 |
| WO | 2013106643 A2 | 7/2013 |
| WO | 2013180834 A3 | 12/2013 |
| WO | 2014057068 A1 | 4/2014 |
| WO | WO 2015/103317 A1 | 7/2015 |
| WO | 2015/130854 A1 | 9/2015 |
| WO | WO 2017/173290 | 10/2017 |

(56) References Cited

FOREIGN PATENT DOCUMENTS

| WO | 2018045054 | 3/2018 | | |
|---|---|---|---|---|
| WO | WO 2019/036460 A1 | 2/2019 | | |
| WO | WO 2019/055590 A1 | 3/2019 | | |
| WO | 2021032933 A1 | 8/2019 | | |
| WO | 2019/186164 | 10/2019 | | |
| WO | WO 2019/211585 A1 | 11/2019 | | |
| WO | 2019231933 A2 | 12/2019 | | |
| WO | WO 2019/231935 A1 | * 12/2019 | ............ | A61K 31/48 |
| WO | 2022035997 A1 | 2/2022 | | |

OTHER PUBLICATIONS

Orsini, F. et al., "Mannan binding lectin-associated serine protease-2 (MASP-2) critically contributes to post-ischemis brain injury independent of MASP-1," Journal of Neuroinflammation (2016)13:213; DOI 10.1186s/12974-016-0684-6.

Asgari, E. et al., "Mannan-binding lectin-associated serine protease 2 is critical for the development of renal ischemia reperfusion injury and mediates tissue injury in the absence of complement C4," The FASEB Journal Research Communication; May 19, 2014; pp. 3996-4003.

Alghadban, S. et al., "Absence of the Lectin Activation Pathway of the Complement Ameliorates Proteinuria-Induced Renal Injury," Front. Immunol. 10:2238; doi: 10.3389/fimmu.2019.02238.

Banda, N. K. et al., "Deconstructing the Lectin Pathway in the Pathogenesis of Experimental Inflammatory Arthritis: Essential Role of the Lectin Ficolin B and Mannose-Binding Protein-Associated Serine Protease 2," J Immunol (2017) 199 (5): 1835-1845; https://doi.org/10.4049/jimmunol.1700119.

Belcher, J. D. et al., "MASP-2 and MASP-3 inhibitors block complement activation, inflammation, and microvascular stasis in a murine model of vaso-occlusion in sickle cell disease," Translational Research, Nov. 2022; pp. 1-12.

Lafayette, R. A. et al., "Safety, Tolerability and Efficacy of Narsoplimab, a Novel MASP-2 Inhibitor for the Treatment of IgA Nephropathy," Kidney International Reports (2020) 5, 2032-2041.

Lafayette Md, R. A. et al. "Long-Term Phase 2 Efficacy of the MASP-2 Inhibitor Narsoplimab for Treatment of Severe IgA Nephropathy," ASN (2021).

Zadlo-Dobrowolska et al., "Enzymatic Ugi Reaction with Amines and Cyclic Imines," Chem. Eur. J., 22:16684-16689 (2016).

Harmat et al., (2004), "The Structure of MBL-associated Serine Protease-2 Reveals that Identical Substrate Specificities of C1s and MASP-2 are Realized Through Different Sets of Enzyme-Substrate Interactions", JMB, 342(5):,XP004844933, https://www.dropbox.com/s/6eto0ib57oqe8pq/D5.pdf?dl=0.

Szakacs et al., (Apr. 5, 2019), "Novel MASP-2 inhibitors developed via directed evolution of human TFPI1 are potent ectin pathway inhibitors", J. Biol. Chem., 294(20):8227-8237, XP055727499, DOI: http://dx.doi.org/10.1074/jbc.RA119.008315.

Pettersen, E. F., et al., "UCSF Chimera—a visualization system for exploratory research and analysis," J Comput Chem 25(13): 1605-1612 (2004).

Yamakawa, I., et al., "Sustained release of insulin by double-layered implant using poly(D,L-lactic acid)," J. Pharm. Sci. 79:505,(1990).

Berge et al., "Pharmaceutical salts," J. Pharm. Sei. 66( 1): 1-19, Jan. 1977.

Berthoux et al., "Predicting the Risk for Dialysis or Death in IgA Nephropathy," J. Am. Soc. Nephrol. 22:752-761, 2011.

Goto et al., "A scoring system to predict renal outcome in IgA nephropathy: a nationwide 10-year prospective cohort study," Nephrol. Dial. Transplant. 24:3068-3074, Jun. 10, 2009.

Ho et al., "Blood and Marrow Transplant Clinical Trials Network Toxicity Committee Consensus Summary: Thrombotic Microangiopathy after Hematopoietic Stem Cell Transplantation," Biology of Blood and Marrow Transplantation 11:571-575, 2005.

Peterlin-Masic et al., "Metabolism-Directed Optimisation of Antithrombotics: The Prodrug Principle," Curr. Pharm. Des. 12(1):73-91, 2006.

Pétursson, "Protecting Groups in Carbohydrate Chemistry," Journal of Chemical Education 74(11): 1297, Nov. 1997.

Rambaldi et al., "Endothelial injury and thrombotic microangiopathy in COVID-19: Treatment with the lectin-pathway inhibitor narsoplimab," Immunobiology 225(152001): 1-10, 2020.

Reich et al., "Remission of Proteinuria Improves Prognosis in IgA Nephropathy," J. Am. Soc. Nephrol. 18:3177-3183,2007.

Schwaeble et al., "Targeting of mannan-binding lectin-associated serine protease-2 confers protection from myocardial and gastrointestinal ischemia/reperfusion injury," PNAS 108( 18):7523-7528, May 3, 2011.

Trost et al., eds., "Comprehensive Organic Synthesis: Selectivity, Strategy & Efficiency in Moden Organic Chemistry" vol. 1, Pergamon Press, Oxford, United Kingdom, 1991.

Wyatt et al., "IgA Nephropathy," N. Engl. J. Med. 368(25):2402-2414, Jun. 20, 2013.

Zipfel et al., "Deletion of Complement Factor H-Related Genes CFHR1 and CFHR3 Is Associated with Atypical Hemolytic Uremic Syndrome," PLOS Genet. 3(3):0387-0392, e41, Mar. 2007.

Office Action (Notice of Allowance and Fees Due (PTOL-85)) dated Sep. 11, 2023 for U.S. Appl. No. 17/112,896 (pp. 1-9).

Office Action (Notice of Allowance and Fees Due (PTOL-85)) dated Sep. 18, 2023 for U.S. Appl. No. 17/112,896 (pp. 1-9).

Nurbo et al., Bioorganic & Medicinal Chemistry (2008), 16(10), 5590-5605 and Supplementary Material on pp. S1-S8. (Year: 2008).

E-EROS Encyclopedia of Reagents for Organic Synthesis; "N-hydroxyacetamide"-preparations, properties and applications; Published Apr. 15, 2001; pp. 1-4, Conference 2008.

Shirk et al.; "Inhibitors of Factor Vlla/Tissue Factor"; Arteriosclerosis, Thrombosis, and Vascular Biology; Sep. 1, 2007; pp. 1895-1900; vol. 27, Issue 9.

Trujillo et al.; "Design, synthesis, and biological evaluation of pyrazinones containing novel P1 needles as inhibitors of TFA/IIa"; Bioorganic & Med Chem Letters; Aug. 15, 2007; pp. 4568-4574; vol. 17, Issue 16.

U.S. Appl. No. 62/688,611, filed Jun. 22, 2018, Demopulos, et al.

Chen, C.B., et al., "Stoichiometry of complexes between mannose-binding protein and its associated serine proteases. Defining functional units for complement activation," J. Biol. Chem., 276(28):25894-25902, (2001).

Feinberg, H., et al., "Crystal structure of the CUB1-EGF-CUB2 region of mannose-binding protein associated serine protease-2," EMBO J. 22:2348-2359, (2003).

Lynch, N.J., et al., "L-ficolin specifically binds to lipoteichoic acid, a cell wall constituent of Gram-positive bacteria, and activates the lectin pathway of complement," J. Immunol. 172:1198-1202, (2004).

Stover, C.M., et al., "Two constituents of the initiation complex of the mannan-binding lectin activation pathway of complement are encoded by a single structural gene," J. Immunol. 162:3481-3490, (1999).

Stover, C.M., et al., "The rat and mouse homologues of MASP-2 and MAp19, components of the lectin activation pathway of complement," J. Immunol. 163:6848-6859, (1999).

Thiel, S., et al., "A second serine protease associated with mannan-binding lectin that activates complement," Nature 386:506-510, (1997).

Thiel, S., et al., "Interaction of C1q and mannan-binding lectin (MBL) with Clr, Cls, MBL-associated serine proteases 1 and 2, and the MBL-associated protein MAp19," J. Immunol. 165:878-887, (2000).

Vorup-Jensen, T., et al., "Distinct pathways of mannan-binding lectin (MBL)- and C1-complex autoactivation revealed by reconstitution of MBL with recombinant MBL-associated serine protease-2," J. Immunol. 165:2093-2100, (2000).

Thielens, N.M., et al., "Interaction properties of human mannan-binding lectin (MBL)-associated serine proteases-1 and -2, MBL-associated protein 19, and Mbl," J. Immunol. 166:5068-5077, (2001).

Matsushita, M., et al., "Cutting edge: complement-activating complex of ficolin and mannose-binding lectin-associated serine protease," J. Immunol. 164:2281-2284, (2000).

(56) References Cited

OTHER PUBLICATIONS

Rodrigues, M.L., et al., "Engineering Fab' fragments for efficient F(ab)2 formation in *Escherichia coli* and for improved in vivo stability," *J. Immunol.* 151(12):6954-6961, (1998).
Riedermann, N.C., et al., "Complement in ischemia reperfusion injury," *Am. J. Pathol.* 162:363-367, (2003).
Matsushita, M., et al., "Activation of the lectin complement pathway by H-ficolin (Hakata antigen)," *J. Immunol.* 168(7):3502-3506, (2002).
Stengaard-Pedersen, K., et al., "Inherited deficiency of mannan-binding lectin-associated serine protease 2," *New England J. Med.* 349:554-560, (2003).
Takahashi, M., et al., "A truncated form of mannose-binding lectin-associated serine protease (MASP)-2 expressed by alternative polyadenylation is a component of the lectin complement pathway," *Int. Immunol.* 11:859-863, (1999).
Ambrus et al., "Natural substrates and inhibitors of mannan-binding lectin-associated serine protease-1 and -2: a study on recombinant catalytic fragments," *J. Immunol.* 170:1374-1382, (2003).
Moller-Kristensen, M., et al., "Levels of mannan-binding lectin-associated serine protease-2 in healthy individuals," *J. Immunol Methods* 282:159-167, (2003).
Dahl, M.R., et al., "MASP-3 and its association with distinct complexes of the mannan-binding lectin complement activation pathway," *Immunity* 15:127-35, (2001).
Petersen, S.V., et al., "An assay for the mannan-binding lectin pathway of complement activation," *J. Immunol. Methods* 257:107-116, (2001).
Liszewski, M.K., et al., "The Complement System," in *Fundamental Immunology*, Third Edition, Raven Press, Ltd., New York, (1993).
Collard, C.D., et al., "Complement activation after oxidative stress: role of the lectin complement pathway," *Am J. Pathol* 156(6):1549-56, (2000).
Lu, J., et al., "Collectins and ficolins: sugar pattern recognition molecules of the mammalian innate immune system," *Biochim Biophys Acta* 1572:387-400, (2002).
Jordan et al., "Inhibition of mannose-binding lectin reduces postischemic myocardial reperfusion injury," *Circulation* 104(12):1413-1418, (2001).
Maynard, Y., et al., "Characterization of a mannose and N-acetylglucosamine-specific lectin present in rat hepatocytes," *J. Biol. Chem.* 257:3788-3794, (1982).
Lee, R.T., et al., "Multivalent ligand binding by serum mannose-binding protein," *Archiv. Biochem. Biophys.* 299:129-136, (1992).
Collard et al., "Endothelial oxidative stress activates the lectin complement pathway: role of cytokeratin 1," *Am. J. Pathol.* 159(3):1045-1054, (2001).
Ji, Y.H., et al., "Activation of the C4 and C2 components of complement by a proteinase in serum bactericidal factor, Ra reactive factor," *J. Immunol.* 150:571-578, (1993).
Kilpatrick, D.C., et al., "Mannan-binding lectin: clinical significance and applications," *Biochim Biophys Acta* 1572:401-413, (2002).
Weis, W.I., et al., "Structure of a C-type mannose-binding protein complexed with an oligosaccharide," *Nature* 360:127-134, (1992).
Kalli, K.R., et al., "Therapeutic uses of recombinant complement protein inhibitors," *Springer Semin. Immunopathol.* 15:417-431, (1994).
Wallis, R., et al., "Localization of the serine protease-binding sites in the collagen-like domain of mannose-binding protein: indirect effects of naturally occurring mutations on protease binding and activation," *J. Biol. Chem.* 279:14065-73, (2004).
Wallis, R., et al., "Interaction of mannose-binding protein with associated serine proteases: effects of naturally occurring mutations," *J. Biol. Chem.* 275:30962-30969, (2000).
Sim, R.B., et al., "Innate Immunity," Biochem. Soc. Trans. 28:545-550, (2000).
Cech, T.R., et al., "Biological catalysis by RNA," *Ann. Rev. Biochem.* 55:599-629, (1986).

Clackson, T., et al., "Making antibody fragments using phage display libraries," *Nature* 352:624-628, (1991).
Chen, P.F., et al., "Development of the non-palindromic adaptor polymerase chain reaction (NPA-PCR) for the amplification of alpha- and beta-chain T-cell receptor cDNAs," *Scand. J. Immunol.* 35:539-549, (1992).
Bird, et al., "Single-chain antigen-binding proteins," *Science* 242(4877):423-426, (1988).
Climie, S., et al., "Chemical synthesis of the thymidylate synthase gene," *Proc. Nat'l Acad. Sci. USA* 87(2):633, (1990).
Carter, P., et al., "Humanization of an anti-p185HER2 antibody for human cancer therapy," *Proc. Nat'l. Acad. Sci. USA* 89(10):4285-4289, (1992).
Altschul, S.F., et al., "Gapped BLAST and PSI-BLAST: a new generation of protein database search programs," *Nucl. Acids Res.* 25:3389-3402, (1997).
Makino, K., "A Microcapsule Self-Regulating Delivery System for Insulin," *J. Controlled Release* 12:235-239, (1990).
Lee, V.H.L., "Protease Inhibitors and Penetration Enhancers as Approaches to Modify Peptide Absorption," *J. Controlled Release* 13:213, (1990).
Jolliffe, L.K., et al., "Humanized antibodies: enhancing therapeutic utility through antibody engineering," *Int'l Rev. Immunol.* 10:241-250, (1993).
Jackson, D.Y., et al., "Potent alpha 4 beta 1 peptide antagonists as potential anti-inflammatory agents," *J. Med. Chem.* 40:3359-68, (1997).
Hori, R., et al., "Enhanced bioavailability of subcutaneously injected insulin coadministered with collagen in rats and humans," *Pharm. Res.* 6:813, (1989).
Daha, M.R., et al., "C3 nephritic factor (C3NeF): stabilization of fluid phase and cell-bound alternative pathway convertase," *J. Immunol.* 116(1):1-7, (1976).
Greenspan, N.S., et al., "Idiotypes: structure and immunogenicity," *FASEB J.* 7(5):437-444, (1993).
Deboer, A.G., et al., "Rectal Absorption Enhancement of Peptide Drugs," *J. Controlled Release* 13:241, (1990).
Fuertges, F., et al., "The Clinical Efficacy of Poly(ethylene Glycol)-modified Proteins," *J. Controlled Release* 11:139, (1990).
Singer, I.I., et al., "Optimal humanization of 1B4, an anti-CD18 murine monoclonal antibody, is achieved by correct choice of human V-region framework sequences," *J. Immun.* 150:2844, (1993).
Siegert, C.E., et al., "The relationship between serum titers of autoantibodies to C1q and age in the general population and in patients with systemic lupus erythematosus," *Clin. Immunol. Immunopathol.* 67:204-9, (1993).
Schwaeble, W., et al., "The mannan-binding lectin-associated serine proteases (MASPs) and MAp19: four components of the lectin pathway activation complex encoded by two genes," *Immunobiology* 205:455-466, (2002).
Sandhu, U.S., "Protein engineering of antibodies," *Crit. Rev. Biotech.* 12:437-462, (1992).
Ravetch, J.V., et al., "Fc receptors," *Annu. Rev. Immunol.* 9:457-492, (1991).
Rosenblatt, J., et al., "The Effect of Collagen Fiber Size Distribution on the Release Rate of Proteins from Collagen Matrices by Diffusion," *J. Controlled Release* 9:195, (1989).
Porter, R.R., "The hydrolysis of rabbit y-globulin and antibodies with crystalline papain," *Biochem. J.* 73:119, (1959).
Merrifield, R.B., "Solid Phase Peptide Synthesis. I. The Synthesis of a Tetrapeptide," in *J. Amer. Chem. Soc.* 85:2149-2154, (1963).
Presta, L.G., "Antibody engineering," *Curr. Op. Struct. Biol.* 2:593-596, (1992).
Lee, V.H.L., "Enzymatic Barriers to Peptide and Protein Absorption," *Crit. Rev. Ther. Drug Carrier Sys.* 5(2):69-97, (1988).
Ohman, E.M., et al., "Early clinical experience with integrelin, an inhibitor of the platelet glycoprotein IIb/IIIa integrin receptor," *European Heart J.* 16:50-55, (1995).
Pack, P., et al., "Improved bivalent miniantibodies, with identical avidity as whole antibodies, produced by high cell density fermentation of *Escherichia coli*," *Bio/Technology* 11:1271, (1993).

(56) References Cited

OTHER PUBLICATIONS

Zhang, L., et al., "A discrete site modulates activation of I domains. Application to integrin alphaMbeta2," *J. Biol. Chem.* 271(47):29953-57, (1996).
Taylor, L.D., et al., "Human immunoglobulin transgenes undergo rearrangement, somatic mutation and class switching in mice that lack endogenous IgM," *Int. Immun.* 6:579, (1994).
Takakura, Y., et al., "Control of pharmaceutical properties of soybean trypsin inhibitor by conjugation with dextran. I: Synthesis and characterization," *J. Pharm. Sci.* 78:117, (1989).
Van de Winkel, J.G., et al., "Human IgG Fc receptor heterogeneity: molecular aspects and clinical implications," *Immunol. Today* 14:215-221, (1993).
Vaughan, T.J., et al., "Human antibodies by design," *Nature Biotechnical* 16:535-539, (1998).
Scatchard, G., "The Attraction of Proteins for Small Molecules and Ions," *NY Acad. Sci.* 51:660-672, (1949).
Green, L.L., et al., "Antigen-specific human monoclonal antibodies from mice engineered with human Ig heavy and light chain YACs," *Nature Genet.* 7:13-21, (1994).
Glover, G.I., et al., "Synthetic peptide inhibitors of complement serine proteases—I. Identification of functionally equivalent protease inhibitor sequences in serpins and inhibition of Cls and D," *Mol. Immunol.* 25:1261, (1988).
Fedor, M.J., et al., "Substrate sequence effects on "hammerhead" RNA catalytic efficiency," *Proc. Natl. Acad. Sci. USA* 87:1668-1672, (1990).
Duncan, A.R., et al., "The binding site for Clq on IgG," *Nature* 332:738-740, (1988).
Dodds, A.W., "Small-scale preparation of complement components C3 and C4," *Methods Enzymol.* 223:46, (1993).
Haseloff, J., et al., "Simple RNA enzymes with new and highly specific endoribonuclease activities," *Nature* 334:585-591, (1988).
Matsushita, M., et al., "Activation of the classical complement pathway by mannose-binding protein in association with a novel Cls-like serine protease," *J. Exp. Med.* 176(6):1497-2284, (2000).
Morgan, B.P., "Clinical complementology: recent progress and future trends," *Eur. J. Clinical Investig.* 24(4):219-228, (1994).
Itakura, K., et al., "Synthesis and use of synthetic oligonucleotides," *Annu. Rev. Biochem.* 53:323, (1984).
Kuntz, I.D., et al., "Structure-based strategies for drug design and discovery," *Science* 257:1078, (1992).
Holmskov, U., et al., "Collections and ficolins: humoral lectins of the innate immune defense," *Annu. Rev. Immunol.* 21:547-578, (2003).
Ikeda, K., et al., "Serum lectin with known structure activates complement through the classical pathway," *J. Biol. Chem.* 262:7451-7454, (1987).
Jensen, J., et al., "Taming of transposable elements by homology-dependent gene silencing," *Nat. Genet.* 21(2):209-12, (1999).
Lloyd, B.H., et al., "Determination of optimal sites of antisense cleavage within TNFalpha mRNA," *Nucleic Acids Res.* 29:3665-3673, (2001).
DesJarlais, R.L., et al., "Structure-based design of nonpeptide inhibitors specific for the human immunodeficiency virus 1 protease," *PNAS* 87:6644-6648, (1990).
Bae, Y.H., et al., "Insulin Permeation Through Thermo-Sensitive Hydrogels," *J. Controlled Release* 9:271, (1989).
Asano, M., et al., "In Vivo Characteristics of Low Molecular Weight Copoly(L-Lactice Acid/Glycolic Acid) Formulations with Controlled Release of Luteinizing Hormone-Releasing Hormone Agonist," *J. Controlled Release* 9:111-112, (1989).
Kohler, G., et al., "Continuous cultures of fused cells secreting antibody of predefined specificity," *Nature* 256:495, (1975).
Kuntz, I.D., et al., "A geometric approach to macromolecule-ligand interactions," *J. Mol. Biol.* 161:269-288, (1982).
Kuhlman, et al., "The human mannose-binding protein functions as an opsonin," *J. Exp. Med.* 169:1733, (1989).
Losman, M.J., et al., "Baboon anti-idiotype antibodies mimic a carcinoembryonic antigen epitope," *Int. J. Cancer* 46:310, (1990).

Lonberg, N., et al., "Antigen-specific human antibodies from mice comprising four distinct genetic modifications," *Nature* 368:856, (1994).
Marks, J.D., et al., "By-passing immunization. Human antibodies from V-gene libraries displayed on phage," *J. Mol. Biol.* 222:581-597, (1991).
Matsushita et al., "A novel human serum lectin with collagen- and fibrinogen-like domains that functions as an opsonin," *J. Biol. Chem.* 271(5):2448-54, (1996).
Mariani, M., et al., "A new enzymatic method to obtain high-yield F(ab)2 suitable for clinical use from mouse IgGI," *Mol. Immunol.* 28:69-71, (1991).
Morrison, S.L., et al., "Chimeric human antibody molecules: mouse antigen-binding domains with human constant region domains," *Proc. Nat'l Acad. Sci. USA* 81:6851-6855, (1984).
Murayama, O., et al., "Novel peptide ligands for integrin alpha 6 beta 1 selected from a phage display library," *J. Biochem.* 120:445-51, (1996).
Nisonoff, A., et al., "Separation of univalent fragments from the bivalent rabbit antibody molecule by reduction of disulfide bonds," *Arch. Biochem. Biophys.* 89:230-244, (1960).
Scherr, M., et al., "Rapid determination and quantitation of the accessibility to native RNAs by antisense oligodeoxynucleotides in murine cell extracts," *Nucleic Acids Res.* 26:5079-5085, (1998).
Isaacs, J.D., et al., "Therapy with monoclonal antibodies. An in vivo model for the assessment of therapeutic potential," *J. Immunol.* 148(10):3062-3071, (1992).
Whitlow, M., et al., "Single-chain Fv Proteins and Their Fusion Proteins," *Methods: A Companion to Methods in Enzymology* 2:97-105, (1991).
Larrick, J.W., et al., "PCR Amplification of Antibody Genes," *Methods: A Companion to Methods in Enzymology* 2:106-110, (1991).
Jones, P. T., et al., "Replacing the complementarity-determining regions in a human antibody with those from a mouse," *Nature* 321:522-525, (1986).
Ward et al., "Genetic Manipulation and Expression of Antibodies," in *Monoclonal Antibodies: Principles and Applications*, Birch et al., (eds.) p. 137, Wiley-Liss, Inc., (1995).
Courtenay-Luck, N.S., "Genetic Manipulation of Monoclonal Antibodies," in *Monoclonal Antibodies: Production, Engineering and Clinical Application*, Ritter et al., (eds.) p. 166, Cambridge University Press, (1995).
Kelley, R.F., "Engineering Therapeutic Antibodies," in *Protein Engineering: Principles and Practice*, Cleland et al., (eds.) John Wiley & Sons, Inc., pp. 399-434, (1996).
Baines et al., "Purification of Immunoglobulin G, (IgG)," in *Methods in Molecular Biology vol. 10: Immunochemical Protocols*, Chapter 8, pp. 79-105, (1992).
Matsushita, M., et al., "The role of ficolins in innate immunity," *Immunobiology*, 205(4-5):490-497, (2002).
Tezel, G., et al., "Oxidative stress and the regulation of complement activation in human glaucoma" *Invest Ophthalmol Vis Sci* 51:5071-5082, (2010).
Harlow, E., et al., *Antibodies: A Laboratory Manual*, Cold Spring Harbor Laboratory, New York, (1988).
Heja, et al., "Monospecific Inhibitors Show That Both Mannan-binding Lectin-associated Serine Protease-1 (MASP-1) and -2 Are Essential for Lectin Pathway Activation and Reveal Structural Plasticity of MASP-2," *The Journal of Biological Chemistry*, 287(24):20290-20300 (2012).
Risitano, A.M., et al., "Complement fraction 3 binding on erythrocytes as additional mechanism of disease in paroxysmal nocturnal hemoglobinuria patients treated by eculizumab," *Blood* 113(17):4094-100, (2009).
Teh, C., et al., "M-ficolin is expressed on monocytes and is a lectin binding to N-acetyl-D-glucosamine and mediates monocyte adhesion and phagocytosis of *Escherichia coli*," *Immunology* 101:225-232, (2000).
Hansen, et al., "Collectin 11 (CL-11, CL-K1) is a MASP-1/3-associated plasma collectin with microbial-binding activity," *J. Immunol* 185(10):6096-6104, (2010).

(56) References Cited

OTHER PUBLICATIONS

Jack, D.L., et al., "Mannose-binding lectin enhances phagocytosis and killing of Neisseria meningitidis by human macrophages" *J Leukoc Biol.*, 77(3):328-36, (2005).
Aoyagi et al., "Role of L-ficolin/mannose-binding lectin-associated serine protease complexes in the opsonophagocytosis of type III group B streptococci," *J Immunol*, 174(1):418-25(2005).
Degn, S.E., et al., "MAp19, the alternative splice product of the MASP2 gene," *J Immunol. Methods*, 373(1-2):89-101, (2011).
Noris M et al. "Atypical Hemolytic-Uremic Syndrome," Nov. 16, 2007 [Updated, Mar. 10, 2011]. In: Pagon RA, Bird TD, Dolan CR, et al., editors. GeneReviews™, Seattle, (WA): University of Washington, Seattle.
Guessous, F., et al., "Shiga toxin 2 and lipopolysaccharide induce human microvascular endothelial cells to release chemokines and factors that stimulate platelet function," *Infect. Immun.*, 73(12): 8306-8316, (2005).
Kaufman, R.J., et al., "Improved vectors for stable expression of foreign genes in mammalian cells by use of the untranslated leader sequence from EMC virus," *Nucleic Acids Research* 19:4485-90, (1991).
Kaufman, R.J., "Selection and coamplification of heterologous genes in mammalian cells," *Methods in Enzymology*, 185:537-66, (1990).
Maniatis, A., et al., "Intermediate-dose melphalan for refractory myeloma," *Blood* 74(3):1177, (1989).
Shea, K.J., "Molecular Imprinting of Synthetic Network Polymers: The De Novo synthesis of Macromolecular Binding and Catalytic Sties," *TRIP* 2(5):166-173, (1994).
Colligan, "Production of Monoclonal Antibosies," *Current Protocols in Immunology*, vol. 1., John Wiley & Sons, pp. 2.5.1-2.6.7, (1991).
Gal et al., "A true autoactivating enzyme. Structural insight into mannose-binding lectin-associated serine protease-2 activations," *J. Biol. Chem.* 280(39):33435-44, (2005).
Ricklin, et al., "Complement: a key system for immune surveillance and homeostasis," *Nat. Immunology* 11(9): 785-797 (2010).
Reichmann, L., et al., "Reshaping human antibodies for therapy," *Nature* 332:323-329, (1988).
Lee, W.A., "Permeation enhancers for the nasal delivery of protein and peptide therapeutics," *Biopharm.* 3:22-25, (1990).
Yoshihiro, I., et al., "An Insulin-Releasing System that is Responsive to Glucose," *J. Controlled Release* 10:195-203, (1989).
Green, J.A., et al., "Production of polyclonal antisera," In: Immunochemical protocols. Methods in molecular biology, vol. 10. Humana Press, Totowa, N.J., p. 1, (1992).
King, L.A., et al., "Propagation, titration and purification of AcMNPV in cell culture," *The Baculovirus Expression System: A Laboratory Guide*, Chapman and Hall Ltd., London, pp. 106-126, (1992).
Gastoldi, S., et al., "C5a/C5aR interaction mediates complement activation and thrombosis on endothelial cells in atypical hemolytic uremic syndrome (aHUS)," *Immunobiology* 217(11):1145-1146, (2012).
Abagyan, R., et al., "Biased probability Monte Carlo conformational searches and electrostatic calculations for peptides and proteins," *J Mol Biol* 235(3):983-1002 (1994).
Abagyan, R., et al., "ICM-A new method for protein modeling and design: Applications to docking and structure prediction from the distorted native conformation," *Journal of Computational Chemistry* 15(5):488-506 (1994).
An, J., et al., "Pocketome via comprehensive identification and classification of ligand binding envelopes," *Mol Cell Proteomics* 4(6):752-761 (2005).
Biela, A., et al., "Ligand binding stepwise disrupts water network in thrombin: enthalpic and entropic changes reveal classical hydrophobic effect," *J Med Chem* 55(13):6094-6110 (2012).
Brady, G. P., Jr., et al., "Fast prediction and visualization of protein binding pockets with Pass," *J Comput Aided Mol Des* 14(4):383-401 (2000).

Brylinski, M., et al., "Prediction of functional sites based on the fuzzy oil drop model," *PLoS Comput Biol* 3(5):e94 (2007).
Brylinski, M., et al., "A threading-based method (FINDSITE) for ligand-binding site prediction and functional annotation," *Proc Natl Acad Sci U S A* 105(1):129-134 (2008).
Chang, D. T., et al., "MEDock: a web server for efficient prediction of ligand binding sites based on a novel optimization algorithm," *Nucleic Acids Res* 33(Web Server issue):W233-238 (2005).
Del Carpio, C. A., et al., "A new approach to the automatic identification of candidates for ligand receptor sites in proteins: (I). Search for pocket regions," *J Mol Graph* 11(1):23-29, 42 (1993).
Delaney, J. S., "Finding and filling protein cavities using cellular logic operations," *J Mol Graph* 10(3): 174-177, 163 (1992).
Donner, A., "The XII factor," *Science-Business eXchange* 7:1-4 (2014).
Dundas, J., et al., "CASTp: computed atlas of surface topography of proteins with structural and topographical mapping of functionally annotated residues," *Nucleic Acids Res* 34(Web Server issue):W116-118 (2006).
Emsley, P., et al., "Features and development of Coot," *Acta Crystallogr D Biol Crystallogr* 66(Pt 4):486-501 (2010).
Fernández-Recio, J., "Prediction of protein binding sites and hot spots," *Wiley Interdiscip Rev Comput Mol Sci* 1(5):680-698 (2011).
Fukunishi, Y., et al., "Prediction of ligand-binding sites of proteins by molecular docking calculation for a random ligand library," *Protein Sci* 20(1):95-106 (2011).
Gelb, M. H., et al., "Substituted isatoic anhydrides: selective inactivators of trypsin-like serine proteases," *J Med Chem* 29(4):585-589 (1986).
Glaser, F., et al., "ConSurf: identification of functional regions in proteins by surface-mapping of phylogenetic information," *Bioinformatics* 19(1):163-164 (2003).
Goodford, P. J., "A computational procedure for determining energetically favorable binding sites on biologically important macromolecules," *J Med Chem* 28(7):849-857 (1985).
Greene, J., et al., "Chemical Function Queries for 3D Database Search," *J Chem Inf Comput Sci* 34(6):1297-1308 (1994).
Grutter, M. G., et al., "Crystal structure of the thrombin-hirudin complex: a novel mode of serine protease inhibition," *EMBO J* 9(8):2361-2365 (1990).
Halgren, T., "New method for fast and accurate binding-site identification and analysis," *Chem Biol Drug Des* 69(2):146-148 (2007).
Hedstrom, L., "Serine protease mechanism and specificity," *Chem Rev* 102(12):4501-4524 (2002).
Hendlich, M., et al., "LIGSITE: automatic and efficient detection of potential small molecule-binding sites in proteins," *J Mol Graph Model* 15(6):359-363, 389 (1997).
Huang, B., et al., "LIGSITEcsc: predicting ligand binding sites using the Connolly surface and degree of conservation," *BMC Struct Biol* 6:19 (2006).
Katz, B. A., et al., "Design of potent selective zinc-mediated serine protease inhibitors," *Nature* 391(6667):608-612 (1998).
Kenawy, H. I., et al., "Complement-Coagulation Cross-Talk: A Potential Mediator of the Physiological Activation of Complement by Low pH," *Front Immunol* 6:215 (2015).
Kleywegt, G. J., et al., "Detection, delineation, measurement and display of cavities in macromolecular structures," *Acta Crystallogr D Biol Crystallogr* 50(Pt 2):178-185 (1994).
Kozarcanin, H., et al., "The lectin complement pathway serine proteases (MASPs) represent a possible crossroad between the coagulation and complement systems in thromboinflammation," *J Thromb Haemost* 14(3):531-545 (2016).
Laskowski, R. A., et al., "LigPlot+: multiple ligand-protein interaction diagrams for drug discovery," *J Chem Inf Model* 51(10):2778-2786 (2011).
Laskowski, R. A., "Surfnet: a program for visualizing molecular surfaces, cavities, and intermolecular interactions," *J Mol Graph* 13(5):323-330, 307-328 (1995).
Laurie, A. T., et al., "Q-SiteFinder: an energy-based method for the prediction of protein-ligand binding sites," *Bioinformatics* 21(9):1908-1916 (2005).

(56) References Cited

OTHER PUBLICATIONS

Levitt, D. G., et al., "POCKET: a computer graphics method for identifying and displaying protein cavities and their surrounding amino acids," *J Mol Graph* 10(4):229-234 (1992).
Lin, C., et al., "Discovery and development of VX-950, a novel, covalent, and reversible inhibitor of hepatitis C virus NS3.4A serine protease," *Infect Disord Drug Targets* 6(1):3-16 (2006).
Moake, J. L., Merck Manual—Hematology and Oncology: Overview of Thrombotic Disorders [updated Oct. 17, 2019]. Available from: https://www.merckmanuals.com/professional/hematology-and-oncology/thrombotic-disorders/overview-of-thrombotic-disorders.
Nayal, M., et al., "On the nature of cavities on protein surfaces: application to the identification of drug-binding sites," *Proteins* 63(4):892-906 (2006).
Ni-NTA Superflow Cartridge Handbook: For manual or FPLC™ purification of His-tagged proteins: QIAGEN; 2007. 32 p.
Pedregosa, F., et al., "Scikit-learn: Machine Learning in Python," *Journal of Machine Learning Research* 12:2825-2830 (2011).
Peters, K. P., et al., "The automatic search for ligand binding sites in proteins of known three-dimensional structure using only geometric criteria," *J Mol Biol* 256(1):201-213 (1996).
Powers, J. C., et al., "Irreversible inhibitors of serine, cysteine, and threonine proteases," *Chem Rev* 102(12):4639-4750 (2002).
Protein Data Bank [Internet]. 3TVJ—Catalytic fragment of MASP-2 in complex with its specific inhibitor developed by directed evolution on SGCI scaffold. 2011 [cited Oct. 22, 2019]. Available from: https://www.resb.org/structure/3tvj.
Ramot, Y., et al., "Drug-induced thrombosis—experimental, clinical, and mechanistic considerations," *Toxicol Pathol* 35(2):208-225 (2007).
Renne, T., et al., "In vivo roles of factor XII," *Blood* 120(22):4296-4303 (2012).
Schechter, I., et al., "On the size of the active site in proteases. I. Papain," *Biochem Biophys Res Commun* 27(2):157-162 (1967).
Smoum, R., et al., "Boron containing compounds as protease inhibitors," *Chem Rev* 112(7):4156-4220 (2012).
Uniprot.org [Internet]. Identifier: O00187, Mannan-binding lectin serine protease 2. 2019 [cited Oct. 22, 2019]. Available from: https://www.uniprot.org/uniprot/O00187.
Venkatachalam, C. M., et al., "LigandFit: a novel method for the shape-directed rapid docking of ligands to protein active sites," *J Mol Graph Model* 21(4):289-307 (2003).
Verdonk, M. L., et al., "SuperStar: a knowledge-based approach for identifying interaction sites in proteins," *J Mol Biol* 289(4):1093-1108 (1999).
Weisel, M., et al., "PocketPicker: analysis of ligand binding-sites with shape descriptors," *Chem Cent J* 1:7 (2007).
Weitz, J. I., et al., "Factors XI and XII as Targets for New Anticoagulants," *Front Med (Lausanne)* 4:19 (2017).
Young, W. B., et al., "Generation of potent coagulation protease inhibitors utilizing zinc-mediated chelation," *Bioorg Med Chem Lett* 16(3):710-713 (2006).
*SciFinder*; Chemical Abstracts Service: Columbus, OH; RN 1223890-82-1 [accessed Nov. 27, 2019]. Available from: https://scifinder.cas.org.
*SciFinder*; Chemical Abstracts Service: Columbus, OH; RN 1242003-50-4 [accessed Nov. 27, 2019]. Available from: https://scifinder.cas.org.
Parlow et al., "Design, Parallel Synthesis, and Crystal Structures of Pyrazinone Antithrombotics as Selective Inhibitors of the Tissue Factor VIIa Complex," *Journal of Medicinal Chemistry*, 46(19):4050-4062 (2003).
Sanderson, et al., "Azaindoles: Moderately Basic P1 Groups for Enhancing the Selectivity of Thrombin Inhibitors," *Biorganic & Medicinal Chemistry Letters*, 13:795-798 (2003).
Staas et al., "Discovery of potent, selective 4-fluoroproline-based thrombin inhibitors with improved metabolic stability," Biorganic & Medicinal Chemistry, 14(20): 6900-16 (2006).
Lange et al., "Orally active thrombin inhibitors. Part 2: Optimization of the P2-moiety," *Biorganic & Medicinal Chemistry*, 16(10): 2648-53 (2006).
Ronn, et al., "Exploration of acyl sulfonamides as carboxylic acid replacements in protease inhibitors of the hepatitis C virus full-length NS3," *Biorganic & Medicinal Chemistry*, 14: 544-559 (2006).
Extended Eurpropean Search Report, dated Mar. 14, 2022 for PCT/US2019/034220.
Belikov, V.G., "Pharmaceutical Chemistry", textbook, 2007, Moscow, "MEDpress-Inform", pp. 27-29.
Dyson G. and P. Mei, "Chemistry of synthetic drugs", translation from English, M: "Mir", 1964, pp. 12-19).
Kümmererer, K. Pharmaceuticals in the environment, Annual Review of Environment and Resources, 2010, V.35, p. 57-75, doi: 10.1146/annurev-environ-052809-16122.
Alexeev, V.V., Optical isomerism and pharmacologic activity of drugs. Soros Educational Journal, 1998, pp. 49-55.
Registry(STN) [online], [search date Aug. 15, 2024]: CAS Registry No. 1325176-10-0, Entry Date Aug. 29, 2011, CAS Registry No. 1321541-78-9, Entry Date Aug. 22, 2011, CAS Registry No. 1300407-49-1, Entry Date May 25, 2011, CAS Registry No. 1277113-31-1, Entry Date Apr. 8, 2011, CAS Registry No. 1277016-41-7, Entry Date Apr. 8, 2011, CAS Registry No. 1240647-23-7, Entry Date Sep. 13, 2010, CAS Registry No. 1009452-72-5, Entry Date Mar. 21, 2008.
Registry(STN) [online], [Retrieved on Jul. 31, 2024]: CAS Registry No. 1348730-54-0, Entry Date Dec. 5, 2011, CAS Registry No. 1348728-96-0, Entry Date Dec. 5, 2011, CAS Registry No. 1348431-17-3, Entry Date Dec. 4, 2011, CAS Registry No. 1348395-03-8, Entry Date Dec. 4, 2011, CAS Registry No. 749177-11-5, Entry Date Sep. 21, 2004.
Endo, Y., "Collaboration of the lectin complement pathway with the blood coagulation system," Japanese Journal of Thrombosis and Hemostasis 22(4): 164-170, 2011.
Ohkuma, K., et al., "Crosstalk between the two systems, blood coagulation and complement," Japanese Journal of Thrombosis and Hemostasis 22(4):171-185, 2011.

\* cited by examiner

- ● Hydrophobic Group
- ⊙ Aromatic Ring
- ○ Hydrogen Bond Donor
- ⊕ Positive Ionizable Group
- ⊗ Hydrogen Bond Acceptor

MASP-2 INHIBITORS AND METHODS OF USE

CROSS-REFERENCE TO RELATED APPLICATIONS

This application is a continuation of pending U.S. application Ser. No. 16/425,791, filed May 29, 2019, which is a continuation of International Patent Application No. PCT/US19/34220 filed May 28, 2019, which claims the benefit of U.S. Provisional Application Ser. No. 62/677,472, filed May 29, 2018, U.S. Provisional Application Ser. No. 62/677,538, filed May 29, 2018, U.S. Provisional Application Ser. No. 62/677,495, filed May 29, 2018, and U.S. Provisional Application Ser. No. 62/677,514, filed May 29, 2018. Each of the foregoing related applications is incorporated herein by reference in its entirety.

STATEMENT REGARDING SEQUENCE LISTING

The sequence listing associated with this application is provided in .xml format in lieu of a paper copy and is hereby incorporated by reference into the specification. The name of the .xml file containing the sequence listing is MP_1_0281_US2_SequenceListing_20221122_ST26. The .xml file is 2,641 bytes, was created on Nov. 22, 2022, and is being submitted via the Patent Center with the filing of the specification.

FIELD

The present disclosure is directed generally to compositions and methods that are useful in the field of medicine. More specifically, the disclosure provides small molecule synthetic inhibitors of mannan-binding lectin-associated serine protease-2 (MASP-2), including small molecule inhibitors that are selective for MASP-2 over thrombin, compositions thereof, and methods for the manufacture and use thereof.

BACKGROUND

The complement system plays a role in the inflammatory response and becomes activated because of tissue damage or microbial infection. Complement activation must be tightly regulated to ensure selective targeting of invading microorganisms and avoid self-inflicted damage (Ricklin et al., Nat. Immunol. 11:785-797, 2010). Currently, it is widely accepted that the complement system can be activated through three distinct pathways: the classical pathway, the lectin pathway, and the alternative pathway. The classical pathway is usually triggered by a complex composed of host antibodies bound to a foreign particle (i.e., an antigen) and generally requires prior exposure to an antigen for the generation of a specific antibody response. Since activation of the classical pathway depends on a prior adaptive immune response by the host, the classical pathway is part of the acquired immune system. In contrast, both the lectin and alternative pathways are independent of adaptive immunity and are part of the innate immune system.

Mannan-binding lectin-associated serine protease-2 (MASP-2) has been shown to be required for the function of the lectin pathway, one of the principal complement activation pathways (Vorup-Jensen et al., J. Immunol 165:2093-2100, 2000; Ambrus et al., J Immunol. 170: 1374-1382, 2003; Schwaeble et al., PNAS 108:7523-7528, 2011). Importantly, inhibition of MASP-2 does not appear to interfere with the antibody-dependent classical complement activation pathway, which is a critical component of the acquired immune response to infection. As described in U.S. Pat. No. 9,011,860 (assigned to Omeros corporation), which is hereby incorporated by reference, discloses a fully human monoclonal antibody targeting human MASP-2 has been generated which binds to human MASP-2 with high affinity and blocks the lectin pathway complement activity and is therefore useful to treat various lectin complement pathway-associated diseases and disorders.

MASP-2-dependent complement activation has been implicated as contributing to the pathogenesis of numerous acute and chronic disease states. Therefore, a need exists for small molecule compounds which are suitable for administration for treatment of subject suffering from MASP-2 complement pathway-associated diseases and disorders.

An important protein for mammalian immunity is the mannan-binding lectin-associated serine protease-2 (MASP-2), which has been shown to be required for the function of the lectin pathway, one of the principal complement activation pathways (Vorup-Jensen et al., J. Immunol 165:2093-2100, 2000; Ambrus et al., J Immunol. 170: 1374-1382, 2003; Schwaeble et al., PNAS 108:7523-7528, 2011). Inhibition of MASP-2 does not appear to interfere with the antibody-dependent classical complement activation pathway, which is a critical component of the acquired immune response to infection. Inhibiting human MASP-2 to block the lectin pathway complement activity is useful to treat various lectin complement pathway-associated diseases and disorders.

Therapeutic compounds and methods of identifying small molecule inhibitors of MASP-2 are needed as they are important to treat various lectin complement pathway-associated diseases and disorders, including diseases that are not suitably or efficiently treated with large molecule biologic inhibitors.

SUMMARY

The present disclosure provides, inter alia, compounds of Formulae (I-1) and (I-2):

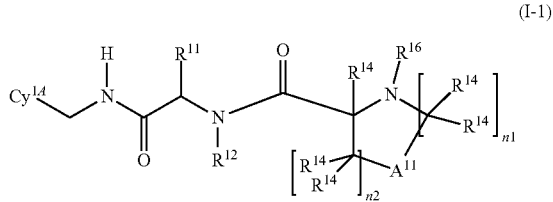

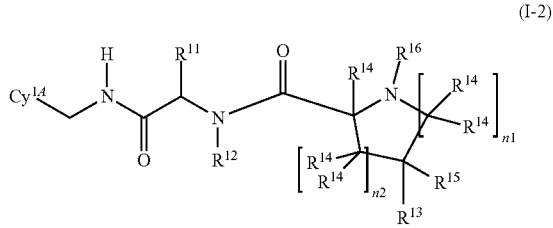

or a salt thereof; wherein the variables are as defined below.

The present disclosure also provides a pharmaceutical composition comprising a compound of Formula (I-1) or (I-2), or a pharmaceutically acceptable salt thereof, and at least one pharmaceutically acceptable carrier or excipient.

The compounds of Formula (I-1) or (I-2) are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Formula (I-1) or (I-2), or a salt thereof.

The present disclosure provides, inter alia, compounds of Formulae (IIA) and (IIB):

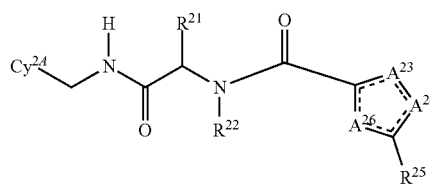

(IIA)

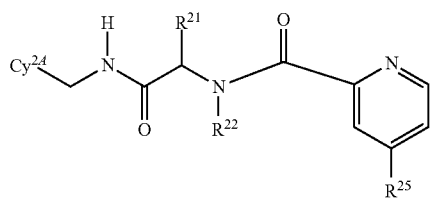

(IIB)

or a salt thereof; wherein the variables are as defined below. Various embodiments of the compounds of Formula (IIA) or (IIB), are also described.

The present disclosure also provides a pharmaceutical composition comprising a compound of Formula (IIA) or (IIB), or a pharmaceutically acceptable salt thereof, and at least one pharmaceutically acceptable carrier or excipient.

The compounds of Formula (IIA) or (IIB) are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Formula (IIA) or (IIB), or a salt thereof.

The present disclosure provides, inter alia, compounds of Formula (III):

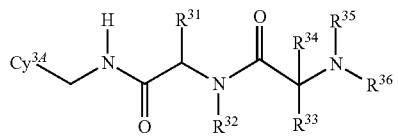

(III)

or a salt thereof; wherein the variables are as defined below. Various embodiments of the compounds of Formula (III), are also described.

The present disclosure also provides a pharmaceutical composition comprising a compound of Formula (III), or a pharmaceutically acceptable salt thereof, and at least one pharmaceutically acceptable carrier or excipient.

The compounds of Formula (III) are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Formula (III), or a salt thereof.

The present disclosure provides, inter alia, compounds of Formulae (IV):

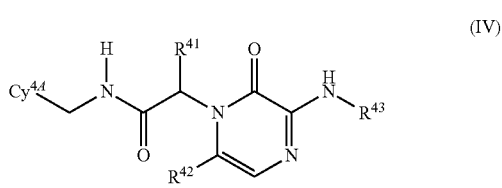

(IV)

or a salt thereof; wherein the variables are as defined below. Various embodiments of the compounds of Formula (IV), are also described.

The present disclosure also provides a pharmaceutical composition comprising a compound of Formula (IV), or a pharmaceutically acceptable salt thereof, and at least one pharmaceutically acceptable carrier or excipient.

The compounds of Formula (IV) are useful as MASP-2 inhibitors. The compounds of Formula (IV) are useful in therapy. The compounds of Formula (IV) are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Formula (IV), or a salt thereof.

The present disclosure provides, inter alia, compounds of Formulae (VA) or (VB):

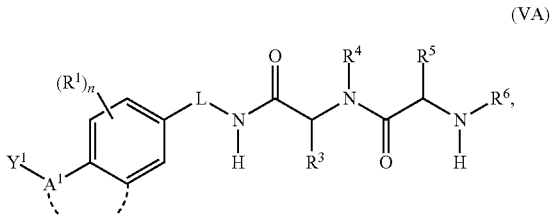

(VA)

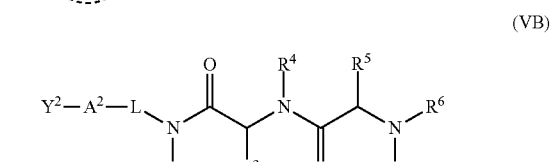

(VB)

or a salt thereof; wherein the variables are as defined below. Various embodiments of the compounds of Formula (VA) or (VB) are also described.

The present disclosure also provides a pharmaceutical composition comprising a compound of Formula (VA) or (VB), or a pharmaceutically acceptable salt thereof, and at least one pharmaceutically acceptable carrier or excipient.

The compounds of Formula (VA) and (VB) are useful as MASP-2 inhibitors. The compounds of Formula (VA) and (VB) are useful in therapy. The compounds of Formula (VA) and (VB) are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Formula (VA) or (VB), or a salt thereof.

The present disclosure provides, inter alia, compounds of Formulae (VIA) or (VIB):

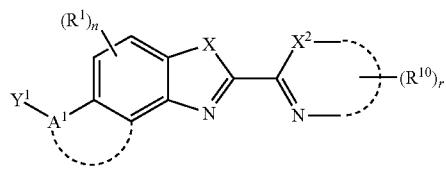

(VIA)

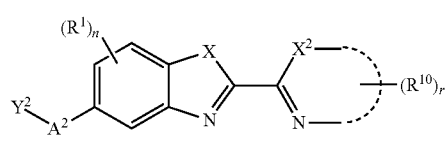

(VIB)

or a salt thereof; wherein the variables are as defined below. Various embodiments of the compounds of Formula (VIA) or (VIB) are also described.

The present disclosure also provides a pharmaceutical composition comprising a compound of Formula (VIA) or (VIB), or a pharmaceutically acceptable salt thereof, and at least one pharmaceutically acceptable carrier or excipient.

The compounds of Formula (VIA) and (VIB) are useful as MASP-2 inhibitors. The compounds of Formula (VIA) and (VIB) are useful in therapy. The compounds of Formula (VIA) and (VIB) are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Formula (VIA) or (VIB), or a salt thereof.

The present disclosure provides, inter alia, compounds of Formulae (VIIA) or (VIIB):

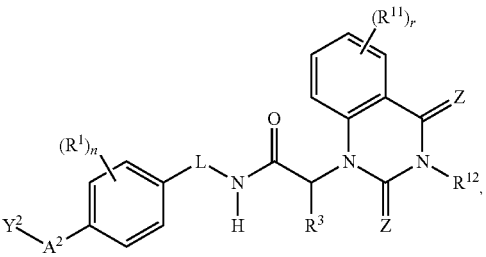

(VIIA)

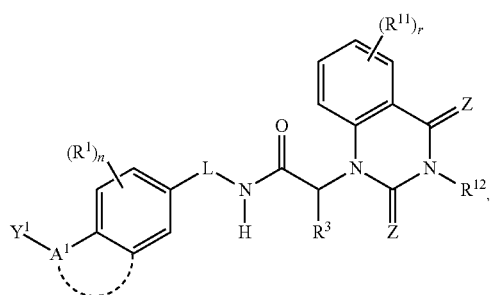

(VIIB)

or a salt thereof; wherein the variables are as defined below. Various embodiments of the compounds of Formula (VIIA) or (VIIB) are also described.

The present disclosure also provides a pharmaceutical composition comprising a compound of Formula (VIIA) or (VIIB), or a pharmaceutically acceptable salt thereof, and at least one pharmaceutically acceptable carrier or excipient.

The compounds of Formula (VIIA) and (VIIB) are useful as MASP-2 inhibitors. The compounds of Formula (VIIA) and (VIIB) are useful in therapy. The compounds of Formula (VIIA) and (VIIB) are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Formula (VIIA) or (VIIB), or a salt thereof.

The present disclosure provides, inter alia, small molecule compounds having MASP-2 inhibitory activity, especially for therapeutic use. The small molecule compound with MASP-2 inhibitory activity interacts with the MASP-2 serine protease domain in an enzyme-inhibitor complex with a plurality of intermolecular interactions. In certain aspects, the small molecule is described with complete specificity and description by the number and type(s) of intermolecular interactions within a MASP-2 binding site, using an empirically derived rule set. The inhibitors follow one or more of the interaction rules.

In certain aspects, the present disclosure provides a small molecule compound with MASP-2 inhibitory activity, for therapeutic use, wherein the compound has one or more such as 1, 2, 3, 4, or 5 of the following interactions (a) to (e):
  a) the compound binds via H-bonds with one or more of PRO 606, ASP 627, SER 628, ARG 630, SER 633, SER 654, GLY 656, SER 657, CYS 660 and GLN 665 in MASP-2;
  b) the compound binds via ionic or electrostatic interactions or hydrogen bonding to one or more of ASP 627 and ARG 630 in MASP-2;
  c) the compound interacts via a water molecule in MASP-2 to one or more of TYR 602, TYR 607, ASP 627, SER 628, SER 657, ASN 659, GLU 662, TRP 655, GLY656, CYS660, GLN 665, TYR 666, VAL 668, and ARG 630 in MASP-2;
  d) the compound interacts via π-π interactions with one or more of PHE 529, TYR 607, and TRP 655 in MASP-2; and
  e) the compound interacts via van der Waals contacts to one or more of ALA 468, ALA 469, HIS 483, ASP 526, ALA 527, GLY 528, PHE 529, LEU 575, PRO 606, TYR 607, PRO 608, SER 611, ASP 627, SER 628, CYS 629, ARG 630, GLY 631, ASP 632, SER 633, GLY 634, GLY 635, VAL 653, SER 654, TRP 655, GLY656, SER 657, MET 658, ASN 659, CYS 660, GLN 665, GLY 667, and TYR 669 in MASP-2, In some embodiments, the compound is not an endogenous MASP-2 ligand.

In some embodiments, the compound is a synthetic small molecule MASP-2 inhibitor.

In some embodiments, the compound selectively inhibits MASP-2 as compared to thrombin.

Various embodiments of the compounds defined by interaction rules are described. The disclosure provides a composition comprising such a compound, or a pharmaceutically acceptable salt thereof, and at least one pharmaceutically acceptable carrier or excipient. The compounds are useful as MASP-2 inhibitors. The compounds are useful in therapy. The compounds are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of defined by interaction rules set forth herein.

The present disclosure provides, inter alia, compounds of Formula (VIII):

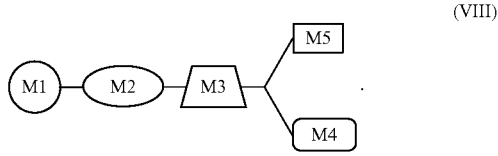

(VIII)

or a salt thereof; wherein the elements of the Formula may have values as described below. Various embodiments of the compounds of Formula (VIII) are also described. The present disclosure also provides a pharmaceutical composition comprising a compound of Formula (VIII), or a pharmaceutically acceptable salt thereof, and at least one pharmaceutically acceptable carrier or excipient. The compounds of Formula (VIII) are useful as MASP-2 inhibitors. The compounds of Formula (VIII) are useful in therapy. The compounds of Formula (VIII) are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Formula (VIII), or a salt thereof.

The present disclosure provides, inter alia, a pharmacophore model for describing small molecule compounds including synthetic compounds that inhibit MASP-2 and compounds defined with specificity by reference to such a pharmacophore model.

In some embodiments, the compounds that are active as inhibitors of MASP-2 may include one or combinations of 2, 3, 4, 5, 6, 7, 8, 9, 10, 11, 12, 13, 14, 15, 16, 17, 18, 19, 20, 21, or 22 of the pharmacophore elements, preferably combinations of 3, 4, 5, 6, 7, 8, 9, 10, 11, 12, 13 or 14 of the pharmacophore elements listed in Table 1. In some embodiments, the compounds may have pharmacophore elements corresponding to those listed in Table 1, wherein the (x, y, z) coordinates of the pharmacophore elements are within four standard deviations, preferably within three standard deviations, more preferably within two standard deviations and most preferably within one standard deviation as listed in Table 1.

In some embodiments, a compound is provided that comprises a combination of pharmacophore elements comprising:
  (a) an S1 pharmacophore group comprising CA1 and N1 pharmacophore elements or CA1 and C5 pharmacophore elements; and/or
  (b) an S2 pharmacophore group comprising H4 and O2 pharmacophore elements; and/or
  (c) an S3 pharmacophore group comprising a C2 pharmacophore element and an N2 or H3 pharmacophore element;
wherein:
  C2 and C5 are hydrophobic groups;
  CA1 is an aromatic ring;
  H3 and H4 are hydrogen bond donors;
  N1 and N2 are positive ionizable groups; and
  O2 is a hydrogen bond acceptor;
  wherein C2, C5, CA1, H3, H4, N1, N2, and O2 have coordinates in the ranges given in Table 3, 4 or 5 below.

In some embodiments, a compound is provided that comprises a combination of pharmacophore elements comprising:
  (a) an S1 pharmacophore group comprising CA1 and N1 pharmacophore elements or CA1 and C5 pharmacophore elements;
  (b) an S2 pharmacophore group comprising H4 and O2 pharmacophore elements; and
  (c) an S3 pharmacophore group comprising a C2 pharmacophore element and an N2 or H3 pharmacophore element.

Various embodiments of the small molecule compounds defined by the pharmacophore model are described. The disclosure provides a composition comprising such a compound, or a pharmaceutically acceptable salt thereof, and at least one pharmaceutically acceptable carrier or excipient. The compounds are useful as MASP-2 inhibitors. The compounds are useful in therapy. The compounds are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of defined by the pharmacophore model.

The present disclosure also provides small molecule compounds with MASP-2 inhibitory activity, wherein the compound interacts with a binding site of MASP-2, wherein the compounds are defined by reference to "binding rules" or "rule sets" derived using virtual docking models of crystallographically-derived MASP-2 enzyme co-crystal structures and binding sites within the MASP-2 enzyme. In certain aspects, the amino acids and their respective atoms of the MASP-2 binding site that are accessible to small molecule MASP-2 inhibitors are described. By using a variety of compounds and their intermolecular interactions, it is possible to design a set of "binding rules" or "rule set" by which MASP-2 inhibitors are specifically described.

In certain aspects, an small molecule MASP-2 inhibitor is described by a rule set. The compound with MASP-2 inhibitory activity interacts with a binding site of MASP-2 such as an enzyme-inhibitor complex, with a plurality of intermolecular interactions. In certain aspects, the molecule is described with complete specificity and a complete description by the number and type(s) of in silico intermolecular interactions between atoms of the MASP-2 amino acid residues of the binding site and atoms of the inhibitor molecule. These rules are empirically derived using virtual docking models of crystallographically-derived MASP-2 enzyme co-crystal structures and binding sites within the MASP-2 enzyme. In certain instances, a plurality of MASP-2 enzyme-inhibitor models can be used such as 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or even more protein models to generate a set of rules.

In some embodiments, the present disclosure provides a compound with MASP-2 inhibitory activity, wherein the compound interacts with a binding site, the interactions being one or more of (a) to (e):
  a) the compound interacts via H-bonds with one or more amino acid residues in the binding site of MASP-2 (SEQ ID NO: 1);
  b) the compound interacts via ionic or electrostatic interactions or hydrogen bonding in the binding site of SEQ ID NO: 1;
  c) the compound interacts via a water molecule in a binding site of SEQ ID NO: 1;
  d) the compound interacts via π-π interactions with one or more amino acid residues in the binding site of SEQ ID NO: 1; and/or
  e) the compound interacts via van der Waals contacts to one or more amino acid residues in the binding site of SEQ ID NO: 1, wherein the compound is not an endogenous ligand or substrate.

In certain aspects, the compound has 1, 2, 3, 4, or 5 of the interactions (a)-(e).

In another embodiment, the present disclosure provides a method for identifying a small molecule capable of inhibiting MASP-2, comprising:
  a) screening small molecule libraries using in silico docking for candidate small molecules that are selectively identified for their ability to target and bind to MASP-2 at a binding site of a MASP-2 model; and
  b) testing/evaluating the candidate agents identified in step (a) through one or more in vitro assays for their ability to target and bind to a MASP-2 binding site, to thereby identify the small molecule capable of inhibiting MASP-2.

In certain aspects, the candidate small molecules comprise unique chemical scaffolds as identified in step (b) and are optimized for their ability to inhibit MASP-2.

These and other aspects, objects and embodiments will become more apparent when read with the detailed description and figures which follow.

DESCRIPTION

I. Definitions

Figure 1:
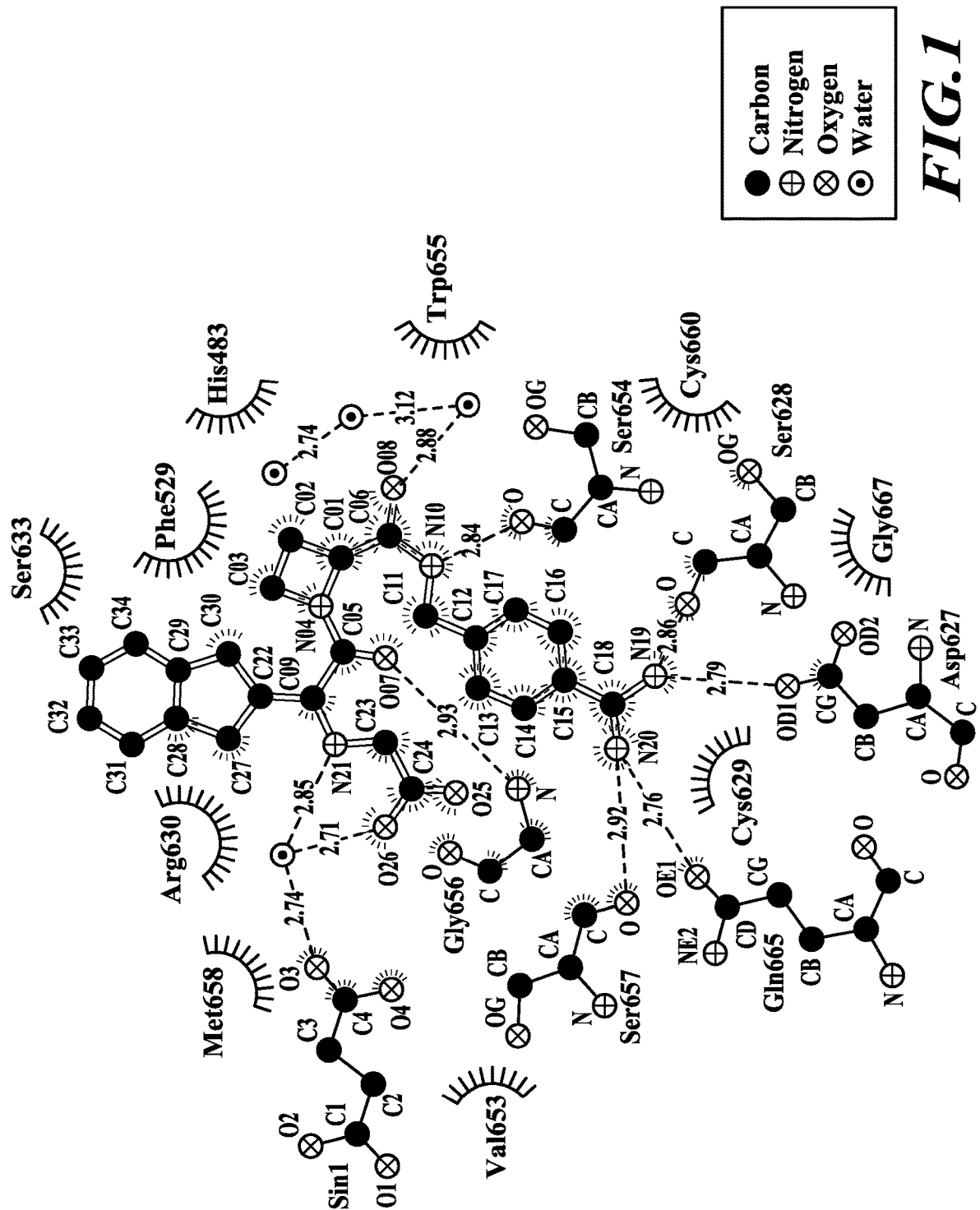
FIG. 1 is a plot illustrating a schematic of one embodiment of the atoms of an inhibitory compound (1129) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting.

In the Summary above, the present Description, and the claims below, reference is made to particular features and aspects of the invention, including method steps. The disclosure of the invention in this specification includes all possible combinations of such particular features within the embodiments of the invention disclosed, at least to the extent that such combinations are non-contradictory. For example, if the description presents aspects A, B, and C of an embodiment, it is understood that this also discloses particular embodiments including both aspects A and B, both aspects B and C, and both aspects A and C, as well as an embodiment with aspects A, B, and C.

a. General Definitions

The terms "a," "an," or "the" not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art.

The terms "about" and "approximately" refer to an acceptable degree of error for the quantity measured given the nature or precision of the measurements. Typical, exemplary degrees of error are within 20 percent (%); preferably, within 10%; and more preferably, within 5% of a given value or range of values. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written support for a claim limitation of, e.g., "0.98X." Alternatively, in biological systems, the terms "about" and "approximately" may mean values that are within an order of magnitude, preferably within 5-fold, and more preferably within 2-fold of a given value. Numerical quantities given herein are approximate unless stated otherwise, meaning that the term "about" or "approximately" can be inferred when not expressly stated. When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11 mg/kg" is equivalent to "about 7, about 9, or about 11 mg/kg."

The term "MASP-2" refers to mannan-binding lectin-associated serine protease-2. Human MASP-2 protein with UniProt accession code O00187 (SEQ ID NO:1). The Serine Protease Domain ('B-chain'=Mannan-binding lectin serine protease 2 B chain, based on UniProtKB—O00187 (MASP-2_HUMAN)) includes residues 445 to 686 (or consists of residues 445 to 686).

The term "MASP-2-dependent complement activation" refers to MASP-2-dependent activation of the lectin pathway, which occurs under physiological conditions (i.e., in the presence of $Ca^{++}$) leading to the formation of the lectin pathway C3 convertase C4b2a and upon accumulation of the C3 cleavage product C3b subsequently to the C5 convertase C4b2a(C3b)n.

The term "MASP-2-dependent complement-associated disease or disorder" refers to a disease or disorder that is associated with MASP-2-dependent complement activation.

The term "MASP-2-associated disease or disorder" refers to a disease or disorder that is associated with activation or activity of MASP-2, including MASP-2-dependent complement-associated disease or disorders, and wherein inhibition of MASP-2 is or is expected to be therapeutically beneficial.

The term "lectin pathway" refers to complement activation that occurs via the specific binding of serum and non-serum carbohydrate-binding proteins including mannan-binding lectin (MBL), CL-11 and the ficolins (H-ficolin, M-ficolin, or L-ficolin).

The term "classical pathway" refers to complement activation that is triggered by an antibody bound to a foreign particle and requires binding of the recognition molecule C1q.

Amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

In the broadest sense, the naturally occurring amino acids can be divided into groups based upon the chemical characteristic of the side chain of the respective amino acids. By "hydrophobic" amino acid is meant either His, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further sub-classed as follows: by "uncharged hydrophilic" amino acid is meant either Ser, Thr, Asn or Gln. By "acidic" amino acid is meant either Glu or Asp. By "basic" amino acid is meant either Lys, Arg or His.

The term "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The term "a subject" includes all mammals, including without limitation, humans, non-human primates, dogs, cats, horses, sheep, goats, cows, rabbits, pigs and rodents.

The terms "small molecule" and "small organic molecule" refers to a small carbon-containing molecule that has a molecular weight of about 2500 daltons or lower. In some embodiments, a small molecule has a molecular weight of about 2000 daltons or lower. In some embodiments, a small molecule has a molecular weight of about 1500 daltons or lower. In some embodiments, a small molecule has a molecular weight of about 1000 daltons or lower. In some embodiments, a small molecule has a molecular weight of about 750 daltons or lower. In some embodiments, a small molecule has a molecular weight of about 500 daltons or lower. In some embodiments, a small molecule has a molecular weight of about 50 daltons or greater. In some embodiments, a small molecule has a molecular weight of about 75 daltons or greater. In some embodiments, a small molecule has a molecular weight of about 100 daltons or greater. In some embodiments, a small molecule has a molecular weight of about 150 daltons or greater. In some embodiments, a small molecule has a molecular weight of about 250 daltons or greater. In some embodiments, small molecules may have a molecular weight in the range from about 50 daltons to about 500 daltons, from about 50 daltons to about 750 daltons, from about 50 daltons to about 1000 daltons, from about 50 daltons to about 1500 daltons, from about 50 daltons to about 2000 daltons, or from about 50 daltons to about 2500 daltons. When the term "compound" is used herein, the term is explicitly intended to include small molecule compounds as defined herein (including any of the embodiments thereof).

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The terms "disorder," "disease," and "condition" are used interchangeably for a condition in a subject. A disorder is a disturbance or derangement that affects the normal function of the body of a subject. A disease is a pathological condition of an organ, a body part, or a system resulting from various causes, such as infection, genetic defect, or environmental stress that is characterized by an identifiable group of symptoms.

The term "effective amount" or "effective dose" means an amount sufficient to achieve the desired result and accordingly will depend on the ingredient and its desired result. Nonetheless, once the desired effect is identified, determining the effective amount is within the skill of a person skilled in the art.

The term "subcutaneous administration" refers to administration of a formulation under all layers of the skin of a subject.

The term "histidine" specifically includes L-histidine unless otherwise specified.

The term "isotonic" refers to a formulation that has essentially the same osmotic pressure as human blood. Isotonic formulations will generally have an osmotic pressure from about 250 to about 350 mOsmol/L. Isotonicity can be measured using a vapor pressure or freezing point depression osmometer, for example.

The term "hypertonic" refers to a formulation with an osmotic pressure above that of human (i.e., greater than 350 mOsm/L).

The term "hydrogen-bonding" is a partially electrostatic attraction between a hydrogen (H) which is bound to a more electronegative atom such as nitrogen (N) or oxygen (O) and another adjacent atom bearing a lone pair of electrons. For example, when it is stated that the nitrogen acts as a "hydrogen bond donor" it means that a hydrogen (H) bound to a nitrogen (N) is donated by the nitrogen as it electrostatically attracted to or accepted by an adjacent atom bearing a lone pair of electrons such as an oxygen. Similarly, when it is stated that an oxygen acts as a "hydrogen bond acceptor," it means that a hydrogen (H) bound to a more electronegative atom such as nitrogen (N) is electrostatically attracted to or "accepted by" an adjacent atom such as oxygen bearing a lone pair of electrons. Sometimes the hydrogen bonded atoms are called out without explicitly stating the origin and presence of an intermediate hydrogen atom. The term "hydrogen bonding" is used wherever LigPlot+ software predicts a hydrogen bonding interaction using its algorithm and applied parameters of 3.35 Å for maximum distance between hydrogen bond donor and acceptor. Not all hydrogen bonds may actually be in place simultaneously; this is evident for atoms that are shown to form 4 putative hydrogen bonds, where however, at any given time only 3 hydrogen bonds are chemically possible.

In general, although crystal structures such as the co-crystal structural information herein does not directly show or detect hydrogen bonding, the software used to describe the co-crystal does predict such H-bonding exists. Therefore, throughout the disclosure when a H-bond is present and described, it may be said to be "predicted" by software to be present.

The term ionic bonding includes a type of chemical bond that involves the electrostatic attraction between oppositely charged ions, and is the primary interaction occurring in ionic compounds.

The term "van der Waals" interaction includes weak, short-range electrostatic attractive forces between uncharged molecules, arising from the interaction of permanent or transient electric dipole moments. As determined by LigPlot+ software employing models derived from the corresponding crystallographic MASP-2 compound co-structures, such interactions include all contacts that are computed using non-bonded contact parameters between hydrophobic to any contacts for interactions with a maximum contact distance of 3.90 Å.

The term "π-π interaction or π-π stacking" interaction includes attractive, noncovalent interactions between aromatic rings that are oriented either roughly parallel or roughly perpendicular (such as in "edge-face" interactions) to each other, since they contain π bonds.

Typically, the active site of serine proteases such as MASP-2 is shaped as a cleft where the polypeptide substrate or inhibitor binds. Schechter and Berger labeled amino acid residues from the N to C terminus of the polypeptide substrate as follows: Pi, . . . , P3, P2, P1, P1', P2', P3', . . . , Pj) and their respective binding sub-sites Si, . . . , S3, S2, S1, S1', S2', S3', . . . , Sj. The cleavage is catalyzed between P1 and P1' (Schechter, I. & Berger, A. On the size of the active site in proteases. I. Papain. Biochem. Biophys. Res. Commun. 27 (1967)).

The term "binding site" is an area on the protein wherein a small molecule can interact with such as a region on the surface of MASP-2, which region does not or only partially overlaps with the active site, but nevertheless render the MASP-2 molecule less active or inactive.

The term "or" refers to an alternative and should in general be construed non-exclusively. For example, a claim to "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

The group "A or B" is equivalent to the group "selected from the group consisting of A and B."

The linking term "comprising" or "comprise" is not closed. For example, "a composition comprising A" must include at least the component A, but it may also include one or more other components (e.g., B; B and C; B, C, and D; and the like). The term "comprising" therefore should in general be construed as not excluding additional ingredients. For example, a claim to "a composition comprising A" would cover compositions that include A and B; A, B, and C; A, B, C, and D; A, B, C, D, and E; and the like.

The term "hypertonic" refers to a formulation with an osmotic pressure above that of human (i.e., greater than 350 mOsm/KglHhO).

The term "agent" refers to a compound or mixture of compounds that, when added to a composition, tend to produce a particular effect on the composition's properties. For example, a composition comprising a thickening agent is likely to be more viscous than an otherwise identical comparative composition that lacks the thickening agent.

A "subject" includes all mammals, including without limitation, humans, non-human primates, dogs, cats, horses, sheep, goats, cows, rabbits, pigs and rodents.

A "synthetic" compound means a compound that is not naturally occurring and that has been synthesized by humans. Reference to a compound herein may be understood to include reference to synthetic compounds, unless the context indicates otherwise.

The terms "treat," "treating," or "treatment" includes administering or applying a composition (e.g., a composition described herein) in an amount, manner (e.g., schedule of administration), and mode (e.g., route of administration) that is effective to improve a disorder or a symptom thereof, or to prevent, to retard, or to slow the progression of a disorder or a symptom thereof. Such improvements can include, but are not limited to, alleviation or amelioration of one or more symptoms or conditions, diminishment of the extent of a disease, stabilizing (i.e., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable.

"Treating" and "treatment" also include prophylactic treatment. In certain embodiments, treatment methods comprise administering to a subject a therapeutically effective amount of an active agent. The administering step may consist of a single administration or may comprise a series of administrations. The length of the treatment period depends on a variety of factors, such as the severity of the condition, the age of the subject, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In one aspect, chronic administration may be required. For example, the compositions are administered to the subject in an amount, and for a duration, sufficient to treat the subject.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

b. Chemical Definitions

At various places in the present specification, certain features of the compounds are disclosed in groups or in ranges. It is specifically intended that such a disclosure include each and every individual subcombination of the members of such groups and ranges. For example, the terms "$C_{1-6}$ alkyl" and "$C_1$-$C_6$ alkyl" are specifically intended to individually disclose (without limitation) methyl, ethyl, $C_3$ alkyl, $C_4$ alkyl, $C_5$ alkyl and $C_6$ alkyl.

At various places in the present specification, variables defining divalent linking groups are described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The phrase "optionally substituted" means substituted or unsubstituted. The term "substituted" means that a hydrogen atom is formally removed and replaced by a substituent. A single divalent substituent, e.g., oxo, can replace two hydrogen atoms.

The terms "$C_{n-m}$" and "$C_n$-$C_m$" where n and m are integers indicates a group that contains from n to m carbon atoms. Examples include $C_{1-4}$, $C_{1-6}$, and the like. The term is intended to expressly disclose every member in the range, i.e., $C_n$, $C_{n+1}$, $C_{n+2}$ . . . $C_{m-2}$, $C_{m-1}$, $C_m$. For example, $C_{1-6}$ is intended to disclose $C_1$, $C_2$, $C_3$, $C_4$, $C_5$, and $C_6$. "$C_{n-m}$" means the same as "$C_n$-$C_m$".

The term "alkyl" employed alone or in combination with other terms, refers to a saturated hydrocarbon group that may be straight-chain or branched. The terms "$C_{n-m}$ alkyl" and "$C_n$-$C_m$ alkyl" refer to an alkyl group having n to m carbon atoms. For example, $C_1$-$C_{12}$ indicates that the group may have from 1 to 12 (inclusive) carbon atoms in it. If not otherwise indicated, an alkyl group about 1 to about 20 carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, 1,1-dimethylpropyl, n-pentyl, 3-pentyl, n-hexyl, 1,2,2-trimethylpropyl, hexyl, heptyl, octyl, nonyl, decyl, dodecyl, and the like. The term "lower alkyl" refers to alkyl groups having from 1 to 6 carbon atoms in the chain. A "substituted alkyl" group is an alkyl group that is substituted with one or more substituents.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The terms "$C_{n-m}$ alkenyl" and "$C_n$-$C_m$ alkenyl" refer to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" and "$C_n$-$C_m$ alkynyl" refer to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bonds replaced by points of attachment of the alkylene group to the remainder of the compound. The term "$C_{n-m}$ alkylene" refers to an alkylene group having n to m carbon atoms. Examples of alkylene groups include, but are not limited to, methylene, ethan-1,2-diyl, propan-1,3-diyl, propan-1,2-diyl, butan-1,4-diyl, butan-1,3-diyl, butan-1,2-diyl, 2-methyl-propan-1,3-diyl and the like. In some embodiments, "$C_{n-m}$ alkylene" can refer to chain of from n to m methylene ($CH_2$) groups, —($CH_2$)n-m-, such as —$CH_2$—, —$CH_2CH_2$—, —$CH_2CH_2CH_2$—, etc.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The term "alkoxyalkyl" refers to an alkyl group in which one or more of the hydrogen atoms has been replaced by an alkoxy group. The term "$C_{n-m}$ alkoxy-$C_{p-q}$ alkyl" refers to a $C_{p-q}$ alkyl group substituted by a $C_{n-m}$ alkoxy group. In some embodiments, the hydroxyalkyl group has one alkoxy group. In some embodiments, the alkoxyalkyl group has one or two alkoxy groups, each on a different carbon atom. Examples may include, but are not limited to, methoxymethyl, ethoxymethyl, 3-ethoxyethyl, and 1-methoxyethyl.

The term "amino" refers to a group of formula —$NH_2$.

The term "carbamyl" refers to a group of formula —C(O)$NH_2$.

The term "carbonyl", employed alone or in combination with other terms, refers to a —C(=O)— group, which also may be written as C(O).

The term "cyano" or "nitrile" refers to a group of formula —C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo is F.

The term "haloalkyl" refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "hydroxyalkyl" refers to an alkyl group in which one or more of the hydrogen atoms has been replaced by a hydroxy. The term "$C_{n-m}$ hydroxyalkyl" refers to a $C_{n-m}$ alkyl group having n to m carbon atoms and from at least one hydroxy group. In some embodiments, the hydroxyalkyl group has one alcohol group. In certain aspects, the hydroxyalkyl group has one or two alcohol groups, each on a different carbon atom. In certain aspects, the hydroxyalkyl group has 1, 2, 3, 4, 5, or 6 alcohol groups. Examples may include, but are not limited to, hydroxymethyl, 2-hydroxyethyl, and 1-hydroxyethyl.

The term "oxo" refers to an oxygen atom as a divalent substituent, forming a carbonyl group when attached to carbon, or attached to a heteroatom forming a sulfoxide or sulfone group, or an N-oxide group.

The term "sulfido" refers to a sulfur atom as a divalent substituent, forming a thiocarbonyl group (C=S) when attached to carbon.

The term "n-membered," where n is an integer, typically describes the number of ring-forming atoms in a moiety where the number of ring-forming atoms is n. The term "n-m membered" wherein n and m are integers describes a range where the number of ring forming atoms is from n to m. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2, 3 or 4 fused rings). The term "$C_n$-m aryl" refers to an aryl group having from n to m ring carbon atoms. Aryl groups include, e.g., phenyl, naphthyl, anthracenyl, phenanthrenyl, indanyl, indenyl, tetracenyl, and the like. In some embodiments, aryl groups have from 6 to about 20 carbon atoms, from 6 to about 18 carbon atoms, from 6 to about 15 carbon atoms, or from 6 to about 10 carbon atoms. In some embodiments, the aryl group is phenyl.

The term "arylalkyl" or "aralkyl" or "alkylaryl" employed alone or in combination with other terms, refers to a group of formula -alkylene-aryl, and refers to an alkyl group as defined herein wherein at least one hydrogen has been replaced by an aryl group as defined herein. In some embodiments, arylalkyl is $C_{6-10}$ aryl-$C_{1-3}$ alkyl. In some embodiments, arylalkyl is $C_{6-10}$ aryl-$C_{1-4}$ alkyl. In some embodiments, arylalkyl is $C_{6-10}$ aryl-$C_{1-3}$ alkyl. In some embodiments, arylalkyl is phenyl-$C_{1-3}$ alkyl. Examples include, but are not limited to, benzyl, 1-phenylethyl, 4-methylbenzyl, and 1,1-dimethyl-1-phenylmethyl. In some embodiments, arylalkyl is benzyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. An "n-membered heteroaryl" or "n-membered heteroaromatic", wherein n is an integer, refers to a heteroaryl having n ring-forming atoms. An "n-m membered heteroaryl" or "n-m membered heteroaromatic", wherein n and m are integers, refers to a heteroaryl having from n to m ring-forming atoms. The number of carbon atoms in the ring is fewer than the number of ring forming atoms by the number of heteroatoms. Thus, in some embodiments, an n-membered heteroaryl may have n-1, n-2, n-3 or n-4 ring carbon atoms and an n-m membered heteroaryl may have from n-1, n-2, n-3 or n-4 ring carbon atoms to m-1, m-2, m-3 or m-4 ring carbon atoms. In some embodiments, an n-m membered heteroaryl may have from 1 to m-1 ring carbon atoms. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, quinoline, isoquinoline, naphthyridine (including 1,2-, 1,3-, 1,4-, 1,5-, 1,6-, 1,7-, 1,8-, 2,3- and 2,6-naphthyridine), indole, azaindole, benzothiophene, benzofuran, benzisoxazole, benzimidazole, imidazo[1,2-b]thiazole, purine, furazane, triazole, tetrazole, 1,2,4-thiadiazole, quinazoline, phthalazine, imidazo[1,2-a]pyridine, imidazo[2,1-b]thiazolyl, or the like.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "heteroarylalkyl," employed alone or in combination with other terms, refers to a group of formula -alkylene-heteroaryl. The term "n-membered heteroarylalkyl" wherein n is an integer refers to a heteroarylalkyl group in which the heteroaryl is n-membered. The term "n-m membered-$C_{p-q}$-alkyl" wherein n, m, p and q are integers refers to heteroarylalkyl group in which the heteroaryl is n to m membered and the alkyl has from p to q carbon atoms. In some embodiments, heteroarylalkyl is 5-10 membered heteroaryl-$C_{1-3}$ alkyl or $C_{1-9}$ heteroaryl-$C_{1-3}$ alkyl, wherein the heteroaryl portion is monocyclic or bicyclic and has 1, 2, 3, 4 or 5 heteroatom ring members independently selected from nitrogen, sulfur and oxygen. In some embodiments, heteroarylalkyl is $C_{1-9}$ heteroaryl-$C_{1-4}$ alkyl, wherein the heteroaryl portion is monocyclic or bicyclic and has 1, 2, 3, or 4 heteroatom ring members independently selected from nitrogen, sulfur and oxygen. Examples include pyridylmethyl, such as 2-pyridylmethyl, 3-pyridylmethyl, or 4-pyridylmethyl.

The term "cycloalkyl," employed alone or in combination with other terms, refers to a non-aromatic, saturated, monocyclic, bicyclic or polycyclic hydrocarbon ring system. The term includes cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, 4,4-dimethylcyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "cycloalkylalkyl," employed alone or in combination with other terms, refers to a group of formula -alkylene-cycloalkyl. The term $C_{n-m}$ cycloalkyl-$C_{p-q}$ alkyl wherein n, m, p and q are integers, refers to a cycloalkyl group having from n to m carbon atoms attached to an alkyl group having from p to q carbon atoms. In some embodiments, cycloalkylalkyl is $C_{3-7}$ cycloalkyl-$C_{1-3}$ alkyl, wherein the cycloalkyl portion is monocyclic or bicyclic. Examples include cyclopropylmethyl, cyclobutylmethyl, cyclopentanemethyl, and cyclohexylmethyl.

The term "heterocycloalkyl", employed alone or in combination with other terms, refers to a non-aromatic ring or ring system, which may optionally contain one or more alkenylene groups as part of the ring structure, which has at least one heteroatom ring member independently selected from nitrogen, sulfur, and oxygen. An "n-membered heterocycloalkyl" wherein n is an integer, refers to a heteroaryl having n ring-forming atoms. An "n-m membered heterocycloalkyl" wherein n and m are integers, refers to a heterocycloalkyl having from n to m ring-forming atoms. The number of carbon atoms in the ring is fewer than the number of ring forming atoms by the number of heteroatoms. Thus, in some embodiments, an n-membered heterocycloalkyl may have n-1, n-2, n-3 or n-4 ring carbon atoms and an n-m membered heterocycloalkyl may have from n-1, n-2, n-3 or n-4 ring carbon atoms to m-1, m-2, m-3 or m-4 ring carbon atoms. In some embodiments, an n-m membered heterocycloalkyl may have from 1 to m-1 ring carbon atoms. In some embodiments, a heterocycloalkyl has 4-12 ring members, 4-10 ring members, 4-7 ring members or 4-6 ring members. Included in heterocycloalkyl groups are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfide group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include azetidine, azepane, dihydrobenzofuran, dihydrofuran, dihydropyran, morpholine, 3-oxa-9-azaspiro[5.5]undecane, 1-oxa-8-azaspiro[4.5]decane, piperidine, piperazine, pyran, pyrrolidine, quinuclidine, tetrahydrofuran, tetrahydropyran, 1,2,3,4-tetrahydroquinoline, tropane, and thiomorpholine.

As used herein, the term "heterocycloalkylalkyl," employed alone or in combination with other terms, refers to a group of formula -alkylene-heterocycloalkyl. The term "n-membered heterocycloalkylalkyl" wherein n is an integer refers to a hereoarylalkylalkyl group in which the heterocycloalkyl is n-membered. The term "n-m membered-$C_{p-q}$-alkyl wherein n, m, p and q are integers refers to heterocycloalkylalkyl group in which the heterocycloalkyl is n to m membered and the alkyl has from p to q carbon atoms. In some embodiments, heterocycloalkylalkyl is 4-10 membered heterocycloalkyl-$C_{1-3}$ alkyl or $C_{1-9}$ heterocycloalkyl-$C_{1-3}$ alkyl, wherein the heterocycloalkyl portion is monocyclic or bicyclic and has 1, 2, 3, 4 or 5 heteroatom ring members independently selected from nitrogen, sulfur and oxygen. In some embodiments, heterocycloalkylalkyl is $C_{2-9}$ heterocycloalkyl-$C_{1-4}$ alkyl or $C_{2-9}$ heterocycloalkyl-$C_{1-3}$ alkyl, wherein the heterocycloalkyl portion is monocyclic or bicyclic and has 1, 2, 3, or 4 heteroatom ring members independently selected from nitrogen, sulfur and oxygen.

At certain places, the definitions or embodiments may refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

When any two groups or two instances of the same substituent group are "independently selected" from a list of alternatives, the groups may be the same or different. For example, if $R^a$ and $R^b$ are independently selected from the group consisting of alkyl, fluoro, amino, and hydroxyalkyl, then a molecule with two $R^a$ groups and two $R^b$ groups could have all groups be alkyl group (e.g., four different alkyl groups). Alternatively, the first $R^a$ could be alkyl, the second $R^a$ could be fluoro, the first $R^b$ could be hydroxyalkyl, and the second $R^b$ could be amino (or any other substituents taken from the group). Alternatively, both $R^a$ and the first $R^b$ could be fluoro, while the second $R^b$ could be alkyl (i.e., some pairs of substituent groups may be the same, while other pairs may be different). Unless otherwise indicated, if two or more groups having the same definition are present, but the definition provides for alternatives, it should be understood that each occurrence of the same group is independently selected from the possible alternatives. For example, if two or more $R^a$ groups are present in a compound, and the definition of $R^a$ provides that $R^a$ can be A, B or C, then it should be understood that each $R^a$ group present in the compound is independently chosen from A, B and C, so that the $R^a$ groups present in the compound can be the same or different.

The compounds described herein can be asymmetric (e.g., having one or more stereocenters). All stereoisomers, such as enantiomers and diastereomers, are intended unless otherwise indicated. Compounds described herein that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds described herein may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution. The disclosure is intended to encompass all such tautomers of the compounds described.

Compounds described herein can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers and isotopes of the structures depicted.

Compounds described herein may include acidic and/or basic groups and be capable of forming salts. It should be understood that the present disclosure is intended to include all salts of compounds that are capable of forming salts, whether or not the possible existence of salts is expressly described, including both acid and base salts of a compound. Furthermore, when a compound is described that is a salt, it is understood that the disclosure of the compound is intended to include all forms of the compound, including the free base or free acid, as well as alternative salt forms thereof. The term "salt" refers to derivatives of the disclosed compounds wherein the parent compound is modified by converting an existing acid or base moiety to its salt form. Examples of salts include, but are not limited to, mineral or organic acid salts of basic residues such as amines; alkali or organic salts of acidic residues such as carboxylic acids; and the like. The terms "a salt thereof," "salt thereof," or "salts thereof" can be applied to any preceding member of an associated Markush group. For example, a group consisting of A, B, C, and salts thereof would include within its scope embodiments that were a salt of A, embodiments that were a salt of B, and embodiments that were a salt of C.

Salts of the compounds disclosed herein include pharmaceutically acceptable salts. The term "pharmaceutically acceptable salts" refers to non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17*th* Ed., (Mack Publishing Company, Easton, 1985), p. 1418, Berge et al., *J. Pharm. Sci.,* 1977, 66(1), 1-19 and in Stahl et al., *Handbook of Pharmaceutical Salts: Properties, Selection, and Use*, (Wiley, 2002). In some embodiments, the compounds described herein include the N-oxide forms. Additional information on suitable pharmaceutically acceptable salts can be found in Remington's, Pharmaceutical Sciences (current edition), Mack Publishing Co., Easton, PA, which is incorporated herein by reference.

Compounds, and salts thereof, including pharmaceutically acceptable salts, can be found together with other substances such as water and solvents (e.g., hydrates and solvates) or can be isolated. When in the solid state, the compounds described herein, and salts thereof may occur in various forms and may, e.g., take the form of solvates, including hydrates. The compounds may be in any solid-state form, such as a polymorph or solvate, so unless clearly indicated otherwise, reference to compounds and salts thereof should be understood as encompassing any solid-state form of the compound.

In some embodiments, the compounds described herein or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

c. Abbreviations

The following abbreviations may be used herein and, unless otherwise noted, have the meanings indicated below: μ (micro); ° C. (degrees Celsius); Ac (acetyl); ACN (acetonitrile); anhyd (anhydrous); aq (aqueous); atm (atmosphere (s)); Bn (benzyl); Boc (tert-butoxycarbonyl); Bu (butyl); calcd (calculated); Cbz (benzyloxycarbonyl); chrom. (chromatography); CPME (cyclopentyl methyl ether); CH$_2$Cl$_2$ (dichloromethane); concd (concentrated); conc (concentration); DCC (N, N'-dicyclohexylcarbodiimide); DIAD (Di-isopropyl azodicarboxylate); DIEA (N,N-diisopropylethyl-amine); DMAP (4-(N,N-dimethylamino)pyridine); DMF (dimethylformamide); DMSO (dimethylsulfoxide); EDC (N-(3-dimethylaminopropyl)-N'-ethylcarbodiimide hydrochloride); equiv (equivalent); ES (electrospray); Et (ethyl); Et$_2$O (diethyl ether); g (gram(s)); h (hour(s)); HATU (N-[(Dimethylamino)-1H-1,2,3-triazolo-[4,5-b]pyridin-1-ylm-ethylene]-N-methylmethanaminium hexafluorophosphate N-oxide); HBTU (O-(Benzotriazol-1-yl)-N,N,N',N'-tetramethyl-O-(1H-benzotriazol-1-yl)uronium hexafluorophosphate); HPLC (high-performance liquid chromatography); HOBt (1-hydroxybenzotriazole hydrate); L (liter(s)); m (milli); m- (meta); M (molar); MeCN (acetonitrile); min (minute(s)); mL (milliliter); mol (mole; molecular (as in mol wt)); Ms (methanesulfonyl); MS (mass spectrometry); MW (molecular weight); NBS (N-bromosuccinimide); NCS (N-chlorosuccinimide); NIS (N-iodosuccinimide); NHS (N-hydroxysuccinimide); NMM (4-methylmorpholine); NMR (nuclear magnetic resonance); o- (ortho); obsd (observed); p- (para); Ph (phenyl); Phth (Phthalimide); ppt (precipitate); Pr (propyl); psi (pounds per square inch); temp (temperature); TFA (trifluoroacetic acid); THF (tetrahydrofuran); TPP (triphenylphosphine); and Tr (trityl). Other abbreviations may also be used and have the meanings that would be understood by the person having skill in the art.

II. Compounds

A. Compounds of Formula I-1

In certain aspects, the present disclosure provides a compound of Formula (I-1):

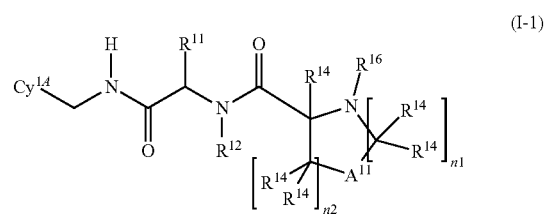

or a salt thereof, wherein:

Cy$^{1A}$ is unsubstituted or substituted C$_{6-10}$ aryl or unsubstituted or substituted 5-10 membered heteroaryl; wherein the ring atoms of the 5-10 membered heteroaryl forming Cy$^{1A}$ consist of carbon atoms and 1, 2, or 3 heteroatoms selected from O, N and S; wherein the substituted C$_{6-10}$ aryl or substituted 5-10 membered heteroaryl forming $Cy^{1A}$ are substituted with 1, 2, 3, 4 or 5 substituents each independently selected from $R^{Cy1A}$, halogen, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $C(=NOR^{a11})NR^{c11}R^{d11}$, $C(=NOC(O)R^{b11})NR^{c11}R^{d11}$, $C(=NR^{e11})NR^{c11}C(O)OR^{a11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

each $R^{Cy1A}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10-membered heterocycloalkyl forming $R^{Cy1A}$ consist of carbon atoms and 1, 2, 3 or 4 heteroatoms selected from O, N and S, wherein each $C_{1-6}$ alkyl, $C_{2-6}$ alkenyl, or $C_{2-6}$ alkynyl forming $R^{Cy1A}$ is independently unsubstituted or substituted with 1, 2 or 3 substituents independently selected from halogen, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo, and wherein each $C_{6-10}$ aryl, 5-10 membered heteroaryl, $C_{3-10}$ cycloalkyl and 4-10 membered heterocycloalkyl forming $R^{Cy1A}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

$R^{11}$ is H or $C_{1-6}$ alkyl, $C_{6-10}$ aryl-$C_{1-6}$ alkyl or 5-10 membered heteroaryl-$C_{1-6}$ alkyl, wherein the $C_{1-6}$ alkyl forming $R^{11}$ is unsubstituted or substituted by 1, 2 or 3 substituents independently selected from halogen, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo, and wherein the $C_{6-10}$ aryl-$C_{1-6}$ alkyl or 5-10 membered heteroaryl-$C_{1-6}$ alkyl forming $R^{11}$ is unsubstituted or substituted by 1, 2 or 3 substituents independently selected from $C_{1-6}$ alkyl, $C_{2-6}$ alkenyl, $C_{2-6}$ alkynyl, $C_{1-6}$ haloalkyl, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

$R^{12}$ is H or $C_{1-6}$ alkyl; or $R^{11}$ and $R^{12}$, together with the groups to which they are attached, form a 4-6 membered heterocycloalkyl ring;

$A^{11}$ is $CR^{13}R^{15}$ or N;

each $R^{13}$ is independently $Cy^{1B}$, $(CR^{13A}R^{13B})_{n3}Cy^{1B}$, $(C_{1-6}$ alkylene$)Cy^{1B}$, $(C_{2-6}$ alkenylene$)Cy^{1B}$, $(C_{2-6}$ alkynylene$)Cy^{1B}$ or $OCy^{1B}$, wherein the $C_{1-6}$ alkylene, $C_{2-6}$ alkenylene, or $C_{2-6}$ alkynylene component of $R^{13}$ is unsubstituted or substituted by 1, 2, 3, 4 or 5 substituents each independently selected from the group consisting of halogen, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

each $R^{14}$ is independently selected from H and $C_{1-6}$ alkyl;

$R^{15}$ is selected from H, $R^{13}$, $C_{1-6}$ alkyl and OH;

a pair of $R^{14}$ groups attached to adjacent carbon atoms, or a pairing of $R^{14}$ and $R^{15}$ groups attached to adjacent carbon atoms, may, independently of other occurrences of $R^{14}$, together be replaced a bond connecting the adjacent carbon atoms to which the pair of $R^{14}$ groups or pairing of $R^{14}$ and $R^{15}$ groups is attached, such that the adjacent carbon atoms are connected by a double bond; or a pair of $R^{14}$ groups attached to the same carbon atom, or a pairing of $R^{13}$ and $R^{15}$ groups attached to the same carbon atom, may, independently of other occurrences of $R^{14}$, and together with the carbon atom to which the pair of $R^{14}$ groups or pairing of $R^{13}$ and $R^{15}$ groups is attached together form a spiro-fused $C_{3-10}$ cycloalkyl or 4-10 membered heterocycloalkyl ring, wherein the ring atoms of the 4-10 membered heterocycloalkyl ring formed consist of carbon atoms and 1, 2, or 3 heteroatoms selected from O, N and S, wherein the spiro-fused $C_{3-10}$ cycloalkyl or 4-10 membered heterocycloalkyl ring formed is optionally further substituted with 1, 2 or 3 substituents independently selected from halogen, $C_{1-6}$ alkyl, $C_{2-6}$ alkenyl, $C_{2-6}$ alkynyl, haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $S(O)_2R^{b11}$, $NR^{c11}S(O)_2R^{b11}$, $S(O)_2NR^{c11}R^{d11}$ and oxo; or pairs of $R^{14}$ groups attached to adjacent carbon atoms, or a pairing of $R^{14}$ and $R^{15}$ groups attached to adjacent carbon atoms, may, independently of other occurrences of $R^{14}$, together with the adjacent carbon atoms to which the pair of $R^{14}$ groups or pairing of $R^{14}$ and $R^{15}$ groups is attached, form a fused $C_{3-10}$ cycloalkyl or 4-10 membered heterocycloalkyl ring, wherein the ring atoms of the 4-10 membered heterocycloalkyl ring formed consist of carbon atoms and 1, 2, or 3 heteroatoms selected from O, N and S, wherein the fused $C_{3-10}$ cycloalkyl or 4-10 membered heterocycloalkyl ring formed is optionally further substituted with 1, 2 or 3 substituents independently selected from halogen, $C_{1-6}$ alkyl, $C_{2-6}$ alkenyl, $C_{2-6}$ alkynyl, haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo; or a grouping of four $R^{14}$ groups attached to two adjacent carbon atoms, or a grouping of two $R^{14}$, one $R^{13}$ and one $R^{15}$ groups attached to two adjacent carbon atoms, may, independently of other occurrences of $R^{14}$, together with the two adjacent carbon atoms to which the grouping of four $R^{14}$ groups or grouping of two $R^{14}$, one $R^{13}$ and one $R^{15}$ groups are attached, form a fused $C_{6-10}$ aryl or 5-10 membered heteroaryl, $C_{3-10}$ cycloalkyl or 4-10 membered heterocycloalkyl ring, wherein the ring atoms of the 5-10 membered heteroaryl or 4-10 membered heterocycloalkyl ring formed consist of carbon atoms and 1, 2, or 3 heteroatoms selected from O, N and S, and wherein the fused $C_{6-10}$ aryl or 5-10 membered heteroaryl, $C_{3-10}$ cycloalkyl or 4-10 membered heterocycloalkyl ring formed is optionally further substituted with 1, 2 or 3 substituents independently selected from halogen, $C_{1-6}$ alkyl, $C_{2-6}$ alkenyl, $C_{2-6}$ alkynyl, haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

n1 is 1 or 2;

n2 is 0, 1 or 2;

provided that the sum of n1 and n2 is 1, 2 or 3;

provided that if n1 is 1 or n2 is 0, then $A^{11}$ is $CR^{13}R^{15}$;

n3 is 0, 1 or 2;

each $R^{13A}$ is independently H or $C_{1-6}$ alkyl;

each $R^{13B}$ is independently H or $C_{1-6}$ alkyl; or or $R^{13A}$ and $R^{13B}$ attached to the same carbon atom, independently of any other $R^{13A}$ and $R^{13B}$ groups, together may form —$(CH_2)_{2-5}$—, thereby forming a 3-6 membered cycloalkyl ring;

$Cy^{1B}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl; wherein the ring atoms of the 5-10 membered heteroaryl or 4-10 membered heterocycloalkyl forming $Cy^{1B}$ consist of carbon atoms and 1, 2 or 3 heteroatoms selected from O, N and S; and wherein the substituted $C_{6-10}$ aryl, substituted 5-10 membered heteroaryl, substituted $C_{3-10}$ cycloalkyl or substituted 4-10 membered heterocycloalkyl forming $Cy^{1B}$ are substituted with 1, 2, 3, 4 or 5 substituents each independently selected from $R^{Cy1B}$, halogen, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $C(=NOR^{a11})NR^{c11}R^{d11}$, $C(=NOC(O)R^{b11})NR^{c11}R^{d11}$, $C(=NR^{e11})NR^{c11}C(O)OR^{a11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

wherein each $R^{Cy1B}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10 membered heterocycloalkyl forming $R^{Cy1B}$ consist of carbon atoms and 1, 2 or 3 heteroatoms selected from O, N and S; wherein each $C_{1-6}$ alkyl, $C_{2-6}$ alkenyl, or $C_{2-6}$ alkynyl forming $R^{Cy1B}$ is independently unsubstituted or substituted with 1, 2 or 3 substituents independently selected from halogen, CN, $OR^{a11}$, $SR^{a11}$, $C(O)R^{b11}$, $C(O)NR^{c11}R^{d11}$, $C(O)OR^{a}n$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo; and wherein each $C_{6-10}$ aryl, 5-10 membered heteroaryl, $C_{3-10}$ cycloalkyl and 4-10 membered heterocycloalkyl forming $R^{Cy1B}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

$R^{16}$ is H, $Cy^{1C}$, $C_{1-6}$ alkyl, $C_{2-6}$ alkenyl, or $C_{2-6}$ alkynyl, wherein the $C_{1-6}$ alkyl, $C_{2-6}$ alkenyl, or $C_{2-6}$ alkynyl forming $R^{16}$ is unsubstituted or substituted by 1, 2, 3, 4 or 5 substituents selected from the group consisting of $Cy^{1C}$, halogen, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo, provided that no more than one of the substituents of $R^{16}$ is $Cy^{1C}$;

$Cy^{1C}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl; wherein the ring atoms of the 5-10 membered heteroaryl or 4-10 membered heterocycloalkyl forming $Cy^{1C}$ consist of carbon atoms and 1, 2 or 3 heteroatoms selected from O, N and S; and wherein the substituted $C_{6-10}$ aryl, substituted 5-10 membered heteroaryl, substituted $C_{3-10}$ cycloalkyl or substituted 4-10 membered heterocycloalkyl forming $Cy^{1C}$ are substituted with 1, 2, 3, 4 or 5 substituents each independently selected from $R^{Cy1C}$, halogen, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $C(=NOR^{a11})NR^{c11}R^{d11}$, $C(=NOC(O)R^{b11})NR^{c11}R^{d11}$, $C(=NR^{e11})NR^{c11}C(O)OR^{a11}$, $NR^{c11}C(=NR^{e11})NR^{c11}R^{d11}$, $S(O)R^{b11}$, $S(O)NR^{c11}R^{d11}$, $S(O)_2 R^{b11}$, $NR^{c11}S(O)_2R^{b11}$, $S(O)_2NR^{c11}R^{d11}$ and oxo;

wherein each $R^{Cy1C}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10 membered heterocycloalkyl forming $R^{Cy1C}$ consist of carbon atoms and 1, 2 or 3 heteroatoms selected from O, N and S; wherein each $C_{1-6}$ alkyl, $C_{2-6}$ alkenyl, or $C_{2-6}$ alkynyl forming $R^{Cy1C}$ is independently unsubstituted or substituted with 1, 2 or 3 substituents independently selected from halogen, CN, $OR^{a11}$, $SR^{a11}$, $C(O)R^{b11}$, $C(O)NR^{c11}R^{d11}$, $C(O)OR^{a}n$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo; and wherein each $C_{6-10}$ aryl, 5-10 membered heteroaryl, $C_{3-10}$ cycloalkyl and 4-10 membered heterocycloalkyl forming $R^{Cy1C}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

$R^{a11}$, $R^{b11}$, $R^{c11}$ and $R^{d11}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a11}$, $R^{b11}$, $R^{c11}$ and $R^{d11}$ are each optionally substituted with 1, 2, 3, 4 or 5 substituents independently selected from $C_{1-6}$ alkyl, halo, CN, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)NR^{c12}R^{d12}$, $NR^{c12}C(O)OR^{a12}$, $C(=NR^{e12})NR^{c12}R^{d12}$, $NR^{c12}C(=NR^{e12})NR^{c12}R^{d12}$, $S(O)R^{b12}$, $S(O)NR^{c12}R^{d12}$, $S(O)_2R^{b12}$, $NR^{c12}S(O)_2R^{b12}$, $S(O)_2NR^{c12}R^{d12}$ and oxo;

or $R^{c11}$ and $R^{d11}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)NR^{c12}R^{d12}$, $NR^{c12}C(O)OR^{a12}$, $C(=NR^{e12})NR^{c12}R^{d12}$, $NR^{c12}C(=NR^{e12})NR^{c12}R^{d12}$, $S(O)R^{b12}$, $S(O)NR^{c12}R^{d12}$, $S(O)_2R^{b12}$, $NR^{c12}S(O)_2R^{b12}$, $S(O)_2NR^{c12}R^{d12}$ and oxo;

$R^{a12}$, $R^{b12}$, $R^{c12}$ and $R^{d12}$ are each independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl forming $R^{a12}$, $R^{b12}$, $R^{c12}$ and $R^{d12}$ are each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl, $C_{1-6}$ haloalkoxy and oxo;

or $R^{c12}$ and $R^{d12}$ attached to the same N atom, together with the N atom to which they are both attached, form a 4-, 5-, 6- or 7-membered heterocycloalkyl group or 5-membered heteroaryl group, each of which is unsubstituted or substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl, $C_{1-6}$ haloalkoxy and oxo; and $R^{e11}$ and $R^{e12}$ are each, independently, H, CN or $NO_2$.

In some embodiments, the compound is of Formula (I-2):

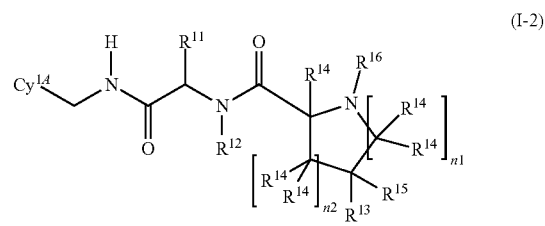

(I-2)

In some embodiments, $Cy^{1A}$ is unsubstituted or substituted aryl.

In some embodiments, $Cy^{1A}$ is unsubstituted or substituted phenyl.

In some embodiments, $Cy^{1A}$ is substituted phenyl.

In some embodiments, $Cy^{1A}$ is substituted with at least one $OR^{a11}$ or at least one $C(=NR^{e11})NR^{c11}R^{d11}$, $C(=NOR^{a11})NR^{c11}R^{d11}$, $C(=NOC(O)R^{b11})NR^{c11}R^{d11}$, or $C(=NR^{e11})NR^{c11}C(O)OR^{a11}$.

In some embodiments, $Cy^{1A}$ is substituted with at least one $OR^{a11}$ and by at least one additional substituent selected from the group consisting of $C_{1-6}$ alkyl, $C_{1-6}$ haloalkyl and halogen.

In some embodiments, $Cy^{1A}$ is substituted with at least one OH and by at least one additional substituent selected from the group consisting of $C_{1-6}$ alkyl, $C_{1-6}$ haloalkyl and halogen.

In some embodiments, $Cy^{1A}$ is substituted with at least one $C(=NR^{e11})NR^{c11}R^{d11}$, $C(=NOR^{a11})NR^{c11}R^{d11}$, $C(=NOC(O)R^{b11})NR^{c11}R^{d11}$, $C(=NR^{e11})NR^{c11}C(O)OR^{a11}$, preferably in the 4-position.

In some embodiments, $Cy^{1A}$ is substituted with at least one $C(=NR^{e11})NR^{c11}R^{d11}$, preferably in the 4-position.

In some embodiments, $Cy^{1A}$ is substituted with at least one $C(=NH)NH_2$, preferably in the 4-position.

In some embodiments, $Cy^{1A}$ is of any one of the following formulae:

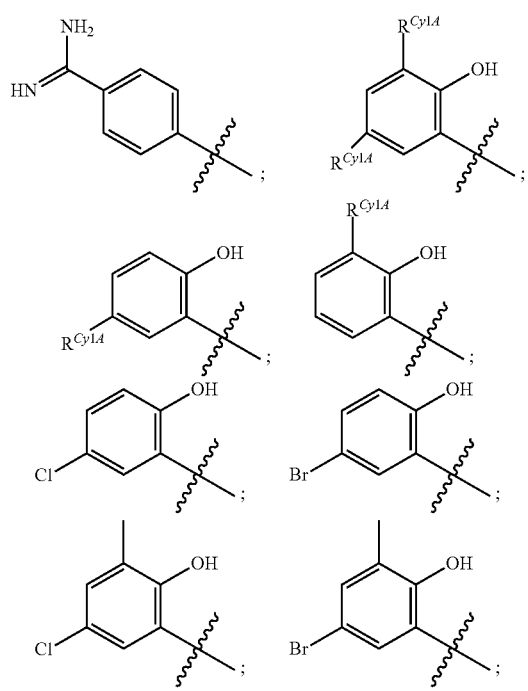

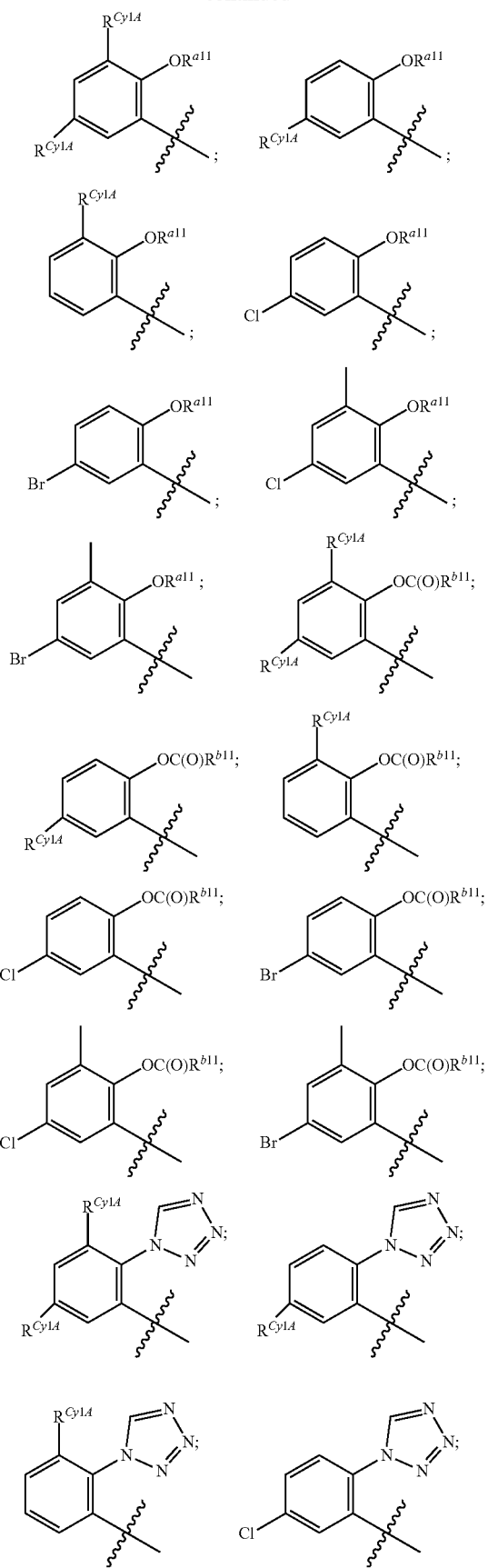

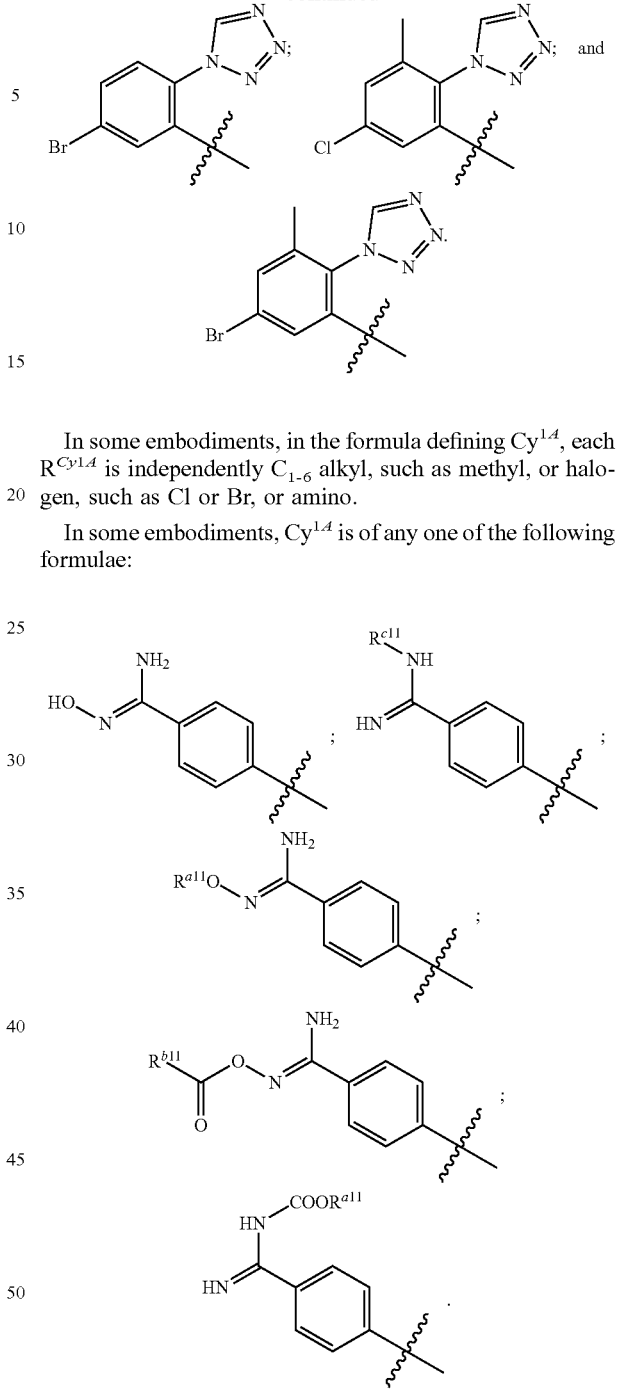

In some embodiments, in the formula defining $Cy^{1A}$, each $R^{Cy1A}$ is independently $C_{1-6}$ alkyl, such as methyl, or halogen, such as Cl or Br, or amino.

In some embodiments, $Cy^{1A}$ is of any one of the following formulae:

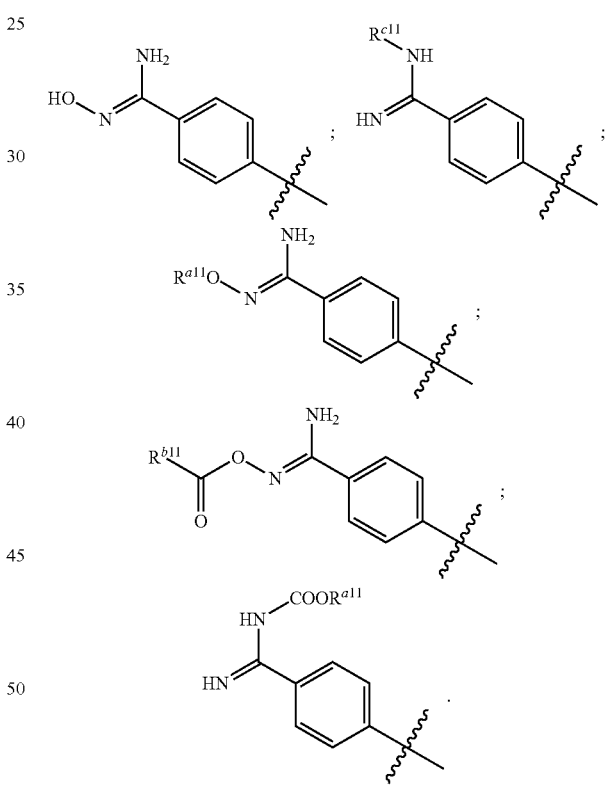

In some embodiments, in the formula defining $Cy^{1A}$, $R^{a11}$ is $C_{1-6}$ alkyl, such as methyl, $R^{b11}$ is $C_{1-6}$ alkyl, such as methyl, $R^{b11}$ is $C_{1-6}$ haloalkyl, such as trifluoromethyl, and $R^{c11}$ is alkyl such as methyl.

In some embodiments, $Cy^{1A}$ is unsubstituted or substituted heteroaryl.

In some embodiments, $Cy^{1A}$ is unsubstituted or substituted pyridin-3-yl, 1H-pyrrolo[2,3-b]pyridine-5-yl, or 1H-benzo[d]imidazol-6-yl.

In some embodiments, $Cy^{1A}$ is of any one of the following formulae:

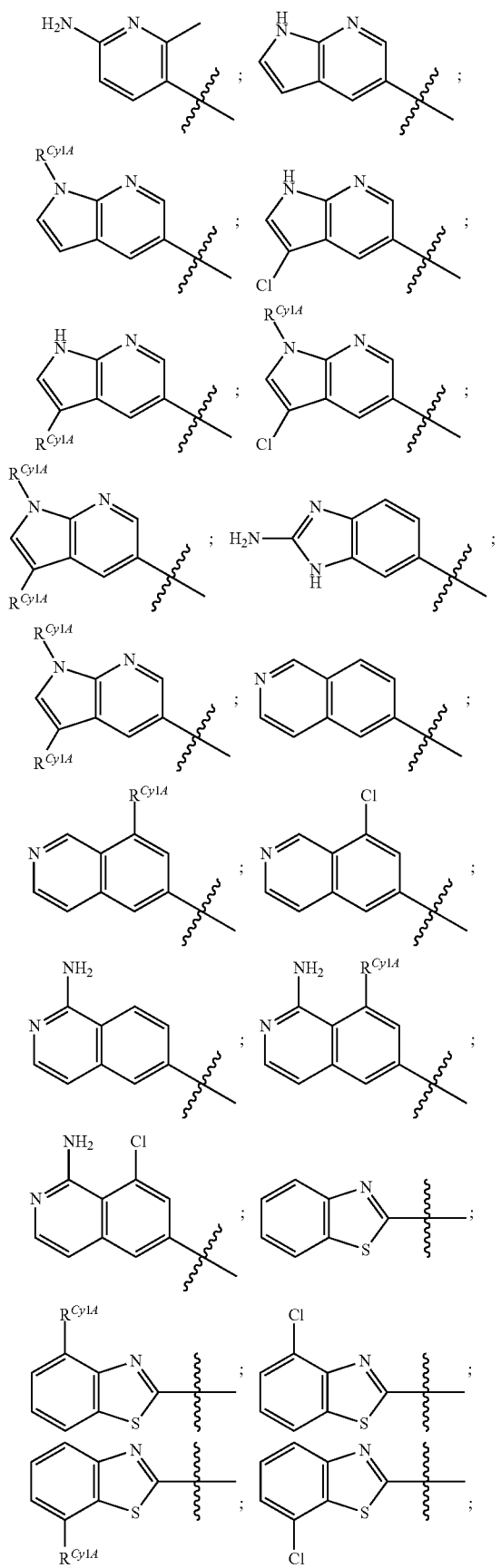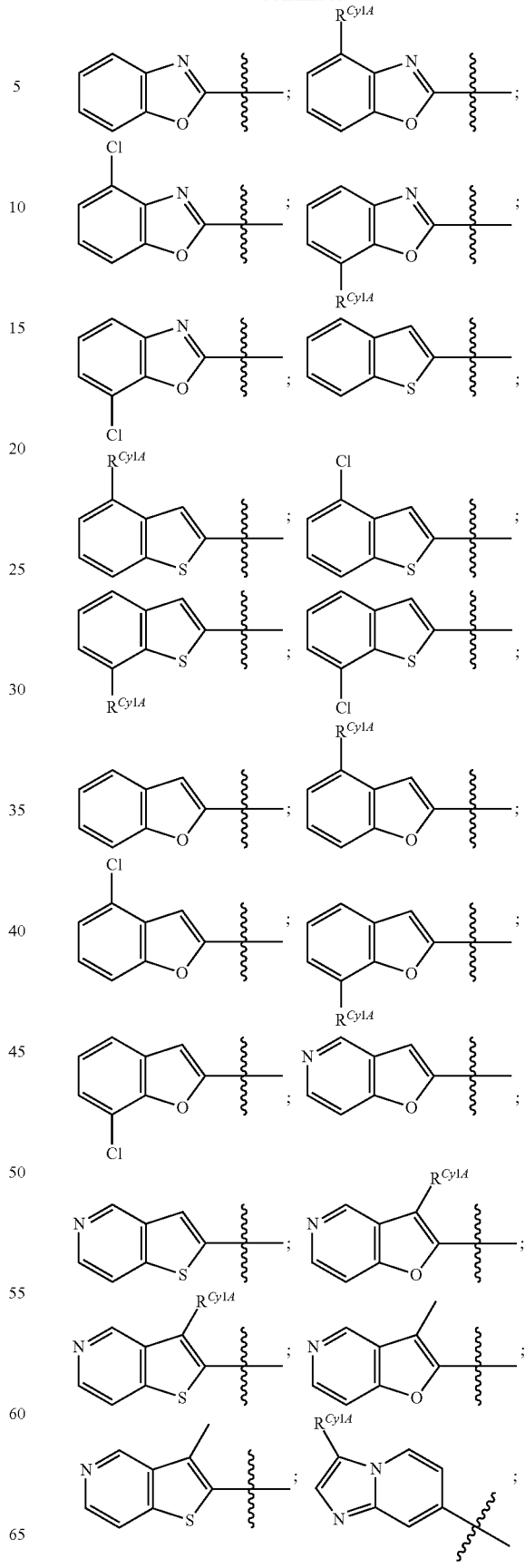

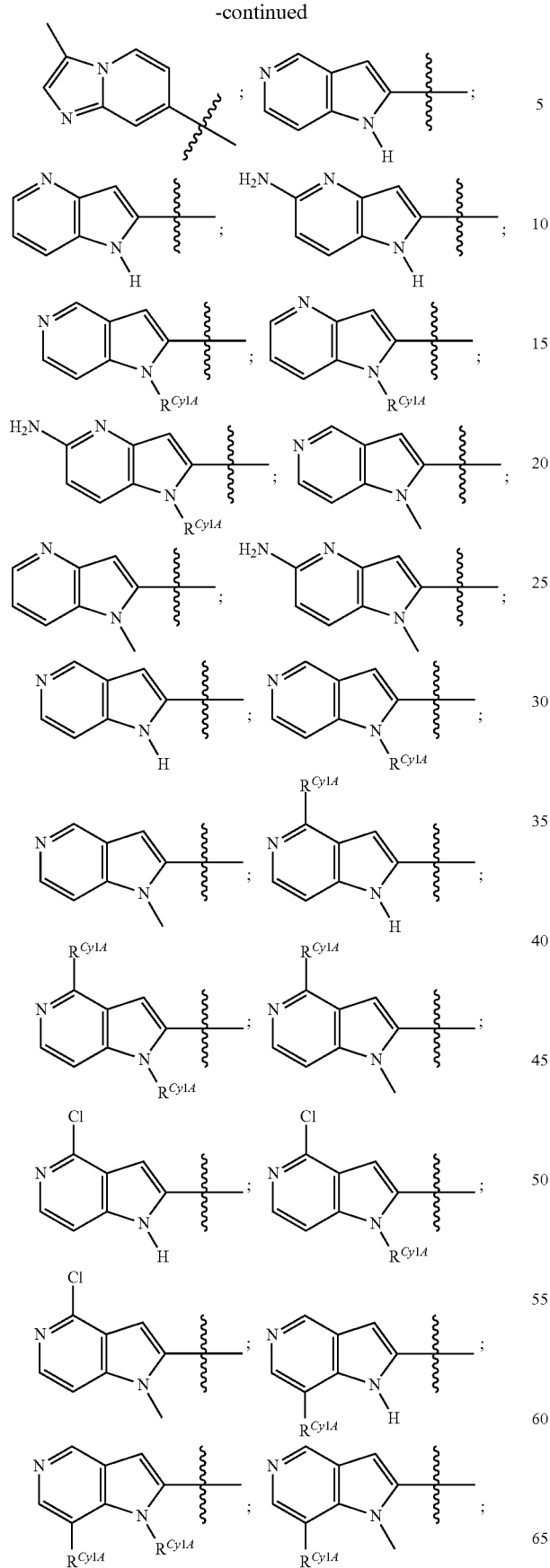
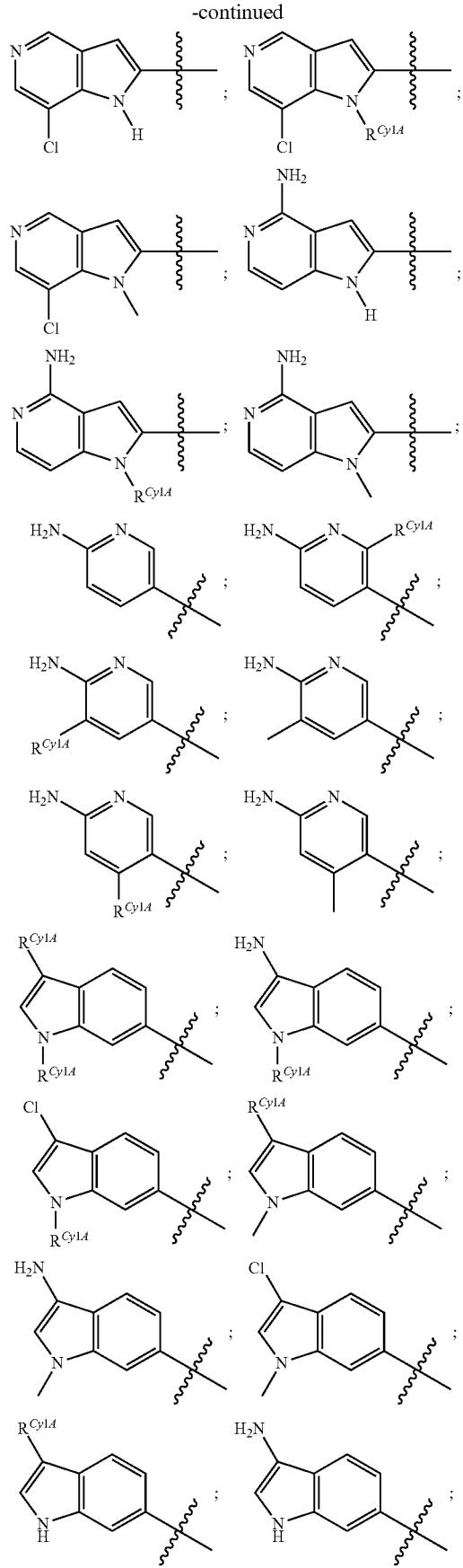

-continued
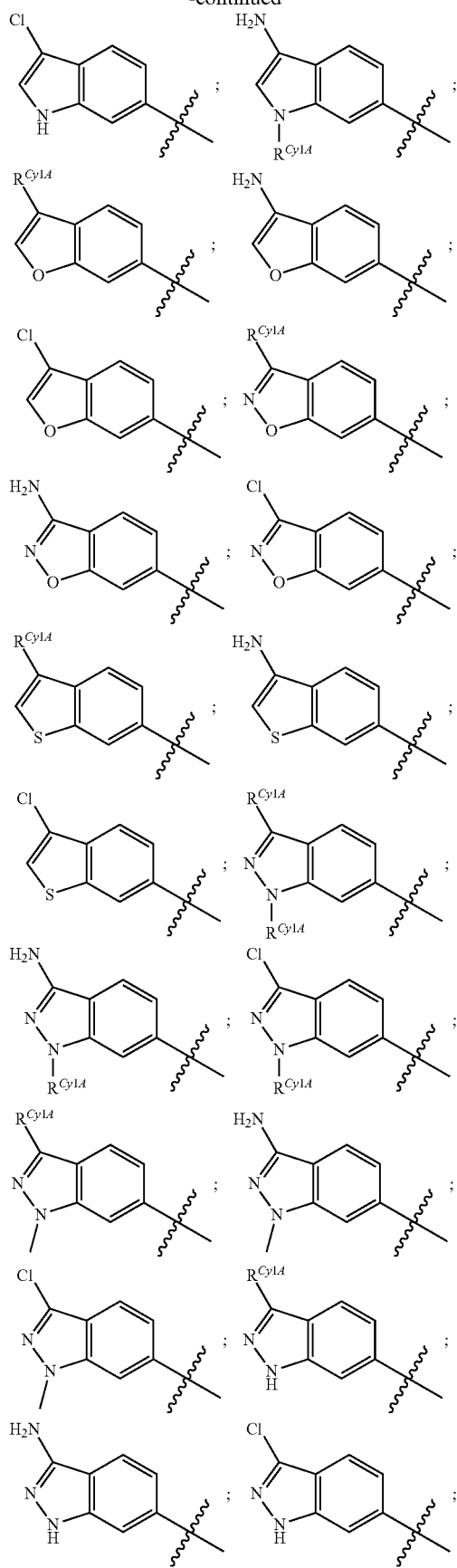
-continued
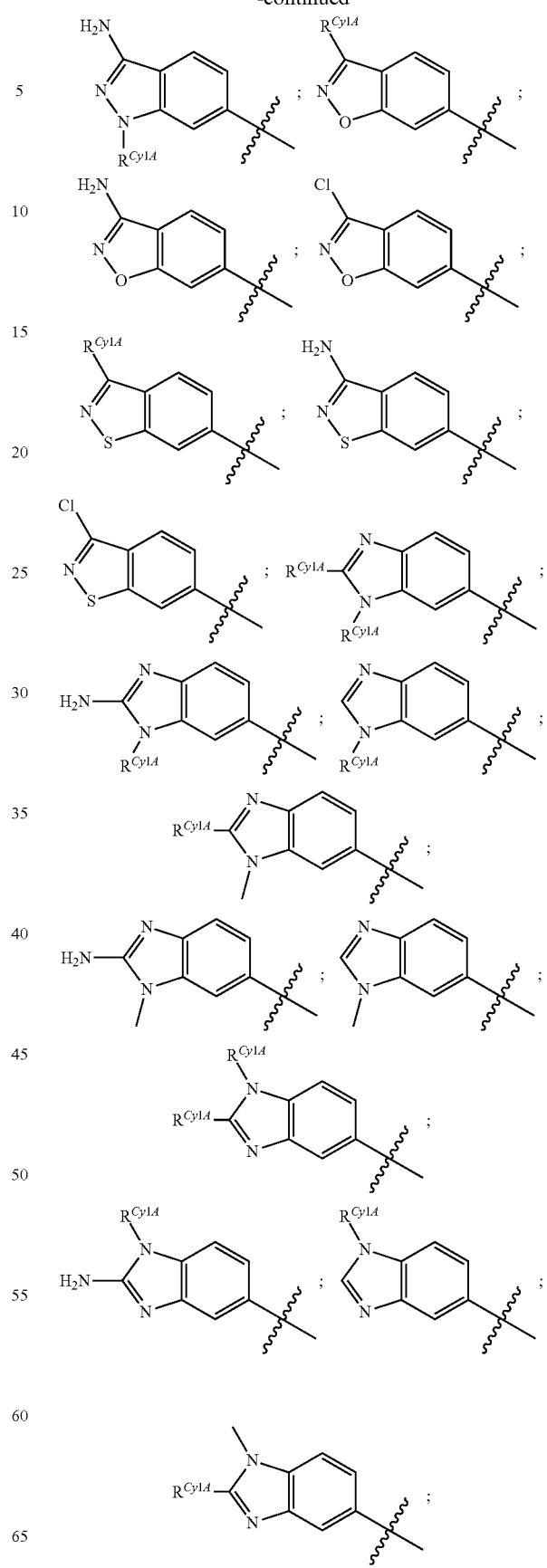

-continued
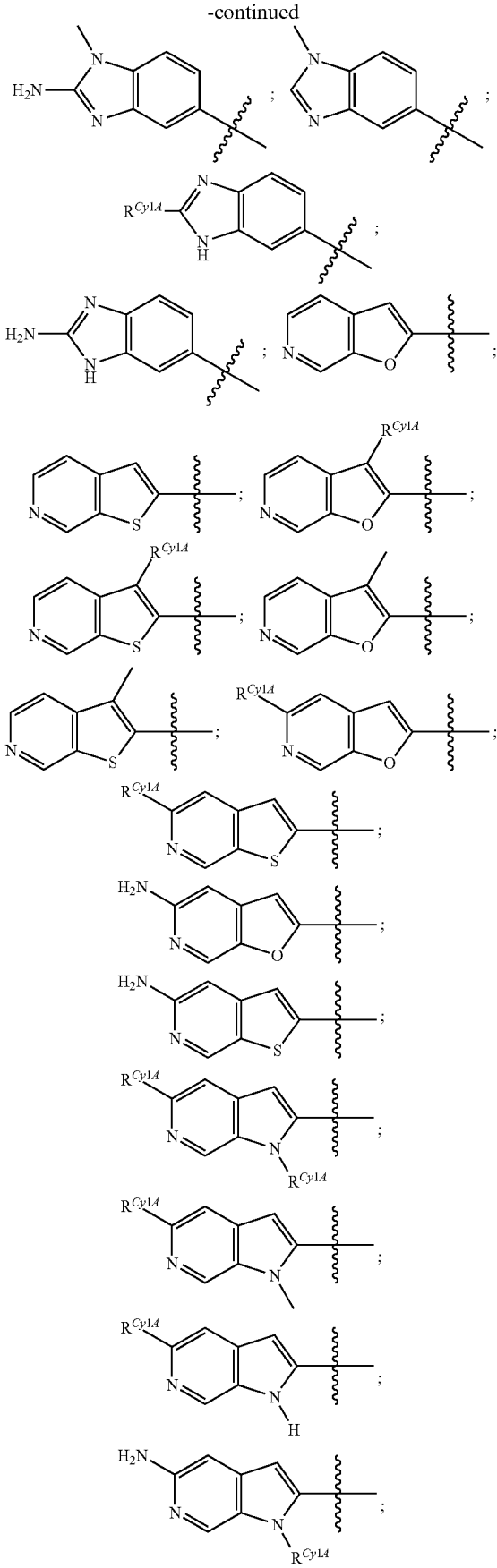
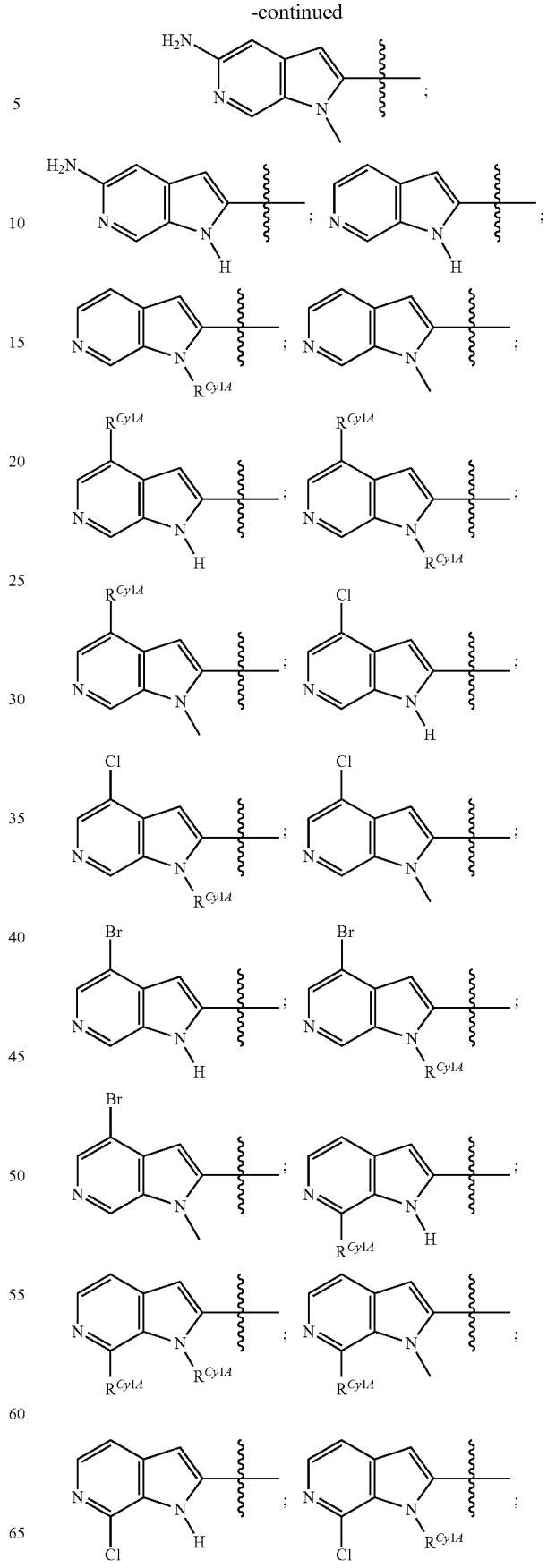

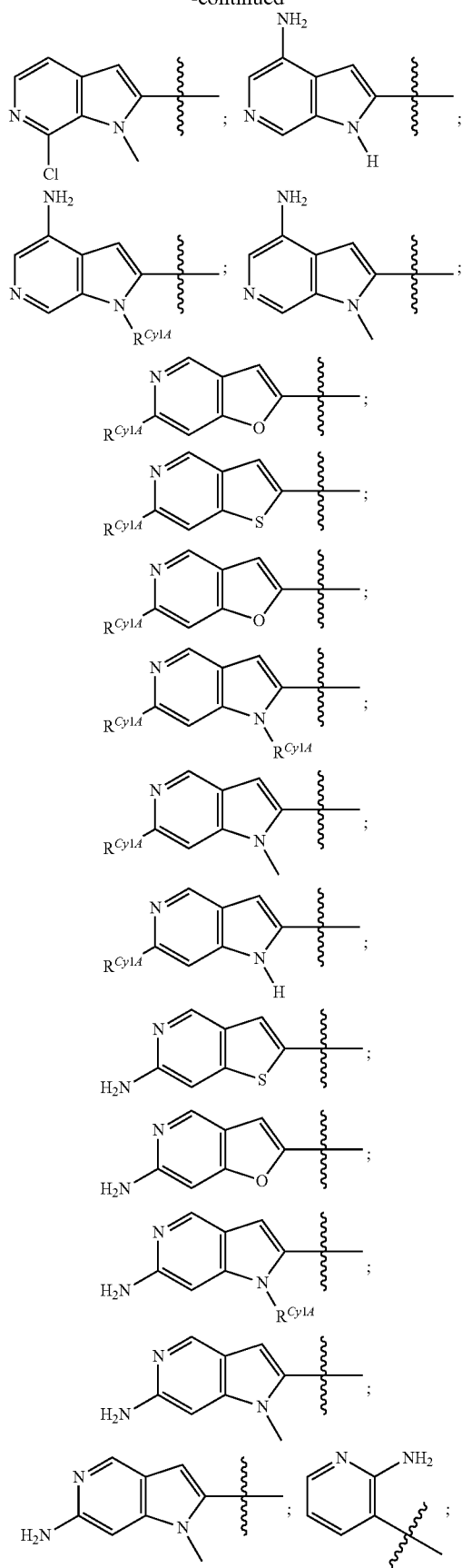
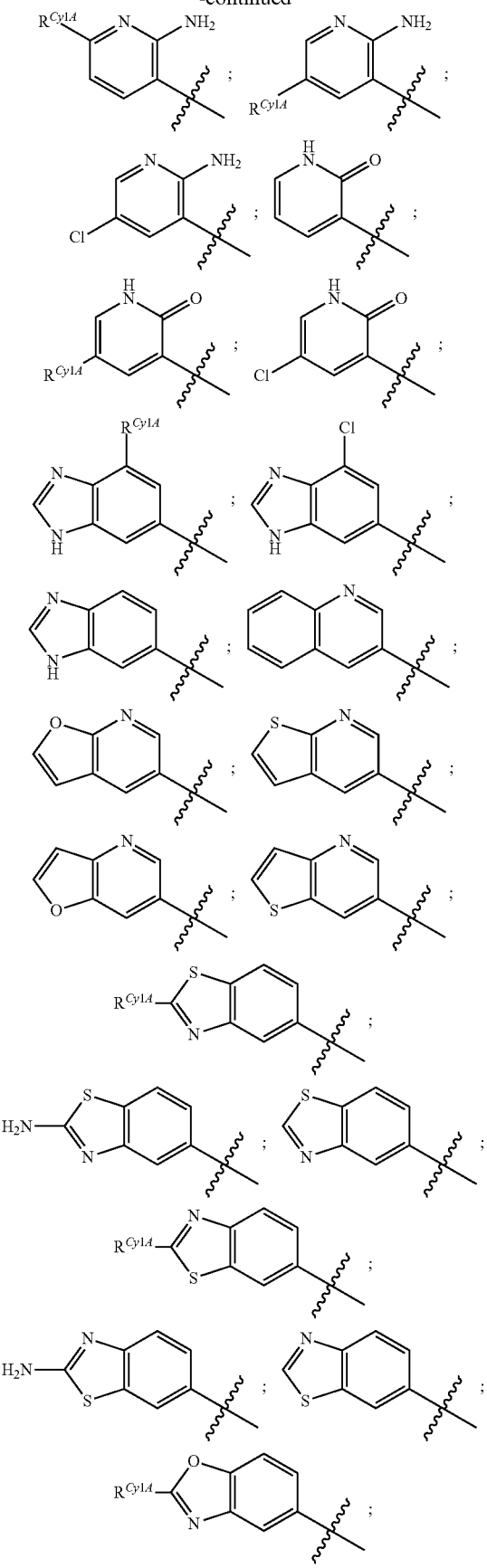

-continued

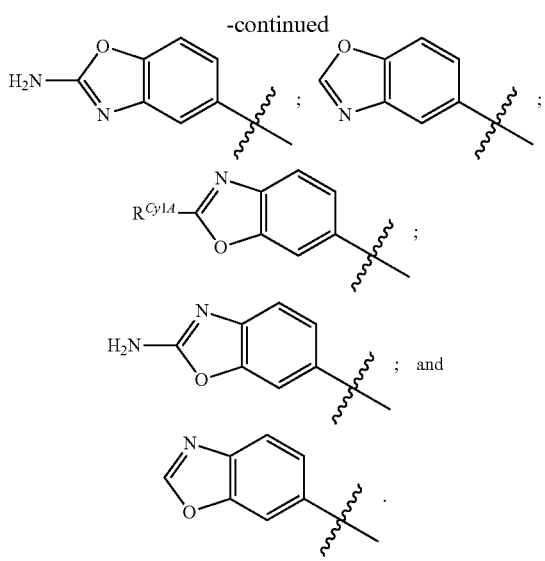

In some embodiments, each $R^{Cy1A}$ in the formula defining $Cy^{1A}$ is independently $C_{1-6}$ alkyl, such as methyl or ethyl, preferably methyl, or halogen such as F, Cl or Br, preferably Cl, or amino.

In some embodiments, each $R^{Cy1A}$ attached to nitrogen in the formula defining $Cy^{1A}$ is $C_{1-6}$ alkyl, such as methyl or ethyl.

In some embodiments, $R^{11}$ is $C_{1-6}$ alkyl.

In some embodiments, $R^{11}$ is methyl.

In some embodiments, $R^{11}$ is H.

In some embodiments, $R^{12}$ is H.

In some embodiments, $R^{12}$ is $C_{1-6}$ alkyl, such as methyl or ethyl, preferably methyl.

In some embodiments, $R^{11}$ and $R^{12}$, together with the groups to which they are attached, form a 4-6 membered heterocycloalkyl ring.

In some embodiments, n1 is 1.

In some embodiments, n1 is 2.

In some embodiments, n2 is 0.

In some embodiments, n2 is 1.

In some embodiments, n2 is 2.

In some embodiments, the compound is according to any of the following Formulae (I-1a) to (I-1f) and (I-2a) to (I-2r):

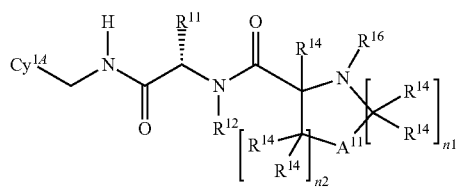
(I-1a)

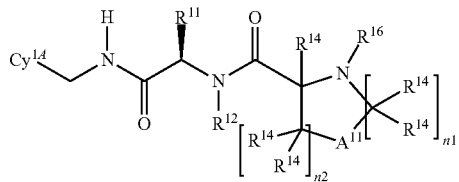
(I-1b)

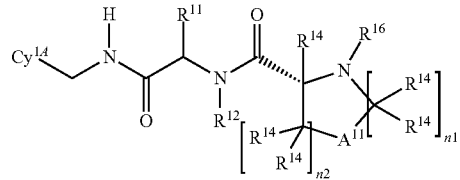
(I-1c)

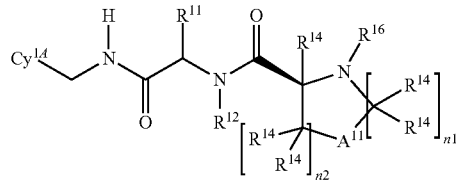
(I-1d)

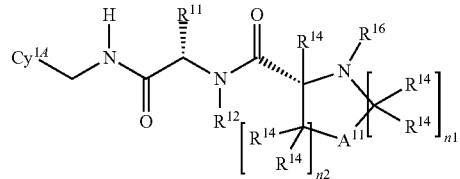
(I-1e)

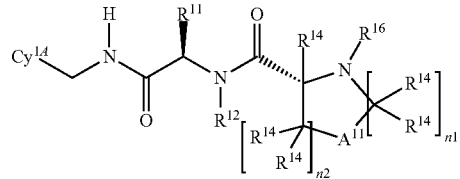
(I-1f)

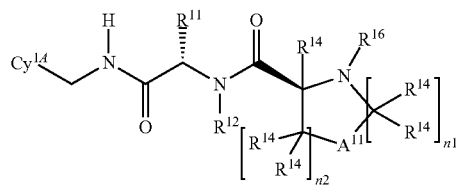
(I-1g)

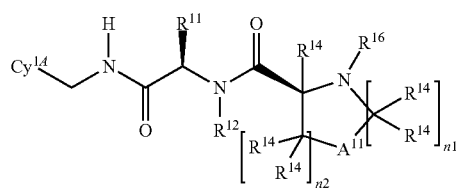
(I-1h)

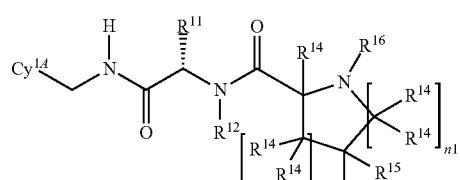
(I-2a)

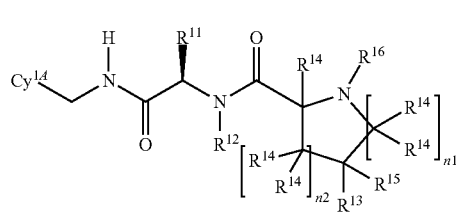
(I-2b)

-continued
(I-2c)
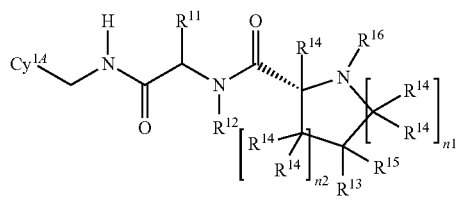
(I-2d)
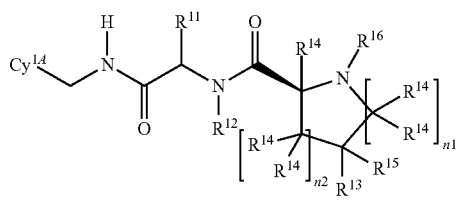
(I-2e)
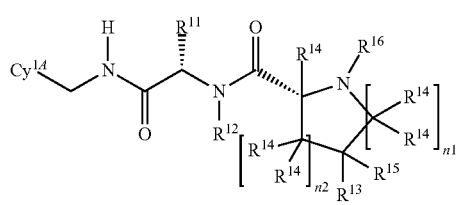
(I-2f)
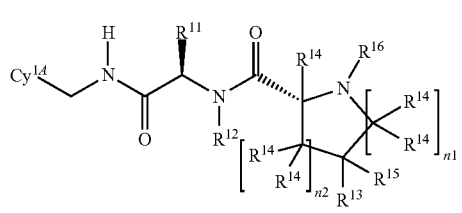
(I-2g)
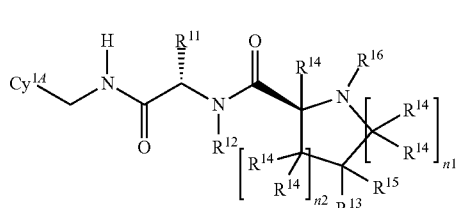
(I-2h)
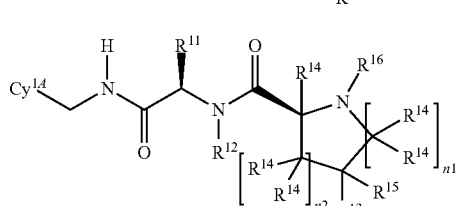
(I-2i)
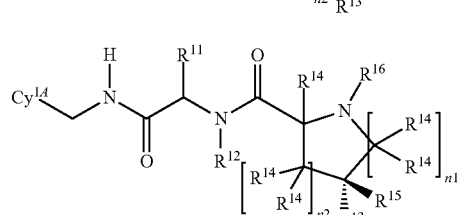
(I-2j)
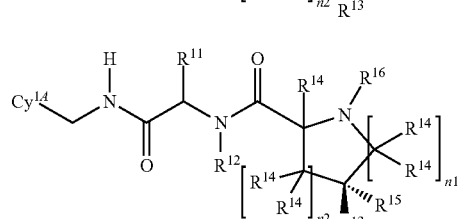
-continued
(I-2k)
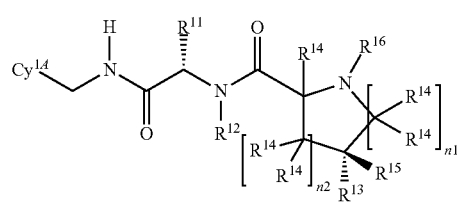
(I-2l)
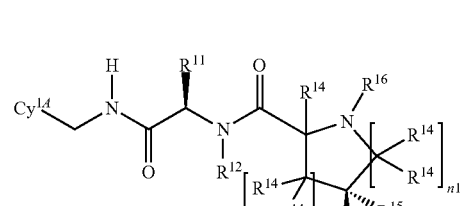
(I-2m)
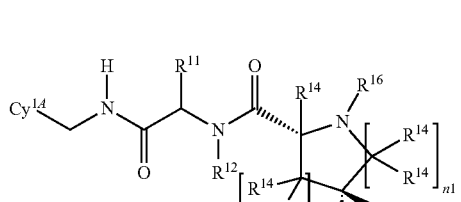
(I-2n)
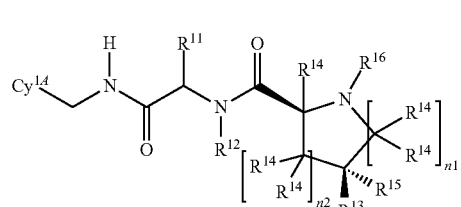
(I-2o)
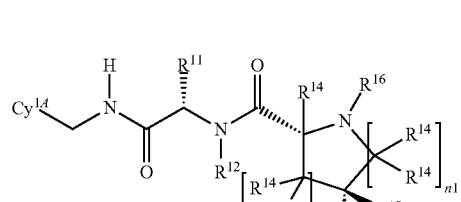
(I-2p)
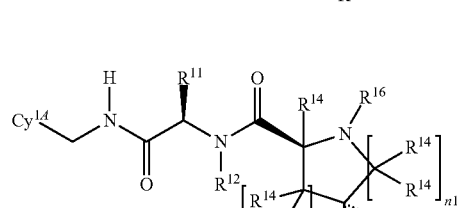
(I-2q)
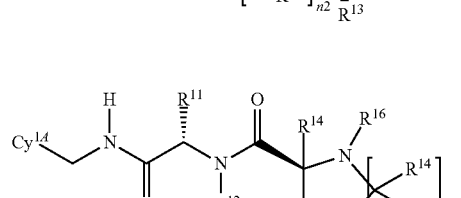

(I-2r)
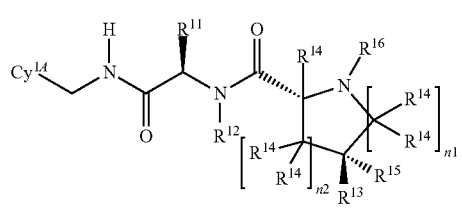
In some embodiments, the compound is according to any of the following Formulae (I-1g) to (I-1o) and (I-2aa) to (I-2az):
(I-1g)
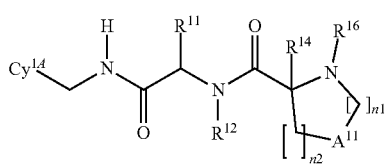
(I-1h)
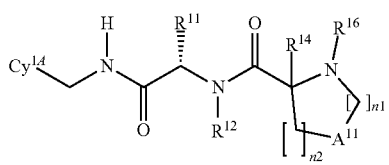
(I-1i)
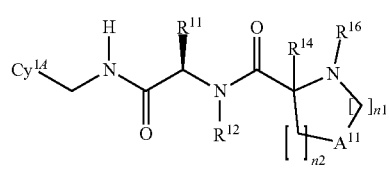
(I-1j)
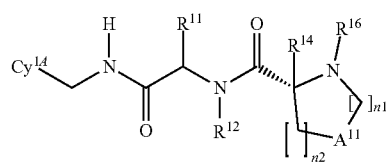
(I-1k)
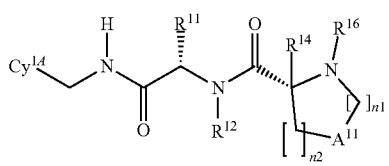
(I-1l)
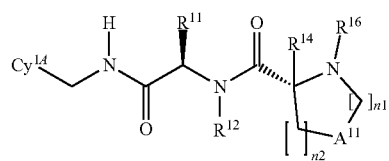
(I-1m)
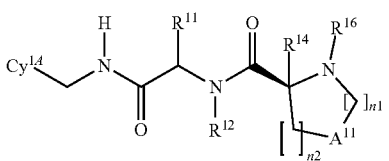
(I-1n)
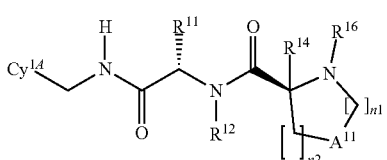
(I-1o)
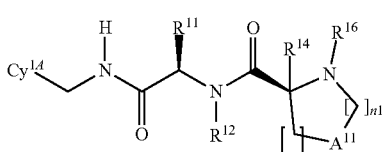
(I-2aa)
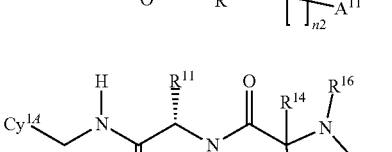
(I-2ab)
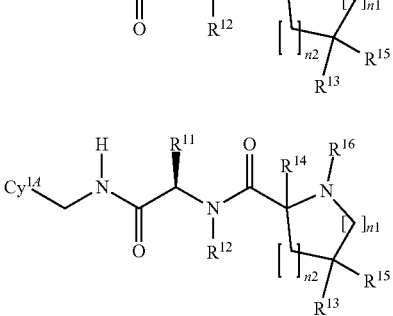
(I-2ac)
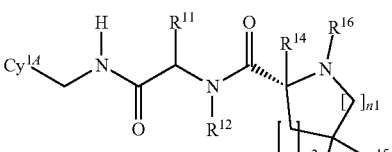
(I-2ad)
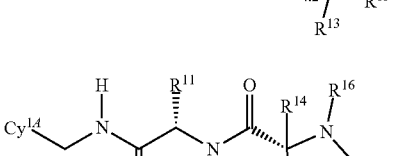
(I-2ae)
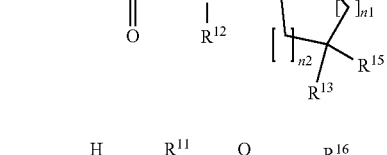
(I-2af)
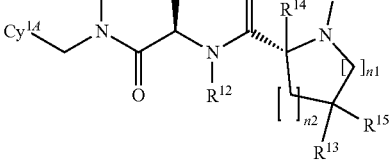

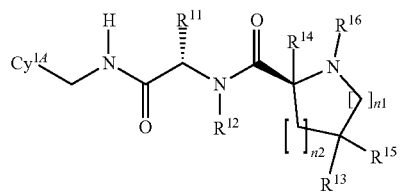
(I-2ag)
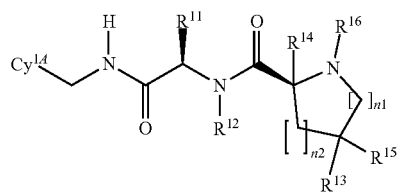
(I-2ah)
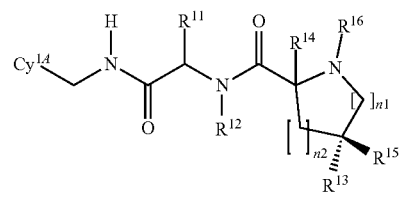
(I-2ai)
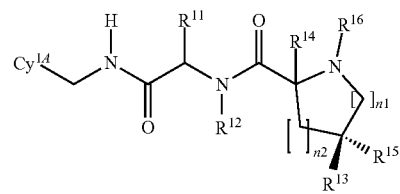
(I-2aj)
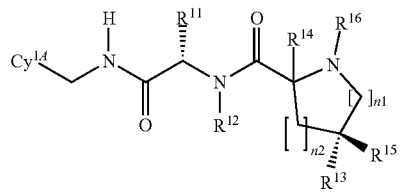
(I-2ak)
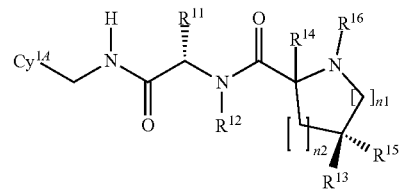
(I-2al)
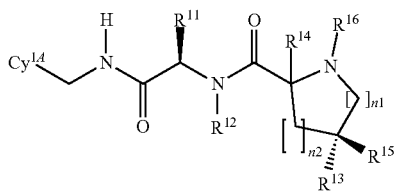
(I-2am)
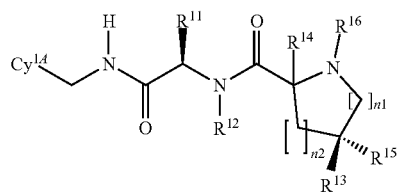
(I-2an)
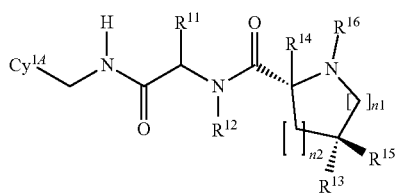
(I-2ao)
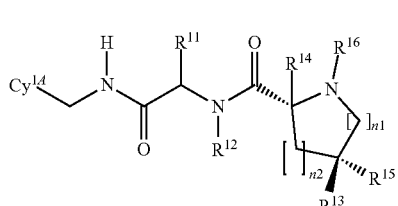
(I-2ap)
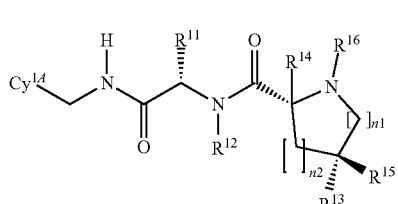
(I-2aq)
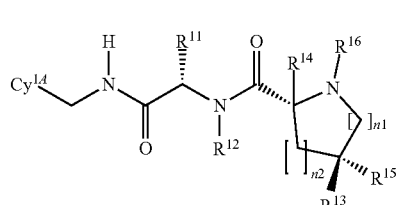
(I-2ar)
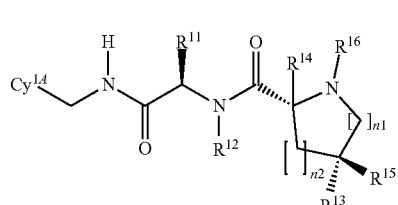
(I-2as)
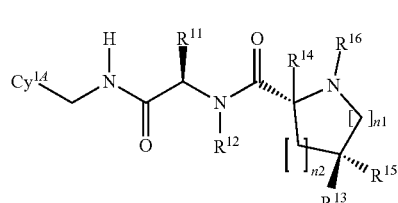
(I-2at)
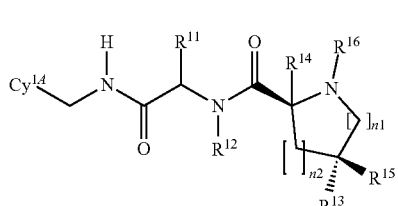
(I-2au)
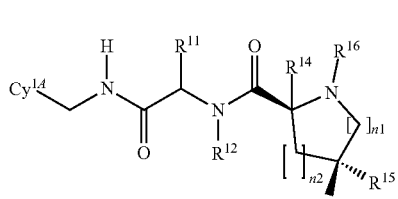
(I-2av)

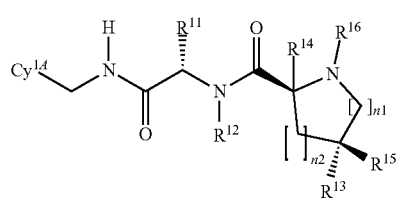 (I-2aw)
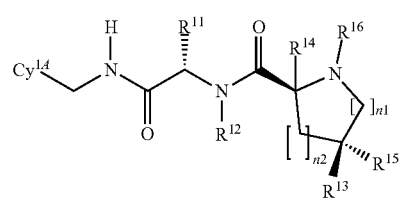 (I-2ax)
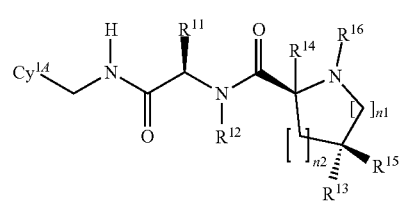 (I-2ay)
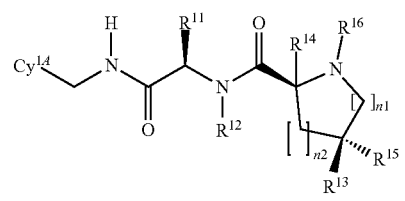 (I-2az)
In some embodiments, the compound is according to any of the following Formulae (I-3) to (I-9):
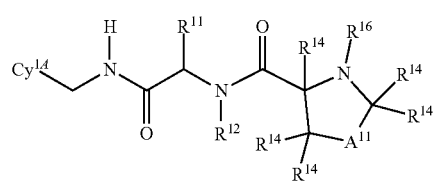 (I-3)
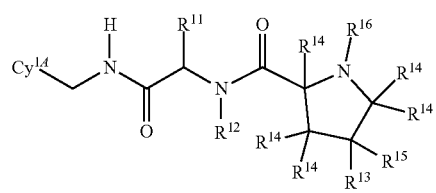 (I-4)
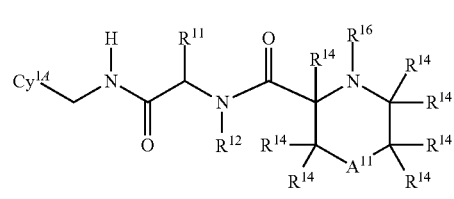 (I-5)
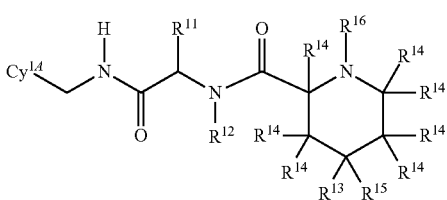 (I-6)
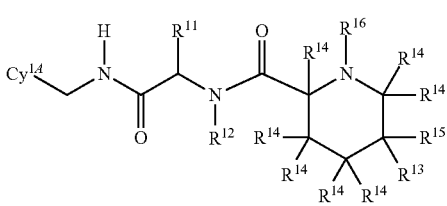 (I-7)
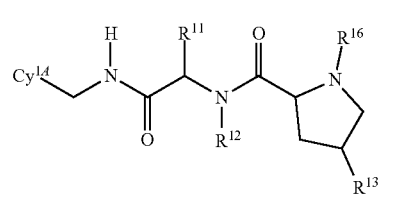 (I-8)
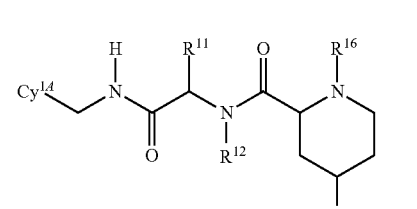 (I-9)
In some embodiments, the compound is according to any of the following Formulae (I-3a) to (1-3 k):
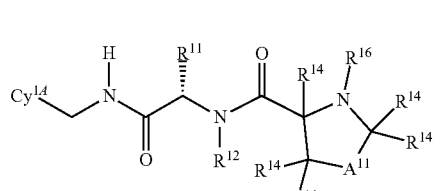 (I-3a)
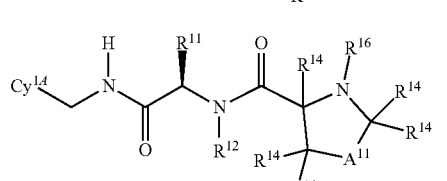 (I-3b)
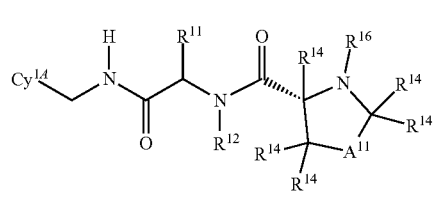 (I-3c)

-continued
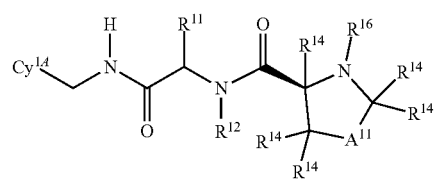
(I-3d)
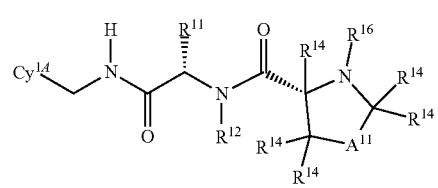
(I-3e)
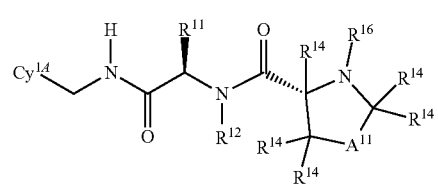
(I-3f)
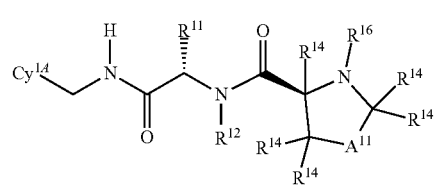
(I-3g)
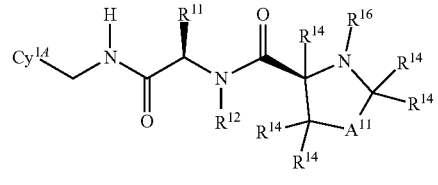
(I-3h)
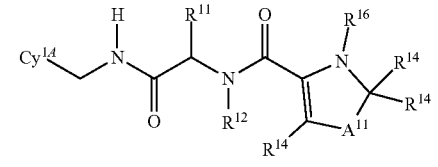
(I-3i)
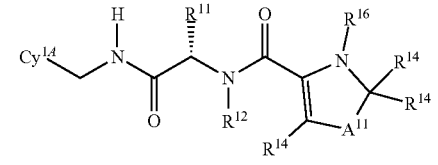
(I-3j)
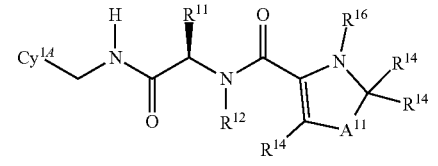
(I-3k)
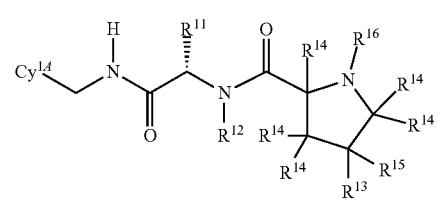
(I-4a)
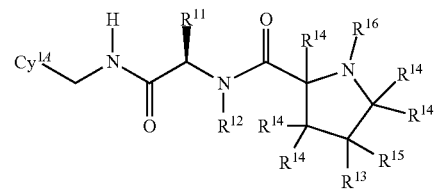
(I-4b)
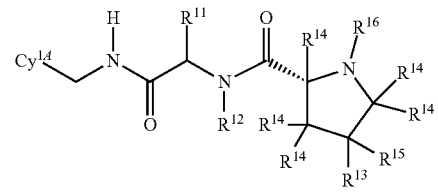
(I-4c)
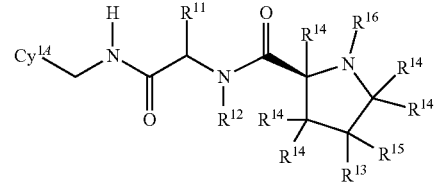
(I-4d)
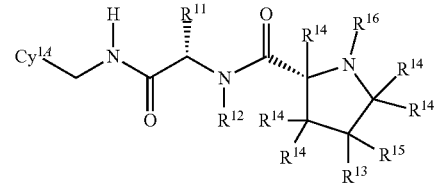
(I-4e)
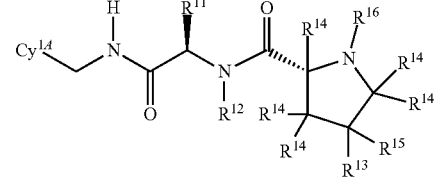
(I-4f)
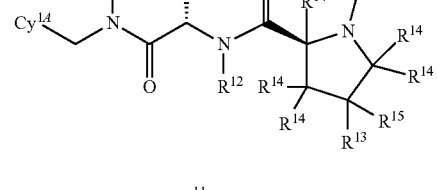
(I-4g)
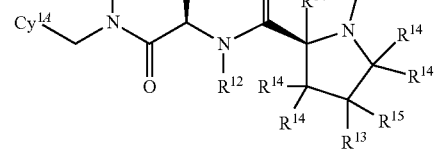
(I-4h)
In some embodiments, the compound is according to any of the following Formulae (I-4a) to (I-4bf):

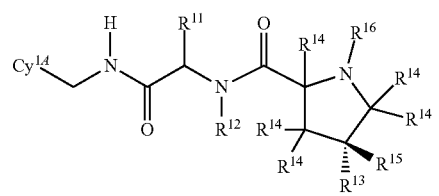
(I-4i)
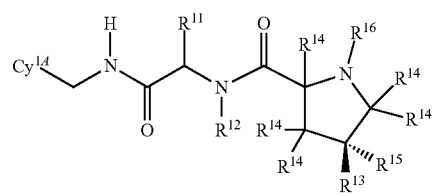
(I-4j)
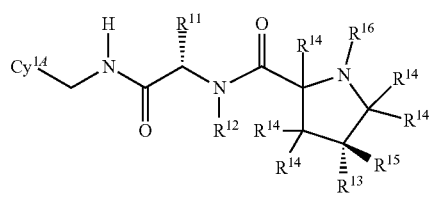
(I-4k)
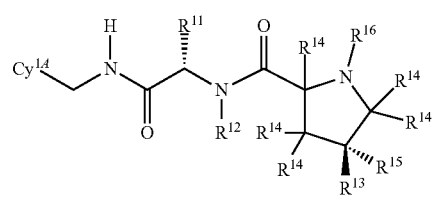
(I-4l)
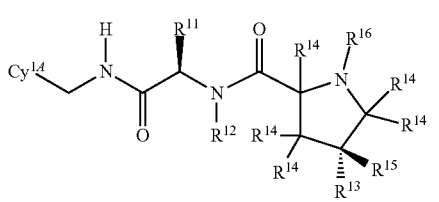
(I-4m)
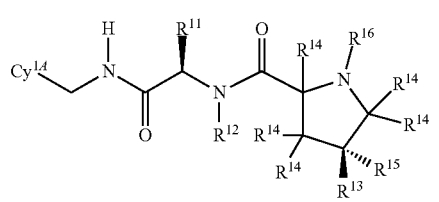
(I-4n)
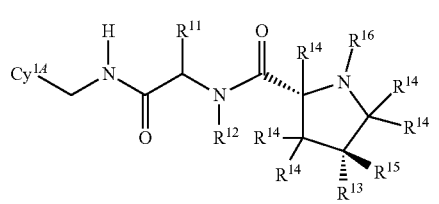
(I-4o)
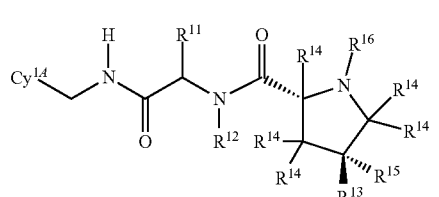
(I-4p)
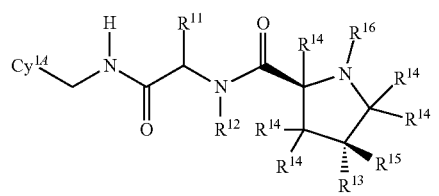
(I-4q)
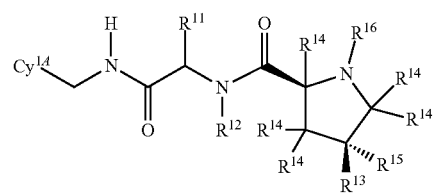
(I-4r)
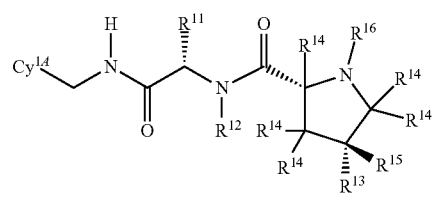
(I-4s)
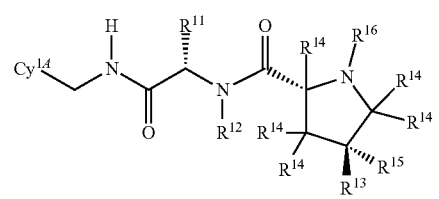
(I-4t)
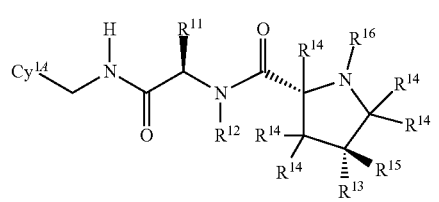
(I-4u)
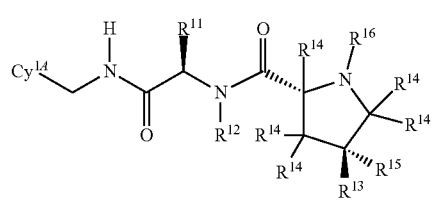
(I-4v)
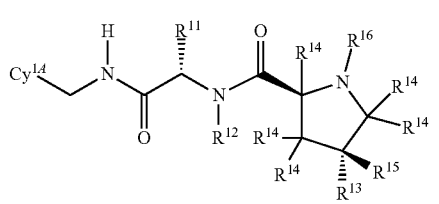
(I-4w)
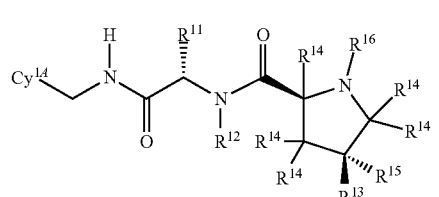
(I-4x)

-continued

-continued
(I-4ar)
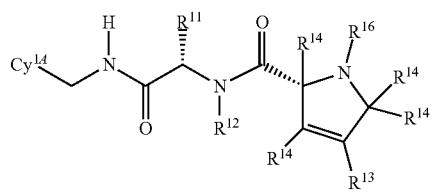
(I-4as)
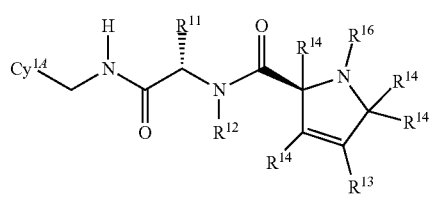
(I-4at)
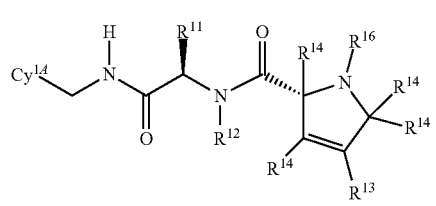
(I-4u)
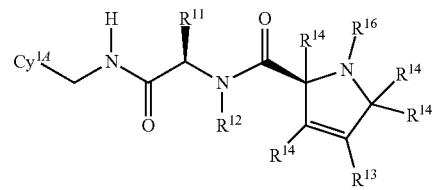
(I-4av)
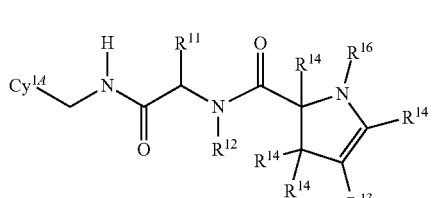
(I-4av)
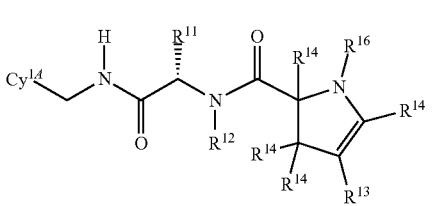
(I-4aw)
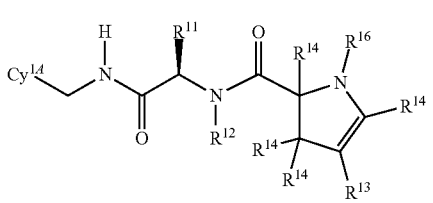
-continued
(I-4ax)
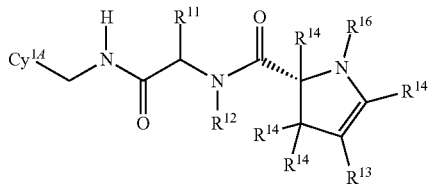
(I-4ay)
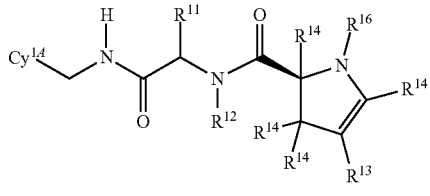
(I-4az)
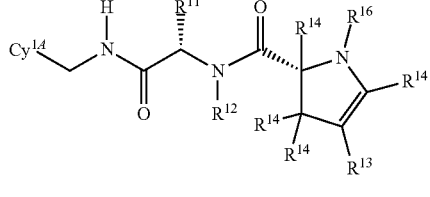
(I-4ba)
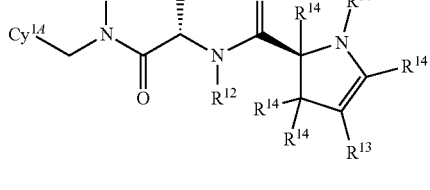
(I-4bb)
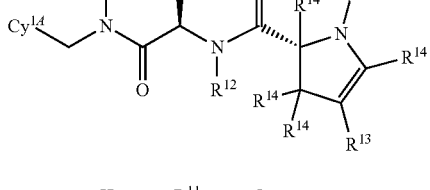
(I-4bc)
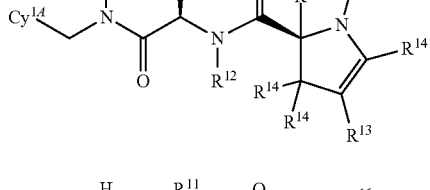
(I-4bd)
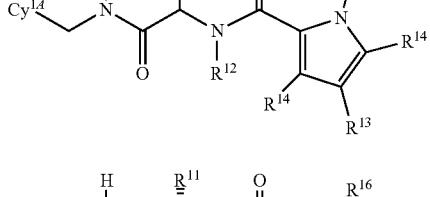
(I-4be)

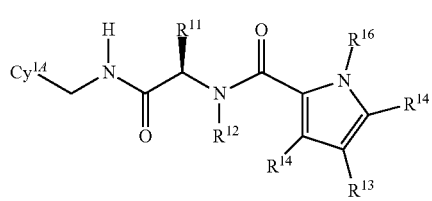
(I-4bf)
In some embodiments, the compound is according to any of the following Formulae (I-5a) to (I-5u):
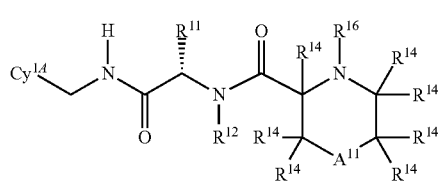
(I-5a)
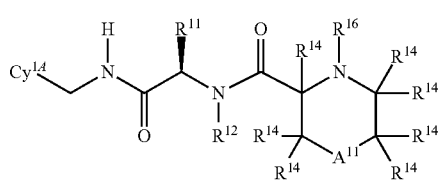
(I-5b)
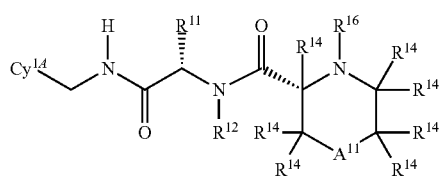
(I-5c)
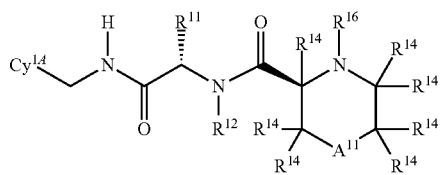
(I-5d)
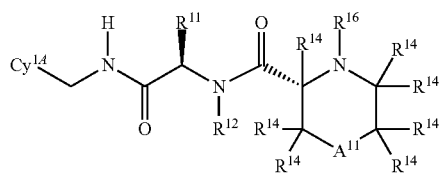
(I-5e)
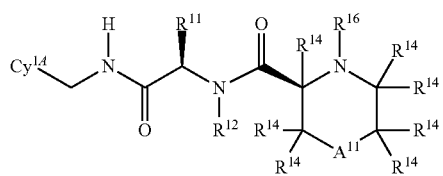
(I-5f)
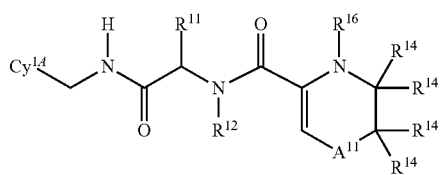
(I-5g)
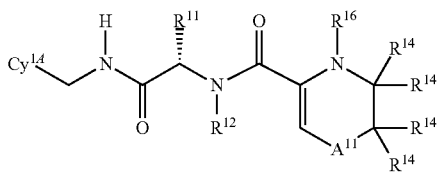
(I-5h)
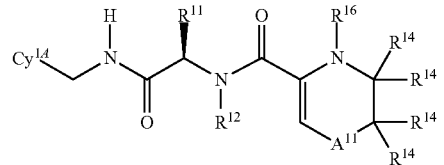
(I-5i)
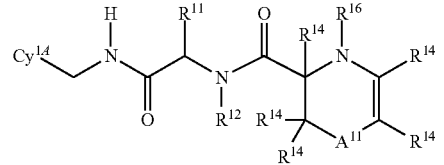
(I-5j)
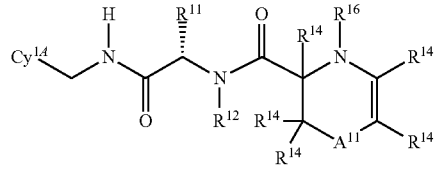
(I-5k)
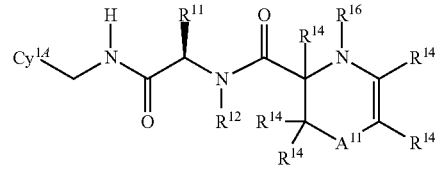
(I-5l)
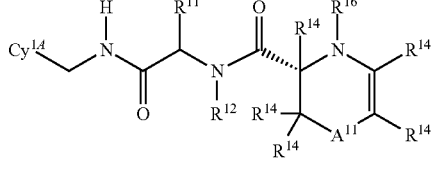
(I-5m)
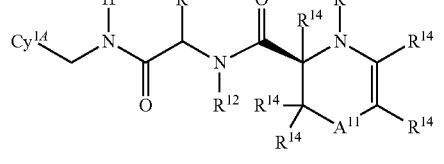
(I-5n)
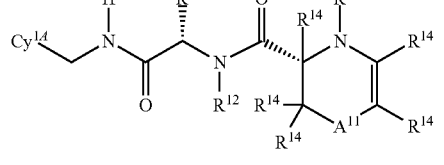
(I-5o)
(I-5p)

(I-5q) 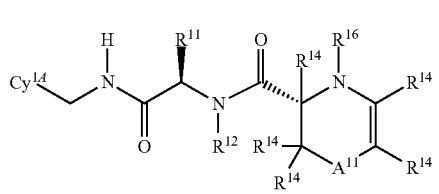
(I-5r) 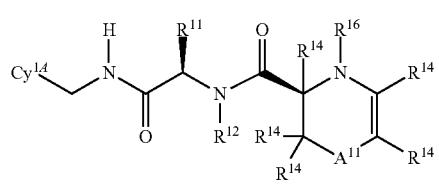
(I-5s) 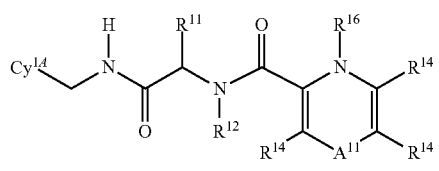
(I-5t) 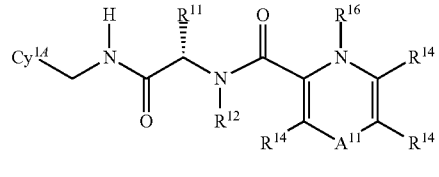
(I-5u) 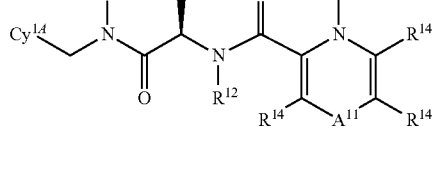
In some embodiments, the compound is according to any of the following Formulae (I-6a) to (I-6cw):
(I-6a) 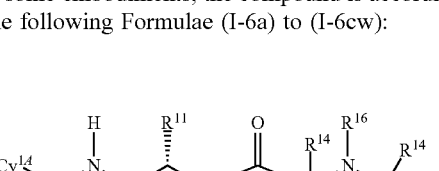
(I-6b) 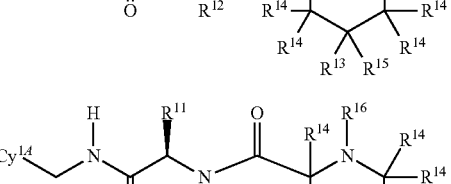
(I-6c) 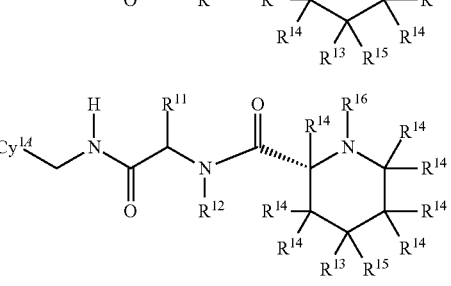
(I-6d) 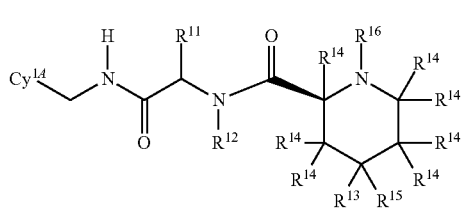
(I-6e) 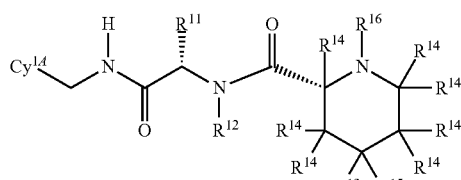
(I-6f) 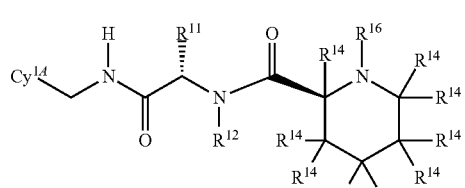
(I-6g) 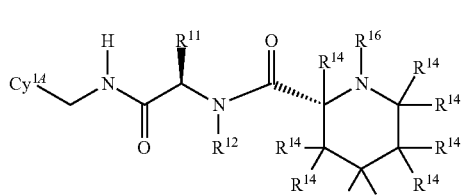
(I-6k) 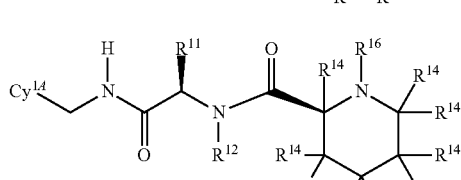
(I-6i) 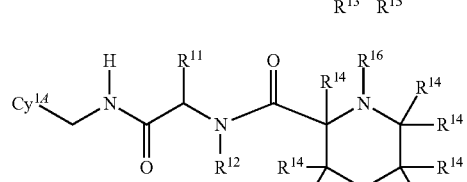
(I-6j) 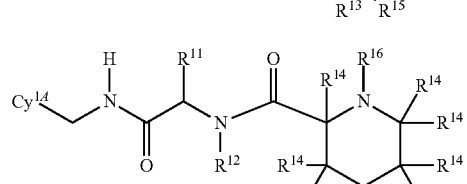
(I-6k) 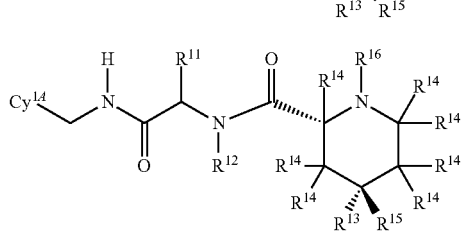

-continued
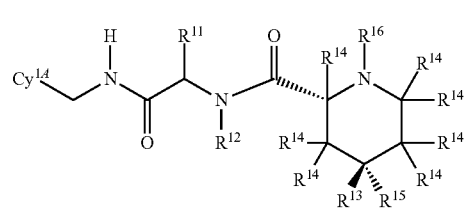
(I-6l)
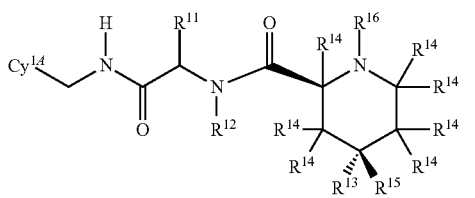
(I-6m)
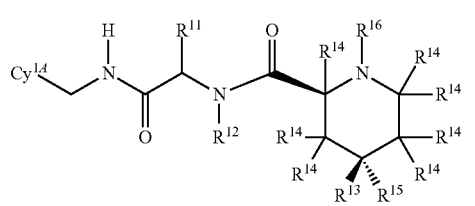
(I-6n)
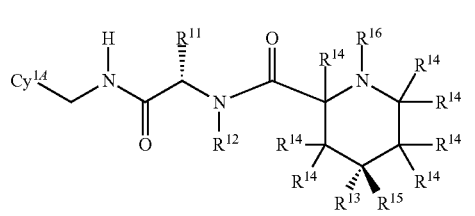
(I-6o)
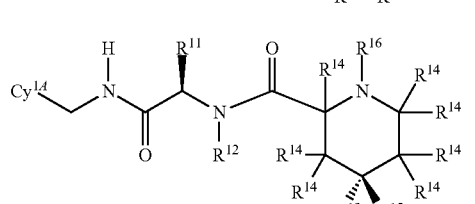
(I-6p)
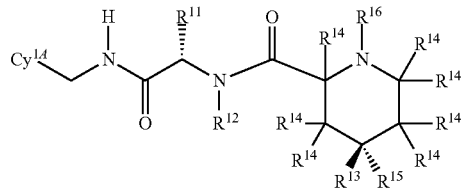
(I-6q)
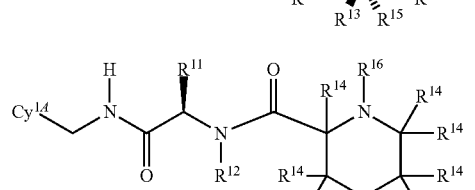
(I-6r)
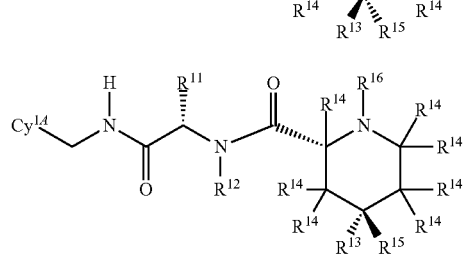
(I-6s)
-continued
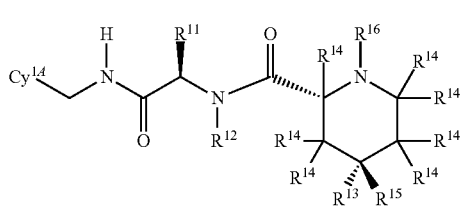
(I-6t)
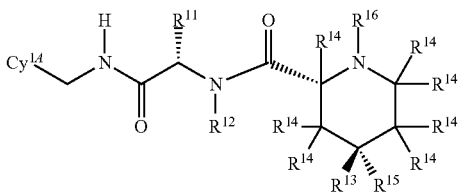
(I-6u)
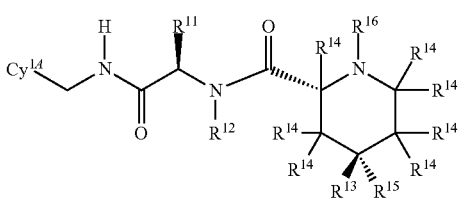
(I-6v)
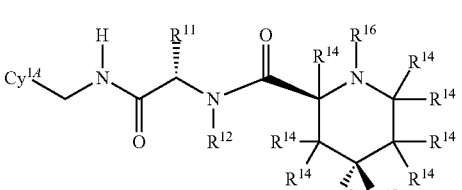
(I-6w)
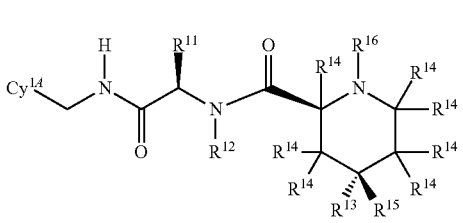
(I-6x)
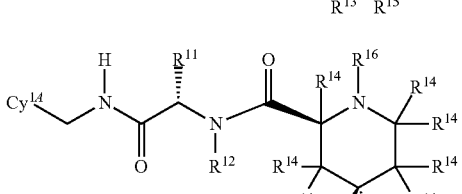
(I-6y)
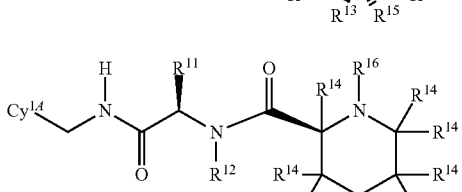
(I-6z)
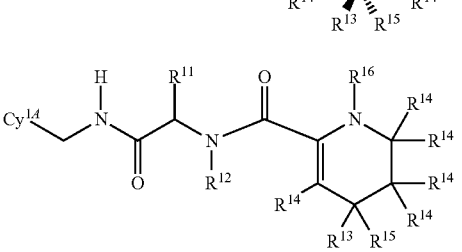
(I-6aa)

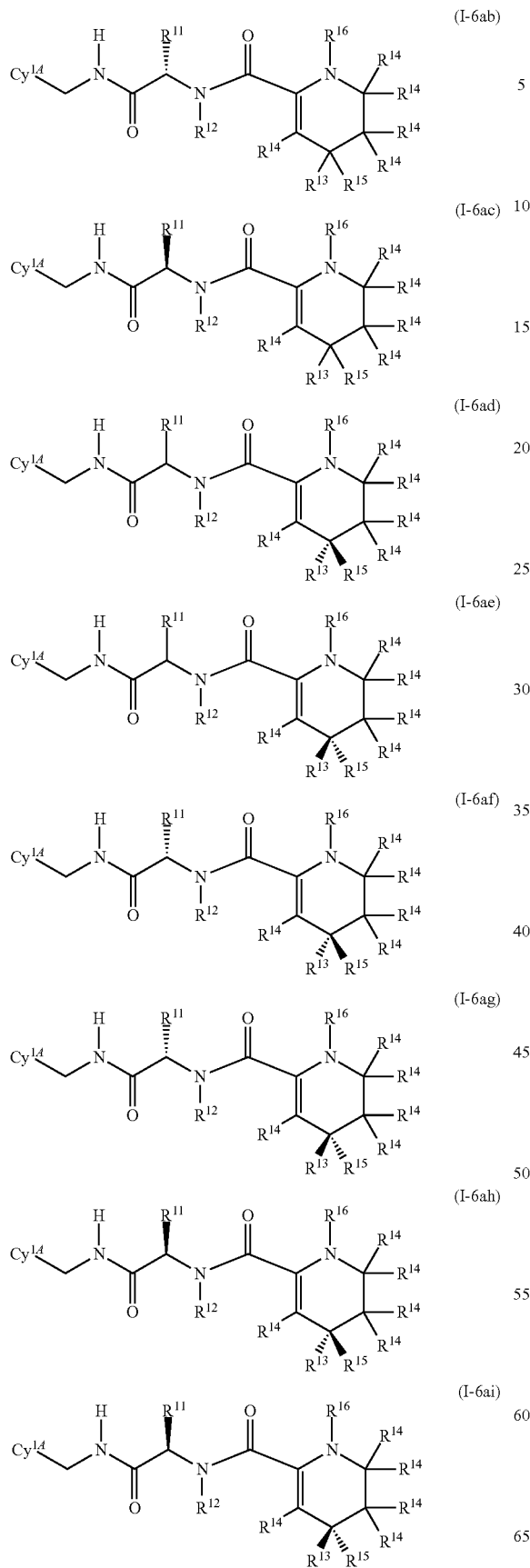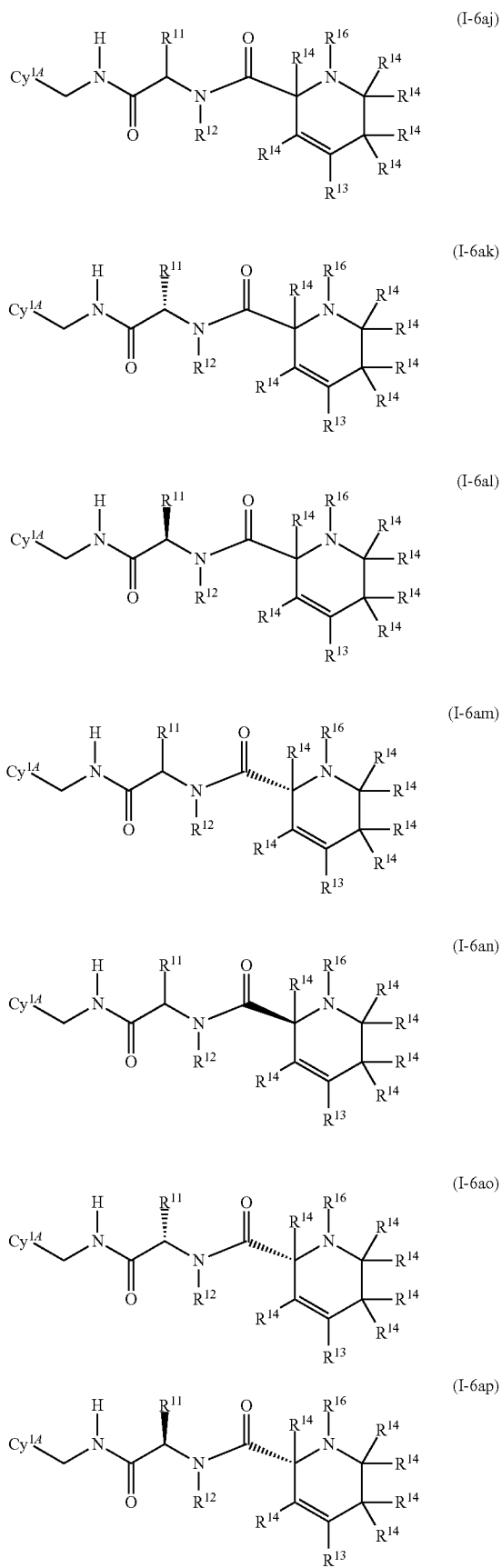

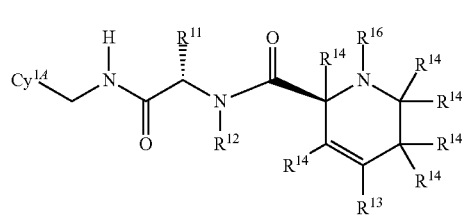
(I-6aq)
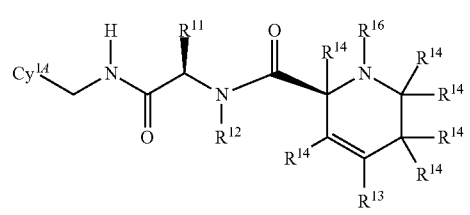
(I-6ar)
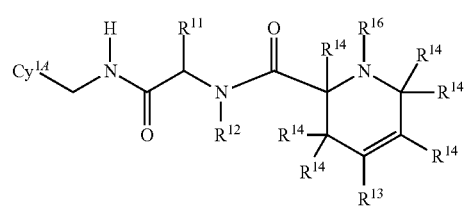
(I-6as)
(I-6at)
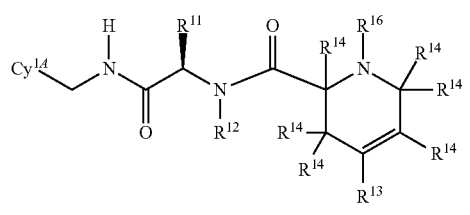
(I-6au)
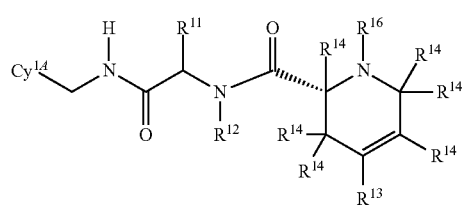
(I-6av)
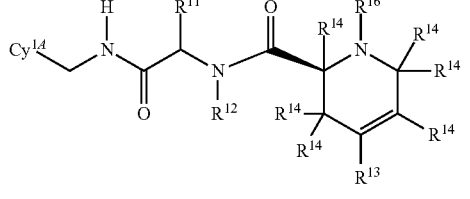
(I-6aw)
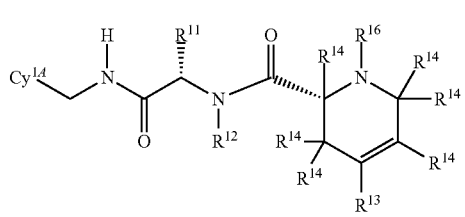
(I-6ax)
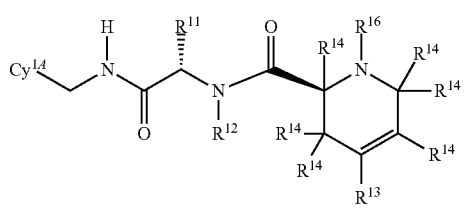
(I-6ay)
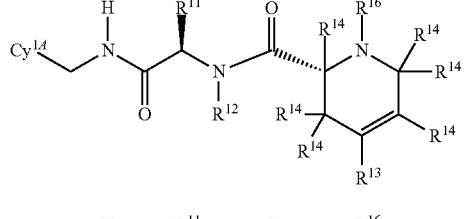
(I-6az)
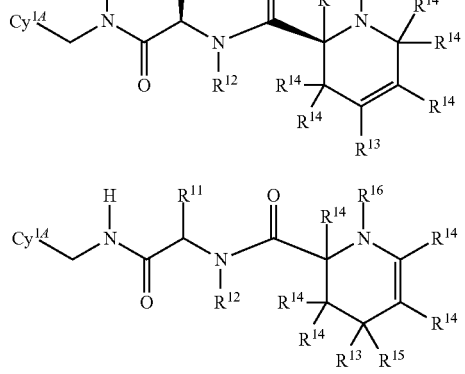
(I-6ba)
(I-6bb)
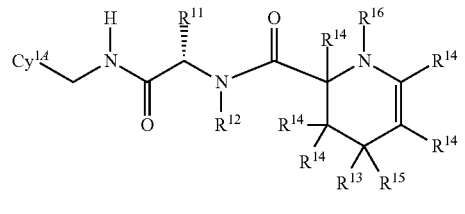
(I-6bc)
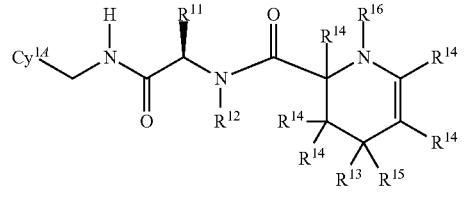
(I-6bd)
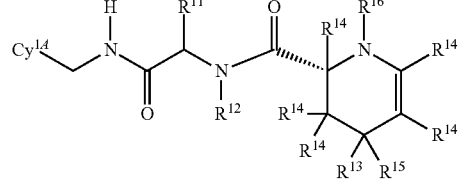
(I-6be)

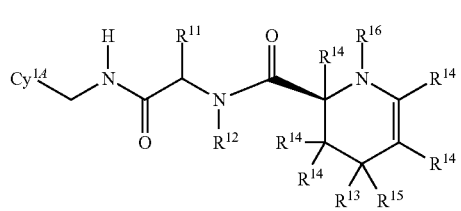
(I-6bf)
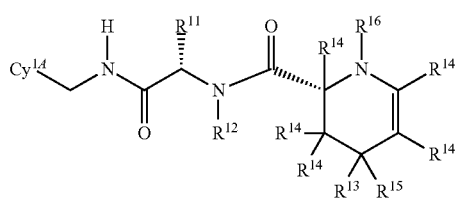
(I-6bg)
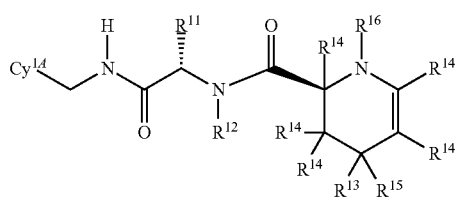
(I-6bh)
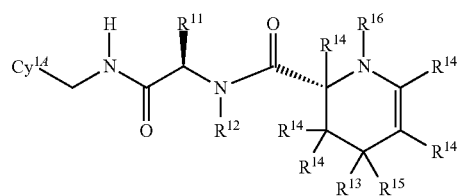
(I-6bi)
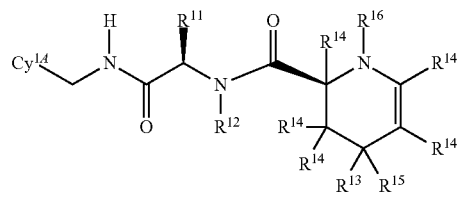
(I-6bj)
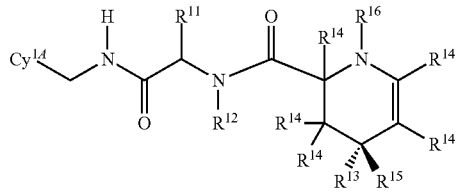
(I-6bk)
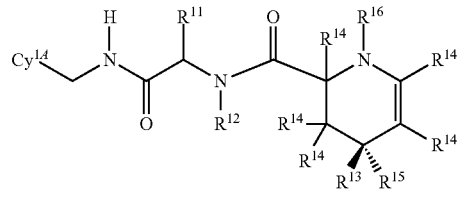
(I-6bl)
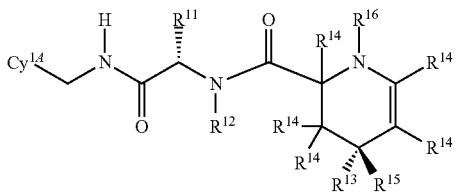
(I-6bm)
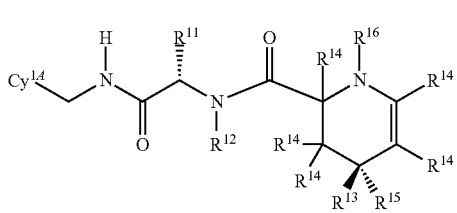
(I-6bn)
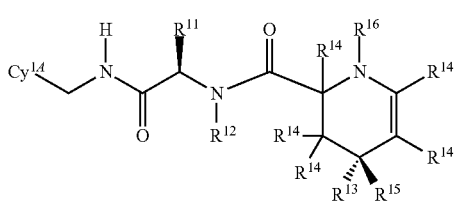
(I-6bo)
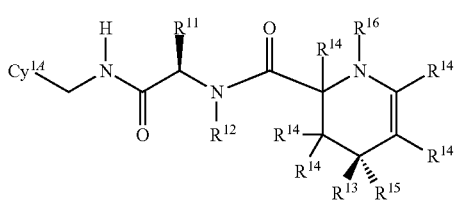
(I-6bp)
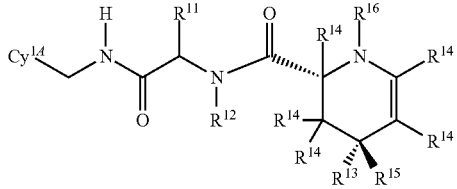
(I-6bq)
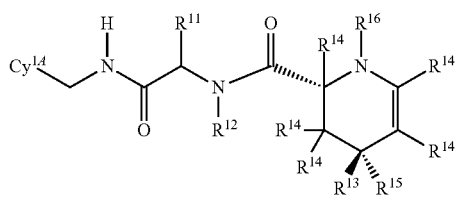
(I-6br)
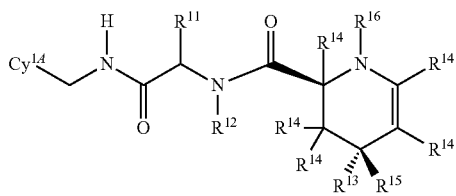
(I-6bs)
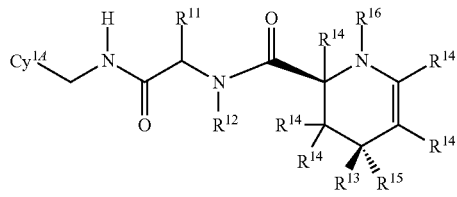
(I-6bt)
(I-6bu)

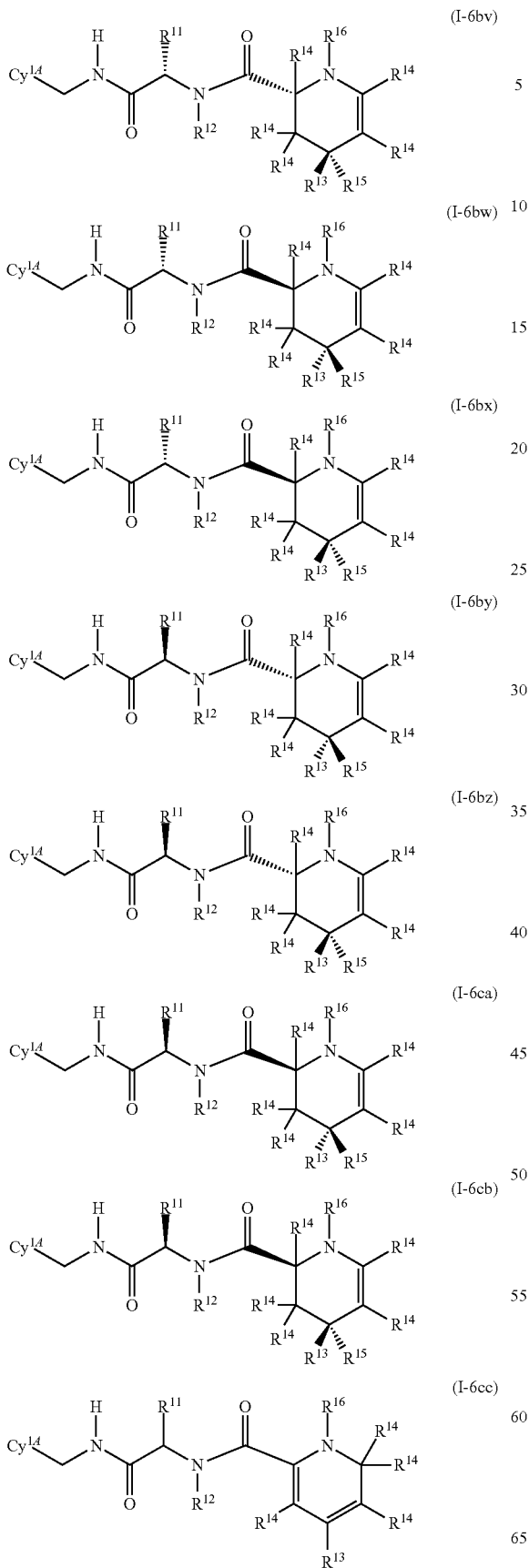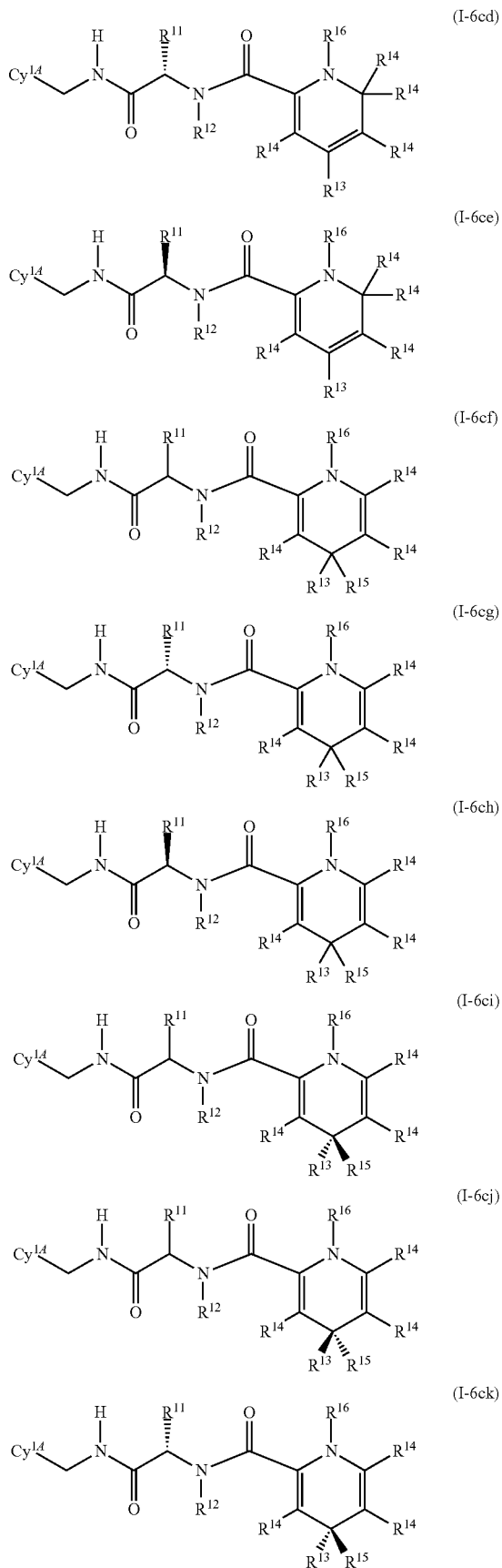

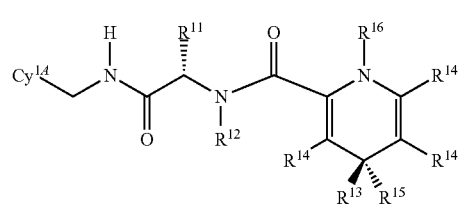
(I-6cl)
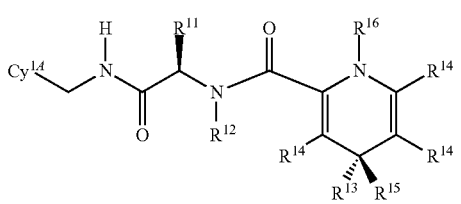
(I-6cm)
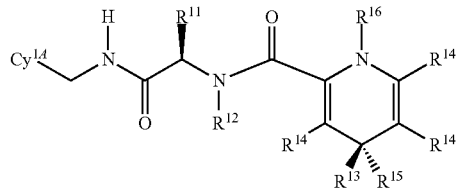
(I-6cn)

(I-6co)
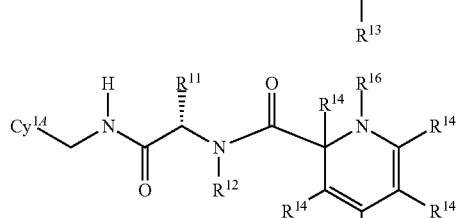
(I-6cp)
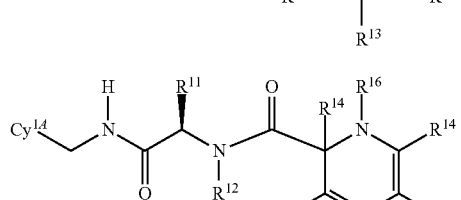
(I-6cq)
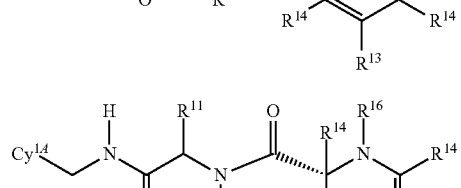
(I-6cr)
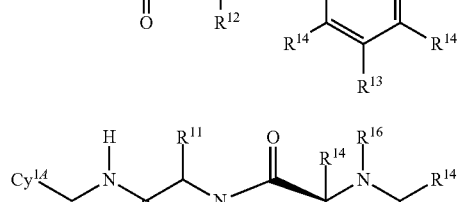
(I-6cs)
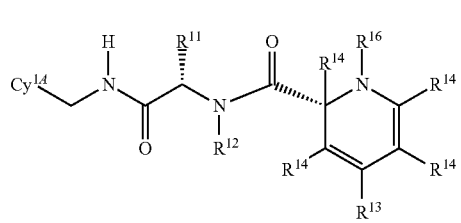
(I-6ct)
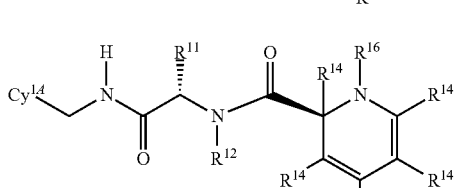
(I-6cu)
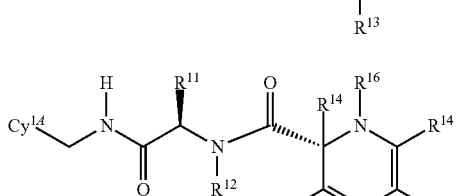
(I-6cv)
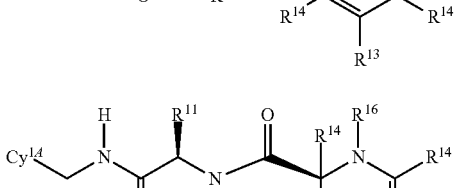
(I-6cw)
In some embodiments, the compound is according to any of the following Formulae (I-7a) to (I-7co):
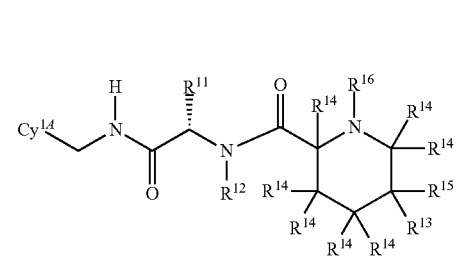
(I-7a)
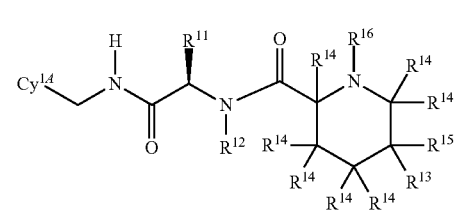
(I-7b)
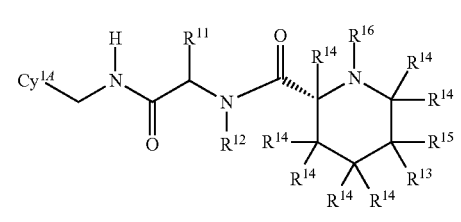
(I-7c)

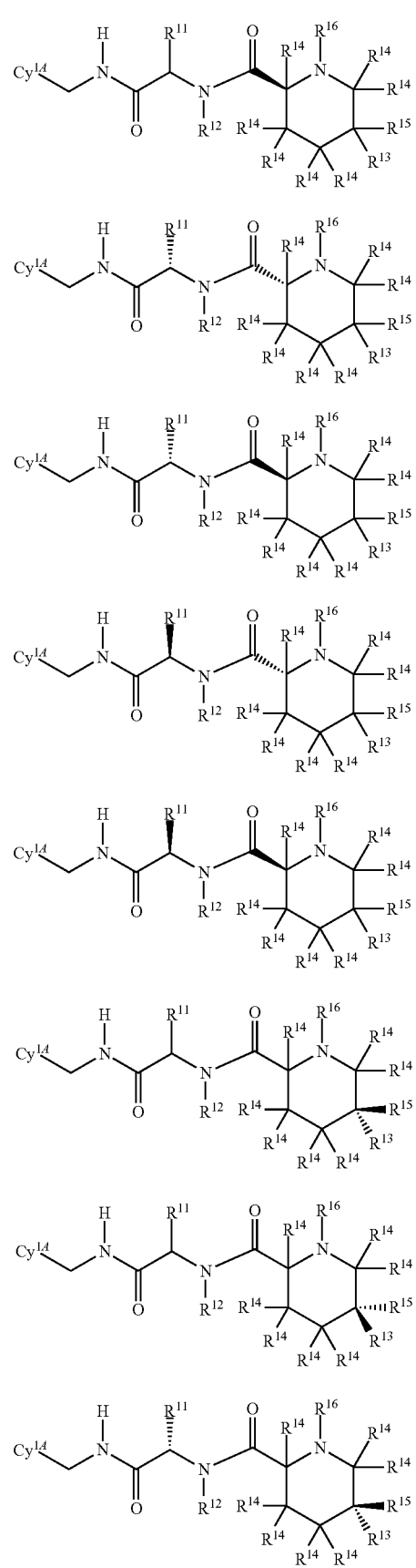
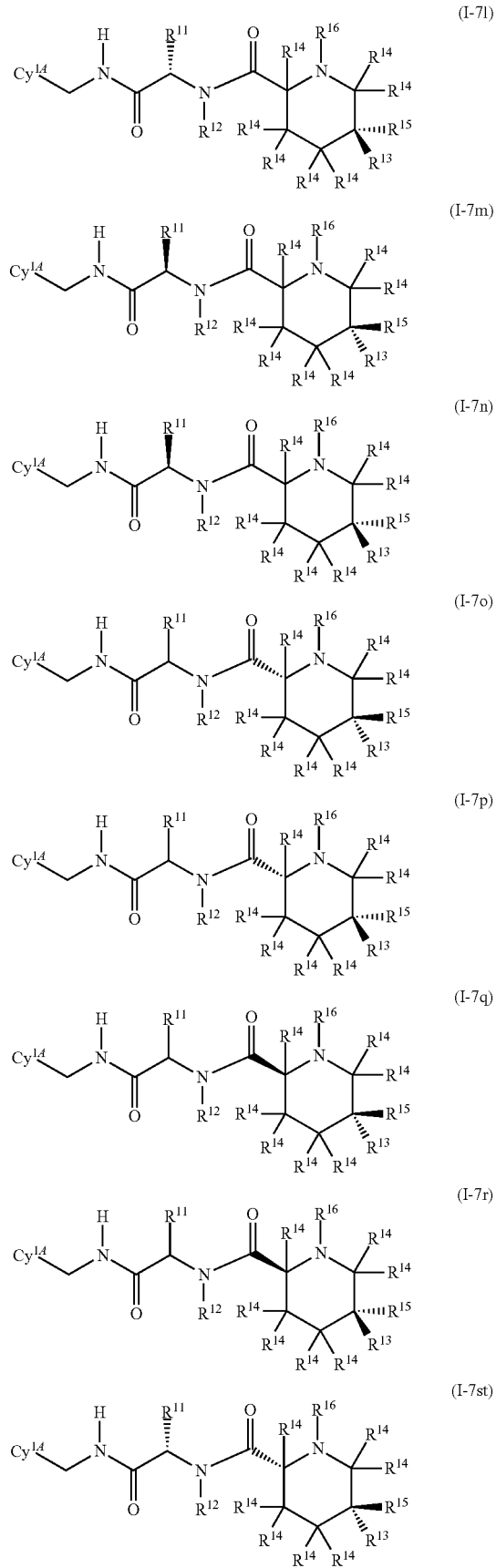

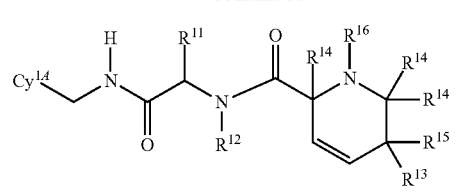
(I-7aj)
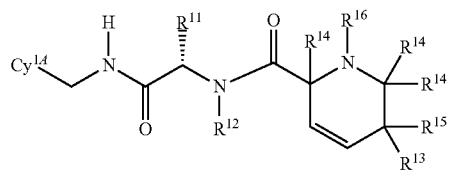
(I-7ak)
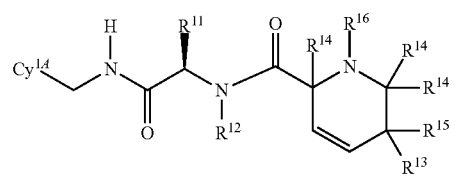
(I-7al)
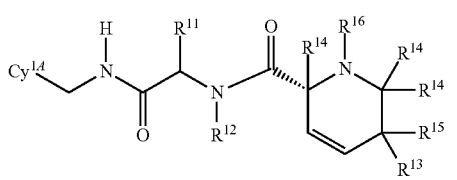
(I-7am)
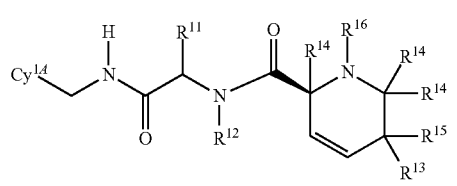
(I-7an)
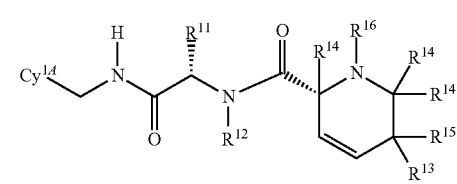
(I-7)
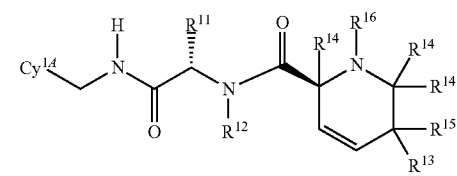
(I-7)
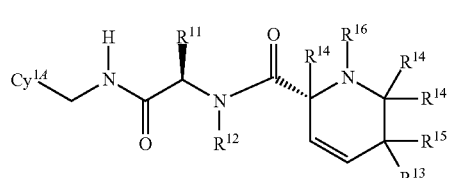
(I-7ao)
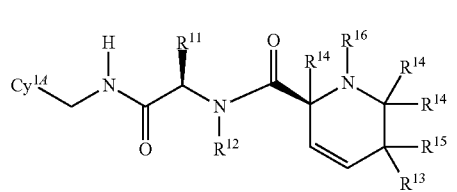
(I-7ap)
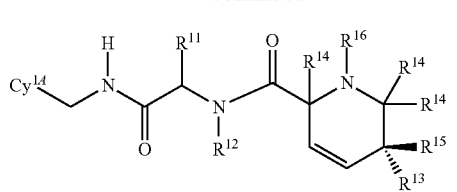
(I-7aq)
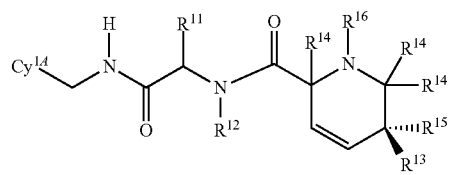
(I-7ar)
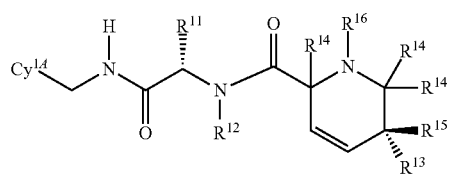
(I-7as)
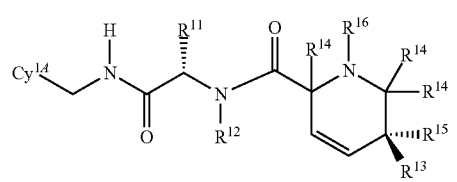
(I-7at)
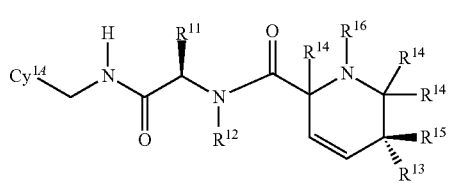
(I-7au)
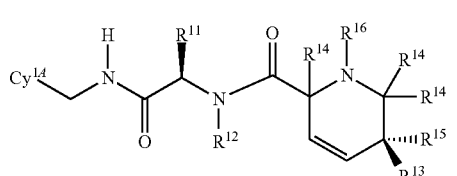
(I-7av)
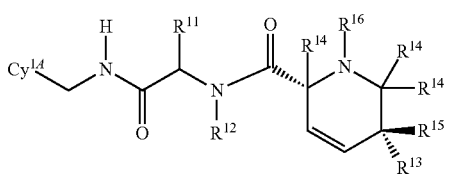
(I-7aw)
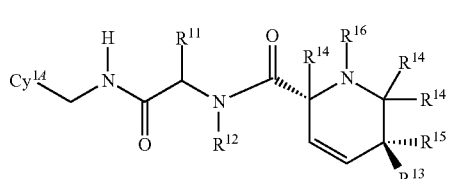
(I-7ax)
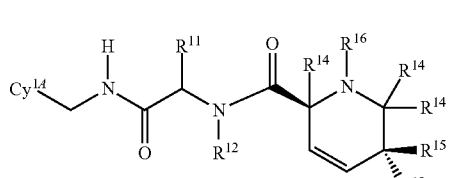
(I-7ay)

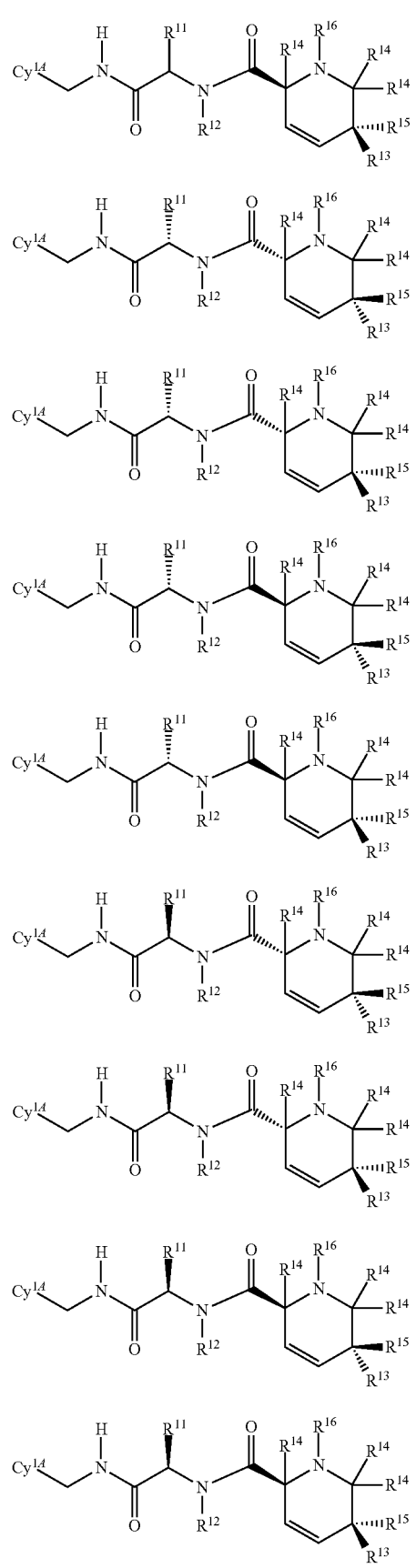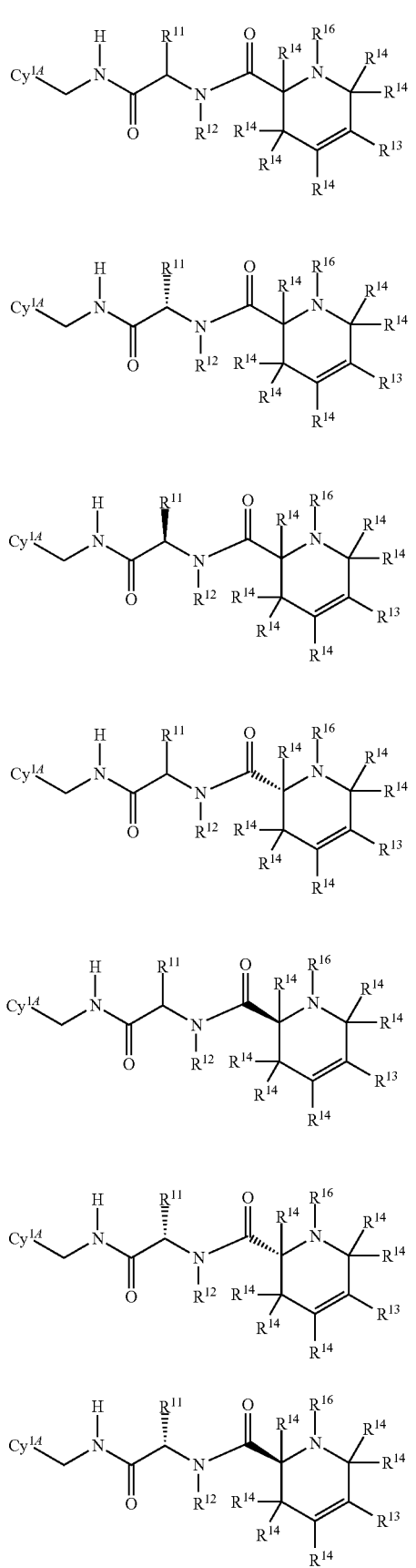

(I-7cf)
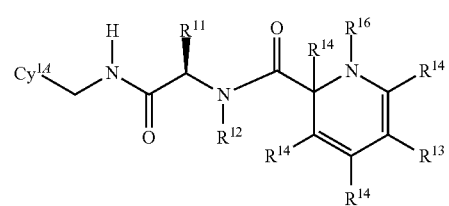
(I-7cg)
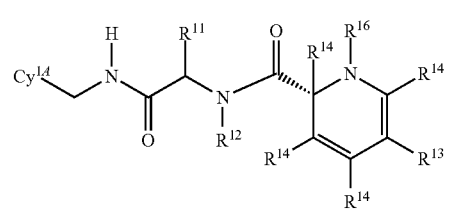
(I-7ch)
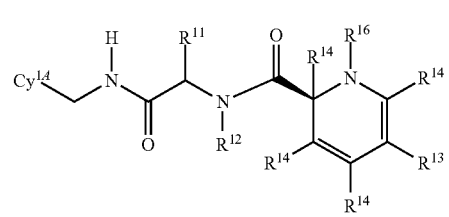
(I-7ci)
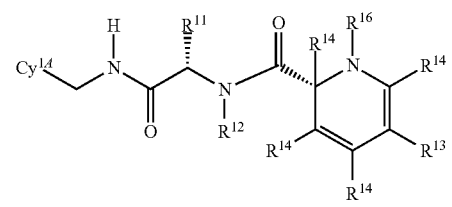
(I-7cj)
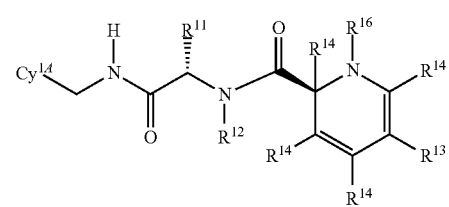
(I-7ck)
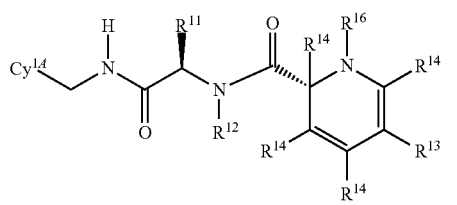
(I-7cl)
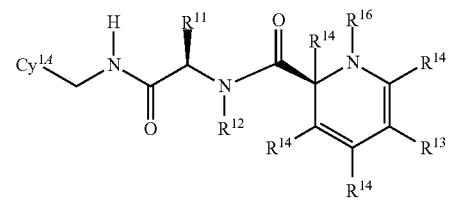
(I-7cm)
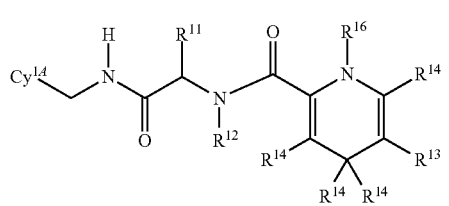
(I-7cn)
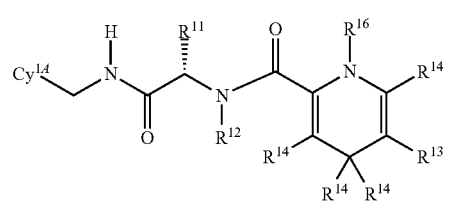
(I-7co)
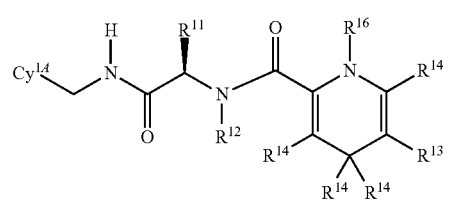
In some embodiments, the compound is according to any of the following Formulae (I-8a) to (I-8z):
(I-8a)
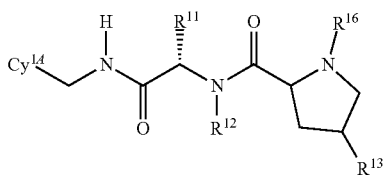
(I-8b)
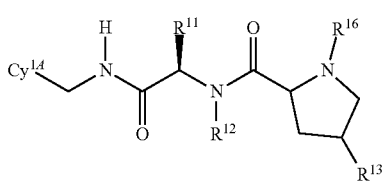
(I-8c)
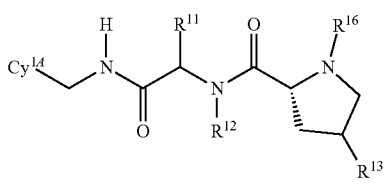
(I-8d)
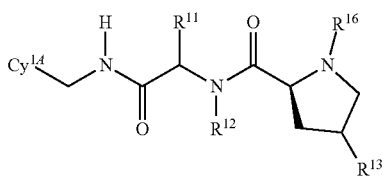

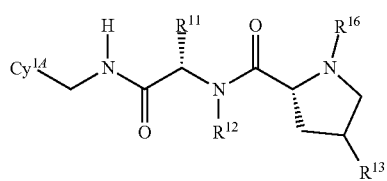
(I-8e)
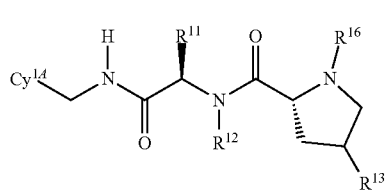
(I-8f)
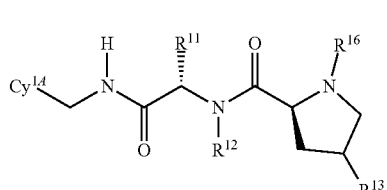
(I-8g)
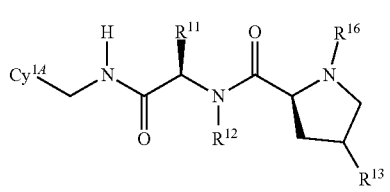
(I-8h)
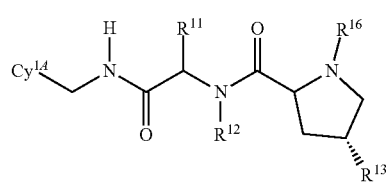
(I-8i)
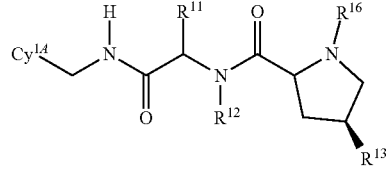
(I-8j)
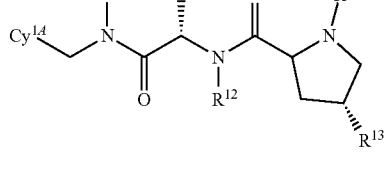
(I-8k)
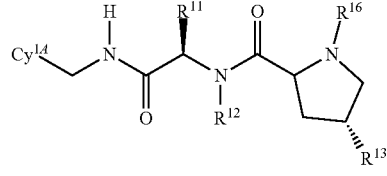
(I-8l)
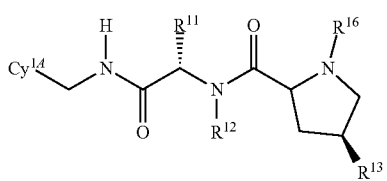
(I-8m)
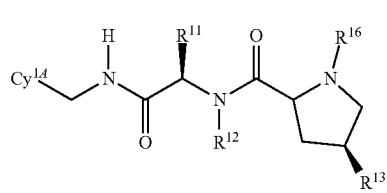
(I-8n)
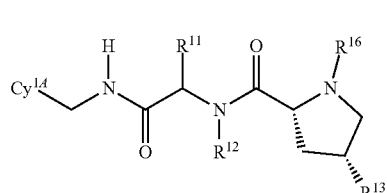
(I-8o)
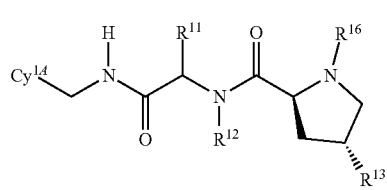
(I-8p)
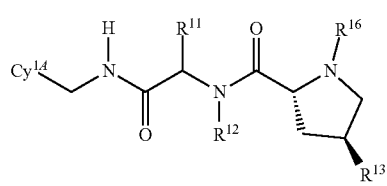
(I-8q)
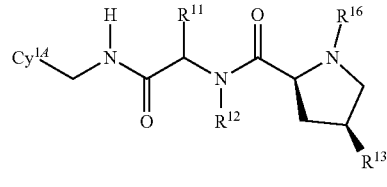
(I-8r)
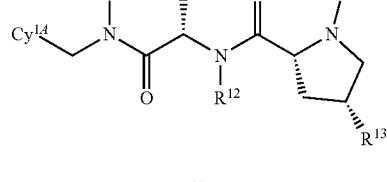
(I-8s)
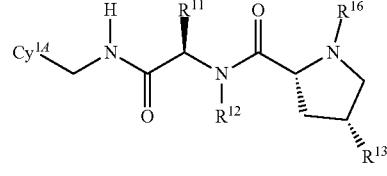
(I-8t)

(I-8u)
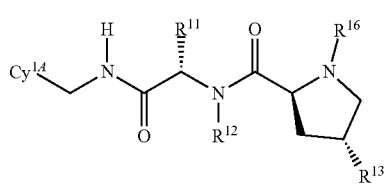
(I-8v)
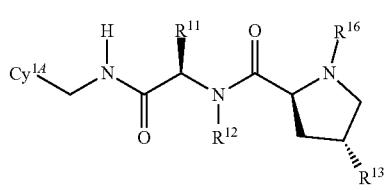
(I-8w)
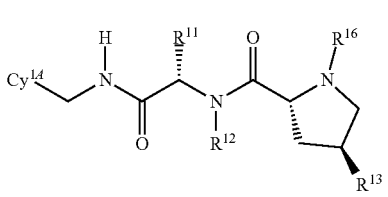
(I-8x)
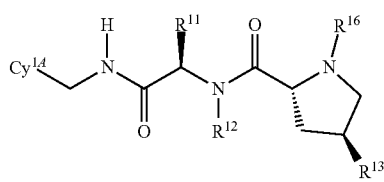
(I-8y)
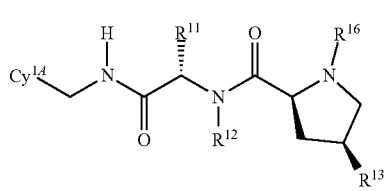
(I-8z)
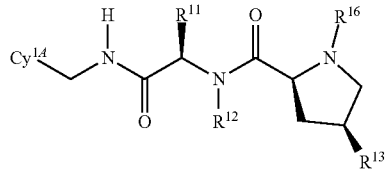
In some embodiments, the compound is according to any of the following Formulae (I-9a) to (I-9z):
(I-9a)
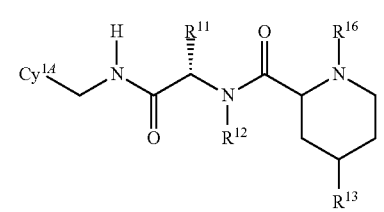
(I-9b)
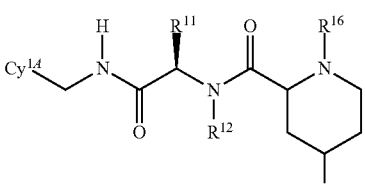
(I-9c)
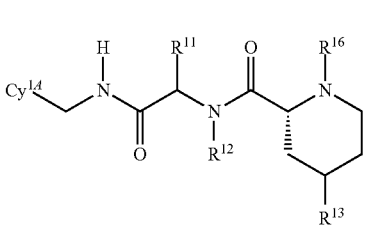
(I-9d)
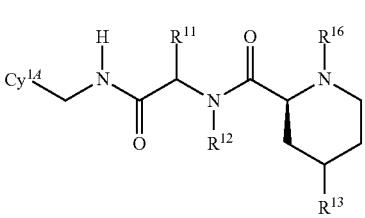
(I-9e)
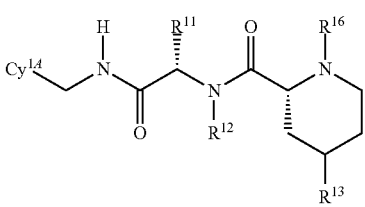
(I-9f)
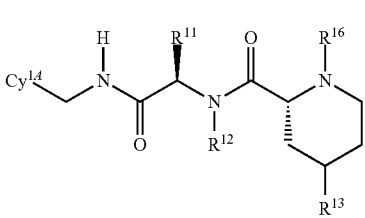
(I-9g)
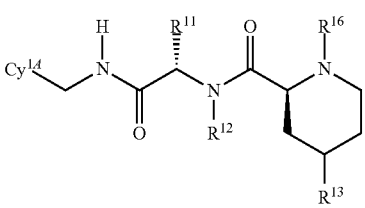
(I-9h)
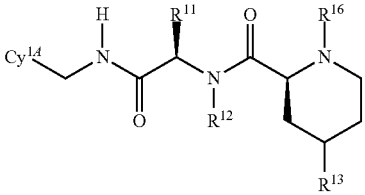

(I-9i)
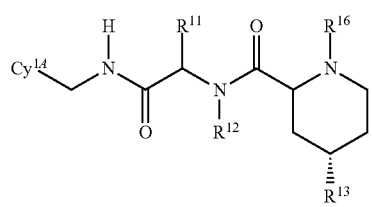
(I-9j)
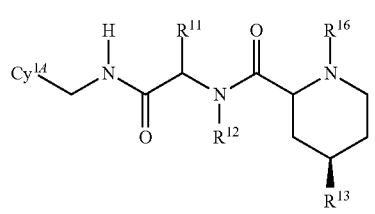
(I-9k)
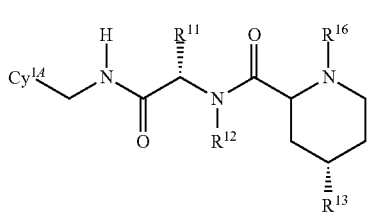
(I-9l)
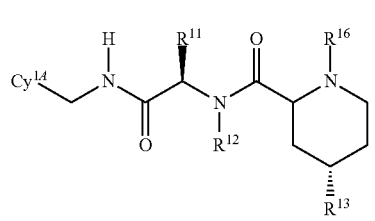
(I-9m)
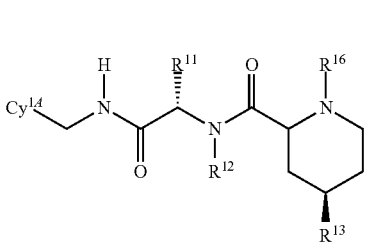
(I-9n)
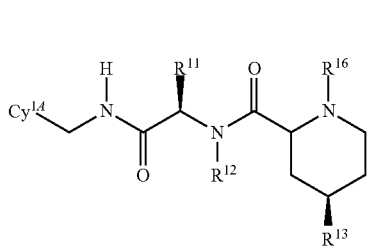
(I-9o)
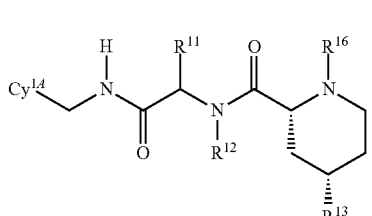
(I-9p)
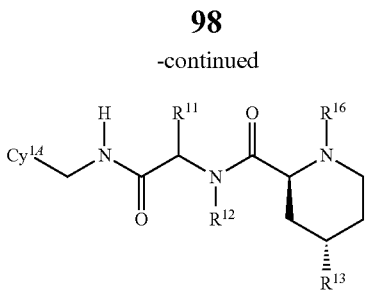
(I-9q)
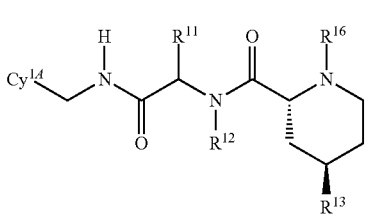
(I-9r)
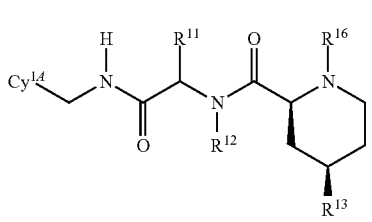
(I-9s)
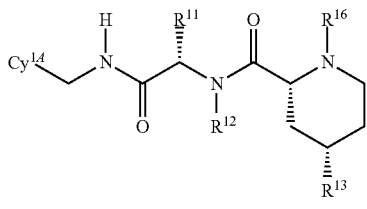
(I-9t)
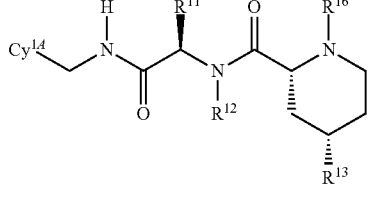
(I-9u)
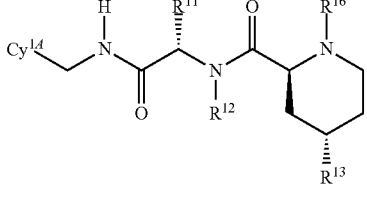
(I-9v)
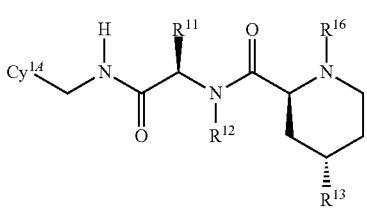

-continued (I-9w)

(I-9x)

(I-9y)

(I-9z)

In some embodiments, $R^{13}$ is $Cy^{1B}$.

In some embodiments, $R^{13}$ is $(C_{1-6}$ alkylene)$Cy^{1B}$, $(C_{2-6}$ alkenylene)$Cy^{1B}$, or $(C_{2-6}$ alkynylene)$Cy^{1B}$. In some embodiments, the $C_{1-6}$ alkylene, $C_{2-6}$ alkenylene, or $C_{2-6}$ alkynylene component of $R^{13}$ is unsubstituted.

In some embodiments, $R^{13}$ is $(CR^{13A}R^{13B})_{n3}Cy^{1B}$.

In some embodiments, each $R^{13A}$ is H.

In some embodiments, each $R^{13B}$ is H.

In some embodiments, n3 is 0.

In some embodiments, n3 is 1.

In some embodiments, n3 is 2.

In some embodiments, $R^{13}$ is $(CH_2)_{0-2}Cy^{1B}$.

In some embodiments, $R^{13}$ is $CH_2Cy^{1B}$.

In some embodiments, $R^{13}$ is $CH_2CH_2Cy^{1B}$.

In some embodiments, $R^{13}$ is $OCy^{1B}$.

In some embodiments, $Cy^{1B}$ is unsubstituted $C_{6-10}$ aryl.

In some embodiments, $Cy^{1B}$ is unsubstituted phenyl.

In some embodiments, $Cy^{1B}$ is unsubstituted naphthyl, such as 1-naphthyl or 2-naphthyl.

In some embodiments, $Cy^{1B}$ unsubstituted 5-10 membered heteroaryl.

In some embodiments, $Cy^{1B}$ is unsubstituted pyridyl, such as unsubstituted 2-, 3-, or 4-pyridyl or unsubstituted quinolyl, such as unsubstituted 2-, 3-, 4-, 5-, 6-, 7-, or 8-quinolyl.

In some embodiments, $Cy^{1B}$ is substituted $C_{6-10}$ aryl.

In some embodiments, $Cy^{1B}$ is substituted phenyl.

In some embodiments, $Cy^{1B}$ is a biphenylyl (i.e., phenyl substituted by phenyl), such as 2-, 3-, or 4-biphenylyl.

In some embodiments, $Cy^{1B}$ is substituted naphthyl, such as 1-naphthyl or 2-naphthyl.

In some embodiments, $Cy^{1B}$ substituted 5-10 membered heteroaryl.

In some embodiments, $Cy^{1B}$ is substituted pyridyl, such as substituted 2-, 3-, or 4-pyridyl or substituted quinolyl, such as substituted 2-, 3-, 4-, 5-, 6-, 7-, or 8-quinolyl.

In some embodiments, $Cy^{1B}$ is substituted with 1, 2, 3, 4 or 5 substituents each independently selected from $R^{Cy1B}$, halogen, and $C_{1-6}$ haloalkyl; wherein each $R^{Cy1B}$ is independently selected from $C_{1-6}$ alkyl, $C_{2-6}$ alkenyl, $C_{2-6}$ alkynyl and $C_{6-10}$ aryl or 5-10 membered heteroaryl, wherein each $C_{6-10}$ aryl or 5-10 membered heteroaryl forming $R^{Cy1B}$ is unsubstituted or substituted with 1, 2 or 3 substituents independently selected from halogen, $C_{1-6}$ alkyl, $C_{2-6}$ alkenyl, $C_{2-6}$ alkynyl, and haloalkyl.

In some embodiments, $R^{13}$ is selected from groups of the following formulae:

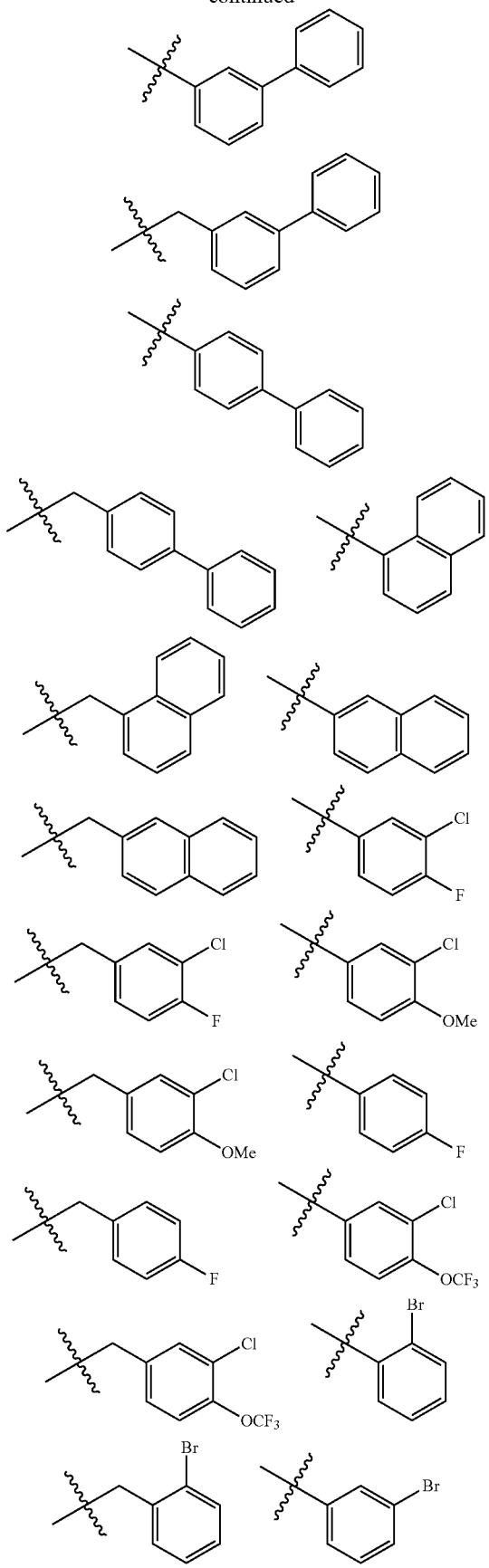
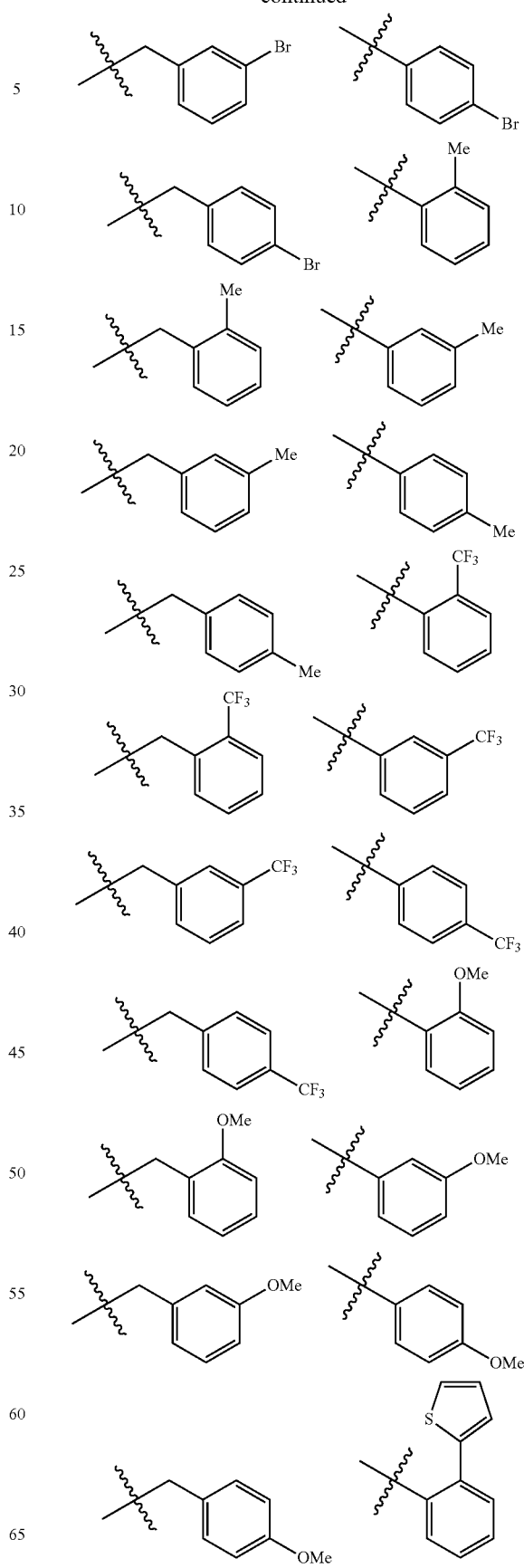

-continued
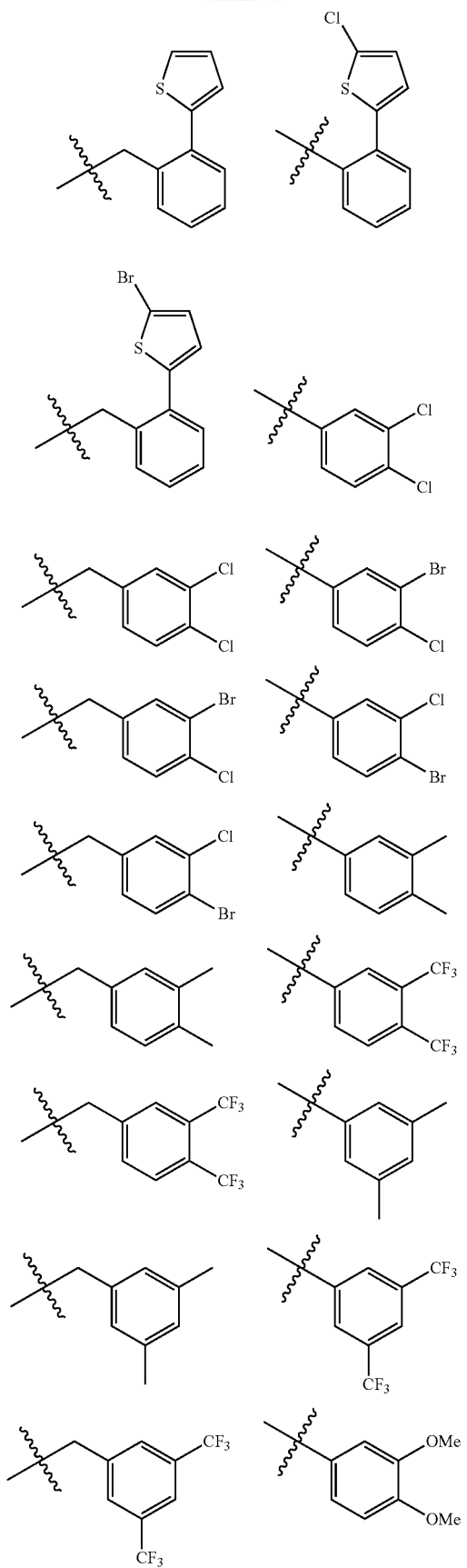
-continued
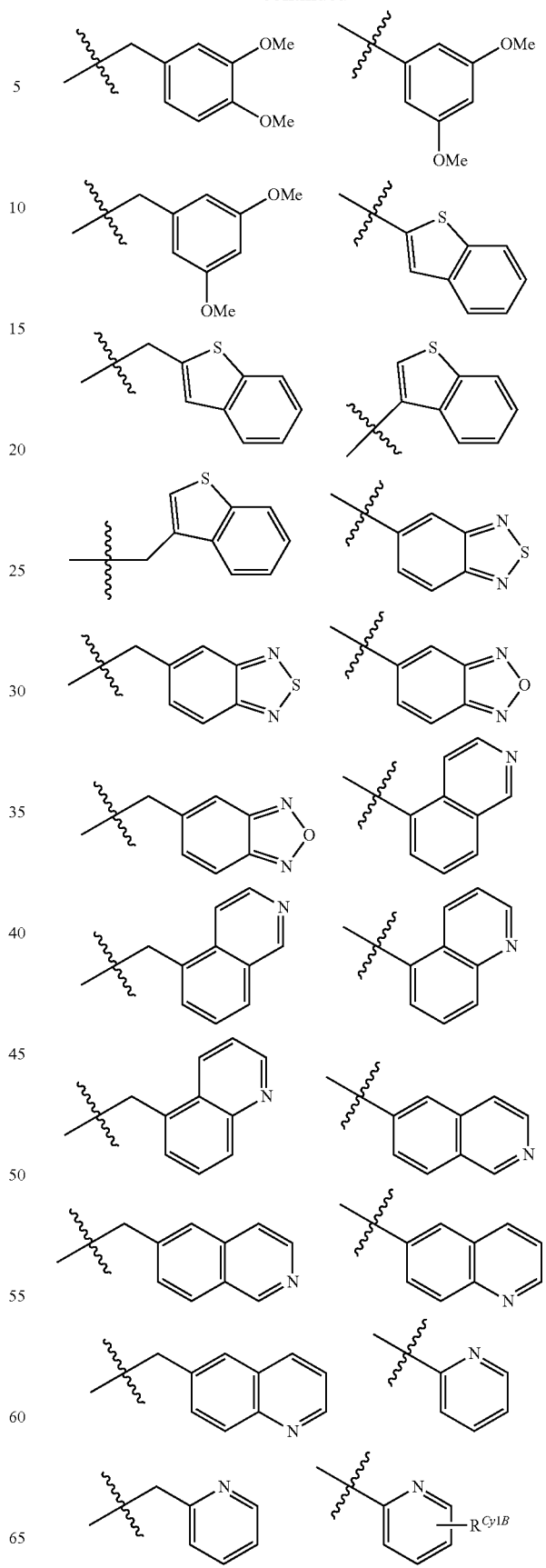

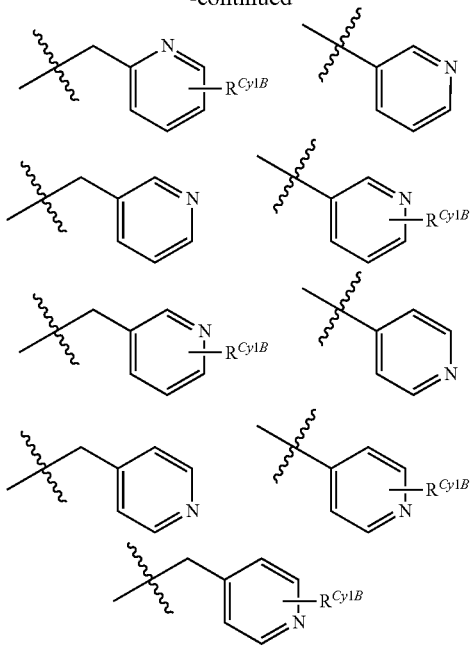

In some embodiments, $R^{Cy1B}$ in the formula representing $R^{13}$ is $C_{1-6}$ alkyl, such as methyl or ethyl, preferably methyl, or halogen, such as fluorine or chlorine, preferably fluorine.

In some embodiments, $R^{Cy1B}$ in the formula representing $R^{13}$ is $C_{1-6}$ alkyl, such as methyl or ethyl, preferably methyl.

In some embodiments, $R^{Cy1B}$ in the formula representing $R^{13}$ is halogen, such as fluorine or chlorine, preferably fluorine.

In some embodiments, no more than one $R^{14}$ is other than hydrogen.

In some embodiments, no more than one $R^{14}$ is other than hydrogen and one $R^{14}$ is $C_{1-6}$ alkyl, such as methyl.

In some embodiments, each $R^{14}$ is hydrogen.
In some embodiments, $A^{11}$ is N.
In some embodiments, $R^{15}$ is hydrogen.
In some embodiments, $R^{15}$ is $C_{1-6}$ alkyl such as methyl.
In some embodiments, $R^{15}$ is hydroxyl.
In some embodiments, $R^{16}$ is hydrogen.
In some embodiments, $R^{16}$ is unsubstituted or substituted $C_{1-6}$ alkyl, $C_{2-6}$ alkenyl, or $C_{2-6}$ alkynyl.
In some embodiments, $R^{16}$ is unsubstituted $C_{1-6}$ alkyl such as methyl.
In some embodiments, $R^{16}$ is substituted $C_{1-6}$ alkyl.
In some embodiments, the substituted $C_{1-6}$ alkyl forming $R^{16}$ is substituted by 1, 2, 3, 4 or 5, such as 1, 2, or 3, or, preferably 1, substituents selected from the group consisting of halogen, CN, $C(O)NR^{c11}R^{d11}$ and $C(O)OR^{a11}$.
In some embodiments, $R^{16}$ is $(CH_2)_{1-6}C(O)OR^{a11}$.
In some embodiments, the $R^{a11}$ defining $R^{16}$ is H or $C_{1-6}$ alkyl such as methyl.
In some embodiments, the $R^{a11}$ defining $R^{16}$ is H.
In some embodiments, $R^{a11}$, $R^{b11}$, $R^{c11}$ and $R^{d11}$, $R^{a12}$, $R^{b12}$, $R^{c12}$ and $R^{d12}$ are each independently selected from H and $C_{1-6}$ alkyl.
In some embodiments, each $R^{e11}$ and each $R^{e12}$ is H.
In some embodiments, the compounds of Formula (I-1), and embodiments thereof, can be in the form of a salt such as a pharmaceutically acceptable salt.

The compounds of Formula (I-1), and embodiments thereof, are useful as inhibitors of MASP-2 and for therapeutic use. The compounds of Formula (I-1), and embodiments thereof, are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Formula (I-1), or an embodiment thereof, optionally in the form of a salt.

In some embodiments the compound Formula (I-1) or an embodiment thereof is provided in the form of a pharmaceutical composition comprising the compound or a salt thereof, such as a pharmaceutically acceptable salt, and at least one pharmaceutically acceptable carrier or excipient.

In certain aspects, the compound is one or more selected from the compounds of Formula (I-1) set forth in the Examples, including the compounds listed in Table 31, e.g., the compounds with selectivity for MASP-2 over thrombin).

In certain aspects, one or more of the variables defining the compounds of Formula (I) (such as $Cy^{1A}$; $R^{Cy1A}$; $R^{11}$; $R^{12}$; $A^{11}$; $R^{13}$; $R^{14}$; $R^{15}$; n1; n2; n3; $R^{13A}$; $R^{13B}$; $Cy^{1B}$; $R^{16}$; $R^{16A}$; $R^{16B}$; $Cy^{1C}$; $R^{Cy1C}$; $R^{a11}$, $R^{b11}$, $R^{c11}$; $R^{d11}$; $R^{e11}$, $R^{a12}$, $R^{b12}$, $R^{c12}$; $R^{d12}$; and $R^{e12}$) is selected from the corresponding substituents in the compounds of Formula (I-1) in the Examples including the compounds listed in Table 31, preferably, those of the compounds with selectivity for MASP-2 over thrombin.

In certain aspects, the invention sets forth a stereochemically pure enantiomer or diastereomer (e.g., an optically active compound with one or more chiral centers). Unless specifically indicated otherwise, for any inventive compound with one or more stereocenters, the present invention is intended to include and to describe both the pure (+) and (−) enantiomers, any other diastereomers, mixtures that are enriched in an enantiomer or diastereomer (e.g., 10%, 20%, 30%, 40%, 50%, 60%, 70% 75%, 80%, 85, 90%, or 95% enantiomeric or diastereomeric excess), and a racemic mixture of enantiomers or diastereomers.

In certain aspects, the invention sets forth a pharmaceutically acceptable salt of the indicated chemical structure (e.g., a hydrohalide, such as a hydrochloride or dihydrochloride). Examples of pharmaceutically acceptable salts are set forth in, e.g., Burge, S. M. et al., J. Pharm. Sci 1977, 66, 1-19. They include chlorides, bromides, iodides, formates, acetates, propionates, oxalates, malonates, succinates, fumarates, maleates, tartrates, citrates, benzoates, phthalates, sulfonates, arylsulfonates, alkylsulfonates, salts of fatty acids, and the like. Salts can be prepared by a variety of methods known to the skilled artisan, including a precipitation with the conjugate acid or base (e.g., treatment with gaseous HCl or an HCl solution).

In certain aspects, the invention sets forth a prodrug. A prodrug is a compound that is converted to a biologically active form under physiological conditions, often by hydrolysis, oxidation, or reduction (e.g., ester to acid form; carbamate to amino or hydroxy group; hydroxyamidine to amidine) Exemplary prodrugs are set forth in, e.g., Tilley, J. W., "Prodrugs of Benzamide," Prodrugs 2007, 191-222; Peterlin-Masic et al. Curr. Pharma. Design 2006, 12, 73-91. Prodrugs for the amidine group include amidoximes, O-alkylamidoximes, acylamidines, carbamates, 1,2,4-oxadiazolin-4-ones, and the like.

In certain aspects, the compound is useful for selectively inhibiting MASP-2 over thrombin, the method comprising administering the compound as described herein. In certain aspects, the selectivity ratio of MASP-2:thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

B. Compounds of Formula IIA and IIB

In certain aspects, the present disclosure provides a compound of Formula (IIA) and (IIB):

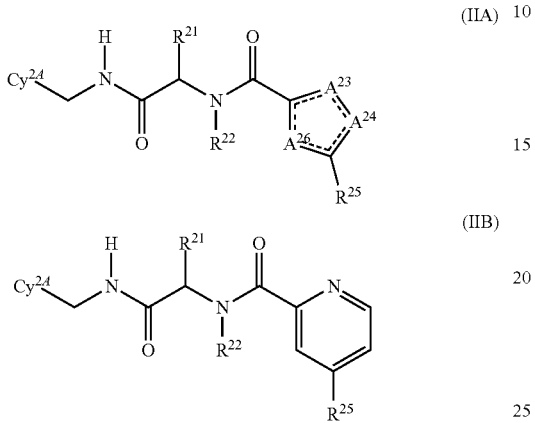

or a salt thereof, wherein:

$Cy^{2A}$ is unsubstituted or substituted $C_{6-10}$ aryl or unsubstituted or substituted 5-10 membered heteroaryl; wherein the ring atoms of the 5-10 membered heteroaryl forming $Cy^{2A}$ consist of carbon atoms and 1, 2, or 3 heteroatoms selected from O, N and S; wherein the substituted $C_{6-10}$ aryl or substituted 5-10 membered heteroaryl forming $Cy^{2A}$ are substituted with 1, 2, 3, 4 or 5 substituents each independently selected from $R^{Cy2A}$, halogen, $C_{1-6}$ haloalkyl, CN, $OR^{21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $C(=NOR^{a21})NR^{c21}R^{d21}$, $C(=NOC(O)R^{b21})NR^{c21}R^{d21}$, $C(=NR^{e21})NR^{c21}C(O)OR^{a21}$, $NR^{c21}C(=NR^{e21})NR^{c21}R^{d21}$, $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo;

each $R^{Cy2A}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10-membered heterocycloalkyl forming $R^{Cy2A}$ consist of carbon atoms and 1, 2, 3 or 4 heteroatoms selected from O, N and S, wherein each $C_{1-6}$ alkyl, $C_{2-6}$ alkenyl, or $C_{2-6}$ alkynyl forming $R^{Cy2A}$ is independently unsubstituted or substituted with 1, 2 or 3 substituents independently selected from halogen, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $NR^{c21}C(=NR^{e21})NR^{c21}R^{d21}$, $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo, and wherein each $C_{6-10}$ aryl, 5-10 membered heteroaryl, $C_{3-10}$ cycloalkyl and 4-10 membered heterocycloalkyl forming $R^{Cy2A}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a21}$, $SR^{a21}$, $C(O)R^{b21}$, $C(O)NR^{c21}R^{d21}$, $C(O)OR^{a21}$, $—OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $NR^{c21}C(=NR^{e21})NR^{c21}R^{d21}$, $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo;

$R^{21}$ is H or $C_{1-6}$ alkyl, $C_{6-10}$ aryl-$C_{1-6}$ alkyl or 5-10 membered heteroaryl-$C_{1-6}$ alkyl, wherein the $C_{1-6}$ alkyl forming $R^{21}$ is unsubstituted or substituted by 1, 2 or 3 substituents independently selected from halogen, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $NR^{c21}C(=NR^{e21})NR^{c21}R^{d21}$, $S(O)R^{b21}$, $S(O)NR^{c21}R^{d21}$ $S(O)_2R^{b21}$, $NR^{c21}S(O)_2R^{b21}$, $S(O)_2NR^{c21}R^{d21}$ and oxo, and wherein the $C_{6-10}$ aryl-$C_{1-6}$ alkyl or 5-10 membered heteroaryl-$C_{1-6}$ alkyl forming $R^{21}$ is unsubstituted or substituted by 1, 2 or 3 substituents independently selected from $C_{1-6}$ alkyl, $C_{2-6}$ alkenyl, $C_{2-6}$ alkynyl, $C_{1-6}$ haloalkyl, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $NR^{c21}C(=NR^{e21})NR^{c21}R^{d21}$, $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo;

$R^{22}$ is H or $C_{1-6}$ alkyl; or $R^{21}$ and $R^{22}$, together with the groups to which they are attached, form a 4-6 membered heterocycloalkyl ring;

$A^{23}$ is N or $NR^{23}$;

$A^{24}$ is $CR^{24}$; N or $NR^{24}$;

$A^{26}$ is $CR^{26}$ or S;

provided that $A^{23}$, $A^{24}$ and $A^{26}$ in Formula (IIA) are selected such that the ring comprising $A^{23}$, $A^{24}$ and $A^{26}$ is a heteroaryl ring and the symbol === represents an aromatic ring (normalized) bond;

$R^{23}$ is H or $C_{1-6}$ alkyl;

$R^{24}$ is H; $C_{1-6}$ alkyl or phenyl;

$R^{25}$ is $Cy^{2B}$, $(CR^{25A}R^{25B})_{n25}Cy^{2B}$, $(C_{1-6}$ alkylene$)Cy^{2B}$, $(C_{2-6}$ alkenylene$)Cy^{2B}$, or $(C_{2-6}$ alkynylene$)Cy^{2B}$, wherein the $C_{1-6}$ alkylene, $C_{2-6}$ alkenylene, or $C_{2-6}$ alkynylene component of $R^{25}$ is unsubstituted or substituted by 1, 2, 3, 4 or 5 substituents each independently selected from the group consisting of halogen, CN, $OR^{a21}$, $SR^{21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $NR^{c21}C(=NR^{e21})NR^{c21}R^{d21}$, $S(O)R^{b21}$, $S(O)NR^{c21}R^{d21}$, $S(O)_2R^{b21}$, $NR^{c21}S(O)_2R^{b21}$, $S(O)_2NR^{c21}R^{a21}$ and oxo;

$R^{26}$ is H or $C_{1-6}$ alkyl;

each $R^{25A}$ is H or $C_{1-6}$ alkyl;

each $R^{25B}$ is H or $C_{1-6}$ alkyl;

n25 is 0, 1 or 2;

$Cy^{2B}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl; wherein the ring atoms of the 5-10 membered heteroaryl or 4-10 membered heterocycloalkyl forming $Cy^{2B}$ consist of carbon atoms and 1, 2 or 3 heteroatoms selected from O, N and S; and wherein the substituted $C_{6-10}$ aryl, substituted 5-10 membered heteroaryl, substituted $C_{3-10}$ cycloalkyl or substituted 4-10 membered heterocycloalkyl forming $Cy^{2B}$ are substituted with 1, 2, 3, 4 or 5 substituents each independently selected from $R^{Cy2B}$, halogen, $C_{1-6}$ haloalkyl, CN, $OR^{21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $C(=NOR^{a21})NR^{c21}R^{d21}$, $C(=NOC(O)R^{b21})NR^{c21}R^{d21}$, $C(=NR^{e21})NR^{c21}C(O)OR^{a21}$, $NR^{c21}C(=NR^{e21})NR^{c21}R^{d21}$, $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo;

wherein each $R^{Cy2B}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10 membered heterocycloalkyl forming $R^{Cy2B}$ consist of carbon atoms and 1, 2 or 3 heteroatoms selected from O, N and S; wherein each $C_{1-6}$ alkyl, $C_{2-6}$ alkenyl, or $C_{2-6}$ alkynyl forming $R^{Cy2B}$ is independently unsubstituted or substituted with 1, 2 or 3 substituents independently selected from halogen, CN, $OR^{a21}$, $SR^{21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $NR^{c21}C(=NR^{e21})NR^{c21}R^{d21}$, $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo; and wherein each $C_{6-10}$ aryl, 5-10 membered heteroaryl, $C_{3-10}$ cycloalkyl and 4-10 membered heterocycloalkyl forming $R^{Cy2B}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a1}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)$ $NR^{c21}R^{d21}$, $NR^{c21}C(O)OR^{a21}$, $C(=NR^{e21})NR^{c21}R^{d21}$, $NR^{c21}C(=NR^{e21})NR^{c21}R^{d21}$, $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo;

$R^{a21}$, $R^{b21}$, $R^{c21}$ and $R^{d21}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a21}$, $R^{b21}$, $R^{c21}$ and $R^{d21}$ are each optionally substituted with 1, 2, 3, 4 or 5 substituents independently selected from $C_{1-6}$ alkyl, halo, CN, $OR^{22}$, $SR^{a22}$, $C(O)R^{b22}$, $C(O)NR^{c22}R^{d22}$, $C(O)OR^{22}$, $OC(O)R^{b22}$, $OC(O)NR^{c22}R^{d22}$, $NR^{c22}R^{d22}$, $NR^{c22}C(O)R^{b22}$, $NR^{c22}C(O)NR^{c22}R^{d22}$, $NR^{c22}C(O)OR^{a22}$, $C(=NR^{e22})NR^{c22}R^{d22}$, $NR^{c22}C(=NR^{e22})NR^{c22}R^{d22}$, $S(O)R^{b22}$, $S(O)NR^{c22}R^{d22}$, $S(O)_2R^{b22}$, $NR^{c22}S(O)_2R^{b22}$, $S(O)_2NR^{c22}R^{d22}$ and oxo;

or $R^{c21}$ and $R^{d21}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, $OR^{22}$, $SR^{22}$, $C(O)R^{b22}$, $C(O)NR^{c22}R^{d22}$, $C(O)OR^{22}$, $OC(O)R^{b22}$, $OC(O)NR^{c22}R^{d22}$, $NR^{c22}R^{d22}$, $NR^{c22}C(O)R^{b22}$, $NR^{c22}C(O)NR^{c22}R^{d22}$, $NR^{c22}C(O)OR^{a22}$, $C(=NR^{e22})NR^{c22}R^{d22}$, $NR^{c22}C(=NR^{e22})NR^{c22}R^{d22}$, $S(O)R^{b22}$, $S(O)NR^{c22}R^{d22}$, $S(O)_2R^{b22}$, $NR^{c22}S(O)_2R^{b22}$, $S(O)_2NR^{c22}R^{d22}$ and oxo;

$R^{a22}$, $R^{b22}$, $R^{c22}$ and $R^{d22}$ are each independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl forming $R^{a22}$, $R^{b22}$, $R^{c22}$ and $R^{d22}$ are each optionally substituted with 1, 2 or 3 substituents independently selected from OH, CN, amino, $NH(C_{1-6}$ alkyl), $N(C_{1-6}$ alkyl$)_2$, halo, $C_{1-6}$ alkyl, $C_{1-6}$ alkoxy, $C_{1-6}$ haloalkyl, $C_{1-6}$ haloalkoxy and oxo;

or $R^{c22}$ and $R^{d22}$ attached to the same N atom, together with the N atom to which they are both attached, form a 4-, 5-, 6- or 7-membered heterocycloalkyl group or 5-membered heteroaryl group, each of which is unsubstituted or substituted with 1, 2 or 3 substituents independently selected from OH, CN, amino, $NH(C_{1-6}$ alkyl), $N(C_{1-6}$ alkyl$)_2$, halo, $C_{1-6}$ alkyl, $C_{1-6}$ alkoxy, $C_{1-6}$ haloalkyl, $C_{1-6}$ haloalkoxy and oxo; and $R^{e21}$ and $R^{e22}$ are each, independently, H, CN or $NO_2$.

In some embodiments, $Cy^{2A}$ is unsubstituted or substituted aryl.

In some embodiments, $Cy^{2A}$ is unsubstituted or substituted phenyl.

In some embodiments, $Cy^{2A}$ is substituted phenyl.

In some embodiments, $Cy^{2A}$ is substituted with at least one $OR^{21}$ or at least one $C(=NR^{e21})NR^{c21}R^{d21}$, $C(=NOR^{a21})NR^{c21}R^{d21}$, $C(=NOC(O)R^{b21})NR^{c21}R^{d21}$, or $C(=NR^{e21})NR^{c21}C(O)OR^{a21}$.

In some embodiments, $Cy^{2A}$ is substituted with at least one $OR^{21}$ and by at least one additional substituent selected from the group consisting of $C_{1-6}$ alkyl, $C_{1-6}$ haloalkyl and halogen.

In some embodiments, $Cy^{2A}$ is substituted with at least one OH and by at least one additional substituent selected from the group consisting of $C_{1-6}$ alkyl, $C_{1-6}$ haloalkyl and halogen.

In some embodiments, $Cy^{2A}$ is substituted with at least one $C(=NR^{e21})NR^{c21}R^{d21}$, $C(=NOR^{a21})NR^{c21}R^{d21}$, $C(=NOC(O)R^{b21})NR^{c21}R^{d21}$, $C(=NR^{e21})NR^{c21}C(O)OR^{a21}$, preferably in the 4-position.

In some embodiments, $Cy^{2A}$ is substituted with at least one $C(=NR^{e21})NR^{c21}R^{d21}$, preferably in the 4-position.

In some embodiments, $Cy^{2A}$ is substituted with at least one $C(=NH)NH_2$, preferably in the 4-position.

In some embodiments, $Cy^{2A}$ is of any one of the following formulae:

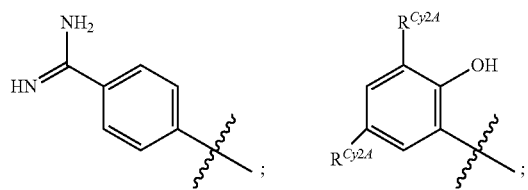

-continued
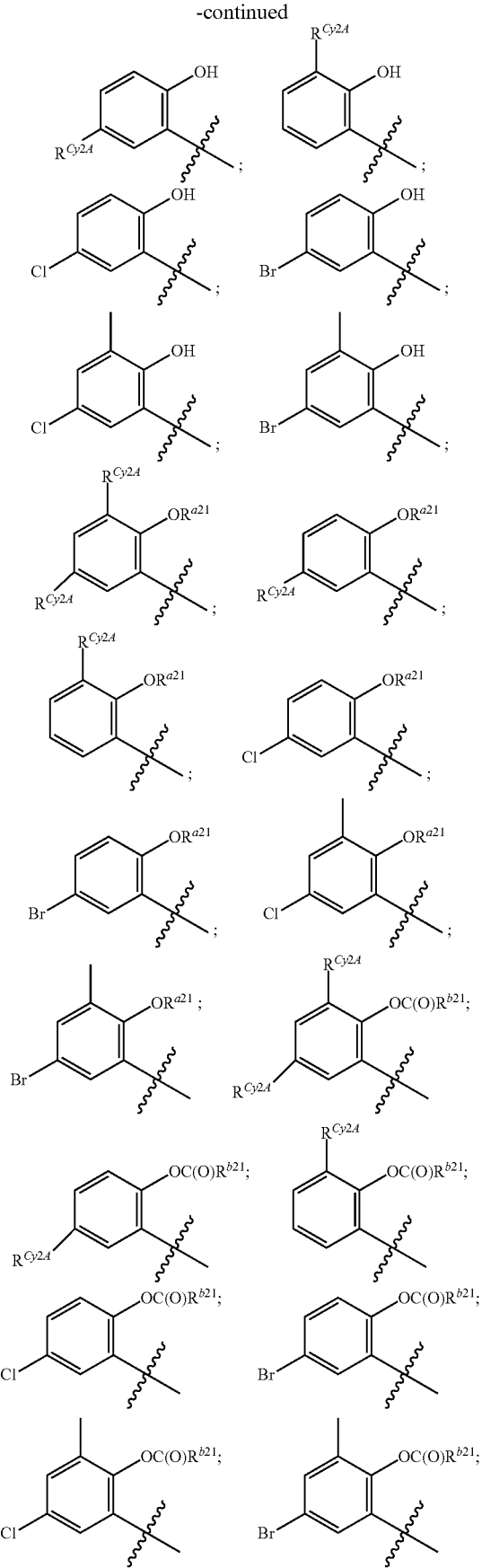
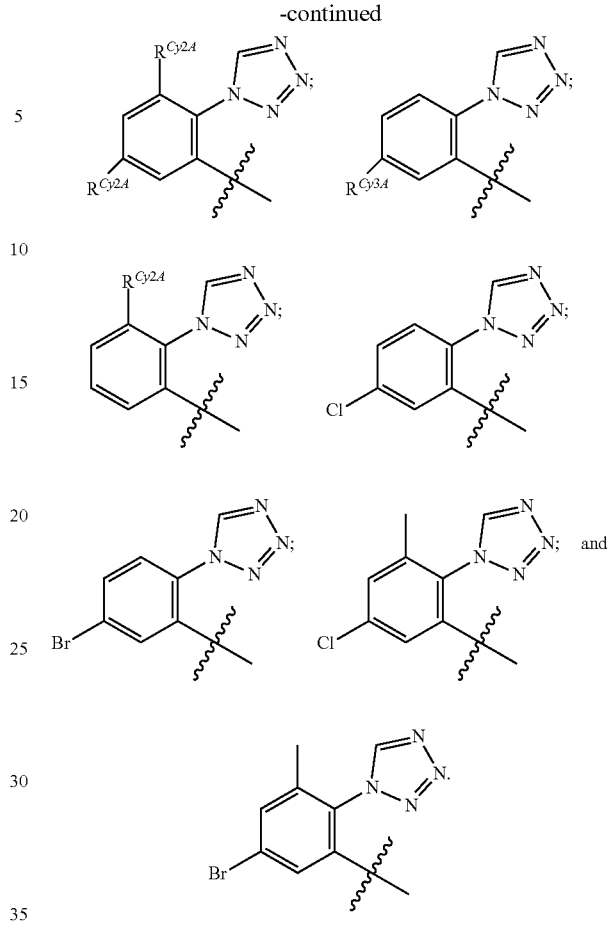
In some embodiments, in the formula defining $Cy^{2A}$, each $R^{Cy2A}$ is independently $C_{1-6}$ alkyl, such as methyl, or halogen, such as Cl or Br, or amino.
In some embodiments, $Cy^{2A}$ is of any one of the following formulae:
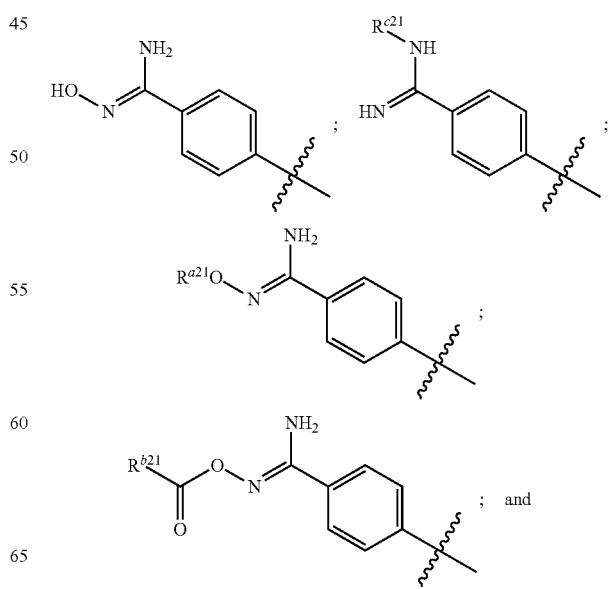

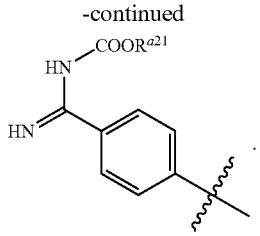
In some embodiments, $R^{21}$ is $C_{1-6}$ alkyl and $R^{b21}$ is $C_{1-6}$ alkyl.
In some embodiments, $Cy^{2A}$ is unsubstituted or substituted heteroaryl, such as pyridin-3-yl, 1H-pyrrolo[2,3-b]pyridine-5-yl, or 1H-benzo[d]imidazol-6-yl.
In some embodiments, $Cy^{2A}$ is of any one of the following formulae:
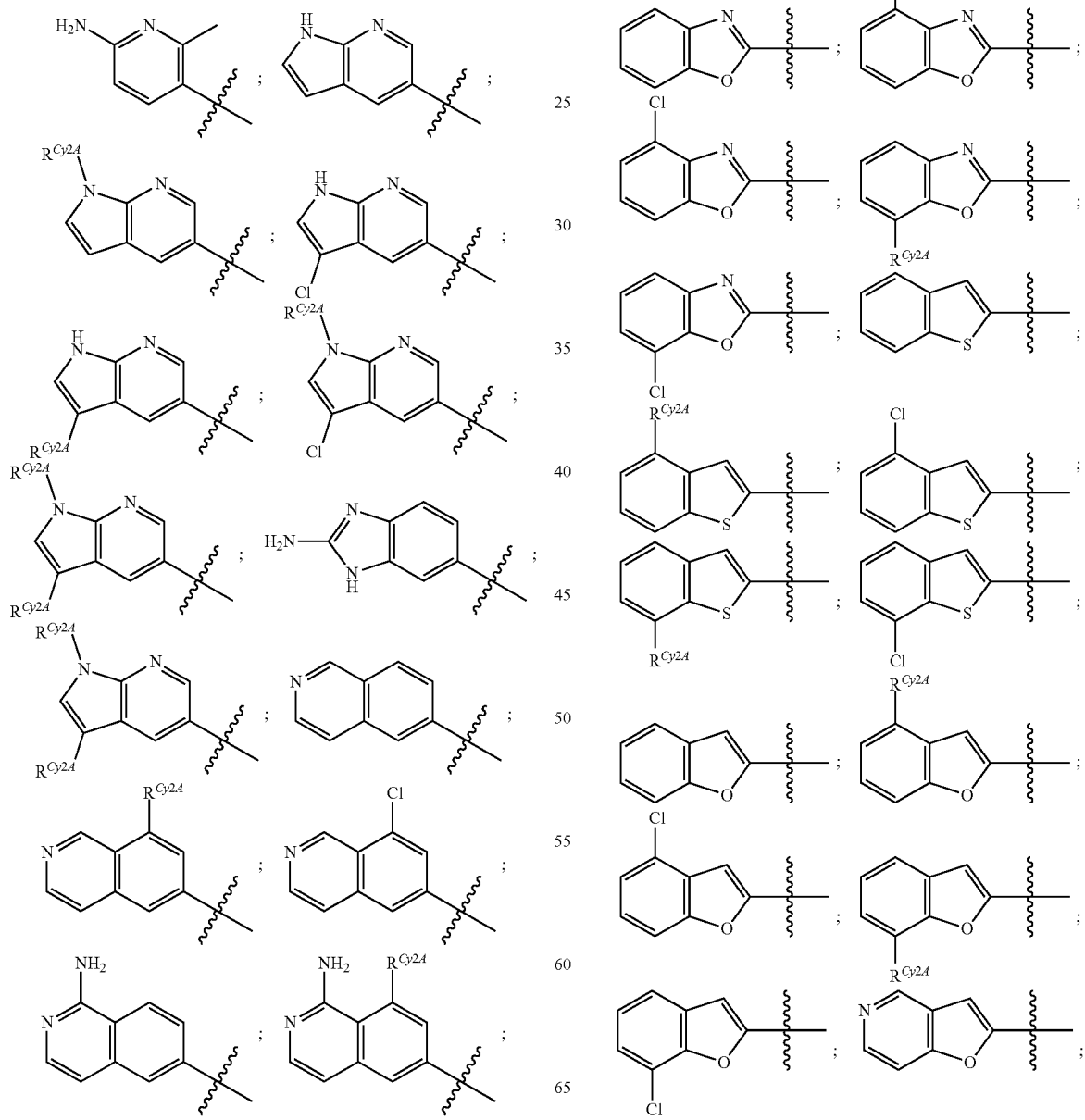
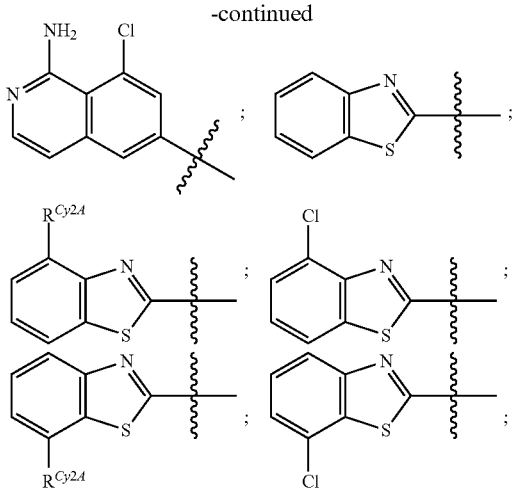

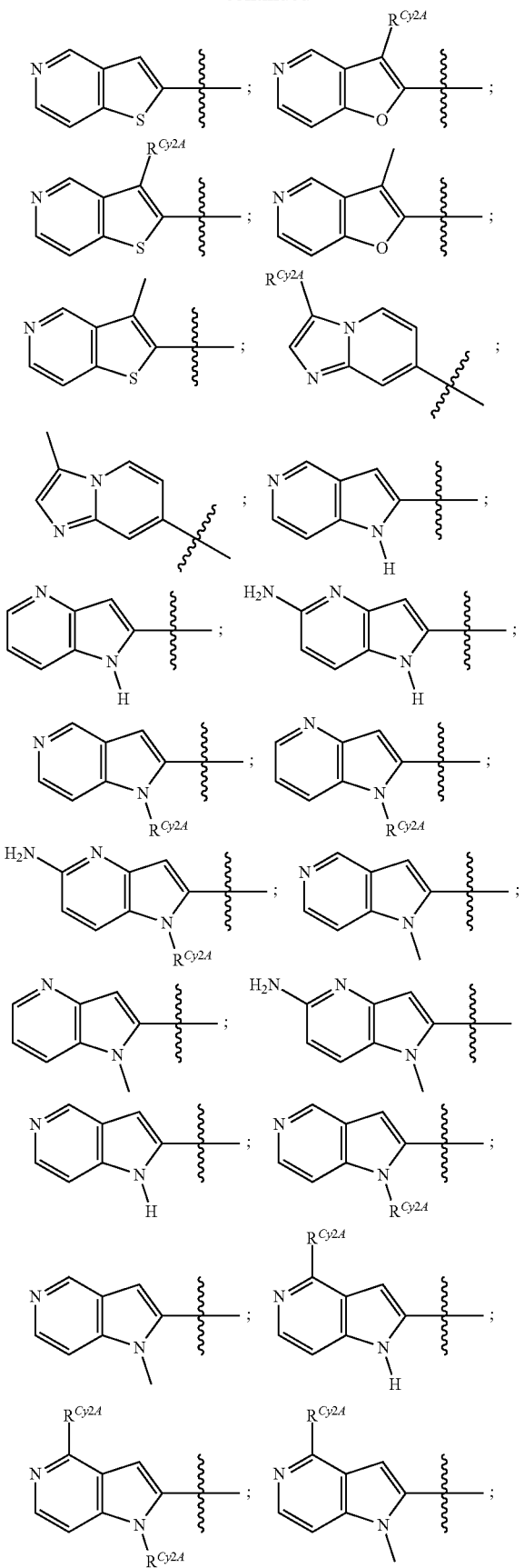
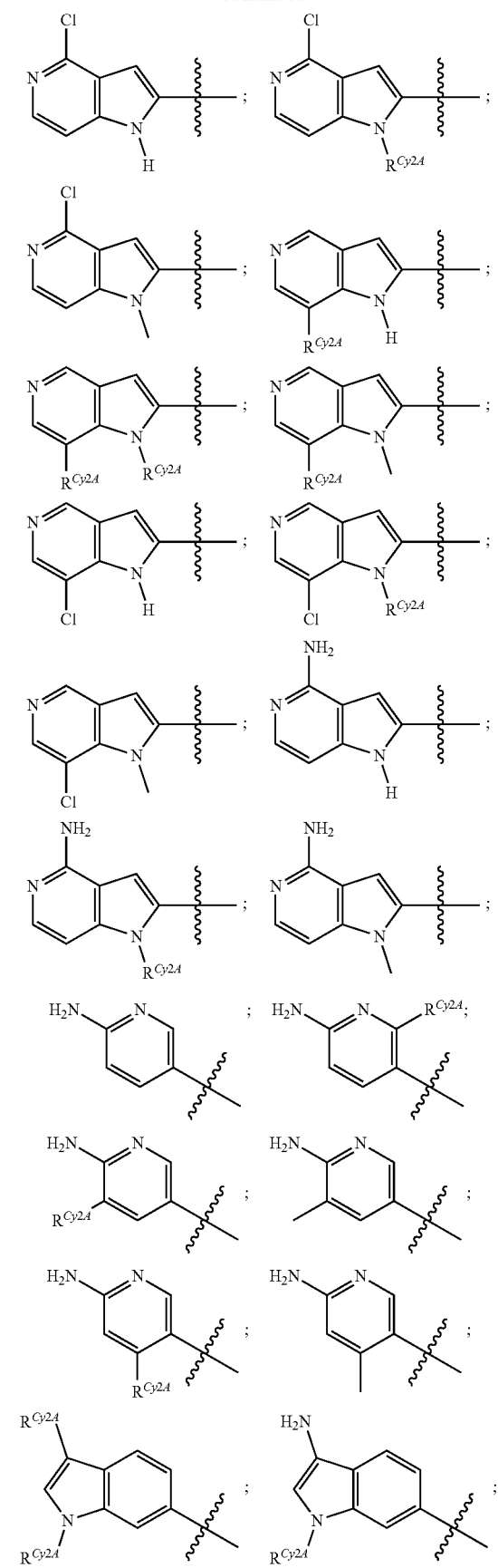

-continued
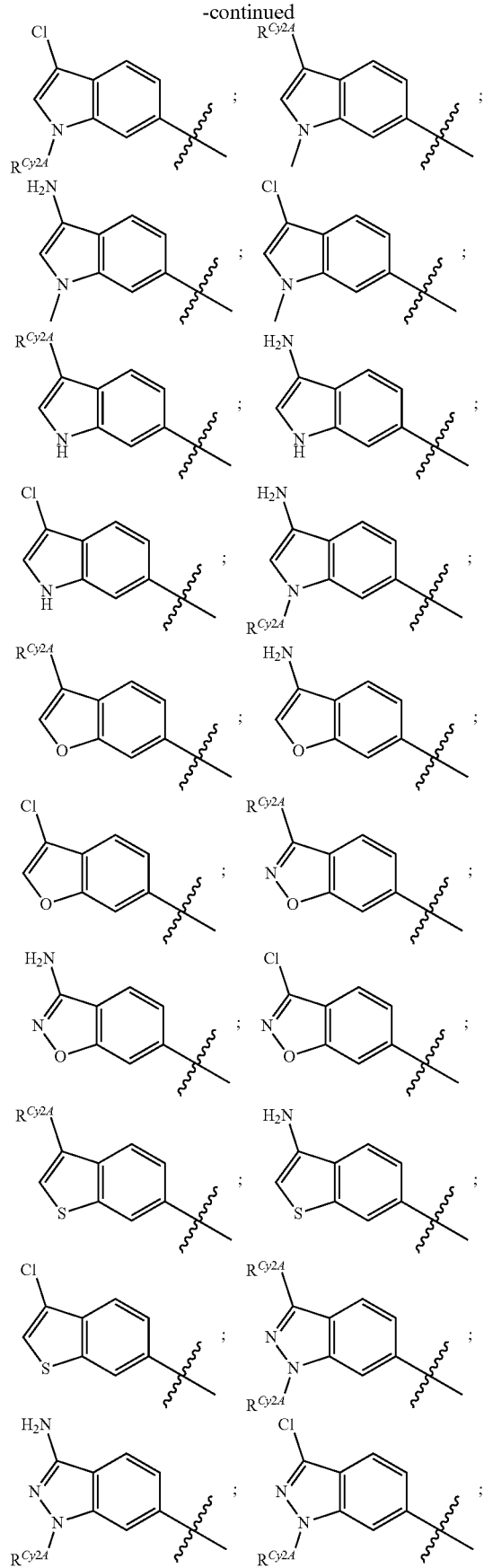
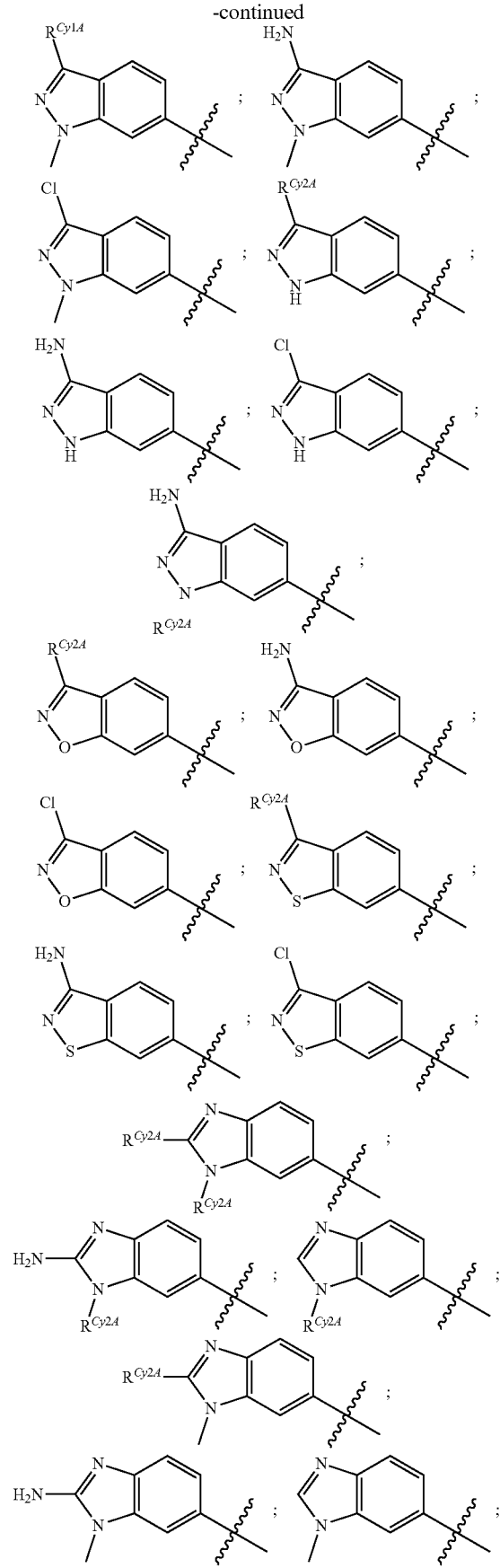

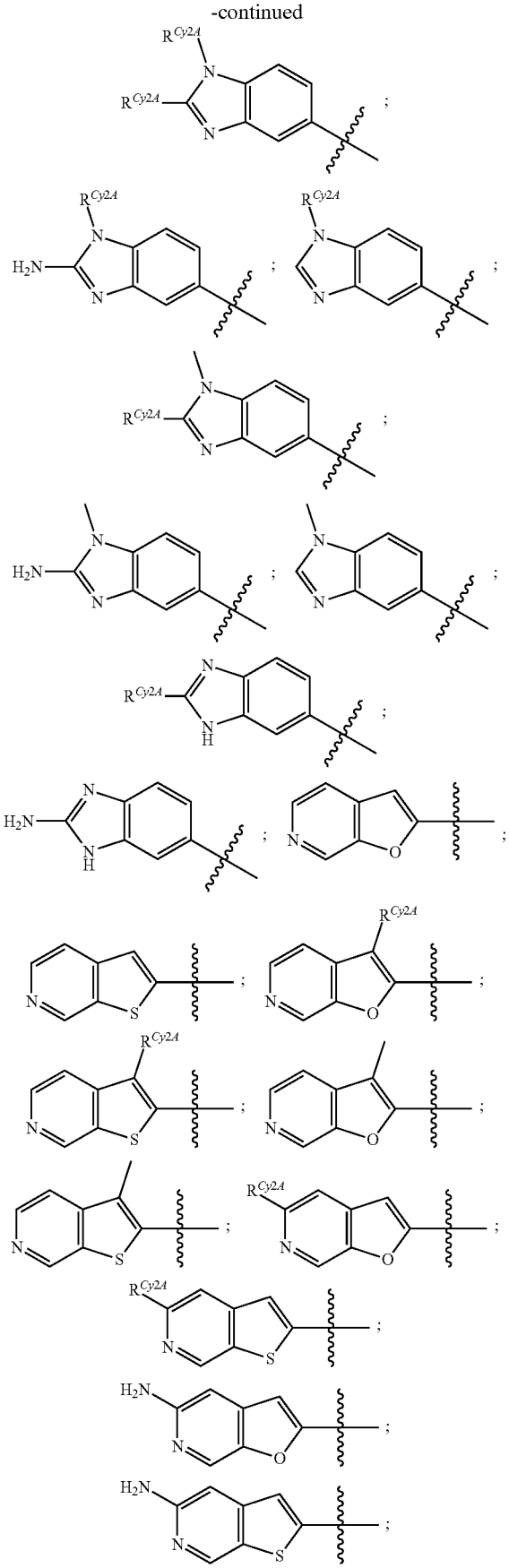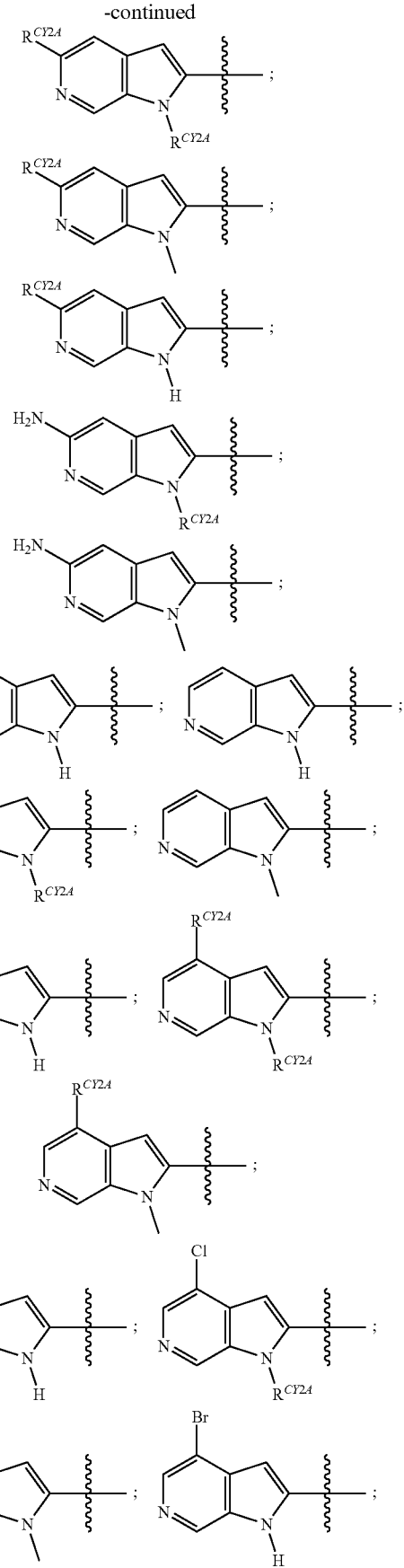

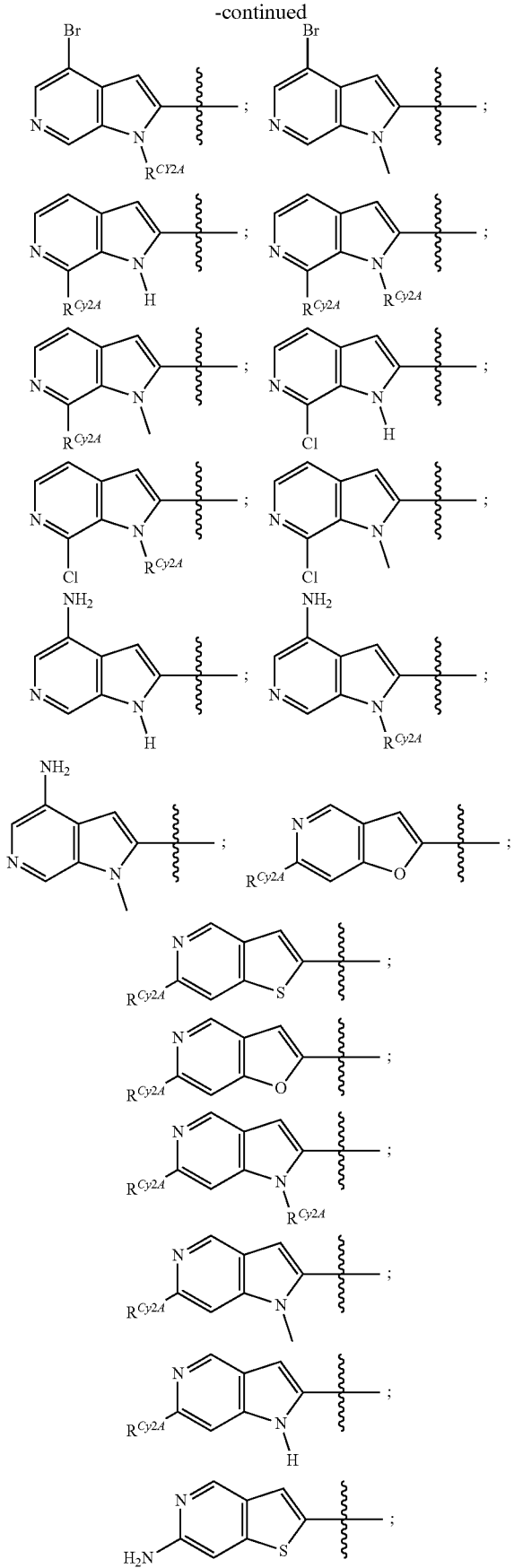
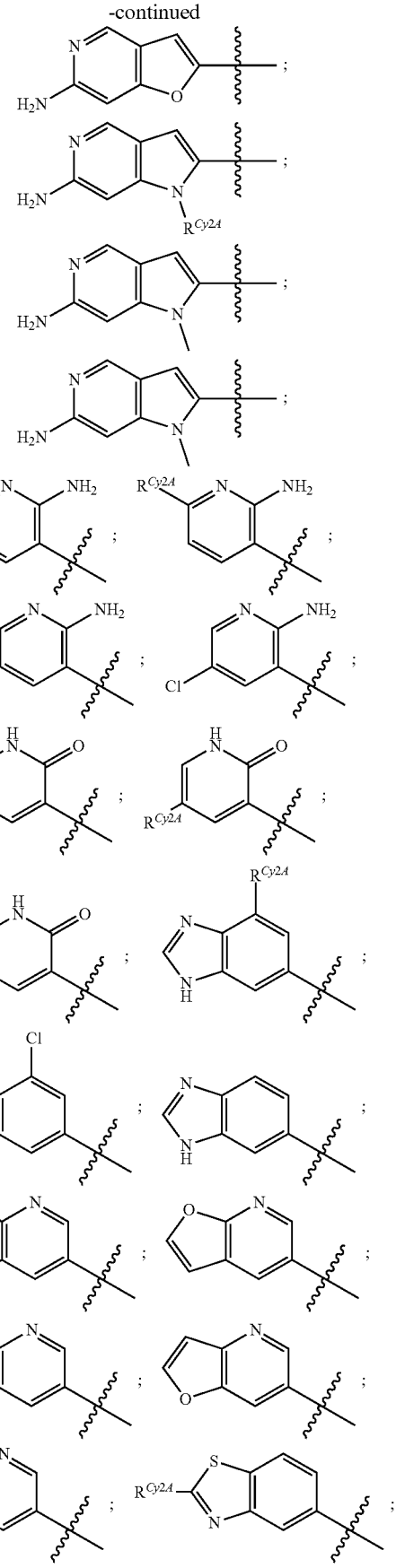

-continued

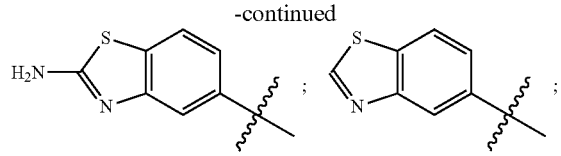

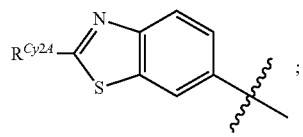

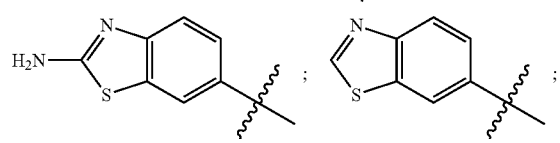

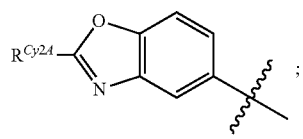

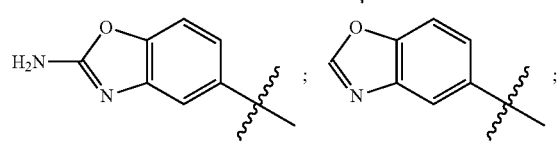

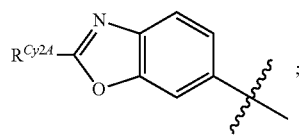

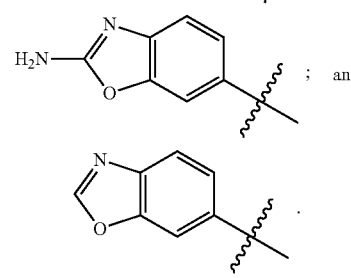

In some embodiments, each $R^{Cy2A}$ in the formula defining $Cy^{2A}$ is independently $C_{1-6}$ alkyl, such as methyl or ethyl, preferably methyl, or halogen such as F, Cl or Br, preferably Cl.

In some embodiments, each $R^{Cy2A}$ attached to nitrogen in the formula defining $Cy^{2A}$ is $C_{1-6}$ alkyl, such as methyl or ethyl.

In some embodiments, $R^{21}$ is $C_{1-6}$ alkyl.

In some embodiments, $R^{21}$ is methyl.

In some embodiments, $R^{21}$ is H.

In some embodiments, $R^{22}$ is H.

In some embodiments, $R^{22}$ is $C_{1-6}$ alkyl.

In some embodiments, $R^{22}$ is methyl.

In some embodiments, $R^{21}$ and $R^{22}$, together with the groups to which they are attached, form a 4-6 membered heterocycloalkyl ring.

In some embodiments, the compound is of Formula (IIA).

In some embodiments, the compound is according to any of the following Formulae (IIA-1a) or (IIA-1b):

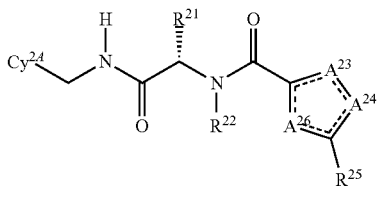
(IIA-1a)

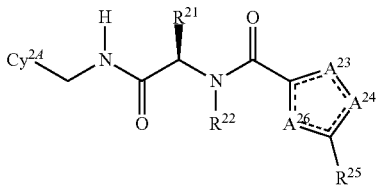
(IIA-1b)

In some embodiments, the compound is according to any of the following Formulae (IIA-2) to (IIA-5):

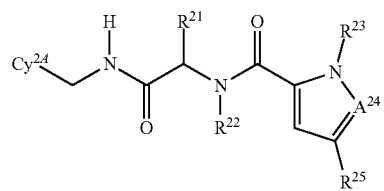
(IIA-2)

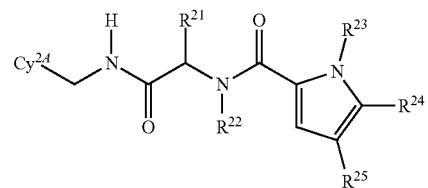
(IIA-3)

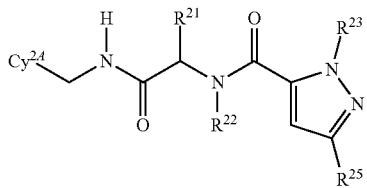
(IIA-4)

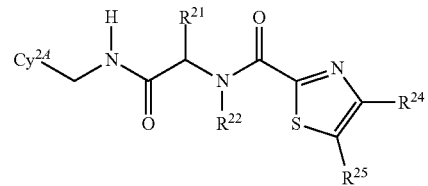
(IIA-5)

In some embodiments, the compound is according to any of the following Formulae (IIA-2a) to (IIA-5b):

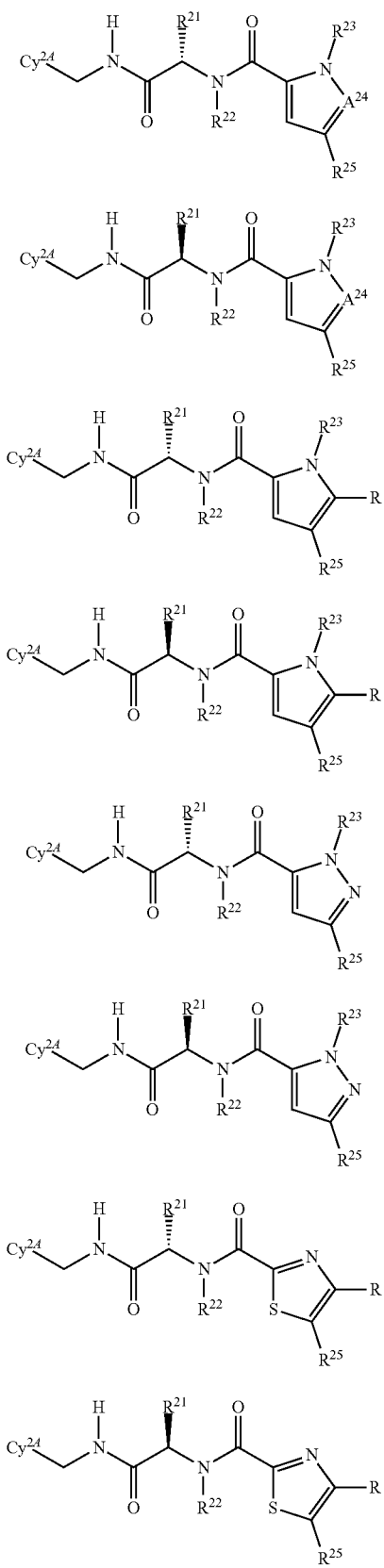

In some embodiments, the compound is of Formula (IIB).

In some embodiments, the compound is according to any of the following Formulae (IIB-1a) or (IIB-1b):

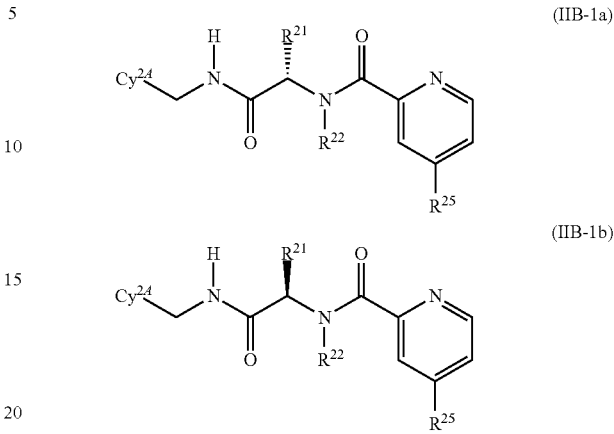

In some embodiments, $R^{23}$ is H.
In some embodiments, $R^{23}$ is $C_{1-6}$ alkyl.
In some embodiments, $R^{24}$ is H.
In some embodiments, $R^{24}$ is $C_{1-6}$ alkyl.
In some embodiments, $R^{24}$ is phenyl.
In some embodiments, $R^{25}$ is $Cy^{2B}$.
In some embodiments, $R^{25}$ is ($C_{1-6}$ alkylene)$Cy^{2B}$, ($C_{2-6}$ alkenylene)$Cy^{2B}$, or ($C_{2-6}$ alkynylene)$Cy^{2B}$, wherein the $C_{1-6}$ alkylene, $C_{2-6}$ alkenylene, or $C_{2-6}$ alkynylene component of $R^{25}$ is unsubstituted or substituted.
In some embodiments, $R^{25}$ is ($C_{1-6}$ alkylene)$Cy^{2B}$, ($C_{2-6}$ alkenylene)$Cy^{2B}$, or ($C_{2-6}$ alkynylene)$Cy^{2B}$, wherein the $C_{1-6}$ alkylene, $C_{2-6}$ alkenylene, or $C_{2-6}$ alkynylene component of $R^{25}$ is unsubstituted.
In some embodiments, $R^{25}$ is $(CR^{25A}R^{25B})_{n25}Cy^{2B}$.
In some embodiments, each $R^{25A}$ is H.
In some embodiments, each $R^{25B}$ is H.
In some embodiments, n25 is 0.
In some embodiments, n25 is 1.
In some embodiments, n25 is 2.
In some embodiments, $R^{25}$ is $CH_2Cy^{2B}$.
In some embodiments, $R^{25}$ is $CH_2CH_2Cy^{2B}$.
In some embodiments, $Cy^{2B}$ is unsubstituted $C_{6-10}$ aryl.
In some embodiments, $Cy^{2B}$ is unsubstituted phenyl.
In some embodiments, $Cy^{2B}$ is unsubstituted naphthyl, such as 1-naphthyl or 2-naphthyl.
In some embodiments, $Cy^{2B}$ unsubstituted 5-10 membered heteroaryl.
In some embodiments, $Cy^{2B}$ is unsubstituted pyridyl, such as unsubstituted 2-, 3-, or 4-pyridyl or unsubstituted quinolyl, such as unsubstituted 2-, 3-, 4-, 5-, 6-, 7-, or 8-quinolyl.
In some embodiments, $Cy^{2B}$ is substituted $C_{6-10}$ aryl.
In some embodiments, $Cy^{2B}$ is substituted phenyl.
In some embodiments, $Cy^{2B}$ is a biphenylyl (i.e., phenyl substituted by phenyl), such as 2-, 3-, or 4-biphenylyl.
In some embodiments, $Cy^{2B}$ is substituted naphthyl, such as 1-naphthyl or 2-naphthyl.
In some embodiments, $Cy^{2B}$ is substituted 5-10 membered heteroaryl.
In some embodiments, $Cy^{2B}$ is substituted pyridyl, such as substituted 2-, 3-, or 4-pyridyl or substituted quinolyl, such as substituted 2-, 3-, 4-, 5-, 6-, 7-, or 8-quinolyl.
In some embodiments, $Cy^{2B}$ is substituted with 1, 2, 3, 4 or 5 substituents each independently selected from $R^{Cy2B}$, halogen, and $C_{1-6}$ haloalkyl; wherein each $R^{Cy2B}$ is independently selected from $C_{1-6}$ alkyl, $C_{2-6}$ alkenyl, $C_{2-6}$ alkynyl and $C_{6-10}$ aryl or 5-10 membered heteroaryl, wherein each $C_{6-10}$ aryl or 5-10 membered heteroaryl forming $R^{Cy2B}$ is unsubstituted or substituted with 1, 2 or 3 substituents independently selected from halogen, $C_{1-6}$ alkyl, $C_{2-6}$ alkenyl, $C_{2-6}$ alkynyl, and haloalkyl.

In some embodiments, $R^{25}$ is selected from groups of the following formulae:

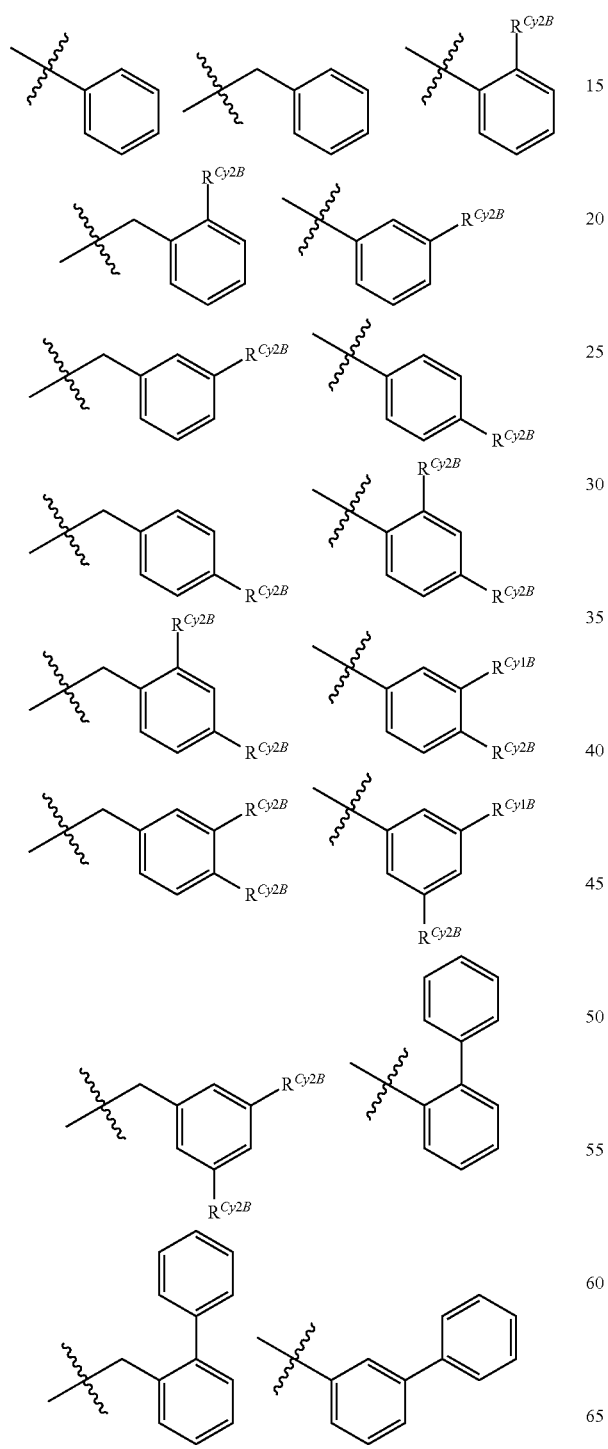

-continued

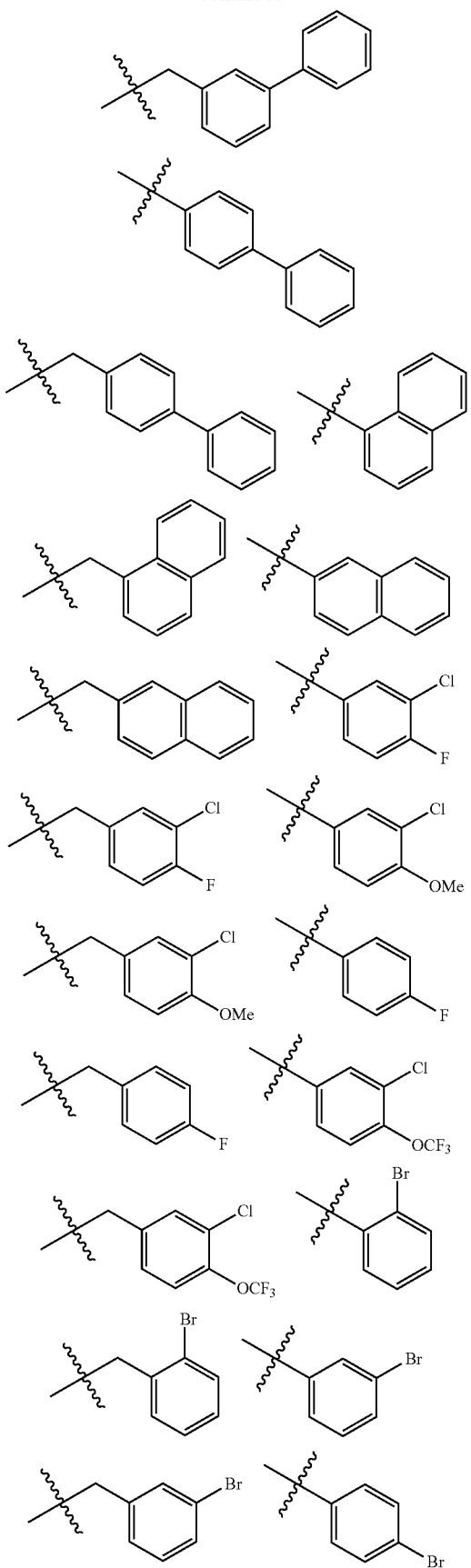

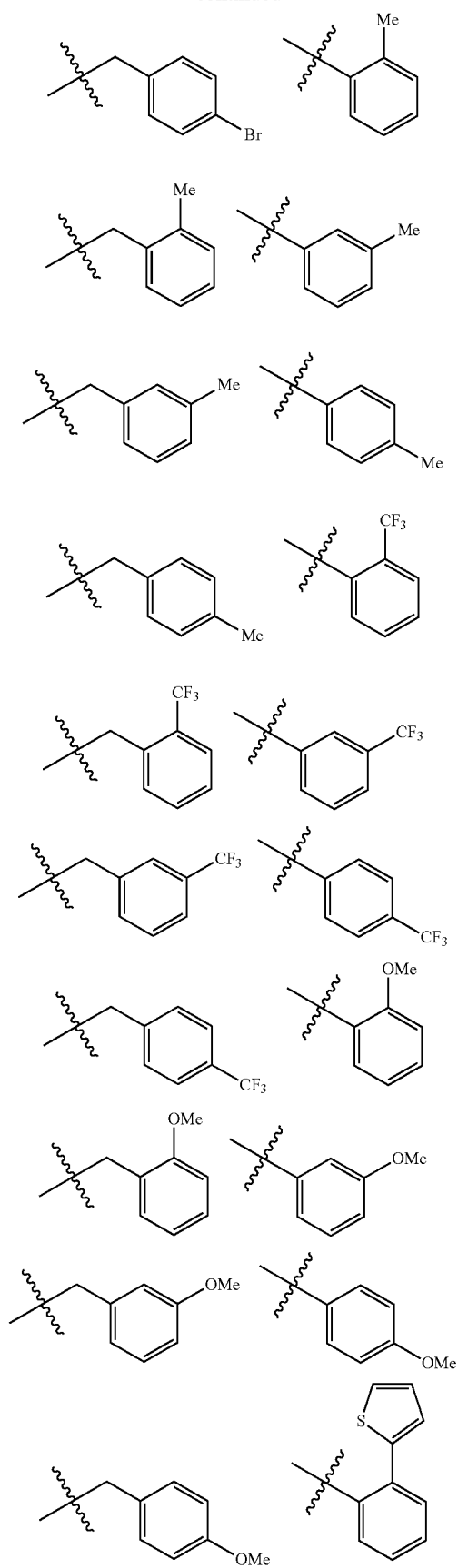
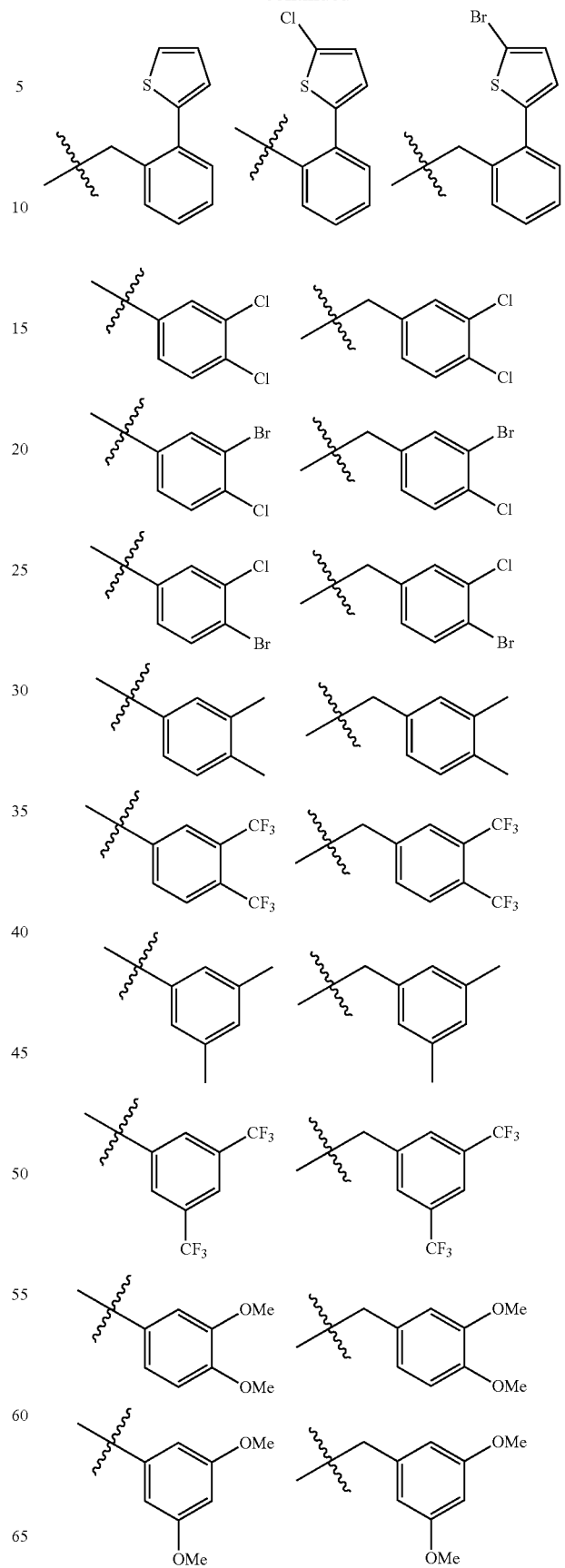

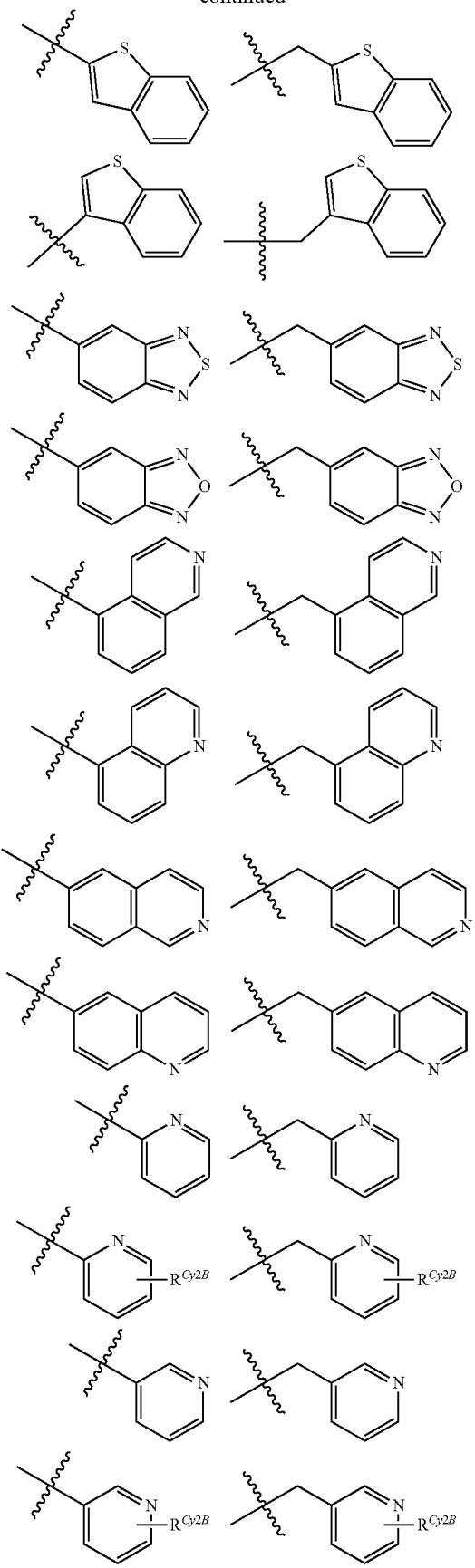

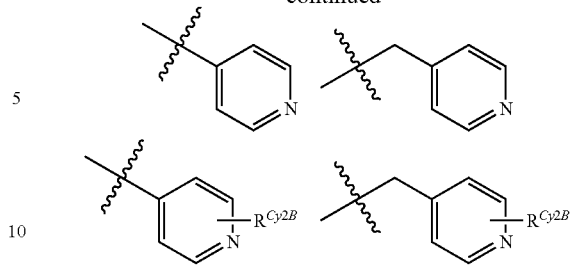

In some embodiments, $R^{Cy2B}$ in the formula representing $R^{25}$ is $C_{1-6}$ alkyl, such as methyl or ethyl, preferably methyl, or halogen, such as fluorine or chlorine, preferably fluorine.

In some embodiments, $R^{Cy2B}$ in the formula representing $R^{25}$ is $C_{1-6}$ alkyl, such as methyl or ethyl, preferably methyl.

In some embodiments, $R^{Cy2B}$ in the formula representing $R^{25}$ is halogen, such as fluorine or chlorine, preferably fluorine.

In some embodiments, $R^{a21}$, $R^{b21}$, $R^{c21}$, $R^{a21}$, $R^{a22}$, $R^{b22}$, $R^{c22}$, $R^{a22}$ are each independently selected from H, $C_{1-6}$ alkyl.

In some embodiments, each $R^{e21}$ and each $R^{e22}$ is H.

The compounds of Formula (IIA) and (IIB), and embodiments thereof, are useful as inhibitors of MASP-2 and for therapeutic use.

In some embodiments, the compounds of Formula (IIA) and (IIB), and embodiments thereof, can be in the form of a salt such as a pharmaceutically acceptable salt.

The compounds of Formula (IIA) and (IIB), and embodiments thereof, are useful as inhibitors of MASP-2 and for therapeutic use. The compounds of Formula (IIA) and (IIB), and embodiments thereof, are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Formula (IIA) or (IIB), or an embodiment thereof, optionally in the form of a salt.

In some embodiments the compound Formula (IIA) or (IIB) or an embodiment thereof is provided in the form of a pharmaceutical composition comprising the compound or a salt thereof, such as a pharmaceutically acceptable salt, and at least one pharmaceutically acceptable carrier or excipient.

In certain aspects, the compound is one or more selected from the compounds of Formula (IIA) and (IIB) set forth in the Examples including the compounds listed in Table 31, e.g., the compounds with selectivity for MASP-2 over thrombin. In certain aspects, one or more of the variables defining the compounds of Formula (IIA) and (IIB) (such as $Cy^{2A}$, $R^{Cy2A}$, $Cy^{2B}$, $R^{Cy2B}$, $A^{23}$, $A^{24}$, $A^{26}$, $R^{21}$, $R^{22}$, $R^{23}$, $R^{24}$, $R^{25}$, $R^{26}$, n25, $R^{a21}$, $R^{b21}$, $R^{c21}$, $R^{d21}$, $R^{e21}$, $R^{a22}$, $R^{b22}$, $R^{c22}$, $R^{d22}$ and $R^{e22}$) is selected from the corresponding substituents in the compounds of Formula (IIA) and (IIB) in the Examples, including the compounds listed in Table 31, preferably, those of the compounds with selectivity for MASP-2 over thrombin.

In certain aspects, the invention sets forth a stereochemically pure enantiomer or diastereomer (e.g., an optically active compound with one or more chiral centers). Unless specifically indicated otherwise, for any inventive compound with one or more stereocenters, the present invention is intended to include and to describe both the pure (+) and (−) enantiomers, any other diastereomers, mixtures that are enriched in an enantiomer or diastereomer (e.g., 10%, 20%, 30%, 40%, 50%, 60%, 70% 75%, 80%, 85, 90%, or 95% enantiomeric or diastereomeric excess), and a racemic mixture of enantiomers or diastereomers.

In certain aspects, the invention sets forth a pharmaceutically acceptable salt of the indicated chemical structure (e.g., a hydrohalide, such as a hydrochloride or dihydrochloride). Examples of pharmaceutically acceptable salts are set forth in, e.g., Burge, S. M. et al., J. Pharm. Sci 1977, 66, 1-19. They include chlorides, bromides, iodides, formates, acetates, propionates, oxalates, malonates, succinates, fumarates, maleates, tartrates, citrates, benzoates, phthalates, sulfonates, arylsulfonates, alkylsulfonates, salts of fatty acids, and the like. Salts can be prepared by a variety of methods known to the skilled artisan, including a precipitation with the conjugate acid or base (e.g., treatment with gaseous HCl or an HCl solution).

In certain aspects, the invention sets forth a prodrug. A prodrug is a compound that is converted to a biologically active form under physiological conditions, often by hydrolysis, oxidation, or reduction (e.g., ester to acid form; carbamate to amino or hydroxy group; hydroxyamidine to amidine) Exemplary prodrugs are set forth in, e.g., Tilley, J. W., "Prodrugs of Benzamide," Prodrugs 2007, 191-222; Peterlin-Masic et al. Curr. Pharma. Design 2006, 12, 73-91. Prodrugs for the amidine group include amidoximes, O-alkylamidoximes, acylamidines, carbamates, 1,2,4-oxadiazolin-4-ones, and the like.

In certain aspects, the compound is useful for selectively inhibiting MASP-2 over thrombin, the method comprising administering the compound as described herein. In certain aspects, the selectivity ratio of MASP-2:thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

C. Compounds of Formula III

In certain aspects, the present disclosure provides a compound of Formula (III).

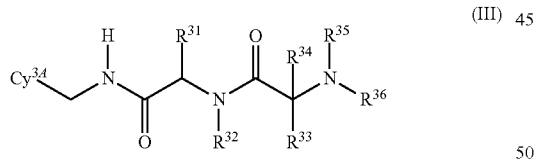

(III)

or a salt thereof, for use in treating a MASP-2-associated disease or disorder, wherein:

$Cy^{3A}$ is unsubstituted or substituted $C_{6-10}$ aryl or unsubstituted or substituted 5-10 membered heteroaryl; wherein the ring atoms of the 5-10 membered heteroaryl forming $Cy^{3A}$ consist of carbon atoms and 1, 2, or 3 heteroatoms selected from O, N and S; wherein the substituted $C_{6-10}$ aryl or substituted 5-10 membered heteroaryl forming $Cy^{3A}$ are substituted with 1, 2, 3, 4 or 5 substituents each independently selected from $R^{Cy3A}$, halogen, $C_{1-6}$ haloalkyl, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $C(=NOR^{a31})NR^{c31}R^{d31}$, $C(=NOC(O)R^{b31})NR^{c31}R^{d31}$, $C(=NR^{e31})NR^{c31}C(O)OR^{a31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo;

each $R^{Cy3A}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10-membered heterocycloalkyl forming $R^{Cy3A}$ consist of carbon atoms and 1, 2, 3 or 4 heteroatoms selected from O, N and S, wherein each $C_{1-6}$ alkyl, $C_{2-6}$ alkenyl, or $C_{2-6}$ alkynyl forming $R^{Cy3A}$ is independently unsubstituted or substituted with 1, 2 or 3 substituents independently selected from halogen, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo, and wherein each $C_{6-10}$ aryl, 5-10 membered heteroaryl, $C_{3-10}$ cycloalkyl and 4-10 membered heterocycloalkyl forming $R^{Cy3A}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo;

$R^{31}$ is H or $C_{1-6}$ alkyl, $C_{6-10}$ aryl-$C_{1-6}$ alkyl or 5-10 membered heteroaryl-$C_{1-6}$ alkyl, wherein the $C_{1-6}$ alkyl forming $R^{31}$ is unsubstituted or substituted by 1, 2 or 3 substituents independently selected from halogen, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo, and wherein the $C_{6-10}$ aryl-$C_{1-6}$ alkyl or 5-10 membered heteroaryl-$C_{1-6}$ alkyl forming $R^{31}$ is unsubstituted or substituted by 1, 2 or 3 substituents independently selected from $C_{1-6}$ alkyl, $C_{2-6}$ alkenyl, $C_{2-6}$ alkynyl, $C_{1-6}$ haloalkyl, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo;

$R^{32}$ is H or $C_{1-6}$ alkyl; or $R^{31}$ and $R^{32}$, together with the groups to which they are attached, form a 4-6 membered heterocycloalkyl ring;

$R^{33}$ is $Cy^{3B}$, $(CR^{33A}R^{33B})_{n33}Cy^{3B}$, $(C_{1-6}$ alkylene)$Cy^{3B}$, $(C_{2-6}$ alkenylene)$Cy^{3B}$, or $(C_{2-6}$ alkynylene)$Cy^{3B}$, wherein the $C_{1-6}$ alkylene, $C_{2-6}$ alkenylene, or $C_{2-6}$ alkynylene component of $R^{35}$ is unsubstituted or substituted by 1, 2, 3, 4 or 5 substituents each independently selected from the group consisting of halogen, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo;

each $R^{33A}$ is independently H or $C_{1-6}$ alkyl;

each $R^{33B}$ is independently H or $C_{1-6}$ alkyl; or or $R^{33A}$ and $R^{33B}$ attached to the same carbon atom, independently of any other $R^{33A}$ and $R^{33B}$ groups, together may form —$(CH_2)_{2-5}$—, thereby forming a 3-6 membered cycloalkyl ring;

n33 is 0, 1, 2 or 3;

$Cy^{3B}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl; wherein the ring atoms of the 5-10 membered heteroaryl or 4-10 membered heterocycloalkyl forming $Cy^{3B}$ consist of carbon atoms and 1, 2 or 3 heteroatoms selected from O, N and S; and wherein the substituted $C_{6-10}$ aryl, substituted 5-10 membered heteroaryl, substituted $C_{3-10}$ cycloalkyl or substituted 4-10 membered heterocycloalkyl forming $Cy^{3B}$ are substituted with 1, 2, 3, 4 or 5 substituents each independently selected from $R^{Cy3B}$, halogen, $C_{1-6}$ haloalkyl, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $C(=NOR^{a31})NR^{c31}R^{d31}$, $C(=NOC(O)R^{b31})NR^{c31}R^{d31}$, $C(=NR^{e31})NR^{c31}C(O)OR^{a31}$, $NR^{c31}C(=NR^{e31})NR^{c31}R^{d31}$, $S(O)R^{b31}$, $S(O)NR^{c31}R^{d31}$, $S(O)_2 R^{b31}$ $NR^{c31}S(O)_2R^{b31}$ $S(O)_2NR^{c31}R^{d31}$ and oxo;

wherein each $R^{Cy3B}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10 membered heterocycloalkyl forming $R^{Cy3B}$ consist of carbon atoms and 1, 2 or 3 heteroatoms selected from O, N and S; wherein each $C_{1-6}$ alkyl, $C_{2-6}$ alkenyl, or $C_{2-6}$ alkynyl forming $R^{Cy3B}$ is independently unsubstituted or substituted with 1, 2 or 3 substituents independently selected from halogen, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo; and wherein each $C_{6-10}$ aryl, 5-10 membered heteroaryl, $C_{3-10}$ cycloalkyl and 4-10 membered heterocycloalkyl forming $R^{Cy3B}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$ $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo;

$R^{34}$ is selected from H and $C_{1-6}$ alkyl;

$R^{35}$ is selected from H, unsubstituted or substituted $C_{1-6}$ alkyl and $Cy^{3C}$, wherein the substituted $C_{1-6}$ alkyl forming $R^{35}$ is substituted by 1, 2, 3, 4 or 5 substituents selected from the group consisting of $Cy^{3C}$, halogen, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo; provided that no more than one of the substituents of $R^{35}$ is $Cy^{3C}$;

$Cy^{3C}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl; wherein the ring atoms of the 5-10 membered heteroaryl or 4-10 membered heterocycloalkyl forming $Cy^{3C}$ consist of carbon atoms and 1, 2 or 3 heteroatoms selected from O, N and S; and wherein the substituted $C_{6-10}$ aryl, substituted 5-10 membered heteroaryl, substituted $C_{3-10}$ cycloalkyl or substituted 4-10 membered heterocycloalkyl forming $Cy^{3C}$ are substituted with 1, 2, 3, 4 or 5 substituents each independently selected from $R^{Cy3C}$, halogen, $C_{1-6}$ haloalkyl, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $C(=NOR^{a31})NR^{c31}R^{d31}$, $C(=NOC(O)R^{b31})NR^{c31}R^{d31}$, $C(=NR^{e31})NR^{c31}C(O)OR^{a31}$, $NR^{c31}C(=NR^{e31})NR^{c31}R^{d31}$, $S(O)R^{b31}$, $S(O)NR^{c31}R^{d31}$, $S(O)_2 R^{b31}$, $NR^{c31}S(O)_2R^{b31}$, $S(O)_2NR^{c31}R^{d31}$ and oxo;

wherein each $R^{Cy3C}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10 membered heterocycloalkyl forming $R^{Cy3C}$ consist of carbon atoms and 1, 2 or 3 heteroatoms selected from O, N and S; wherein each $C_{1-6}$ alkyl, $C_{2-6}$ alkenyl, or $C_{2-6}$ alkynyl forming $R^{Cy3C}$ is independently unsubstituted or substituted with 1, 2 or 3 substituents independently selected from halogen, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo; and wherein each $C_{6-10}$ aryl, 5-10 membered heteroaryl, $C_{3-10}$ cycloalkyl and 4-10 membered heterocycloalkyl forming $R^{Cy3C}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a31}$, $SR^{a3}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$ $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo;

$R^{36}$ is selected from H and $C_{1-6}$ alkyl;

$R^{a3}$, $R^{b31}$, $R^{c31}$ and $R^{d31}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a3}$, $R^{b31}$, $R^{c31}$ and $R^{d31}$ are each optionally substituted with 1, 2, 3, 4 or 5 substituents independently selected from $C_{1-6}$ alkyl, halo, CN, $OR^{12}$, $SR^{a32}$, $C(O)R^{b32}$, $C(O)NR^{c32}R^{d32}$, $C(O)OR^{32}$, $OC(O)R^{b32}$, $OC(O)NR^{c32}R^{d32}$, $NR^{c32}R^{d32}$, $NR^{c32}C(O)R^{b32}$, $NR^{c32}C(O)NR^{c32}R^{d32}$, $NR^{c32}C(O)OR^{32}$, $C(=NR^{32})$ NR$^{c32}$R$^{d32}$, NR$^{c32}$C(=NR$^{e32}$)NR$^{c32}$R$^{d32}$, S(O)R$^{b32}$, S(O)NR$^{c32}$R$^{d32}$, S(O)$_2$R$^{b32}$, NR$^{c32}$S(O)$_2$R$^{b32}$, S(O)$_2$NR$^{c32}$R$^{d32}$ and oxo;

or R$^{c31}$ and R$^{d31}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from C$_{1-6}$ alkyl, halo, CN, OR$^{12}$, SR$^{32}$, C(O)R$^{b32}$, C(O)NR$^{c32}$R$^{d32}$, C(O)OR$^{32}$, OC(O)R$^{b32}$, OC(O)NR$^{c32}$R$^{d32}$, NR$^{c32}$R$^{d32}$, NR$^{c32}$C(O)R$^{b32}$, NR$^{c32}$C(O)NR$^{c32}$R$^{d32}$, NR$^{c32}$C(O)OR$^{a32}$, C(=NR$^{e32}$)NR$^{c32}$R$^{d32}$, NR$^{c32}$C(=NR$^{e32}$)NR$^{c32}$R$^{d32}$, S(O)R$^{b32}$, S(O)NR$^{c32}$R$^{d32}$, S(O)$_2$R$^{b32}$, NR$^{c32}$S(O)$_2$R$^{b32}$, S(O)$_2$NR$^{c32}$R$^{d32}$ and oxo;

R$^{a32}$, R$^{b32}$, R$^{c32}$ and R$^{d32}$ are each independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-3}$ alkyl, 5-6 membered heteroaryl-C$_{1-3}$ alkyl, C$_{3-7}$ cycloalkyl-C$_{1-3}$ alkyl and 4-7 membered heterocycloalkyl-C$_{1-3}$ alkyl, wherein said C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-3}$ alkyl, 5-6 membered heteroaryl-C$_{1-3}$ alkyl, C$_{3-7}$ cycloalkyl-C$_{1-3}$ alkyl and 4-7 membered heterocycloalkyl-C$_{1-3}$ alkyl forming R$^{a32}$, R$^{b32}$, R$^{c32}$ and R$^{d32}$ are each optionally substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl, C$_{1-6}$ haloalkoxy and oxo;

or R$^{c32}$ and R$^{d32}$ attached to the same N atom, together with the N atom to which they are both attached, form a 4-, 5-, 6- or 7-membered heterocycloalkyl group or 5-membered heteroaryl group, each of which is unsubstituted or substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl, C$_{1-6}$ haloalkoxy and oxo; and R$^{e31}$ and R$^{e32}$ are each, independently, H, CN or NO$_2$.

In some embodiments, Cy$^{3A}$ is unsubstituted or substituted aryl.

In some embodiments, Cy$^{3A}$ is unsubstituted or substituted phenyl.

In some embodiments, Cy$^{3A}$ is substituted phenyl.

In some embodiments, Cy$^{3A}$ is substituted with at least one OR$^{a31}$ or at least one C(=NR$^{e31}$)NR$^{c31}$R$^{d31}$, C(=NOR$^{a31}$)NR$^{c31}$R$^{d31}$, C(=NOC(O)R$^{b31}$)NR$^{c31}$R$^{d31}$, or C(=NR$^{e31}$)NR$^{c31}$C(O)OR$^{a31}$.

In some embodiments, Cy$^{3A}$ is substituted with at least one OR$^{a31}$ and by at least one additional substituent selected from the group consisting of C$_{1-6}$ alkyl, C$_{1-6}$ haloalkyl and halogen.

In some embodiments, Cy$^{3A}$ is substituted with at least one OH and by at least one additional substituent selected from the group consisting of C$_{1-6}$ alkyl, C$_{1-6}$ haloalkyl and halogen.

In some embodiments, Cy$^{3A}$ is substituted with at least one C(=NR$^{e31}$)NR$^{c31}$R$^{d31}$, C(=NOR$^{a31}$)NR$^{c31}$R$^{d31}$, C(=NOC(O)R$^{b31}$)NR$^{c31}$R$^{d31}$, C(=NR$^{e31}$)NR$^{c31}$C(O)OR$^{a31}$, preferably in the 4-position.

In some embodiments, Cy$^{3A}$ is substituted with at least one C(=NR$^{e31}$)NR$^{c31}$R$^{d31}$, preferably in the 4-position.

In some embodiments, Cy$^{3A}$ is substituted with at least one C(=NH)NH$_2$, preferably in the 4-position.

In some embodiments, Cy$^{3A}$ is of any one of the following formulae:

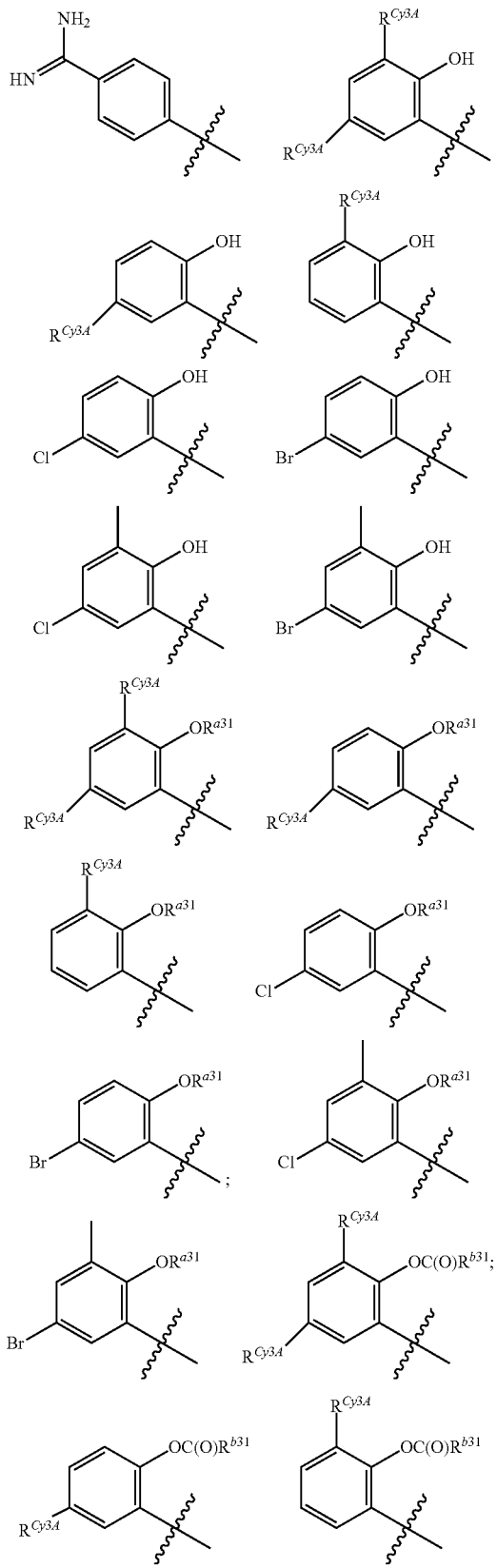

-continued

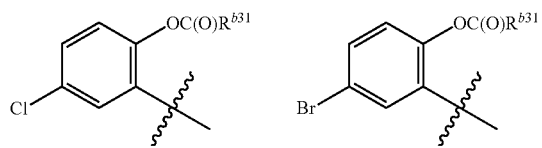

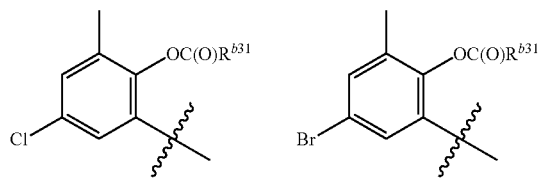

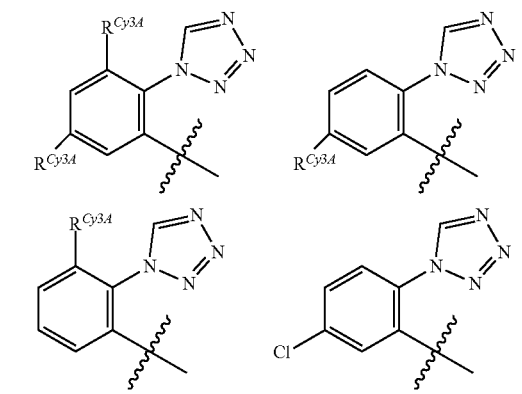

In some embodiments, Cy$^{3A}$ is of any one of the following formulae:

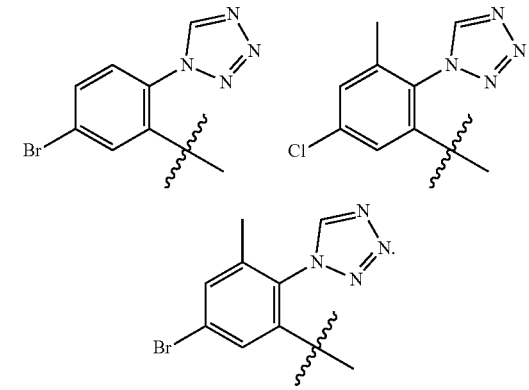

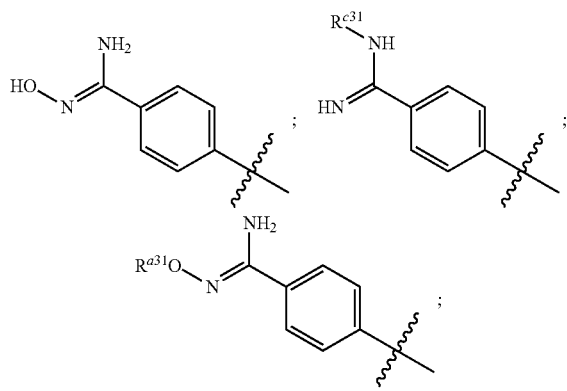

-continued

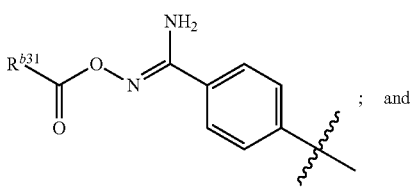; and

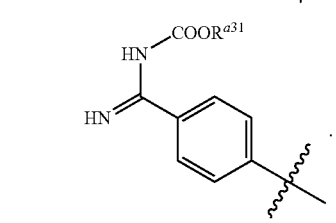.

In some embodiments, in the formula defining Cy$^{3A}$, R$^{a31}$ is C$_{1-6}$ alkyl, such as methyl; R$^{b31}$ is C$_{1-6}$ alkyl, such as methyl, or R$^{b31}$ is C$_{1-6}$ haloalkyl, such as trifluoromethyl and R$^{c31}$ is alkyl such as methyl.

In some embodiments, Cy$^{3A}$ is unsubstituted or substituted heteroaryl.

In some embodiments, Cy$^{3A}$ is unsubstituted or substituted pyridin-3-yl, 1H-pyrrolo[2,3-b]pyridine-5-yl, or 1H-benzo[d]imidazol-6-yl.

In some embodiments, Cy$^{3A}$ is of any one of the following formulae:

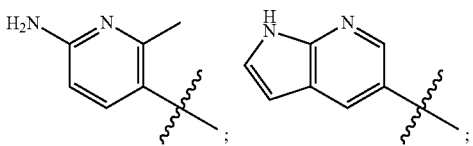

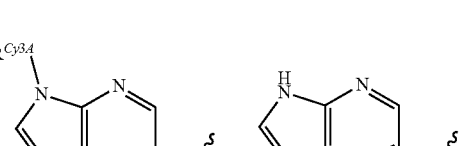

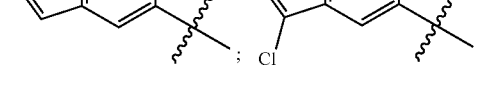

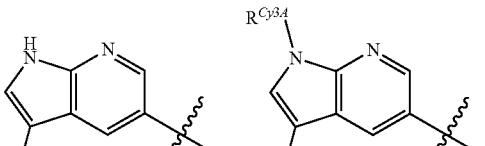

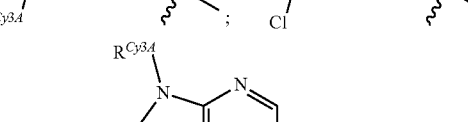

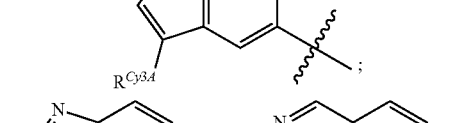

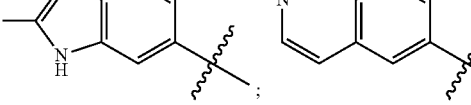

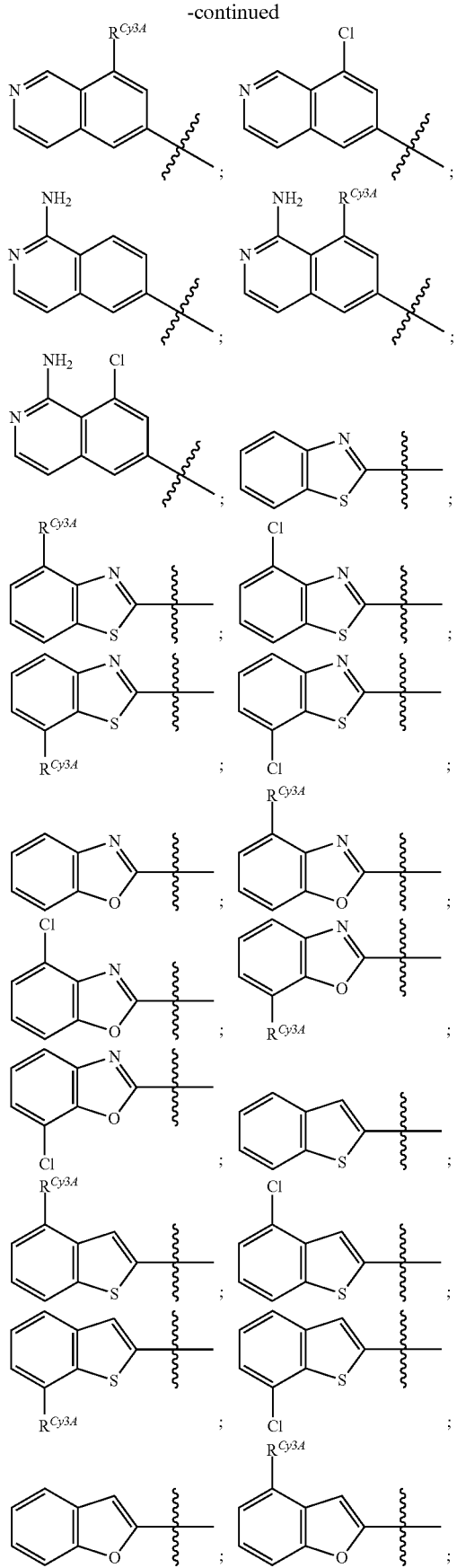
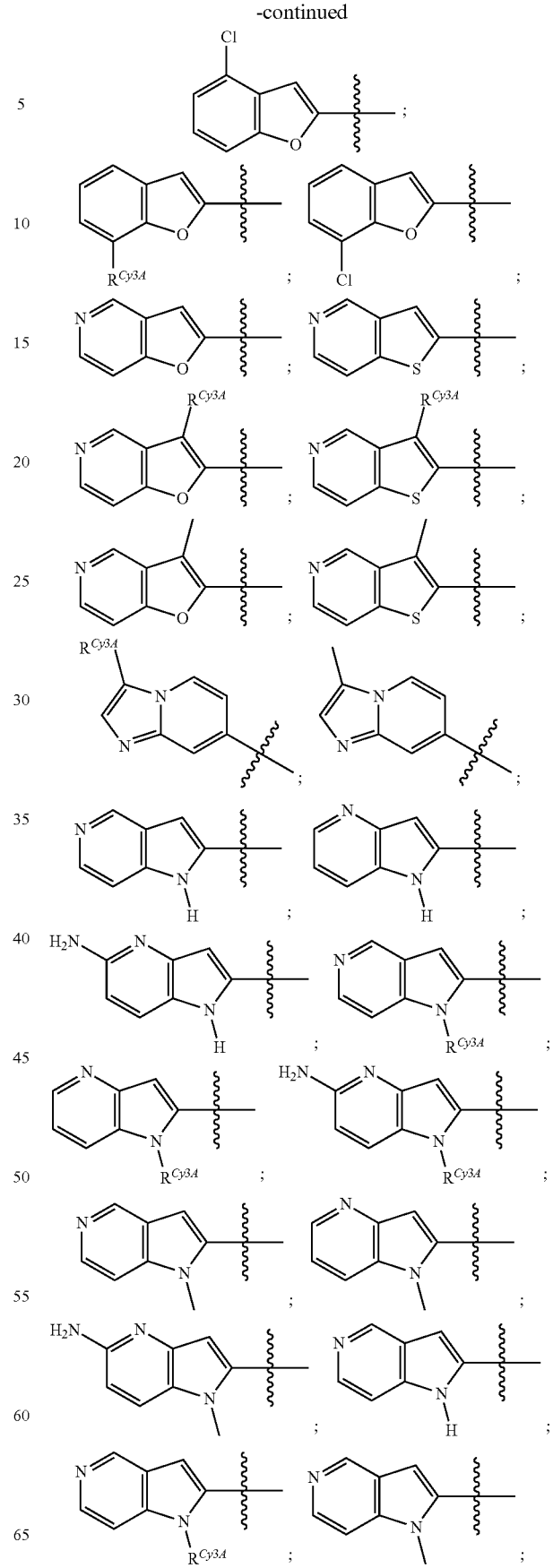

-continued
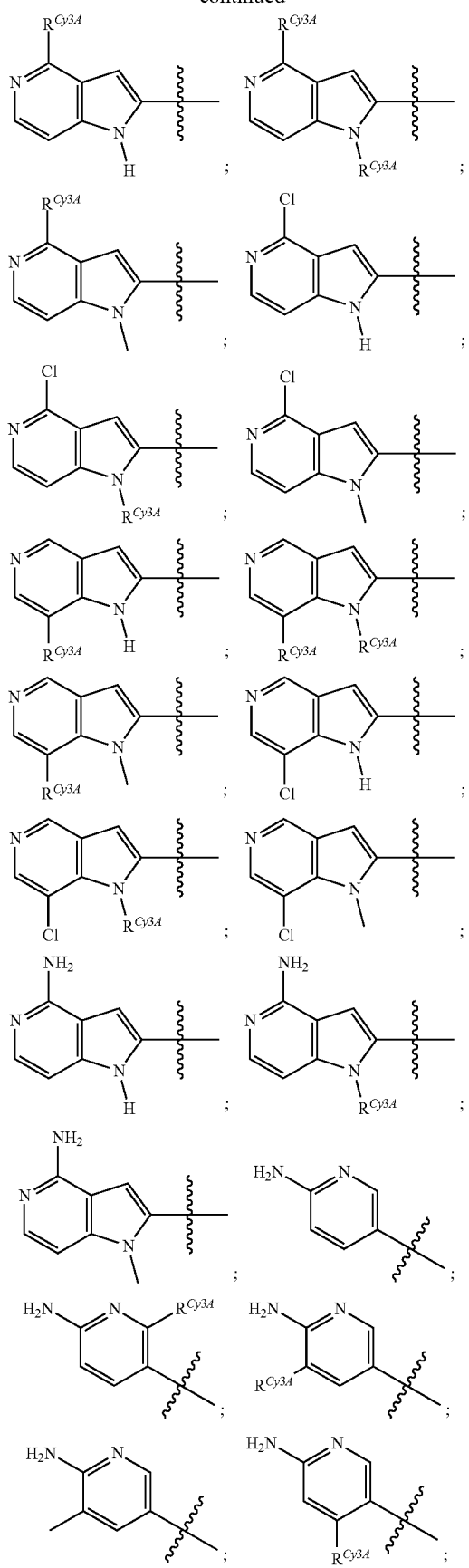
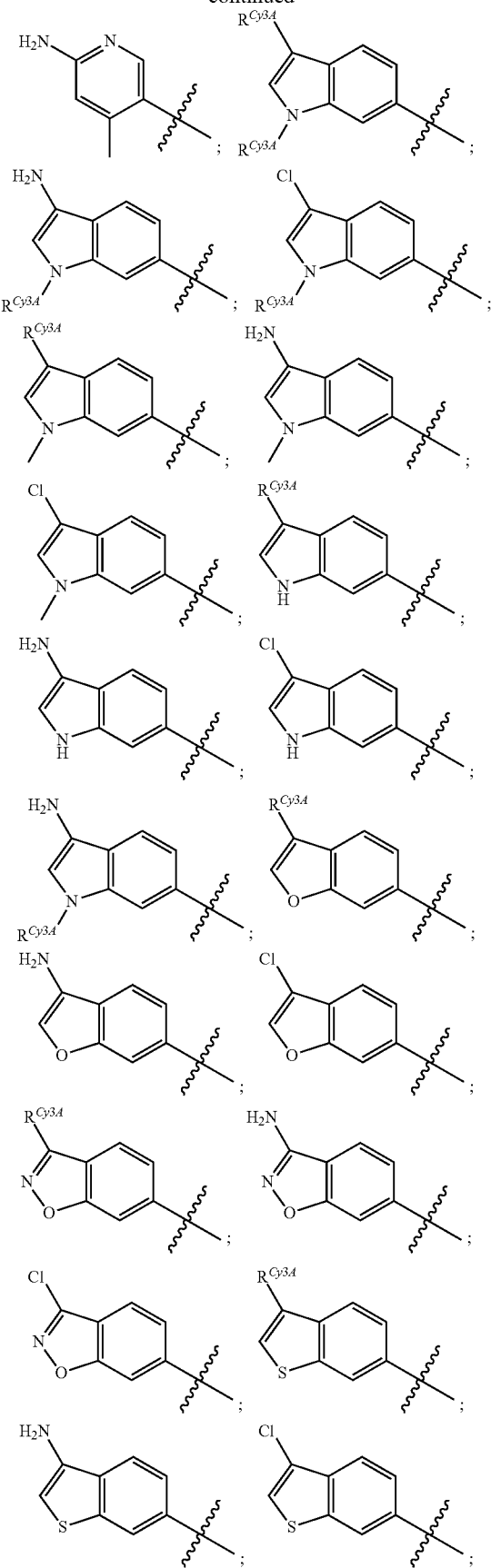

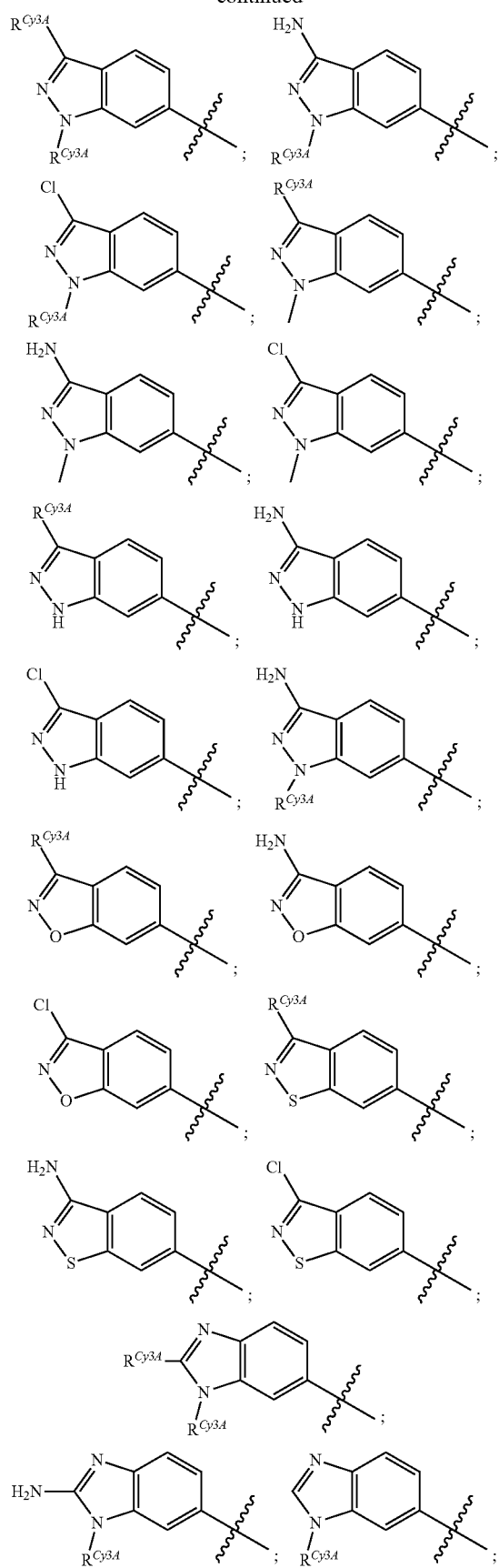
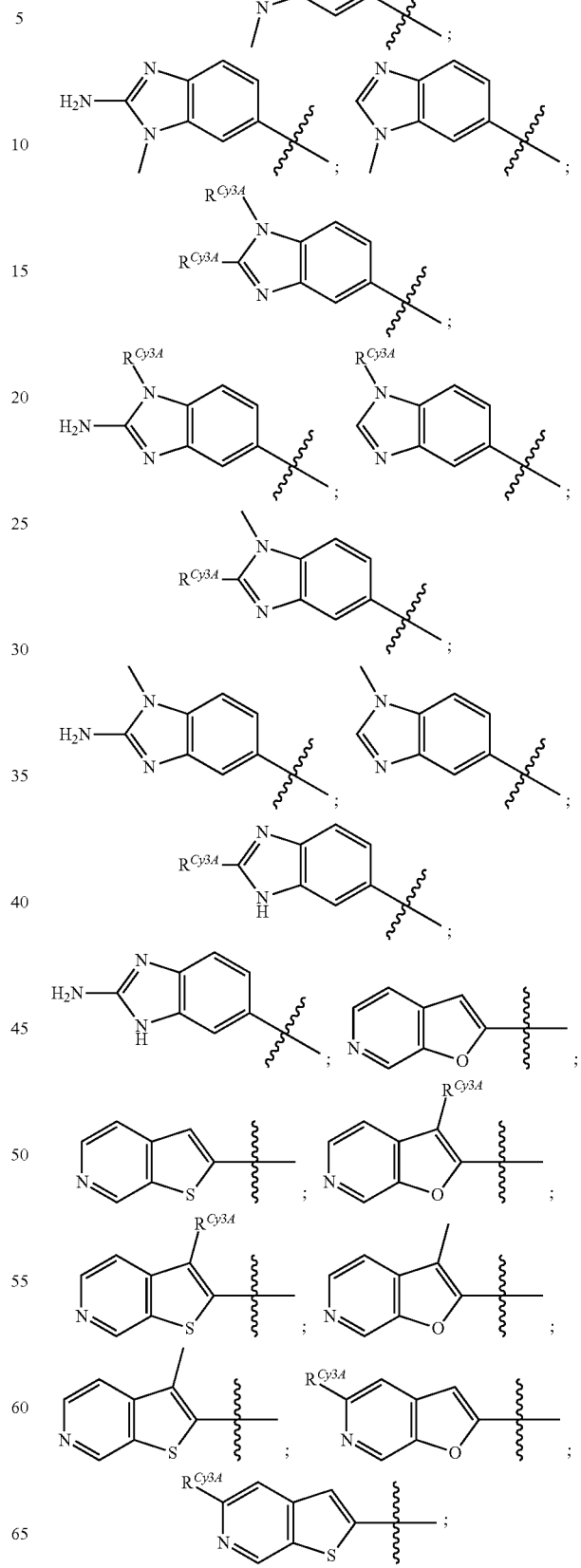

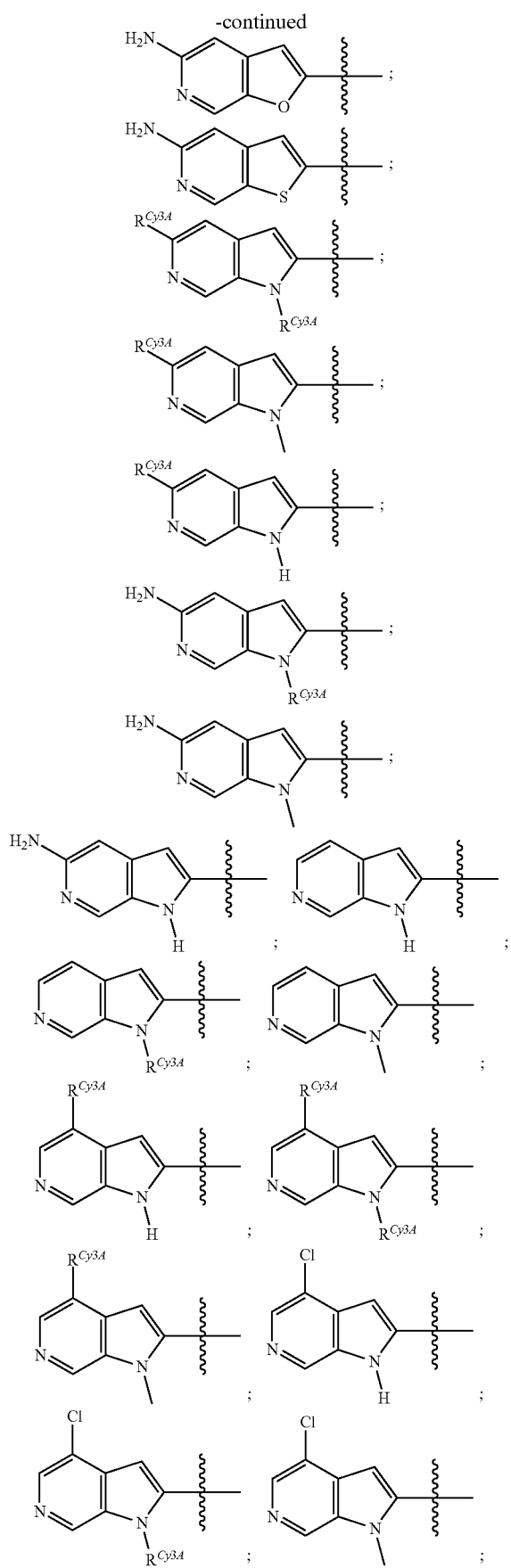
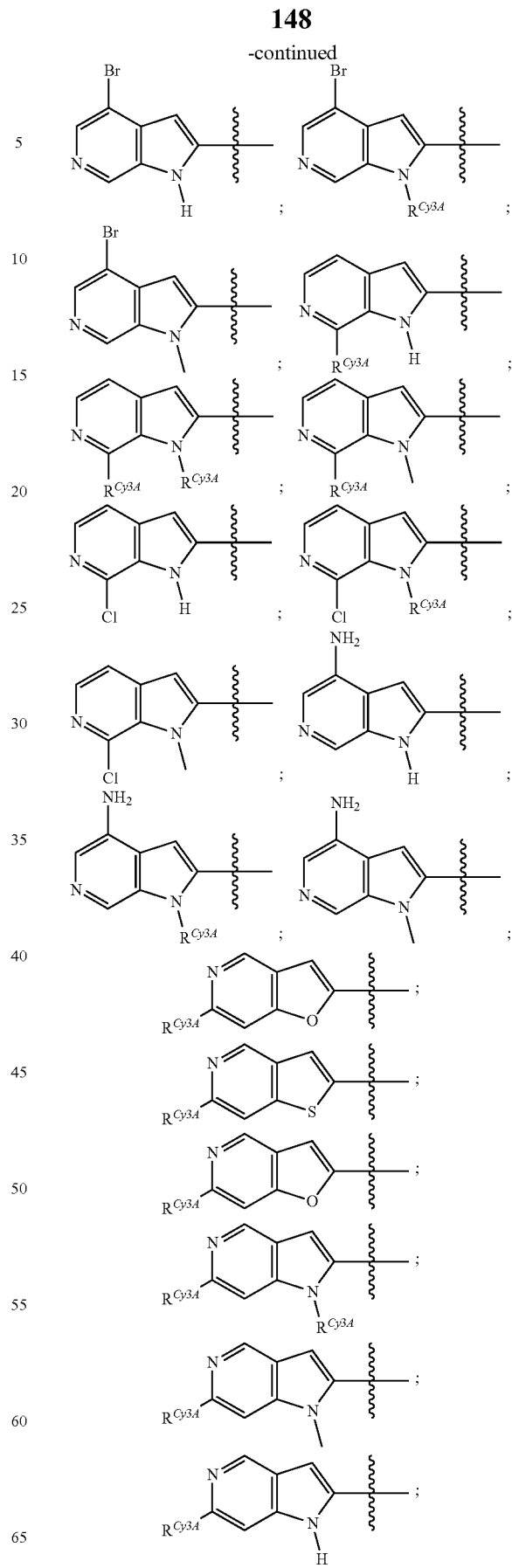

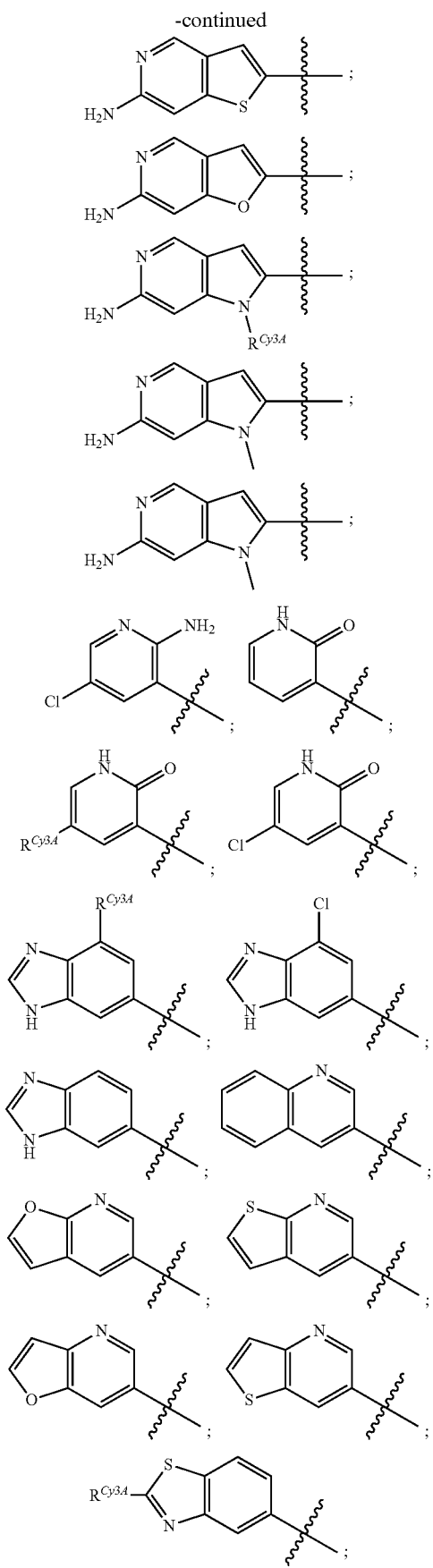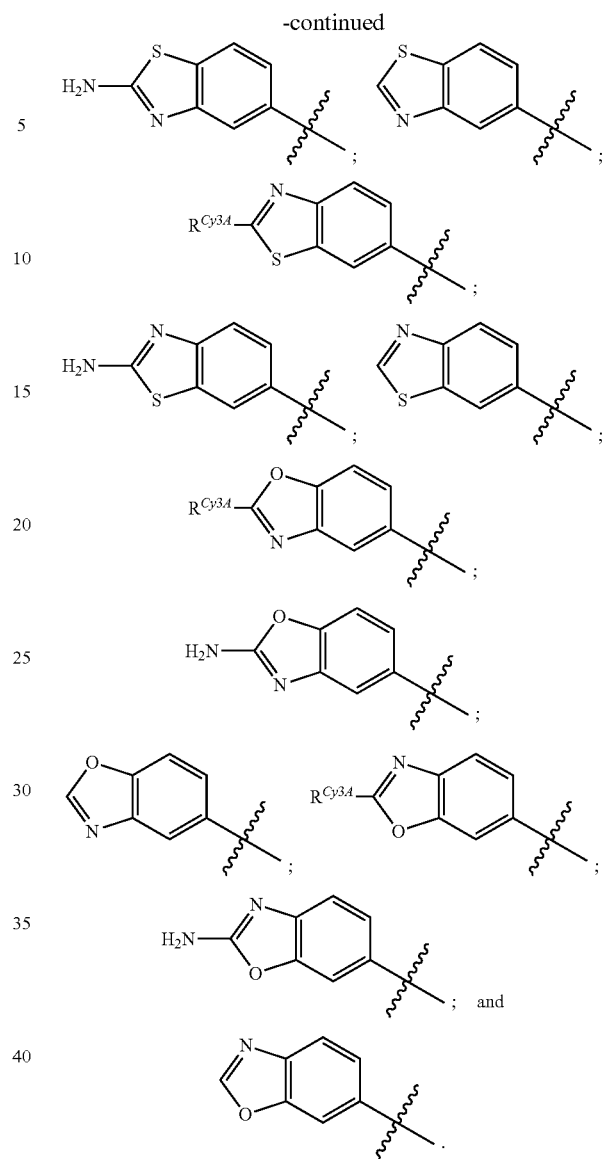

In some embodiments, each $R^{Cy3A}$ in the formula defining $Cy^{3A}$ is independently $C_{1-6}$ alkyl, such as methyl or ethyl, preferably methyl, or halogen such as F, Cl or Br, preferably Cl, or amino.

In some embodiments, each $R^{Cy3A}$ attached to nitrogen in the formula defining $Cy^{3A}$ is $C_{1-6}$ alkyl, such as methyl or ethyl.

In some embodiments, $R^{31}$ is $C_{1-6}$ alkyl.

In some embodiments, $R^{31}$ is methyl.

In some embodiments, $R^{31}$ is H.

In some embodiments, $R^{32}$ is H.

In some embodiments, $R^{32}$ is $C_{1-6}$ alkyl.

In some embodiments, $R^{32}$ is methyl.

In some embodiments, $R^{31}$ and $R^{32}$, together with the groups to which they are attached, form a 4-6 membered heterocycloalkyl ring.

In some embodiments, the compound is according to any of the following Formulae (III-1a) to (III-1h):

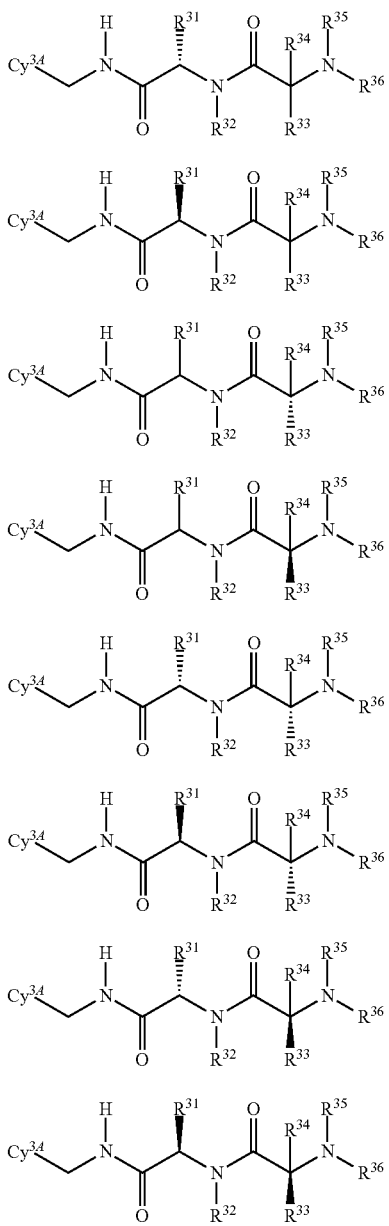

(III-1a)
(III-1b)
(III-1c)
(III-1d)
(III-1e)
(III-1f)
(III-1g)
(III-1h)

In some embodiments, $R^{33}$ is $Cy^{3B}$.

In some embodiments, $R^{33}$ is. ($C_{1-6}$ alkylene)$Cy^{3B}$, ($C_{2-6}$ alkenylene)$Cy^{3B}$, or ($C_{2-6}$ alkynylene)$Cy^{3B}$, wherein the $C_{1-6}$ alkylene, $C_{2-6}$ alkenylene, or $C_{2-6}$ alkynylene component of $R^{35}$ is unsubstituted.

In some embodiments, $R^{33}$ is ($C_{1-6}$ alkylene)$Cy^{3B}$, ($C_{2-6}$ alkenylene)$Cy^{3B}$, or ($C_{2-6}$ alkynylene)$Cy^{3B}$, wherein the $C_{1-6}$ alkylene, $C_{2-6}$ alkenylene, or $C_{2-6}$ alkynylene component of $R^{35}$ is substituted by 1, 2, 3, 4 or 5 substituents each independently selected from the group consisting of halogen, CN, $OR^{a31}$, $SR^{a31}$, $C(O)R^{b31}$, $C(O)NR^{c31}R^{d31}$, $C(O)OR^{a1}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a1}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo.

In some embodiments, $R^{33}$ is $Cy^{3B}$, $(CR^{33A}R^{33B})_{n33}Cy^{3B}$.

In some embodiments, each $R^{33A}$ is H.

In some embodiments, each $R^{33B}$ is H.

In some embodiments, n33 is 0.

In some embodiments, n33 is 1.

In some embodiments, n33 is 2.

In some embodiments, n33 is 3.

In some embodiments, $R^{33}$ is $CH_2Cy^{3B}$.

In some embodiments, $R^{33}$ is $CH_2CH_2Cy^{3B}$.

In some embodiments, the compound is according to any of the following Formulae (III-2) to (III-4):

(III-2)

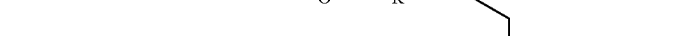

(III-3)

(III-4)


In some embodiments, the compound is according to any of the following Formulae (III-2a) to (III-2h):

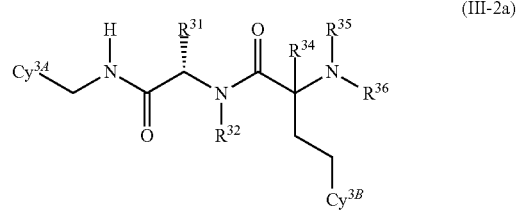

(III-2a)

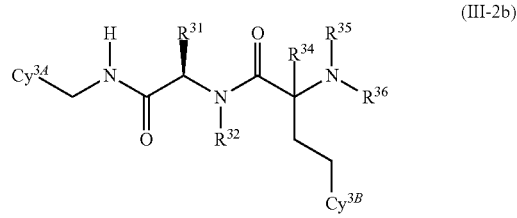

(III-2b)

(III-2c)
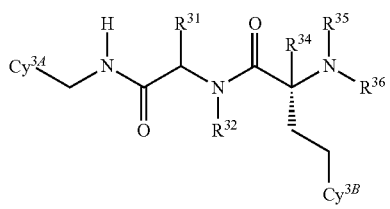
(III-2d)
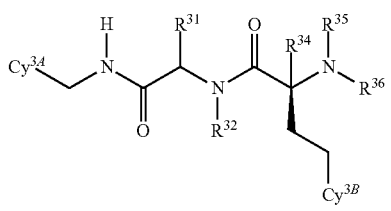
(III-2e)
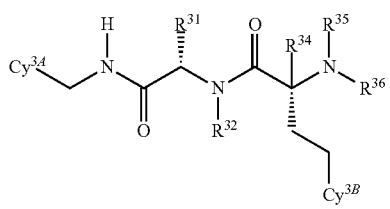
(III-2f)
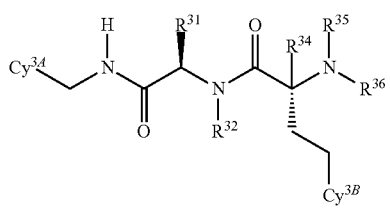
(III-2g)
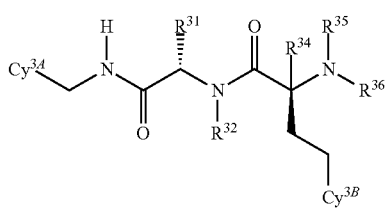
(III-2h)
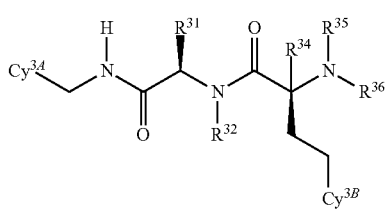
In some embodiments, the compound is according to any of the following Formulae (III-3a) to (III-3h):
(III-3a)
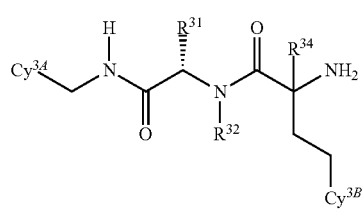
(III-3b)
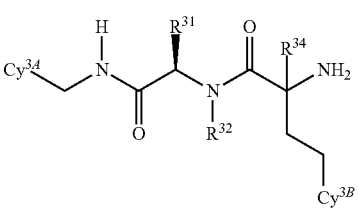
(III-3c)
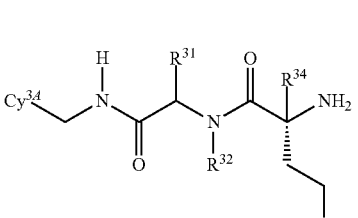
(III-3d)
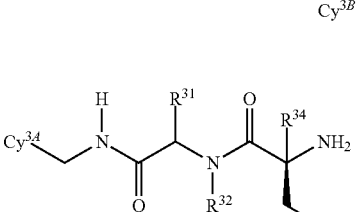
(III-3e)
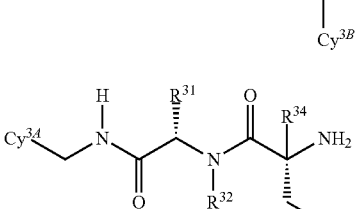
(III-3f)
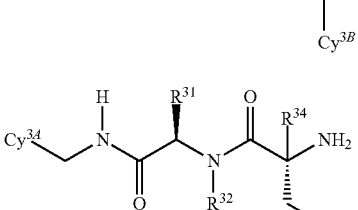
(III-3g)
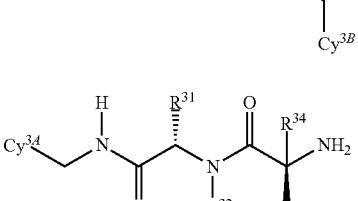
(III-3h)
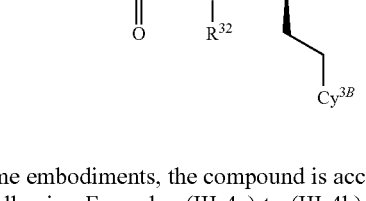
In some embodiments, the compound is according to any of the following Formulae (III-4a) to (III-4h):

(III-4a) 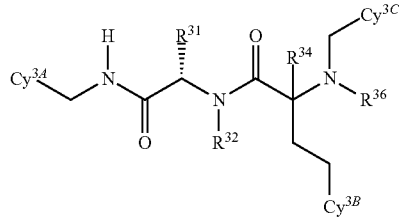

(III-4b) 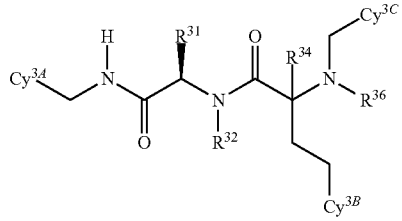

(III-4c) 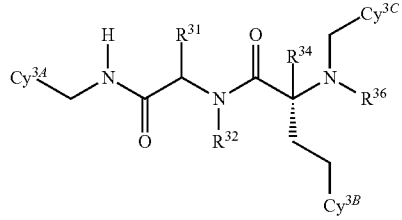

(III-4d) 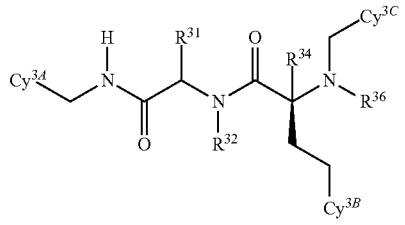

(III-4e) 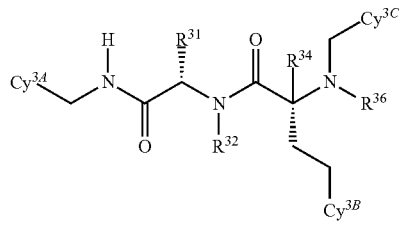

(III-4f) 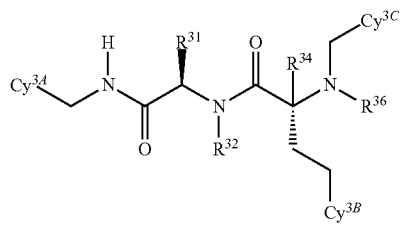

(III-4g) 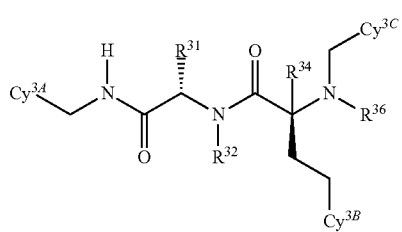

(III-4h) 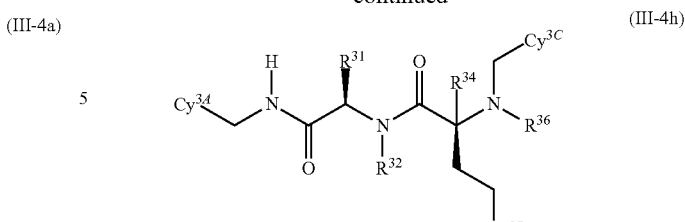

In some embodiments, $R^{33}$ is $CH_2CH_2CH_2Cy^{3B}$.

In some embodiments, $Cy^{3B}$ is unsubstituted $C_{6-10}$ aryl.

In some embodiments, $Cy^{3B}$ is unsubstituted phenyl.

In some embodiments, $R^{33}$ is $CH_2CH_2Ph$.

In some embodiments, $Cy^{3B}$ is unsubstituted naphthyl, such as 1-naphthyl or 2-naphthyl.

In some embodiments, $R^{33}$ is $CH_2CH_2$-1-naphthyl or $CH_2CH_2$-2-naphthyl.

In some embodiments, $Cy^{3B}$ unsubstituted 5-10 membered heteroaryl.

In some embodiments, $Cy^{3B}$ is unsubstituted pyridyl, such as unsubstituted 2-, 3-, or 4-pyridyl, unsubstituted quinolyl, such as unsubstituted 2-, 3-, 4-, 5-, 6-, 7-, or 8-quinolyl, unsubstituted benzo[b]thiophenyl such as unsubstituted 2-, 3-, 4-, 5-, 6-, or 7-benzo[b]thiophenyl, or unsubstituted indolyl, such as unsubstituted indol-2-yl, -3-yl, -4-yl, -5-yl, -6-yl or -7-yl.

In some embodiments, $Cy^{3B}$ unsubstituted $C_{3-10}$ cycloalkyl.

In some embodiments, $Cy^{3B}$ is unsubstituted cyclopentyl, cyclohexyl, or cycloheptyl.

In some embodiments, $Cy^{3B}$ unsubstituted 4-10 membered heterocycloalkyl.

In some embodiments, $Cy^{3B}$ is substituted $C_{6-10}$ aryl.

In some embodiments, $Cy^{3B}$ is substituted phenyl.

In some embodiments, $Cy^{3B}$ is substituted naphthyl, such as 1-naphthyl or 2-naphthyl.

In some embodiments, $Cy^{3B}$ substituted 5-10 membered heteroaryl.

In some embodiments, $Cy^{3B}$ is substituted pyridyl, such as substituted 2-, 3-, or 4-pyridyl, substituted quinolyl, such as substituted 2-, 3-, 4-, 5-, 6-, 7-, or 8-quinolyl, substituted benzo[b]thiophenyl such as substituted 2-, 3-, 4-, 5-, 6-, or 7-benzo[b]thiophenyl, or substituted indolyl, such as substituted indol-2-yl, -3-yl, -4-yl, -5-yl, -6-yl or -7-yl.

In some embodiments, $Cy^{3B}$ substituted $C_{3-10}$ cycloalkyl.

In some embodiments, $Cy^{3B}$ is substituted cyclopentyl, cyclohexyl, or cycloheptyl.

In some embodiments, $Cy^{3B}$ substituted 4-10 membered heterocycloalkyl

In some embodiments, $Cy^{3B}$ is substituted with 1, 2, 3, 4 or 5 substituents each independently selected from $R^{Cy3B}$, halogen, and $C_{1-6}$ haloalkyl; wherein each $R^{Cy3B}$ is independently selected from $C_{1-6}$ alkyl, $C_{2-6}$ alkenyl, $C_{2-6}$ alkynyl and $C_{6-10}$ aryl or 5-10 membered heteroaryl, wherein each $C_{6-10}$ aryl or 5-10 membered heteroaryl forming $R^{Cy3B}$ is unsubstituted or substituted with 1, 2 or 3 substituents independently selected from halogen, $C_{1-6}$ alkyl, $C_{2-6}$ alkenyl, $C_{2-6}$ alkynyl, and haloalkyl.

In some embodiments, $R^{33}$ is selected from the following groups: phenyl; benzyl; 2-phenylethyl; 2,3-dihydro-1H-inden-2-yl; 2-(2-methylphenyl)ethyl; 2-(3-methylphenyl) ethyl; 2-(4-methylphenyl)ethyl; 2-(2,4-dimethylphenyl) ethyl; 2-(2,5-dimethylphenyl)ethyl; 2-(3,5-dimethylphenyl) ethyl; 2-(2-ethylphenyl)ethyl; 2-(3-ethylphenyl)ethyl; 2-(4- ethylphenyl)ethyl; 2-(2,4-diethylphenyl)ethyl; 2-(2,5-dimethylphenyl)ethyl; 2-(3,5-dimethylphenyl)ethyl; 2-(2-trifluoromethylphenyl)ethyl; 2-(3-trifluoromethylphenyl)ethyl; 2-(4-trifluoromethylphenyl)ethyl; 2-(2-fluorophenyl)ethyl; 2-(3-fluorophenyl)ethyl; 2-(4-fluorophenyl)ethyl; 2-(2,4-difluorophenyl)ethyl; 2-(2,5-difluorophenyl)ethyl; 2-(3,5-difluorophenyl)ethyl; 2-(2-chlorophenyl)ethyl; 2-(3-chlorophenyl)ethyl; 2-(4-chlorophenyl)ethyl; 2-(2,4-dichlorophenyl)ethyl; 2-(2,5-dichlorophenyl)ethyl; 2-(3,5-dichlorophenyl)ethyl; 2-(2-methoxyphenyl)ethyl; 2-(3-methoxyphenyl)ethyl; 2-(4-methoxyphenyl)ethyl; 2-(2,4-dimethoxyphenyl)ethyl; 2-(2,5-dimethoxyphenyl)ethyl; 2-(3,5-dimethoxyphenyl)ethyl; 2-(cyclopentyl)ethyl; 2-(cyclohexyl)ethyl; 2-(cycloheptyl)ethyl; 2-(2-(aminomethyl)phenyl)ethyl; 2-(3-(aminomethyl)phenyl)ethyl; 2-(4-(aminomethyl)phenyl)ethyl; 2-(2-cyanophenyl)ethyl; 2-(3-cyanophenyl)ethyl; and 2-(4-cyanophenyl)ethyl; and groups of the following formulae:

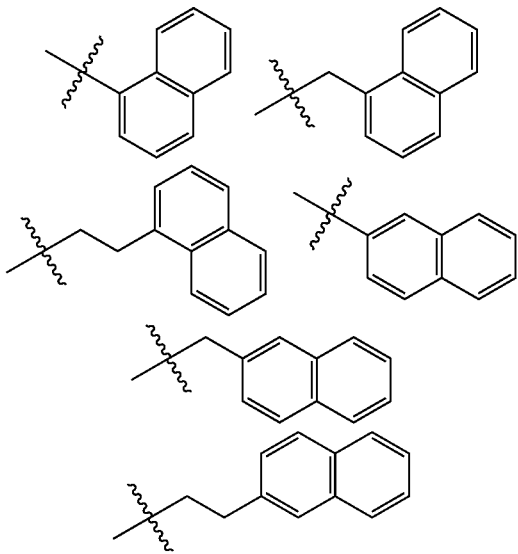

In some embodiments, $R^{34}$ is hydrogen.
In some embodiments, $R^{34}$ is $C_{1-6}$ alkyl, such as methyl.
In some embodiments, $R^{35}$ is H.
In some embodiments, $R^{35}$ is $Cy^{3C}$.
In some embodiments, $R^{35}$ is unsubstituted $C_{1-6}$ alkyl.
In some embodiments, $R^{35}$ is substituted $C_{1-6}$ alkyl.
In some embodiments, the substituted $C_{1-6}$ alkyl forming $R^{35}$ is substituted by at least one substituent, wherein the substituents of $R^{35}$ are independently selected from: 1, 2, or 3 substituents selected from the group consisting of $Cy^{3C}$, halogen, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo.
In some embodiments, the substituted $C_{1-6}$ alkyl forming $R^{35}$ is substituted by at least one substituent, wherein the substituents include $Cy^{3C}$.
In some embodiments, the substituted $C_{1-6}$ alkyl forming $R^{35}$ is substituted by one substituent, wherein the substituent is $Cy^{3C}$.
In some embodiments, $R^{35}$ is $(CH_2)_{1-5}Cy^{3C}$.
In some embodiments, $R^{35}$ is $CH_2Cy^{3C}$.

In some embodiments, $Cy^{3C}$ is unsubstituted $C_{6-10}$ aryl.
In some embodiments, $Cy^{3C}$ is unsubstituted phenyl or naphthyl, such as 1-naphthyl or 2-naphthyl.
In some embodiments, $Cy^{3C}$ is unsubstituted 5-10 membered heteroaryl.
In some embodiments, $Cy^{3C}$ is unsubstituted pyridyl, such as unsubstituted 2-, 3-, or 4-pyridyl, unsubstituted quinolyl, such as unsubstituted 2-, 3-, 4-, 5-, 6-, 7-, or 8-quinolyl, unsubstituted benzo[b]thiophenyl such as unsubstituted 2-, 3-, 4-, 5-, 6-, or 7-benzo[b]thiophenyl, or unsubstituted indolyl, such as unsubstituted indol-2-yl, -3-yl, -4-yl, -5-yl, -6-yl or -7-yl.
In some embodiments, $Cy^{3C}$ is unsubstituted $C_{3-10}$ cycloalkyl, such as cyclopropyl, cyclobutyl, cyclopentyl, cyclohexyl, or cycloheptyl.
In some embodiments, $Cy^{3C}$ is unsubstituted 4-10 membered heterocycloalkyl.
In some embodiments, $Cy^{3C}$ is substituted $C_{6-10}$ aryl.
In some embodiments, $Cy^{3C}$ is substituted phenyl, or substituted naphthyl, such as substituted 1-naphthyl or 2-naphthyl.
In some embodiments, $Cy^{3C}$ substituted 5-10 membered heteroaryl.
In some embodiments, $Cy^{3C}$ is substituted pyridyl, such as substituted 2-, 3-, or 4-pyridyl, substituted quinolyl, such as substituted 2-, 3-, 4-, 5-, 6-, 7-, or 8-quinolyl, substituted benzo[b]thiophenyl such as substituted 2-, 3-, 4-, 5-, 6-, or 7-benzo[b]thiophenyl, or substituted indolyl, such as substituted indol-2-yl, -3-yl, -4-yl, -5-yl, -6-yl or -7-yl.
In some embodiments, $Cy^{3C}$ is substituted $C_{3-10}$ cycloalkyl such as substituted cyclopropyl, cyclobutyl, cyclopentyl, cyclohexyl, or cycloheptyl.
In some embodiments, $Cy^{3C}$ is substituted 4-10 membered heterocycloalkyl.
In some embodiments, $R^{36}$ is H.
In some embodiments, $R^{36}$ is $C_{1-6}$ alkyl such as methyl.
In some embodiments, $R^{a31}$, $R^{b31}$, $R^{c31}$, $R^{d31}$, $R^{a32}$, $R^{b32}$, $R^{c32}$ and $R^{d32}$ are each independently selected from H and $C_{1-6}$ alkyl.
In some embodiments, each $R^{e31}$ and each $R^{e32}$ is H.
The compounds of Formula (III), and embodiments thereof, are useful as inhibitors of MASP-2 and for therapeutic use.
In some embodiments, the compounds of Formula (III), and embodiments thereof, can be in the form of a salt such as a pharmaceutically acceptable salt.
The compounds of Formula (III), and embodiments thereof, are useful as inhibitors of MASP-2 and for therapeutic use. The compounds of Formula (III), and embodiments thereof, are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Formula (III), or an embodiment thereof, optionally in the form of a salt.
In some embodiments the compound Formula (III) or an embodiment thereof is provided in the form of a pharmaceutical composition comprising the compound or a salt thereof, such as a pharmaceutically acceptable salt, and at least one pharmaceutically acceptable carrier or excipient.
In certain aspects, the compound is one or more selected from the compounds of Formula (III) set forth in the Examples, including the compounds listed in Table 31, e.g., the compounds with selectivity for MASP-2 over thrombin.
In certain aspects, one or more of the variables defining the compounds of Formula (III) (such as $Cy^{3A}$, $R^{Cy3A}$ $Cy^{3B}$, $R^{Cy3B}$, $Cy^{3C}$, $R^{Cy3C}$, $R^{31}$, $R^{32}$, $R^{33}$, $R^{33A}$, $R^{33B}$, $R^{34}$, $R^{35}$, $R^{36}$, n33, $R^{a31}$, $R^{b31}$, $R^{c31}$, $R^{d31}$, $R^{e31}$, $R^{a32}$, $R^{b32}$, $R^{c32}$, $R^{d32}$ and $R^{e32}$) is selected from the corresponding substituents in the compounds of Formula (III) of the Examples, including the compounds listed in Table 31, preferably, those of the compounds with selectivity for MASP-2 over thrombin.

In certain aspects, the invention sets forth a stereochemically pure enantiomer or diastereomer (e.g., an optically active compound with one or more chiral centers). Unless specifically indicated otherwise, for any inventive compound with one or more stereocenters, the present invention is intended to include and to describe both the pure (+) and (−) enantiomers, any other diastereomers, mixtures that are enriched in an enantiomer or diastereomer (e.g., 10%, 20%, 30%, 40%, 50%, 60%, 70% 75%, 80%, 85, 90%, or 95% enantiomeric or diastereomeric excess), and a racemic mixture of enantiomers or diastereomers.

In certain aspects, the invention sets forth a pharmaceutically acceptable salt of the indicated chemical structure (e.g., a hydrohalide, such as a hydrochloride or dihydrochloride). Examples of pharmaceutically acceptable salts are set forth in, e.g., Burge, S. M. et al., J. Pharm. Sci 1977, 66, 1-19. They include chlorides, bromides, iodides, formates, acetates, propionates, oxalates, malonates, succinates, fumarates, maleates, tartrates, citrates, benzoates, phthalates, sulfonates, arylsulfonates, alkylsulfonates, salts of fatty acids, and the like. Salts can be prepared by a variety of methods known to the skilled artisan, including a precipitation with the conjugate acid or base (e.g., treatment with gaseous HCl or an HCl solution).

In certain aspects, the invention sets forth a prodrug. A prodrug is a compound that is converted to a biologically active form under physiological conditions, often by hydrolysis, oxidation, or reduction (e.g., ester to acid form; carbamate to amino or hydroxy group; hydroxyamidine to amidine) Exemplary prodrugs are set forth in, e.g., Tilley, J. W., "Prodrugs of Benzamide," Prodrugs 2007, 191-222; Peterlin-Masic et al. Curr. Pharma. Design 2006, 12, 73-91. Prodrugs for the amidine group include amidoximes, O-alkylamidoximes, acylamidines, carbamates, 1,2,4-oxadiazolin-4-ones, and the like.

In certain aspects, the compound is useful for selectively inhibiting MASP-2 over thrombin, the method comprising administering the compound as described herein. In certain aspects, the selectivity ratio of MASP-2:thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

D. Compounds of Formula IV

In certain aspects, the present disclosure provides a compound of Formula (IV).

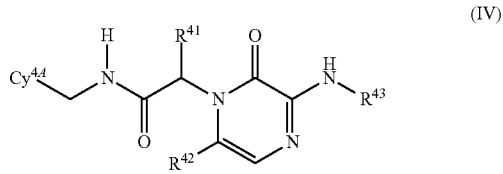

(IV)

or a salt thereof, for use in treating a MASP-2-associated disease or disorder, wherein:

$Cy^{4A}$ is unsubstituted or substituted $C_{6-10}$ aryl or unsubstituted or substituted 5-10 membered heteroaryl; wherein the ring atoms of the 5-10 membered heteroaryl forming $Cy^{4A}$ consist of carbon atoms and 1, 2, or 3 heteroatoms selected from O, N and S; wherein the substituted $C_{6-10}$ aryl or substituted 5-10 membered heteroaryl forming $Cy^{4A}$ are substituted with 1, 2, 3, 4 or 5 substituents each independently selected from $R^{Cy4A}$, halogen, $C_{1-6}$ haloalkyl, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $C(=NOR^{a41})NR^{c41}R^{d41}$, $C(=NOC(O)R^{b41})NR^{c41}R^{d41}$, $C(=NR^{e41})NR^{c41}C(O)OR^{a41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo;

each $R^{Cy4A}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10-membered heterocycloalkyl forming $R^{Cy4A}$ consist of carbon atoms and 1, 2, 3 or 4 heteroatoms selected from O, N and S, wherein each $C_{1-6}$ alkyl, $C_{2-6}$ alkenyl, or $C_{2-6}$ alkynyl forming $R^{Cy4A}$ is independently unsubstituted or substituted with 1, 2 or 3 substituents independently selected from halogen, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo, and wherein each $C_{6-10}$ aryl, 5-10 membered heteroaryl, $C_{3-10}$ cycloalkyl and 4-10 membered heterocycloalkyl forming $R^{Cy4A}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo;

$R^{41}$ is H or $C_{1-6}$ alkyl, $C_{6-10}$ aryl-$C_{1-6}$ alkyl or 5-10 membered heteroaryl-$C_{1-6}$ alkyl, wherein the $C_{1-6}$ alkyl forming $R^{41}$ is unsubstituted or substituted by 1, 2 or 3 substituents independently selected from halogen, CN, $OR^{a41}$, $SR^{a41}$, $C(O)R^{11}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo, and wherein the $C_{6-10}$ aryl-$C_{1-6}$ alkyl or 5-10 membered heteroaryl-$C_{1-6}$ alkyl forming $R^{41}$ is unsubstituted or substituted by 1, 2 or 3 substituents independently selected from $C_{1-6}$ alkyl, $C_{2-6}$ alkenyl, $C_{2-6}$ alkynyl, $C_{1-6}$ haloalkyl, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b11}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo;

$R^{42}$ is H, $C_{1-6}$ alkyl, $C_{2-6}$ alkenyl, $C_{2-6}$ alkynyl, or $Cy^{4B}$; wherein each of the $C_{1-6}$ alkyl, $C_{2-6}$ alkenyl, or $C_{2-6}$ alkynyl, forming $R^{42}$ is unsubstituted or substituted by 1, 2, 3, 4 or 5 substituents selected from the group consisting of $Cy^{4B}$, halogen, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b1}$, $S(O)NR^{c41}R^{d41}$, $S(O)_2R^{b41}$, $NR^{c41}S(O)_2R^{b41}$, $S(O)_2NR^{c41}R^{d41}$ and oxo; provided that no more than one of the substituents is $Cy^{4B}$;

$Cy^{4B}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl; wherein the ring atoms of the 5-10 membered heteroaryl or unsubstituted or substituted 4-10 membered heterocycloalkyl forming $Cy^{4B}$ consist of carbon atoms and 1, 2 or 3 heteroatoms selected from O, N and S; and wherein the substituted $C_{6-10}$ aryl, substituted 5-10 membered heteroaryl substituted $C_{3-10}$ cycloalkyl, or 4-10 membered heterocycloalkyl forming $Cy^{4B}$ is substituted with 1, 2, 3, 4 or 5 substituents each independently selected from $R^{Cy4B}$, halogen, $C_{1-6}$ haloalkyl, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $C(=NOR^{a41})NR^{c41}R^{d41}$, $C(=NOC(O)R^{b41})NR^{c41}R^{d41}$, $C(=NR^{e41})NR^{c41}C(O)OR^{a41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo;

wherein each $R^{Cy4B}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10-membered heterocycloalkyl forming $R^{Cy4B}$ consist of carbon atoms and 1, 2, or 3 heteroatoms selected from O, N and S, and wherein each $C_{1-6}$ alkyl, $C_{2-6}$ alkenyl, or $C_{2-6}$ alkynyl forming $R^{Cy4B}$ is independently unsubstituted or substituted with 1, 2 or 3 substituents independently selected from halogen, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)$ $NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo; and each $C_{6-10}$ aryl, 5-10 membered heteroaryl, $C_{3-10}$ cycloalkyl and 4-10 membered heterocycloalkyl forming each $R^{Cy4B}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo;

or $R^{41}$ and $R^{42}$, together with the atoms to which they are attached and the nitrogen atom linking the atoms to which $R^{41}$ and $R^{42}$ are attached, form a 4-7 membered heterocycloalkyl ring; which is optionally further substituted by 1, 2, 3, 4 or 5 substituents each independently selected from $R^{Cy4B}$, halogen, $C_{1-6}$ haloalkyl, CN, $OR^{a41}$, $SR^{a41}$, $C(O)R^{b1}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $C(=NOR^{a41})NR^{c41}R^{d41}$, $C(=NOC(O)R^{b41})NR^{c41}R^{d41}$, $C(=NR^{e41})NR^{c41}C(O)OR^{a41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo;

$R^{43}$ is H, $C_{1-6}$ alkyl, $C_{2-6}$ alkenyl, $C_{2-6}$ alkynyl, or $Cy^{4C}$; wherein each of the $C_{1-6}$ alkyl, $C_{2-6}$ alkenyl, or $C_{2-6}$ alkynyl forming $R^{43}$ is unsubstituted or substituted by 1, 2, 3, 4 or 5 substituents each independently selected from: 0, 1, 2, 3, 4 or 5 substituents selected from the group consisting of $Cy^{4C}$, halogen, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo, provided that no more than one substituent of the $C_{1-6}$ alkyl, $C_{2-6}$ alkenyl, or $C_{2-6}$ alkynyl forming $R^{43}$ is $Cy^{4C}$;

$Cy^{4C}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl; wherein the ring atoms of the 5-10 membered heteroaryl or unsubstituted or substituted 4-10 membered heterocycloalkyl forming $Cy^{4B}$ consist of carbon atoms and 1, 2 or 3 heteroatoms selected from O, N and S; and wherein the substituted $C_{6-10}$ aryl, substituted 5-10 membered heteroaryl substituted $C_{3-10}$ cycloalkyl, or 4-membered heterocycloalkyl forming $Cy^{4C}$ is substituted with 1, 2, 3, 4 or 5 substituents each independently selected from $R^{Cy4C}$, halogen, $C_{1-6}$ haloalkyl, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $C(=NOR^{a41})NR^{c41}R^{d41}$, $C(=NOC(O)R^{b41})NR^{c41}R^{d41}$, $C(=NR^{e41})NR^{c41}C(O)OR^{a41}$, $NR^{c41}C(=NR^{e41})NR^{c41}R^{d41}$, $S(O)R^{c41}$, $S(O)NR^{c41}R^{d41}$, $S(O)_2R^{b41}$, $NR^{c41}S(O)_2R^{b41}$, $S(O)_2NR^{c41}R^{d41}$ and oxo;

each $R^{Cy4C}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10-membered heterocycloalkyl forming $R^{Cy4C}$ consist of carbon atoms and 1, 2, or 3 heteroatoms selected from O, N and S, wherein each $C_{1-6}$ alkyl, $C_{2-6}$ alkenyl, or $C_{2-6}$ alkynyl forming $R^{Cy4C}$ is independently unsubstituted or substituted with 1, 2 or 3 substituents independently selected from halogen, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo; and wherein each $C_{6-10}$ aryl, 5-10 membered heteroaryl, $C_{3-10}$ cycloalkyl and 4-10 membered heterocycloalkyl forming each $R^{Cy4A}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, NR$^{c41}$C(=NR$^{e41}$)NR$^{c41}$R$^{d41}$, S(O)R$^{b41}$, S(O)NR$^{c41}$R$^{d41}$, S(O)$_2$R$^{b41}$, NR$^{c41}$S(O)$_2$R$^{11}$, S(O)$_2$NR$^{c41}$R$^{d41}$ and oxo;

R$^{a41}$, R$^{b41}$, R$^{c41}$ and R$^{d41}$ are each independently selected from H, C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl forming R$^{a41}$, R$^{b41}$, R$^{c41}$ and R$^{d41}$ are each optionally substituted with 1, 2, 3, 4 or 5 substituents independently selected from C$_{1-6}$ alkyl, halo, CN, OR$^{a42}$, SR$^{a42}$, C(O)R$^{42}$, C(O)NR$^{c42}$R$^{d42}$, C(O)OR$^{a42}$, OC(O)R$^{b42}$, OC(O)NR$^{c42}$R$^{d42}$, NR$^{c42}$R$^{d42}$, NR$^{c42}$C(O)R$^{b42}$, NR$^{c42}$C(O)NR$^{c42}$R$^{d42}$, NR$^{c42}$C(O)OR$^{a42}$, C(=NR$^{e42}$)NR$^{c42}$R$^{d42}$, NR$^{c42}$C(=NR$^{e42}$)NR$^{c42}$R$^{d42}$, S(O)R$^{b42}$, S(O)NR$^{c42}$R$^{d42}$, S(O)$_2$R$^{b42}$, NR$^{c42}$S(O)$_2$R$^{b42}$, S(O)$_2$NR$^{c42}$R$^{d42}$ and oxo;

or R$^{c41}$ and R$^{d41}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from C$_{1-6}$ alkyl, halo, CN, OR$^{a42}$, SR$^{a42}$, C(O)R$^{b42}$, C(O)NR$^{c42}$R$^{d42}$, C(O)OR$^{a42}$, OC(O)R$^{b42}$, OC(O)NR$^{c42}$R$^{d42}$, NR$^{c42}$R$^{d42}$, NR$^{c42}$C(O)R$^{b42}$, NR$^{c42}$C(O)NR$^{c42}$R$^{d42}$, NR$^{c42}$C(O)OR$^{a42}$, C(=NR$^{e42}$)NR$^{c42}$R$^{d42}$, NR$^{c42}$C(=NR$^{e42}$)NR$^{c42}$R$^{d42}$, S(O)R$^{b42}$, S(O)NR$^{c42}$R$^{d42}$, S(O)$_2$R$^{b42}$, NR$^{c42}$S(O)$_2$R$^{b42}$, S(O)$_2$NR$^{c42}$R$^{d42}$ and oxo;

R$^{a42}$, R$^{b42}$, R$^{c42}$ and R$^{d42}$ are each independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-3}$ alkyl, 5-6 membered heteroaryl-C$_{1-3}$ alkyl, C$_{3-7}$ cycloalkyl-C$_{1-3}$ alkyl and 4-7 membered heterocycloalkyl-C$_{1-3}$ alkyl, wherein said C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-3}$ alkyl, 5-6 membered heteroaryl-C$_{1-3}$ alkyl, C$_{3-7}$ cycloalkyl-C$_{1-3}$ alkyl and 4-7 membered heterocycloalkyl-C$_{1-3}$ alkyl forming R$^{a42}$, R$^{b42}$, R$^{c42}$ and R$^{d42}$ are each optionally substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl, C$_{1-6}$ haloalkoxy and oxo;

or R$^{c42}$ and R$^{d42}$ attached to the same N atom, together with the N atom to which they are both attached, form a 4-, 5-, 6- or 7-membered heterocycloalkyl group or 5-membered heteroaryl group, each of which is unsubstituted or substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl, C$_{1-6}$ haloalkoxy and oxo; and R$^{e41}$ and R$^{e42}$ are each, independently, H, CN or NO$_2$.

In some embodiments, Cy$^{4A}$ is unsubstituted or substituted aryl.

In some embodiments, Cy$^{4A}$ is unsubstituted or substituted phenyl.

In some embodiments, Cy$^{4A}$ is substituted phenyl.

In some embodiments, Cy$^{4A}$ is substituted with at least one OR$^{a41}$ or at least one C(=NR$^{e41}$)NR$^{c41}$R$^{d41}$, C(=NOR$^{a41}$)NR$^{c41}$R$^{d41}$, C(=NOC(O)R$^{b41}$)NR$^{c41}$R$^{d41}$, or C(=NR$^{e41}$)NR$^{c41}$C(O)OR$^{a41}$.

In some embodiments, Cy$^{4A}$ is substituted with at least one OR$^{a41}$ and by at least one additional substituent selected from the group consisting of C$_{1-6}$ alkyl, C$_{1-6}$ haloalkyl and halogen.

In some embodiments, Cy$^{4A}$ is substituted with at least one OH and by at least one additional substituent selected from the group consisting of C$_{1-6}$ alkyl, C$_{1-6}$ haloalkyl and halogen.

In some embodiments, Cy$^{4A}$ is substituted with at least one C(=NR$^{e41}$)NR$^{c41}$R$^{d41}$, C(=NOR$^{a41}$)NR$^{c41}$R$^{d41}$, C(=NOC(O)R$^{b41}$)NR$^{c41}$R$^{d41}$, C(=NR$^{e41}$)NR$^{c41}$C(O)OR$^{a41}$, preferably in the 4-position.

In some embodiments, Cy$^{4A}$ is substituted with at least one C(=NR$^{e41}$)NR$^{c41}$R$^{d41}$, such as C(=NH)NH$_2$, preferably in the 4-position.

In some embodiments, Cy$^{4A}$ is of any one of the following formulae:

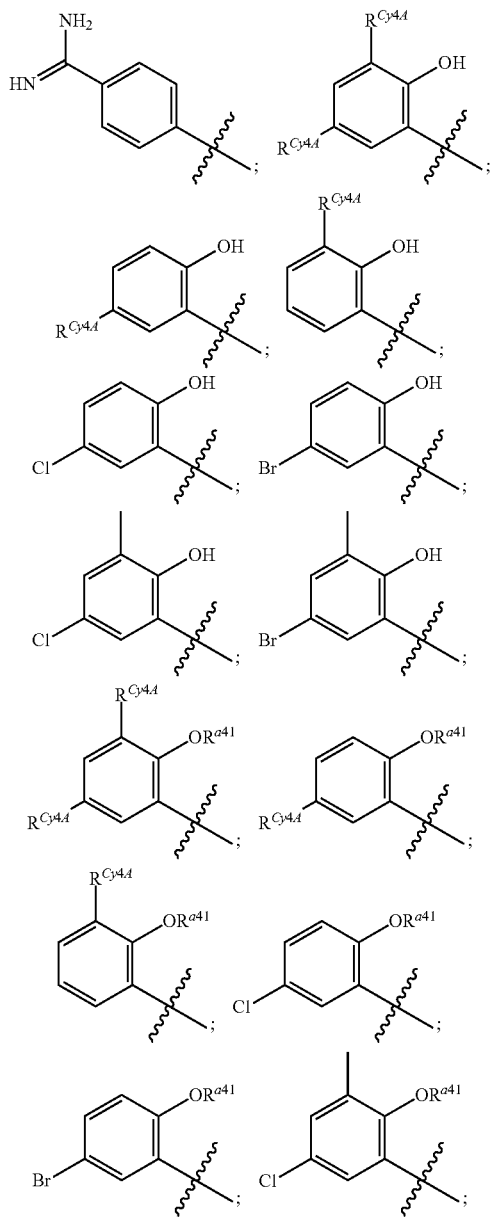

-continued

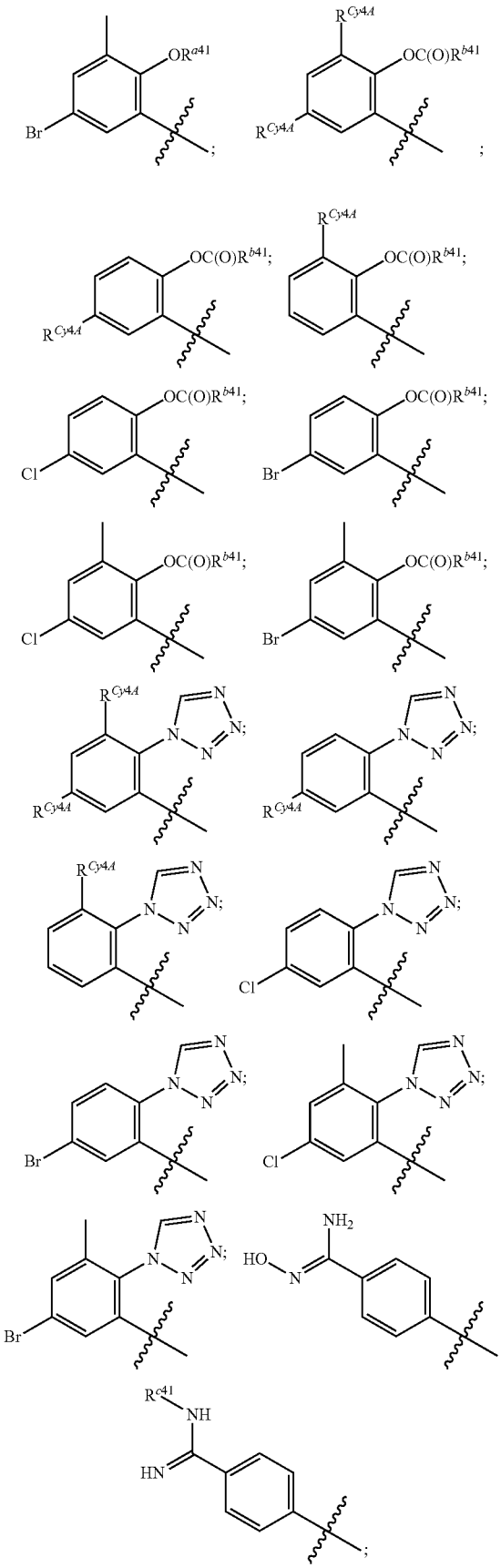

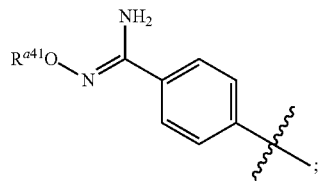

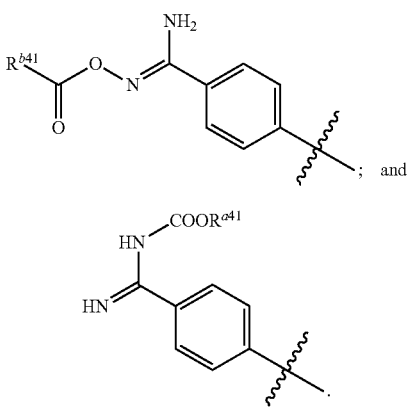

In some embodiments, in the formula defining $Cy^{4A}$, $R^{a41}$ is $C_{1-6}$ alkyl, such as methyl, $R^{b41}$ is $C_{1-6}$ alkyl, such as methyl, $R^{b41}$ is $C_{1-6}$ haloalkyl, such as trifluoromethyl, and $R^{c41}$ is alkyl such as methyl.

In some embodiments, $Cy^{4A}$ is unsubstituted or substituted heteroaryl.

In some embodiments, $Cy^{4A}$ is unsubstituted or substituted pyridin-3-yl, 1H-pyrrolo[2,3-b]pyridine-5-yl, or 1H-benzo[d]imidazol-6-yl.

In some embodiments, $Cy^{4A}$ is of any one of the following formulae:

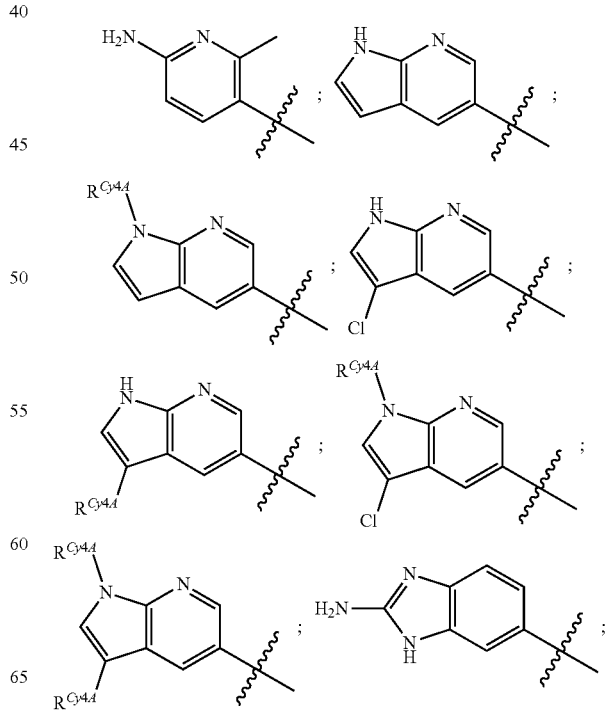

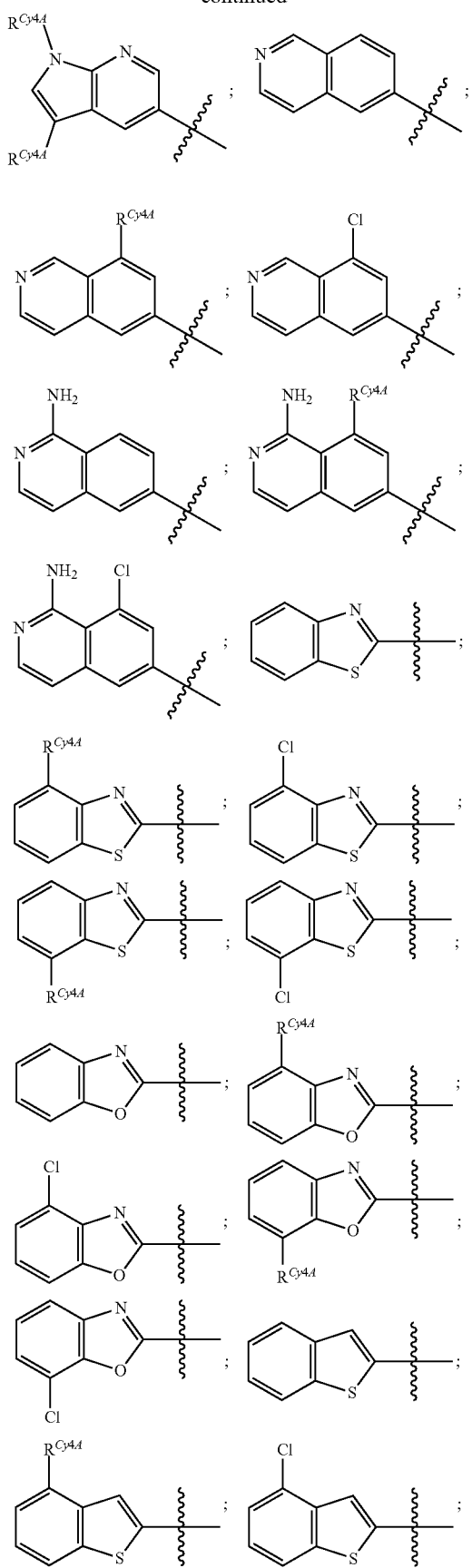
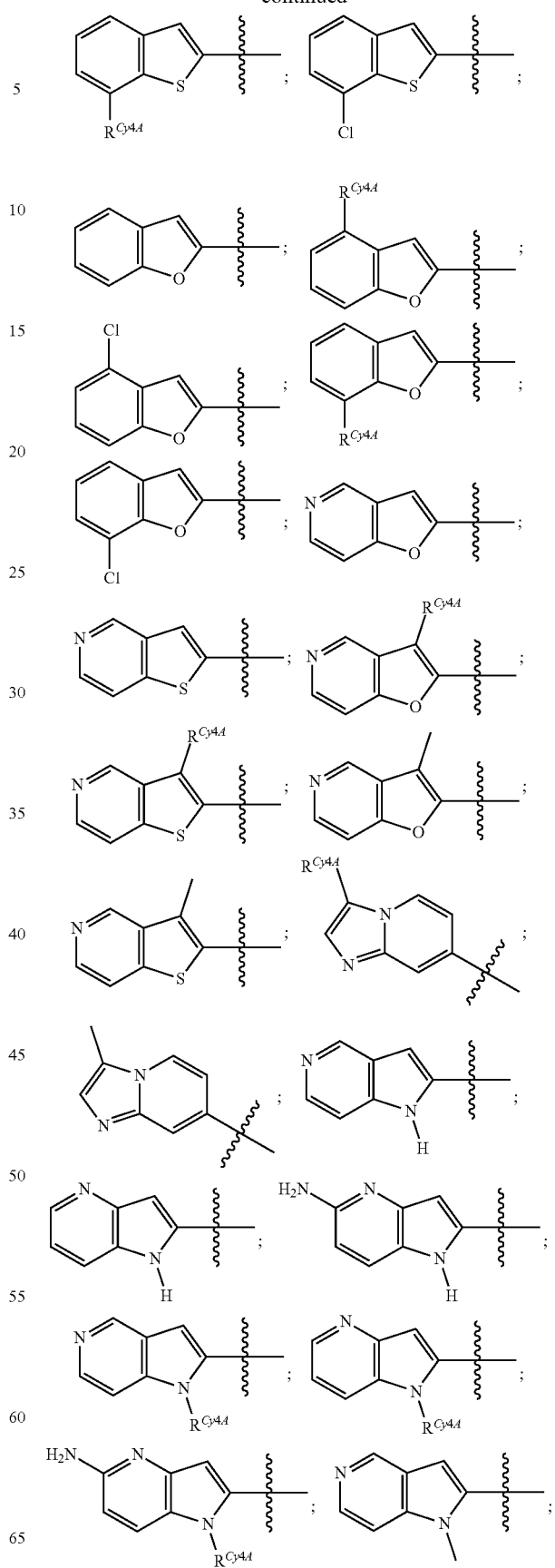

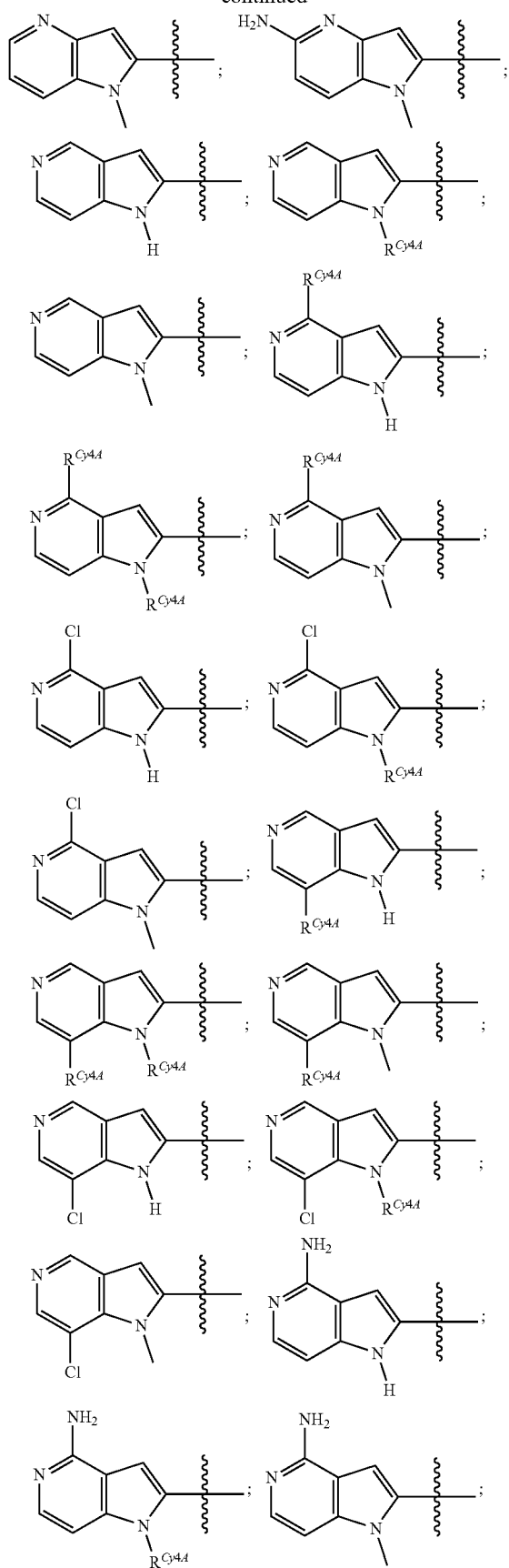
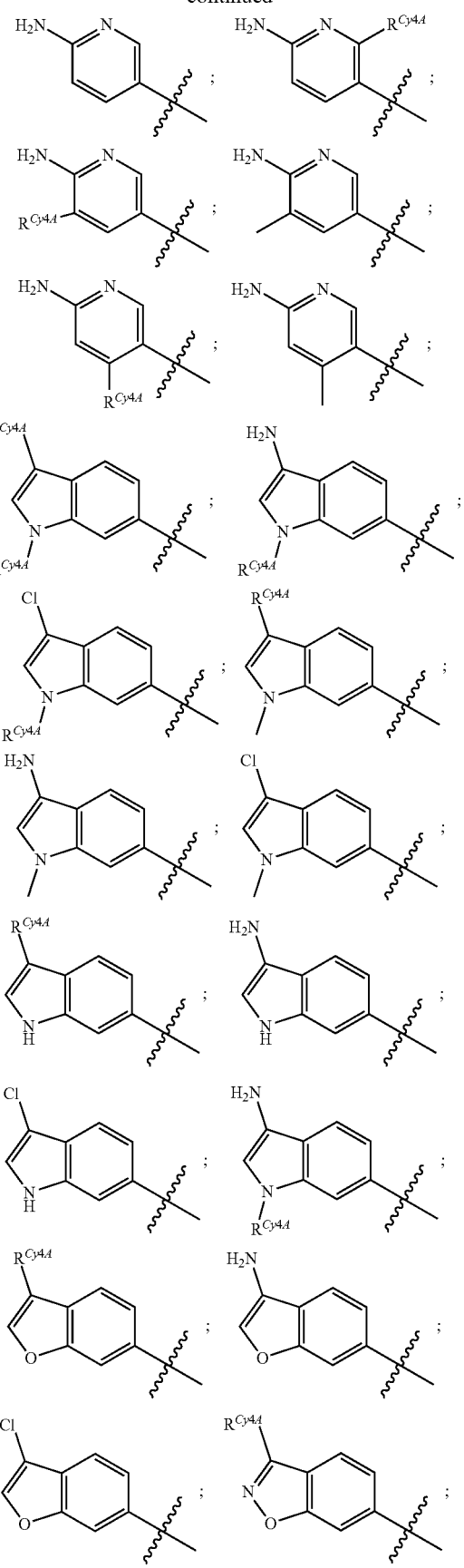

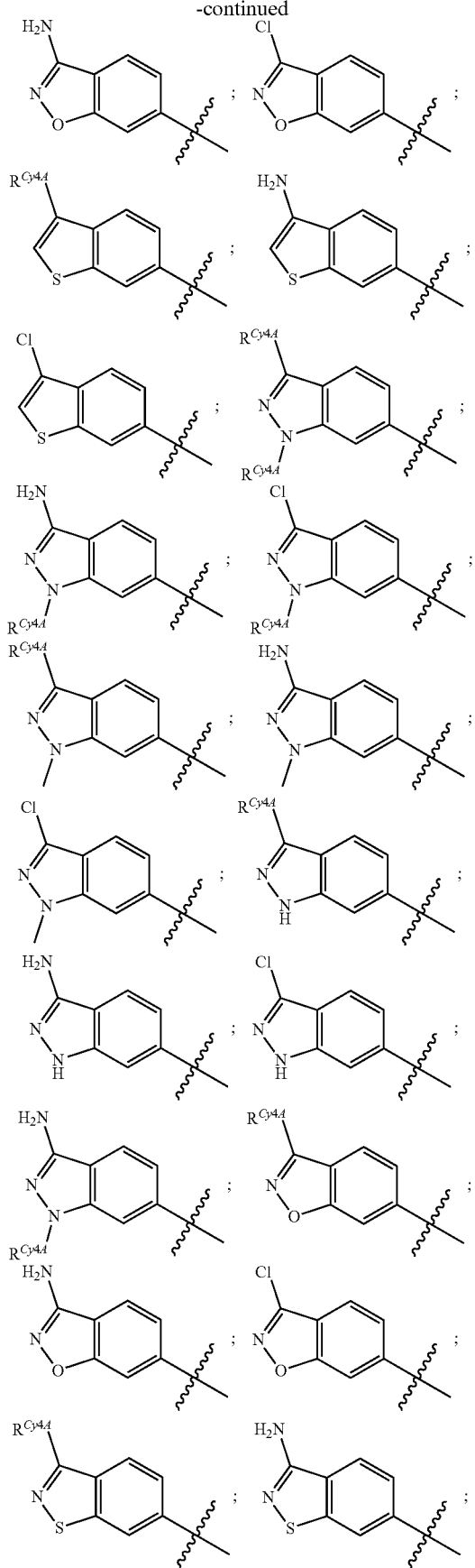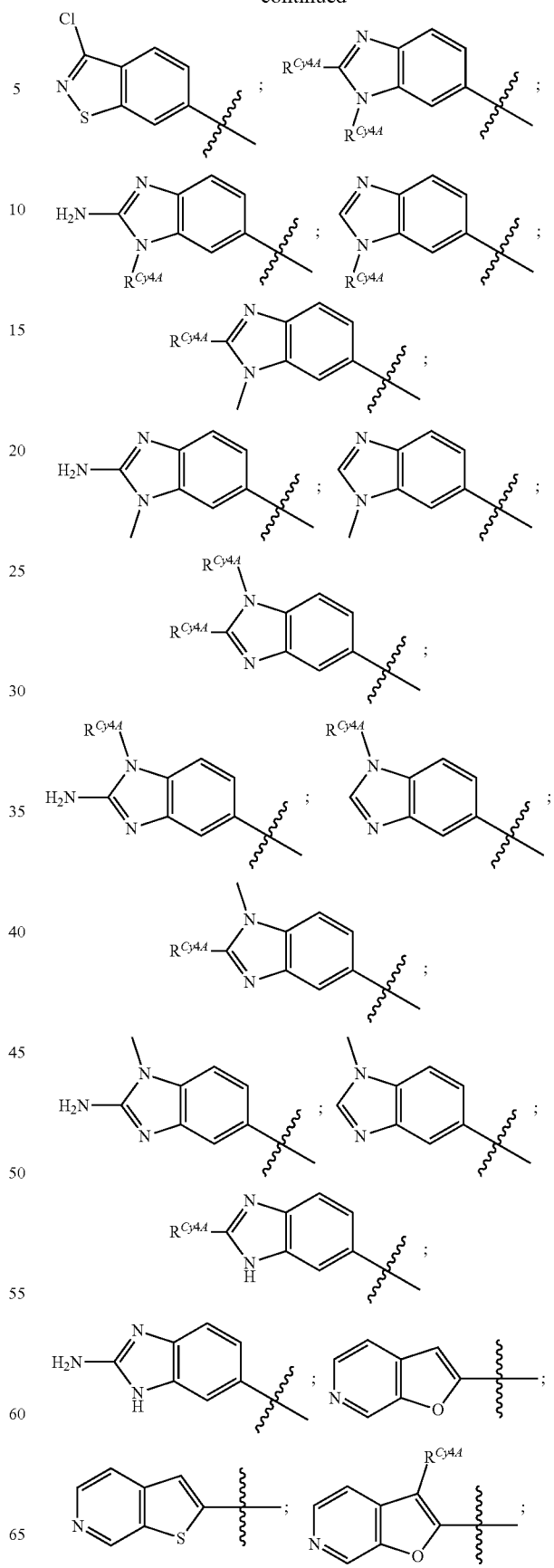

-continued
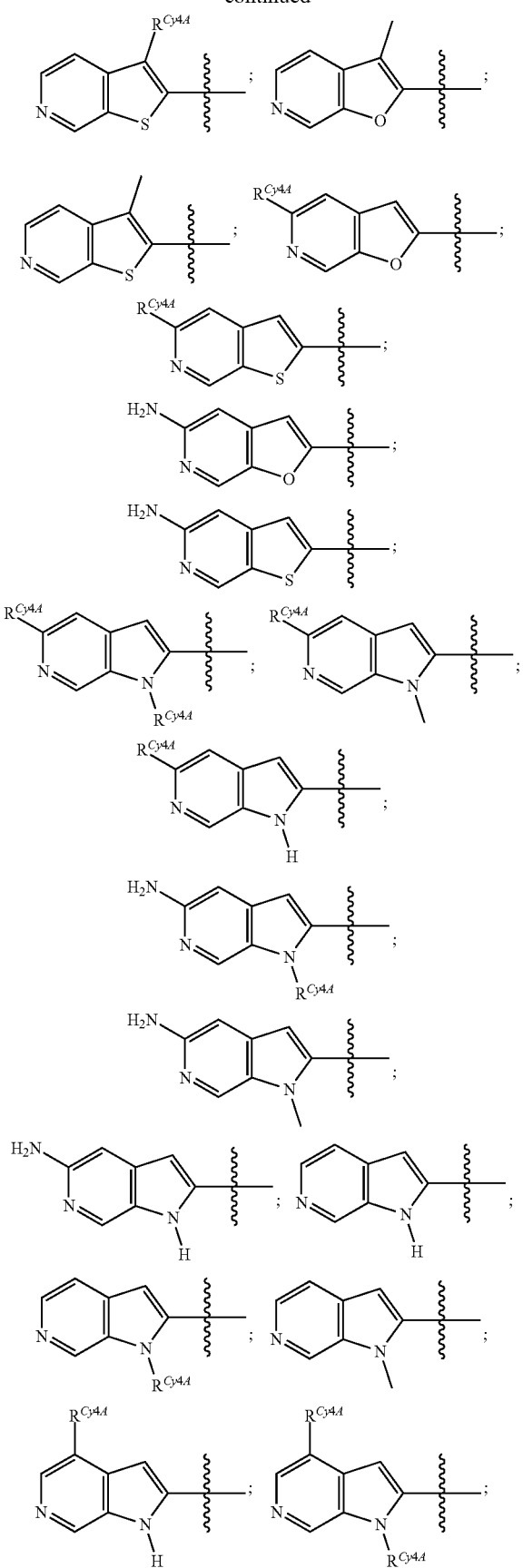
-continued
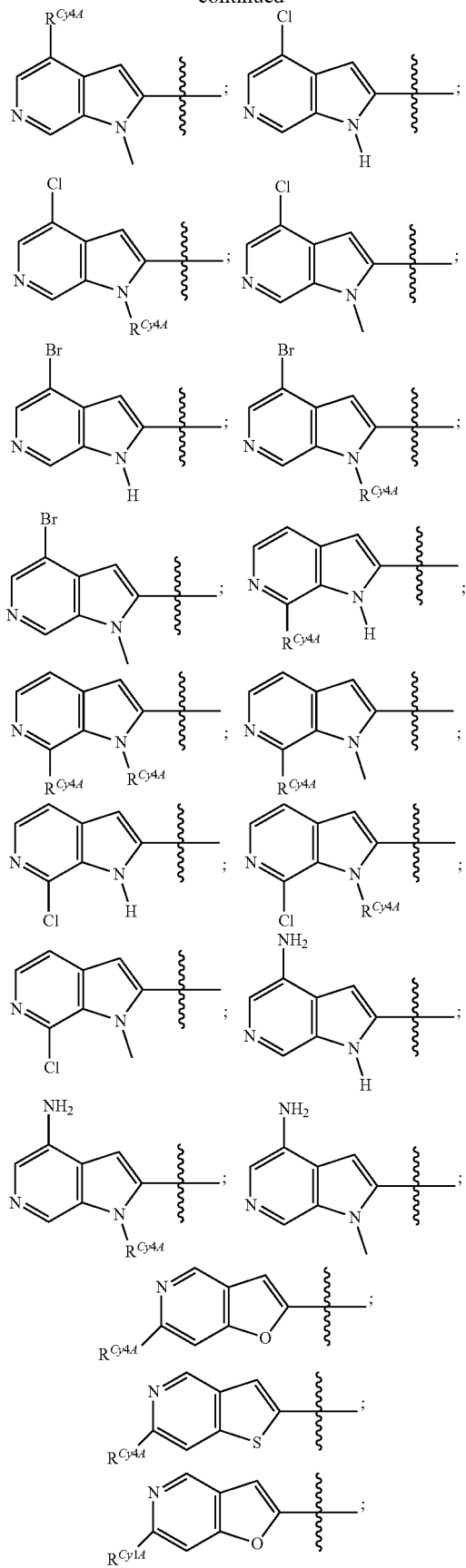

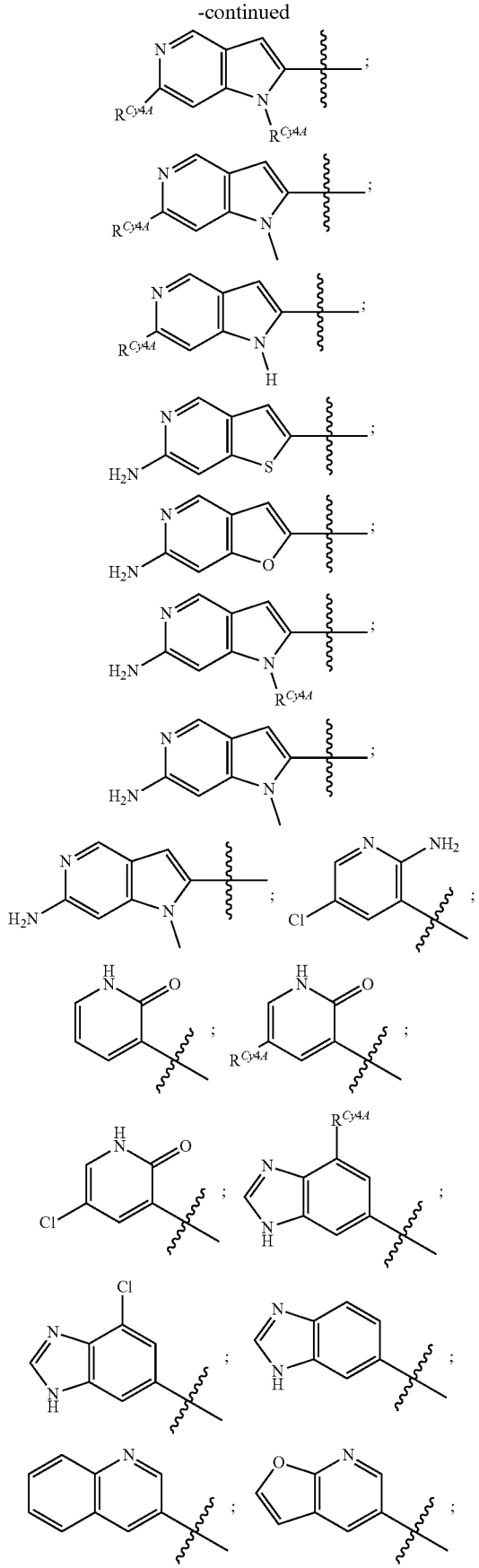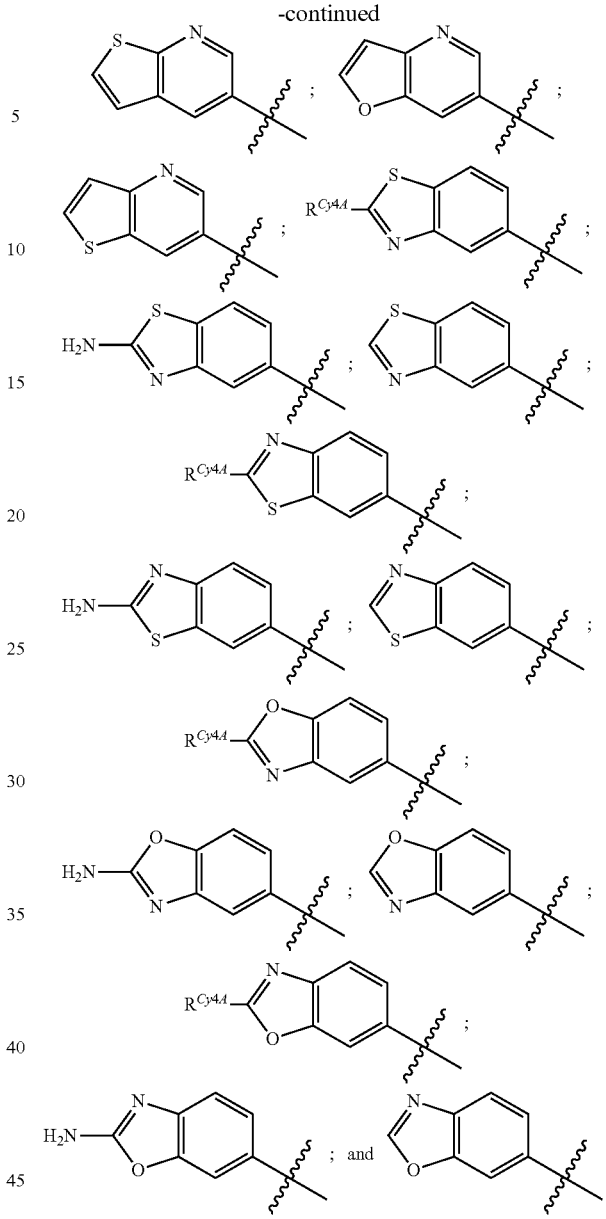

In some embodiments, each $R^{Cy4A}$ in the formula defining $Cy^{4A}$ is independently $C_{1-6}$ alkyl, such as methyl or ethyl, preferably methyl, or halogen such as F, Cl or Br, preferably Cl.

In some embodiments, each $R^{Cy4A}$ attached to nitrogen in the formula defining $Cy^{4A}$ is $C_{1-6}$ alkyl, such as methyl or ethyl.

In some embodiments, $R^{41}$ is $C_{1-6}$ alkyl.
In some embodiments, $R^{41}$ is H.
In some embodiments, $R^{41}$ is methyl.
In some embodiments, $R^{42}$ is H.
In some embodiments, $R^{42}$ is unsubstituted $C_{1-6}$ alkyl, such as methyl.
In some embodiments, $R^{42}$ is $Cy^{4B}$.
In some embodiments, $R^{42}$ is substituted $C_{1-6}$ alkyl, $C_{2-6}$ alkenyl, or $C_{2-6}$ alkynyl.
In some embodiments, $R^{42}$ is substituted $C_{1-6}$ alkyl.
In some embodiments, $R^{42}$ is substituted $C_{1-6}$ alkyl, wherein the $C_{1-6}$ alkyl forming $R^{42}$ is substituted by 1, 2, or 3 substituents selected from the group consisting of $Cy^{4B}$, halogen, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo; provided that no more than one of the substituents is $Cy^{4B}$.

In some embodiments, the substituted $C_{1-6}$ alkyl forming $R^{42}$ is substituted by at least one substituent, wherein the substituents include $Cy^{4B}$.

In some embodiments, the substituted $C_{1-6}$ alkyl forming $R^{35}$ is substituted by one substituent, wherein the substituent is $Cy^{4B}$.

In some embodiments, $R^{42}$ is $(CH_2)_{1-5}Cy^{4B}$.

In some embodiments, $R^{42}$ is $CH_2Cy^{4B}$.

In some embodiments, $Cy^{4B}$ is unsubstituted $C_{6-10}$ aryl such as unsubstituted phenyl or naphthyl, such as 1-naphthyl or 2-naphthyl, $Cy^{4B}$ is unsubstituted 5-10 membered heteroaryl, such as unsubstituted pyridyl, such as unsubstituted 2-, 3-, or 4-pyridyl, unsubstituted quinolyl, such as unsubstituted 2-, 3-, 4-, 5-, 6-, 7-, or 8-quinolyl, unsubstituted benzo[b]thiophenyl such as unsubstituted 2-, 3-, 4-, 5-, 6-, or 7-benzo[b]thiophenyl, or unsubstituted indolyl, such as unsubstituted indol-2-yl, -3-yl, -4-yl, -5-yl, -6-yl or -7-yl, $Cy^{4B}$ is unsubstituted $C_{3-10}$ cycloalkyl, such as cyclopropyl, cyclobutyl, cyclopentyl, cyclohexyl, or cycloheptyl, or $Cy^{4B}$ is unsubstituted 4-10 membered heterocycloalkyl.

In some embodiments, $Cy^{4B}$ is substituted $C_{6-10}$ aryl such as substituted phenyl or naphthyl, such as 1-naphthyl or 2-naphthyl, $Cy^{4B}$ is substituted 5-10 membered heteroaryl, such as substituted pyridyl, such as substituted 2-, 3-, or 4-pyridyl, substituted quinolyl, such as substituted 2-, 3-, 4-, 5-, 6-, 7-, or 8-quinolyl, substituted benzo[b]thiophenyl such as substituted 2-, 3-, 4-, 5-, 6-, or 7-benzo[b]thiophenyl, or substituted indolyl, such as substituted indol-2-yl, -3-yl, -4-yl, -5-yl, -6-yl or -7-yl, $Cy^{4B}$ is substituted $C_{3-10}$ cycloalkyl, such as cyclopropyl, cyclobutyl, cyclopentyl, cyclohexyl, or cycloheptyl, or $Cy^{4B}$ is substituted 4-10 membered heterocycloalkyl.

In some embodiments, $R^{41}$ and $R^{42}$, together with the atoms to which they are attached and the nitrogen atom linking the atoms to which $R^{41}$ and $R^{42}$ are attached, form a 4-7 membered heterocycloalkyl ring; which is optionally further substituted by 1, 2, 3, 4 or 5 substituents each independently selected from $R^{Cy4B}$, halogen, $C_{1-6}$ haloalkyl, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $C(=NOR^{a41})NR^{c41}R^{d41}$, $C(=NOC(O)R^{b41})NR^{c41}R^{d41}$, $C(=NR^{e41})C(O)OR^{a41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo.

In some embodiments, $R^{41}$ and $R^{42}$, together with the atoms to which they are attached and the nitrogen atom linking the atoms to which $R^{41}$ and $R^{42}$ are attached, form a 5 or 6 membered heterocycloalkyl ring.

In some embodiments, the compound is according to any of the following Formulae (IV-1), (IV-2), (IV-1a), (IV-1b), (IV-2a), or (IV-2b),

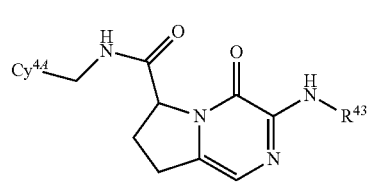

(IV-1)

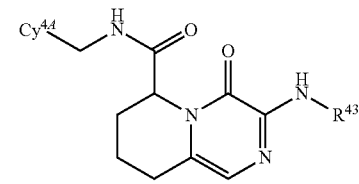

(IV-2)

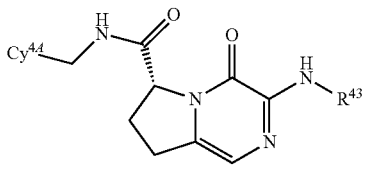

(IV-1a)

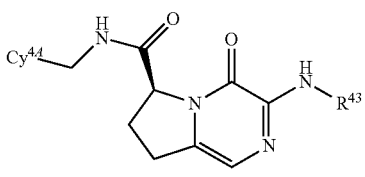

(IV-1b)

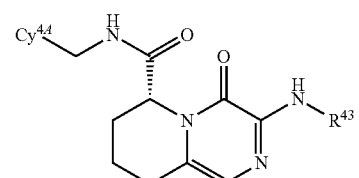

(IV-2a)

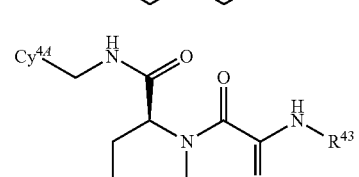

(IV-2b)

In some embodiments, $R^{43}$ is $Cy^{4C}$.
In some embodiments, $R^{43}$ is unsubstituted $C_{1-6}$ alkyl.
In some embodiments, $R^{43}$ is substituted $C_{1-6}$ alkyl.
In some embodiments, the substituted $C_{1-6}$ alkyl forming $R^{43}$ is substituted by at least one substituent independently selected from: 1, 2, or 3 substituents selected from the group consisting of $Cy^{4C}$, halogen, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo.

In some embodiments, the substituted $C_{1-6}$ alkyl forming $R^{43}$ is substituted by at least one substituent, wherein the substituents include $Cy^{4C}$.

In some embodiments, the substituted $C_{1-6}$ alkyl forming $R^{43}$ is substituted by one substituent, wherein the substituent is $Cy^{4C}$.

In some embodiments, $R^{43}$ is $(CH_2)_{1-5}Cy^{4C}$.
In some embodiments, $R^{43}$ is $CH_2Cy^{4C}$.
In some embodiments, $R^{43}$ is $CH_2CH_2Cy^{4C}$.

In some embodiments, $R^{43}$ is $CF_2Cy^{4C}$ or $CF_2CH_2Cy^{4C}$.

In some embodiments, $Cy^{4C}$ is unsubstituted $C_{6-10}$ aryl, such as phenyl, 1-naphthyl or 2-naphthyl.

In some embodiments, $Cy^{4C}$ is unsubstituted 5-10 membered heteroaryl, such as unsubstituted pyridyl, such as unsubstituted 2-, 3-, or 4-pyridyl, unsubstituted quinolyl, such as unsubstituted 2-, 3-, 4-, 5-, 6-, 7-, or 8-quinolyl, unsubstituted benzo[b]thiophenyl such as unsubstituted 2-, 3-, 4-, 5-, 6-, or 7-benzo[b]thiophenyl, or unsubstituted indolyl, such as unsubstituted indol-2-yl, -3-yl, -4-yl, -5-yl, -6-yl or -7-yl.

In some embodiments, $Cy^{4C}$ is unsubstituted $C_{3-10}$ cycloalkyl, such as cyclopropyl, cyclobutyl, cyclopentyl, cyclohexyl, or cycloheptyl.

In some embodiments, $Cy^{4C}$ is unsubstituted 4-10 membered heterocycloalkyl.

In some embodiments, $Cy^{4C}$ is substituted $C_{6-10}$ aryl, such as substituted phenyl, substituted 1-naphthyl or substituted 2-naphthyl.

In some embodiments, $Cy^{4C}$ is substituted 5-10 membered heteroaryl, such as substituted pyridyl, such as substituted 2-, 3-, or 4-pyridyl, substituted quinolyl, such as substituted 2-, 3-, 4-, 5-, 6-, 7-, or 8-quinolyl, substituted benzo[b]thiophenyl such as substituted 2-, 3-, 4-, 5-, 6-, or 7-benzo[b]thiophenyl, or substituted indolyl, such as substituted indol-2-yl, -3-yl, -4-yl, -5-yl, -6-yl or -7-yl.

In some embodiments, $Cy^{4C}$ is substituted $C_{3-10}$ cycloalkyl such as substituted cyclopropyl, cyclobutyl, cyclopentyl, cyclohexyl, or cycloheptyl.

In some embodiments, $Cy^{4C}$ is substituted 4-10 membered heterocycloalkyl.

In some embodiments, the compound is according to any of the following Formulae (IV-3)-(IV-7), (IV-3a), (IV-3b), (IV-5a), (IV-5b), (IV-7a), or (IV-7b):

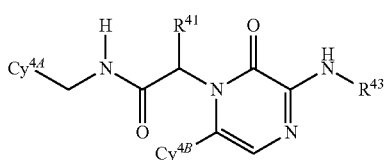
(IV-3)

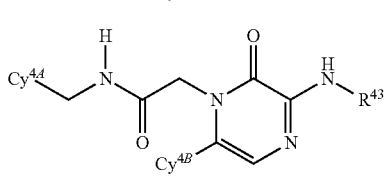
(IV-4)

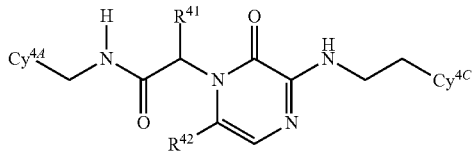
(IV-5)

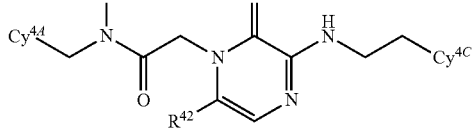
(IV-6)

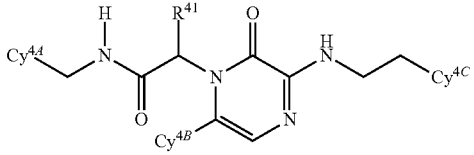
(IV-7)

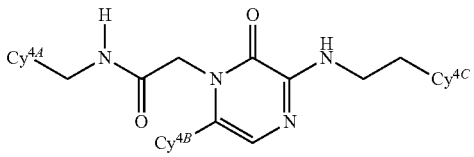
(IV-8)

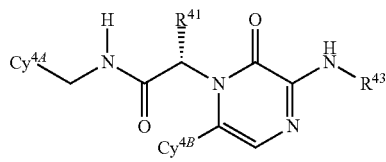
(IV-3a)

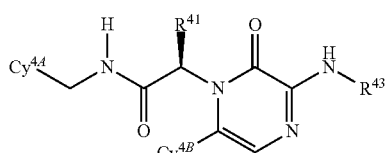
(IV-3b)

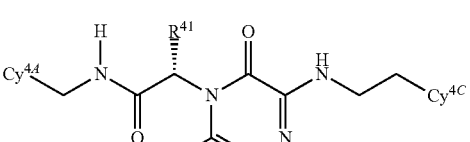
(IV-5a)

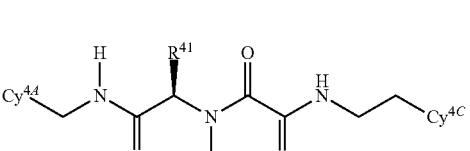
(IV-5b)

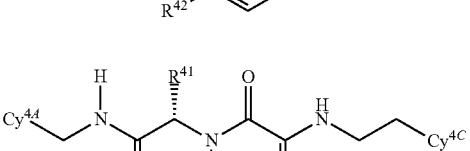
(IV-7a)

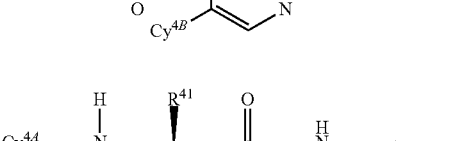
(IV-7b)

In some embodiments, $R^{a41}$, $R^{b41}$, $R^{c41}$, $R^{d41}$, $R^{a42}$, $R^{b42}$, $R^{c42}$ and $R^{d42}$ are each independently selected from H and $C_{1-6}$ alkyl.

In some embodiments, each $R^{e41}$ and each $R^{e42}$ is H.

In some embodiments, the compounds of Formula (IV), and embodiments thereof, can be in the form of a salt such as a pharmaceutically acceptable salt.

The compounds of Formula (Iv), and embodiments thereof, are useful as inhibitors of MASP-2 and for therapeutic use. The compounds of Formula (IV), and embodiments thereof, are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Formula (IV), or an embodiment thereof, optionally in the form of a salt.

In some embodiments the compound Formula (IV) or an embodiment thereof is provided in the form of a pharmaceutical composition comprising the compound or a salt thereof, such as a pharmaceutically acceptable salt, and at least one pharmaceutically acceptable carrier or excipient.

In certain aspects, the compound is one or more selected from the compounds of Formula (IV) set forth in the Examples, including the compounds listed in Table 31, (e.g., the compounds with selectivity for MASP-2 over thrombin). In certain aspects, one or more of the variables defining the compounds of Formula (IV) (such as $Cy^{4A}$, $R^{Cy4A}$, $Cy^{4B}$, $R^{Cy4B}$, $Cy^{4C}$, $R^{Cy4C}$, $R^{41}$, $R^{42}$, $R^{43}$, $R^{a41}$, $R^{b41}$, $R^{c41}$, $R^{d41}$, $R^{e41}$, $R^{a42}$, $R^{b42}$, $R^{c42}$, $R^{d42}$ and $R^{e42}$) is selected from the corresponding substituents in the compounds of Formula (IV) of the Examples, including the compounds listed in Table 31, preferably, those of the compounds with selectivity for MASP-2 over thrombin.

In certain aspects, the invention sets forth a stereochemically pure enantiomer or diastereomer (e.g., an optically active compound with one or more chiral centers). Unless specifically indicated otherwise, for any inventive compound with one or more stereocenters, the present invention is intended to include and to describe both the pure (+) and (−) enantiomers, any other diastereomers, mixtures that are enriched in an enantiomer or diastereomer (e.g., 10%, 20%, 30%, 40%, 50%, 60%, 70% 75%, 80%, 85, 90%, or 95% enantiomeric or diastereomeric excess), and a racemic mixture of enantiomers or diastereomers.

In certain aspects, the invention sets forth a pharmaceutically acceptable salt of the indicated chemical structure (e.g., a hydrohalide, such as a hydrochloride or dihydrochloride). Examples of pharmaceutically acceptable salts are set forth in, e.g., Burge, S. M. et al., J. Pharm. Sci 1977, 66, 1-19. They include chlorides, bromides, iodides, formates, acetates, propionates, oxalates, malonates, succinates, fumarates, maleates, tartrates, citrates, benzoates, phthalates, sulfonates, arylsulfonates, alkylsulfonates, salts of fatty acids, and the like. Salts can be prepared by a variety of methods known to the skilled artisan, including a precipitation with the conjugate acid or base (e.g., treatment with gaseous HCl or an HCl solution).

In certain aspects, the invention sets forth a prodrug. A prodrug is a compound that is converted to a biologically active form under physiological conditions, often by hydrolysis, oxidation, or reduction (e.g., ester to acid form; carbamate to amino or hydroxy group; hydroxyamidine to amidine) Exemplary prodrugs are set forth in, e.g., Tilley, J. W., "Prodrugs of Benzamide," *Prodrugs* 2007, 191-222; Peterlin-Masic et al. *Curr. Pharma. Design* 2006, 12, 73-91. Prodrugs for the amidine group include amidoximes, O-alkylamidoximes, acylamidines, carbamates, 1,2,4-oxadiazolin-4-ones, and the like.

In certain aspects, the compound is useful for selectively inhibiting MASP-2 over thrombin, the method comprising administering the compound as described herein. In certain aspects, the selectivity ratio of MASP-2:thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

E. Compounds of Formula VA, VB, VIA, VIB, VIIA and VIIB

1. Additional Chemical Definitions

The following definitions apply herein in the present section (II)(E) and the claims directed to the compounds of Formulae (VA), (VB), (VIA), (VIB), (VIIA) and (VIIB) disclosed herein.

The term "alkoxy" refers to a straight or branched chain saturated or unsaturated hydrocarbon containing at least one oxygen atom in an ether group (e.g., EtO—). The chain may contain an indicated number of carbon atoms. For example, "$C_1$-$C_{12}$ alkoxy" indicates that the group may have from 1 to 12 (inclusive) carbon atoms and at least one oxygen atom. Examples of $C_1$-$C_{12}$ alkoxy groups include, but are not limited to, methoxy, ethoxy, isopropoxy, butoxy, n-pentoxy, isopentoxy, neopentoxy, and hexoxy.

The term "alkyl" includes an aliphatic hydrocarbon chain that may be straight chain or branched. The chain may contain an indicated number of carbon atoms: For example, $C_1$-$C_{12}$ indicates that the group may have from 1 to 12 (inclusive) carbon atoms in it. If not otherwise indicated, an alkyl group about 1 to about 20 carbon atoms. In one aspect, alkyl groups have 1 to about 12 carbon atoms in the chain. In another aspect, alkyl groups ("lower alkyl") have 1 to about 6 carbon atoms in the chain. Examples may include, but are not limited to, methyl, ethyl, propyl, isopropyl (iPr), 1-butyl, 2-butyl, isobutyl (iBu), tert-butyl, pentyl, 2-methylbutyl, 1,1-dimethylpropyl, hexyl, heptyl, octyl, nonyl, decyl, dodecyl, cyclopentyl, or cyclohexyl. In one aspect, an alkyl group can exclude methyl (e.g., 2 to 6 carbon atoms in the chain).

The term "aryl" as used herein includes cyclic aromatic carbon ring systems containing from 6 to 18 carbons. Examples of an aryl group include, but are not limited to, phenyl, naphthyl, anthracenyl, tetracenyl, biphenyl and phenanthrenyl.

The terms "arylalkyl" and "aralkyl," which are used interchangeably, include an alkyl group as defined herein where at least one hydrogen substituent has been replaced with an aryl group as defined herein. Examples include, but are not limited to, benzyl, 1-phenylethyl, 4-methylbenzyl, and 1,1-dimethyl-1-phenylmethyl.

The term "cycloalkyl" as used herein includes a cyclic hydrocarbon group that may contain an indicated number of carbon atoms: For example, $C_3$-$C_{12}$ indicates that the group may have from 3 to 12 (inclusive) carbon atoms in it. If not otherwise indicated, a cycloalkyl group includes about 3 to about 20 carbon atoms. In one aspect, cycloalkyl groups have 3 to about 12 carbon atoms in the group. In another aspect, cycloalkyl groups have 3 to about 7 carbon atoms in the group. Examples may include, but are not limited to, cyclopropyl, cyclobutyl, cyclopentyl, cyclohexyl, 4,4-dimethylcyclohexyl, and cycloheptyl.

As used herein, "halo" or "halogen" includes fluoro, chloro, bromo, or iodo. In one aspect, "halo" includes fluoro or chloro (preferably chloro).

The term "heteroaryl" includes mono and bicyclic aromatic groups of about 4 to about 14 ring atoms (e.g., 4 to 10 or 5 to 10 atoms) containing at least one heteroatom. Heteroatom as used in the term heteroaryl refers to oxygen, sulfur and nitrogen. A nitrogen atom of a heteroaryl is optionally oxidized to the corresponding N-oxide. Examples include, but are not limited to, pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl.

As used herein, "heterocyclyl" includes a non-aromatic saturated monocyclic or multicyclic ring system of about 4 to about 10 ring atoms (e.g., 5 to about 8 ring atoms, or 5 to about 6 ring atoms), in which one or more of the atoms in the ring system is an element or elements other than carbon, e.g., nitrogen, oxygen or sulfur. A heterocyclyl group optionally comprises at least one sp²-hybridized atom (e.g., a ring incorporating a carbonyl, endocyclic olefin, or exocyclic olefin). In some embodiments, a nitrogen or sulfur atom of the heterocyclyl is optionally oxidized to the corresponding N-oxide, S-oxide or S,S-dioxide. Examples of monocyclic heterocyclyl rings include, but are not limited to, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, and tetrahydrothiopyranyl.

As used herein, the term "hydroxyalkyl" includes an alkyl group where at least one hydrogen substituent has been replaced with an alcohol (—OH) group. In certain aspects, the hydroxyalkyl group has one alcohol group. In certain aspects, the hydroxyalkyl group has one or two alcohol groups, each on a different carbon atom. In certain aspects, the hydroxyalkyl group has 1, 2, 3, 4, 5, or 6 alcohol groups. Examples may include, but are not limited to, hydroxymethyl, 2-hydroxyethyl, and 1-hydroxyethyl.

The term "hypertonic" refers to a formulation with an osmotic pressure above that of human (i.e., greater than 350 mOsm/KglHhO).

When any two substituent groups or any two instances of the same substituent group are "independently selected" from a list of alternatives, the groups may be the same or different. For example, if $R^a$ and $R^b$ are independently selected from the group consisting of alkyl, fluoro, amino, and hydroxyalkyl, then a molecule with two $R^a$ groups and two $R^b$ groups could have all groups be alkyl group (e.g., four different alkyl groups). Alternatively, the first $R^a$ could be alkyl, the second $R^a$ could be fluoro, the first $R^b$ could be hydroxyalkyl, and the second $R^b$ could be amino (or any other substituents taken from the group). Alternatively, both $R^a$ and the first $R^b$ could be fluoro, while the second $R^b$ could be alkyl (i.e., some pairs of substituent groups may be the same, while other pairs may be different).

As used herein, the term "salt" refers to acid or base salts of a compound, e.g., ZNA or another 2-(acylamino)imidazole. Illustrative examples of pharmaceutically acceptable salts are cationic salts such as alkali and alkaline earth metal (such as sodium, lithium, potassium, calcium, and magnesium) salts, ammonium (ammonium, trimethyl ammonium, diethylammonium, and tris-(hydroxymethyl)-methyl-ammonium) salts, mineral acid (hydrochloric acid, hydrobromic acid, phosphoric acid, and the like) salts, organic carboxylic acid (acetic acid, propionic acid, glutamic acid, citric acid, and the like) salts, organic sulfonic acid (methanesulfonic acid) salts, and quaternary ammonium (methyl iodide, ethyl iodide, and the like) salts. Additional information on suitable pharmaceutically acceptable salts can be found in Remington's, Pharmaceutical Sciences (current edition), Mack Publishing Co., Easton, PA, which is incorporated herein by reference.

The terms "a salt thereof," "salt thereof," or "salts thereof" can be applied to any preceding member of an associated Markush group. For example, a group consisting of A, B, C, and salts thereof would include within its scope embodiments that were a salt of A, embodiments that were a salt of B, and embodiments that were a salt of C.

2. Compounds of Formula VA and VB

In certain aspects, the present disclosure provides a compound is of the Formula (VA) or (VB):

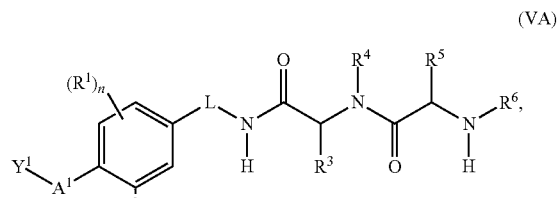

(VA)

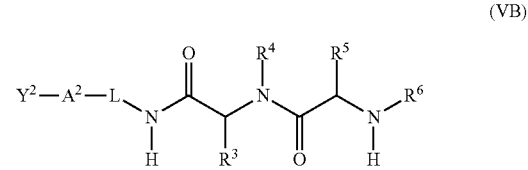

(VB)

or a salt thereof; wherein:

$A^1$ is a member selected from the group consisting of —(C=NH)—, —(C=NOR$^a$)—, —[C=NO(C=O)R$^a$]—, —[C=N[O(C=O)ZR$^b$]]—, a fused 5- or 6-member heterocyclyl, and a fused 5- or 6-member heteroaryl;

when $A^1$ is —(C=NH)—, $Y^1$ is selected from the group consisting of —NH$_2$, —NH(C=O)R$^a$, and —NH(C=O)ZR$^b$;

when $A^1$ is —(C=NOR$^a$)—, —[C=NO(C=O)R$^a$]—, or —{C=N[O(C=O)ZR$^b$]}—, $Y^1$ is —NH$_2$;

when $A^1$ is fused heterocyclyl or heteroaryl, $Y^1$ is —NH$_2$ or halo, and $A^1$ is substituted with m additional $R^1$ groups;

each $R^a$ and $R^b$ is independently selected from the group consisting of $C_1$-$C_6$ alkyl, $C_3$-$C_{10}$ cycloalkyl, $C_6$-$C_{10}$ aryl, and $C_7$-$C_{12}$ arylalkyl; wherein $R^a$ has m substituents selected from the group consisting of $C_1$-$C_6$ alkyl, hydroxyl, hydroxyl($C_1$-$C_6$ alkyl), $C_1$-$C_6$ alkoxy, $C_2$-$C_9$ alkoxyalkyl, amino, $C_1$-$C_6$ alkylamino, and halo; or, alternatively, $R^a$ and $R^b$ join to form a heterocyclyl ring with m substituents selected from the group consisting of $C_1$-$C_6$ alkyl, hydroxyl, $C_1$-$C_6$ alkoxy, and halo;

each Z is independently selected from the group consisting of O and S;

$A^2$ is a member selected from the group consisting of $C_3$-$C_6$ heteroaryl, $C_6$ aryl, and $C_2$-$C_6$ alkyl;

when $A^2$ is $C_3$-$C_6$ heteroaryl, $Y^2$ is selected from the group consisting of —NH$_2$, —CH$_2$NH$_2$, chloro, —(C=NH)NH$_2$, —(C=NH)NH(C=O)R$^a$, —(C=NH)NH(C=O)ZR$^b$, —(C=NOR$^a$)NH$_2$, —[C=NO(C=O)R$^a$]NH$_2$, and —{C=N[O(C=O)ZR$^b$]}NH$_2$; and $A^2$ is substituted with m additional $R^1$ groups;

when $A^2$ is $C_6$ aryl, $Y^2$ is selected from the group consisting of aminomethyl, hydroxy, and halo, and $A^2$ is substituted with m additional $R^1$ groups;

when $A^2$ is $C_2$-$C_6$ alkyl, $Y^2$ is selected from the group consisting of —NH(C=NH)NH$_2$, —NH(C=NH)NH(C=O)R$^a$, and —NH(C=NH)NH(C=O)ZR$^b$;

each $R^1$ is a member independently selected from the group consisting of $C_1$-$C_6$ alkyl, hydroxyl, $C_1$-$C_6$ alkoxy, amino, $C_1$-$C_6$ alkylamino, and halo;

each m and n is an independently selected integer from 0 to 3;

L is —(O)$_p$—(C(R$^{2a}$)(R$^{2b}$))$_q$—, each $R^{2a}$ or $R^{2b}$ is a member independently selected from the group consisting of hydrogen and fluoro;

p is an integer from 0 to 1;

q is an integer from 1 to 2;

$R^3$ is a member selected from the group consisting of hydrogen, $C_1$-$C_6$ alkyl, $C_1$-$C_6$ fluoroalkyl, and carboxy($C_1$-$C_6$ alkyl); or, alternatively, $R^3$ and $R^4$ join to form an azetidine, pyrrolidine, or piperidine ring;

$R^4$ is a member selected from the group consisting of hydrogen and $C_1$-$C_6$ alkyl; or, alternatively, $R^4$ and $R^3$ join to form an azetidine, pyrrolidine, or piperidine ring;

$R^5$ is a member selected from the group consisting of $C_3$-$C_7$ cycloalkyl, $C_4$-$C_8$ cycloalkylalkyl, heteroaryl, and $C_7$-$C_{12}$ arylalkyl or heteroarylalkyl with from 0 to 3 $R^{13}$ substituents; or, alternatively, $R^5$ and $R^6$ join to form a heterocyclic ring with from 0 to 3 $R^{13}$ substituents;

$R^6$ is a member selected from the group consisting of hydrogen, $C_1$-$C_6$ alkyl, $C_3$-$C_7$ cycloalkyl, carboxy($C_1$-$C_6$ alkyl), $C_7$-$C_{12}$ arylalkyl or heteroarylalkyl with from 0 to 3 $R^{13}$ substituents, amino($C_1$-$C_8$ alkyl); and amido($C_1$-$C_8$ alkyl); or, alternatively, $R^6$ and $R^5$ join to form a heterocyclylic ring with from 0 to 3 $R^{13}$ substituents; and each $R^{13}$ is a member independently selected from the group consisting of $C_1$-$C_6$ alkyl, $C_6$-$C_{10}$ aryl, ($C_6$-$C_{10}$ aryl)$C_1$-$C_6$ alkyl, carboxy($C_1$-$C_6$ alkyloxy), heteroaryl, ($C_6$-$C_{10}$ heteroaryl)$C_1$-$C_6$ alkyl, heterocyclyl, hydroxyl, hydroxyl($C_1$-$C_6$ alkyl), $C_1$-$C_6$ alkoxy, $C_2$-$C_9$ alkoxyalkyl, amino, $C_1$-$C_6$ amido, $C_1$-$C_6$ alkylamino, and halo; or, alternatively, two $R^{13}$ groups join to form a fused $C_6$-$C_{10}$ aryl, $C_6$-$C_{10}$ heteroaryl, or $C_5$-$C_7$ cycloalkyl ring.

In certain aspects, the present disclosure provides a compound is of the Formula (VA) or (VB):

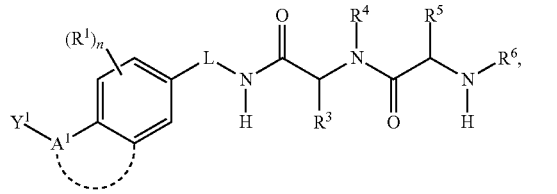

(VA)

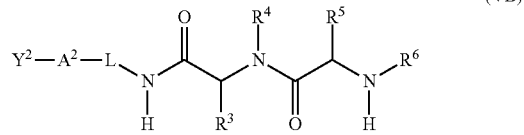

(VB)

or a salt thereof; wherein:

$A^1$ is a member selected from the group including —(C=NH)—, —(C=NOR$^a$)—, —[C=NO(C=O)R$^a$]—, —[C=N[O(C=O)ZR$^b$]]—, a fused 5- or 6-member heterocyclyl, and a fused 5- or 6-member heteroaryl;

when $A^1$ is —(C=NH)—, $Y^1$ is selected from the group including —NH$_2$, —NH(C=O)R$^a$, and —NH(C=O)ZR$^b$;

when $A^1$ is —(C=NOR$^a$)—, —[C=NO(C=O)R$^a$]—, or —{C=N[O(C=O)ZR$^b$]}—, $Y^1$ is —NH$_2$;

when $A^1$ is fused heterocyclyl or heteroaryl, $Y^1$ is —NH$_2$ or halo, and $A^1$ is substituted with m additional $R^1$ groups;

each $R^a$ and $R^b$ is independently selected from the group including $C_1$-$C_6$ alkyl, $C_3$-$C_{10}$ cycloalkyl, $C_6$-$C_{10}$ aryl, and $C_7$-$C_{12}$ arylalkyl; wherein $R^a$ has m substituents selected from the group including $C_1$-$C_6$ alkyl, hydroxyl, hydroxyl($C_1$-$C_6$ alkyl), $C_1$-$C_6$ alkoxy, $C_2$-$C_9$ alkoxyalkyl, amino, $C_1$-$C_6$ alkylamino, and halo; or, alternatively, $R^a$ and $R^b$ join to form an heterocyclyl ring with m substituents selected from the group including $C_1$-$C_6$ alkyl, hydroxyl, $C_1$-$C_6$ alkoxy, and halo;

each Z is independently selected from the group including O and S;

$A^2$ is a member selected from the group including $C_3$-$C_6$ heteroaryl, $C_6$ aryl, and $C_2$-$C_6$ alkyl;

when $A^2$ is $C_3$-$C_6$ heteroaryl, $Y^2$ is selected from the group including —NH$_2$, —CH$_2$NH$_2$, chloro, —(C=NH)NH$_2$, —(C=NH)NH(C=O)R$^a$, —(C=NH)NH(C=O)ZR$^b$, —(C=NOR$^a$)NH$_2$, —[C=NO(C=O)R$^a$]NH$_2$, and —{C=N[O(C=O)ZR$^b$]}NH$_2$; and $A^2$ is substituted with m additional $R^1$ groups;

when $A^2$ is $C_6$ aryl, $Y^2$ is selected from the group including aminomethyl, hydroxy, and halo, and $A^2$ is substituted with m additional $R^1$ groups;

when $A^2$ is $C_2$-$C_6$ alkyl, $Y^2$ is selected from the group including —NH(C=NH)NH$_2$, —NH(C=NH)NH(C=O)R$^a$, and —NH(C=NH)NH(C=O)ZR$^b$;

each $R^1$ is a member independently selected from the group including $C_1$-$C_6$ alkyl, hydroxyl, $C_1$-$C_6$ alkoxy, amino, $C_1$-$C_6$ alkylamino, and halo;

each m and n is an independently selected integer from 0 to 3;

L is —(O)$_p$—(C(R$^{2a}$)(R$^{2b}$))$_q$—, each $R^{2a}$ or $R^{2b}$ is a member independently selected from the group including hydrogen and fluoro;

p is an integer from 0 to 1;

q is an integer from 1 to 2;

$R^3$ is a member selected from the group including hydrogen, $C_1$-$C_6$ alkyl, $C_1$-$C_6$ fluoroalkyl, and carboxy($C_1$-$C_6$ alkyl); or, alternatively, $R^3$ and $R^4$ join to form an azetidine, pyrrolidine, or piperidine ring;

$R^4$ is a member selected from the group including hydrogen and $C_1$-$C_6$ alkyl; or, alternatively, $R^4$ and $R^3$ join to form an azetidine, pyrrolidine, or piperidine ring;

$R^5$ is a member selected from the group including $C_3$-$C_7$ cycloalkyl, $C_4$-$C_8$ cycloalkylalkyl, heteroaryl, and $C_7$-$C_{12}$ arylalkyl or heteroarylalkyl with from 0 to 3 $R^{13}$ substituents; or, alternatively, $R^5$ and $R^6$ join to form a heterocyclic ring with from 0 to 3 $R^{13}$ substituents;

$R^6$ is a member selected from the group including hydrogen, $C_1$-$C_6$ alkyl, $C_3$-$C_7$ cycloalkyl, carboxy($C_1$-$C_6$ alkyl), $C_7$-$C_{12}$ arylalkyl or heteroarylalkyl with from 0 to 3 $R^{13}$ substituents, amino($C_1$-$C_8$ alkyl); and amido ($C_1$-$C_8$ alkyl); or, alternatively, $R^6$ and $R^5$ join to form a heterocyclic ring with from 0 to 3 $R^{13}$ substituents; and each $R^{13}$ is a member independently selected from the group including $C_1$-$C_6$ alkyl, $C_6$-$C_{10}$ aryl, carboxy($C_1$-$C_6$ alkyloxy), heteroaryl, heterocyclyl, hydroxyl, hydroxyl($C_1$-$C_6$ alkyl), $C_1$-$C_6$ alkoxy, $C_2$-$C_9$ alkoxyalkyl, amino, $C_1$-$C_6$ amido, $C_1$-$C_6$ alkylamino, and halo; or, alternatively, two $R^{13}$ groups join to form a fused $C_6$-$C_{10}$ aryl, $C_6$-$C_{10}$ heteroaryl, or $C_5$-$C_7$ cycloalkyl ring, with the proviso that the compound is not melagatran.

In certain aspects, the compound is of Formula VA.

In certain aspects, $A^1$ is —(C=NH)—. In certain aspects, $A^1$ is —NH(C=O)$R^a$. In certain aspects, $A^1$ is —NH(C=O)Z$R^b$. In certain aspects, Z is O, S, or N.

In certain aspects, $A^1$ is —(C=NH)—. In certain aspects, $Y^1$ is —$NH_2$. In certain aspects, $Y^1$ is —NH(C=O)$R^a$. In certain aspects, $Y^1$ is —NH(C=O)Z$R^b$.

In certain aspects, $A^1$ is —(C=NOR$^a$)—. In certain aspects, $Y^1$ is —$NH_2$. In certain aspects, $Y^1$ is —NH(C=O)$R^a$. In certain aspects, $Y^1$ is —NH(C=O)Z$R^b$.

In certain aspects, $R^a$ or $R^b$ is $C_1$-$C_6$ alkyl, such as methyl, ethyl, n-propyl, isopropyl, n-butyl, or t-butyl. In certain aspects, $R^a$ or $R^b$ is $C_3$-$C_{10}$ cycloalkyl, such as cyclohexyl, cyclopentyl, or cyclopropyl. In certain aspects, $R^a$ or $R^b$ is $C_6$-$C_{10}$ aryl, such as phenyl or substituted phenyl (e.g., 4-methoxyphenyl). In certain aspects, $R^a$ or $R^b$ is $C_7$-$C_{12}$ arylalkyl, such as benzyl or 4-methoxybenzyl.

In certain aspects, $A^1$ is a fused heteroaryl. In certain aspects, $A^1$ is a quinolone. In certain aspects, $A^1$ is an isoquinoline. In certain aspects, $A^1$ is a benzimidazole. In certain aspects, $Y^1$ is —$NH_2$.

In certain aspects, $Y^1$ is -$NH_2$.

In certain aspects, the compound is of Formula VB.

In certain aspects, $A^2$ is $C_6$ aryl. In certain aspects, $A^2$ is $C_3$-$C_6$ heteroaryl.

In certain aspects, $A^2$ is substituted with m additional $R^1$ groups, such as halo, hydroxyl, $C_2$-$C_6$ alkyl, or $C_1$-$C_4$ methoxy, In certain aspects, $Y^2$ is halo (e.g., chloro). In certain aspects, $Y^2$ is 3-chloro. In certain aspects, $Y^2$ is aminomethyl (e.g., 4-aminomethyl).

In certain aspects, $A^2$ is $C_2$-$C_6$ alkyl.

In certain aspects, $Y^2$ is —NH(C=NH)$NH_2$.

In certain aspects, $Y^2$ is selected from the group consisting of —NH(C=NH)$NH_2$, —NH(C=NH)NH(C=O)$R^a$, and —NH(C=NH)NH(C=O)Z$R^b$. In certain aspects, $Y^2$ is —NH(C=NH)$NH_2$. In certain aspects, $Y^2$ is —NH(C=NH)NH(C=O)$R^a$. In certain aspects, $Y^2$ is —NH(C=NH)NH(C=O)Z$R^b$.

In certain aspects, the compound has an $R^3$ stereochemistry of

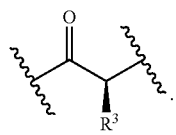

In certain aspects, $R^3$ is a member selected from the group including hydrogen or methyl. In certain aspects, $R^3$ is hydrogen. In certain aspects, $R^3$ is methyl.

In certain aspects, $R^4$ is a member selected from the group including hydrogen or methyl. In certain aspects, $R^4$ is hydrogen.

In certain aspects, $R^3$ and $R^4$ join to form an azetidine, pyrrolidine, or piperidine ring. In certain aspects, $R^3$ and $R^4$ join to form a pyrrolidine ring. In certain aspects, $R^3$ and $R^4$ join to form a piperidine ring.

In certain aspects, $R^5$ is a member selected from the group including 2,3-dihydro-1H-inden-2-yl, cyclohexyl, cyclohexylmethyl, phenyl, benzyl, phenethyl, and phenpropyl with from 0 to 3 $R^{13}$ substituents.

In certain aspects, $R^5$ is a member selected from the group including phenethyl, 4-methylphenethyl, 4-chlorophenethyl, 4-fluorophenethyl, and phenpropyl. In certain aspects, $R^5$ is a member selected from the group including phenethyl, 4-methylphenethyl, 4-chlorophenethyl, 4-fluorophenethyl, 3-methylphenethyl, 3-chlorophenethyl, 3-fluorophenethyl, 2-methylphenethyl, 2-chlorophenethyl, 2-fluorophenethyl, phenpropyl, 4-methylphenpropyl, 4-chlorophenpropyl, 4-fluorophenpropyl, 3-methylphenpropyl, 3-chlorophenpropyl, 3-fluorophenpropyl, 2-methylphenpropyl, 2-chlorophenpropyl, and 2-fluorophenpropyl.

In certain aspects, $R^6$ is a member selected from the group including amino($C_1$-$C_8$ alkyl). and $C_7$-$C_{12}$ arylalkyl with from 0 to 3 $R^{13}$ substituents.

In certain aspects, $R^6$ is a member selected from the group including hydrogen and carboxymethyl.

In certain aspects, $R^6$ and $R^5$ join to form a pyrrolidine, octahydro-1H-indole, 3-phenylpyrrolidine, piperidine, 1,2,3,4-tetrahydroisoquinoline, 2,5-dihydro-1H-pyrrole, or 1,2,3,6-tetrahydropyridine ring.

In certain aspects, $R^1$ is hydroxyl or $C_1$-$C_6$ alkoxy. In certain aspects, $R^1$ is hydroxyl (e.g., 2-hydroxy; 3-hydroxy). In certain aspects, $R^1$ is methoxy (e.g., 2-methoxy).

In certain aspects, m is 0. In certain aspects, m is 1. In certain aspects, n is 0. In certain aspects, n is 1. In certain aspects, both m and n are 0.

In certain aspects, p is 0. In certain aspects, p is 1.

In certain aspects, q is 1. In certain aspects, p is 0 and q is 1.

In certain aspects, each $R^{2a}$ or $R^{2b}$ is hydrogen. In certain aspects, L is methylene. In certain aspects, L is ethylene.

In certain aspects, the compound of Formula (VA) is selected from compounds of Formulae (VC), (VD), (VE) and (VF):

(VC)

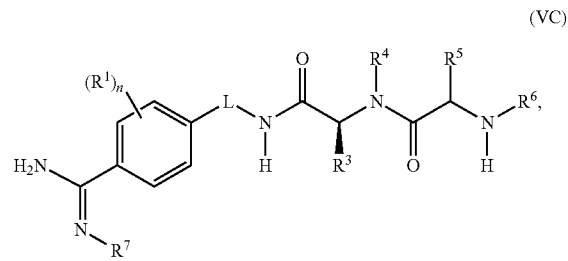

(VD)

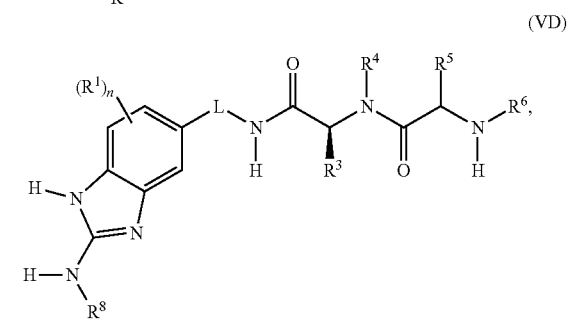

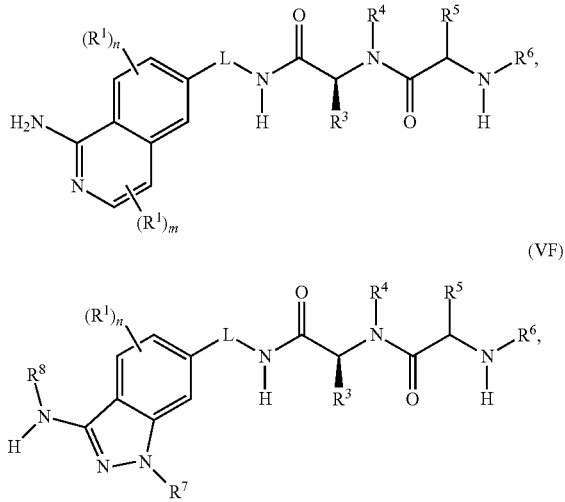

and salts thereof; wherein:

R$^7$ is a member selected from the group including hydrogen, hydroxyl, and C$_1$-C$_6$ alkyl;

R$^8$ is a member selected from the group including hydrogen and C$_1$-C$_6$ alkyl; and each m and n is an independently selected integer from 0 to 2.

In certain aspects, the compound is of Formula (VC). In certain aspects, the compound is of Formula (VD). In certain aspects, the compound is of Formula (VE). In certain aspects, the compound is of Formula (VF).

In certain aspects, R$^7$ is hydrogen. In certain aspects, R$^8$ is hydrogen.

The compounds of Formula (VA) and (VB), and embodiments thereof, including compounds of Formula (VC), (VD), (VE) and (VF), are useful as inhibitors of MASP-2 and for therapeutic use. The compounds of Formula (VA) and (VB), and embodiments thereof, are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Formula (VA) or (VB), or an embodiment thereof, optionally in the form of a salt.

In some embodiments the compound Formula (VA) or (VB) or an embodiment thereof is provided in the form of a pharmaceutical composition comprising the compound or a salt thereof, such as a pharmaceutically acceptable salt, and at least one pharmaceutically acceptable carrier or excipient.

In certain aspects, the compound is one or more selected from the compounds of Formula (VA) and (VB) in the Examples, including the compounds listed in Table 31, e.g., the compounds with selectivity for MASP-2 over thrombin. In certain aspects, one or more of R$^1$, R$^a$, R$^b$, R$^{2a}$, R$^{2b}$, R$^3$, R$^4$, R$^5$, R$^6$, or R$^{13}$ is selected from the corresponding substituents in the compounds of (VA) and (VB) in the Examples, including the compounds listed in Table 31 preferably, those of the compounds with selectivity for MASP-2 over thrombin.

In certain aspects, the invention sets forth a stereochemically pure enantiomer or diastereomer (e.g., an optically active compound with one or more chiral centers). Unless specifically indicated otherwise, for any inventive compound with one or more stereocenters, the present invention is intended to include and to describe both the pure (+) and (−) enantiomers, any other diastereomers, mixtures that are enriched in an enantiomer or diastereomer (e.g., 10%, 20%, 30%, 40%, 50%, 60%, 70% 75%, 80%, 85, 90%, or 95% enantiomeric or diastereomeric excess), and a racemic mixture of enantiomers or diastereomers.

In certain aspects, the invention sets forth a pharmaceutically acceptable salt of the indicated chemical structure (e.g., a hydrohalide, such as a hydrochloride or dihydrochloride). Examples of pharmaceutically acceptable salts are set forth in, e.g., Burge, S. M. et al., J. Pharm. Sci 1977, 66, 1-19. They include chlorides, bromides, iodides, formates, acetates, propionates, oxalates, malonates, succinates, fumarates, maleates, tartrates, citrates, benzoates, phthalates, sulfonates, arylsulfonates, alkylsulfonates, salts of fatty acids, and the like. Salts can be prepared by a variety of methods known to the skilled artisan, including a precipitation with the conjugate acid or base (e.g., treatment with gaseous HCl or an HCl solution).

In certain aspects, the invention sets forth a prodrug. A prodrug is a compound that is converted to a biologically active form under physiological conditions, often by hydrolysis, oxidation, or reduction (e.g., ester to acid form; carbamate to amino or hydroxy group; hydroxyamidine to amidine) Exemplary prodrugs are set forth in, e.g., Tilley, J. W., "Prodrugs of Benzamide," Prodrugs 2007, 191-222; Peterlin-Masic et al. Curr. Pharma. Design 2006, 12, 73-91. Prodrugs for the amidine group include amidoximes, O-alkylamidoximes, acylamidines, carbamates, 1,2,4-oxadiazolin-4-ones, and the like.

In certain aspects, the compound is useful for selectively inhibiting MASP-2 over thrombin, the method comprising administering the compound as described herein. In certain aspects, the selectivity ratio of MASP-2:thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

3. Compounds of Formula (VIA) and (VIB)

In certain aspects, the present disclosure provides a MASP-2 inhibitory compound for therapeutic use, wherein the compound is of the Formula (VIA) or (VIB):

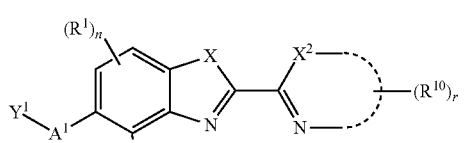

(VIA)

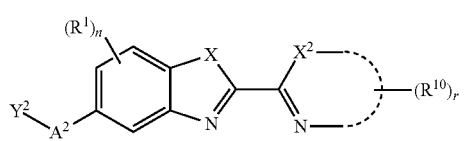

(VIB)

or a salt thereof; wherein:

A$^1$ is a member selected from the group consisting of —(C=NH)—, —(C=NOR$^a$)—, —[C=NO(C=O)R$^a$]—, —[C=N[O(C=O)ZR$^b$]]—, a fused 5- or 6-member heterocyclyl, and a fused 5- or 6-member heteroaryl;

when A¹ is —(C═NH)—, Y¹ is selected from the group consisting of —NH₂, —NH(C═O)Rᵃ, and —NH(C═O)ZRᵇ;

when A¹ is —(C═NORᵃ)—, —[C═NO(C═O)Rᵃ]—, or —{C═N[O(C═O)ZRᵇ]}—, Y¹ is —NH₂;

when A¹ is fused heterocyclyl or heteroaryl, Y¹ is —NH₂ or halo, and A¹ is substituted with m additional R¹ groups;

each Rᵃ and Rᵇ is independently selected from the group consisting of C₁-C₆ alkyl, C₃-C₁₀ cycloalkyl, C₆-C₁₀ aryl, and C₇-C₁₂ arylalkyl; wherein Rᵃ has m substituents selected from the group consisting of C₁-C₆ alkyl, hydroxyl, hydroxyl(C₁-C₆ alkyl), C₁-C₆ alkoxy, C₂-C₉ alkoxyalkyl, amino, C₁-C₆ alkylamino, and halo; or, alternatively, Rᵃ and Rᵇ join to form an heterocyclyl ring with m substituents selected from the group consisting of C₁-C₆ alkyl, hydroxyl, C₁-C₆ alkoxy, and halo;

each Z is independently selected from the group consisting of O and S;

A² is a member selected from the group consisting of C₃-C₆ heteroaryl and C₂-C₆ alkyl;

when A² is C₃-C₆ heteroaryl, Y² is selected from the group consisting of —NH₂, —CH₂NH₂, chloro, —(C═NH)NH₂, —(C═NH)NH(C═O)Rᵃ, —(C═NH)NH(C═O)ZRᵇ, —(C═NORᵃ)NH₂, —[C═NO(C═O)Rᵃ]NH₂, and —{C═N[O(C═O)ZRᵇ]}NH₂; and A² is substituted with m additional R¹ groups;

when A² is C₂-C₆ alkyl, Y² is selected from the group consisting of —NH(C═NH)NH₂, —NH(C═NH)NH(C═O)Rᵃ, and —NH(C═NH)NH(C═O)ZRᵇ;

each R¹ is a member independently selected from the group consisting of C₁-C₆ alkyl, hydroxyl, C₁-C₆ alkoxy, amino, C₁-C₆ alkylamino, and halo;

each m and n is an independently selected integer from 0 to 3;

X and X² are each a member selected from the group consisting of NR⁸, CH, and CR¹⁰ (preferably, NR⁸); or, alternatively, the X and X² R¹⁰ groups join to form a fused C₆ aryl, heteroaryl, or C₅-C₇ cycloalkyl ring with from 0 to 3 R¹³ substituents;

each R⁸ is a member independently selected from the group consisting of hydrogen and C₁-C₆ alkyl;

each R¹⁰ is a member independently selected from the group consisting of C₁-C₆ alkyl, heteroaryl or C₆-C₁₀ aryl with from 0 to 3 R¹³ substituents, hydroxyl, hydroxyl(C₁-C₆ alkyl), C₁-C₆ alkoxy, C₂-C₉ alkoxyalkyl, amino, C₁-C₆ alkylamino, and halo; or, alternatively, two R¹⁰ groups join to form a fused C₆ aryl, heteroaryl, or C₅-C₇ cycloalkyl ring with from 0 to 3 R¹³ substituents;

r is an integer from 0 to 4; and each R¹³ is a member independently selected from the group consisting of C₁-C₆ alkyl, C₆-C₁₀ aryl, carboxy (C₁-C₆ alkyloxy), heteroaryl, heterocyclyl, hydroxyl, hydroxyl(C₁-C₆ alkyl), C₁-C₆ alkoxy, C₂-C₉ alkoxyalkyl, amino, C₁-C₆ amido, C₁-C₆ alkylamino, and halo; or, alternatively, two R¹³ groups join to form a fused C₆-C₁₀ aryl, C₆-C₁₀ heteroaryl, or C₅-C₇ cycloalkyl ring or a salt thereof.

In certain aspects, the compound is of Formula (VIA).

In certain aspects, the compound is of Formula (VIB).

In certain aspects, the compound is of Formula (VIC) or (VID):

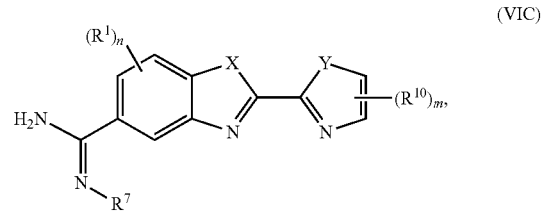

(VIC)

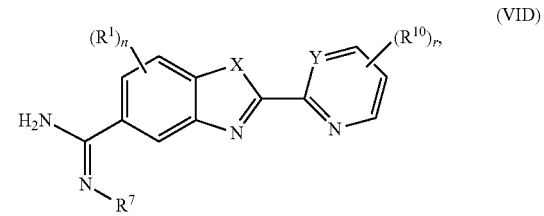

(VID)

or a salt thereof.

In certain aspects, each R⁷ is a member selected from the group consisting of hydrogen, hydroxyl, and C₁-C₆ alkyl; and m is an integer from 0 to 2.

In certain aspects, (i) the compound is of Formula (VIA) or a salt thereof, and m is 0; or (ii) the compound is (VIB) or a salt thereof, and r is 0.

In certain aspects, X is NR⁸.

In certain aspects, R⁸ is hydrogen.

In certain aspects, X² is CH or CR¹⁰.

In certain aspects, R¹⁰ is a member independently selected from the group consisting of C₁-C₆ alkyl, C₆ aryl with from 0 to 3 R¹³ substituents, C₁-C₆ alkoxy, and C₂-C₉ alkoxyalkyl.

In certain aspects, two R¹⁰ groups join to form a fused C₆ aryl ring with from 0 to 3 R¹³ substituents.

In certain aspects, R⁷ is hydrogen.

In certain aspects, R³ is a member selected from the group consisting of hydrogen or methyl. In certain aspects, R³ is methyl.

In certain aspects, Z is O.

In certain aspects, R¹¹ is (R¹⁴)(R¹⁴)N(CO)—.

In certain aspects, R¹¹ is (R¹⁴)(H)N(CO)—.

In certain aspects, R¹⁴ is C₁-C₆ alkyl, C₃-C₇ cycloalkyl, or C₄-C₈ cycloalkylalkyl.

In certain aspects, R¹² is hydrogen or C₇-C₁₄ arylalkyl.

In certain aspects, R¹ is hydroxyl or C₁-C₆ alkoxy.

In certain aspects, each R²ᵃ or R²ᵇ is hydrogen.

In certain aspects, L is methylene.

In certain aspects, A¹ is —(C═NH)—. In certain aspects, Y¹ is —NH₂. In certain aspects, Y¹ is —NH(C═O)Rᵃ. In certain aspects, Y¹ is —NH(C═O)ZRᵇ.

In certain aspects, A¹ is —(C═NORᵃ)—. In certain aspects, Y¹ is —NH₂. In certain aspects, Y¹ is —NH(C═O)Rᵃ. In certain aspects, Y¹ is —NH(C═O)ZRᵇ.

In certain aspects, A¹ is —(C═NH)—. In certain aspects, A¹ is —NH(C═O)Rᵃ. In certain aspects, A¹ is —NH(C═O)ZRᵇ. In certain aspects, Z is O, S, or N.

In certain aspects, A¹ is a fused heteroaryl. In certain aspects, A¹ is a quinolone. In certain aspects, A¹ is an isoquinoline. In certain aspects, A¹ is a benzimidazole. In certain aspects, Y¹ is —NH₂.

In certain aspects, Rᵃ or Rᵇ is C₁-C₆ alkyl, such as methyl, ethyl, n-propyl, isopropyl, n-butyl, or t-butyl. In certain aspects, Rᵃ or Rᵇ is C₃-C₁₀ cycloalkyl, such as cyclohexyl, cyclopentyl, or cyclopropyl. In certain aspects, Rᵃ or Rᵇ is C₆-C₁₀ aryl, such as phenyl or substituted phenyl (e.g., 4-methoxyphenyl). In certain aspects, $R^a$ or $R^b$ is $C_7$-$C_{12}$ arylalkyl, such as benzyl or 4-methoxybenzyl.

In certain aspects, $R^7$ is hydrogen.
In certain aspects, the compound is of Formula (VIB).
In certain aspects, $A^2$ is $C_3$-$C_6$ heteroaryl.
In certain aspects, $A^2$ is substituted with m additional $R^1$ groups, such as halo, $C_2$-$C_6$ alkyl, or $C_1$-$C_4$ methoxy, In certain aspects, $Y^2$ is selected from the group consisting of —NH(C=NH)NH$_2$, —NH(C=NH)NH(C=O)$R^a$, and —NH(C=NH)NH(C=O)Z$R^b$. In certain aspects, $Y^2$ is —NH(C=NH)NH$_2$. In certain aspects, $Y^2$ is —NH(C=NH)NH(C=O)$R^a$. In certain aspects, $Y^2$ is —NH(C=NH)NH(C=O)Z$R^b$.

In certain aspects, $Y^2$ is halo (e.g., chloro, such as 3-chloro). In certain aspects, $Y^2$ is aminomethyl (e.g., 4-aminomethyl).

In certain aspects, $A^2$ is $C_2$-$C_6$ alkyl.
In certain aspects, X is $NR^8$ (e.g., NH or NMe). In certain aspects, X is CH. In certain aspects, X is $CR^{10}$ (e.g., CMe).
In certain aspects, each Z is a member independently selected from the group consisting of O and $NR^8$; and each $R^8$ is a member independently selected from the group consisting of hydrogen and $C_1$-$C_6$ alkyl. In certain aspects, one Z or each Z is $NR^b$. In certain aspects, each $R^8$ is hydrogen.

In certain aspects, $X^2$ is $NR^8$ (e.g., NH or NMe). In certain aspects, B is CH. In certain aspects, $X^2$ is $CR^{10}$ (e.g., CMe).
In certain aspects, the compound has an $R^3$ stereochemistry of

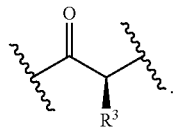

In certain aspects, $R^3$ is a member selected from the group consisting of hydrogen or methyl. In certain aspects, $R^3$ is hydrogen. In certain aspects, $R^3$ is methyl.

In certain aspects, $R^1$ is hydroxyl or $C_1$-$C_6$ alkoxy. In certain aspects, $R^1$ is hydroxyl (e.g., 2-hydroxy; 3-hydroxy). In certain aspects, $R^1$ is methoxy (e.g., 2-methoxy).

In certain aspects, m is 0. In certain aspects, m is 1. In certain aspects, n is 0. In certain aspects, n is 1. In certain aspects, both m and n are 0.

In certain aspects, p is 0. In certain aspects, p is 1.
In certain aspects, q is 1. In certain aspects, p is 0 and q is 1.

In certain aspects, each $R^{2a}$ or $R^{2b}$ is hydrogen. In certain aspects, L is methylene In certain aspects, L is ethylene.

In certain aspects, each $R^{13}$ is a member independently selected from the group consisting of $C_1$-$C_6$ alkyl, heteroaryl or $C_6$-$C_{10}$ aryl with from 0 to 3 $R^{13}$ substituents, hydroxyl, hydroxyl($C_1$-$C_6$ alkyl), $C_1$-$C_6$ alkoxy, $C_2$-$C_9$ alkoxyalkyl, amino, $C_1$-$C_6$ alkylamino, and halo; or, alternatively, two $R^{10}$ groups join to form a fused $C_6$ aryl, heteroaryl, or $C_5$-$C_7$ cycloalkyl ring with from 0 to 3 $R^{13}$ substituents. In certain aspects, an $R^{10}$ is amino. In certain aspects, an $R^{10}$ and an $R^1$ are amino.

In certain aspects, r is an integer from 0 to 5 (i.e., 0, 1, 2, 3, 4, or 5). In certain aspects, r is an integer from 0 to 4 (i.e., 0, 1, 2, 3, and 4). In certain aspects, r is an integer from 0 to 3 (i.e., 0, 1, 2, or 3).

In certain aspects, each $R^{13}$ is a member independently selected from the group consisting of $C_1$-$C_6$ alkyl, $C_6$-$C_{10}$ aryl, carboxy($C_1$-$C_6$ alkyloxy), heteroaryl, heterocyclyl, hydroxyl, hydroxyl($C_1$-$C_6$ alkyl), $C_1$-$C_6$ alkoxy, $C_2$-$C_9$ alkoxyalkyl, amino, $C_1$-$C_6$ amido, $C_1$-$C_6$ alkylamino, and halo; or, alternatively, two $R^{13}$ groups join to form a fused $C_6$-$C_{10}$ aryl, $C_6$-$C_{10}$ heteroaryl, or $C_5$-$C_7$ cycloalkyl ring or a salt thereof. In certain aspects, $R^{13}$ is phenyl. In certain aspects, $R^{13}$ is substituted phenyl.

The compounds of Formula (VIA) and (VIB), and embodiments thereof, including compounds of Formula (VIC) and (VID), are useful as inhibitors of MASP-2 and for therapeutic use. The compounds of Formula (VIA) and (VIB), and embodiments thereof, are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Formula (VIA) and (VIB), or an embodiment thereof, optionally in the form of a salt.

In some embodiments the compound Formula (VIA) and (VIB) or an embodiment thereof is provided in the form of a pharmaceutical composition comprising the compound or a salt thereof, such as a pharmaceutically acceptable salt, and at least one pharmaceutically acceptable carrier or excipient.

In certain aspects, the compound is one or more selected from the compounds of Formula (VIA) and (VIB) in the Examples, including the compounds listed in Table 31, e.g., the compounds with selectivity for MASP-2 over thrombin. In certain aspects, one or more of $R^1$, $R^a$, $R^b$, $R^{2a}$, $R^{2b}$, $R^3$, $R^4$, $R^5$, $R^6$, or $R^{13}$ is selected from the corresponding substituents in the compounds of (VIA) and (VIB) in the Examples, including the compounds listed in Table 31 preferably, those of the compounds with selectivity for MASP-2 over thrombin.

In certain aspects, the invention sets forth a stereochemically pure enantiomer or diastereomer (e.g., an optically active compound with one or more chiral centers). Unless specifically indicated otherwise, for any inventive compound with one or more stereocenters, the present invention is intended to include and to describe both the pure (+) and (−) enantiomers, any other diastereomers, mixtures that are enriched in an enantiomer or diastereomer (e.g., 10%, 20%, 30%, 40%, 50%, 60%, 70% 75%, 80%, 85, 90%, or 95% enantiomeric or diastereomeric excess), and a racemic mixture of enantiomers or diastereomers.

In certain aspects, the invention sets forth a pharmaceutically acceptable salt of the indicated chemical structure (e.g., a hydrohalide, such as a hydrochloride or dihydrochloride). Examples of pharmaceutically acceptable salts are set forth in, e.g., Burge, S. M. et al., J. Pharm. Sci 1977, 66, 1-19. They include chlorides, bromides, iodides, formates, acetates, propionates, oxalates, malonates, succinates, fumarates, maleates, tartrates, citrates, benzoates, phthalates, sulfonates, arylsulfonates, alkylsulfonates, salts of fatty acids, and the like. Salts can be prepared by a variety of methods known to the skilled artisan, including a precipitation with the conjugate acid or base (e.g., treatment with gaseous HCl or an HCl solution).

In certain aspects, the invention sets forth a prodrug. A prodrug is a compound that is converted to a biologically active form under physiological conditions, often by hydrolysis, oxidation, or reduction (e.g., ester to acid form; carbamate to amino or hydroxy group; hydroxyamidine to amidine) Exemplary prodrugs are set forth in, e.g., Tilley, J. W., "Prodrugs of Benzamide," *Prodrugs* 2007, 191-222;

Peterlin-Masic et al. *Curr. Pharma. Design* 2006, 12, 73-91. Prodrugs for the amidine group include amidoximes, O-alkylamidoximes, acylamidines, carbamates, 1,2,4-oxadiazolin-4-ones, and the like.

In certain aspects, the compound is useful for selectively inhibiting MASP-2 over thrombin, the method comprising administering the compound as described herein. In certain aspects, the selectivity ratio of MASP-2:thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

4. Compounds of Formula VIIA and VIIB

In certain aspects, the present disclosure provides a MASP-2 inhibitory compound for therapeutic use, wherein the compound is of the Formula (VIIA) or (VIIB):

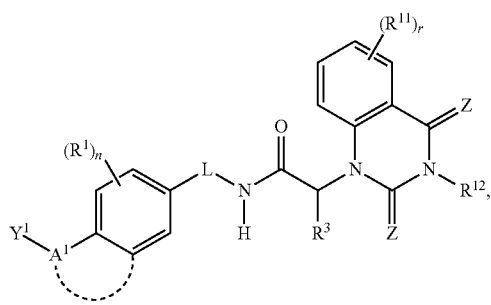

(VIIA)

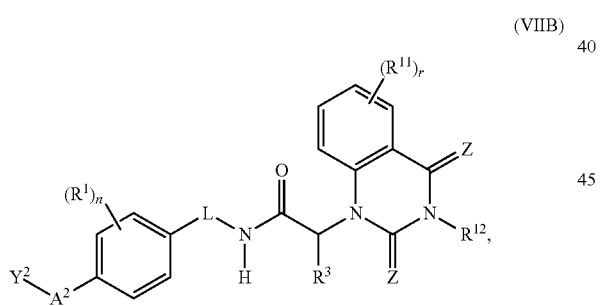

(VIIB)

or a salt thereof; wherein:

$A^1$ is a member selected from the group consisting of —(C=NH)—, —(C=NOR$^a$)—, —[C=NO(C=O)R$^a$]—, —[C=N[O(C=O)ZR$^b$]]—, a fused 5- or 6-member heterocyclyl, and a fused 5- or 6-member heteroaryl;

when $A^1$ is —(C=NH)—, $Y^1$ is selected from the group consisting of —NH$_2$, —NH(C=O)R$^a$, and —NH(C=O)ZR$^b$;

when $A^1$ is —(C=NOR$^a$)—, —[C=NO(C=O)R$^a$]—, or —{C=N[O(C=O)ZR$^b$]}—, $Y^1$ is —NH$_2$;

when $A^1$ is fused heterocyclyl or heteroaryl, $Y^1$ is —NH$_2$ or halo, and $A^1$ is substituted with m additional $R^1$ groups;

each $R^a$ and $R^b$ is independently selected from the group consisting of $C_1$-$C_6$ alkyl, $C_3$-$C_{10}$ cycloalkyl, $C_6$-$C_{10}$ aryl, and $C_7$-$C_{12}$ arylalkyl; wherein $R^a$ has m substituents selected from the group consisting of $C_1$-$C_6$ alkyl, hydroxyl, hydroxyl($C_1$-$C_6$ alkyl), $C_1$-$C_6$ alkoxy, $C_2$-$C_9$ alkoxyalkyl, amino, $C_1$-$C_6$ alkylamino, and halo; or, alternatively, $R^a$ and $R^b$ join to form an heterocyclyl ring with m substituents selected from the group consisting of $C_1$-$C_6$ alkyl, hydroxyl, $C_1$-$C_6$ alkoxy, and halo;

each Z is independently selected from the group consisting of O and S;

$A^2$ is a member selected from the group consisting of $C_3$-$C_6$ heteroaryl and $C_2$-$C_6$ alkyl;

when $A^2$ is $C_3$-$C_6$ heteroaryl, $Y^2$ is selected from the group consisting of —NH$_2$, —CH$_2$NH$_2$, chloro, —(C=NH)NH$_2$, —(C=NH)NH(C=O)R$^a$, —(C=NH)NH(C=O)ZR$^b$, —(C=NOR$^a$)NH$_2$, —[C=NO(C=O)R$^a$]NH$_2$, and —{C=N[O(C=O)ZR$^b$]}NH$_2$; and $A^2$ is substituted with m additional $R^1$ groups;

when $A^2$ is $C_2$-$C_6$ alkyl, $Y^2$ is selected from the group consisting of —NH(C=NH)NH$_2$, —NH(C=NH)NH(C=O)R$^a$, and —NH(C=NH)NH(C=O)ZR$^b$;

each $R^1$ is a member independently selected from the group consisting of $C_1$-$C_6$ alkyl, hydroxyl, $C_1$-$C_6$ alkoxy, amino, $C_1$-$C_6$ alkylamino, and halo;

each m and n is an independently selected integer from 0 to 3;

L is —(O)$_p$—(C(R$^{2a}$)(R$^{2b}$))$_q$—, each $R^{2a}$ or $R^{2b}$ is a member independently selected from the group consisting of hydrogen and fluoro;

p is an integer from 0 to 1;

q is an integer from 1 to 2;

$R^3$ is a member selected from the group consisting of hydrogen, $C_1$-$C_6$ alkyl, and carboxy($C_1$-$C_6$ alkyl);

each $R^{11}$ is a member independently selected from the group consisting of $C_1$-$C_6$ alkyl, hydroxyl, $C_1$-$C_6$ alkoxy, amino, $C_1$-$C_6$ alkylamino, halo, and (R$^{14}$)(R$^{14}$)N(CO)—; or, alternatively, two $R^{11}$ groups join to form a fused $C_6$ aryl, heteroaryl, or $C_5$-$C_7$ cycloalkyl ring with from 0 to 3 $R^{13}$ substituents;

r is an integer from 0 to 4; and each Z is a member independently selected from the group consisting of O and NR$^8$;

each $R^8$ is a member independently selected from the group consisting of hydrogen and $C_1$-$C_6$ alkyl;

each $R^{12}$ is a member independently selected from the group consisting of hydrogen, $C_1$-$C_6$ alkyl, and $C_7$-$C_{14}$ arylalkyl with from 0 to 3 $R^{13}$ substituents;

each $R^{13}$ is a member independently selected from the group consisting of $C_1$-$C_6$ alkyl, hydroxyl, hydroxyl($C_1$-$C_6$ alkyl), $C_1$-$C_6$ alkoxy, $C_2$-$C_9$ alkoxyalkyl, amino, $C_1$-$C_6$ alkylamino, and halo; or, alternatively, two $R^{13}$ groups join to form a fused $C_6$ aryl, heteroaryl, or $C_5$-$C_7$ cycloalkyl ring; and each $R^{14}$ is a member independently selected from the group consisting of hydrogen, $C_1$-$C_6$ alkyl, $C_3$-$C_7$ cycloalkyl, $C_4$-$C_8$ cycloalkylalkyl, $C_7$-$C_{14}$ arylalkyl, and heteroaryl($C_1$-$C_6$ alkyl); or, alternatively, two $R^{13}$ groups join to form a fused heterocyclyl ring.

In certain aspects, the compound is of Formula (VIIA).

In certain aspects, the compound is of Formula (VIIB).

In certain aspects, the compound is of Formula (VIIC):

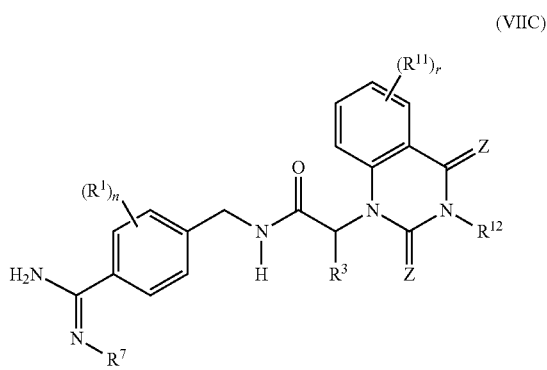

(VIIC)

in which each $R^7$ is a member selected from the group consisting of hydrogen, hydroxyl, and $C_1$-$C_6$ alkyl.

In certain aspects, $R^7$ is hydrogen.
In certain aspects, X is $NR^8$.
In certain aspects, $R^8$ is hydrogen.
In certain aspects, $X^2$ is CH or $CR^{10}$.
In certain aspects, $R^{10}$ is a member independently selected from the group consisting of $C_1$-$C_6$ alkyl, $C_6$ aryl with from 0 to 3 $R^{13}$ substituents, $C_1$-$C_6$ alkoxy, and $C_2$-$C_9$ alkoxyalkyl.
In certain aspects, two $R^{10}$ groups join to form a fused $C_6$ aryl ring with from 0 to 3 R13 substituents.
In certain aspects, $R^7$ is hydrogen.
In certain aspects, $R^3$ is a member selected from the group consisting of hydrogen or methyl. In certain aspects, $R^3$ is methyl.
In certain aspects, Z is O.
In certain aspects, $R^{11}$ is $(R^{14})(R^{14})N(CO)$—.
In certain aspects, $R^{11}$ is $(R^{14})(H)N(CO)$—.
In certain aspects, $R^{14}$ is $C_1$-$C_6$ alkyl, $C_3$-$C_7$ cycloalkyl, or $C_4$-$C_8$ cycloalkylalkyl.
In certain aspects, $R^{12}$ is hydrogen or $C_7$-$C_{14}$ arylalkyl.
In certain aspects, $R^1$ is hydroxyl or $C_1$-$C_6$ alkoxy.
In certain aspects, each $R^{2a}$ or $R^{2b}$ is hydrogen.
In certain aspects, L is methylene.
In certain aspects, $A^1$ is —(C=NH)—. In certain aspects, $Y^1$ is —$NH_2$. In certain aspects, $Y^1$ is —NH(C=O)$R^a$. In certain aspects, $Y^1$ is —NH(C=O)Z$R^b$.
In certain aspects, $A^1$ is —(C=NO$R^a$)—. In certain aspects, $Y^1$ is —$NH_2$. In certain aspects, $Y^1$ is —NH(C=O)$R^a$. In certain aspects, $Y^1$ is —NH(C=O)Z$R^b$.
In certain aspects, $A^1$ is —(C=NH)—. In certain aspects, $A^1$ is —NH(C=O)$R^a$. In certain aspects, $A^1$ is —NH(C=O)Z$R^b$. In certain aspects, Z is O, S, or N.
In certain aspects, $A^1$ is a fused heteroaryl. In certain aspects, $A^1$ is a quinolone. In certain aspects, $A^1$ is an isoquinoline. In certain aspects, $A^1$ is a benzimidazole. In certain aspects, $Y^1$ is —$NH_2$.
In certain aspects, $R^a$ or $R^b$ is $C_1$-$C_6$ alkyl, such as methyl, ethyl, n-propyl, isopropyl, n-butyl, or t-butyl. In certain aspects, $R^a$ or $R^b$ is $C_3$-$C_{10}$ cycloalkyl, such as cyclohexyl, cyclopentyl, or cyclopropyl. In certain aspects, $R^a$ or $R^b$ is $C_6$-$C_{10}$ aryl, such as phenyl or substituted phenyl (e.g., 4-methoxyphenyl). In certain aspects, $R^a$ or $R^b$ is $C_7$-$C_{12}$ arylalkyl, such as benzyl or 4-methoxybenzyl.
In certain aspects, $R^7$ is hydrogen.
In certain aspects, the compound is of Formula (VIIB).
In certain aspects, $A^2$ is $C_3$-$C_6$ heteroaryl.

In certain aspects, $A^2$ is substituted with m additional $R^1$ groups, such as halo, $C_2$-$C_6$ alkyl, or $C_1$-$C_4$ methoxy,
In certain aspects, $Y^2$ is selected from the group consisting of —NH(C=NH)$NH_2$, —NH(C=NH)NH(C=O)$R^a$, and —NH(C=NH)NH(C=O)Z$R^b$. In certain aspects, $Y^2$ is —NH(C=NH)$NH_2$. In certain aspects, $Y^2$ is —NH(C=NH)NH(C=O)$R^a$. In certain aspects, $Y^2$ is —NH(C=NH)NH(C=O)Z$R^b$.
In certain aspects, $Y^2$ is halo (e.g., chloro, such as 3-chloro). In certain aspects, $Y^2$ is aminomethyl (e.g., 4-aminomethyl).
In certain aspects, $A^2$ is $C_2$-$C_6$ alkyl.
In certain aspects, X is $NR^8$ (e.g., NH or NMe). In certain aspects, X is CH. In certain aspects, X is $CR^{10}$ (e.g., CMe).
In certain aspects, each Z is a member independently selected from the group consisting of O and $NR^8$; and each $R^1$ is a member independently selected from the group consisting of hydrogen and $C_1$-$C_6$ alkyl. In certain aspects, one Z or each Z is $NR^8$. In certain aspects, each $R^8$ is hydrogen.
In certain aspects, $X^2$ is $NR^8$ (e.g., NH or NMe). In certain aspects, B is CH. In certain aspects, $X^2$ is $CR^{10}$ (e.g., CMe).
In certain aspects, the compound has an $R^3$ stereochemistry of

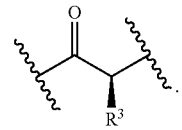

In certain aspects, $R^3$ is a member selected from the group consisting of hydrogen or methyl. In certain aspects, $R^3$ is hydrogen. In certain aspects, $R^3$ is methyl.
In certain aspects, $R^1$ is hydroxyl or $C_1$-$C_6$ alkoxy. In certain aspects, $R^1$ is hydroxyl (e.g., 2-hydroxy; 3-hydroxy). In certain aspects, $R^1$ is methoxy (e.g., 2-methoxy).
In certain aspects, m is 0. In certain aspects, m is 1. In certain aspects, n is 0. In certain aspects, n is 1. In certain aspects, both m and n are 0.
In certain aspects, p is 0. In certain aspects, p is 1.
In certain aspects, q is 1. In certain aspects, p is 0 and q is 1.
In certain aspects, each $R^{2a}$ or $R^{2b}$ is hydrogen. In certain aspects, L is methylene In certain aspects, L is ethylene.
In certain aspects, each $R^{13}$ is a member independently selected from the group consisting of $C_1$-$C_6$ alkyl, heteroaryl or $C_6$-$C_{10}$ aryl with from 0 to 3 $R^{13}$ substituents, hydroxyl, hydroxyl($C_1$-$C_6$ alkyl), $C_1$-$C_6$ alkoxy, $C_2$-$C_9$ alkoxyalkyl, amino, $C_1$-$C_6$ alkylamino, and halo; or, alternatively, two $R^{10}$ groups join to form a fused $C_6$ aryl, heteroaryl, or $C_5$-$C_7$ cycloalkyl ring with from 0 to 3 $R^{13}$ substituents. In certain aspects, an $R^{10}$ is amino. In certain aspects, an $R^{10}$ and an $R^1$ are amino.
In certain aspects, r is an integer from 0 to 5 (i.e., 0, 1, 2, 3, 4, or 5). In certain aspects, r is an integer from 0 to 4 (i.e., 0, 1, 2, 3, and 4). In certain aspects, r is an integer from 0 to 3 (i.e., 0, 1, 2, or 3).
In certain aspects, each $R^{13}$ is a member independently selected from the group consisting of $C_1$-$C_6$ alkyl, $C_6$-$C_{10}$ aryl, carboxy($C_1$-$C_6$ alkyloxy), heteroaryl, heterocyclyl, hydroxyl, hydroxyl($C_1$-$C_6$ alkyl), $C_1$-$C_6$ alkoxy, $C_2$-$C_9$ alkoxyalkyl, amino, $C_1$-$C_6$ amido, $C_1$-$C_6$alkylamino, and halo; or, alternatively, two $R^{13}$ groups join to form a fused $C_6$-$C_{10}$ aryl, $C_6$-$C_{10}$ heteroaryl, or $C_5$-$C_7$ cycloalkyl ring or a salt thereof. In certain aspects, $R^{13}$ is phenyl. In certain aspects, $R^{13}$ is substituted phenyl.

The compounds of Formula (VIIA) and (VIIB), and embodiments thereof, including compounds of Formula (VIIC) and (VIID), are useful as inhibitors of MASP-2 and for therapeutic use. The compounds of Formula (VIIA) and (VIIB), and embodiments thereof, are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Formula (VIIA) and (VIIB), or an embodiment thereof, optionally in the form of a salt.

In some embodiments the compound Formula (VIIA) and (VIIB) or an embodiment thereof is provided in the form of a pharmaceutical composition comprising the compound or a salt thereof, such as a pharmaceutically acceptable salt, and at least one pharmaceutically acceptable carrier or excipient.

In certain aspects, the compound is one or more selected from the compounds of Formula (VIIA) and (VIIB) in the Examples, including the compounds listed in Table 31, e.g., the compounds with selectivity for MASP-2 over thrombin. In certain aspects, one or more of $R^1$, $R^a$, $R^b$, $R^{2a}$, $R^{2b}$, $R^3$, $R^4$, $R^5$, $R^6$, or $R^{13}$ is selected from the corresponding substituents in the compounds of (VIIA) and (VIIB) in the Examples, including the compounds listed in Table 31 preferably, those of the compounds with selectivity for MASP-2 over thrombin.

In certain aspects, the invention sets forth a stereochemically pure enantiomer or diastereomer (e.g., an optically active compound with one or more chiral centers). Unless specifically indicated otherwise, for any inventive compound with one or more stereocenters, the present invention is intended to include and to describe both the pure (+) and (−) enantiomers, any other diastereomers, mixtures that are enriched in an enantiomer or diastereomer (e.g., 10%, 20%, 30%, 40%, 50%, 60%, 70% 75%, 80%, 85, 90%, or 95% enantiomeric or diastereomeric excess), and a racemic mixture of enantiomers or diastereomers.

In certain aspects, the invention sets forth a pharmaceutically acceptable salt of the indicated chemical structure (e.g., a hydrohalide, such as a hydrochloride or dihydrochloride). Examples of pharmaceutically acceptable salts are set forth in, e.g., Burge, S. M. et al., J. Pharm. Sci 1977, 66, 1-19. They include chlorides, bromides, iodides, formates, acetates, propionates, oxalates, malonates, succinates, fumarates, maleates, tartrates, citrates, benzoates, phthalates, sulfonates, arylsulfonates, alkylsulfonates, salts of fatty acids, and the like. Salts can be prepared by a variety of methods known to the skilled artisan, including a precipitation with the conjugate acid or base (e.g., treatment with gaseous HCl or an HCl solution).

In certain aspects, the invention sets forth a prodrug. A prodrug is a compound that is converted to a biologically active form under physiological conditions, often by hydrolysis, oxidation, or reduction (e.g., ester to acid form; carbamate to amino or hydroxy group; hydroxyamidine to amidine) Exemplary prodrugs are set forth in, e.g., Tilley, J. W., "Prodrugs of Benzamide," *Prodrugs* 2007, 191-222; Peterlin-Masic et al. *Curr. Pharma. Design* 2006, 12, 73-91. Prodrugs for the amidine group include amidoximes, O-alkylamidoximes, acylamidines, carbamates, 1,2,4-oxadiazolin-4-ones, and the like.

In certain aspects, the compound is useful for selectively inhibiting MASP-2 over thrombin, the method comprising administering the compound as described herein. In certain aspects, the selectivity ratio of MASP-2:thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

F. Compounds Defined by Reference to Binding Rules

In certain aspects, the present disclosure provides compounds having MASP-2 inhibitory activity, especially for therapeutic use. The compound with MASP-2 inhibitory activity interacts with the MASP-2 serine protease domain in an enzyme-inhibitor complex with a plurality of intermolecular interactions. In certain aspects, the molecule is described with complete specificity and description by the number and type(s) of intermolecular interactions within a MASP-2 binding site, using an empirically derived rule set such as an interaction rule set.

In certain aspects, the compounds with MASP-2 inhibitory activity interact with the MASP-2 serine protease domain as an enzyme-inhibitor complex. The compound having MASP-2 inhibitory activity has between 1 and 100 intermolecular interactions between itself and MASP-2 such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more intermolecular interactions with the serine protease domain of MASP-2 (residues 445-686 of SEQ ID NO: 1). These intermolecular interactions types can be a hydrogen-bond, an ionic bond, an electrostatic bond, π-π interactions, a van der Waals interaction, binding of a water molecule or combinations thereof. The numbers within the various types of intermolecular interactions are counted to reach a total.

In certain aspects, a plurality of the same type of intermolecular interactions exists. For example, the enzyme-inhibitor complex may have 1-40 hydrogen-bonds, 1-40 ionic bonds, 1-40 electrostatic bonds, 1-40 π-π interactions, 1-40 van der Waals interactions, 1-40 binding of water molecules and combinations of thereof, wherein each of the foregoing 1-40 range means 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more interactions. In certain aspects, a plurality or multiple intermolecular interactions may exist with the same amino acid within the binding site.

In certain instances, an inhibitory molecule is described by a rule set. The compound with MASP-2 inhibitory activity interacts with the MASP-2 serine protease domain in an enzyme-inhibitor complex with a plurality of intermolecular interactions or rules. In certain aspects, the molecule is described with complete structural and functional specificity and description by the number and type(s) of intermolecular interactions. These rules have been empirically derived and discovered using crystallographic data with a number of enzyme-inhibitor complex co-crystals. In certain instances, the crystallographic data are from at least 1, 10, 20, 30, 40, 50, up to 100 enzyme-inhibitor complex crystals. For example, 30 co-crystals can be used, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or even more enzyme-inhibitor complex crystals can be used to generate a set of rules. Using the co-crystal structural information, it is possible to describe the binding site and inhibitory compounds within Angstrom detail and definition.

In certain instances, a plurality of amino acids within the MASP-2 serine protease domain are involved in the intermolecular interactions. Amino acids within the MASP-2 serine protease domain (amino acid residues 445-686 of SEQ ID NO:1) include, but are not limited to, ASP 627, SER 628, SER 654, GLY 656, GLN 665, SER 657, PHE 529, TYR 607, TRP 655, GLY 667, SER 633, ARG 630, CYS 629, HIS 483, PRO 606, PRO 608, SER 611, VAL 653, MET 658, TYR 669, ASN 659, CYS 660, GLN 665.

In certain aspects, the number of amino acids within the serine protease domain that interact with a compound having MASP-2 inhibitory activity or that make up a rule set is about 1-50, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acid residues within the MASP-2 serine protease domain.

In certain instances, an inhibitor of the present disclosure is bound to MASP-2, rendering MASP-2 inactive. The amino acids of MASP-2 interact through intermolecular interactions with the inhibitor compound and the types of interactions are now described in more detail.

In certain aspects, the type of interactions include a hydrogen bond (H-bond). The enzyme-inhibitor complex may include 1-40 intermolecular H-bonds with one or more of the following 8 amino acids: ASP 627, SER 628, SER 654, GLY 656, GLN 665, ARG 630, PRO 606 and SER 657. The enzyme-inhibitor complex may include 1-40 intermolecular H-bonds with one or more of the following 6 amino acids: ASP 627, SER 628, SER 654, GLY 656, GLN 665 and SER 657. The 1-40 intermolecular H-bonds can include one or more atoms of the inhibitor with one or more atoms of ASP 627, SER 628, SER 654, GLY 656, GLN 665, ARG 630, PRO 606 and SER 657. The 1-40 intermolecular H-bonds can include one or more atoms of the inhibitor with one or more atoms of ASP 627, SER 628, SER 654, GLY 656, GLN 665 and SER 657. Each amino acid can have more than one H-bond interaction with an inhibitor. In certain instances, the same atom can be hydrogen bonded to one or more partners. In other words, a single atom of an inhibitory molecule can interact with 2 or more atoms on the protein. In certain instances, there are 1-10H-bonds, or 2-8H-bonds, or 1, 2, 3, 4, 5, 6, 7, 8, 9, or 10H-bonds per compounds.

In certain aspects, the type of interactions include an ionic and/or an electrostatic interaction. The enzyme-inhibitor complex may include 1-10 intermolecular ionic and/or electrostatic interactions with ASP 627 or ARG 630. The enzyme-inhibitor complex may include 1-10 intermolecular ionic and/or electrostatic interactions with ASP 627. ASP 627 can have more than one ionic and or electrostatic interaction with an inhibitor.

In certain other aspects, the type of interaction is binding of a water molecule with ASP 627, GLN 665, SER 657, ASN 659, SER 628, GLU 662, ARG 630, VAL 668, TYR 602, TYR 607. The enzyme-inhibitor complex may include 1-30 bound water molecules 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 to various amino acids, other water molecules, to the compounds or combinations thereof.

In certain other instances, the type of interaction includes one or more (e.g., a plurality or 1-40) π-π interactions with one or more of the following amino acids PHE 529, TYR 607, and/or TRP 655, 1, 2 or 3 amino acids. Each of the foregoing amino acids can have more than one π-π interaction.

In certain aspects, the type of interaction also includes one or more such as 1-40, van der Waals interactions with ALA 468, ALA 469, HIS 483, ASP 526, ALA 527, GLY 528, PHE 529, LEU 575, PRO 606, TYR 607, PRO 608, SER 611, ASP627, SER 628, CYS 629, ARG 630, GLY 631, ASP 632, SER 633, GLY634, GLY 635, VAL 653, SER 654, TRP 655, GLY656, SER 657, MET 658, ASN 659, CYS 660, GLN 665, GLY 667, TYR 669 and combinations thereof, which interactions are specific MASP-2 amino acids within the serine protease domain of MASP-2.

In certain aspects, the type of interaction also includes one or more such as 1-40, van der Waals interactions with HIS 483, PHE 529, PRO 606, TYR 607, PRO 608, SER 611, ASP 627, SER 628, CYS 629, ARG 630, SER 633, VAL 653, SER 654, TRP 655, GLY 656, SER 657, MET 658, ASN 659, CYS 660, GLN 665, GLY 667 and TYR 669 and combinations thereof, which interactions are specific MASP-2 amino acids within the serine protease domain of MASP-2.

In certain aspects, the MASP-2 inhibitory compound can be a compound as described elsewhere herein, including the compounds of Formulae (I), (II), (III), (IV), (V), (VI) or (VII), or any of the embodiments thereof.

In certain aspects, compounds having MASP-2 inhibitory activity comprise the compounds of Formula (VIII):

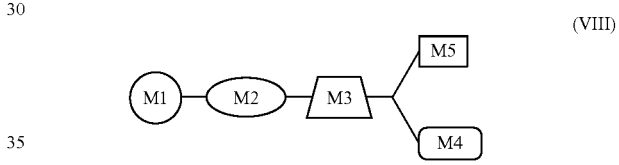

(VIII)

In certain aspects, the compounds of the disclosure can have 5 segments identified as $M_1$, $M_2$, $M_3$, $M_4$ and $M_5$. The segments or regions bind the active binding site of MASP-2. In certain aspects, the various segments bind with affinity to the active site. The inhibitor recognition site or pocket includes the binding site for the inhibitor. Using the nomenclature of Schechter and Berger, P1-P1' denotes the peptide residues of the scissile bond of the substrate (inhibitor), whereas S1-S1' denote the corresponding enzyme binding pocket for these segments. The inhibitor-MASP-2 interactions extends beyond the S1 site and includes additional binding of the inhibitor to MASP-2. In one aspect, $M_1$-$M_5$ may substantially bind to one or more binding pockets of MASP-2. These binding pockets correspond to S1', S1, S2, S3, and S4'.

In certain aspects, the disclosure provides compounds wherein $M_1$ is a member selected from the group consisting of:

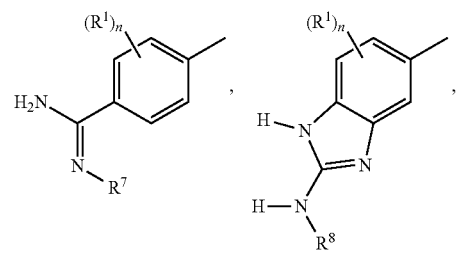

-continued

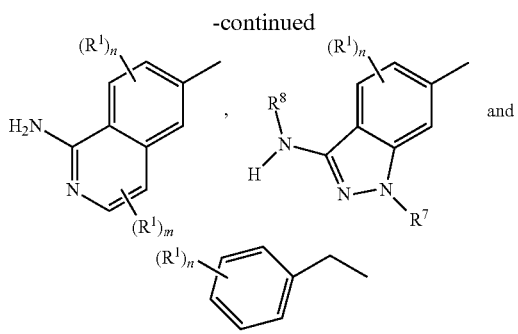

wherein each $R^1$ is a member independently selected from the group consisting of $C_1$-$C_6$ alkyl, hydroxyl, $C_1$-$C_6$ alkoxy, amino, $C_1$-$C_6$ alkylamino, and halo (e.g., chloro);
each n is an independently selected integer from 0 to 4;
$R^7$ is a member selected from the group consisting of hydrogen, hydroxyl, and $C_1$-$C_6$ alkyl; and
$R^8$ is a member selected from the group consisting of hydrogen and $C_1$-$C_6$ alkyl.
In certain aspects, $M_5$ has the formula:

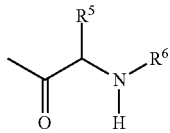

$R^5$ is a member selected from the group including $C_3$-$C_7$ cycloalkyl, $C_4$-$C_8$ cycloalkylalkyl, heteroaryl, and $C_7$-$C_{12}$ arylalkyl or heteroarylalkyl with from 0 to 3 $R^{13}$ substituents; or, alternatively, $R^5$ and $R^6$ join to form a heterocyclic ring with from 0 to 3 $R^{13}$ substituents;
$R^6$ is a member selected from the group consisting of hydrogen, $C_1$-$C_6$ alkyl, $C_3$-$C_7$ cycloalkyl, carboxy($C_1$-$C_6$ alkyl), $C_7$-$C_{12}$ arylalkyl or heteroarylalkyl with from 0 to 3 $R^{13}$ substituents, amino($C_1$-$C_8$ alkyl); and amido ($C_1$-$C_8$ alkyl); or, alternatively, $R^6$ and $R^5$ join to form a heterocyclic ring with from 0 to 3 $R^{13}$ substituents; and
each $R^{13}$ is a member independently selected from the group including $C_1$-$C_6$ alkyl, $C_6$-$C_{10}$ aryl, carboxy($C_1$-$C_6$ alkyloxy), heteroaryl, heterocyclyl, hydroxyl, hydroxyl($C_1$-$C_6$ alkyl), $C_1$-$C_6$ alkoxy, $C_2$-$C_9$ alkoxyalkyl, amino, $C_1$-$C_6$ amido, $C_1$-$C_6$ alkylamino, and halo; or, alternatively, two $R^{13}$ groups join to form a fused $C_6$-$C_{10}$ aryl, $C_6$-$C_{10}$ heteroaryl, or $C_5$-$C_7$ cycloalkyl ring.
In certain aspects, $M_{2-4}$ has the formula:

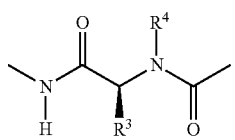

wherein $R^3$ is a member selected from the group including hydrogen, $C_1$-$C_6$ alkyl, $C_1$-$C_6$ fluoroalkyl, and carboxy ($C_1$-$C_6$ alkyl); or, alternatively, $R^3$ and $R^4$ join to form an azetidine, pyrrolidine, or piperidine ring; and $R^4$ is a member selected from the group including hydrogen and $C_1$-$C_6$ alkyl; or, alternatively, $R^4$ and $R^3$ join to form an azetidine, pyrrolidine, or piperidine ring.

In certain aspects, the compounds having MASP-2 inhibitory activity of Formula VIII have Formula VIIIA as follows:

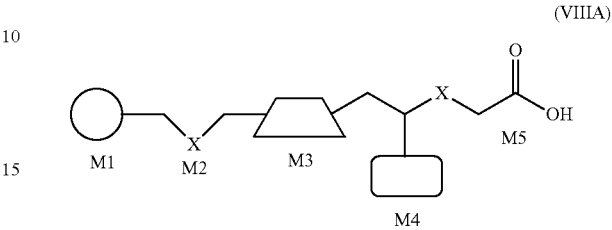

(VIIIA)

Figure 77A:
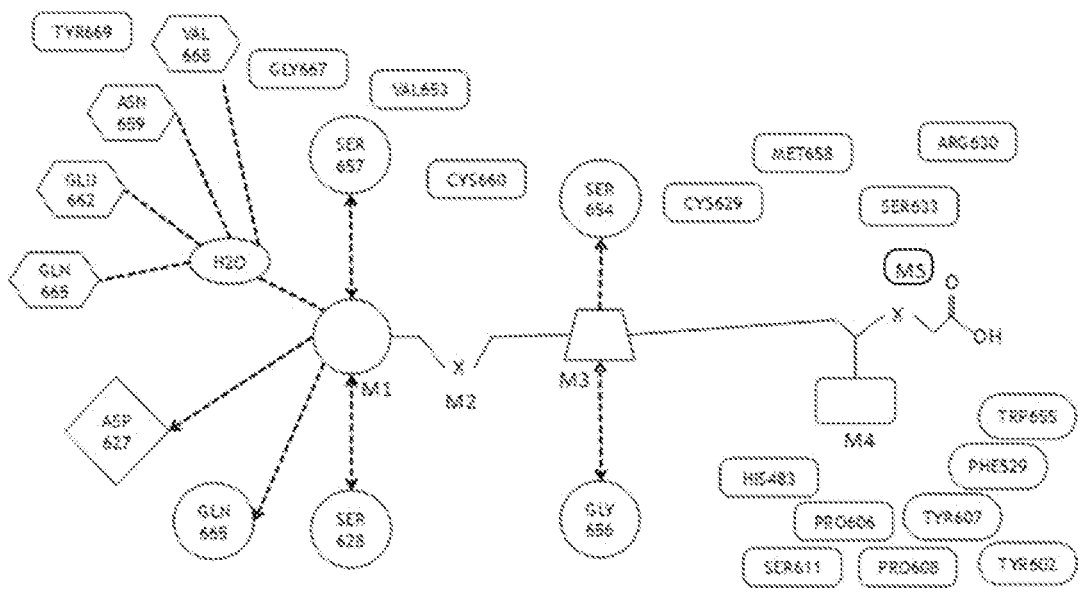
FIGS. 77A and 77B illustrate various interactions between a compound of Formula VIIIA and the MASP-2 active site.
Figure 77B:
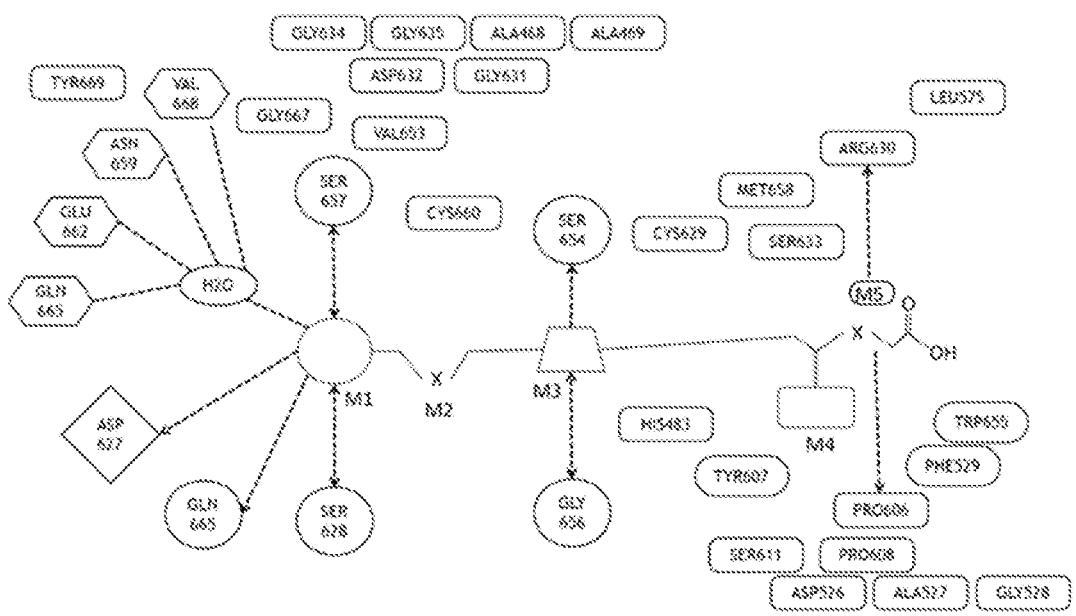

Various interactions between a compound of Formula VIIIA and the MASP-2 active site may exist as is shown in FIGS. 77A and 77B.

Segment $M_1$ of the compounds of Formula (VIIIA) can have an interaction which is an ionic type interaction between an ASP 627 carboxyl group and a positive (protonatable group) moiety in a compound of Formula (VIIIA). For example, as shown above, a nitrogen on the amidine can be a protonatable moiety and ionically interact with ASP 627.

In certain other aspects, with respect to hydrogen bonding analysis, certain of the compounds of the disclosure interact through intermolecular hydrogen bonding with one or more of the following amino acids: ASP 627, SER 628, SER 654, GLY 656, GLN 665, ARG630, PRO606, SER 633, CYS660 and SER 657 in MASP-2. In certain aspects, the compounds interact through intermolecular hydrogen bonding with one or more of the following acids: ASP 627, SER 628, SER 654, GLY 656, GLN 665 and SER 657 in MASP-2.

In certain aspects, the compound binds via H-bonds with 1, 2, 3, 4, 5 or all of the following residues: ASP 627, SER 628, SER 654, GLY 656, GLN 665, ARG630, PRO606, SER 633, CYS660 and SER 657. In certain aspects, the compound binds via H-bonds with 1, 2, 3, 4, 5 or all of the following residues: ASP 627, SER 628, SER 654, GLY 656, GLN 665 and SER 657. There may be more than one H-bond per amino acid. In certain aspects, the number of hydrogen bonds between an inhibitory molecule and the active site can be 1-40. In certain aspects, one amino acid (e.g., GLY 656) may have more than 1 hydrogen bond. A compound of the disclosure may have about 1 to about 10 hydrogen bonds, such as 2, 3, 4, 5, 6, 7, 8, 9 or 10H-bonds.

In general, although crystal structural information does not directly show or detect hydrogen bonding, the LigPlot+ software used to describe the co-crystal structural information does include algorithms to evaluate the presence of (or "predict") such H-bonding based on, e.g., bond distances. Therefore, throughout the disclosure when a H-bond is said to be present and described, it may be said to have been evaluated by software to be present based on the crystallographic data.

In certain aspects, the compound binds via ionic or electrostatic interactions or hydrogen bonding to ASP 627 or ARG630. In certain aspects, the compound does not bind via ionic interaction with ASP 627 or ARG630. In certain aspects, the compound does bind via ionic interaction with ASP 627 or ARG630. In certain aspects, the compound binds via ionic or electrostatic interactions or hydrogen bonding to ASP 627. In certain aspects, the compound does not bind via ionic interaction with ASP 627. In certain aspects, the compound does bind via ionic interaction with ASP 627.

As shown above, a hydrogen from a compound of Formula (VIIIA) in segment $M_1$ hydrogen-bonds with SER 628 and another hydrogen from the compound hydrogen-bonds with SER 657. In addition, hydrogens on SER 628 and another on SER 657 hydrogen-bonds with nitrogens on the compound in segment $M_1$. In general, a hydrogen bond is a partially electrostatic attraction between a hydrogen (H) which is bound to a more electronegative atom such as nitrogen (N) or oxygen (O) and another adjacent atom bearing a lone pair of electrons.

As shown, in certain aspects, atoms in segment $M_3$ interact with SER 654. In certain aspects, an atom such as a nitrogen in segment $M_3$ hydrogen bonds with SER 654. In addition, in certain aspects, an atom such as nitrogen in $M_3$ is both a hydrogen bonding acceptor and donor with GLY 656. In another aspect, an atom such as an oxygen in segment $M_3$ interacts with a water molecule.

In certain aspects, an inhibitory compound interacts via a water molecule. The water molecule may be bound to both the compound and an amino acid residue, only the compounds, only the amino acid or a combination thereof. The water molecule may bridge by binding $M_1$ and 1, 2, 3, 4, 5, 6, or 7 MASP-2 residues ASP 627, GLN 665, SER 657, ASN 659, SER 628, GLU 662, ARG 630, VAL 668, TYR 602, TYR 607, VAL 668.

In certain aspects, the $M_4$ segment of a compound interacts through π-π stacking interactions with either TYR 607 and/or PHE 529 and in the vicinity of TRP 655. In certain other aspects, the compound interacts via π-π interactions with 1, 2, 3 or all of the following residues: PHE 529, TYR 607, and TRP 655. In certain aspects, π-π interactions of the edge-face or T-type interaction are present.

In yet certain other aspects, in order to minimize interactions with serine proteases other than MASP-2, such as thrombin, bulky aromatic groups at segment $M_4$ of the compounds increase specificity for MASP-2 over thrombin.

In yet certain other aspects, to minimize interactions with serine proteases other than MASP-2, such as thrombin, methylated chloroazaindole $M_1$ segments of the compounds increase specificity for MASP-2 over thrombin.

In yet certain other aspects, to minimize interactions with serine proteases other than MASP-2, such as thrombin, large substituents such as glutaminyl derivatives or small substituents such as fluorine on the glycine carbon or substitutions on the Nitrogen atom of the center glycine of $M_3$ moieties increase specificity for MASP-2 over thrombin In yet certain other aspects, to minimize interactions with serine protease other than MASP-2, such as thrombin, planar aromatic groups such as 5-membered rings such as pyrazole connecting the $M_3$ region with the M4 segments of the compounds increase specificity for MASP-2 over thrombin.

In certain aspects, a compound binds via 3H-bonds with 2 residues: SER 654 and GLY 656. In certain aspects, there are two (2) H-bonds to GLY 656. For example, in certain instances, only 3 hydrogen bonds exist between the compound and the active site of MASP-2. In certain aspects, π-π stacking interaction (T-type or edge-face) can occur with either TYR 607 or PHE 529 and in the vicinity of TRP 655. In other aspects, no ionic bonds exist between the inhibitory compound and the active site of MASP-2. In other aspects, ionic bonds exist between the inhibitory compound and the active site of MASP-2.

Figure 57:
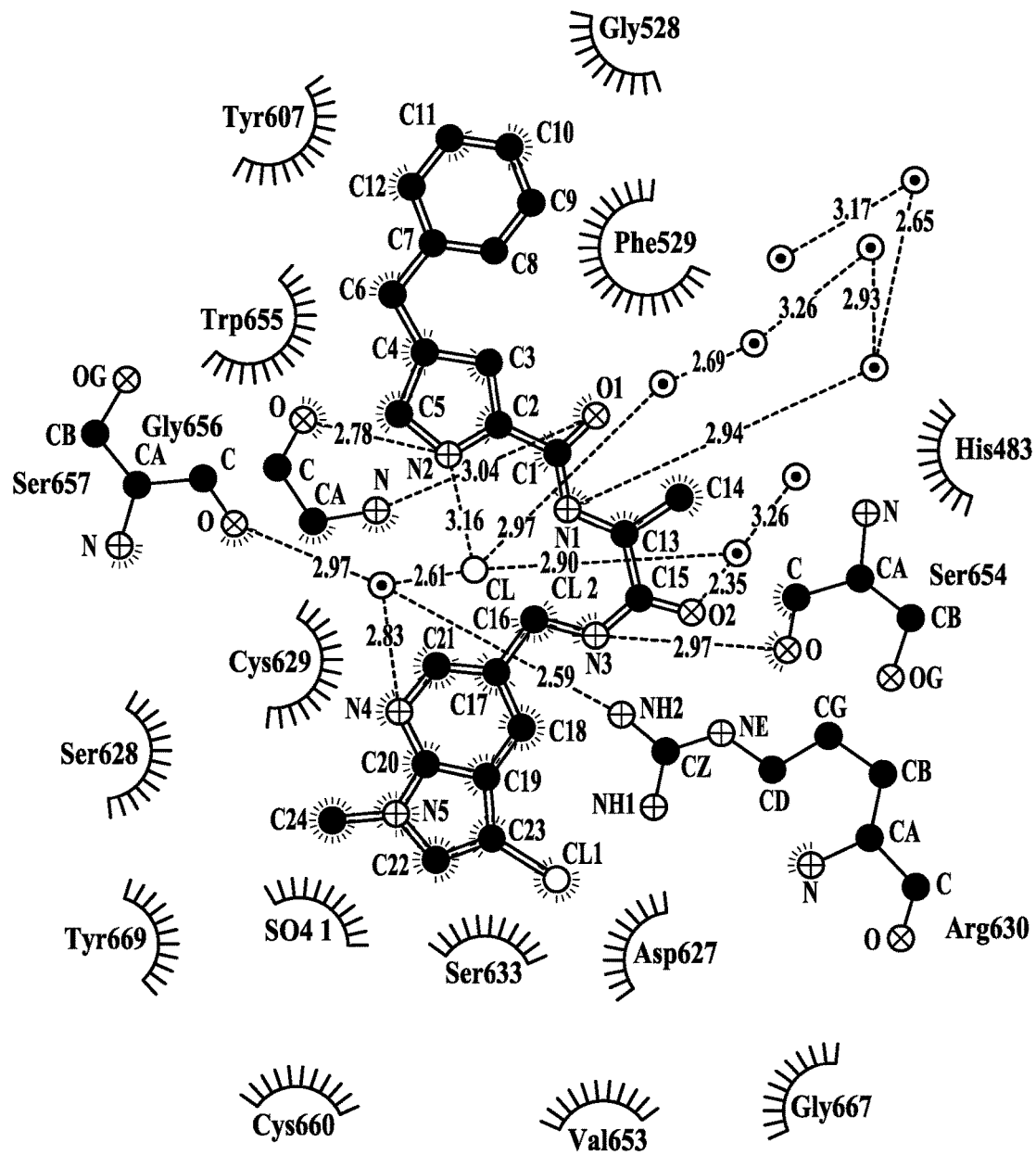
FIG. 57 is a plot showing the binding of compound (1450) to MASP-2 showing hydrogen bonds as computed by LigPlot+ software.

In certain aspects, FIGS. 1-57 show certain of the amino acids of MASP-2 having arcs with radiating lines showing interactions, such as van der Waals interactions, with atoms of inhibitors of the present disclosure.

In certain aspects, the compound interacts via van der Waals contacts to 1, 2, 3, 4, 5, 6, 7, 8, 9, 10, 11, 12, 13, 14, 15, 16, 17, 18, 19, 20, 21 or all of the following residues: ALA 468, ALA 469, HIS 483, ASP 526, ALA527, GLY528, PHE 529, LEU 575, PRO 606, TYR 607, PRO608, SER 611, ASP627, SER 628, CYS 629, ARG 630, GLY 631, ASP 632, SER 633, GLY634, GLY 635, VAL 653, SER 654, TRP 655, GLY656, SER 657, MET 658, ASN 659, CYS 660, GLN 665, GLY 667, TYR 669 and combinations thereof.

In certain aspects, the compound interacts via van der Waals contacts to 1, 2, 3, 4, 5, 6, 7, 8, 9, 10, 11, 12, 13, 14, 15, 16, 17, 18, 19, 20, 21 or all of the following residues: GLY 667, SER 657, GLY 656, TRP 655, SER 654, SER 633, ARG 630, CYS 629, SER 628, ASP 627, PHE 529, HIS 483, PRO 606, TYR 607, PRO 608, SER 611, VAL 653, MET 658, TYR 669, ASN 659, CYS 660, GLN 665 and combinations thereof.

FIGS. 1-57 represent 2D ligand-MASP-2 interaction diagrams for specific compounds of this disclosure. These figures are schematic depictions of atoms from various compounds with those of MASP-2 amino acids as computed by LigPlot++ software settings for hydrogen-bond calculation parameters employing models derived from the corresponding crystallographic MASP-2-compound co-structures. Atoms for amino acids that interact with compound atoms as well as compound atoms that have sufficient 2fo-fc electron density from crystallographic data are depicted. MASP-2 amino acid residue numbering (MASP-2 AA #) is according to Uniprot accession code O00187, atom numbering for amino acids (AA atom) according to conventions established by the Protein Data Bank and correspond to those in Table A1 (Appendix). Hydrogen bonds and polar contacts are depicted as broken lines with distances provided in units of Angstrom.

Turning now to FIG. 1, an illustration of MASP-2 CCP2-SP amino acid interactions with (1129) through hydrogen bonds.

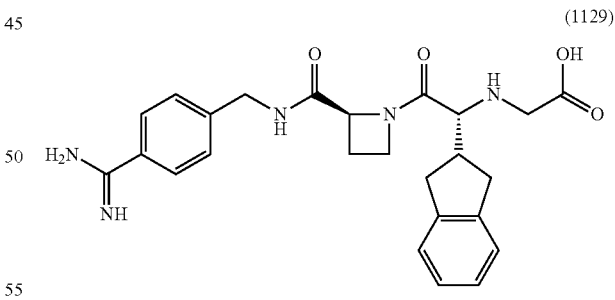

(1129)

As shown therein, six different hydrogen bonds are present between the (1129) compound atoms and the MASP-2 amino acid residue atoms. In addition, a total of four water molecules are shown in this area of the active site to be included within the crystal structure, two of which are shown to be participating in hydrogen bonding, either with one or more atoms of the (1129) compound, or as a bridging water molecule between particular (1129) compound atoms and MASP-2 amino acid residue atoms. As shown therein, an amidine nitrogen N19 interacts with an oxygen OD1 of ASP 627 as a hydrogen bond donor. As used herein, when it is stated that the nitrogen acts as a "hydrogen bond donor" it means that a hydrogen (H) bound to a more electronegative atom such as nitrogen (N) is electrostatically attracted to an adjacent atom bearing a lone pair of electrons such as an oxygen. Nitrogen N19 also interacts with an oxygen of SER628 as a hydrogen bond donor. In addition, N20 of the amidine interacts with oxygen OE1 of GLN 665 and O of SER 657 as a hydrogen bond donor. The nitrogen N10 of the amide bond interacts by H-bonding as a donor with an oxygen of SER 654. Further, oxygen O07 interacts by H-bonding with the nitrogen of GLY 656 as a hydrogen bond acceptor. Similarly, as above, when it is stated that an oxygen acts as a "hydrogen bond acceptor," it means that a hydrogen (H) bound to a more electronegative atom such as nitrogen (N) is electrostatically attracted to or "accepted by" an adjacent atom such as oxygen bearing a lone pair of electrons. The oxygen O08 interacts with a water molecule near TRP 655. The oxygen of O26 interacts with a water molecule, as does the secondary amine N21, while the same water molecule further interacts with oxygen O3 of a nearby buffer molecule succinic acid (Sin1). In addition, the compound binds via ionic or electrostatic interaction to ASP 627 (not shown).

(1034)

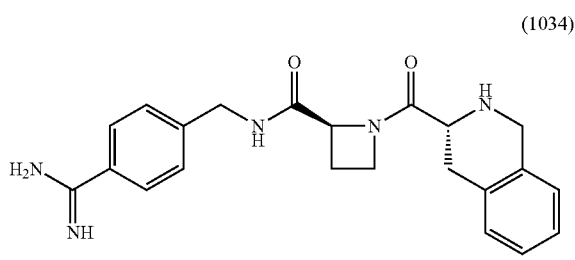 [SMILES: N=C(N)c1ccc(CNC(=O)[C@@H]2CCN2C(=O)[C@H]2Cc3ccccc3CN2)cc1]

Figure 2:
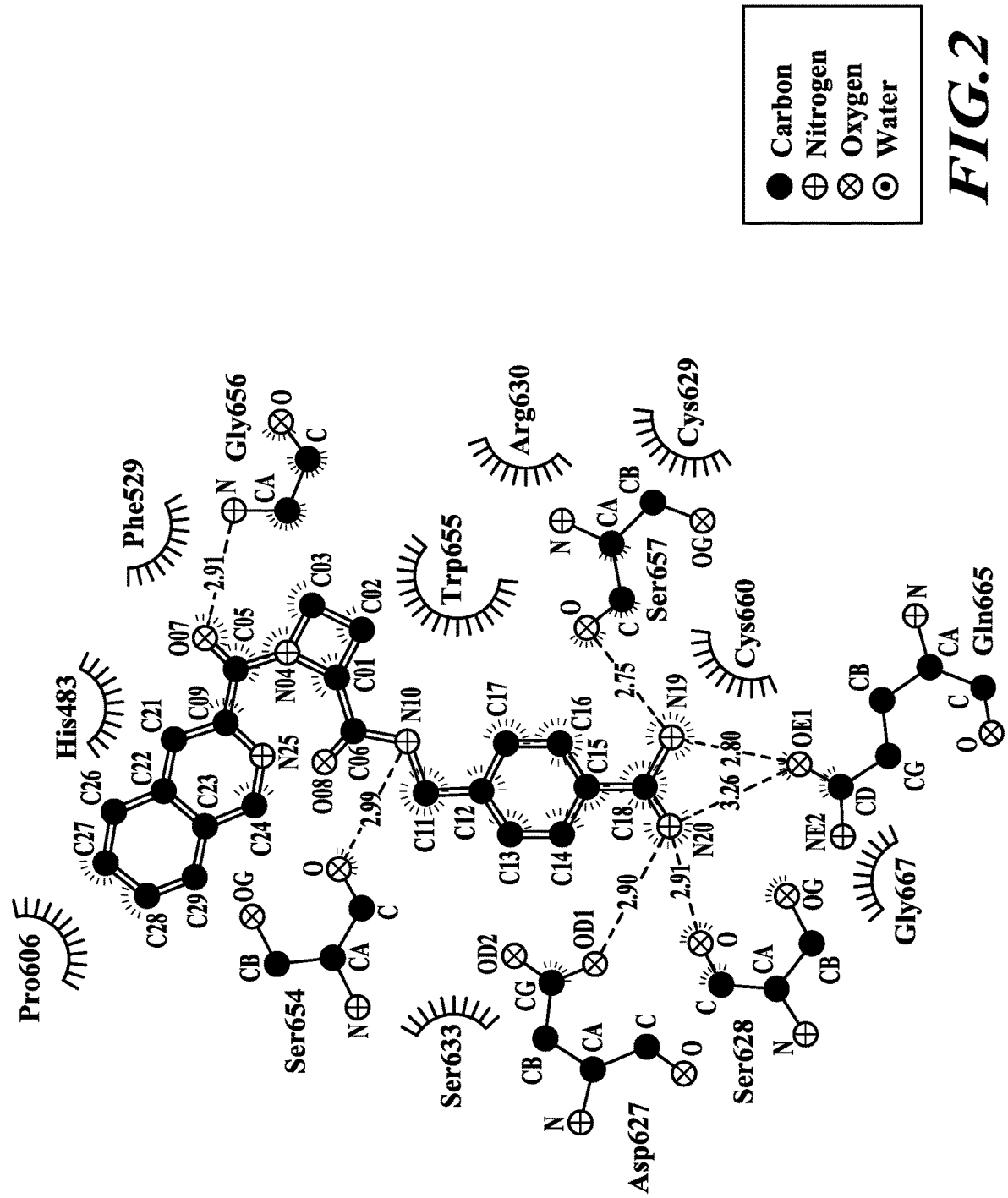
FIG. 2 is a plot illustrating a schematic of one embodiment of the atoms of an inhibitory compound (1034) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 2 is an illustration of MASP-2 CCP2-SP amino acid interactions with (1034) through hydrogen bonds. As shown therein, seven different hydrogen bonds are present between the (1034) compound atoms and the MASP-2 amino acid residue atoms. The figure does not depict the presence of any water molecules in the crystal structure. The amidine nitrogen N19 interacts with an oxygen of SER657 as a hydrogen bond donor. N19 also interacts with oxygen OE1 of GLN665 as a hydrogen bond donor. Nitrogen N20 interacts with oxygen OE1 of GLN665, an oxygen of SER628, and the OD1 oxygen of ASP627 as a hydrogen bond donor. N10 nitrogen interacts with oxygen of SER654 by H-bonding as a donor. Oxygen O07 interacts with a nitrogen on GLY656 by H-bonding as an acceptor. In addition, the compound binds via ionic or electrostatic interaction to ASP 627 (not shown).

(1024)

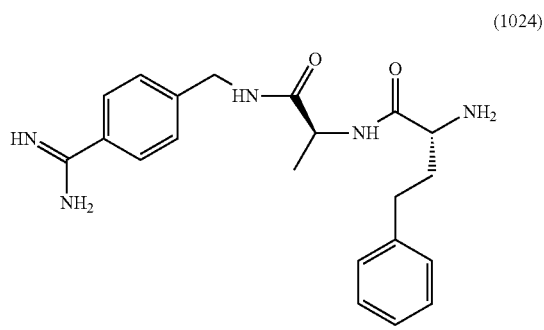 [SMILES: C[C@H](NC(=O)[C@H](N)CCc1ccccc1)C(=O)NCc1ccc(C(=N)N)cc1]

Figure 3:
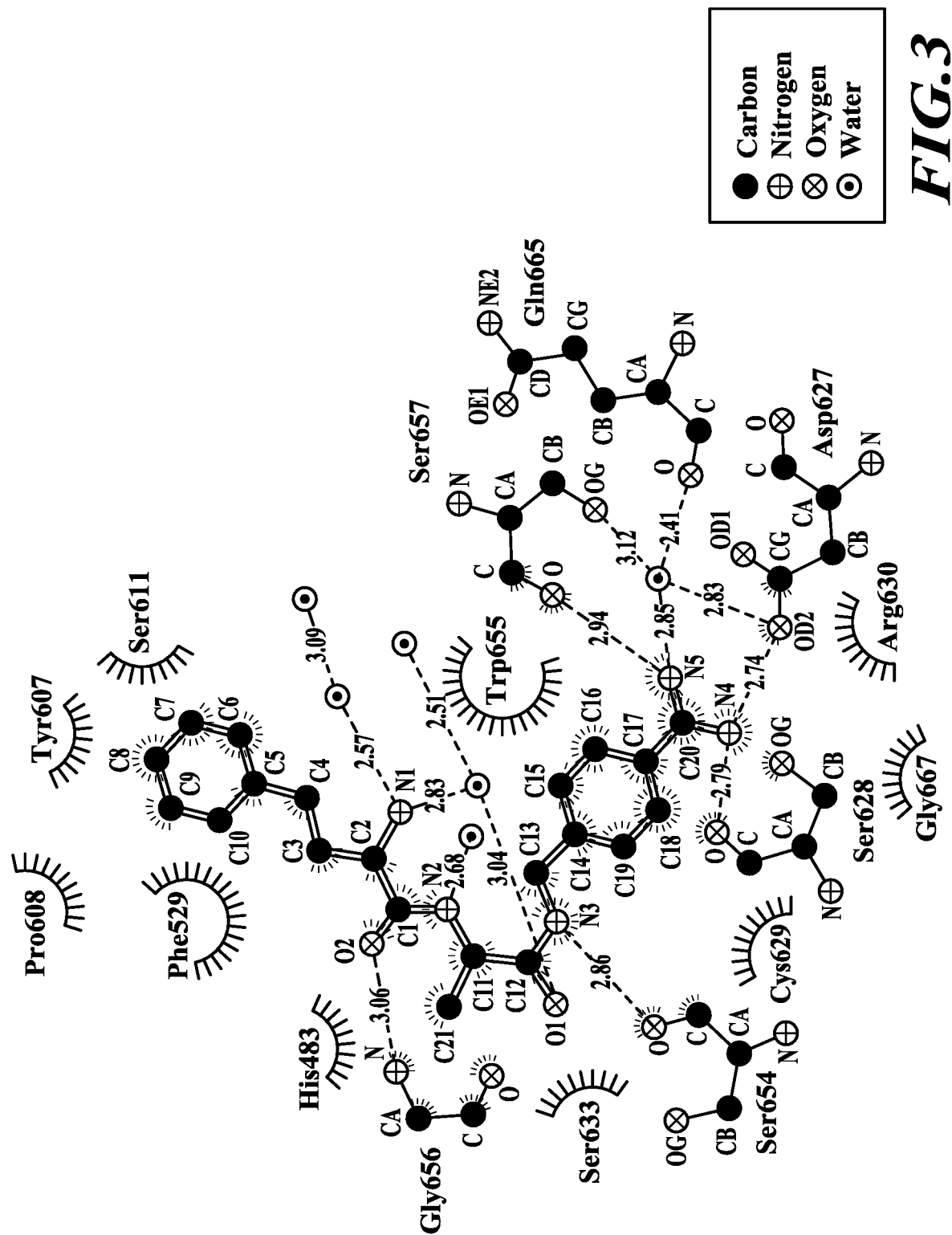
FIG. 3 is a plot illustrating a schematic of one embodiment of the atoms of an inhibitory compound (1024) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 3 is an illustration of MASP-2 CCP2-SP amino acid interactions with (1024) through hydrogen bonds. As shown therein, five different hydrogen bonds are present between atoms of the (1024) compound and MASP-2 residue atoms. In addition, a total of six water molecules are shown in the active site depicted to be included within the crystal structure, four of which are shown to be participating in hydrogen bonding, either with one or more atoms of the (1024) compound, or as a bridging water molecule between particular (1024) compound atoms and MASP-2 amino acid residue atoms. As shown therein, the O2 oxygen interacts with a nitrogen of GLY 656 as a hydrogen bond acceptor. Nitrogen N1 interacts with two different water molecules near TRP 655, one of which also interacts with oxygen O1. Nitrogen N2 interacts with another water molecule. The N3 nitrogen interacts with an oxygen of SER 654 as a hydrogen bond donor. Amidine nitrogen N4 interacts with an oxygen of SER628 by H-bonding as a donor and OD2 oxygen of ASP 627 by H-bonding as a donor. The other amidine nitrogen N5 interacts with an oxygen of SER 657 as a hydrogen bond donor and a nearby water molecule. The same water molecule that is interacting with nitrogen N5 also interacts with oxygen OG of SER 657, an oxygen of GLN 665 via a hydrogen bond, and oxygen OD2 of ASP 627 as a bridging water molecule. In addition, the compound binds via ionic or electrostatic interaction ASP 627 (not shown).

(1059)

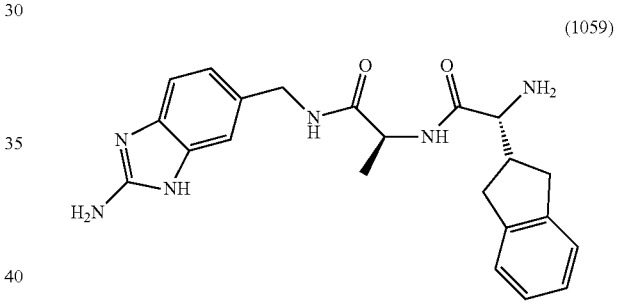

Figure 4:
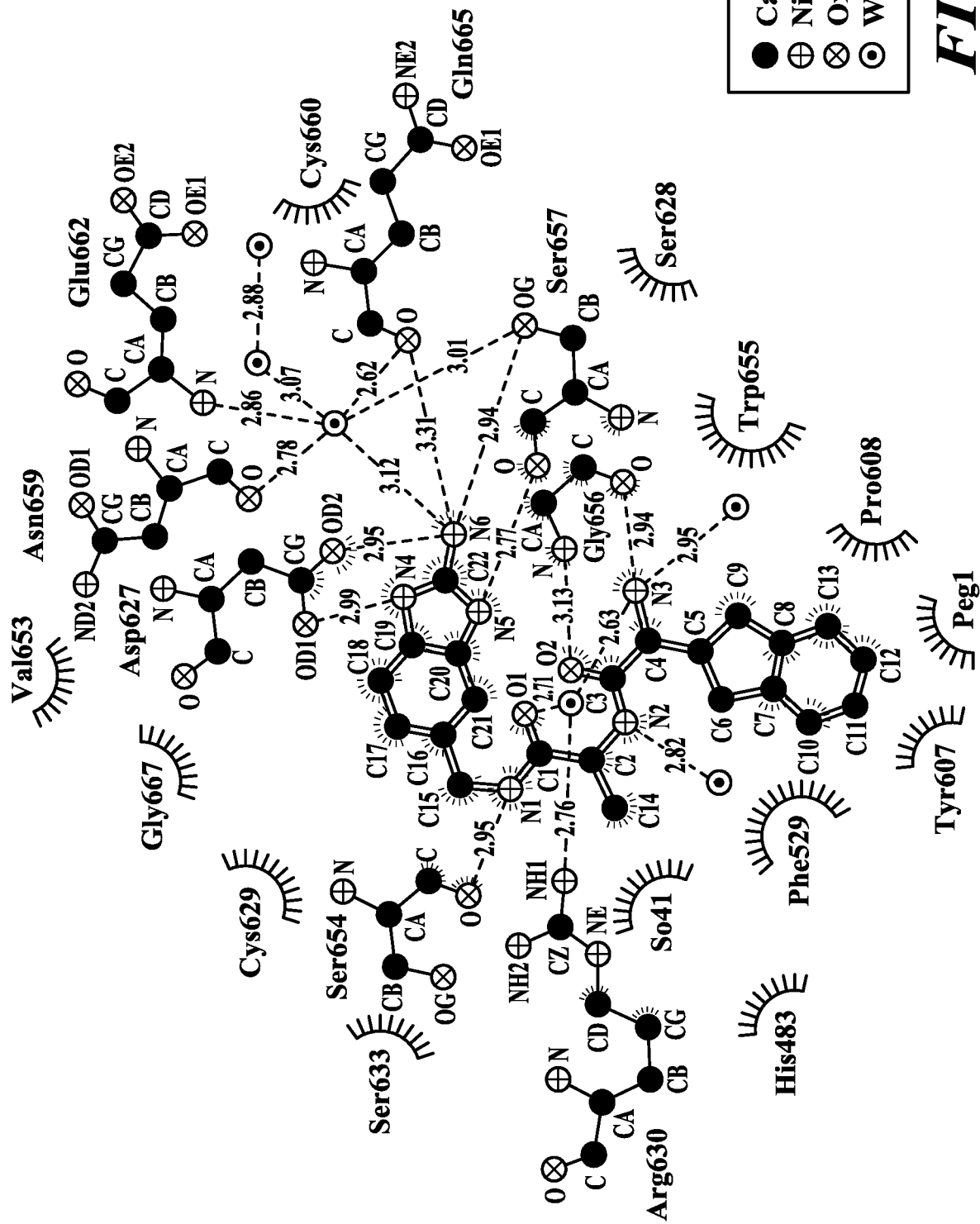
FIG. 4 is a plot illustrating a schematic of one embodiment of the atoms of an inhibitory compound (1059) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 4 is an illustration of MASP-2 CCP2-SP amino acid interactions with (1059) through hydrogen bonds. As shown therein, eight different H-bonds between the (1059) compound atoms and the MASP-2 residue atoms. In addition, a total of six water molecules are shown in the active site depicted to be included within the crystal structure, four of which are shown to be participating in hydrogen bonding, either with one or more atoms of the (1059) compound, or as a bridging water molecule between particular (1059) compound atoms and MASP-2 amino acid residue atoms. As shown therein, the amine nitrogen of the benzimidazole moiety, N6, forms hydrogen bonds as a donor with the OD2 oxygen of ASP 627, an oxygen of GLN 665, and the oxygen OG of SER 657. Nitrogen N6 may also interact with a water molecule. The same water molecule that is interacting with nitrogen N6 also interacts with oxygen OG of SER657 and an oxygen of ASN 659 as a bridging water molecule. The hydrogen of the benzimidazole can tautomerize between N4 and N5. Although there is only one hydrogen, software shows that the benzimidazole nitrogen N4 interacts as a H-bond donor with oxygen OD1 of ASP 627 and the other imidazole nitrogen N5 interacts with an oxygen of SER 657 as a hydrogen bond donor. Nitrogen N1 interacts with an oxygen of SER 654 as a hydrogen bond donor. Oxygen O1 interacts with a nearby water molecule, which is a bridging water molecule that further interacts with nitrogen NH1 of ARG 630 (an encircled cross) and nitrogen N3 of (1059). The N3 nitrogen interacts with another water molecule near TRP 655 as well as an oxygen of GLY 656 as a hydrogen bond donor. Oxygen O2 interacts with the nitrogen of GLY 656 as a hydrogen bond acceptor. The N2 nitrogen interacts with a water molecule close to PHE 529. In addition, the compound binds via ionic or electrostatic interaction to ASP 627 (not shown). The molecule labeled So41 designates a sulfate ion.

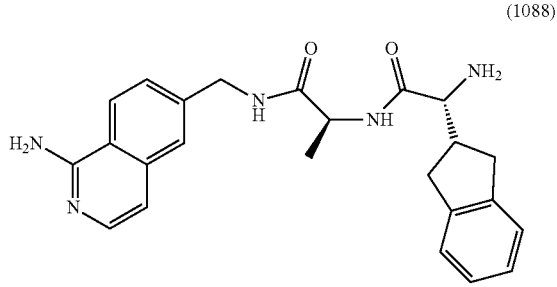 [SMILES: C[C@H](NC(=O)[C@H](N)C1Cc2ccccc2C1)C(=O)NCc1ccc2c(N)nccc2c1]

Figure 5:
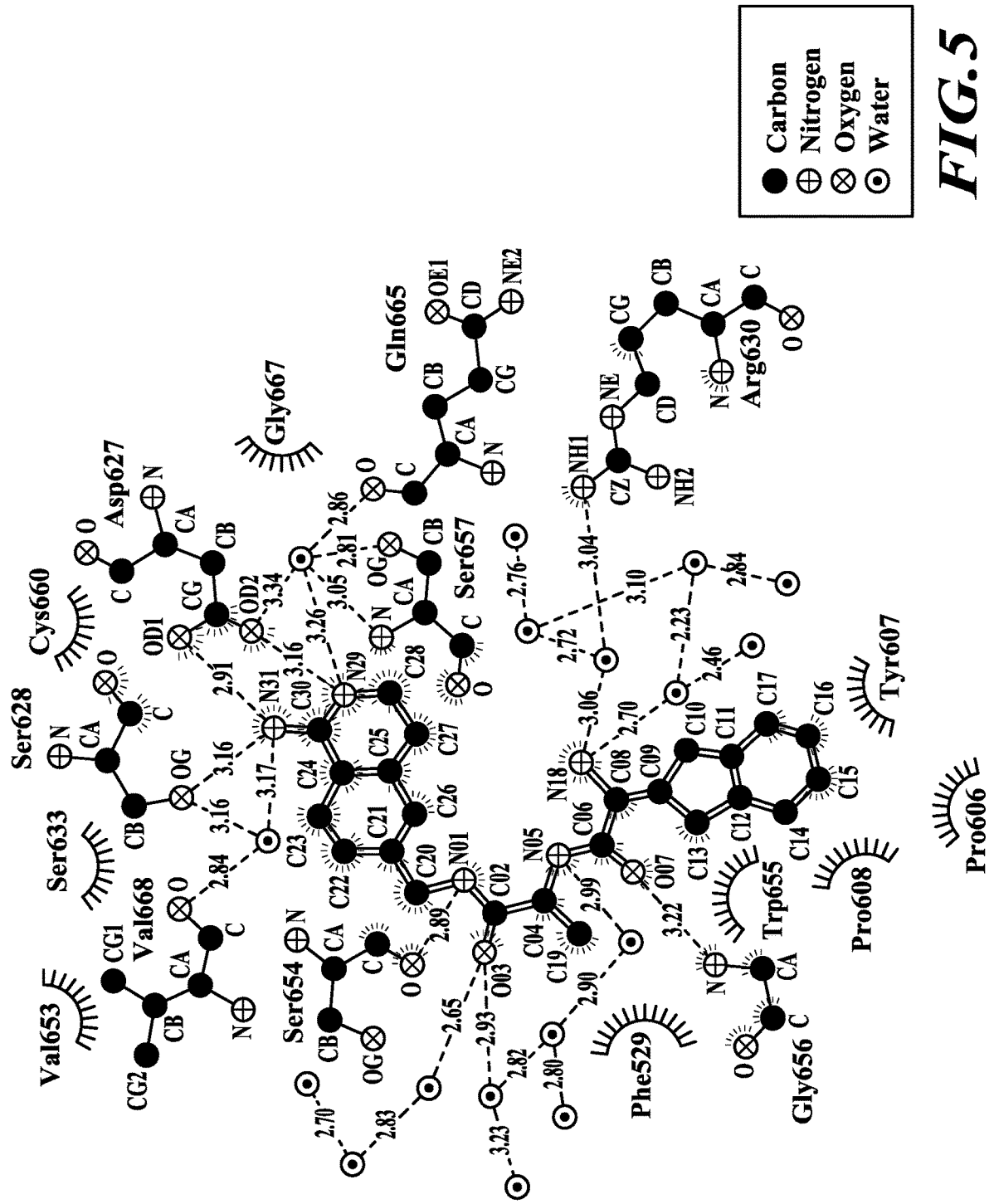
FIG. 5 is a plot illustrating a schematic of one embodiment of the atoms of an inhibitory compound (1088) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 5 is an illustration of MASP-2 CCP2-SP amino acid interactions with (1088) through hydrogen bonds. As shown therein, five different hydrogen bonds are present between atoms of the (1088) compound and atoms of the MASP-2 amino acid residues. In addition, a total of 17 water molecules are shown to be included within the active site of the crystal structure, seven of which are shown to be participating in hydrogen bonding with compound (1088), either with one or more atoms of the (1088), or as a bridging water molecule between particular (1088) compound atoms and MASP-2 amino acid residue atoms. As shown therein, nitrogen N31, the primary amine nitrogen of the isoquinoline moiety, interacts with the OG oxygen of SER 628 and the OD1 oxygen of ASP 627 as a hydrogen bond donor. The N31 nitrogen also interacts with a nearby water molecule. The same water molecule that is interacting with nitrogen N31 also interacts with oxygen OG of SER628 and an oxygen of VAL 668 as a bridging water molecule. The nitrogen of the isoquinoline ring, N29, forms a hydrogen bond as a donor with oxygen OD2 of ASP 627 and also forms a contact with a nearby water molecule. The same water molecule that is interacting with nitrogen N29 also interacts with oxygen OD2 of ASP 627, both a nitrogen and oxygen OG of SER 657, and an oxygen atom of GLN665 as a bridging water molecule. Nitrogen N01 interacts with an oxygen of SER654 as a hydrogen bond donor. Nitrogen N05 interacts with a water molecule near GLY 656 and PHE 529, and oxygen O03 also interacts with two different water molecules that are located between PHE 529 and SER 654. Oxygen O07 interacts with the nitrogen of GLY 656 as a hydrogen bond acceptor. The N18 nitrogen interacts with two different water molecules, in which one of the water molecules also interacts with nitrogen NH1 of ARG 630 as a bridging water molecule. In addition, the compound binds via ionic or electrostatic interaction to ASP 627 (not shown).

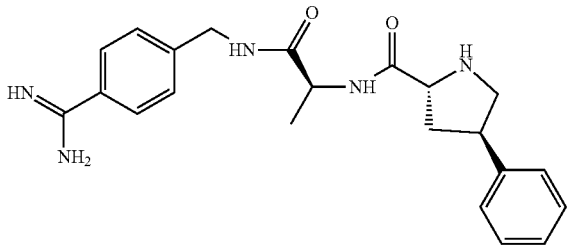

Figure 6:
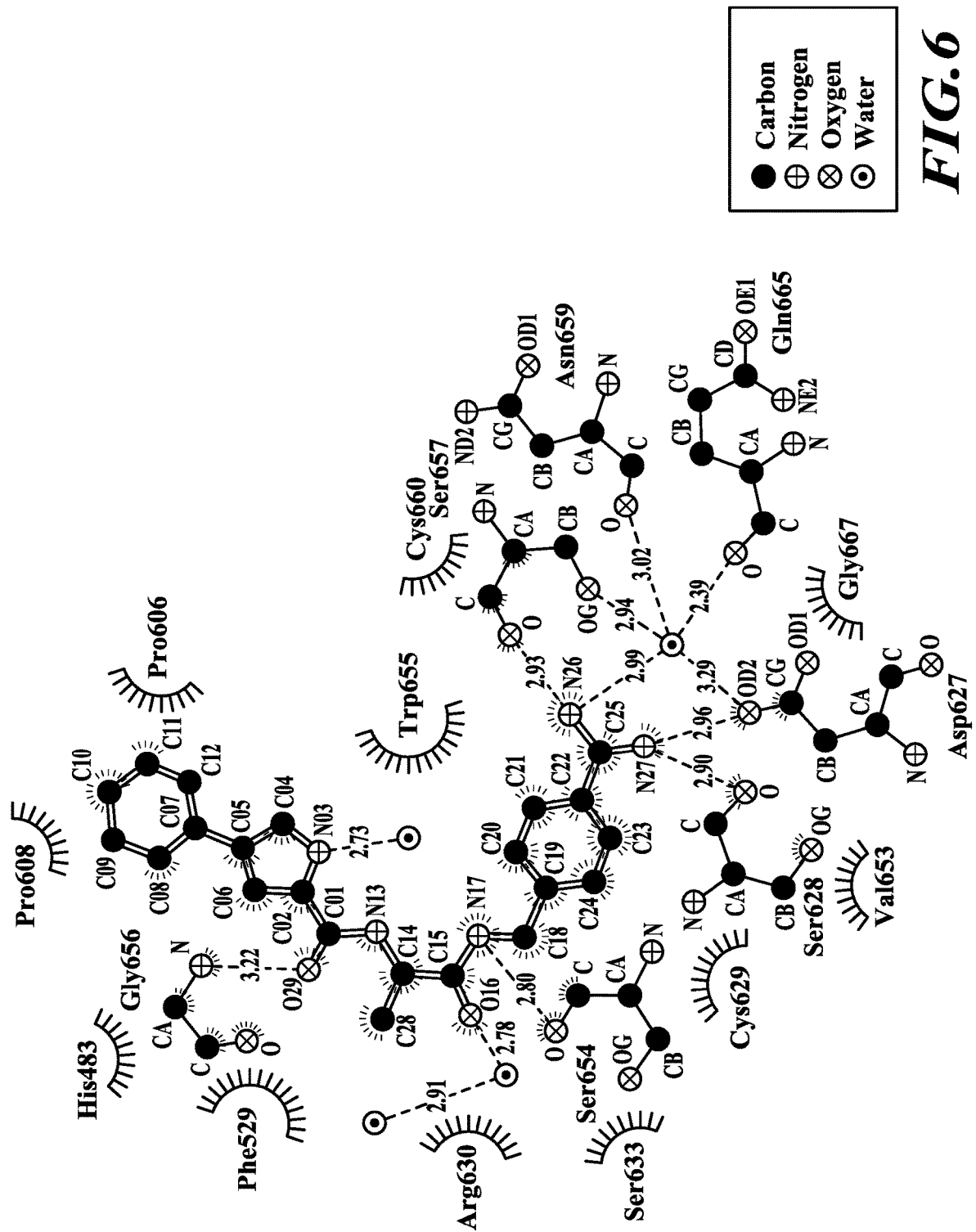
FIG. 6 is a plot illustrating a schematic of one embodiment of the atoms of an inhibitory compound (1036) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 6 is an illustration of MASP-2 CCP2-SP amino acid interactions with (1036) through hydrogen bonds. As shown therein, six different hydrogen bonds are present between the (1036) compound atoms and the atoms of the MASP-2 residues. In addition, a total of four water molecules are shown to be included within the crystal structure, three of which are shown to be participating in hydrogen bonding, either with one or more atoms of the (1036) compound, or as a bridging water molecule between particular (1036) compound atoms and MASP-2 amino acid residue atoms. As shown therein, an amidine nitrogen N26 interacts with an oxygen of SER 657 as a hydrogen bond donor. Nitrogen N26 also interacts with a water molecule. The same water molecule that is interacting with nitrogen N26 also interacts with oxygen OG of SER 657, an oxygen of ASN 659, an oxygen of GLN 665, and oxygen OD2 of ASP 627 as a bridging water molecule. In addition, N27 of the amidine forms hydrogen bonds as a donor with oxygen OD2 of ASP 627 and an oxygen of SER 628. Nitrogen N17 interacts with an oxygen of SER 654 as a hydrogen bond donor and oxygen O16 interacts with a water molecule positioned between ARG 630 and SER 654. Oxygen O29 interacts with a nitrogen of GLY 656 as a hydrogen bond acceptor and the nitrogen of the pyrrolidine moiety, N03, interacts with a water molecule. In addition, the compound binds via ionic or electrostatic interaction to ASP 627 (not shown).

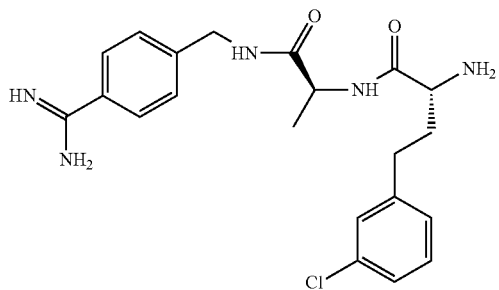

Figure 7:
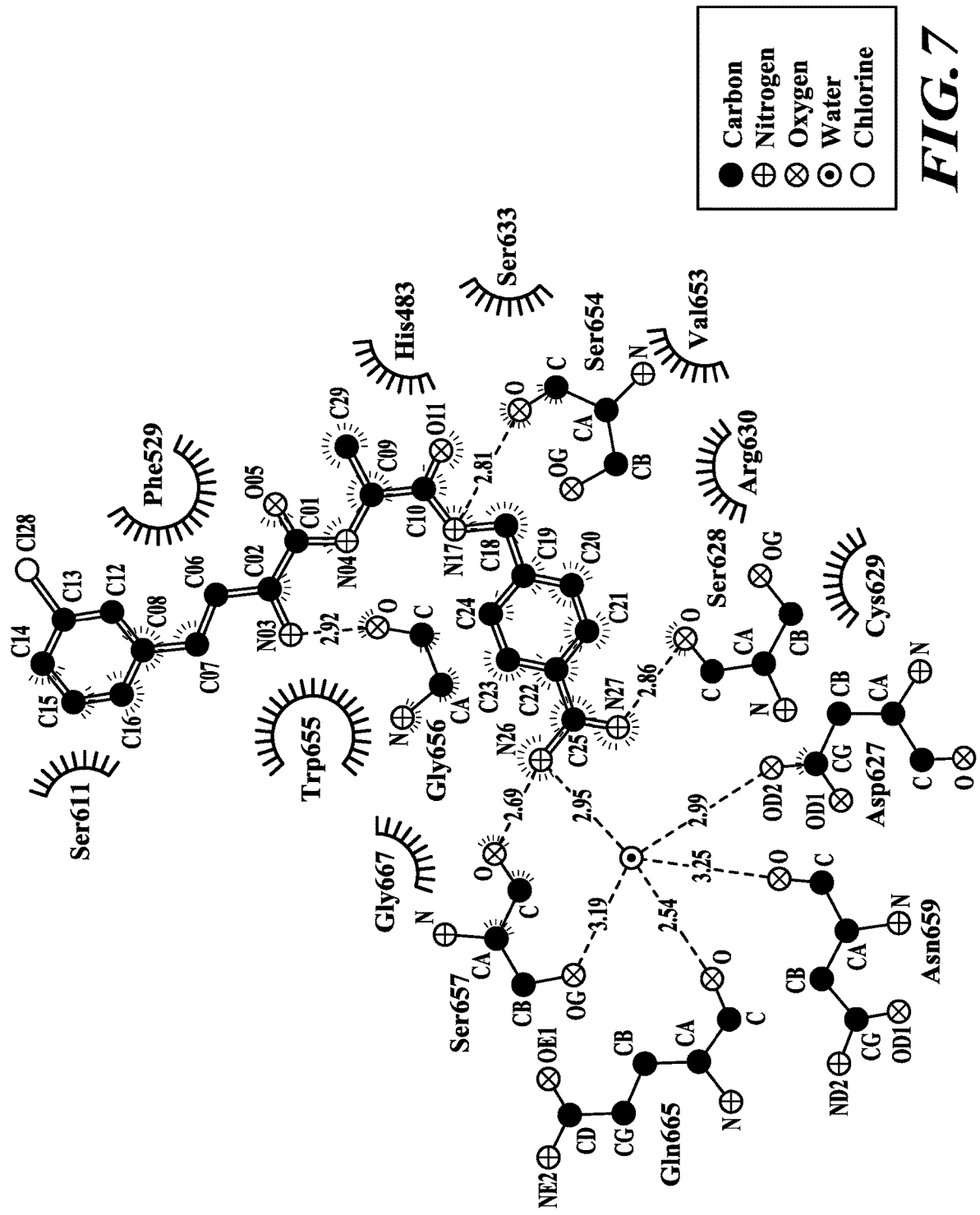
FIG. 7 is a plot illustrating a schematic of one embodiment of the atoms of an inhibitory compound (1081) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 7 is an illustration of MASP-2 CCP2-SP amino acid interactions with (1081) through hydrogen bonds. As shown therein, four different hydrogen bonds are present between atoms of the (1081) compound and atoms of the MASP-2 amino acid residues. In addition, a single water molecule is shown to be included within the crystal structure, which is shown to be participating in hydrogen bonding as a water molecule, bridging between one atom of the compound and multiple MASP-2 amino acid residue atoms. As shown therein, an amidine nitrogen N26 interacts with an oxygen of SER 657 as a hydrogen donor. Nitrogen N26 also interacts with a water molecule. The same water molecule that is interacting with nitrogen N26 also interacts with oxygen OG of SER 657, an oxygen atom of GLN665, an oxygen atom of ASN 659, and oxygen OD2 of ASP 627 as a bridging water molecule. The other amidine nitrogen, N27, interacts with an oxygen of SER 628 as a hydrogen bond donor. Nitrogen N17 interacts with an oxygen of SER 654 as a hydrogen bond donor and nitrogen N03 interacts with an oxygen of GLY 656 as a hydrogen bond donor. In addition, the compound binds via ionic or electrostatic interaction ASP 627 (not shown).

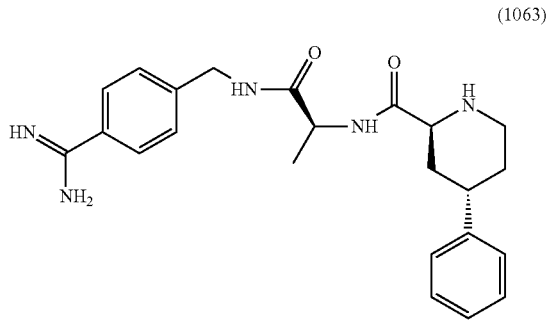 [SMILES: C[C@H](NC(=O)[C@@H]1C[C@@H](c2ccccc2)CCN1)C(=O)NCc1ccc(C(=N)N)cc1]

(1063)

Figure 8:

FIG. 8 is a plot illustrating a schematic of one embodiment of the atoms of an inhibitory compound (1063) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 8 is an illustration of MASP-2 CCP2-SP amino acid interactions with (1063) through hydrogen bonds. As shown therein, four different hydrogen bonds are present between the (1063) compound atoms and the MASP-2 amino acid residue atoms. In addition, a total of two water molecules are shown to be included within the crystal structure, one of which is shown to be participating in hydrogen bonding with one atom of the (1063) compound. As shown therein, the amidine nitrogen N5 interacts with an oxygen of SER 657 as a hydrogen bond donor and the other amidine nitrogen N4 interacts with an oxygen of SER 628 as a hydrogen bond donor. Nitrogen N3 interacts with an oxygen of SER 654 as a hydrogen bond donor, oxygen O2 interacts with a nearby water molecule, and oxygen O1 interacts with the nitrogen of GLY 656 as a hydrogen bond acceptor. In addition, the compound binds via ionic or electrostatic interaction ASP 627 (not shown).

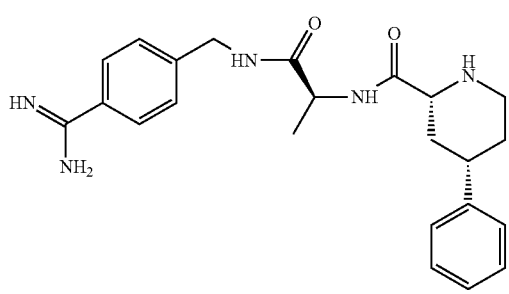

(1065)

Figure 9:
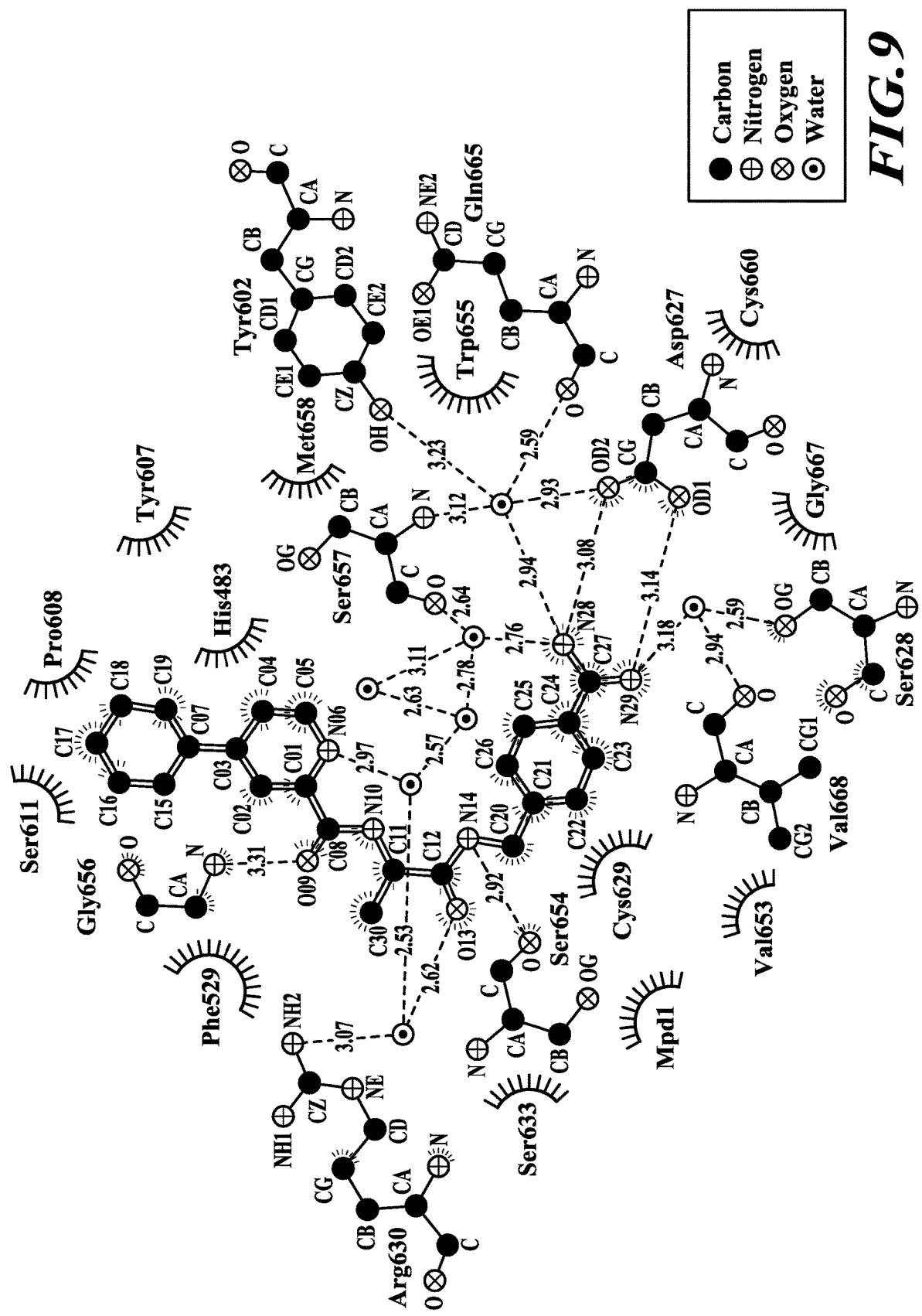
FIG. 9 is a plot illustrating a schematic of one embodiment of the atoms of an inhibitory compound (1065) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 9 is an illustration of MASP-2 CCP2-SP amino acid interactions with (1065) through hydrogen bonds. As shown therein, four different hydrogen bonds are present between the (1065) compound atoms and the MASP-2 residue atoms. In addition, a total of seven water molecules are shown to be included within the crystal structure, five of which are shown to be participating in hydrogen bonding, either with one or more atoms of the (1065) compound, or as a bridging water molecule between particular (1065) compound atoms and MASP-2 amino acid residue atoms. As shown therein, the amidine nitrogen N28 interacts with two different bridging water molecules, in which one of said water molecules further interacts with an oxygen atom of SER 657, while the second water molecule interacts with a nitrogen atom of SER 657, an oxygen OH of TYR 602, an oxygen atom of GLN 665, and oxygen OD2 of ASP 627. Nitrogen N28 also forms a hydrogen bond as a donor with oxygen OD2 of ASP 627. The other amidine nitrogen N29 interacts as a hydrogen bond donor with the OD1 oxygen of ASP627. Nitrogen N29 also interacts with a nearby water molecule, bridging between N29, an oxygen atom of VAL 668, and oxygen OG of SER6 28. Nitrogen N14 interacts with an oxygen of SER 654 as a hydrogen bond donor and oxygen O13 interacts with a water molecule. The same water molecule that is interacting with O13 also interacts with an oxygen atom of ARG 630 as a bridging water molecule. Oxygen O09 interacts with the nitrogen of GLY 656 as a hydrogen bond acceptor and the nitrogen of the piperidine moiety, N06, interacts with a nearby water molecule. In addition, the compound binds via ionic or electrostatic interaction to ASP 627 (not shown).

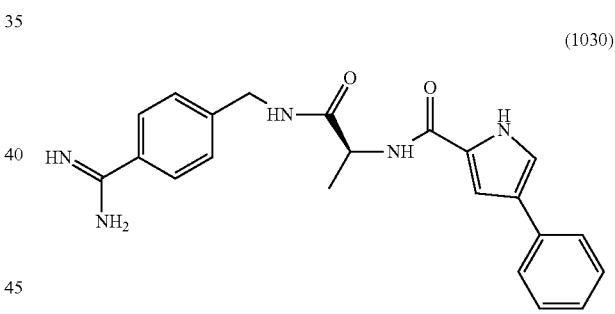

(1030)

Figure 10:
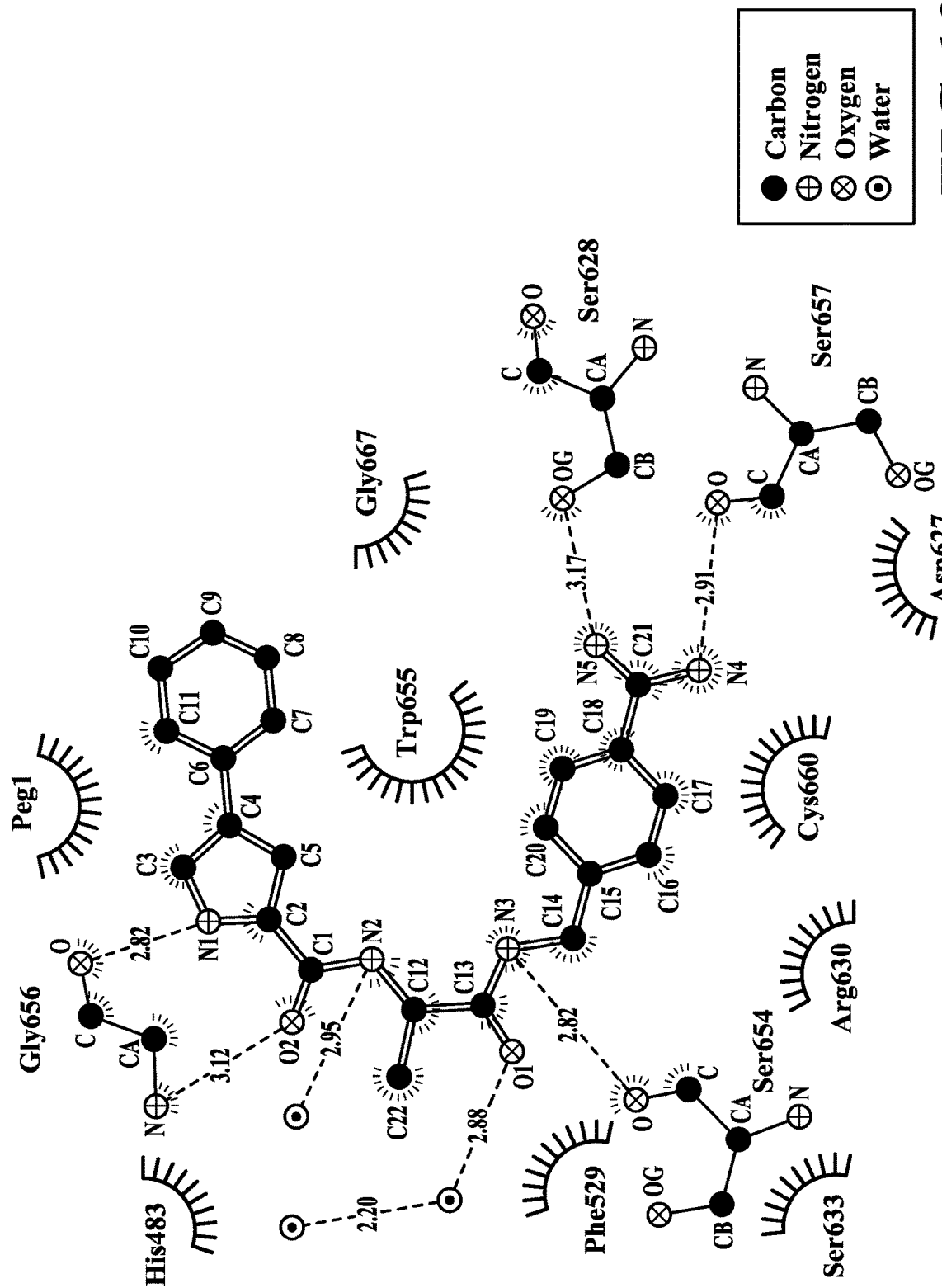
FIG. 10 is a plot illustrating a schematic of one embodiment of the atoms of an inhibitory compound (1030) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 10 is an illustration of MASP-2 CCP2-SP amino acid interactions with (1030) through hydrogen bonds. As shown therein, five different H-bonds are present between the (1030) compound atoms and the MASP-2 atoms. In addition, a total of three water molecules are shown to be included within the crystal structure, two of which are shown to be participating in hydrogen bonding with two different atoms of the compound. As shown therein, the amidine nitrogen N4 interacts with an oxygen of SER 657 as a hydrogen bond donor and the other amidine nitrogen N5 interacts with oxygen OG of SER 628 as a hydrogen bond donor. Nitrogen N3 interacts with an oxygen of SER 654 as a hydrogen bond donor, oxygen O1 interacts with a water molecule near PHE 529, and nitrogen N2 interacts with another nearby water molecule. Oxygen O2 interacts with the nitrogen of GLY 656 as a hydrogen bond acceptor, while the nitrogen of the pyrrole moiety, N1, interacts with the oxygen of GLY 656 as a hydrogen bond donor. In addition, the compound binds via ionic or electrostatic interaction to ASP 627 (not shown).

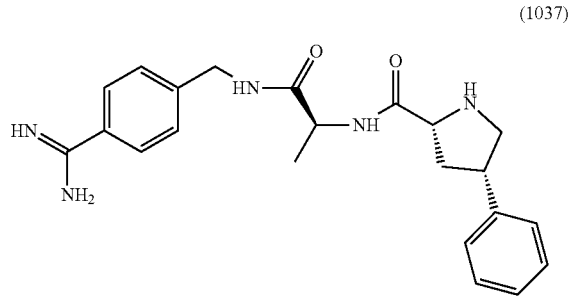 [SMILES: C[C@H](NC(=O)[C@H]1C[C@@H](c2ccccc2)CN1)C(=O)NCc1ccc(C(=N)N)cc1]

(1037)

Figure 11:
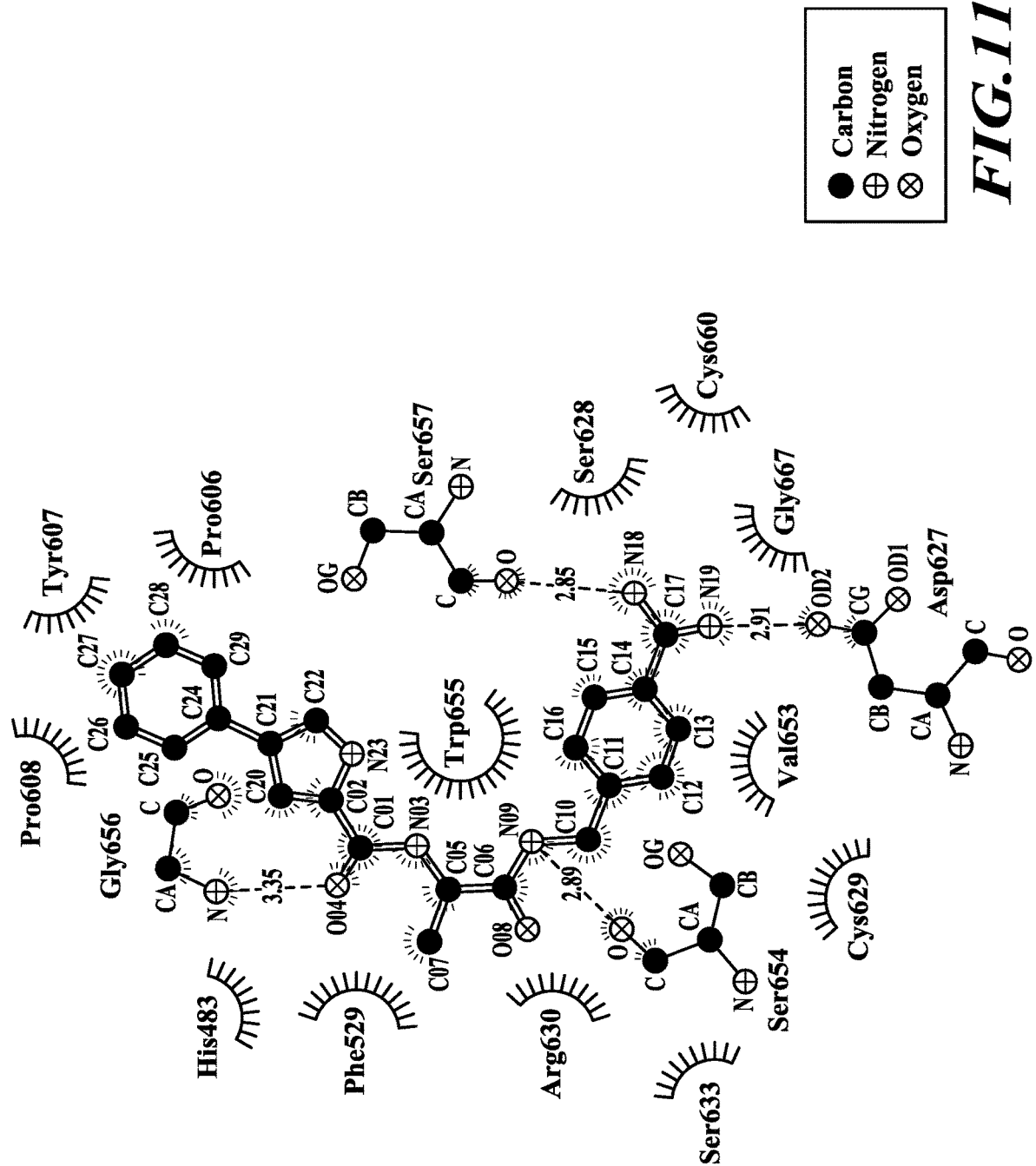
FIG. 11 is a plot illustrating a schematic of one embodiment of the atoms of an inhibitory compound (1037) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 11 is an illustration of MASP-2 CCP2-SP amino acid interactions with (1037) through hydrogen bonds. As shown therein, four different hydrogen bonds are present between the (1037) molecule atoms and the MASP-2 amino acid residue atoms. The figure does not depict the presence of any water molecules in the crystal structure. An amidine nitrogen N18 interacts with an oxygen of SER 657 as a hydrogen bond donor. The other amidine nitrogen N19 forms a hydrogen bond as a donor with oxygen OD2 of ASP 627. Nitrogen O9 interacts with an oxygen of SER 654 as a hydrogen donor and oxygen O04 interacts relatively weakly as a hydrogen acceptor with the nitrogen of GLY 656. In addition, the compound binds via ionic or electrostatic interaction to ASP 627 (not shown).

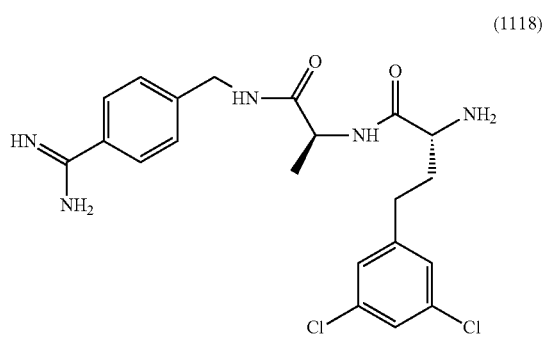 [SMILES: C[C@H](NC(=O)[C@H](N)CCc1cc(Cl)cc(Cl)c1)C(=O)NCc1ccc(C(=N)N)cc1]

(1118)

Figure 12:
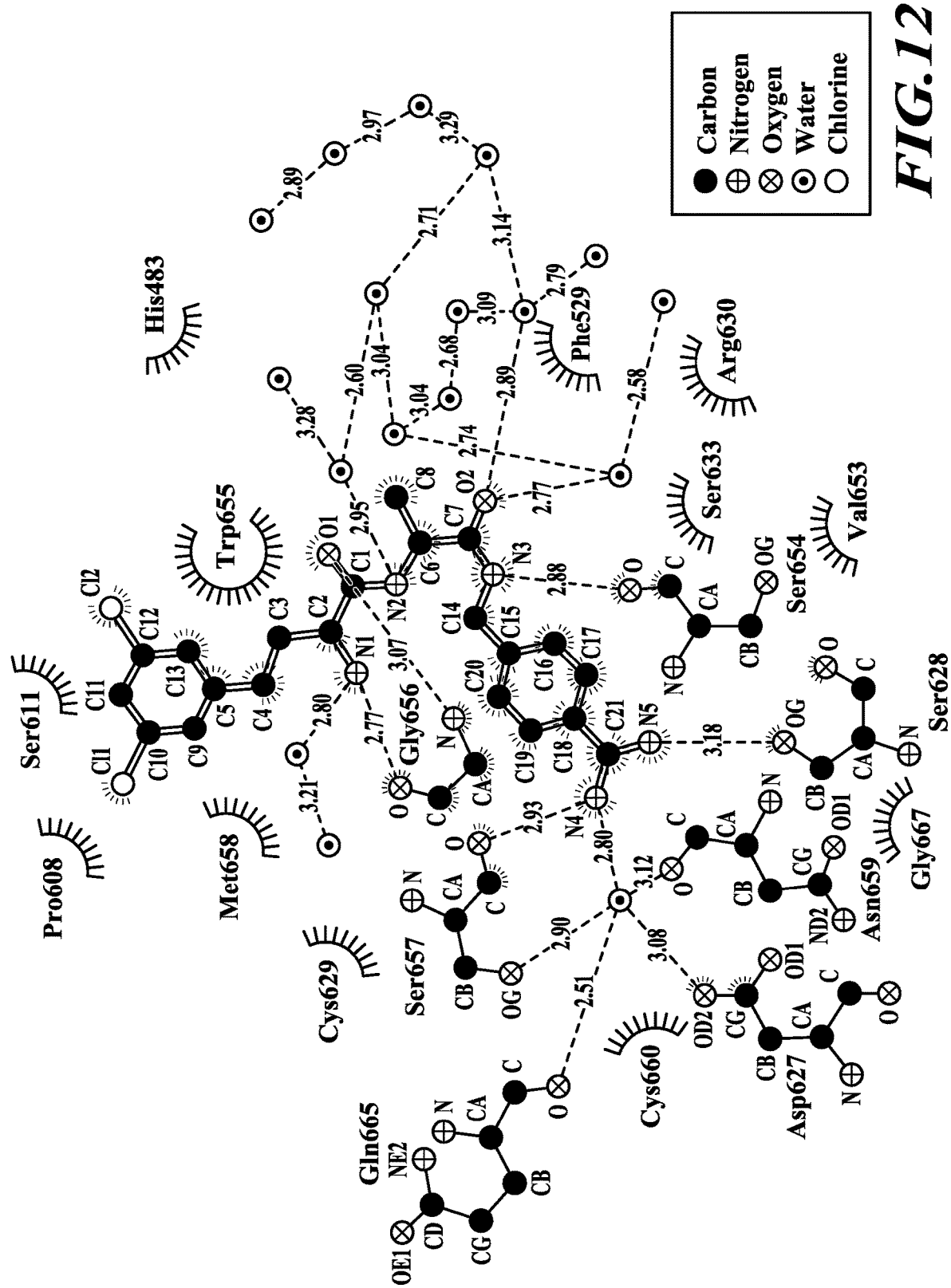
FIG. 12 is a plot illustrating a schematic of one embodiment of the atoms of an inhibitory compound (1118) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 12 is an illustration of MASP-2 CCP2-SP amino acid interactions with (1118) through hydrogen bonds. As shown therein, five different hydrogen bonds are present between the atoms of (1118) and the atoms of MASP-2 amino acids. In addition, a total of 17 water molecules are shown to be included within the crystal structure, five of which are shown to be participating in hydrogen bonding, either with single atoms of the (1118) compound, or as a bridging water molecule between particular (1118) compound atoms and MASP-2 amino acid residue atoms. As shown therein, one of the amidine nitrogens, N4, interacts with an oxygen of SER 657 as a hydrogen bond donor. Nitrogen N4 also interacts with a bridging water molecule, bridging between N4, oxygen OG of SER 657, an oxygen atom of GLN 665, oxygen OD2 of ASP 627, and an oxygen atom of ASN 659. The other amidine nitrogen N5 interacts with oxygen OG of SER 628 as a hydrogen bond donor. Nitrogen N3 forms a hydrogen bond as a donor with an oxygen of SER 654 and oxygen O2 interacts with two different water molecules close to PHE 529. Nitrogen N2 interacts with a nearby water molecule as well. Oxygen O1 interacts with the nitrogen atom of GLY 656 as a hydrogen bond acceptor, while nitrogen N1 interacts with the oxygen atom of GLY 656 as a hydrogen bond donor. Nitrogen N1 also interacts with a water molecule. In addition, the compound binds via ionic or electrostatic interaction to ASP 627 (not shown).

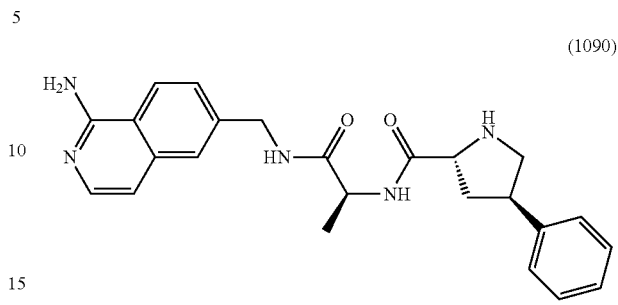

(1090)

Figure 13:
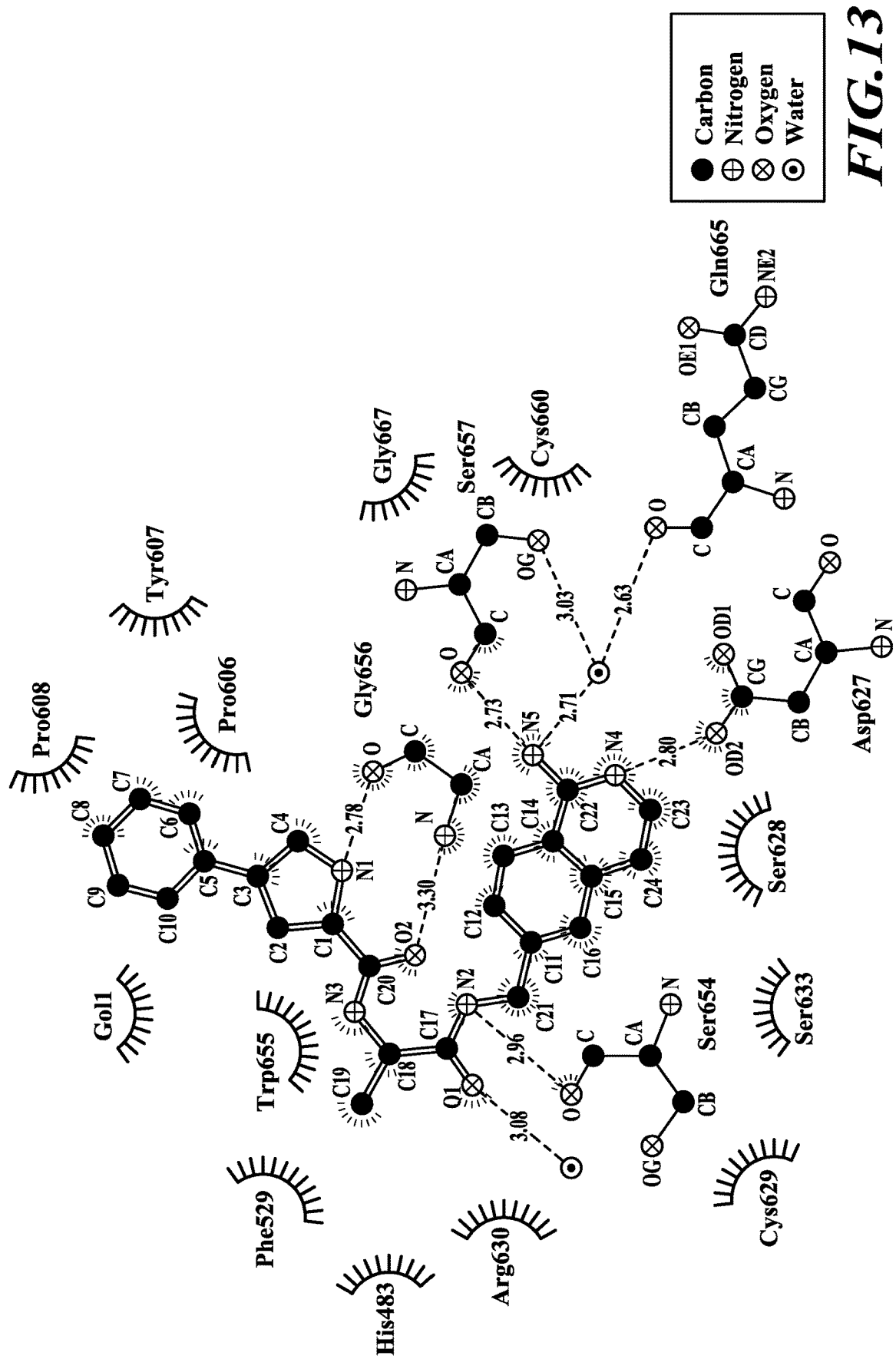
FIG. 13 is a plot illustrating a schematic of one embodiment of the atoms of an inhibitory compound (1090) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 13 is an illustration of MASP-2 CCP2-SP amino acid interactions with (1090) through hydrogen bonds. As shown therein, five different hydrogen bonds are present between the (1090) atoms and the MASP-2 residue atoms. In addition, a total of two water molecules are shown to be included within the crystal structure, both of which are shown to be participating in hydrogen bonding, either with a single atom of (1090) or as a water molecule, bridging between one atom of the (1090) compound and multiple MASP-2 amino acid residue atoms. As shown therein, nitrogen N5, the amine nitrogen of the isoquinoline moiety, interacts with a nearby water molecule. This water molecule also interacts with oxygen OG of SER 657 and an oxygen atom of GLN 665 as a bridging water molecule. Nitrogen N5 also interacts with an oxygen of SER 657 as a hydrogen bond donor. The nitrogen of the isoquinoline ring, N4, interacts with oxygen OD2 of ASP 627 as a hydrogen bond donor. Nitrogen N2 interacts with an oxygen of SER 654 as a hydrogen bond donor and oxygen O1 interacts with a nearby water molecule positioned next to SER 654. Oxygen O2 interacts with the nitrogen atom of GLY 656 as a hydrogen bond acceptor and the nitrogen of the pyrrolidine moiety, N1, interacts with the oxygen atom of GLY 656 as a hydrogen bond donor.

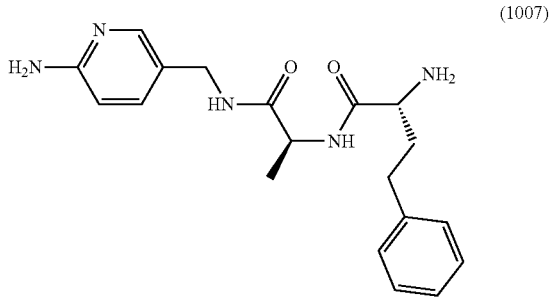 [SMILES: C[C@H](NC(=O)[C@H](N)CCc1ccccc1)C(=O)NCc1ccc(N)nc1]

(1007)

Figure 14:
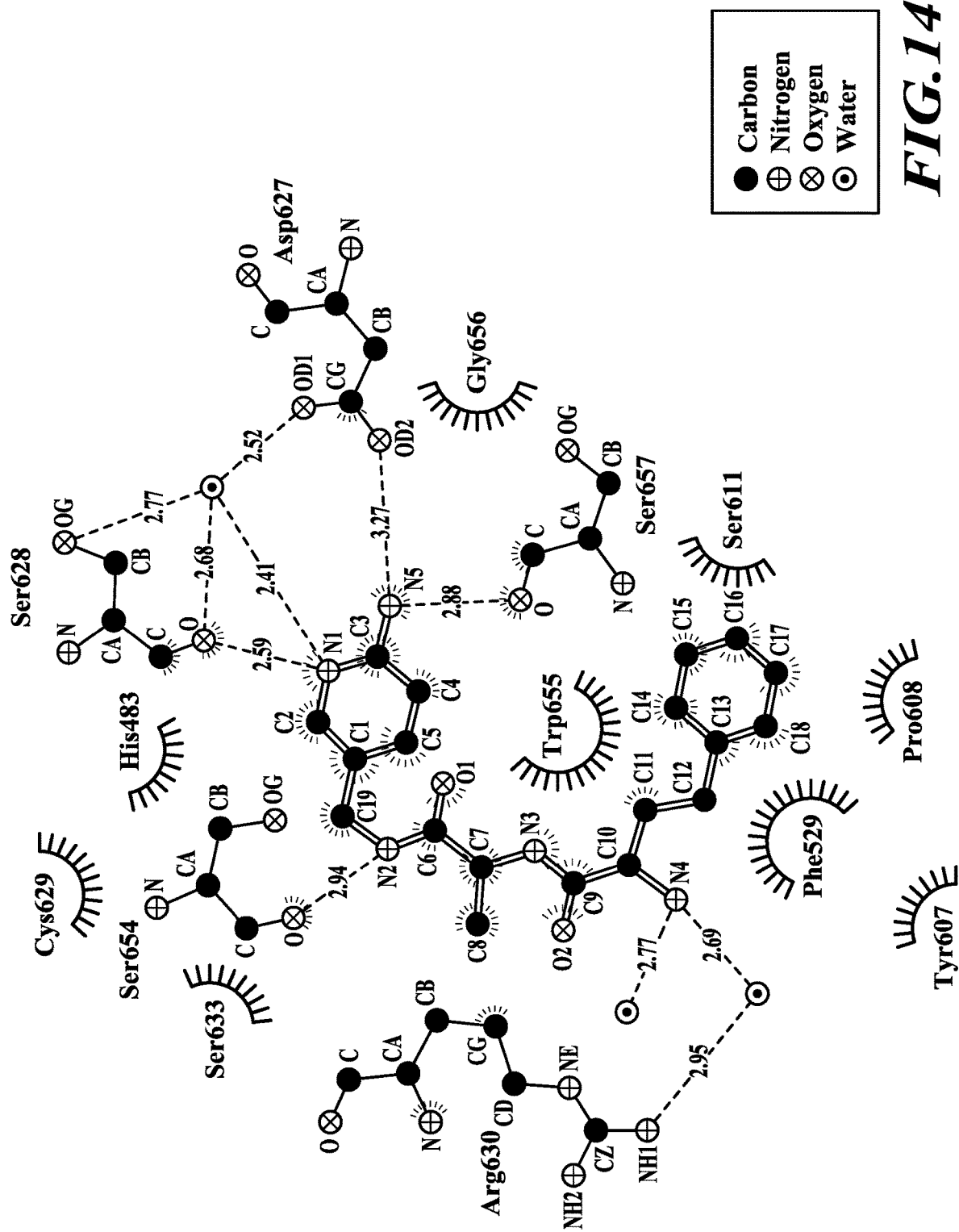
FIG. 14 is a plot illustrating a schematic of one embodiment of the atoms of an inhibitory compound (1007) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 14 is an illustration of MASP-2 CCP2-SP amino acid interactions with (1007) through hydrogen bonds. As shown therein, four different hydrogen bonds exist between the (1007) compound atoms and the MASP-2 amino acid residue atoms. In addition, a total of three water molecules are shown to be included within the crystal structure, all of which are shown to be participating in hydrogen bonding, either with single atoms of the (1007) compound, or as a bridging water molecule between particular (1007) compound atoms and MASP-2 amino acid residue atoms. As shown therein, nitrogen N5, the amine nitrogen of the pyridine moiety, interacts with OD2 oxygen of ASP 627 and an oxygen of SER 657 as a hydrogen bond donor. The nitrogen of the pyridine ring, N1, interacts with an oxygen of SER 628 as a hydrogen bond donor. Nitrogen N1 also interacts with a water molecule. This water molecule bridges between N1 of (1007), oxygen OD1 of ASP 627, oxygen OG of SER 628, as well as the other oxygen atom of SER628. Nitrogen atom N2 interacts with an oxygen of SER 654 as a hydrogen bond donor and nitrogen atom N4 interacts with two different water molecules, one of which is a bridging water molecule which interacts with NH1 of ARG 630. In addition, the compound binds via ionic or electrostatic interaction to ASP 627 (not shown).

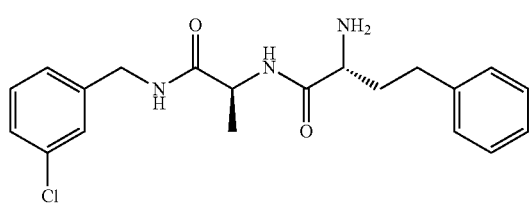

(1021)

Figure 15:
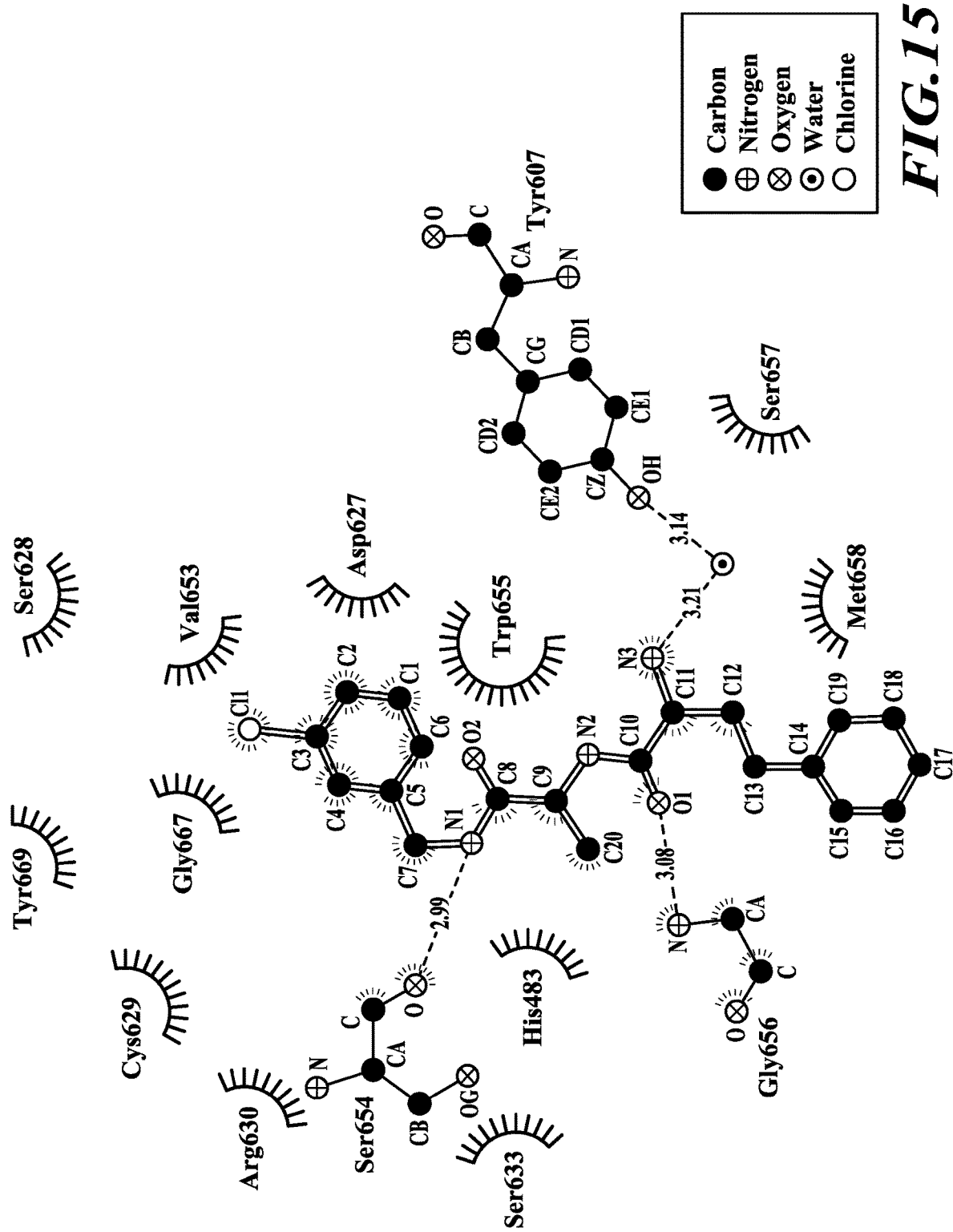
FIG. 15 is a plot illustrating a schematic of one embodiment of the atoms of an inhibitory compound (1021) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 15 is an illustration of MASP-2 CCP2-SP amino acid interactions with (1021) through hydrogen bonds. As shown therein, two different hydrogen bonds are present between (1021) and MASP-2 amino acid atoms. In addition, a single water molecule is shown to be included within the crystal structure, which is shown to be participating in hydrogen bonding as a water molecule, bridging between one atom of the (1021) compound and an atom of a MASP-2 amino acid residue. As shown therein, the amide nitrogen N1 interacts with an oxygen of SER 654 as a hydrogen bond donor. The amino nitrogen N3 interacts with a bridging water molecule which also interacts with the phenolic OH-group of TYR 607. Oxygen O1 interacts with the nitrogen of GLY 656 as a hydrogen bond acceptor. In addition, the compound does not bind via ionic or electrostatic interaction to ASP 627.

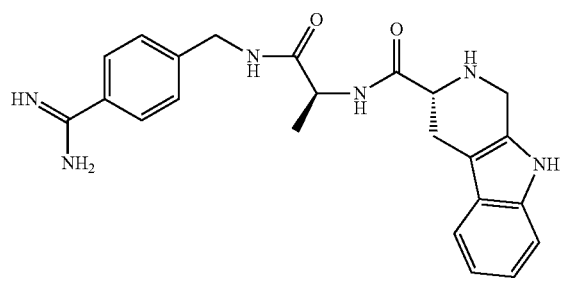

(1097)

Figure 16:
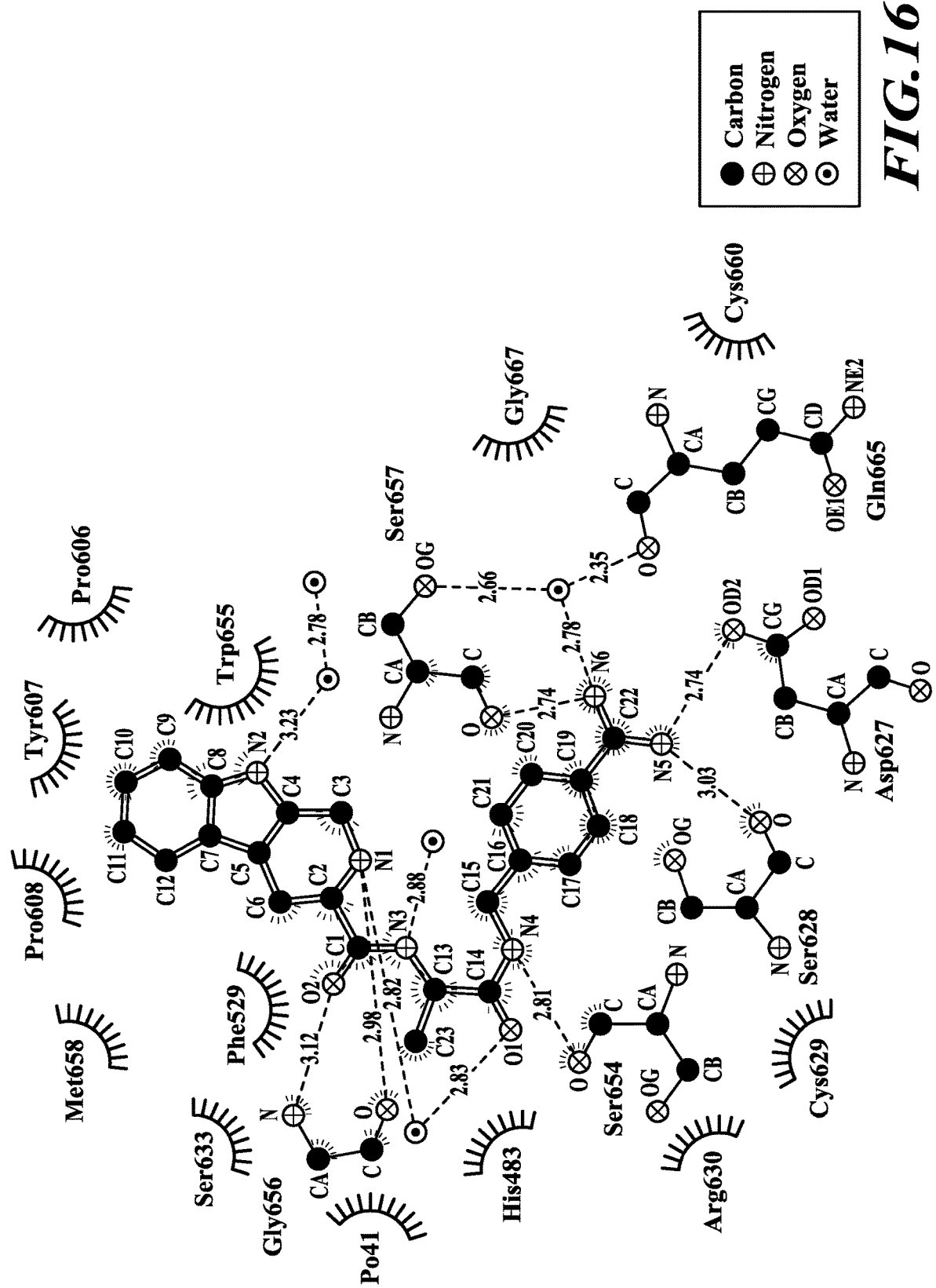
FIG. 16 is a plot illustrating a schematic of one embodiment of the atoms of an inhibitory compound (1097) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 16 is an illustration of MASP-2 CCP2-SP amino acid interactions with (1097) through hydrogen bonds. As shown therein, six different H-bonds are present between the (1097) compound atoms and the MASP-2 residue atoms. In addition, a total of five water molecules are shown to be included within the crystal structure, four of which are shown to be participating in hydrogen bonding, either with one or more atoms of the (1097) compound, or as a bridging water molecule between particular (1097) compound atoms and MASP-2 amino acid residue atoms. As shown therein, an amidine nitrogen, N6, interacts with an oxygen of SER 657 as a hydrogen bond donor. Nitrogen N6 also interacts with a bridging water molecule that is positioned between and interacting with oxygen OG of SER 657 and an oxygen atom of GLN665. In addition, N5 of the amidine interacts with oxygen OD2 of ASP 627 and an oxygen atom of SER 628 as a hydrogen bond donor. Nitrogen N4 forms a hydrogen bond as a donor with an oxygen of SER 654 and nitrogen N3 interacts with a nearby water molecule. Oxygen O1 (in the backbone) and nitrogen N1 in the piperidinyl ring of the fused tetrahydro-pyrido-indole system interact with the same bridging water molecule positioned between HIS 483 and GLY 656. The N1 nitrogen also interacts with the oxygen of GLY 656 as a hydrogen bond donor and the O2 oxygen interacts with the nitrogen atom of the GLY 656 as a hydrogen bond acceptor. Nitrogen N2 in the indole ring of the fused tetrahydro-pyrido-indole system interacts with a water molecule shown between TRP 655 and SER 657. In addition, the compound binds via ionic or electrostatic interaction to ASP 627 (not shown).

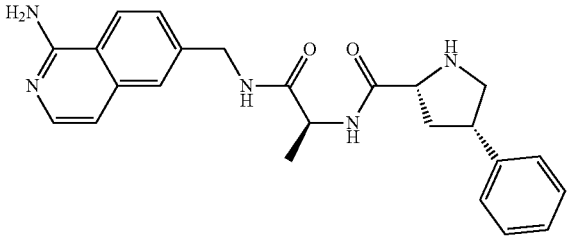

(1089)

Figure 17:
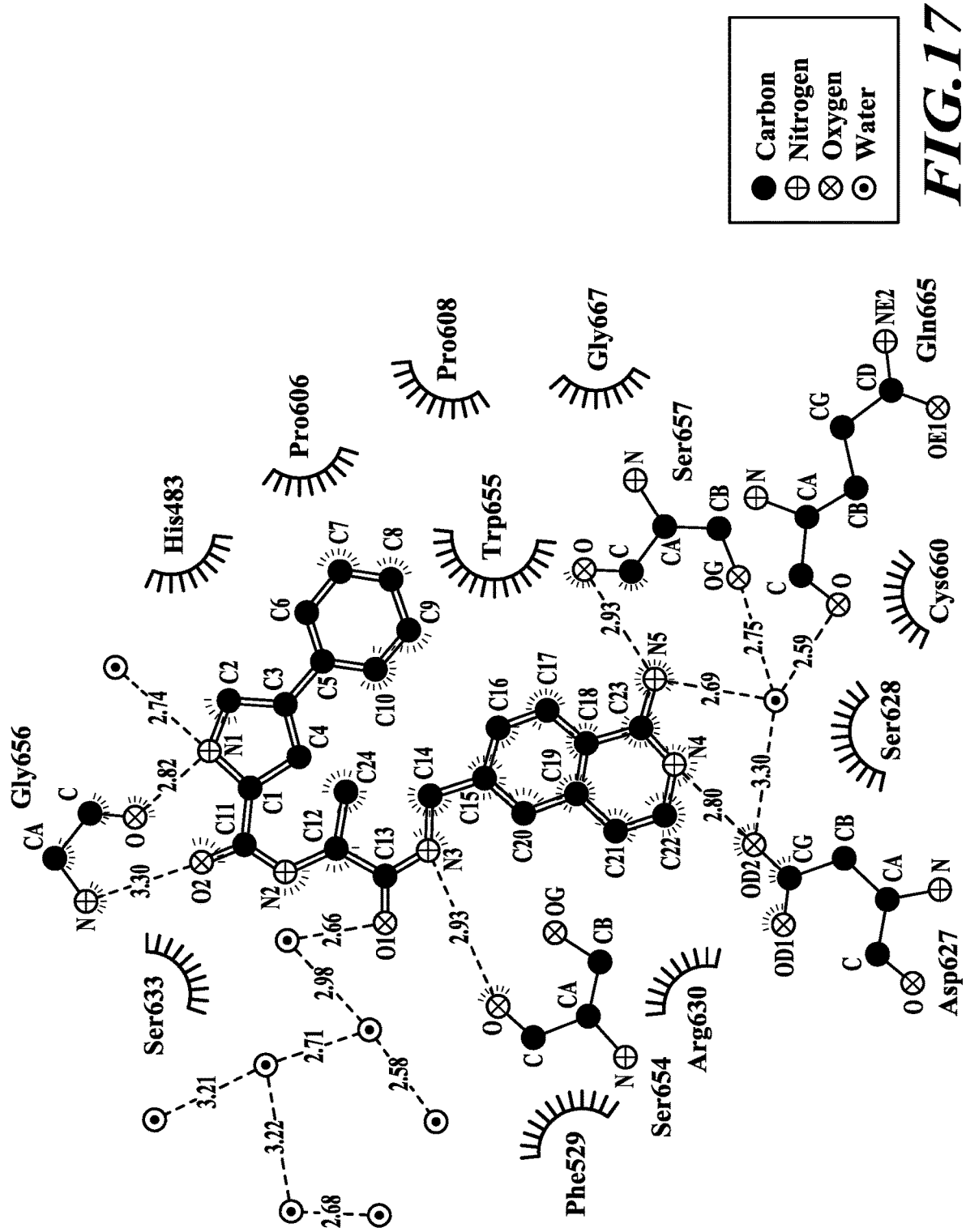
FIG. 17 is a plot illustrating a schematic of one embodiment of the atoms of an inhibitory compound (1089) with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 17 is an illustration of MASP-2 CCP2-SP amino acid interactions with (1089) through hydrogen bonds. As shown therein, five different hydrogen bonds are present between atoms of the (1089) compound and the atoms of the MASP-2 amino acid residues. In addition, a total of nine water molecules are shown to be included within the crystal structure, three of which are shown to be participating in hydrogen bonding, either with single atoms of the (1089) compound, or as a bridging water molecule between particular (1089) compound atoms and MASP-2 amino acid residue atoms. As shown therein, nitrogen N5, the primary amine nitrogen of the isoquinoline moiety, interacts with an oxygen atom of SER 657 as a hydrogen bond donor. The N5 nitrogen also interacts with a bridging water molecule that is positioned between and interacting with oxygen OG of SER 657, an oxygen atom of GLN 665, and oxygen OD2 of ASP627. The nitrogen of the isoquinoline ring, N4, interacts with oxygen OD2 of ASP 627 as a hydrogen bond donor. Nitrogen N3 forms a hydrogen bond as a donor with an oxygen of SER654 and oxygen O1 interacts with a nearby water molecule. The oxygen O2 forms a hydrogen bond as an acceptor with the nitrogen atom of GLY 656, while the pyrrolidinyl nitrogen N1 interacts with the oxygen atom of GLY 656 as a hydrogen bond donor. Nitrogen N1 also interacts with a nearby water molecule. In addition, the compound binds via ionic or electrostatic interaction to ASP 627 (not shown).

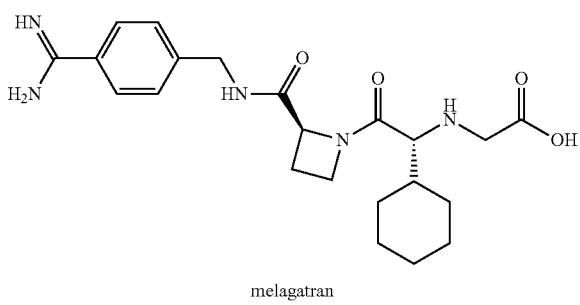 [SMILES: N=C(N)c1ccc(CNC(=O)[C@@H]2CCN2C(=O)[C@H](NCC(=O)O)C2CCCCC2)cc1]

melagatran

Figure 18:
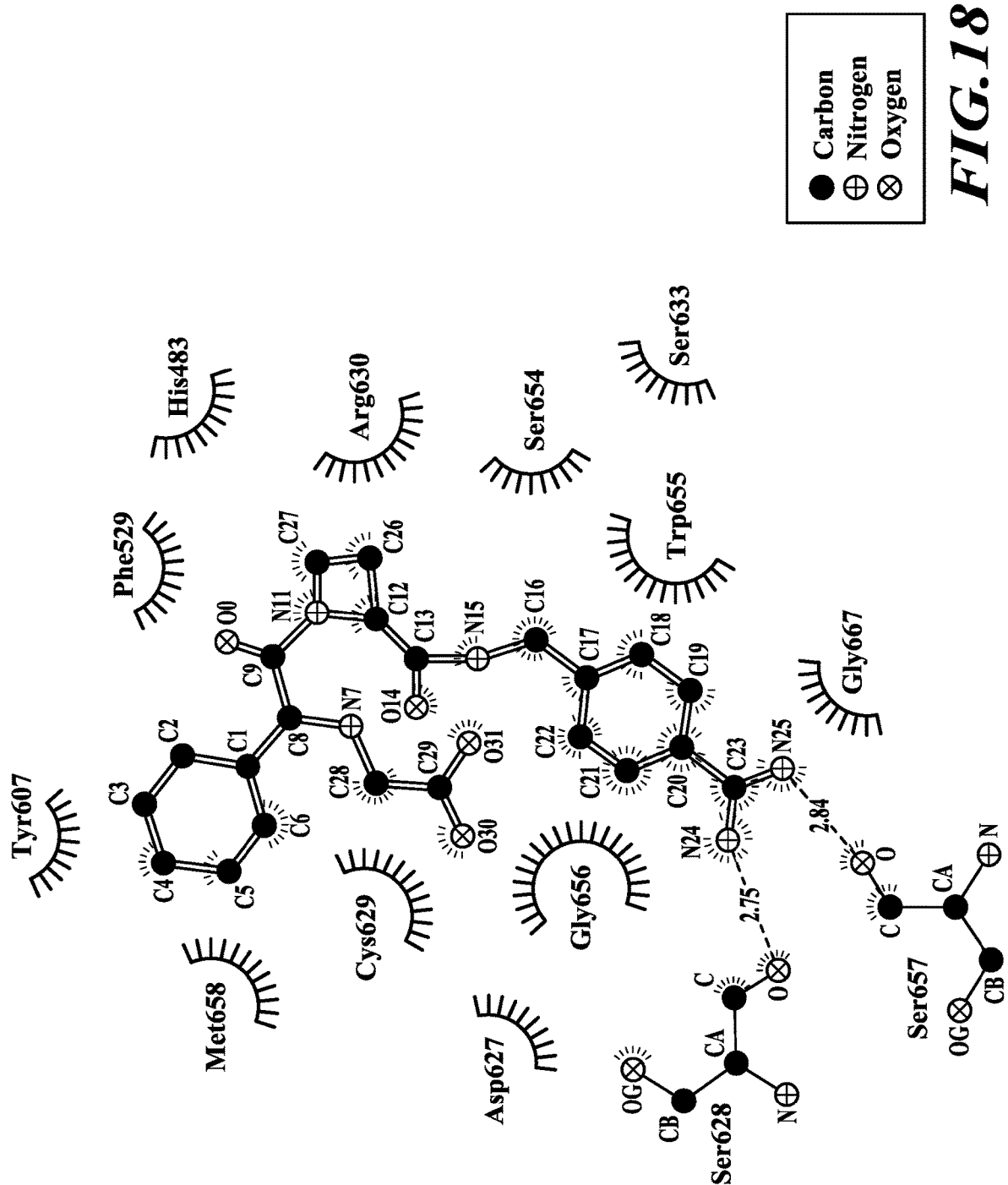
FIG. 18 is a plot illustrating a schematic of one embodiment of the atoms of an inhibitory compound melagatran with those of MASP-2 amino acids as computed by LigPlot+ software settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures.

FIG. 18 is an illustration of MASP-2 CCP2-SP amino acid interactions with melagatran via hydrogen bonds. As shown therein, two different H-bonds exist between the atoms of melagatran and the atoms of the MASP-2 residues. The figure does not depict the presence of any water molecules in the crystal structure. One of the amidine nitrogens, N25, interacts with an oxygen of SER 657 as a hydrogen bond donor and the other amidine nitrogen N24 interacts with an oxygen of SER 628 as a hydrogen bond donor. In addition, the compound binds via ionic or electrostatic interactions or hydrogen bonding to ASP 627 (not shown).

Figure 19:
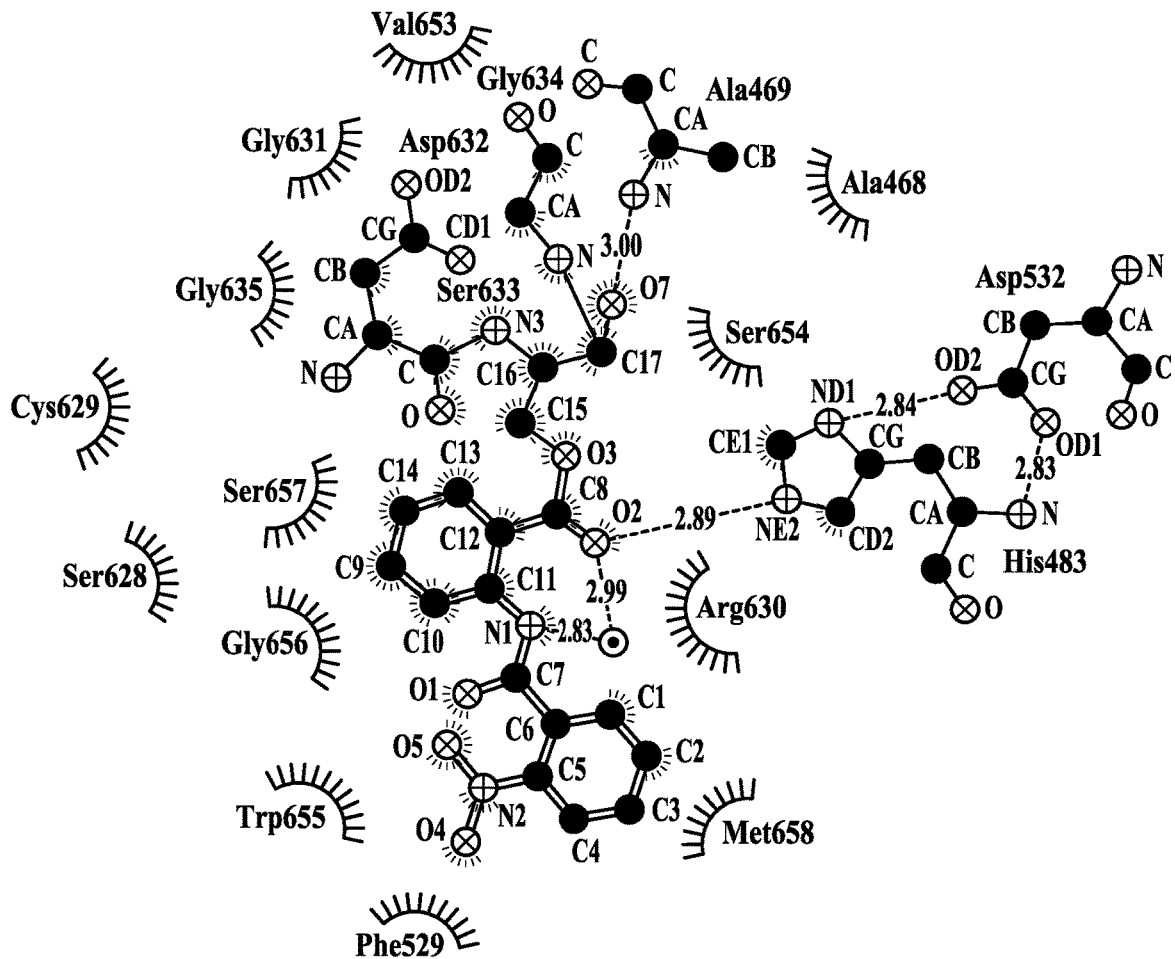
FIG. 19 is a plot showing the binding of compound (14) to MASP-2 showing hydrogen bonds as computed by LigPlot+ software.

FIG. 19 is an illustration of MASP-2 CCP2-SP amino acid interactions with compound 14 via hydrogen bonds. The compound binds covalently to SER 633 with opening of the oxazin-4-one ring. The carbonyl oxygen atom O2 of the resulting ester linkage forms a hydrogen bond with nitrogen NE2 of HIS 483 as a hydrogen bond acceptor. Furthermore, the same carbonyl oxygen atom also forms a hydrogen bond with water molecule 66 as a hydrogen bond acceptor.

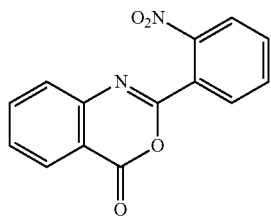

(14)

Figure 20:
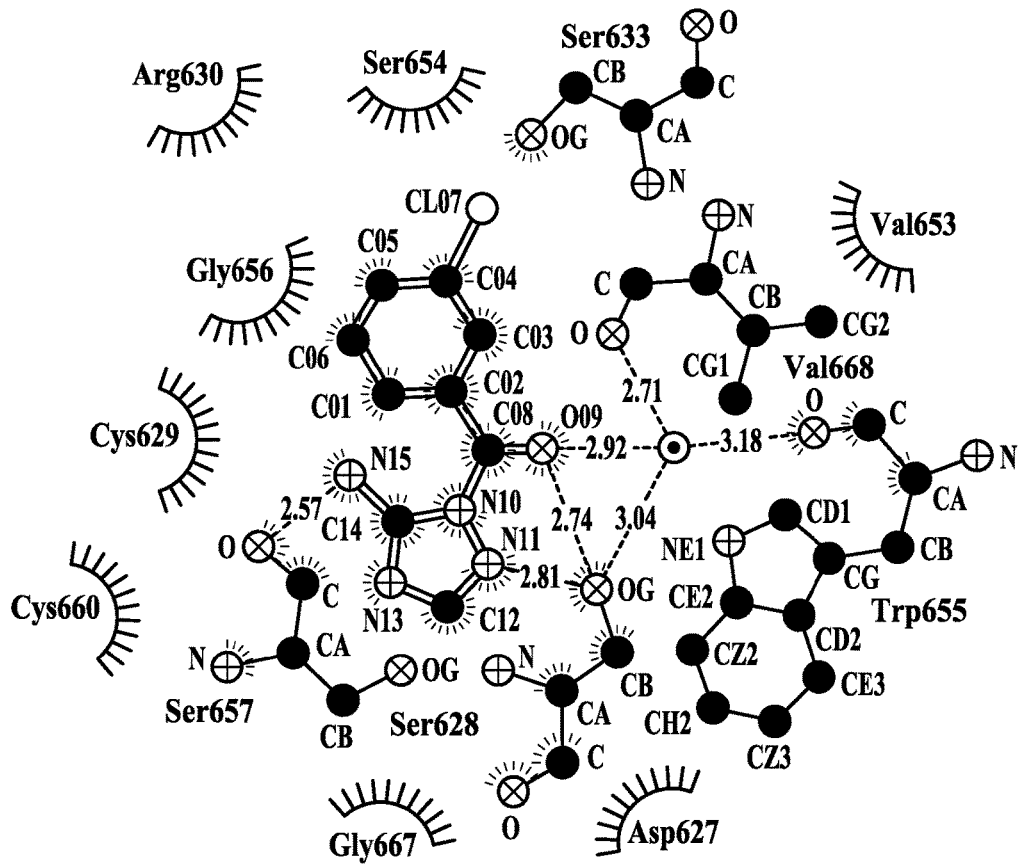
FIG. 20 is a plot showing the binding of compound (54) to MASP-2 showing hydrogen bonds as computed by LigPlot+ software.

FIG. 20 is an illustration of MASP-2 CCP2-SP amino acid interactions with compound (54) via hydrogen bonds. As shown therein, two different H-bonds exist between the atoms of compound (54) and the atoms of the MASP-2 residues. The carbonyl oxygen atom O09, interacts with an oxygen of SER 628 as a hydrogen bond acceptor and the amino nitrogen atom N15 interacts with a carbonyl oxygen of SER 657 as a hydrogen bond donor. In addition, one water molecule is included within the crystal structure, which is shown to be participating as a bridging water molecule between the carbonyl oxygen atom O09 of compound (54) and MASP-2 amino acid residue atoms of SER 628, TRP 655 and VAL 668.

(54)

Figure 21:
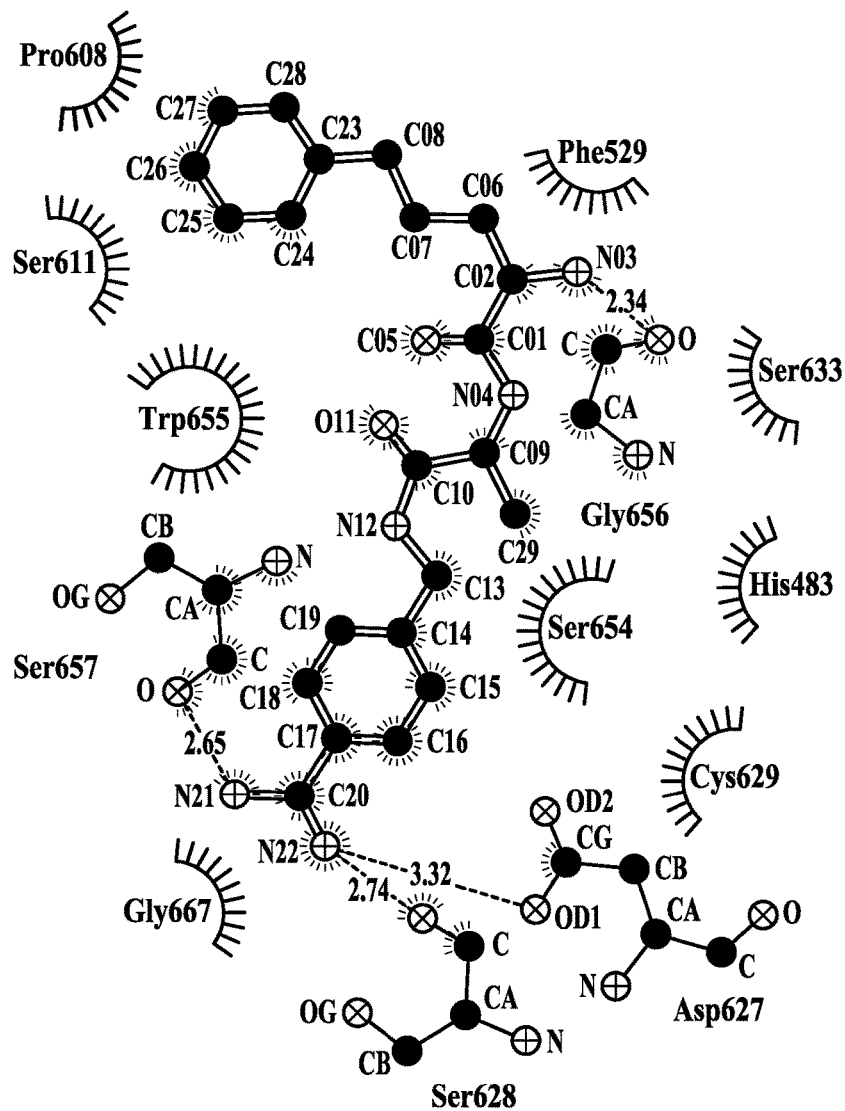
FIG. 21 is a plot showing the binding of compound (1042) to MASP-2 showing hydrogen bonds as computed by LigPlot+ software.

FIG. 21 is an illustration of MASP-2 CCP2-SP amino acid interactions with compound (1042) through hydrogen bonds. As shown therein, four different hydrogen bonds are present between the compound (1042) atoms and the MASP-2 amino acid residue atoms. As shown therein, an amidine nitrogen N21 interacts with a carbonyl oxygen O of SER 657 as a hydrogen bond donor. The other amidine nitrogen N22 interacts with a carbonyl oxygen O of SER 628 as a hydrogen bond donor and with a carboxylate group oxygen OD1 of ASP 627 as a hydrogen bond donor. The amino group nitrogen N03 interacts with a carbonyl oxygen of GLY 656 as a hydrogen bond donor.

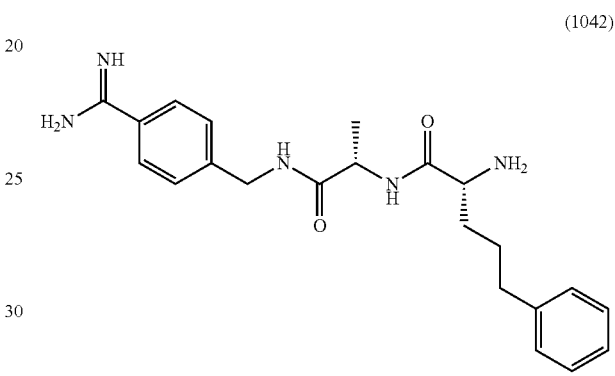

(1042)

Figure 22:
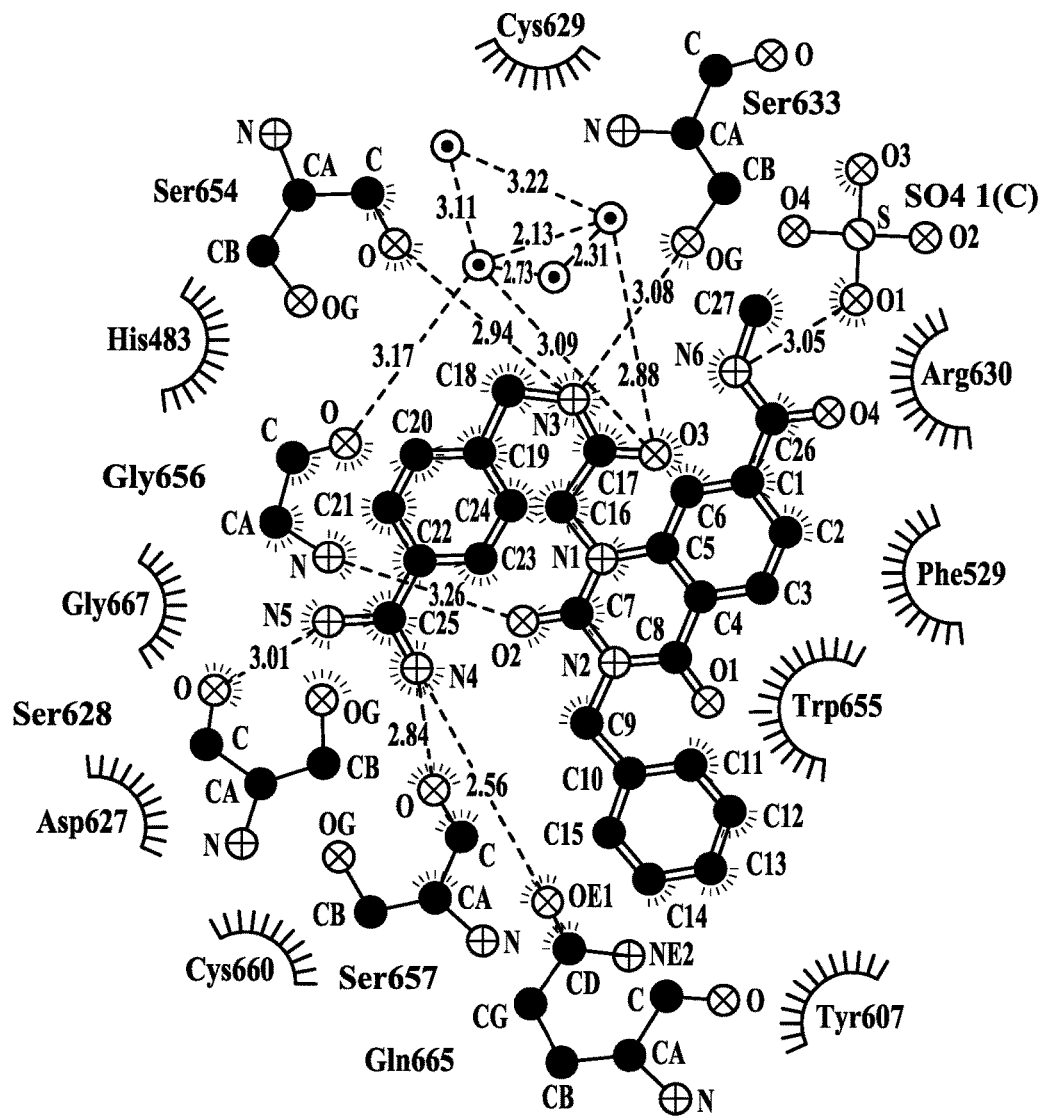
FIG. 22 is a plot showing the binding of compound (2018) to MASP-2 showing hydrogen bonds as computed by LigPlot+ software.

FIG. 22 is an illustration of MASP-2 CCP2-SP amino acid interactions with compound (2018) through hydrogen bonds. As shown therein, six different hydrogen bonds are present between the compound (2018) compound atoms and the MASP-2 amino acid residue atoms. As shown therein, one of the amidine nitrogens, N4, interacts with a carbonyl oxygen O of SER 657 as a hydrogen bond donor and with a carbonyl oxygen OE1 of SER 657 as a hydrogen bond donor. The other amidine nitrogen N5 interacts with an oxygen of SER 628 as a hydrogen bond donor. The amide nitrogen N3 interacts with the carbonyl oxygen O of SER 654 as a hydrogen bond donor, and with the hydroxyl oxygen OG of SER 633 as a hydrogen bond acceptor. The carbonyl oxygen O2 interacts with the nitrogen N of GLY 656 as a hydrogen bond acceptor. A total of four water molecules are shown in this area of the active site to be included within the crystal structure, two of which are shown to be participating in hydrogen bonding with one or more atoms of the compound (2018) compound, or as a bridging water molecule between particular compound (2018) compound atoms and MASP-2 amino acid residue atoms. A sulfate ion is also present in the crystal structure and interacts with amide nitrogen N6 of compound (2018) as a hydrogen bond acceptor.

(2018)

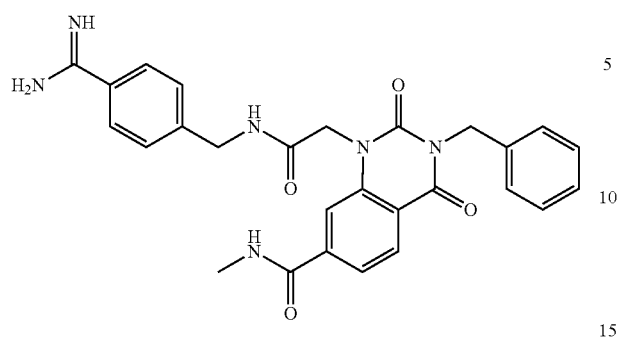

Figure 23:
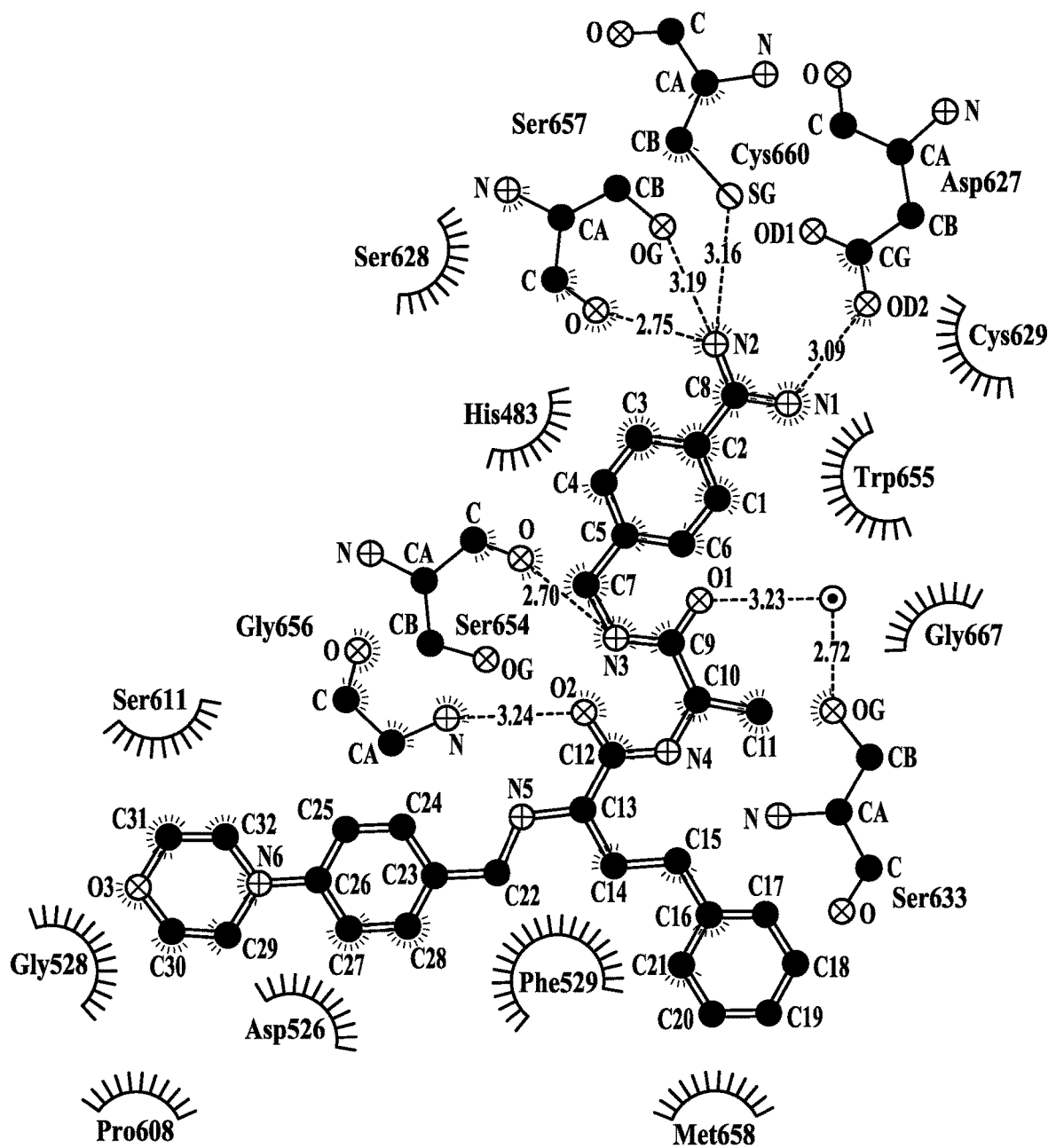
FIG. 23 is a plot showing the binding of compound (1149) to MASP-2 showing hydrogen bonds as computed by LigPlot+ software.

FIG. 23 is an illustration of MASP-2 CCP2-SP amino acid interactions with compound (1149) through hydrogen bonds. As shown therein, six different hydrogen bonds are present between the compound (1149) atoms and the MASP-2 amino acid residue atoms. As shown therein, an amidine nitrogen N1 interacts with a carboxylate oxygen OD2 of ASP 627 as a hydrogen bond donor. The other amidine nitrogen N2 interacts with the carbonyl oxygen O of SER 657 as a hydrogen bond donor and can interact with a hydroxyl oxygen OG of SER 657 as a hydrogen bond donor, or with the sulfur atom SG of CYS 660 as a hydrogen bond donor. The amide nitrogen N3 interacts with carbonyl oxygen O of SER 654 as a hydrogen bond donor. The carbonyl oxygen O2 interacts with a nitrogen atom of GLY 656 as a hydrogen bond acceptor. In addition, one water molecule is shown to be included within the crystal structure in this area of the active site, which participates in hydrogen bonding with the carbonyl oxygen O1 of the compound (1149).

(1149)

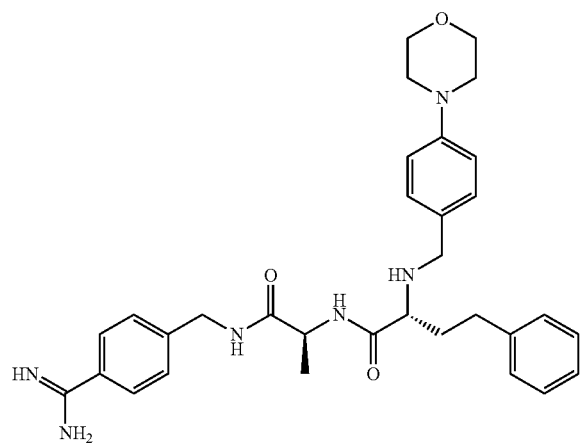

Figure 24:
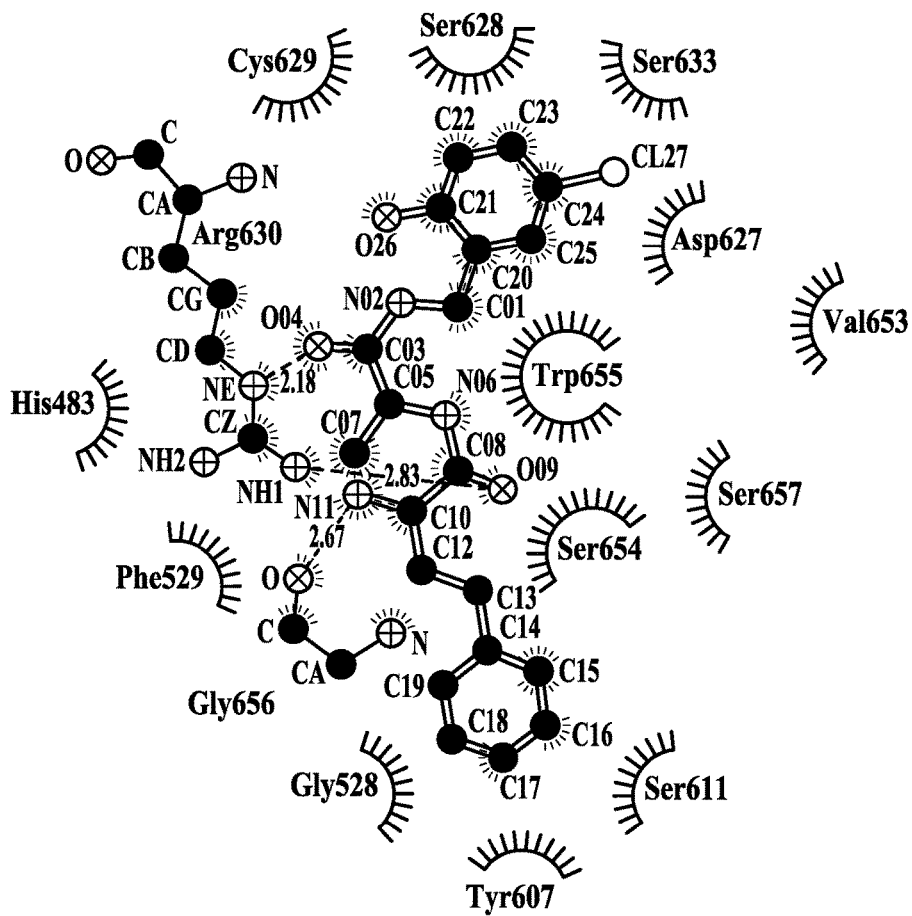
FIG. 24 is a plot showing the binding of compound (1031) to MASP-2 showing hydrogen bonds as computed by LigPlot+ software.

FIG. 24 is an illustration of MASP-2 CCP2-SP amino acid interactions with compound (1031) through hydrogen bonds. As shown therein, three different hydrogen bonds are present between the compound (1031) and the MASP-2 amino acid residue atoms. The carbonyl oxygen O04 interacts with a guanidine nitrogen NE of ARG 630 as a hydrogen bond acceptor. The carbonyl oxygen O09 interacts with a guanidine nitrogen NH1 of ARG 630 as a hydrogen bond acceptor. The amino group nitrogen N11 interacts with a carbonyl oxygen O of GLY 656 as a hydrogen bond donor.

(1031)

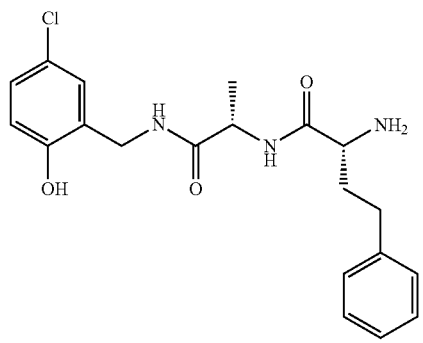

Figure 25:

FIG. 25 is a plot showing the binding of compound (1153) to MASP-2 showing hydrogen bonds as computed by LigPlot+ software.

FIG. 25 is an illustration of MASP-2 CCP2-SP amino acid interactions with compound (1153) through hydrogen bonds. As shown therein, six different hydrogen bonds are present between the compound (1153) compound atoms and the MASP-2 amino acid residue atoms. As shown therein, an amidine nitrogen N1 interacts with a carboxylate oxygen O of SER 657 as a hydrogen bond donor and with a carboxylate oxygen OD2 of ASP 627 as a hydrogen bond donor. The other amidine nitrogen N2 interacts with a hydroxyl oxygen OG of SER 628 as a hydrogen bond donor. The carbonyl oxygen O1 interacts with guanidine nitrogen NH2 of ARG 630 as a hydrogen bond acceptor. The amine nitrogen N5 interacts with a carbonyl oxygen of GLY 656 as a hydrogen bond donor. The carbonyl oxygen O2 interacts with a nitrogen atom of GLY 656 as a hydrogen bond acceptor. In addition, one water molecule is shown to be included within the crystal structure in this area of the active site, which participates in hydrogen bonding with amide nitrogen N3 of the compound (1153).

(1153)

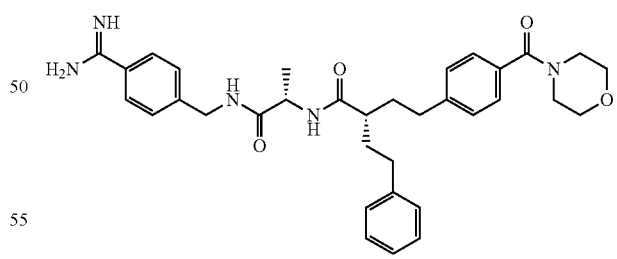

Figure 26:
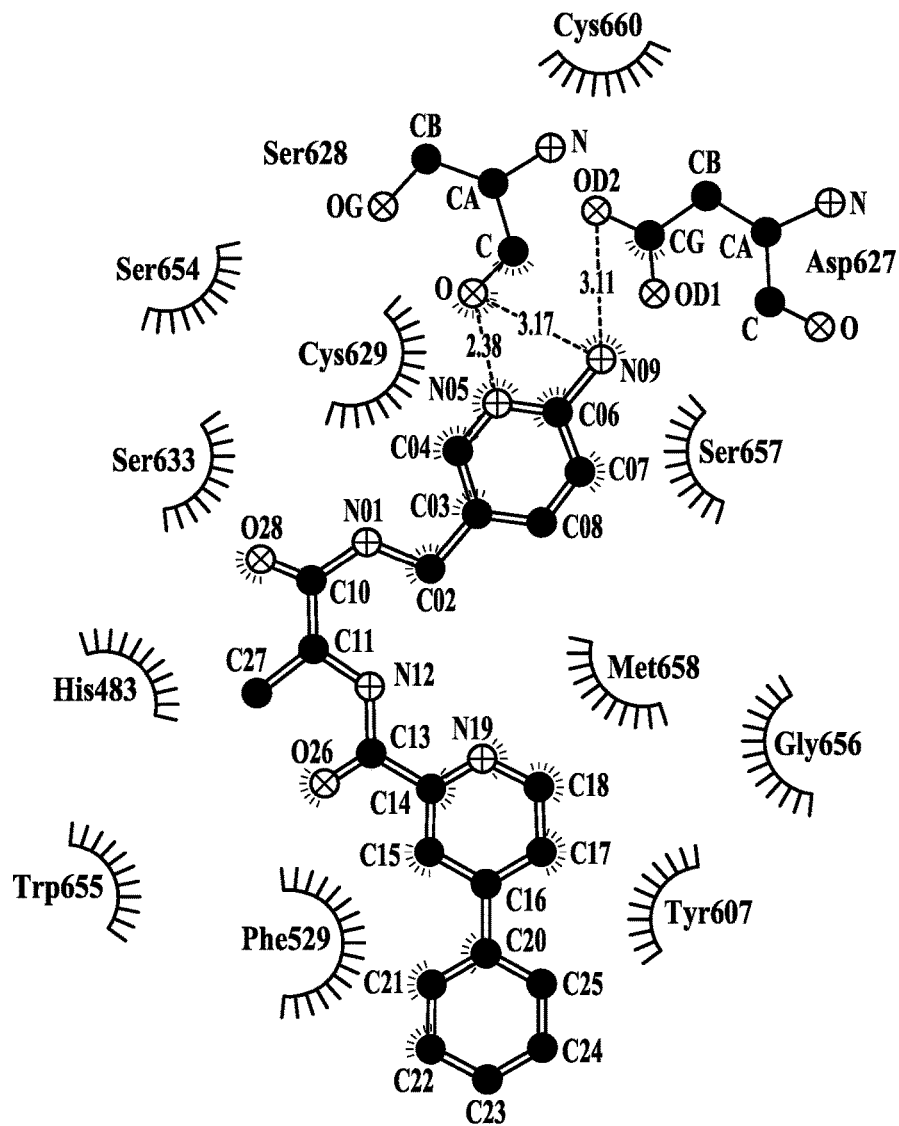
FIG. 26 is a plot showing the binding of compound (1025) to MASP-2 showing hydrogen bonds as computed by LigPlot+ software.

FIG. 26 is an illustration of MASP-2 CCP2-SP amino acid interactions with compound (1025) through hydrogen bonds. As shown therein, three different hydrogen bonds are present between the compound (1025) atoms and the MASP-2 amino acid residue atoms. Amine nitrogen N09 interacts with carboxylate oxygen OD2 of ASP 627 as a hydrogen bond donor and also with a carbonyl oxygen O of SER 628 as a hydrogen bond donor. The pyridine nitrogen N05 also interacts with carbonyl oxygen O of SER 628 as a hydrogen bond donor.

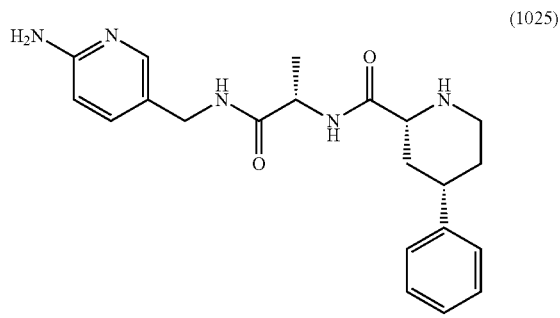 [SMILES: C[C@H](NC(=O)[C@H]1C[C@@H](c2ccccc2)CCN1)C(=O)NCc1ccc(N)nc1]

(1025)

Figure 27:
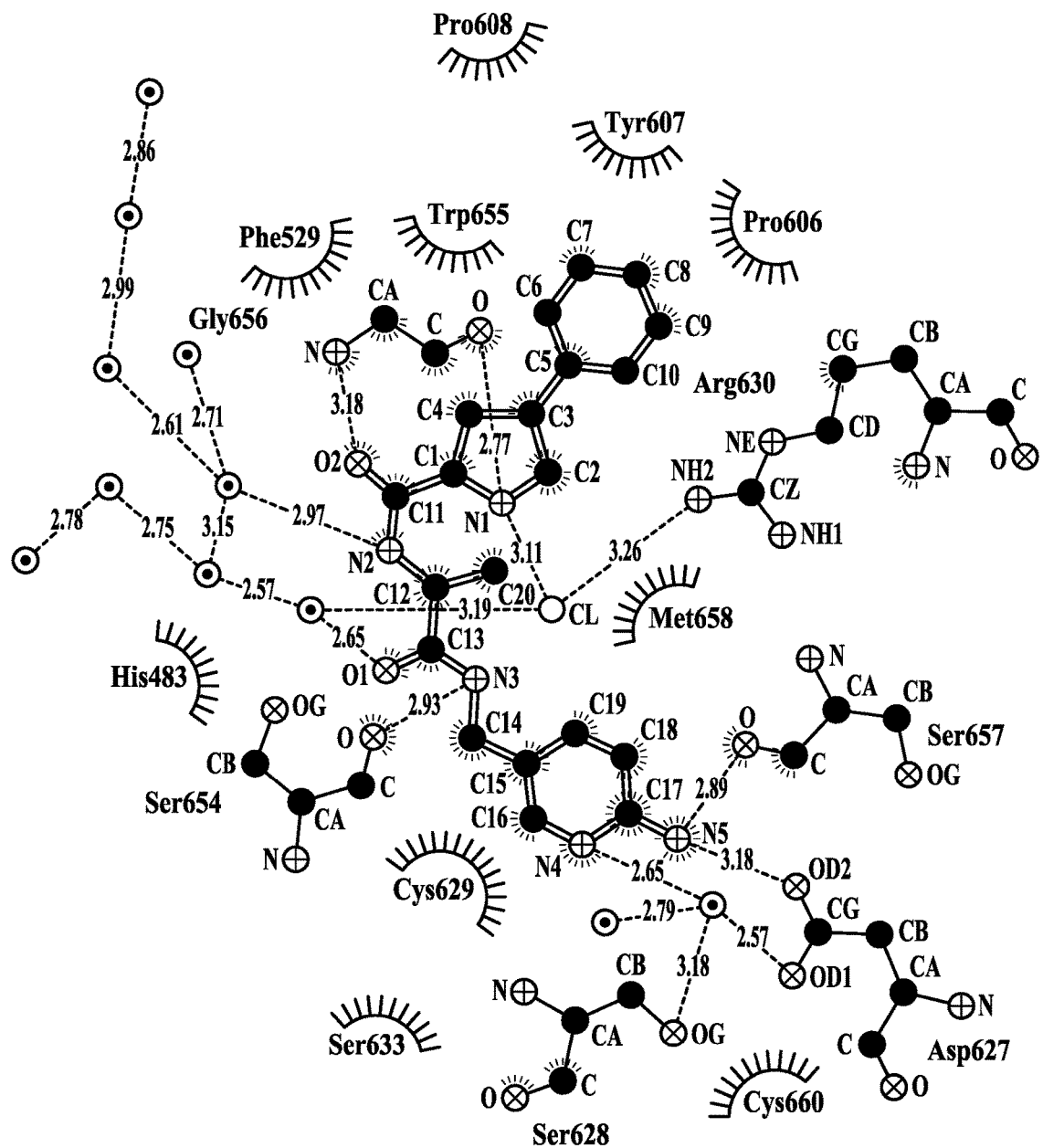
FIG. 27 is a plot showing the binding of compound (1012) to MASP-2 showing hydrogen bonds as computed by LigPlot+ software.

FIG. 27 is an illustration of MASP-2 CCP2-SP amino acid interactions with compound (1012) through hydrogen bonds. As shown therein, five different hydrogen bonds are present between the compound (1012) atoms and the MASP-2 amino acid residue atoms. As shown therein, an amine nitrogen N5 interacts with a carboxylate oxygen OD2 of ASP 627 as a hydrogen bond donor and also with a carbonyl oxygen O of SER 657 as a hydrogen bond donor. The amide nitrogen N3 interacts with a carbonyl oxygen of SER 654 as a hydrogen bond donor. The pyrrolidine nitrogen N1 interacts with a carbonyl oxygen of GLY 656 as a hydrogen bond donor. The carbonyl oxygen O1 interacts with a nitrogen atom of GLY 656 as a hydrogen bond acceptor. In addition, a total of eleven water molecules are shown in this area of the active site to be included within the crystal structure, three of which are shown to be participating in hydrogen bonding, either with one or more atoms of the compound (1012), or as a bridging water molecule between particular compound (1012) atoms and MASP-2 amino acid residue atoms. One of the water atoms forms a bridge between the pyridine nitrogen N4 and the carboxylate carbon OD1 of ASP 627 and the hydroxyl oxygen OG of SER 628. A chloride ion is also present in the crystal structure, bridging N1 of compound (1012) to NH2 of ARG630 and a water molecule 141.

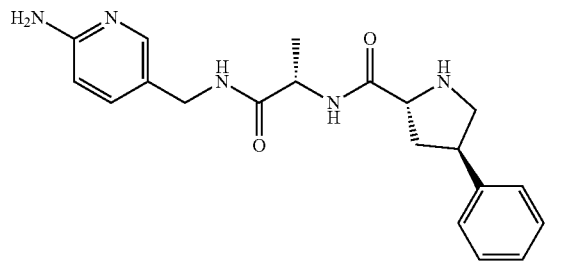

(1012)

Figure 28:
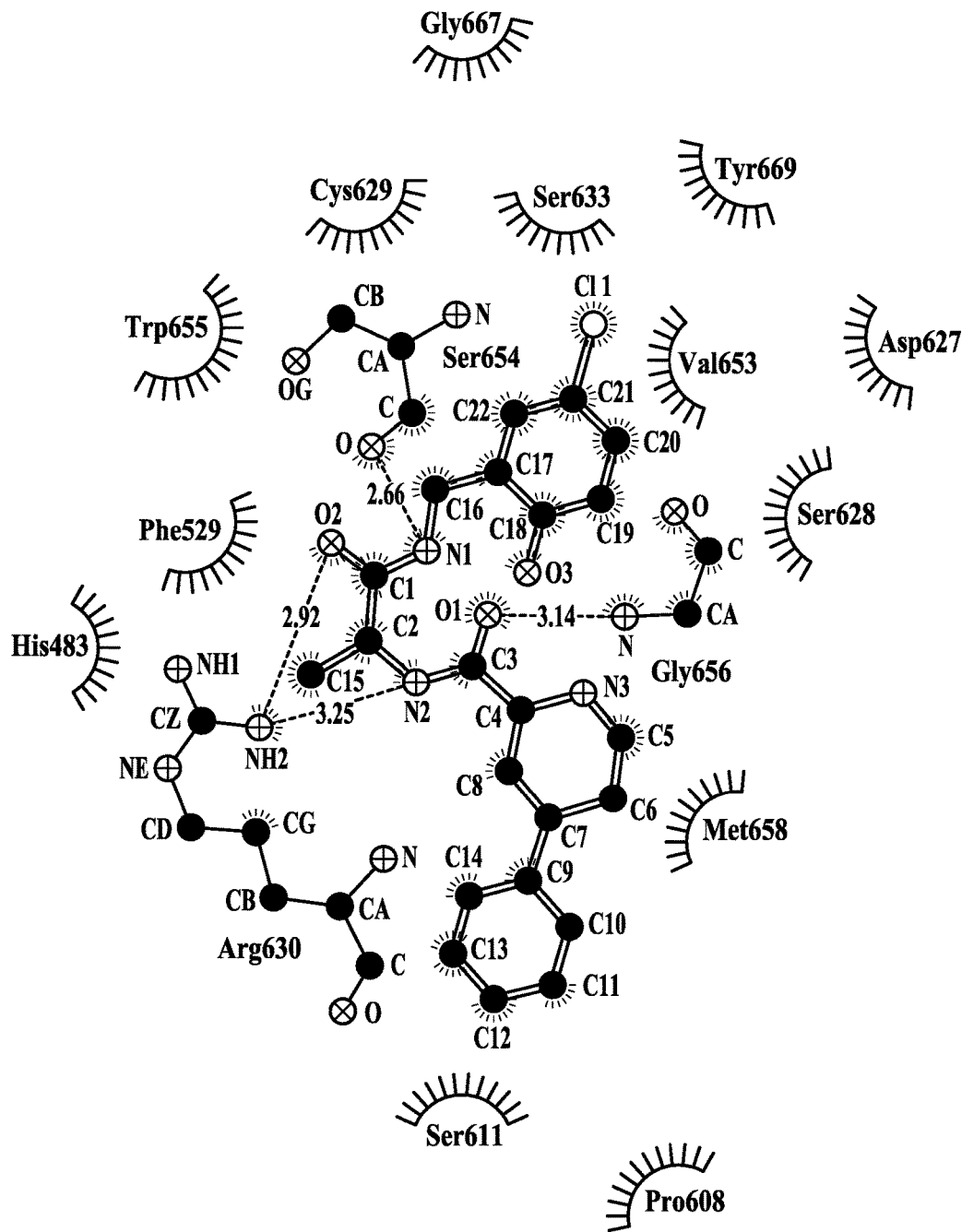
FIG. 28 is a plot showing the binding of compound (1078) to MASP-2 showing hydrogen bonds as computed by LigPlot+ software.

FIG. 28 is an illustration of MASP-2 CCP2-SP amino acid interactions with compound (1078) through hydrogen bonds. As shown therein, three different hydrogen bonds are present between the compound (1078) atoms and the MASP-2 amino acid residue atoms. The carbonyl oxygen O2 interacts with a guanidine nitrogen NH2 of ARG 630 as a hydrogen bond acceptor. The amide nitrogen N2 also interacts with the guanidine nitrogen NH2 of ARG 630, but as a hydrogen bond donor. The amide nitrogen N1 interacts with carbonyl oxygen O of SER 654 as a hydrogen bond donor. The carbonyl oxygen O1 interacts with a nitrogen N of GLY 656 as a hydrogen bond acceptor.

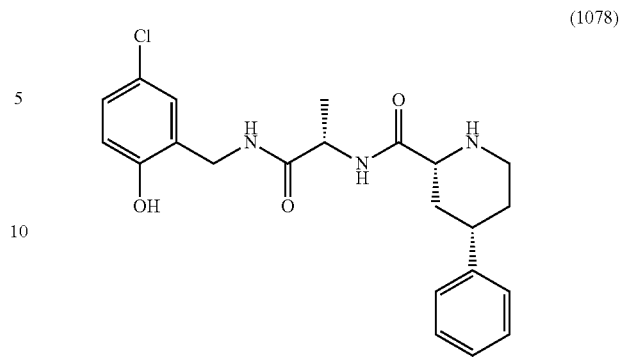

(1078)

Figure 29:
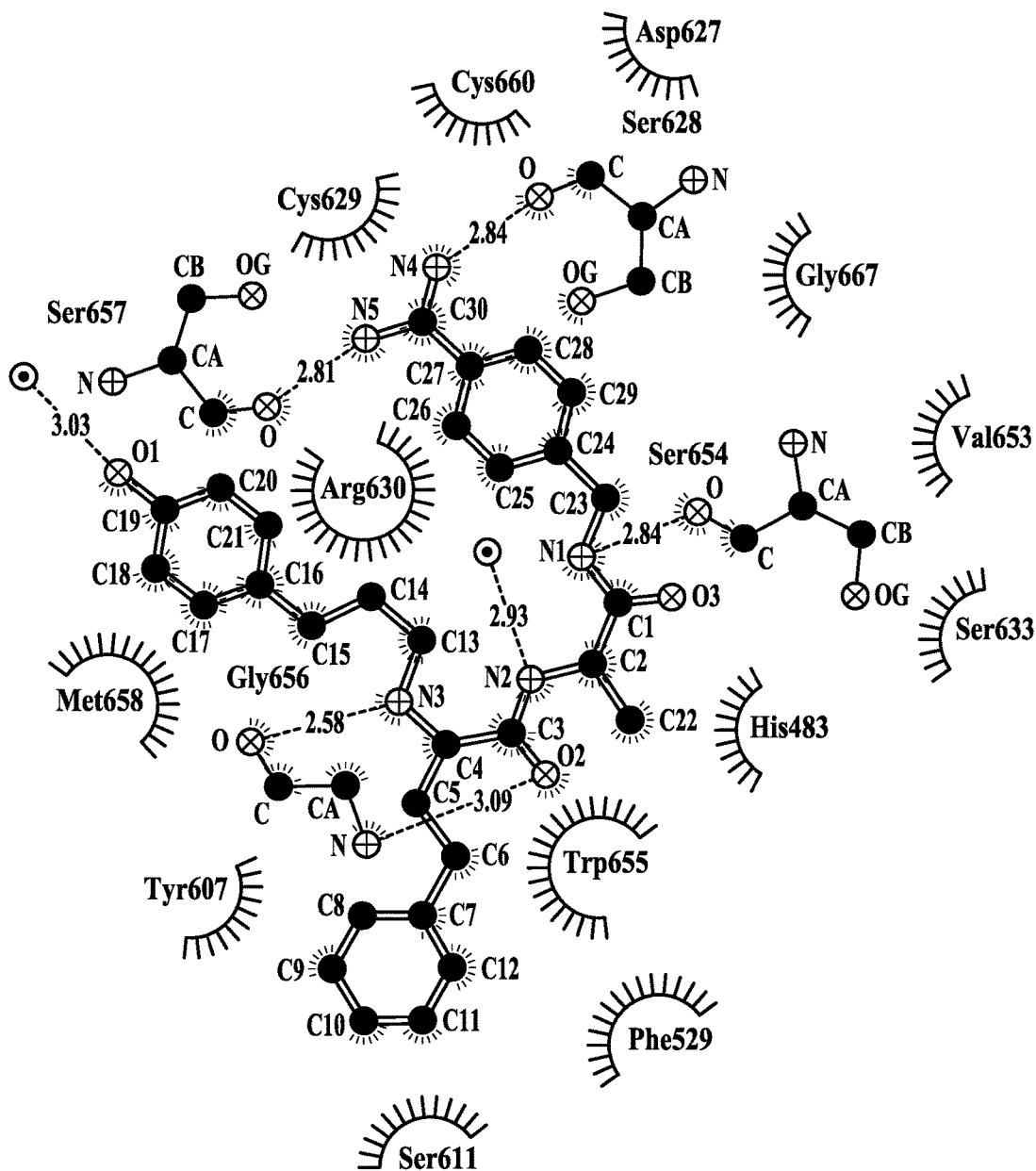
FIG. 29 is a plot showing the binding of compound (1145) to MASP-2 showing hydrogen bonds as computed by LigPlot+ software.

FIG. 29 is an illustration of MASP-2 CCP2-SP amino acid interactions with compound (1145) through hydrogen bonds. As shown therein, five different hydrogen bonds are present between the compound (1145) compound atoms and the MASP-2 amino acid residue atoms. As shown therein, an amidine nitrogen N5 interacts with a carbonyl oxygen O of SER 657 as a hydrogen bond donor. The other amidine nitrogen N4 interacts with a carbonyl oxygen O of SER 628 as a hydrogen bond donor. Amide nitrogen N1 interacts with carbonyl oxygen atom O of SER 654 as a hydrogen bond donor. The amine nitrogen N3 interacts with a carbonyl oxygen of GLY 656 as a hydrogen bond donor. The carbonyl oxygen O2 interacts with a nitrogen atom of GLY 656 as a hydrogen bond acceptor. In addition, two water molecules are shown to be included within the crystal structure in this area of the active site, which participates in hydrogen bonding with the phenolic hydroxyl O1 and amide nitrogen N2 of the compound (1145).

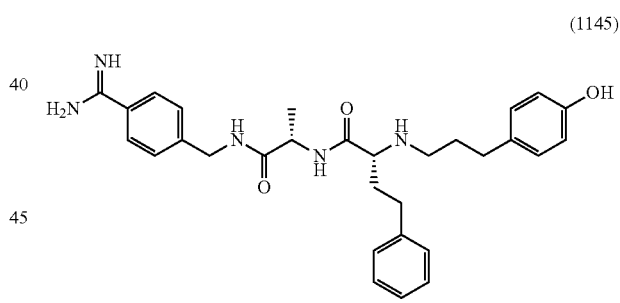

(1145)

Figure 30:
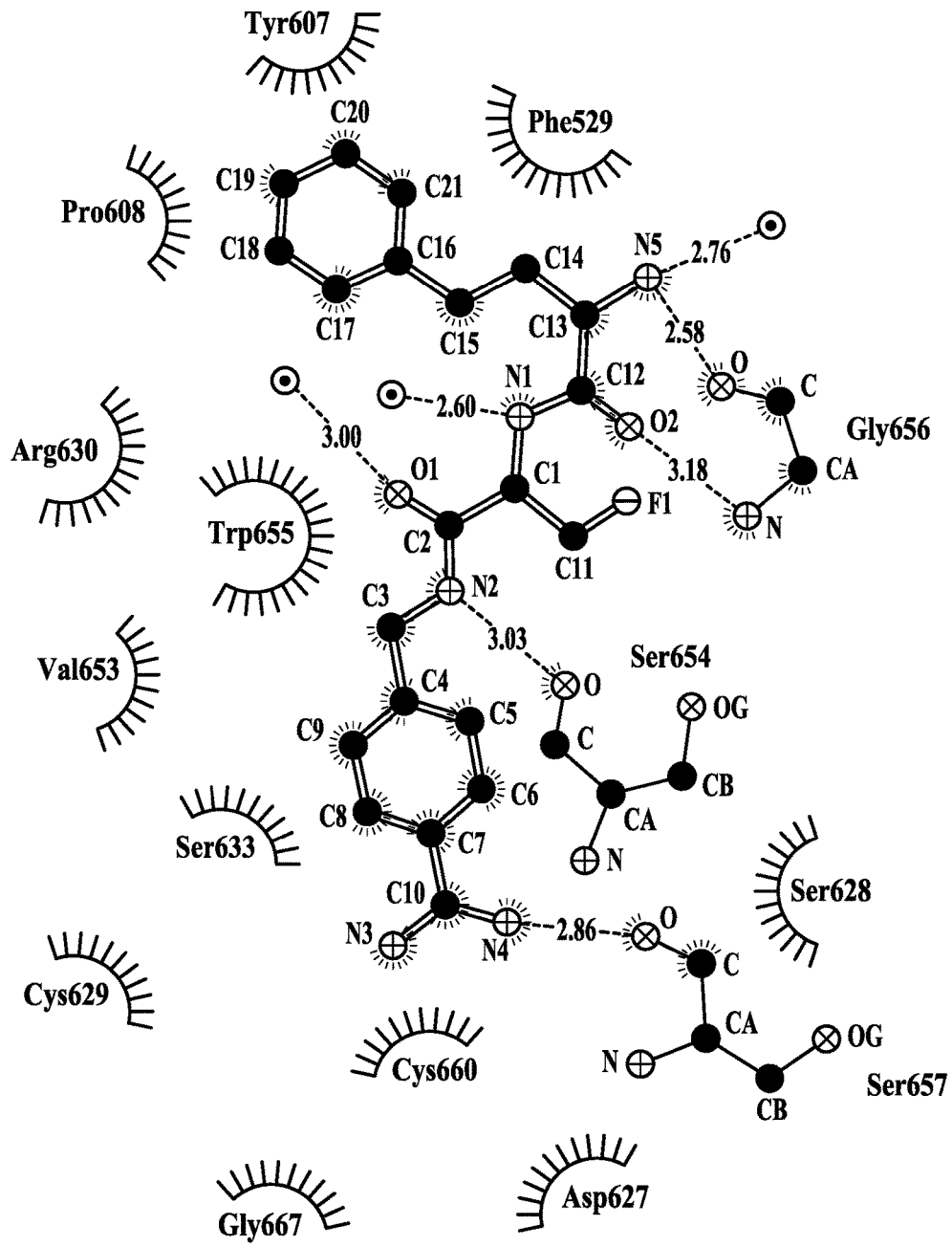
FIG. 30 is a plot showing the binding of compound (1050) to MASP-2 showing hydrogen bonds as computed by LigPlot+ software.

FIG. 30 is an illustration of MASP-2 CCP2-SP amino acid interactions with compound (1050) through hydrogen bonds. As shown therein, four different hydrogen bonds are present between the compound (1050) atoms and the MASP-2 amino acid residue atoms. As shown therein, an amidine nitrogen N4 interacts with a carbonyl oxygen O of SER 657 as a hydrogen bond donor. The amide nitrogen N2 interacts with a carbonyl oxygen O of SER 654 as a hydrogen bond donor. The amino group nitrogen N5 interacts with a carbonyl oxygen of GLY 656 as a hydrogen bond donor. The carbonyl oxygen O2 interacts with a nitrogen atom of GLY 656 as a hydrogen bond acceptor. In addition, three water molecules are shown to be included within the crystal structure in this area of the active site, each of which participate in hydrogen bonding with the compound (1050).

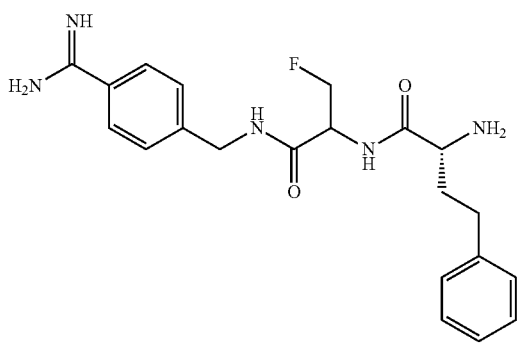

(1050)

Figure 31:
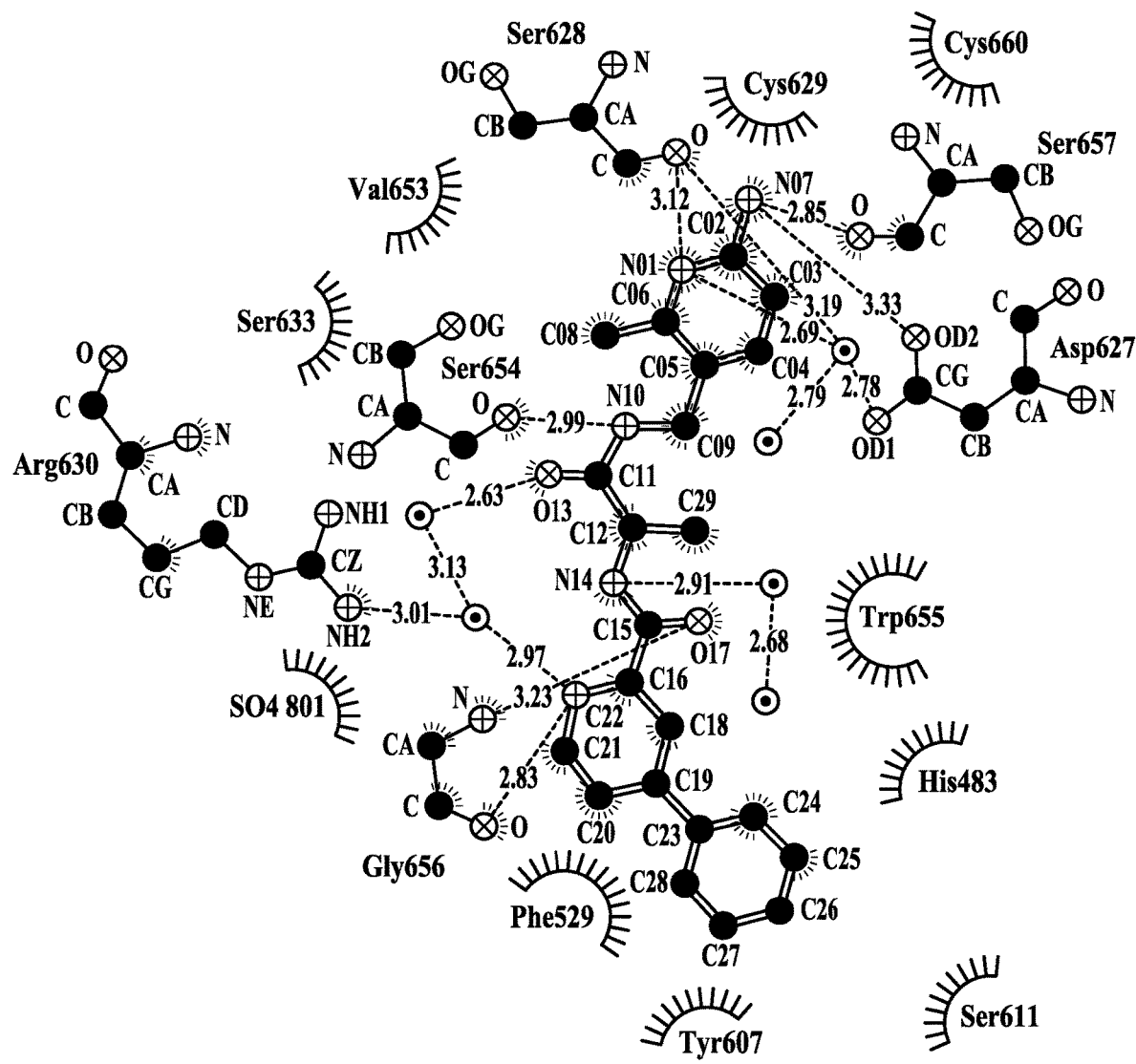
FIG. 31 is a plot showing the binding of compound (1253) to MASP-2 showing hydrogen bonds as computed by LigPlot+ software.

FIG. 31 is an illustration of MASP-2 CCP2-SP amino acid interactions with compound (1253) through hydrogen bonds. As shown therein, six different hydrogen bonds are present between the compound (1253) atoms and the MASP-2 amino acid residue atoms. Amine nitrogen N07 interacts with carboxylate oxygen OD2 of ASP 627 as a hydrogen bond donor and also with a carbonyl oxygen O of SER 657 as a hydrogen bond donor. The pyridine nitrogen N01 may interact with carbonyl oxygen O of SER 628 as a hydrogen bond donor and is in H-bonding distance to a water molecule 16 which it may interact with as an acceptor or donor. Amide nitrogen N10 interacts with carbonyl oxygen O of SER 654 as a hydrogen bond donor. Piperidine nitrogen N22 interacts with carbonyl oxygen O of GLY 656 as a hydrogen bond donor. Carbonyl oxygen O17 interacts with a nitrogen N of GLY 656 as a hydrogen bond acceptor. Six water molecules are shown to be included within the crystal structure in this area of the active site, four of which are involved in hydrogen bonding, either with one or more atoms of the compound (1253), or as a bridging water molecule between particular compound (1253) atoms and MASP-2 amino acid residue atoms.

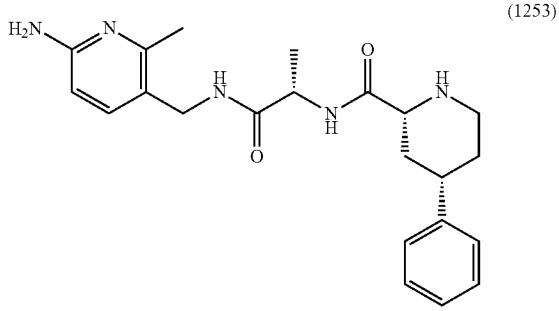 [SMILES: Cc1nc(N)ccc1CNC(=O)[C@H](C)NC(=O)[C@H]1C[C@@H](c2ccccc2)CCN1]

(1253)

Figure 32:
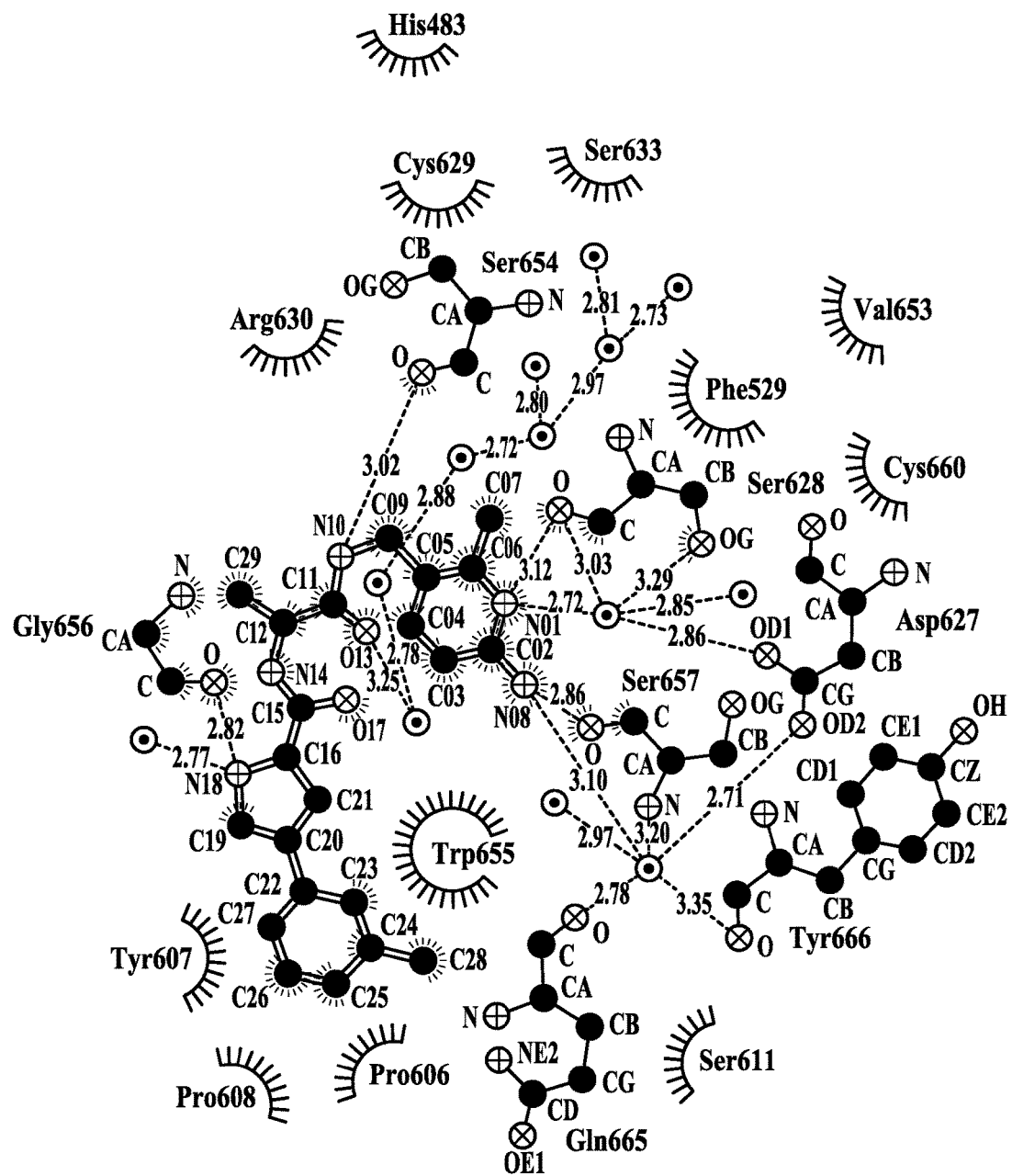
FIG. 32 is a plot showing the binding of compound (1257) to MASP-2 showing hydrogen bonds as computed by LigPlot+ software.

FIG. 32 is an illustration of MASP-2 CCP2-SP amino acid interactions with compound (1257) through hydrogen bonds. As shown therein, four different hydrogen bonds are present between the compound (1257) compound atoms and the MASP-2 amino acid residue atoms. As shown therein, an amine nitrogen N08 interacts with a carbonyl oxygen O of SER 657 as a hydrogen bond donor. The pyridine nitrogen N01 may interact with carbonyl oxygen O of SER 628 as a hydrogen bond donor and is in H-bonding distance to a water molecule which it may interact with as an acceptor or donor. The amide nitrogen N10 interacts with a carbonyl oxygen of SER 654 as a hydrogen bond donor. The pyrrolidine nitrogen N18 interacts with a carbonyl oxygen of GLY 656 as a hydrogen bond donor. In addition, a total of thirteen water molecules are shown in this area of the active site to be included within the crystal structure, four of which are shown to be participating in hydrogen bonding, either with one or more atoms of the compound (1257), or as a bridging water molecule between particular compound (1257) atoms and MASP-2 amino acid residue atoms

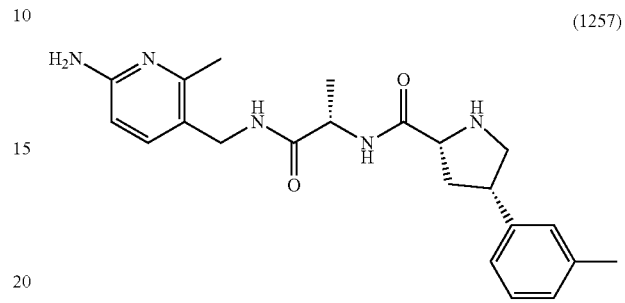

(1257)

Figure 33:
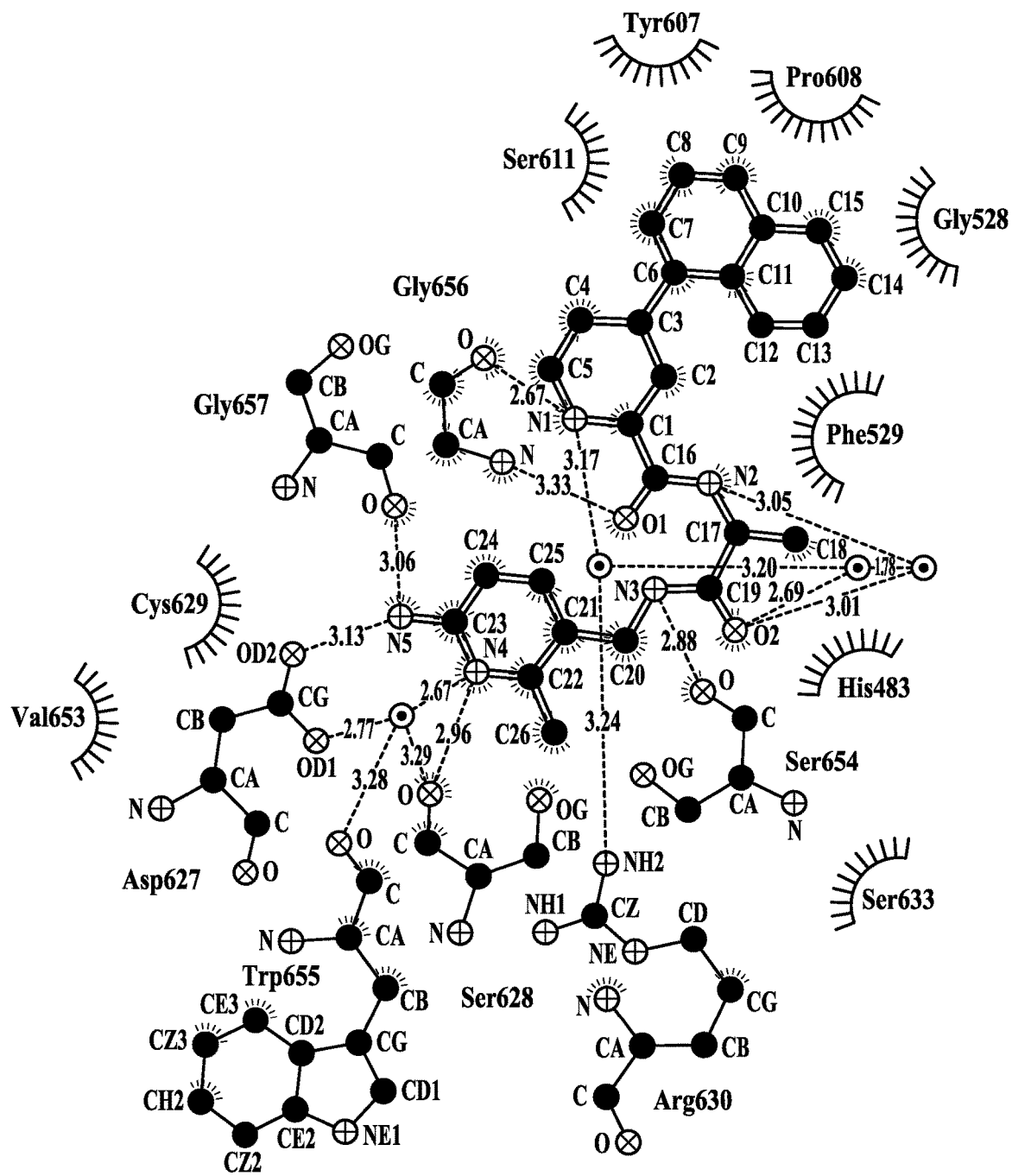
FIG. 33 is a plot showing the binding of compound (1297) to MASP-2 showing hydrogen bonds as computed by LigPlot+ software.

FIG. 33 is an illustration of MASP-2 CCP2-SP amino acid interactions with compound (1297) through hydrogen bonds. As shown therein, six different hydrogen bonds are present between the compound (1297) atoms and the MASP-2 amino acid residue atoms. The amino group nitrogen N5 interacts with a carboxyl group oxygen OD2 of ASP 627 as a hydrogen bond donor and also with a carbonyl group oxygen O of SER 657 as a hydrogen bond donor. The pyridine nitrogen N4 interacts with a carbonyl oxygen O of SER 628 as a hydrogen bond donor. The amide nitrogen N3 interacts with a carbonyl oxygen of SER 654 as a hydrogen bond donor. The piperidine nitrogen N1 interacts with a carbonyl oxygen of GLY 656 as a hydrogen bond donor. The carbonyl oxygen O1 interacts with a nitrogen atom of GLY 656 as a hydrogen bond acceptor. In addition, a total of four water molecules are shown in this area of the active site to be included within the crystal structure, which are shown to be participating in hydrogen bonding, either with one or more atoms of the compound (1297), or as a bridging water molecule between particular compound (1297) atoms and MASP-2 amino acid residue atoms.

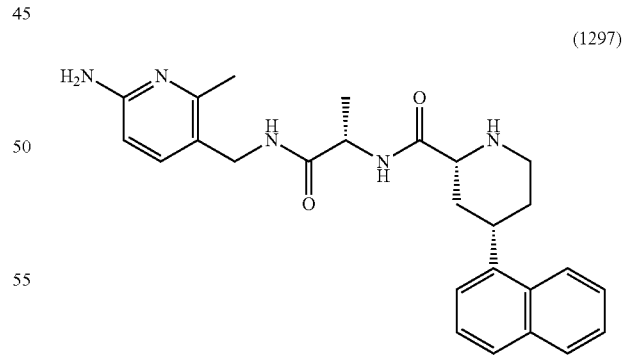

(1297)

Figure 34:
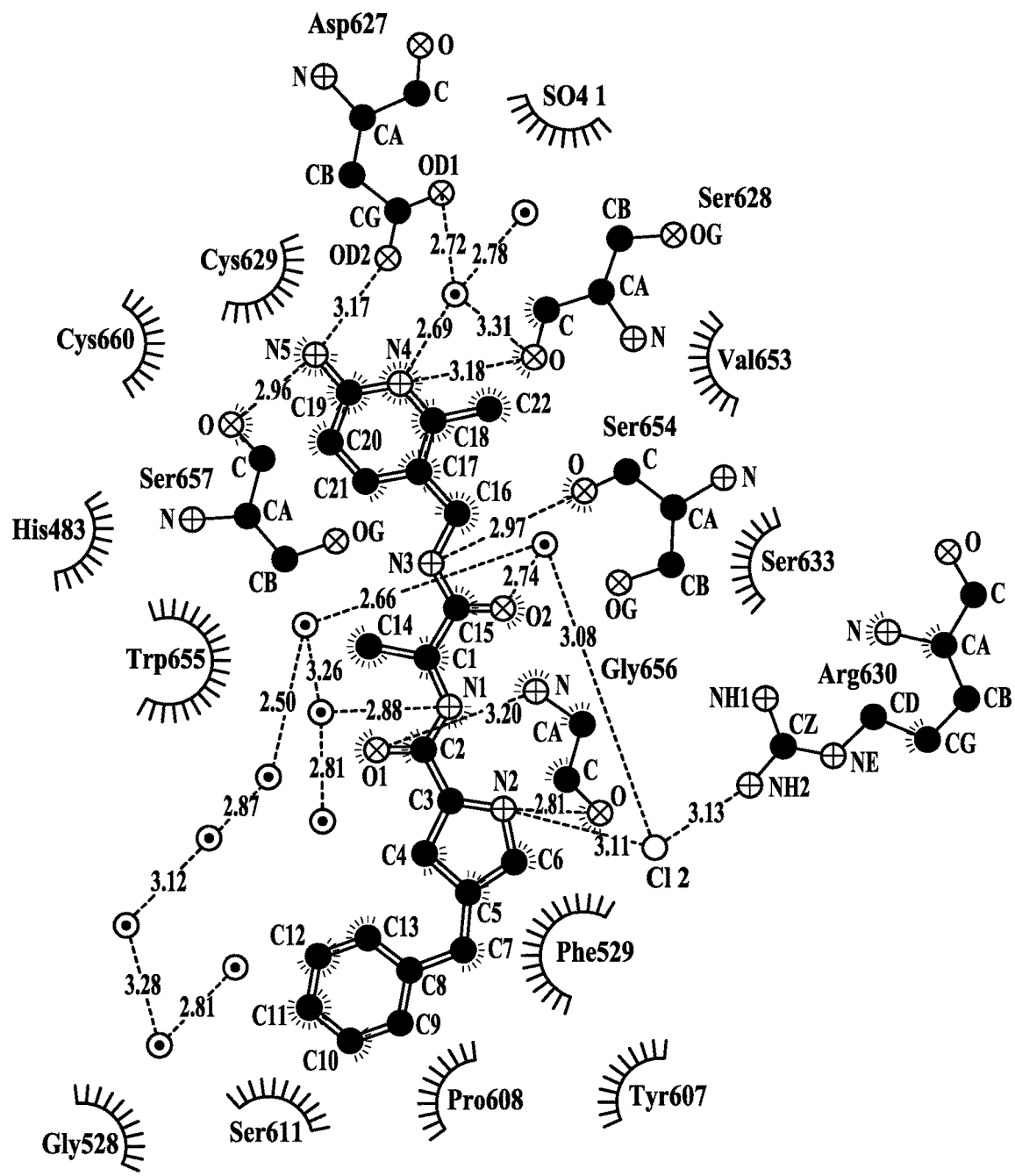
FIG. 34 is a plot showing the binding of compound (1304) to MASP-2 showing hydrogen bonds as computed by LigPlot+ software.

FIG. 34 is an illustration of MASP-2 CCP2-SP amino acid interactions with compound (1304) through hydrogen bonds. As shown therein, six different hydrogen bonds are present between the compound (1304) atoms and the MASP-2 amino acid residue atoms. An amine nitrogen N5 interacts with a carboxyl group oxygen OD2 of ASP 627 as a hydrogen bond donor and also with a carbonyl oxygen O of SER 657 as a hydrogen bond donor. The pyridine nitrogen N4 may interact with carbonyl oxygen O of SER 628 as a hydrogen bond donor and is in H-bonding distance to a water molecule which it may interact with as an acceptor or donor. The amide nitrogen N3 interacts with a carbonyl oxygen of SER 654 as a hydrogen bond donor. The pyrrolidine nitrogen N2 interacts with a carbonyl oxygen of GLY 656 as a hydrogen bond donor. The carbonyl oxygen O1 interacts with a nitrogen atom of GLY 656 as a hydrogen bond acceptor. In addition, a total of eleven water molecules are shown to be included within the crystal structure in this area of the active site, three of which are shown to be participating in hydrogen bonding, either with one or more atoms of the compound (1304), or as a bridging water molecule between particular compound (1304) atoms and MASP-2 amino acid residue atoms. A chloride ion is also present in the crystal structure in this area of the active site, which interacts with the pyrrolidine nitrogen N2 as a hydrogen bond acceptor.

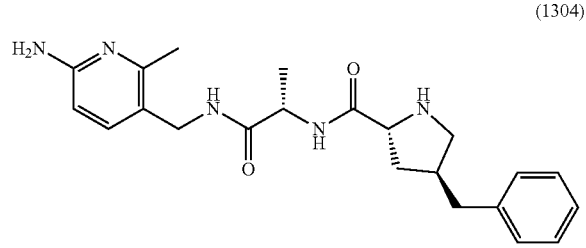 [SMILES: Cc1nc(N)ccc1CNC(=O)[C@H](C)NC(=O)[C@H]1C[C@H](Cc2ccccc2)CN1]

(1304)

Figure 35:
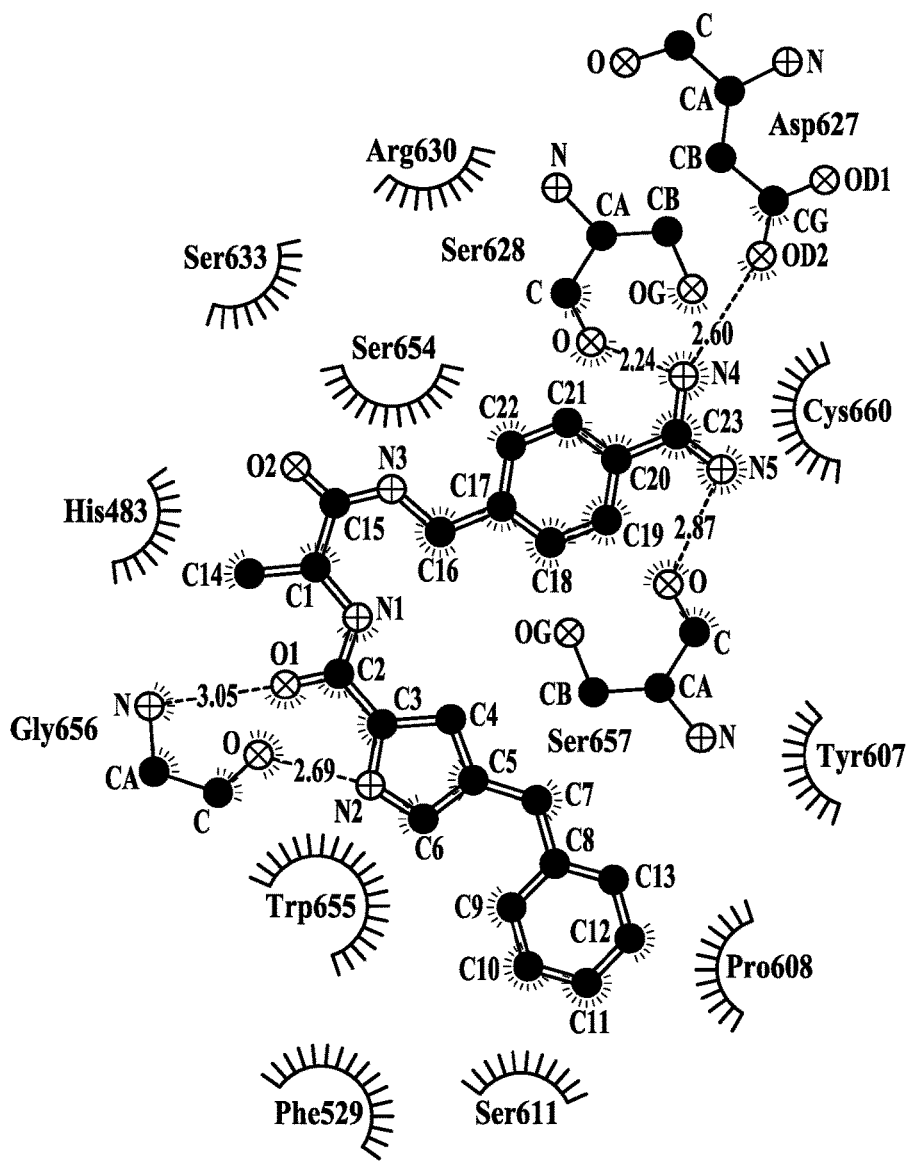
FIG. 35 is a plot showing the binding of compound (1306) to MASP-2 showing hydrogen bonds as computed by LigPlot+ software.

FIG. 35 is an illustration of MASP-2 CCP2-SP amino acid interactions with compound (1306) through hydrogen bonds. As shown therein, five different hydrogen bonds are present between the compound (1306) atoms and the MASP-2 amino acid residue atoms. As shown therein, one of the amidine nitrogens, N5, interacts with a carbonyl oxygen of SER 657 as a hydrogen bond donor and the other amidine nitrogen N4 interacts with a carbonyl group oxygen of SER 628 as a hydrogen bond donor and with a carboxyl group oxygen OD2 of ASP 627 as a hydrogen bond donor. The pyrrolidine nitrogen N2 interacts with a carbonyl oxygen of GLY 656 as a hydrogen bond donor. The carbonyl oxygen O1 interacts with a nitrogen atom of GLY 656 as a hydrogen bond acceptor.

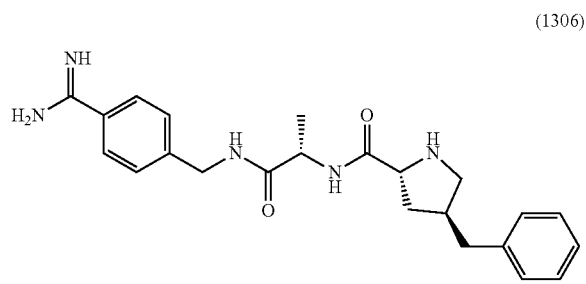 [SMILES: C[C@H](NC(=O)[C@H]1C[C@H](Cc2ccccc2)CN1)C(=O)NCc1ccc(C(=N)N)cc1]

(1306)

Figure 36:
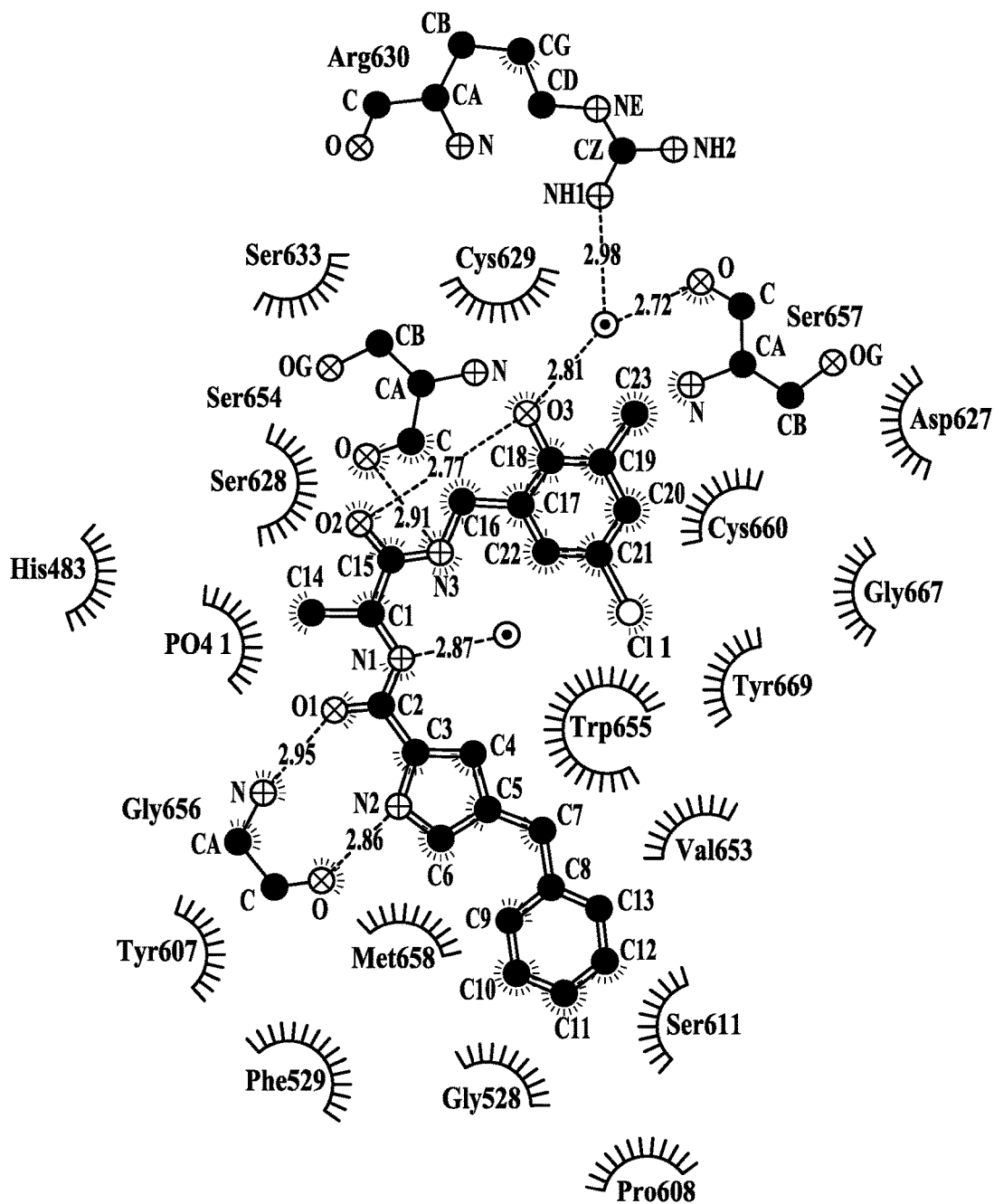
FIG. 36 is a plot showing the binding of compound (1307) to MASP-2 showing hydrogen bonds as computed by LigPlot+ software.

FIG. 36 is an illustration of MASP-2 CCP2-SP amino acid interactions with compound (1307) through hydrogen bonds. As shown therein, three different hydrogen bonds are present between the compound (1307) atoms and the MASP-2 amino acid residue atoms. The amide nitrogen N3 interacts with a carbonyl oxygen of SER 654 as a hydrogen bond donor. The pyrrolidine nitrogen N2 interacts with a carbonyl oxygen of GLY 656 as a hydrogen bond donor. The carbonyl oxygen O1 interacts with a nitrogen atom of GLY 656 as a hydrogen bond acceptor. Two water molecules are shown to be included within the crystal structure in this area of the active site, both of which are shown to be participating in hydrogen bonding, either with one or more atoms of the compound (1307), or as a bridging water molecule between particular compound (1307) atoms and MASP-2 amino acid residue atoms. The phenolic oxygen atom forms an intramolecular H-bond with O2 serving as an H-bond donor and it interacts as a hydrogen bond acceptor with a water molecule that further interacts with a nitrogen atom NH1 of ARG 630 as a hydrogen bond acceptor and a carbonyl oxygen of SER 657 as a hydrogen bond donor.

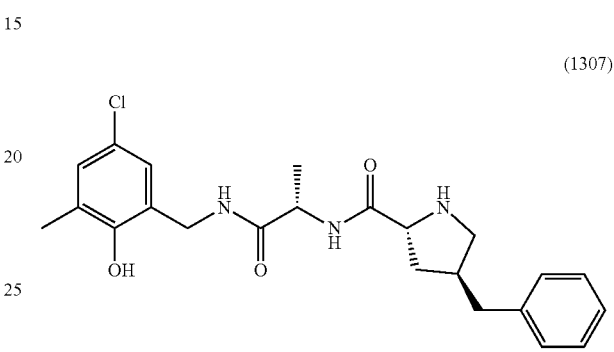

(1307)

Figure 37:
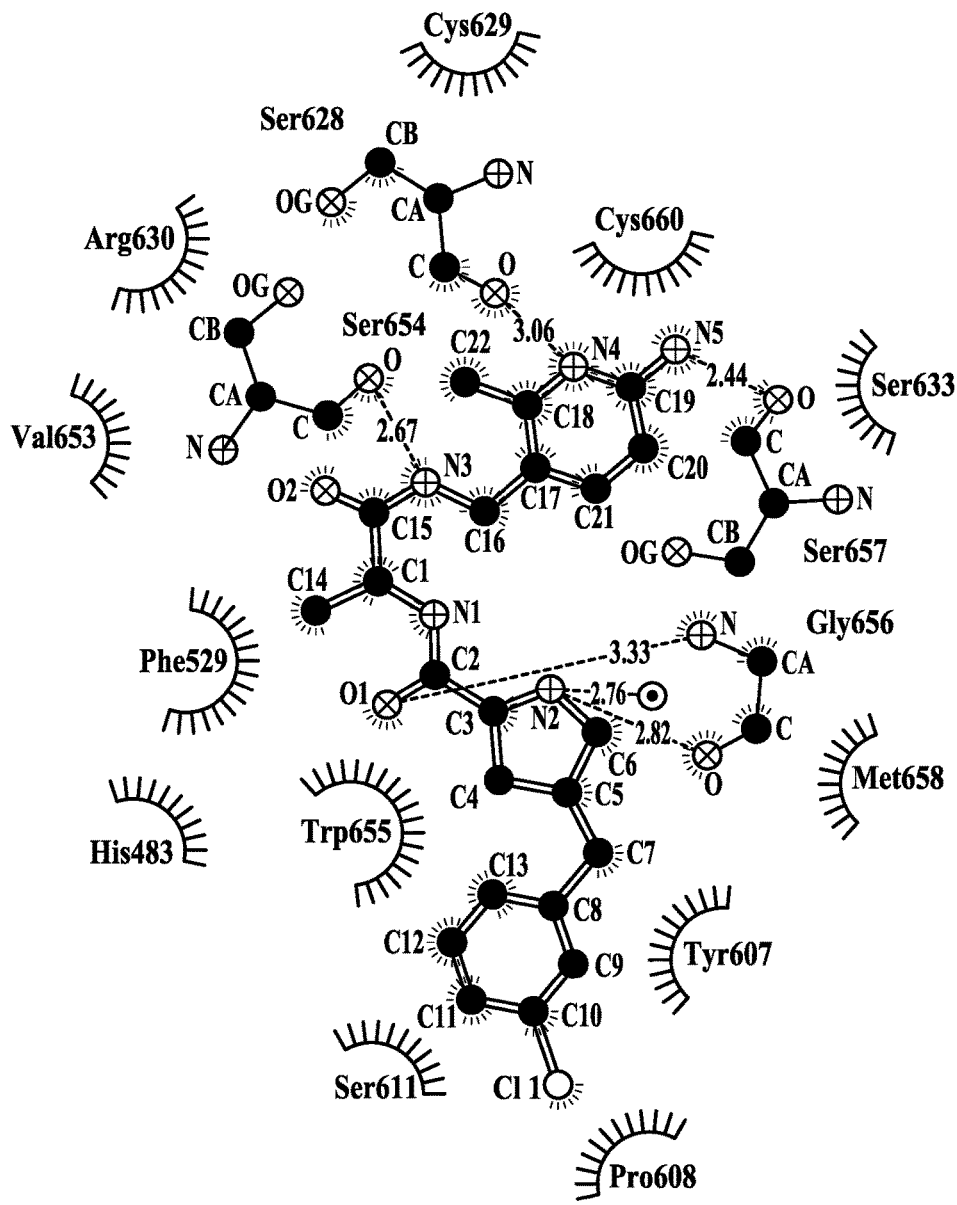
FIG. 37 is a plot showing the binding of compound (1328) to MASP-2 showing hydrogen bonds as computed by LigPlot+ software.

FIG. 37 is an illustration of MASP-2 CCP2-SP amino acid interactions with compound (1328) through hydrogen bonds. As shown therein, five different hydrogen bonds are present between the compound (1328) atoms and the MASP-2 amino acid residue atoms. The amino group nitrogen N5 interacts with a carbonyl oxygen O of SER 657 as a hydrogen bond donor. The pyridine nitrogen N4 interacts with a carbonyl oxygen O of SER 628 as a hydrogen bond donor. The amide nitrogen N3 interacts with a carbonyl oxygen of SER 654 as a hydrogen bond donor. The pyrrolidine nitrogen N2 interacts with a carbonyl oxygen of GLY 656 as a hydrogen bond donor. The carbonyl oxygen O1 interacts with a nitrogen atom of GLY 656 as a hydrogen bond acceptor. In addition, one water molecule is shown in this area of the active site to be included within the crystal structure in this area of the active site, which participates in hydrogen bonding with the pyrrolidine nitrogen (N2) of the compound (1328).

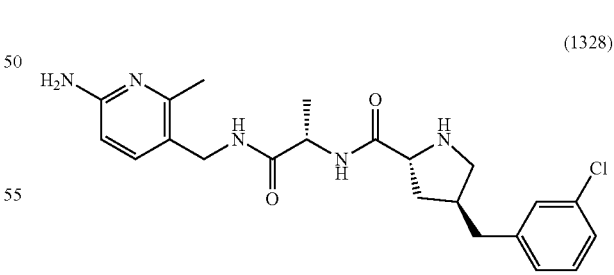

(1328)

Figure 38:
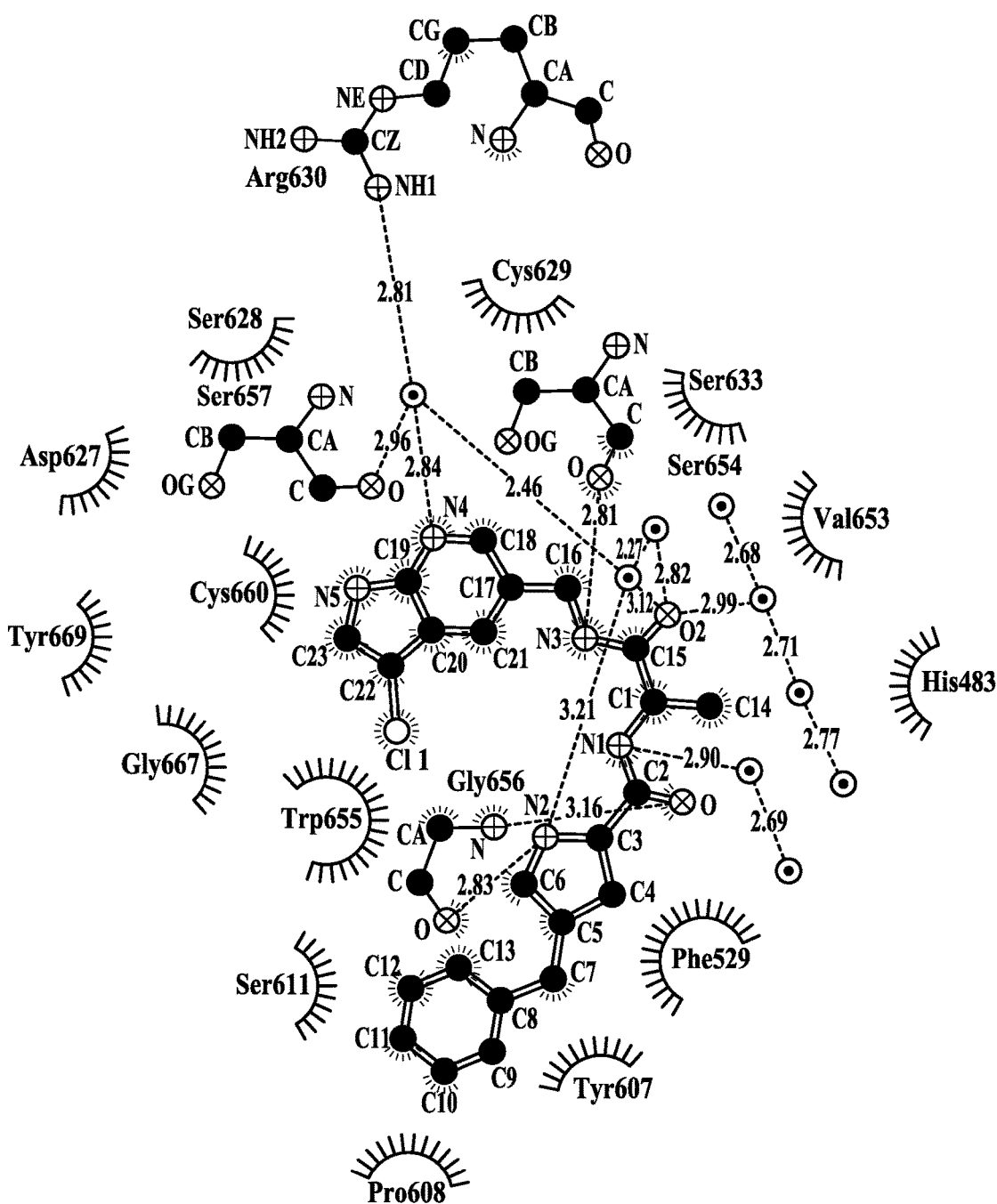
FIG. 38 is a plot showing the binding of compound (1334) to MASP-2 showing hydrogen bonds as computed by LigPlot+ software.

FIG. 38 is an illustration of MASP-2 CCP2-SP amino acid interactions with compound (1334) through hydrogen bonds. As shown therein, three different hydrogen bonds are present between the compound (1334) atoms and the MASP-2 amino acid residue atoms. The amide nitrogen N3 interacts with a carbonyl oxygen of SER 654 as a hydrogen bond donor. The pyrrolidine nitrogen N2 interacts with a carbonyl oxygen of GLY 656 as a hydrogen bond donor. The carbonyl oxygen O1 interacts with a nitrogen atom of GLY 656 as a hydrogen bond acceptor. Nine water molecules are shown to be included within the crystal structure in this area of the active site, five of which are shown to be participating in hydrogen bonding, either with one or more atoms of the compound (1334), or as a bridging water molecule between particular compound (1334) atoms and MASP-2 amino acid residue atoms.

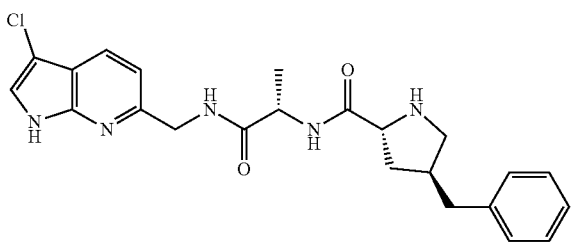

(1334)

Figure 39:
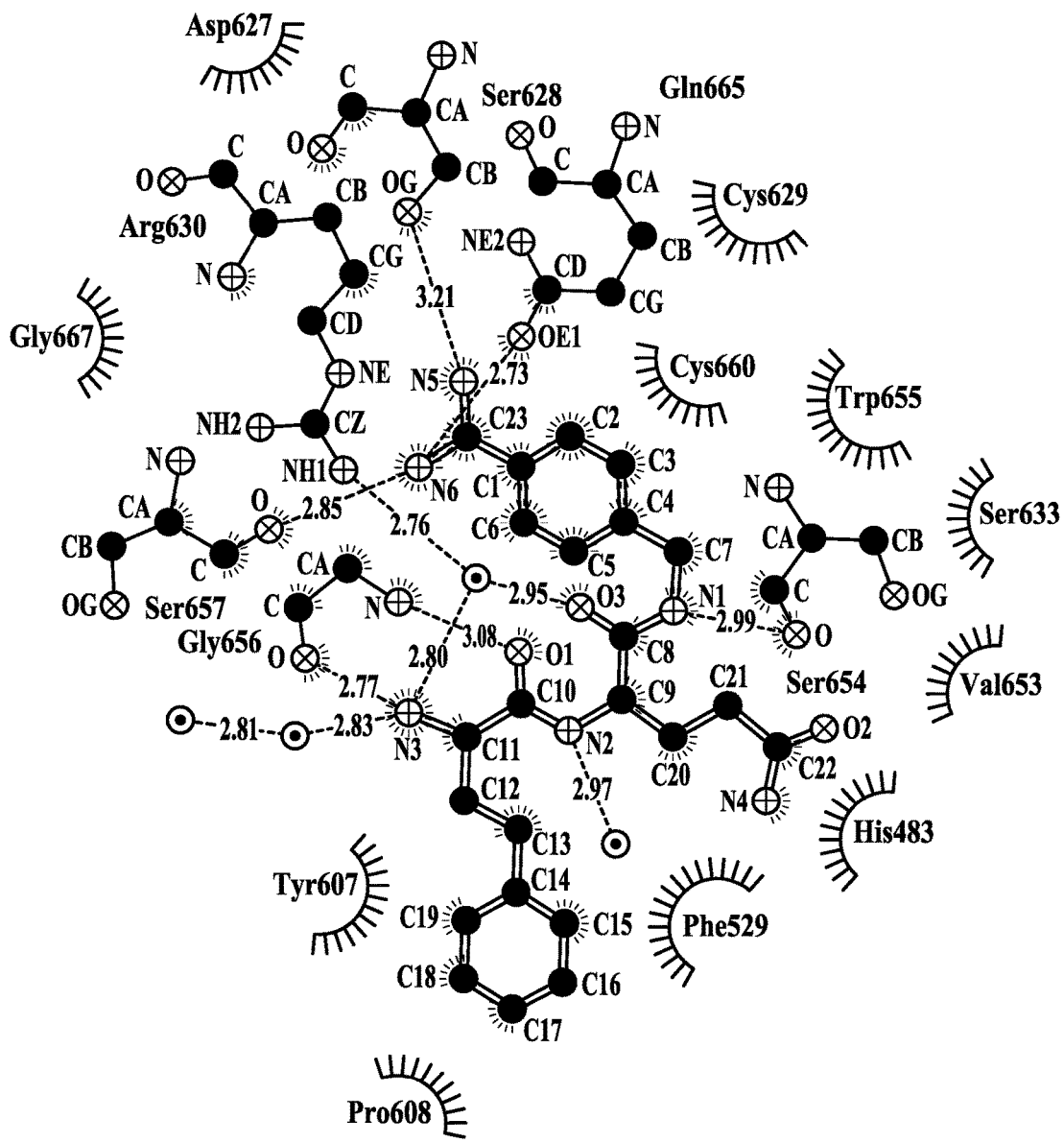
FIG. 39 is a plot showing the binding of compound (1335) to MASP-2 showing hydrogen bonds as computed by LigPlot+ software.

FIG. 39 is an illustration of MASP-2 CCP2-SP amino acid interactions with compound (1335) through hydrogen bonds. As shown therein, six different hydrogen bonds are present between the compound (1335) atoms and the MASP-2 amino acid residue atoms. An amidine nitrogen N6 interacts with a carbonyl oxygen O of SER 657 as a hydrogen bond donor and with an amide group carbonyl oxygen OE1 of GLN 665 as a hydrogen bond donor. The other amidine nitrogen N5 interacts with a hydroxyl group oxygen OG of SER 628 as a hydrogen bond donor. The amide nitrogen N1 interacts with a carbonyl oxygen of SER 654 as a hydrogen bond donor. The amino group nitrogen N3 interacts with a carbonyl oxygen of GLY 656 as a hydrogen bond donor. The carbonyl oxygen O1 interacts with a nitrogen atom of GLY 656 as a hydrogen bond acceptor. In addition, four water molecules are shown in this area of the active site to be included within the crystal structure, three of which are shown to be participating in hydrogen bonding, either with one or more atoms of the compound (1335), or as a bridging water molecule between particular compound (1335) atoms and MASP-2 amino acid residue atoms.

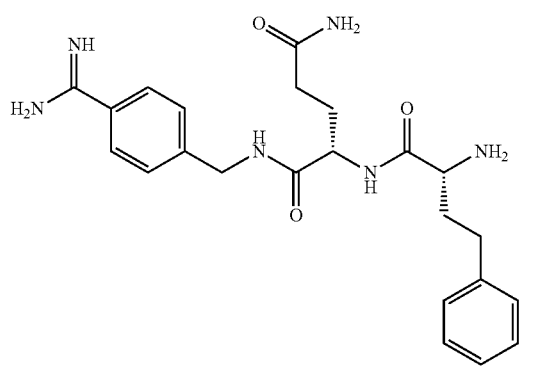

(1335)

Figure 40:
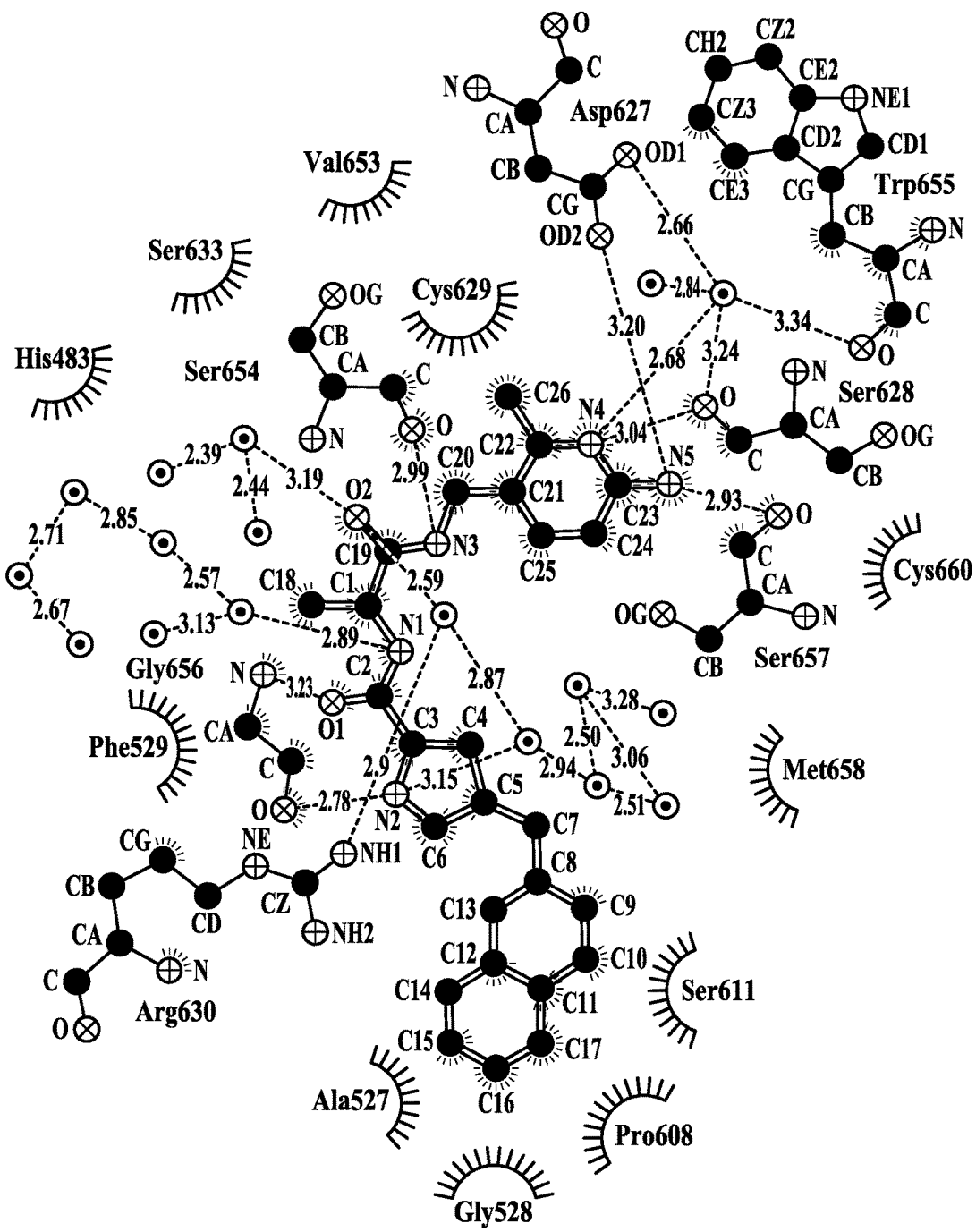
FIG. 40 is a plot showing the binding of compound (1338) to MASP-2 showing hydrogen bonds as computed by LigPlot+ software.

FIG. 40 is an illustration of MASP-2 CCP2-SP amino acid interactions with compound (1338) through hydrogen bonds. As shown therein, six different hydrogen bonds are present between the compound (1338) atoms and the MASP-2 amino acid residue atoms. An amino group nitrogen N5 interacts with a carboxyl group oxygen OD2 of ASP 627 as a hydrogen bond donor and also with a carbonyl oxygen O of SER 657 as a hydrogen bond donor. The pyridine nitrogen N4 may interact with carbonyl oxygen O of SER 628 as a hydrogen bond donor and is in H-bonding distance to a water molecule which it may interact with as an acceptor or donor. The amide nitrogen N3 interacts with a carbonyl oxygen of SER 654 as a hydrogen bond donor. The pyrrolidine nitrogen N2 interacts with a carbonyl oxygen of GLY 656 as a hydrogen bond donor. The carbonyl oxygen O1 interacts with a nitrogen atom of GLY 656 as a hydrogen bond acceptor. In addition, a total of seventeen water molecules are shown to be included within the crystal structure in this area of the active site, three of which are shown to be participating in hydrogen bonding, either with one or more atoms of the compound (1338), or as a bridging water molecule between particular compound 1338 atoms and MASP-2 amino acid residue atoms.

(1338)

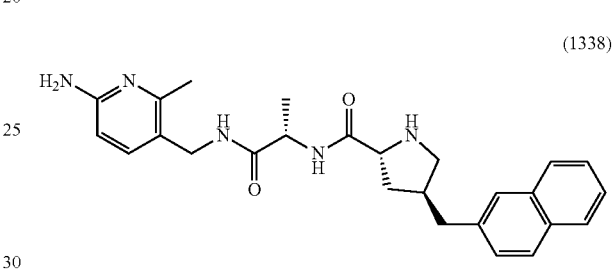

Figure 41:
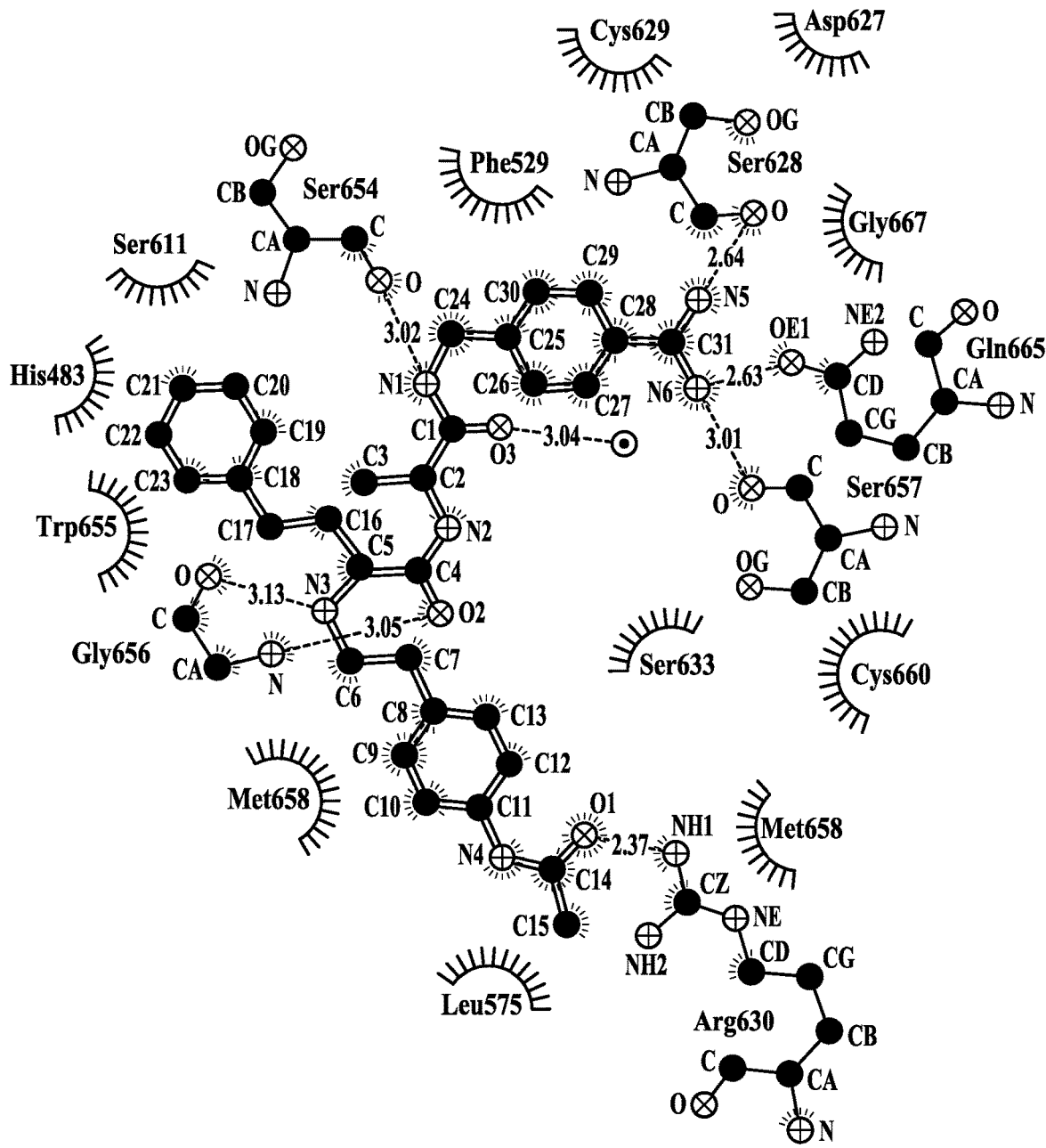
FIG. 41 is a plot showing the binding of compound (1345) to MASP-2 showing hydrogen bonds as computed by LigPlot+ software.

FIG. 41 is an illustration of MASP-2 CCP2-SP amino acid interactions with compound (1345) through hydrogen bonds. As shown therein, seven different hydrogen bonds are present between the compound (1345) atoms and the MASP-2 amino acid residue atoms. An amidine nitrogen N6 interacts with a carbonyl oxygen O of SER 657 as a hydrogen bond donor and with a carbonyl oxygen OE1 of GLN 665 as a hydrogen bond donor. The other amidine nitrogen N5 interacts with a carbonyl oxygen O of SER 628 as a hydrogen bond donor. The amide nitrogen N1 interacts with a carbonyl oxygen O of SER 654 as a hydrogen bond donor. The secondary amine nitrogen N3 interacts with a carbonyl oxygen of GLY 656 as a hydrogen bond donor. The carbonyl oxygen O1 interacts with guanidine nitrogen NH1 of ARG 630 as a hydrogen bond acceptor. The carbonyl oxygen O2 interacts with a nitrogen atom of GLY 656 as a hydrogen bond acceptor. In addition, one water molecule is shown to be included within the crystal structure in this area of the active site, which participates in hydrogen bonding as a hydrogen bond donor with carbonyl oxygen O3 of the compound (1345).

(1345)

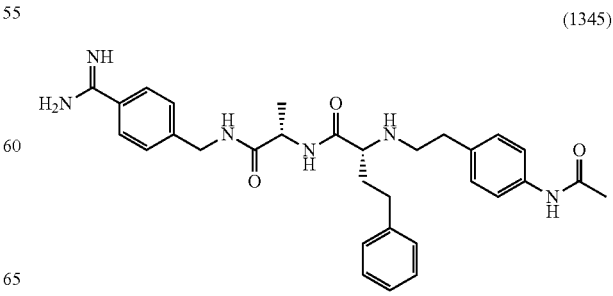

Figure 42:
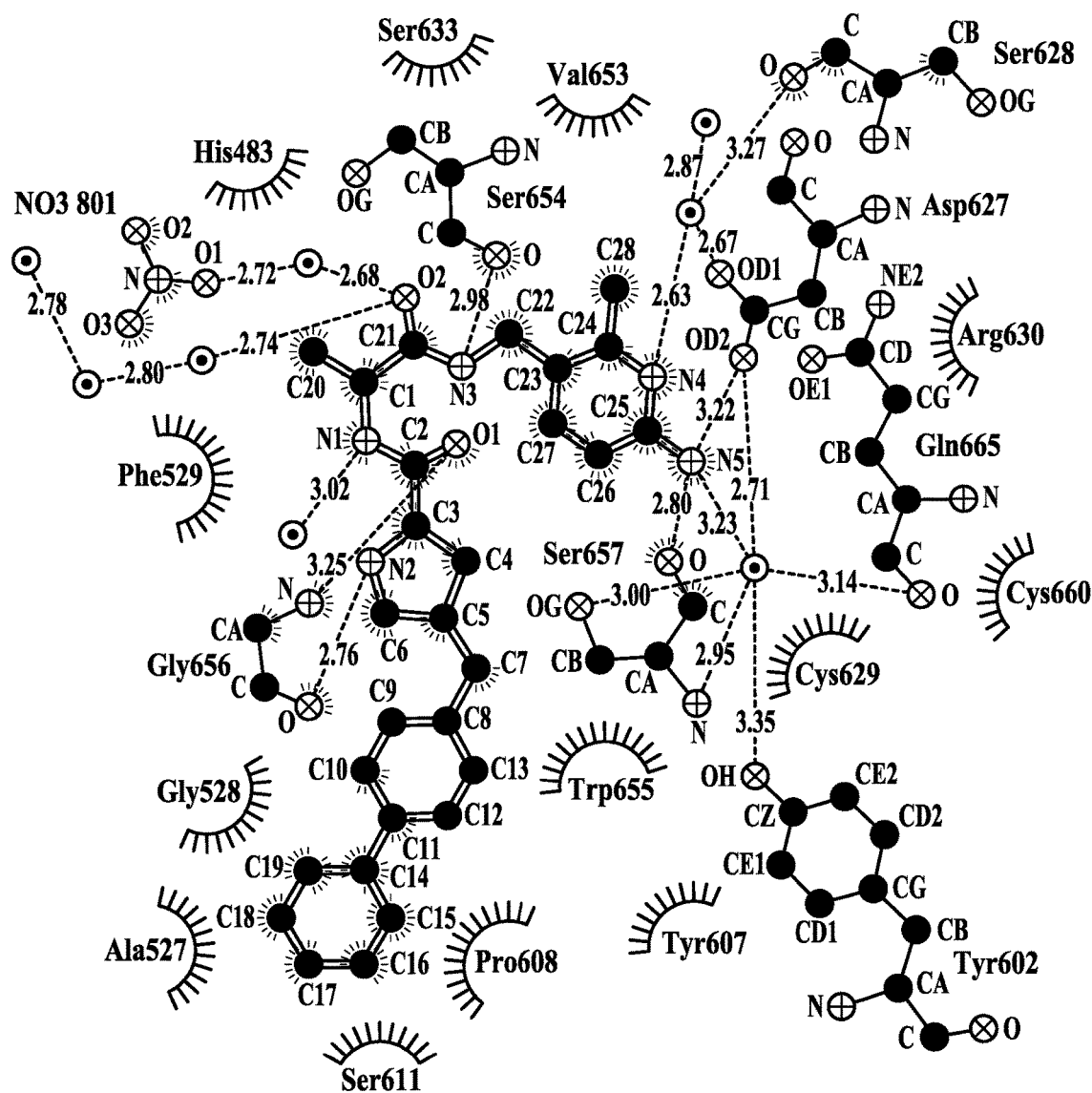
FIG. 42 is a plot showing the binding of compound (1351) to MASP-2 showing hydrogen bonds as computed by LigPlot+ software.

FIG. 42 is an illustration of MASP-2 CCP2-SP amino acid interactions with compound (1351) through hydrogen bonds. As shown therein, five different hydrogen bonds are present between the compound (1351) atoms and the MASP-2 amino acid residue atoms. An amino group nitrogen N5 interacts with a carboxylate group oxygen OD2 of ASP 627 as a hydrogen bond donor and also with a carbonyl oxygen O of SER 657 as a hydrogen bond donor. The amide nitrogen N3 interacts with a carbonyl oxygen of SER 654 as a hydrogen bond donor. The pyrrolidine nitrogen N2 interacts with a carbonyl oxygen of GLY 656 as a hydrogen bond donor. The carbonyl oxygen O1 interacts with a nitrogen atom of GLY 656 as a hydrogen bond acceptor. In addition, a total of eight water molecules are shown to be included within the crystal structure in this area of the active site, five of which are shown to be participating in hydrogen bonding, either with one or more atoms of the compound (1351), or as a bridging water molecule between particular compound (1351) atoms and MASP-2 amino acid residue atoms.

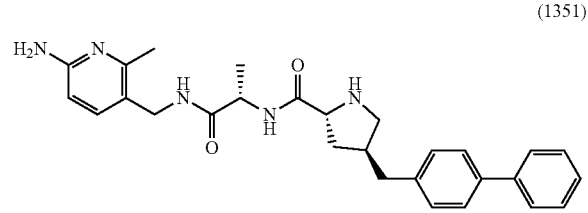 [SMILES: Cc1nc(N)ccc1CNC(=O)[C@H](C)NC(=O)[C@H]1C[C@H](Cc2ccc(-c3ccccc3)cc2)CN1]

(1351)

Figure 43:
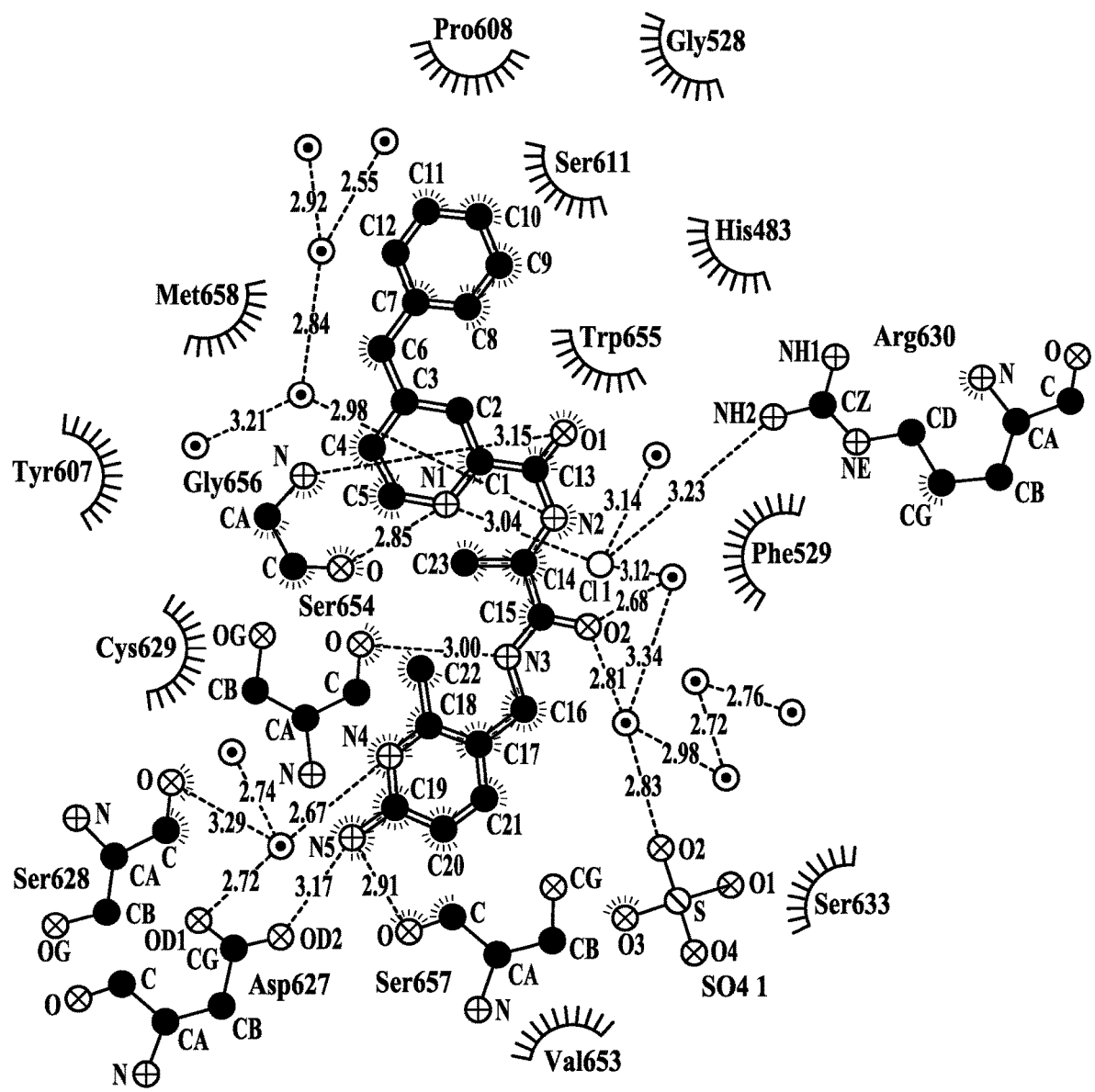
FIG. 43 is a plot showing the binding of compound (1353) to MASP-2 showing hydrogen bonds as computed by LigPlot+ software.

FIG. 43 is an illustration of MASP-2 CCP2-SP amino acid interactions with compound (1353) through hydrogen bonds. As shown therein, five different hydrogen bonds are present between the compound (1353) atoms and the MASP-2 amino acid residue atoms. As shown therein, an amino group nitrogen N5 interacts with a carboxylate group oxygen OD2 of ASP 627 as a hydrogen bond donor and also with a carbonyl oxygen O of SER 657 as a hydrogen bond donor. The amide nitrogen N3 interacts with a carbonyl oxygen of SER 654 as a hydrogen bond donor. The piperidine nitrogen N1 interacts with a carbonyl oxygen of GLY 656 as a hydrogen bond donor. The carbonyl oxygen O1 interacts with a nitrogen atom of GLY 656 as a hydrogen bond acceptor. A total of thirteen water molecules are shown to be included within the crystal structure in this area of the active site, four of which are shown to be participating in hydrogen bonding, either with one or more atoms of the compound (1353), or as a bridging water molecule between particular compound (1353) atoms and MASP-2 amino acid residue atoms. In addition, a chloride ion is present, which interacts with the piperidine nitrogen N1 as a hydrogen bond acceptor. A sulfate ion is also present.

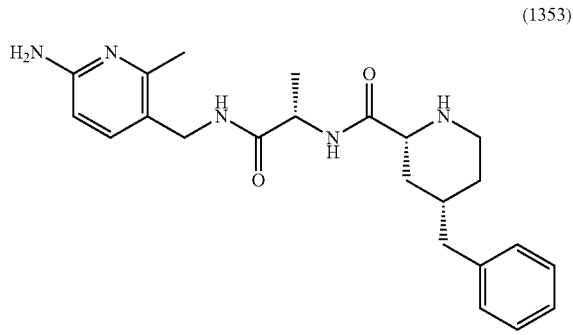 [SMILES: Cc1nc(N)ccc1CNC(=O)[C@H](C)NC(=O)[C@H]1C[C@@H](Cc2ccccc2)CCN1]

(1353)

Figure 44:
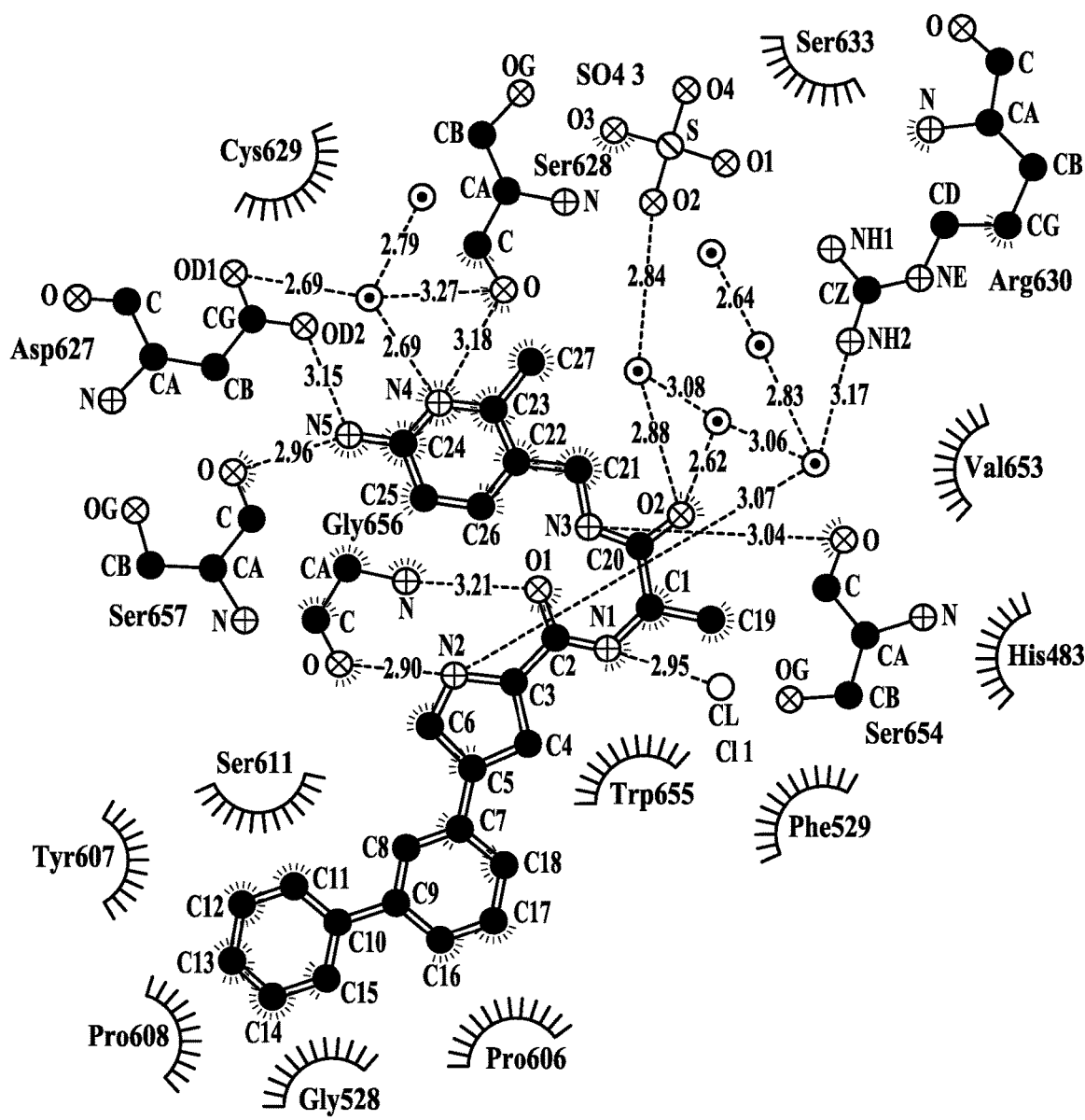
FIG. 44 is a plot showing the binding of compound (1360) to MASP-2 showing hydrogen bonds as computed by LigPlot+ software.

FIG. 44 is an illustration of MASP-2 CCP2-SP amino acid interactions with compound (1360) through hydrogen bonds. As shown therein, six different hydrogen bonds are present between the compound (1360) atoms and the MASP-2 amino acid residue atoms. An amino group nitrogen N5 interacts with a carboxylate group oxygen OD2 of ASP 627 as a hydrogen bond donor and also with a carbonyl oxygen O of SER 657 as a hydrogen bond donor. The amide nitrogen N3 interacts with a carbonyl oxygen of SER 654 as a hydrogen bond donor. The pyridine nitrogen N4 interacts with a carbonyl oxygen of SER 628 as a hydrogen bond donor, and is in H-bonding distance to a water molecule which it may interact with as an acceptor or donor. The pyrrolidine nitrogen N2 interacts with a carbonyl oxygen of GLY 656 as a hydrogen bond donor. The carbonyl oxygen O1 interacts with a nitrogen atom of GLY 656 as a hydrogen bond acceptor. In addition, a total of seven water molecules are shown to be included within the crystal structure in this area of the active site, four of which are shown to be participating in hydrogen bonding, either with one or more atoms of the compound (1360), or as a bridging water molecule between particular compound (1360) atoms and MASP-2 amino acid residue atoms. A sulfate ion and a chloride ion is also present.

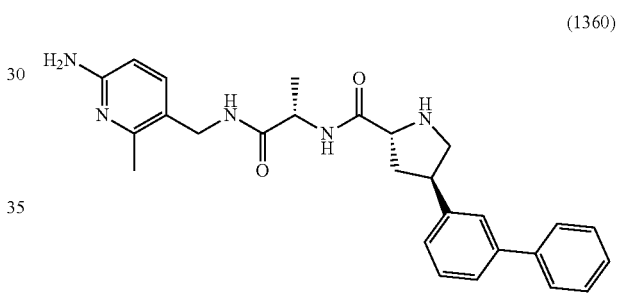

(1360)

Figure 45:
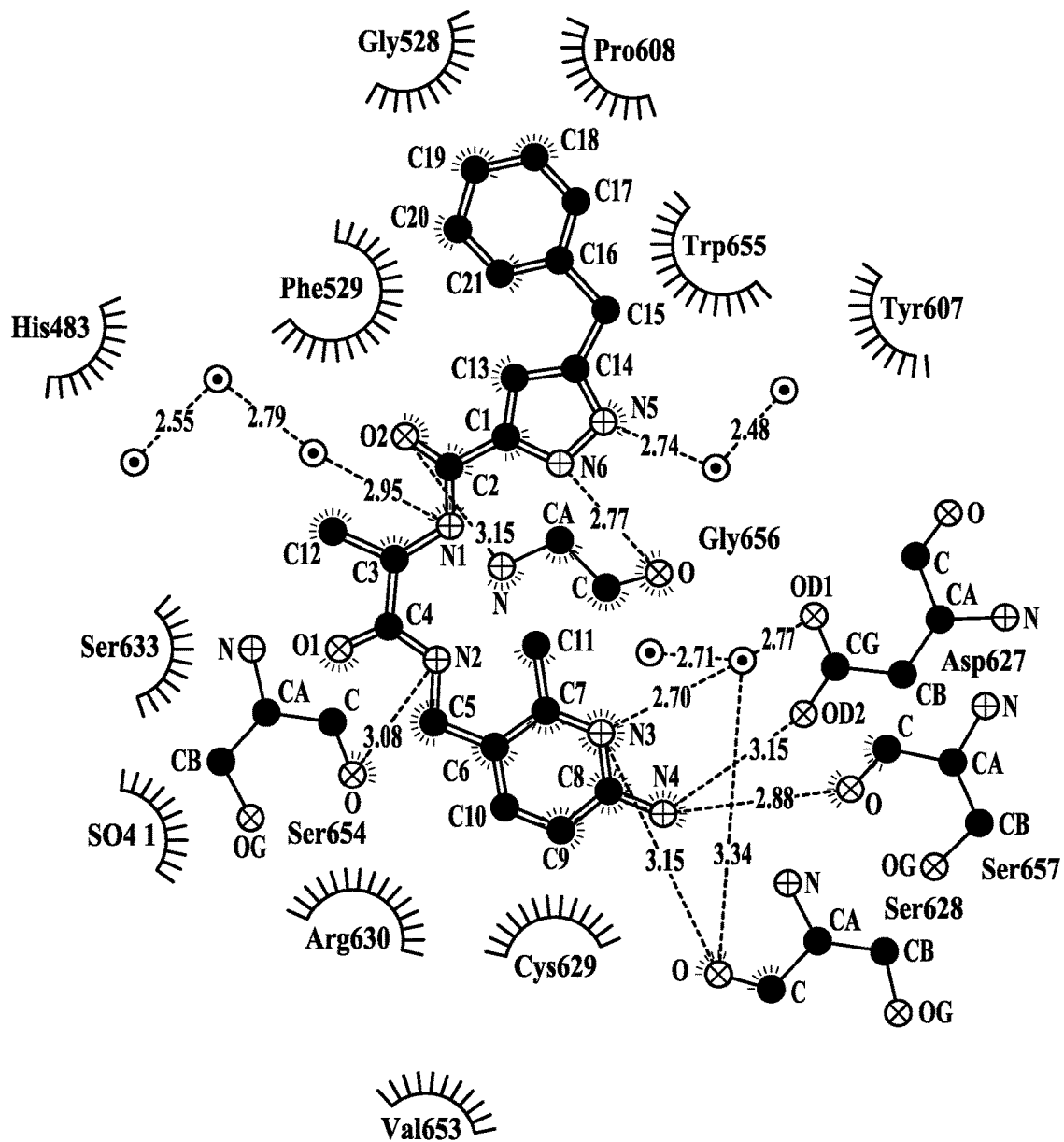
FIG. 45 is a plot showing the binding of compound (1367) to MASP-2 showing hydrogen bonds as computed by LigPlot+ software.

FIG. 45 is an illustration of MASP-2 CCP2-SP amino acid interactions with compound (1367) through hydrogen bonds. As shown therein, six different hydrogen bonds are present between the compound (1367) atoms and the MASP-2 amino acid residue atoms. An amino group nitrogen N4 interacts with a carboxylate group oxygen OD2 of ASP 627 as a hydrogen bond donor and also with a carbonyl oxygen O of SER 657 as a hydrogen bond donor. The pyridine nitrogen N3 may interact with carbonyl oxygen O of SER 628 as a hydrogen bond donor and is in H-bonding distance to a water molecule which it may interact with as an acceptor or donor. The amide nitrogen N2 interacts with a carbonyl oxygen of SER 654 as a hydrogen bond donor. The pyrazole nitrogen N6 interacts with a carbonyl oxygen of GLY 656 as a hydrogen bond donor. The carbonyl oxygen O2 interacts with a nitrogen atom of GLY 656 as a hydrogen bond acceptor. In addition, a total of seven water molecules are to be included within the crystal structure shown in this area of the active site, three of which are shown to be participating in hydrogen bonding, either with one or more atoms of the compound (1367), or as a bridging water molecule between particular compound (1367) atoms and MASP-2 amino acid residue atoms.

(1367)

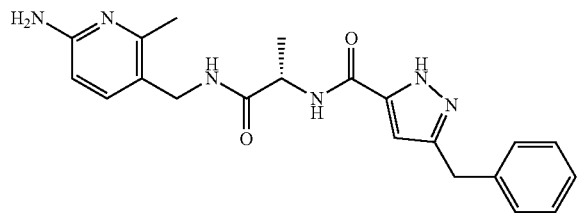

(1371)

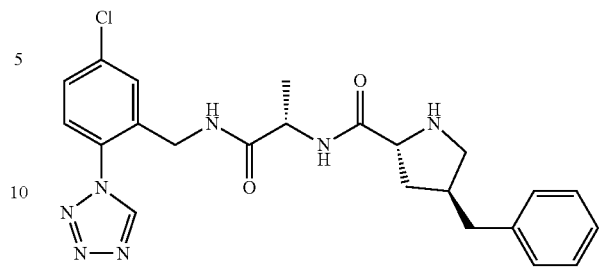

Figure 46:
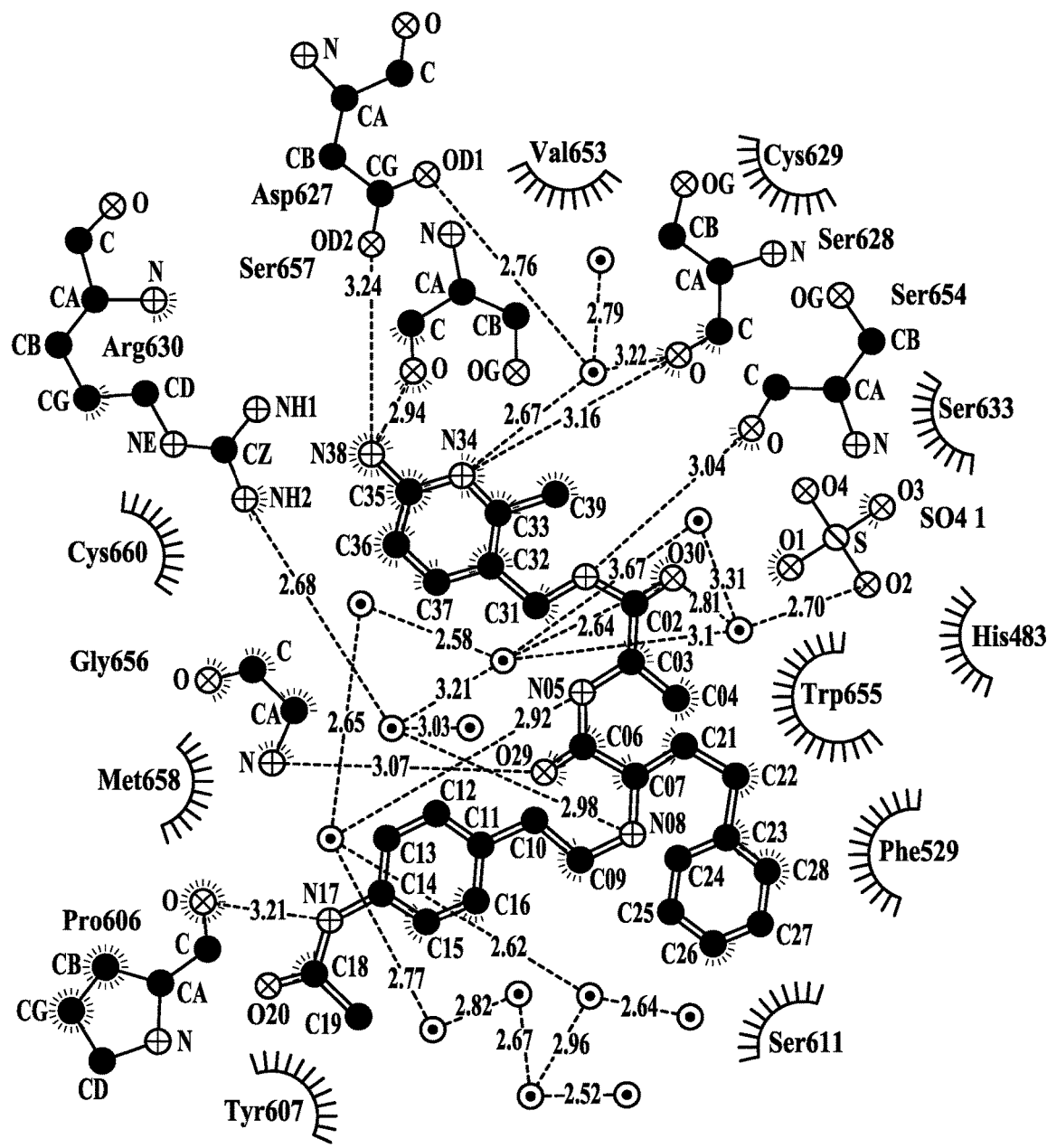
FIG. 46 is a plot showing the binding of compound (1368) to MASP-2 showing hydrogen bonds as computed by LigPlot+ software.

FIG. 46 is an illustration of MASP-2 CCP2-SP amino acid interactions with compound (1368) through hydrogen bonds. As shown therein, six different hydrogen bonds are present between the compound (1368) atoms and the MASP-2 amino acid residue atoms. As shown therein, an amino group nitrogen N38 interacts with a carbonyl oxygen O of SER 657 as a hydrogen bond donor and also with a carboxyl group oxygen OD2 of ASP 627 as a hydrogen bond donor. The pyridine nitrogen N34 may interact with carbonyl oxygen O of SER 628 as a hydrogen bond donor and is in H-bonding distance to a water molecule which it may interact with as an acceptor or donor. The amide nitrogen N01 interacts with a carbonyl oxygen of SER 654 as a hydrogen bond donor. The carbonyl oxygen O29 interacts with a nitrogen of GLY 656 as a hydrogen bond acceptor. The acetamide group nitrogen N17 interacts with a carbonyl oxygen of PRO 606 as a hydrogen bond donor. In addition, a total of fifteen water molecules are shown in this area of the active site to be included within the crystal structure, five of which are shown to be participating in hydrogen bonding, either with one or more atoms of the compound (1368), or as a bridging water molecule between particular compound (1368) atoms and MASP-2 amino acid residue atoms. A sulfate ion is also present.

Figure 48:
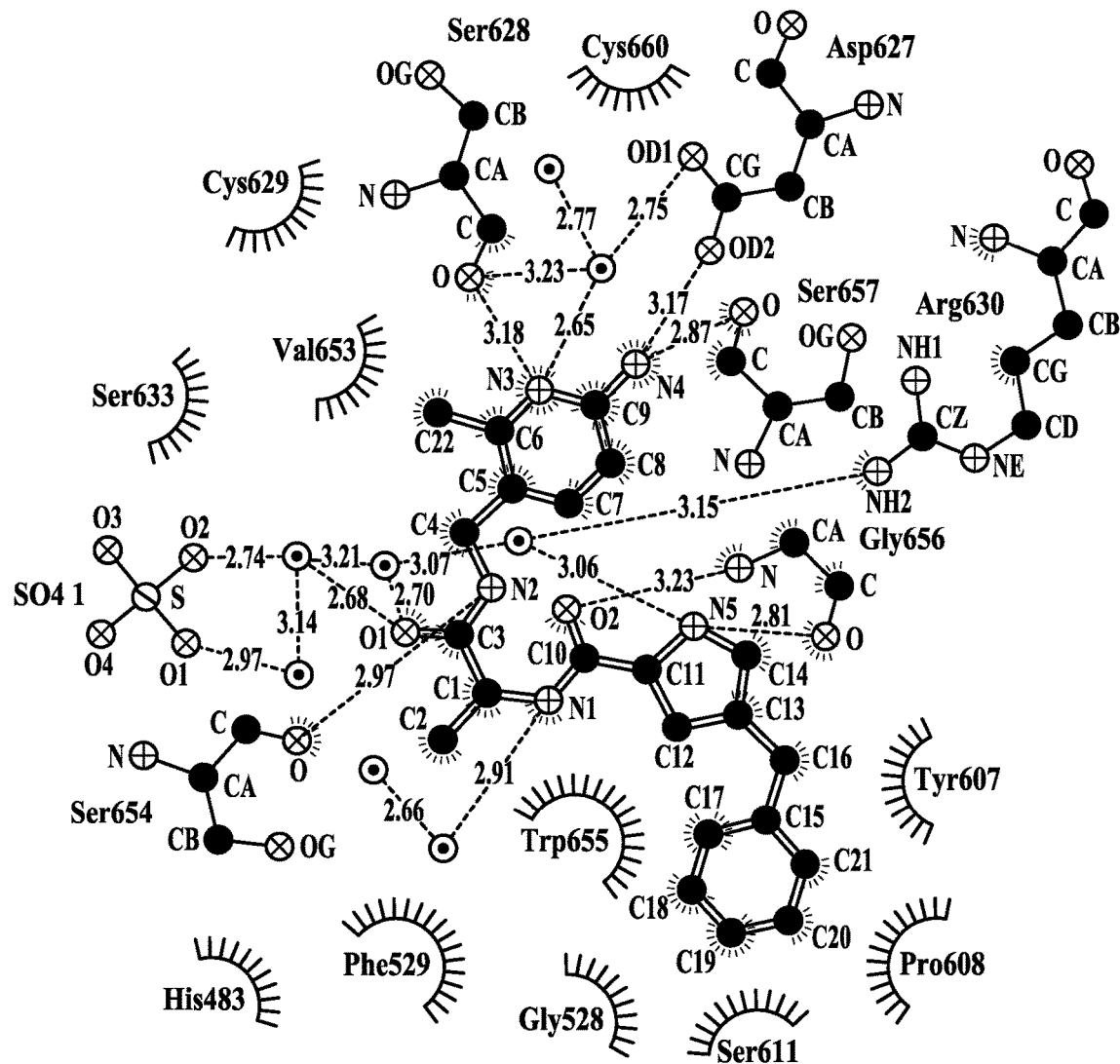
FIG. 48 is a plot showing the binding of compound (1372) to MASP-2 showing hydrogen bonds as computed by LigPlot+ software.

FIG. 48 is an illustration of MASP-2 CCP2-SP amino acid interactions with compound (1372) through hydrogen bonds. As shown therein, eight different hydrogen bonds are present between the compound (1372) atoms and the MASP-2 amino acid residue atoms. An amino group nitrogen N4 interacts with a carbonyl oxygen O of SER 657 as a hydrogen bond donor and with a carboxyl group oxygen atom O2 of ASP 627 as a hydrogen bond donor. The pyridine nitrogen N3 may interact with carbonyl oxygen O of SER 628 as a hydrogen bond donor and is in H-bonding distance to a water molecule which it may interact with as an acceptor or donor. The amide nitrogen N2 interacts with a carbonyl oxygen of SER 654 as a hydrogen bond donor. The pyrrolidine nitrogen N5 interacts with a carbonyl oxygen of GLY 656 as a hydrogen bond donor. The carbonyl oxygen O2 interacts with a nitrogen atom of GLY 656 as a hydrogen bond acceptor. In addition, a total of eight water molecules are shown to be included within the crystal structure in this area of the active site, four of which are shown to be participating in hydrogen bonding, either with one or more atoms of the compound (1372), or as a bridging water molecule between particular compound (1372) atoms and MASP-2 amino acid residue atoms. A sulfate ion is also present.

(1368)

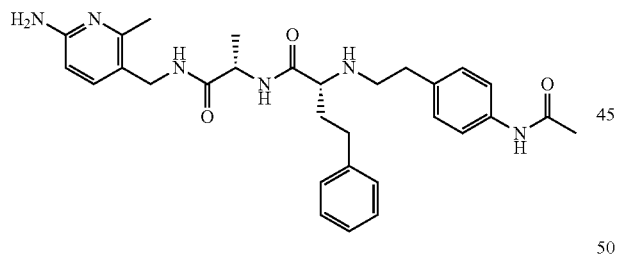

(1372)

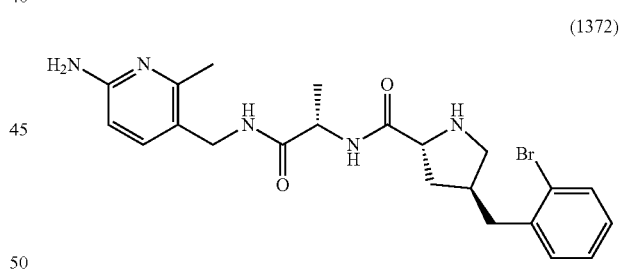

Figure 47:
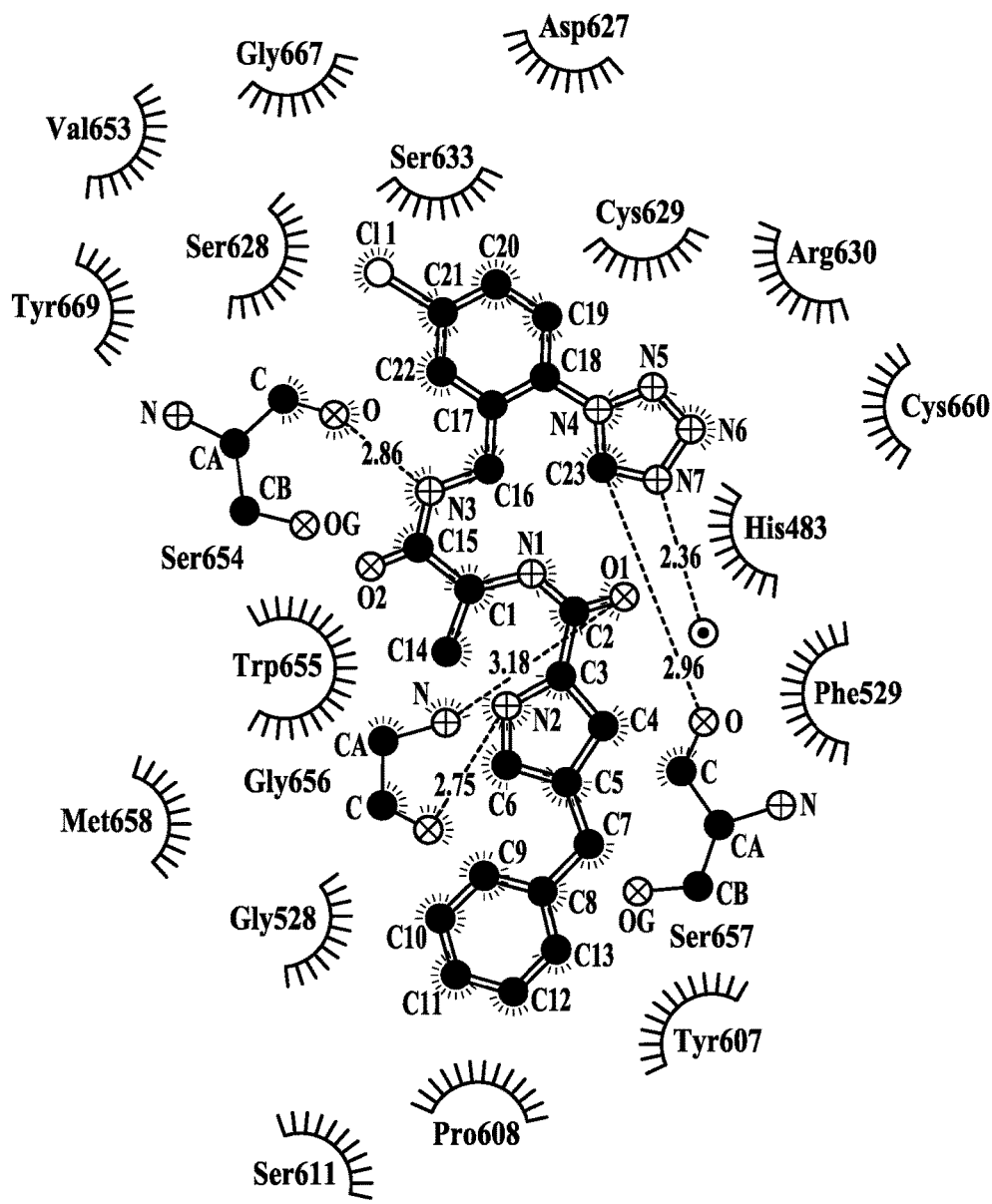
FIG. 47 is a plot showing the binding of compound (1371) to MASP-2 showing hydrogen bonds as computed by LigPlot+ software.

FIG. 47 is an illustration of MASP-2 CCP2-SP amino acid interactions with compound (1371) through hydrogen bonds. As shown therein, four different hydrogen bonds are present between the compound (1371) atoms and the MASP-2 amino acid residue atoms. The amide nitrogen N3 interacts with a carbonyl oxygen of SER 654 as a hydrogen bond donor. The pyrrolidine nitrogen N2 interacts with a carbonyl oxygen of GLY 656 as a hydrogen bond donor. The carbonyl oxygen O1 interacts with a nitrogen atom of GLY 656 as a hydrogen bond acceptor. A tetrazole nitrogen N7 interacts with a water molecule as a hydrogen bond acceptor. C23 interacts with a carbonyl oxygen O of SER657 as a hydrogen bond donor. One water molecule is shown in this area of the active site to be included within the crystal structure, which participates in hydrogen bonding with tetrazole nitrogen N6 of the compound (1371).

Figure 49:
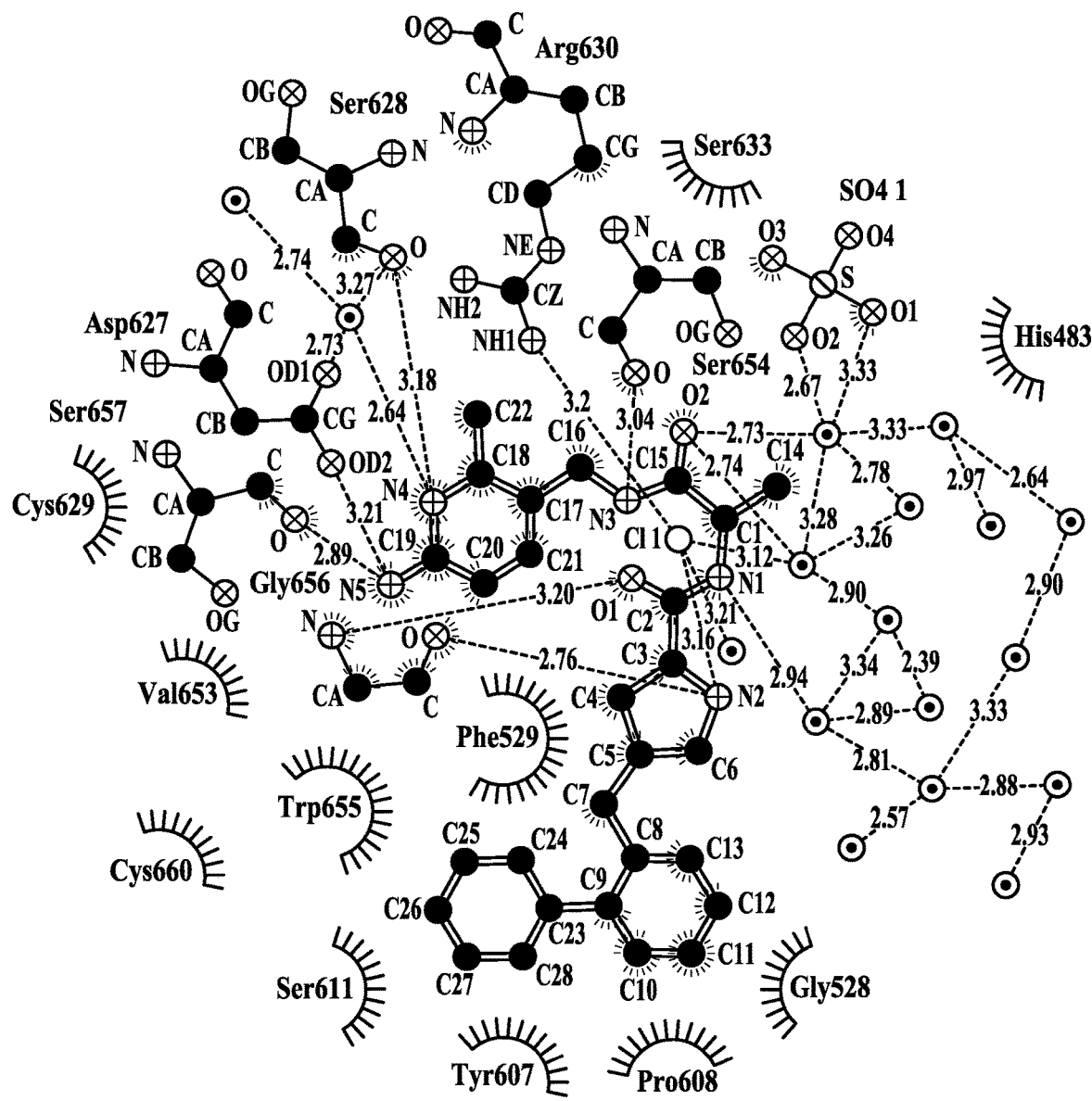
FIG. 49 is a plot showing the binding of compound (1373) to MASP-2 showing hydrogen bonds as computed by LigPlot+ software.

FIG. 49 is an illustration of MASP-2 CCP2-SP amino acid interactions with compound (1373) through hydrogen bonds. As shown therein, six different hydrogen bonds are present between the compound (1373) atoms and the MASP-2 amino acid residue atoms. An amino group nitrogen N5 interacts with a carbonyl oxygen O of SER 657 as a hydrogen bond donor and with a carboxylate group oxygen atom OD2 of ASP 627 as a hydrogen bond donor. The pyridine nitrogen N3 may interact with carbonyl oxygen O of SER 628 as a hydrogen bond donor and is in H-bonding distance to a water molecule which it may interact with as an acceptor or donor. The amide nitrogen N3 interacts with a carbonyl oxygen of SER 654 as a hydrogen bond donor. The pyrrolidine nitrogen N2 interacts with a carbonyl oxygen of GLY 656 as a hydrogen bond donor. The carbonyl oxygen O1 interacts with a nitrogen atom of GLY 656 as a hydrogen bond acceptor. In addition, a total of seventeen water molecules are shown in this area of the active site to be included within the crystal structure, three of which are shown to be participating in hydrogen bonding, either with one or more atoms of the compound (1373), or as a bridging water molecule between particular compound (1373) atoms and MASP-2 amino acid residue atoms. Chloride and sulfate ions are also present.

(1373)

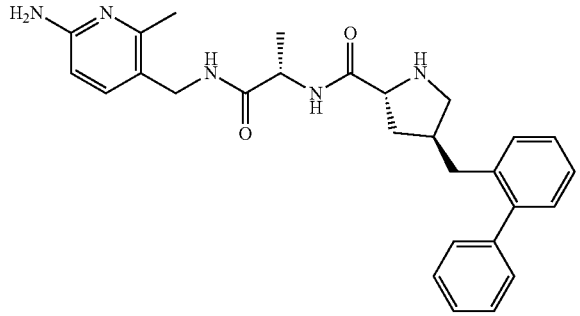

Figure 50:
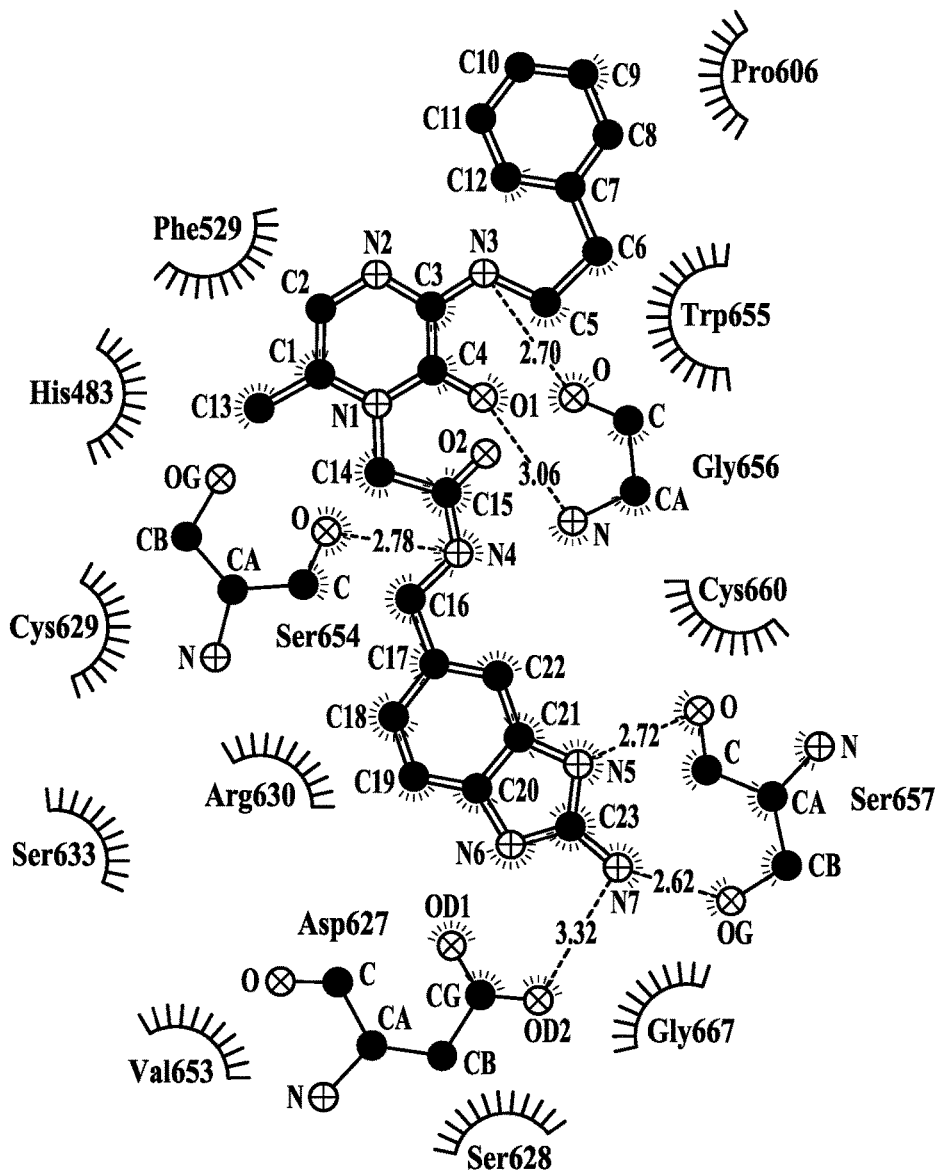
FIG. 50 is a plot showing the binding of compound (1492) to MASP-2 showing hydrogen bonds as computed by LigPlot+ software.

FIG. 50 is an illustration of MASP-2 CCP2-SP amino acid interactions with compound (1492) through hydrogen bonds. As shown therein, seven different hydrogen bonds are present between the compound (1492) atoms and the MASP-2 amino acid residue atoms. A benzimidazole nitrogen N5 interacts with a carbonyl oxygen O of SER 657 as a hydrogen bond donor. A benzimidazole nitrogen ND6 interacts with a carboxyl group oxygen atom OD1 of ASP 627 as a hydrogen bond donor. An amino group nitrogen N7 interacts with a carboxyl group oxygen atom OD2 of ASP 627 as a hydrogen bond donor and also with a carbonyl oxygen atom O of GLN 665 as a hydrogen bond donor. The amide nitrogen N4 interacts with a carbonyl oxygen of SER 654 as a hydrogen bond donor. The nitrogen N3 interacts with a carbonyl oxygen of GLY 656 as a hydrogen bond donor. The carbonyl oxygen O1 interacts with a nitrogen atom of GLY 656 as a hydrogen bond acceptor.

(1492)

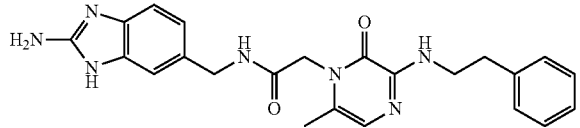

Figure 51:
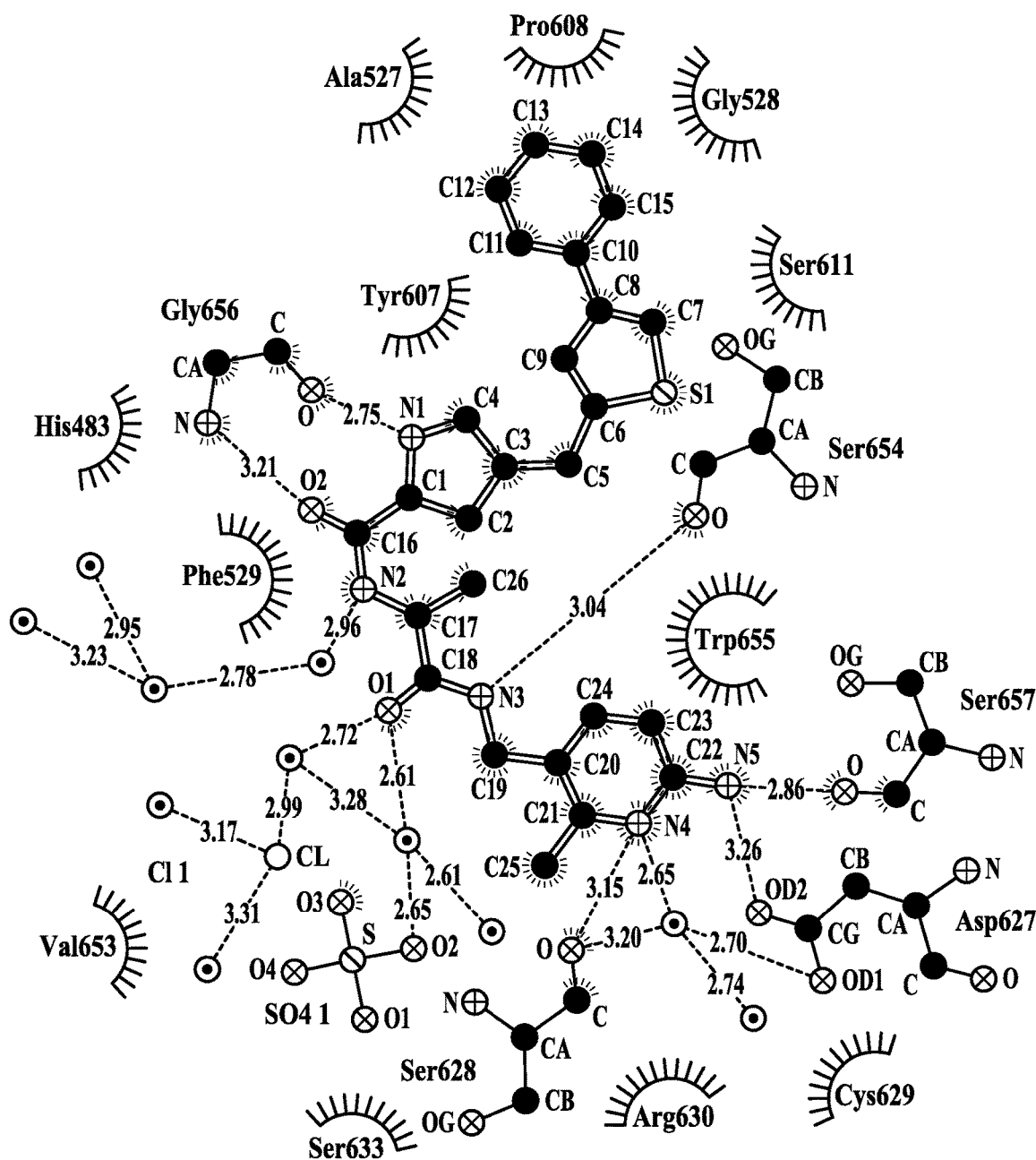
FIG. 51 is a plot showing the binding of compound (1399) to MASP-2 showing hydrogen bonds as computed by LigPlot+ software.

FIG. 51 is an illustration of MASP-2 CCP2-SP amino acid interactions with compound (1399) through hydrogen bonds. As shown therein, six different hydrogen bonds are present between the compound (1399) atoms and the MASP-2 amino acid residue atoms. An amino group nitrogen N5 interacts with a carbonyl oxygen O of SER 657 as a hydrogen bond donor and with a carboxylate oxygen atom OD2 of ASP 627 as a hydrogen bond donor. The pyridine nitrogen N4 may interact with carbonyl oxygen O of SER 628 as a hydrogen bond donor and is in H-bonding distance to a water molecule which it may interact with as an acceptor or donor. The amide nitrogen N3 interacts with a carbonyl oxygen of SER 654 as a hydrogen bond donor. The pyrrolidine nitrogen N1 interacts with a carbonyl oxygen of GLY 656 as a hydrogen bond donor. The carbonyl oxygen O1 interacts with a nitrogen atom of GLY 656 as a hydrogen bond acceptor. In addition, a total of eleven water molecules are shown in this area of the active site to be included within the crystal structure, four of which are shown to be participating in hydrogen bonding, either with one or more atoms of the compound (1399), or as a bridging water molecule between particular compound (1399) atoms and MASP-2 amino acid residue atoms. Chloride and sulfate ions are also present and shown to be interacting in hydrogen bonding with water in the crystal structure.

(1399)

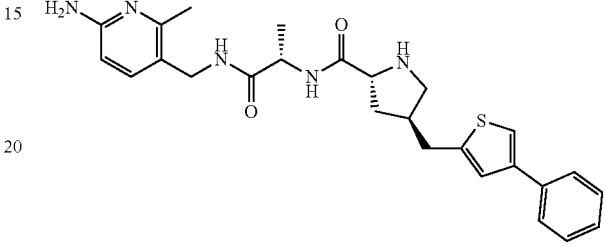

Figure 52:
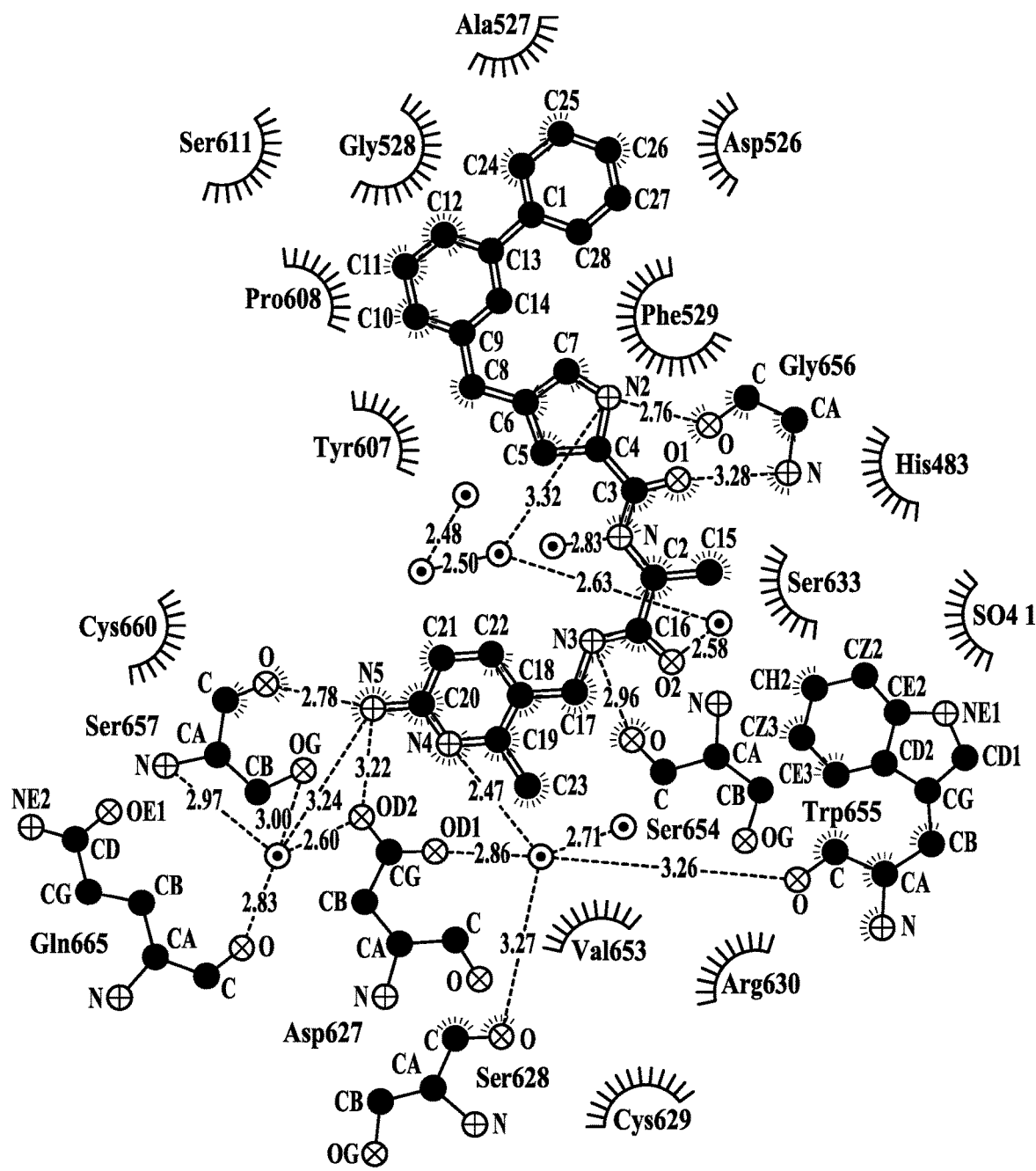
FIG. 52 is a plot showing the binding of compound (1406) to MASP-2 showing hydrogen bonds as computed by LigPlot+ software.

FIG. 52 is an illustration of MASP-2 CCP2-SP amino acid interactions with compound (1406) through hydrogen bonds. As shown therein, five different hydrogen bonds are present between the compound (1406) atoms and the MASP-2 amino acid residue atoms. An amino group nitrogen N5 interacts with a carbonyl oxygen O of SER 657 as a hydrogen bond donor and with a carboxyl group oxygen atom OD2 of ASP 627 as a hydrogen bond donor. The amide nitrogen N3 interacts with a carbonyl oxygen of SER 654 as a hydrogen bond donor. The pyrrolidine nitrogen N2 interacts with a carbonyl oxygen of GLY 656 as a hydrogen bond donor. The carbonyl oxygen O1 interacts with a nitrogen atom of GLY 656 as a hydrogen bond acceptor. In addition, a total of eight water molecules are shown in this area of the active site to be included within the crystal structure, four of which are shown to be participating in hydrogen bonding, either with one or more atoms of the compound (1406), or as a bridging water molecule between particular compound (1406) atoms and MASP-2 amino acid residue atoms.

(1406)

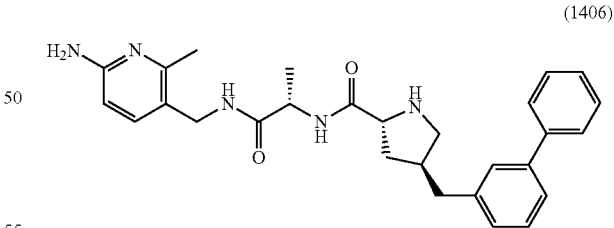

Figure 53:

FIG. 53 is a plot showing the binding of compound (1411) to MASP-2 showing hydrogen bonds as computed by LigPlot+ software.

FIG. 53 is an illustration of MASP-2 CCP2-SP amino acid interactions with compound (1411) through hydrogen bonds. As shown therein, six different hydrogen bonds are present between the compound (1411) atoms and the MASP-2 amino acid residue atoms. An amino group nitrogen N5 interacts with a carbonyl oxygen O of SER 657 as a hydrogen bond donor and with a carboxyl group oxygen atom OD2 of ASP 627 as a hydrogen bond donor. The pyridine nitrogen N4 may interact with carbonyl oxygen O of SER 628 as a hydrogen bond donor and is in H-bonding distance to a water molecule which it may interact with as an acceptor or donor. The amide nitrogen N1 interacts with a carbonyl oxygen of SER 654 as a hydrogen bond donor. The carbonyl oxygen O2 interacts with a nitrogen atom of GLY 656 as a hydrogen bond acceptor. The carboxylate oxygen O3 interacts with a guanidine nitrogen NH2 of ARG 630 as a hydrogen bond acceptor. In addition, a total of four water molecules are shown in this area of the active site to be included within the crystal structure, three of which are shown to be participating in hydrogen bonding, either with one or more atoms of the compound (1411), or as a bridging water molecule between particular compound (1411) atoms and MASP-2 amino acid residue atoms.

(1411)

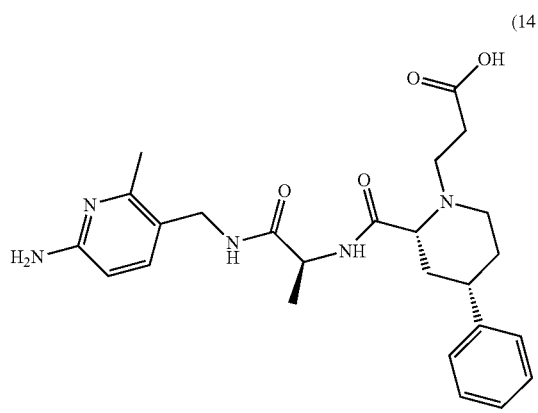

Figure 54:
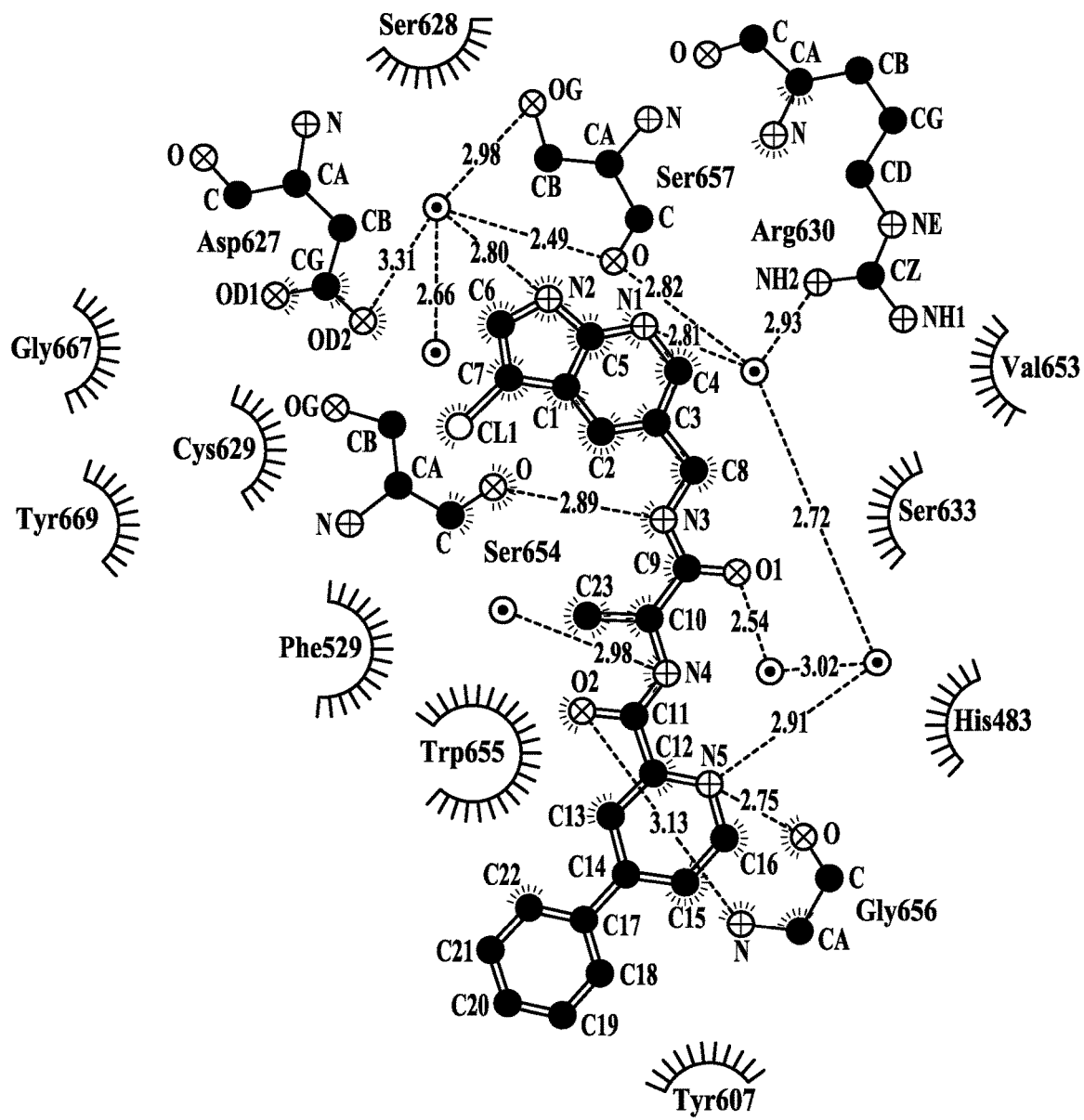
FIG. 54 is a plot showing the binding of compound (1433) to MASP-2 showing hydrogen bonds as computed by LigPlot+ software.

FIG. 54 is an illustration of MASP-2 CCP2-SP amino acid interactions with compound (1433) through hydrogen bonds. As shown therein, three different hydrogen bonds are present between the compound (1433) atoms and the MASP-2 amino acid residue atoms. Amide nitrogen N3 interacts with carbonyl oxygen O of SER 654 as a hydrogen bond donor. Piperidine nitrogen N5 interacts with carbonyl oxygen O of GLY 656 as a hydrogen bond donor. Carbonyl oxygen O2 interacts with a nitrogen N of GLY 656 as a hydrogen bond acceptor. Six water molecules are shown to be included within the crystal structure in this area of the active site, four of which are involved in hydrogen bonding, either with one or more atoms of the compound (1433), or as a bridging water molecule between particular compound (1433) atoms and MASP-2 amino acid residue atoms.

(1433)

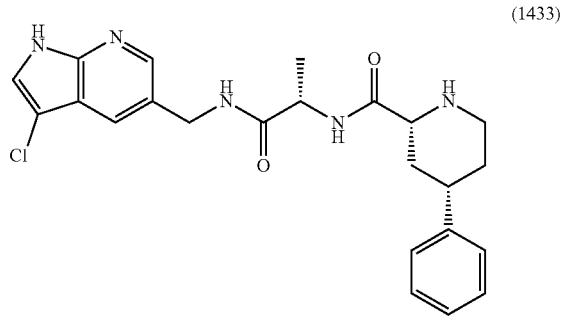 [SMILES: C[C@H](NC(=O)[C@H]1C[C@@H](c2ccccc2)CCN1)C(=O)NCc1cnc2[nH]cc(Cl)c2c1]

Figure 55:
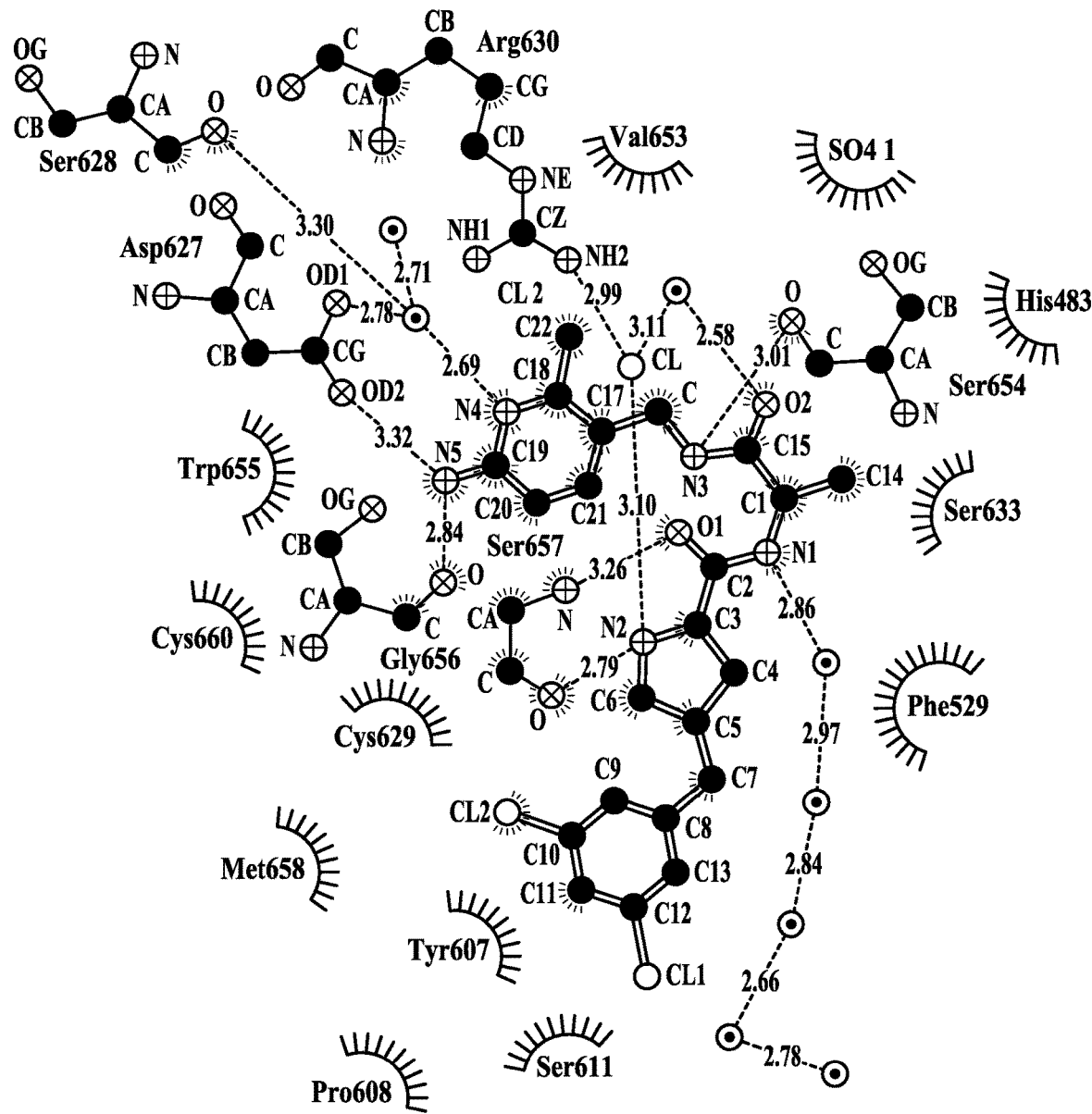
FIG. 55 is a plot showing the binding of compound (1435) to MASP-2 showing hydrogen bonds as computed by LigPlot+ software.

FIG. 55 is an illustration of MASP-2 CCP2-SP amino acid interactions with compound (1435) through hydrogen bonds. As shown therein, five different hydrogen bonds are present between the compound (1435) atoms and the MASP-2 amino acid residue atoms. The amino group nitrogen N5 interacts with carboxylate oxygen OD2 of ASP 627 as a hydrogen bond donor and with carbonyl oxygen O of SER 657 as a hydrogen bond donor. The amide nitrogen N3 interacts with a carbonyl oxygen of SER 654 as a hydrogen bond donor. The pyrrolidine nitrogen N2 interacts with a carbonyl oxygen of GLY 656 as a hydrogen bond donor. The carbonyl oxygen O1 interacts with a nitrogen atom of GLY 656 as a hydrogen bond acceptor. In addition, eight water molecules are shown in this area of the active site to be included within the crystal structure in this area of the active site, three of which are involved in hydrogen bonding, either with one or more atoms of the compound (1435), or as a bridging water molecule between particular compound (1435) atoms and MASP-2 amino acid residue atoms. A chloride ion is also present, which may participate in hydrogen bonding with the pyrrolidine nitrogen N2.

(1435)

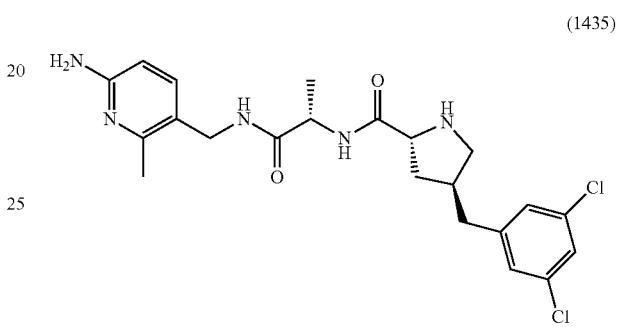

Figure 56:
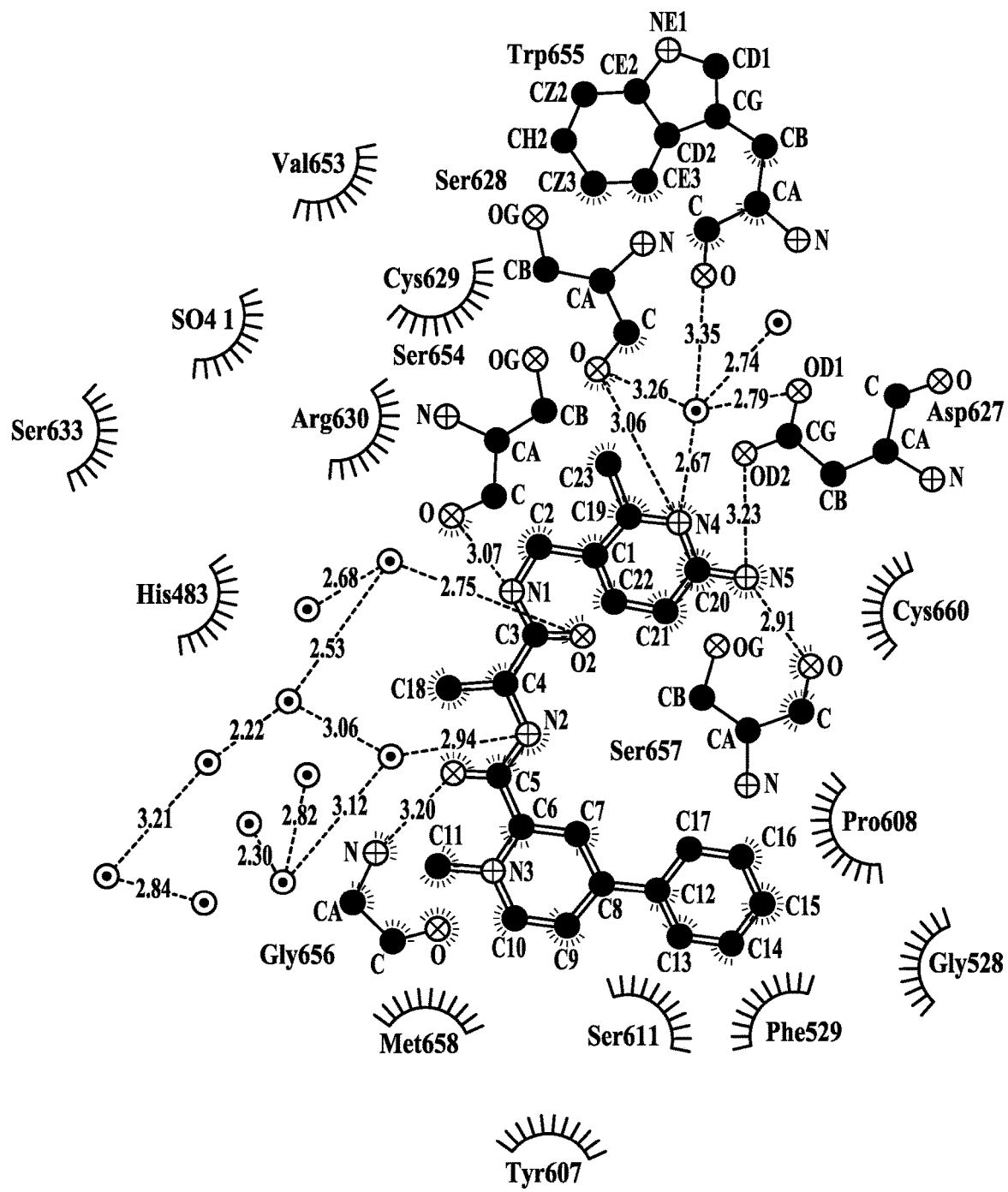
FIG. 56 is a plot showing the binding of compound (1441) to MASP-2 showing hydrogen bonds as computed by LigPlot+ software.

FIG. 56 is an illustration of MASP-2 CCP2-SP amino acid interactions with compound (1441) through hydrogen bonds. As shown therein, five different hydrogen bonds are present between the compound (1441) atoms and the MASP-2 amino acid residue atoms. An amino group nitrogen N5 interacts with a carbonyl oxygen O of SER 657 as a hydrogen bond donor and with a carboxyl group oxygen atom OD2 of ASP 627 as a hydrogen bond donor. The pyridine nitrogen N4 may interact with carbonyl oxygen O of SER 628 as a hydrogen bond donor and is in H-bonding distance to a water molecule which it may interact with as an acceptor or donor. The amide nitrogen N1 interacts with a carbonyl oxygen of SER 654 as a hydrogen bond donor. The carbonyl oxygen O1 interacts with a nitrogen atom of GLY 656 as a hydrogen bond acceptor. In addition, a total of twelve water molecules are shown in this area of the active site to be included within the crystal structure, three of which are shown to be participating in hydrogen bonding, either with one or more atoms of the compound (1441), or as a bridging water molecule between particular compound (1441) atoms and MASP-2 amino acid residue atoms.

(1441)

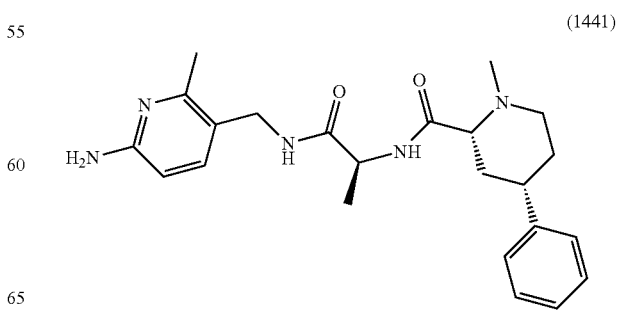

FIG. 57 is an illustration of MASP-2 CCP2-SP amino acid interactions with compound (1450) through hydrogen bonds. As shown therein, three different hydrogen bonds are present between the compound (1450) atoms and the MASP-2 amino acid residue atoms. Amide nitrogen N3 interacts with carbonyl oxygen O of SER 654 as a hydrogen bond donor. Pyrrolidine nitrogen N2 interacts with carbonyl oxygen O of GLY 656 as a hydrogen bond donor. Carbonyl oxygen O1 interacts with a nitrogen N of GLY 656 as a hydrogen bond acceptor. Nine water molecules are shown to be included within the crystal structure in this area of the active site, three of which are involved in hydrogen bonding, either with one or more atoms of the compound (1450), or as a bridging water molecule between particular compound (1450) atoms and MASP-2 amino acid residue atoms. A chloride ion is also present, which participates in hydrogen bonding with the pyrrolidine nitrogen atom N2.

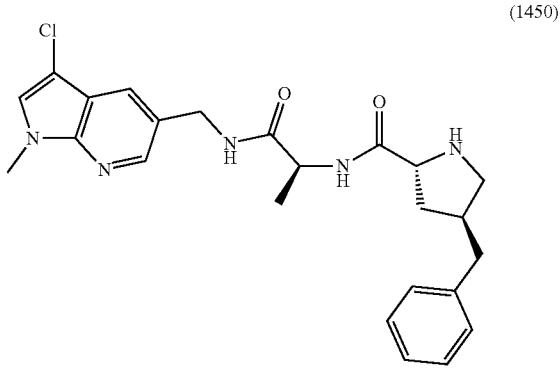 [SMILES: C[C@H](NC(=O)[C@H]1C[C@H](Cc2ccccc2)CN1)C(=O)NCc1cnc2c(c1)c(Cl)cn2C]

(1450)

In certain aspects, the present disclosure provides a compound with MASP-2 inhibitory activity, for therapeutic use in the treatment of a MASP-2-associated disease or disorder, wherein the compound has one or more such as 1, 2, 3, 4, or 5 of the following interactions (a) to (e):
  a) the compound binds via H-bonds with one or more of PRO 606, ASP 627, SER 628, ARG 630, SER 633, SER 654, GLY 656, SER 657, CYS 660 and GLN 665 in MASP-2;
  b) the compound binds via ionic or electrostatic interactions or hydrogen bonding to one or more of ASP 627 and ARG 630 in MASP-2;
  c) the compound interacts via a water molecule in MASP-2 to one or more of TYR 602, TYR 607, ASP 627, SER 628, SER 657, ASN 659, GLU 662, TRP 655, GLY656, CYS660, GLN 665, TYR 666, VAL 668, and ARG 630 in MASP-2;
  d) the compound interacts via π-π interactions with one or more of PHE 529, TYR 607, and TRP 655 in MASP-2; and
  e) the compound interacts via van der Waals contacts to one or more of ALA 468, ALA 469, HIS 483, ASP 526, ALA 527, GLY 528, PHE 529, LEU 575, PRO 606, TYR 607, PRO 608, SER 611, ASP 627, SER 628, CYS 629, ARG 630, GLY 631, ASP 632, SER 633, GLY 634, GLY 635, VAL 653, SER 654, TRP 655, GLY656, SER 657, MET 658, ASN 659, CYS 660, GLN 665, GLY 667, and TYR 669 in MASP-2,
  wherein the compound is not an endogenous MASP-2 ligand or substrate.

In certain aspects, the present disclosure provides a compound with MASP-2 inhibitory activity, for therapeutic use in the treatment of a MASP-2-associated disease or disorder, wherein the compound has one or more such as 1, 2, 3, 4, or 5 of the following interactions (a) to (e):
  a) the compound binds via H-bonds with 1, 2, 3, 4, 5, 6 or 7 of PRO 606, ARG 630, SER 633, SER 654, SER 657, CYS 660 and GLN 665 in MASP-2;
  b) the compound interacts via van der Waals contacts to 1, 2, 3, 4, 5, 6, 7 or 8 of ALA 469, GLY 634, GLY 635, SER 657, ASN 659, CYS 660, GLN 665, and TYR 669 in MASP-2.

Protein Data Bank access code 3TVJ). The following MASP-2 residues were identified to bind to peptide SGMI-2 via hydrogen bonds: GLY 656 (2H-bonds), ASP 627, SER 628 (2H-bonds), SER 633 (2H-bonds), GLY 631, THR 467 (3H-bonds), GLY 464, GLY 465, MET 658 and via van der Waals interactions with PRO 608, PHE 529, TYR 602, TYR 607, TRP 655, HIS 483, ALA 484, VAL 653, LEU 575, LEU 581, ALA 468, THR 466 and ARG 630. An analysis of the associated structure 3TVJ with LigPlot Plus produced the following amino acids being involved in non-bonded contacts: GLY 464, GLY 465, THR 466, THR 467, ALA 468, HIS 483, ALA 484, HIS 525, ASP 526, ALA 527, GLY 528, PHE 529, LEU 575, LEU 581, TYR 602, PRO 606, TYR 607, PRO 608, ARG 609, GLY 610, SER 611, ASP 627, SER 628, CYS 629, ARG 630, GLY 631, ASP 632, SER 633, VAL 653, SER 654, TRP655, GLY 656, MET 658, GLY 667.

In certain aspects, the present disclosure provides a compound with MASP-2 inhibitory activity, for therapeutic use in the treatment of a MASP-2-associated disease or disorder, wherein the compound has one or more such as 1, 2, 3, 4, or 5 of the following interactions (a) to (e):
  a) the compound binds via H-bonds with one or more of ASP 627, SER 628, SER 654, GLY 656, GLN 665, and SER 657 in MASP-2;
  b) the compound binds via ionic or electrostatic interactions or hydrogen bonding to ASP 627 in MASP-2;
  c) the compound interacts via a water molecule in MASP-2 to one or more of ASP 627, GLN 665, SER 657, ASN 659, SER 628, GLU 662, VAL 668, TYR607, TYR602, ARG630 in MASP-2;
  d) the compound interacts via π-π interactions with one or more of PHE 529, TYR 607, and TRP 655 in MASP-2; and
  e) the compound interacts via van der Waals contacts to one or more of HIS 483, PHE 529, PRO 606, TYR 607, PRO 608, SER 611, ASP 627, SER 628, CYS 629, ARG 630, SER 633, VAL 653, SER 654, TRP 655, GLY 656, SER 657, MET 658, ASN 659, CYS 660, GLN 665, GLY 667 and TYR 669 in MASP-2,
  wherein the compound is not an endogenous MASP-2 ligand or substrate.

In certain aspects, the compound interacts with 1, 2, 3, 4, or 5 of the features (a) to (e) above in any combination. The compound is not an endogenous MASP-2 ligand or substrate.

In some embodiments, the compound binds via H-bonds with one or more of the following: PRO 606, ASP 627, SER 628, SER 633, SER 654, GLY 656, SER 657, CYS 660 and GLN 665 in MASP-2.

In some embodiments, the compound binds via H-bonds with one or more of the following: ASP 627, SER 628, SER 654, GLY 656, GLN 665 and SER 657 in MASP-2.

In some embodiments, the compound binds via 1-10H-bonds.

In some embodiments, the compound binds via 3H-bonds to SER 654 and GLY 656, wherein there are two H-bonds to GLY 656 in MASP-2.

In some embodiments, the compound binds via ionic or electrostatic interactions or hydrogen bonding to one or both of ASP 627 and ARG 630 in MASP-2.

In some embodiments, the compound binds via ionic or electrostatic interactions or hydrogen bonding to ASP 627 in MASP-2.

In some embodiments, the compound does not bind via ionic interactions to ASP 627 or ARG 630 in MASP-2.

In some embodiments, the compound does not bind via ionic interactions to ASP 627 in MASP-2.

In some embodiments, the compound binds via a water molecule in MASP-2 to one or more of TYR 602, TYR 607, ASP 627, SER 628, SER 657, ASN 659, GLU 662, TRP 655, GLY 656, CYS 660, GLN 665, TYR 666, VAL 668, and ARG 630 in MASP-2.

In some embodiments, the compound binds via a water molecule in MASP-2 to one or more of ASP 627, GLN 665, SER 657, ASN 659, SER 628, GLU 662, VAL 668, TYR 607, TYR 602, and ARG 630.

In some embodiments, the compound binds via 1-20 water molecule(s) in MASP-2.

In some embodiments, the compound binds via 1, 2, 3, 4, 5, 6, 7, 8, 9, 10, 11, 12, 13, 14, 15, 16, or 17 water molecule(s) in MASP-2.

In some embodiments, the compound interacts via π-π interactions with one or more of PHE 529, TYR 607, and TRP 655 in MASP-2.

In some embodiments, the compound interacts via van der Waals contacts to one or more of ALA 468, ALA 469, HIS 483, ASP 526, ALA 527, GLY 528, PHE 529, LEU 575, PRO 606, TYR 607, PRO 608, SER 611, ASP 627, SER 628, CYS 629, ARG 630, GLY 631, ASP 632, SER 633, GLY 634, GLY 635, VAL 653, SER 654, TRP 655, GLY 656, SER 657, MET 658, ASN 659, CYS 660, GLN 665, GLY 667, and TYR 669 in MASP-2.

In some embodiments, the compound interacts via van der Waals contacts to one or more of HIS 483, PHE 529, PRO 606, TYR 607, PRO 608, SER 611, ASP 627, SER 628, CYS 629, ARG 630, SER 633, VAL 653, SER 654, TRP 655, GLY 656, SER 657, MET 658, ASN 659, CYS 660, GLN 665, GLY 667 and TYR 669 in MASP-2.

The foregoing set of rules for interactions was developed to increase inhibition of MASP-2, while at the same time reducing inhibition of thrombin. More specifically the above-described rules provide for compounds that preferentially inhibit MASP-2 relative to inhibition of thrombin. In certain aspects, the selectivity ratio of MASP-2:thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

Crystallographic data and evidence aided in the development and discovery of the rules.

The foregoing ligand-MASP-2 atom contacts represent polar interactions. Ligand atom to MASP-2 atom polar contacts (hydrogen bonds and ionic bonding) are included for pair-wise distances with a maximum contact distance of 3.35 Å between donor and acceptor atom as computed by LigPlot+ software settings for hydrogen-bond calculation parameters employing models derived from the corresponding crystallographic MASP-2 compound co-structures. MASP-2 amino acid residue numbering (MASP-2 AA #) is according to Uniprot accession code O00187, atom numbering for amino acids (AA atom) according to conventions established by the Protein Data Bank and atom ligand numbering assigned as depicted in FIGS. 1-57. Table A1 (Appendix) illustrates interaction of ligand atoms, which are D for hydrogen bond donor, and A for hydrogen bond acceptor. Distance units are in Angstrom.

MASP-2 specific peptide inhibitors have been developed previously (Kocsis et al., 2010, Héja et al., 2012). Small molecule inhibitors with drug-like characteristics, however, have not been reported in the published literature. The interaction of an artificially evolved MASP-2 specific 38-mer polypeptide, named SGMI-2, with MASP-2 was determined by crystallographic analysis (Héja et al., 2012, Protein Data Bank access code 3TVJ). The following MASP-2 residues were identified to bind to peptide SGMI-2 via hydrogen bonds: GLY 656 (2H-bonds), ASP 627, SER 628 (2H-bonds), SER 633 (2H-bonds), GLY 631, THR 467 (3H-bonds), GLY 464, GLY 465, MET 658 and via van der Waals interactions with PRO 608, PHE 529, TYR 602, TYR 607, TRP 655, HIS 483, ALA 484, VAL 653, LEU 575, LEU 581, ALA 468, THR 466 and ARG 630. An analysis of the associated structure 3TVJ with LigPlot+ produced the following amino acids being involved in non-bonded contacts: GLY 464, GLY 465, THR 466, THR 467, ALA 468, HIS 483, ALA 484, HIS 525, ASP 526, ALA 527, GLY 528, PHE 529, LEU 575, LEU 581, TYR 602, PRO 606, TYR 607, PRO 608, ARG 609, GLY 610, SER 611, ASP 627, SER 628, CYS 629, ARG 630, GLY 631, ASP 632, SER 633, VAL 653, SER 654, TRP 655, GLY 656, MET 658, GLY 667. The interaction of SGMI-2 with MASP-2 is reported to cause substantial distortions within the MASP-2 molecule and Héja et al. (2012) point out that such a distortion might cause an energy penalty, potentially weakening the binding strength for MASP-2. (see, Dávid Héja, Veronika Harmat, Krisztián Fodor, Matthias Wilmanns, József Dobó, Katalin A. Kékesi, Péter Závodszky, Péter Gál, Gábor Pál. Monospecific Inhibitors Show That Both Mannan-binding Lectin-associated Serine Protease-1 (MASP-1) and -2 Are Essential for Lectin Pathway Activation and Reveal Structural Plasticity of MASP-2. Journal of Biological Chemistry 287, 20290-20300 (2012) incorporated herein by reference).

In Table A2 (Appendix) ligand-MASP-2 atom contacts for van der Waals-type interactions between MASP-2 and compounds disclosed herein are given. Ligand atom to MASP-2 atom contacts are included for pair-wise interactions with a minimum distance of 2.9 Å and a maximum contact distance of 3.9 Å as computed by LigPlot+ software settings for non-bonded contact parameters employing models derived from the corresponding crystallographic MASP-2-compound co-structures. MASP-2 amino acid residue numbering (MASP-2 AA #) is according to Uniprot accession code O00187, atom numbering for amino acids (AA atom) according to conventions established by the Protein Data Bank and atom ligand numbering assigned as depicted in FIGS. 1-18. Distance units are in Angstrom.

In certain aspects, the compounds having MASP-2 inhibitory activity have a molecular weight of about 300 g/mol to about 600 g/mol, or about 350 g/mol to about 550 g/mol, or about 350 to about 500 g/mol, such as about 350, 360, 370, 380, 390, 400, 410, 420, 430, 440, 450, 460, 470, 480, 490 or about 500 g/mol. Typically, a small molecule has a molecular weight in these ranges.

In certain aspects, the present disclosure provides compounds that are selective for MASP-2 over thrombin. In other words, the compounds of interest have a greater affinity for MASP-2 (i.e., a smaller Ki for MASP-2) than the same compound for thrombin (i.e., the Ki for thrombin is larger). In certain aspects, the selectivity ratio of MASP-2:thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

As will be described in more detail, the active site for MASP-2 has a "V" shaped crevice, which allows for and accommodates a sterically larger molecule. The V-shaped crevice of MASP-2, accepts 'long' sterically bulky moieties such as a rotatable aromatic residue in the $M_4$-region of certain of the molecules of the disclosure.

As will be described in more detail, the active site for MASP-2 has a "S1 indentation", which allows for and accommodates a sterically larger molecule. The S1 indentation of MASP-2, accepts 'small' moieties such as a methyl group in a chloroazaindole residue in the M1-region of certain of the molecules of the disclosure.

As will be described in more detail, the active site for MASP-2 has a "S2 shelf", which allows for and accommodates a sterically larger molecule. The S2 shelf of MASP-2, accepts 'large' moieties such as a glutaminyl groups in the M3-region of certain of the molecules of the disclosure.

As will be described in more detail, the active site for MASP-2 has a "S3 entry indentation", which allows for and accommodates a sterically larger molecule. The S3 entry indentation of MASP-2, accepts 'planar aromatic' moieties such as a pyrazole ring connecting the M3 with the M4 segments of certain of the molecules of the disclosure.

On the other hand, the backside of the active site in thrombin is closed. Therefore, larger or bulky groups are not sterically accommodated in the same manner as thrombin due to this closure. Thrombin does not have a crevice in the active site. As such, bulky groups in the $M_4$ region are not well accommodated.

Moreover, the crystallographic evidence indicates that key amino acids making up the V shaped crevice of MASP-2 are one or more of the following 6 amino acids: PHE 529, GLY 528, TRP 655, SER 611, PRO 608, TYR 607, PRO 606, such as 1, 2, 3, 4, 5, or all 6 amino acids.

In addition, it was discovered that thrombin possesses a ridge, creating a barrier for large bulky residues ($M_4$) preventing occupation of this site. The ridge includes the amino acids ASN 98, LEU 99, and ILE 174 (defined using Protein Data Bank structure 1K22 numbering) or GLU130 and ILE209 (defined using numbering of Protein Data Bank structure file 4BAH). In the corresponding region in MASP-2 however, a crevice exists that is lined by amino acids PHE 529, GLY 528, TRP 655, SER 611, PRO 608, TYR 607, and PRO 606. As there is no corresponding barrier to large bulky residues in MASP-2, large bulky residues can bind and, provide a means to design specificity for MASP-2 over thrombin or other similar proteases.

Based on crystallographic models, certain of the compounds of this disclosure have a specificity for binding to MASP-2 as compared to thrombin.

Figure 58:
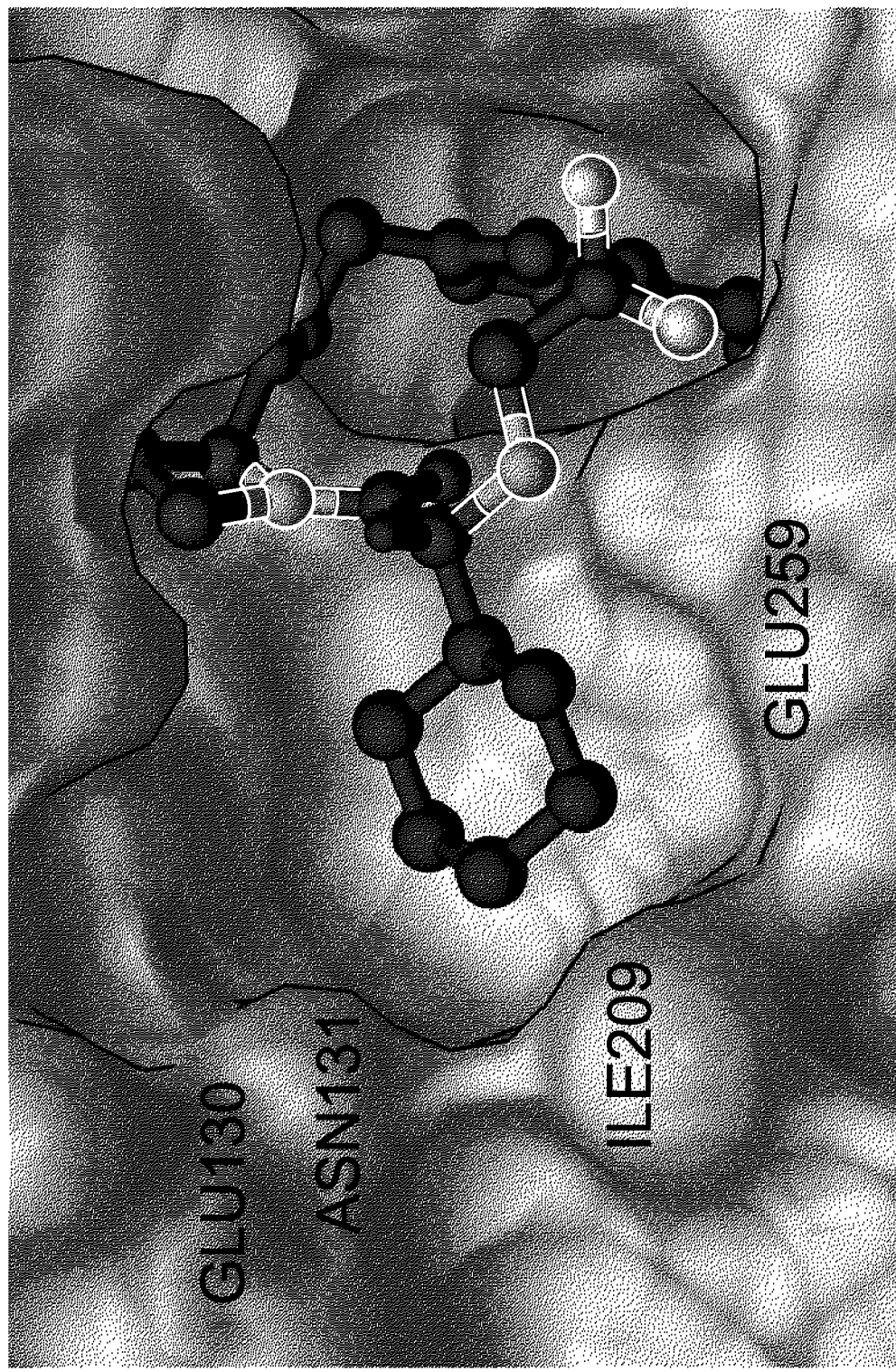
FIG. 58 is a plot depicting melagatran bound to thrombin.
Figure 59:
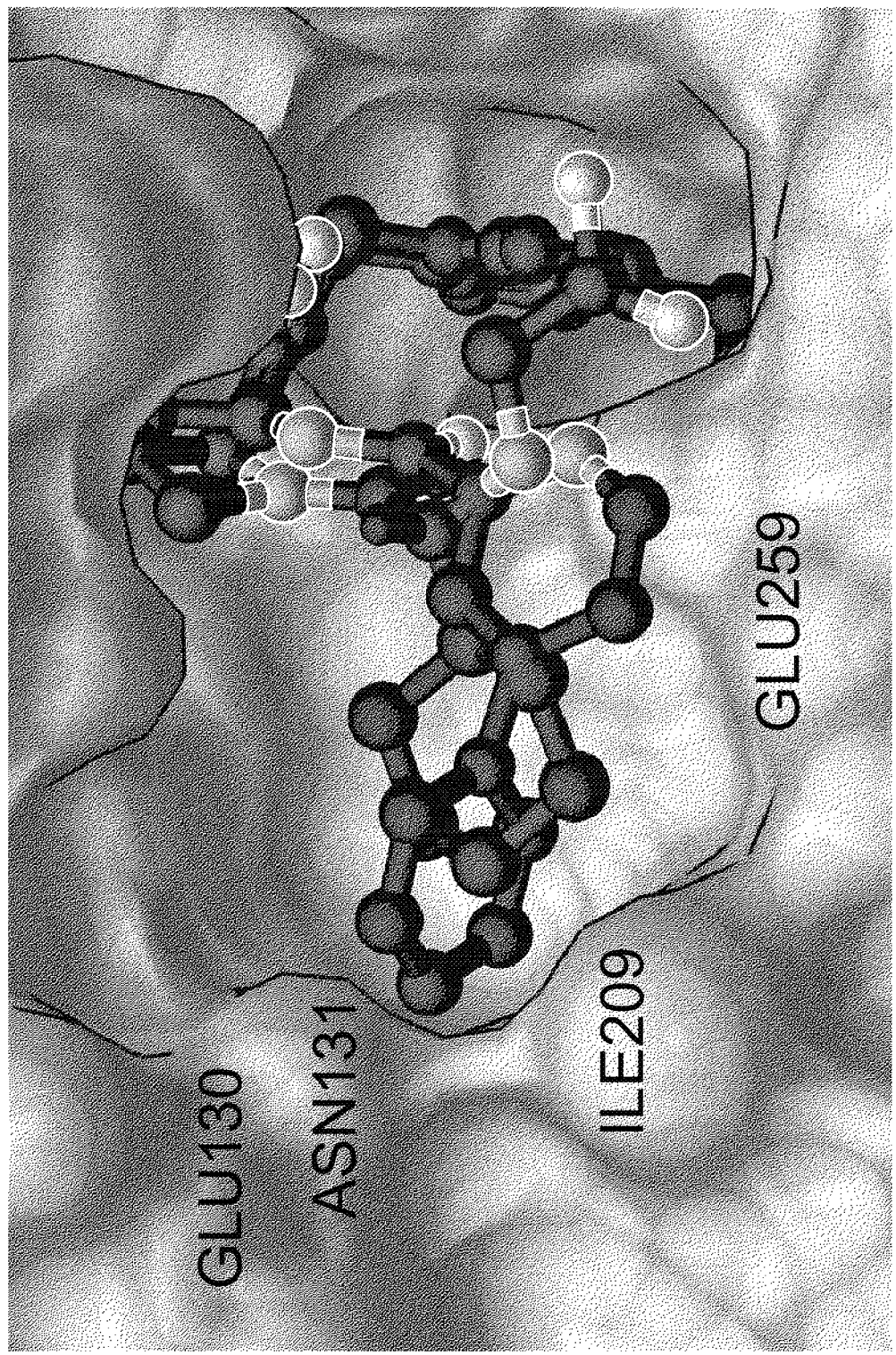
FIG. 59 is a plot showing melagatran bound to thrombin overlaid with a MASP-2 selective compound (1065) bound to MASP-2.
Figure 60:
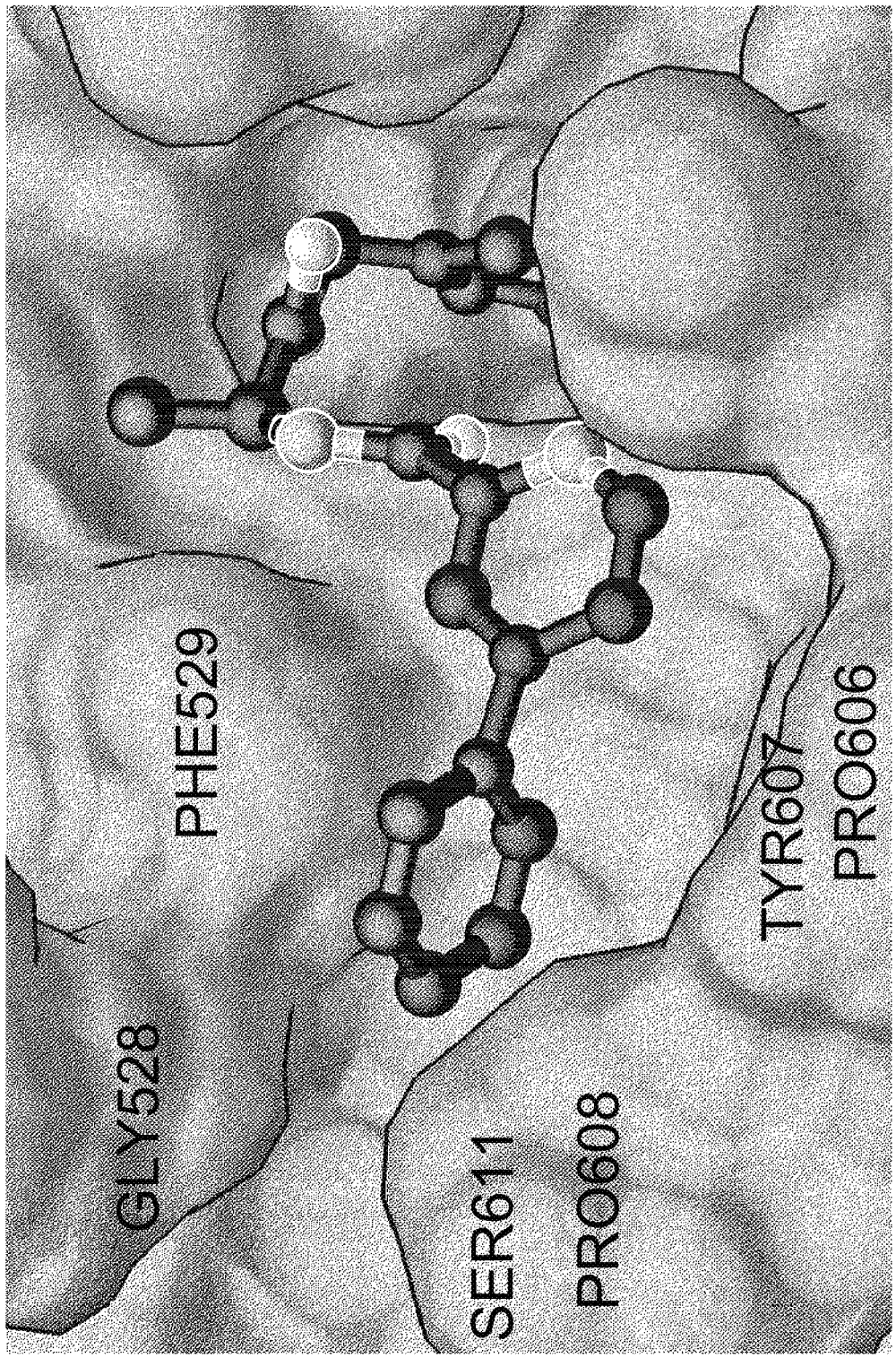
FIG. 60 is a plot showing compound (1065) bound to the SP domain of MASP-2.
Figure 61:
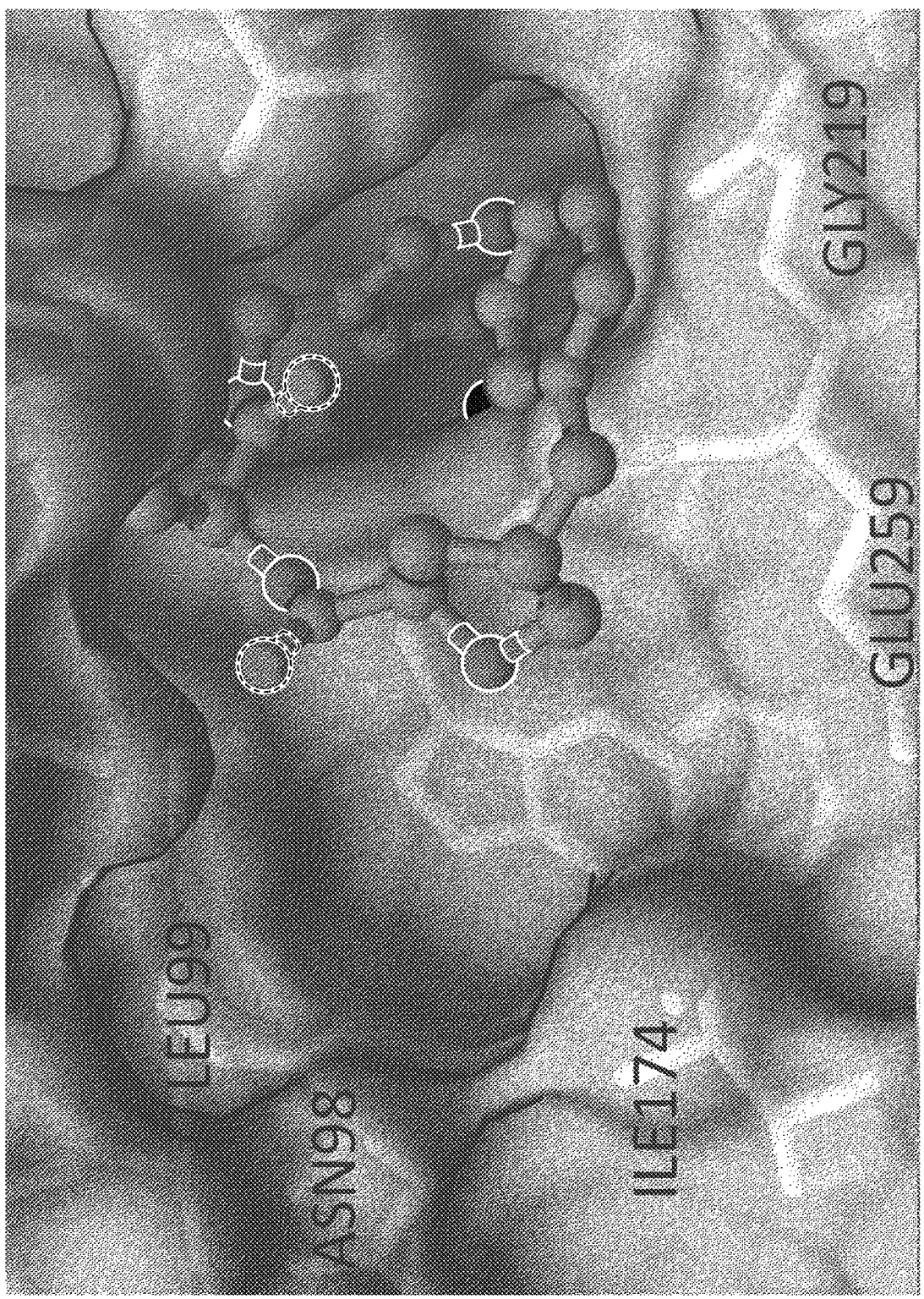
FIG. 61 is a plot showing compound (1334) bound to thrombin.
Figure 62:
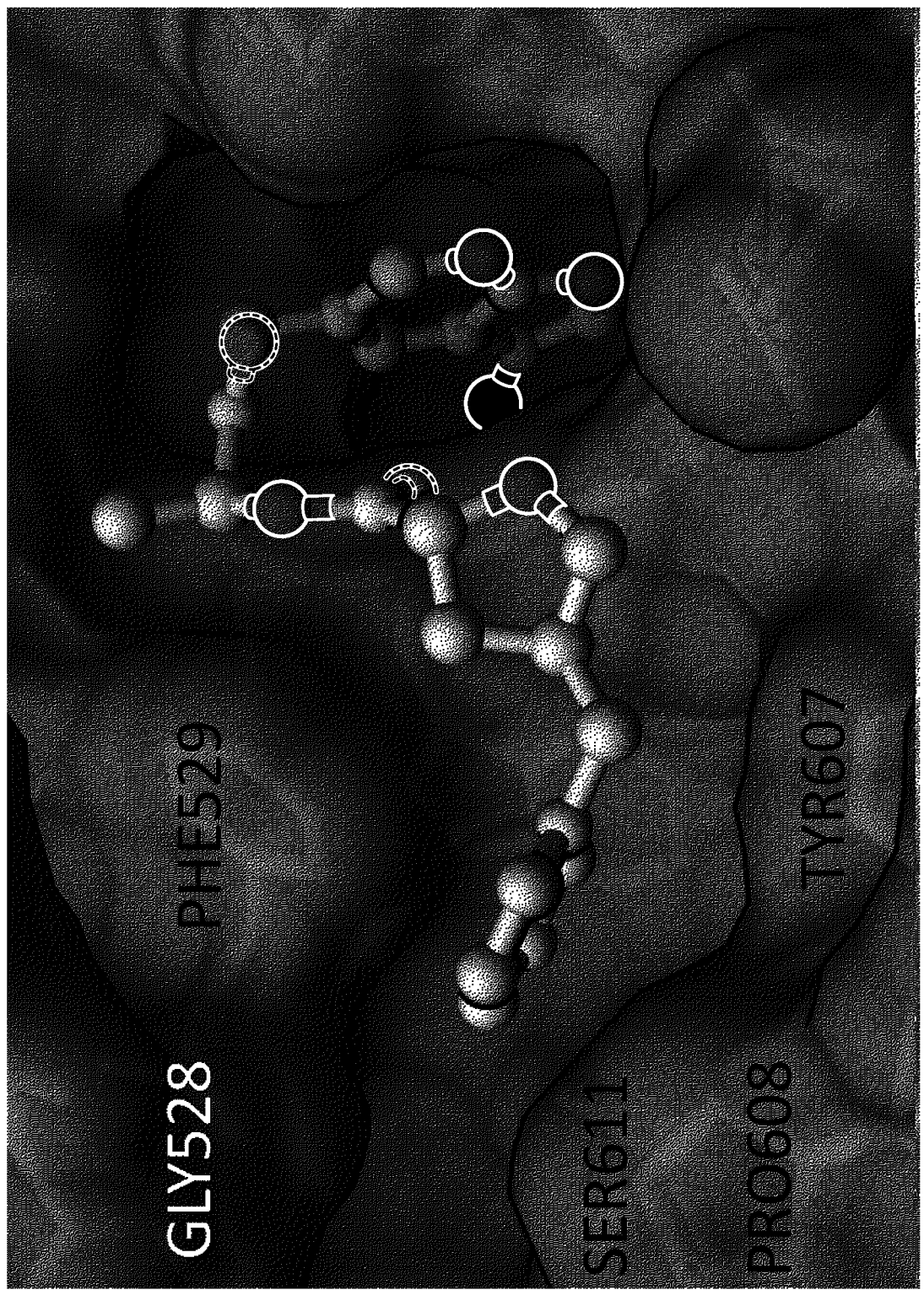
FIG. 62 is a plot showing compound (1334) bound to the SP domain of MASP-2.

FIG. 58 to 63 show a region of the S3-S4 binding pockets of thrombin, compared to the S3-S4 binding pockets of MASP-2, with protein surface residues depicted as a surface and the bound small molecules depicted as ball and stick. FIG. 58, FIG. 59, FIG. 61 and FIG. 63 show a region of the S3-S4 binding pockets of thrombin, whereas the S3-S4 binding pockets of MASP-2 are shown in FIG. 60 and FIG. 62.

FIG. 58 depicts melagatran bound to thrombin (Protein Data Bank accession code 4BAH) with its cyclohexyl group embedded in a pocket that is lined by a ridge formed by GLU 130, ASN 131, ILE 209 and GLU 259. The benzamidine functional group of melagatran is located in a deep pocket (S1) of thrombin on the right-hand side of the image.

FIG. 59 shows melagatran bound to thrombin overlaid with a MASP-2 selective compound (1065) bound to MASP-2. The overlay reproduces the location of the benz-amidine function of both molecules (1065) bound to MASP-2 and melagatran bound to thrombin, and as shown, there is a clash with the ridge formed by ASN 131 and ILE 209.

FIG. 60 is a plot showing compound (1065) bound to the SP domain of MASP-2 with its bulky phenyl group fitting into a crevice that is formed by MASP-2 residues GLY 528 and PHE 529 on one side, and SER 611, PRO 608, TYR 607 and PRO 606 on the opposite side.

FIG. 61 depicts compound (1334) bound to thrombin with its benzyl group folded back onto a surface that is lined by a ridge formed by GLU 259, and GLY 219. The chloroazaindole functional group of compound (1334) is located in a deep pocket (S1) of thrombin on the right-hand side of the image.

FIG. 62 illustrates compound (1334) bound to the SP domain of MASP-2 with its bulky phenyl group fitting into a crevice that is formed by MASP-2 residues GLY 528 and PHE 529 on one side, and SER 611, PRO 608, TYR 607 and PRO 606 on the opposite side.

Figure 63:
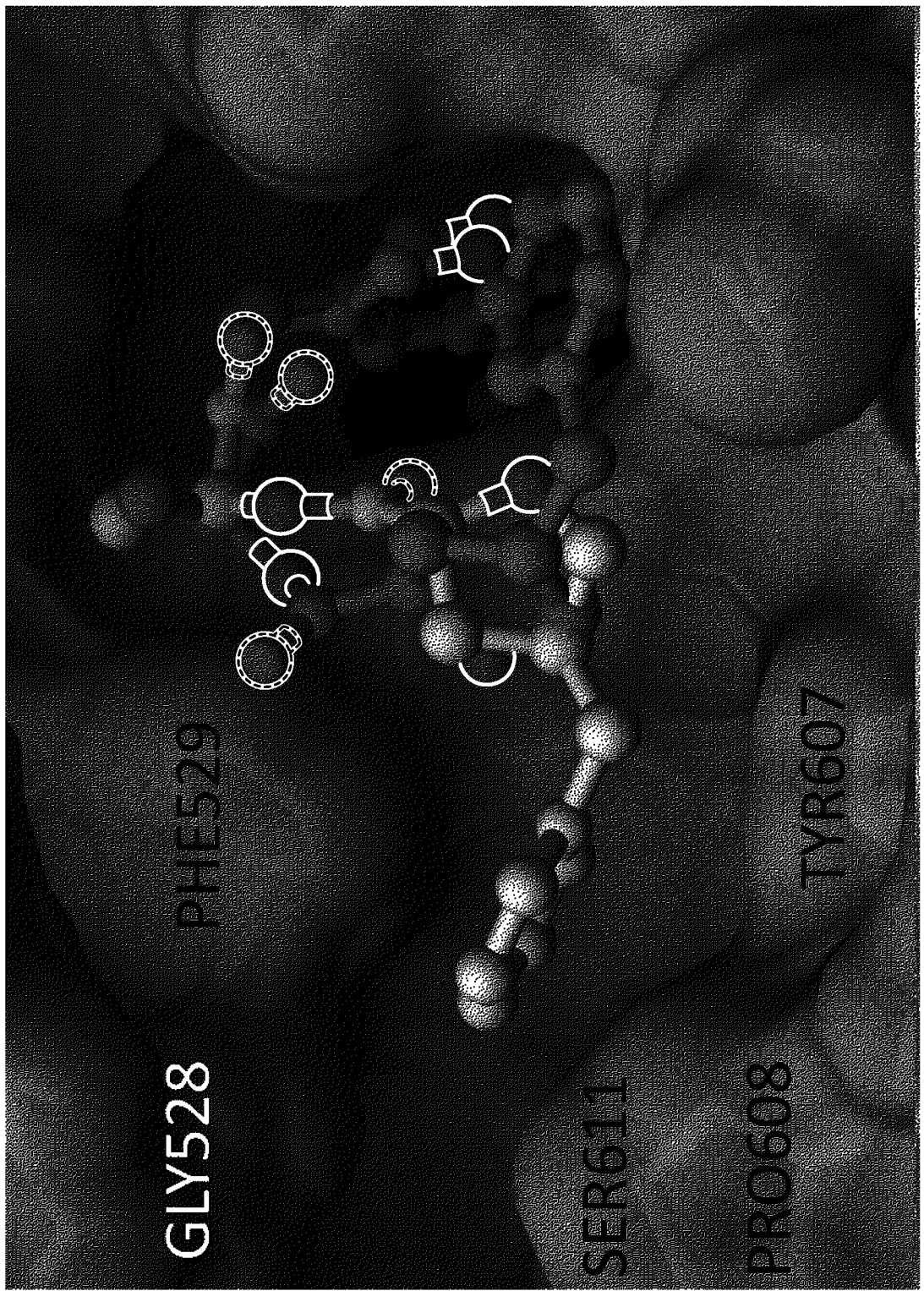
FIG. 63 is a plot showing compound (1334) bound to MASP-2 overlaid with compound (1334) bound to thrombin.

FIG. 63 is a plot showing the MASP-2 selective compound (1334) bound to MASP-2 overlaid with compound (1334) bound to thrombin. The overlay reproduces the location of the chloroazaindole function of the molecule compound (1334) bound to MASP-2 and compound (1334) bound to thrombin.

The difference between the closed pocket in thrombin to the open crevice in MASP-2 provides a mechanism to design compounds with selectivity to MASP-2 over thrombin. For example, elongated and bulky moieties fit into the MASP-2 crevice, but would clash with the ridge in thrombin.

Figure 65:
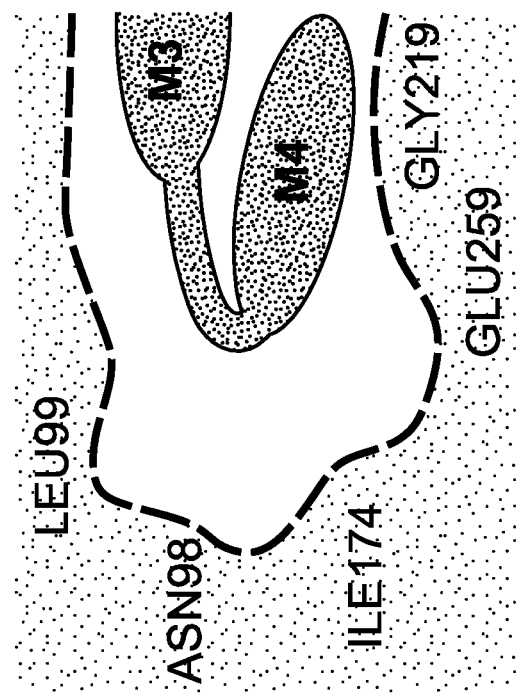
FIG. 65 is a plot illustrating the S3-S4 binding pockets of thrombin.
Figure 64:
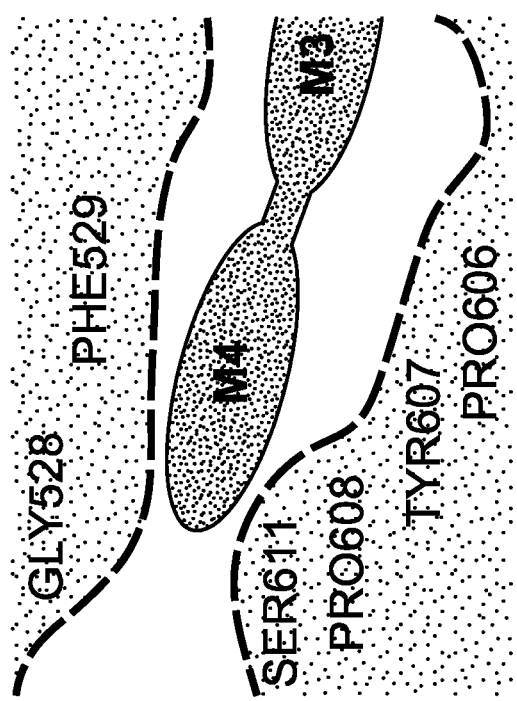
FIG. 64 is a plot illustrating the S3-S4 binding pockets of MASP-2.

FIGS. 64 and 65 illustrate a schematic depiction of selectivity for MASP-2 vs thrombin in region S3-S4, based on analysis of crystallographic models. FIG. 64 illustrates the S3-S4 binding pockets of MASP-2, whereas FIG. 65 illustrates S3-S4 binding pockets of thrombin. Both are shown with the protein in grey and the bound small molecules depicted as dark grey ellipsoids. As shown in FIG. 65, in thrombin, only small moieties of $M_4$ (e.g. cyclohexyl groups) can fit into a pocket formed by LEU99, ASN98, ILE174, GLU259, GLY219. FIG. 64 shows a small molecule bound to the equivalent S3-S4 pocket in the SP domain of MASP-2 that reaches further into a crevice formed by MASP-2 residues GLY 528 and PHE 529 on one side, and SER 611, PRO 608, TYR 607 and PRO 606 on the opposite side. Hence, larger molecules with elongated and bulky groups in $M_4$ can fit into the crevice in MASP-2, but cannot bind to the small S3-S4 pocket in thrombin. FIG. 64 shows the open crevice in MASP-2 provides a mechanism to design compounds with selectivity to MASP-2 over thrombin accommodating sterically bulky groups in $M_4$.

Without being limited by any theory, based on the analysis of the structures, structural features of the MASP-2 and thrombin and the way that molecules interact with such features in MASP-2 and thrombin can be used to identify binding rules and structural features of compounds that contribute to selectivity for MASP-2 and thrombin.

S1-indentation: While not being limited by any theory, it is understood that the S1 pocket of MASP-2 may accept molecules of certain sizes and shapes that are unlikely to fit into the S1 pocket of thrombin. This site can be occupied, e.g., by moieties $M_1$ of compounds as described herein. In fact, the S1 pocket of MASP-2 is lined with an amino acid sequence comprising GLY 656, SER 657, MET 658, ASN 659 and CYS 660. The corresponding sequence is shorter by one amino acid in thrombin (comprising the amino acids GLY 216, GLU 217, GLY 219 and Cys220, defined using Protein Data Bank structure 1K22 numbering). This section in MASP-2 forms a concave space in the S1 pocket, whereas in thrombin there is less space, hence restricting the size of ligand molecules that may bind into the S1 pocket. Certain MASP-2 selective compounds were found to form H-bonds and van der Waals contacts with surface lining residues of the S1 pocket of MASP-2, including ASP 627, SER 628, CYS 629, SER 633, TRP 655, GLY 656, SER 657, CYS 660, GLY 667, and TYR 669. Thus, it is understood that compounds having selectivity for inhibiting MASP-2 over thrombin can be compounds that make interactions with the amino acids lining the S-1 pocket of MASP-2. For example, the MASP-2 selective inhibitors can include compounds that make, e.g., 1, 2, 3, 4, or 5 or more H-bonding interactions, and/or, e.g., 1, 2, 3, 4, or 5 van der Waals interactions with 1 or more amino acids of MASP-2 lining the S1 pocket of MASP-2, such as those amino acids selected from the group consisting of including ASP 627, SER 628, CYS 629, SER 633, TRP 655, GLY 656, SER 657, CYS 660, GLY 667, and TYR 669.

S2 shelf: While not being limited by any theory, it is understood that selectivity for MASP-2 inhibition over thrombin can be increased by including groups that interact with the S2 region of MASP-2. For example, $M_3$ moieties can provide selective MASP-2 inhibition over thrombin by the introduction of substituents on a glycine carbon or nitrogen. The S2 region of MASP-2 can accommodate both large and small substituents, which can form H-bonds and van der Waals contacts with surface lining residues (such as the peptide backbone of SER 654, the peptide backbone and carbonyl of TRP 655 and GLY 656, and the side-chain of HIS 483), but a similar binding pose in thrombin is unfavored due to steric interactions. Thus, it is understood that compounds having selectivity for inhibiting MASP-2 over thrombin can be compounds that make interactions with the amino acids in the S-2 region of MASP-2. For example, the MASP-2 selective inhibitors can include compounds that make, e.g., 1, 2, 3, 4, or 5 or more H-bonding interactions, and/or, e.g., 1, 2, 3, 4, or 5 van der Waals interactions with 1 or more amino acids of MASP-2 in the S2 region of MASP-2, such as those amino acids selected from the group consisting of SER 654, TRP 655, GLY 656, and HIS 483.

S3 entry indentation: While not being limited by any theory, it is understood that selectivity for MASP-2 inhibition over thrombin can be favored by introducing groups that interact with the S3 entry site in MASP-2, e.g., as a linker element connecting $M_3$ and $M_4$ moieties, such as planar aromatic groups and/or groups that can form a hydrogen bond acceptor via the carbonyl group of GLY 656. In MASP-2 the S3 entry site is composed of the first two amino acids of the 5 amino acid sequence that includes the amino acids GLY 656, SER 657, MET 658, ASN 659 and CYS 660, while in thrombin (1 k22.pdb) the corresponding site is composed of only the first of a 4 amino acid sequence (comprising the amino acids GLY 216, GLU 217, GLY 219 and Cys220). As a result of the corresponding shortened sequence in thrombin, the GLY 216 carbonyl group is displaced and cannot form favorable interactions with compounds that interact with the corresponding region of MASP-2. Thus, it is understood that compounds having selectivity for inhibiting MASP-2 over thrombin can be compounds that make interactions with the amino acids at the S3 entry site of MASP-2. For example, the MASP-2 selective inhibitors can include compounds that make, e.g., 1, 2, 3, 4, or 5 or more H-bonding interactions, and/or, e.g., 1, 2, 3, 4, or 5 van der Waals interactions with 1 or more amino acids of MASP-2 lining at the S3 entry site of MASP-2, such as those amino acids selected from the group consisting of GLY 656, SER 657, MET 658, ASN 659 and CYS 660.

G. Compounds Defined by Reference to a Pharmacophore Model

The present disclosure also provides small molecules inhibitors of MASP-2 that may be described by reference to a pharmacophore model. It has been found that compounds that are capable of binding to and inhibiting MASP-2, and, in particular, compounds that bind to MASP-2 according to the binding rules described above can be described in terms of their structural features using a pharmacophore model.

The pharmacophore model described in Table 1 and its properties displayed in FIG. 67-75 represents averaged pharmacophore elements of MASP-2 inhibitors as obtained by PHASE analysis after protein preparation and protein structure alignment with the Small-Molecule Drug Discovery Suite 2018-4 (Schrödinger, LLC, New York, NY 2018) and clustered with KMeans from sklearn (version 0.20.3; Machine Learning in Python, Pedregosa et al., JMLR 12, pp. 2825-2830, 2011).

The PHASE methodology for pharmacophore analysis has been described generally in Dixon et al., *J. Comput. Aided Mol. Des.*, 2006, 20, 647-671, and Dixon et al., *Chem. Biol. Drug Des.*, 2006, 67, 370-372. The analysis was performed with Prody (Bakan et al., *Bioinformatics*, 2011, 27(11), 1575-1577; Bakan et al., *Bioinformatics*, 2014, 30(18), 2681-2683), and the Python programing language.

Briefly, the crystal structures of small molecule inhibitors described herein bound to human MASP-2 small molecule crystal structures were prepared within Maestro version 2018-4 (Schrödinger, LLC). Hydrogens were added, protonation states were adjusted, and hydrogen bond interactions optimized. In cases where several molecules with different conformations and/or binding modes were identified in the asymmetric unit (ASU), these were split and treated as separate protein ligand complexes. In addition, disordered small molecules were treated as separate ligand conformation. The heavy atom coordinates were not modified, i.e., through minimization.

The prepared structures were then aligned by using all backbone atoms within 10 Å of each small molecule without residues 594-611 of SEQ ID NO:1.

Protein atoms, solvent atoms and ions are deleted to obtain an alignment of small molecule poses only.

The program create_molSites from Schrödinger, LLC was used to convert each small molecule into separate 3-dimensional pharmacophores. Besides the standard feature definitions, an additional pharmacophore element was created to consider that positive ionizable groups can also be hydrogen bond donors. In later analysis this feature was merged with the standard hydrogen bond donor feature. The definition of positive ionizable groups (N) was extended to include groups with pKa≥6.0 (as calculated using Epik (Schrödinger, LLC)). An alignment of pharmacophore elements from the small molecules is obtained.

KMeans from sklearn is used to cluster the so obtained alignment of all pharmacophore elements by cartesian coordinates. After several tries the number of cluster centers for each pharmacophore feature was chosen to mimic experimentally observed SAR, and few pharmacophore elements were deleted. All cluster centers represent the averaged features of the overall pharmacophore.

Python 3.6 and Prody were used to perform the analysis.

In the PHASE method, each ligand structure is represented by a set of points in 3D space, which coincide with various chemical features that may facilitate non-covalent binding between the ligand and its target receptor. These pharmacophore sites can be characterized by type, location and, if applicable, directionality. Pharmacophore elements include: hydrogen bond acceptor (O), hydrogen bond donor (H), hydrophobic group (C), negative ionizable group (X), positive ionizable group (N), and aromatic ring (CA).

A hydrogen bond acceptor site (O) is positioned on a surface-accessible atom that carries one or more donatable lone pairs, and a vector attribute is assigned to each idealized hydrogen bond axis, according to the hybridization of the acceptor atom.

A hydrogen bond donor site (H) is centered on each donatable hydrogen atom, and a single vector feature is directed along its idealized hydrogen bond axis.

Hydrophobic groups (C) are assigned using a procedure that has been described by Greene et al., *J. Chem. Inf. Comput. Sci.* 1994, 34, 1297. Rings, isopropyl groups, t-butyl groups, various halogenated moieties, and chains as long as four carbons are each treated as a single hydrophobic site. Chains of five or more carbons are broken into smaller fragments containing between two and four carbons and each fragment is designated as a separate hydrophobic site. The location of a given hydrophobic site is a weighted average ($r_H$) of the positions of the non-hydrogen atoms in the associated fragment.

$$r_H = \frac{\sum_i s_i t_i r_i}{\sum_i s_i t_i}$$

Here, $s_i$ is the solvent-accessible surface area of atom i, computed using a probe radius of 1.4 Å, and $t_i$ is a hydrophobicity factor that ranges between 0 and 1 (polar atoms (O, N, S) are assigned a hydrophobicity of 0, carbons and halogens at least three bonds from any polar atom receive a value of 1; and intermediate hydrophobicities are assigned to carbons and halogens when polar atoms are within a distance of two bonds).

Positive ionizable groups (N) and negative ionizable groups (X) are modeled as a single point located on a formally charged atom, or at the centroid of a group of atoms over which the ionic charge is shared. As noted above, in the present analysis, the definition of positive ionizable groups was extended to include positive ionizable groups with a pKa≥6.0. Thus, a positive ionizable group pharmacophore element as described herein should be understood to include positive ionizable groups with a pKa≥6.0 (as calculated using Epik (Schrödinger, LLC)).

Aromatic rings (CA) may be distinguished from other hydrophobic groups, and are designated as a separate type of pharmacophore feature, represented by a single site placed at the centroid of each aromatic ring, and a two-headed vector normal to the plane of the ring is associated with the site.

For this analysis presented herein, only the position of each pharmacophore element was used, and vector type information was not considered.

The pharmacophore analysis found that compounds active as MASP-2 inhibitors included combinations of one or more, for example, combinations of the elements listed in Table 1. Table 1 lists the pharmacophore elements of MASP-2 inhibitor compounds designated according to element type and cartesian coordinates (x, y, z) identifying the relative position of the pharmacophore elements on an angstrom scale. The origin of the cartesian system is defined based on the average position of all the pharmacophore elements O2, which was defined as (0.0, 0.0, 0.0). The cartesian coordinates given represent average (mean) values for the coordinates of each pharmacophore element. Table 1 lists standard deviations for the values of the x, y, and z coordinates for the ligands studied.

While not being limited by any theory, it is understood that compounds that are active as inhibitors of MASP-2 will include at least one or two and preferably combinations of three or more of the pharmacophore elements listed in Table 1. For example, the compounds that are active as inhibitors of MASP-2 may include one or combinations of 2, 3, 4, 5, 6, 7, 8, 9, 10, 11, 12, 13, 14, 15, 16, 17, 18, 19, 20, 21, or 22 of the pharmacophore elements, preferably combinations of 3, 4, 5, 6, 7, 8, 9, 10, 11, 12, 13 or 14 or more of the pharmacophore elements listed in Table 1.

While not being limited by any theory, it is understood that a compound is considered to include a pharmacophore element or combination of pharmacophore elements as listed in Table 1 if the pharmacophore element or combination of pharmacophore elements is present in the compound and the compound has an accessible conformation at physiological temperature (37° C.) which can place the pharmacophore element(s) within four standard deviations, preferably within three standard deviations, more preferably within two standard deviations and most preferably within one standard deviation of the mean value for x, y and z listed in Table 1. The range defined by the mean value of each of the x, y, and z coordinates and error allowed for (plus or minus four, three, two or one standard deviation) can be considered to define a box within which the pharmacophore elements should be found for an active MASP-2 inhibitor compound.

Table 2A lists the coordinates of the pharmacophore elements listed as ranges of the mean (x, y, z) coordinates plus or minus one or two standard deviations. Table 2B lists the coordinates of the pharmacophore elements listed as ranges of the mean (x, y, z) coordinates plus or minus three or four standard deviations.

TABLE 1

Pharmacophore Elements for MASP-2 Inhibitors and their Coordinates

| Pharmacophore Element Type | Label | x value (average) | standard deviation of x | y value (average) | standard deviation of y | z value (average) | standard deviation of z |
| --- | --- | --- | --- | --- | --- | --- | --- |
| Hydrophobic group | C2 | 0.30 | 1.18 | 1.17 | 1.35 | −2.76 | 1.59 |
| Hydrophobic group | C3 | −0.41 | 0.89 | −2.85 | 1.66 | 4.64 | 0.12 |
| Hydrophobic group | C4 | 4.09 | 1.32 | 5.54 | 0.95 | −4.66 | 1.24 |

TABLE 1-continued

Pharmacophore Elements for MASP-2 Inhibitors and their Coordinates

| Pharmacophore Element Type | Label | x value (average) | standard deviation of x | y value (average) | standard deviation of y | z value (average) | standard deviation of z |
|---|---|---|---|---|---|---|---|
| Hydrophobic group | C5 | 2.64 | 0.22 | −4.84 | 0.22 | 4.79 | 0.29 |
| Hydrophobic group | C6 | 6.01 | 0.75 | 2.84 | 0.54 | −2.56 | 0.34 |
| Hydrophobic group | C7 | −0.85 | 0.35 | −5.92 | 0.29 | 0.26 | 0.85 |
| Aromatic ring | CA1 | −0.61 | 0.50 | −3.55 | 0.38 | 2.50 | 0.57 |
| Aromatic ring | CA2 | 4.00 | 0.48 | 3.49 | 0.32 | −3.49 | 0.36 |
| Aromatic ring | CA3 | −5.29 | 0.84 | −1.15 | 1.48 | −2.77 | 1.09 |
| Aromatic ring | CA4 | 4.02 | 1.46 | 5.89 | 0.76 | −3.90 | 0.21 |
| Aromatic ring | CA5 | 1.84 | 1.28 | 2.62 | 1.27 | −5.13 | 0.90 |
| Aromatic ring | CA6 | −1.88 | 1.11 | 2.21 | 0.59 | −1.85 | 1.73 |
| H bond donor | H1 | −8.33 | 0.06 | −1.98 | 0.05 | −5.56 | 0.06 |
| H bond donor | H2 | −2.25 | 0.35 | −2.33 | 0.70 | 2.28 | 0.96 |
| H bond donor | H3 | −0.36 | 0.59 | −3.03 | 2.11 | −0.98 | 1.00 |
| H bond donor | H4 | −0.28 | 0.75 | −1.61 | 1.68 | 3.01 | 0.56 |
| Positive Ionizable Group | N1 | 0.10 | 0.57 | −5.35 | 1.00 | 1.66 | 0.89 |
| Positive Ionizable Group | N2 | −0.49 | 0.37 | −0.11 | 0.48 | −2.46 | 0.37 |
| H bond acceptor | O1 | −2.52 | 0.68 | 0.57 | 0.72 | 2.02 | 0.57 |
| H bond acceptor | O2 | 0.00 | 0.74 | 0.00 | 0.67 | 0.00 | 0.88 |
| H bond acceptor | O3 | −6.82 | 2.89 | −1.48 | 3.03 | −5.36 | 3.59 |
| H bond acceptor | O4 | −1.97 | 0.77 | −3.24 | 0.66 | 2.08 | 0.53 |

TABLE 2A

Pharmacophore Elements Coordinate Ranges MASP-2 Inhibitors

| | Range for (x, y, z) ± 1 standard deviation | | | Range for (x, y, z) ± 2 standard deviations | | |
|---|---|---|---|---|---|---|
| Label | x | y | z | x | y | z |
| C2 | 0.30 ± 1.18 | 1.17 ± 1.35 | −2.76 ± 1.59 | 0.30 ± 2.37 | 1.17 ± 2.69 | −2.76 ± 3.18 |
| C3 | −0.41 ± 0.89 | −2.85 ± 1.66 | 4.64 ± 0.12 | −0.41 ± 1.78 | −2.85 ± 3.32 | 4.64 ± 0.23 |
| C4 | 4.09 ± 1.32 | 5.54 ± 0.95 | −4.66 ± 1.24 | 4.09 ± 2.63 | 5.54 ± 1.89 | −4.66 ± 2.49 |
| C5 | 2.64 ± 0.22 | −4.84 ± 0.22 | 4.79 ± 0.29 | 2.64 ± 0.43 | −4.84 ± 0.45 | 4.79 ± 0.59 |
| C6 | 6.01 ± 0.75 | 2.84 ± 0.54 | −2.56 ± 0.34 | 6.01 ± 1.50 | 2.84 ± 1.07 | −2.56 ± 0.67 |
| C7 | −0.85 ± 0.35 | −5.92 ± 0.29 | 0.26 ± 0.85 | −0.85 ± 0.70 | −5.92 ± 0.58 | 0.26 ± 1.71 |
| CA1 | −0.61 ± 0.50 | −3.55 ± 0.38 | 2.50 ± 0.57 | −0.61 ± 1.00 | −3.55 ± 0.76 | 2.50 ± 1.13 |
| CA2 | 4.00 ± 0.48 | 3.49 ± 0.32 | −3.49 ± 0.36 | 4.00 ± 0.96 | 3.49 ± 0.65 | −3.49 ± 0.72 |
| CA3 | −5.29 ± 0.84 | −1.15 ± 1.48 | −2.77 ± 1.09 | −5.29 ± 1.68 | −1.15 ± 2.96 | −2.77 ± 2.17 |
| CA4 | 4.02 ± 1.46 | 5.89 ± 0.76 | −3.90 ± 0.21 | 4.02 ± 2.92 | 5.89 ± 1.52 | −3.90 ± 0.41 |
| CA5 | 1.84 ± 1.28 | 2.62 ± 1.27 | −5.13 ± 0.90 | 1.84 ± 2.55 | 2.62 ± 2.53 | −5.13 ± 1.80 |
| CA6 | −1.88 ± 1.11 | 2.21 ± 0.59 | −1.85 ± 1.73 | −1.88 ± 2.23 | 2.21 ± 1.18 | −1.85 ± 3.46 |
| H1 | −8.33 ± 0.06 | −1.98 ± 0.05 | −5.56 ± 0.06 | −8.33 ± 0.12 | −1.98 ± 0.11 | −5.56 ± 0.11 |
| H2 | −2.25 ± 0.35 | −2.33 ± 0.70 | 2.28 ± 0.96 | −2.25 ± 0.69 | −2.33 ± 1.41 | 2.28 ± 1.93 |
| H3 | −0.36 ± 0.59 | −3.03 ± 2.11 | −0.98 ± 1.00 | −0.36 ± 1.17 | −3.03 ± 4.21 | −0.98 ± 2.01 |
| H4 | −0.28 ± 0.75 | −1.61 ± 1.68 | 3.01 ± 0.56 | −0.28 ± 1.49 | −1.61 ± 3.35 | 3.01 ± 1.12 |
| N1 | 0.10 ± 0.57 | −5.35 ± 1.00 | 1.66 ± 0.89 | 0.10 ± 1.13 | −5.35 ± 2.00 | 1.66 ± 1.78 |
| N2 | −0.49 ± 0.37 | −0.11 ± 0.48 | −2.46 ± 0.37 | −0.49 ± 0.74 | −0.11 ± 0.96 | −2.46 ± 0.75 |
| O1 | −2.52 ± 0.68 | 0.57 ± 0.72 | 2.02 ± 0.57 | −2.52 ± 1.35 | 0.57 ± 1.44 | 2.02 ± 1.13 |
| O2 | 0.00 ± 0.74 | 0.00 ± 0.67 | 0.00 ± 0.88 | 0.00 ± 1.49 | 0.00 ± 1.33 | 0.00 ± 1.77 |
| O3 | −6.82 ± 2.89 | −1.48 ± 3.03 | −5.36 ± 3.59 | −6.82 ± 5.78 | −1.48 ± 6.06 | −5.36 ± 7.19 |
| O4 | −1.97 ± 0.77 | −3.24 ± 0.66 | 2.08 ± 0.53 | −1.97 ± 1.54 | −3.24 ± 1.33 | 2.08 ± 1.06 |

TABLE 2B

Pharmacophore Elements Coordinate Ranges MASP-2 Inhibitors

| | Range for (x, y, z) ± 3 standard deviations | | | Range for (x, y, z) ± 4 standard deviations | | |
|---|---|---|---|---|---|---|
| Label | x | y | z | x | y | z |
| C2 | 0.30 ± 3.55 | 1.17 ± 4.04 | −2.76 ± 4.77 | 0.30 ± 4.74 | 1.17 ± 5.38 | −2.76 ± 6.36 |
| C3 | −0.41 ± 2.67 | −2.85 ± 4.98 | 4.64 ± 0.35 | −0.41 ± 3.56 | −2.85 ± 6.64 | 4.64 ± 0.47 |
| C4 | 4.09 ± 3.95 | 5.54 ± 2.84 | −4.66 ± 3.73 | 4.09 ± 5.26 | 5.54 ± 3.79 | −4.66 ± 4.97 |
| C5 | 2.64 ± 0.65 | −4.84 ± 0.67 | 4.79 ± 0.88 | 2.64 ± 0.86 | −4.84 ± 0.89 | 4.79 ± 1.17 |
| C6 | 6.01 ± 2.25 | 2.84 ± 1.61 | −2.56 ± 1.01 | 6.01 ± 3.00 | 2.84 ± 2.14 | −2.56 ± 1.34 |
| C7 | −0.85 ± 1.04 | −5.92 ± 0.87 | 0.26 ± 2.56 | −0.85 ± 1.39 | −5.92 ± 1.16 | 0.26 ± 3.41 |

TABLE 2B-continued

Pharmacophore Elements Coordinate Ranges MASP-2 Inhibitors

| Label | Range for (x, y, z) ± 3 standard deviations | | | Range for (x, y, z) ± 4 standard deviations | | |
|---|---|---|---|---|---|---|
| | x | y | z | x | y | z |
| CA1 | −0.61 ± 1.49 | −3.55 ± 1.15 | 2.50 ± 1.70 | −0.61 ± 1.99 | −3.55 ± 1.53 | 2.5 ± 2.26 |
| CA2 | 4.00 ± 1.43 | 3.49 ± 0.97 | −3.49 ± 1.07 | 4.00 ± 1.91 | 3.49 ± 1.29 | −3.49 ± 1.43 |
| CA3 | −5.29 ± 2.52 | −1.15 ± 4.44 | −2.77 ± 3.26 | −5.29 ± 3.36 | −1.15 ± 5.92 | −2.77 ± 4.35 |
| CA4 | 4.02 ± 4.37 | 5.89 ± 2.29 | −3.90 ± 0.62 | 4.02 ± 5.83 | 5.89 ± 3.05 | −3.9 ± 0.83 |
| CA5 | 1.84 ± 3.83 | 2.62 ± 3.80 | −5.13 ± 2.70 | 1.84 ± 5.11 | 2.62 ± 5.06 | −5.13 ± 3.60 |
| CA6 | −1.88 ± 3.34 | 2.21 ± 1.76 | −1.85 ± 5.19 | −1.88 ± 4.46 | 2.21 ± 2.35 | −1.85 ± 6.92 |
| H1 | −8.33 ± 0.18 | −1.98 ± 0.16 | −5.56 ± 0.17 | −8.33 ± 0.24 | −1.98 ± 0.22 | −5.56 ± 0.23 |
| H2 | −2.25 ± 1.04 | −2.33 ± 2.11 | 2.28 ± 2.89 | −2.25 ± 1.38 | −2.33 ± 2.82 | 2.28 ± 3.86 |
| H3 | −0.36 ± 1.76 | −3.03 ± 6.32 | −0.98 ± 3.01 | −0.36 ± 2.34 | −3.03 ± 8.43 | −0.98 ± 4.01 |
| H4 | −0.28 ± 2.24 | −1.61 ± 5.03 | 3.01 ± 1.68 | −0.28 ± 2.99 | −1.61 ± 6.71 | 3.01 ± 2.24 |
| N1 | 0.10 ± 1.70 | −5.35 ± 3.00 | 1.66 ± 2.68 | 0.10 ± 2.26 | −5.35 ± 4.00 | 1.66 ± 3.57 |
| N2 | −0.49 ± 1.11 | −0.11 ± 1.45 | −2.46 ± 1.12 | −0.49 ± 1.48 | −0.11 ± 1.93 | −2.46 ± 1.50 |
| O1 | −2.52 ± 2.03 | 0.57 ± 2.16 | 2.02 ± 1.70 | −2.52 ± 2.70 | 0.57 ± 2.88 | 2.02 ± 2.27 |
| O2 | 0.00 ± 2.23 | 0.00 ± 2.00 | 0.00 ± 2.65 | 0.00 ± 2.98 | 0.00 ± 2.66 | 0.00 ± 3.54 |
| O3 | −6.82 ± 8.67 | −1.48 ± 9.09 | −5.36 ± 10.78 | −6.82 ± 11.56 | −1.48 ± 12.12 | −5.36 ± 14.37 |
| O4 | −1.97 ± 2.32 | −3.24 ± 1.99 | 2.08 ± 1.59 | −1.97 ± 3.09 | −3.24 ± 2.65 | 2.08 ± 2.12 |

The present disclosure provides a compound for use in the treatment of MASP-2-associated diseases or disorders, wherein the compound comprises a combination of pharmacophore elements comprising:
(a) an S1 pharmacophore group comprising CA1 and N1 pharmacophore elements or CA1 and C5 pharmacophore elements; and/or
(b) an S2 pharmacophore group comprising H4 and O2 pharmacophore elements; and/or
(c) an S3 pharmacophore group comprising a C2 pharmacophore element and an N2 or H3 pharmacophore element;
wherein:
C2 and C5 are hydrophobic groups;
CA1 is an aromatic ring;
H3 and H4 are hydrogen bond donors;
N1 and N2 are positive ionizable groups; and
O2 is a hydrogen bond acceptor;
wherein C2, C5, CA1, H3, H4, N1, N2, and O2 have coordinates in the ranges given in Table 3, 4, or 5 below.

In some embodiments, the compound comprises a combination of pharmacophore elements comprising:
(a) an S1 pharmacophore group comprising CA1 and N1 pharmacophore elements or CA1 and C5 pharmacophore elements; and
(b) an S2 pharmacophore group comprising H4 and O2 pharmacophore elements; and
(c) an S3 pharmacophore group comprising a C2 pharmacophore element and an N2 or H3 pharmacophore element.
wherein C2, C5, CA1, H3, H4, N1, N2, and O2 have coordinates in the ranges given in Table 3, 4, or 5 below.

In some embodiments, C2, C5, CA1, H3, H4, N1, N2, and O2 have coordinates in the ranges given in Table 3 below:

TABLE 3

| Pharmacophore element | x coordinate | y coordinate | z coordinates |
|---|---|---|---|
| C2 | 0.30 ± 3.55 | 1.17 ± 4.04 | −2.76 ± 4.77 |
| C5 | 2.64 ± 0.65 | −4.84 ± 0.67 | 4.79 ± 0.88 |
| CA1 | −0.61 ± 1.49 | −3.55 ± 1.15 | 2.50 ± 1.70 |
| H3 | −0.36 ± 1.76 | −3.03 ± 6.32 | −0.98 ± 3.01 |

TABLE 3-continued

| Pharmacophore element | x coordinate | y coordinate | z coordinates |
|---|---|---|---|
| H4 | −0.28 ± 2.24 | −1.61 ± 5.03 | 3.01 ± 1.68 |
| N1 | 0.10 ± 1.70 | −5.35 ± 3.00 | 1.66 ± 2.68 |
| N2 | −0.49 ± 1.11 | −0.11 ± 1.45 | −2.46 ± 1.12 |
| O2 | 0.00 ± 2.23 | 0.00 ± 2.00 | 0.00 ± 2.65 |

In some embodiments, C2, C5, CA1, H3, H4, N1, N2, and O2 have coordinates in the ranges given in Table 4 below:

TABLE 4

| Pharmacophore element | x coordinate | y coordinate | z coordinates |
|---|---|---|---|
| C2 | 0.30 ± 2.37 | 1.17 ± 2.69 | −2.76 ± 3.18 |
| C5 | 2.64 ± 0.43 | −4.84 ± 0.45 | 4.79 ± 0.59 |
| CA1 | −0.61 ± 1.00 | −3.55 ± 0.76 | 2.50 ± 1.13 |
| H3 | −0.36 ± 1.17 | −3.03 ± 4.21 | −0.98 ± 2.01 |
| H4 | −0.28 ± 1.49 | −1.61 ± 3.35 | 3.01 ± 1.12 |
| N1 | 0.10 ± 1.13 | −5.35 ± 2.00 | 1.66 ± 1.78 |
| N2 | −0.49 ± 0.74 | −0.11 ± 0.96 | −2.46 ± 0.75 |
| O2 | 0.00 ± 1.49 | 0.00 ± 1.33 | 0.00 ± 1.77 |

In some embodiments, C2, C5, CA1, H3, H4, N1, N2, and O2 have coordinates in the ranges given in Table 5 below:

TABLE 5

| Pharmacophore element | x coordinate | y coordinate | z coordinates |
|---|---|---|---|
| C2 | 0.30 ± 1.18 | 1.17 ± 1.35 | −2.76 ± 1.59 |
| C5 | 2.64 ± 0.22 | −4.84 ± 0.22 | 4.79 ± 0.29 |
| CA1 | −0.61 ± 0.5 | −3.55 ± 0.38 | 2.5 ± 0.57 |
| H3 | −0.36 ± 0.59 | −3.03 ± 2.11 | −0.98 ± 1.00 |
| H4 | −0.28 ± 0.75 | −1.61 ± 1.68 | 3.01 ± 0.56 |
| N1 | 0.10 ± 0.57 | −5.35 ± 1.00 | 1.66 ± 0.89 |
| N2 | −0.49 ± 0.37 | −0.11 ± 0.48 | −2.46 ± 0.37 |
| O2 | 0.00 ± 0.74 | 0.00 ± 0.67 | 0.00 ± 0.88 |

In some embodiments, the S1 pharmacophore group comprises CA1 and N1 pharmacophore elements.

In some embodiments, the S1 pharmacophore group further comprises a C3 pharmacophore element, wherein C3 is a hydrophobic group and has coordinates in the ranges given in Table 6 below.

TABLE 6

| Pharmacophore element | x coordinate | y coordinate | z coordinates |
|---|---|---|---|
| C3 | −0.41 ± 2.67 | −2.85 ± 4.98 | 4.64 ± 0.35 |

In some embodiments, C3 has coordinates in the ranges given in Table 7 below.

TABLE 7

| Pharmacophore element | x coordinate | y coordinate | z coordinates |
|---|---|---|---|
| C3 | −0.41 ± 1.78 | −2.85 ± 3.32 | 4.64 ± 0.23 |

In some embodiments, C3 has coordinates in the ranges given in Table 8 below.

TABLE 8

| Pharmacophore element | x coordinate | y coordinate | z coordinates |
|---|---|---|---|
| C3 | −0.41 ± 0.89 | −2.85 ± 1.66 | 4.64 ± 0.12 |

In some embodiments, the S1 pharmacophore group comprises CA1 and C5 pharmacophore elements.

In some embodiments, the S1 pharmacophore group further comprises 1, 2, or 3 pharmacophore elements selected from the group consisting of C7, H2 and O4, wherein:
C7 is a hydrophobic group;
H2 is a hydrogen bond donor; and
O4 is a hydrogen bond acceptor; and
wherein C7, H2 and O4 have the coordinates in the ranges given in Table 9 below:

TABLE 9

| Pharmacophore element | x coordinate | y coordinate | z coordinates |
|---|---|---|---|
| C7 | −0.85 ± 1.04 | −5.92 ± 0.87 | 0.26 ± 2.56 |
| H2 | −2.25 ± 1.04 | −2.33 ± 2.11 | 2.28 ± 2.89 |
| O4 | −1.97 ± 2.32 | −3.24 ± 1.99 | 2.08 ± 1.59 |

In some embodiments, C7, H2 and O4 have coordinates in the ranges given in Table 10 below:

TABLE 10

| Pharmacophore element | x coordinate | y coordinate | z coordinates |
|---|---|---|---|
| C7 | −0.85 ± 0.70 | −5.92 ± 0.58 | 0.26 ± 1.71 |
| H2 | −2.25 ± 0.69 | −2.33 ± 1.41 | 2.28 ± 1.93 |
| O4 | −1.97 ± 1.54 | −3.24 ± 1.33 | 2.08 ± 1.06 |

In some embodiments, C7, H2 and O4 have coordinates in the ranges given in Table 11 below:

TABLE 11

| Pharmacophore element | x coordinate | y coordinate | z coordinates |
|---|---|---|---|
| C7 | −0.85 ± 0.35 | −5.92 ± 0.29 | 0.26 ± 0.85 |
| H2 | −2.25 ± 0.35 | −2.33 ± 0.7 | 2.28 ± 0.96 |
| O4 | −1.97 ± 0.77 | −3.24 ± 0.66 | 2.08 ± 0.53 |

In some embodiments, the S1 pharmacophore group comprises a C7 pharmacophore element.

In some embodiments, the S1 pharmacophore group comprises an H2 pharmacophore element.

In some embodiments, the S1 pharmacophore group comprises an O4 pharmacophore element.

In some embodiments, the S2 pharmacophore group further comprises 1 or 2 pharmacophore elements selected from the group consisting of CA6 and O1, wherein:
CA6 is an aromatic ring;
O1 is a hydrogen bond acceptor;
wherein CA6 and O1 have coordinates in the ranges given in Table 12 below:

TABLE 12

| Pharmacophore element | x coordinate | y coordinate | z coordinates |
|---|---|---|---|
| CA6 | −1.88 ± 3.34 | 2.21 ± 1.76 | −1.85 ± 5.19 |
| O1 | −2.52 ± 2.03 | 0.57 ± 2.16 | 2.02 ± 1.70 |

In some embodiments, CA6 and O1 have coordinates in the ranges given in Table 13 below:

TABLE 13

| Pharmacophore element | x coordinate | y coordinate | z coordinates |
|---|---|---|---|
| CA6 | −1.88 ± 2.23 | 2.21 ± 1.18 | −1.85 ± 3.46 |
| O1 | −2.52 ± 1.35 | 0.57 ± 1.44 | 2.02 ± 1.13 |

In some embodiments, CA6 and O1 have coordinates in the ranges given in Table 14 below:

TABLE 14

| Pharmacophore element | x coordinate | y coordinate | z coordinates |
|---|---|---|---|
| CA6 | −1.88 ± 1.11 | 2.21 ± 0.59 | −1.85 ± 1.73 |
| O1 | −2.52 ± 0.68 | 0.57 ± 0.72 | 2.02 ± 0.57 |

In some embodiments, the S1 pharmacophore group comprises a CA6 pharmacophore element.

In some embodiments, the S1 pharmacophore group comprises an O1 pharmacophore element.

In some embodiments, the S3 pharmacophore group comprises C2 and N2 pharmacophore elements.

In some embodiments, the S3 pharmacophore group further comprises an H3 pharmacophore element.

In some embodiments, the compound further comprises an S4 pharmacophore group;
wherein the S4 pharmacophore group comprises a C4, CA2, CA4 or CA5 pharmacophore element; wherein
C4 is a hydrophobic group; and
CA2, CA4, and CA5 are aromatic rings; and
wherein C4, CA2, CA4, and CA5 have coordinates in the ranges given in Table 15 below:

TABLE 15

| Pharmacophore element | x coordinate | y coordinate | z coordinates |
|---|---|---|---|
| C4 | 4.09 ± 3.95 | 5.54 ± 2.84 | −4.66 ± 3.73 |
| CA2 | 4.00 ± 1.43 | 3.49 ± 0.97 | −3.49 ± 1.07 |
| CA4 | 4.02 ± 4.37 | 5.89 ± 2.29 | −3.90 ± 0.62 |
| CA5 | 1.84 ± 3.83 | 2.62 ± 3.80 | −5.13 ± 2.70 |

In some embodiments, C4, CA2, CA4, and CA5 have coordinates in the ranges given in Table 16 below:

TABLE 16

| Pharmacophore element | x coordinate | y coordinate | z coordinates |
|---|---|---|---|
| C4 | 4.09 ± 2.63 | 5.54 ± 1.89 | −4.66 ± 2.49 |
| CA2 | 4.00 ± 0.96 | 3.49 ± 0.65 | −3.49 ± 0.72 |
| CA4 | 4.02 ± 2.92 | 5.89 ± 1.52 | −3.90 ± 0.41 |
| CA5 | 1.84 ± 2.55 | 2.62 ± 2.53 | −5.13 ± 1.80 |

In some embodiments, C4, CA2, CA4, and CA5 have coordinates in the ranges given in Table 17 below:

TABLE 17

| Pharmacophore element | x coordinate | y coordinate | z coordinates |
|---|---|---|---|
| C4 | 4.09 ± 1.32 | 5.54 ± 0.95 | −4.66 ± 1.24 |
| CA2 | 4.00 ± 0.48 | 3.49 ± 0.32 | −3.49 ± 0.36 |
| CA4 | 4.02 ± 1.46 | 5.89 ± 0.76 | −3.90 ± 0.21 |
| CA5 | 1.84 ± 1.28 | 2.62 ± 1.27 | −5.13 ± 0.90 |

In some embodiments, the S4 pharmacophore group comprises C4.

In some embodiments, the S4 pharmacophore group comprises CA2.

In some embodiments, the S4 pharmacophore group comprises CA4.

In some embodiments, the S4 pharmacophore group comprises CA5.

In some embodiments, the S4 pharmacophore group further comprises 1, 2, 3, or 4 additional pharmacophore elements selected from the group consisting of C6, C7, CA4 and CA5, wherein:

C6 and C7 are hydrophobic groups; and

CA4 and CA5 are aromatic rings; and wherein C6, C7, CA4, and CA5 have coordinates in the ranges given in Table 18 below:

TABLE 18

| Pharmacophore element | x coordinate | y coordinate | z coordinates |
|---|---|---|---|
| C6 | 6.01 ± 2.25 | 2.84 ± 1.61 | −2.56 ± 1.01 |
| C7 | −0.85 ± 1.04 | −5.92 ± 0.87 | 0.26 ± 2.56 |
| CA4 | 4.02 ± 4.37 | 5.89 ± 2.29 | −3.90 ± 0.62 |
| CA5 | 1.84 ± 3.83 | 2.62 ± 3.80 | −5.13 ± 2.70 |

In some embodiments, C6, C7, CA4, and CA5 have coordinates in the ranges given in Table 19 below:

TABLE 19

| Pharmacophore element | x coordinate | y coordinate | z coordinates |
|---|---|---|---|
| C6 | 6.01 ± 1.50 | 2.84 ± 1.07 | −2.56 ± 0.67 |
| C7 | −0.85 ± 0.70 | −5.92 ± 0.58 | 0.26 ± 1.71 |
| CA4 | 4.02 ± 2.92 | 5.89 ± 1.52 | −3.90 ± 0.41 |
| CA5 | 1.84 ± 2.55 | 2.62 ± 2.53 | −5.13 ± 1.80 |

In some embodiments, C6, C7, CA4, and CA5 have coordinates in the ranges given in Table 20 below:

TABLE 20

| Pharmacophore element | x coordinate | y coordinate | z coordinates |
|---|---|---|---|
| C6 | 6.01 ± 0.75 | 2.84 ± 0.54 | −2.56 ± 0.34 |
| C7 | −0.85 ± 0.35 | −5.92 ± 0.29 | 0.26 ± 0.85 |
| CA4 | 4.02 ± 1.46 | 5.89 ± 0.76 | −3.90 ± 0.21 |
| CA5 | 1.84 ± 1.28 | 2.62 ± 1.27 | −5.13 ± 0.90 |

In some embodiments, the S4 pharmacophore group comprises a C6 pharmacophore element.

In some embodiments, the S4 pharmacophore group comprises a C7 pharmacophore element.

In some embodiments, the S4 pharmacophore group comprises a CA4 pharmacophore element.

In some embodiments, the S4 pharmacophore group comprises a CA5 pharmacophore element.

In some embodiments, the compound further comprises an RM pharmacophore group; wherein the RM pharmacophore group comprises a CA3 pharmacophore element, wherein CA3 is an aromatic ring that has coordinates in the ranges given in Table 21 below:

TABLE 21

| Pharmacophore element | x coordinate | y coordinate | z coordinates |
|---|---|---|---|
| CA3 | −5.29 ± 2.52 | −1.15 ± 4.44 | −2.77 ± 3.26 |

In some embodiments, CA3 has coordinates in the ranges given in Table 22 below:

TABLE 22

| Pharmacophore element | x coordinate | y coordinate | z coordinates |
|---|---|---|---|
| CA3 | −5.29 ± 1.68 | −1.15 ± 2.96 | −2.77 ± 2.17 |

In some embodiments, CA3 has coordinates in the ranges given in Table 23 below: Table 23.

TABLE 23

| Pharmacophore element | x coordinate | y coordinate | z coordinates |
|---|---|---|---|
| CA3 | −5.29 ± 0.84 | −1.15 ± 1.48 | −2.77 ± 1.09 |

In some embodiments, the RM pharmacophore group further comprises 1 or 2 additional pharmacophore elements selected from the group consisting of H1 and O3, wherein:

H1 is a hydrogen bond donor; and

O3 is a hydrogen bond acceptor; and wherein H1 and O3 have coordinates in the ranges given in Table 24 below:

TABLE 24

| Pharmacophore element | x coordinate | y coordinate | z coordinates |
|---|---|---|---|
| H1 | −8.33 ± 0.18 | −1.98 ± 0.16 | −5.56 ± 0.17 |
| O3 | −6.82 ± 8.67 | −1.48 ± 9.09 | −5.36 ± 10.78 |

In some embodiments, H1 and O3 have coordinates in the ranges given in Table 25 below:

TABLE 25

| Pharmacophore element | x coordinate | y coordinate | z coordinates |
|---|---|---|---|
| H1 | −8.33 ± 0.12 | −1.98 ± 0.11 | −5.56 ± 0.11 |
| O3 | −6.82 ± 5.78 | −1.48 ± 6.06 | −5.36 ± 7.19 |

In some embodiments, H1 and O3 have coordinates in the ranges given in Table 26 below:

TABLE 26

| Pharmacophore element | x coordinate | y coordinate | z coordinates |
|---|---|---|---|
| H1 | −8.33 ± 0.06 | −1.98 ± 0.05 | −5.56 ± 0.06 |
| O3 | −6.82 ± 2.89 | −1.48 ± 3.03 | −5.36 ± 3.59 |

In some embodiments, the RM pharmacophore group comprises H1.

In some embodiments, the RM pharmacophore group comprises O3.

Figure 66:
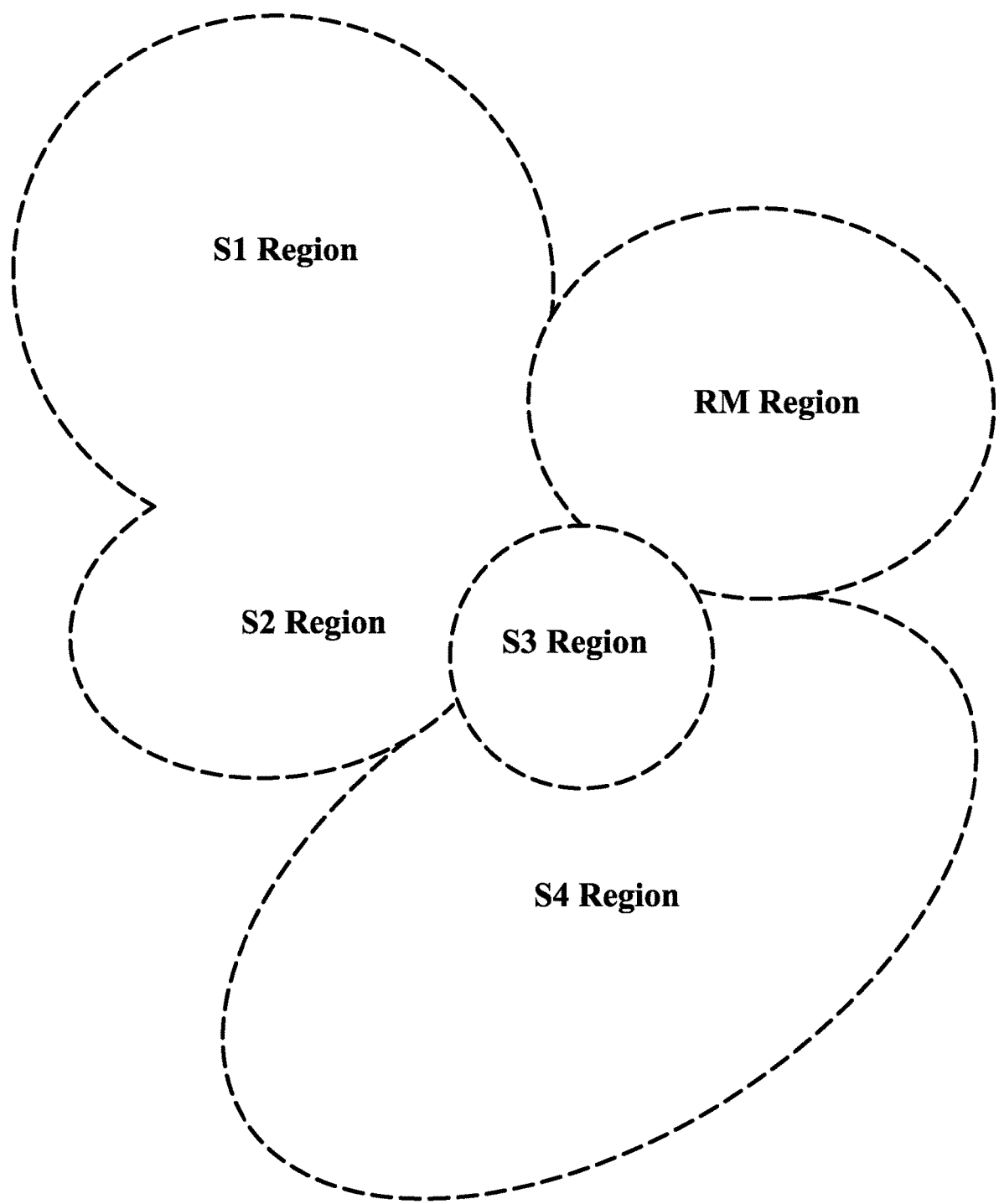
FIG. 66 is a plot showing a representation of the MASP-2 binding sub-pockets.

FIG. 66 shows a schematic representation of the MASP+2 binding sub-pockets. While not being limited by any theory, it is understood that certain pharmacophore groups and elements are associated with binding to certain regions of the MASP-2 protein. For clarity reasons only, some of the sub-pockets are shown and referred to in the discussion and additional figures below.

Certain combinations of the pharmacophore elements listed in Table 1 were found to be favorable and associated with more potent activity. In particular, in some embodiments, effective MASP-2 inhibitors can include S1, S2 and/or S3 pharmacophore groups. In some embodiments, effective MASP-2 inhibitors can include S1, S2, S3 and/or S4 pharmacophore groups.

In some embodiments, the S1 pharmacophore group can be selected from the pharmacophore groups S1a, S1b and S1c, wherein:
the S1a pharmacophore group includes the pharmacophore elements CA1 and N1;
the S1b pharmacophore group includes the pharmacophore elements CA1, N1 and C3; and
the S1c pharmacophore group includes the pharmacophore elements CA1 and C5 elements, and can also optionally include 1, 2, 3 or 4 of the pharmacophore elements C5, C7, H2 and/or O4.

The S2 pharmacophore group includes the pharmacophore elements H4 and O2, and can optionally also include the pharmacophore elements O1 and/or CA6.

In some embodiments, the S3 pharmacophore group can be selected from the pharmacophore groups S3a and S3b, wherein:
the S3a pharmacophore group includes the pharmacophore elements C2 and N2, and can optionally also include the pharmacophore element H3; and
the S3b pharmacophore group includes the pharmacophore elements C3 and H3.

The compounds can also include an S4 pharmacophore group.

In some embodiments, the S4 pharmacophore group can be selected from the pharmacophore groups S4a, S4b, S4c, S4d, S4e and S4f, wherein:
the S4a pharmacophore group includes the pharmacophore element CA2, and can optionally also include 1, 2, 3, or 4 of the pharmacophore elements C6, C7, CA4 and/or CA5;
the S4b pharmacophore group includes the pharmacophore element CA2;
the S4c pharmacophore group includes the pharmacophore elements CA2 and CA4;
the S4d pharmacophore group includes the pharmacophore elements CA2 and C6;
the S4e pharmacophore group includes the pharmacophore element CA5; and
the S4e pharmacophore group includes the pharmacophore element C4.

The compounds can also include an RM pharmacophore group, which includes the pharmacophore element CA3. The RM pharmacophore group can also optionally include 1 or 2 pharmacophore elements selected from H1 and/or H3.

Preferred are combinations where S1, S2, S3 and S4 pharmacophore groups are present. An RM pharmacophore group can also optionally be present.

Table 27 provides a listing of pharmacophore group elements and combinations. Optional elements are shown in parentheses.

TABLE 27

Listing of Pharmacophore Group Elements and Combinations

| Pharmacophore groups | Pharmacophore elements |
|---|---|
| S1a | CA1, N1 |
| S1b | CA1, N1, C3 |
| S1c | CA1, C5, (C7), (O4), (H2) |
| S2 | H4, (O1), O2, (CA6) |
| S3a | N2, (H3), C2 |
| S3b | H3, C2 |
| S4a | CA2, (CA4), (CA5), (C6), (C7) |
| S4b | CA2 |
| S4c | CA2, CA4 |
| S4d | CA2, C6 |
| S4e | CA5 |
| S4f | C4 |
| RM | CA3, (O3), (H1) |

Elements in parentheses may be matched.

Distances between said pharmacophore elements and the closest atom of each ligand in its crystallized conformation are summarized in Table A4 (Appendix), distances and bond and torsion angles separating atoms matched by said pharmacophore elements are summarized in Tables A5-A7 (Appendix) and defined in FIGS. 67-75, and distances between pharmacophore elements and the nearest binding site residue (Table A8).

Table A4 describes the distances between individual averaged pharmacophore elements and a small molecule for a conformation of the small molecule as it binds into the binding site of hMASP-2. The ligand-protein complexes were experimentally determined by X-ray crystallography. The statistical values used for description in the text are summarizing all values for a specific distance. A missing value indicates that the averaged pharmacophore element is not present in the molecule.

Table A5 describes the distances between specific atoms in a molecule as it binds into the binding site of hMASP-2 matched by select pharmacophore elements The ligand-protein complexes were experimentally determined by X-ray crystallography. The statistical values used for description in the text are summarizing all values for each distance. A missing value indicates that either one or two pharmacophore elements are not present in the molecule.

Table A6 describes the angles between specific atoms in a molecule as it binds into the binding site of hMASP-2 matched by select pharmacophore elements. The ligand-protein complexes were experimentally determined by X-ray crystallography. The statistical values used for description in the text are summarizing all values for each angle. A missing value indicates that either one, two or three pharmacophore elements are not present in the molecule.

Table A7 describes the torsion angles between specific atoms in a molecule as it binds into the binding site of hMASP-2 matched by select pharmacophore elements. The ligand-protein complexes were experimentally determined by X-ray crystallography. The statistical values used for description in the text are summarizing all values for each torsion angle. A missing value indicates that either one, two, three or four pharmacophore elements are not present in the molecule.

Table A8 describes the shortest distances between each pharmacophore element and binding site residues of all hMASP-2 crystal structures. Starting from aligned ligand-protein complexes the small molecule in every structure was replaced by the averaged pharmacophore model. Each pharmacophore element can interact with several binding site residues. Furthermore, different atoms of a residue can form shortest distances with a pharmacophore element. The summary statistics of all distances between a pharmacophore element and a residue form the basis for the description in the text.

The center of a pharmacophore is defined as S2 region (FIGS. 67 and 68) (Table 27) including hydrogen bond donating group H4, hydrogen bond accepting group O1, and hydrogen bond accepting group O2, which are highly conserved among all compounds. An additional aromatic ring (CA6) can be matched. Potent MASP-2 inhibitor compounds match one of 4 of these pharmacophore elements. The distance d(H4,O1) between H4 and O1 is an average of 3.984 Å with a standard deviation of 1.071 Å, a minimum of 2.084 Å, and a maximum of 6.969. Between HA and O2 the distance d(H4,O2) is an average of 3.975 Å with a standard deviation of 1.125 Å, a minimum of 2.420 Å, and a maximum of 8.835 Å. The distance d(O1,O2) between O1 and O2 is an average of 3.585 Å with a standard deviation of 1.034 Å, a minimum of 2.286 Å, and a maximum of 9.569 Å. The bond angle (O1,O2,H4) as defined by O1, O2 and H4 between O1, O2 and H4 is an average of 125.220 with a standard deviation of 16.57°, a minimum of 61.95°, and a maximum of 156.25°. The average distance d(CA6,O1) between CA6 and O1 is 5.186 Å with a standard deviation of 1.781 Å, a minimum value of 2.732 Å, and a maximum value of 7.041 Å. The average distance d(CA6,O2) between CA6 and O2 is 3.797 Å with a standard deviation of 2.477 Å, a minimum value of 1.127 Å and a maximum value of 8.449 Å. The average bond angle ∠(O1,CA6,O2) between O1, CA6 and O2 is 106.010 with a standard deviation of 33.54°, a minimum value of 75.74° and a maximum value of 159.18°. The average torsion angle ∠(CA6,O1,H4,O2) as defined by CA6, O1, H4 and O2 is 17.400 with a standard deviation of 29.14°, a minimum value of −19.90° and a maximum value of 55.30°.

Figure 67:
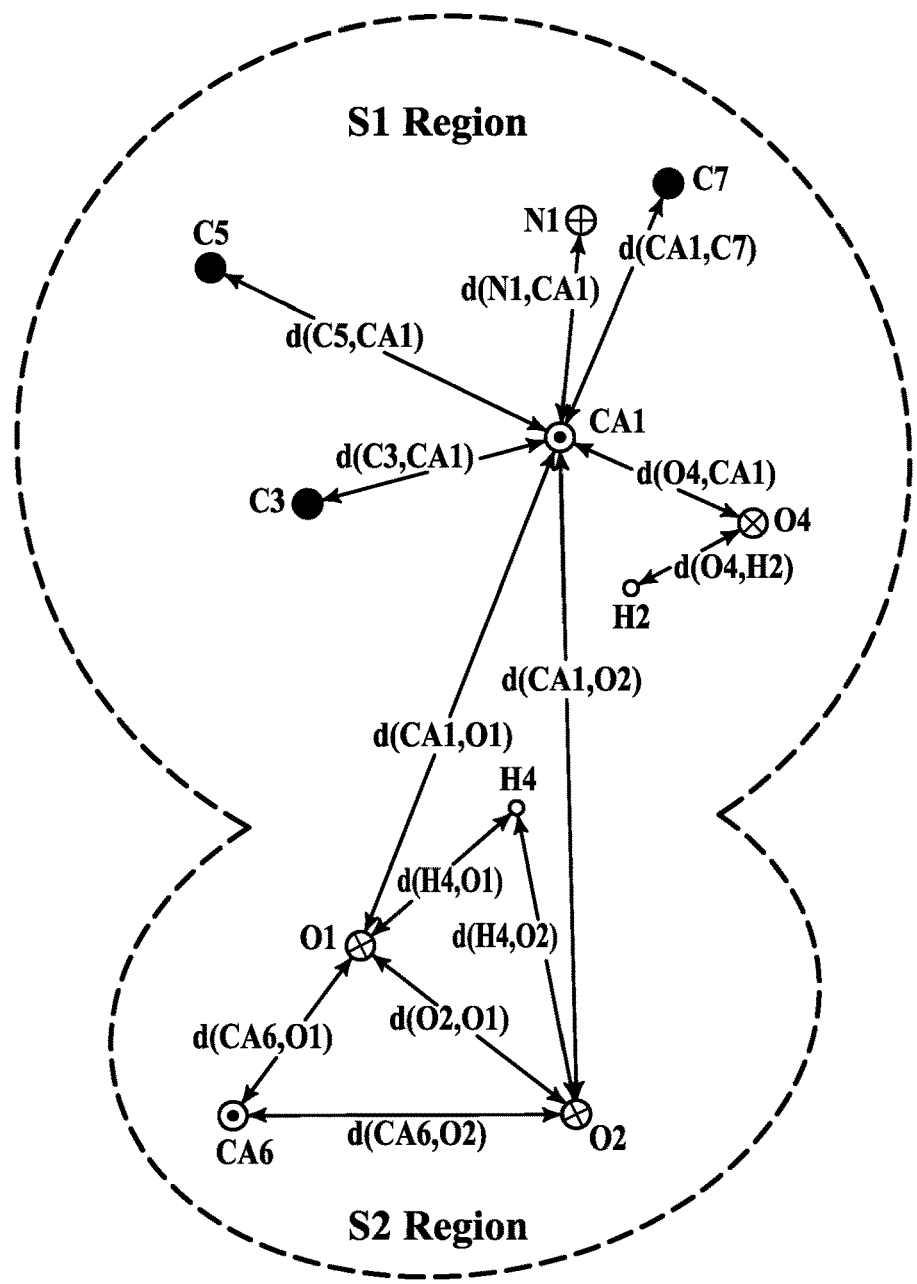
FIG. 67 is a depiction of the distances between pharmacophore elements describing the S1 and S2 regions. The S2 region comprises H4, O1, O2 and CA6. The S1 region area consists of H2, O4, CA1, C3, C5, C7, and N1. Distances mentioned in the text are shown.
Figure 68:
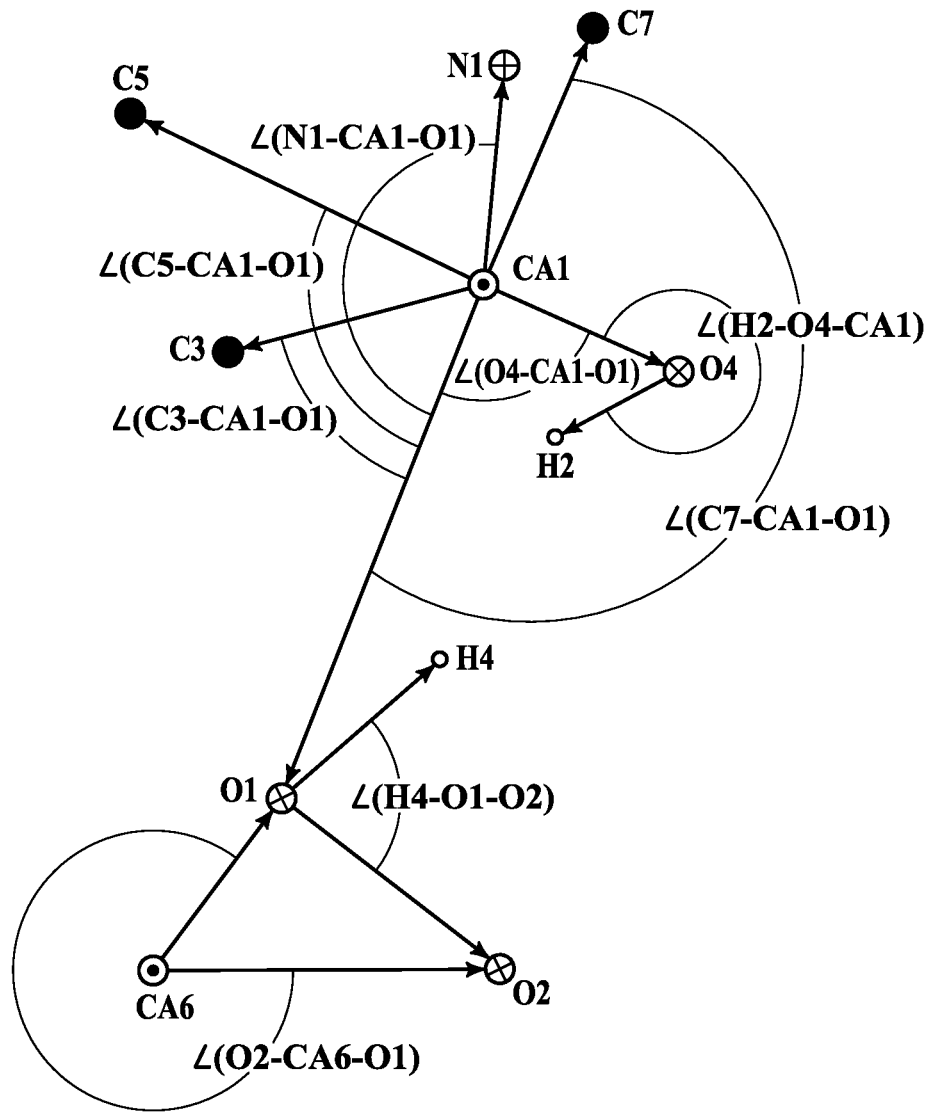
FIG. 68 is a plot depicting the angles between pharmacophore elements describing the S1 and S2 region.

The pharmacophore elements in the S1 region as defined in FIGS. 67 and 68 and Table 27 represent a collection of pharmacophore subsets that are preferred for effective MASP-2 inhibition. Subsets have in common an aromatic ring CA1 which forms with O1 and O2 a bond angle ∠(CA1, O1, O2) of an average of 109.450 with a standard deviation of 12.06°, a minimum value of 72.650 and a maximum value of 151.69°. The average torsion angle ∠(CA1,O2,H4,O1) as defined by CA1, O2, H4 and O1 is −76.06° with a standard deviation of 50.45°, a minimum value of −175.49° and a maximum value of 150.81°. The average distance d(CA1, O1) between CA1 and O1 is 4.703 Å and the standard deviation is 0.647 Å, the minimum value is 3.345 Å and the maximum value is 7.586 Å. The average distance d(CA1, O2) between CA1 and O2 4.524 Å and the standard deviation is 0.948 Å, with a minimum value of 3.506 Å and a maximum value of 9.417 Å.

For the S1a pharmacophore group in Table 27 a positively charged group N1 is preferred for the compounds to be efficient MASP-2 inhibitors. The average distance d(CA1, N1) between CA1 and N1 is 3.463 Å and a standard deviation of 0.426 Å, with a minimum value of 1.849 Å and a maximum value of 3.658 Å. The average bond angle ∠(N1,CA1,O1) between N1, CA1 and O1 is 164.290 with a standard deviation of 5.24°, a minimum value of 153.110 and a maximum value of 176.16°. The average torsion angle ∠(N1,CA1,O2,H4) as defined by N1, CA1, O2 and H4 is −92.19° with a standard deviation of 67.16°, a minimum value of −159.59° and a maximum value of 106.51°.

Pharmacophore group S1b in Table 27 represents an extension of pharmacophore group S1a with an additional hydrophobic group C3. The average bond distance d(C3, CA1) between C3 and CA1 is 2.858 Å with a standard deviation of 0.010 Å, a minimum value of 2.842 Å and a maximum value of 2.882 Å. The average bond angle ∠(C3, CA1,O1) between C3, CA1 and O1 is 149.91 degree with a standard deviation of 0.51°, a minimum value of 148.890 and a maximum value of 151.05°. The average torsion angle ∠(C3,CA1,O1,H4) as defined by C3, CA1, O1 and H4 is 28.540 with a standard deviation of 9.82°, a minimum value of 21.760 and a maximum value of 66.00°. The average distance d(CA1, N1) between CA1 and N1 is 1.374 Å and a standard deviation of 0.014, a minimum of 1.336, and maximum value of 1.392 Å. The average bond angle ∠(N1, CA1,O1) between N1, CA1 and O1 is 173.400 with a standard deviation of 2.20°, a minimum of 161.820 and maximum of 175.41°. The average torsion angle ∠(N1,CA1, O1,H4) as defined by N1, CA1, O1 and H4 is 2.570 with a standard deviation of 29.67°, a minimum value of −107.13° and a maximum value of 58.16°.

The pharmacophore group S1c comprises the pharmacophore elements aromatic ring CA1 and a hydrophobic group C5, an optional hydrogen bond acceptor O4, or hydrophobic group C7 or an optional hydrogen bond donating group H2. The average distance d(CA1,O4) between CA2 and O4 is 2.592 Å with a standard deviation of 0.367 Å, a minimum of 1.737 Å and maximum value of 2.836 Å. The average bond angle ∠(O1,CA1,O4) between O1, CA1 and O4 is 64.900 with a standard deviation of 5.55°, a minimum value of 51.330 and a maximum value of 73.28°. The average torsion angle ∠(O4,CA1,O1,H4) as defined by O4, CA1, O1 and H4 is −51.12° with a standard deviation of 146.72°, a minimum value of −176.00° and a maximum value of 175.38°. The average distance d(CA1, C5) between CA1 and C5 is 3.173 Å with a standard deviation of 0.128 Å, a minimum value of 3.084 Å and a maximum value 3.547 Å. The average bond angle ∠(C5,CA1,O1) between C5, CA1 and O1 is an average of 159.21° with a standard deviation of 4.12°, a minimum value of 150.20° and a maximum value of 164.79°. The average torsion angle ∠(C5,CA1,O1,H4) as defined by C5, CA1, O1 and H4 is −2.73° with a standard deviation of 39.57°, a minimum value of −110.81° and a maximum value of 38.04°. The average distance d(CA1, C7) between CA1 and C7 is 2.992 Å with a standard deviation of 0.067 Å, a minimum value of 2.903 Å, and a maximum value of 3.065 Å. The average bond angle ∠(C7,CA1,O1) between C7, CA1 and O1 is 132.370 with a standard deviation of 8.18°, a minimum value of 121.010 and a maximum value of 139.92°. The average torsion angle ∠(C7,CA1,O1,H4) as defined by C7, CA1, O1 and H4 is −157.34° with a standard deviation of 4.95°, a minimum value of −161.01° and a maximum value of −150.35°. The average distance d(O4,H2) between O4 and H2 is 0.973 Å with a standard deviation of 0.007 Å, a minimum value of 0.962, and a maximum value of 0.983. The average bond angle ∠(CA1,O4,H2) between CA1, O4 and H2 is 126.980 with a standard deviation of 2.30°, a minimum value of 122.200 and a maximum value of 131.81°. The average torsion angle ∠(H2,O4,CA1,O1) as defined by H2, O4, CA1 and O1 is 29.820 with a standard deviation of 60.96°, a minimum value of −12.92° and a maximum value of 174.89°. The S3 region as defined in Table 27 and FIGS. 66 and 72 includes a protonatable N2 and or a hydrogen bond donor H3 and a hydrophobic group C2. In the collection of pharmacophore elements S3a,b the hydrogen bond donating group H3 and/or the positive ionizable group N2 (Table 27) are preferred to provide potent inhibitors of human MASP-2. The average distance d(O2, H3) between O2 and H3 is 3.993 Å with a standard deviation of 1.422 Å, a minimum value of 1.266 Å and a maximum value of 8.995 Å. The average bond angle ∠(O1,O2,H3) is 141.41°, with a standard deviation of 17.50°, a minimum value of 25.95°, and maximum value of 170.92°. The average torsion angle ∠(H4,O1,O2,H3) as defined by H4, O1, O2 and H3 is 17.91° with a standard deviation of 88.16°, a minimum value of −176.95° and a maximum value of 162.81°. The distance d(O2,N2) between O2 and N2 is 2.830 Å with a standard deviation of 0.295 Å, a minimum value of 2.404 Å and a maximum value of 4.424 Å. The bond angle ∠(O1,O2,N2) is 139.320 with a standard deviation of 16.79°, a minimum value of 44.760 and a maximum value of 175.07°. The average torsion angle ∠(H4,O1,O2,N2) as defined by H4, O1, O2 and N2 is 47940 with a standard deviation of 124.93°, a minimum value of −178.39° and a maximum value of 177.59°. The average distance d(N2,C2) between N2 and C2 is 2.220 Å with a standard deviation of 1.638 Å, a minimum value of 1.321 Å and a maximum value of 8.529 Å. The average bond angle ∠(O2, N2,C2) between O2, N2 and C2 is 130.190 with a standard deviation of 11.79°, a minimum value of 100.680 and a maximum value of 168.69°. The average torsion angle ∠(O1,O2,N2,C2) as defined by O1, O2, N2 and C2 is 99.050 with a standard deviation of 59.50°, a minimum value of −139.940 and maximum value of 151.54°.

Figure 72:
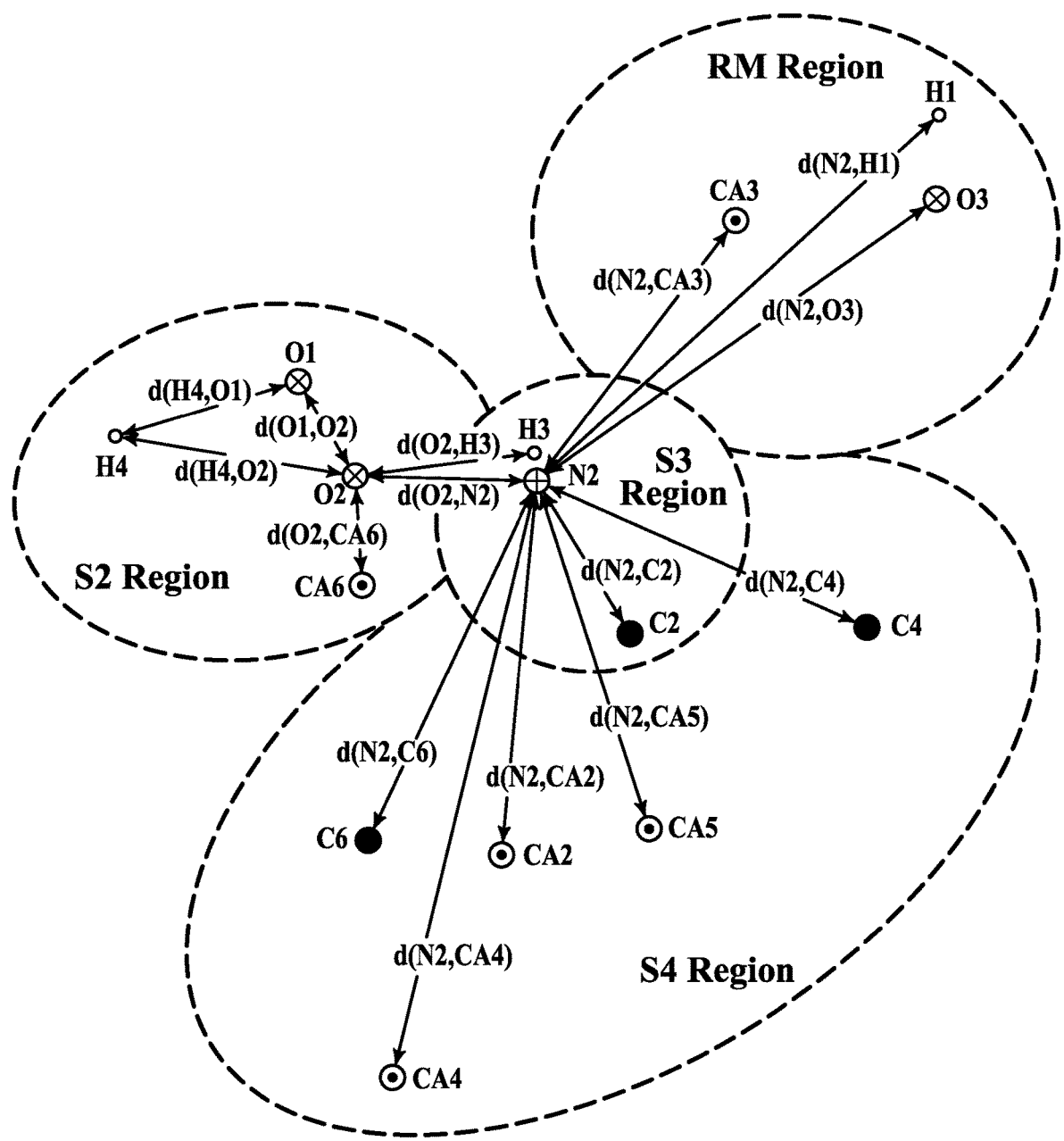
FIG. 72 is a plot depicting the distances between pharmacophore elements describing the S2, S4 and RM region.
Figure 73:
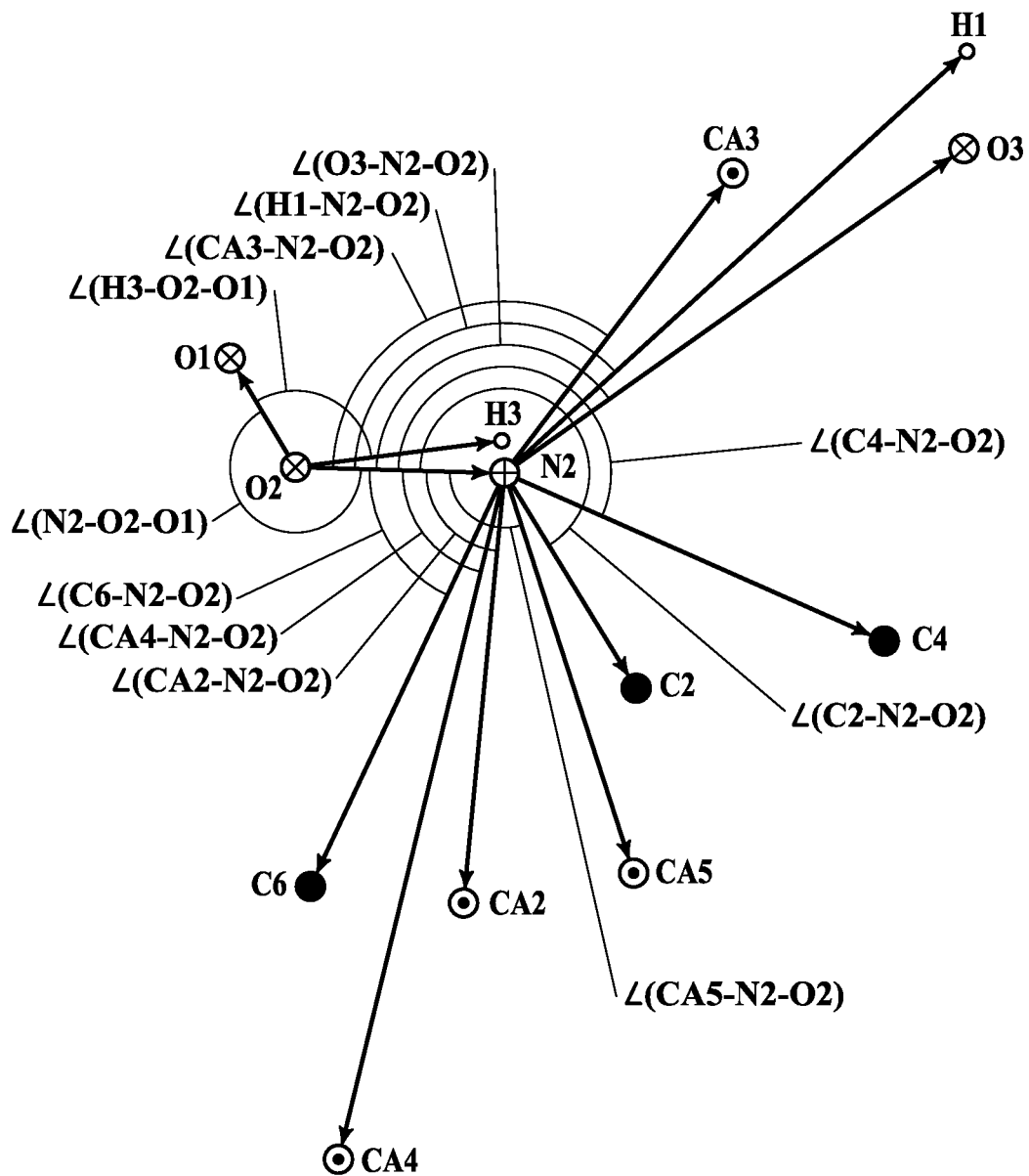
FIG. 73 is a plot depicting the definitions of angles used in the text.
Figure 74:
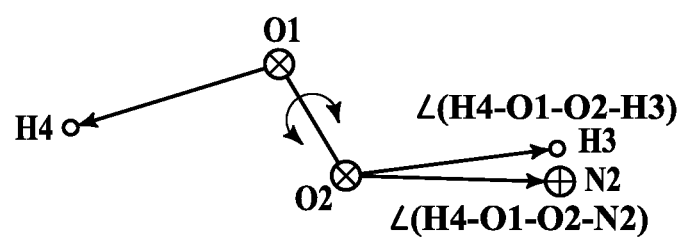
FIG. 74 is a plot depicting the definitions of torsion angles used in the text.

The S4 region contains a cluster of hydrophobic groups and aromatic rings, which can be matched individually or in combination (see Table 27 and FIGS. 72-74 for details).

The average distance d(N2,C4) between N2 and C4 is 7.669 Å with a standard deviation of 0.619 Å, a minimum value of 6.056 Å and a maximum value of 8.240 Å. The average bond angle ∠(O2,N2,C4) between O2, N2 and C4 is 109.140 with a standard deviation of 22.13°, a minimum value of 49.800 and a maximum value of 127.51°. The torsion angle ∠(O1,O2,N2,C4) as defined by O1, O2, N2 and C4 is 118.880 with a standard deviation of 15.36°, a minimum value of 103.260 and a maximum value of 145.41°.

CA5 has an average distance (d(N2,CA5)) of 4.939 to N2 with a standard deviation of 0.623, a minimum value of 3.723 Å and a maximum value of 6.599 Å. The standard bond angle ∠(CA5,N2,O2) between CA5, N2 and O2 is 152.850 with a standard deviation of 12.41°, a minimum value of 111.73° and a maximum value of 161.77°. The average torsion angle ∠(O1,O2,N2,CA5) as defined by O1, O2, N2 and CA5 is 113.480 with a standard deviation of 68.44°, a minimum value of −161.98° and a maximum value of 148.15°.

The average distance d(N2,CA2) between CA2 and N2 is 5.909 Å with a standard deviation of 0.414 Å, a minimum value of 5.064 Å and a maximum value of 8.317 Å. The average bond angle ∠(CA2,N2,O2) between CA2, N2 and O2 is 155.190 with a standard deviation of 2.86°, a minimum value of 145.050 and a maximum value of 163.85°. The average torsion angle ∠(O1,O2,N2,CA2) as defined by O1, O2, N2 and CA2 is 114.960 with a standard deviation of 55.79°, a minimum value of −157.89° and a maximum value of 159.770.

The average distance d(N2,CA4) between CA4 and N2 is 7.669 Å with a standard deviation of 0.620 Å, a minimum value of 6.056 Å and a maximum value of 8.240 Å. The average bond angle ∠(CA4,N2,O2) between CA4, N2 and O2 is 160.71° with a standard deviation of 2.46°, a minimum value of 154.82° and a maximum value of 164.21°. The average torsion angle ∠(O1,O2,N2,CA4) as defined by O1, O2, N2 and CA4 is 113.64° with a standard deviation of 14.37°, a minimum value of 101.00° and a maximum value of 155.91°.

The average distance d(N2, C6) between C6 and N2 is 6.993 Å with a standard deviation of 1.011 Å, a minimum value of 5.556 Å and a maximum value of 8.271 Å. The average bond angle ∠(C6,N2,O2) between C2, N2 and O2 is 102.26° with a standard deviation of 9.84°, a minimum value of 88.59° and a maximum value of 115.79°. The average torsion angle ∠(O1,O2,N2,C6) as defined by O1, O2, N2 and C6 is 143.73° with a standard deviation of 4.82°, a minimum value of 137.30° and a maximum value of 150.07°.

Compounds can also match one or more of the features in another pharmacophore cluster in the RM region (Table 27, FIGS. 66, 72-75). This pharmacophore cluster consists of an aromatic ring CA3, the hydrogen bond accepting group O3 and the hydrogen bond donating group H1.

The average distance d(N2,CA3) between N2 and CA3 is 5.057 Å with a standard deviation of 0.668 Å, a minimum value of 3.779 Å and a maximum value of 5.595 Å. The average bond angle ∠(O2,N2,CA3) between O2, N2 and CA3 is 157.18° with a standard deviation of 3.95°, a minimum value of 151.660 and a maximum value of 161.48°. The average torsion angle ∠(O1,O2,N2,CA3) as defined by O1, O2, N2 and CA3 is −13.65° with a standard deviation of 20.56°, a minimum value of −34.52°, and maximum value of 24.87°.

The average distance d(N2,O3) between O3 and N2 is 8.488 Å with a standard deviation of 0.670 Å, a minimum value of 7.778 Å and a maximum value of 9.724 Å. The average bond angle ∠(O3,N2,O2) between O3, N2 and O2 is 166.020 with a standard deviation of 2.30°, a minimum value of 162.760 and a maximum value of 168.41°. The average torsion angle ∠(O1,O2,N2,O3) as defined by O1, O2, N2 and O3 is −25.81° with a standard deviation of 57.02°, a minimum value of −144.09° and a maximum value of 43.95°.

The average distance d(N2,H1) between H1 and N2 is 8.663 Å with a standard deviation of 0.021 Å, a minimum value of 8.642 Å and a maximum value of 8.684 Å. The average bond angle ∠(H1,N2,O2) between H1, N2 and O2 is 168.740 with a standard deviation of 0.08°, a minimum value of 168.660 and a maximum value of 168.81°. The average torsion angle ∠(O1,O2,N2,H1) as defined by O1, O2, N2 and H1 is −16.54° with a standard deviation of 0.57°, a minimum of −17.10°, and maximum value of −16.97°.

The pharmacophore model is illustrated by the FIG. 66-75.

FIG. 66 is a schematic representation of the pharmacophore model related to elements of the binding site in its entirety. In subsequent figures, only parts of the subsection are shown for clarity.

FIG. 67 is a depiction of the distances between pharmacophore elements describing the S1 and S2 regions. The S2 region comprises H4, O1, O2 and CA6. The S1 region area consists of H2, O4, CA1, C3, C5, C7, and N1. Distances mentioned in the text are shown.

FIG. 68 is a depiction of the angles between the pharmacophore elements describing the S1 and S2 region. The S2 region comprises H4, O1, O2 and CA6. The S1 region consists of H2, O4, CA1, C3, C5, C7, and N1. Bond angles mentioned in the text are shown. Region definitions are omitted for clarity reasons.

Figure 69:
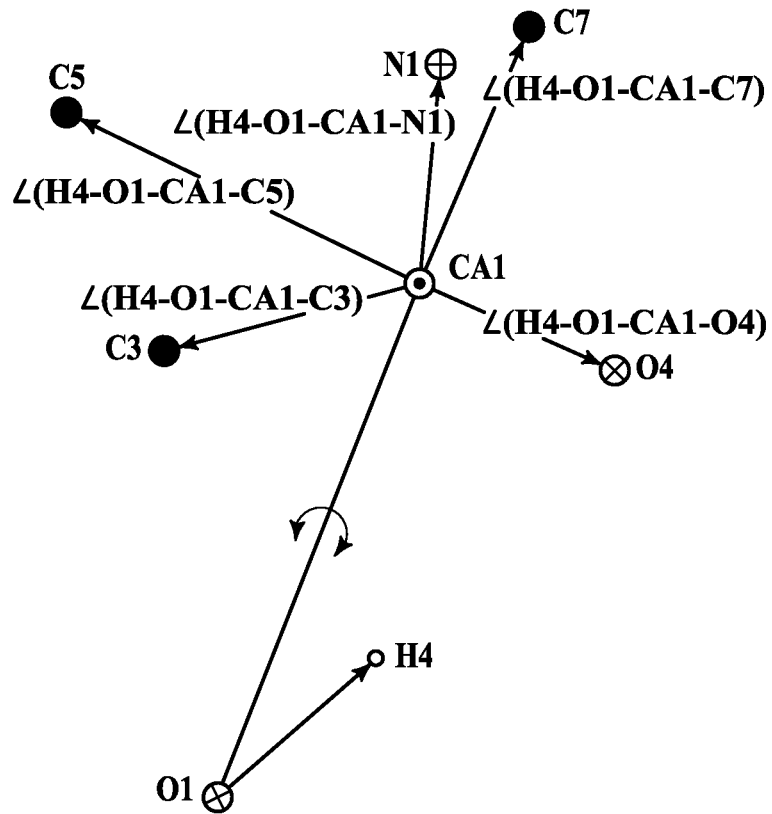
FIG. 69 is a plot depicting the definitions of torsion angles used in the text.

FIG. 69 is a depiction of the definitions of torsion angles used in the text. The torsion angle is formed by 3 consecutive vectors and is defined as the angle of the two outer vectors with arrow heads at their end. Region definitions are omitted for clarity reasons.

Figure 70:
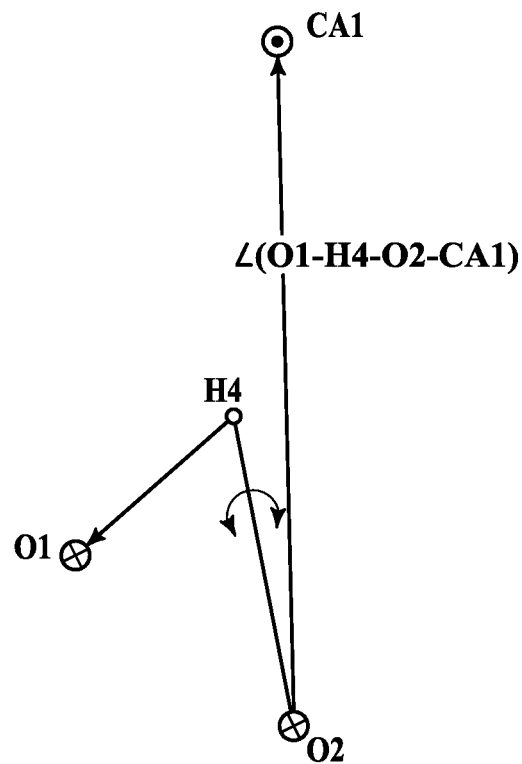
FIG. 70 is a plot depicting the definitions of torsion angles used in the text.

FIG. 70 is a depiction of the definitions of torsion angles used in the text. The torsion angle is formed by 3 consecutive vectors and is defined as the angle of the two outer vectors with arrow heads at their end. Region definitions are omitted for clarity reasons.

Figure 71:
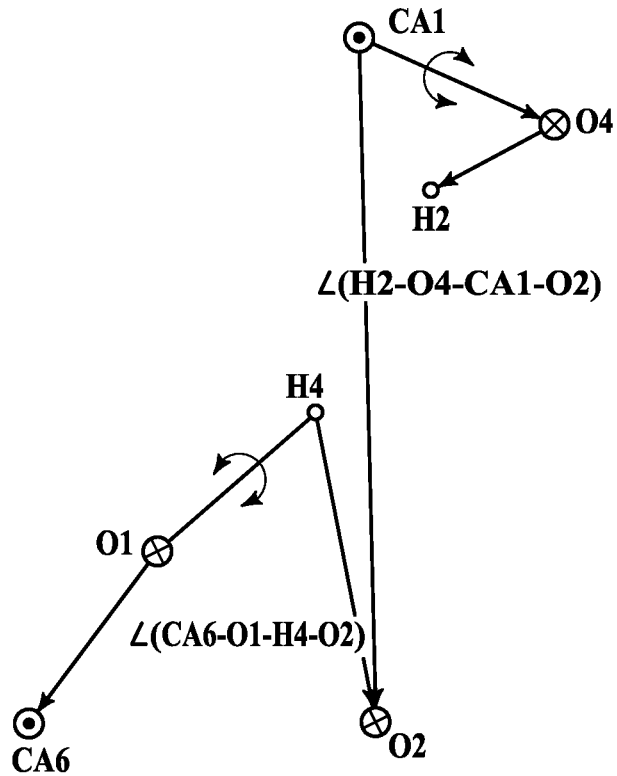
FIG. 71 is a plot depicting the definitions of torsion angles used in the text.

FIG. 71 is a depiction of the definitions of torsion angles used in the text. The torsion angle is formed by 3 consecutive vectors and is defined as the angle of the two outer vectors with arrow heads at their end. Region definitions are omitted for clarity reasons.

FIG. 72 is a depiction of the distances between pharmacophore elements describing the S2, S4 and RM region. The S2 region comprises H4, O1, O2 and CA6. The S4 region consists of H3, N2, C2, C4, CA5, CA2, CA4, C6. The RM region comprises CA3, H1, O3. Distances mentioned in the text are shown.

FIG. 73 is a depiction of bond angles mentioned in the text. Region definitions are omitted for clarity reasons.

FIG. 74 is a depiction of the definitions of torsion angles used in the text. The torsion angle is formed by 3 consecutive vectors and is defined as the angle of the two outer vectors with arrow heads at their end. Region definitions are omitted for clarity reasons.

Figure 75:
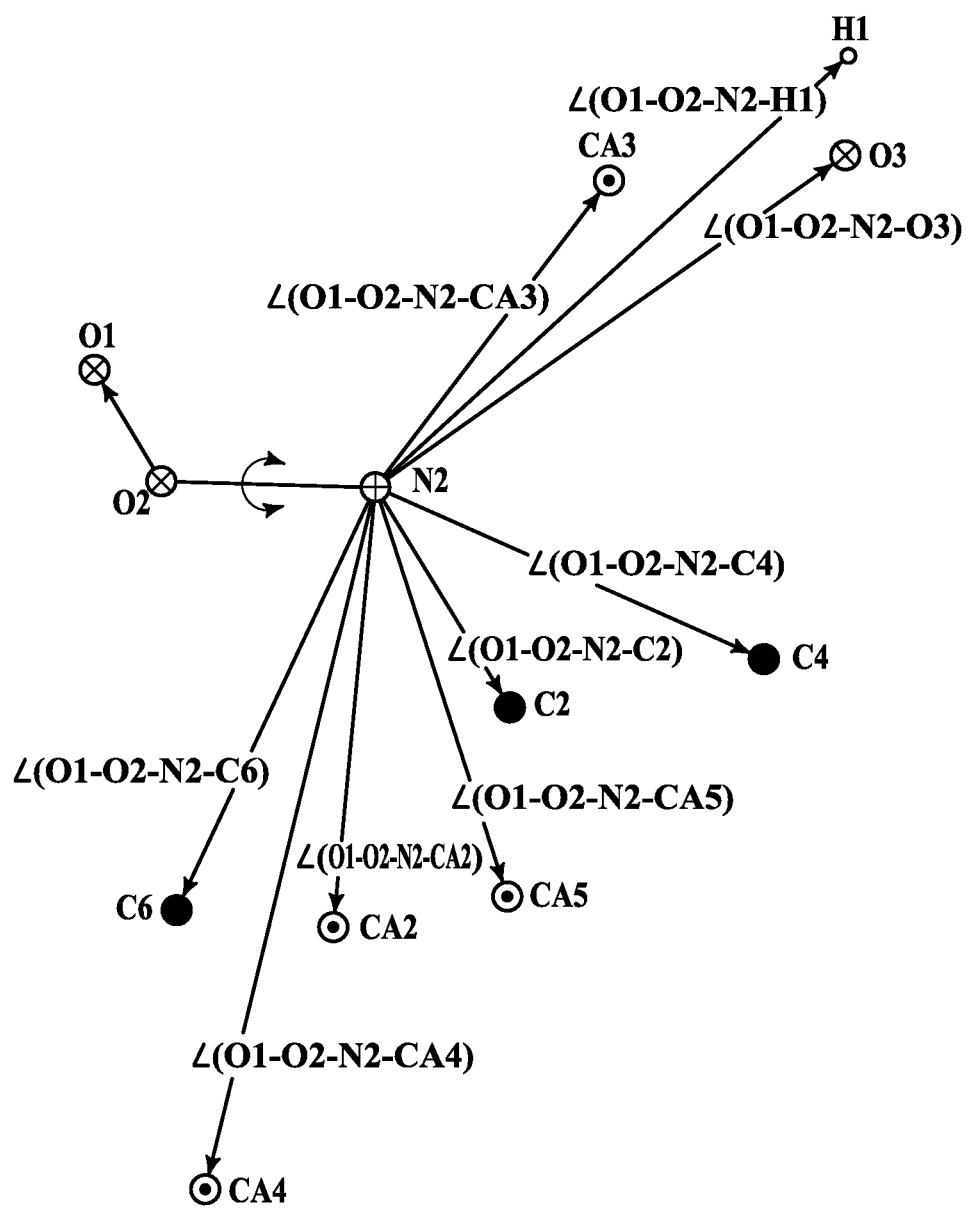
FIG. 75 is a plot depicting the definitions of torsion angles used in the text.

FIG. 75 is a depiction of torsion angles used in the text. The torsion angle is formed by 3 consecutive vectors and is defined as the angle of the two outer vectors with arrow heads at their end. Region definitions are omitted for clarity reasons.

Without being limited by any theory, it is understood that certain pharmacophore elements may interact with particular elements of the MASP-2 binding site. The interactions that are considered to be the more important interactions are discussed below.

The S2 region pharmacophore elements (Table 27) are understood to form classical hydrogen bond interactions with the S4 shelf in the MASP-2 binding site. The average distance between H4 and the O atom in SER 654 is 2.308 Å with a standard deviation of 0.157, a minimum value of 2.037 Å and a maximum value of 2.787 Å. The average distance between O2 and the H atom in GLY 656 is 2.425 Å with a standard deviation of 0.159 Å, a minimum value of 2.027 Å and a maximum value of 2.943 Å. The average distance between CA6 and the HZ atom in PHE 529 is 3.243 Å with a standard deviation of 0.263 Å, a minimum value of 2.558 Å and a maximum value of 4.535 Å.

Pharmacophore element C3 in the S1 region (FIG. 67, Table 27) is understood to form a hydrophobic interaction with VAL 653 based on the shortest average distance of 2.762 Å. The standard deviation is 0.147 Å, the minimum value is 1.963 Å and the maximum value is 3.038 Å. Based on the nature of C5 in the S1 region it can form with TYR 669 a pi-interaction. The shortest average distance is 3.701 Å with a standard deviation of 0.246 Å, a minimum value of 1.820 Å, and maximum value of 4.327 Å.

The aromatic ring pharmacophore group CA1 is understood to form interactions with GLY 656. The shortest average distance is 3.494 Å with a standard deviation of 0.283 Å, a minimum value of 3.001 Å and a maximum value of 4.517 Å. CA1 interacts also with TRP 655 as exemplified by the shortest average distance with HA. The shortest average distance is 3.563 Å, with a standard deviation of 0.142 Å, a minimum value of 3.220 Å and a maximum value of 3.955 Å. CA1 interacts also with CYS 629. The shortest average distance is 3.051 Å with a standard deviation of 0.178 Å, a minimum value of 2.199 Å, and maximum value of 3.620 Å.

The protonatable group N1 is understood to form an ionic interaction with ASP 627. The shortest average distance is 3.750 Å, with a standard deviation of 0.633 Å, a minimum value of 2.670 Å, and maximum value of 5.269 Å.

The hydrophobic pharmacophore element C7 is understood to form interactions with CYS 660. The shortest average distance is 2.438 Å with a standard deviation of 0.332 Å, a minimum value of 1.070 Å and maximum value of 3.816 Å. C7 is also understood for form an interaction with GLY 656. The shortest average distance is 3.400 Å with a standard deviation of 0.298 Å, a minimum value of 2.707 Å and maximum value of 4.358 Å. It is understood that C7 can also contact with SER 657. The shortest average distance is 2.873 Å with a standard deviation of 0.228 Å, a minimum value of 2.384 Å, and maximum value of 3.497 Å. C7 forms contacts with ASP 627. The shortest average distance is 3.411 Å with a standard deviation of 0.570 Å, a minimum value of 2.634 Å, and maximum value of 5.201 Å. It is understood that C7 can also interact with SER 628. The shortest average distance is 3.623 Å with a standard deviation of 0.215 Å, a minimum value of 3.136 Å, and a maximum value of 5.000 Å. Furthermore, C7 can also interact with CYS 629. The shortest average distance is 3.495 Å, a standard deviation of 0.197 Å, a minimum value of 2.608 Å, and a maximum value of 3.889 Å.

The hydrogen acceptor O4 is understood to form interactions with ARG 630. The shortest average distance is 3.187 Å, with a standard deviation of 0.366 Å, a minimum value of 2.071 Å, and maximum value of 4.572 Å. O4 may also form interactions with CYS 629. The shortest average distance is 3.311 Å with a standard deviation of 0.156 Å, a minimum value of 2.756 Å, and a maximum value of 3.746 Å.

In the S3 region (Table 27, FIG. 72) it is understood that the pharmacophore element N2 forms a hydrogen bond with O of GLY 656. The average distance is 2.771 Å with a standard deviation of 0.242 Å, a minimum value of 2.184 Å and a maximum value of 3.695 Å.

It is understood that the pharmacophore element H3 forms a hydrogen bond with O of GLY 656. The average distance is 2.612 Å with a standard deviation of 0.236 Å, a minimum value of 1.956 Å, and maximum value of 3.613.

In the S4 region, it is understood that the pharmacophore element CA2 forms aromatic pi interactions with PHE 529. The shortest average distance is 3.136 Å with a standard deviation of 0.295 Å, a minimum of 2.490 and a maximum distance of 3.838 Å. It is understood that CA2 also forms hydrophobic interactions with PRO 608. The shortest average distance is 3.561 Å, with a standard deviation of 0.545, a minimum value of 2.400 Å and a maximum value of 4.978 Å. It is further understood that CA2 also forms hydrophobic interactions with TYR 607. The shortest average distance id 3.617 Å with a standard deviation of 0.437 Å, a minimum value of 2.644 Å, and a maximum value of 4.896 Å.

It is understood that the aromatic ring CA4 forms hydrophobic interactions with GLY 528. The shortest average distance is 3.182 Å, with a standard deviation of 0.215 Å, a minimum value of 2.235 Å, and a maximum value of 3.450 Å. CA4 also forms hydrophobic interactions with PRO 608. The shortest average distance is 3.514 Å with a standard deviation of 0.681 Å, a minimum value of 2.077 Å and a maximum value of 5.235 Å. CA4 form aromatic pi interactions with PHE 529. The shortest average distance is 3.921 Å with a standard deviation of 0.237 Å, a minimum value of 3.306 Å, and a maximum value of 4.762 Å.

CA5 is understood to form hydrophobic interactions with TYR 607. The shortest average distance is 3.520 Å, with a standard deviation of 0.419 Å, a minimum value of 2.463 Å, and maximum value of 4.374 Å.

It is understood that C2 forms hydrophobic interactions with TYR 607. The shortest average distance is 3.621 Å with a standard deviation of 0.449 Å, a minimum value of 2.780 Å, and maximum value of 5.630 Å. C2 also is understood to form hydrophobic interactions with GLY 656. The shortest average distance is 3.501 Å, with a standard deviation of 0.247 Å, a minimum value of 2.920 Å, and maximum value of 4.091 Å. Furthermore, it is understood that C2 can interact with TRP 655. The shortest average distance is 3.888 Å, with a standard deviation of 0.185 Å, a minimum value of 3.090 Å, and maximum value of 4.320 Å.

C4 is understood to form hydrophobic interactions with PRO 608. The shortest average distance is 3.282 Å, with a standard deviation of 0.607 Å, a minimum value of 2.206 Å, and a maximum value of 4.992 Å.

It is understood that C6 forms a hydrophobic interaction with TRP 655. The shortest average distance is 3.698 Å, with a standard deviation of 0.231 Å, a minimum value of 3.087 Å, and maximum value of 4.113 Å. Furthermore, it is understood that C6 forms hydrophobic interactions with PHE 529. The shortest average distance is 3.006 Å, with a standard deviation of 0.251 Å, a minimum value of 2.420, and a maximum value of 3.836 Å. It is understood that C6 also interacts with SER 611. The shortest average distance is 2.603 Å, with a standard deviation of 0.298 Å, a minimum value of 1.991 Å, and a maximum value of 3.322 Å. C6 is also understood to form hydrophobic interactions with PRO 608. The shortest average distance is 3.835 Å, with a standard deviation of 0.360 Å, a minimum value of 2.970 Å, and a maximum value of 4.919 Å. C6 can also form hydrophobic interactions with GLY 528. The shortest average distance is 3.610 Å, with a standard deviation of 0.213 Å, a minimum value of 2.993 Å, and a maximum value of 4.666 Å.

In the RM region, it is understood that CA3 forms a hydrophobic interaction with MET 658. The shortest average distance is 2.533 Å, with a standard deviation of 0.472 Å, a minimum value of 1.072 Å, and a maximum value of 3.890 Å. It is understood that CA3 also forms interactions with ARG 630. The shortest average distance is 2.861 Å, with a standard deviation of 0.958 Å, a minimum value of 0.155 Å, and a maximum value of 5.371 Å.

It is understood that O3 also forms interactions with ARG 630. The shortest average distance is 3.766, with a standard deviation of 0.893 Å, a minimum value of 1.734 Å, and a maximum value of 5.839 Å.

Finally, it is understood H1 forms interactions with MET 658. The shortest average distance is 3.371 Å, with a standard deviation of 0.510 Å, a minimum value of 0.739 Å, and maximum value of 5.284 Å.

A small molecule compound can be evaluated in accordance with the methods described herein to determine matching with pharmacophore elements as described herein by determining low energy conformations of the compound using molecular mechanics calculations or other computational methods. In addition, or alternatively, conformations can be identified in accordance with methods described herein, or otherwise, by docking compounds to any MASP-2 structure derived by any theoretical or experimental method such as homology modelling, comparative modelling or ab initio modeling, or such as X-ray diffraction or cryo electron microscopy. For example, 1Q3X is a SP-CCP2 human MASP-2 structure which could be used for docking, or a MASP-2 homology model obtained from a MASP-1 crystal structure used as structural template, in accordance with the teachings of the present disclosure. Once conformations of the molecule have been identified, as disclosed herein, the compound can be evaluated as disclosed herein for a match to the parameters of the pharmacophore model as described above. The matching may be performed using standard software known to the person having skill in the art such as the tools available in the Discovery Suite available from Schrödinger, LLC or other commercially available molecular modelling software.

H. Compounds Defined by Reference to Computationally-Derived Binding Rules

The present disclosure provides compounds with MASP-2 inhibitory activity, wherein the compound interacts with a binding site of MASP-2. The binding site(s) on the MASP-2 protein are identified using the methods described herein. The compounds of the disclosure interact with amino acids residues of the binding site. By identifying the binding sites and ways the compounds of the disclosure interact with a binding site such as surface amino acid residues, it is possible to design a set of "binding rules" or "rule set" by which a MASP-2 inhibitor can also be specifically described. By using a variety of compounds, including those disclosed herein, the rule set describes the compounds with complete specificity. In other words, by identifying such amino acids and how the inhibitor interacts with the amino acids, it is possible to specifically define the inhibitor itself.

In one embodiment, the present disclosure provides a method for determining virtual binding sites and thereby providing virtual binding sites of the MASP-2 protein. As will be apparent herein, the newly identified binding sites provide an alternative method to structurally describe MASP-2 inhibitors by describing the structural interactions between the inhibitory compounds and MASP-2 interactions, all in accordance with the present disclosure.

The methods described herein involve one or more computational experiments (i.e., in silico docking methods or virtual docking methods) used in accordance with the present disclosure to model the interaction between MASP-2 protein surface residues, which have been derived from experimental crystallographic structure information, and known MASP-2 small molecule inhibitors. Such virtual or in silico docking methods identify binding sites of MASP-2 and their interaction with small molecule inhibitors. In certain aspects of the present disclosure, the identity of amino acids and their respective atoms on the protein surface that are accessible to small molecule binding often contribute significantly to the overall binding energy (Fernández-Recio et al., Comput Mol Sci, 680-698, 2011).

The series of computational experiments that employ experimental crystallographic structure information with known inhibitors provides virtual binding sites, or three-dimensional models of their interaction with MASP-2.

The virtual binding or docking methods described herein, allow for identification of the amino acids that interact with the inhibitor. By identifying such amino acids and how the inhibitor interacts in accordance with the present disclosure, it is possible to specifically define and describe the inhibitor itself.

In certain aspects, the inhibitor is a reversible inhibitor, an irreversible inhibitor which is covalently bound or alternatively, a reversible covalently bound inhibitor. In certain aspects, the inhibitors herein are designed to interact with their biological targets under equilibrium binding conditions, wherein the desired drug-protein interaction is a rapid and reversible process. In other aspects, the inhibitor is a covalent inhibitor, which is designed to bind to a protein binding site through traditional reversible interactions, but also undergo a covalent bond-forming event that produces a durable drug-protein linkage. In yet other aspects, the inhibitors herein can form reversible covalent bonds with their respective binding site targets.

In certain aspects, the inhibitors herein are covalent inhibitors. In contrast to conventional reversible drugs, irreversible inhibitors achieve complete neutralization of their bimolecular targets such as MASP-2 given enough time. Covalent inhibitors have high biochemical efficiencies and therefore have lower doses and reduced frequency of dosing. In addition, covalent inhibitors have lower or reduced off-target effects. In addition, in certain instances, the covalent inhibitors herein overcome competing endogenous substrates as they bind to the same target. Moreover, covalent inhibitors reduce the amount of drug resistance. Advantageously, covalent inhibitors address alternative protein binding site targets that can be shallow and therefore previously believed to be undrugable sites.

In certain aspects, the inhibitors herein are boron containing protease inhibitors. (see, Smoum et al. Chem. Rev. 2012, 112, 4156-4220). For example, peptidyl boronic acids are among the most potent inhibitors of serine proteases known, achieving sub-nanomolar affinity from interaction with the S-subsites alone. As one example, MeO-Suc-Ala-Ala-ProboroPhe-OH inhibited α-chymotrypsin with a $K_i$ value of 0.16 nM. In certain instances, the inhibitors are functionalized aryl boronic acid derivatives.

In still yet other aspects, the inhibitors herein are derivatives of isatoic anhydrides, oxazinediones and benzoxazinones. (see, Gelb et al. J Med Chem., 1986, 29, 585-589). These derivatives are generally irreversible inhibitors. Further, other irreversible inhibitors are designed by taking a good reversible inhibitor herein and attaching a reactive warhead to that structure such as an alkylating agent. For example, diazo compounds or haloketones can be used as warheads. Other strategies use X-ray crystallography and the co-crystals described herein. Moieties that form covalent bonds are installed using the co-crystal structures (see, Power et al. Chem Rev. 2002, 102, 4639-4750).

In certain aspects, the inhibitors herein are zinc mediated inhibitors such as derivatives of bis(5-amidino-2-benzimidazolyl)methane (BABIM) (see, Katz et al. Nature, Vol. 391. February 1998, p. 608-612). In certain instances, the MASP-2 protein is inhibited by a coordinating $Zn^{2+}$ in the presence of BABIM-like chelators, and is susceptible to potent $Zn^{2+}$-mediated inhibition.

In certain aspects, the inhibitors are irreversible protease inhibitors comprising electrophilic warheads such as aldehydes, boronates and α-keto functionalities. (see, Lin et al. *Infectious Disorders—Drug Targets,* 2006 6, 3-16).

1. Methods to Identify Virtual Binding Sites

Step 1—Prepare Initial MASP-2 Models

Figure 76:
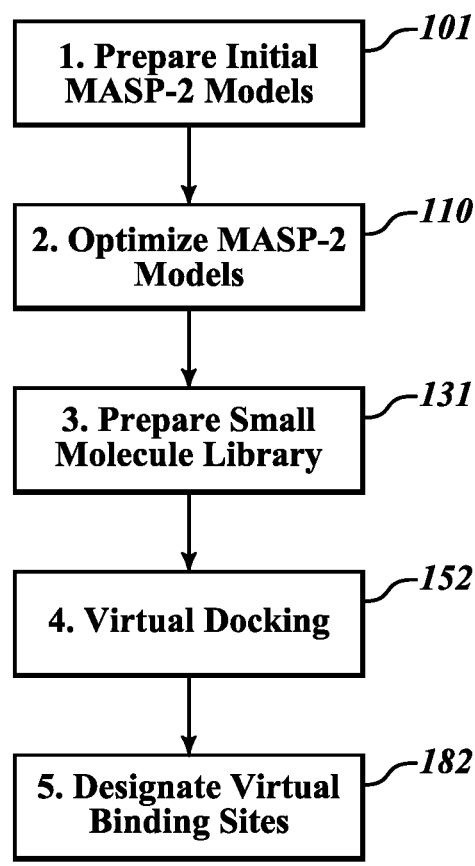
FIG. 76 is a flow chart illustrating one embodiment of a process of this disclosure.

Turning now to FIG. 76, in order to identify and characterize a binding site on MASP-2, in certain aspects, multiple models of MASP-2 are prepared. In some aspects, multiple MASP-2 models are prepared by computationally reproducing experimental crystallographic structures.

In certain aspects, a modified MolSite approach (Fukunishi and Nakamura, Protein Science, 20, 95-106, 2011) is used to produce MASP-2 protein models. The MolSite approach has been shown to correctly predict binding sites with about 80-99% accuracy. For the purposes of the instant disclosure, the MolSite method is modified by employing crystallographic MASP-2 structures to identify in silico those interacting residues that have a propensity for ligand binding, such as small molecule binding as established by the crystallographic data.

As shown in FIG. 76, in certain aspects, the present disclosure computationally reproduces the experimental crystallographic structures of small molecules interacting with particular amino acid residues within a MASP-2 binding site (step 101). The MASP-2 protein models can be computationally derived from the crystallographic data and thereafter verified via RMSD (root mean square deviation) superimposition on the respective crystal structures. In some aspects, initial MASP-2 protein models are derived by computationally reproducing each of the crystallographically derived MASP-2-bound small molecule inhibitor co-crystals (see, FIG. 1-57). In some embodiments, the second complement control protein module (CCP2) chain, all solvent and water molecules, counter ions, and the bound inhibitor molecule are removed from the crystallographic parameters prior to computationally deriving the initial MASP-2 protein models. In some aspects, initial MASP-2 protein models are derived by computationally reproducing each of the crystallographically derived MASP-2-bound small molecule inhibitor co-crystals (FIG. 1-57), followed by removing the second complement control protein module (CCP2) chain, all solvent and water molecules, counter ions, and the bound inhibitor molecule from the MASP-2 model parameters. The docking parameters from these initial MASP-2 models are then optimized in the next step.

Step 2—Prepare Optimized MASP-2 Models

Next, the docking parameters of the initial MASP-2 models are optimized by adding polar hydrogens, employing energy minimization algorithms using a force field, followed by assigning charges to protein atoms (AMBER) and using manual inspection and correction (step 110). Solvent molecules can be added back to locations where such molecules are observed crystallographically. In some aspects, all water molecule are added back to locations where such molecules are observed crystallographically. In some aspects, the CCP2 chain is optionally added back to the crystallographically observed location. Further adjustments are then made to account for dipoles without altering net charges on any residues. A plurality or multiple MASP-2 protein models are produced from the optimization step to account for conformational differences observed in the crystallographic co-structures of MASP-2. As mentioned above, this disclosure describes 57 co-crystals with small molecule inhibitors. Each optimized MASP-2 model with optimized and MASP-2 specific docking parameters is used in successive virtual docking processes or campaigns (i.e., computational docking experiments) including, re-docking of the crystallographically observed small molecule inhibitor and cross-docking of the small molecules selected from the small molecule library. The fidelity of the outcome of such crossand re-docking experiments will inform the optimization of the MASP-2 model and docking parameters.

Step 3—Prepare Small Molecule Library

In certain aspects, a database is populated with digital representations of small molecules known to inhibit the activity of MASP-2 (for example, compounds selected from Tables 28 or 31) (see, step 131). The digital representations of each small molecule within the library are energy minimized three dimensional structures of the small molecules that are produced using known computational methods. In some aspects, the crystallographically observed small molecule inhibitors of each of the 57 co-crystals are computationally reproduced as energy minimized three dimensional structures using known computational methods. Such computational algorithms involve the identification of ionizable and polarizable groups within each small molecule structure, and rendering digital representations of each small molecule in both a charged state and a neutral state, and with and without, or only a subset of crystallographically identified bound solvent molecules.

The small molecule library includes ligands which are known to bind to MASP-2 as well as molecules that do not bind to MASP-2. The small molecules that are known to inhibit MASP-2 (i.e., bind to MASP-2) are referred to as "hits." The small molecules that do not exhibit any MASP-2 inhibitory activity (i.e., known to not bind to or inhibit MASP-2) are referred to as "decoys." The docking behavior of both the hits and the decoys included in the database are thereafter assessed in the next step (step 4) of the method.

Step 4—Virtual Docking

In certain aspects, software such as GLIDE software (Friesner et al., 2016; Schrödinger, LLC) can be used to carry out rigid as well as flexible computational docking of small molecules onto each MASP-2 model (step 152). As used herein, the term "cross-docking" refers to the computational docking of a compound selected from the set of 57 MASP-2 crystallographic co-structures onto two or more MASP-2 models, the latter of which being different from the MASP-2 model derived with that bound small molecule. The term "re-docking" refers to the computational docking of the crystallographically observed small molecule inhibitor representation back onto the same MASP-2 model which was derived from its corresponding co-crystal structure. In these virtual docking processes or campaigns, the docking experiments are limited to exposed residues on the surface only. Resulting docked ligand positions are thereafter sampled, scored and binned and, assigned a distance cutoff to match ligand atoms to MASP-2 surface exposed atoms. For docking campaigns, primarily preferred surface sites are used, namely those that have been identified crystallographically to bind, via hydrogen bonding and van der Waals contacts, certain small molecules. Such surface sites are prone to binding of small molecules and hence this information is used to serve as anchor points for those small molecule compounds selected from HTS hits (see Table 28).

In certain aspects, other software programs such as the following can be used in this step.

In certain aspects, ICM Pro software is used. (Abagyan & Totrov, Journal of Computational Chemistry, Volume 15, Issue 5, May 1994, Pages 488-506; and Abagyan et al., Journal of Molecular Biology Volume 235, Issue 3, 20 Jan. 1994, Pages 983-1002).

In certain aspects, GRID is used which is described as follows: Protein-probe energies computed by Lennard-Jones, electrostatic and hydrogen bonding potentials are mapped onto a grid around the protein. (See, Goodford, P. J. A computational procedure for determining energetically favorable binding sites on biologically important macromolecules. J. Med. Chem., 1985, 28, 849-857).

In certain aspects, Pocket is used which is described as follows: A 3 Å probe scans the protein along a Cartesian grid for line segments not overlapping with protein but surrounded by overlapping segments. (See, Levitt, D. G.; Banaszak L. J. POCKET: a computer graphics method for identifying and displaying protein cavities and their surrounding amino acids. J. Mol. Graph., 1992, 10, 229-234).

In certain aspects, Delaney is used which is described as follows: Expansion and contraction of surface probes is used to detect pockets where probe particles concentrate. (See, Delaney, J. S. Finding and filling protein cavities using cellular logic operations. J. Mol. Graph., 1992 10, 174-177).

In certain aspects, Del Carpio is used which is described as follows: Closest distances between the protein's center of gravity and protein surface points are used to identify pockets. (See, Del Carpio C. A.; Takahashi Y.; Sasaki S. A new approach to the automatic identification of candidates for ligand receptor sites in proteins: (I). Search for pocket regions. J. Mol. Graph., 1993, 11, 23-29).

In certain aspects, VOIDOO is used which is described as follows: Cavities are detected by stepwise increase of Van-der-Waals radii of all protein atoms. After a floodfill algorithm, sealed off localizations can be identified as cavities. (See, Kleywegt, G. J.; Jones, T. A. Efficient Rebuilding of Protein Structures. Acta Crystallogr. Sect. D: Biol. Crystallogr., 1994, 50, 178-185).

In certain aspects, SurfNet is used which is described as follows: Spheres between two atoms containing no other atoms are created and scanned for the cluster of spheres with the largest volume. (See, Laskowski, R. A. SURFNET: A program for visualizing molecular surfaces, cavities, and intermolecular interactions. J. Mol. Graph., 1995, 13, 323-330).

In certain aspects, APROPOS is used which is described as follows: Protein pockets are determined employing an alpha-shape algorithm that allows for a complete global envelope of the protein. (See, Peters, K. P.; Fauck, J.; Frömmel, C. The automatic search for ligand binding sites in proteins of known three-dimensional structure using only geometric criteria. J. Mol. Biol., 1996, 256, 201-213).

In certain aspects, LIGSITE is used which is described as follows: On a regular grid around the protein, lines are drawn from each grid point along the x/y/z-axis as well as the cubic diagonals. Segments of lines that are enclosed by protein from both sides are considered as cavities. (See, Hendlich, M.; Rippmann, F.; Barnickel, G. LIGSITE: automatic and efficient detection of potential small-molecule binding sites in proteins. J. Mol. Graph. Model., 1997, 15, 359-363).

In certain aspects, Superstar is used which is described as follows: Creates propensity maps of basic molecular probes along the protein surface. (See, Verdonk, M. L.; Cole, J. C.; Taylor, R. SuperStar: a knowledge based approach for identifying interaction sites in proteins. J. Mol. Biol., 1999, 289, 1093-1108).

In certain aspects, PASS is used which is described as follows: The algorithm repeats filtering and expanding a set of initial probe spheres on the protein surface to eventually find "active site points" (See, Brady G. P.; Stouten P. F. Fast prediction and visualization of protein binding pockets with PASS. J. Comput. Aided Mol. Des., 2000, 14, 383-401).

In certain aspects, ConSurf is used which is described as follows: Identifying functional sites on proteins by determining the conservation of sequence homologues. (See, Glaser, F.; Pupko, T.; Paz, I.; Bell, R. E.; Bechor-Shental, D.; Martz, E.; Ben-Tal, N. ConSurf: identification of functional regions in proteins by surface-mapping of phylogenetic information. Bioinformatics, 2003, 19, 163-164).

In certain aspects, CASTp is used which is described as follows: Uses alpha shape theory and triangulation methods to predict pockets. (See, Dundas, J.; Ouyang, Z.; Tseng, J.; Binkowski, A.; Turpaz with structural and topographical mapping of functionally annotated residues. Nucleic Acids Res., 2006, 34, W116-W118).

In certain aspects, LigandFit is used which is described as follows: Identifies possible binding sites using a flood-filling-algorithm and docks ligands using a Monte Carlo conformational search (See, Venkatachalam, C. M.; Jiang, X.; Oldfield, T.; Waldman, M. LigandFit: a novel method for the shape-directed rapid docking of ligands to protein active sites. J. Mol. Graph. Model., 2003, 21, 289-307).

In certain aspects, Q-SiteFinder is used which is described as follows: Energetically based method: clusters of protein surface regions that show favorable Van der Waals interactions with a methyl-group are collected and ranked (See, Laurie, A. T. R.; Jackson, R. M. Q-SiteFinder: an energy-based method for the prediction of protein-ligand binding sites. Bioinformatics, 2005, 21, 1908-1916).

In certain aspects, DrugSite is used which is described as follows: Predicts binding sites on the basis of Van der Waals potential grid point maps (See, An, J.; Totrov, M.; Abagyan, R. Pocketome via comprehensive identification and classification of ligand binding envelopes. Mol. Cell. Proteomics, 2005, 4, 752-761).

In certain aspects, MEDock is used which is described as follows: Evolutionary algorithm utilizing the maximum entropy (ME) property of the Gaussian probability distribution (See, Chang, D. T.-H.; Oyang, Y.-J.; Lin, H.-H. MEDock: a web server for efficient prediction of ligand binding sites based on a novel optimization algorithm. Nucleic Acids Res., 2005, 33, W233-W238).

In certain aspects, LIGSITEcsc is used which is described as follows: In extension to the traditional LigSite method, the Connolly surface area is calculated and grid points are scanned for surface-solvent-surface events. Additionally, the top three predicted pockets are re-ranked according to sequence conservation. (Huang, B.; Schroeder, M. LIGSITEcsc: predicting ligand binding sites using the Connolly surface and degree of conservation. BMC Struct. Biol., 2006, 6, 19).

In certain aspects, Screen/Mark-Us is used which is described as follows: Cavities are geometrically determined via the difference between the molecular surface and the probe-specified molecular envelope and statistical analysis. (See, Nayal, M.; Honig, B. On the nature of cavities on protein surfaces: application to the identification of drug-binding sites. Proteins, 2006, 63, 892-906).

In certain aspects, Pocket-Picker is used which is described as follows: A rectangular grid is used to segregate relevant points along the protein surface which are then clustered and ranked according to shape descriptors. (See, Weisel, M.; Proschak, E.; Schneider, G. PocketPicker: analysis of ligand binding-sites with shape descriptors. Chem. Cent. J., 2007, 1, 7).

In certain aspects, Fuzzy-Oil-Drop is used which is described as follows: Analyzes the protein for regions with high hydrophobic deficiency, i.e. the difference between observed and idealized hydrophobicity distribution declared by the 'Fuzzy Oil Drop Model' (See, Brylinski, M.; Prymula, K.; Jurkowski, W.; Kochanczyk, M.; Stawowczyk, E.; Konieczny, L.; Roterman, I. Prediction of functional sites based on the fuzzy oil drop model. PLoS Comput. Biol., 2007, 3, e94).

In certain aspects, SiteMap is used which is described as follows: Sets of relevant points are identified by geometric and energetic means and analyzed for hydrophobicity and other physicochemical properties (See, Halgren, T. New Method for Fast and Accurate Binding-site Identification and Analysis. Chem. Biol. Drug Des., 2007, 69, 146-148).

In certain aspects, FINDSITE is used which is described as follows: The method uses protein threading to identify ligand bound templates which are then superimposed and analyzed for similarities in the ligand binding sites (See, Brylinski, M.; Skolnick, J. A threading-based method (FINDSITE) for ligand-binding for ligand-binding site prediction and functional annotation. PNAS, 2008, 105, 129-134).

Step 5—Designate Virtual Binding Sites

As shown in FIG. 76, step 182, after visual inspection of such identified interaction sites, binding hot spots are grouped by normalizing the docking score by the number of ligand atoms prior to sorting the pairings of ligand and site atom pairings. In addition, Volume and Enclosure (for example, as computed via MAESTRO, Schrödinger, LLC) of the interacting sites and rank clusters of such ligand/site atom pairings as hot spots with respect to number and size of interactions. The highest ranked ligand/site atom pairing will be designated 'virtual binding site' for each of the compounds in Table 28. Other compounds from compound libraries with known MASP-2 inhibition activity described below are also used.

TABLE 28

| Compound No. | Chemical Structure | Molecular Weight | MASP-2 Ki (µM) | Thrombin Ki (µM) |
|---|---|---|---|---|
| 1# | 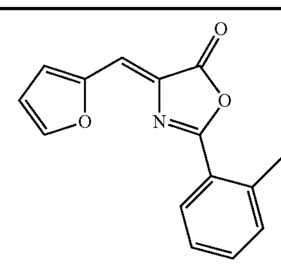 | 253.26 | * | * |

TABLE 28-continued
| Compound No. | Chemical Structure | Molecular Weight | MASP-2 Ki (μM) | Thrombin Ki (μM) |
|---|---|---|---|---|
| 2# | 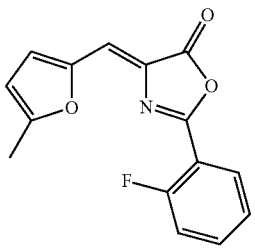 [SMILES: Cc1ccc(/C=C2\N=C(c3ccccc3F)OC2=O)o1] | 271.25 | *** | * |
| 3# | 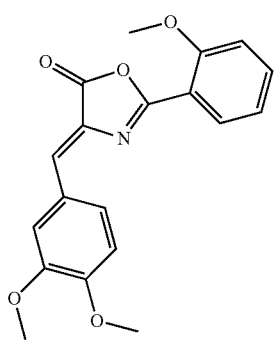 [SMILES: COc1ccc(/C=C2\N=C(c3ccccc3OC)OC2=O)cc1OC] | 388.22 | * | *** |
| 4# | 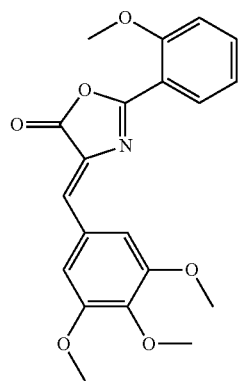 [SMILES: COc1ccccc1C1=N/C(=C\c2cc(OC)c(OC)c(OC)c2)C(=O)O1] | 369.38 | *** | * |
| 5# | 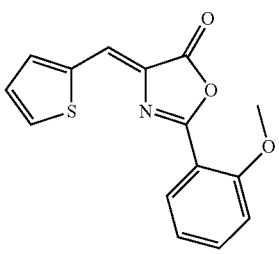 [SMILES: COc1ccccc1C1=N/C(=C\c2cccs2)C(=O)O1] | 285.32 |  |  |
| 6# | 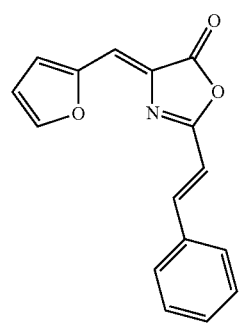 [SMILES: O=C1OC(/C=C/c2ccccc2)=NC/1=C\c1ccco1] | 265.27 | *** | * |

TABLE 28-continued

| Compound No. | Chemical Structure | Molecular Weight | MASP-2 Ki (μM) | Thrombin Ki (μM) |
| --- | --- | --- | --- | --- |
| 7# | 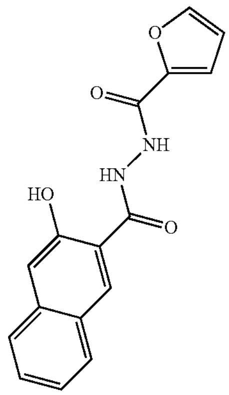 [SMILES: O=C(NNC(=O)c1cc2ccccc2cc1O)c1ccco1] | 296.29 | * | * |
| 8 | 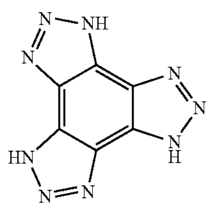 [SMILES: n1nc2c([nH]1)c1nn[nH]c1c1nn[nH]c21] | 201.15 | ** | No Activity |
| 9 | 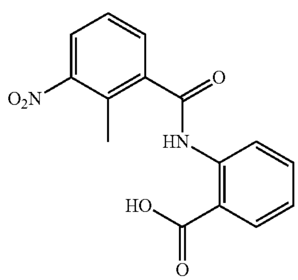 [SMILES: Cc1c(C(=O)Nc2ccccc2C(=O)O)cccc1[N+](=O)[O-]] | 300.27 | * | * |
| 10 | 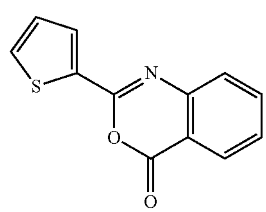 [SMILES: O=c1oc(-c2cccs2)nc2ccccc12] | 229.26 | *** | * |
| 11 | 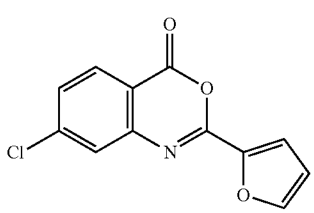 [SMILES: O=c1oc(-c2ccco2)nc2cc(Cl)ccc12] | 247.63 | *** | No Activity |
| 12# | 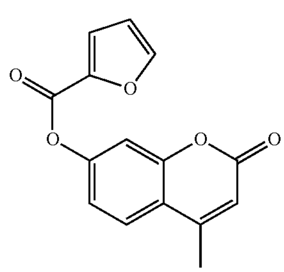 [SMILES: Cc1cc(=O)oc2cc(OC(=O)c3ccco3)ccc12] | 270.24 | * | * |

TABLE 28-continued
| Compound No. | Chemical Structure | Molecular Weight | MASP-2 Ki (μM) | Thrombin Ki (μM) |
|---|---|---|---|---|
| 13# | 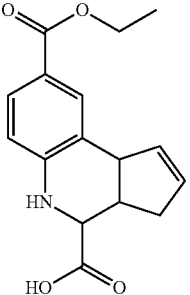 [SMILES: CCOC(=O)c1ccc2c(c1)C1C=CCC1C(C(=O)O)N2] | 287.31 | * | No activity |
| 14 | 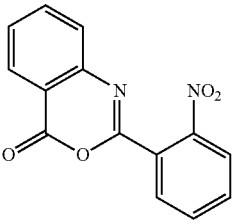 [SMILES: O=c1oc(-c2ccccc2[N+](=O)[O-])nc2ccccc12] | 268.23 | * | * |
| 15 | 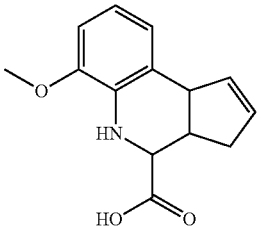 [SMILES: COc1cccc2c1NC(C(=O)O)C1CC=CC21] | 245.27 | * | No activity |
| 16 | 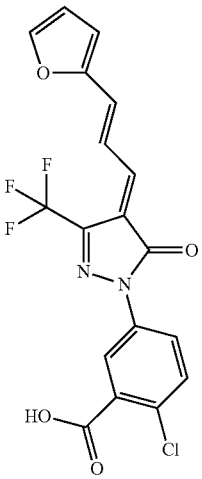 [SMILES: O=C(O)c1cc(N2N=C(C(F)(F)F)/C(=C\C=C\c3ccco3)C2=O)ccc1Cl] | 410.73 | * | No activity |

TABLE 28-continued

| Compound No. | Chemical Structure | Molecular Weight | MASP-2 Ki (μM) | Thrombin Ki (μM) |
|---|---|---|---|---|
| 17# | 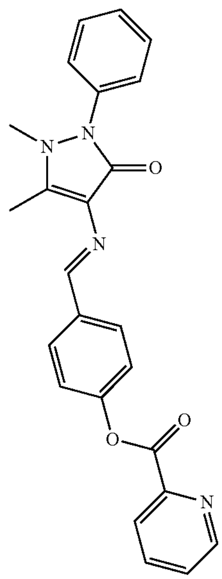 [SMILES: Cc1c(/N=C/c2ccc(OC(=O)c3ccccn3)cc2)c(=O)n(-c2ccccc2)n1C] | 412.45 | *** | * |
| 18 | 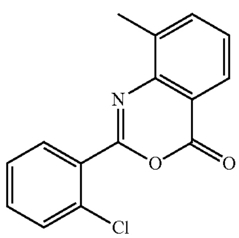 [SMILES: Cc1cccc2c(=O)oc(-c3ccccc3Cl)nc12] | 271.71 | * | * |
| 19# | 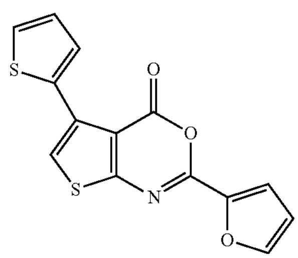 [SMILES: O=c1oc(-c2ccco2)nc2scc(-c3cccs3)c12] | 301.34 | *** | * |
| 20# | 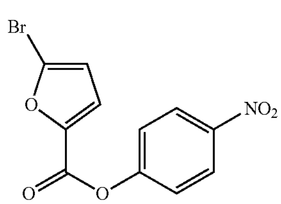 [SMILES: O=C(Oc1ccc([N+](=O)[O-])cc1)c1ccc(Br)o1] | 312.07 | *** | No Activity |
| 21# | 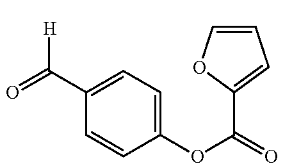 [SMILES: O=Cc1ccc(OC(=O)c2ccco2)cc1] | 216.18 | * | * |

TABLE 28-continued

| Compound No. | Chemical Structure | Molecular Weight | MASP-2 Ki (μM) | Thrombin Ki (μM) |
|---|---|---|---|---|
| 22 | 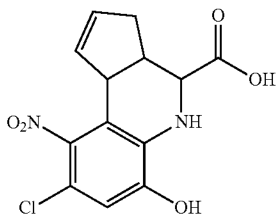 [SMILES: O=C(O)C1Nc2c(O)cc(Cl)c([N+](=O)[O-])c2C2C=CCC12] | 310.68 | ** | No Activity |
| 23 | 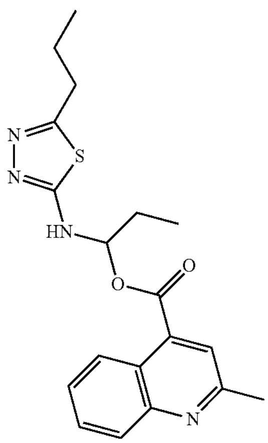 [SMILES: CCCc1nnc(NC(CC)OC(=O)c2cc(C)nc3ccccc23)s1] | 370.46 | *** | No Activity |
| 24# | 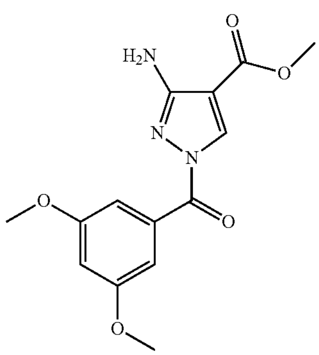 | 305.29 | * |  |
| 25 | 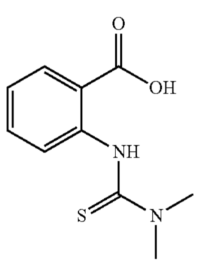 | 305.29 | * | No activity |
| 26# | 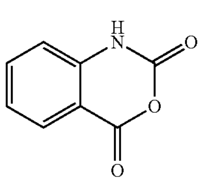 [SMILES: O=c1[nH]c2ccccc2c(=O)o1] | 163.13 | *** | * |

TABLE 28-continued
| Compound No. | Chemical Structure | Molecular Weight | MASP-2 Ki (μM) | Thrombin Ki (μM) |
| --- | --- | --- | --- | --- |
| 27# | 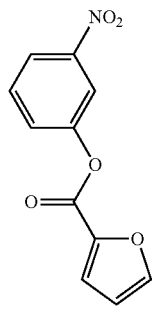 [SMILES: O=C(Oc1cccc([N+](=O)[O-])c1)c1ccco1] | 233.18 | *** | * |
| 28 | 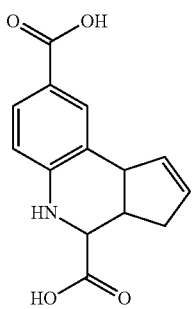 | 259.26 | * | No activity |
| 29 | 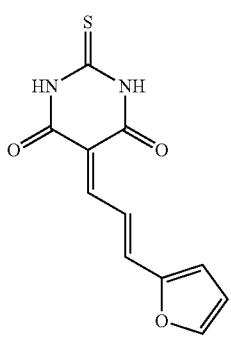 [SMILES: O=C1NC(=S)NC(=O)C1=C/C=C/c1ccco1] | 248.26 | *** | * |
| 30 | 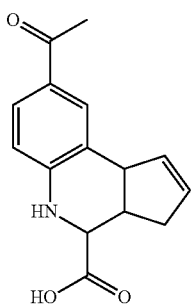 [SMILES: CC(=O)c1ccc2c(c1)C1C=CCC1C(C(=O)O)N2] | 257.29 | * | No activity |

TABLE 28-continued
| Compound No. | Chemical Structure | Molecular Weight | MASP-2 Ki (µM) | Thrombin Ki (µM) |
|---|---|---|---|---|
| 31# | 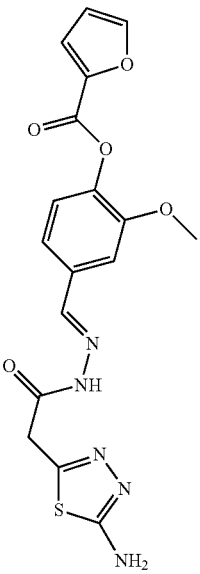 [SMILES: COc1cc(/C=N/NC(=O)Cc2nnc(N)s2)ccc1OC(=O)c1ccco1] | 401.40 | *** | No activity |
| 32# | 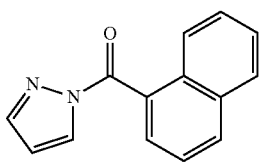 [SMILES: O=C(c1cccc2ccccc12)n1cccn1] | 222.24 | *** | No activity |
| 33 | 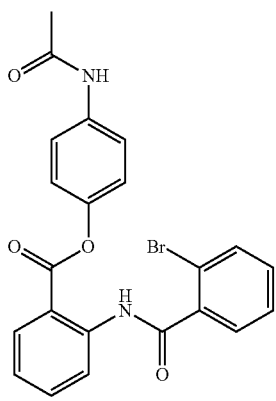 [SMILES: CC(=O)Nc1ccc(OC(=O)c2ccccc2NC(=O)c2ccccc2Br)cc1] | 453.30 | * | * |

TABLE 28-continued
| Compound No. | Chemical Structure | Molecular Weight | MASP-2 Ki (μM) | Thrombin Ki (μM) |
|---|---|---|---|---|
| 34# | 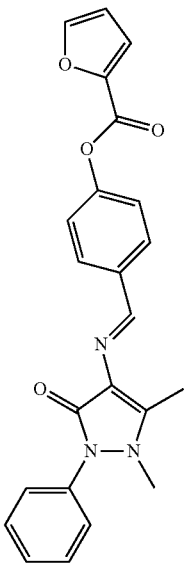 [SMILES: Cc1c(/N=C/c2ccc(OC(=O)c3ccco3)cc2)c(=O)n(-c2ccccc2)n1C] | 401.43 | *** | * |
| 35 | 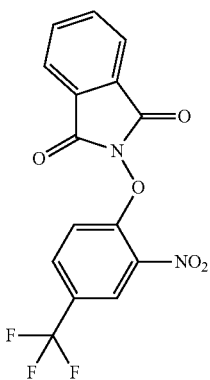 [SMILES: O=C1c2ccccc2C(=O)N1Oc1ccc(C(F)(F)F)cc1[N+](=O)[O-]] | 352.23 | * | * |
| 36 | 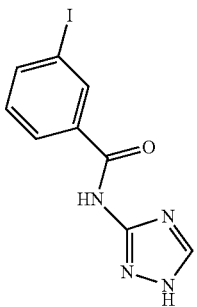 [SMILES: O=C(Nc1nc[nH]n1)c1cccc(I)c1] | 314.08 | *** | * |

TABLE 28-continued

| Compound No. | Chemical Structure | Molecular Weight | MASP-2 Ki (μM) | Thrombin Ki (μM) |
|---|---|---|---|---|
| 37 | 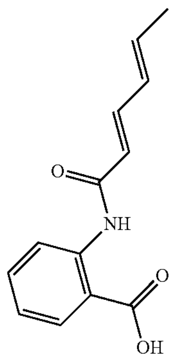 [SMILES: C/C=C/C=C/C(=O)Nc1ccccc1C(=O)O] | 231.25 | * | No activity |
| 38 | 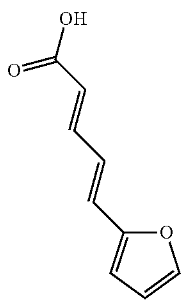 [SMILES: O=C(O)/C=C/C=C/c1ccco1] | 164.16 |  |  |
| 39# | 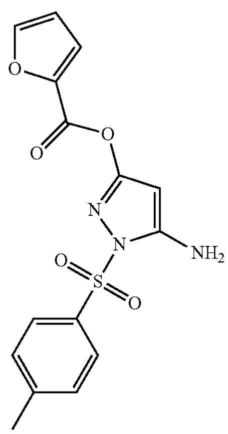 [SMILES: Cc1ccc(S(=O)(=O)n2nc(OC(=O)c3ccco3)cc2N)cc1] | 347.35 | * |  |
| 40# | 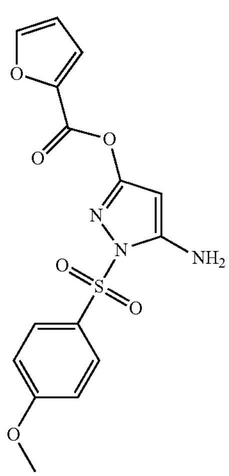 [SMILES: COc1ccc(S(=O)(=O)n2nc(OC(=O)c3ccco3)cc2N)cc1] | 363/35 | * | * |

TABLE 28-continued

| Compound No. | Chemical Structure | Molecular Weight | MASP-2 Ki (μM) | Thrombin Ki (μM) |
| --- | --- | --- | --- | --- |
| 41# | 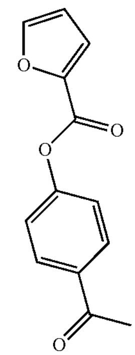 [SMILES: CC(=O)c1ccc(OC(=O)c2ccco2)cc1] | 230.22 | *** | No activity |
| 42# | 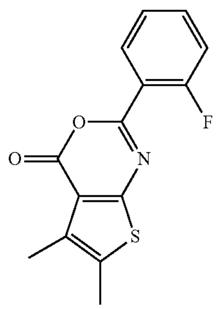 [SMILES: Cc1sc2nc(-c3ccccc3F)oc(=O)c2c1C] | 275.30 | *** | * |
| 43# | 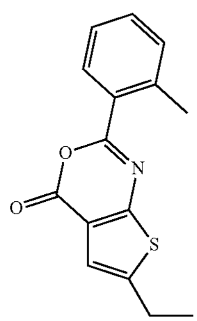 [SMILES: CCc1cc2c(=O)oc(-c3ccccc3C)nc2s1] | 271.43 | *** | * |
| 44# | 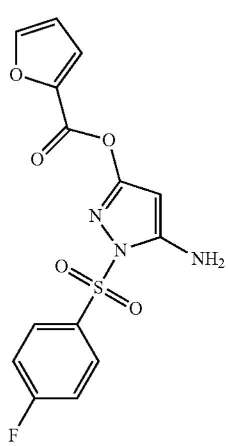 [SMILES: Nc1cc(OC(=O)c2ccco2)nn1S(=O)(=O)c1ccc(F)cc1] | 351.32 | *** | * |

TABLE 28-continued

| Compound No. | Chemical Structure | Molecular Weight | MASP-2 Ki (μM) | Thrombin Ki (μM) |
|---|---|---|---|---|
| 45# | 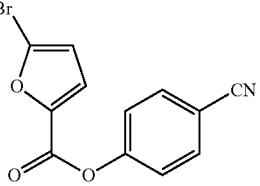 | 292.09 | *** | * |
| 46 | 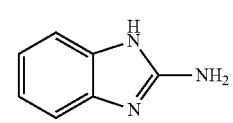 | 133.15 | * | No activity |
| 47[a] | 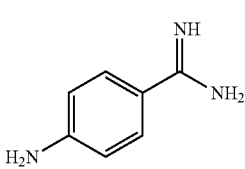 | 135.17 | * | No activity |
| 51 | 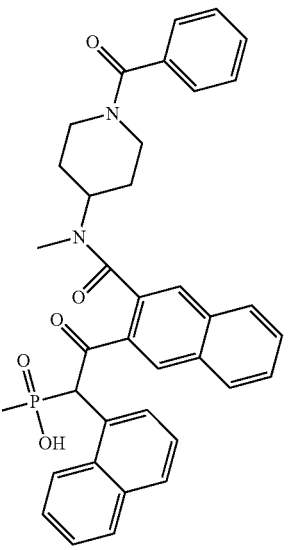 | 620.63 | ** | No activity |
| 53 | 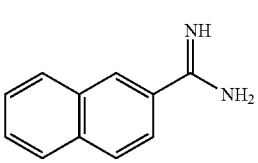 [SMILES: N=C(N)c1ccc2ccccc2c1] | 170.21 | * |  |

\# = irreversible inhibitor;
[a]HCl salt;
[b]HCl hydrate salt;
[c]HNO₃ salt
Key: MASP-2 and Thrombin Inhibition
*** (Ki < 10 μM)
** (Ki: 10-25 μM)
* (Ki: 25-100 μM)

In addition to the compounds of Table 28, it is possible to screen other compound libraries for identification of binding sites. Certain of the molecular interaction data presented herein is derived from 57 co-crystals of MASP-2 and specific inhibitors (see FIGS. 1-57).

In certain aspects, the NCI Diversity Set, which is a compound collection representing a universally diverse group of "drug-like" small molecules chosen on the basis of their three dimensional pharmacophoric scaffolds, which represent diverse, biologically relevant pharmacophoric scaffolds from within the NCI parent library is used.

In addition, the Chembridge library can also be screened. This library has been selected from their master database of (>5 million compounds) ensuring computational diversity of the discrete chemical moieties, drug-like properties, as well as medicinal chemistry pharmacokinetics.

Moreover, the Maybridge library is another alternative collection that is comprised of 60,000 organic compounds, produced by innovative synthetic techniques, representing 400,000 pharmacophores identified within the world drug index.

Alternative compound libraries are available and a very recent compilation of one million commercially accessible compounds, including a natural product library, was made available for web-accessible database searching and docking through ZINC (http://blaster.docking.org/zinc) DOCK Blaster is a public access service for structure-based ligand discovery.

In certain aspects, a ChemDiv library (12760 High Bluff Drive, Suite 370, San Diego, CA 92130 USA) is used. The ChemDiv library offers a wide variety of compounds including more than 1.5 M individual solid screening compounds.

In one aspect, parameters are controlled and adjusted to increase the fidelity of the above process by comparing computationally identified hot spots from those obtained crystallographically. Specifically, the binding of decoy compounds and ligand/site atom pairings in the binding pocket for inhibitors for which we have identified key residues and their respective ligand atom/site atom pairings to computed ligand/site atom pairings are compared and used to assess the fidelity of the identification of virtual binding sites.

2. Binding Sites

In some aspects, a virtual binding site identified on MASP-2 is at least one amino acid residue of SEQ ID NO: 1. In some aspects, a virtual binding site identified on MASP-2 is one amino acid residue to 100 amino acid residues of SEQ ID NO: 1. In some aspects, a virtual binding site identified on MASP-2 is two to 90 amino acid residues of SEQ ID NO: 1, or three to 85, four to 80, five to 75, six to 70, seven to 65, eight to 60, nine to 55, 10 to 50, 11 to 45, 12 to 40, 13 to 35, 14 to 30, or 15 to 25 amino acid residues of SEQ ID NO: 1. In some aspects, a virtual binding site identified on MASP-2 is five to 50 amino acid residues of SEQ ID NO: 1, or five to 25, five to 20, five to 10, or 10 to 40, 10 to 35, or 15 to 35 amino acid residues of SEQ ID NO: 1. In some aspects, a virtual binding site identified on MASP-2 is one amino acid residue of SEQ ID NO: 1, or two, three, four, five, six, seven, eight, nine, 10, 11, 12, 13, 14, 15, 16, 17, 18, 19, 20, 21, 22, 23, 24, 25, 26, 27, 28, 29, 30, 35, 40, 45, or 50 amino acid residues of SEQ ID NO: 1. In some aspects, a virtual binding site identified on MASP-2 is about five to 30 amino acid residues of SEQ ID NO: 1. In some aspects, a virtual binding site identified on MASP-2 is about 10 to 20 amino acid residues of SEQ ID NO: 1. In some aspects, a virtual binding site identified on MASP-2 is about 10 amino acid residue of SEQ ID NO: 1.

In some aspects, one or more virtual binding sites are identified on MASP-2. In some embodiments, one to 100 virtual binding sites are identified on MASP-2, or one to 40, one to 30, one to 25, one to 20, one to 15, one to 10, or one to 5 (1, 2, 3, 4, 5) virtual binding sites are identified on MASP-2. In some embodiments, one virtual binding site is identified on MASP-2. In some embodiments, two virtual binding sites are identified on MASP-2, or three, four, five, six, seven, eight, nine, 10, 11, 12, 13, 14, 15, 16, 17, 18, 19, 20, 25, 30, 35, 40, 45, or 50 virtual binding sites are identified on MASP-2.

In some aspects, the amino acids of the MASP-2 virtual binding sites are hydrophobic, hydrophilic, or a mixture thereof. In some aspects, the amino acids are of the MASP-2 virtual binding site are hydrophobic. In some aspects, the amino acids of the MASP-2 virtual binding sites are hydrophilic. In some aspects, the amino acids of the MASP-2 virtual binding sites are a mixture of hydrophobic and hydrophilic amino acid residues.

In some aspects, the MASP-2 virtual binding sites contain one or more hydrophobic amino acid residues. In some aspects, the one or more hydrophobic amino acid residues are two or more hydrophobic amino acid residues, three or more hydrophobic amino acid residues, four or more hydrophobic amino acid residues, five or more hydrophobic amino acid residues, six or more hydrophobic amino acid residues, seven or more hydrophobic amino acid residues, eight or more hydrophobic amino acid residues, nine or more hydrophobic amino acid residues, 10 or more hydrophobic amino acid residues, 11 or more hydrophobic amino acid residues, 12 or more hydrophobic amino acid residues, 13 or more hydrophobic amino acid residues, 14 or more hydrophobic amino acid residues, 15 or more hydrophobic amino acid residues, 20 or more hydrophobic amino acid residues, or 25 or more hydrophobic amino acids.

In some aspects, the MASP-2 virtual binding sites contain one or more hydrophilic amino acid residues. In some aspects, the one or more hydrophilic amino acid residues are two or more hydrophilic amino acid residues, three or more hydrophilic amino acid residues, four or more hydrophilic amino acid residues, five or more hydrophilic amino acid residues, six or more hydrophilic amino acid residues, seven or more hydrophilic amino acid residues, eight or more hydrophilic amino acid residues, nine or more hydrophilic amino acid residues, 10 or more hydrophilic amino acid residues, 11 or more hydrophilic amino acid residues, 12 or more hydrophilic amino acid residues, 13 or more hydrophilic amino acid residues, 14 or more hydrophilic amino acid residues, 15 or more hydrophilic amino acid residues, 20 or more hydrophilic amino acid residues, or 25 or more hydrophilic amino acids.

In some aspects, a virtual binding site identified on MASP-2 is at least one amino acid residue selected from the MET 1 to LYS 350 region of SEQ ID NO: 1. In some aspects, a virtual binding site identified on MASP-2 is at least one amino acid residue selected from the ASP 351 to PHE 686 region of SEQ ID NO: 1. In some aspects, a virtual binding site identified on MASP-2 is at least one amino acid residue selected from the MET 1 to LYS 350 region of SEQ ID NO: 1 and at least one amino acid residue selected from the ASP 351 to PHE 686 region of SEQ ID NO: 1. In some aspects, a virtual binding site identified on MASP-2 is at least one amino acid residue selected from the MET1 to THR50 region of SEQ ID NO: 1, or the ALA 51 to ALA 100 region, PRO 101 to PRO 150, THR 151 to GLU 200, TYR 201 to THR 250, ASP 251 to CYS 300, PRO 301 to LYS 350, ASP 351 to PHE 400, TYR 401 to LYS 450, ALA 451 to GLY 500, THR 501 to PRO 550, ILE 551 to ALA 600, ALA 601 to GLY 650, the GLY 651 to PHE 686 region of SEQ ID NO: 1, or combinations thereof.

In some aspects, the one or more virtual binding sites identified on MASP-2 are one or more of the residues of the of the serine protease domain residues 445-686 of SEQ ID NO: 1. In one aspect, one or more of the catalytic triad is included, HIS 483, ASP 532 and SER 633.

In some aspects, the one or more virtual binding sites identified on MASP-2 are one or more of the following residues: LEU 621, ALA 663, GLY 664, TYR 666, VAL 429, CYS 430, GLU 431, PRO 432, VAL 433, CYS 434, ILE 544, ASN 545, ALA 527, GLY 528, GLU 378, ARG 376, GLU 397, GLU 398, ASP 475, SER 374, LEU 473, TYR 474, PRO 550, ILE 551, CYS 552, LYS 541, VAL 542, VAL 543, ILE 544, ASN 545, SER 546, ASN 547, ILE 548, THR 549, GLY 574, ILE 363, THR 440, THR 441, PHE 400, TYR 401, ASP 532, ASP 526, HIS 525, TYR 523, THR 466, ILE 661, GLU 662, LEU 575, PRO 605, VAL 485, TYR 486, GLU 487, GLN 488, LYS 489, HIS 490, GLY 631, LEU 581, THR 467, GLY 667, SER 657, GLY 656, TRP 655, SER 654, SER 633, ARG 630, CYS 629, SER 628, ASP 627, PHE 529, HIS 483, PRO 606, PRO 608, SER 611, VAL 653, MET 658, TYR 669, TYR 607, ASN 659, CYS 660, GLN 665, and combinations thereof. In some aspects, the one or more virtual binding sites identified on MASP-2 are one or more of the following residues: LEU 621, ALA 663, GLY 664, TYR 666, VAL 429, CYS 430, GLU 431, PRO 432, VAL 433, CYS 434, ILE 544, ASN 545, ALA 527, GLY 528, GLU 378, ARG 376, GLU 397, GLU 398, ASP 475, SER 374, LEU 473, TYR 474, PRO 550, ILE 551, CYS 552, LYS 541, VAL 542, VAL 543, ILE 544, ASN 545, SER 546, ASN 547, ILE 548, THR 549, GLY 574, ILE 363, THR 440, THR 441, PHE 400, TYR 401, ASP 532, ASP 526, HIS 525, TYR 523, THR 466, ILE 661, GLU 662, LEU 575, PRO 605, VAL 485, TYR 486, GLU 487, GLN 488, LYS 489, HIS 490, GLY 631, LEU 581, THR 467, and combinations thereof. In some aspects, the one or more virtual binding sites identified on MASP-2 are one or more of the following residues: GLY 667, SER 657, GLY 656, TRP 655, SER 654, SER 633, ARG 630, CYS 629, SER 628, ASP 627, PHE 529, HIS 483, PRO 606, PRO 608, SER 611, VAL 653, MET 658, TYR 669, TYR 607, ASN 659, CYS 660, GLN 665, and combinations thereof.

In some aspects, proteins interact with small molecules on their surface and when strongly bound, can be resolved crystallographically. Such small molecules often originate from buffer components or cryoprotectants that are added to the protein sample to aid crystallization or protein crystal cryo-protection. Using crystallographic structures of MASP-2 with bound compounds (see, FIG. 1-57), a number of such small molecules bound to MASP-2 (Tables 29 and Table 30) have been identified, such as polyethylene glycol (PEG), succinic acid (SIN), sulfate ($SO_4$), glycerol (GOL), 2-methyl-2,4-pentanediol (MPD), phosphate ($PO_4$), acetic acid (ACT) as well as ligand (LIG) molecules that are bound at a location that is different from the canonical binding site and away from the active site. The hydrogen bonding pattern, as well as their van der Waals interaction pattern with MASP-2 surface atoms may be of utility in identifying binding sites for inhibitor molecules. MASP-2 amino acids and their respective experimentally determined hydrogen bond forming residues and atoms are listed in Table 29, which shows the hydrogen bonding pattern of MASP-2 serine protease residues and corresponding atoms with small molecules. Hydrogen bond donor and acceptor distances are provided, as well as the respective residue identity and corresponding numbering. In short, such H-bond forming amino acids constitute THR 466, HIS 483, GLU 487, TYR 523, GLY 528, LYS 541, ARG 578, ARG 583, ASN 584, ARG 630, GLY 631, SER 633, THR 644 and MET 658. Likewise, MASP-2 amino acids and specific atoms therein that form van der Waals with such small molecules are listed in Table 30. In short, such van der Waals contact forming amino acids include GLY465, THR466, THR467, ALA468, TYR474, ASN476, HIS483, GLU487, ASP526, GLY528, PHE529, CYS552, LEU575, ARG 578, GLY579, LEU581, ALA582, ARG583, ASN584, MET586, PRO606, TYR607, PRO608, ARG630, GLY631, SER633, ASP641, THR644, ARG646, SER657, MET658, ALE683, SER684.

TABLE 29

Hydrogen bonding pattern of MASP-2 serine protease residues and corresponding atoms with small molecules. Hydrogen bond donor and acceptor distances are provided, as well as the respective residue identity and corresponding numbering.

| Compound No. | Small molecule | DONOR Residue or molecule | # | Atom | ACCEPTOR Residue or molecule | # | Atom | Distance [Å] |
|---|---|---|---|---|---|---|---|---|
| 1129 | PEG | LYS | 541 | NZ | PEG | 1 | O4 | 2.87 |
| 1129 | SIN | MET | 658 | N | SIN | 1 | O1 | 2.78 |
| 1059 | SO4_1 | SER | 633 | OG | SO4 | 1 | O3 | 3.15 |
| 1059 | SO4_1 | SER | 633 | OG | SO4 | 1 | O1 | 2.62 |
| 1059 | SO4_1 | GLY | 631 | N | SO4 | 1 | O1 | 2.88 |
| 1059 | SO4_1 | HIS | 483 | NE2 | SO4 | 1 | O3 | 2.61 |
| 1059 | SO4_2 | ASN | 584 | ND2 | SO4 | 2 | O1 | 3.11 |
| 1059 | SO4_2 | ASN | 584 | N | SO4 | 2 | O1 | 3.12 |
| 1059 | SO4_2 | ARG | 583 | NH2 | SO4 | 2 | O4 | 2.82 |
| 1059 | SO4_2 | ARG | 583 | NE | SO4 | 2 | O2 | 3.19 |
| 1059 | SO4_2 | ARG | 583 | N | SO4 | 2 | O2 | 2.86 |
| 1059 | SO4_2 | ARG | 578 | NH1 | SO4 | 2 | O3 | 2.51 |
| 1088 | Lig2 | LIG | 2 | N31 | GLY | 528 | O | 3.01 |
| 1088 | Lig2 | LIG | 2 | N29 | GLY | 528 | O | 3.03 |
| 1088 | Lig2 | LIG | 2 | N31 | TYR | 523 | OH | 2.8 |
| 1088 | Lig1 | LIG | 1 | N31 | GLU | 487 | OE2 | 3.02 |
| 1088 | Lig1 | LIG | 1 | N29 | GLU | 487 | OE1 | 2.78 |
| 1065 | MPD1 | SER | 633 | OG | MPD | 1 | O2 | 2.6 |
| 1065 | MPD1 | GLY | 631 | N | MPD | 1 | O2 | 2.88 |
| 1030 | SO4_1 | ASN | 584 | ND2 | SO4 | 1 | O1 | 3.21 |
| 1030 | SO4_1 | ASN | 584 | N | SO4 | 1 | O1 | 3.04 |
| 1030 | SO4_1 | ARG | 583 | NH1 | SO4 | 1 | O4 | 2.92 |
| 1030 | SO4_1 | ARG | 583 | NE | SO4 | 1 | O2 | 3 |
| 1030 | SO4_1 | ARG | 583 | N | SO4 | 1 | O2 | 2.76 |
| 1030 | SO4_1 | ARG | 578 | NH2 | SO4 | 1 | O3 | 2 |
| 1030 | SO4_2 | SER | 633 | OG | SO4 | 2 | O1 | 2.52 |
| 1030 | SO4_2 | GLY | 631 | N | SO4 | 2 | O1 | 2.83 |
| 1030 | SO4_2 | ARG | 630 | NH2 | SO4 | 2 | O4 | 3.03 |

TABLE 29-continued

Hydrogen bonding pattern of MASP-2 serine protease residues and corresponding atoms with small molecules. Hydrogen bond donor and acceptor distances are provided, as well as the respective residue identity and corresponding numbering.

| Compound No. | Small molecule | DONOR Residue or molecule | # | Atom | ACCEPTOR Residue or molecule | # | Atom | Distance [Å] |
|---|---|---|---|---|---|---|---|---|
| 1030 | SO4_2 | ARG | 630 | NE | SO4 | 2 | O4 | 2.63 |
| 1030 | SO4_2 | HIS | 483 | NE2 | SO4 | 2 | O3 | 2.59 |
| melagatran | ACT | THR | 644 | OG1 | ACT | 1 | OXT | 2.67 |
| 1090 | GOL | SER | 633 | OG | GOL | 1 | O1 | 2.5 |
| 1090 | GOL | GLY | 631 | N | GOL | 1 | O1 | 3.32 |
| 1090 | GOL | THR | 466 | OG1 | GOL | 1 | O2 | 2.84 |
| 1089 | Lig2 | Lig | 2 | N5 | GLU | 487 | OE2 | 3 |
| 1089 | Lig2 | Lig | 2 | N4 | GLU | 487 | OE1 | 2.66 |
| 1097 | PO4_1 | SER | 633 | OG | PO4 | 1 | O3 | 2.55 |
| 1097 | PO4_1 | GLY | 631 | N | PO4 | 1 | O3 | 2.85 |
| 1097 | PO4_1 | HIS | 483 | NE2 | PO4 | 1 | O1 | 2 |
| 1097 | PO4_2 | SER | 633 | OG | PO4 | 2 | O1 | 2.51 |
| 1097 | PO4_2 | GLY | 631 | N | PO4 | 2 | O1 | 2.92 |
| 1097 | PO4_2 | HIS | 483 | NE2 | PO4 | 2 | O4 | 3.03 |
| 1097 | PO4_2 | THR | 466 | OG1 | PO4 | 2 | O2 | 3.33 |

Abbreviations used: polyethylene glycol (PEG), succinic acid (SIN), sulfate (SO$_4$), glycerol (GOL), 2-methyl-2,4-pentanediol (MPD), phosphate (PO$_4$), acetic acid (ACT), surplus ligand (LIG) molecules.

TABLE 30 van der Waals contact pattern of MASP-2 serine protease residues and corresponding atoms with small molecules. Inter atomic contact distances are provided, as well as the respective residue identity and corresponding numbering.

| Compound No. | Small molecule | ATOM 1 | | ATOM 2 | | | Distance [Å] |
|---|---|---|---|---|---|---|---|
| 1129 | PEG | PEG | O1 | SER | 684 | CA | 3.58 |
| 1129 | PEG | PEG | O2 | ILE | 683 | CG2 | 3.78 |
| 1129 | PEG | PEG | C1 | ILE | 683 | CG2 | 3.81 |
| 1129 | PEG | PEG | C1 | ILE | 683 | O | 3.61 |
| 1129 | PEG | PEG | C4 | ASN | 476 | OD1 | 3.77 |
| 1129 | PEG | PEG | C3 | ASN | 476 | OD1 | 3.58 |
| 1129 | PEG | PEG | O4 | ASN | 476 | CG | 3.55 |
| 1129 | PEG | PEG | C4 | TYR | 474 | CG | 3.89 |
| 1129 | PEG | PEG | C3 | TYR | 474 | CG | 3.75 |
| 1129 | PEG | PEG | O4 | TYR | 474 | CB | 3.67 |
| 1129 | PEG | PEG | C4 | TYR | 474 | CB | 3.79 |
| 1129 | SIN | SIN | O3 | MET | 658 | SD | 3.75 |
| 1129 | SIN | SIN | O3 | MET | 658 | CG | 3.73 |
| 1129 | SIN | SIN | O1 | MET | 658 | CB | 3.41 |
| 1129 | SIN | SIN | O1 | MET | 658 | CA | 3.71 |
| 1129 | SIN | SIN | O1 | SER | 657 | CB | 3.58 |
| 1129 | SIN | SIN | O1 | SER | 657 | C | 3.6 |
| 1129 | SIN | SIN | O4 | SER | 657 | C | 3.88 |
| 1129 | SIN | SIN | O1 | SER | 657 | CA | 3.49 |
| 1129 | SIN | SIN | C1 | TYR | 607 | OH | 3.25 |
| 1129 | SIN | SIN | C3 | TYR | 607 | OH | 3.78 |
| 1129 | SIN | SIN | O1 | TYR | 607 | CZ | 3.9 |
| 1129 | SIN | SIN | O2 | PRO | 606 | CD | 3.88 |
| 1129 | SIN | SIN | C2 | PRO | 606 | CG | 3.79 |
| 1129 | SIN | SIN | C3 | PRO | 606 | CG | 3.62 |
| 1059 | SO4_1 | SO4 | S | SER | 633 | OG | 3.48 |
| 1059 | SO4_1 | SO4 | O3 | SER | 633 | CB | 3.88 |
| 1059 | SO4_1 | SO4 | O1 | SER | 633 | CB | 3.38 |
| 1059 | SO4_1 | SO4 | O1 | GLY | 631 | CA | 3.86 |
| 1059 | SO4_1 | SO4 | O1 | ARG | 630 | C | 3.59 |
| 1059 | SO4_1 | SO4 | O4 | ARG | 630 | CG | 3.25 |
| 1059 | SO4_1 | SO4 | O1 | ARG | 630 | CB | 3.89 |
| 1059 | SO4_1 | SO4 | O4 | ARG | 630 | CB | 3.46 |
| 1059 | SO4_1 | SO4 | O1 | ARG | 630 | CA | 3.32 |
| 1059 | SO4_1 | SO4 | O3 | HIS | 483 | CD2 | 3.15 |
| 1059 | SO4_1 | SO4 | O3 | HIS | 483 | CE1 | 3.82 |
| 1059 | SO4_2 | SO4 | O3 | MET | 586 | CE | 3.63 |
| 1059 | SO4_2 | SO4 | O1 | MET | 586 | CE | 3.1 |
| 1059 | SO4_2 | SO4 | S | MET | 586 | CE | 3.83 |
| 1059 | SO4_2 | SO4 | O1 | ASN | 584 | CG | 3.74 |
| 1059 | SO4_2 | SO4 | O1 | ASN | 584 | CB | 3.44 |
| 1059 | SO4_2 | SO4 | O1 | ASN | 584 | CA | 3.8 |
| 1059 | SO4_2 | SO4 | S | ARG | 583 | NH2 | 3.81 |
| 1059 | SO4_2 | SO4 | O4 | ARG | 583 | CZ | 3.82 |
| 1059 | SO4_2 | SO4 | O2 | ARG | 583 | CG | 3.77 |
| 1059 | SO4_2 | SO4 | O2 | ARG | 583 | CB | 3.54 |
| 1059 | SO4_2 | SO4 | O2 | ARG | 583 | CA | 3.79 |
| 1059 | SO4_2 | SO4 | S | ARG | 583 | N | 3.57 |
| 1059 | SO4_2 | SO4 | O2 | ALA | 582 | C | 3.69 |
| 1059 | SO4_2 | SO4 | O1 | ALA | 582 | C | 3.89 |
| 1059 | SO4_2 | SO4 | O1 | ALA | 582 | CB | 3.86 |
| 1059 | SO4_2 | SO4 | O3 | ALA | 582 | CA | 3.62 |
| 1059 | SO4_2 | SO4 | O2 | ALA | 582 | CA | 3.63 |
| 1059 | SO4_2 | SO4 | O1 | ALA | 582 | CA | 3.86 |
| 1059 | SO4_2 | SO4 | S | ARG | 578 | NH1 | 3.56 |
| 1059 | SO4_2 | SO4 | O3 | ARG | 578 | CZ | 3.51 |
| 1059 | PEG1 | PEG | C1 | PRO | 606 | O | 3.77 |
| 1059 | PEG1 | PEG | C4 | PRO | 606 | CG | 3.07 |
| 1059 | PEG1 | PEG | C4 | PRO | 606 | CB | 3.83 |
| 1088 | Lig2 | LIG | C15 | GLY | 631 | CA | 3.64 |
| 1088 | Lig2 | LIG | C14 | GLY | 631 | CA | 3.8 |
| 1088 | Lig2 | LIG | C15 | GLY | 631 | N | 3.57 |
| 1088 | Lig2 | LIG | C14 | GLY | 631 | N | 3.57 |
| 1088 | Lig2 | LIG | C15 | ARG | 630 | C | 3.74 |
| 1088 | Lig2 | LIG | C17 | ARG | 630 | CB | 3.76 |
| 1088 | Lig2 | LIG | C16 | ARG | 630 | CB | 3.82 |
| 1088 | Lig2 | LIG | C11 | ARG | 630 | CB | 3.86 |
| 1088 | Lig2 | LIG | C15 | LEU | 581 | CD2 | 3.83 |
| 1088 | Lig2 | LIG | C16 | LEU | 575 | CG | 3.8 |
| 1088 | Lig2 | LIG | N31 | PHE | 529 | CE2 | 3.7 |
| 1088 | Lig2 | LIG | C30 | PHE | 529 | CE2 | 3.48 |
| 1088 | Lig2 | LIG | N29 | PHE | 529 | CE2 | 3.88 |
| 1088 | Lig2 | LIG | C24 | PHE | 529 | CE2 | 3.7 |
| 1088 | Lig2 | LIG | C30 | PHE | 529 | CZ | 3.43 |
| 1088 | Lig2 | LIG | N29 | PHE | 529 | CZ | 3.47 |
| 1088 | Lig2 | LIG | C28 | PHE | 529 | CZ | 3.55 |
| 1088 | Lig2 | LIG | C27 | PHE | 529 | CZ | 3.67 |
| 1088 | Lig2 | LIG | C25 | PHE | 529 | CZ | 3.76 |
| 1088 | Lig2 | LIG | C24 | PHE | 529 | CZ | 3.62 |
| 1088 | Lig2 | LIG | N29 | PHE | 529 | CE1 | 3.66 |

TABLE 30-continued van der Waals contact pattern of MASP-2 serine protease residues and corresponding atoms with small molecules. Inter atomic contact distances are provided, as well as the respective residue identity and corresponding numbering.

| Compound No. | Small molecule | ATOM 1 | | ATOM 2 | | Distance [Å] |
|---|---|---|---|---|---|---|
| 1088 | Lig2 | LIG | C28 | PHE | 529 CE1 | 3.64 |
| 1088 | Lig2 | LIG | C30 | GLY | 528 O | 3.41 |
| 1088 | Lig2 | LIG | N29 | GLY | 528 C | 3.57 |
| 1088 | Lig2 | LIG | N29 | GLY | 528 CA | 3.67 |
| 1088 | Lig2 | LIG | C28 | GLY | 528 N | 3.64 |
| 1088 | Lig2 | LIG | N29 | ASP | 526 C | 3.64 |
| 1088 | Lig2 | LIG | C28 | ASP | 526 C | 3.67 |
| 1088 | Lig1 | LIG | C16 | GLY | 579 O | 3.7 |
| 1088 | Lig1 | LIG | C15 | GLY | 579 O | 3.61 |
| 1088 | Lig1 | LIG | C16 | LEU | 575 CD2 | 3.78 |
| 1088 | Lig1 | LIG | C15 | LEU | 575 CD2 | 3.51 |
| 1088 | Lig1 | LIG | C14 | LEU | 575 CD2 | 3.86 |
| 1088 | Lig1 | LIG | C30 | GLU | 487 OE2 | 3.58 |
| 1088 | Lig1 | LIG | C30 | GLU | 487 OE1 | 3.77 |
| 1088 | Lig1 | LIG | C28 | GLU | 487 OE1 | 3.38 |
| 1088 | Lig1 | LIG | N31 | GLU | 487 CD | 3.83 |
| 1088 | Lig1 | LIG | N29 | GLU | 487 CD | 3.32 |
| 1088 | Lig1 | LIG | C28 | THR | 466 CG2 | 3.77 |
| 1088 | Lig1 | LIG | C27 | THR | 466 CG2 | 3.52 |
| 1088 | Lig1 | LIG | C30 | GLY | 465 O | 3.59 |
| 1088 | Lig1 | LIG | C24 | GLY | 465 O | 3.68 |
| 1088 | Lig1 | LIG | N31 | GLY | 465 CA | 3.84 |
| 1065 | MPD1 | MPD | C1 | SER | 633 OG | 3.55 |
| 1065 | MPD1 | MPD | CM | SER | 633 OG | 3.61 |
| 1065 | MPD1 | MPD | C2 | SER | 633 OG | 3.42 |
| 1065 | MPD1 | MPD | O2 | SER | 633 CB | 3.38 |
| 1065 | MPD1 | MPD | CM | SER | 633 CB | 3.85 |
| 1065 | MPD1 | MPD | O2 | GLY | 631 CA | 3.69 |
| 1065 | MPD1 | MPD | C4 | GLY | 631 N | 3.72 |
| 1065 | MPD1 | MPD | O2 | ARG | 630 C | 3.76 |
| 1065 | MPD1 | MPD | C3 | ARG | 630 NH1 | 3.58 |
| 1065 | MPD1 | MPD | C3 | ARG | 630 CZ | 3.66 |
| 1065 | MPD1 | MPD | O2 | ARG | 630 CA | 3.71 |
| 1065 | MPD1 | MPD | CM | THR | 467 O | 3.89 |
| 1065 | MPD1 | MPD | C5 | THR | 467 O | 3 |
| 1065 | MPD1 | MPD | C4 | THR | 467 O | 3.14 |
| 1065 | MPD1 | MPD | C5 | THR | 467 C | 3.67 |
| 1065 | MPD1 | MPD | C5 | THR | 467 CB | 3.88 |
| 1065 | MPD1 | MPD | C5 | THR | 467 CA | 3.74 |
| 1065 | MPD1 | MPD | C5 | THR | 467 N | 3.17 |
| 1065 | MPD1 | MPD | CM | THR | 466 CB | 3.87 |
| 1065 | MPD1 | MPD | C5 | THR | 466 CB | 3.72 |
| 1030 | SO4_1 | SO4 | O1 | MET | 586 CE | 3 |
| 1030 | SO4_1 | SO4 | O1 | ASN | 584 CG | 3.84 |
| 1030 | SO4_1 | SO4 | O1 | ASN | 584 CB | 3.5 |
| 1030 | SO4_1 | SO4 | O1 | ASN | 584 CA | 3.77 |
| 1030 | SO4_1 | SO4 | S | ARG | 583 NH1 | 3.88 |
| 1030 | SO4_1 | SO4 | O2 | ARG | 583 CZ | 3.79 |
| 1030 | SO4_1 | SO4 | O4 | ARG | 583 CZ | 3.85 |
| 1030 | SO4_1 | SO4 | O2 | ARG | 583 CD | 3.83 |
| 1030 | SO4_1 | SO4 | O2 | ARG | 583 CG | 3.5 |
| 1030 | SO4_1 | SO4 | O2 | ARG | 583 CB | 3.36 |
| 1030 | SO4_1 | SO4 | O2 | ARG | 583 CA | 3.62 |
| 1030 | SO4_1 | SO4 | S | ARG | 583 N | 3.49 |
| 1030 | SO4_1 | SO4 | O2 | ALA | 582 C | 3.71 |
| 1030 | SO4_1 | SO4 | O1 | ALA | 582 CB | 3.75 |
| 1030 | SO4_1 | SO4 | O3 | ALA | 582 CA | 3.81 |
| 1030 | SO4_1 | SO4 | O2 | ALA | 582 CA | 3.73 |
| 1030 | SO4_1 | SO4 | O1 | ALA | 582 CA | 3.88 |
| 1030 | SO4_1 | SO4 | S | ARG | 578 NH2 | 3.7 |
| 1030 | SO4_2 | SO4 | S | SER | 633 OG | 3.38 |
| 1030 | SO4_2 | SO4 | O3 | SER | 633 CB | 3.75 |
| 1030 | SO4_2 | SO4 | O1 | SER | 633 CB | 3.19 |
| 1030 | SO4_2 | SO4 | O1 | GLY | 631 CA | 3.8 |
| 1030 | SO4_2 | SO4 | S | GLY | 631 N | 3.86 |
| 1030 | SO4_2 | SO4 | O1 | ARG | 630 C | 3.67 |
| 1030 | SO4_2 | SO4 | O4 | ARG | 630 CZ | 3.26 |
| 1030 | SO4_2 | SO4 | O4 | ARG | 630 CD | 3.73 |
| 1030 | SO4_2 | SO4 | O4 | ARG | 630 CB | 3.69 |
| 1030 | SO4_2 | SO4 | O1 | ARG | 630 CA | 3.56 |
| 1030 | SO4_2 | SO4 | O3 | HIS | 483 CD2 | 3.13 |
| 1030 | SO4_2 | SO4 | O3 | HIS | 483 CE1 | 3.79 |
| 1030 | PEG | PEG | O2 | PRO | 608 CD | 3.6 |
| 1030 | PEG | PEG | O2 | TYR | 607 CD1 | 3.5 |
| 1030 | PEG | PEG | C4 | PHE | 529 CD2 | 3.8 |
| 1030 | PEG | PEG | C4 | GLY | 528 CA | 3.77 |
| 1030 | PEG | PEG | O4 | GLY | 528 CA | 3 |
| melagatran | ACT | ACT | OXT | ARG | 646 CG | 3.65 |
| melagatran | ACT | ACT | OXT | ARG | 646 CB | 3.44 |
| melagatran | ACT | ACT | OXT | THR | 644 CG2 | 3.88 |
| melagatran | ACT | ACT | C | THR | 644 OG1 | 3.8 |
| melagatran | ACT | ACT | OXT | THR | 644 CB | 3.57 |
| melagatran | ACT | ACT | C | ASP | 641 OD2 | 3.45 |
| melagatran | ACT | ACT | CH3 | CYS | 552 SG | 3.79 |
| melagatran | ACT | ACT | CH3 | CYS | 552 CB | 3.78 |
| 1090 | GOL | GOL | C1 | SER | 633 OG | 3.59 |
| 1090 | GOL | GOL | O1 | SER | 633 CB | 3.17 |
| 1090 | GOL | GOL | C2 | GLY | 631 N | 3.75 |
| 1090 | GOL | GOL | C1 | HIS | 483 NE2 | 3.82 |
| 1090 | GOL | GOL | O3 | THR | 466 CG2 | 3.88 |
| 1090 | GOL | GOL | O2 | THR | 466 CB | 3.75 |
| 1089 | Lig2 | LIG | C23 | GLU | 487 OE2 | 3.61 |
| 1089 | Lig2 | LIG | C23 | GLU | 487 OE1 | 3.66 |
| 1089 | Lig2 | LIG | C22 | GLU | 487 OE1 | 3.36 |
| 1089 | Lig2 | LIG | N5 | GLU | 487 CD | 3.79 |
| 1089 | Lig2 | LIG | N4 | GLU | 487 CD | 3.36 |
| 1089 | Lig2 | LIG | C23 | GLY | 465 O | 3.53 |
| 1089 | Lig2 | LIG | C18 | GLY | 465 O | 3.68 |
| 1097 | PO4_1 | PO4 | O3 | SER | 633 CB | 3.34 |
| 1097 | PO4_1 | PO4 | O1 | SER | 633 CB | 3.64 |
| 1097 | PO4_1 | PO4 | P | SER | 633 CB | 3.73 |
| 1097 | PO4_1 | PO4 | O4 | SER | 633 CB | 3.51 |
| 1097 | PO4_1 | PO4 | O3 | GLY | 631 CA | 3.63 |
| 1097 | PO4_1 | PO4 | O3 | ARG | 630 C | 3.78 |
| 1097 | PO4_1 | PO4 | O3 | ARG | 630 CG | 3.89 |
| 1097 | PO4_1 | PO4 | O2 | ARG | 630 CG | 3.54 |
| 1097 | PO4_1 | PO4 | O3 | ARG | 630 CA | 3.75 |
| 1097 | PO4_1 | PO4 | O1 | HIS | 483 CD2 | 3.14 |
| 1097 | PO4_1 | PO4 | O4 | ALA | 468 CB | 3.82 |
| 1097 | PO4_1 | PO4 | O4 | ALA | 468 CA | 3.86 |
| 1097 | PO4_1 | PO4 | O4 | THR | 467 C | 3.77 |
| 1097 | PO4_2 | PO4 | O3 | SER | 633 CB | 3.54 |
| 1097 | PO4_2 | PO4 | O1 | SER | 633 CB | 3.06 |
| 1097 | PO4_2 | PO4 | P | SER | 633 CB | 3.63 |
| 1097 | PO4_2 | PO4 | O4 | SER | 633 CB | 3.64 |
| 1097 | PO4_2 | PO4 | O1 | GLY | 631 CA | 3.73 |
| 1097 | PO4_2 | PO4 | O1 | ARG | 630 C | 3.82 |
| 1097 | PO4_2 | PO4 | O2 | ARG | 630 CG | 3.6 |
| 1097 | PO4_2 | PO4 | O1 | ARG | 630 CA | 3.76 |
| 1097 | PO4_2 | PO4 | O4 | HIS | 483 CD2 | 3.22 |
| 1097 | PO4_2 | PO4 | O3 | ALA | 468 CB | 3.73 |
| 1097 | PO4_2 | PO4 | O3 | THR | 467 C | 3.75 |

Abbreviations used: polyethylene glycol (PEG), succinic acid (SIN), sulfate (SO₄), glycerol (GOL), 2-methyl-2,4-pentanediol (MPD), phosphate (PO₄), acetic acid (ACT), surplus ligand (LIG) molecules.

Advantageously, after one or more binding sites has been identified as above it is then possible to identify each of the amino acids that participate in the binding. These specific amino acids interact with the candidate molecules through hydrogen-bonding, ionic bonding and van der Waals interactions such as short-range electrostatic attractive forces between uncharged molecules.

After a docking campaign has been performed, it is possible to analyze the intermolecular interactions and prepare a rule set which describes the interactions.

The compound with MASP-2 inhibitory activity interacts with a MASP-2 binding site in an enzyme-inhibitor complex with a plurality of intermolecular interactions. In certain aspects, the molecule is described with complete specificity and description by the number and type(s) of intermolecular interactions within a MASP-2 binding site, using an empirically derived rule set such as an interaction rule set.

3. Rule Sets

In certain aspects, the compounds with MASP-2 inhibitory activity interact with the MASP-2 binding site as an enzyme-inhibitor complex. The compound having MASP-2 inhibitory activity has between 1 and 100 intermolecular interactions between itself and MASP-2 such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more intermolecular interactions with the binding site of MASP-2. These intermolecular interactions types can be a hydrogen-bond, an ionic bond, an electrostatic bond, π-π interactions, a van der Waals interaction, binding of a water molecule or combinations thereof. The numbers within the various types of intermolecular interactions are counted to reach a total.

In certain aspects, a plurality of the same type of intermolecular interactions exists. For example, the enzyme-inhibitor complex may have 1-40 hydrogen-bonds, 1-40 ionic bonds, 1-40 electrostatic bonds, 1-40 π-π interactions, 1-40 van der Waals interactions, 1-40 binding of water molecules and combinations of thereof, wherein each of the foregoing 1-40 range means 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more interactions. In certain aspects, a plurality or multiple intermolecular interactions may exist with the same amino acid within the binding site.

In certain instances, an inhibitory molecule is described by a rule set. The compound with MASP-2 inhibitory activity interacts with the MASP-2 binding site with a plurality of intermolecular interactions or rules. In certain aspects, the molecule is described with complete structural and functional specificity and description by the number and type(s) of intermolecular interactions. These rules have been empirically derived and discovered using the methods herein.

In certain instances, the present disclosure provides a compound with MASP-2 inhibitory activity, wherein the compound interacts with a binding site, the interactions being one or more of (a) to (e):

a) the compound interacts via H-bonds with one or more amino acid residues in the binding site of SEQ ID NO: 1;
b) the compound interacts via ionic or electrostatic interactions or hydrogen bonding in the binding site of SEQ ID NO: 1;
c) the compound interacts via a water molecule in a binding site of SEQ ID NO: 1;
d) the compound interacts via π-π interactions with one or more amino acid residues in the binding site of SEQ ID NO: 1; and/or
e) the compound interacts via van der Waals contacts to one or more amino acid residues in the binding site of SEQ ID NO: 1, wherein the compound is not an endogenous ligand.

In certain aspects, the compound has 1, 2, 3, 4, or 5 of the interactions (a)-(e).

In addition to identifying virtual binding sites, it is also useful to use crystallographic data derived from a number of enzyme-inhibitor complex co-crystals to derive rule sets. In certain instances, the crystallographic data from at least 1, 10, 20, 30, 40, 50, up to 100. For example, 30 co-crystals can be used 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or even more enzyme-inhibitor complex crystals can be used to generate a set of rules. Using the co-crystal structural data, it is possible to describe the binding site and inhibitory compounds within angstrom detail and definition. The following rule set was empirically derived using crystallographic data with a number of enzyme-inhibitor complex co-crystals.

In certain instances, an inhibitory molecule is described by a rule set. The compound with MASP-2 inhibitory activity interacts with the MASP-2 serine protease domain in an enzyme-inhibitor complex with a plurality of intermolecular interactions or rules. In certain aspects, the molecule is described with complete structural and functional specificity and description by the number and type(s) of intermolecular interactions. These rules have been empirically derived and discovered using crystallographic data with a number of enzyme-inhibitor complex co-crystals. In certain instances, the crystallographic data from at least 1, 10, 20, 30, 40, 50, up to 100. For example, 30 co-crystals can be used 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or even more enzyme-inhibitor complex crystals can be used to generate a set of rules. Using the co-crystal structure information, it is possible to describe the binding site and inhibitory compounds within angstrom detail and definition.

In certain instances, a plurality of amino acids within the MASP-2 serine protease domain are involved in the intermolecular interactions. Amino acids within the MASP-2 serine protease domain include, but are not limited to, ASP 627, SER 628, SER 654, GLY 656, GLN 665, SER 657, PHE 529, TYR 607, TRP 655, GLY 667, SER 633, ARG 630, CYS 629, HIS 483, PRO 606, PRO 608, SER 611, VAL 653, MET 658, TYR 669, ASN 659, CYS 660, GLN 665.

In certain aspects, the number of amino acids within the serine protease domain that interact with a compound having MASP-2 inhibitory activity or that make up a rule set is about 1-50, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids within the MASP-2 serine protease domain.

In certain instances, an inhibitor of the present disclosure is bound to MASP-2, rendering MASP-2 inactive. The amino acids of MASP-2 interact through intermolecular interactions with the inhibitor compound and the types of interactions are now described in more detail.

In certain aspects, the type of interactions include a hydrogen bond (H-bond). The enzyme-inhibitor complex may include 1-40 intermolecular H-bonds with one or more of the following 6 amino acids: ASP 627, SER 628, SER 654, GLY 656, GLN 665 and SER 657. The 1-40 intermolecular H-bonds can include one or more atoms of the inhibitor with one or more atoms of ASP 627, SER 628, SER 654, GLY 656, GLN 665 and SER 657. Each amino acid can have more than one H-bond interaction with an inhibitor. In certain instances, the same atom can be hydrogen bonded to one or more partners. In other words, a single atom of an inhibitory molecule can interact with 2 or more atoms on the protein. In certain instances, there are 1-10H-bonds, or 2-8H-bonds, or 1, 2, 3, 4, 5, 6, 7, 8, 9, or 10H-bonds per compounds.

In certain aspects, the type of interactions include an ionic and/or an electrostatic interaction. The enzyme-inhibitor complex may include 1-10 intermolecular ionic and/or electrostatic interactions with ASP 627. ASP 627 can have more than one ionic and or electrostatic interaction with an inhibitor.

In certain other aspects, the type of interaction is binding of a water molecule with ASP 627, GLN 665, SER 657, ASN 659, SER 628, GLU 662, ARG 630, VAL 668, TYR 602, TYR 607. The enzyme-inhibitor complex may include 1-30 bound water molecules 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 to various amino acids, other water molecules, to the compounds or combinations thereof.

In certain other instances, the type of interaction includes one or more (e.g., a plurality or 1-40) π-π interactions with one or more of the following amino acids PHE 529, TYR 607, and/or TRP 655, 1, 2 or 3 amino acids. Each of the foregoing amino acids can have more than one π-π interaction.

In certain aspects, the type of interaction also includes one or more such as 1-40, van der Waals interactions with GLY 667, SER 657, GLY 656, TRP 655, SER 654, SER 633, ARG 630, CYS 629, SER 628, ASP 627, PHE 529, HIS 483, PRO 606, TYR 607, PRO 608, SER 611, VAL 653, MET 658, TYR 669, ASN 659, CYS 660, GLN 665 and combinations thereof, which interactions are specific MASP-2 amino acids within the serine protease domain of MASP-2.

III. Synthesis

Compounds described herein, including salts thereof, can be prepared using known organic synthesis techniques and can be synthesized according to any of numerous possible synthetic routes, such as those illustrated in the Examples below.

The reactions for preparing compounds described herein can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, Protecting Groups, (Thieme, 2007); Robertson, Protecting Group Chemistry, (Oxford University Press, 2000); Smith et al., March's Advanced Organic Chemistry: Reactions, Mechanisms, and Structure, 6th Ed. (Wiley, 2007); Peturssion et al., "Protecting Groups in Carbohydrate Chemistry," *J. Chem. Educ.*, 1997, 74(11), 1297; and Wuts et al., Protective Groups in Organic Synthesis, 4th Ed., (Wiley, 2006).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry or by chromatographic methods such as high performance liquid chromatography (HPLC) or thin layer chromatography (TLC).

The particular synthetic methods used in the Examples provide general guidance in connection with preparing the compounds of the invention. One skilled in the art would understand that the preparations can be modified or optimized using general knowledge of organic chemistry to prepare various compounds within the scope of the present disclosure.

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry*, Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2nd Edition, 2004); Katritzky et al. (Ed.), *Comprehensive Heterocyclic Chemistry* (Pergamon Press, 1984); Katritzky et al., *Comprehensive Heterocyclic Chemistry II* (Pergamon Press, 1996); Smith et al., *March's Advanced Organic Chemistry: Reactions, Mechanisms, and Structure*, 6th Ed. (Wiley, 2007); Trost et al. (Ed.), *Comprehensive Organic Synthesis* (Pergamon Press, 1991).

IV. Methods of Treatment

In another aspect, the present disclosure provides a method of treating a patient suffering from, or at risk for developing a MASP-2-associated disease or disorder such as a MASP-2-dependent complement-associated disease or disorder comprising administering a small molecule inhibitor of MASP-2.

The compound can be any small molecule inhibitor of MASP-2. In some embodiments, the compound can be a small molecule inhibitor of MASP-2 that binds to the serine protease domain of MASP-2. In some embodiments, the compound can be a small molecule inhibitor such as a synthetic small molecule inhibitor of MASP-2. In some embodiments, the compound can be a small molecule inhibitor of MASP-2 that binds to the catalytic, substrate-binding region of MASP-2. In some embodiments, the compound selectively inhibits MASP-2 as compared to thrombin. In some embodiments, the compound can be any small molecule inhibitor of MASP-2 that binds to a binding site comprising the S1, S2 and S3 regions, and optionally, further comprises the S4 and RM regions, of the MASP-2 enzyme described herein. In some embodiments, the compound can be any small molecule that binds to a binding site of comprising the amino acids ALA 468, ALA 469, HIS 483, ASP 526, ALA 527, GLY 528, PHE 529, LEU 575, TYR 602, PRO 606, TYR 607, PRO 608, SER 611, ASP 627, SER 628, CYS 629, ARG 630, GLY 631, ASP 632, SER 633, GLY 634, GLY 635, VAL 653, SER 654, TRP 655, GLY 656, SER 657, MET 658, ASN 659, CYS 660, GLU 662, GLN 665, TYR 666, GLY 667, VAL 668, and TYR 669, or any subset of any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 of the amino acids ALA 468, ALA 469, HIS 483, ASP 526, ALA 527, GLY 528, PHE 529, LEU 575, TYR 602, PRO 606, TYR 607, PRO 608, SER 611, ASP 627, SER 628, CYS 629, ARG 630, GLY 631, ASP 632, SER 633, GLY 634, GLY 635, VAL 653, SER 654, TRP 655, GLY 656, SER 657, MET 658, ASN 659, CYS 660, GLU 662, GLN 665, TYR 666, GLY 667, VAL 668, and/or TYR 669.

The compound can be any small molecule inhibitor of MASP-2 as disclosed herein. In some embodiments, the compound can be any of the compounds disclosed above under "II. Compounds" above, or any embodiment thereof.

As described in U.S. Pat. Nos. 7,919,094; 8,840,893; 8,652,477; 8,951,522, 9,011,860, 9,475,885, 9,644,035, U.S. Patent Application Publication Nos. US2013/0344073, US2013/0266560, US 2015/0166675, US2017/0137537, US2017/0166660, US2017/0189525, US2017/0267781, US2017/0283508, US2017/0253667, US2018/0105604, WO2018/045054, WO2019/036460 and U.S. Patent Application Ser. No. 62/688,611 (each of which is assigned to Omeros Corporation, the assignee of the instant application, each of which is hereby incorporated by reference), MASP-2-dependent complement activation has been implicated as contributing to the pathogenesis of numerous acute and chronic disease states. For example, as described in U.S. Pat. No. 8,951,522, the primary function of the complement system, a part of the innate immune system, is to protect the host against infectious agents, however, inappropriate or over-activation of the complement system can lead to serious disease, such as thrombotic microangiopathies (TMAs, including aHUS, TTP and HUS) in which endothelial damage as well as fibrin and platelet-rich thrombi in the microvasculature lead to organ damage. The lectin pathway plays a dominant role in activating complement in settings of endothelial cell stress or injury, and preventing the activation of MASP-2 and the lectin pathway halts the sequence of enzymatic reactions that lead to the formation of the membrane attack complex, platelet activation and leukocyte recruitment. As described in U.S. Pat. No. 8,652,477, in addition to initiation of the lectin pathway, MASP-2 can also activate the coagulation system and is capable of cleaving prothrombin to thrombin.

Accordingly, in some embodiments, the method comprises administering to a patient suffering from or at risk for developing a MASP-2-dependent complement-associated disease or disorder an amount of a compound of the disclosure in an amount sufficient to inhibit MASP-2 dependent complement activation in said mammalian subject to thereby treat the disease or disorder. In some embodiments, the method can further comprise, prior to administering a compound of the disclosure to the patient, determining that the patient is afflicted with the lectin complement-associated disease or disorder.

In some embodiments, the MASP-2-dependent complement-associated disease or disorder is selected from the group consisting of a thrombotic microangiopathy (TMA), a renal condition, an inflammatory reaction resulting from tissue or organ transplantation, an ischemia reperfusion injury, a complication associated with diabetes, a cardiovascular disease or disorder, an inflammatory gastrointestinal disorder, a pulmonary disorder, an ophthalmic disease or disorder, disseminated intravascular coagulation, graft-versus-host disease, veno-occlusive disease and diffuse alveolar hemorrhage.

In some embodiments, the MASP-2-dependent complement-associated disease or disorder is a thrombotic microangiopathy (TMA) including thrombotic thrombocytopenic purpura (TTP), refractory TTP, Upshaw-Schulman Syndrome (USS), hemolytic uremic syndrome (HUS), atypical hemolytic syndrome (aHUS), non-Factor H-dependent atypical hemolytic syndrome, aHUS secondary to an infection, plasma therapy-resistant aHUS, a TMA secondary to cancer, a TMA secondary to chemotherapy, a TMA secondary to transplantation, or a TMA associated with hematopoietic stem cell transplant.

In some embodiments, the method comprises administering to a patient suffering from or at risk for developing graft-versus-host disease (GVHD), including acute GVHD, chronic GVHD or steroid-resistant GVHD an amount of a compound of the disclosure in an amount sufficient to inhibit MASP-2 dependent complement activation in said mammalian subject to thereby treat the disease or disorder. In some embodiments, the subject suffering from or at risk for developing GVHD has previously undergone, is undergoing, or will undergo a hematopoietic stem cell transplant.

In some embodiments, the method comprises administering to a patient suffering from, or at risk for developing diffuse alveolar hemorrhage (DAH) an amount of a compound of the disclosure in an amount sufficient to inhibit MASP-2 dependent complement activation in said mammalian subject to thereby treat the disease or disorder. In some embodiments, the subject suffering from, or at risk for developing DAH has previously undergone, is undergoing, or will undergo a hematopoietic stem cell transplant.

In some embodiments, the method comprises administering to a patient suffering from, or at risk for developing veno-occlusive disease (VOD) an amount of a compound of the disclosure in an amount sufficient to inhibit MASP-2 dependent complement activation in said mammalian subject to thereby treat the disease or disorder. In some embodiments, the subject suffering from, or at risk for developing VOD has previously undergone, is undergoing, or will undergo a hematopoietic stem cell transplant.

In some embodiments, the MASP-2-dependent complement-associated disease or disorder is a renal condition including, but not limited to, mesangioproliferative glomerulonephritis, membranous glomerulonephritis, membranoproliferative glomerulonephritis (mesangiocapillary glomerulonephritis), acute post infectious glomerulonephritis (poststreptococcal glomerulonephritis), C3 glomerulopathy, cryoglobulinemic glomerulonephritis, pauci-immune necrotizing crescentic glomerulonephritis, lupus nephritis, Henoch-Schonlein purpura nephritis and IgA nephropathy.

In some embodiments, the MASP-2-dependent complement-associated disease or disorder is renal fibrosis (e.g., tubulointerstitial fibrosis) and/or proteinuria in a subject suffering from or at risk for developing chronic kidney disease, chronic renal failure, glomerular disease (e.g., focal segmental glomerulosclerosis), an immune complex disorder (e.g., IgA nephropathy, membranous nephropathy), lupus nephritis, nephrotic syndrome, diabetic nephropathy, tubulointerstitial damage and glomerulonepthritis (e.g., C3 glomerulopathy), or a disease or condition associated with proteinuria, including, but not limited to, nephrotic syndrome, pre-eclampsia, eclampsia, toxic lesions of kidneys, amyloidosis, collagen vascular diseases (e.g., systemic lupus erythematosus), dehydration, glomerular diseases (e.g., membranous glomerulonephritis, focal segmental glomerulonephritis, C3 glomerulopathy, minimal change disease, lipoid nephrosis), strenuous exercise, stress, benign orthostatis (postural) proteinuria, focal segmental glomerulosclerosis, IgA nephropathy (i.e., Berger's disease), IgM nephropathy, membranoproliferative glomerulonephritis, membranous nephropathy, minimal change disease, sarcoidosis, Alport's syndrome, diabetes mellitus (diabetic nephropathy), drug-induced toxicity (e.g., NSAIDS, nicotine, penicillamine, lithium carbonate, gold and other heavy metals, ACE inhibitors, antibiotics (e.g., adriamycin) or opiates (e.g., heroin) or other nephrotoxins); Fabry's disease, infections (e.g., HIV, syphilis, hepatitis A, B or C, poststreptococcal infection, urinary schistosomiasis); aminoaciduria, Fanconi syndrome, hypertensive nephrosclerosis, interstitial nephritis, sickle cell disease, hemoglobinuria, multiple myeloma, myoglobinuria, organ rejection (e.g., kidney transplant rejection), ebola hemorrhagic fever, Nail patella syndrome, familial Mediterranean fever, HELLP syndrome, systemic lupus erythematosus, Wegener's granulomatosis, Rheumatoid arthritis, Glycogen storage disease type 1, Goodpasture's syndrome, Henoch-Schonlein purpura, urinary tract infection which has spread to the kidneys, Sjogren's syndrome and post-infections glomerulonepthritis.

In some embodiments, the MASP-2-dependent complement-associated disease or disorder is an inflammatory reaction resulting from tissue or solid organ transplantation including, but not limited to, allotransplantation or xenotransplantation of whole organs (e.g., kidney, heart, liver, pancreas, lung, cornea, and the like) or tissue grafts (e.g., valves, tendons, bone marrow, and the like).

In some embodiments, the MASP-2-dependent complement-associated disorder is an ischemia reperfusion injury (I/R), including but not limited to, myocardial I/R, gastrointestinal I/R, renal I/R, and I/R following an aortic aneurism repair, I/R associated with cardiopulmonary bypass, cerebral I/R, stroke, organ transplant or reattachment of severed or traumatized limbs or digits; revascularization to transplants and/or replants, and hemodynamic resuscitation following shock and/or surgical procedures.

In some embodiments, the MASP-2-dependent complement-associated disease or disorder is a complication associated with non-obese diabetes (Type-1 diabetes or Insulin-dependent diabetes mellitus) and/or complications associated with Type-1 or Type-2 (adult onset) diabetes including, but not limited to diabetic angiopathy, diabetic neuropathy, diabetic retinopathy or diabetic macular edema.

In some embodiments, the MASP-2-dependent complement-associated disease or disorder is a cardiovascular disease or disorder, including but not limited to, Henoch-Schonlein purpura nephritis, systemic lupus erythematosus-associated vasculitis, vasculitis associated with rheumatoid arthritis (also called malignant rheumatoid arthritis), immune complex vasculitis, and Takayasu's disease; dilated cardiomyopathy; diabetic angiopathy; Kawasaki's disease (arteritis); venous gas embolus (VGE); and inhibition of restenosis following stent placement, rotational atherectomy and/or percutaneous transluminal coronary angioplasty (PTCA).

In some embodiments, the MASP-2-dependent complement-associated disease or disorder is an inflammatory gastrointestinal disorder, including but not limited to, pancreatitis, diverticulitis and bowel disorders including Crohn's disease, ulcerative colitis, irritable bowel syndrome and inflammatory bowel disease (IBD).

In some embodiments, the MASP-2-dependent complement-associated disease or disorder is a pulmonary disorder, including but not limited to, acute respiratory distress syndrome, transfusion-related acute lung injury, ischemia/reperfusion acute lung injury, chronic obstructive pulmonary disease, asthma, Wegener's granulomatosis, antiglomerular basement membrane disease (Goodpasture's disease), meconium aspiration syndrome, aspiration pneumonia, bronchiolitis obliterans syndrome, idiopathic pulmonary fibrosis, acute lung injury secondary to burn, non-cardiogenic pulmonary edema, transfusion-related respiratory depression and emphysema.

In some embodiments, the MASP-2-dependent complement-associated disease or disorder is an extracorporeal exposure-triggered inflammatory reaction and the method comprises treating a subject undergoing an extracorporeal circulation procedure including, but not limited to, hemodialysis, plasmapheresis, leukopheresis, extracorporeal membrane oxygenation (ECMO), heparin-induced extracorporeal membrane oxygenation LDL precipitation (HELP) and cardiopulmonary bypass (CPB).

In some embodiments, the MASP-2-dependent complement-associated disease or disorder is selected from inflammatory or non-inflammatory arthritides and other musculoskeletal disorders, including but not limited to, osteoarthritis, rheumatoid arthritis, juvenile rheumatoid arthritis, gout, neuropathic arthropathy, psoriatic arthritis, ankylosing spondylitis or other spondyloarthropathies and crystalline arthropathies, muscular dystrophy and systemic lupus erythematosus (SLE).

In some embodiments, the MASP-2-dependent complement-associated disease or disorder is a skin disorder, including, but not limited to, psoriasis, autoimmune bullous dermatoses, eosinophilic spongiosis, bullous pemphigoid, epidermolysis bullosa acquisita, atopic dermatitis, herpes gestationis and other skin disorders, and for the treatment of thermal and chemical burns including capillary leakage caused thereby.

In some embodiments, the MASP-2-dependent complement-associated disease or disorder is a peripheral nervous system (PNS) and/or central nervous system (CNS) disorder or injury including, but not limited to, multiple sclerosis (MS), myasthenia gravis (MG), Huntington's disease (HD), amyotrophic lateral sclerosis (ALS), Guillain Barre syndrome, reperfusion following stroke, degenerative discs, cerebral trauma, Parkinson's disease (PD), Alzheimer's disease (AD), Miller-Fisher syndrome, cerebral trauma and/or hemorrhage, traumatic brain injury, demyelination and meningitis.

In some embodiments, the MASP-2-dependent complement-associated disease or disorder is sepsis or a condition resulting from sepsis including without limitation severe sepsis, septic shock, acute respiratory distress syndrome resulting from sepsis, hemolytic anemia, systemic inflammatory response syndrome, or hemorrhagic shock.

In some embodiments, the MASP-2-dependent complement-associated disease or disorder is a urogenital disorder including, but not limited to, painful bladder disease, sensory bladder disease, chronic abacterial cystitis and interstitial cystitis, male and female infertility, placental dysfunction and miscarriage and pre-eclampsia.

In some embodiments, the MASP-2-dependent complement-associated disease or disorder is an inflammatory reaction in a subject being treated with chemotherapeutics and/or radiation therapy, including without limitation for the treatment of cancerous conditions.

In some embodiments, the MASP-2-dependent complement-associated disease or disorder is an angiogenesis-dependent cancer, including but not limited to, a solid tumor(s), blood borne tumor(s), high-risk carcinoid tumors and tumor metastases.

In some embodiments, the MASP-2-dependent complement-associated disease or disorder is an angiogenesis-dependent benign tumor, including but not limited to, hemangiomas, acoustic neuromas, neurofibromas, trachomas, carcinoid tumors and pyogenic granulomas.

In some embodiments, the MASP-2-dependent complement-associated disease or disorder is an endocrine disorder including, but not limited to, Hashimoto's thyroiditis, stress, anxiety and other potential hormonal disorders involving regulated release of prolactin, growth or insulin-like growth factor, and adrenocorticotropin from the pituitary.

In some embodiments, the MASP-2-dependent complement-associated disease or disorder is an ophthalmic disease or disorder including, but not limited to, age-related macular degeneration, glaucoma and endophthalmitis.

In some embodiments, the MASP-2-dependent complement-associated disease or disorder is an ocular angiogenic disease or condition including, but not limited to age-related macular degeneration, uveitis, ocular melanoma, corneal neovascularization, primary pterygium, HSV stromal keratitis, HSV-1-induced corneal lymphangiogenesis, proliferative diabetic retinopathy, diabetic macular edema, retinopathy of prematurity, retinal vein occlusion, corneal graft rejection, neovascular glaucoma, vitreous hemorrhage secondary to proliferative diabetic retinopathy, neuromyelitis optica and rubeosis.

In some embodiments, the MASP-2-dependent complement-associated disease or disorder is disseminated intravascular coagulation (DIC) or other complement mediated coagulation disorder, including DIC secondary to sepsis, severe trauma, including neurological trauma (e.g., acute head injury, see Kumura et al, Acta Neurochirurgica 55:23-28 (1987), infection (bacterial, viral, fungal, parasitic), cancer, obstetrical complications, liver disease, severe toxic reaction {e.g., snake bite, insect bite, transfusion reaction), shock, heat stroke, transplant rejection, vascular aneurysm, hepatic failure, cancer treatment by chemotherapy or radiation therapy, burn, or accidental radiation exposure.

In some embodiments, the MASP-2-dependent complement-associated disease or disorder is selected from the group consisting of acute radiation syndrome, dense deposit disease, Degos Disease, Catastrophic Antiphospholipid Syndrome (CAPS), Behcet's disease, cryoglobulinemia; paroxysmal nocturnal hemoglobinuria ("PNH") and cold agglutinin disease.

In some embodiments, the MASP-2-dependent complement-associated disease or disorder is selected from the group consisting of aHUS, HSCT-TMA, IgAN, and Lupus Nepthritis (LN).

In some embodiments, the method comprises administering to a patient suffering from, or at risk for developing a disease, disorder or condition associated with fibrin-induced activation of the complement system and the associated activation of the coagulation and/or contact systems an amount of a compound of the disclosure in an amount sufficient to inhibit MASP-2 dependent complement activation in said mammalian subject to thereby treat the disease or disorder. In some embodiments, the subject is suffering from, or at risk of developing, a disease, disorder or condition associated with complement-related inflammation, excessive coagulation or contact system activation initiated by fibrin or activated platelets. In some embodiments, the subject is suffering from a disease or disorder selected from the group consisting of arterial thrombosis, venous thrombosis, deep vein thrombosis, post-surgical thrombosis, restenosis following coronary artery bypass graft and/or an interventional cardiovascular procedure (e.g., angioplasty or stent placement), atherosclerosis, plaque rupture, plaque instability, restenosis, hypotension, acute respiratory distress syndrome (ARDS), systemic inflammatory response syndrome (SIRS), disseminated intravascular coagulation (DIC), veno-occlusive disease (VOD), thrombotic microangiopathy, lupus nephritis, superficial thrombophlebitis, Factor V Leiden mutation, ischemic/reperfusion injury, human immunodeficiency virus (HIV) infection, undergoing hormone-replacement therapy (HRT), Alzheimer's disease and/or suffering from a hypercoagulable state. In some embodiments, the subject is suffering from, or at risk for developing an acquired hypercoagulable state due to at least one or more of the following: undergoing therapy with a drug selected from the group consisting of 5-FU, GM-CSF, cisplatin, heparin, COX-2 inhibitor, contrast media, corticosteroids and antipsychotics; venous stasis (immobilization, surgery, etc.), antiphospholipid syndrome, cancer (promyelocytic leukemia, lung, breast, prostate, pancreas, stomach and colon tumors), tissue injury due to trauma or surgery, presence of a catheter in a central vein, acquired deficiency of a protein involved in clot formation (e.g., protein C), paroxysmal nocturnal hemoglobinuria (PNH), elevated levels of homocysteine, heart failure, presence of a mechanical valve, pulmonary hypertension with in-situ thrombosis, atrial fibrillation, heparin-induced thrombocytopenia (HIT), heparin-induced thrombocytopenia and thrombosis (HITT), Kawasaki disease with in-situ thrombus, Takayasu arteritis with in-situ thrombus, thrombophilia of metastatic cancer, elevated Factor VIII levels, pregnancy, inflammatory bowel disease (IBD), or due to a genetic defect that causes or increases the risk of developing, a hypercoagulable state, such as a genetic defect selected from the group consisting of a Prothrombin 20210 gene mutation, an MTHFR mutation, a deficiency of protein C, a deficiency of protein S, a deficiency of protein A, a deficiency of protein Z, an antithrombin deficiency and a genetic disorder producing thrombophilia. In some embodiments, the subject is suffering from, or at risk for developing, a disease or disorder that is amenable to treatment with a kallikrein inhibitor. In some embodiments, the subject is suffering from, or at risk for developing a disease or disorder amenable to treatment with a kallikrein inhibitor is selected from the group consisting of hereditary angioedema, diabetic macular edema and bleeding during cardiopulmonary bypass. In some embodiments, the subject is suffering from, or at risk for developing, a disease or disorder that is amenable to treatment with a thrombin inhibitor, such as arterial thrombosis, venous thrombosis, pulmonary embolism, atrial fibrillation, heparin-induced thrombocytopenia, conversion from one anticoagulant to another, or off-label use for extracorporeal circuit patency of continuous renal replacement therapy (CRRT) in critically ill patients with HIT (maintenance). In some embodiments, the subject has previously experienced, is currently suffering from, or is at risk for developing atrial fibrillation and the MASP-2 inhibitory compound is administered in an amount sufficient to reduce the risk of stroke in said subject. In some embodiments, the subject is suffering from, or at risk for developing, a disease or disorder that is amenable to treatment with a factor XII inhibitor, such as deep vein thrombosis (both primary prophylaxis and extended therapy), pulmonary embolism, nonvalvular atrial fibrillation, prevention of recurrent ischemia after acute coronary syndrome in subjects with or without atrial fibrillation, end-stage renal disease, cerebral ischemia, angina, or to reduce or prevent clotting associated with medical devices (e.g., valves, small caliber grafts, etc.) and/or extracorporeal circuits. In some embodiments, the subject has previously experienced, is currently suffering from, or is at risk for developing nonvalvular atrial fibrillation and the MASP-2 inhibitory compound is administered in an amount sufficient to reduce the risk of stroke and/or embolism in said subject. In some embodiments, the subject has an acquired disease or disorder that increases the propensity for thromboembolism, such as a disease or disorder selected from the group consisting of atherosclerosis, antiphospholipid antibodies, cancer (e.g., promyelocytic leukemia, lung, breast, prostate, pancreatic, stomach and colon), hyperhomocysteinemia, infection, tissue injury, venous stasis (such as due to surgery, orthopedic or paralytic immobilization, heart failure, pregnancy, or obesity) and a subject taking oral contraceptives that contain estrogen. In some embodiments, the subject is in need of anticoagulant therapy and the MASP-2 inhibitory compound is used as a replacement for standard anticoagulant therapy (e.g., Warfarin). In some embodiments, the subject has a condition that normally prohibits standard anticoagulant therapy, such as CNS amyloid angiopathy. In some embodiments of the method, the MASP-2 inhibitory compound is administered as a bridging agent perioperatively in a subject otherwise on standard anticoagulation therapy. In some embodiments, the subject has sickle cell disease which is a vaso-occlusive disorder involving activation of platelets.

Atypical Hemolytic Uremic Syndrome (aHUS).

Atypical hemolytic uremic syndrome (aHUS) is part of a group of conditions termed "Thrombotic microangiopathies." In the atypical form of HUS (aHUS), the disease is associated with defective complement regulation and can be either sporadic or familial. Familial cases of aHUS are associated with mutations in genes coding for complement activation or complement regulatory proteins, including complement factor H, factor I, factor B, membrane cofactor CD46 as well as complement factor H-related protein 1 (CFHR1) and complement factor H-related protein 3 (CFHR3). (Zipfel, P. F., et al., PloS Genetics 3(3):e41 (2007)). The unifying feature of this diverse array of genetic mutations associated with aHUS is a predisposition to enhanced complement activation on cellular or tissue surfaces. A subject is a risk for developing aHUS upon the onset of at least one or more symptoms indicative of aHUS (e.g., the presence of anemia, thrombocytopenia and/or renal insufficiency) and/or the presence of thrombotic microangiopathy in a biopsy obtained from the subject. The determination of whether a subject is at risk for developing aHUS comprises determining whether the subject has a genetic predisposition to developing aHUS, which may be carried out by assessing genetic information (e.g. from a database containing the genotype of the subject), or performing at least one genetic screening test on the subject to determine the presence or absence of a genetic marker associated with aHUS (i.e., determining the presence or absence of a genetic mutation associated with aHUS in the genes encoding complement factor H (CFH), factor I (CFI), factor B (CFB), membrane cofactor CD46, C3, complement factor H-related protein 1 (CFHR1), or THBD (encoding the anticoagulant protein thrombodulin) or complement factor H-related protein 3 (CFHR3), or complement factor H-related protein 4 (CFHR4)) either via genome sequencing or gene-specific analysis (e.g., PCR analysis), and/or determining whether the subject has a family history of aHUS. Methods of genetic screening for the presence or absence of a genetic mutation associated with aHUS are well established, for example, see Noris M et al. "Atypical Hemolytic-Uremic Syndrome," 2007 Nov. 16 [Updated 2011 Mar. 10]. In: Pagon R A, Bird T D, Dolan C R, et al., editors. GeneReviews™, Seattle (Wash.): University of Washington, Seattle.

Hematopoietic Stem Cell Transplant-Associated TMA (HSCT-TMA)

Hematopoietic stem cell transplant-associated TMA (HSCT-TMA) is a life-threatening complication that is triggered by endothelial injury. The kidney is the most commonly affected organ, though HSCT-TMA can be a multi-system disease that also involves the lung, bowel, heart and brain. The occurrence of even mild TMA is associated with long-term renal impairment. Development of post-allogeneic HSCT-associated TMA differs in frequency based on varying diagnostic criteria and conditioning and graft-versus-host disease prophylaxis regimens, with calcineurin inhibitors being the most frequent drugs implicated (Ho V T et al., Biol Blood Marrow Transplant, 11(8):571-5, 2005).

Immunoglobulin A Nephropathy (IgAN)

Immunoglobulin A nephropathy (IgAN) is an autoimmune kidney disease resulting in intrarenal inflammation and kidney injury. IgAN is the most common primary glomerular disease globally. With an annual incidence of approximately 2.5 per 100,000, it is estimated that 1 in 1400 persons in the U.S. will develop IgAN. As many as 40% of patients with IgAN will develop end-stage renal disease (ESRD). Patients typically present with microscopic hematuria with mild to moderate proteinuria and variable levels of renal insufficiency (Wyatt R. J., et al., NEnglJ Med 36S(25): 2402-4, 2013). Clinical markers such as impaired kidney function, sustained hypertension, and heavy proteinuria (over 1 g per day) are associated with poor prognosis (Goto M et al., Nephrol Dial Transplant 24(10):3068-74, 2009; Berthoux F. et al., J Am Soc Nephrol 22(4):752-61, 2011). Proteinuria is the strongest prognostic factor independent of other risk factors in multiple large observational studies and prospective trials (Coppo R. et al., J Nephrol 18(5):503-12, 2005; Reich H. N., et al., J Am Soc Nephrol 18(12):3177-83, 2007). It is estimated that 15-20% of patients reach ESRD within 10 years of disease onset if left untreated (D'Amico G., Am J Kidney Dis 36(2):227-37, 2000). The diagnostic hallmark of IgAN is the predominance of IgA deposits, alone or with IgG, IgM, or both, in the glomerular mesangium.

Lupus Nephritis (LN)

A main complication of systemic lupus erythematosus (SLE) is nephritis, also known as lupus nephritis, which is classified as a secondary form of glomerulonephritis. Up to 60% of adults with SLE have some form of kidney involvement later in the course of the disease (Koda-Kimble et al., Koda-Kimble and Young's Applied Therapeutics: the clinical use of drugs, 10th Ed, Lippincott Williams & Wilkins: pages 792-9, 2012) with a prevalence of 20-70 per 100,000 people in the US. Lupus nephritis often presents in patients with other symptoms of active SLE, including fatigue, fever, rash, arthritis, serositis, or central nervous system disease (Pisetsky D. S. et al., Med Clin North Am 81(1): 113-28, 1997). Some patients have asymptomatic lupus nephritis; however, during regular follow-up, laboratory abnormalities such as elevated serum creatinine levels, low albumin levels, or urinary protein or sediment suggest active lupus nephritis.

V. Compositions, Dosage and Administration

The compounds as described herein can be administered in a manner compatible with the dosage formulation, and in such amount as will be effective or suitable for treatment.

The quantity to be administered depends on a variety of factors including, e.g., the age, body weight, physical activity, and diet of the individual, and the desired effect. In certain embodiments, the size of the dose may also be determined by the existence, nature, and extent of any adverse side effects that accompany the administration of the compound in a particular individual.

It will be understood, however, that the specific dose level and frequency of dosage for any particular patient may be varied by a physician and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In certain embodiments, the dose may take the form of solid, semi-solid, or liquid forms, preferably in unit dosage forms suitable for simple administration of precise dosages.

As used herein, the term "unit dosage form" refers to physically discrete units suitable as unitary dosages for humans and other mammals, each unit containing a predetermined quantity of an active agent calculated to produce the desired onset, tolerability, and/or efficacious effects, in association with a suitable pharmaceutical excipient (e.g., an ampoule). In addition, more concentrated dosage forms may be prepared, from which the more dilute unit dosage forms may then be produced.

The compounds described herein can be administered to a subject in need of treatment using methods known in the art, such as by oral administration or by injection. The injection can be subcutaneous, intravenous, intraperitoneal, intramuscular. As described herein, parenteral formulations can be prepared in dosage unit form for ease of administration and uniformity of dosage. As used herein the term "unit dosage form" refers to physically discrete units suited as unitary dosages for the subject to be treated; each unit containing a predetermined quantity of active compound calculated to produce the desired therapeutic effect.

The pharmaceutical compositions of the present application comprise a therapeutically effective amount of a compound of the present application formulated together with one or more pharmaceutically acceptable carriers or excipient. As used herein, the term "pharmaceutically acceptable carrier" means a non-toxic, inert solid, semi-solid or liquid filler, diluent, encapsulating material or formulation auxiliary of any type. The pharmaceutical compositions of this application can be administered to humans and other animals orally, rectally, parenterally, intracistemally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier or excipient and any needed preservatives or buffers as may be required.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present application, disorders are treated or prevented in a subject, such as a human or other animal, by administering to the subject a therapeutically effective amount of a compound of the application, in such amounts and for such time as is necessary to achieve the desired result. The term "therapeutically effective amount" of a compound of the application, as used herein, means a sufficient amount of the compound so as to decrease the symptoms of a disorder in a subject. As is well understood in the medical arts a therapeutically effective amount of a compound of this application will be at a reasonable benefit/risk ratio applicable to any medical treatment.

In general, compounds of the application will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors.

In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 250 mg, about 5 mg to about 150 mg, about 5 mg to about 100 mg, about 10 mg to about 75 mg, about 10 mg to about 50 mg, such as 10, 20, 30, 40, or about 50 mg, conveniently administered, e.g., in divided doses up to four times a day or in retard form. Suitable unit dosage forms for oral administration comprise from ca. 1 to 60 mg active ingredient.

In certain embodiments, a therapeutic amount or dose of the compounds of the present application may range from about 0.1 mg/kg to about 500 mg/kg, alternatively from about 1 to about 50 mg/kg. In general, treatment regimens according to the present application comprise administration to a patient in need of such treatment from about 10 mg to about 1000 mg of the compound(s) of this application per day in single or multiple doses. Therapeutic amounts or doses will also vary depending on route of administration, as well as the possibility of co-usage with other agents.

Upon improvement of a subject's condition, a maintenance dose of a compound, composition or combination of this application may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The application also provides for a pharmaceutical combinations, e.g., a kit, comprising a) a first agent which is a compound of the application as disclosed herein, in free form or in pharmaceutically acceptable salt form, and b) at least one co-agent. The kit can comprise instructions for its administration.

Methods for preparing such dosage forms are known to those skilled in the art (see, e.g., REMINGTON'S PHARMACEUTICAL SCIENCES, 18th ED., Mack Publishing Co., Easton, PA (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, 18th ED., Mack Publishing Co., Easton, PA (1990)).

EXAMPLES

The following examples are provided by way of illustration only and not by way of limitation. Those of skill will readily recognize a variety of noncritical parameters which could be changed or modified to yield essentially similar results.

General Methods

If not otherwise stated, chromatography refers to flash chromatography conducted on silica gel.

HPLC purification was performed by one of two methods. Method 1: on a Gilson preparative reverse phase HPLC system with the combination of UV/ELS detectors (254 nm and 280 nm) and ThermoFisher Hypersil GOLD Agilent (21.2×250 mm) 5 µm C-18 column. Eluents were a mixture of water and acetonitrile (with 0.05% trifluoroacetic acid). Flow rate was typically 20 mL/min with a linear gradient of water in acetonitrile from 2-90% in 45 minutes. The injection volume was from 1 to 3 mL with maximum 20 mg per load. Method 2: on a Waters preparative reverse phase HPLC system with the combination of UV/MS detectors (254 nm and 280 nm) and XBridge Prep (19×50 mm) C18 10 µM OBD column. Eluents were a mixture of water and acetonitrile (with 0.05% trifluoroacetic acid). Flow rate was typically 50 mL/min with a linear gradient of water in acetonitrile from 5-95% in 8 minutes. The injection volume was from 0.2 to 1 mL with maximum 20 mg per load.

Example 1: Preparation of ((R)-2-((S)-2-((4-Carbamindoylbenzyl(carbamoyl)azetidin-1-ylcyclopropyl-2-oxoethyl)glycine (1028)

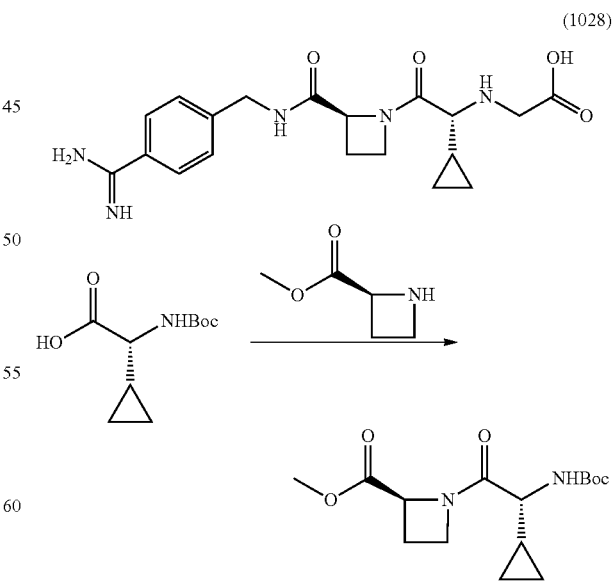

Step 1: To a stirred solution of Boc-D-cyclopropyl glycine (300 mg, 1.4 mmol), methyl (S)-azetidine-2-carboxylate hydrochloride (211 mg, 1.4 mmol) and DMAP (255 mg, 2.4 mmol) in MeCN (5 mL) at 5° C. was added EDC (293 mg, 1.5 mmol). The mixture was stirred for 48 h, then concentrated under vacuum. The residue was dissolved in EtOAc and washed with H₂O, 0.5 M KHSO₄ twice, saturated aqueous NaHCO₃, H₂O and brine, then dried (Na₂SO₄) and concentrated under vacuum. Chromatography (EtOAc-hexanes) gave methyl (S)-1-((R)-2-((tert-butoxycarbonyl)amino)-2-cyclopropylacetyl)azetidine-2-carboxylate (381 mg, 88% yield).

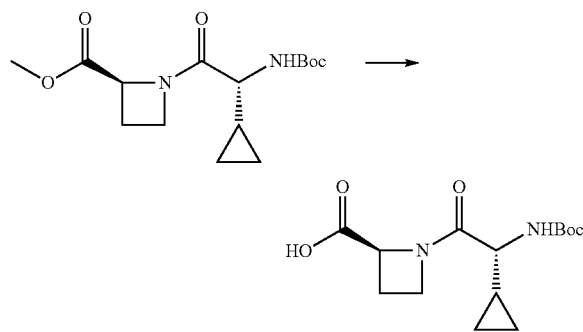

Step 2: To a solution of methyl (S)-1-((R)-2-((tert-butoxycarbonyl)amino)-2-cyclopropylacetyl)azetidine-2-carboxylate (381 mg) in THF (6 mL) was added 5 equiv of LiOH. The mixture was stirred for 16 h at room temperature, then diluted with EtOAc, and adjusted to pH 3 with the slow addition of 10% KHSO₄. The mixture was saturated with NaCl, and the layers were separated. The aqueous layer was extracted with EtOAc (3×10 mL) and the combined organics were dried (Na₂SO₄) and concentrated under vacuum to give (S)-1-((R)-2-((tert-butoxycarbonyl)amino)-2-cyclopropylacetyl)azetidine-2-carboxylic acid as a solid foam that was used without further purification (380 mg crude).

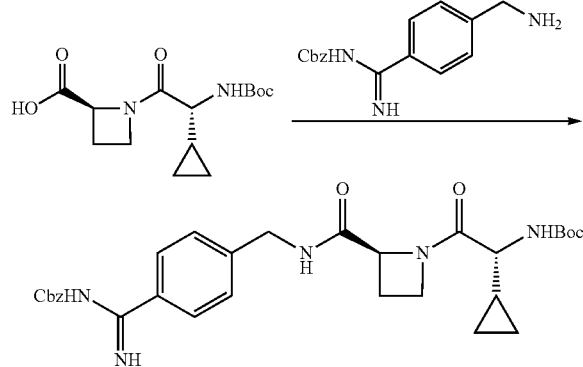

Step 3: (S)-1-((R)-2-((tert-Butoxycarbonyl)amino)-2-cyclopropylacetyl)azetidine-2-carboxylic acid was coupled with benzyl ((4-(aminomethyl)phenyl)(imino)methyl)carbamate following compound 1028, step 1. Chromatography (EtOAc-hexanes) gave tert-butyl ((R)-2-((S)-2-((4-(N-((benzyloxy)carbonyl)carbamimidoyl)benzyl)carbamoyl)azetidin-1-yl)-1-cyclopropyl-2-oxoethyl)carbamate as a white foam (180 mg).

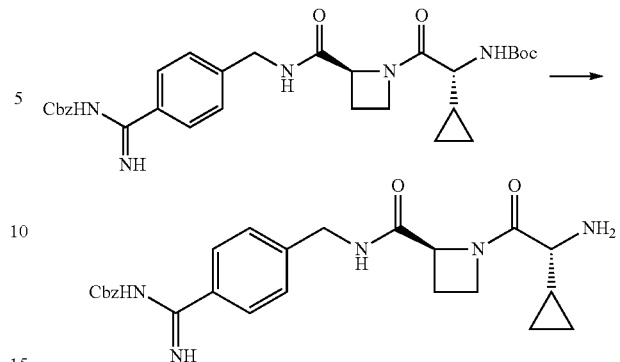

Step 4: A solution of tert-butyl ((R)-2-((S)-2-((4-(N-((benzyloxy)carbonyl)carbamimidoyl)benzyl)carbamoyl)azetidin-1-yl)-1-cyclopropyl-2-oxoethyl)carbamate (180 mg) in EtOAc was cooled in an ice bath. Hydrogen chloride was bubbled through the solution for approximately 5 min. The mixture was allowed to reach room temp and stirred for 30 min. Et₂O was added to the solution upon which a ppt formed. After the mixture was left at room temp for 16 h, the product was isolated by filtration, washed with Et₂O and dried under vacuum. The resulting solid was dissolved in H₂O, made alkaline with 2 M NaOH and extracted with CH₂Cl₂ (3×10 mL). The combined organics were washed with brine, dried over Na₂SO₄ and concentrated under vacuum to give benzyl ((4-(((S)-1-((R)-2-amino-2-cyclopropylacetyl)azetidine-2-carboxamido)methyl)phenyl)(imino)methyl)carbamate as a white foam (115 mg, 78% yield over two steps).

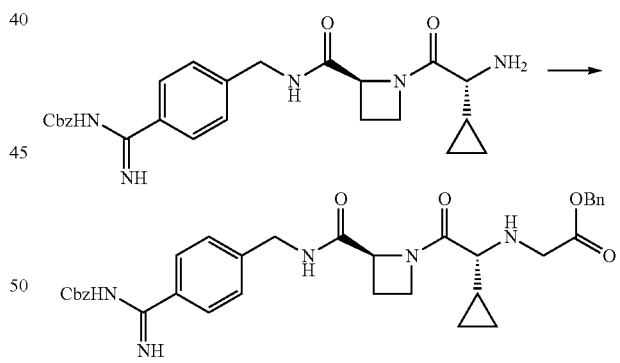

Step 5: To a solution of benzyl ((4-(((S)-1-((R)-2-amino-2-cyclopropylacetyl)azetidine-2-carboxamido)methyl)phenyl)(imino)methyl)carbamate (103 mg, 0.22 mmol) in MeCN (10 mL) was added bromobenzyl acetate (39 μL, 0.245 mmol) and K₂CO₃ (77 mg, 0.556 mmol). The mixture was heated to 60° C. and stirred for 16 h. The mixture was concentrated under vacuum and the residue was dissolved in EtOAc, washed with H₂O, dried over Na₂SO₄ and concentrated under vacuum. Chromatography (100% EtOAc then 0-10% MeOH—CH₂Cl₂) gave benzyl ((R)-2-((S)-2-((4-(N-((benzyloxy)carbonyl)carbamimidoyl)benzyl)carbamoyl)azetidin-1-yl)-1-cyclopropyl-2-oxoethyl)glycinate (20 mg, 15% yield).

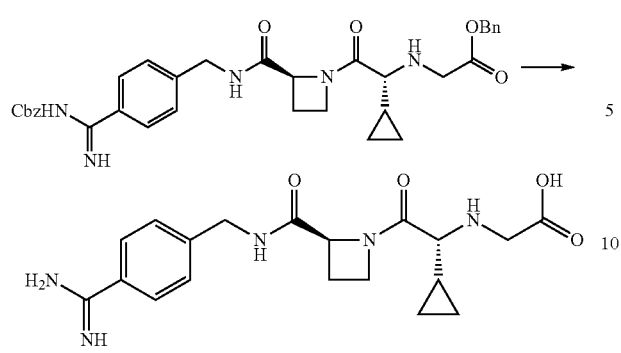

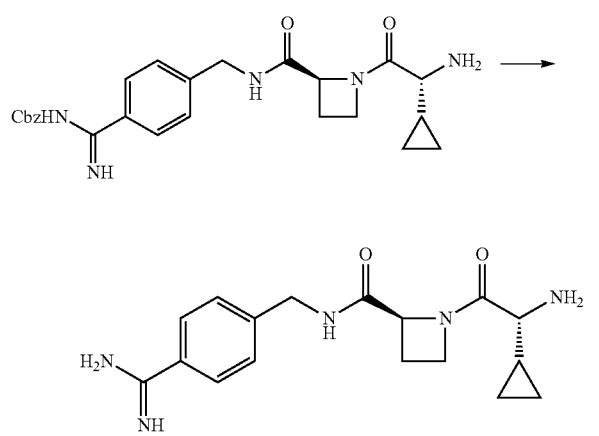

Step 6: To a degassed solution of benzyl ((R)-2-((S)-2-((4-(N-((benzyloxy)carbonyl)carbamimidoyl)benzyl)carbamoyl)azetidin-1-yl)-1-cyclopropyl-2-oxoethyl)glycinate (20 mg, 0.033 mmol) in EtOH was added 10% Pd/C (~2 mg). The mixture was stirred under 1 atm H₂ for 24 h. The mixture was filtered (0.2 µM syringe filter) and the filtrate was concentrated under vacuum to give ((R)-2-((S)-2-((4-carbamimidoylbenzyl)carbamoyl)azetidin-1-yl)-1-cyclopropyl-2-oxoethyl)glycine (12 mg).

Example 2: Preparation of (S)-1-((R)-2-Amino-2-cyclopropylacetyl)-N-(4-carbamimidoylbenzyl)azetidine-2-carboxamide (1002)

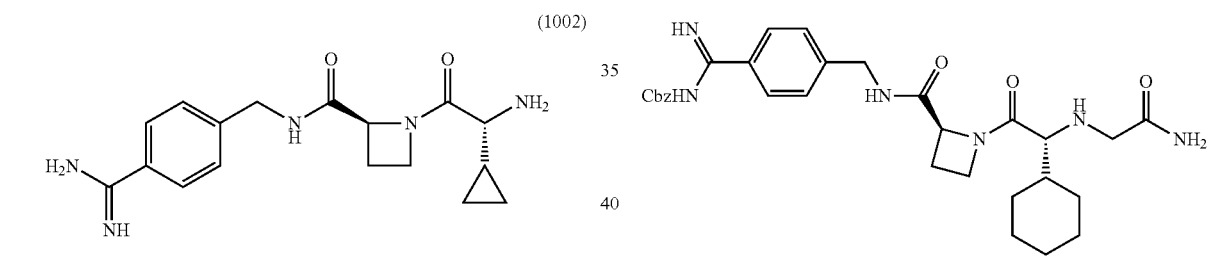

Benzyl ((4-(((S)-1-((R)-2-amino-2-cyclopropylacetyl)azetidine-2-carboxamido)methyl)phenyl)(imino)methyl)carbamate was hydrogenated according to the method for compound 1028, step 6 to provide (S)-1-((R)-2-amino-2-cyclopropylacetyl)-N-(4-carbamimidoylbenzyl)azetidine-2-carboxamide.

Example 3: Preparation of (S)-1-((R)-2-((2-amino-2-oxoethyl)amino)-2-cyclohexylacetyl)-N-(4-carbamimidoylbenzyl)azetidine-2-carboxamide (1102)

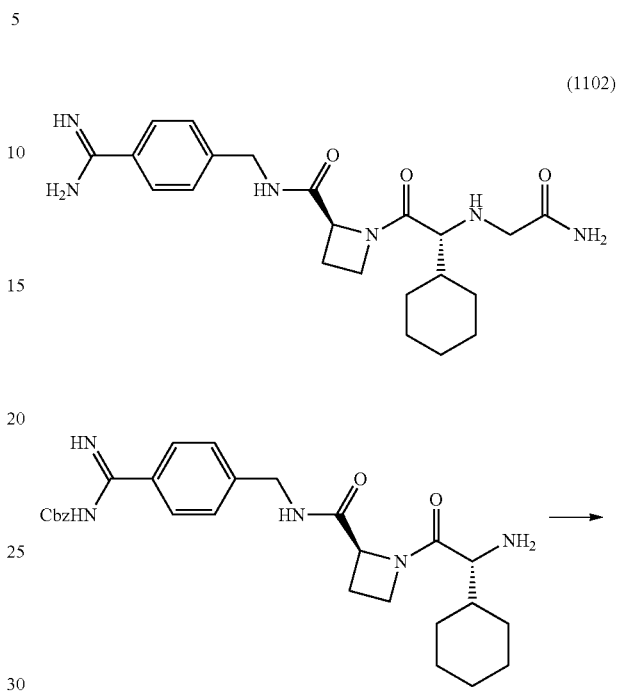

Step 1: Benzyl ((4-(((S)-1-((R)-2-amino-2-cyclohexylacetyl)azetidine-2-carboxamido)methyl)phenyl)(imino)methyl)carbamate was synthesized according to the foregoing procedures with the appropriate starting materials. Reaction of benzyl ((4-(((S)-1-((R)-2-amino-2-cyclohexylacetyl)azetidine-2-carboxamido)methyl)phenyl)(imino)methyl)carbamate with bromoacetamide (1.2 equiv) and K₂CO₃ (2.5 equiv) according to the procedure for compound 1028, step 5 gave benzyl ((4-(((S)-1-((R)-2-((2-amino-2-oxoethyl)amino)-2-cyclohexylacetyl)azetidine-2-carboxamido)methyl)phenyl)(imino)methyl)carbamate (76% yield).

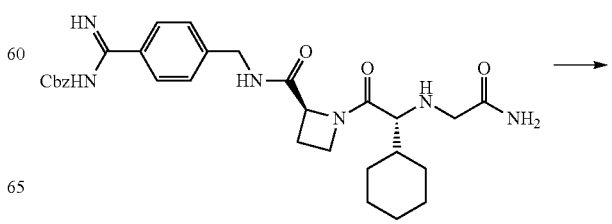

-continued

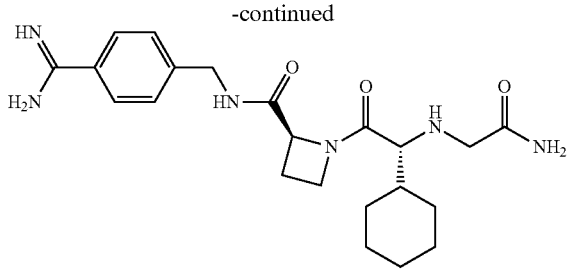

Step 2: Deprotection of benzyl ((4-(((S)-1-((R)-2-((2-amino-2-oxoethyl)amino)-2-cyclohexylacetyl)azetidine-2-carboxamido)methyl)phenyl)(imino)methyl)carbamate according to compound 1028, step 6 provided (S)-1-((R)-2-((2-amino-2-oxoethyl)amino)-2-cyclohexylacetyl)-N-(4-carbamimidoylbenzyl)azetidine-2-carboxamide (83% yield).

Example 4: Preparation of (S)-1-((R)-2-Acetamido-2-cyclohexylacetyl)-N-(4-carbamimidoylbenzyl)azetidine-2-carboxamide (1154)

(1154)

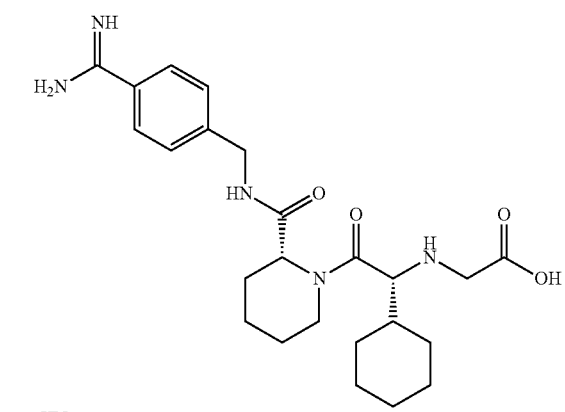

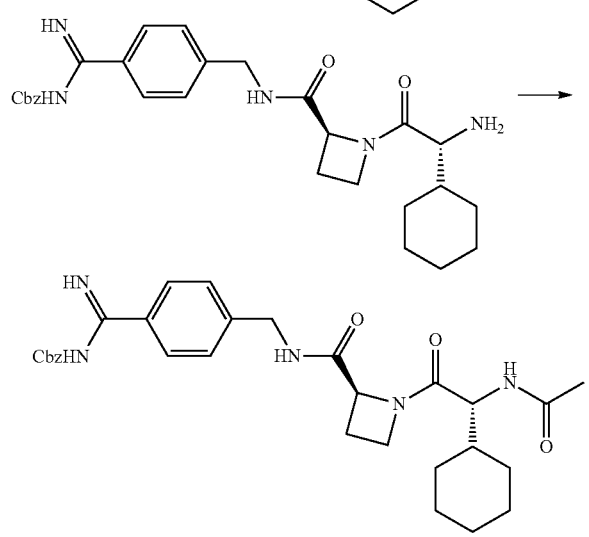

Step 1: To a solution of benzyl ((4-(((S)-1-((R)-2-amino-2-cyclohexylacetyl)azetidine-2-carboxamido)methyl)phenyl)(imino)methyl)carbamate (170 mg, 0.337 mmol) in anhydrous CH$_2$Cl$_2$ (5 mL) at was added Et$_3$N (138 μL, 1.0 mmol), acetic anhydride (41 μL, 0.405 mmol) and DMAP (2 mg). The mixture was stirred at room temp overnight then concentrated under vacuum. The residue was dissolved in EtOAc, washed with H$_2$O and dried (Na$_2$SO$_4$). Chromatography (100% EtOAc then 0-10% MeOH—CH$_2$Cl$_2$) gave benzyl ((4-(((S)-1-((R)-2-acetamido-2-cyclohexylacetyl)azetidine-2-carboxamido)methyl)phenyl)(imino)methyl)carbamate (125 mg, 68% yield).

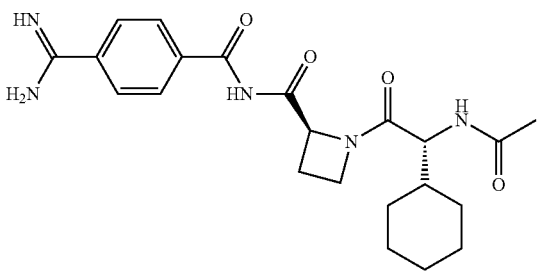

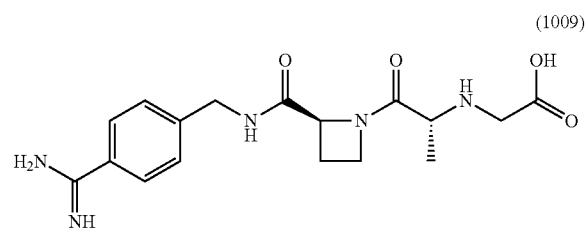 [SMILES: C[C@@H](NCC(=O)O)C(=O)N1CC[C@H]1C(=O)NCc1ccc(C(=N)N)cc1]

Step 2: Deprotection of benzyl ((4-(((S)-1-((R)-2-acetamido-2-cyclohexylacetyl)azetidine-2-carboxamido)methyl)phenyl)(imino)methyl)carbamate according to compound 1028, step 6 provided (S)-1-((R)-2-acetamido-2-cyclohexylacetyl)-N-(4-carbamimidoylbenzyl)azetidine-2-carboxamide (70 mg, 74% yield).

Example 5: Preparation of ((R)-1-((S)-2-((4-Carbamimidoylbenzyl)carbamoyl)azetidin-1-yl)-1-oxopropan-2-yl)glycine (1009)

(1009)

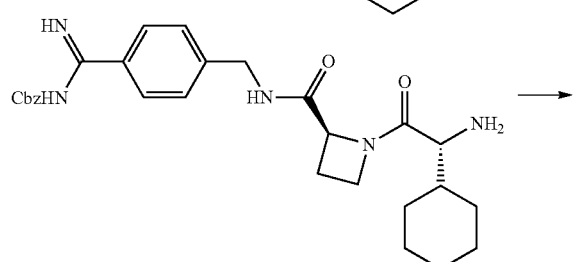

((R)-1-((S)-2-((4-Carbamimidoylbenzyl)carbamoyl)azetidin-1-yl)-1-oxopropan-2-yl) glycine was synthesized according to the method for compound 1028, except that Boc deprotection was performed in MeOH instead of EtOAc.

Example 6: Preparation of (S)-1-((R)-2-Amino-2-(2,3-dihydro-1H-inden-2-yl)acetyl)-N-(4-carbamimidoylbenzyl)azetidine-2-carboxamide (1058)

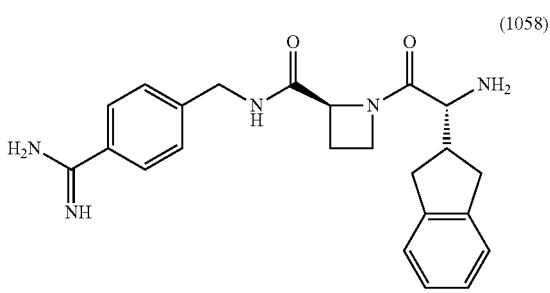 [SMILES: N=C(N)c1ccc(CNC(=O)[C@@H]2CCN2C(=O)[C@H](N)C2Cc3ccccc3C2)cc1]
(1058)

(S)-1-((R)-2-Amino-2-(2,3-dihydro-1H-inden-2-yl)acetyl)-N-(4-carbamimidoylbenzyl)azetidine-2-carboxamide was synthesized according to the method for compound 1028 except that methyl ester hydrolysis was conducted with 1.5 equiv of LiOH in 1:1 THF-H$_2$O.

Example 7: Preparation of (S)-1-((R)-2-amino-2-phenylacetyl)-N-(4-carbamimidoylbenzyl)azetidine-2-carboxamide (1011)

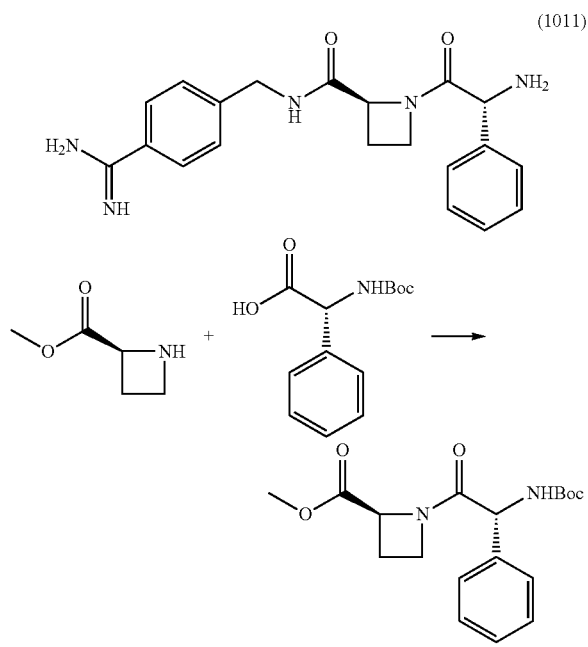

A solution of methyl (S)-azetidine-2-carboxylate (100 mg, 0.66 mmol), (R)-2-((tert-butoxycarbonyl)amino)-2-phenylacetic acid (150 mg, 0.60 mmol), pyridine (0.16 mL) and EtOAc (0.33 mL) were cooled at −20 to −10° C. A solution of propylphosphonic anhydride in EtOAc (50% solution, 0.84 mL) was added dropwise at a rate to maintain the internal temperature below 0° C. The yellow solution was stirred at 0° C. for 18 h, then cooled to −10° C. and 1 M HCl (~1 mL) was added dropwise. The reaction was stirred at room temp for 2 h. EtOAc was added, the aqueous layer separated and dried over Na$_2$SO$_4$. Concentration under vacuum followed by chromatography (50% EtOAc-hexanes) gave methyl (S)-1-((R)-2-((tert-butoxycarbonyl)amino)-2-phenylacetyl)azetidine-2-carboxylate (80 mg). The remaining steps for the synthesis of compound 1011, (S)-1-((R)-2-amino-2-phenylacetyl)-N-(4-carbamimidoylbenzyl)azetidine-2-carboxamide, were conducted according to the procedures for compound 1058.

Example 8: Preparation of (S)-1-(D-Prolyl)-N-(4-carbamimidoylbenzyl)azetidine-2-carboxamide (1156)

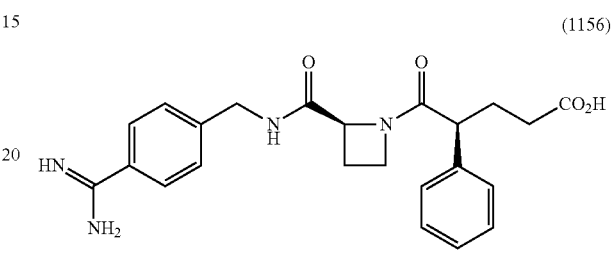
(1156)

(S)-1-(D-prolyl)-N-(4-carbamimidoylbenzyl)azetidine-2-carboxamide was synthesized according to the procedures for compound 1058, except that methyl ester hydrolysis was conducted with 1.1 equiv LiOH and Boc removal was conducted with TFA-CH$_2$Cl$_2$ (0.2 M) at 0° C. to room temp.

Example 9: Preparation of ((R)-2-((S)-2-((4-Carbamimidoyl-3-hydroxybenzyl)carbamoyl)azetidin-1-yl)-1-cyclohexyl-2-oxoethyl)glycine (1116)

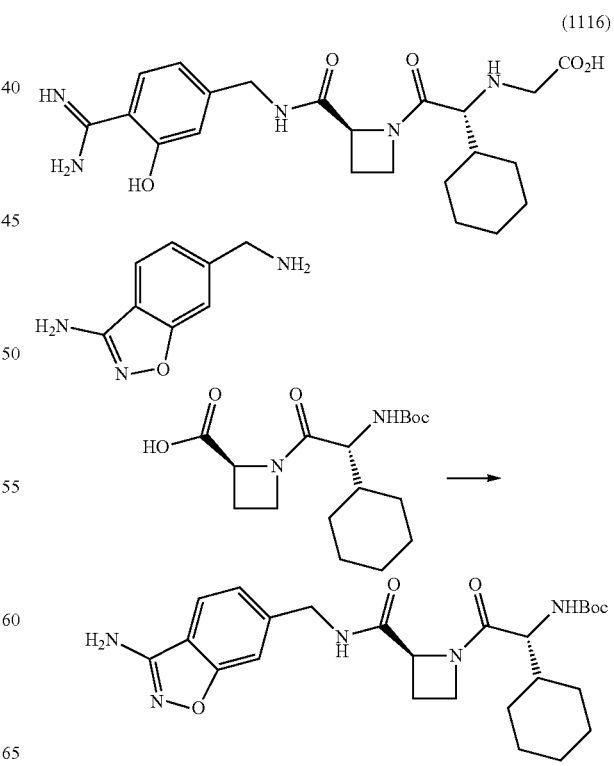

Step 1: to an ice-cold solution of (S)-1-((R)-2-((tert-butoxycarbonyl)amino)-2-cyclohexylacetyl)azetidine-2-carboxylic acid (260 mg, 0.76 mmol) and DIEA (0.42 mL, 2.4 mmol) in anhyd MeCN (15 mL) was added EDC (166 mg, 0.87 mmol) and HOBt (112 mg, 0.83 mmol). The mixture was stirred for 5 min then 6-(aminomethyl)benzo[d]isoxazol-3-amine hydrochloride (183 mg, 0.92 mmol, prepared according to WO 2001079195) was added. The mixture was stirred for 18 h, allowed to warm to room temp, then concentrated under vacuum. The residue was dissolved in EtOAc, washed with H₂O and brine, dried over Na₂SO₄ and chromatographed with 65-100% EtOAc-hexanes to give 305 mg of tert-butyl ((R)-2-((S)-2-(((3-aminobenzo[d]isoxazol-6-yl)methyl)carbamoyl)azetidin-1-yl)-1-cyclohexyl-2-oxoethyl)carbamate.

Step 2: Boc removal was conducted according to the procedure for compound 1028, except using MeOH-EtOAc as the solvent, gave (S)-1-((R)-2-amino-2-cyclohexylacetyl)-N-((3-aminobenzo[d]isoxazol-6-yl)methyl)azetidine-2-carboxamide hydrochloride.

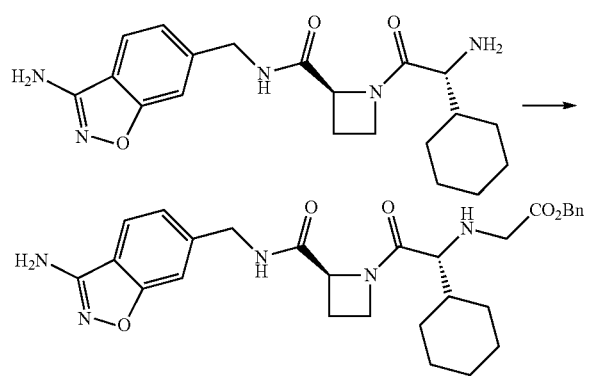

Step 3: To a solution of (S)-1-((R)-2-amino-2-cyclohexylacetyl)-N-((3-aminobenzo [d]isoxazol-6-yl)methyl)azetidine-2-carboxamide hydrochloride (160 mg, 0.38 mmol) in anhyd MeCN (10 mL) under Ar was added DIEA (0.25 mL) and bromobenzylacetate (0.08 mL, 0.50 mmol). The mixture was stirred at room temp. for 15 h then concentrated under vacuum and re-dissolved in EtOAc. The solution was washed with H₂O and brine, dried (Na₂SO₄) and chromatographed with 55-100% EtOAc-hexanes to give 144 mg of benzyl ((R)-2-((S)-2-(((3-aminobenzo[d]isoxazol-6-yl)methyl)carbamoyl)azetidin-1-yl)-1-cyclohexyl-2-oxoethyl) glycinate.

Step 4: Benzyl ((R)-2-((S)-2-(((3-aminobenzo[d]isoxazol-6-yl)methyl)carbamoyl) azetidin-1-yl)-1-cyclohexyl-2-oxoethyl)glycinate was converted to compound 1116 following the procedure of compound 1028, step 6.

Example 10: Preparation of (S)-1-((R)-2-Amino-2-cyclohexylacetyl)-N-((1-aminoisoquinolin-6-yl)methyl)azetidine-2-carboxamide dihydrochloride (1041)

(1041)

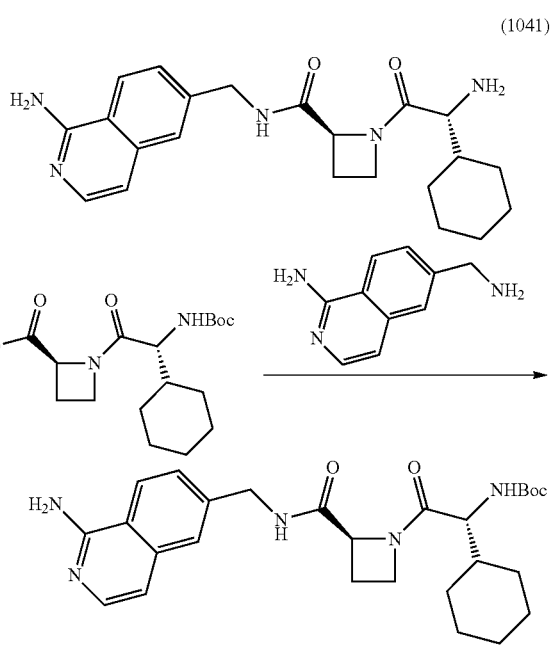

Step 1: 6-(Aminomethyl)isoquinolin-1-amine and (S)-1-((R)-2-((tert-butoxycarbonyl) amino)-2-cyclohexylacetyl) azetidine-2-carboxylic acid were coupled following the procedure of compound 1116, step 1. After 15 h reaction time, additional DIEA (1 equiv) was added and stirring was continued for 24 h. Following concentration under vacuum, the residue was dissolved in EtOAc and washed with NaHCO₃ solution, H₂O, and brine then dried (Na₂SO₄). Chromatography (0-10% MeOH—CH₂Cl₂) gave tert-butyl ((R)-2-((S)-2-(((1-aminoisoquinolin-6-yl)methyl)carbamoyl)azetidin-1-yl)-1-cyclohexyl-2-oxoethyl)carbamate (51% yield).

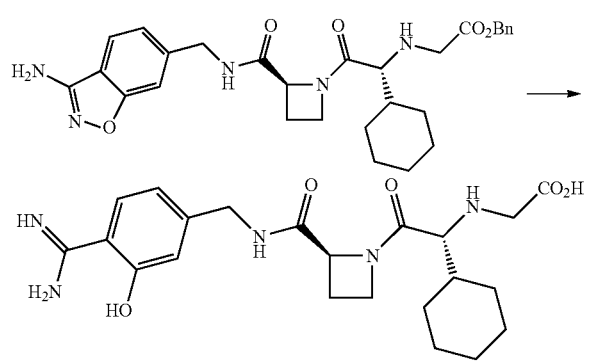

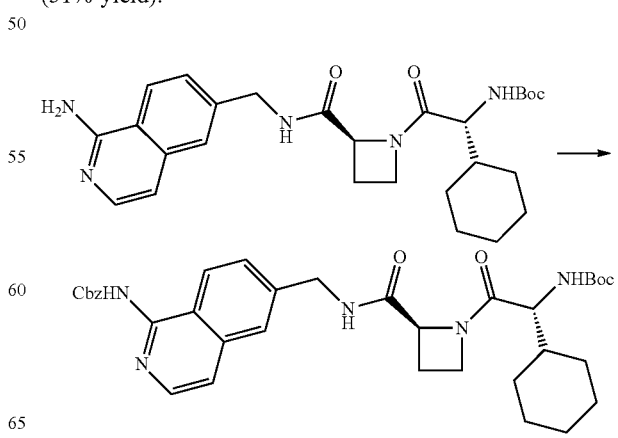

Step 2: To a solution of tert-butyl ((R)-2-((S)-2-(((1-aminoisoquinolin-6-yl)methyl)carbamoyl)azetidin-1-yl)-1-cyclohexyl-2-oxoethyl)carbamate (0.51 g, 1.0 mmol) in anhyd CH₂Cl₂ under Ar was added NMM (0.5 mL, 4.5 mmol) and benzylchloroformate (0.2 mL, 1.4 mmol) dropwise. After stirring at room temp for 1.5 h, additional benzylchloroformate ((0.15 mL, 1.0 mmol) was added and the mixture was stirred for 2.5 h. After conc under vacuum, EtOAc and saturated aqueous NaHCO₃ were added and the layers were separated. The org layer was washed with brine and dried (Na₂SO₄). Chromatography (75-100% EtOAc-hexanes) provided benzyl (6-(((S)-1-((R)-2-((tert-butoxycarbonyl)amino)-2-cyclohexylacetyl)azetidine-2-carboxamido)methyl)isoquinolin-1-yl)carbamate (79% yield).

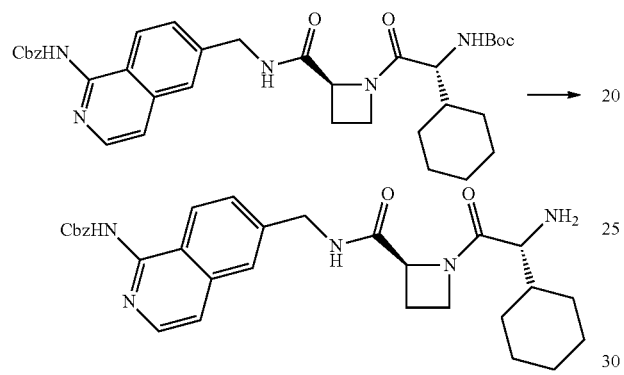

Step 3: The Boc group of benzyl (6-(((S)-1-((R)-2-((tert-butoxycarbonyl)amino)-2-cyclohexylacetyl)azetidine-2-carboxamido)methyl)isoquinolin-1-yl)carbamate was removed according to the procedure for compound 1116, step 2 followed by aqueous extractive work-up (sat aqueous NaHCO₃/CH₂Cl₂) gave benzyl (6-(((S)-1-((R)-2-amino-2-cyclohexylacetyl)azetidine-2-carboxamido)methyl)isoquinolin-1-yl)carbamate (88% yield).

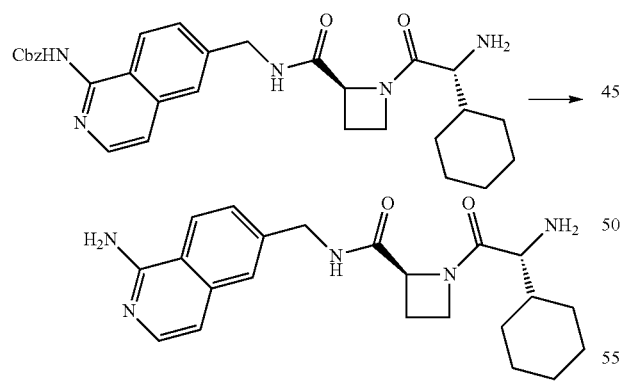

Step 4: Benzyl (6-(((S)-1-((R)-2-amino-2-cyclohexylacetyl)azetidine-2-carboxamido) methyl)isoquinolin-1-yl)carbamate (163 mg, 0.31 mmol) was subjected to hydrogenolysis in MeOH with 10% Pd/C (24 mg) under 1 atm H₂. After the reaction did not proceed to completion with extended reaction time (42 h); 6 M HCl (0.5 mL, 3 mmol) was added. The mixture was reacted under 1 atm H₂ for 21 h then filtered (0.2 μM syringe filter). Chromatography on a 12 g Biotage C-18 column (5-30% MeCN—H₂O) gave 49 mg of compound 1041 as a white solid in 40% yield.

Example 11: Preparation of (S)-1-((R)-2-Amino-2-cyclohexylacetyl)-N-(4-guanidinobutyl)azetidine-2-carboxamide Dihydrochloride (1006)

(1006)

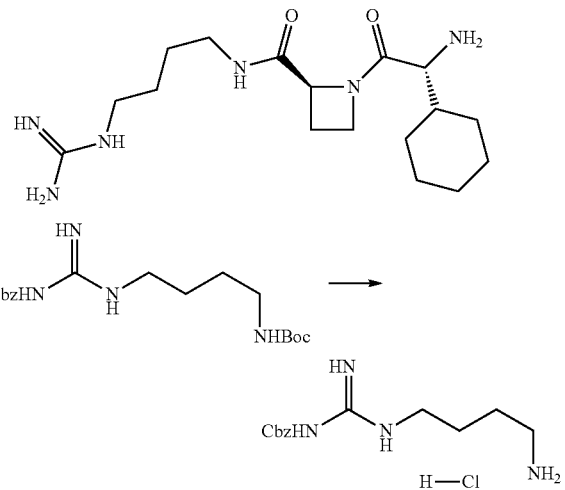

Step 1: To an ice-cold solution of Boc-Agm (Z) (3.0 g, 8.2 mmol, synthesized according to the procedure of WO9429335) in EtOAc-MeOH (20 mL, 1:1) was added 4 M HCl-dioxane (10 mL). After 10 min, the solution was allowed to warm to room temp and stirred for 3 h. The mixture was concentrated under vacuum and the residue was dissolved in EtOAc-MeOH and concentrated under vacuum. This procedure was repeated to give benzyl N—[N-(4-aminobutyl)carbamimidoyl]carbamate hydrochloride as a foam (2.045 g, 82% yield).

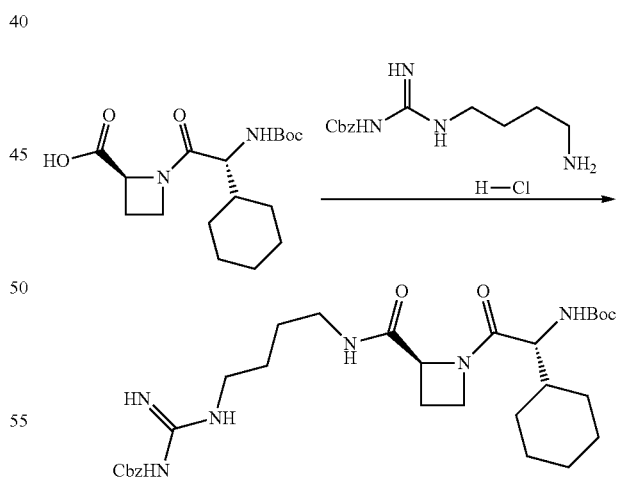

Step 2: (S)-1-((R)-2-((tert-Butoxycarbonyl)amino)-2-cyclohexylacetyl)azetidine-2-carboxylic acid and benzyl N—[N-(4-aminobutyl)carbamimidoyl]carbamate hydrochloride were coupled according to the procedure for compound 1116, step 1. Chromatography (0-6% MeOH—CH₂Cl₂) provided tert-butyl ((R)-1-cyclohexyl-2-((S)-2-((4-(3-Cbz-guanidino)butyl)carbamoyl)azetidin-1-yl)-2-oxoethyl)carbamate as a white foam (435 mg, 84% yield).

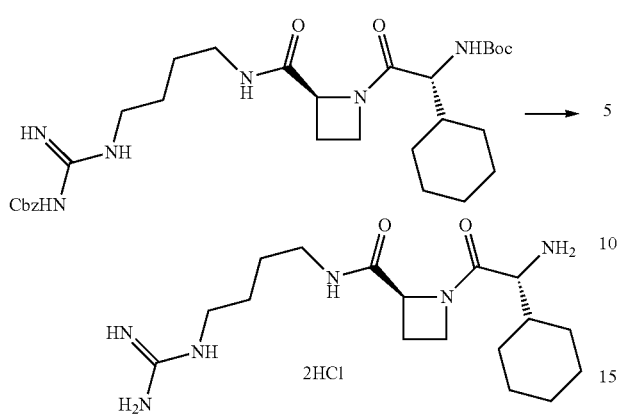

Step 3: Boc removal according to the procedure for compound 1116, step 2 provided intermediate (S)-1-((R)-2-amino-2-cyclohexylacetyl)-N-(4-(3-Cbz-guanidino)butyl)azetidine-2-carboxamide dihydrochloride as a white foam.

Step 4: Removal of the Cbz group of (S)-1-((R)-2-amino-2-cyclohexylacetyl)-N-(4-(3-Cbz-guanidino)butyl)azetidine-2-carboxamide dihydrochloride was conducted according to compound 1028, step 6 followed by the addition of concd HCl (~3 mmol), filtration (0.2 µM syringe filter) and concentrated under vacuum gave an orange oil. A MeOH solution of the crude product was treated with finely divided charcoal and heated at 30° C. for 30 min. After cooling to room temp, the mixture was filtered (0.2 µM syringe filter) and concentrated under vacuum to give (S)-1-((R)-2-amino-2-cyclohexylacetyl)-N-(4-guanidinobutyl)azetidine-2-carboxamide dihydrochloride as a beige foam (306 mg).

Example 12: Preparation of (S)-1-((R)-2-Amino-2-cyclohexylacetyl)-N-(3-guanidinopropyl)azetidine-2-carboxamide Hydrochloride (1004)

(1004)

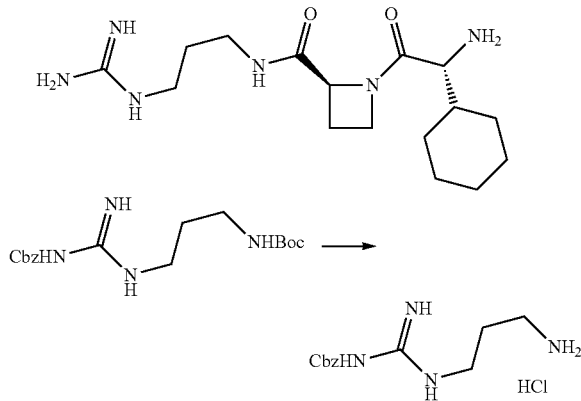

Step 1: 10-Oxa-2,4,8-triazadodecanoic acid, 3-imino-11,11-dimethyl-9-oxo-, phenylmethyl ester (synthesized according to the procedure of WO9429335) was deprotected according to the procedure for compound 1006, step 1 to give carbamic acid, [[(3-aminopropyl)amino]iminomethyl]-, benzyl ester hydrochloride as a white foam.

Step 2: (S)-1-((R)-2-((tert-Butoxycarbonyl)amino)-2-cyclohexylacetyl)azetidine-2-carboxylic acid and carbamic acid, [[(4-aminopropyl)amino]iminomethyl]-, benzyl ester hydrochloride were coupled and subsequently deprotected according to the procedure for compound 1006 to give (S)-1-((R)-2-amino-2-cyclohexylacetyl)-N-(3-guanidinopropyl)azetidine-2-carboxamide hydrochloride as a white foam (279 mg, 74% yield for three steps).

Example 13: Preparation of (S)-2-((R)-2-Amino-2-(2,3-dihydro-1H-inden-2-yl)acetamido)-N-((1-aminoisoquinolin-6-yl)methyl)propanamide Dihydrochloride (1088)

(1088)

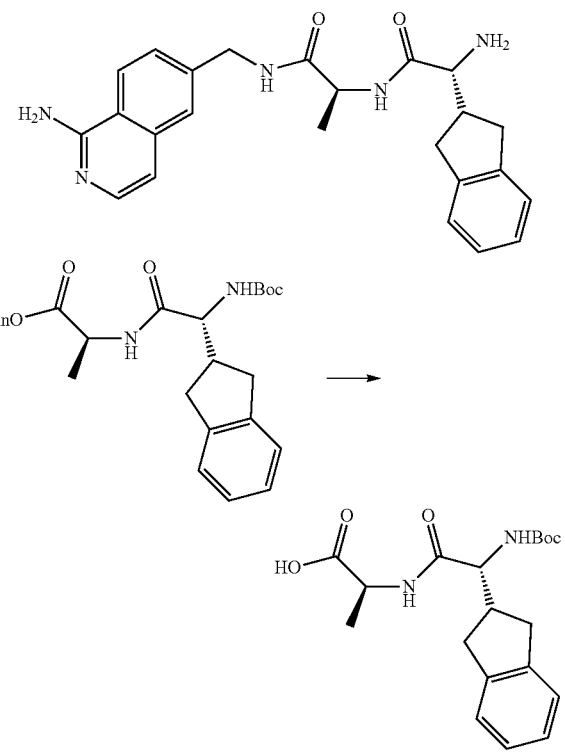

Step 1: Benzyl ((R)-2-((tert-butoxycarbonyl)amino)-2-(2,3-dihydro-1H-inden-2-yl)acetyl)-L-alaninate (3.6 g, 7.96 mmol, prepared according to the procedure for compound 1116, step 1) was hydrogenated with 10% Pd/C in MeOH according to the procedure for compound 1028, step 6. The crude material was crystallized from warm EtOH-H₂O; the solid that was collected on a fritted funnel and rinsed with H₂O to give ((R)-2-((tert-butoxycarbonyl)amino)-2-(2,3-dihydro-1H-inden-2-yl)acetyl)-L-alanine as a white powder (2.45 g, 85% yield).

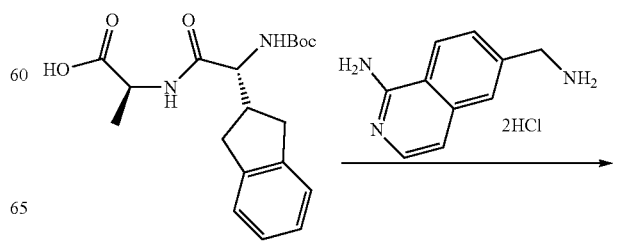

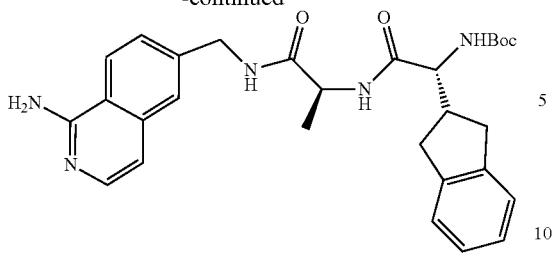

Step 2: To a solution of ((R)-2-((tert-butoxycarbonyl)amino)-2-(2,3-dihydro-1H-inden-2-yl)acetyl)-L-alanine (291 mg, 0.80 mmol) in anhyd DMF (2.5 mL) was added 6-(aminomethyl)isoquinolin-1-amine dihydrochloride (252 mg, 1.0 mmol) and DIEA (0.54 mL, 3.1 mmol) to give a tan suspension. HBTU (349 mg, 0.92 mmol) was added in two aliquots then additional anhyd DMF (0.4 mL). After stirring for 50 min at room temp, additional HBTU (18 mg, 0.05 mmol) was added. The reaction was stirred for 90 min then concentrated under vacuum. The residue was dissolved in EtOAc-CH$_2$Cl$_2$ then washed with 5% aqueous NaHCO$_3$ and brine, then dried (Na$_2$SO$_4$). Chromatography (0-10% MeOH—CH$_2$Cl$_2$) gave tert-butyl ((R)-2-(((S)-1-(((1-aminoisoquinolin-6-yl)methyl)amino)-1-oxopropan-2-yl)amino)-1-(2,3-dihydro-1H-inden-2-yl)-2-oxoethyl)carbamate (398 mg, 95% yield).

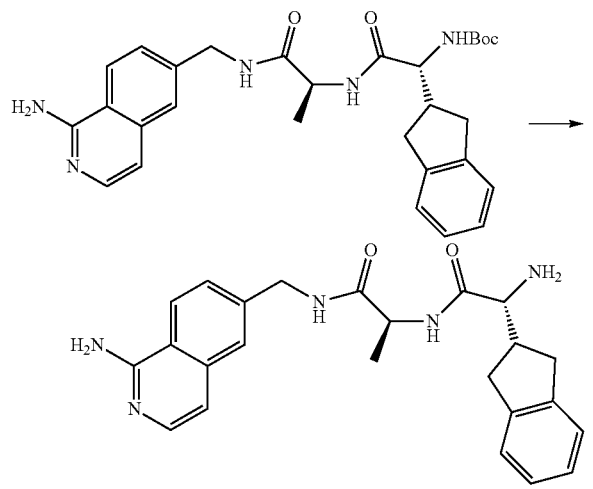

Step 3: To an ice-cold solution of tert-butyl ((R)-2-(((S)-1-(((1-aminoisoquinolin-6-yl)methyl)amino)-1-oxopropan-2-yl)amino)-1-(2,3-dihydro-1H-inden-2-yl)-2-oxoethyl)carbamate (130 mg, 0.25 mmol) in MeOH (2 mL) was added 4 M HCl-dioxane (3 mL). The mixture was stirred for 40 min then allowed to warm to room temperature. After stirring for 4 h total, the solution was concentrated under vacuum. The residue was dissolved in a minimal amount of MeOH and triturated with Et$_2$O. The mixture was warmed for 30 min at 30-40° C. then cooled to room temp. The solid was collected on a fritted funnel and rinsed with Et$_2$O. The solid was dried under vacuum at room temp to give (S)-2-((R)-2-amino-2-(2,3-dihydro-1H-inden-2-yl)acetamido)-N-((1-aminoisoquinolin-6-yl)methyl)propanamide as an off-white solid (107 mg, 93% yield).

Example 14: Preparation of (S)-2-((R)-2-Amino-2-(2,3-dihydro-1H-inden-2-yl)acetamido)-N-(4-(N-methylcarbamimidoyl)benzyl)propenamide Dihydrochloride (1062)

(1062)

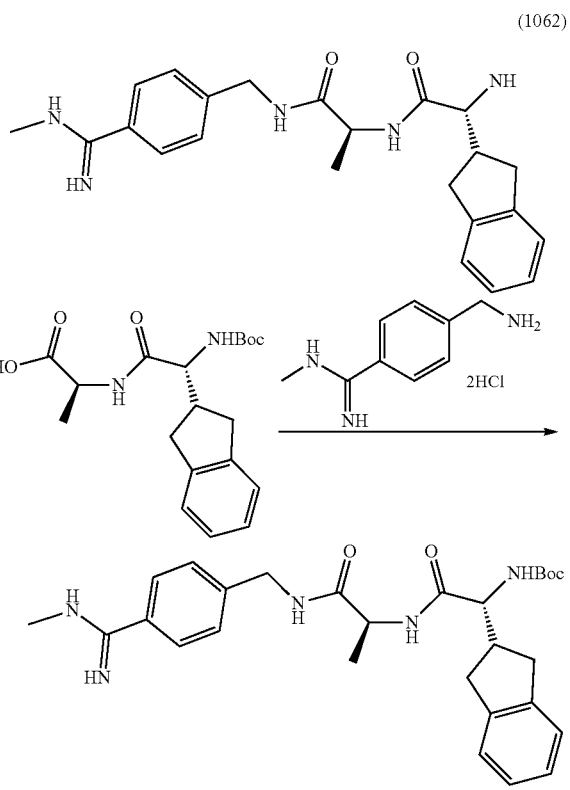

Step 1: ((R)-2-((tert-Butoxycarbonyl)amino)-2-(2,3-dihydro-1H-inden-2-yl)acetyl)-L-alanine was coupled to 4-(aminomethyl)-N-methylbenzimidamide dihydrochloride (synthesized according to WO2003028729, except that one Boc protecting group was used in the synthetic sequence) were coupled according to the procedure of compound 1088, step 2 at 15° C. to room temp for 16 h. After extractive workup with 10% MeOH—CH$_2$Cl$_2$, chromatography (0-10% (7 M NH$_3$-MeOH)—CH$_2$Cl$_2$) provided tert-butyl ((R)-1-(2,3-dihydro-1H-inden-2-yl)-2-(((S)-1-((4-(N-methylcarbamimidoyl)benzyl)amino)-1-oxopropan-2-yl)amino)-2-oxoethyl)carbamate that was contaminated with the dimethyl benzamidine derivative. Purification by HPLC (4-45%, then 70% MeCN—H$_2$O) gave moderate separation of the two products. Lyophilization of the purest fractions gave tert-butyl ((R)-1-(2,3-dihydro-1H-inden-2-yl)-2-(((S)-1-((4-(N-methylcarbamimidoyl)benzyl)amino)-1-oxopropan-2-yl)amino)-2-oxoethyl)carbamate as a white solid (73 mg, 23% yield.

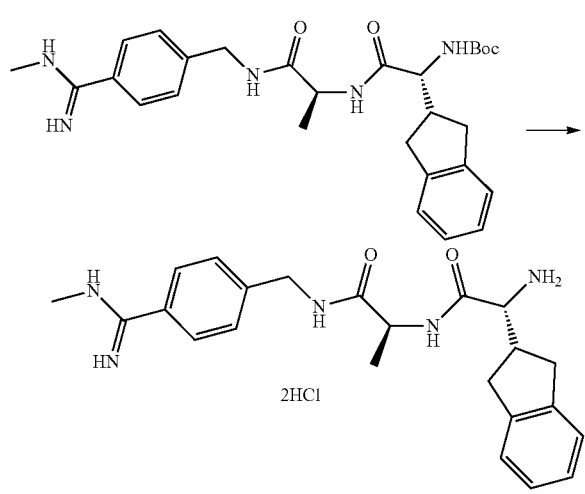

Step 2: tert-Butyl ((R)-1-(2,3-dihydro-1H-inden-2-yl)-2-(((S)-1-((4-(N-methyl carbamimidoyl)benzyl)amino)-1-oxopropan-2-yl)amino)-2-oxoethyl)carbamate was deprotected according to the procedure of compound 1088, step 3. The residue was triturated with Et₂O-EtOAc with sonication to give (S)-2-((R)-2-amino-2-(2,3-dihydro-1H-inden-2-yl)acetamido)-N-(4-(N-methylcarbamimidoyl)benzyl)propenamide dihydrochloride as a light yellow solid (62 mg).

Example 15: Preparation of (R)-2-Amino-N—((S)-1-((2-(6-aminopyridin-3-yl)ethyl)amino)-1-oxopropan-2-yl)-4-phenylbutanamide Dihydrochloride (1015)

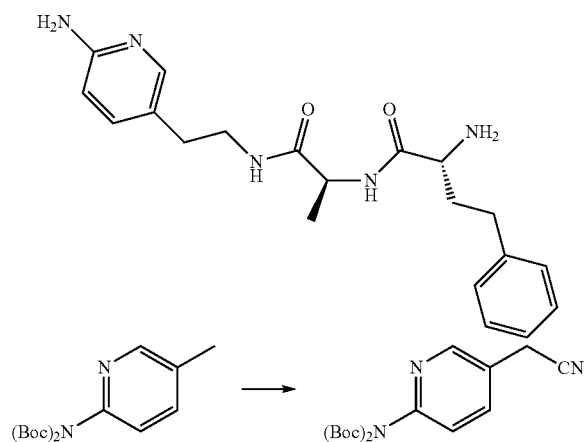

Step 1: tert-Butyl N-[(tert-butoxy)carbonyl]-N-(5-methylpyridin-2-yl)carbamate (synthesized according to WO2010141406) was brominated following a modified procedure also reported in WO2010141406 as follows. Tert-butyl N-[(tert-butoxy)carbonyl]-N-(5-methylpyridin-2-yl)carbamate (2.118 g, 6.87 mmol) was partially dissolved in CCl₄ (60 mL). To this mixture was added NBS (1.22 g, 6.86 mmol) and benzoyl peroxide (0.21 g, 0.65 mmol). The mixture was heated at 80° C. for 20 h. After cooling to room temp, the mixture was diluted with CH₂Cl₂ and washed with saturated aqueous NaHCO₃ 2×, 5% aqueous NaHCO₃ and brine then dried (Na₂SO₄) and concentrated under vacuum to give crude di-tert-butyl 5-(bromomethyl)pyridin-2-yliminodicarbonate (2.6 g).

Step 2: To a solution of crude di-tert-butyl 5-(bromomethyl)pyridin-2-yliminodicarbonate (2.2 g) in CH₂Cl₂ (40 mL) was added H₂O, NaCN (0.85 g, 17.3 mmol) and Bu₄NI (6.4 g, 17.3 mmol). The mixture was stirred vigorously at room temp for 19 h then diluted with CH₂Cl₂ and washed with saturated aqueous NaHCO₃ 2×, H₂O and brine. Dried (Na₂SO₄) and concentrated under vacuum then chromatographed (0-40% EtOAc-hexanes) to give di-tert-butyl 5-(cyanomethyl)pyridin-2-yliminodicarbonate (0.84 g).

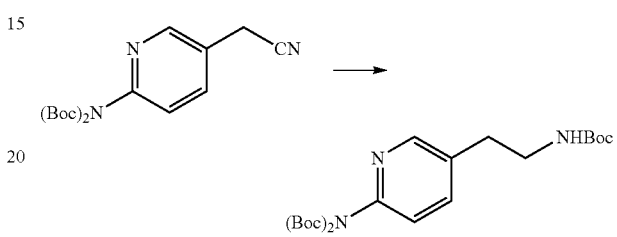

Step 3: To a solution of di-tert-butyl 5-(cyanomethyl)pyridin-2-yliminodicarbonate (370 mg, 1.1 mmol) in MeOH (5 mL) was added CoCl₂·6H₂O (292 mg, 1.2 mmol) and di-tert-butyl dicarbonate (470 mg, 2.2 mmol). The solution was cooled over an ice/EtOH bath for 4 min, then NaBH₄ (165 mg, 4.4 mmol) was added in three aliquots over 25 min. The mixture was stirred for 20 min then allowed to warm to room temp and stirred for 75 min. The reaction was quenched with 0.5 M KHSO₄ in 0.5 mL aliquots until pH=2. The aqueous mixture was extracted with 5% MeOH—CH₂Cl₂ several times then the aqueous layer was adjusted to pH 4-5 with the addition of several drops of 2 M NaOH. Additional extractions with CH₂Cl₂ were conducted. The combined organics were washed with brine, dried (Na₂SO₄) and concentrated under vacuum to give a yellow oil. Chromatography (0-45% EtOAc-hexanes) gave tert-butyl (tert-butoxycarbonyl)(5-(2-((tert-butoxycarbonyl)amino)ethyl)pyridin-2-yl)carbamate that was contaminated with 10% of the starting material (320 mg, 66% crude yield).

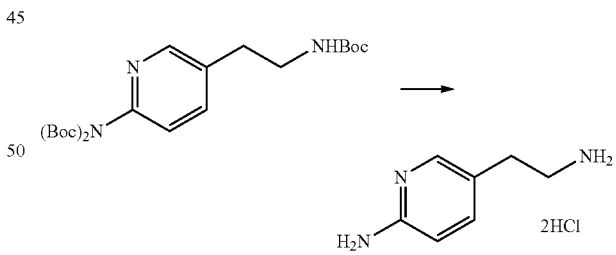

Step 4: tert-Butyl (tert-butoxycarbonyl)(5-(2-((tert-butoxycarbonyl)amino)ethyl)pyridin-2-yl)carbamate (320 mg, 0.73 mmol) was reacted with a concentrated solution of HCl-MeOH (4 mL) prepared by saturating MeOH with HCl (g). After stirring for 4 h, Et₂O was added and the mixture was concentrated under vacuum. Trituration with MeOH-Et₂O gave a ppt that was collected on a fritted funnel and rinsed with Et₂O and hexanes. 5-(Aminoethyl)pyridin-2-amine dihydrochloride was isolated (135 mg, 76% yield).

Step 5: ((R)-2-((tert-Butoxycarbonyl)amino)-4-phenylbutanoyl)-L-alanine was coupled with 5-(2-aminoethyl)pyridin-2-amine dihydrochloride to provide tert-butyl ((R)-1-

(((S)-1-((2-(6-aminopyridin-3-yl)ethyl)amino)-1-oxopropan-2-yl)amino)-1-oxo-4-phenylbutan-2-yl)carbamate following the procedure for compound 1088, step 2 at 10° C. to room temp for 3 h (94% yield).

Step 6: Deprotection of tert-butyl ((R)-1-(((S)-1-((2-(6-aminopyridin-3-yl)ethyl)amino)-1-oxopropan-2-yl)amino)-1-oxo-4-phenylbutan-2-yl)carbamate with HCl-MeOH afforded (R)-2-amino-N—((S)-1-((2-(6-aminopyridin-3-yl)ethyl)amino)-1-oxopropan-2-yl)-4-phenylbutanamide dihydrochloride after crystallization from MeOH-MeCN (49 mg, 27% yield).

Example 16: Preparation of (R)-2-Amino-N—((S)-1-(((4-aminoquinazolin-7-yl)methyl)amino)-1-oxopropan-2-yl)-4-phenylbutanamide Dihydrochloride (1060)

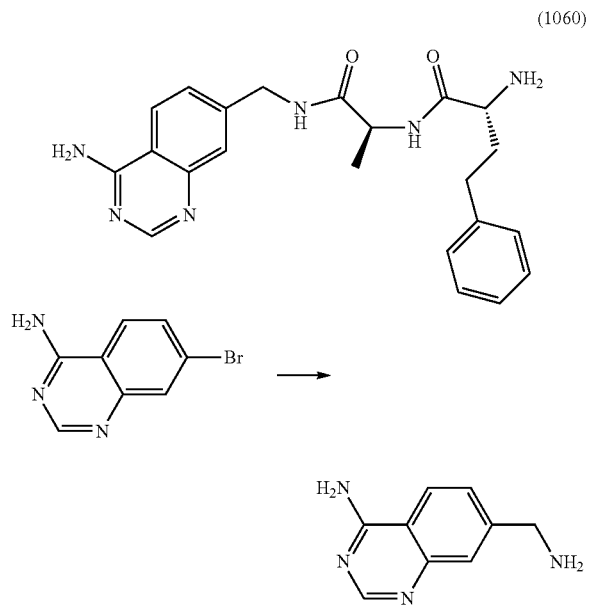

Step 1: 7-(Aminomethyl)quinazolin-4-amine was synthesized from 7-bromoquinazolin-4-amine in two steps by the procedure reported in WO2015103317.

Step 2: tert-Butyl ((R)-1-(((S)-1-(((4-aminoquinazolin-7-yl)methyl)amino)-1-oxopropan-2-yl)amino)-1-oxo-4-phenylbutan-2-yl)carbamate was synthesized by coupling 7-(aminomethyl)quinazolin-4-amine and ((R)-2-((tert-butoxycarbonyl)amino)-4-phenylbutanoyl)-L-alanine according to the procedure for compound 1088, step 2 at 0-5° C.

Step 3: Deprotection of tert-butyl ((R)-1-(((S)-1-(((4-aminoquinazolin-7-yl)methyl)amino)-1-oxopropan-2-yl)amino)-1-oxo-4-phenylbutan-2-yl)carbamate with MeOH and 3 M HCl-CPME provided (R)-2-amino-N—((S)-1-(((4-aminoquinazolin-7-yl)methyl)amino)-1-oxopropan-2-yl)-4-phenylbutanamide dihydrochloride as a white powder (50 mg, 96% yield).

Example 17: Preparation of (R)-2-Amino-N—((S)-1-(((1-aminoisoquinolin-6-yl)methyl)amino)-1-oxopropan-2-yl)-N-methyl-4-(3-(trifluoromethyl)phenyl)butanamide Dihydrochloride (1139)

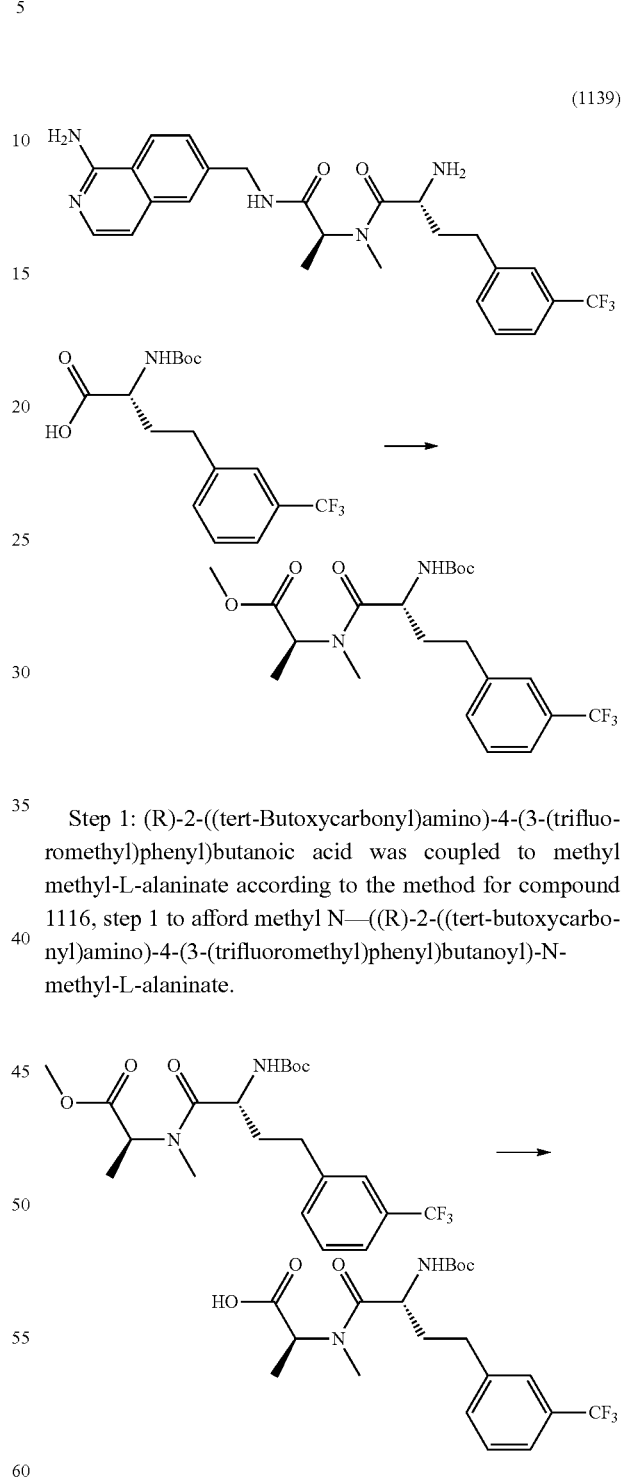

Step 1: (R)-2-((tert-Butoxycarbonyl)amino)-4-(3-(trifluoromethyl)phenyl)butanoic acid was coupled to methyl methyl-L-alaninate according to the method for compound 1116, step 1 to afford methyl N—((R)-2-((tert-butoxycarbonyl)amino)-4-(3-(trifluoromethyl)phenyl)butanoyl)-N-methyl-L-alaninate.

Step 2: N—((R)-2-((tert-Butoxycarbonyl)amino)-4-(3-(trifluoromethyl)phenyl)butanoyl)-N-methyl-L-alanine was synthesized from methyl N—((R)-2-((tert-butoxycarbonyl)amino)-4-(3-(trifluoromethyl)phenyl)butanoyl)-N-methyl-L-alaninate according to the procedure for ester hydrolysis for compound 1058.

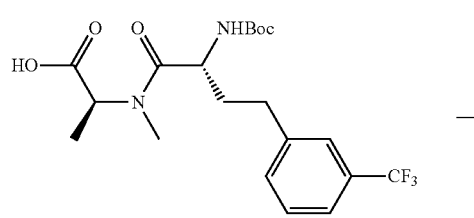

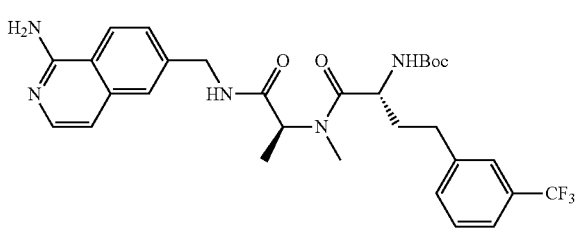

Step 3: N—((R)-2-((tert-Butoxycarbonyl)amino)-4-(3-(trifluoromethyl)phenyl)butanoyl)-N-methyl-L-alanine was coupled with 6-(aminomethyl)isoquinolin-1-amine dihydrochloride according to the foregoing procedures to provide tert-butyl ((R)-1-(((S)-1-(((1-aminoisoquinolin-6-yl)methyl)amino)-1-oxopropan-2-yl)(methyl)amino)-1-oxo-4-(3-(trifluoromethyl)phenyl)butan-2-yl)carbamate.

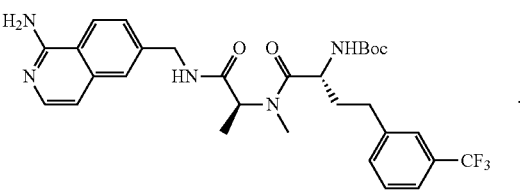

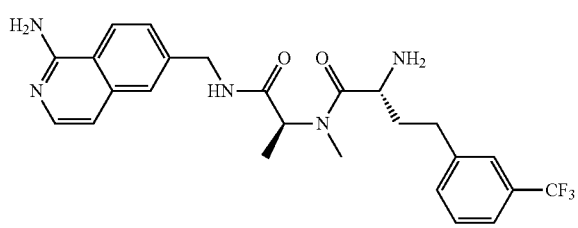

Step 4: tert-Butyl ((R)-1-(((S)-1-(((1-aminoisoquinolin-6-yl)methyl)amino)-1-oxopropan-2-yl)(methyl)amino)-1-oxo-4-(3-(trifluoromethyl)phenyl)butan-2-yl)carbamate was deprotected with MeOH and 3 M HCl-CPME according to the foregoing procedures to give (R)-2-amino-N—((S)-1-(((1-aminoisoquinolin-6-yl)methyl)amino)-1-oxopropan-2-yl)-N-methyl-4-(3-(trifluoromethyl)phenyl)butanamide dihydrochloride.

Example 18: Preparation of 2-Amino-N—((S)-1-(((2-amino-1H-benzo[d]imidazol-6-yl)methyl)amino)-1-oxopropan-2-yl)-4-phenylbutanamide Di-trifluoroacetate salt (1040)

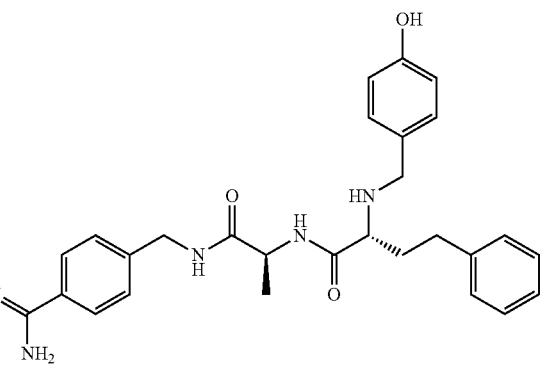

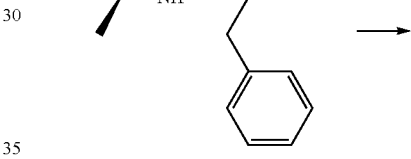

Step 1: ((R)-2-((tert-Butoxycarbonyl)amino)-4-phenylbutanoyl)-L-alanine was coupled with 6-(aminomethyl)-1H-benzo[d]imidazol-2-amine dihydrochloride according to the procedure of compound 1088, step 2 except that the reaction was conducted at room temp and the 6-(aminomethyl)-1H-benzo[d]imidazol-2-amine dihydrochloride was added to the reaction mixture last. The reaction was stirred for 18 h after which the mixture was concentrated under vacuum. The residue was diluted with $CH_2Cl_2$ and washed with 5% aqueous $NaHCO_3$, dried ($Na_2SO_4$) and chromatographed with 10% MeOH (containing 7 M $NH_3$)—$CH_2Cl_2$ to give tert-butyl ((R)-1-(((S)-1-(((2-amino-1H-benzo[d]imidazol-6-yl)methyl)amino)-1-oxopropan-2-yl)amino)-1-oxo-4-phenylbutan-2-yl)carbamate in 32% yield.

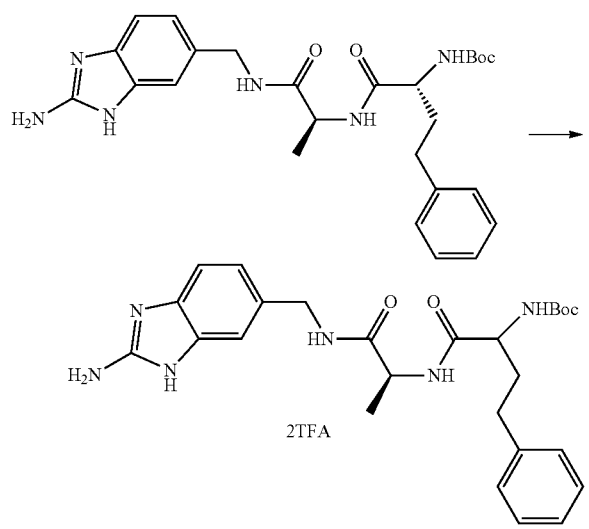

Step 2: tert-Butyl ((R)-1-(((S)-1-(((2-amino-1H-benzo[d]imidazol-6-yl)methyl)amino)-1-oxopropan-2-yl)amino)-1-oxo-4-phenylbutan-2-yl)carbamate was deprotected with HCl-MeOH as described in foregoing procedures to give 2-amino-N—((S)-1-(((2-amino-1H-benzo[d]imidazol-6-yl)methyl)amino)-1-oxopropan-2-yl)-4-phenylbutanamide dihydrochloride. The compound was purified by HPLC (2-15-35-90% MeCN—H₂O) to give 2-amino-N—((S)-1-(((2-amino-1H-benzo[d]imidazol-6-yl)methyl)amino)-1-oxopropan-2-yl)-4-phenylbutanamide di-trifluoroacetate salt, isomer 2.

Example 19: Preparation of (R)-2-Amino-N—((S)-1-((2-(2-aminopyridin-4-yl)ethyl)amino)-1-oxopropan-2-yl)-4-phenylbutanamide Dihydrochloride (1016)

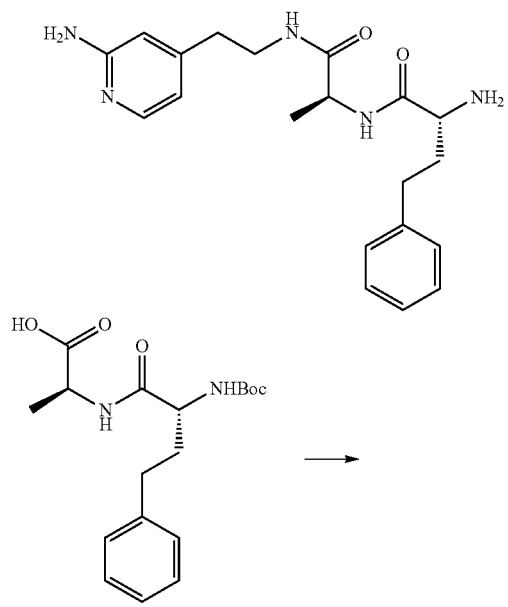

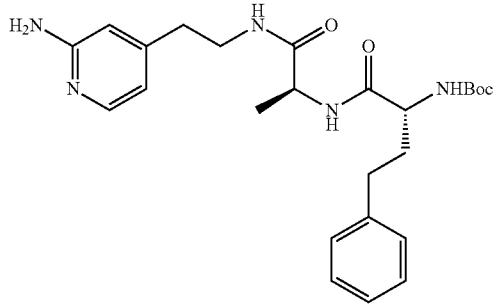

Step 1: ((R)-2-((tert-Butoxycarbonyl)amino)-4-phenylbutanoyl)-L-alanine was coupled with 4-(2-aminoethyl)pyridin-2-amine dihydrochloride to provide tert-butyl ((R)-1-(((S)-1-((2-(2-aminopyridin-4-yl)ethyl)amino)-1-oxopropan-2-yl)amino)-1-oxo-4-phenylbutan-2-yl)carbamate according to the procedure of compound 1088, step 2, except that the reaction was conducted at 10-15° C. to room temp.

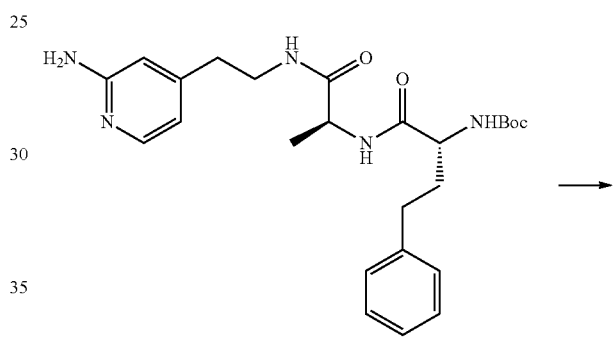

Step 2: tert-Butyl ((R)-1-(((S)-1-((2-(2-aminopyridin-4-yl)ethyl)amino)-1-oxopropan-2-yl)amino)-1-oxo-4-phenylbutan-2-yl)carbamate was deprotected with HCl-MeOH according to the foregoing procedures to give compound 1016 (80 mg, 89% yield).

Example 20: Preparation of (R)-2-Amino-N—((S)-1-((4-carbamimidoylbenzyl)amino)-1-oxopropan-2-yl)-4-(4-(trifluoromethyl)phenyl)butanamide Dihydrochloride (1119)

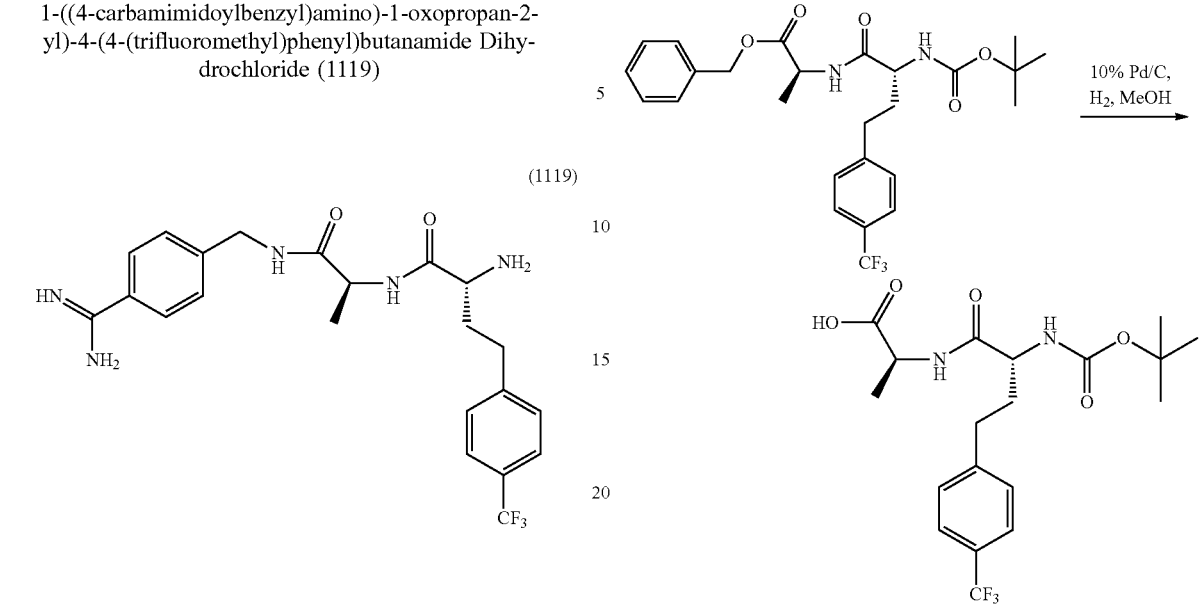

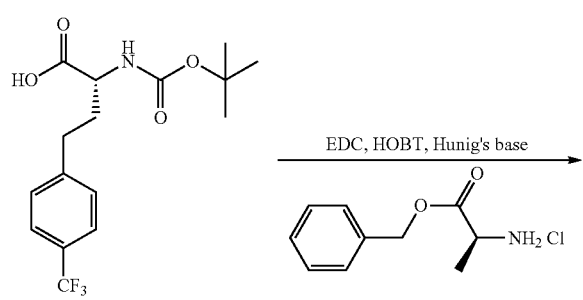

Step 1: To a solution of (R)-2-((tert-butoxycarbonyl)amino)-4-(4-(trifluoromethyl)phenyl)butanoic acid (500 mg, 1.44 mmol) in anhydrous MeCN (30 mL) was added HOBt (1.1 equiv, 1.58 mmol), DIEA (4.0 equiv, 5.76 mmol) and EDC (1.1 equiv, 1.58 mmol) with stirring at room temp. for 30 min. Benzyl L-alaninate hydrochloride (1.1 equiv, 1.58 mmol) was added and stirred overnight. The solution was evaporated to dryness and the residue was partitioned with EtOAc (60 mL) and 10% KHSO₄ (50 mL). The organic layer was separated and washed with H₂O (30 mL), saturated Na₂CO₃ (60 mL), dried (Na₂SO₄) and evaporated leaving benzyl ((R)-2-((tert-butoxycarbonyl)amino)-4-(4-(trifluoromethyl)phenyl)butanoyl)-L-alaninate (512 mg, 70%) as an oil pure enough to use in the next step.

Step 2: A solution of benzyl ((R)-2-((tert-butoxycarbonyl)amino)-4-(4-(trifluoromethyl)phenyl)butanoyl)-L-alaninate (512 mg, 1.01 mmol) in MeOH (20 mL) was degassed with a stream of Ar for 2-3 min. 10% Pd/C (50 mg) was added and a vacuum was pulled for approx. 3 min. A balloon of H₂ was added and the reaction was monitored for the consumption of starting material (typically 1-4 h). The catalyst was removed by filtration and the solution was evaporated to dryness leaving ((R)-2-((tert-butoxycarbonyl)amino)-4-(4-(trifluoromethyl)phenyl)butanoyl)-L-alanine as a fluffy white solid (420 mg, 100%).

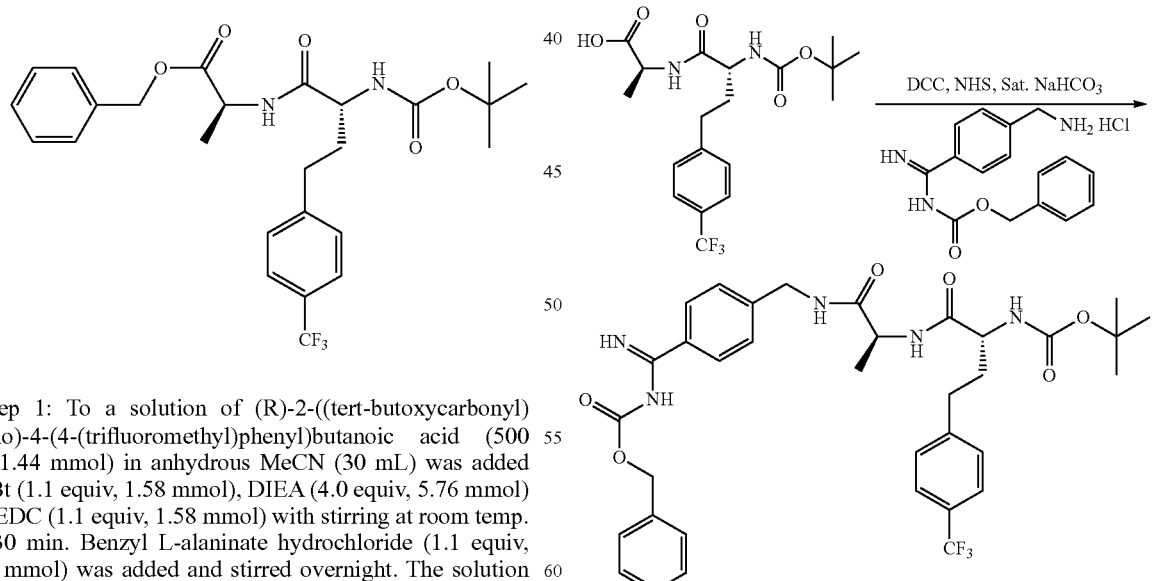

Step 3: To a solution of ((R)-2-((tert-butoxycarbonyl)amino)-4-(4-(trifluoromethyl)phenyl)butanoyl)-L-alanine (400 mg, 0.956 mmol) in CH₂Cl₂ (15 mL) was added NHS (1.1 equiv, 1.05 mmol) with stirring at room temp. until dissolved. DCC (1.1 equiv, 1.05 mmol) was added and stirred for 1.0 h. This mixture was poured into a separatory funnel containing saturated NaHCO₃ (15 mL), and benzyl ((4-(aminomethyl)phenyl)(imino)methyl)carbamate hydrochloride (1.2 equiv, 1.15 mmol) and then shaken for 5 min. The organic layer was filtered over a bed of anhyd Na₂SO₄ and evaporated to dryness. Flash chromatography (3% 7 N NH₃ in MeOH/CH₂Cl₂) gave tert-butyl ((R)-1-(((S)-1-((4-(N-((benzyloxy)carbonyl)carbamimidoyl)benzyl)amino)-1-oxopropan-2-yl)amino)-1-oxo-4-(4-(trifluoromethyl)phenyl)butan-2-yl)carbamate as an oil (477 mg, 73%). [In certain cases, products were able to be collected by filtration after a reduction in volume of the CH₂Cl₂ layer. These products contained a small amount of DCU which was removed in the final step of the synthesis by filtration from H₂O.]

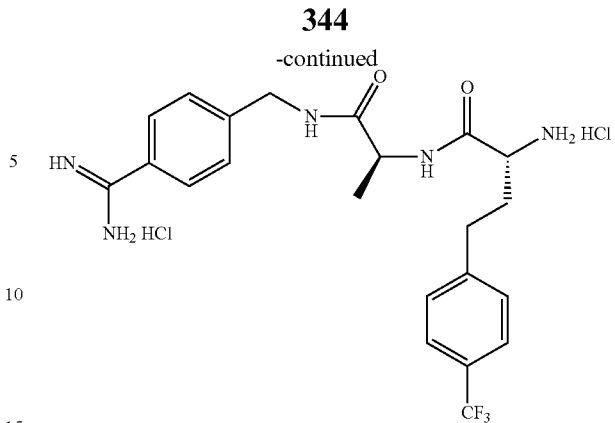

Step 5: A solution of benzyl ((4-(((S)-2-((R)-2-amino-4-(4-(trifluoromethyl)phenyl)butanamido)propanamido)methyl)phenyl)(imino)methyl)carbamate hydrochloride (420 mg, 0.677 mmol) in MeOH (10 mL) was degassed with a stream of Ar for 2-3 min. 10% Pd/C (50 mg) was added and a vacuum was pulled for approx. 3 min. A balloon of H₂ was applied and the reaction was monitored for the consumption of starting material (typically 1-2 h). The catalyst was removed by filtration then 4 drops of concentrated HCl was added and the solution was evaporated to dryness. To the residue was added H₂O (2-3 mL). The mixture was filtered then and lyophilized, giving (R)-2-amino-N—((S)-1-((4-carbamimidoylbenzyl)amino)-1-oxopropan-2-yl)-4-(4-(trifluoromethyl)phenyl)butanamide dihydrochloride as an off white solid (350 mg, 100%).

Example 21: Preparation of (R)-2-Amino-N—((S)-1-((4-(N-hydroxycarbamimidoyl)benzyl)amino)-1-oxopropan-2-yl)-4-phenylbutanamide Dihydrochloride (1157)

(1157)

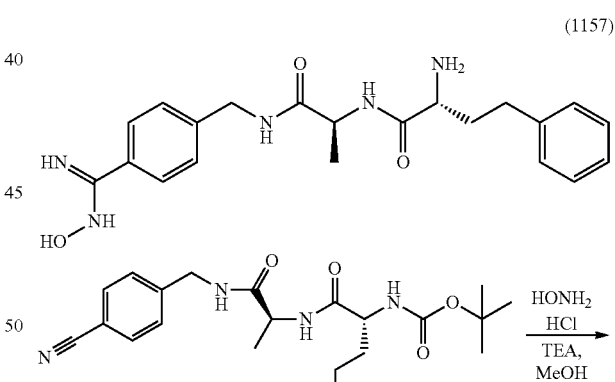

Step 4: To tert-butyl ((R)-1-(((S)-1-((4-(N-((benzyloxy)carbonyl)carbamimidoyl)benzyl)amino)-1-oxopropan-2-yl)amino)-1-oxo-4-(4-(trifluoromethyl)phenyl)butan-2-yl)carbamate (460 mg, 0.673 mmol) was added a solution of MeOH/HCl (5.0 mL, 227 mg HCl/mL) with stirring at room temp while monitoring for the consumption of starting material. The solution was evaporated to dryness and MeOH (15 mL) was added and evaporated to dryness giving benzyl ((4-(((S)-2-((R)-2-amino-4-(4-(trifluoromethyl)phenyl)butanamido)propanamido)methyl)phenyl)(imino)methyl)carbamate hydrochloride as a white solid pure enough to use in the next step (420 mg, 100%).

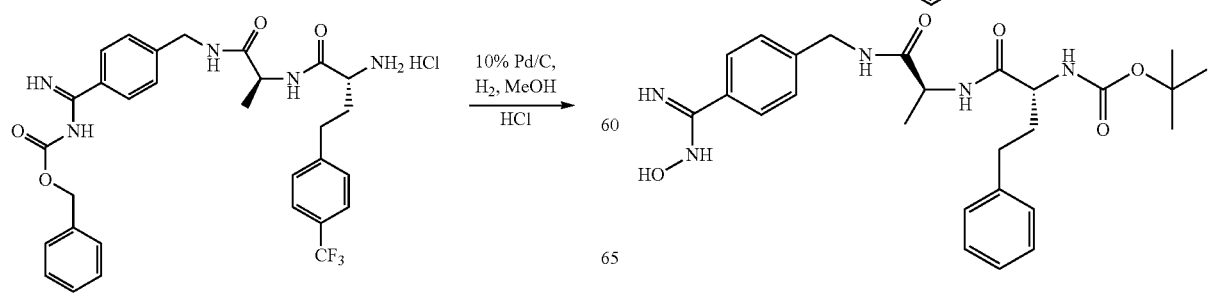

Step 1: To a solution of tert-butyl ((R)-1-(((S)-1-((4-cyanobenzyl)amino)-1-oxopropan-2-yl)amino)-1-oxo-4-phenylbutan-2-yl)carbamate (660 mg, 1.42 mmol, prepared according to compound 1119, step 3 using 4-cyanobenzyl amine HCl in MeOH (20 mL) was added hydroxylamine HCl (1.5 equiv, 2.13 mmol) and Et₃N (1.5 equiv, 2.13 mmol). This mixture was heated at reflux for 4 h, evaporated to dryness, and then partitioned between H₂O (15 mL) and EtOAc (2×30 mL.) The combined organic layers were dried over anhyd Na₂SO₄ and evaporated. Chromatography (50% EtOAc-hexanes) gave tert-butyl ((R)-1-(((S)-1-((4-(N-hydroxycarbamimidoyl)benzyl)amino)-1-oxopropan-2-yl)amino)-1-oxo-4-phenylbutan-2-yl)carbamate as a white solid (417 mg, 59%).

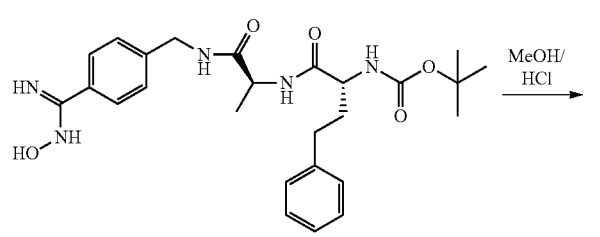

MeOH/HCl

Step 2: The intermediate was deprotected according to the procedure for compound 1119, step 4, to provide (R)-2-amino-N—((S)-1-((4-(N-hydroxycarbamimidoyl)benzyl)amino)-1-oxopropan-2-yl)-4-phenylbutanamide dihydrochloride (i.e., compound 1157).

Example 22: Preparation of (R)—N—(S)-1-((4-Carbamimidoylbenzyl)amino)-1-oxopropan-2-yl)-4-phenyl-2,5-dihydro-1H-pyrrole-2-carboxamide Di-trifluoroacetate (1032)

(1032)

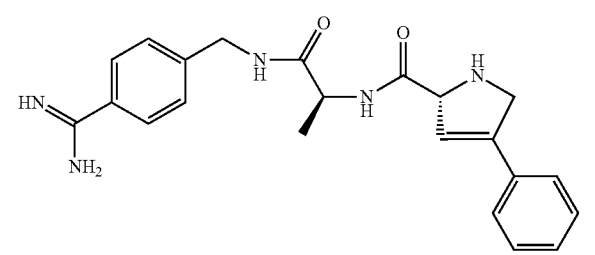

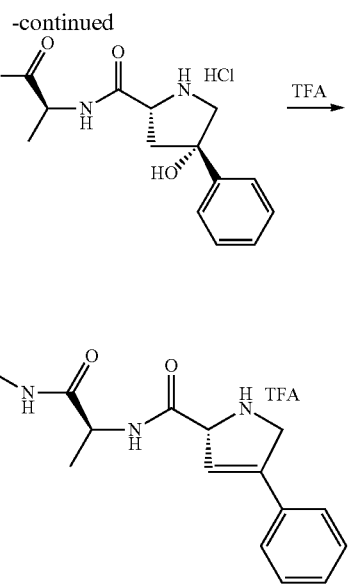

TFA (2R,4S)—N—((S)-1-((4-Carbamimidoylbenzyl)amino)-1-oxopropan-2-yl)-4-hydroxy-4-phenylpyrrolidine-2-carboxamide dihydrochloride (45 mg, 0.093 mmol) was stirred in TFA (5.0 mL) for 48 h at room temp. The solution was evaporated to dryness and the residue was subjected to purification using reverse phase HPLC (5-45-75-90% MeCN—H₂O). (R)—N—(S)-1-((4-Carbamimidoylbenzyl)amino)-1-oxopropan-2-yl)-4-phenyl-2,5-dihydro-1H-pyrrole-2-carboxamide di-trifluoroacetate was isolated as a white solid (15 mg, 26% yield).

Example 23: Preparation of (2R)-2-Amino-N-(1-((4-carbamimidoylbenzyl)amino)-3-fluoro-1-oxopropan-2-yl)-4-phenylbutanamide Dihydrochloride (1050)

(1050)

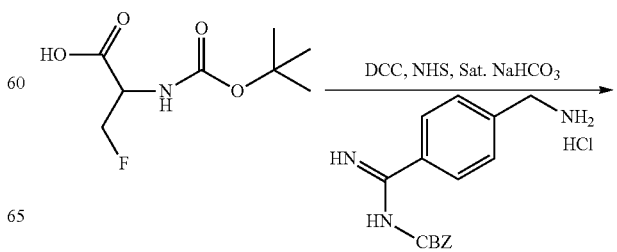

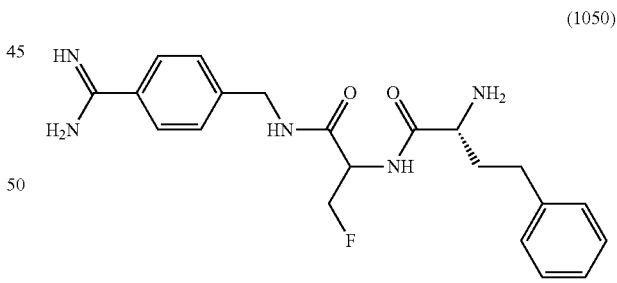

DCC, NHS, Sat. NaHCO₃

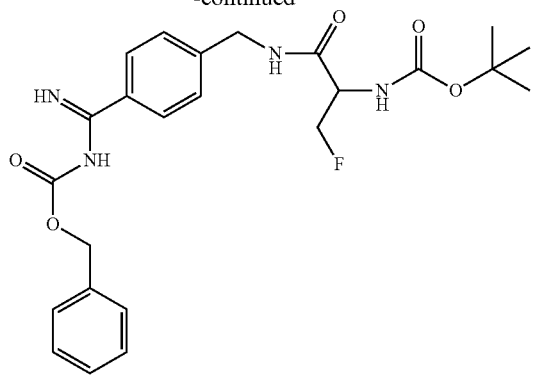

Step 1: tert-Butyl (1-((4-(N-((benzyloxy)carbonyl)carbamimidoyl)benzyl)amino)-3-fluoro-1-oxopropan-2-yl)carbamate was synthesized from 2-((tert-butoxycarbonyl)amino)-3-fluoropropanoic acid and benzyl ((4-(aminomethyl)phenyl)(imino)methyl)carbamate hydrochloride according to the procedure for compound 1119, step 3.

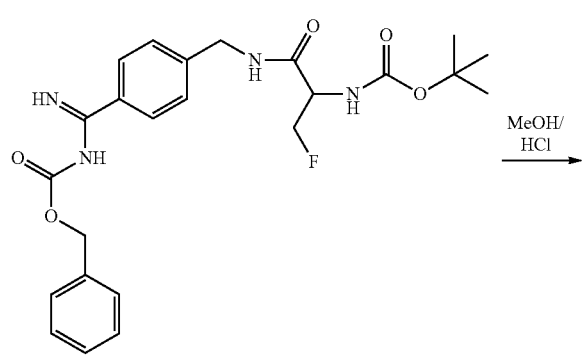

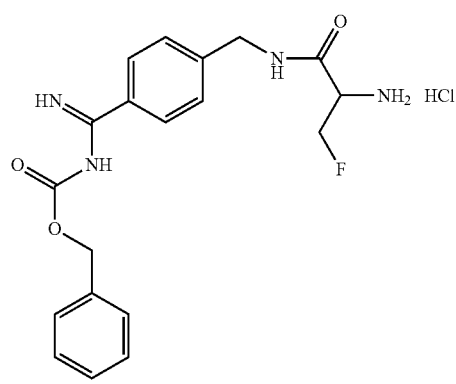

Step 2: tert-Butyl (1-((4-(N-((benzyloxy)carbonyl)carbamimidoyl)benzyl)amino)-3-fluoro-1-oxopropan-2-yl)carbamate was deprotected according to the procedure for compound 1119, step 4 to give benzyl ((4-((2-amino-3-fluoropropanamido)methyl)phenyl) (imino)methyl)carbamate hydrochloride.

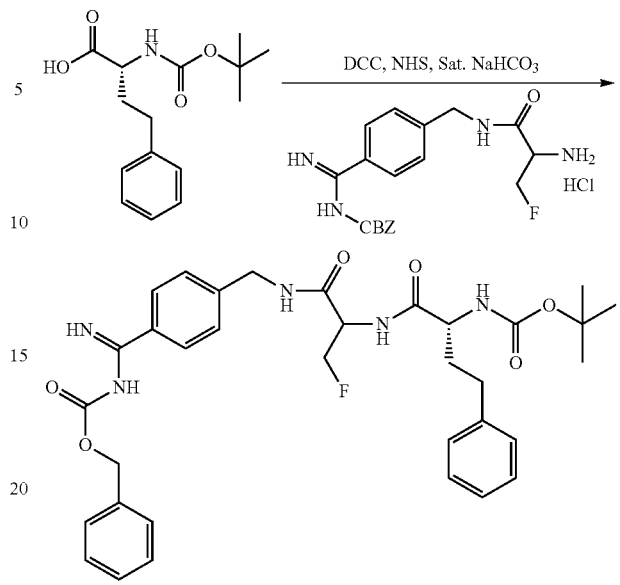

Step 3: Benzyl ((4-((2-((R)-2-amino-4-phenylbutanamido)-3-fluoropropanamido)methyl)phenyl)(imino)methyl)carbamate hydrochloride was synthesized from benzyl ((4-((2-amino-3-fluoropropanamido)methyl)phenyl) (imino)methyl)carbamate hydrochloride and (R)-2-((tert-butoxycarbonyl)amino)-4-phenylbutanoic acid according to the procedure for compound 1119, step 3.

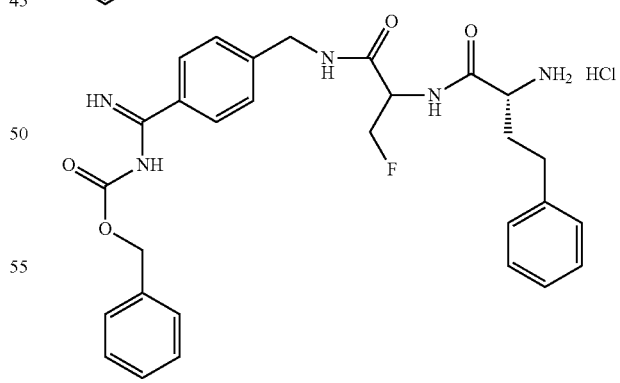

Step 4: Benzyl ((4-((2-((R)-2-amino-4-phenylbutanamido)-3-fluoropropanamido)methyl)phenyl)(imino)methyl)carbamate hydrochloride was synthesized from benzyl ((4-((2-((R)-2-amino-4-phenylbutanamido)-3-fluoropropanamido)methyl)phenyl)(imino)methyl)carbamate hydrochloride according to the procedure for compound 1119, step 4.

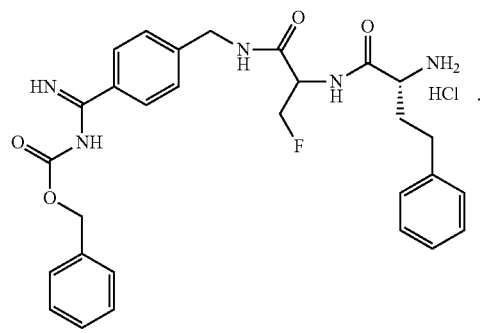

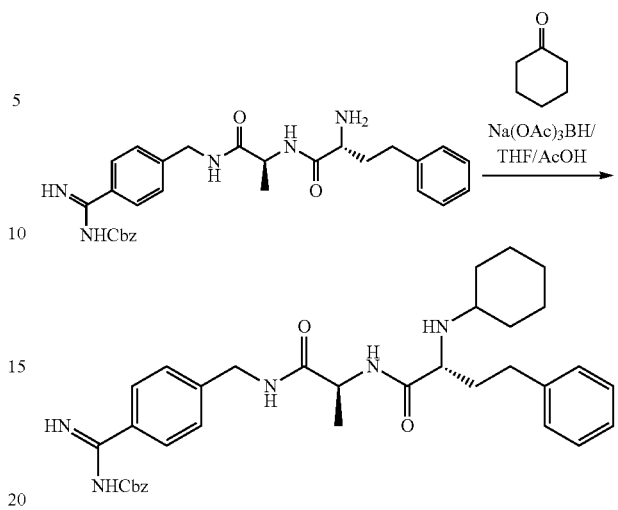

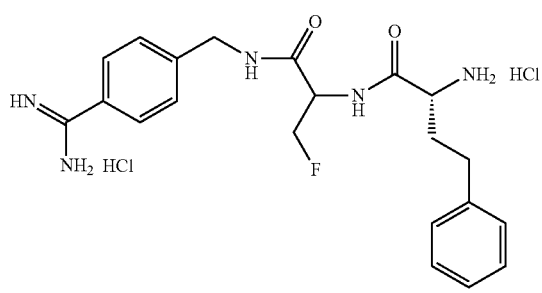

Step 5: (2R)-2-Amino-N-(1-((4-carbamimidoylbenzyl)amino)-3-fluoro-1-oxopropan-2-yl)-4-phenylbutanamide dihydrochloride (1050) was synthesized from benzyl ((4-((2-((R)-2-amino-4-phenylbutanamido)-3-fluoropropanamido)methyl)phenyl)(imino)methyl)carbamate hydrochloride according to the procedure for compound 1119, step 5.

Example 24: Preparation of (R)—N—((S)-1-((4-Carbamimidoylbenzyl)amino)-1-oxopropan-2-yl)-2-(cyclohexylamino)-4-phenylbutanamide Dihydrochloride (1130)

(1130)

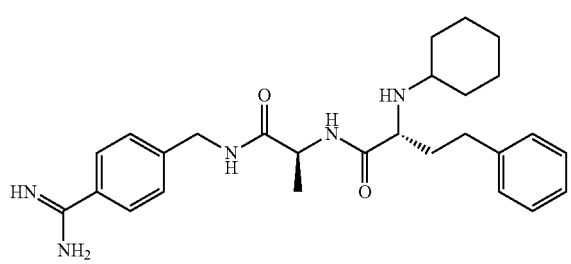

Step 1: Benzyl ((4-(((S)-2-((R)-2-amino-4-phenylbutanamido)propanamido) methyl)phenyl)(imino)methyl)carbamate (1.9 g, 41% yield in 4 steps) was synthesized by a method similar to that used for compound 1119, except the crude product was purified by chromatography (10% MeOH—CH$_2$Cl$_2$ and then 5% 7 N NH$_3$ in MeOH—CH$_2$Cl$_2$).

Step 2: To a 20-mL scintillation vial, benzyl ((4-(((S)-2-((R)-2-amino-4-phenylbutanamido)propanamido)methyl)phenyl)(imino)methyl)carbamate (55.1 mg, 0.107 mmol) was added and followed by THF (400 µL). The solution was treated with cyclohexanone (15 µL, 0.145 mmol) at room temp followed by Na(OAc)$_3$ solid (32 mg, 0.151 mmol) and HOAc (10 µL, 0.175 mmol). After purging with N$_2$, the vial was capped. The reaction was stirred at room temp for 4 h and quenched with about 15 mL saturated NaHCO$_3$ solution. The resulting mixture was extracted with 15 mL CH$_2$Cl$_2$ (3 times). The organic layers were combined, washed with brine, dried (Na$_2$SO$_4$) vacuum filtered, and evaporated under vacuum. The crude product was dissolved in CH$_2$Cl$_2$ and adsorbed on silica gel. Purification by chromatography (0-5% MeOH—CH$_2$Cl$_2$) gave benzyl ((4-(((S)-2-((R)-2-(cyclohexylamino)-4-phenylbutanamido)propanamido)methyl)phenyl)(imino)methyl)carbamate (44 mg, 69% yield).

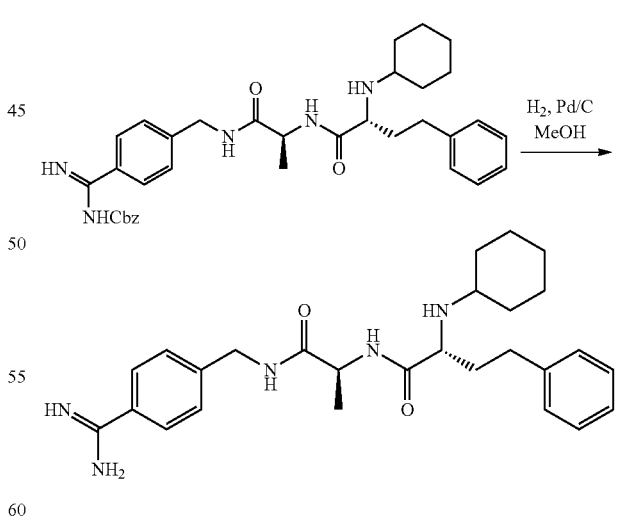

Step 3: To a solution of benzyl ((4-(((S)-2-((R)-2-(cyclohexylamino)-4-phenylbutanamido)propanamido)methyl)phenyl)(imino)methyl)carbamate (44 mg, 0.0736 mmol) in MeOH (1.0 mL) was treated with 10% Pd/C (8.1 mg, 0.00761 mmol) at room temp. Air was removed from the reaction apparatus by in-house N$_2$ line (5 times). H$_2$ was added via a balloon while stirring overnight. The reaction was filtered through a 0.25 m syringe filter. Volatiles were evaporated under vacuum to give (R)—N—((S)-1-((4-carbamimidoylbenzyl)amino)-1-oxopropan-2-yl)-2-(cyclohexylamino)-4-phenylbutanamide, compound 1130 (25.3 mg, 69% yield).

Example 25: Preparation of (R)—N—((S)-1-((4-Carbamimidoylbenzyl)amino)-1-oxopropan-2-yl)-2-((4-hydroxybenzyl)amino)-4-phenylbutanamide Dihydrochloride (1140)

(1140)

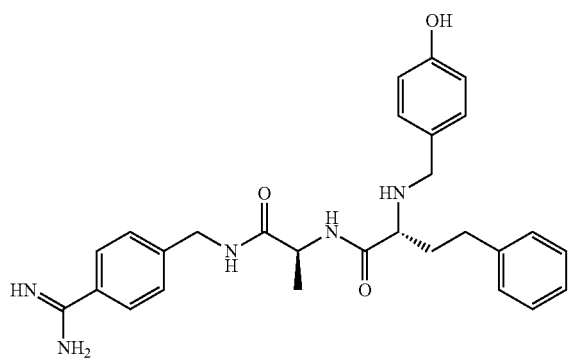

(R)—N—((S)-1-((4-Carbamimidoylbenzyl)amino)-1-oxopropan-2-yl)-2-((4-hydroxybenzyl)amino)-4-phenylbutanamide (17.7 mg, 30% yield in 2 steps) was synthesized by a method similar to that used for compound 1130, except the crude product was purified by reverse phase HPLC (5-45-75-90% MeCN—H$_2$O).

Example 26: Preparation of (R)—N—((S)-1-((4-Carbamimidoylbenzyl)amino)-1-oxopropan-2-yl)-4-phenyl-2-((4-(piperazin-1-yl)benzyl)amino)butanamide, Trifluoroacetate Salt (1148)

(1148)

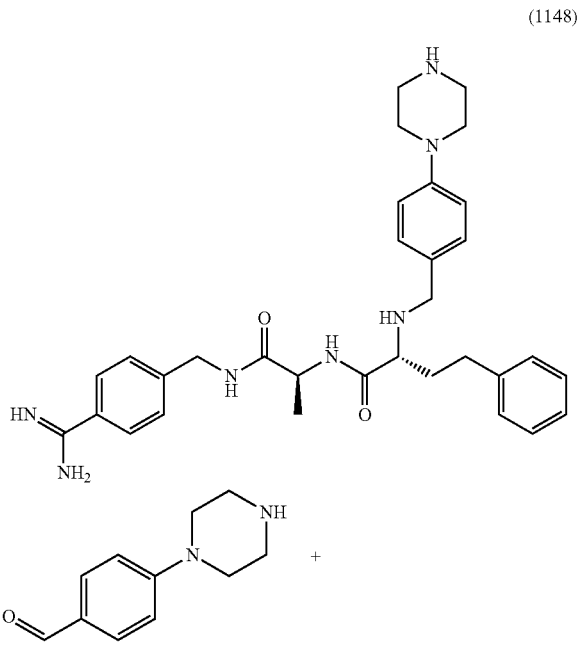

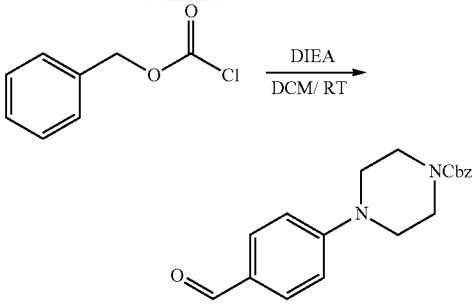

Step 1: A clear solution of 4-(piperazin-1-yl)benzaldehyde (502 mg, 2.68 mmol) in CH$_2$Cl$_2$ (10 mL) was treated with DIEA (0.900 mL, 5.17 mmol) at room temp under N$_2$ and the reaction changed to clear yellow solution. Benzyl chloroformate (0.450 mL, 3.19 mmol) was added. The reaction gradually changed to deep clear red solution. After stirring at room temp overnight, the reaction was washed with 20 mL 1 N HCl solution (2 times). The organic layer was washed with brine, dried (Na$_2$SO$_4$), vacuum filtered, and evaporated under vacuum. Purification by flash chromatography (0-100% EtOAc-hexanes) gave benzyl 4-(4-formylphenyl)piperazine-1-carboxylate (606 mg, 70% yield).

Step 2: (R)—N—((S)-1-((4-Carbamimidoylbenzyl)amino)-1-oxopropan-2-yl)-4-phenyl-2-((4-(piperazin-1-yl)benzyl)amino)butanamide (3.4 mg, 2.8% yield in 2 steps) was synthesized by a method similar to compound 1130, steps 1 and 2, except the crude product was purified by reverse phase HPLC condition (5-15-90% MeCN—H$_2$O) similar to that used for compound 1140.

Example 27: Preparation of (R)-2-((5-Aminopentyl)amino)-N—((S)-1-((4-carbamimidoylbenzyl)amino)-1-oxopropan-2-yl)-4-phenylbutanamide Trihydrochloride (1132)

(1132)

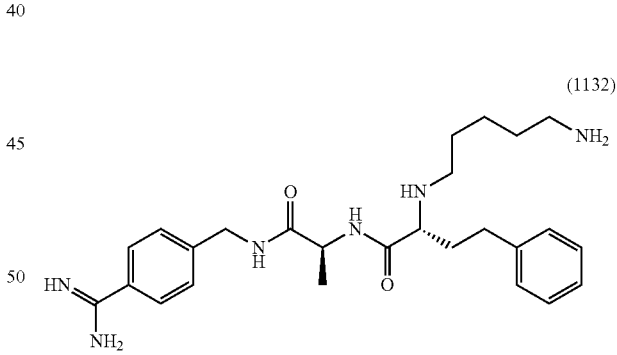

Step 1: tert-Butyl (5-(((R)-1-(((S)-1-((4-carbamimidoylbenzyl)amino)-1-oxopropan-2-yl)amino)-1-oxo-4-phenylbutan-2-yl)amino)pentyl)carbamate was synthesized by a method similar to step 1 that used for compound 1130 (461.4 mg, 63% yield).

Step 2: Benzyl ((4-(((S)-2-((R)-2-((5-aminopentyl)amino)-4-phenylbutanamido)propanamido)methyl)phenyl)(imino)methyl)carbamate (crude) was synthesized by a method similar to that used for compound 1119.

Step 3: (R)-2-((5-Aminopentyl)amino)-N—((S)-1-((4-carbamimidoylbenzyl)amino)-1-oxopropan-2-yl)-4-phenylbutanamide was synthesized by a method similar to step 2 used for compound 1130 (18.4 mg, 21% yield in 2 steps)

except the crude product was purified by reverse phase HPLC (5-45-75-90% MeCN—H₂O); (18.4 mg, 21% yield in 2 steps).

Example 28: Preparation of (R)-2-(((R)-2-Amino-3-phenylpropyl)amino)-N—((S)-1-((4-carbamimidoyl-benzyl)amino)-1-oxopropan-2-yl)-4-phenylbutana-mide, Tri-trifluoroacetate Salt (1144)

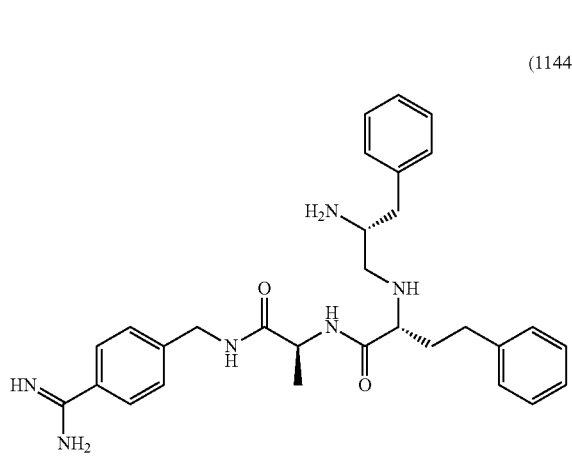 [SMILES: C[C@H](NC(=O)[C@@H](CCc1ccccc1)NC[C@H](N)Cc1ccccc1)C(=O)NCc1ccc(C(=N)N)cc1]

(1144)

(R)-2-(((R)-2-Amino-3-phenylpropyl)amino)-N—((S)-1-((4-carbamimidoylbenzyl)amino)-1-oxopropan-2-yl)-4-phenylbutanamide was synthesized by a method similar to that used for compound 1132 except the crude product was purified by reverse phase HPLC condition (5-60-90% MeCN—H₂O); (13.6 mg, 12% yield in 3 steps).

Example 29: Preparation of (S)-2-(((R)-2-Amino-4-phenylbutyl)amino)-N-(4-carbamimidoylbenzyl) propanamide Dihydrochloride (1013)

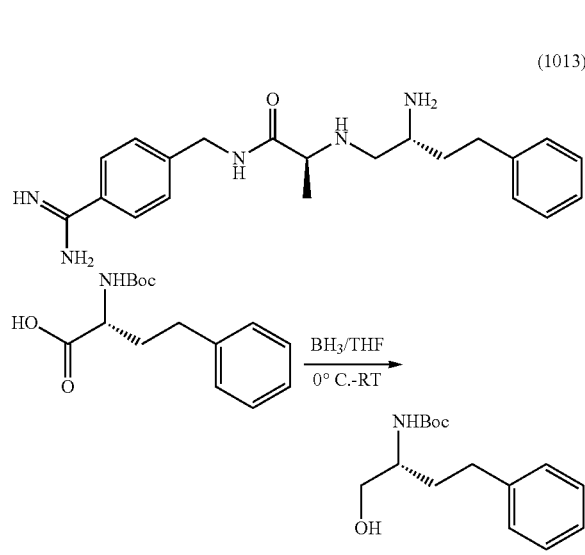

(1013)

Step 1: A solution of (R)-2-((tert-butoxycarbonyl)amino)-4-phenylbutanoic acid (694.9 mg, 2.49 mmol) in THF (1 mL) was treated with 1 M borane-tetrahydrofuran complex solution (4.2 mL, 4.2 mmol) at 0° C. in an ice bath under N₂. Gas was produced moderately. The reaction was warmed to room temp while stirring for 4 h. H₂O was added slowly via syringe. Gas was produced violently. The resulting mixture was extracted with 30 mL CH₂Cl₂ (3 times) after adding 30 mL saturated NH₄Cl solution. The organic layers were combined, dried (Na₂SO₄), vacuum filtered, and evaporated under vacuum. Purification by chromatography (0-100% EtOAc-hexanes) gave tert-butyl (R)-(1-hydroxy-4-phenylbutan-2-yl)carbamate (263.4 mg, 40% yield).

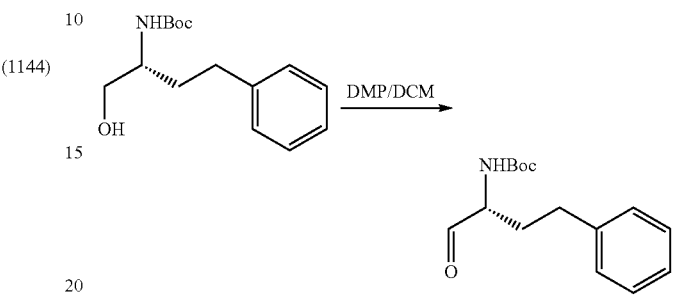

Step 2: A solution of tert-butyl (R)-(1-hydroxy-4-phenylbutan-2-yl)carbamate (263.4 mg, 0.993 mmol) in CH₂Cl₂ (17 mL) was treated with Dess-Martin periodinane (468.9 mg, 1.10 mmol, 1.1 eq) at 0° C. The reaction was stirred at the same temperature for 2.5 h. The reaction became opaque and was added to a solution of 1 M Na₂S₂O₃ (20 mL) and 1 M NaHCO₃ (20 mL) at room temp. The resulting mixture was stirred at room temp for 15 min and became colorless. The organic was separated and the aqueous layer was extracted with CH₂Cl₂ (2×20 mL). The organic layer was combined, washed once with saturated NaHCO₃ solution, dried over Na₂SO₄, vacuum filtered, and evaporated under vacuum. Purification by chromatography (0-100% EtOAc-hexanes) gave tert-butyl (R)-(1-oxo-4-phenylbutan-2-yl)carbamate (199 mg, 76%).

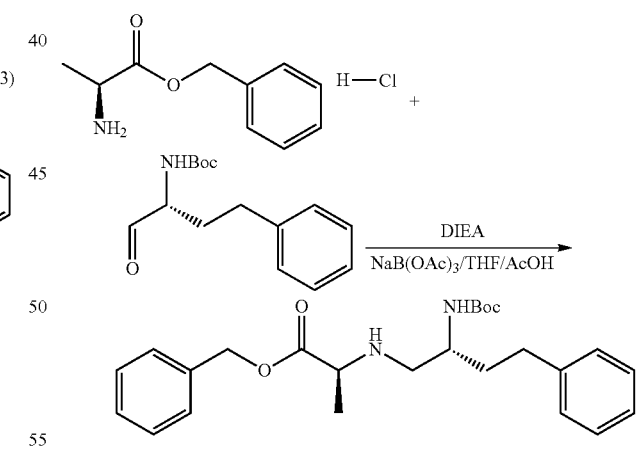

Step 3: A solution of tert-butyl (R)-(1-oxo-4-phenylbutan-2-yl)carbamate (199 mg, 0.756 mmol) in THF (1.8 mL) was treated with benzyl L-alaninate hydrochloride (102.6 mg, 0.476 mmol) followed by DIEA (240 μL, 1.38 mmol). The resulting colorless solution was treated with NaBH(OAc)₃ (148.6 mg, 0.701 mmol) and HOAc (85 μL, 1.49 mmol). After purging with N₂, the vial was capped. The reaction was stirred at room temp for 4 h and quenched with about 20 mL saturated NaHCO₃ solution. The resulting mixture was extracted with 20 mL CH₂Cl₂ (3 times). The organic layers were combined, washed with brine, dried (Na₂SO₄), vacuum filtered, and evaporated under vacuum. The crude product was dissolved in $CH_2Cl_2$ and adsorbed onto silica gel. Purification by chromatography (0-100% EtOAc-hexanes) gave benzyl ((R)-2-((tert-butoxycarbonyl)amino)-4-phenylbutyl)-L-alaninate (127 mg, 63% yield).

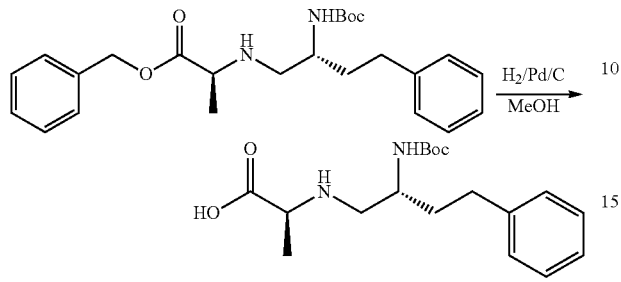

Step 4: ((R)-2-((tert-Butoxycarbonyl)amino)-4-phenylbutyl)-L-alanine (99 mg, 100% yield) was synthesized by a method similar to step 2, used for compound 1130.

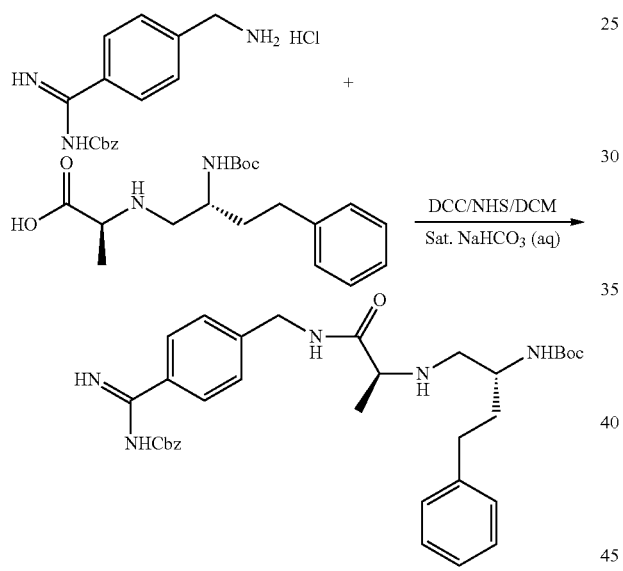

Step 5: tert-Butyl ((R)-1-(((S)-1-((4-(N-((benzyloxy)carbonyl)carbamimidoyl)benzyl)amino)-1-oxopropan-2-yl)amino)-4-phenylbutan-2-yl)carbamate (66.8 mg, 38% yield) was synthesized by a method similar to that used for compound 1119, except the crude product was purified by chromatography (10% MeOH—$CH_2Cl_2$).

Step 6: Benzyl ((4-(((S)-2-(((R)-2-amino-4-phenylbutyl)amino)propanamido)methyl)phenyl)(imino)methyl)carbamate was synthesized by a method similar to that used for compound 1119, except the crude product was purified by flash chromatography (10% MeOH—$CH_2Cl_2$ and then 5% 7 N $NH_3$ in MeOH—$CH_2Cl_2$). This procedure yielded 15.1 mg (27% yield) of material.

Step 7: (S)-2-(((R)-2-Amino-4-phenylbutyl)amino)-N-(4-carbamimidoylbenzyl)propanamide (i.e., compound 1013) was synthesized by a method similar to step 2 that used for compound 1130, except the crude product was purified by reverse phase HPLC (2-15-35-90% MeCN—$H_2O$) similar to that used for compound 1140. This procedure yielded 10.3 mg (72% yield) of material.

Example 30: Preparation of (R)-2-Amino-N—((S)-1-((5-chloro-2-hydroxybenzyl)amino)-1-oxopropan-2-yl)-4-phenylbutanamide Hydrochloride (1031)

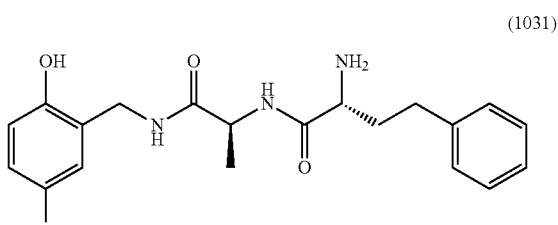

(1031)

(R)-2-Amino-N—((S)-1-((5-chloro-2-hydroxybenzyl)amino)-1-oxopropan-2-yl)-4-phenylbutanamide was prepared following similar protocols as reported for compound 1119, steps 1-4 using the appropriate starting materials.

Example 31: Preparation of (S)-1-((R)-2-Amino-4-phenylbutanoyl)-N-(5-chloro-2-hydroxybenzyl)pyrrolidine-2-carboxamide Hydrochloride (1079)

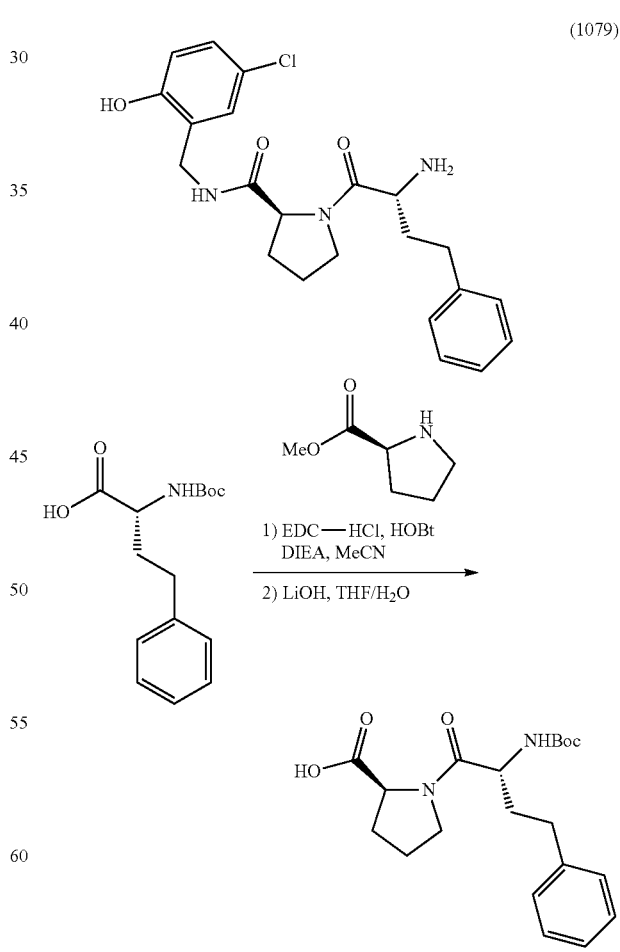

Steps 1-2: ((R)-2-((tert-Butoxycarbonyl)amino)-4-phenylbutanoyl)-L-proline was prepared following similar protocols as compound 1028, but with steps 1-2 using the appropriate starting materials.

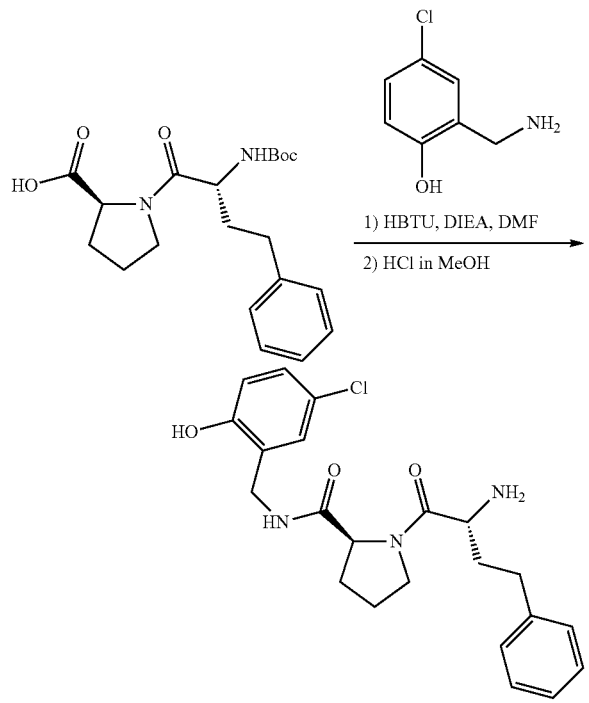

Steps 3-4: (S)-1-((R)-2-Amino-4-phenylbutanoyl)-N-(5-chloro-2-hydroxybenzyl)pyrrolidine-2-carboxamide was prepared following similar protocols as reported for compound 1060, step 2 using the appropriate starting materials.

Example 32: Preparation of (R)-2-Amino-N—((S)-1-((5-chloro-2-(2-(ethylamino)-2-oxoethoxy)benzyl)amino)-1-oxopropan-2-yl)-4-phenylbutanamide, Trifluoroacetate Salt (1137)

(1137)

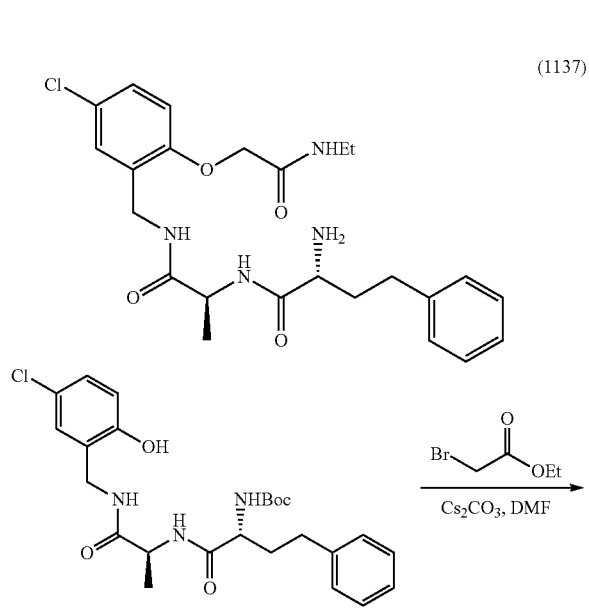

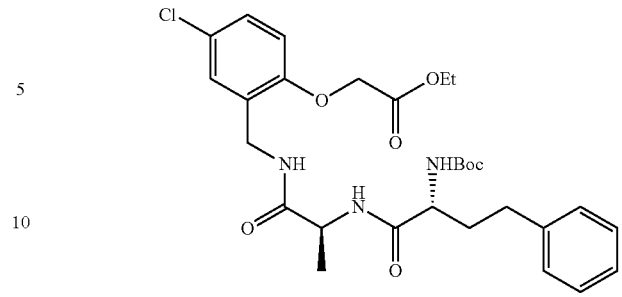

Step 1: tert-Butyl ((R)-1-(((S)-1-((5-chloro-2-hydroxybenzyl)amino)-1-oxopropan-2-yl)amino)-1-oxo-4-phenylbutan-2-yl)carbamate (436 mg, 0.89 mmol, as prepared for compound 1031) was suspended in DMF (4 mL) and treated with ethyl bromoacetate (148 μL, 1.34 mmol) and Cs₂CO₃ (725 mg, 2.23 mmol). The reaction mixture was allowed to stir for 18 h, then diluted with EtOAc and washed with H₂O, 5% aqueous LiCl and brine. The organic layer was dried over MgSO₄ and concentrated under vacuum, then purified by chromatography (40-80% EtOAc-hexanes) to yield ethyl 2-(4-chloro-2-((4S,7R)-4,11,11-trimethyl-3,6,9-trioxo-7-phenethyl-10-oxa-2,5,8-triazadodecyl)phenoxy)acetate as a white powder (370 mg, 72% yield).

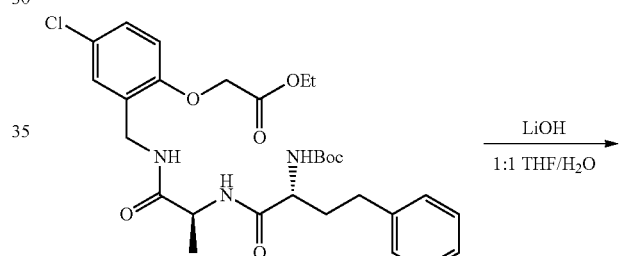

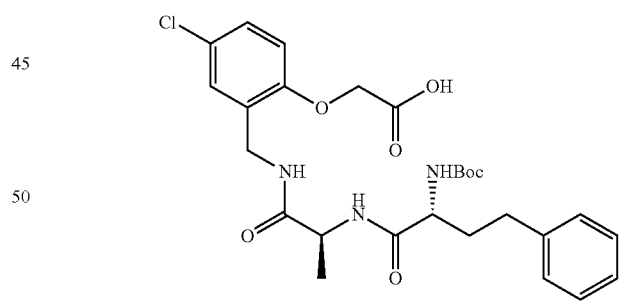

Step 2: A reaction vessel was charged with ethyl 2-(4-chloro-2-((4S,7R)-4,11,11-trimethyl-3,6,9-trioxo-7-phenethyl-10-oxa-2,5,8-triazadodecyl)phenoxy)acetate (370 mg, 0.64 mmol), LiOH (31 mg, 1.28 mmol), THF (3 mL) and H₂O (3 mL). The reaction mixture was allowed to stir at room temp for 4 h, then THF was removed under vacuum and the residue was treated with 10% aq. KHSO₄ (3 mL). The resulting ppt was filtered and washed with water and hexanes to provide 2-(4-chloro-2-((4S,7R)-4,11,11-trimethyl-3,6,9-trioxo-7-phenethyl-10-oxa-2,5,8-triazadodecyl)phenoxy)acetic acid as a white solid (281 mg, 80% yield).

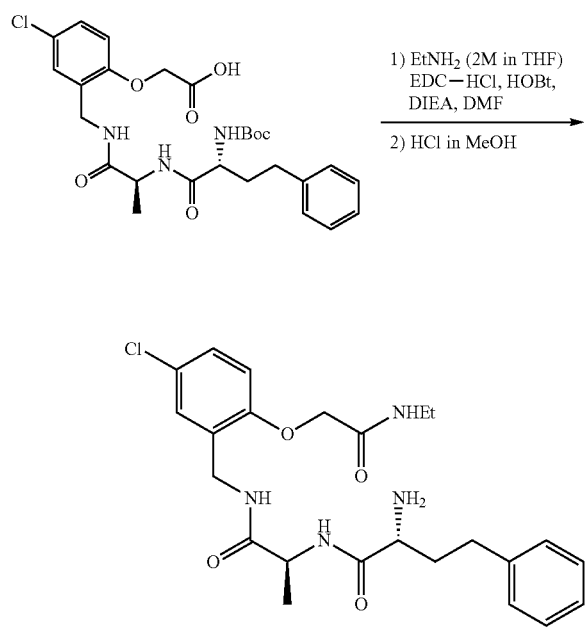

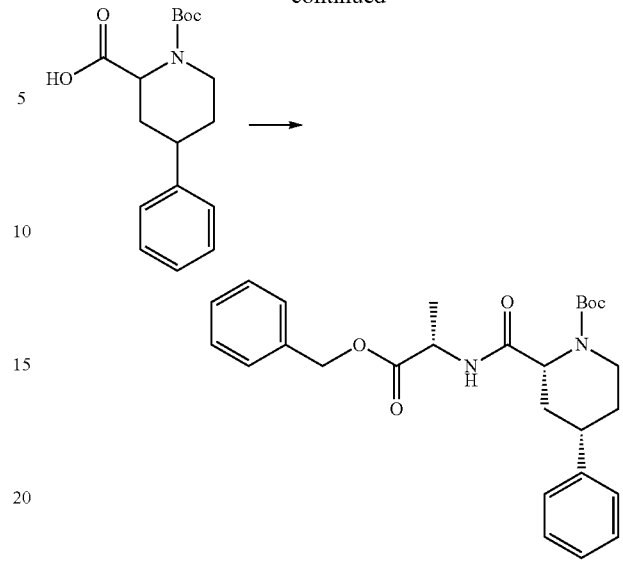

Steps 3-4: 2-(4-Chloro-2-((4S,7R)-4,11,11-trimethyl-3,6,9-trioxo-7-phenethyl-10-oxa-2,5,8-triazadodecyl)phenoxy)acetic acid (24 mg, 0.04 mmol) and HOBt (5.9 mg, 0.044 mmol) were dissolved in DMF (1 mL). EDC (8.4 mg, 0.044 mmol) was then added in a single portion, followed by ethylamine (2 M in THF, 150 μL) and DIEA (21 μL, 0.12 mmol). The resulting solution was allowed to stir at room temp for 60 h. The reaction mixture was then diluted with EtOAc, washed with 10% aqueous KHSO$_4$, 5% aqueous LiCl, saturated NaHCO$_3$ (×2) and brine. The crude mixture was treated with HCl in MeOH and filtered through diatomaceous earth, then purified by preparative HPLC (5% to 95% MeCN in H$_2$O containing 0.1% TFA) to provide (R)-2-amino-N—((S)-1-((5-chloro-2-(2-(ethylamino)-2-oxoethoxy)benzyl)amino)-1-oxopropan-2-yl)-4-phenylbutanamide as a white solid (2.4 mg, 11% yield).

Example 33. Preparation of (2R,4S)—N—((S)-1-((4-Carbamimidoylbenzyl)amino)-1-oxopropan-2-yl)-4-phenylpiperidine-2-carboxamide Dihydrochloride (1230)

(1230)

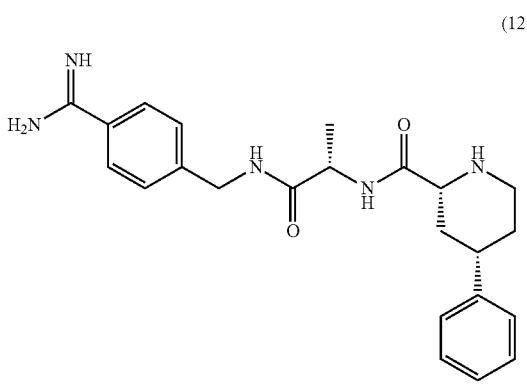

Step 1: To a solution of (2R,4S)-1-(tert-butoxycarbonyl)-4-phenylpiperidine-2-carboxylic acid (5.0 g, 16.4 mmol) in MeCN (300 mL, 0.05 M) was added HOBt (2.g, 3.77 mmol), DIEA (11.4 mL, 13.7 mmol), and EDC (2.8 g, 3.77 mmol). After stirring for 30 min at room temperature, benzyl L-alanine hydrochloride (814 mg, 18 mmol) was added and stirred for 16 h. The reaction mixture was conc in vacuo and the residue was partitioned with EtOAc and 10% KHSO$_4$ solution. The organic layer was separated and washed with H$_2$O and saturated aq NaHCO$_3$. The organic layer was dried over anhyd Na$_2$SO$_4$ and conc under vacuum. The residue was purified by chromatography (0-20% EtOAc-hexanes; the 3$^{rd}$ UVActive material eluting from the column) to give tert-butyl (2R,4S)-2-(((S)-1-(benzyloxy)-1-oxopropan-2-yl)carbamoyl)-4-phenylpiperidine-1-carboxylate (2.59 g, 34% yield).

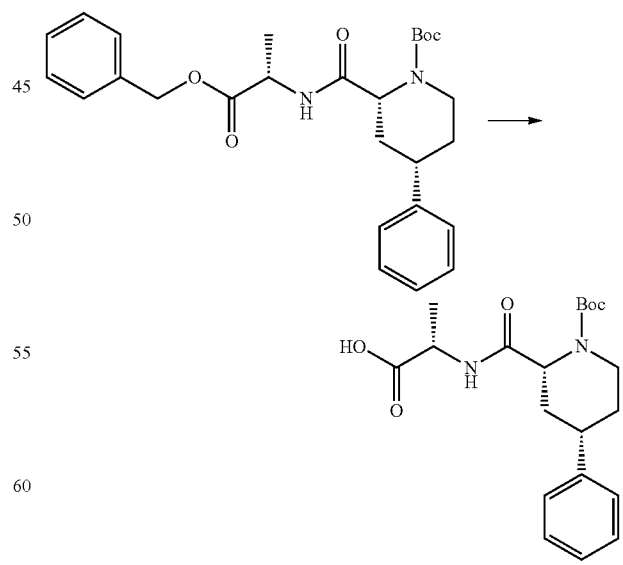

Step 2: A solution of tert-butyl (2R,4S)-2-(((S)-1-(benzyloxy)-1-oxopropan-2-yl)carbamoyl)-4-phenylpiperidine-1-carboxylate (2.59 mg, 5.54 mmol) was degassed with a stream of Ar for 2 min. 10% Pd/C (130 mg) was added and a vacuum was pulled for 1 min. A balloon of H₂ was added and the reaction was monitored for the consumption of starting material for 1.5 h. The catalyst was removed by filtration and the solution was evaporated to give ((2R,4S)-1-(tert-butoxycarbonyl)-4-phenylpiperidine-2-carbonyl)-L-alanine (1.8 g, 86%).

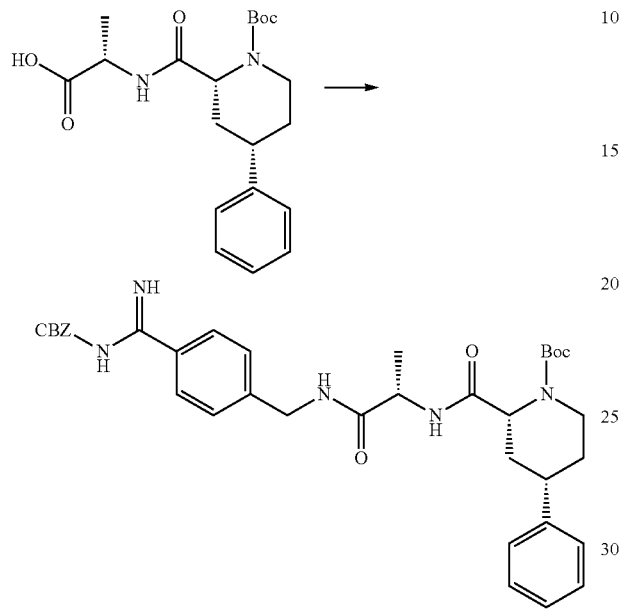

Step 3: tert-Butyl (2R,4S)-2-(((S)-1-((4-(N-((benzyloxy)carbonyl)carbamimidoyl)benzyl)amino)-1-oxopropan-2-yl)carbamoyl)-4-phenylpiperidine-1-carboxylate was synthesized according to the procedure for compound 0194.

Step 4: Benzyl (imino(4-(((S)-2-((2R,4S)-4-phenylpiperidine-2-carboxamido)propanamido)methyl)phenyl)methyl)

carbamate hydrochloride was synthesized according to the procedure for compound 0195.

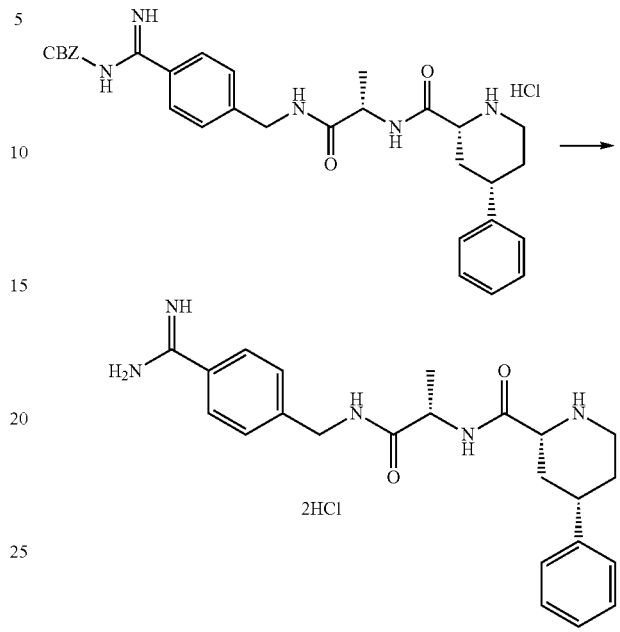

Step 5: (2R,4S)—N—((S)-1-((4-carbamimidoylbenzyl)amino)-1-oxopropan-2-yl)-4-phenylpiperidine-2-carboxamide dihydrochloride was synthesized according to the procedure for compound 0196.

Example 34. Preparation of (2R,4S)—N—((S)-1-((4-Carbamimidoylbenzyl)amino)-1-oxopropan-2-yl)-4-(m-tolyl)piperidine-2-carboxamide Dihydrochloride (1231)

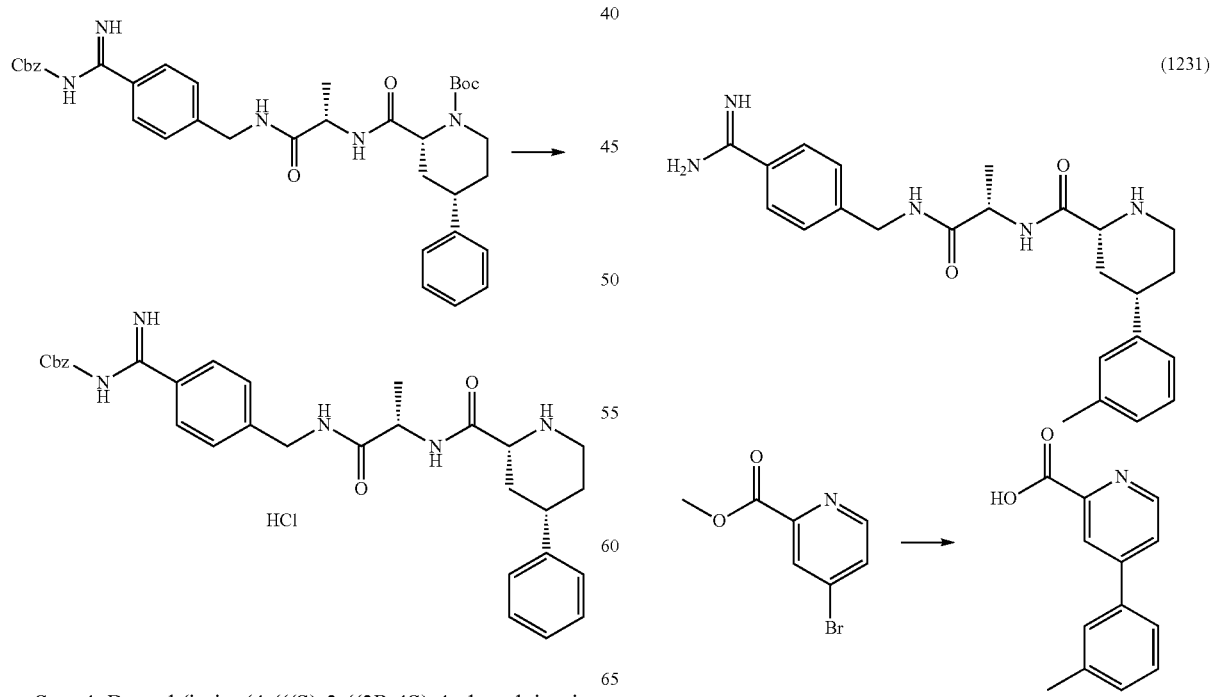

Step 1: To a solution of dioxane: 2 M K$_2$CO$_3$ (1:1, 116 ml total) was added methyl 4-bromopicolinate 10.0 g (46.29 mmol) and m-tolylboronic acid (55.6 mmol, 1.2 eq.). The solution was degassed with a stream of Ar for 5 min. Pd(PPh$_3$)$_4$ (0.05 eq.) was added and the solution was refluxed for 48 h. Dioxane was removed by evaporation followed by the addition of H$_2$O (50 ml) and EtOAc (100 ml) with stirring. The aqueous layer was separated, and the pH adjusted to approx. 5 with the addition of solid KHSO$_4$. The product was collected by filtration, washed with H$_2$O and dried giving 4-(m-tolyl)picolinic acid (9.07 g, 92% yield).

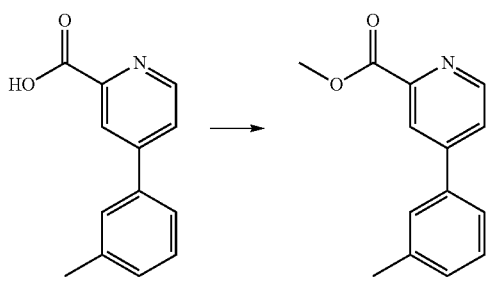 [SMILES: Cc1cccc(-c2ccnc(C(=O)O)c2)c1 ; COC(=O)c1cc(-c2cccc(C)c2)ccn1]

Step 2: To a solution of 4-(m-tolyl)picolinic acid (9.05 g., 42.4 mmol) in anhyd MeOH (50 ml) was added H$_2$SO$_4$ (5 ml) with refluxing for 24 h. MeOH was removed by evaporation and the residue partitioned between sat. NaHCO$_3$ and CH$_2$Cl$_2$. The organic layer was dried over Na$_2$SO$_4$ and evaporated. Column chrom. (40% EtOAc/hexanes) gave methyl 4-(m-tolyl)picolinate (6.05 g, 63% yield) as a yellow oil.

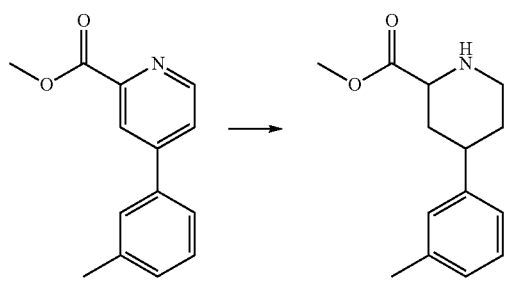 [SMILES: COC(=O)c1cc(-c2cccc(C)c2)ccn1 ; COC(=O)C1CC(c2cccc(C)c2)CCN1]

Step 3: To a solution of acetic acid (40 ml) was added methyl 4-(m-tolyl)picolinate (2.4 g, 10.6 mmol) with degassing with Ar for 2 min. PtO$_2$ (240 mg) was added and a vacuum pulled for 5 min. A balloon of H$_2$ was added with stirring for 26 h. The catalyst was removed by filtration followed by evaporation. Purification by chromatography (1% MeOH—CH$_2$Cl$_2$) gave methyl 4-(m-tolyl)piperidine-2-carboxylate (1.6 g, 65% yield) as an oil.

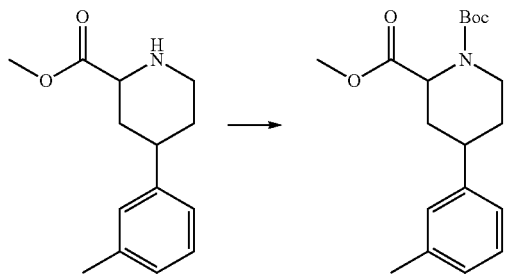 [SMILES: COC(=O)C1CC(c2cccc(C)c2)CCN1 ; COC(=O)C1CC(c2cccc(C)c2)CCN1C(=O)OC(C)(C)C]

Step 4: To a solution of THF-sat. NaHCO$_3$ (1:1, 35 ml total) was added methyl 4-(m-tolyl)piperidine-2-carboxylate (1.6 g, 6.9 mmol) and di-tert-butyl dicarbonate (1.05 equiv, 7.25 mmol) with stirring overnight. THF was removed by evaporation with extraction with CH$_2$Cl$_2$ (2×30 ml). The organic layer was dried over Na$_2$SO$_4$ and evaporated to dryness. 1-(tert-Butyl) 2-methyl 4-(m-tolyl)piperidine-1,2-dicarboxylate (2.34 g, 100% yield) was used in the next step.

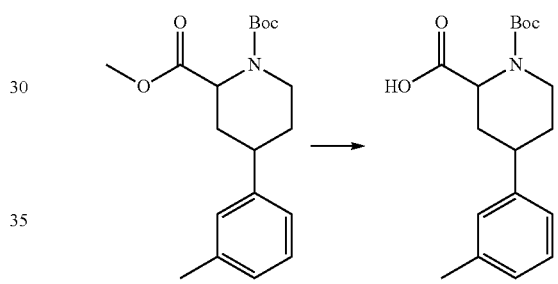

Step 5: To a solution of THF-H$_2$O (1:1, 30 ml) was added 1-(tert-butyl) 2-methyl 4-(m-tolyl)piperidine-1,2-dicarboxylate (2.34 g, 7.0 mmol) and LiOH (35.0 mmol, 5.0 equiv.) with stirring for 6 h. THF was removed by evaporation and the pH adjusted to 5 with 10% KHSO$_4$. The product was collected by filtration, washed with H$_2$O and dried. 1-(tert-Butoxycarbonyl)-4-(m-tolyl)piperidine-2-carboxylic acid (1.81 g, 81% yield) as a pale yellow solid.

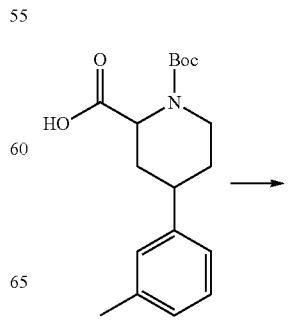

-continued

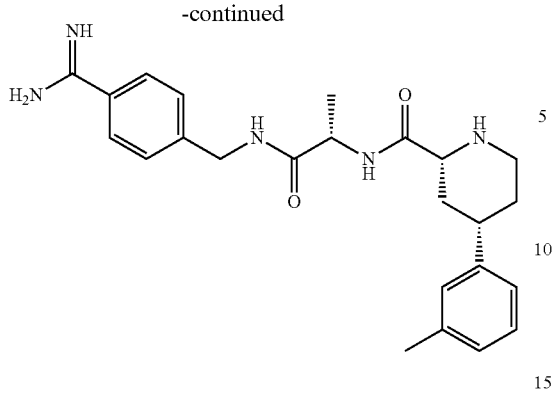

Steps 6-11: (2R,4S)—N—((S)-1-((4-carbamimidoylbenzyl)amino)-1-oxopropan-2-yl)-4-(m-tolyl)piperidine-2-carboxamide was synthesized according to the procedures for compound (1230). The third UVActive material eluting from the column in step 6 was carried forward.

Example 35. Preparation of (R)—N—((S)-1-((4-Carbamimidoylbenzyl)amino)-1-oxopropan-2-yl)-2-((2-(4-methylpiperazin-1-yl)benzyl)amino)-4-phenylbutanamide Di-trifluoroacetate salt (1232)

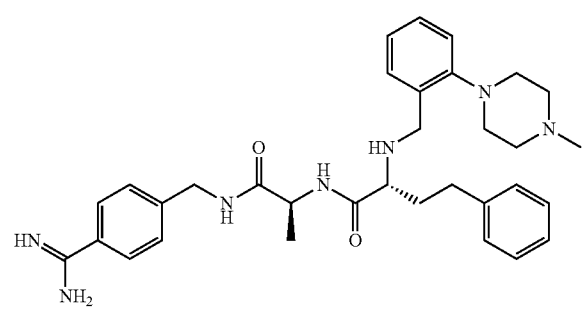

(1232)

Step 1: Benzyl (imino(4-(((S)-2-((R)-2-((2-(4-methylpiperazin-1-yl)benzyl)amino)-4-phenylbutanamido)propanamido)methyl)phenyl)methyl)carbamate was synthesized according to the procedure for compound 1130, step 2.

Step 2: Deprotection of benzyl (imino(4-(((S)-2-((R)-2-((2-(4-methylpiperazin-1-yl)benzyl)amino)-4-phenylbutanamido)propanamido)methyl)phenyl)methyl)carbamate according to the procedure for compound 1130, step 3 afforded (R)—N—((S)-1-((4-carbamimidoylbenzyl)amino)-1-oxopropan-2-yl)-2-((2-(4-methylpiperazin-1-yl)benzyl)amino)-4-phenylbutanamide.

Step 3: (R)—N—((S)-1-((4-Carbamimidoylbenzyl)amino)-1-oxopropan-2-yl)-2-((2-(4-methylpiperazin-1-yl)benzyl)amino)-4-phenylbutanamide di-trifluoroacetate salt was formed according to the procedure for compound (1368), step 2.

Example 36. Preparation of (R)-2-((4-(1H-Tetrazol-5-yl)benzyl)amino)-N—((S)-1-((4-carbamimidoylbenzyl)amino)-1-oxopropan-2-yl)-4-phenylbutanamide Di-trifluoroacetate salt (1233)

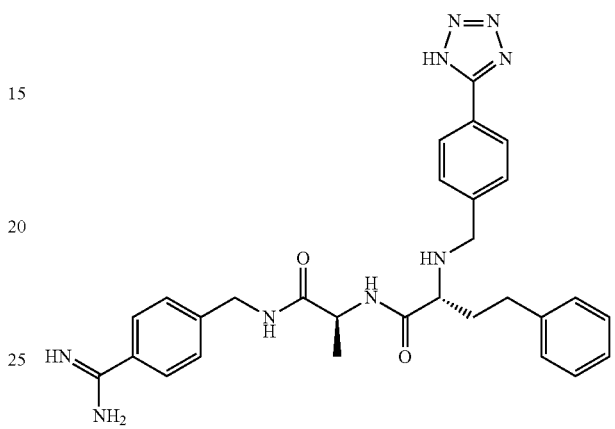

(1233)

Step 1: Benzyl ((4-(((S)-2-((R)-2-((4-(1H-tetrazol-5-yl)benzyl)amino)-4-phenylbutanamido)propanamido)methyl)phenyl)(imino)methyl)carbamate was synthesized according to the procedure for compound 1130, step 2.

Step 2: Deprotection of benzyl ((4-(((S)-2-((R)-2-((4-(1H-tetrazol-5-yl)benzyl)amino)-4-phenylbutanamido)propanamido)methyl)phenyl)(imino)methyl)carbamate according to the procedure for compound 1130, step 3. Purification by reverse phase HPLC (5-75-90% MeCN—H₂O) afforded (R)-2-((4-(1H-tetrazol-5-yl)benzyl)amino)-N—((S)-1-((4-carbamimidoylbenzyl)amino)-1-oxopropan-2-yl)-4-phenylbutanamide di-trifluoroacetate salt.

Example 37. Preparation of (S)—N-(1-((4-Carbamimidoylbenzyl)amino)-1-oxopropan-2-yl)-4-(naphthalen-1-yl)-1H-pyrrole-2-carboxamide (1234)

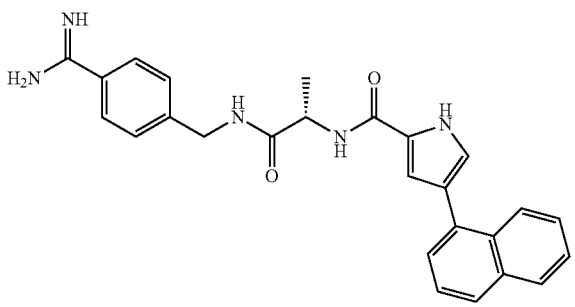

(1234)

367

-continued

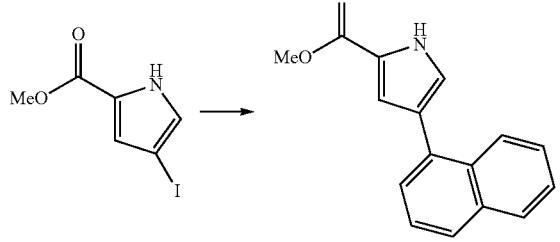

Step 1: In a 50 mL round bottom flask equipped with a stir bar and septum was added methyl 4-iodo-1H-pyrrole-2-carboxylate (300 mg, 1.19 mmol), 1-naphthyl boronic acid (246 mg, 1.43), Pd(OAc)$_2$ (13 mg, 0.06 mmol), potassium carbonate (330 mg, 2.39 mmol), acetone (2.7 mL) and water (1.3 mL). The resulting mixture was degassed by bubbling N$_2$ through the solution for 5 min. The reaction was then heated to 75° C. for 5 h. Upon cooling to room temperature, the reaction solution was filtered through diatomaceous earth, eluted with EtOAc, concentrated and purified by chromatography using EtOAc-hexanes to afford methyl 4-(naphthalen-1-yl)-1H-pyrrole-2-carboxylate (260 mg, 86% yield) as a colorless solid.

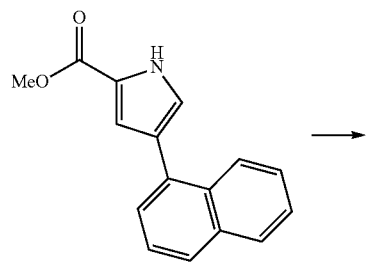

Step 2: 4-(Naphthalen-1-yl)-1H-pyrrole-2-carboxylic acid (180 mg, 82%) was synthesized from methyl 4-(naphthalen-1-yl)-1H-pyrrole-2-carboxylate (260 mg, 1.03 mmol) according to the procedure for compound (1328), step 1.

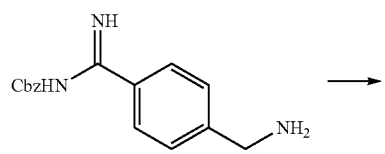

368

-continued

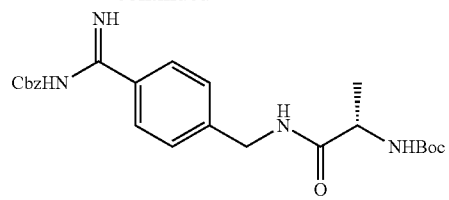

Step 3: To a solution of (tert-butoxycarbonyl)-L-alanine (300 mg, 1.58 mmol) in CH$_2$Cl$_2$ (11 mL) was added NHS (200 mg, 1.74 mmol) with stirring at ambient temperature until dissolution. DCC (359 mg, 1.74 mmol) was added and stirred for 1.0 h. This mixture was poured into a separatory funnel containing sat. NaHCO$_3$ (10 mL), and benzyl ((4-(aminomethyl)phenyl)(imino)methyl)carbamate hydrochloride (540 mg, 1.90 mmol) and then shaken for 5 min. The organic layer was filtered over a bed of anhyd Na$_2$SO$_4$ and evaporated to dryness. Flash chromatography using EtOAc-hexanes gave tert-butyl (S)-(1-((4-(N-((benzyloxy)carbonyl)carbamimidoyl)benzyl)amino)-1-oxopropan-2-yl)carbamate as a solid (560 mg, 80% yield).

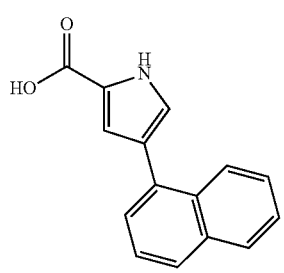

Step 4: Benzyl (S)-((4-((2-aminopropanamido)methyl)phenyl)(imino)methyl)carbamate hydrochloride (380 mg, 90%) was synthesized from tert-butyl (S)-(1-((4-(N-((benzyloxy)carbonyl)carbamimidoyl)benzyl)amino)-1-oxopropan-2-yl)carbamate (560 mg, 1.23 mmol) according to the procedure for compound (1304), step 6.

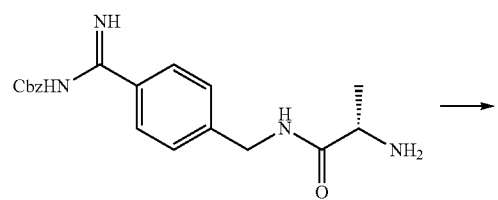

-continued

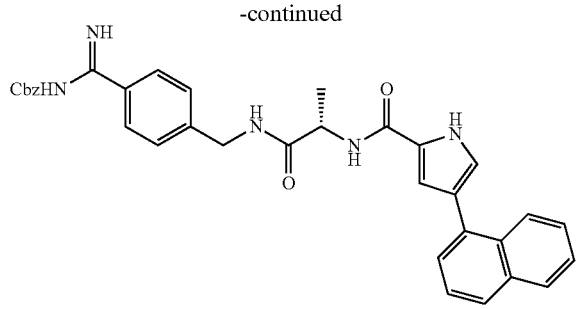

Step 5: Benzyl (S)-(imino(4-((2-(4-(naphthalen-1-yl)-1H-pyrrole-2-carboxamido)propanamido)methyl)phenyl)methyl)carbamate (35 mg, 45% yield) was synthesized from benzyl (S)-((4-((2-aminopropanamido)methyl)phenyl)(imino)methyl)carbamate hydrochloride (60 mg, 0.17 mmol) according to the procedure for compound (1304), step 7.

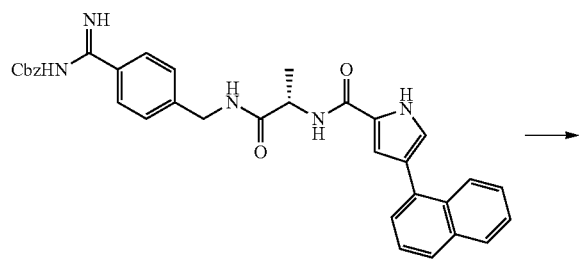 →

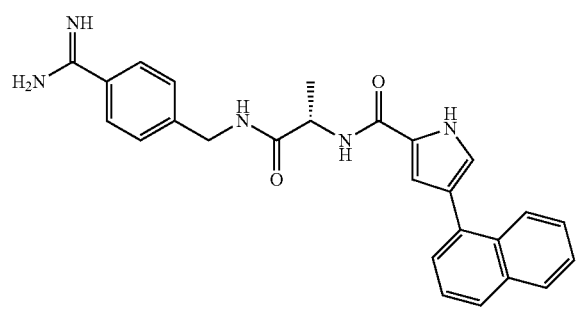

Step 6: (S)—N-(1-((4-Carbamimidoylbenzyl)amino)-1-oxopropan-2-yl)-4-(naphthalen-1-yl)-1H-pyrrole-2-carboxamide (25.3 mg, 94% yield) was synthesized from benzyl (S)-(imino(4-((2-(4-(naphthalen-1-yl)-1H-pyrrole-2-carboxamido)propanamido)methyl)phenyl)methyl)carbamate (35 mg, 0.06 mmol) according to the procedure for compound (1304), step 4.

Example 38. Preparation of (S)—N-(1-((4-Carbamimidoylbenzyl)amino)-1-oxopropan-2-yl)-4-(3-fluoro-4-methylphenyl)-1H-pyrrole-2-carboxamide (1235)

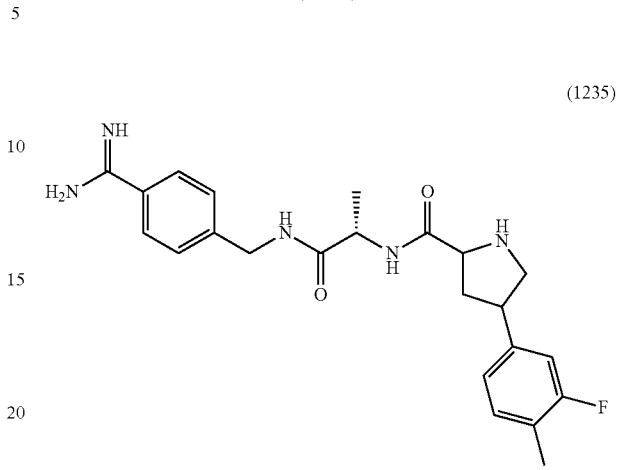

(S)—N-(1-((4-Carbamimidoylbenzyl)amino)-1-oxopropan-2-yl)-4-(3-fluoro-4-methylphenyl)-1H-pyrrole-2-carboxamide was synthesized according to the procedures for compound (1234).

Example 39. Preparation of (R)—N—((S)-1-((4-Carbamimidoylbenzyl)amino)-1-oxopropan-2-yl)-2-((4-(2-hydroxyethoxy)benzyl)amino)-4-phenylbutanamide Di-trifluoroacetate salt (1236)

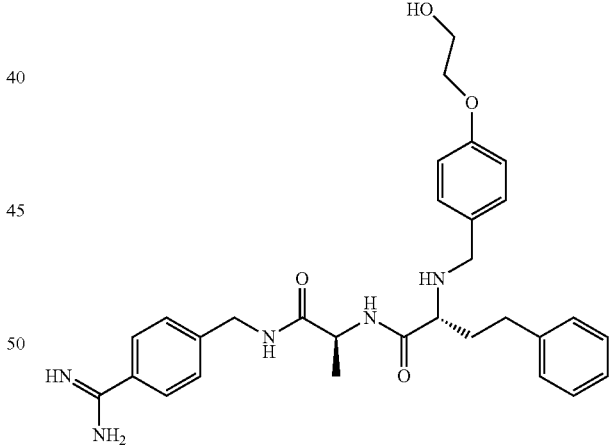

Step 1: Benzyl ((4-(((S)-2-((R)-2-((4-(2-hydroxyethoxy)benzyl)amino)-4-phenylbutanamido)propanamido)methyl)phenyl)(imino)methyl)carbamate was synthesized according to the procedure for compound 1130, step 2.

Step 2: Deprotection of benzyl ((4-(((S)-2-((R)-2-((4-(2-hydroxyethoxy)benzyl)amino)-4-phenylbutanamido)propanamido)methyl)phenyl)(imino)methyl)carbamate according to the procedure for compound 1130, step 3. Purification by reverse phase HPLC (5-75-90% MeCN—H$_2$O) afforded (R)—N—((S)-1-((4-carbamimidoylbenzyl)amino)-1-oxopropan-2-yl)-2-((4-(2-hydroxyethoxy)benzyl)amino)-4-phenylbutanamide di-trifluoroacetate salt.

Example 40. Preparation of (R)-2-amino-N—((S)-1-((5-chloro-2-(2-((3-hydroxypropyl)amino)-2-oxoethoxy)benzyl)amino)-1-oxopropan-2-yl)-4-phenylbutanamide Hydrochloride (1237)

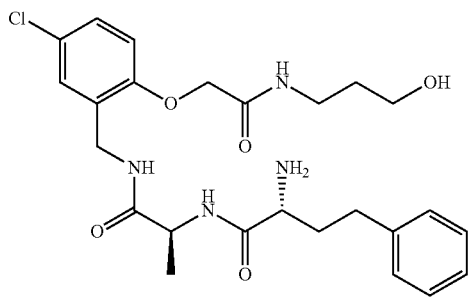

(1237)

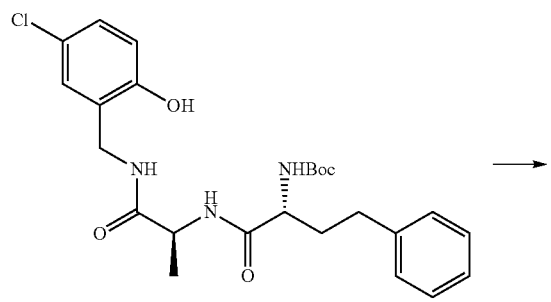

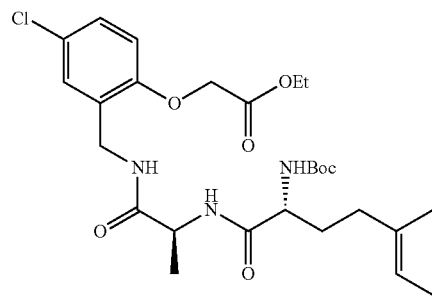

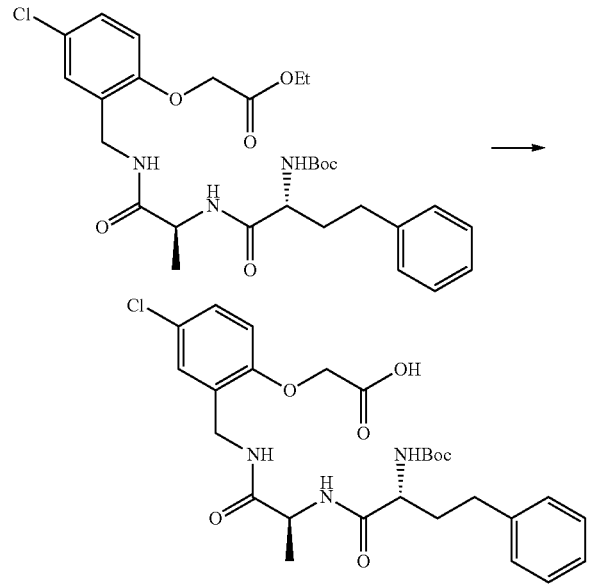

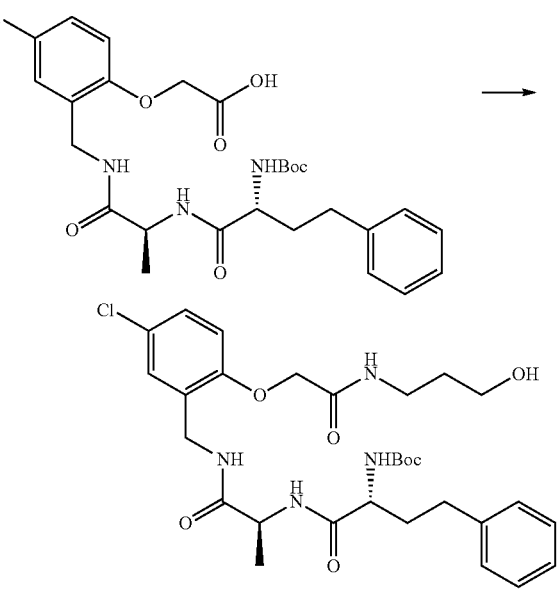

Step 1: tert-Butyl ((R)-1-(((S)-1-((5-chloro-2-hydroxybenzyl)amino)-1-oxopropan-2-yl)amino)-1-oxo-4-phenylbutan-2-yl)carbamate (436 mg, 0.89 mmol, as prepared for compound 1031) was suspended in DMF (4 mL) and treated with ethyl bromoacetate (148 μL, 1.34 mmol) and Cs$_2$CO$_3$ (725 mg, 2.23 mmol). The reaction mixture was allowed to stir for 18 h, then diluted with EtOAc and washed with H$_2$O, 5% aqueous LiCl and brine. The organic layer was dried over MgSO$_4$ and concentrated under vacuum, then purified by chromatography (40-80% EtOAc-hexanes) to yield ethyl 2-(4-chloro-2-((4S,7R)-4,11,11-trimethyl-3,6,9-trioxo-7-phenethyl-10-oxa-2,5,8-triazadodecyl)phenoxy)acetate as a white powder (370 mg, 72% yield).

Step 2: A reaction vessel was charged with ethyl 2-(4-chloro-2-((4S,7R)-4,11,11-trimethyl-3,6,9-trioxo-7-phenethyl-10-oxa-2,5,8-triazadodecyl)phenoxy)acetate (370 mg, 0.64 mmol), LiOH (31 mg, 1.28 mmol), THF (3 mL) and H$_2$O (3 mL). The reaction mixture was allowed to stir at room temp for 4 h, then THF was removed under vacuum and the residue was treated with 10% aq. KHSO$_4$ (3 mL). The resulting ppt was filtered and washed with water and hexanes to provide 2-(4-chloro-2-((4S,7R)-4,11,11-trimethyl-3,6,9-trioxo-7-phenethyl-10-oxa-2,5,8-triazadodecyl)phenoxy)acetic acid as a white solid (281 mg, 80% yield).

Step 3: 2-(4-Chloro-2-((4S,7R)-4,11,11-trimethyl-3,6,9-trioxo-7-phenethyl-10-oxa-2,5,8-triazadodecyl)phenoxy)acetic acid (51 mg, 0.09 mmol) and NHS (14 mg) were dissolved in ACN (1 mL). DCC (14 mg, 0.1 mmol) was then added in a single portion, followed by 3-aminopropan-1-ol (22 μL, 0.29 mmol) and DIEA (47 μL, 0.27 mmol). The resulting solution was allowed to stir at room temp for 16 h. The reaction mixture was then diluted with EtOAc, washed with 10% aq KHSO₄, brine and sat. aq NaHCO₃. The organic layer was dried over Na₂SO₄ and concentrated under vacuum, then purified by chromatography (7-9% MeOH—CH₂Cl₂) to yield tert-butyl ((R)-1-(((S)-1-((5-chloro-2-(2-((3-hydroxypropyl)amino)-2-oxoethoxy)benzyl)amino)-1-oxopropan-2-yl)amino)-1-oxo-4-phenylbutan-2-yl) carbamate as a colorless oil (25 mg, 44% yield).

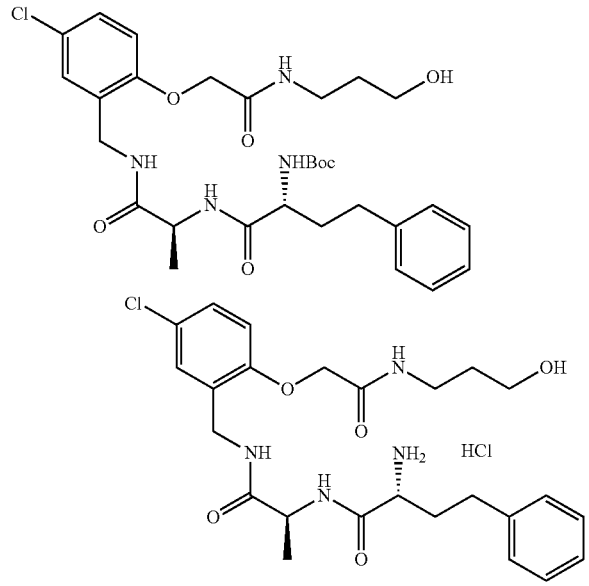

Step 4: ((R)-1-(((S)-1-((5-Chloro-2-(2-((3-hydroxypropyl)amino)-2-oxoethoxy)benzyl)amino)-1-oxopropan-2-yl)amino)-1-oxo-4-phenylbutan-2-yl)carbamate carbamate was deprotected according to the procedure for compound 1119, step 4 to provide the title compound as a white solid (21 mg, 95% yield).

Example 41. Preparation of (S)—N-(1-((4-Carbamimidoylbenzyl)amino)-1-oxopropan-2-yl)-4-(4-methoxyphenyl)-1H-pyrrole-2-carboxamide Trifluoroacetate salt (1238)

(1238)

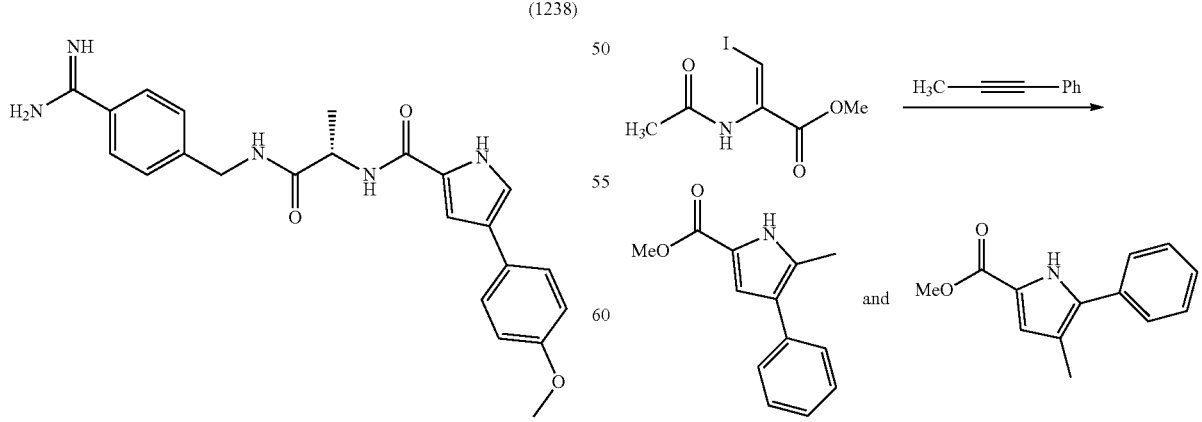

(S)—N-(1-((4-Carbamimidoylbenzyl)amino)-1-oxopropan-2-yl)-4-(4-methoxyphenyl)-1H-pyrrole-2-carboxamide trifluoroacetate salt was synthesized according to the procedures for compound (1234), except that the final product was purified using reverse-phase HPLC.

Example 42. Preparation of (S)—N-(1-((4-Carbamimidoylbenzyl)amino)-1-oxopropan-2-yl)-5-methyl-4-phenyl-1H-pyrrole-2-carboxamide Trifluoroacetate salt (1239)

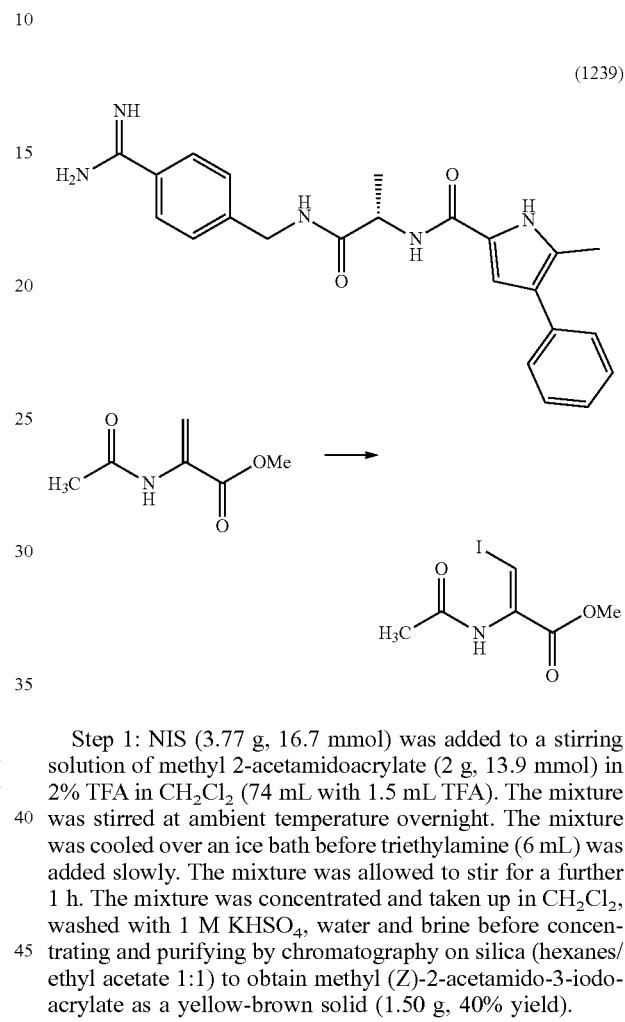

Step 1: NIS (3.77 g, 16.7 mmol) was added to a stirring solution of methyl 2-acetamidoacrylate (2 g, 13.9 mmol) in 2% TFA in CH₂Cl₂ (74 mL with 1.5 mL TFA). The mixture was stirred at ambient temperature overnight. The mixture was cooled over an ice bath before triethylamine (6 mL) was added slowly. The mixture was allowed to stir for a further 1 h. The mixture was concentrated and taken up in CH₂Cl₂, washed with 1 M KHSO₄, water and brine before concentrating and purifying by chromatography on silica (hexanes/ethyl acetate 1:1) to obtain methyl (Z)-2-acetamido-3-iodoacrylate as a yellow-brown solid (1.50 g, 40% yield).

Step 2: Methyl (Z)-2-acetamido-3-iodoacrylate (500 mg, 1.86 mmol), LiCl (78.4 mg, 1.86 mmol), K₂CO₃ (1.28 g, 9.29 mmol) and Pd(OAc)$_2$ (42 mg, 0.18 mmol) were dissolved in DMF (18 mL) and treated with the prop-1-yn-1-ylbenzene (648 mg, 5.57 mmol). The solution was degassed, placed under Argon atmosphere, and heated to 65° C. with stirring for 12 h. The solution was filtered to remove solids, diluted with EtOAc (50 mL), washed with water (25 mL), brine (25 mL), and the organic layer dried over Na$_2$SO$_4$. After conc in vacuo, chromatography (EtOAc-hexanes) afforded methyl 5-methyl-4-phenyl-1H-pyrrole-2-carboxylate (85 mg, 30% yield) and by-product (75 mg, 25% yield).

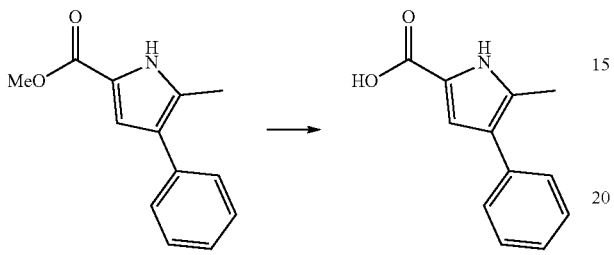

Step 3: 5-Methyl-4-phenyl-1H-pyrrole-2-carboxylic acid (40 mg, 85% yield) was synthesized from methyl 5-methyl-4-phenyl-1H-pyrrole-2-carboxylate (45 mg, 0.21 mmol) according to the procedure for compound (1328), step 1.

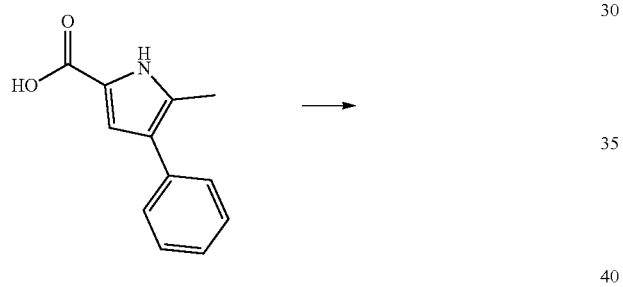

TFA

Step 4: (S)—N-(1-((4-Carbamimidoylbenzyl)amino)-1-oxopropan-2-yl)-5-methyl-4-phenyl-1H-pyrrole-2-carboxamide trifluoroacetate salt was synthesized according to the procedures for compound (1234), step 5 to step 6, except that the final product was purified using reverse-phase HPLC.

Example 43. Preparation of (S)—N-(1-((4-Carbamimidoylbenzyl)amino)-1-oxopropan-2-yl)-4,5-diphenyl-1H-pyrrole-2-carboxamide (1240)

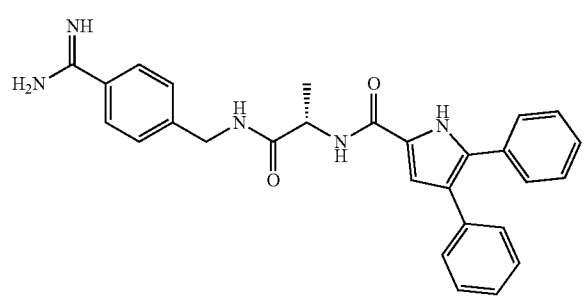

(1240)

(S)—N-(1-((4-Carbamimidoylbenzyl)amino)-1-oxopropan-2-yl)-4,5-diphenyl-1H-pyrrole-2-carboxamide was synthesized according to the procedures for compound (1239).

Example 44. Preparation of (2R,4R)—N—((S)-1-((4-Carbamimidoylbenzyl)amino)-1-oxopropan-2-yl)-4-(m-tolyl)piperidine-2-carboxamide Dihydrochloride (1241)

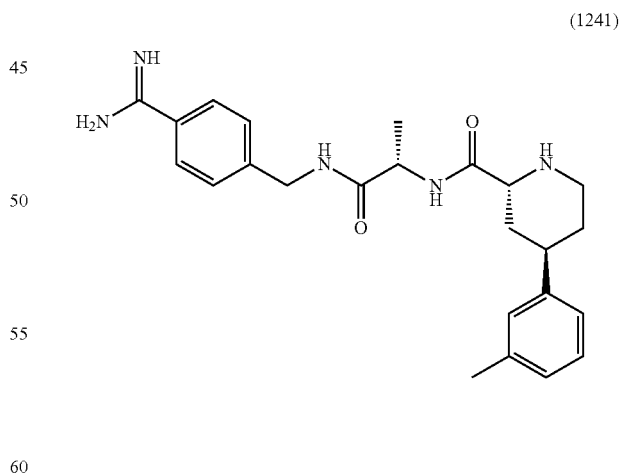

(1241)

(2R,4R)—N—((S)-1-((4-Carbamimidoylbenzyl)amino)-1-oxopropan-2-yl)-4-(m-tolyl)piperidine-2-carboxamide was synthesized according to the procedures for compound (1231) (9). The first UVActive material eluting from the column in step 6 was carried forward.

Example 45. Preparation of (2R,4R)—N—((S)-1-((5-Chloro-2-hydroxybenzyl)amino)-1-oxopropan-2-yl)-4-phenylpyrrolidine-2-carboxamide (1242)

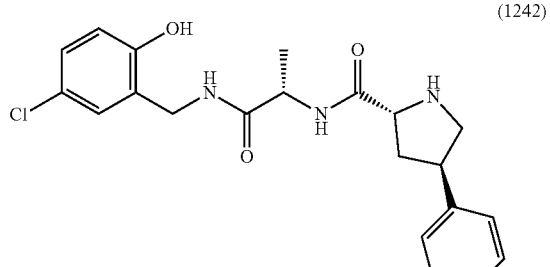
(1242)

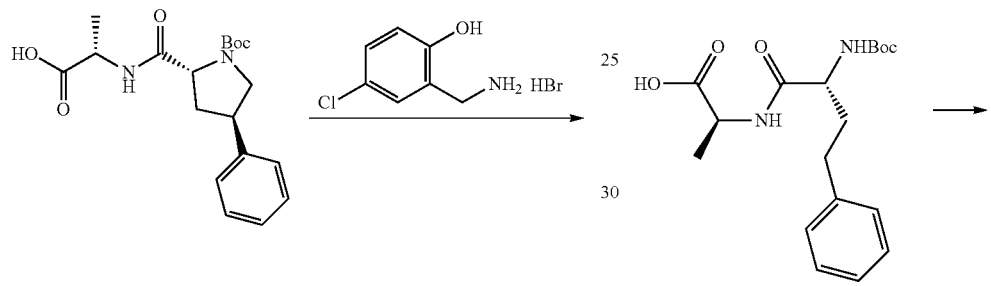

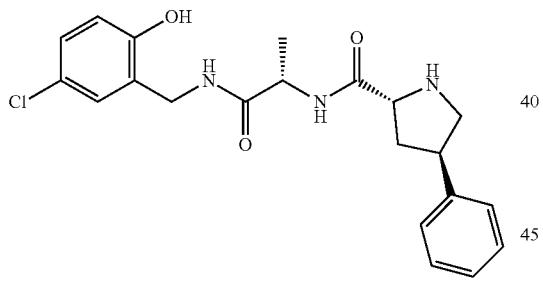

Steps 1-2: To a solution of ((2R,4R)-1-(tert-butoxycarbonyl)-4-phenylpyrrolidine-2-carbonyl)-L-alanine (22 mg, 0.06 mmol) and 2-(aminomethyl)-4-chlorophenol hydrobromide (15 mg, 0.06 mmol) in anhyd DMF (1 mL) at 0° C. was added HBTU (349 mg, 0.92 mmol) and DIEA (31 μL, mmol). The reaction mixture was slowly warmed to ambient temperature and stirred for 2 h, then diluted with EtOAc and washed with 10% aq KHSO$_4$ and brine. The organic layer was dried over Na$_2$SO$_4$ and concentrated under vacuum, then purified by chromatography (70% EtOAc-hexanes) to provide tert-butyl (2R,4R)-2-(((S)-1-(((5-chloro-2-hydroxybenzyl)amino)-1-oxopropan-2-yl)carbamoyl)-4-phenylpyrrolidine-1-carboxylate as a colorless oil. The residue was then taken up in MeOH (1 mL) and treated with 3 M HCl in CPME (2 mL). After 4 h, the reaction mixture was concentrated and purified by chromatography (7% MeOH/CH$_2$CL$_2$ containing 2.5% 7 N NH$_3$-MeOH) to yield the title compound as a white solid (12.2 mg, 51% yield over 2 steps).

Example 46. Preparation of (R)-2-Amino-N—((S)-1-(((6-amino-4-methylpyridin-3-yl)methyl)amino)-1-oxopropan-2-yl)-4-phenylbutanamide Dihydrochloride (1243)

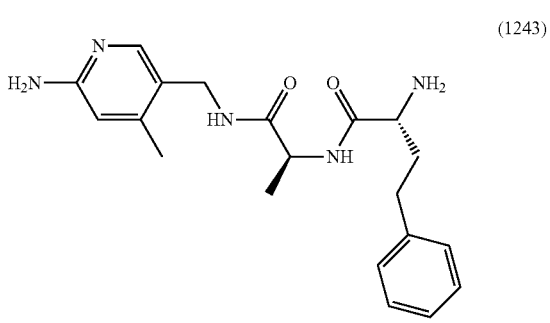
(1243)

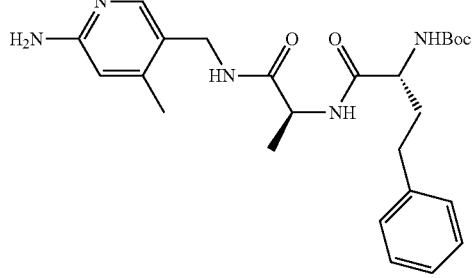

Step 1: To a solution of ((R)-2-((tert-butoxycarbonyl)amino)-4-phenylbutanoyl)-L-alanine (152 mg, 0.43 mmol) in anhyd DMF (3.5 mL) under Ar was added DIEA (0.10 mL, 0.57 mmol) and 5-(aminomethyl)-4-methylpyridin-2-amine (65 mg, 0.47 mmol). The mixture was cooled over ice then HBTU (172 mg, 0.45 mmol) was added: the reaction was stirred for 30 min then stored at 2-8° C. overnight. The reaction mixture was conc in vacuo then the residue was dissolved in EtOAc and washed with H$_2$O, diluted NaHCO$_3$ solution and brine. The solution was dried (Na$_2$SO$_4$) and conc in vacuo. The residue was purified by chromatography with 0-10% MeOH—CH$_2$Cl$_2$ to give tert-butyl ((R)-1-(((S)-1-(((6-amino-4-methylpyridin-3-yl)methyl)amino)-1-oxopropan-2-yl)amino)-1-oxo-4-phenylbutan-2-yl)carbamate (25 mg, 12% yield).

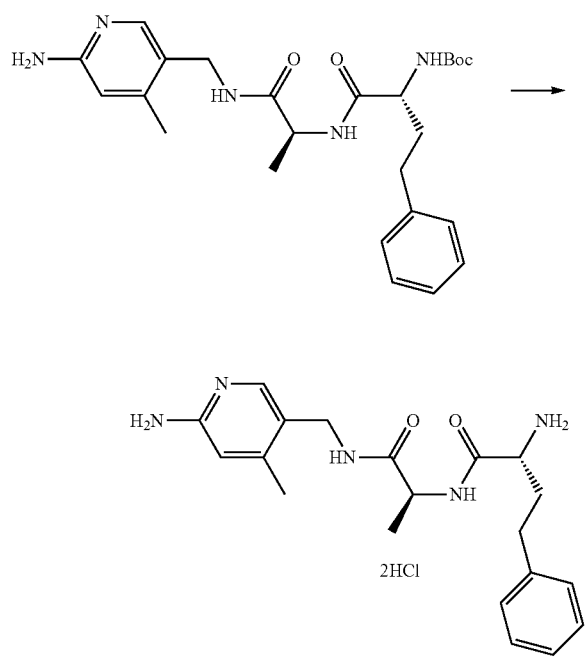

Step 2: To a solution of tert-butyl ((R)-1-(((S)-1-(((6-amino-4-methylpyridin-3-yl)methyl)amino)-1-oxopropan-2-yl)amino)-1-oxo-4-phenylbutan-2-yl)carbamate (25 mg, 0.05 mol) in MeOH (2 mL) was added a solution of HCl-CPME (3 M, 4 mL). The mixture was stirred for 2 h then conc in vacuo. The residue was dissolved in MeOH and conc in vacuo then partitioned between H$_2$O and CH$_2$Cl$_2$. The H$_2$O layer was washed with CH$_2$Cl$_2$ and the volatiles removed in vacuo. The aqueous solution was lyophilized to give (R)-2-amino-N—((S)-1-(((6-amino-4-methylpyridin-3-yl)methyl)amino)-1-oxopropan-2-yl)-4-phenylbutanamide dihydrochloride as a white powder (22.8 mg, 97% yield; 85:15 diastereomer mixture).

Example 47. Preparation of (R)-2-Amino-N—((S)-1-(((6-amino-5-methylpyridin-3-yl)methyl)amino)-1-oxopropan-2-yl)-4-phenylbutanamide Dihydrochloride (1244)

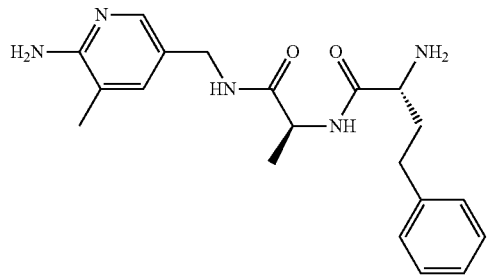

(R)-2-Amino-N—((S)-1-(((6-amino-5-methylpyridin-3-yl)methyl)amino)-1-oxopropan-2-yl)-4-phenylbutanamide dihydrochloride was synthesized according to the procedures for compound (1243).

Example 48. Preparation of (R)-2-Amino-N—((S)-1-(((6-amino-2-methylpyridin-3-yl)methyl)amino)-1-oxopropan-2-yl)-4-phenylbutanamide Dihydrochloride (1245)

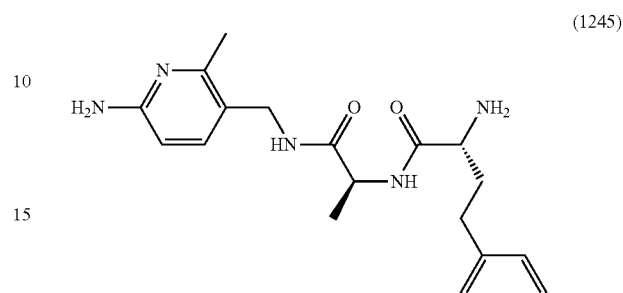

tert-Butyl ((R)-1-(((S)-1-(((6-amino-2-methylpyridin-3-yl)methyl)amino)-1-oxopropan-2-yl)amino)-1-oxo-4-phenylbutan-2-yl)carbamate was synthesized according to the procedure for compound (1243), step 1, except that additional HBTU (0.34 eq.) was added after stirring for 3.5 h over ice bath. Following purification of the intermediate, deprotection was achieved according to the procedure for compound (1243), step 2.

Example 49. Preparation of (R)-2-Amino-N—((S)-1-((5-chloro-2-nitrobenzyl)amino)-1-oxopropan-2-yl)-4-phenylbutanamide Hydrochloride (1246)

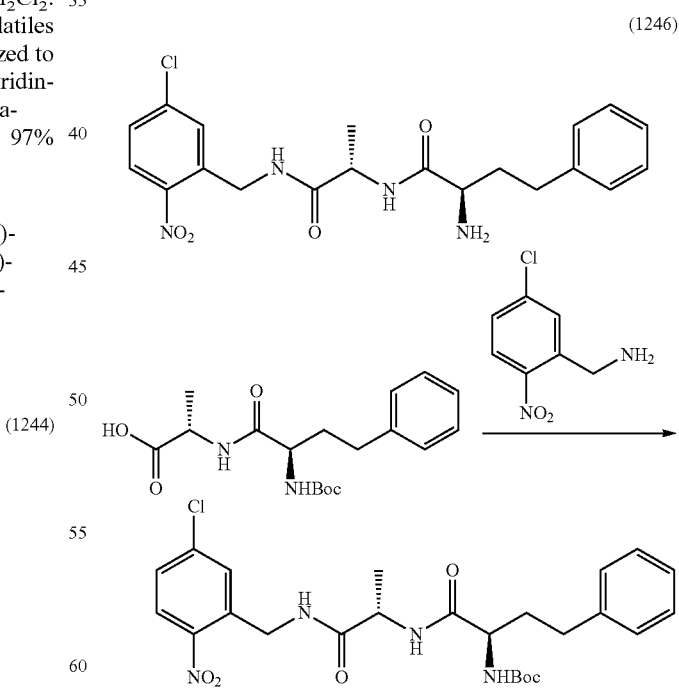

Step 1: tert-Butyl ((R)-1-(((S)-1-((5-chloro-2-nitrobenzyl)amino)-1-oxopropan-2-yl)amino)-1-oxo-4-phenylbutan-2-yl)carbamate synthesized according to step 1 of the procedure for compound (1242) using the appropriate starting materials.

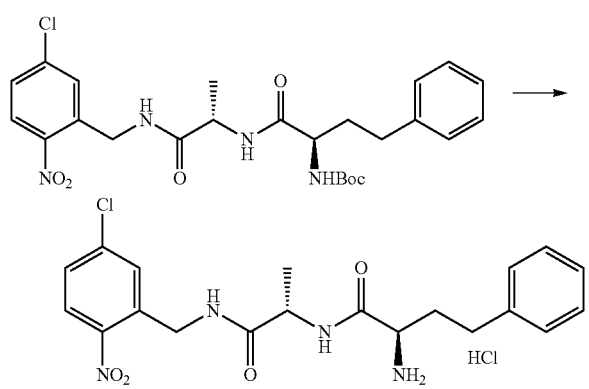

Step 2: To tert-butyl ((R)-1-(((S)-1-((5-chloro-2-nitrobenzyl)amino)-1-oxopropan-2-yl)amino)-1-oxo-4-phenylbutan-2-yl)carbamate (12 mg, 0.025 mmol) was added conc HCl in MeOH (1 mL). The reaction mixture was allowed to stir at ambient temperature overnight, then evaporated to dryness. The residue was taken up in $H_2O$-ACN (~1:1) and lyophilized overnight to yield (R)-2-amino-N—((S)-1-((5-chloro-2-nitrobenzyl)amino)-1-oxopropan-2-yl)-4-phenylbutanamide, hydrochloride as a yellow powder (8.3 mg, 73%).

Example 50. Preparation of (2R,4S)—N—((S)-1-((4-Carbamimidoylbenzyl)amino)-1-oxopropan-2-yl)-4-(m-tolyl)pyrrolidine-2-carboxamide Dihydrochloride (1247)

(1247)

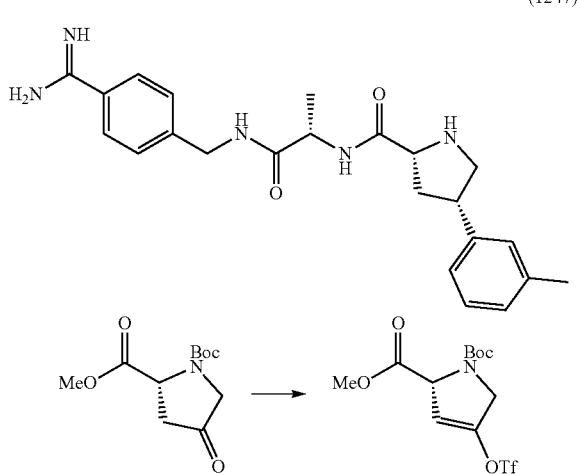

Step 1: To a stirred solution of 1-(tert-butyl) 2-methyl (R)-4-oxopyrrolidine-1,2-dicarboxylate (1.50 g, 6.16 mmol) in THF (15 mL) at −78° C. was slowly added lithium bis(trimethylsilyl)amide (7.40 mL, 7.40 mmol, 1 M in THF) under Ar. After stirring for 1 h at −78° C., Comins' reagent (2.99 g, 7.40 mmol) in THF (5 mL) was added and the stirring continued for an additional 1 h. The reaction mixture was stirred at −20° C. for additional 18 h. The reaction mixture was quenched with 20 mL water and extracted with diethyl ether (3×60 mL). The combined extracts were washed with 2 N NaOH solution, dried over $Na_2SO_4$, filtered and concentrated under vacuum. The residue was purified by chromatography (EtOAc-hexanes) to give 1-(tert-butyl) 2-methyl (R)-4-(((trifluoromethyl)sulfonyl)oxy)-2,5-dihydro-1H-pyrrole-1,2-dicarboxylate (1.85 g, 80% yield).

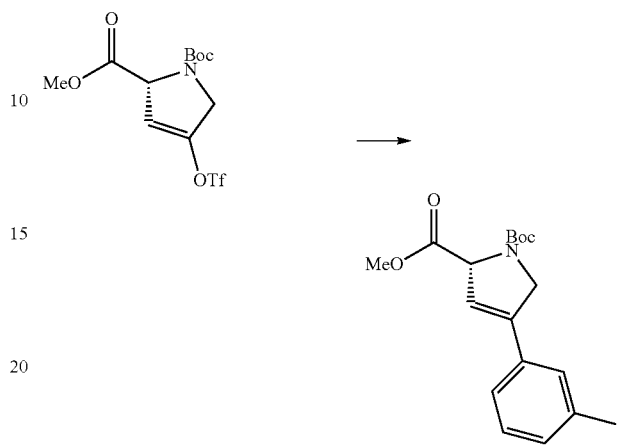

Step 2: In a 50 mL round bottom flask equipped with a stir bar and septum was added 1-(tert-butyl) 2-methyl (R)-4-(((trifluoromethyl)sulfonyl)oxy)-2,5-dihydro-1H-pyrrole-1,2-dicarboxylate (400 mg, 1.06 mmol), m-tolyl boronic acid (215 mg, 1.17), Pd(PPh$_3$)$_4$ (123 mg, 0.11 mmol), $K_2CO_3$ (442 mg, 3.20 mmol), dioxane (7.1 mL) and water (1.5 mL). The resulting mixture was degassed by bubbling $N_2$ through the solution for 10 min. The reaction was then heated to 80° C. for 2 h. Upon cooling to ambient temperature, the reaction solution was filtered through diatomaceous earth, eluting with EtOAc, concentrated and purified by chromatography using EtOAc-hexanes to afford 1-(tert-butyl) 2-methyl (R)-4-(m-tolyl)-2,5-dihydro-1H-pyrrole-1,2-dicarboxylate (330 mg, 86% yield) as a colorless solid.

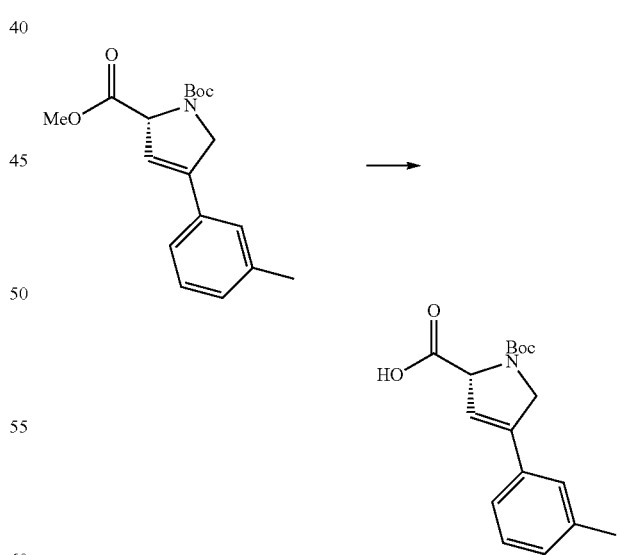

Step 3: To a stirred solution of 1-(tert-butyl) 2-methyl (R)-4-(m-tolyl)-2,5-dihydro-1H-pyrrole-1,2-dicarboxylate (317 mg, 1 mmol) in THF (24 mL), MeOH (12 mL), and water (12 mL) was added LiOH (360 mg, 15 mmol) at ambient temperature. The resulting reaction mixture was stirred at ambient temperature overnight. 12 mL of 1 M HCl was added to the reaction mixture and organic volatiles were removed under vacuum. The aqueous layer was extracted with EtOAc (3×20 mL). The combined organic extracts were thoroughly dried using Na₂SO₄, filtered, and concentrated to afford (R)-1-(tert-butoxycarbonyl)-4-(m-tolyl)-2,5-dihydro-1H-pyrrole-2-carboxylic acid (288 mg crude, 95% yield) that was directly used in the next step without further purification.

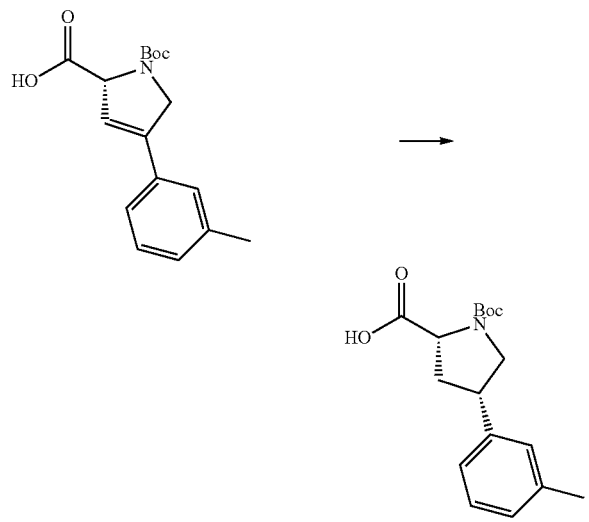

Step 4: A solution of (R)-1-(tert-butoxycarbonyl)-4-(m-tolyl)-2,5-dihydro-1H-pyrrole-2-carboxylic acid (288 mg, 0.95 mmol) in MeOH (8 mL) was bubbled with Ar gas for 5 min. 10% Pd/C (28 mg) was added to the reaction mixture and that was stirred under 1 atm of H₂ for 4 h. The reaction mixture was filtered (0.2 μm syringe filter) and the filtrate was concentrated under vacuum to give (2R,4S)-1-(tert-butoxycarbonyl)-4-(m-tolyl)pyrrolidine-2-carboxylic acid (265 mg, 92% yield).

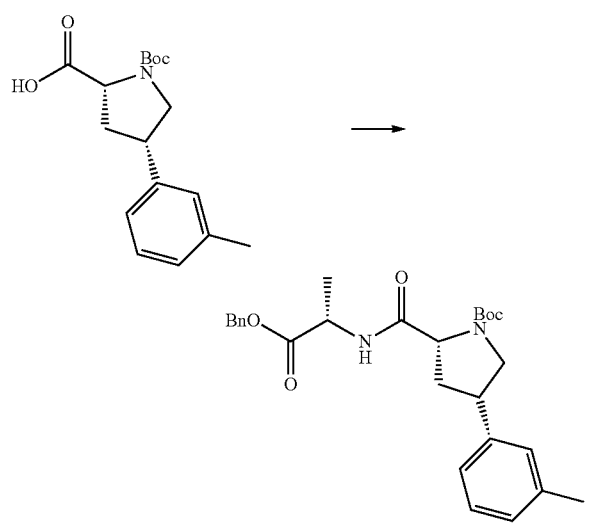

Step 5: tert-Butyl (2R,4S)-2-(((S)-1-(benzyloxy)-1-oxopropan-2-yl)carbamoyl)-4-(m-tolyl)pyrrolidine-1-carboxylate (404 mg, 74% yield) was synthesized from (2R,4S)-1-(tert-butoxycarbonyl)-4-(m-tolyl)pyrrolidine-2-carboxylic acid (360 mg, 1.18 mmol) according to the procedure for compound (1304), step 7.

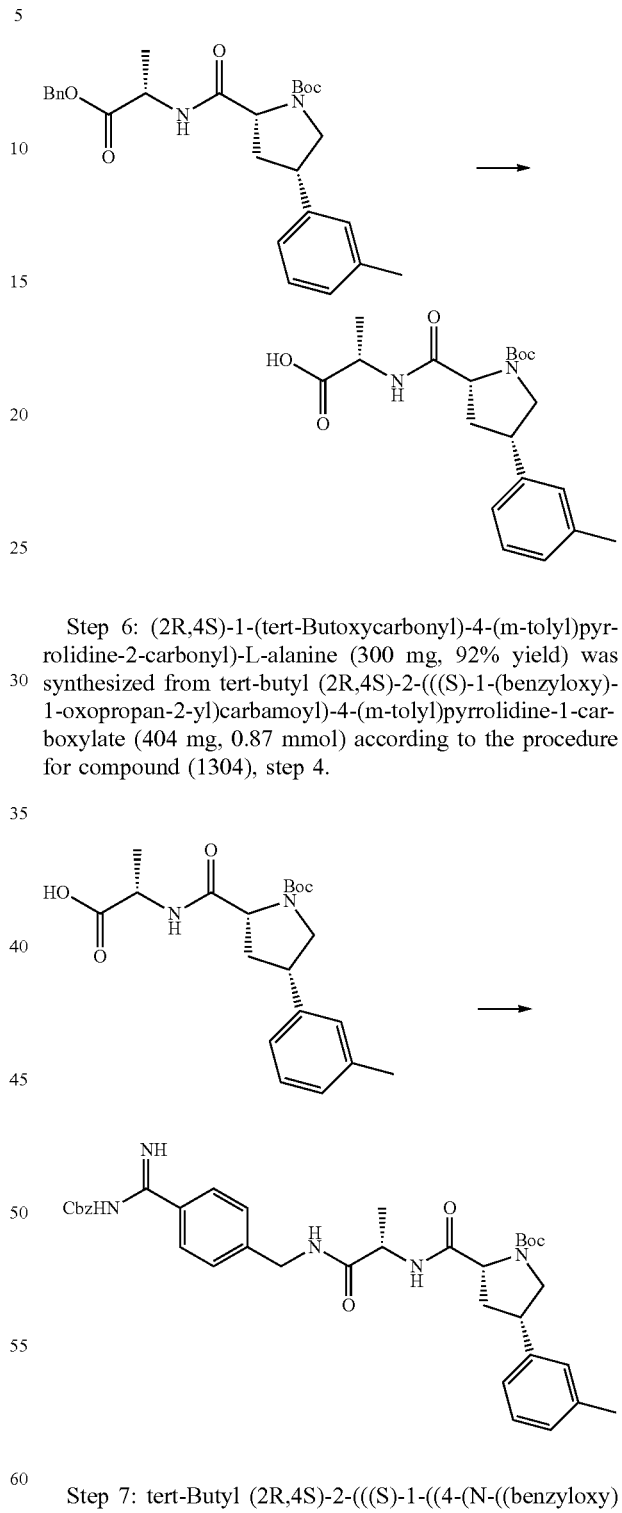

Step 6: (2R,4S)-1-(tert-Butoxycarbonyl)-4-(m-tolyl)pyrrolidine-2-carbonyl)-L-alanine (300 mg, 92% yield) was synthesized from tert-butyl (2R,4S)-2-(((S)-1-(benzyloxy)-1-oxopropan-2-yl)carbamoyl)-4-(m-tolyl)pyrrolidine-1-carboxylate (404 mg, 0.87 mmol) according to the procedure for compound (1304), step 4.

Step 7: tert-Butyl (2R,4S)-2-(((S)-1-((4-(N-((benzyloxy)carbonyl)carbamimidoyl)benzyl)amino)-1-oxopropan-2-yl)carbamoyl)-4-(m-tolyl)pyrrolidine-1-carboxylate (154 mg, 75% yield) was synthesized from (2R,4S)-1-(tert-butoxycarbonyl)-4-(m-tolyl)pyrrolidine-2-carbonyl)-L-alanine (100 mg, 0.26 mmol) according to the procedure for compound (1234), step 3.

385

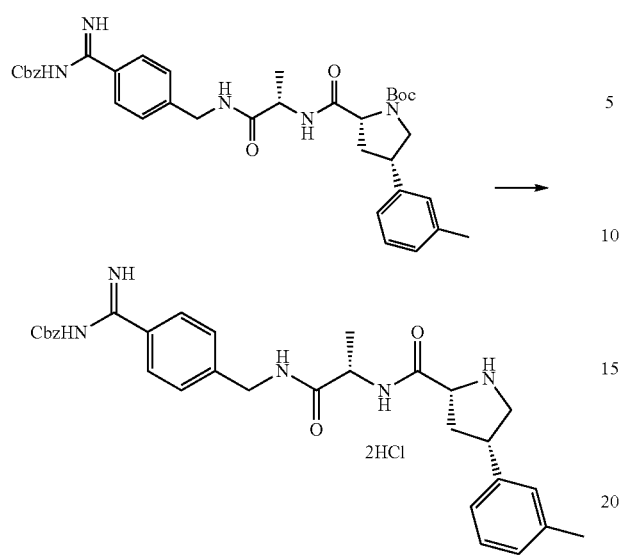

Step 8: Benzyl (imino(4-(((S)-2-((2R,4S)-4-(m-tolyl)pyrrolidine-2-carboxamido)propanamido)methyl)phenyl)methyl)carbamate dihydrochloride (83 mg, 90% yield) was synthesized from tert-butyl (2R,4S)-2-(((S)-1-((4-(N-((benzyloxy)carbonyl)carbamimidoyl)benzyl)amino)-1-oxopropan-2-yl)carbamoyl)-4-(m-tolyl)pyrrolidine-1-carboxylate (110 mg, 0.17 mmol) according to the procedure for compound (1304), step 8.

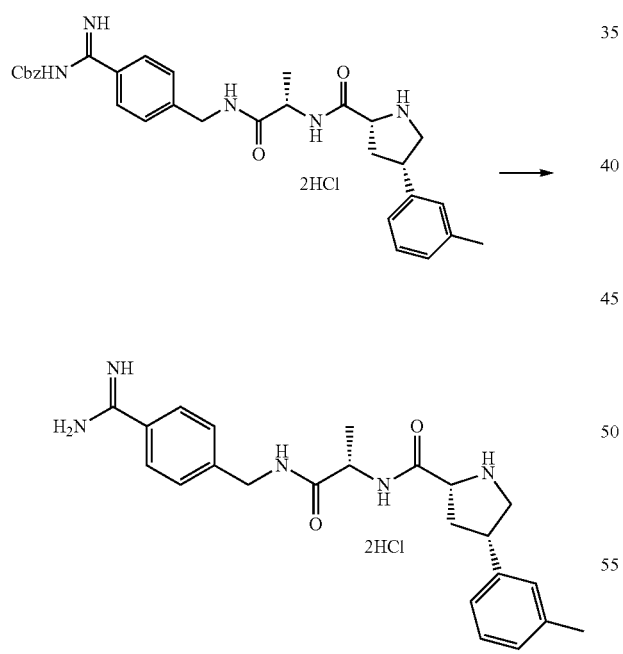

Step 9: (2R,4S)—N—((S)-1-((4-Carbamimidoylbenzyl)amino)-1-oxopropan-2-yl)-4-(m-tolyl)pyrrolidine-2-carboxamide dihydrochloride (64 mg, 86%) was synthesized from benzyl (imino(4-(((S)-2-((2R,4S)-4-(m-tolyl)pyrrolidine-2-carboxamido)propanamido)methyl)phenyl)methyl)carbamate (55 mg, 0.15 mmol) according to the procedure for compound (1304), step 4.

386

Example 51. Preparation of (2R,4R)—N—((S)-1-((4-Carbamimidoylbenzyl)amino)-1-oxopropan-2-yl)-4-(p-tolyl)piperidine-2-carboxamide Dihydrochloride (1248)

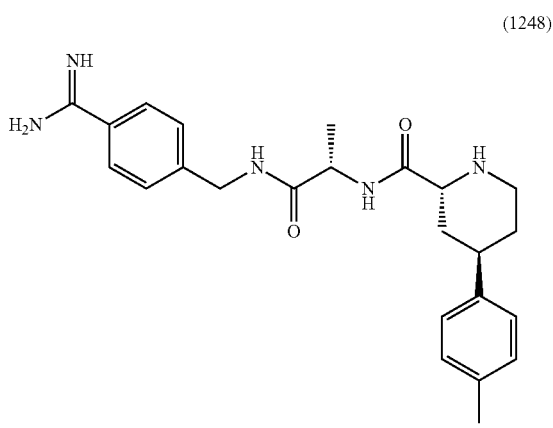 [SMILES: Cc1ccc([C@@H]2CCN[C@@H](C(=O)N[C@@H](C)C(=O)NCc3ccc(C(=N)N)cc3)C2)cc1]

(1248)

(2R,4R)—N—((S)-1-((4-Carbamimidoylbenzyl)amino)-1-oxopropan-2-yl)-4-(p-tolyl)piperidine-2-carboxamide dihydrochloride was synthesized according to the procedures for compound (1241). The first UVActive material eluting from the column in step 6 was carried forward.

Example 52. Preparation of (2R,4S)—N—((S)-1-((4-Carbamimidoylbenzyl)amino)-1-oxopropan-2-yl)-4-(p-tolyl)piperidine-2-carboxamide Dihydrochloride (1249)

(1249)

(2R,4S)—N—((S)-1-((4-Carbamimidoylbenzyl)amino)-1-oxopropan-2-yl)-4-(p-tolyl)piperidine-2-carboxamide was synthesized according to the procedures for compound (1231) (9). The third UVActive material eluting from the column in step 6 was carried forward.

Example 53. Preparation of (R)—N—((S)-1-((4-Carbamimidoylbenzyl)amino)-1-oxopropan-2-yl)-2-((4-(4-(methylsulfonyl)piperazin-1-yl)benzyl)amino)-4-phenylbutanamide Di-trifluoroacetate salt (1250)

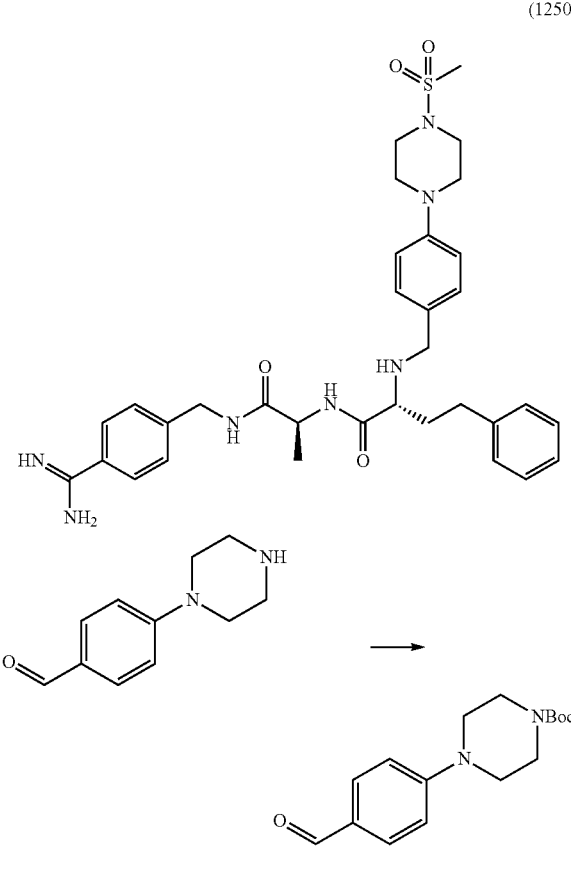

(1250)

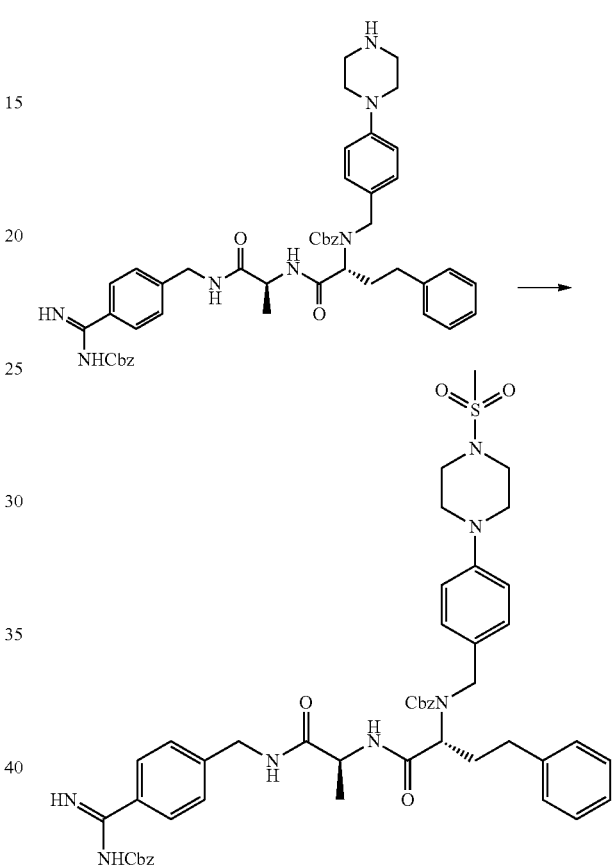

Step 1: To a solution of 4-(piperazin-1-yl)benzaldehyde (450.0 mg, 2.37 mmol) in THF (6 mL) and CH$_2$Cl$_2$ (6 mL), di-tert-butyl dicarbonate (650 mg, 2.98 mmol) was added. After purging with N$_2$, the reaction was stirred at room temp for 16 h. The reaction was quenched with 50 mL sat. NH$_4$Cl solution and extracted with 50 mL CH$_2$Cl$_2$ (3 times). The organic layers were combined, dried (Na$_2$SO$_4$), vacuum filtered, and evaporated under vacuum. The crude product was dissolved in CH$_2$Cl$_2$ and adsorbed on silica gel. Purification by chromatography (0-100% EtOAc-hexanes) afforded tert-butyl 4-(4-formylphenyl)piperazine-1-carboxylate (632.6 mg, 92% yield).

Step 2: tert-Butyl 4-(4-((((R)-1-(((S)-1-((4-(N-((benzyloxy)carbonyl)carbamimidoyl)benzyl)amino)-1-oxopropan-2-yl)amino)-1-oxo-4-phenylbutan-2-yl)amino)methyl)phenyl)piperazine-1-carboxylate was synthesized according to the procedure for compound 1130, step 2.

Step 3: tert-Butyl 4-(4-(((((benzyloxy)carbonyl)((R)-1-(((S)-1-((4-(N-((benzyloxy)carbonyl)carbamimidoyl)benzyl)amino)-1-oxopropan-2-yl)amino)-1-oxo-4-phenylbutan-2-yl)amino)methyl)phenyl)piperazine-1-carboxylate was synthesized according to the procedure for compound 1148, step 1.

Step 4: Deprotection of tert-butyl 4-(4-(((((benzyloxy)carbonyl)((R)-1-(((S)-1-((4-(N-((benzyloxy)carbonyl)car-bamimidoyl)benzyl)amino)-1-oxopropan-2-yl)amino)-1-oxo-4-phenylbutan-2-yl)amino)methyl)phenyl)piperazine-1-carboxylate was conducted according to the procedure for compound 1015, step 4 except the crude product was purified by chromatography (5% 7 N NH$_3$ in MeOH—CH$_2$Cl$_2$) to afford benzyl ((R)-1-(((S)-1-((4-(N-((benzyloxy)carbonyl)carbamimidoyl)benzyl)amino)-1-oxopropan-2-yl)amino)-1-oxo-4-phenylbutan-2-yl)(4-(piperazin-1-yl)benzyl)carbamate.

Step 5: To a solution of benzyl ((R)-1-(((S)-1-((4-(N-((benzyloxy)carbonyl)carbamimidoyl)benzyl)amino)-1-oxopropan-2-yl)amino)-1-oxo-4-phenylbutan-2-yl)(4-(piperazin-1-yl)benzyl)carbamate (54.4 mg, 0.066 mmol) in DCE (500 μL) and TEA (14 μL) was added MsCl (6 μL) at 0° C. The reaction was warmed to room temp and stirred for 16 h. The reaction was quenched with 1 mL 0.5 M NaOH solution and extracted with 20 mL CH$_2$Cl$_2$ (3 times). The organic layers were combined, washed with brine, dried (Na$_2$SO$_4$), vacuum filtered, and evaporated under vacuum. The crude product was dissolved in CH$_2$Cl$_2$ and adsorbed on silica gel. Purification by chromatography (0-10% MeOH—CH$_2$Cl$_2$) afforded benzyl ((R)-1-(((S)-1-((4-(N-((benzyloxy)carbonyl)carbamimidoyl)benzyl)amino)-1-oxopropan-2-yl)amino)-1-oxo-4-phenylbutan-2-yl)(4-(4-(methylsulfonyl)piperazin-1-yl)benzyl)carbamate.

Step 6: Deprotection of benzyl ((R)-1-(((S)-1-((4-(N-((benzyloxy)carbonyl)carbamimidoyl)benzyl)amino)-1-oxopropan-2-yl)amino)-1-oxo-4-phenylbutan-2-yl)(4-(4-(methylsulfonyl)piperazin-1-yl)benzyl)carbamate according to the procedure for compound 1130, step 3. Purification by reverse phase HPLC (5-75-90% MeCN—H$_2$O) afforded (R)—N—((S)-1-((4-carbamimidoylbenzyl)amino)-1-oxo-propan-2-yl)-2-((4-(4-(methylsulfonyl)piperazin-1-yl)benzyl)amino)-4-phenylbutanamide di-trifluoroacetate salt.

Example 54. Preparation of (R)-2-amino-N—((S)-1-((4-carbamimidoyl-2-methoxybenzyl)amino)-1-oxopropan-2-yl)-4-phenylbutanamide Di-trifluoroacetate salt (1251)

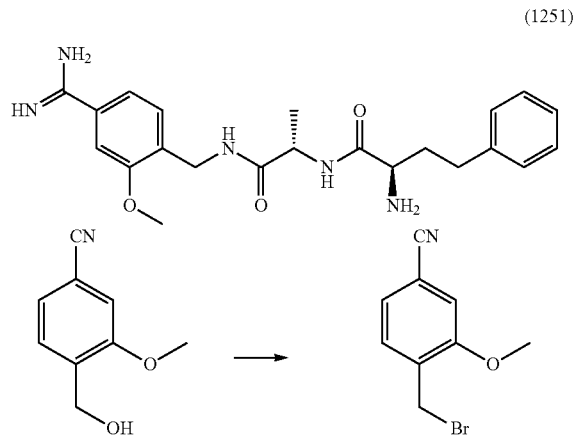

(1251)

Step 1: A dry round bottom flask was charged with 4-(hydroxymethyl)-3-methoxybenzonitrile (950 mg, 5.8 mmol), CBr$_4$ (2.12 g, 6.4 mmol) and CH$_2$Cl$_2$ (20 mL), then cooled to 0° C. PPh$_3$ (1.68 g, 6.4 mmol) was added and the reaction mixture stirred for 2 h at ambient temperature. Upon completion, the reaction mixture was concentrated and then purified by chromatography (40% EtOAc-hexanes) to furnish 4-(bromomethyl)-3-methoxybenzonitrile as a white powder (1.1 g, 85% yield).

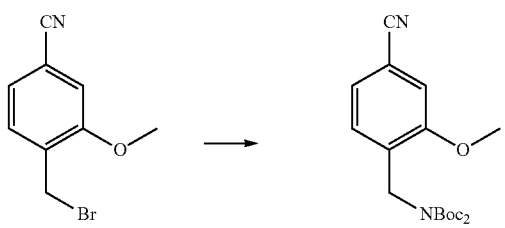

Step 2: In a dry round bottom flask under Ar, NaH (60% in mineral oil; 508 mg, 12.7 mmol) was washed 3× with hexanes. Anhyd THF was added and the suspension cooled to 0° C. A solution of 4-(bromomethyl)-3-methoxybenzonitrile (1.1 g, 4.88 mmol) was added followed by dropwise addition of di-tert-butyl-iminodicarboxylate (1.38 g, 6.36 mmol) in THF. Reaction mixture was stirred for 16 h at ambient temperature then quenched with H$_2$O. THF was removed in vacuo and the aqueous layer filtered through a fritted funnel. The crude product was recrystallized with hot EtOAc to furnish tert-butyl (tert-butoxycarbonyl)(4-cyano-2-methoxybenzyl)carbamate as a white crystalline solid (1.11 g, 63% yield).

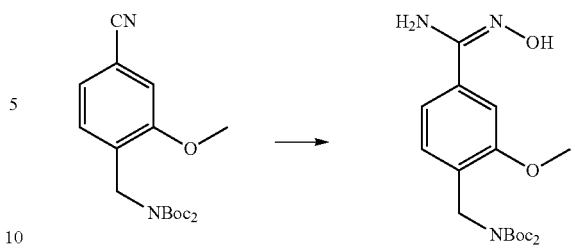

Step 3: A 100 mL round bottom flask was charged with tert-butyl (tert-butoxycarbonyl)(4-cyano-2-methoxybenzyl)carbamate (1.11 g, 3.07 mmol) and anhyd MeOH (10 mL), followed by hydroxylamine hydrochloride (1.07 g, 15.3 mmol) and DIEA (2.67 mL, 15.3 mmol). The reaction flask was equipped with a condenser and heated at reflux for 3 h. Upon cooling, the reaction mixture was then concentrated and the product precipitated with H$_2$O. Crude product was collected by suction filtration, dissolved in CH$_2$Cl$_2$, washed with brine and dried over Na$_2$SO$_4$. Organic layers were collected and concentrated to furnish tert-butyl (E)-(tert-butoxycarbonyl)(4-(N'-hydroxycarbamimidoyl)-2-methoxybenzyl)carbamate as a white powder (1.12 g, 93% yield)

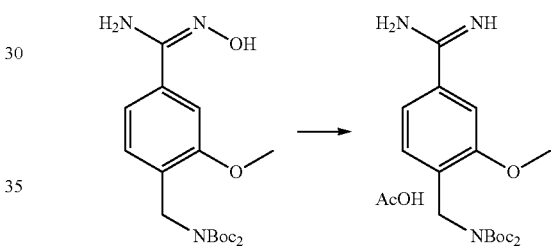

Step 4: A 100 mL round bottom flask was charged with (E)-(tert-butoxycarbonyl)(4-(N'-hydroxycarbamimidoyl)-2-methoxybenzyl)carbamate (1.12 g, 2.83 mmol), Ac$_2$O (320 μL, 3.35 mmol) and AcOH (5 mL). The flask was evacuated and backfilled with Ar then charged with 10% Pd/C (cat.). The flask was again evacuated and backfilled with H$_2$ and allowed to stir at ambient temperature for 16 h. Reaction mixture was filtered through a 0.2 μm syringe filter and concentrated in vacuo to give tert-butyl (tert-butoxycarbonyl)(4-carbamimidoyl-2-methoxybenzyl)carbamate as a white solid (1.25 g, quant.)

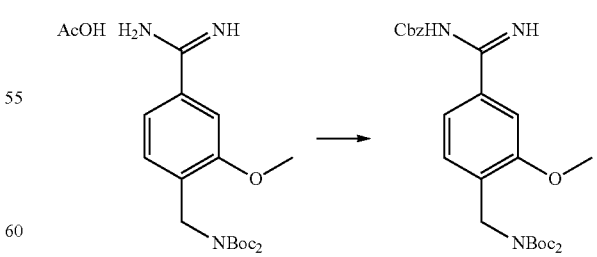

Step 5: To a solution of (tert-butoxycarbonyl)(4-carbamimidoyl-2-methoxybenzyl)carbamate (1.25 g, 2.83 mmol) in THF (7 mL) was added sat. aq NaHCO$_3$ (7 mL) and N-(benzyloxycarbonyloxy)succinimide (741 mg, 3 mmol). The reaction mixture was stirred at ambient temperature for 16 h then diluted with EtOAc and washed with brine. The organic layer was dried over MgSO₄ and concentrated. The residue was then triturated with diethyl ether to provide tert-butyl (4-(N-((benzyloxy)carbonyl)carbamimidoyl)-2-methoxybenzyl)(tert-butoxycarbonyl)carbamate as a white powder (704 mg, 48% yield).

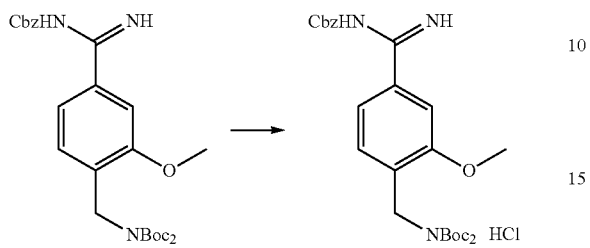

Step 6: tert-Butyl (4-(N-((benzyloxy)carbonyl)carbamimidoyl)-2-methoxybenzyl)(tert-butoxycarbonyl)carbamate (103 mg, 0.2 mmol) was deprotected according to the procedure for compound 1015, step 4 to provide benzyl ((4-(aminomethyl)-3-methoxyphenyl)(imino)methyl)carbamate hydrochloride as a mint-green powder (68 mg, 97% yield).

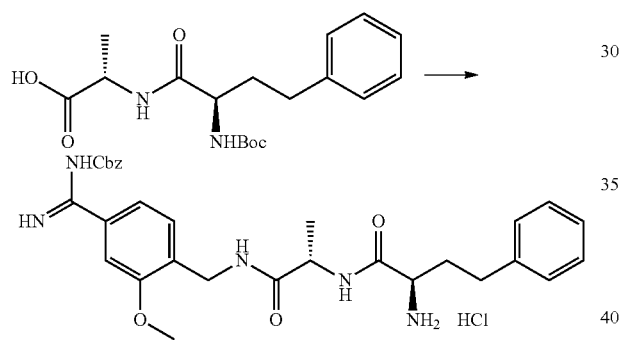

Steps 7-8: Benzyl ((4-(((S)-2-((R)-2-amino-4-phenylbutanamido)propanamido)methyl)-3-methoxyphenyl)(imino)methyl)carbamate was synthesized according to steps 1-2 of the procedure for compound (1246) using the appropriate starting materials except the crude material was carried on without purification to the following step.

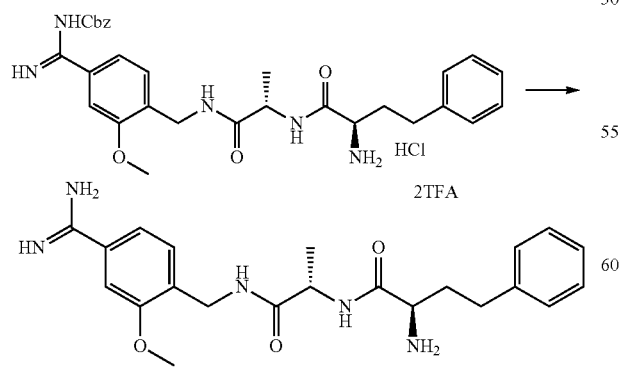

Step 9: Removal of the Cbz group of benzyl ((4-(((S)-2-((R)-2-amino-4-phenylbutanamido)propanamido)methyl)-3-methoxyphenyl)(imino)methyl)carbamate was carried out according to the procedure for compound 1028, step 6. The crude product was purified by reverse-phase HPLC (35-65% MeCN-H₂O+TFA) and the fractions lyophilized to furnish the title compound as a white powder.

Example 55. Preparation of (2R,4S)—N—((S)-1-((4-Carbamimidoylbenzyl)amino)-1-oxopropan-2-yl)-4-(p-tolyl)pyrrolidine-2-carboxamide Dihydrochloride (1252)

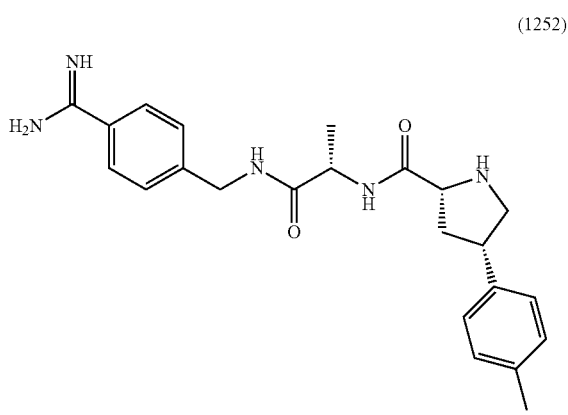 [SMILES: Cc1ccc([C@H]2CN[C@@H](C(=O)N[C@@H](C)C(=O)NCc3ccc(C(=N)N)cc3)C2)cc1]

(2R,4S)—N—((S)-1-((4-Carbamimidoylbenzyl)amino)-1-oxopropan-2-yl)-4-(p-tolyl)pyrrolidine-2-carboxamide dihydrochloride was synthesized according to the procedures for compound (1247).

Example 56. Preparation of (2R,4S)—N—((S)-1-(((6-Amino-2-methylpyridin-3-yl)methyl)amino)-1-oxopropan-2-yl)-4-phenylpiperidine-2-carboxamide Dihydrochloride (1253)

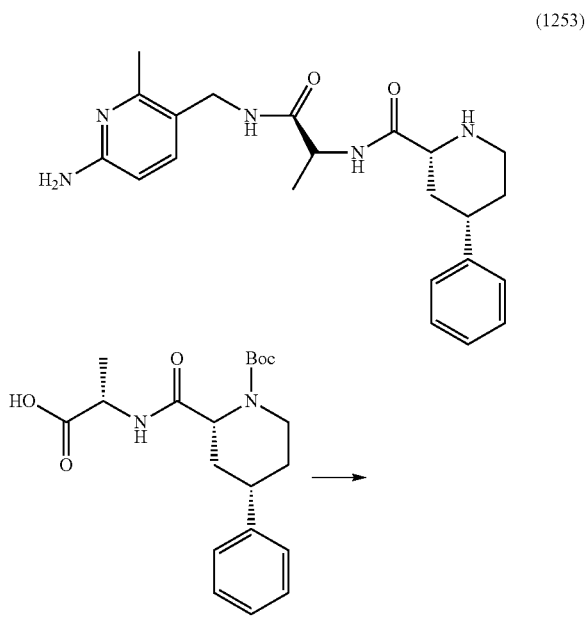

-continued

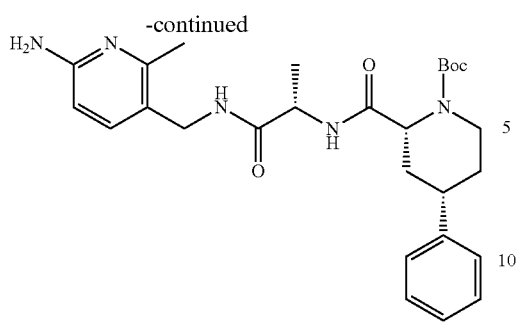

Step 1: To a solution of ((R)-2-((tert-butoxycarbonyl)amino)-4-(4-(trifluoromethyl)phenyl)butanoyl)-L-alanine (100 mg, 0.266 mmol) in CH₂Cl₂ (5 mL) was added NHS (1.1 equiv, 1.05 mmol) with stirring at room temp. until dissolved. DCC (1.1 equiv, 1.05 mmol) was added and stirred for 1.0 h then 5-(aminomethyl)-6-methylpyridin-2-amine (0.319 mmol, 1.2 equiv.) was added with sonication and stirred overnight at room temp. The solution was filtered and evaporated to dryness. Flash chromatography (3% 7 N NH₃ in MeOH/CH₂Cl₂) gave tert-butyl (2R,4S)-2-(((S)-1-(((6-amino-2-methylpyridin-3-yl)methyl)amino)-1-oxopropan-2-yl)carbamoyl)-4-phenylpiperidine-1-carboxylate (91 mg, 69%) as a white solid.

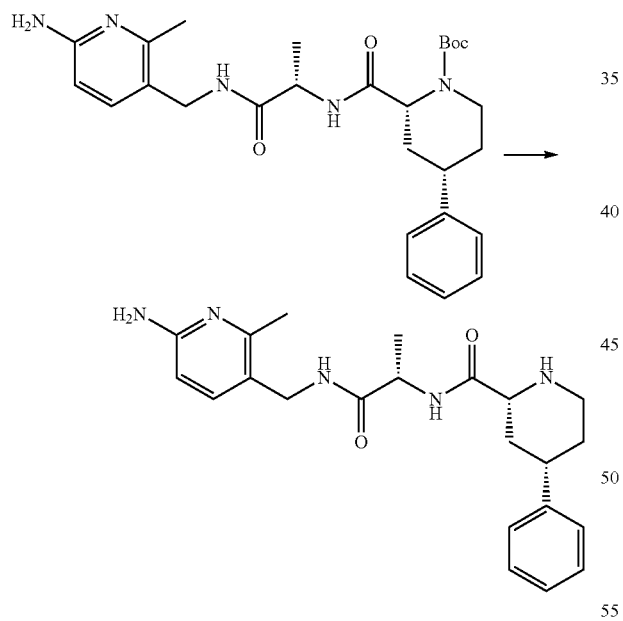

Step 2: To tert-butyl (2R,4S)-2-(((S)-1-(((6-amino-2-methylpyridin-3-yl)methyl)amino)-1-oxopropan-2-yl)carbamoyl)-4-phenylpiperidine-1-carboxylate (84 mg, 0.169 mmol) was added a solution of MeOH—HCl (5.0 mL, 227 mg HCl/mL) with stirring at room temp while monitoring for the consumption of starting material. The solution was evaporated to dryness and MeOH (15 mL) was added and evaporated to dryness giving (2R,4S)—N—((S)-1-(((6-amino-2-methylpyridin-3-yl)methyl)amino)-1-oxopropan-2-yl)-4-phenylpiperidine-2-carboxamide as a white solid (80 mg, 100% yield).

Example 57. Preparation of (2R,4S)—N—((S)-1-((5-Chloro-2-hydroxybenzyl)amino)-1-oxopropan-2-yl)-4-(m-tolyl)pyrrolidine-2-carboxamide Hydrochloride (1254)

(1254)

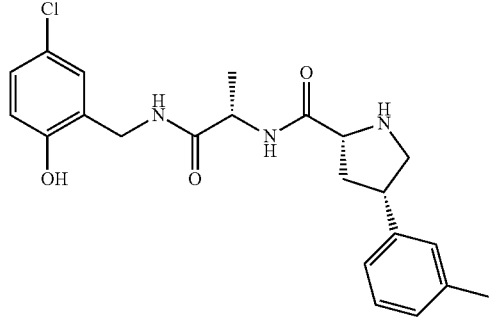

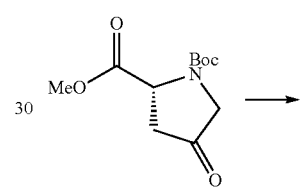

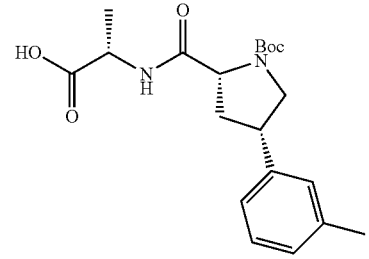

Step 1: (2R,4S)-1-(tert-Butoxycarbonyl)-4-(m-tolyl)pyrrolidine-2-carbonyl)-L-alanine was synthesized from 1-(tert-butyl) 2-methyl (R)-4-oxopyrrolidine-1,2-dicarboxylate according to the procedure for compound (1247), step 1 to step 6.

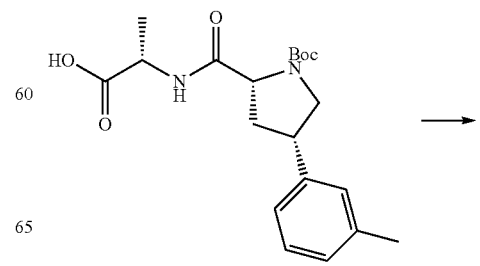

-continued

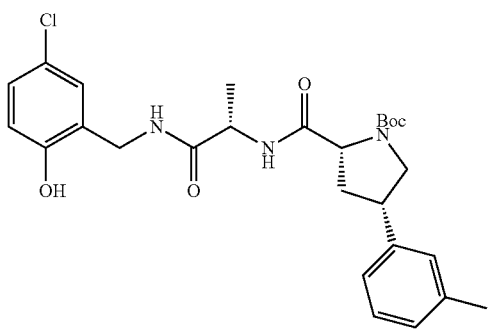

Step 2: tert-Butyl (2R,4S)-2-(((S)-1-((5-chloro-2-hydroxybenzyl)amino)-1-oxopropan-2-yl)carbamoyl)-4-(m-tolyl)pyrrolidine-1-carboxylate (57 mg, 70% yield) was synthesized from (2R,4S)-1-(tert-butoxycarbonyl)-4-(m-tolyl)pyrrolidine-2-carbonyl)-L-alanine (60 mg, 0.16 mmol) according to the procedure for compound (1234), step 3.

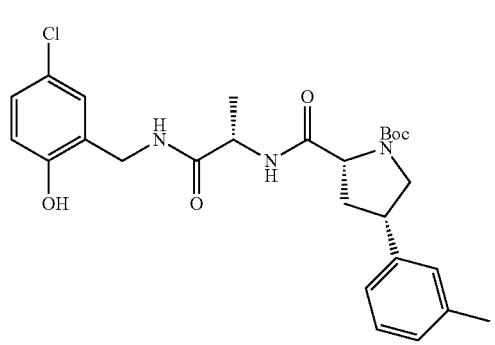

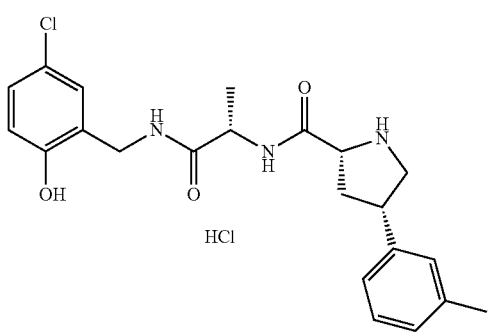

Step 3: (2R,4S)—N—((S)-1-((5-Chloro-2-hydroxybenzyl)amino)-1-oxopropan-2-yl)-4-(m-tolyl)pyrrolidine-2-carboxamide hydrochloride (50.7 mg, 90% yield) was synthesized from tert-butyl (2R,4S)-2-(((S)-1-((5-chloro-2-hydroxybenzyl)amino)-1-oxopropan-2-yl)carbamoyl)-4-(m-tolyl)pyrrolidine-1-carboxylate (57 mg, 0.11 mmol) according to the procedure for compound (1304), step 8.

Example 58. Preparation of (2R,4S)—N—((S)-1-(((6-Aminopyridin-3-yl)methyl)amino)-1-oxopropan-2-yl)-4-phenylpyrrolidine-2-carboxamide Dihydrochloride (1255)

(1255)

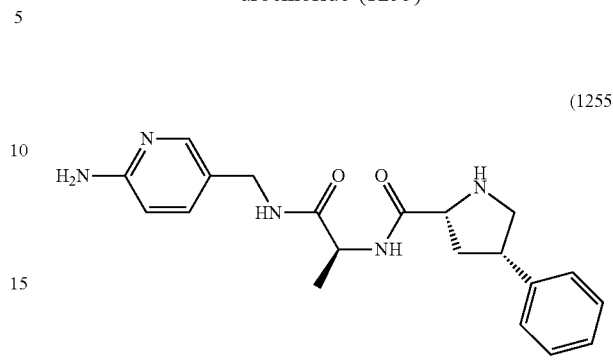

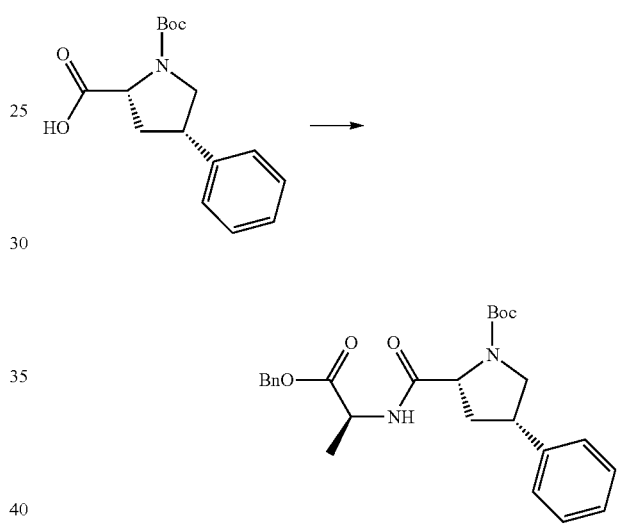

Step 1: To a solution of (2R,4S)-1-(tert-butoxycarbonyl)-4-phenylpyrrolidine-2-carboxylic acid (1 g, 3.4 mmol) in MeCN (25 mL) was added EDC (0.786 g, 4.1 mmol), HOBt (0.553 g, 4.1 mmol) and DIEA (3 mL, 17 mmol). The mixture was stirred at ambient temperature for 15 min then benzyl L-alanine hydrochloride (0.884 g, 4.1 mmol) was added. The mixture was stirred overnight then cone in vacuo. The residue was dissolved in EtOAc and washed with 0.5 M KHSO₄, sat. NaHCO₃ 3×, brine and H₂O, dried (Na₂SO₄) and conc in vacuo. Purification by chromatography (5-40% EtOAc-hexanes) gave ((2R,4S)-1-(tert-butoxycarbonyl)-4-phenylpyrrolidine-2-carbonyl)-L-alanine (1.05 g, 70% yield).

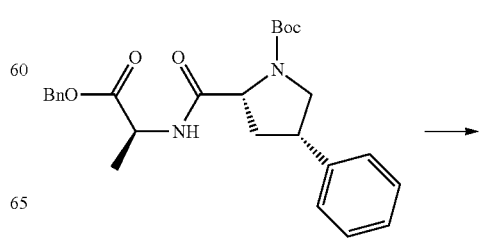

-continued

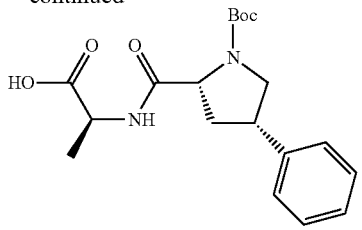

Step 2: To a degassed solution of ((2R,4S)-1-(tert-butoxycarbonyl)-4-phenylpyrrolidine-2-carbonyl)-L-alanine (1.05 g, 2.3 mmol) in anhyd MeOH (20 mL) was added 10% Pd/C (0.30 g). The mixture was degassed then put under H$_2$ atm. After stirring overnight at ambient temperature, the mixture was filtered (0.20 μm syringe filter) then conc in vacuo to give 0.825 g of ((2R,4S)-1-(tert-butoxycarbonyl)-4-phenylpyrrolidine-2-carbonyl)-L-alanine which was used without further purification (0.825 g, 98% yield).

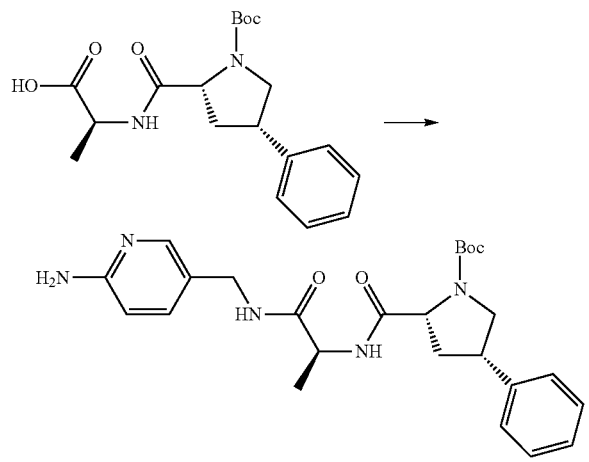

Step 3: ((2R,4S)-1-(tert-Butoxycarbonyl)-4-phenylpyrrolidine-2-carbonyl)-L-alanine was coupled to 5-(aminomethyl)pyridin-2-amine according to the procedure for compound (1243), step 1 to give tert-butyl (2R,4S)-2-(((S)-1-(((6-aminopyridin-3-yl)methyl)amino)-1-oxopropan-2-yl)carbamoyl)-4-phenylpyrrolidine-1-carboxylate (150 mg, 73% yield).

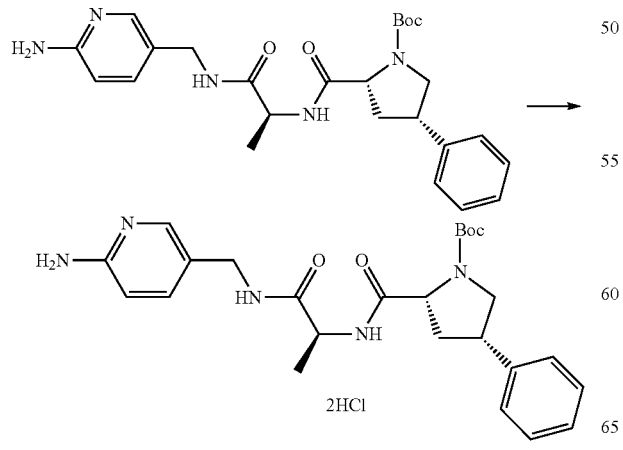

Step 4: tert-Butyl (2R,4S)-2-(((S)-1-(((6-aminopyridin-3-yl)methyl)amino)-1-oxopropan-2-yl)carbamoyl)-4-phenylpyrrolidine-1-carboxylate was deprotected according to the procedure for compound (1243), step 2 except that 5-6 N HCl-IPA was used to give (2R,4S)—N—((S)-1-(((6-aminopyridin-3-yl)methyl)amino)-1-oxopropan-2-yl)-4-phenylpyrrolidine-2-carboxamide dihydrochloride (127 mg, 90% yield).

Example 59. Preparation of (R)—N—((S)-1-((4-Carbamimidoylbenzyl)amino)-1-oxopropan-2-yl)-2-(((6-hydroxynaphthalen-2-yl)methyl)amino)-4-phenylbutanamide Di-trifluoroacetate salt (1256)

(1256)

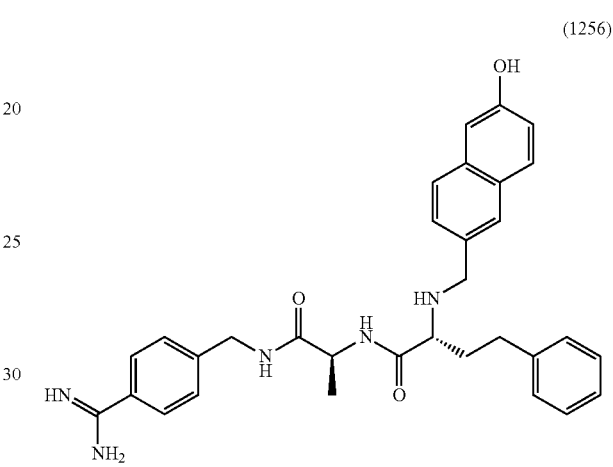

Step 1: Benzyl ((4-(((S)-2-((R)-2-(((6-hydroxynaphthalen-2-yl)methyl)amino)-4-phenylbutanamido)propanamido)methyl)phenyl)(imino)methyl)carbamate was synthesized according to the procedure for compound 1130, step 2.

Step 2: Deprotection of benzyl ((4-(((S)-2-((R)-2-(((6-hydroxynaphthalen-2-yl)methyl)amino)-4-phenylbutanamido)propanamido)methyl)phenyl)(imino)methyl)carbamate according to the procedure for compound 1130, step 3. Purification by reverse phase HPLC (5-75-90% MeCN—H$_2$O) afforded (R)—N—((S)-1-((4-carbamimidoylbenzyl)amino)-1-oxopropan-2-yl)-2-(((6-hydroxynaphthalen-2-yl)methyl)amino)-4-phenylbutanamide di-trifluoroacetate salt.

Example 60. Preparation of (2R,4S)—N—((S)-1-(((6-Amino-2-methylpyridin-3-yl)methyl)amino)-1-oxopropan-2-yl)-4-(m-tolyl)pyrrolidine-2-carboxamide Dihydrochloride (1257)

(1257)

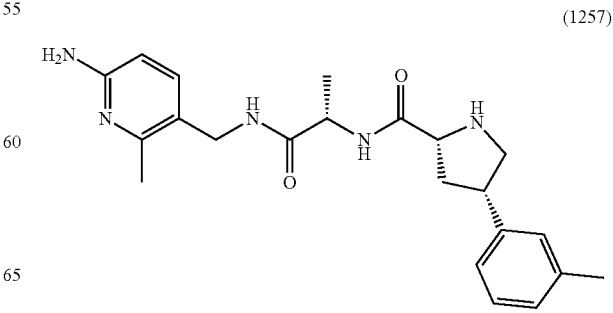

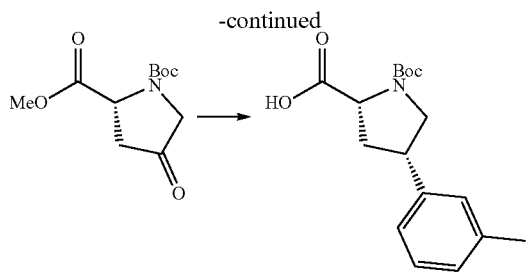

Step 1: (2R,4S)-1-(tert-Butoxycarbonyl)-4-(m-tolyl)pyrrolidine-2-carboxylic acid was synthesized from 1-(tert-butyl) 2-methyl (R)-4-oxopyrrolidine-1,2-dicarboxylate according to the procedures for compound (1247), step 1 to step 4.

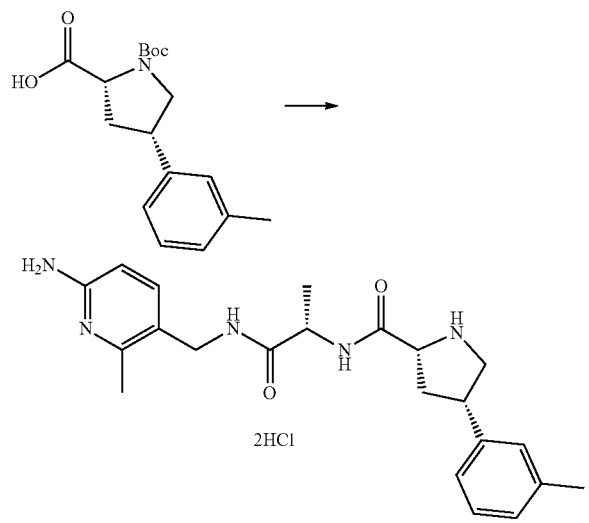

Step 2: (2R,4S)—N—((S)-1-(((6-Amino-2-methylpyridin-3-yl)methyl)amino)-1-oxopropan-2-yl)-4-(m-tolyl)pyrrolidine-2-carboxamide dihydrochloride was synthesized according to the procedures for compound (1304), step 7 to step 8.

Example 61. Preparation of Methyl (imino(4-(((S)-2-((2R,4R)-4-phenylpyrrolidine-2-carboxamido)propanamido)methyl)phenyl)methyl)carbamate (1258)

(1258)

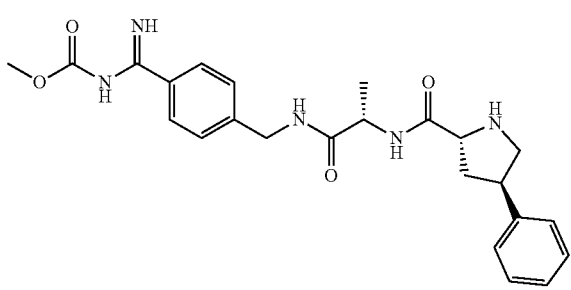

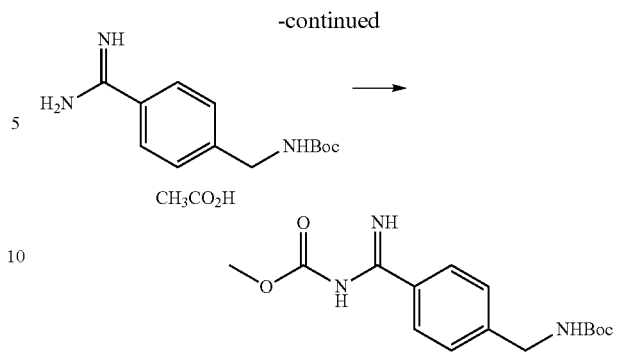

Step 1: To a 0° C. solution of tert-butyl (4-carbamimidoylbenzyl)carbamate acetate salt (100 mg, 0.32 mmol) in $CH_2Cl_2$ (8 mL, 0.04 M) was added DIEA (0.23 mL, 1.3 mmol), DMAP (6.3 mg, 0.05 mmol), and methyl chloroformate (0.03 mL, 0.36 mmol). After stirring for 16 h at room temp, the reaction was quenched by addition of sat. aq $NaHCO_3$. The resulting mixture was extracted with $CH_2Cl_2$, dried over anhyd $Na_2SO_4$, and conc under vacuum. The residue was purified by chromatography (0-100% EtOAc-hexanes) to give methyl ((4-(((tert-butoxycarbonyl)amino)methyl)phenyl)(imino)methyl)carbamate (57 mg, 57% yield) as a white solid.

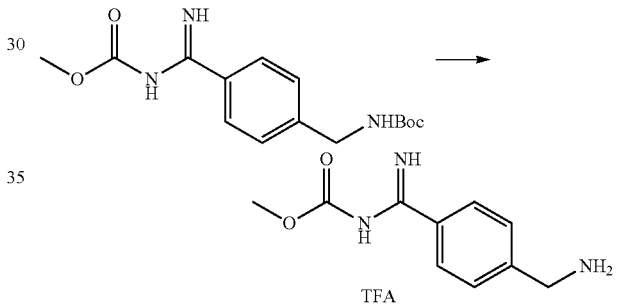

Step 2: Deprotection of ((4-(((tert-butoxycarbonyl)amino)methyl)phenyl) (imino)methyl)carbamate (121 mg, 0.39 mmol) was conducted according to the procedure for compound (1259), step 2 to give methyl ((4-(aminomethyl)phenyl)(imino)methyl)carbamate trifluoroacetate salt (125 mg, 100% yield).

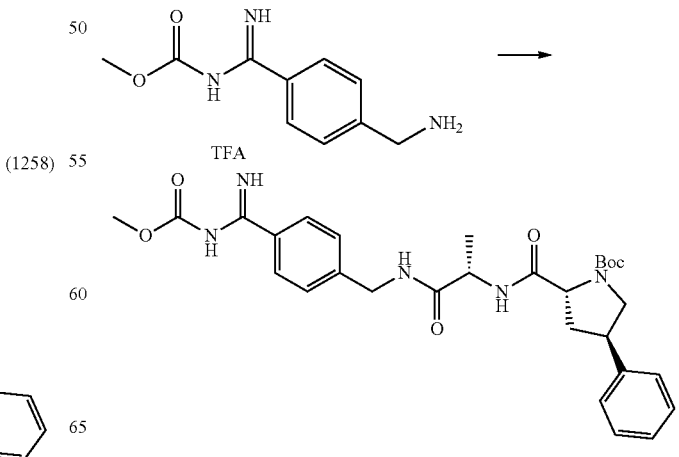

Step 3: Methyl ((4-(aminomethyl)phenyl)(imino)methyl)carbamate trifluoroacetate salt (230 mg, 0.72 mmol) was coupled with ((2R,4R)-1-(tert-butoxycarbonyl)-4-phenylpyrrolidine-2-carbonyl)-L-alanine according to the procedure for compound (1259), step 3 to give tert-butyl (2R,4R)-2-(((S)-1-((4-(N-(methoxycarbonyl)carbamimidoyl)benzyl)amino)-1-oxopropan-2-yl)carbamoyl)-4-phenylpyrrolidine-1-carboxylate (200 mg, 61% yield).

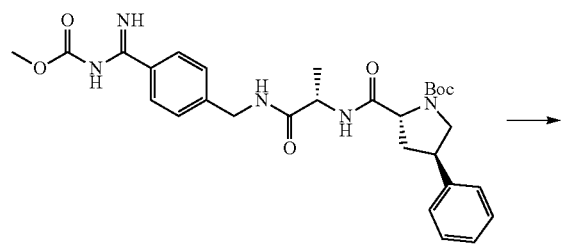

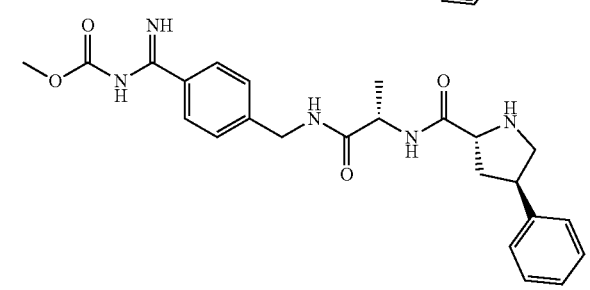

Step 4: Deprotection of tert-butyl (2R,4R)-2-(((S)-1-((4-(N-(methoxycarbonyl)carbamimidoyl)benzyl)amino)-1-oxopropan-2-yl)carbamoyl)-4-phenylpyrrolidine-1-carboxylate (172 mg, 0.31 mmol) was conducted according to the procedure for compound (1259), step 4 to give methyl (imino(4-(((S)-2-((2R,4R)-4-phenylpyrrolidine-2-carboxamido)propanamido)methyl)phenyl)methyl)carbamate (98 mg, 70% yield).

Example 62. Preparation of Benzyl (imino(4-(((S)-2-((2R,4R)-4-phenylpyrrolidine-2-carboxamido)propanamido)methyl)phenyl)methyl)carbamate (1259)

(1259)

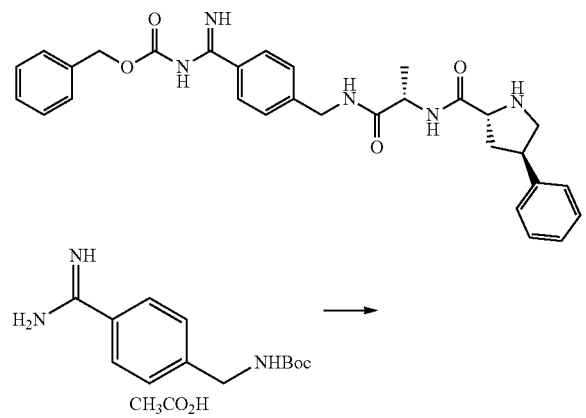

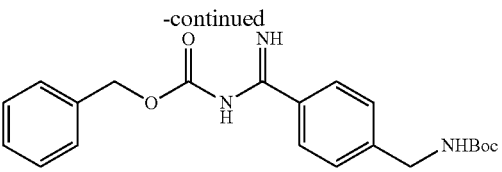

Step 1: To a solution of tert-butyl (4-carbamimidoylbenzyl)carbamate acetate salt (100 mg, 0.32 mmol) in DMF (3 mL, 0.1 M) was added DIEA (0.23 mL, 1.3 mmol) and benzyl chloroformate (30% in toluene, 0.31 mL, 0.65 mmol). After stirring for 16 h at room temperature, $H_2O$ was added and the solvents were removed under vacuum. The residue was partitioned with EtOAc and $H_2O$. The organic layer was separated and washed with sat. aq $NH_4Cl$, $H_2O$, $NaHCO_3$. The organic layer was dried over anhyd $Na_2SO_4$ and cone under vacuum. The residue was purified by chromatography (50-100% EtOAc-hexanes) to give benzyl ((4-(((tert-butoxycarbonyl)amino)methyl)phenyl)(imino)methyl)carbamate (77 mg, 62% yield) as a white solid.

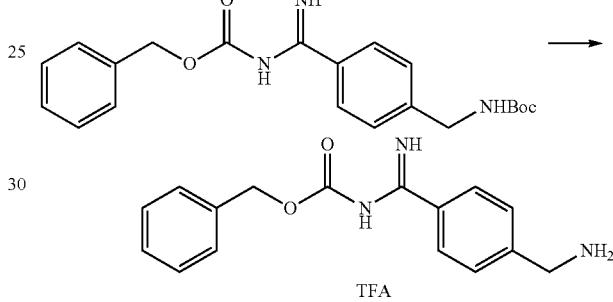

Step 2: To a 0° C. solution of benzyl ((4-(((tert-butoxycarbonyl)amino)methyl)phenyl)(imino)methyl)carbamate (66 mg, 0.17 mmol) in $CH_2Cl_2$ (1.5 mL, 0.1 M) was added 20% TFA in $CH_2Cl_2$ (1.5 mL). After stirring for 2 h at room temperature, the reaction mixture was concentrated to give benzyl ((4-(aminomethyl)phenyl)(imino)methyl)carbamate trifluoroacetate salt (48 mg, 100% yield).

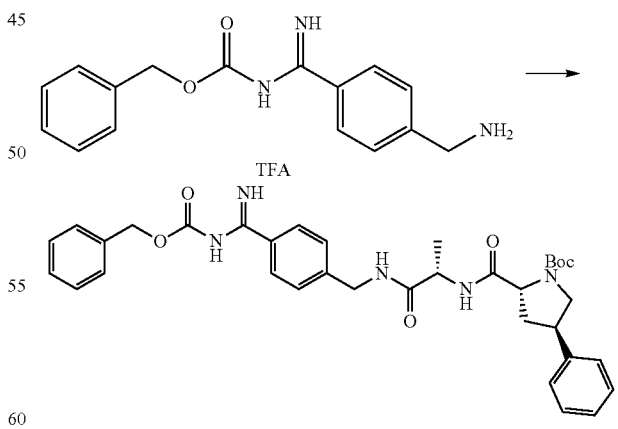

Step 3: To a solution of ((2R,4R)-1-(tert-butoxycarbonyl)-4-phenylpyrrolidine-2-carbonyl)-L-alanine (93 mg, 0.26 mmol) in $CH_2Cl_2$ (5 mL, 0.05 M) was added NHS (33 mg, 0.28 mmol) with stirring at room temp until dissolved. DCC (59 mg, 0.28 mmol) was added and stirred for 1 h. The mixture was poured into a separatory funnel containing sat.

aq NaHCO₃ (5 mL) and benzyl ((4-(aminomethyl)phenyl)(imino)methyl)carbamate trifluoroacetate salt (123 mg, 0.31 mmol) and then shaken for 15 min. The organic layer was filtered through over a bed of anhyd Na₂SO₄ and evaporated to dryness. The residue was purified by chromatography (50-100% EtOAc-hexanes) to give tert-butyl (2R,4R)-2-(((S)-1-((4-(N-((benzyloxy)carbonyl)carbamimidoyl)benzyl)amino)-1-oxopropan-2-yl)carbamoyl)-4-phenylpyrrolidine-1-carboxylate (128 mg, 79% yield).

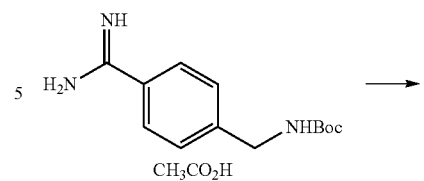

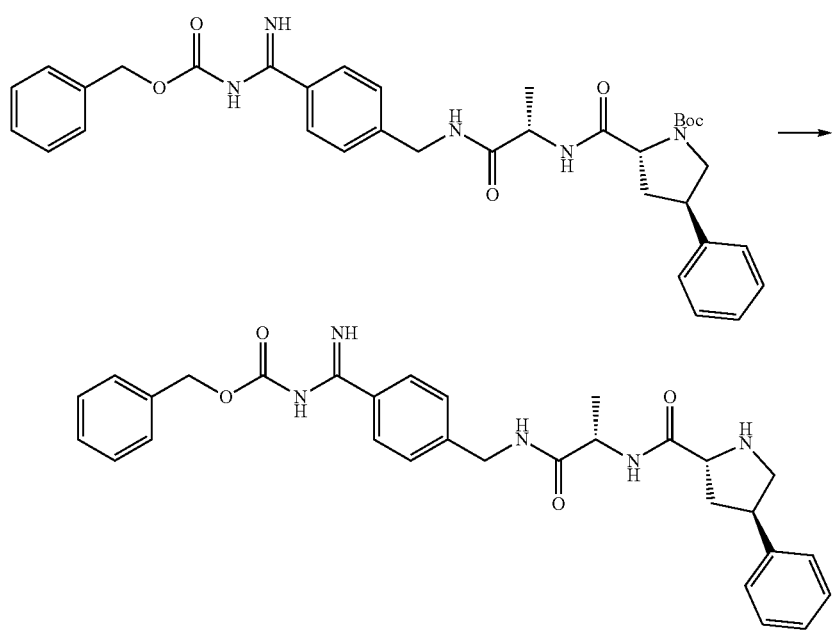

Step 4: To a suspension of tert-butyl (2R,4R)-2-(((S)-1-((4-(N-((benzyloxy)carbonyl)carbamimidoyl)benzyl)amino)-1-oxopropan-2-yl)carbamoyl)-4-phenylpyrrolidine-1-carboxylate (128 mg, 0.2 mmol) in methanol (2 mL, 0.1 M), was added a solution of HCl/MeOH (2 mL, 227 mg HCl/mL). After stirring for 4 h at room temperature, the reaction mixture was concentrated. The residue was purified by chromatography (0-100% [5% 7 N NH₃ in MeOH/CH₂Cl₂]—CH₂Cl₂) to give benzyl (imino(4-(((S)-2-((2R,4R)-4-phenylpyrrolidine-2-carboxamido)propanamido)methyl)phenyl)methyl)carbamate (60 mg, 56% yield).

Example 63. Preparation of Hexyl (imino(4-(((S)-2-((2R,4R)-4-phenylpyrrolidine-2-carboxamido)propanamido)methyl)phenyl)methyl)carbamate (1260)

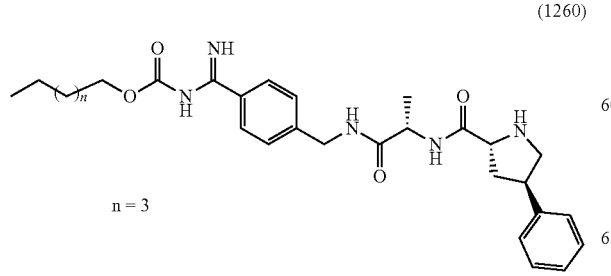

(1260)

n = 3

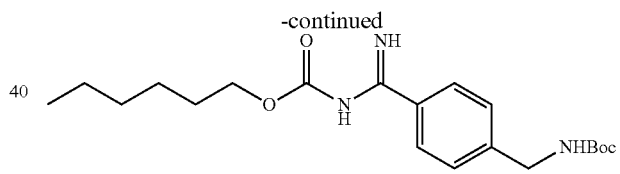

Step 1: To a 0° C. solution of tert-butyl (4-carbamimidoylbenzyl)carbamate acetate salt (200 mg, 0.65 mmol) in CH₂Cl₂ (8 mL, 0.08 M) was added DIEA (0.23 mL, 1.3 mmol). After stirring for 15 min at the same temperature, hexyl chloroformate (0.13 mL, 0.78 mmol) was added dropwise. After stirring for 1 h at the same temperature, the reaction was quenched by addition of H₂O. The resulting mixture was extracted with CH₂Cl₂, dried over anhyd Na₂SO₄, and conc under vacuum. The residue was purified by chromatography (0-100% EtOAc-hexanes) to give tert-butyl (4-(N-((hexyloxy)carbonyl)carbamimidoyl)benzyl)carbamate (151 mg, 62% yield).

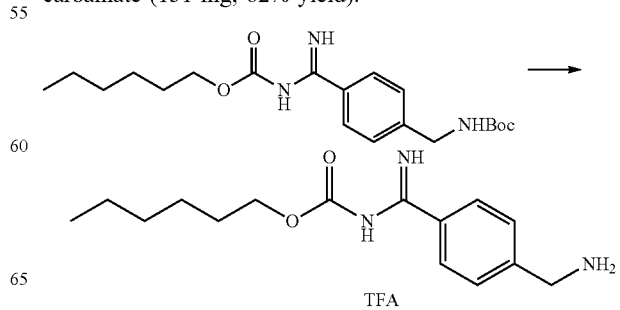

TFA

Step 2: Deprotection of tert-butyl (4-(N-((hexyloxy)carbonyl)carbamimidoyl)benzyl)carbamate (150 mg, 0.4 mmol) was conducted according to the procedure for compound (1259), step 2 to give hexyl ((4-(aminomethyl)phenyl)(imino)methyl)carbamate trifluoroacetate salt (155 mg, 100% yield).

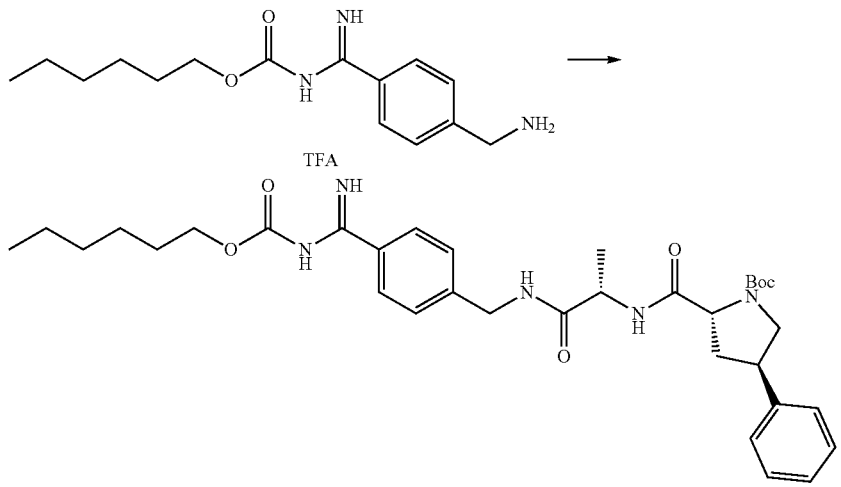

Step 3: Hexyl ((4-(aminomethyl)phenyl)(imino)methyl) carbamate trifluoroacetate salt (140 mg, 0.39 mmol) was coupled with ((2R,4R)-1-(tert-butoxycarbonyl)-4-phenylpyrrolidine-2-carbonyl)-L-alanine according to the procedure for compound (1259), step 3 to give tert-butyl (2R,4R)-2-(((S)-1-((4-(N-((hexyloxy)carbonyl)carbamimidoyl)benzyl)amino)-1-oxopropan-2-yl)carbamoyl)-4-phenylpyrrolidine-1-carboxylate (230 mg, 96% yield).

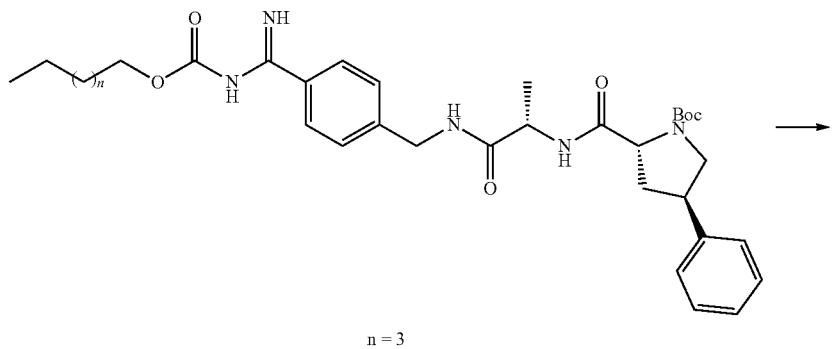

n = 3

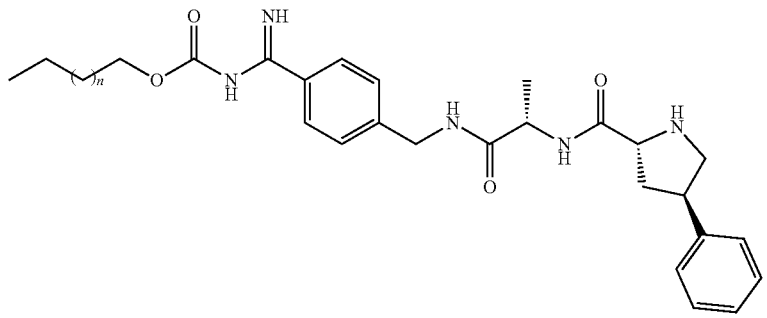

n = 3

Step 4: To a 0° C. solution of tert-butyl (2R,4R)-2-(((S)-1-((4-(N-((hexyloxy)carbonyl)carbamimidoyl)benzyl)amino)-1-oxopropan-2-yl)carbamoyl)-4-phenylpyrrolidine-1-carboxylate (230 mg, 0.37 mmol) in CH$_2$Cl$_2$ (3.5 mL, 0.11 M) was added 20% TFA in CH$_2$Cl$_2$ (3.5 mL). After stirring for 3 h at room temp, the reaction mixture was concentrated. The residue was purified by chromatography (0-100% [5% 7 N NH$_3$ in MeOH/CH$_2$Cl$_2$]—CH$_2$Cl$_2$) to give hexyl (imino (4-(((S)-2-((2R,4R)-4-phenylpyrrolidine-2-carboxamido)propanamido)methyl)phenyl)methyl)carbamate (131 mg, 68% yield).

Example 64. Preparation of (R, E)-2-Amino-N—((S)-1-(((6-aminopyridin-3-yl)methyl)amino)-1-oxopropan-2-yl)-5-phenylpent-4-enamide Dihydrochloride (1261)

(1261)

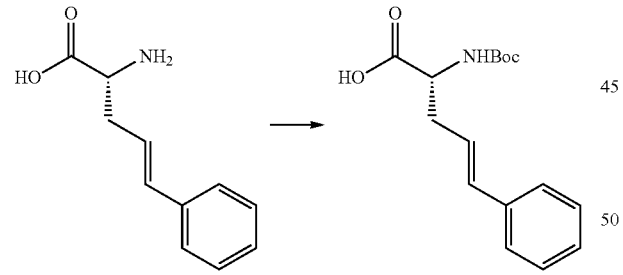

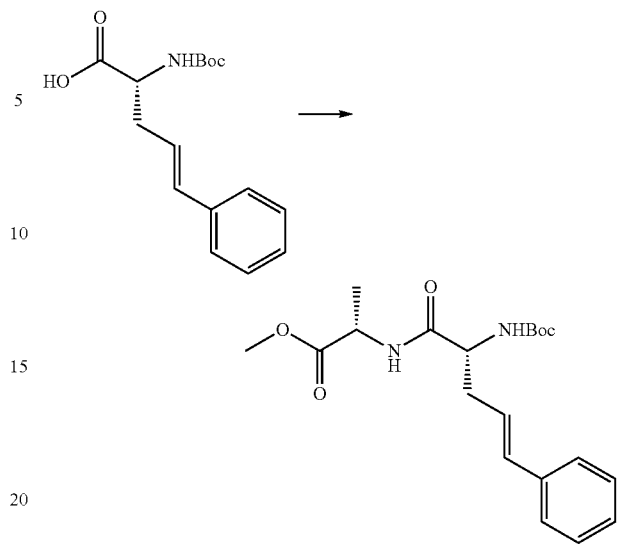

Step 2: To a solution of (R, E)-2-((tert-butoxycarbonyl)amino)-5-phenylpent-4-enoic acid (1.53 g, 5.25 mmol) in anhyd MeCN (27 mL) under Ar was added DIEA (2.0 mL, 11.5 mmol). EDC (1.1 g, 5.7 mmol) and HOBt (0.79 g, 5.8 mmol) were added and the mixture was stirred for 35 min. Methyl L-alaninate hydrochloride (0.89 g, 6.4 mmol) was added and the reaction stirred overnight. The mixture was conc in vacuo and the residue was dissolved in EtOAc, washed with 0.5 M KHSO$_4$ 2×, H$_2$O, then sat NaHCO$_3$. The solution was dried (Na$_2$SO$_4$), conc in vacuo and purified by chromatography (0-35% EtOAc-hexanes) to give a sticky solid which was dissolved in MeCN—H$_2$O and lyophilized. 1.3 g Of methyl ((R,E)-2-((tert-butoxycarbonyl)amino)-5-phenylpent-4-enoyl)-L-alaninate was isolated (66% yield).

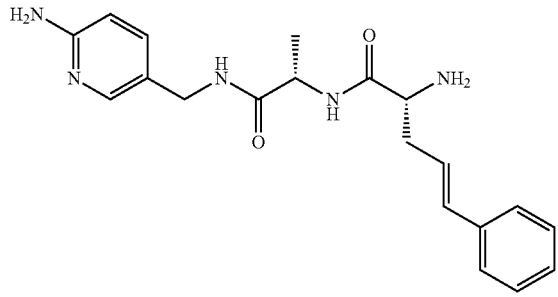

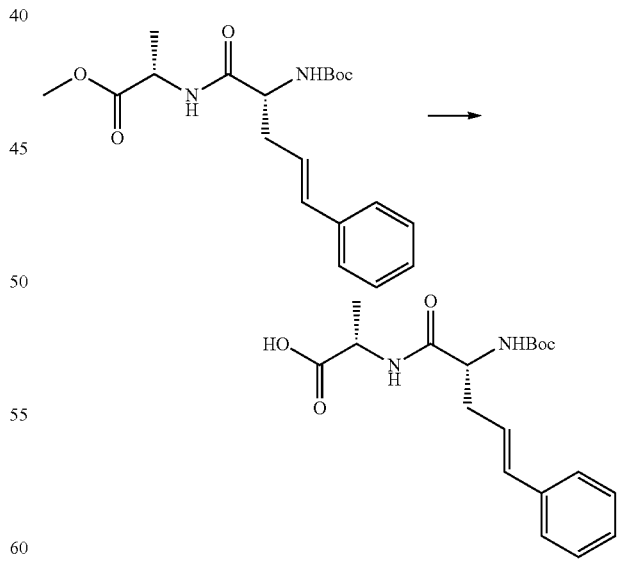

Step 1: To a solution of (R, E)-2-amino-5-phenylpent-4-enoic acid (0.97 g, 5.07 mmol) in THF (15 mL), di-tert-butyl dicarbonate (1.1 g, 5.04 mmol) was added followed by a solution of NaHCO$_3$ (1.2 g, 14.3 mmol) in H$_2$O (15 mL). The reaction mixture was cooled briefly over an ice bath and stirred for 1.5 h. Additional THF (10 mL) and sat. NaHCO$_3$ (1 mL) were added. The mixture was stirred overnight then EtOAc was added and the mixture acidified with 0.5 M KHSO$_4$. The layers were separated, the aq layer was saturated with NaCl and extracted twice with EtOAc. The combined organics were washed with brine, dried (Na$_2$SO$_4$) and conc in vacuo to give (R, E)-2-((tert-butoxycarbonyl)amino)-5-phenylpent-4-enoic acid (1.53 g, quant. yield).

Step 3: Methyl ((R,E)-2-((tert-butoxycarbonyl)amino)-5-phenylpent-4-enoyl)-L-alaninate was hydrolyzed according to the procedure for compound 1058 to give ((R,E)-2-((tert-butoxycarbonyl)amino)-5-phenylpent-4-enoyl)-L-alanine (484 mg, quant. yield).

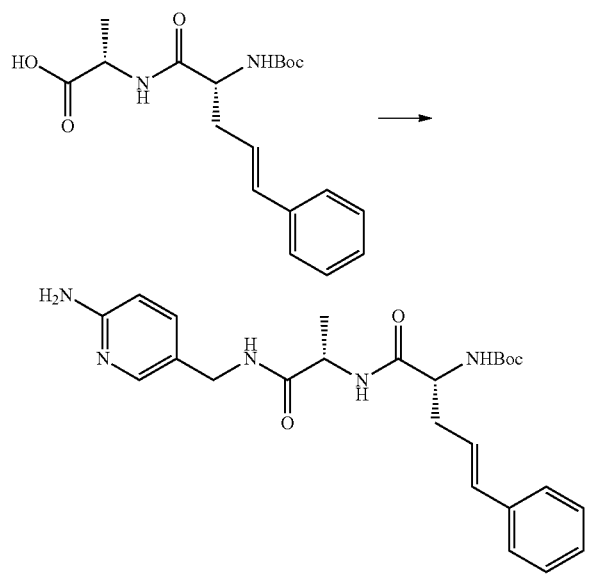

Step 4: ((R,E)-2-((tert-Butoxycarbonyl)amino)-5-phenyl-pent-4-enoyl)-L-alanine was coupled to 5-(aminomethyl)pyridin-2-amine according to the procedure for compound (1243), step 1 to give tert-butyl ((R,E)-1-(((S)-1-(((6-aminopyridin-3-yl)methyl)amino)-1-oxopropan-2-yl)amino)-1-oxo-5-phenylpent-4-en-2-yl)carbamate (116 mg, 91% yield).

Step 5: tert-Butyl ((R,E)-1-(((S)-1-(((6-aminopyridin-3-yl)methyl)amino)-1-oxopropan-2-yl)amino)-1-oxo-5-phenylpent-4-en-2-yl)carbamate was deprotected according to the procedure for compound (1255) to give (R,E)-2-amino-N—((S)-1-(((6-aminopyridin-3-yl)methyl)amino)-1-oxopropan-2-yl)-5-phenylpent-4-enamide dihydrochloride (101 mg, 93% yield).

Example 65. Preparation of (2R,4S)—N—((S)-1-((4-Carbamimidoylbenzyl)amino)-1-oxopropan-2-yl)-4-(3-methoxyphenyl)pyrrolidine-2-carboxamide Dihydrochloride (1262)

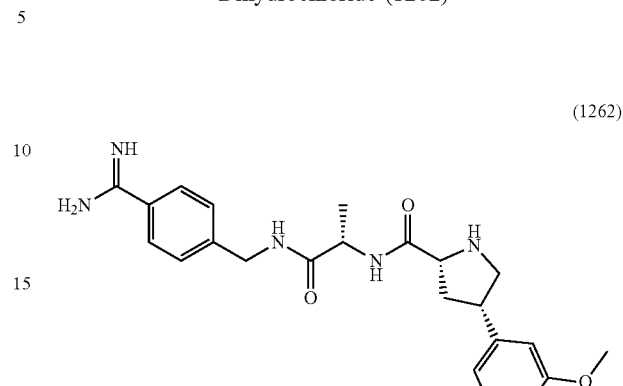

(2R,4S)—N—((S)-1-((4-Carbamimidoylbenzyl)amino)-1-oxopropan-2-yl)-4-(3-methoxyphenyl)pyrrolidine-2-carboxamide dihydrochloride was synthesized according to the procedures for compound (1247).

Example 66. Preparation of Propyl (imino(4-(((S)-2-((2R,4R)-4-phenylpyrrolidine-2-carboxamido)propanamido)methyl)phenyl)methyl)carbamate (1263)

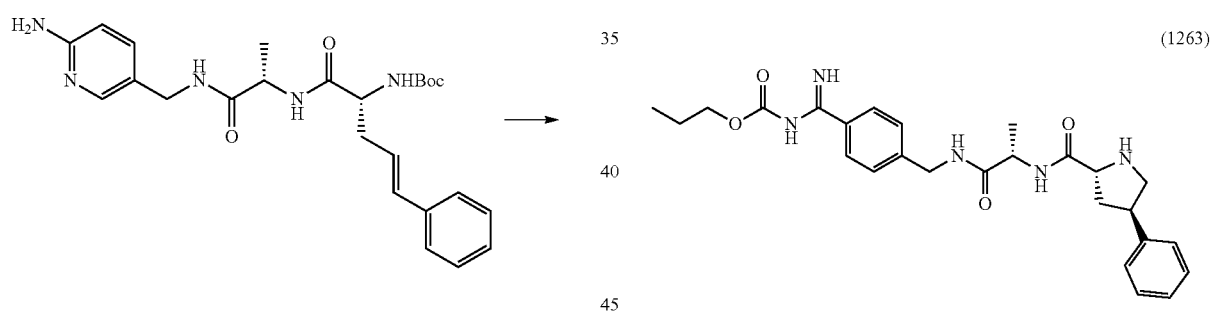

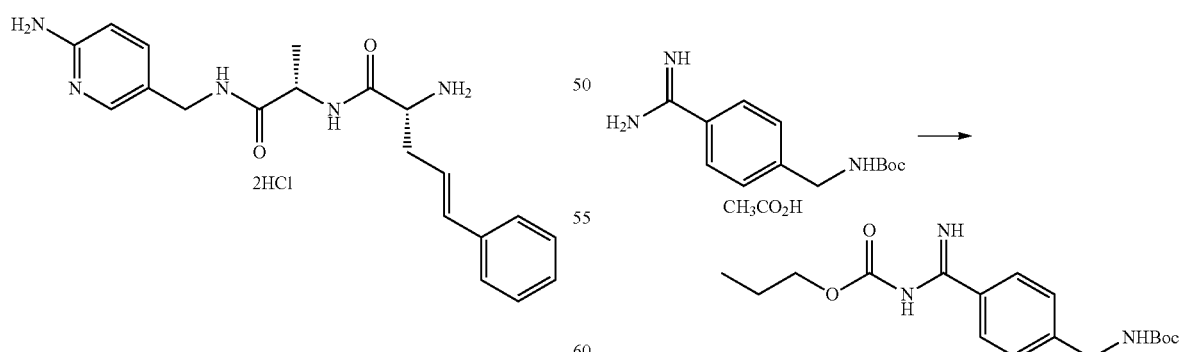

Step 1: tert-Butyl (4-(N-(propoxycarbonyl)carbamimidoyl)benzyl)carbamate (108 mg, 50% yield) was synthesized from tert-butyl (4-carbamimidoylbenzyl)carbamate acetate salt (198 mg, 0.64 mmol) and propyl chloroformate according to the procedure for compound (1260), step 1.

411

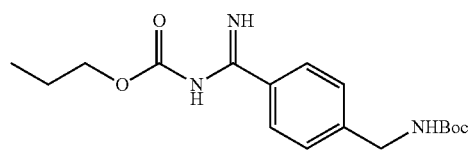

412

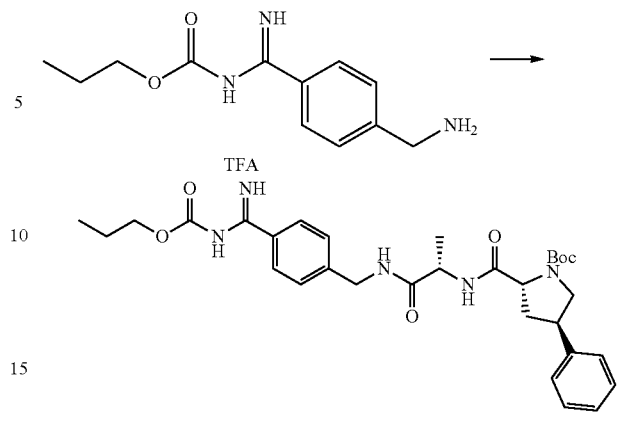

Step 2: Deprotection of tert-butyl (4-(N-(propoxycarbonyl)carbamimidoyl)benzyl)-carbamate (108 mg, 0.32 mmol) was conducted according to the procedure for compound (1259), step 2 to give propyl ((4-(aminomethyl)phenyl)(imino)methyl)carbamate trifluoroacetate salt (112 mg, 100% yield).

Step 3: Propyl ((4-(aminomethyl)phenyl)(imino)methyl)carbamate trifluoroacetate salt (125 mg, 0.32 mmol) was coupled with ((2R,4R)-1-(tert-butoxycarbonyl)-4-phenylpyrrolidine-2-carbonyl)-L-alanine according to the procedure for compound (1259), step 3 to give tert-butyl (2R,4R)-2-(((S)-1-oxo-1-((4-(N-(propoxycarbonyl)carbamimidoyl)benzyl)amino)propan-2-yl)carbamoyl)-4-phenylpyrrolidine-1-carboxylate (176 mg, 95% yield).

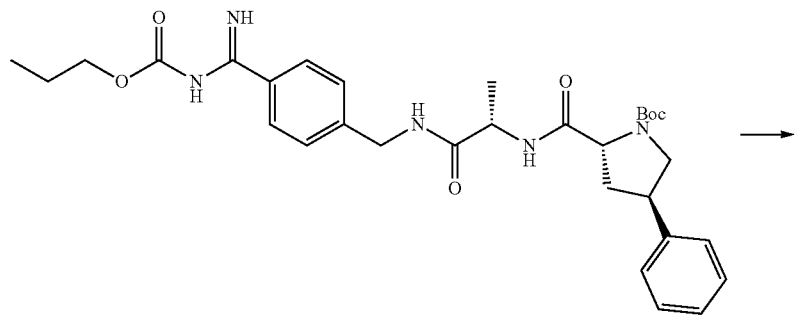

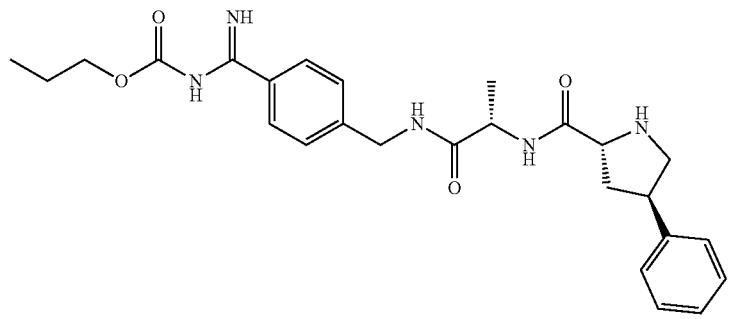

Step 4: Deprotection of tert-butyl (2R,4R)-2-(((S)-1-oxo-1-((4-(N-(propoxycarbonyl)carbamimidoyl)benzyl)amino)propan-2-yl)carbamoyl)-4-phenylpyrrolidine-1-carboxylate (176 mg, 0.3 mmol) was conducted according to the procedure for compound (1260), step 4 to give propyl (imino(4-(((S)-2-((2R,4R)-4-phenylpyrrolidine-2-carboxamido)propanamido)methyl)phenyl)methyl)carbamate (89 mg, 62% yield).

Example 67. Preparation of (2R,4R)—N—((S)-1-((4-((Z)—N'-Acetoxycarbamimidoyl)benzyl)amino)-1-oxopropan-2-yl)-4-phenylpyrrolidine-2-carboxamide (1264)

(1264)

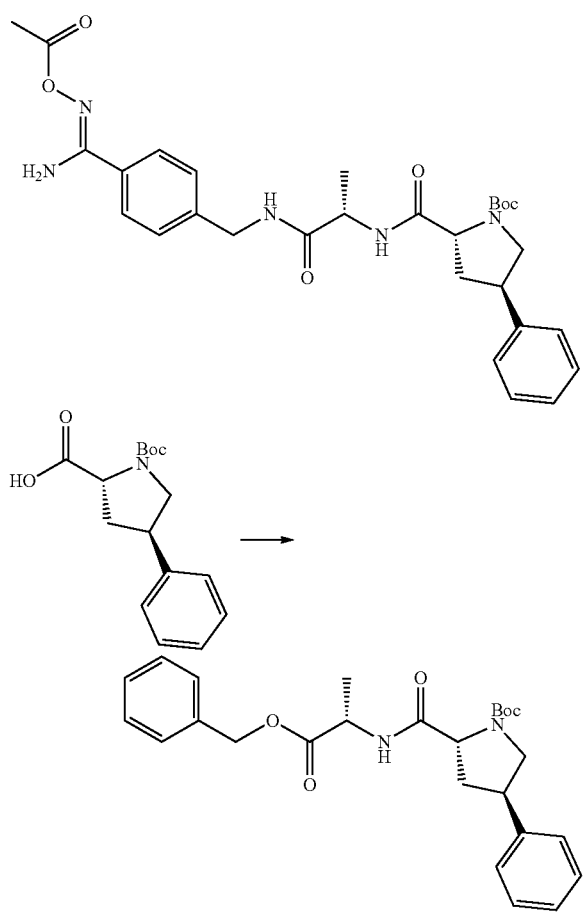

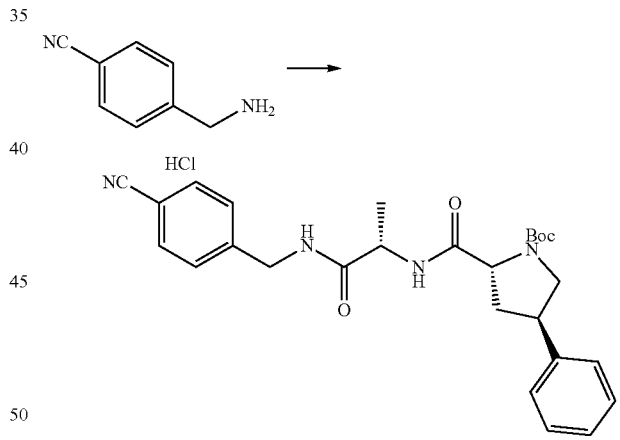

Step 2: A solution of the crude tert-butyl (2R,4R)-2-(((S)-1-(benzyloxy)-1-oxopropan-2-yl)carbamoyl)-4-phenylpyrrolidine-1-carboxylate (1.55 g, 3.42 mmol) was degassed with a stream of Ar for 2 min. 10% Pd/C (70 mg) was added and a vacuum was pulled for 1 min. A balloon of $H_2$ was added and the reaction was monitored for the consumption of starting material for 1.5 h. The catalyst was removed by filtration and the solution was evaporated to give ((2R,4R)-1-(tert-butoxycarbonyl)-4-phenylpyrrolidine-2-carbonyl)-L-alanine (1.24 g, 100% yield).

Step 1: To a solution of (2R,4R)-1-(tert-butoxycarbonyl)-4-phenylpyrrolidine-2-carboxylic acid (1.0 g, 3.43 mmol) in MeCN (70 mL, 0.05 M) was added HOBt (577 mg, 3.77 mmol), DIEA (2.39 mL, 13.7 mmol), and EDC (585 mg, 3.77 mmol). After stirring for 30 min at room temperature, benzyl L-alanine hydrochloride (814 mg, 3.77 mmol) was added and stirred for 16 h. The reaction mixture was conc and the residue was partitioned with EtOAc and 10% $KHSO_4$ solution. The organic layer was separated and washed with $H_2O$ and sat. aq $NaHCO_3$. The organic layer was dried over anhyd $Na_2SO_4$ and conc under vacuum to give the crude tert-butyl (2R,4R)-2-(((S)-1-(benzyloxy)-1-oxopropan-2-yl)carbamoyl)-4-phenylpyrrolidine-1-carboxylate (1.33 g, 86% yield) which was used in the next step without further purification.

Step 3: To a solution of ((2R,4R)-1-(tert-butoxycarbonyl)-4-phenylpyrrolidine-2-carbonyl)-L-alanine (1.16 g, 3.2 mmol) in $CH_2Cl_2$ (50 mL, 0.06 M) was added NHS (405 mg, 3.52 mmol) with stirring at room temp until dissolved. DCC (726 mg, 3.52 mmol) was added and stirred for 1 h. The mixture was poured into a separatory funnel containing sat. aq $NaHCO_3$ (50 mL) and 4-(aminomethyl)benzonitrile hydrochloride (647 mg, 3.84 mmol) and then shaken for 15 min. The organic layer was filtered through over a bed of anhyd $Na_2SO_4$ and evaporated to dryness. The residue was purified by chromatography (50-100% EtOAc-hexanes) to give tert-butyl (2R,4R)-2-(((S)-1-((4-cyanobenzyl)amino)-1-oxopropan-2-yl)carbamoyl)-4-phenylpyrrolidine-1-carboxylate (1.3 g, 85% yield) as a white solid.

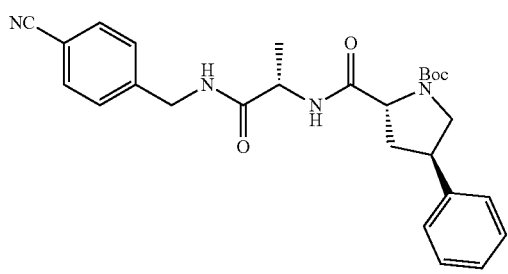

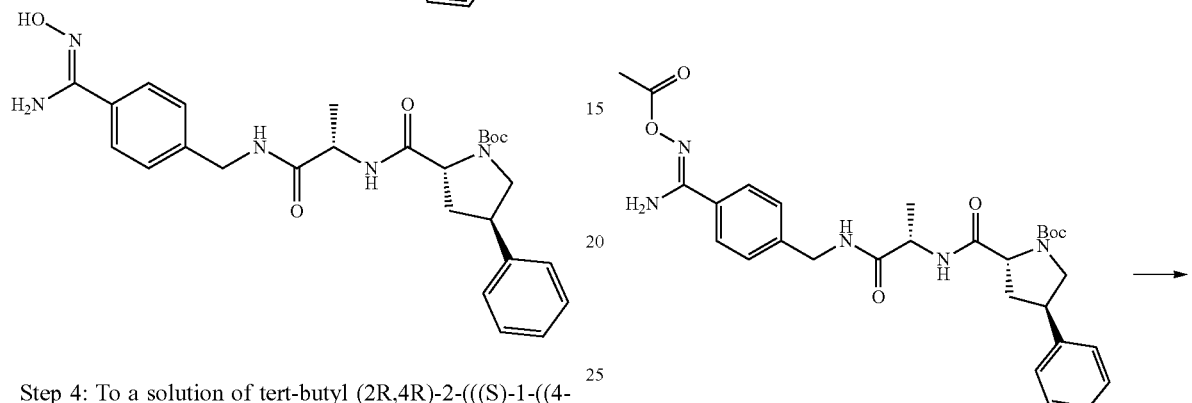

Step 4: To a solution of tert-butyl (2R,4R)-2-(((S)-1-((4-cyanobenzyl)amino)-1-oxopropan-2-yl)carbamoyl)-4-phenylpyrrolidine-1-carboxylate (870 mg, 1.83 mmol) in MeOH (20 mL, 0.09 mmol) was added hydroxylamine hydrochloride (507 mg, 7.3 mmol) and DIEA (1.27 mL, 7.3 mmol). After stirring for 4 h at reflux, the reaction mixture was evaporated to dryness. The residue was purified by chromatography (0-100% EtOAc-hexanes) to give tert-butyl (2R,4R)-2-(((S)-1-((4-((Z)—N'-hydroxycarbamimidoyl)benzyl)amino)-1-oxopropan-2-yl)carbamoyl)-4-phenylpyrrolidine-1-carboxylate (670 mg, 72% yield).

Step 5: To a suspension of tert-butyl (2R,4R)-2-(((S)-1-((4-((Z)—N-hydroxycarbamimidoyl)benzyl)amino)-1-oxopropan-2-yl)carbamoyl)-4-phenylpyrrolidine-1-carboxylate (239 mg, 0.47 mmol) in acetic acid (5 mL) was added acetic anhydride (1 mL). After stirring for 17 h at room temperature, the reaction mixture was concd. The residue was purified by chromatography (0-100% EtOAc-hexanes) to give tert-butyl (2R,4R)-2-(((S)-1-((4-((Z)—N-acetoxycarbamimidoyl)benzyl)amino)-1-oxopropan-2-yl)carbamoyl)-4-phenylpyrrolidine-1-carboxylate (180 mg, 70% yield).

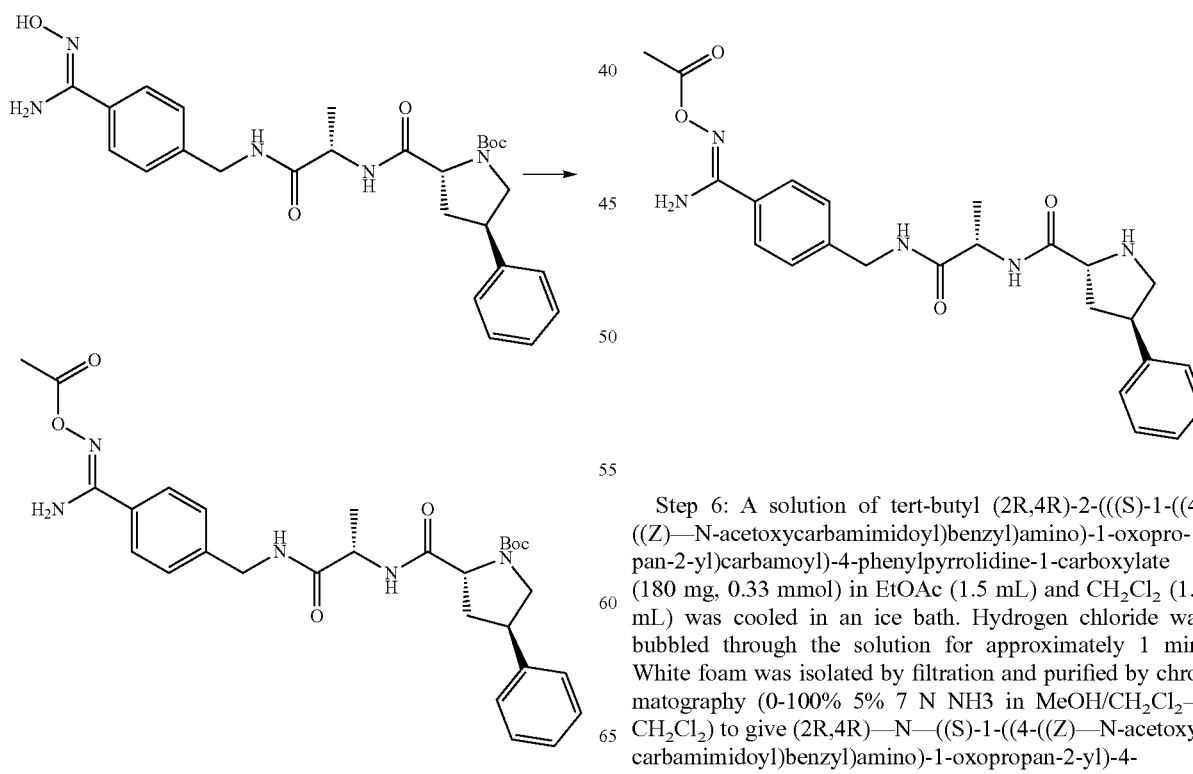

Step 6: A solution of tert-butyl (2R,4R)-2-(((S)-1-((4-((Z)—N-acetoxycarbamimidoyl)benzyl)amino)-1-oxopropan-2-yl)carbamoyl)-4-phenylpyrrolidine-1-carboxylate (180 mg, 0.33 mmol) in EtOAc (1.5 mL) and $CH_2Cl_2$ (1.5 mL) was cooled in an ice bath. Hydrogen chloride was bubbled through the solution for approximately 1 min. White foam was isolated by filtration and purified by chromatography (0-100% 5% 7 N NH3 in MeOH/$CH_2Cl_2$—$CH_2Cl_2$) to give (2R,4R)—N—((S)-1-((4-((Z)—N-acetoxycarbamimidoyl)benzyl)amino)-1-oxopropan-2-yl)-4-phenylpyrrolidine-2-carboxamide (62 mg, 42% yield).

Example 68. Preparation of (2R,4R)—N—((S)-1-(((6-Amino-2-methylpyridin-3-yl)methyl)amino)-1-oxopropan-2-yl)-4-phenylpyrrolidine-2-carboxamide Dihydrochloride (1265)

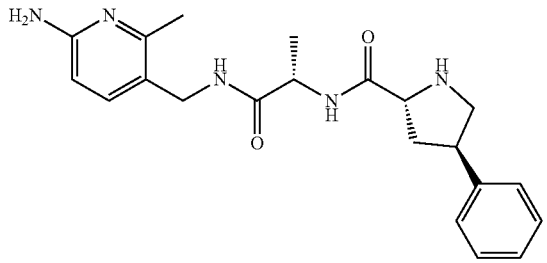
(1265)

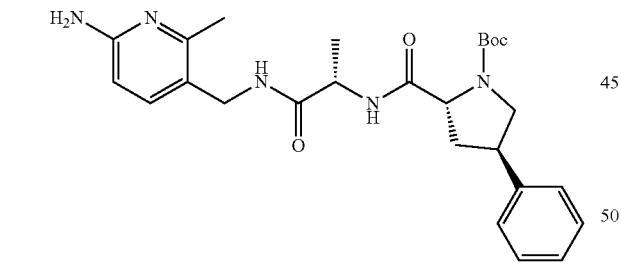

Step 1: To a solution of ((2R,4R)-1-(tert-butoxycarbonyl)-4-phenylpyrrolidine-2-carbonyl)-L-alanine (93 mg, 0.26 mmol, prepared according to the procedure for compound (1255) in CH$_2$Cl$_2$ (5 mL) was added NHS (33 mg, 0.28 mmol). The mixture was stirred for 70 min then DCC was added. After stirring for 70 min, 5-(aminomethyl)-6-methylpyridin-2-amine (47 mg, 0.34 mmol) was added. The mixture was stirred for 3 h then conc in vacuo to a smaller volume, filtered through a cotton plug and rinsed with 5% EtOAC-CH$_2$Cl$_2$. The filtrate was conc in vacuo then purified by chromatography (0-10% MeOH—CH$_2$Cl$_2$) to give tert-butyl (2R,4R)-2-(((S)-1-(((6-amino-2-methylpyridin-3-yl)methyl)amino)-1-oxopropan-2-yl)carbamoyl)-4-phenylpyrrolidine-1-carboxylate (93 mg, 75% yield).

Step 2: tert-Butyl (2R,4R)-2-(((S)-1-(((6-amino-2-methylpyridin-3-yl)methyl)amino)-1-oxopropan-2-yl)carbamoyl)-4-phenylpyrrolidine-1-carboxylate was deprotected according to the procedure for compound (1255). The lyophilized solid was dissolved in MeOH, treated with Darco® charcoal (10 mg), warmed, then cooled to ambient temperature and filtered (0.20 μm syringe filter). The filtrate was conc in vacuo to give (2R,4R)—N—((S)-1-(((6-amino-2-methylpyridin-3-yl)methyl)amino)-1-oxopropan-2-yl)-4-phenylpyrrolidine-2-carboxamide (81.8 mg, 93% yield).

Example 69. Preparation of (R)-2-Amino-N—((S)-1-(((6-amino-5-methoxypyridin-3-yl)methyl)amino)-1-oxopropan-2-yl)-4-phenylbutanamide Dihydrochloride (1266)

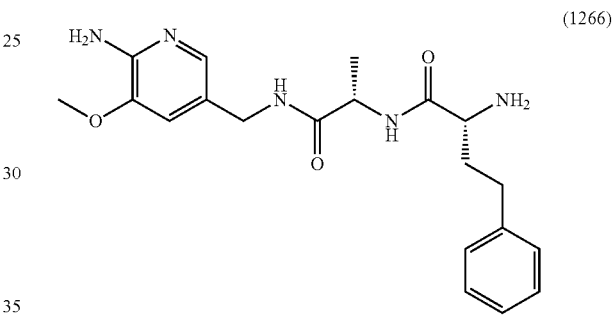
(1266)

(R)-2-Amino-N—((S)-1-(((6-amino-5-methoxypyridin-3-yl)methyl)amino)-1-oxopropan-2-yl)-4-phenylbutanamide dihydrochloride was synthesized according to the procedure for compound (1243).

Example 70. Preparation of (R)-2-amino-N—((S)-1-(((6-amino-5-fluoropyridin-3-yl)methyl)amino)-1-oxopropan-2-yl)-4-phenylbutanamide Dihydrochloride (1267)

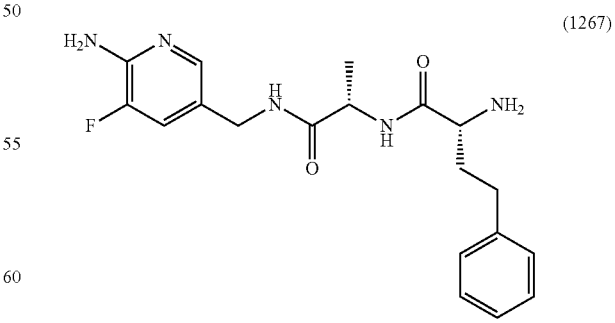
(1267)

(R)-2-Amino-N—((S)-1-(((6-amino-5-fluoropyridin-3-yl)methyl)amino)-1-oxopropan-2-yl)-4-phenylbutanamide dihydrochloride was synthesized according to the procedure for compound (1243).

419

Example 71. Preparation of 4-((((R)-1-(((S)-1-((4-Carbamimidoylbenzyl)amino)-1-oxopropan-2-yl)amino)-1-oxo-4-phenylbutan-2-yl)amino)methyl)benzamide Di-trifluoroacetate salt 1268)

(1268)

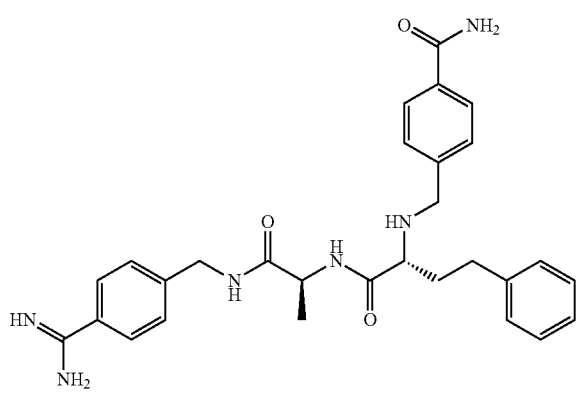

Step 1: Benzyl ((4-(((S)-2-((R)-2-((4-carbamoylbenzyl)amino)-4-phenylbutanamido)propanamido)methyl)phenyl)(imino)methyl)carbamate was synthesized according to the procedure for compound 1130, step 2.

Step 2: Deprotection of benzyl ((4-(((S)-2-((R)-2-((4-carbamoylbenzyl)amino)-4-phenylbutanamido)propanamido)methyl)phenyl)(imino)methyl)carbamate according to the procedure for compound 1130, step 3. Purification by reverse phase HPLC (5-75-90% MeCN—H₂O) afforded 4-((((R)-1-(((S)-1-((4-carbamimidoylbenzyl)amino)-1-oxopropan-2-yl)amino)-1-oxo-4-phenylbutan-2-yl)amino)methyl)benzamide di-trifluoroacetate salt.

Example 72. Preparation of (2R,4R)—N—((S)-1-((2-Acetamido-5-chlorobenzyl)amino)-1-oxopropan-2-yl)-4-phenylpyrrolidine-2-carboxamide Hydrochloride (1269)

(1269)

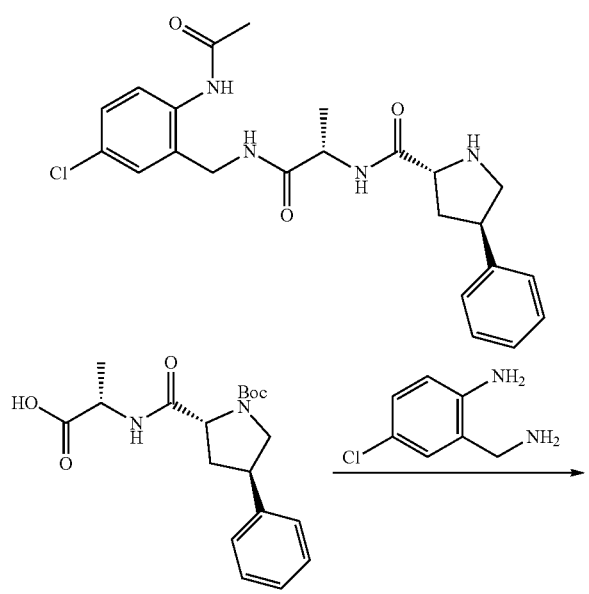

420

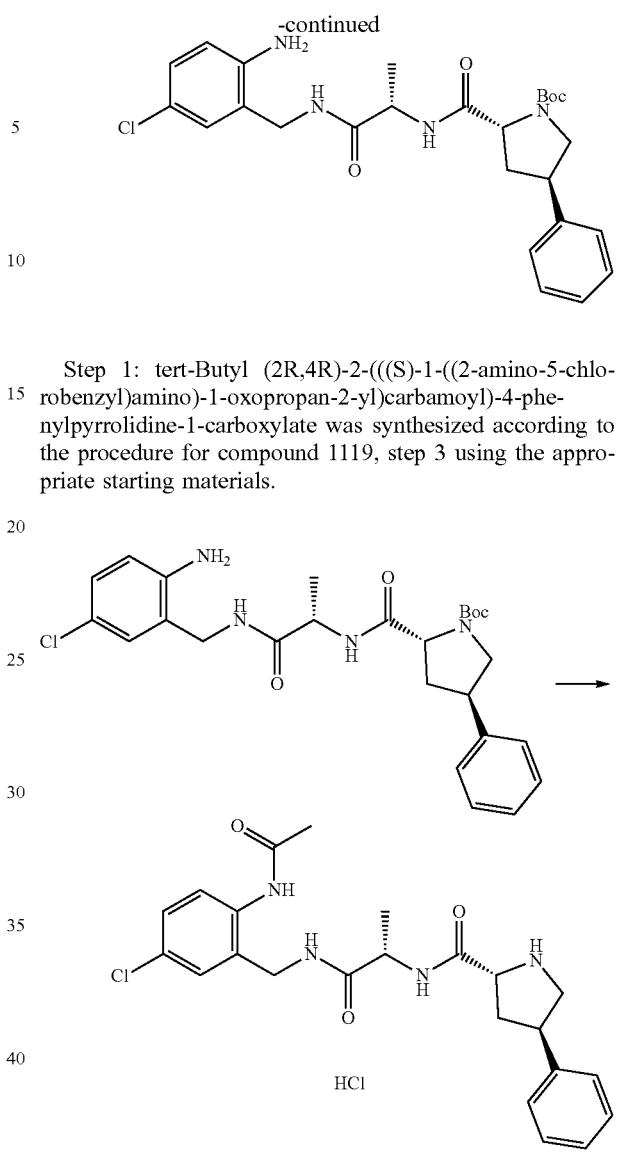

Step 1: tert-Butyl (2R,4R)-2-(((S)-1-((2-amino-5-chlorobenzyl)amino)-1-oxopropan-2-yl)carbamoyl)-4-phenylpyrrolidine-1-carboxylate was synthesized according to the procedure for compound 1119, step 3 using the appropriate starting materials.

Steps 2-3: tert-Butyl (2R,4R)-2-(((S)-1-((2-amino-5-chlorobenzyl)amino)-1-oxopropan-2-yl)carbamoyl)-4-phenylpyrrolidine-1-carboxylate (30 mg, 0.06 mmol) was dissolved in CH₂Cl₂ (1 mL) and treated with Ac₂O (28 µL, 0.3 mmol) and Et₃N (42 µL, 0.06 mmol) then stirred for 6 h at ambient temperature. The reaction mixture was diluted with CH₂Cl₂ and washed with 10% aq KHSO₄, brine and sat. aq NaHCO₃. The organic layer was dried over Na₂SO₄ and concentrated, then the residue purified by chromatography (80-95% EtOAc-hexanes) to furnish tert-butyl (2R,4R)-2-(((S)-1-((2-acetamido-5-chlorobenzyl)amino)-1-oxopropan-2-yl)carbamoyl)-4-phenylpyrrolidine-1-carboxylate as a colorless oil. Removal of the Boc protecting group was achieved upon treatment with 3 M HCl in iPrOH overnight at ambient temperature. Removal of iPrOH and lyophilization in a mixture of 1:1 ACN/H₂O gave the title compound as a white powder (15.9 mg, 52% yield over 2 steps).

Example 73. Preparation of (R)-2-Amino-N—((S)-1-(((6-carbamimidoylpyridin-3-yl)methyl)amino)-1-oxopropan-2-yl)-4-phenylbutanamide Di-trifluoroacetate salt (1270)

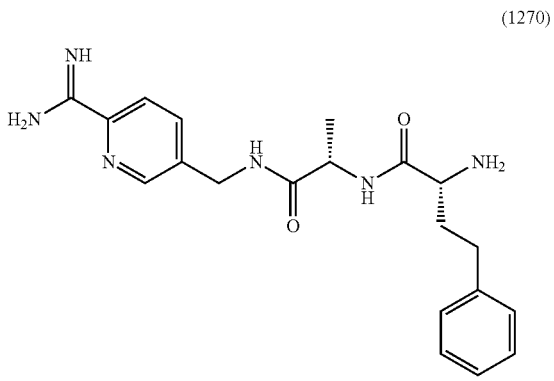 [SMILES: C[C@H](NC(=O)[C@H](N)CCc1ccccc1)C(=O)NCc1ccc(C(=N)N)nc1]

(R)-2-Amino-N—((S)-1-(((6-carbamimidoylpyridin-3-yl)methyl)amino)-1-oxopropan-2-yl)-4-phenylbutanamide di-trifluoroacetate salt was synthesized according to the procedures for compound 1119 except using benzyl ((5-(aminomethyl)pyridin-2-yl)(imino)methyl)carbamate (PCT Int. Appl., 2001087854, 22 Nov. 2001) in step 3. Purification was achieved by using the procedure for compound 1032.

Example 74. Preparation of (2R,4S)—N—((S)-1-(benzylamino)-1-oxopropan-2-yl)-4-phenylpiperidine-2-carboxamide Dihydrochloride (1271)

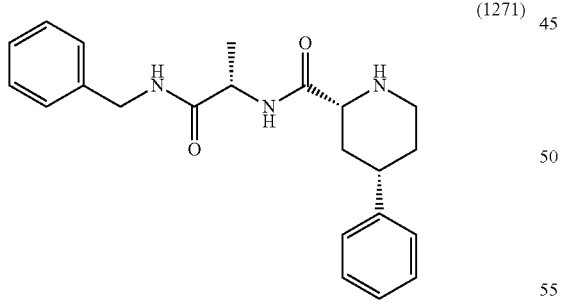

(2R,4S)—N—((S)-1-(Benzylamino)-1-oxopropan-2-yl)-4-phenylpiperidine-2-carboxamide was synthesized according to the procedures for compound (1230), except using benzyl amine in step 3.

Example 75. Preparation of (2R,4R)—N—((S)-1-(((6-Carbamimidoylpyridin-3-yl)methyl)amino)-1-oxopropan-2-yl)-4-phenylpyrrolidine-2-carboxamide Di-trifluoroacetate (1272)

(2R,4R)—N—((S)-1-(((6-Carbamimidoylpyridin-3-yl)methyl)amino)-1-oxopropan-2-yl)-4-phenylpyrrolidine-2-carboxamide di-trifluoroacetate salt was synthesized according to the procedures for compound 1119 except using (2R,4R)-1-(tert-butoxycarbonyl)-4-phenylpyrrolidine-2-carboxylic acid in step 1 and benzyl ((5-(aminomethyl)pyridin-2-yl)(imino)methyl)carbamate in step 3. Purification was achieved by using the procedure for compound 1032.

Example 76. Preparation of 5-(((S)-2-((2R,4R)-4-Phenylpyrrolidine-2-carboxamido)propanamido)methyl)picolinamide Dihydrochloride (1273)

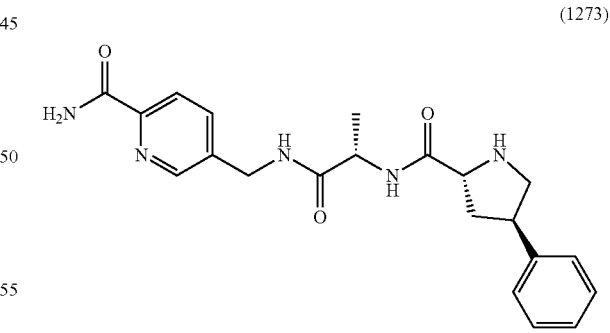

5-(((S)-2-((2R,4R)-4-Phenylpyrrolidine-2-carboxamido)propanamido)methyl)picolinamide was isolated as a byproduct in the synthesis of (1272).

Example 77. Preparation of (2R,4R)—N—((S)-1-((5-chloro-2-(methylsulfonamido)benzyl)amino)-1-oxopropan-2-yl)-4-phenylpyrrolidine-2-carboxamide, hydrochloride (1274)

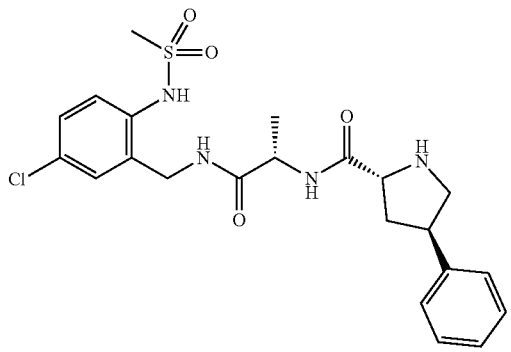
(1274)

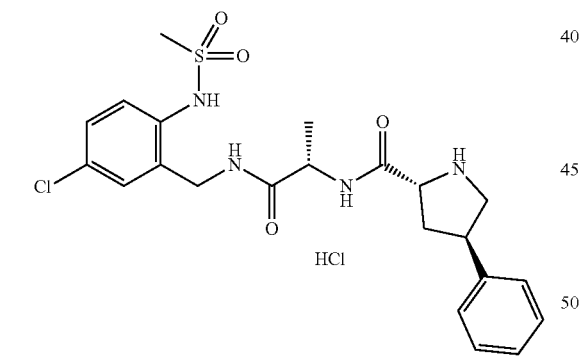
HCl

Step 1: tert-Butyl (2R,4R)-2-(((S)-1-((2-amino-5-chlorobenzyl)amino)-1-oxopropan-2-yl)carbamoyl)-4-phenylpyrrolidine-1-carboxylate (30 mg, 0.06 mmol) (as synthesize in Step 1 for compound (1269)) was dissolved in CH₂Cl₂ (1 mL) and treated with MsCl (7 µL, 0.09 mmol) and Et₃N (25 µL, 0.18 mmol), then stirred for 16 h at ambient temperature. The reaction mixture was diluted with CH₂Cl₂ and washed with 10% aq KHSO₄, brine and sat. aq NaHCO₃. The organic layer was dried over Na₂SO₄ and concentrated, then the residue purified by chromatography (80-90% EtOAc/hexanes) to furnish tert-butyl (2R,4R)-2-(((S)-1-((5-chloro-2-(methylsulfonamido)benzyl)amino)-1-oxopropan-2-yl)carbamoyl)-4-phenylpyrrolidine-1-carboxylate as a colorless oil. Removal of the Boc protecting group was achieved upon treatment with 3 M HCl in iPrOH overnight at ambient temperature. Removal of iPrOH and lyophilization in a mixture of 1:1 ACN/H₂O gave the title compound as a pink-tinged fluffy solid (1.9 mg, 6% yield over 2 steps).

Example 78. Preparation of (R)-2-Amino-N—((S)-1-(((6-amino-5-chloropyridin-3-yl)methyl)amino)-1-oxopropan-2-yl)-4-phenylbutanamide Dihydrochloride (1275)

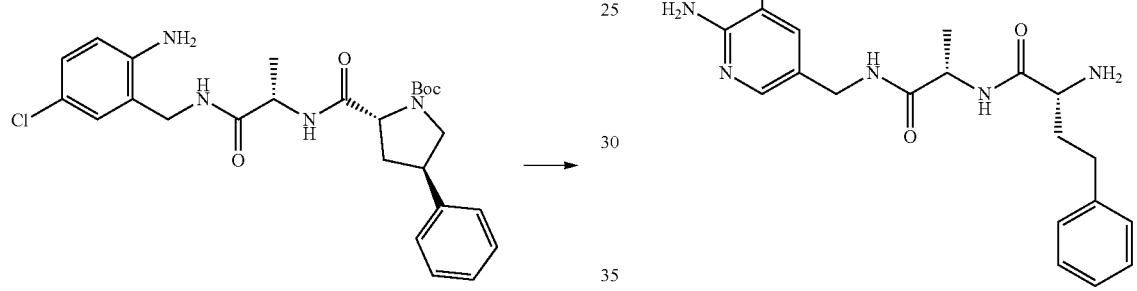
(1275)

(R)-2-Amino-N—((S)-1-(((6-amino-5-chloropyridin-3-yl)methyl)amino)-1-oxopropan-2-yl)-4-phenylbutanamide dihydrochloride was synthesized according to the procedure for compound (1243).

Example 79. Preparation of (2R,4S)—N—((S)-1-((4-Carbamimidoylbenzyl)amino)-1-oxopropan-2-yl)-4-(3-(trifluoromethyl)phenyl)pyrrolidine-2-carboxamide Dihydrochloride (1276)

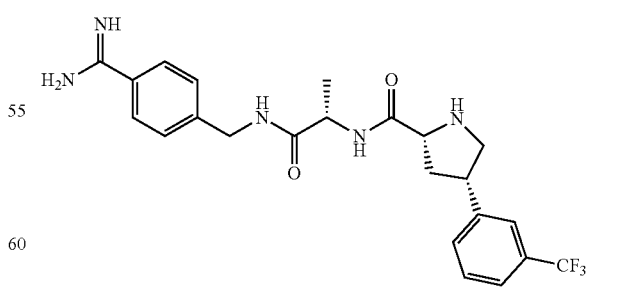
(1276)

(2R,4S)—N—((S)-1-((4-Carbamimidoylbenzyl)amino)-1-oxopropan-2-yl)-4-(3-(trifluoromethyl)phenyl)pyrrolidine-2-carboxamide dihydrochloride was synthesized according to the procedures for compound (1247).

Example 80. Preparation of (2R,4S)-4-(3-(Aminomethyl)phenyl)-N—((S)-1-((4-carbamimidoylbenzyl)amino)-1-oxopropan-2-yl)pyrrolidine-2-carboxamide Trihydrochloride (1277)

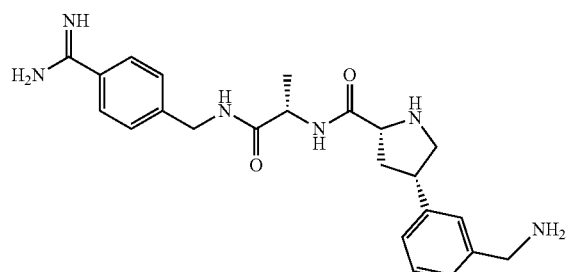

(1277)

(2R,4S)-4-(3-(Aminomethyl)phenyl)-N—((S)-1-((4-carbamimidoylbenzyl)amino)-1-oxopropan-2-yl)pyrrolidine-2-carboxamide trihydrochloride was synthesized according to the procedures for compound (1247).

Example 81. Preparation of (2R,4S)—N—((S)-1-((4-Carbamimidoylbenzyl)amino)-1-oxopropan-2-yl)-4-(3-cyanophenyl)pyrrolidine-2-carboxamide Dihydrochloride (1278)

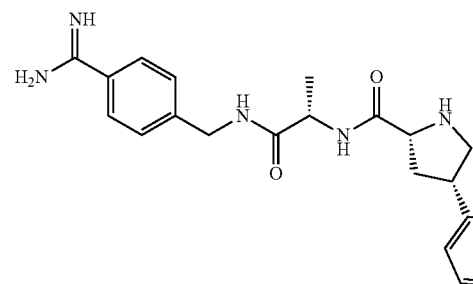

(1278)

(2R,4S)—N—((S)-1-((4-Carbamimidoylbenzyl)amino)-1-oxopropan-2-yl)-4-(3-cyanophenyl)pyrrolidine-2-carboxamide dihydrochloride was synthesized according to the procedures for compound (1247).

Example 82. Preparation of (R)-2-amino-N—((S)-1-((5-bromo-2-hydroxybenzyl)amino)-1-oxopropan-2-yl)-4-phenylbutanamide, hydrochloride (1279)

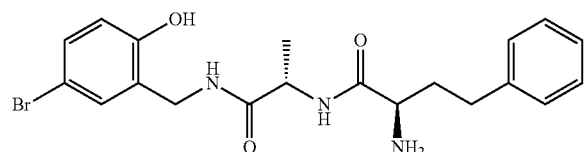

(1279)

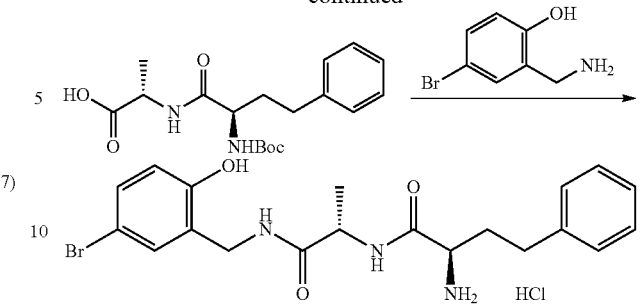

Steps 1-2: (R)-2-amino-N—((S)-1-((5-bromo-2-hydroxybenzyl)amino)-1-oxopropan-2-yl)-4-phenylbutanamide, hydrochloride was synthesized as a white fluffy powder according to steps 1-2 of the procedure for compound (1246) using the appropriate starting materials (31.4 mg, 44% yield over two steps).

Example 83. Preparation of (R)-2-Amino-N—((S)-1-(((6-(aminomethyl)pyridin-3-yl)methyl)amino)-1-oxopropan-2-yl)-4-phenylbutanamide Dihydrochloride (1280)

(1280)

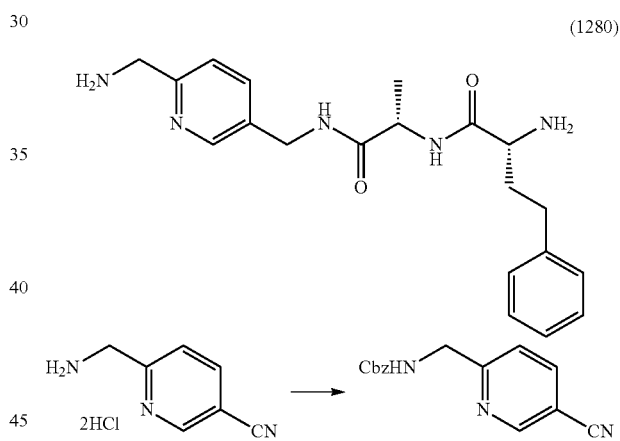

Step 1: To a suspension of 6-(aminomethyl)nicotinonitrile (2.05 g, 9.95 mmol) in THF (50 mL) was added sat. NaHCO₃ (50 mL). The mixture was stirred 30 min then benzyl chloroformate (1.6 mL, 11.3 mmol) was added. After stirring vigorously for 2 h, the mixture was diluted with EtOAc and the layers were separated. The aqueous layer was extracted with EtOAc and the combined organics were washed with brine, dried (Na₂SO₄) and conc in vacuo. The crude material was crystallized from warm hexanes-Et₂O. The solid was collected by filtration, rinsed with Et₂O-hexanes and ~10% EtOAc-hexanes and air dried to give benzyl ((5-cyanopyridin-2-yl)methyl)carbamate (805 mg, 30% yield).

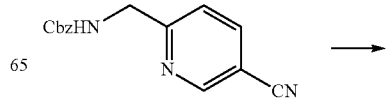

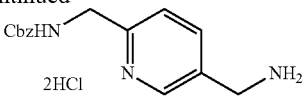

Step 2: To a solution of benzyl ((5-cyanopyridin-2-yl)methyl)carbamate (0.80 g, 2.99 mmol) in MeOH (50 mL) was added NiCl₂ (0.43 g, 3.29 mmol) and di-tert-butyl dicarbonate (2.05 g, 9.4 mmol). The mixture was cooled over an ice bath and NaBH₄ (0.445 g, 11.8 mmol) was added in two aliquots over 10 min. The reaction was allowed to warm to ambient temperature, stirred overnight, then conc in vacuo. The residue was dissolved in EtOAc and 0.5 M KHSO₄. The layers were separated, and the aqueous layer was adjusted to pH 10 with sat. NaHCO₃ and 2 M NaOH. After extraction with EtOAc, the combined organics were washed with H₂O and dilute aqueous NH₄OH solution containing brine. The solution was dried (Na₂SO₄) and conc in vacuo. Purification by chromatography (10-80% EtOAc-hexanes) provided benzyl ((5-(((tert-butoxycarbonyl)amino)methyl)pyridin-2-yl)methyl)carbamate (527 mg, 47% yield).

Step 3: To a solution of benzyl ((5-(((tert-butoxycarbonyl)amino)methyl)pyridin-2-yl)methyl)carbamate (527 mg, 1.42 mmol) in MeOH (10 mL) was added 3 M HCl-CPME (10 mL). After stirring for 3 h, EtOAc was added to the slurry. The solid was collected by filtration, rinsed with EtOAc and hexanes and dried to give benzyl ((5-(aminomethyl)pyridin-2-yl)methyl)carbamate dihydrochloride (412 mg, 94% yield).

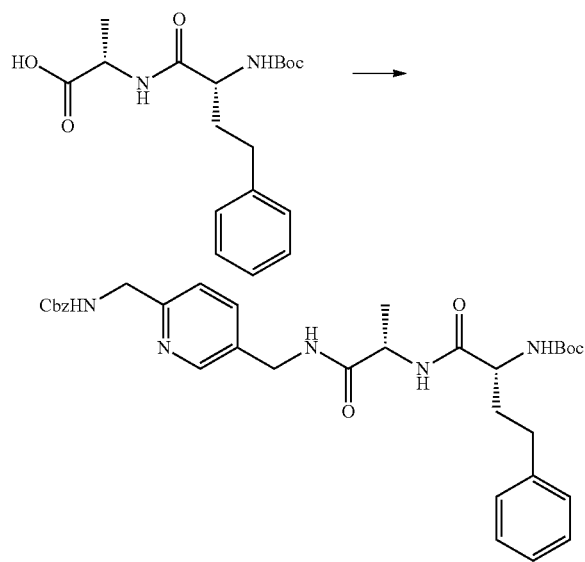

Step 4: To a solution of ((R)-2-((tert-butoxycarbonyl)amino)-4-phenylbutanoyl)-L-alanine (122 mg, 0.35 mmol) and NHS (44 mg, 0.38 mmol) in CH₂Cl₂ (8 mL) was added DCC (77 mg, 0.37 mmol) and the mixture was stirred for 1 h. In a separate vial, benzyl ((5-(aminomethyl)pyridin-2-yl)methyl)carbamate dihydrochloride (140 mg, 0.45 mmol) was treated with CH₂Cl₂ (2 mL) and sat. NaHCO₃ (2.5 mL). This biphasic mixture was added to the reaction and stirred for 70 min. The layers were separated then the organic layers washed with H₂O and brine, then dried (Na₂SO₄) and conc in vacuo. Purification by chromatography (50-100%) EtOAc gave tert-butyl ((R)-1-(((S)-1-(((6-((((benzyloxy)carbonyl)amino)methyl)pyridin-3-yl)methyl)amino)-1-oxopropan-2-yl)amino)-1-oxo-4-phenylbutan-2-yl)carbamate (113 mg, 54% yield).

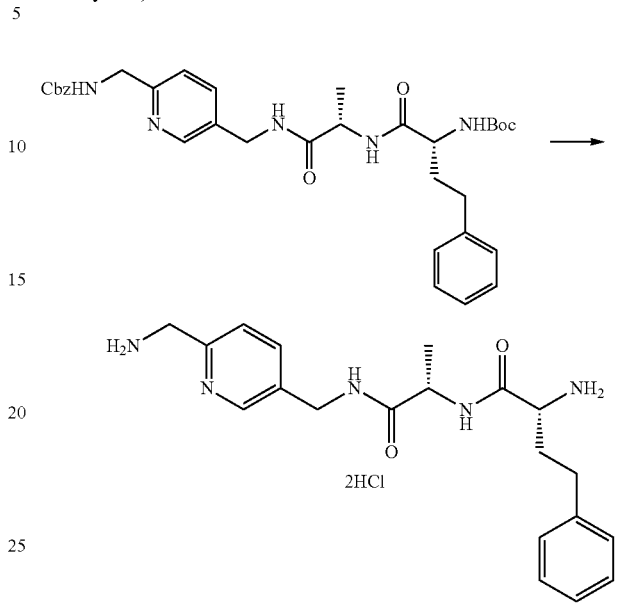

Step 5: tert-Butyl ((R)-1-(((S)-1-(((6-((((benzyloxy)carbonyl)amino)methyl)pyridin-3-yl)methyl)amino)-1-oxopropan-2-yl)amino)-1-oxo-4-phenylbutan-2-yl)carbamate was deprotected with 3 M HCl-CPME according to the procedure for (1315), except that the reaction mixture was conc in vacuo to give benzyl ((5-(((S)-2-((R)-2-amino-4-phenylbutanamido)propanamido)methyl)pyridin-2-yl)methyl)carbamate dihydrochloride.

Step 6: To a degassed solution benzyl ((5-(((S)-2-((R)-2-amino-4-phenylbutanamido)propanamido)methyl)pyridin-2-yl)methyl)carbamate from the previous step in MeOH (8 mL) was added 10% Pd/C (18 mg). The mixture was placed under H₂ atm and stirred at ambient temperature overnight. After degassing the mixture, 1 M HCl (0.5 mL) was added then the slurry was filtered (0.2 μm syringe filter) and conc in vacuo. The residue was dissolved in H₂O, washed with CH₂Cl₂ 3× then conc in vacuo. Dissolution of the residue in EtOAc-MeOH followed by conc in vacuo gave (R)-2-amino-N—((S)-1-(((6-(aminomethyl)pyridin-3-yl)methyl)amino)-1-oxopropan-2-yl)-4-phenylbutanamide dihydrochloride as an off-white solid (88 mg, quant. yield).

Example 84. Preparation of (2R,4R)—N-((2S)-1-(((2-Amino-4,5,6,7-tetrahydrobenzo[d]thiazol-6-yl)methyl)amino)-1-oxopropan-2-yl)-4-phenylpyrrolidine-2-carboxamide Di-trifluoroacetate salt (1281)

(1281)

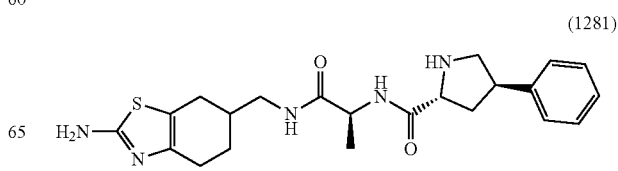

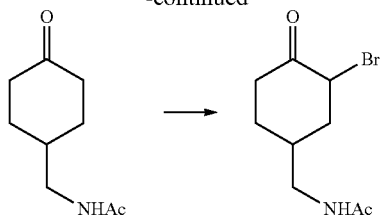

Step 1: To a 25-mL round bottom flask, commercially available N-((4-oxocyclohexyl)methyl)acetamide (467.0 mg, 2.76 mmol) was added and followed by $CH_2Cl_2$ (5 mL). After purging with $N_2$, a solution of $Br_2$ (140 μL, 2.73 mmol) in $CH_2Cl_2$ (10 mL) was added dropwise at room temp by a syringe pump at the rate of 0.317 mL per min. After the addition, the reaction was heated to reflux for 1 h. Volatiles was evaporated under vacuum to afford the crude N-((3-bromo-4-oxocyclohexyl)methyl)acetamide.

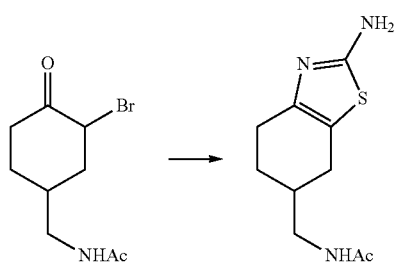 [SMILES: CC(=O)NCC1CCC(=O)C(Br)C1 ; CC(=O)NCC1CCc2nc(N)sc2C1]

Step 2: To a 25-mL round bottom flask, the crude N-((3-bromo-4-oxocyclohexyl)methyl)acetamide was added and followed by EtOH (8 mL) and thiourea at room temp. After purging with $N_2$, the reaction was heated to reflux for 2 h. Volatiles was evaporated under vacuum. The crude product was diluted with water (10 mL) and followed by slow addition of 1M NaOH solution to become basic (pH about 13). The basic solution was extracted with 15 mL EtOAc (3 times). The organic layers were combined, washed with brine, dried ($Na_2SO_4$), vacuum filtered, and evaporated under vacuum. The crude product was dissolved in $CH_2Cl_2$ and adsorbed on silica gel. Purification by chromatography (0-15% MeOH—$CH_2Cl_2$) gave N-((2-amino-4,5,6,7-tetrahydrobenzo[d]thiazol-6-yl)methyl)acetamide (48.5 mg, 8% yield).

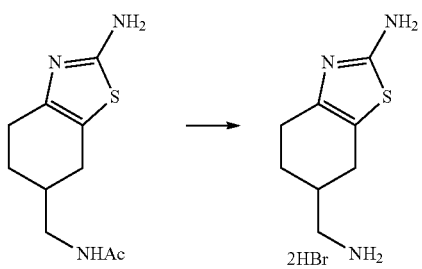 [SMILES: CC(=O)NCC1CCc2nc(N)sc2C1 ; NCC1CCc2nc(N)sc2C1]

Step 3: To a 25-mL round bottom flask, N-((2-amino-4,5,6,7-tetrahydrobenzo[d]thiazol-6-yl)methyl)acetamide (48.5 mg, 0.213 mmol) was added and followed by the addition of commercially available aqueous HBr solution (2 mL, 48% in water). After purging with $N_2$, the reaction was heated to reflux for 18 h. Volatiles was evaporated under vacuum to afford crude 6-(aminomethyl)-4,5,6,7-tetrahydrobenzo[d]thiazol-2-amine dihydrobromide salt.

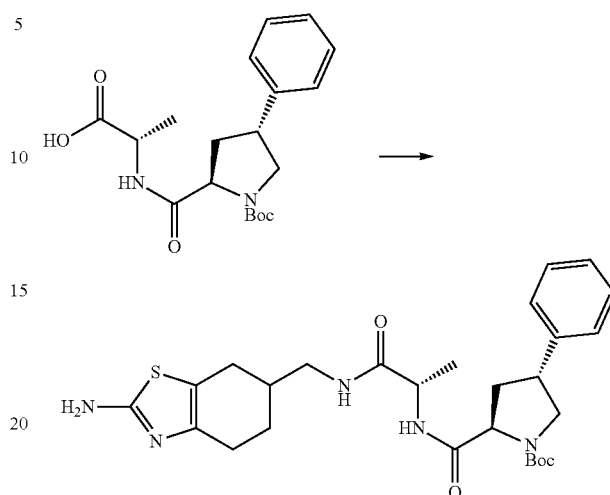

Step 4: ((2R,4R)-1-(tert-Butoxycarbonyl)-4-phenylpyrrolidine-2-carbonyl)-L-alanine (69.0 mg, 0.190 mmol) was coupled with the crude 6-(aminomethyl)-4,5,6,7-tetrahydrobenzo[d]thiazol-2-amine dihydrobromide according to the procedure for compound 1116, step 1 to afford tert-butyl (2R,4R)-2-(((2S)-1-(((2-amino-4,5,6,7-tetrahydrobenzo[d]thiazol-6-yl)methyl)amino)-1-oxopropan-2-yl)carbamoyl)-4-phenylpyrrolidine-1-carboxylate (64.1 mg, 64% yield).

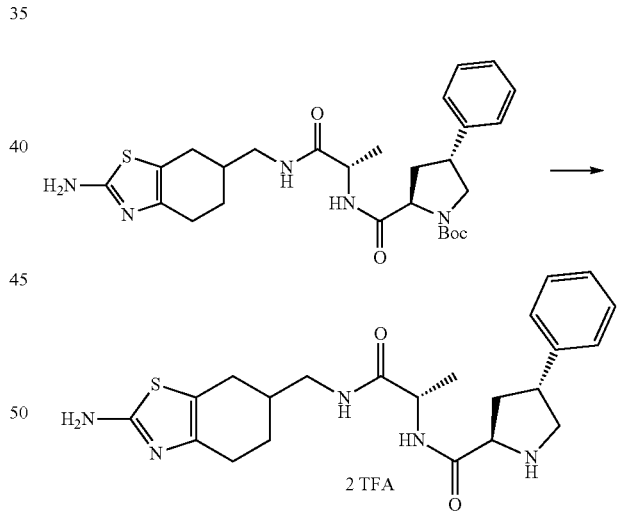

Step 5: Deprotection of tert-butyl (2R,4R)-2-(((2S)-1-(((2-amino-4,5,6,7-tetrahydrobenzo[d]thiazol-6-yl)methyl)amino)-1-oxopropan-2-yl)carbamoyl)-4-phenylpyrrolidine-1-carboxylate (64.1 mg, 0.121 mmol) was done according to the procedure for compound 1119, step 2. Purification by reverse phase HPLC (5-45-75-90% MeCN—$H_2O$) afforded (2R,4R)—N-((2S)-1-(((2-amino-4,5,6,7-tetrahydrobenzo[d]'thiazol-6-yl)methyl)amino)-1-oxopropan-2-yl)-4-phenylpyrrolidine-2-carboxamide di-trifluoroacetate salt (16.0 mg, 31% yield).

Example 85. Preparation of (2S,4R)—N—((S)-1-(((6-Amino-2-methylpyridin-3-yl)methyl)amino)-1-oxopropan-2-yl)-4-benzylpyrrolidine-2-carboxamide Dihydrochloride (1282)

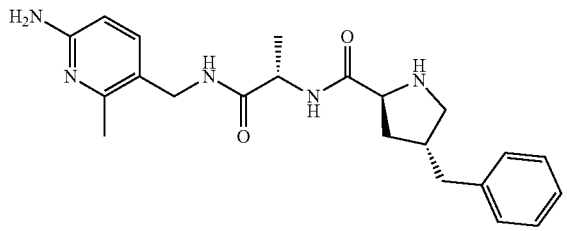

(1282)

(2S,4R)—N—((S)-1-(((6-Amino-2-methylpyridin-3-yl)methyl)amino)-1-oxopropan-2-yl)-4-benzylpyrrolidine-2-carboxamide dihydrochloride was synthesized according to the procedures for compound (1304), steps 7 and 8 starting from commercially available (2S,4R)-4-benzyl-1-(tert-butoxycarbonyl)pyrrolidine-2-carboxylic acid.

Example 86. Preparation of (2R,4R)—N—((S)-1-(((6-Amino-2-methylpyridin-3-yl)methyl)amino)-1-oxopropan-2-yl)-4-benzylpyrrolidine-2-carboxamide Dihydrochloride (1283)

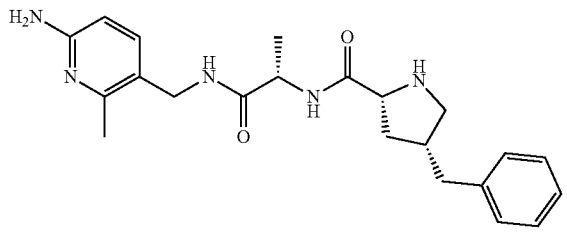

(1283)

(2R,4R)—N—((S)-1-(((6-Amino-2-methylpyridin-3-yl)methyl)amino)-1-oxopropan-2-yl)-4-benzylpyrrolidine-2-carboxamide dihydrochloride was synthesized according to the procedures for compound (1304), steps 7 and 8 starting from commercially available (2R,4R)-4-benzyl-1-(tert-butoxycarbonyl)pyrrolidine-2-carboxylic acid.

Example 87. Preparation of (2R,4R)-4-Benzyl-N—((S)-1-((4-carbamimidoylbenzyl)amino)-1-oxopropan-2-yl)pyrrolidine-2-carboxamide Di-trifluoroacetate salt (1284)

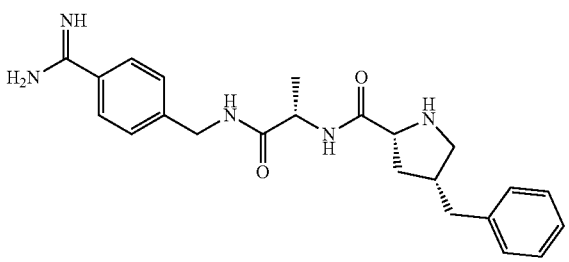

(1284)

(2R,4R)-4-Benzyl-N—((S)-1-((4-carbamimidoylbenzyl)amino)-1-oxopropan-2-yl)pyrrolidine-2-carboxamide di-trifluoroacetate salt was synthesized according to the procedures for compound (1247), except that the final product was purified using reverse-phase HPLC.

Example 88. Preparation of (2S,4R)-4-Benzyl-N—((S)-1-((4-carbamimidoylbenzyl)amino)-1-oxopropan-2-yl)pyrrolidine-2-carboxamide Dihydrochloride (1285)

(1285)

[structure 1285]

(2S,4R)-4-Benzyl-N—((S)-1-((4-carbamimidoylbenzyl)amino)-1-oxopropan-2-yl)pyrrolidine-2-carboxamide dihydrochloride was synthesized according to the procedures for compound (1247).

Example 89. Preparation of (S)—N-(1-((4-Carbamimidoylbenzyl)amino)-1-oxopropan-2-yl)-4-phenylthiazole-2-carboxamide Hydrochloride (1286)

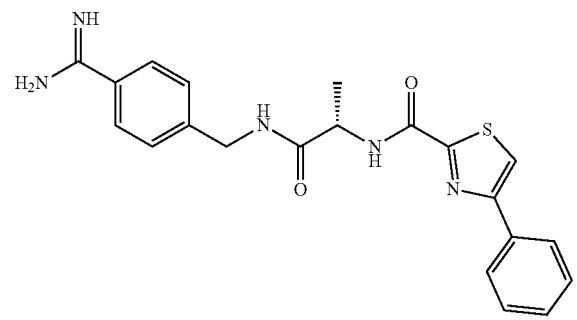

(1286)

(S)—N-(1-((4-Carbamimidoylbenzyl)amino)-1-oxopropan-2-yl)-4-phenylthiazole-2-carboxamide hydrochloride was synthesized according to the procedures for compound (1234), except that a few drops of conc HCl was added to the reaction mixture during the benzyl carbamate deprotection step.

Example 90. Preparation of (R)-2-amino-N—((S)-1-((5-Chloro-2-(hydroxymethyl)benzyl)amino)-1-oxopropan-2-yl)-4-phenylbutanamide Hydrochloride (1287)

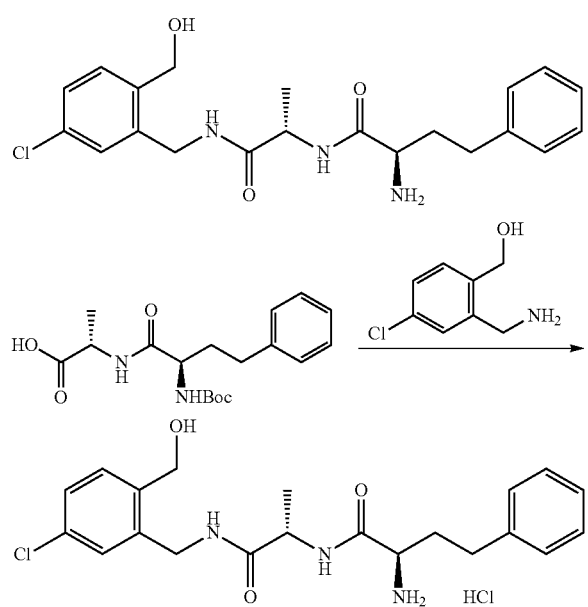

(1287)

Steps 1-2: The title compound was synthesized as a white powder according to steps 1-2 of the procedure for compound (1246) using the appropriate starting materials (27.5 mg, 31% yield over two steps).

Example 91. Preparation of 2,2,2-Trichloroethyl (imino(4-(((S)-2-((2R,4R)-4-phenylpyrrolidine-2-carboxamido)propanamido)methyl)phenyl)methyl)carbamate (1288)

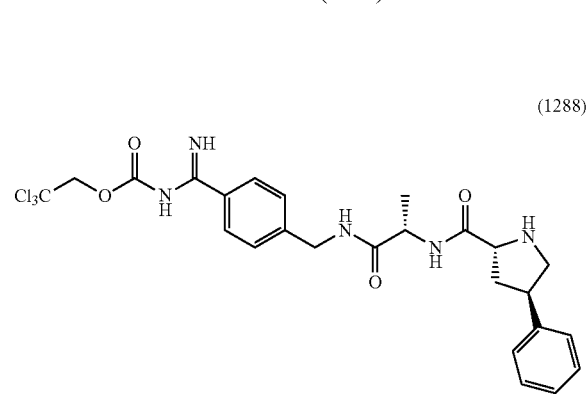

(1288)

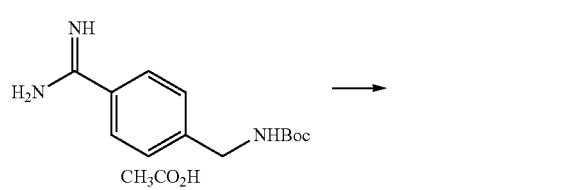

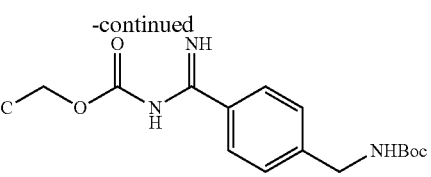

Step 1: To a 0° C. solution of tert-butyl (4-carbamimidoylbenzyl)carbamate acetate salt (100 mg, 0.32 mmol) in DMF (2 mL, 0.16 M) was added trichloroethyl chloroformate (0.09 mL, 0.65 mmol) and Et₃N (0.18 mL, 1.29 mmol). After stirring for 1 h at the same temperature, the reaction was quenched by addition of H₂O. The resulting mixture was extracted with EtOAc, dried over anhyd Na₂SO₄, and conc under vacuum. The residue was purified by chromatography (0-100% EtOAc-hexanes) to give tert-butyl (4-(N-((2,2,2-trichloroethoxy)carbonyl)carbamimidoyl)benzyl)carbamate (82 mg, 60% yield).

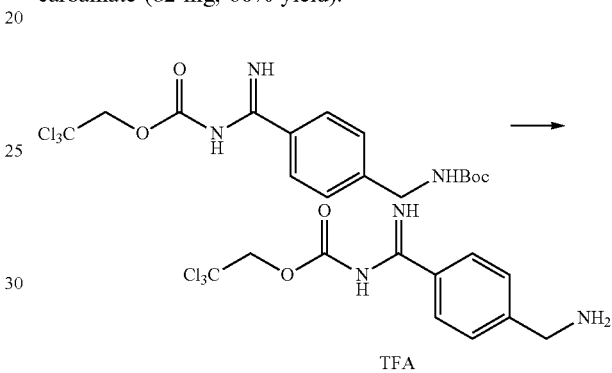

Step 2: Deprotection of tert-butyl (4-(N-((2,2,2-trichloroethoxy)carbonyl)carbamimidoyl)benzyl)carbamate (165 mg, 0.39 mmol) was conducted according to the procedure for compound (1259), step 2 to give 2,2,2-trichloroethyl ((4-(aminomethyl)phenyl)(imino)methyl)carbamate trifluoroacetate salt (126 mg, 100% yield).

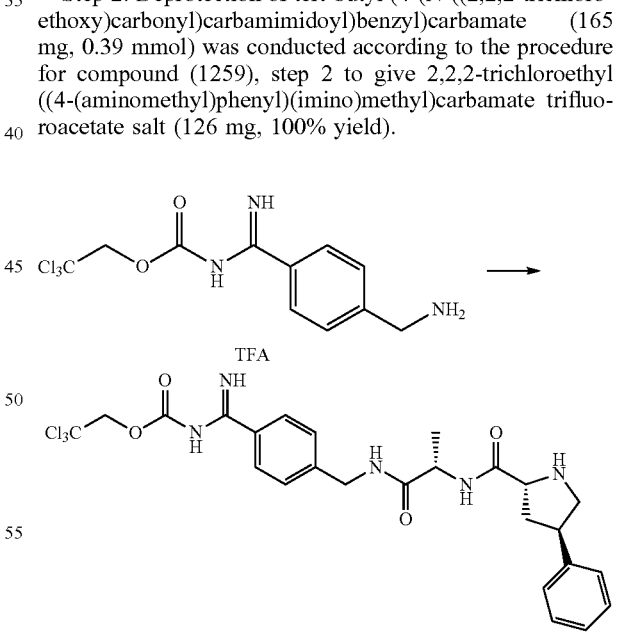

Step 3: 2,2,2-Trichloroethyl ((4-(aminomethyl)phenyl)(imino)methyl)carbamate trifluoroacetate salt (170 mg, 0.39 mmol) was coupled with ((2R,4R)-1-(tert-butoxycarbonyl)-4-phenylpyrrolidine-2-carbonyl)-L-alanine according to the procedure for compound (1259), step 3 to give 2,2,2-trichloroethyl (imino(4-(((S)-2-((2R,4R)-4-phenylpyrrolidine-2-carboxamido)propanamido)methyl)phenyl)methyl)carbamate (180 mg, 83% yield).

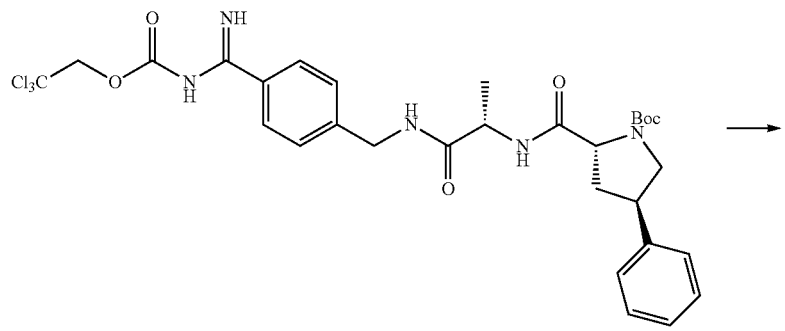

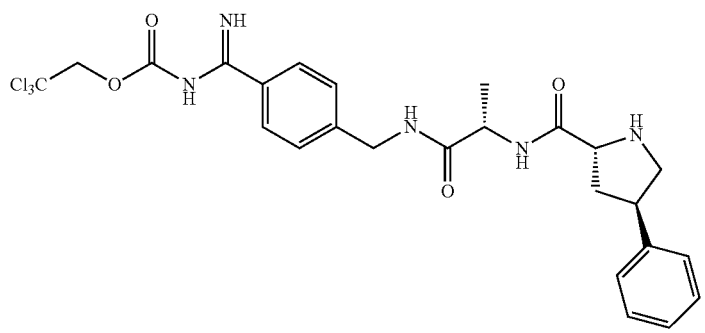

Step 4: Deprotection of (imino(4-(((S)-2-((2R,4R)-4-phenylpyrrolidine-2-carboxamido)propanamido)methyl)phenyl)methyl)carbamate (180 mg, 0.27 mmol) was conducted according to the procedure for compound (1260), step 4 to give 2,2,2-trichloroethyl (imino(4-(((S)-2-((2R,4R)-4-phenylpyrrolidine-2-carboxamido)propanamido)methyl)phenyl)methyl)carbamate (112 mg, 73% yield).

Example 92. Preparation of (R)-2-Amino-N—((S)-1-((4-carbamimidoylbenzyl)amino)-1-oxobutan-2-yl)-4-phenylbutanamide Dihydrochloride (1289)

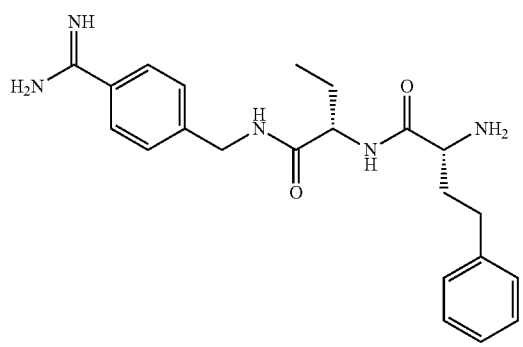

(1289)

(R)-2-Amino-N—((S)-1-((4-carbamimidoylbenzyl)amino)-1-oxobutan-2-yl)-4-phenylbutanamide dihydrochloride was synthesized using (S)-2-((tert-butoxycarbonyl)amino)butanoic acid in step 1 according to the procedures for compound 1050.

Example 93. Preparation of (2R,4R)—N—((S)-1-((4-carbamimidoylbenzyl)amino)-1-oxobutan-2-yl)-4-phenylpyrrolidine-2-carboxamide Dihydrochloride (1290)

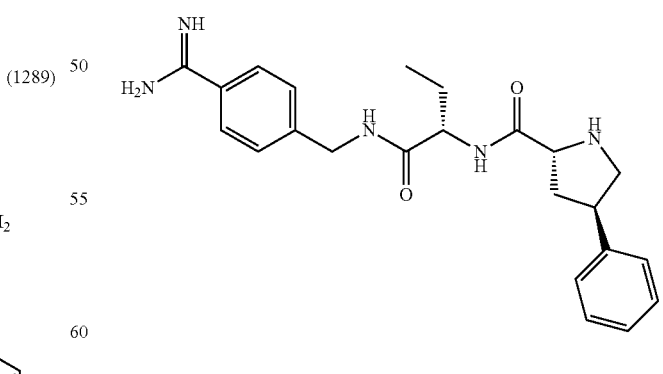

(1290)

(2R,4R)—N—((S)-1-((4-carbamimidoylbenzyl)amino)-1-oxobutan-2-yl)-4-phenylpyrrolidine-2-carboxamide was synthesized using (S)-2-((tert-butoxycarbonyl)amino)butanoic acid in step 1 and (2R,4R)-1-(tert-butoxycarbonyl)-4-phenylpyrrolidine-2-carboxylic acid in step 3 according to the procedures for compound 1050.

Example 94. Preparation of (2R,4S)—N—((S)-1-(((6-Amino-2-methylpyridin-3-yl)methyl)amino)-1-oxopropan-2-yl)-4-(3-(aminomethyl)phenyl)pyrrolidine-2-carboxamide Dihydrochloride (1291)

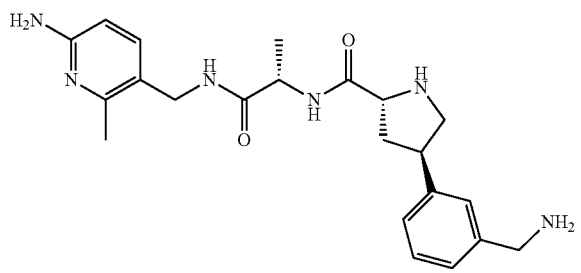

(1291)

(2R,4S)—N—((S)-1-(((6-Amino-2-methylpyridin-3-yl)methyl)amino)-1-oxopropan-2-yl)-4-(3-(aminomethyl)phenyl)pyrrolidine-2-carboxamide dihydrochloride was synthesized according to the procedures for compound (1257).

Example 95. Preparation of (R)—N-(4-((Z)—N'-Hydroxycarbamimidoyl)benzyl)-2-methyl-4-oxo-4-((2R,4R)-4-phenylpyrrolidin-2-yl)butanamide (1292)

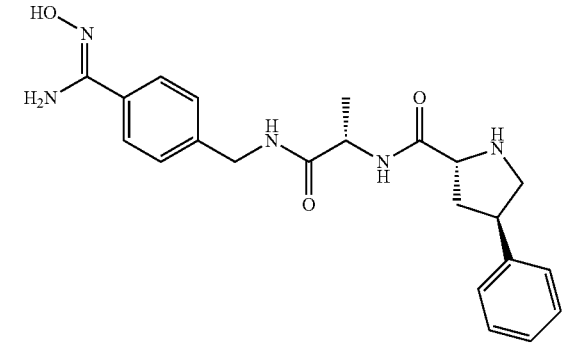

(1292)

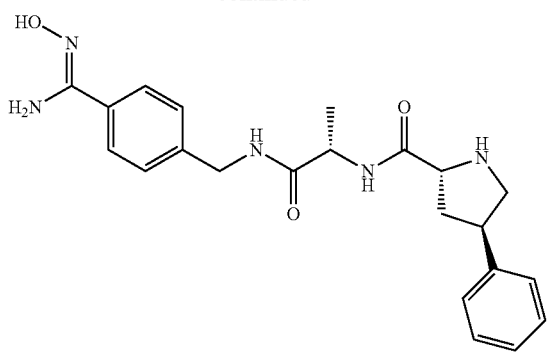

Deprotection of tert-butyl (2R,4R)-2-(((S)-1-((4-((Z)—N'-hydroxycarbamimidoyl)benzyl)amino)-1-oxopropan-2-yl)carbamoyl)-4-phenylpyrrolidine-1-carboxylate (173 mg, 0.34 mmol) was conducted according to the procedure for compound (1260), step 4 to give (R)—N-(4-((Z)—N'-hydroxycarbamimidoyl)benzyl)-2-methyl-4-oxo-4-((2R,4R)-4-phenylpyrrolidin-2-yl)butanamide (103 mg, 71% yield).

Example 96. Preparation of Isobutyl (imino(4-(((S)-2-((2R,4R)-4-phenylpyrrolidine-2-carboxamido)propanamido)methyl)phenyl)methyl)carbamate (1293)

(1293)

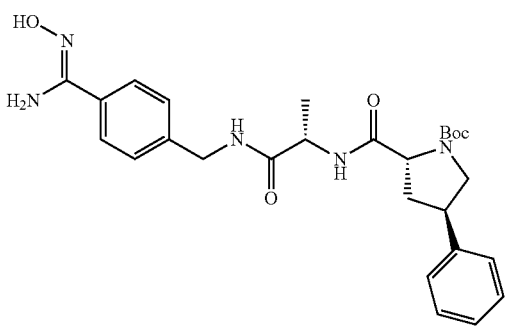

Step 1: tert-Butyl (4-(N-(isobutoxycarbonyl)carbamimidoyl)benzyl)carbamate (145 mg, 64% yield) was synthesized from tert-butyl (4-carbamimidoylbenzyl)carbamate acetate salt (200 mg, 0.65 mmol) and isobutyl chloroformate according to the procedure for compound (1288), step 1.

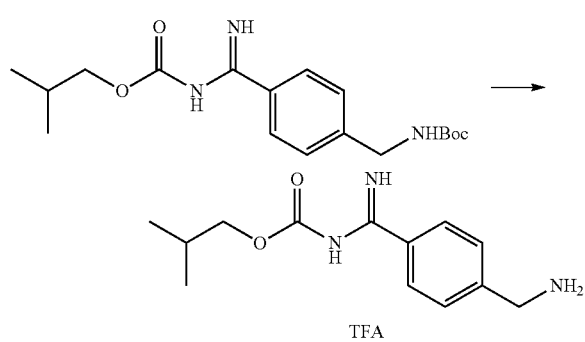

Step 2: Deprotection of tert-butyl (4-(N-(isobutoxycarbonyl)carbamimidoyl)benzyl)carbamate (145 mg, 0.42 mmol) was conducted according to the procedure for compound (1259), step 2 to give isobutyl ((4-(aminomethyl)phenyl)(imino)methyl)carbamate trifluoroacetate salt (150 mg, 100% yield).

Step 3: Isobutyl ((4-(aminomethyl)phenyl)(imino)methyl)carbamate trifluoroacetate salt (150 mg, 0.42 mmol) was coupled with ((2R,4R)-1-(tert-butoxycarbonyl)-4-phenylpyrrolidine-2-carbonyl)-L-alanine according to the procedure for compound (1259), step 3 to give tert-butyl (2R,4R)-2-(((S)-1-((4-(N-(isobutoxycarbonyl)carbamimidoyl)benzyl)amino)-1-oxopropan-2-yl)carbamoyl)-4-phenylpyrrolidine-1-carboxylate (173 mg, 84% yield).

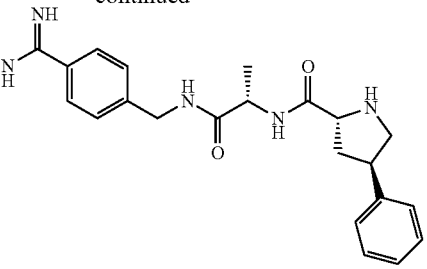

Step 4: Deprotection of tert-butyl (2R,4R)-2-(((S)-1-((4-(N-(isobutoxycarbonyl)carbamimidoyl)benzyl)amino)-1-oxopropan-2-yl)carbamoyl)-4-phenylpyrrolidine-1-carboxylate (173 mg, 0.29 mmol) was conducted according to the procedure for compound (1260), step 4 to give isobutyl (imino(4-(((S)-2-((2R,4R)-4-phenylpyrrolidine-2-carboxamido)propanamido)methyl)phenyl)methyl)carbamate (111 mg, 77% yield).

Example 97. Preparation of Ethyl (imino(4-(((S)-2-((2R,4R)-4-phenylpyrrolidine-2-carboxamido)propanamido)methyl)phenyl)methyl)carbamate (1294)

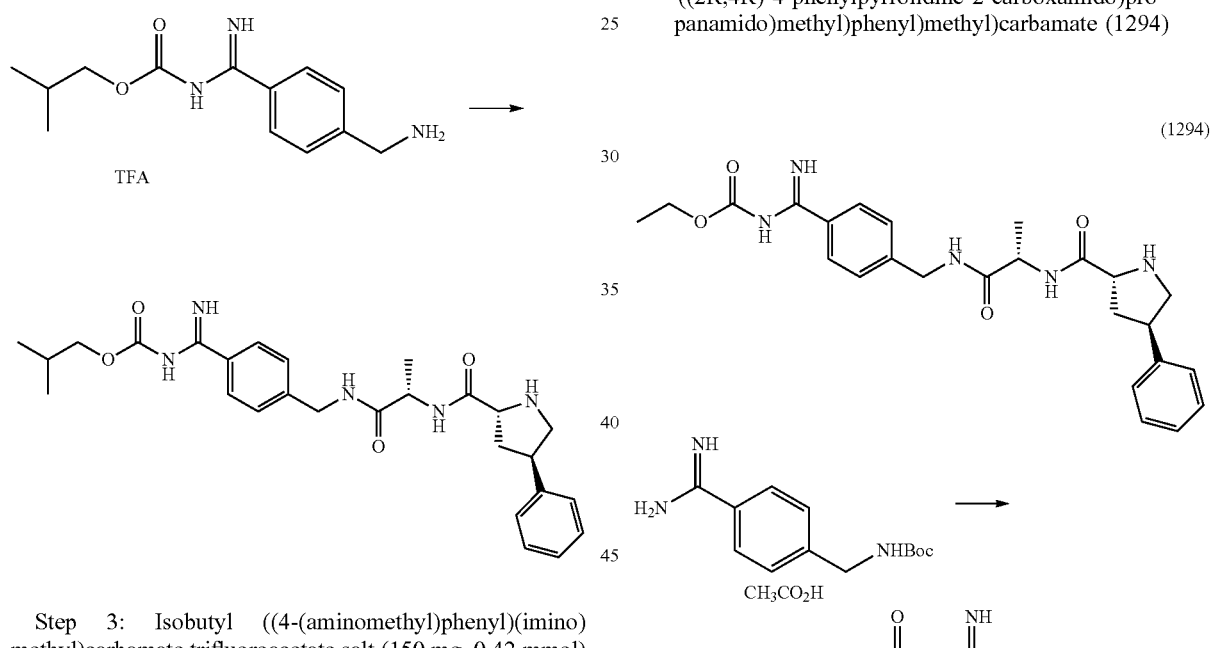

Step 1: tert-Butyl (4-(N-(ethoxycarbonyl)carbamimidoyl)benzyl)carbamate (142 mg, 68% yield) was synthesized from tert-butyl (4-carbamimidoylbenzyl)carbamate acetic acid (200 mg, 0.65 mmol) and ethyl chloroformate according to the procedure for compound (1288), step 1.

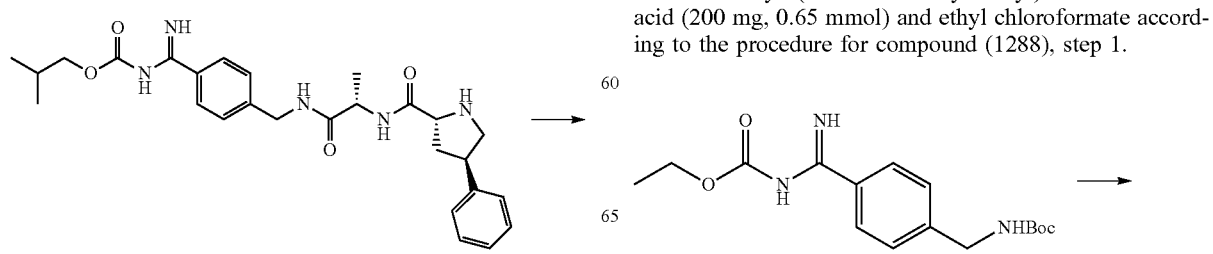

-continued

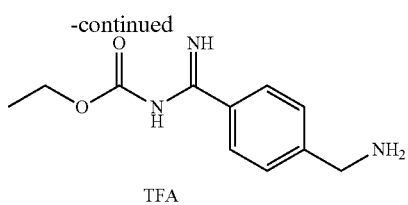

Step 2: Deprotection of tert-butyl (4-(N-(ethoxycarbonyl)carbamimidoyl)benzyl)carbamate (142 mg, 0.44 mmol) was conducted according to the procedure compound (1259), step 2 to give ethyl ((4-(aminomethyl)phenyl)(imino)methyl)carbamate trifluoroacetate salt (148 mg, 100% yield).

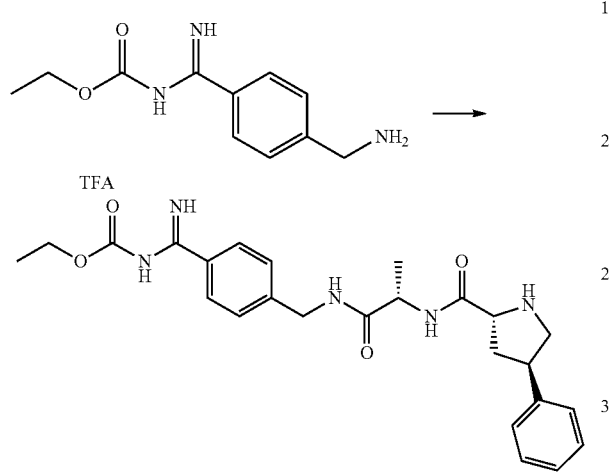

Step 3: Ethyl ((4-(aminomethyl)phenyl)(imino)methyl) carbamate trifluoroacetate salt (130 mg, 0.39 mmol) was coupled with ((2R,4R)-1-(tert-butoxycarbonyl)-4-phenylpyrrolidine-2-carbonyl)-L-alanine according to the procedure for compound (1259), step 3 to give tert-butyl (2R,4R)-2-(((S)-1-((4-(N-(ethoxycarbonyl)carbamimidoyl)benzyl)amino)-1-oxopropan-2-yl)carbamoyl)-4-phenylpyrrolidine-1-carboxylate (168 mg, 91% yield).

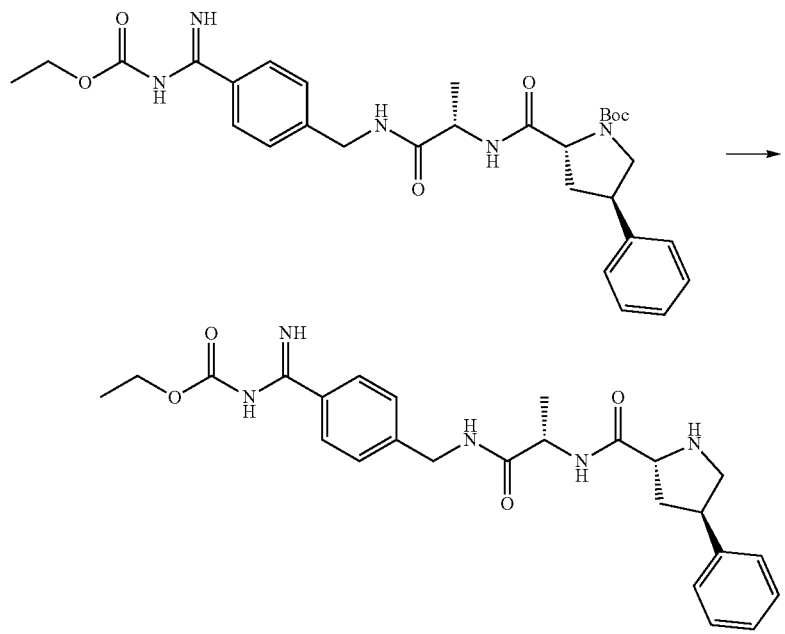

Step 4: Deprotection of tert-butyl (2R,4R)-2-(((S)-1-((4-(N-(ethoxycarbonyl)carbamimidoyl)benzyl)amino)-1-oxopropan-2-yl)carbamoyl)-4-phenylpyrrolidine-1-carboxylate (168 mg, 0.3 mmol) was conducted according to the procedure for compound (1260), step 4 to give ethyl (imino(4-(((S)-2-((2R,4R)-4-phenylpyrrolidine-2-carboxamido)propanamido)methyl)phenyl)methyl)carbamate (102 mg, 74% yield).

Example 98. Preparation of (S)—N-(1-((4-Carbamimidoylbenzyl)amino)-1-oxopropan-2-yl)-3-phenyl-1H-pyrazole-5-carboxamide (1295)

(1295)

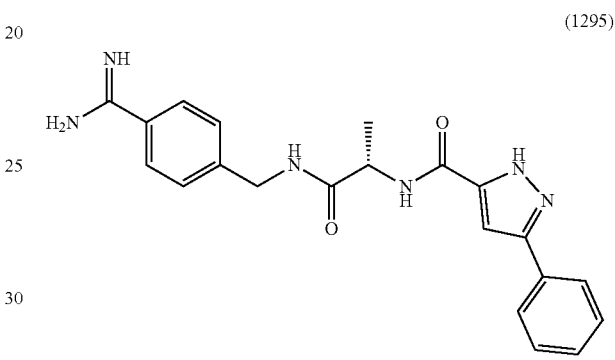

(S)—N-(1-((4-Carbamimidoylbenzyl)amino)-1-oxopropan-2-yl)-3-phenyl-1H-pyrazole-5-carboxamide was synthesized according to the procedures for compound (1234).

Example 99. Preparation of (R)-2-Amino-N—((S)-1-(((2-aminopyridin-4-yl)methyl)amino)-1-oxopropan-2-yl)-4-phenylbutanamide Dihydrochloride (1296)

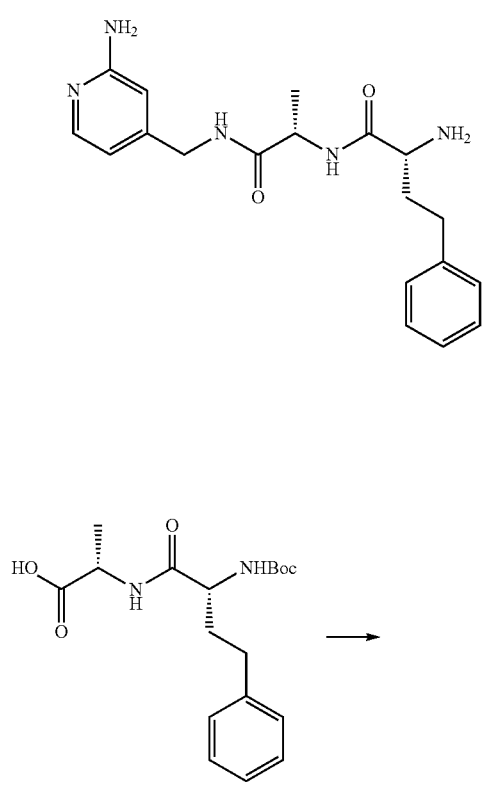

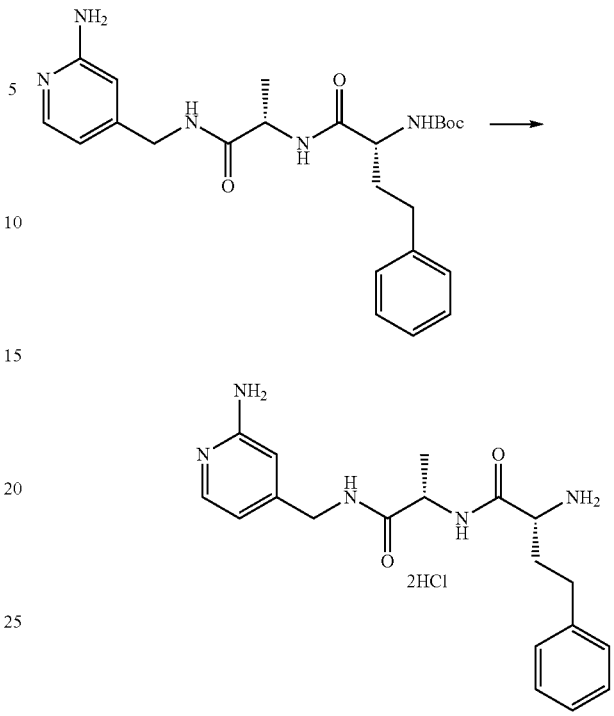

Step 1: ((R)-2-((tert-Butoxycarbonyl)amino)-4-phenylbutanoyl)-L-alanine was coupled with 4-(aminomethyl)pyridin-2-amine according to the procedure for compound (1265) step 1, except that a small amount of sat. NaHCO₃ was added to the reaction mixture. Following extractive workup, purification by chromatography (0-10% MeOH—CH₂Cl₂) gave tert-butyl ((R)-1-(((S)-1-(((2-aminopyridin-4-yl)methyl)amino)-1-oxopropan-2-yl)amino)-1-oxo-4-phenylbutan-2-yl)carbamate (90 mg, 57% yield).

Step 2: tert-Butyl ((R)-1-(((S)-1-(((2-aminopyridin-4-yl)methyl)amino)-1-oxopropan-2-yl)amino)-1-oxo-4-phenylbutan-2-yl)carbamate was deprotected according to the procedure for compound (1243) to give (R)-2-amino-N—((S)-1-(((2-aminopyridin-4-yl)methyl)amino)-1-oxopropan-2-yl)-4-phenylbutanamide dihydrochloride (85 mg, quant. yield).

Example 100. Preparation of (2R,4S)—N—((S)-1-(((6-Amino-2-methylpyridin-3-yl)methyl)amino)-1-oxopropan-2-yl)-4-(naphthalen-1-yl)piperidine-2-carboxamide Dihydrochloride (1297)

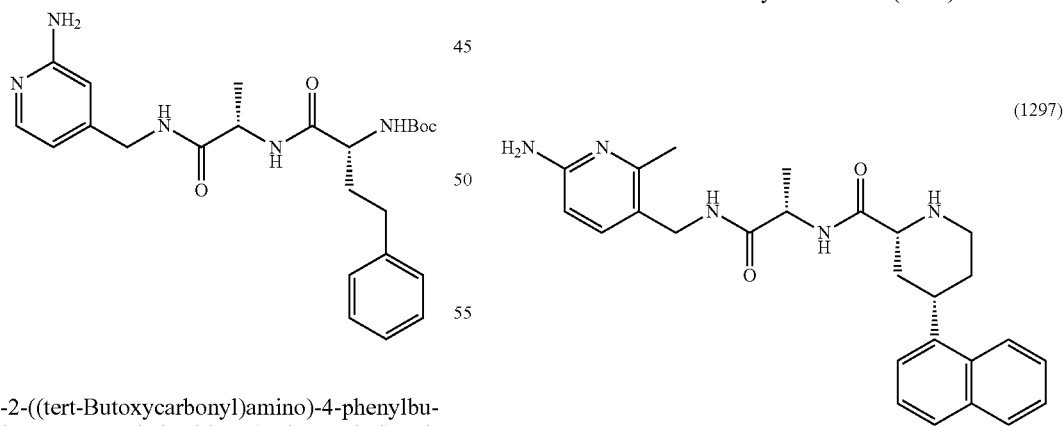

(2R,4S)—N—((S)-1-(((6-Amino-2-methylpyridin-3-yl)methyl)amino)-1-oxopropan-2-yl)-4-(naphthalen-1-yl)piperidine-2-carboxamide dihydrochloride was synthesized according to the procedures for compound (1231) (9) (the third UVActive material eluting from the column in step 6 was carried forward) and compound (1253) steps 1 and 2.

Example 101. Preparation of (2R,4R)—N—((S)-1-((5-chloro-2-hydroxy-3-methylbenzyl)amino)-1-oxopropan-2-yl)-4-phenylpyrrolidine-2-carboxamide Hydrochloride (1298)

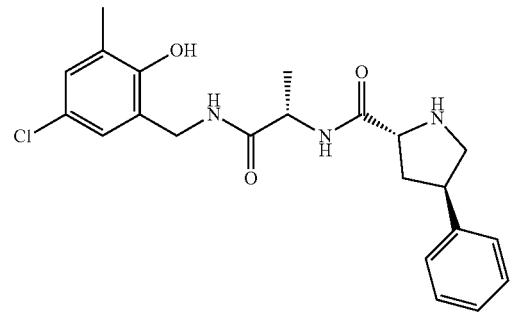
(1298)

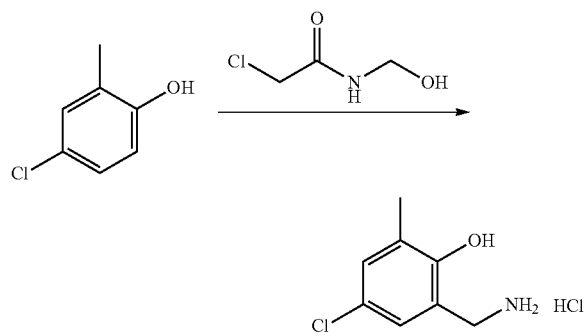

Step 1: A 100 mL round bottom flask was charged with AcOH (18 mL) and H$_2$SO$_4$ (2 mL), then cooled to 0° C. Cl—N-(hydroxymethyl)acetamide (4.32 g, 35 mmol) and 4-chloro-2-methylphenol (5 g, 35 mmol) were added portionwise to the stirring acidic solution, then the reaction mixture allowed to warm to ambient temperature overnight. The reaction mixture was poured into ice-cold H$_2$O then extracted with CH$_2$Cl$_2$×3. Combined organic layers were washed with brine, dried over Na$_2$SO$_4$ and concentrated to produce a colorless oil. The intermediate was dissolved in EtOH (10 mL), treated with conc. HCl (3 mL) and refluxed for 2 h. The resulting yellow suspension was then stored at −10° C. overnight and filtered with EtOH to yield 2-(aminomethyl)-4-chloro-6-methylphenol, hydrochloride as a white fluffy solid (1.67 g, 23% yield).

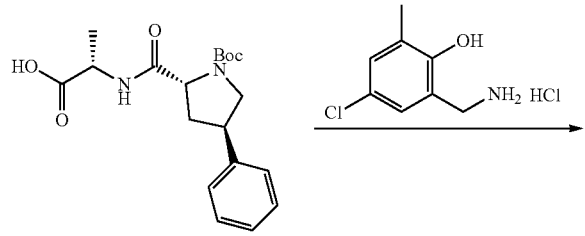

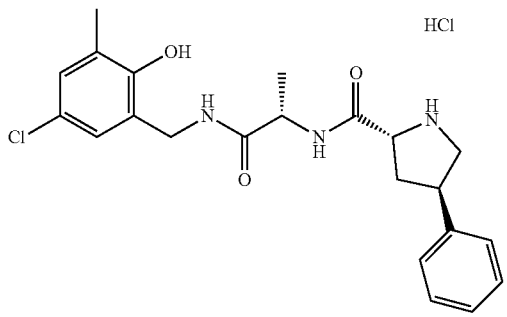

Steps 2-3: The title compound was synthesized as a white powder according to steps 1-2 of the procedure for compound (1246) using the appropriate starting materials (36.7 mg, 25% yield over two steps).

Example 102. Preparation of (R)-2-Amino-N—((S)-1-((5-chloro-2-hydroxy-3-methylbenzyl)amino)-1-oxopropan-2-yl)-4-phenylbutanamide Hydrochloride (1299)

(1299)

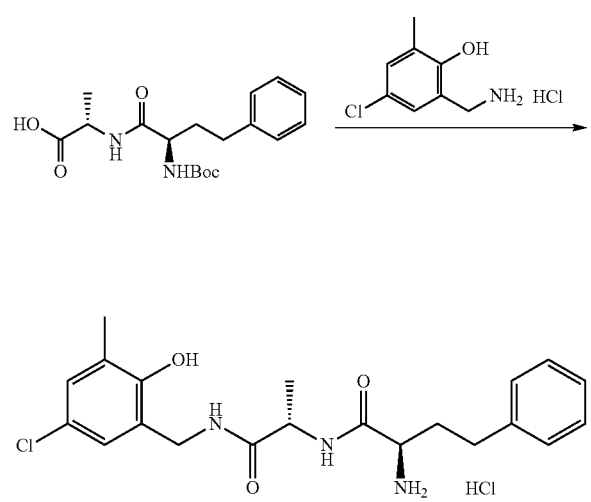

Steps 1-2: The title compound was synthesized as a white granular solid according to steps 1-2 of the procedure for compound (1246) using the appropriate starting materials (65 mg, 59% yield over two steps).

Example 103. Preparation of (2R,4R)—N—((S)-1-((4-Carbamimidoyl-3-fluorobenzyl)amino)-1-oxopropan-2-yl)-4-phenylpyrrolidine-2-carboxamide Di-trifluoroacetate salt (1300)

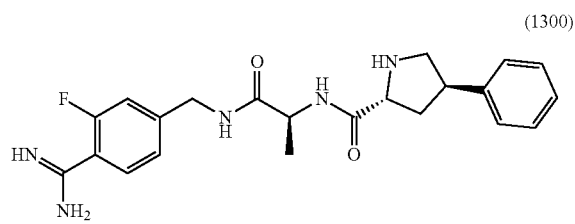

(1300)

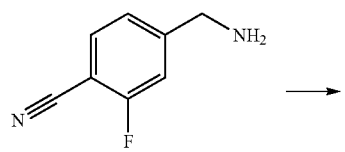

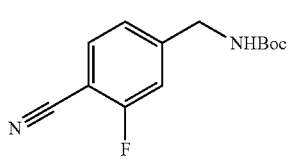

Step 1: To a solution of 4-(aminomethyl)-2-fluorobenzonitrile (986.0 mg, 6.57 mmol) in MeCN (5.5 mL) was added DIEA (1.2 mL, 6.89 mmol) and di-tert-butyl dicarbonate (1.44 g, 6.60 mmol) at room temp. After purging with N₂, the reaction was stirred at room temp for 16 h. Volatiles was evaporated under vacuum. The crude product was diluted with EtOAc (200 mL) and washed with 10% KHSO₄ solution (100 mL, 2 times). The organic layer was washed with brine, dried (Na₂SO₄), vacuum filtered, and evaporated under vacuum. The crude product was dissolved in CH₂Cl₂ and adsorbed on silica gel. Purification by chromatography (0-15% MeOH—CH₂Cl₂) afforded tert-butyl (4-cyano-3-fluorobenzyl)carbamate (1.19 g, 73% yield).

Step 2: Benzyl ((4-(aminomethyl)-2-fluorophenyl)(imino)methyl)carbamate hydrochloride was synthesized according to the procedure for compound 1251, steps 3-6.

Step 3: Benzyl ((2-fluoro-4-(((S)-2-((2R,4R)-4-phenylpyrrolidine-2-carboxamido)propanamido)methyl)phenyl)(imino)methyl)carbamate was synthesized according to the procedure for compound (1281), steps 4-5.

Step 4: Deprotection of benzyl ((2-fluoro-4-(((S)-2-((2R,4R)-4-phenylpyrrolidine-2-carboxamido)propanamido)methyl)phenyl)(imino)methyl)carbamate according to the procedure for compound 1130, step 3. Purification by reverse phase HPLC (5-75-90% MeCN—H₂O) afforded (2R,4R)—N—((S)-1-((4-carbamimidoyl-3-fluorobenzyl)amino)-1-oxopropan-2-yl)-4-phenylpyrrolidine-2-carboxamide di-trifluoroacetate salt.

Example 104. Preparation of (2R,4R)—N—((S)-1-(((5-Chloro-2-oxo-1,2-dihydropyridin-3-yl)methyl)amino)-1-oxopropan-2-yl)-4-phenylpyrrolidine-2-carboxamide Hydrochloride (1301)

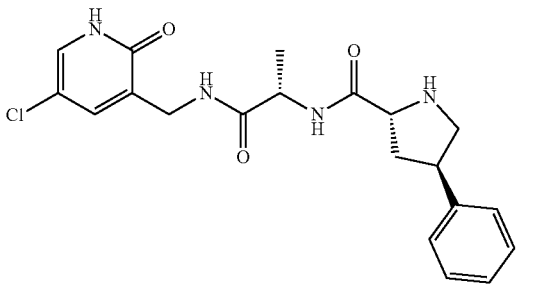

(1301)

(2R,4R)—N—((S)-1-(((5-Chloro-2-oxo-1,2-dihydropyridin-3-yl)methyl)amino)-1-oxopropan-2-yl)-4-phenylpyrrolidine-2-carboxamide hydrochloride was synthesized according to the procedure given for compound (1296).

Example 105. Preparation of (2R,4S)—N—((S)-1-((4-Carbamimidoylbenzyl)amino)-1-oxopropan-2-yl)-4-(3-ethylphenyl)pyrrolidine-2-carboxamide Dihydrochloride (1302)

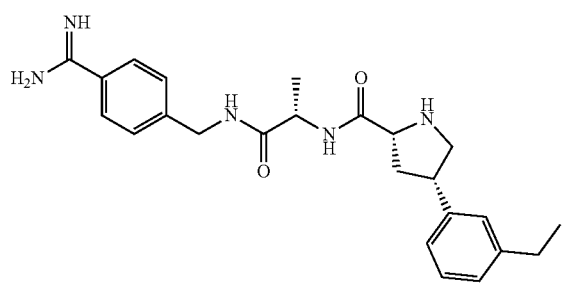

(1302)

(2R,4S)—N—((S)-1-((4-Carbamimidoylbenzyl)amino)-1-oxopropan-2-yl)-4-(3-ethylphenyl)pyrrolidine-2-carboxamide dihydrochloride was synthesized according to the procedures for compound (1247).

Example 106. Preparation of (2R,4S)—N—((S)-1-(((6-Amino-2-methylpyridin-3-yl)methyl)amino)-1-oxopropan-2-yl)-4-(3-ethylphenyl)pyrrolidine-2-carboxamide Dihydrochloride (1303)

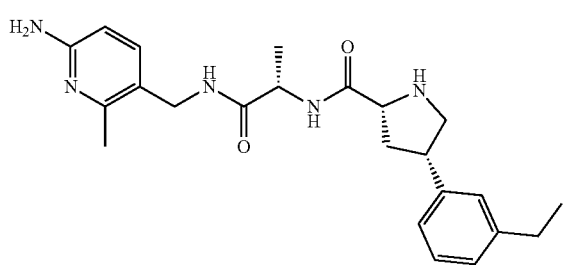

(1303)

The first four steps to synthesize (2R,4S)—N—((S)-1-(((6-amino-2-methylpyridin-3-yl)methyl)amino)-1-oxopropan-2-yl)-4-(3-ethylphenyl)pyrrolidine-2-carboxamide dihydrochloride was performed according to the procedures for compound (1257).

Example 107. Preparation of (2R,4S)—N—((S)-1-(((6-Amino-2-methylpyridin-3-yl)methyl)amino)-1-oxopropan-2-yl)-4-benzylpyrrolidine-2-carboxamide Dihydrochloride (1304)

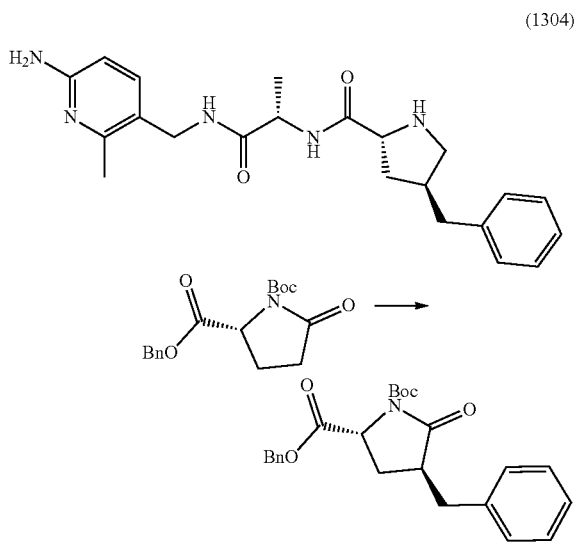

(1304)

Step 1: To a stirred solution of 2-benzyl 1-(tert-butyl) (R)-5-oxopyrrolidine-1,2-dicarboxylate (1.50 g, 4.70 mmol) in THF (31 mL) at −78° C. was slowly added lithium bis(trimethylsilyl)amide (5.17 mL, 5.17 mmol, 1 M in THF) under Ar atmosphere. After stirring for 1 h at −78° C., benzyl bromide (0.653 mL, 5.65 mmol) was added and the stirring continued for an additional 2 h. The reaction mixture was quenched with sat. NH$_4$Cl solution and extracted with diethyl ether (3×60 mL). The combined extracts were dried over Na$_2$SO$_4$, filtered and concentrated under vacuum. The residue was purified by chromatography (EtOAc-hexanes) gave 2-benzyl 1-(tert-butyl) (2R,4S)-4-benzyl-5-oxopyrrolidine-1,2-dicarboxylate (1.60 g, 83% yield).

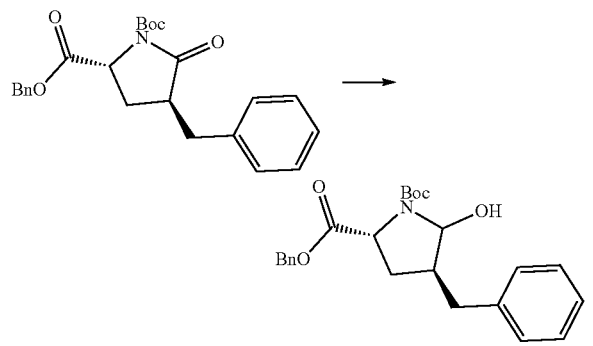

Step 2: To a solution of 2-benzyl 1-(tert-butyl) (2R,4S)-4-benzyl-5-oxopyrrolidine-1,2-dicarboxylate (1.60 g, 3.91 mmol) in THF (26 mL) at −78° C. was added lithium triethylborohydride solution (4.30 mL, 4.30 mmol, 1 M in THF) under Ar atmosphere. After 30 min, the reaction mixture was quenched with sat. NaHCO$_3$ solution (8.60 mL) and warmed to 0° C. At 0° C., 30% H$_2$O$_2$ (about 25 drops) was added and the reaction mixture was stirred at same temperature for 30 min. The organic volatiles were removed under vacuum and the aqueous layer was extracted with CH$_2$Cl$_2$ (3×40 mL). The combined organic extracts were thoroughly dried using Na$_2$SO$_4$, filtered, concentrated to afford 2-benzyl 1-(tert-butyl) (2R,4S)-4-benzyl-5-hydroxypyrrolidine-1,2-dicarboxylate (1.70 g crude) that was directly used in the next step without further purification.

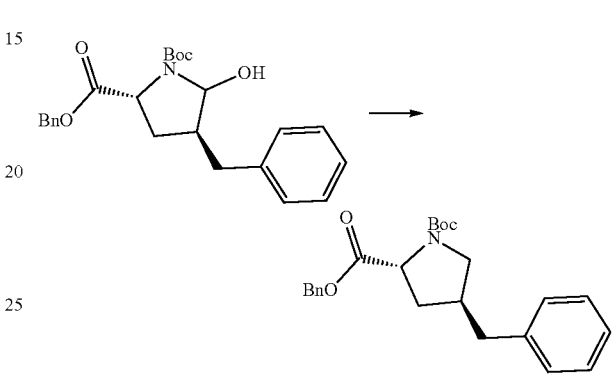

Step 3: To a stirred solution of 2-benzyl 1-(tert-butyl) (2R,4S)-4-benzyl-5-hydroxypyrrolidine-1,2-dicarboxylate (1.70 g crude) and triethylsilane (0.685 mL, 4.30 mmol) in CH$_2$Cl$_2$ (20 mL) at −78° C. was drop wise added boron trifluoride diethyl etherate (0.531 mL, 4.30 mmol) under Ar atmosphere. After 30 min at same temperature additional triethylsilane (0.685 mL, 4.30 mmol) and boron trifluoride diethyl etherate (0.531 mL, 4.30 mmol) were added. After stirring for 2 h at −78° C., the reaction mixture was quenched with sat. aqueous NaHCO$_3$ solution (10 mL) and extracted with CH$_2$Cl$_2$ (3×40 mL). The combined extracts were dried over Na$_2$SO$_4$, filtered and conc under vacuum. The residue was purified by chromatography (EtOAc-hexanes) to afford 2-benzyl 1-(tert-butyl) (2R,4S)-4-benzylpyrrolidine-1,2-dicarboxylate (1.00 g, 65% yield in two steps).

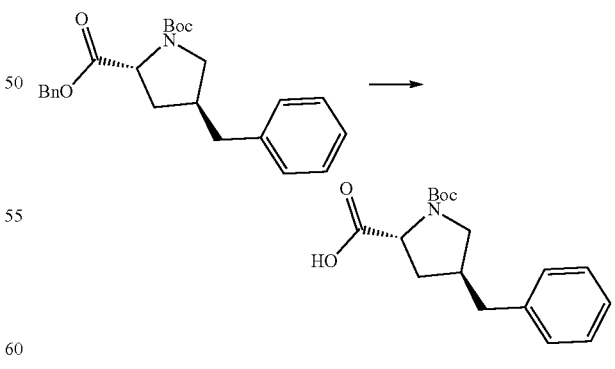

Step 4: A solution of 2-benzyl 1-(tert-butyl) (2R,4S)-4-benzylpyrrolidine-1, 2-dicarboxylate (1.00 g, 2.53 mmol) in MeOH (20 mL) was bubbled with Ar gas for 5 minutes. 10% Pd/C (100 mg) was added to the reaction mixture and that was stirred under 1 atmosphere of H$_2$ for 3 h. The reaction mixture was filtered (0.2 µM syringe filter) and the filtrate was concentrated under vacuum to give (2R,4S)-4-benzyl-1-(tert-butoxycarbonyl)pyrrolidine-2-carboxylic acid (700 mg, 91% yield).

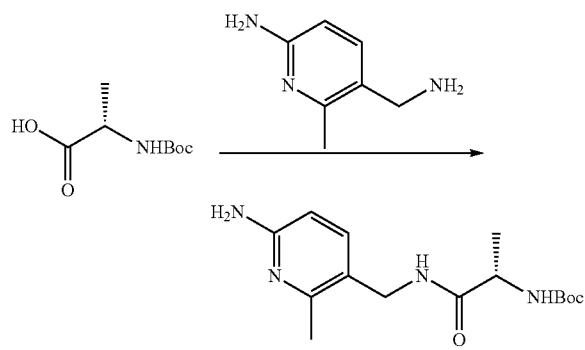

Step 5: To a stirred solution of (tert-butoxycarbonyl)-L-alanine (1.96 g, 10.38 mmol) in CH$_2$Cl$_2$ (55 mL) was added NHS (1.25 g, 10.89 mmol) at room temperature. To the reaction mixture DCC (2.25 g 10.9 mmol) was added and the reaction mixture stirred for 1.0 h. 5-(Aminomethyl)-6-methylpyridin-2-amine was added to the reaction mixture and sonicated for 5 min. The 5-(aminomethyl)-6-methylpyridin-2-amine was completely dissolved and stirred the reaction mixture at ambient temperature for 1 h. The crude reaction mixture was filtered and conc under reduced pressure. The crude reaction mixture was purified by chromatography (MeOH/CH$_2$Cl$_2$) to afford tert-butyl (S)-(1-(((6-amino-2-methylpyridin-3-yl)methyl)amino)-1-oxopropan-2-yl)carbamate (2.35 g, 70% yield) as a white solid.

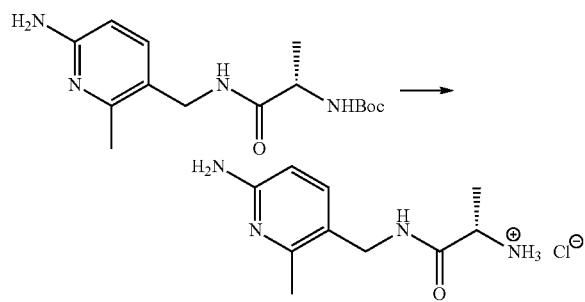

Step 6: To tert-butyl (S)-(1-(((6-amino-2-methylpyridin-3-yl)methyl)amino)-1-oxopropan-2-yl)carbamate (2.35 g, 7.62 mmol) was added a solution of MeOH—HCl (19 mL, 2 M) with stirring at ambient temperature while monitoring for the consumption of starting material (typically 1 h). The solution was evaporated to dryness and MeOH (50 mL) was added and evaporated to dryness to remove residual HCl gas to give (S)-2-amino-N-((6-amino-2-methylpyridin-3-yl)methyl)propanamide hydrochloride (1.60 g, 90% yield) as an off white solid (hygroscopic).

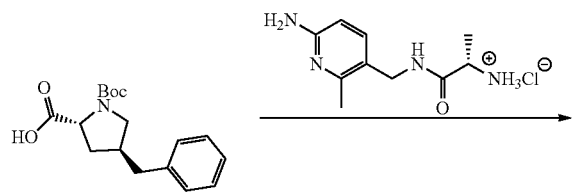

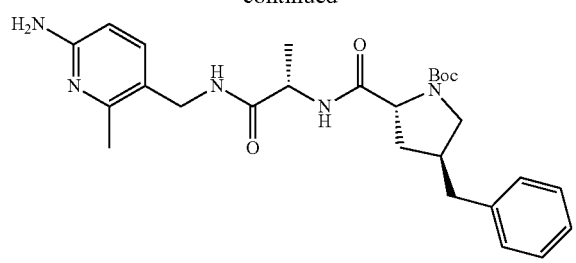

Step 7: To a stirred solution of (2R,4S)-4-benzyl-1-(tert-butoxycarbonyl)pyrrolidine-2-carboxylic acid (100 mg, 0.33 mmol) in anhydrous DMF (3.3 mL) was added HOBt (50 mg, 0.36 mmol), DIEA (0.23 mL, 1.32 mmol) and EDC (69 mg, 0.36 mmol) at ambient temperature. The reaction mixture was stirred for 30 min at ambient temperature. (S)-2-Amino-N-((6-amino-2-methylpyridin-3-yl)methyl)propanamide hydrochloride (97 mg, 0.396 mmol) was added to the reaction mixture and stirred overnight. The solution was evaporated to dryness and the residue was partitioned with EtOAc (20 mL) and 10% KHSO$_4$ (15 mL). The organic layer was separated and washed with sat. NaHCO$_3$ solution (20 ml), dried over anhydrous Na$_2$SO$_4$ and conc under vacuum. The crude reaction mixture was purified by chromatography using MeOH—CH$_2$Cl$_2$ to afford tert-butyl (2R,4S)-2-(((S)-1-(((6-amino-2-methylpyridin-3-yl)methyl)amino)-1-oxopropan-2-yl)carbamoyl)-4-benzylpyrrolidine-1-carboxylate (124 mg, 76% yield) as a white solid.

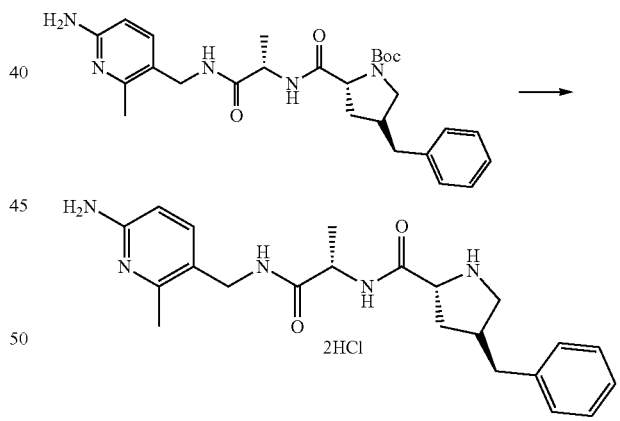

Step 8: To tert-butyl (2R,4S)-2-(((S)-1-(((6-amino-2-methylpyridin-3-yl)methyl)amino)-1-oxopropan-2-yl)carbamoyl)-4-benzylpyrrolidine-1-carboxylate (124 mg, 0.25 mmol) was added a solution of MeOH—HCl (2.0 mL, 2 M) with stirring at ambient temperature while monitoring for the consumption of starting material (30 min to 1 h). The solution was evaporated to dryness and MeOH (10 mL) was added and evaporated to dryness to remove residual HCl gas to yield (2R,4S)—N—((S)-1-(((6-amino-2-methylpyridin-3-yl)methyl)amino)-1-oxopropan-2-yl)-4-benzylpyrrolidine-2-carboxamide dihydrochloride (94 mg, 95% yield) as a white solid.

Example 108. Preparation of 2,2,2-Trifluoroethyl (imino(4-(((S)-2-((2R,4R)-4-phenylpyrrolidine-2-carboxamido)propanamido)methyl)phenyl)methyl) carbamate (1305)

(1305)

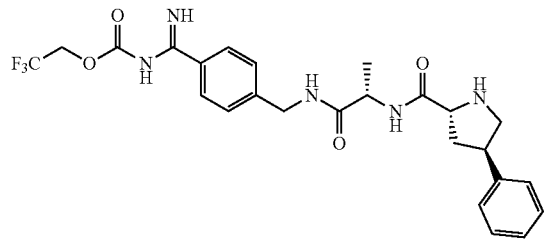

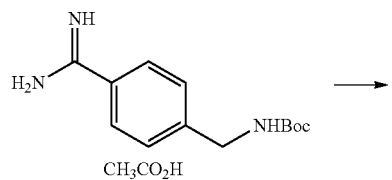

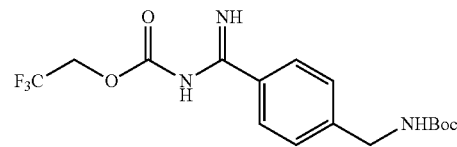

Step 1: tert-Butyl (4-(N-(ethoxycarbonyl)carbamimidoyl)benzyl)carbamate (139 mg, 57% yield) was synthesized from tert-butyl (4-carbamimidoylbenzyl)carbamate acetate salt (200 mg, 0.65 mmol) and trifluoroethyl chloroformate according to the procedure for compound (1288), step 1.

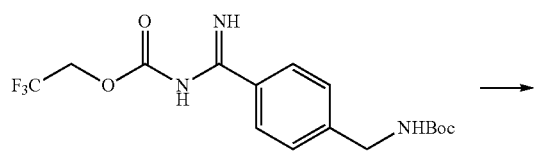

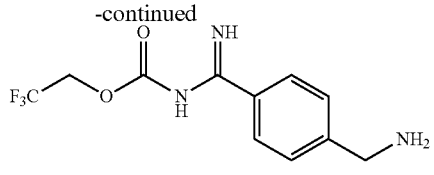

Step 2: Deprotection of tert-butyl (4-(N-(ethoxycarbonyl)carbamimidoyl)benzyl)carbamate (139 mg, 0.37 mmol) was conducted according to the procedure for compound (1259), step 2 to give 2,2,2-trifluoroethyl ((4-(aminomethyl)phenyl)(imino)methyl)carbamate trifluoroacetate salt (144 mg, 100% yield).

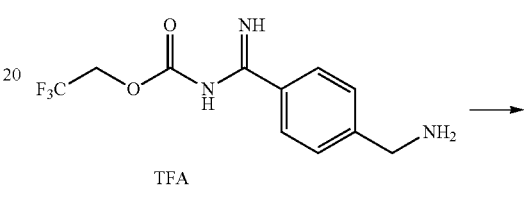

Step 3: 2,2,2-Trifluoroethyl ((4-(aminomethyl)phenyl)(imino)methyl)carbamate trifluoroacetate salt (144 mg, 0.37 mmol) was coupled with ((2R,4R)-1-(tert-butoxycarbonyl)-4-phenylpyrrolidine-2-carbonyl)-L-alanine according to the procedure for compound (1259), step 3 to give tert-butyl (2R,4R)-2-(((S)-1-oxo-1-((4-(N-((2,2,2-trifluoroethoxy)carbonyl)carbamimidoyl)benzyl)amino)propan-2-yl)carbamoyl)-4-phenylpyrrolidine-1-carboxylate (168 mg, 88% yield).

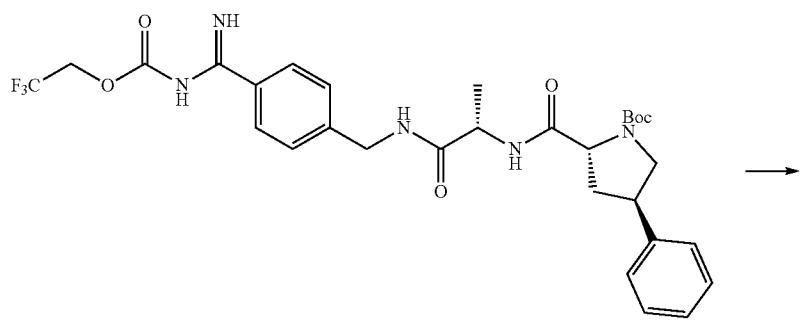

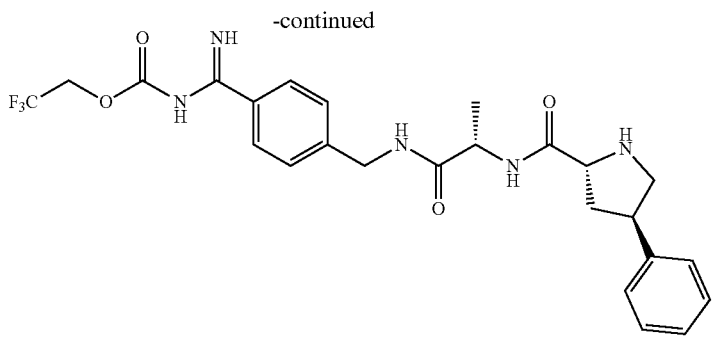

Step 4: Deprotection of tert-butyl (2R,4R)-2-(((S)-1-oxo-1-((4-(N-((2,2,2-trifluoroethoxy)carbonyl)carbamimidoyl)benzyl)amino)propan-2-yl)carbamoyl)-4-phenylpyrrolidine-1-carboxylate (168 mg, 0.27 mmol) was conducted according to the procedure for compound (1260), step 4 to give 2,2,2-trifluoroethyl (imino(4-(((S)-2-((2R,4R)-4-phenylpyrrolidine-2-carboxamido)propanamido)methyl)phenyl)methyl)carbamate (60 mg, 43% yield).

Example 109. Preparation of (2R,4S)-4-Benzyl-N—((S)-1-((4-carbamimidoylbenzyl)amino)-1-oxopropan-2-yl)pyrrolidine-2-carboxamide Dihydrochloride (1306)

(1306)

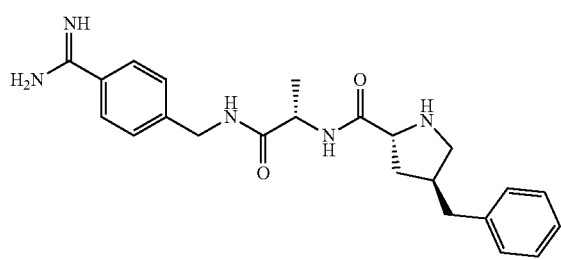

(2R,4S)-4-Benzyl-N—((S)-1-((4-carbamimidoylbenzyl)amino)-1-oxopropan-2-yl)pyrrolidine-2-carboxamide dihydrochloride was synthesized according to the procedures for compound (1304), step 1 to step 4 and compound (1247), step 5 to step 9.

Example 110. Preparation of (2R,4S)-4-Benzyl-N—((S)-1-((5-chloro-2-hydroxy-3-methylbenzyl)amino)-1-oxopropan-2-yl)pyrrolidine-2-carboxamide Hydrochloride (1307)

(1307)

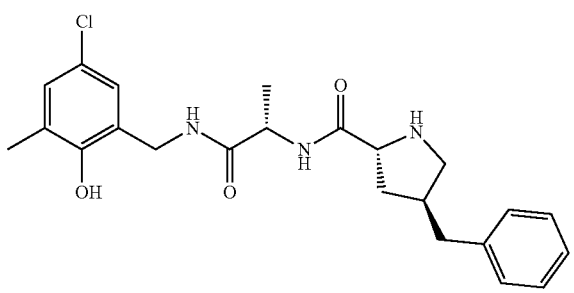

-continued

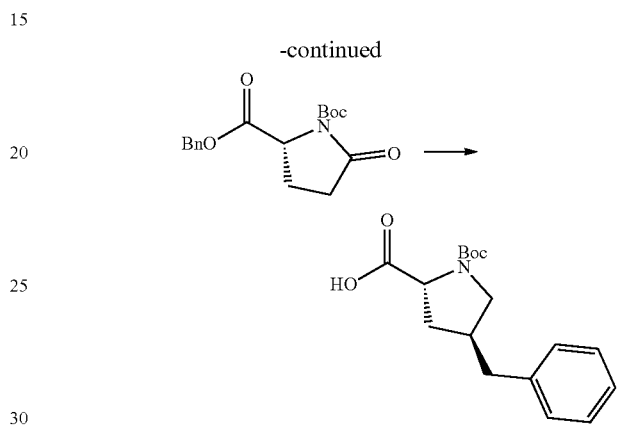

Step 1: (2R,4S)-4-Benzyl-1-(tert-butoxycarbonyl)pyrrolidine-2-carboxylic acid was synthesized from 2-benzyl 1-(tert-butyl) (R)-5-oxopyrrolidine-1,2-dicarboxylate according to the procedures for compound (1304), step 1 to step 4.

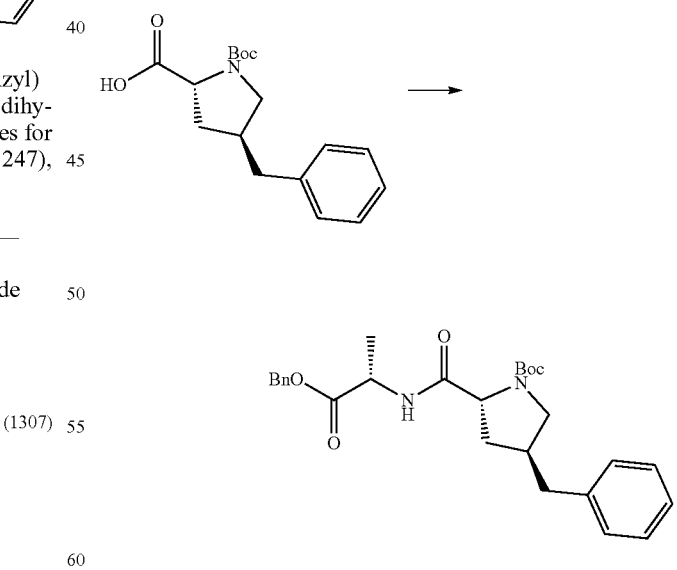

Step 2: tert-Butyl (2R,4S)-4-benzyl-2-(((S)-1-(benzyloxy)-1-oxopropan-2-yl)carbamoyl)pyrrolidine-1-carboxylate (350 mg, 66% yield) was synthesized from (2R,4S)-4-benzyl-1-(tert-butoxycarbonyl)pyrrolidine-2-carboxylic acid (350 mg, 1.14 mmol) according to the procedures for compound (1304), step 7.

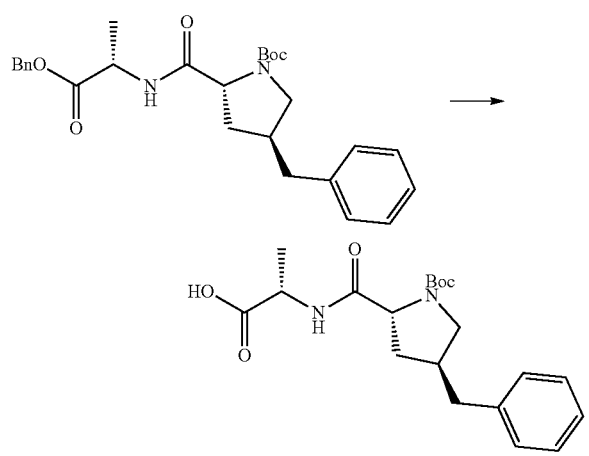

Step 3: ((2R,4S)-4-Benzyl-1-(tert-butoxycarbonyl)pyrrolidine-2-carbonyl)-L-alanine (254 mg, 90% yield) was synthesized from tert-butyl (2R,4S)-4-benzyl-2-(((S)-1-(benzyloxy)-1-oxopropan-2-yl)carbamoyl)pyrrolidine-1-carboxylate (350 mg, 0.75 mmol) according to the procedures for compound (1304), step 4.

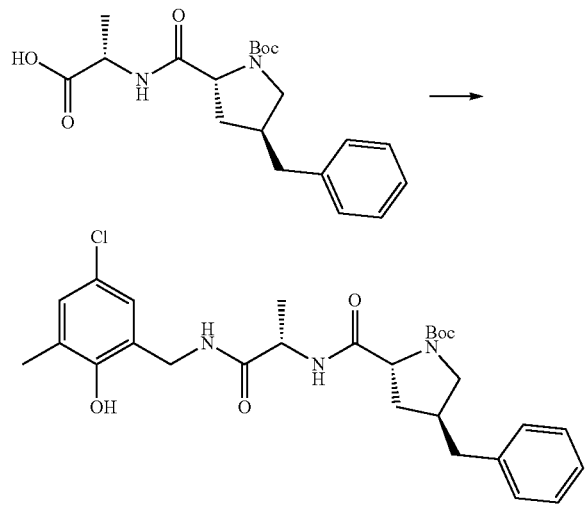

Step 4: tert-Butyl (2R,4S)-4-benzyl-2-(((S)-1-((5-chloro-2-hydroxy-3-methylbenzyl)amino)-1-oxopropan-2-yl)carbamoyl)pyrrolidine-1-carboxylate (66 mg, 70% yield) was synthesized from ((2R,4S)-4-benzyl-1-(tert-butoxycarbonyl)pyrrolidine-2-carbonyl)-L-alanine (67 mg, 0.18 mmol) according to the procedure for compound (1234), step 3.

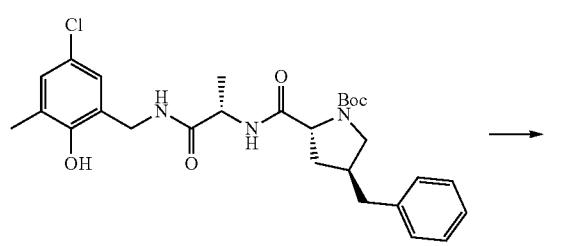

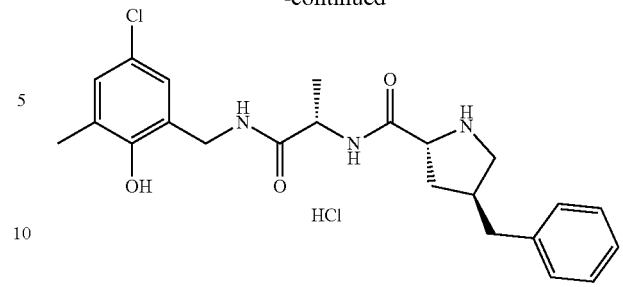

Step 5: (2R,4S)-4-Benzyl-N—((S)-1-((5-chloro-2-hydroxy-3-methylbenzyl)amino)-1-oxopropan-2-yl)pyrrolidine-2-carboxamide hydrochloride (41 mg, 80% yield) was synthesized from tert-butyl (2R,4S)-4-benzyl-2-(((S)-1-((5-chloro-2-hydroxy-3-methylbenzyl)amino)-1-oxopropan-2-yl)carbamoyl)pyrrolidine-1-carboxylate (66 mg, 0.12 mmol) according to the procedure for compound (1234), step 3.

Example 111. Preparation of (2R,4R)—N—((S)-1-(((6-Amino-2-methylpyridin-3-yl)methyl)amino)-1-oxopropan-2-yl)-4-phenylpiperidine-2-carboxamide Dihydrochloride (1308)

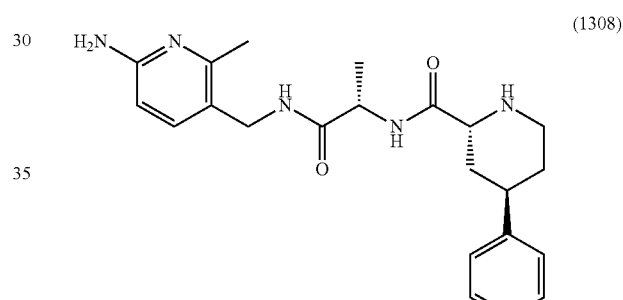

(2R,4R)—N—((S)-1-(((6-Amino-2-methylpyridin-3-yl)methyl)amino)-1-oxopropan-2-yl)-4-phenylpiperidine-2-carboxamide dihydrochloride was synthesized according to the procedures for compound (1253).

Example 112. Preparation of (R)—N—((S)-1-(((6-Amino-2-methylpyridin-3-yl)methyl)amino)-1-oxopropan-2-yl)-4-(naphthalen-1-yl)piperazine-2-carboxamide Dihydrochloride (1309)

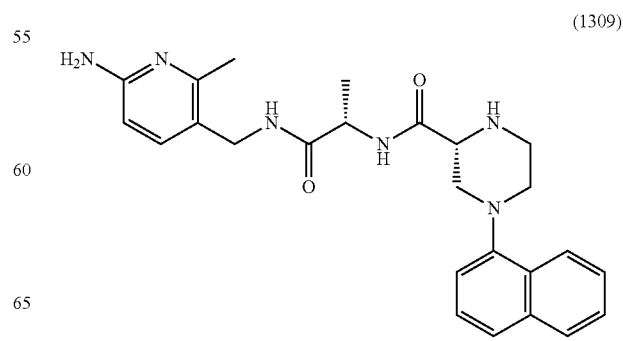

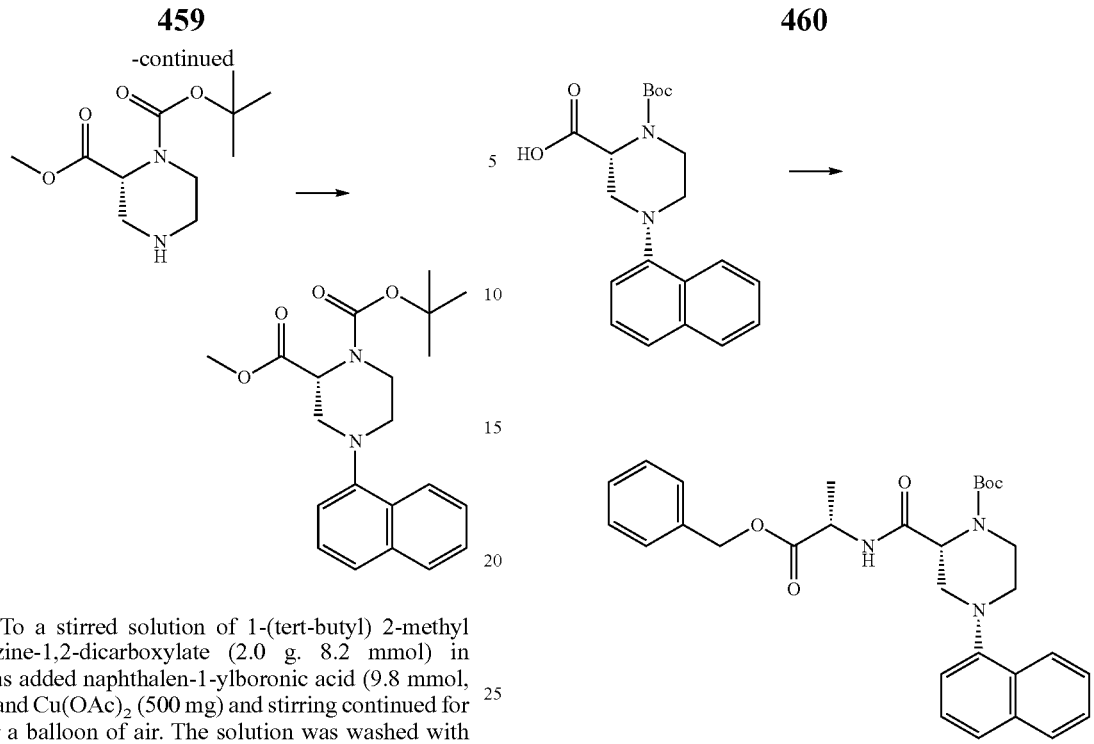

Step 1: To a stirred solution of 1-(tert-butyl) 2-methyl (R)-piperazine-1,2-dicarboxylate (2.0 g. 8.2 mmol) in $CH_2Cl_2$ was added naphthalen-1-ylboronic acid (9.8 mmol, 1.2 equiv) and $Cu(OAc)_2$ (500 mg) and stirring continued for 48 h under a balloon of air. The solution was washed with $H_2O$, dried over $Na_2SO_4$ and evaporated. Column chromatography (20% EtOAc-hexanes) gave 1-(tert-butyl) 2-methyl (R)-4-(naphthalen-1-yl)piperazine-1,2-dicarboxylate (402 mg, 13% yield) as an oil.

Step 2: To a stirred solution of 1-(tert-butyl) 2-methyl (R)-4-(naphthalen-1-yl)piperazine-1,2-dicarboxylate (390 mg, 1.05 mmol) in $MeOH—H_2O$ was added LiOH (3.15 mmol, 3.0 equiv.) with heating at 60° C. for 3 h. The solution is evaporated to dryness and $H_2O$ was added with swirling. The pH was adjusted to 5 with 10% $KHSO_4$ and the product was collected by filtration, washed with $H_2O$ and dried. (R)-1-(Tert-butoxycarbonyl)-4-(naphthalen-1-yl)piperazine-2-carboxylic acid was isolated (335 mg, 89% yield) as a tan solid.

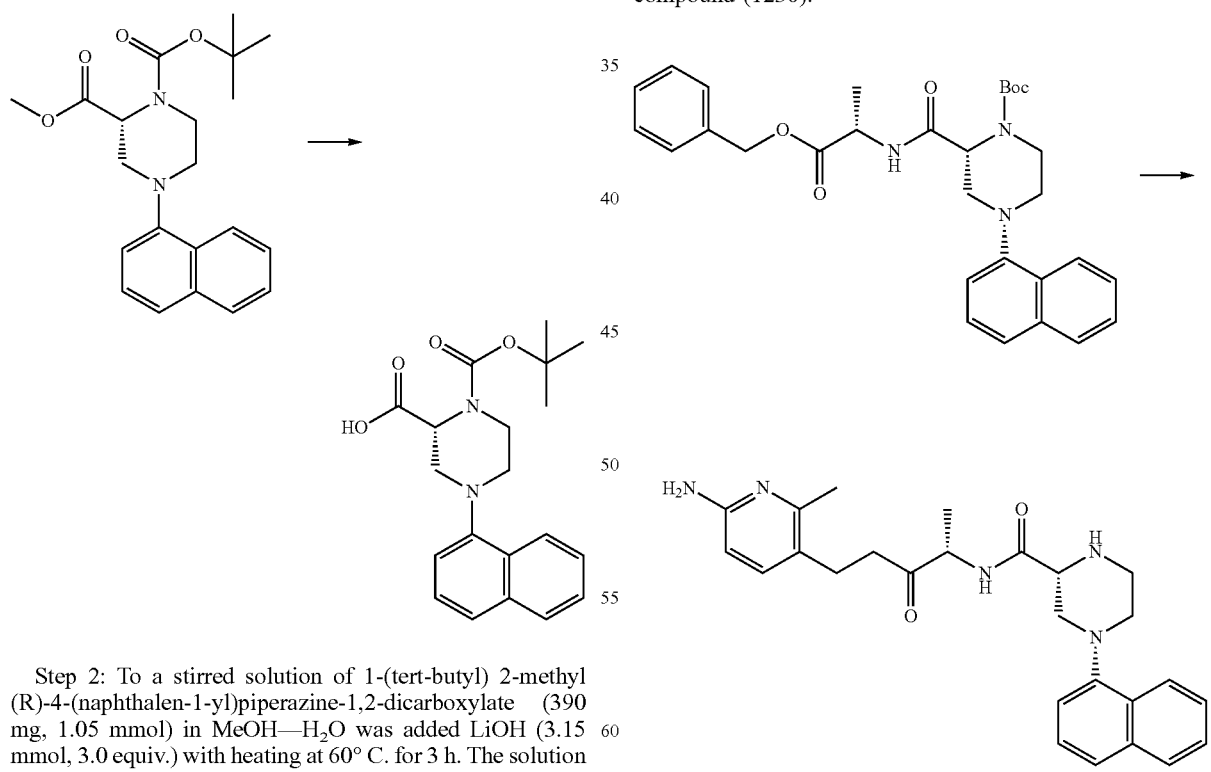

Step 3: tert-Butyl (R)-2-(((S)-1-(benzyloxy)-1-oxopropan-2-yl)carbamoyl)-4-(naphthalen-1-yl)piperazine-1-carboxylate was synthesized according to the procedure for compound (1230).

Steps 4-6: (R)—N—((S)-5-(6-Amino-2-methylpyridin-3-yl)-3-oxopentan-2-yl)-4-(naphthalen-1-yl)piperazine-2-carboxamide was synthesized according to the procedures for compound (1253).

Example 113. Preparation of (2R,4R)—N—((S)-1-(((6-Amino-2-methylpyridin-3-yl)methyl)amino)-1-oxopropan-2-yl)-4-phenoxypyrrolidine-2-carboxamide Dihydrochloride (1310)

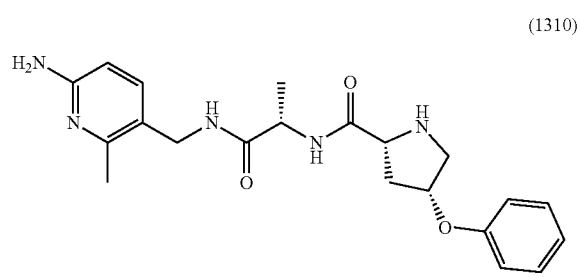 [SMILES: Cc1nc(N)ccc1CNC(=O)[C@H](C)NC(=O)[C@H]1C[C@@H](Oc2ccccc2)CN1]

(1310)

(2R,4R)—N—((S)-1-(((6-Amino-2-methylpyridin-3-yl)methyl)amino)-1-oxopropan-2-yl)-4-phenoxypyrrolidine-2-carboxamide dihydrochloride was synthesized according to the procedures for compound (1304).

Example 114. Preparation of (2R,4R)—N—((S)-1-(((1H-Pyrrolo[2,3-b]pyridin-5-yl)methyl)amino)-1-oxopropan-2-yl)-4-phenylpyrrolidine-2-carboxamide Dihydrochloride (1311)

(1311)

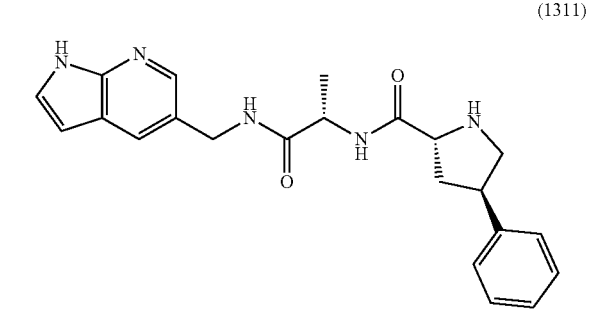

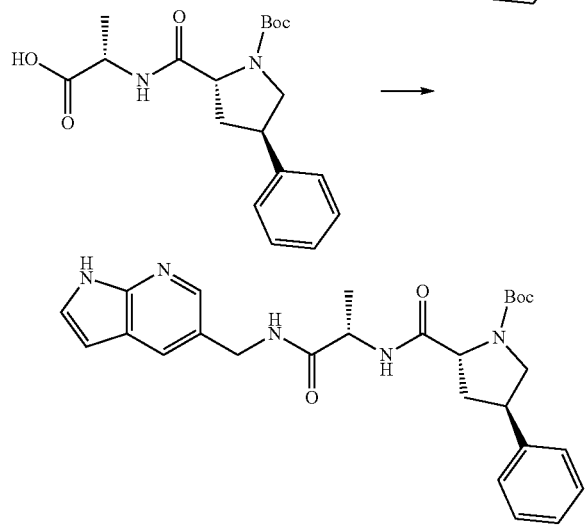

Step 1: ((2R,4R)-1-(tert-Butoxycarbonyl)-4-phenylpyrrolidine-2-carbonyl)-L-alanine was coupled to (1H-pyrrolo[2,3-b]pyridin-5-yl)methanamine according to the procedure given for compound (1265), step 1. Purification by chromatography (0-10% MeOH—CH$_2$Cl$_2$) gave tert-butyl (2R,4R)-2-(((S)-1-(((1H-pyrrolo[2,3-b]pyridin-5-yl)methyl)amino)-1-oxopropan-2-yl)carbamoyl)-4-phenylpyrrolidine-1-carboxylate (100 mg, 69% yield).

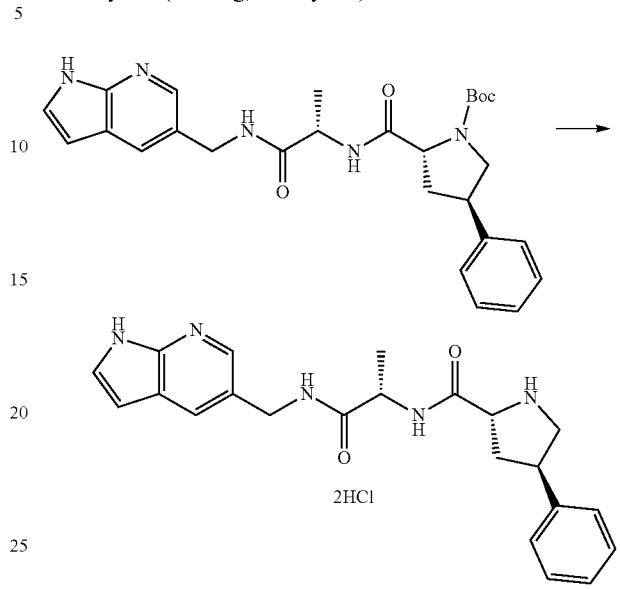

Step 2: tert-Butyl (2R,4R)-2-(((S)-1-(((1H-pyrrolo[2,3-b]pyridin-5-yl)methyl)amino)-1-oxopropan-2-yl)carbamoyl)-4-phenylpyrrolidine-1-carboxylate was deprotected according to the procedure given for compound (1243) to give (2R,4R)—N—((S)-1-(((1H-pyrrolo[2,3-b]pyridin-5-yl)methyl)amino)-1-oxopropan-2-yl)-4-phenylpyrrolidine-2-carboxamide dihydrochloride (89.9 mg, 95% yield).

Example 115. Preparation of (R)—N—((S)-1-((4-Carbamimidoylbenzyl)amino)-1-oxopropan-2-yl)-2-((3-(3-hydroxyphenyl)propyl)amino)-4-phenylbutanamide Di-trifluoroacetate salt (1312)

(1312)

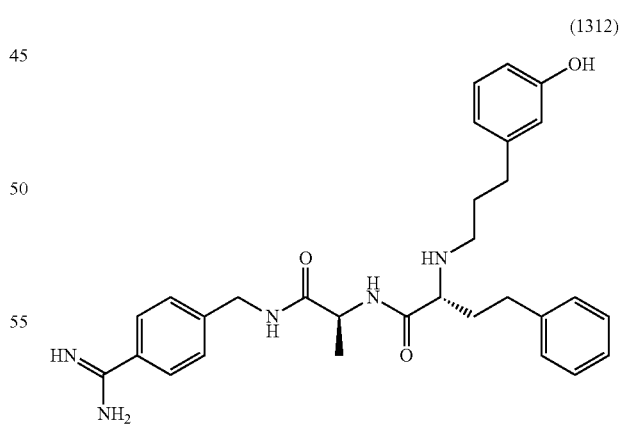

Step 1: Benzyl ((4-(((S)-2-((R)-2-((3-(3-hydroxyphenyl)propyl)amino)-4-phenylbutanamido)propanamido)methyl)phenyl)(imino)methyl)carbamate was synthesized according to the procedure for compound 1130, step 2.

Step 2: Deprotection of benzyl ((4-(((S)-2-((R)-2-((3-(3-hydroxyphenyl)propyl)amino)-4-phenylbutanamido)propanamido)methyl)phenyl)(imino)methyl)carbamate according to the procedure for compound 1130, step 3. Purification by reverse phase HPLC (5-45-90% MeCN—H₂O) afforded (R)—N—((S)-1-((4-carbamimidoylbenzyl)amino)-1-oxopropan-2-yl)-2-((3-(3-hydroxyphenyl)propyl)amino)-4-phenylbutanamide di-trifluoroacetate salt.

Example 116. Preparation of (2R,5S)-5-Amino-N-(5-chloro-2-cyanobenzyl)-2-methyl-4-oxo-7-phenylheptanamide Trifluoroacetate salt (1313)

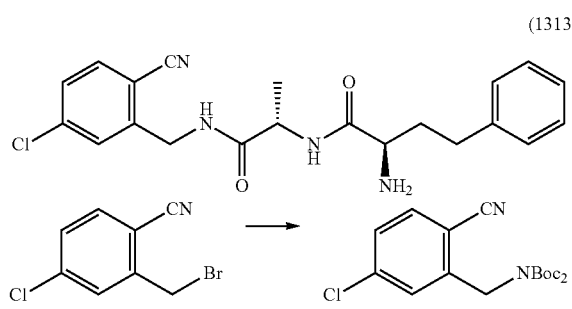

Step 1: A dry 50 mL round bottom flask was charged with NaH (60% in mineral oil) (246 mg, 6.16 mmol) and washed with hexanes 3× under Ar. Dry THF (5 mL) was then added and the suspension cooled to 0° C. 2-(Bromomethyl)-4-chlorobenzonitrile (650 mg, 2.8 mmol) was dissolved in THF (5 mL) and added to the stirring suspension, followed by di-tert-butyl-iminodicarboxylate (679 mg, 3.1 mmol) in THF (5 mL) dropwise. The reaction mixture was allowed to warm to ambient temperature overnight, then quenched with H₂O, poured into sat. aq NH₄Cl and extracted with EtOAc 2×. The combined organic layers were washed with brine and dried over Na₂SO₄. The crude product was then loaded onto silica gel and purified by chromatography (0-30% EtOAc/hexanes) to yield both di-tert-butyl (5-chloro-2-cyanobenzyl)iminodicarbonate (672 mg, 65% yield) and tert-butyl (5-chloro-2-cyanobenzyl)carbamate (158 mg, 21% yield).

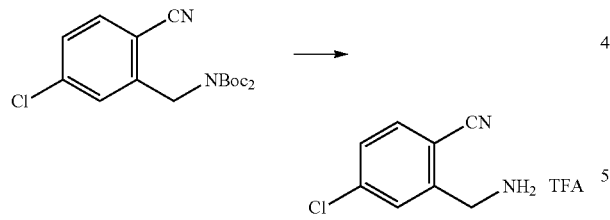

Step 2: Di-tert-butyl (5-chloro-2-cyanobenzyl)iminodicarbonate (110 mg, 0.3 mmol) was dissolved in CH₂Cl₂ and treated with TFA (300 µL) at ambient temperature. After 2 hours, the reaction mixture was concentrated in vacuo to yield 2-(aminomethyl)-4-chlorobenzonitrile, trifluoroacetate as a white powder (79 mg, quant. yield).

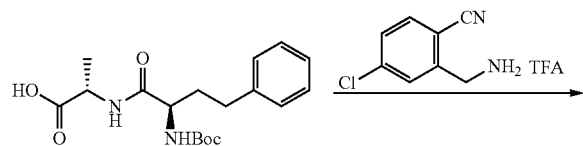

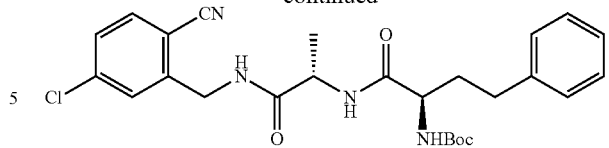

Step 3: tert-Butyl ((R)-1-(((S)-1-((5-chloro-2-cyanobenzyl)amino)-1-oxopropan-2-yl)amino)-1-oxo-4-phenylbutan-2-yl)carbamate was synthesized according to step 1 of the procedure for compound (1246) using the appropriate starting materials.

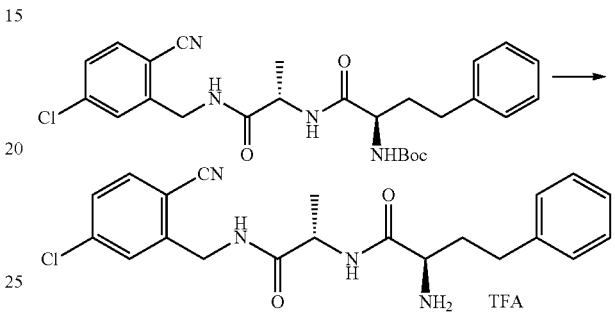

Step 4: tert-Butyl ((R)-1-(((S)-1-((5-chloro-2-cyanobenzyl)amino)-1-oxopropan-2-yl)amino)-1-oxo-4-phenylbutan-2-yl)carbamate (120 mg, 0.24 mmol) was dissolved in CH₂Cl₂ (2 mL) and treated with TFA (~500 µL). After stirring at ambient temperature overnight, the reaction mixture was concentrated, taken up in ACN/H₂O and lyophilized to yield the title compound as a white solid (17 mg, 14% yield over two steps).

Example 117. Preparation of (R)-2-Amino-N—((S)-1-((5-cyano-2-hydroxybenzyl)amino)-1-oxopropan-2-yl)-4-phenylbutanamide Trifluoroacetate salt (1314)

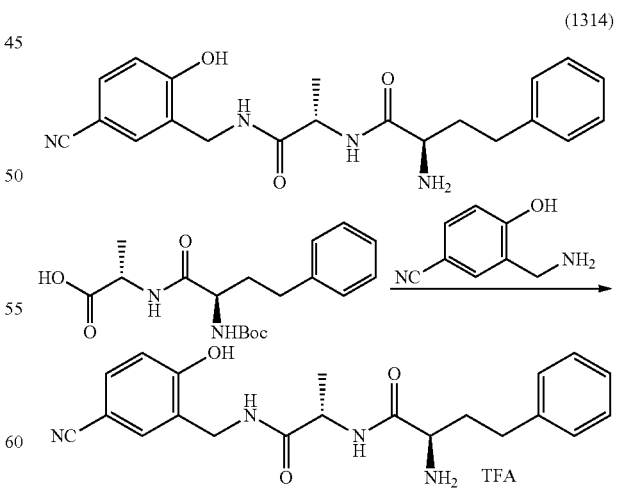

Steps 1-2: The title compound was synthesized as a white solid according to steps 3-4 of the procedure for compound (1313) using the appropriate starting materials (17 mg, 17% yield over two steps).

Example 118. Preparation of (S)-1-((4-Carbamimidoylbenzyl)amino)-1-oxopropan-2-yl (R)-2-amino-4-phenylbutanoate Hydrochloride (1315)

(1315)

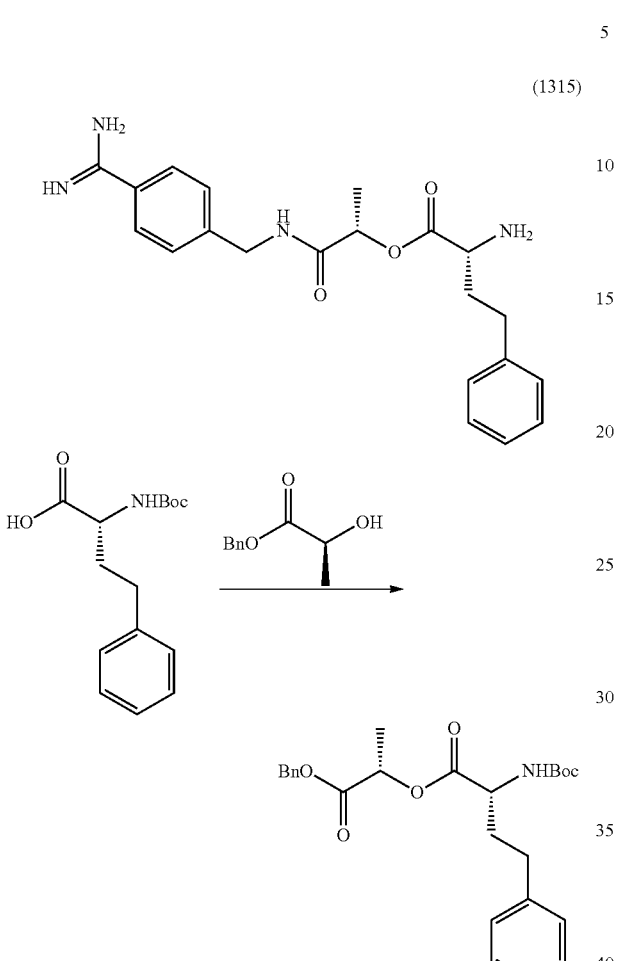

Step 1: To a stirred solution of (R)-2-((tert-butoxycarbonyl)amino)-4-phenylbutanoic acid (838 mg, 3 mmol)), benzyl (S)-lactate (507 µL, 3.15 mmol) and DMAP (403 mg, 3.3 mmol) in CH$_2$Cl$_2$ (15 mL) was added DCC (681 mg, 3.3 mmol). The mixture was stirred for 18 h, then diluted with CH$_2$Cl$_2$ and washed with 10% aq KHSO$_4$, brine and sat. aq. NaHCO$_3$. The organic layer was dried over Na$_2$SO$_4$ and concentrated in vacuo. Chromatography (20% EtOAc/hexanes) gave (S)-1-(benzyloxy)-1-oxopropan-2-yl (R)-2-((tert-butoxycarbonyl)amino)-4-phenylbutanoate (1 g, 76% yield).

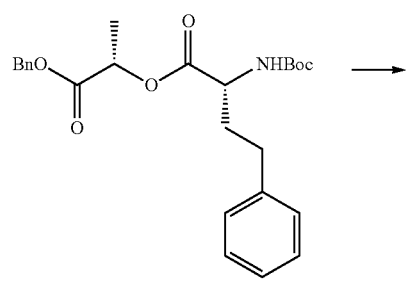

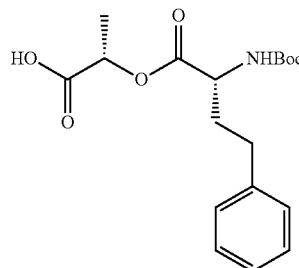

Step 2: Removal of the benzyl group of (S)-1-(benzyloxy)-1-oxopropan-2-yl (R)-2-((tert-butoxycarbonyl)amino)-4-phenylbutanoate was carried out according to the procedure for compound 1028, step 6.

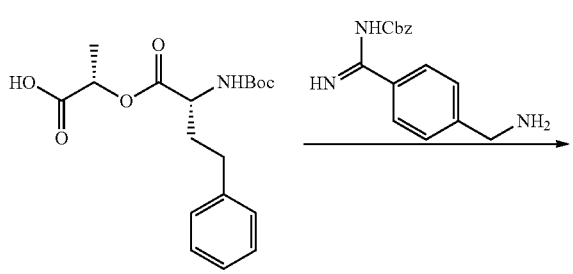

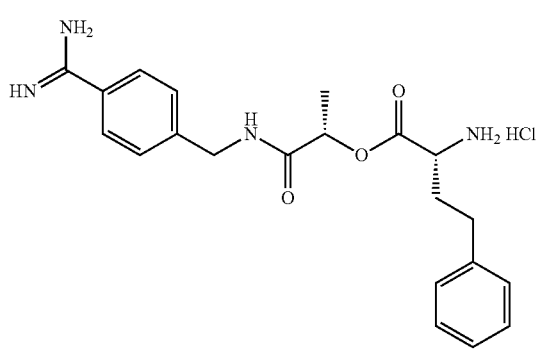

Steps 3-5: (S)-1-((4-Carbamimidoylbenzyl)amino)-1-oxopropan-2-yl (R)-2-amino-4-phenylbutanoate hydrochloride was synthesized as a white granular solid according to steps 3-5 of the procedure for compound 1119 using the appropriate starting materials.

Example 119. Preparation of (2R,4S)—N—((S)-1-((4-Carbamimidoylbenzyl)amino)-1-oxopropan-2-yl)-4-(3-isopropylphenyl)pyrrolidine-2-carboxamide Dihydrochloride (1316)

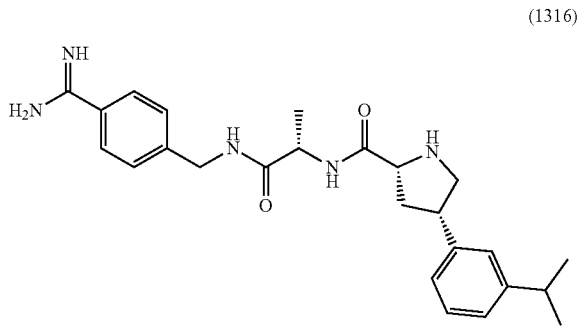 [SMILES: CC(C)c1cccc([C@H]2CN[C@@H](C(=O)N[C@@H](C)C(=O)NCc3ccc(C(=N)N)cc3)C2)c1]
(1316)

(2R,4S)—N—((S)-1-((4-Carbamimidoylbenzyl)amino)-1-oxopropan-2-yl)-4-(3-isopropylphenyl)pyrrolidine-2-carboxamide dihydrochloride was synthesized according to the procedures for compound (1247).

Example 120. Preparation of (R)—N—((S)-1-((5-Chloro-2-hydroxy-3-methylbenzyl)amino)-1-oxopropan-2-yl)-4-(naphthalen-1-yl)piperazine-2-carboxamide Hydrochloride (1317)

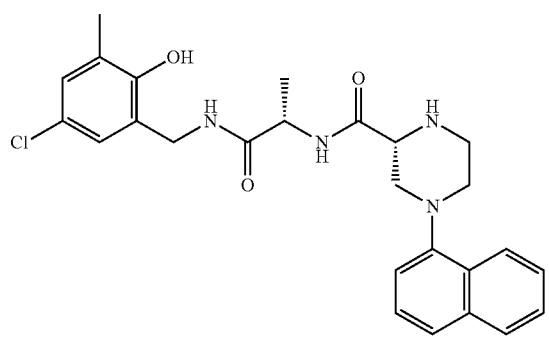
(1317)

(R)—N—((S)-1-((5-Chloro-2-hydroxy-3-methylbenzyl)amino)-1-oxopropan-2-yl)-4-(naphthalen-1-yl)piperazine-2-carboxamide hydrochloride was synthesized according to the procedures for compound (1230), except using (R)-1-(tert-butoxycarbonyl)-4-(naphthalen-1-yl)piperazine-2-carboxylic acid in step 1 and 2-(aminomethyl)-4-chloro-6-methylphenol in step 3.

Example 121. Preparation of (2R,4S)—N—((S)-1-(((6-Amino-2-methylpyridin-3-yl)methyl)amino)-1-oxopropan-2-yl)-4-(3-(trifluoromethyl)benzyl)pyrrolidine-2-carboxamide Dihydrochloride (1318)

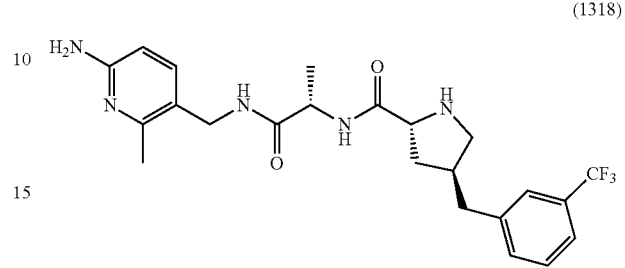
(1318)

(2R,4S)—N—((S)-1-(((6-Amino-2-methylpyridin-3-yl)methyl)amino)-1-oxopropan-2-yl)-4-(3-(trifluoromethyl)benzyl)pyrrolidine-2-carboxamide dihydrochloride was synthesized according to the procedures for compound (1304).

Example 122. Preparation of (R)—N—((S)-1-(((6-Amino-2-methylpyridin-3-yl)methyl)amino)-1-oxopropan-2-yl)-2-((3-(3-hydroxyphenyl)propyl)amino)-4-phenylbutanamide Dihydrochloride salt (1319)

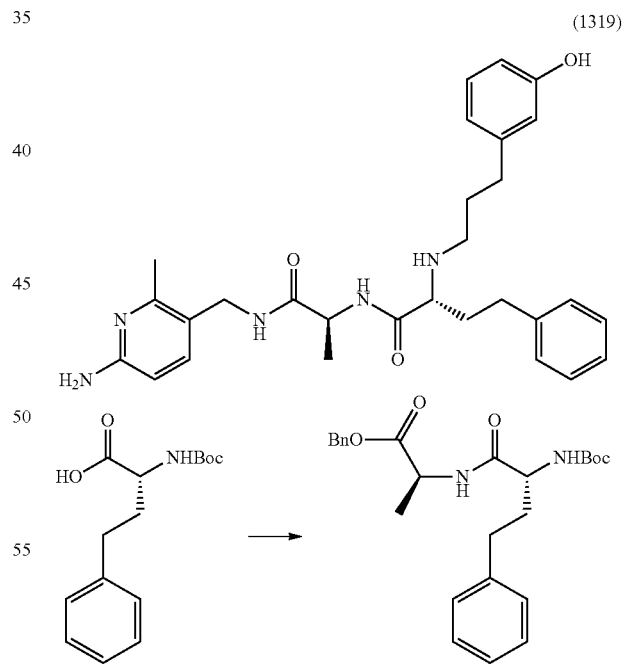
(1319)

Step 1: (R)-2-((tert-Butoxycarbonyl)amino)-4-phenylbutanoic acid (5.0 g, 17.9 mmol) was coupled with commercially available benzyl L-alaninate hydrochloride (4.8 g, 22.3 mmol) according to the procedure for compound 1119, step 1 to afford benzyl ((R)-2-((tert-butoxycarbonyl)amino)-4-phenylbutanoyl)-L-alaninate (6.9 g, 87% yield).

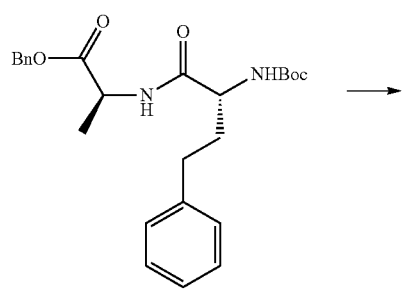

Step 2: Deprotection of benzyl ((R)-2-((tert-butoxycarbonyl)amino)-4-phenylbutanoyl)-L-alaninate (6.9 g, 15.7 mmol)) according to the procedure for compound 1119, step 2 afforded ((R)-2-((tert-butoxycarbonyl)amino)-4-phenylbutanoyl)-L-alanine (5.3 g, 96% yield).

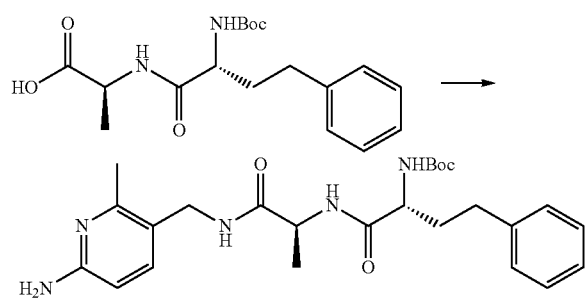

Step 3: ((R)-2-((tert-Butoxycarbonyl)amino)-4-phenylbutanoyl)-L-alanine (470.0 mg, 1.34 mmol) was coupled with commercially available 5-(aminomethyl)-6-methylpyridin-2-amine (560.0 mg, 1.75 mmol) according to the procedure for compound 1088, step 2 except HBTU was added to the reaction at 0° C. afforded tert-butyl ((R)-1-(((S)-1-(((6-amino-2-methylpyridin-3-yl)methyl)amino)-1-oxopropan-2-yl)amino)-1-oxo-4-phenylbutan-2-yl)carbamate (181.6 mg, 29% yield).

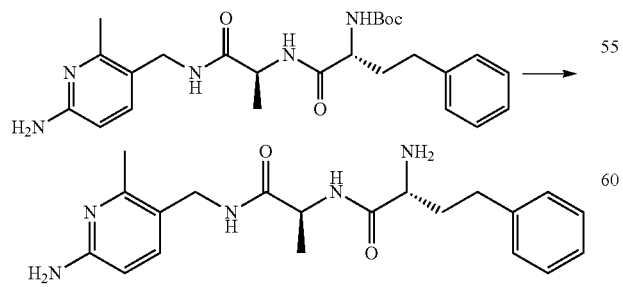

Step 4: Deprotection of tert-butyl ((R)-1-(((S)-1-(((6-amino-2-methylpyridin-3-yl)methyl)amino)-1-oxopropan-2-yl)amino)-1-oxo-4-phenylbutan-2-yl)carbamate (181.6 mg, 0.387 mmol) according to the procedure for compound 1119, step 4 afforded (R)-2-amino-N—((S)-1-(((6-amino-2-methylpyridin-3-yl)methyl)amino)-1-oxopropan-2-yl)-4-phenylbutanamide (115.7 mg, 81% yield).

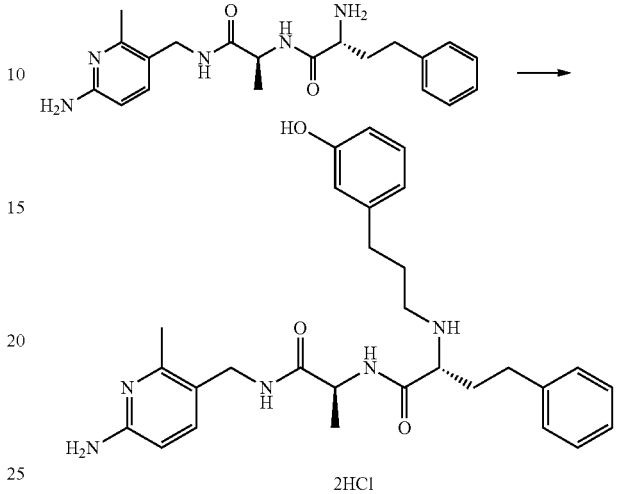

Step 5: (R)-2-Amino-N—((S)-1-(((6-amino-2-methylpyridin-3-yl)methyl)amino)-1-oxopropan-2-yl)-4-phenylbutanamide (115.7 mg, 0.313 mmol) was reacted with 3-(3-hydroxyphenyl)propanal (68.0 mg, 0.453 mmol) according to the procedure for compound 1130, step 2. The crude product was dissolved in $CH_2Cl_2$ and adsorbed onto silica gel. Purification by chromatography (0-15% MeOH—$CH_2Cl_2$) afforded (R)—N—((S)-1-(((6-amino-2-methylpyridin-3-yl)methyl)amino)-1-oxopropan-2-yl)-2-((3-(3-hydroxyphenyl)propyl)amino)-4-phenylbutanamide (42.3 mg, 27% yield).

Step 6: To a solution of R)—N—((S)-1-(((6-Amino-2-methylpyridin-3-yl)methyl)amino)-1-oxopropan-2-yl)-2-((3-(3-hydroxyphenyl)propyl)amino)-4-phenylbutanamide in MeOH (1 mL) was added HCl in MeOH (0.5 mL, ca. 4 M). Volatile was evaporated under vacuum to afford (R)—N—((S)-1-(((6-Amino-2-methylpyridin-3-yl)methyl)amino)-1-oxopropan-2-yl)-2-((3-(3-hydroxyphenyl)propyl)amino)-4-phenylbutanamide dihydrochloride salt.

Example 123. Preparation of (2R,4S)—N—((S)-1-(((6-Amino-2-methylpyridin-3-yl)methyl)amino)-1-oxopropan-2-yl)-5-oxo-4-(3-(trifluoromethyl)benzyl)pyrrolidine-2-carboxamide Di-trifluoroacetate salt (1320)

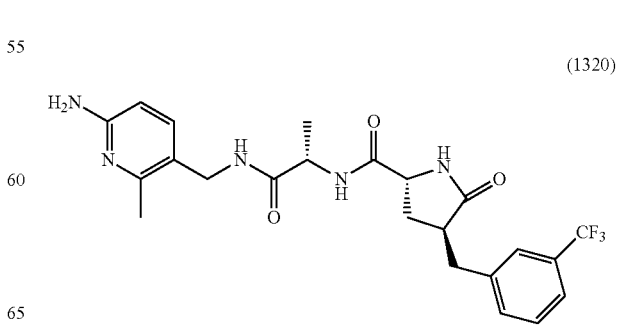

(2R,4S)—N—((S)-1-(((6-Amino-2-methylpyridin-3-yl)methyl)amino)-1-oxopropan-2-yl)-5-oxo-4-(3-(trifluoromethyl)benzyl)pyrrolidine-2-carboxamide di-trifluoroacetate salt was synthesized according to the procedures for compound (1304) except that the final product was purified using reverse-phase HPLC.

Example 124. Preparation of (2R,4S)—N—((R)-1-(((6-Amino-2-methylpyridin-3-yl)methyl)amino)-1-oxopropan-2-yl)-5-oxo-4-(3-(trifluoromethyl)benzyl)pyrrolidine-2-carboxamide Di-trifluoroacetate salt (1321)

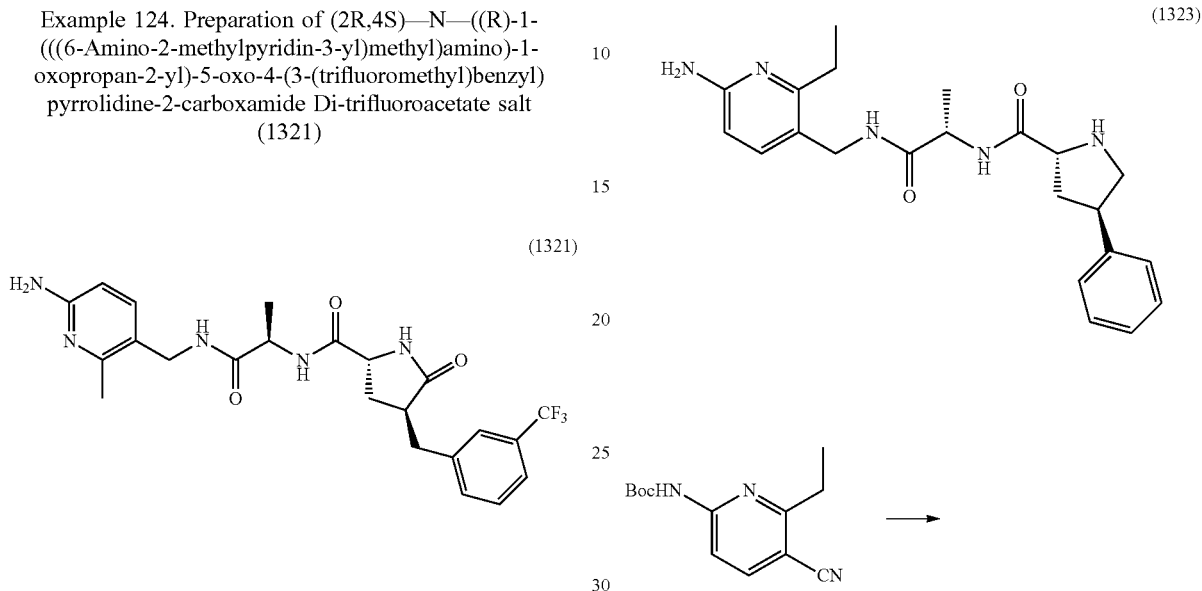

(2R,4S)—N—((R)-1-(((6-Amino-2-methylpyridin-3-yl)methyl)amino)-1-oxopropan-2-yl)-5-oxo-4-(3-(trifluoromethyl)benzyl)pyrrolidine-2-carboxamide di-trifluoroacetate salt was synthesized according to the procedures for compound (1304), except that the final product was purified using reverse-phase HPLC.

Example 125. Preparation of (2R,4R)—N—((S)-1-(((6-Amino-2-methylpyridin-3-yl)methyl)amino)-1-oxopropan-2-yl)-4-phenethylpyrrolidine-2-carboxamide Dihydrochloride (1322)

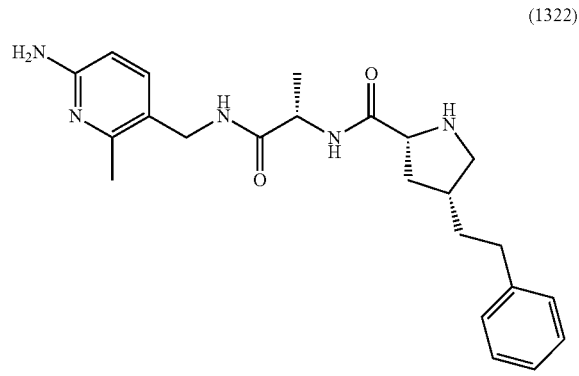 [SMILES: Cc1nc(N)ccc1CNC(=O)[C@H](C)NC(=O)[C@H]1C[C@@H](CCc2ccccc2)CN1]

(2R,4R)—N—((S)-1-(((6-Amino-2-methylpyridin-3-yl)methyl)amino)-1-oxopropan-2-yl)-4-phenethylpyrrolidine-2-carboxamide dihydrochloride was synthesized according to the procedures for compound (1247).

Example 126. Preparation of (2R,4R)—N—((S)-1-(((6-Amino-2-ethylpyridin-3-yl)methyl)amino)-1-oxopropan-2-yl)-4-phenylpyrrolidine-2-carboxamide Dihydrochloride (1323)

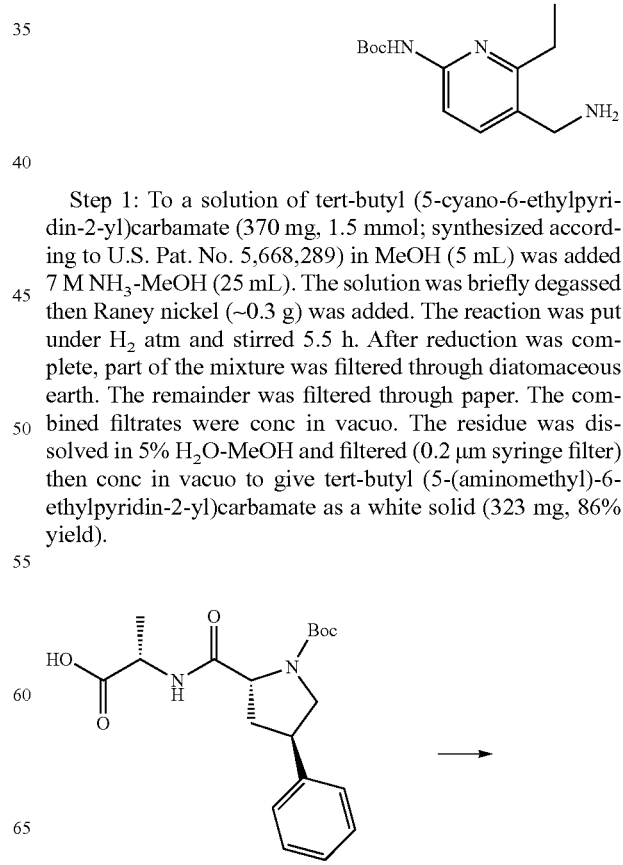

Step 1: To a solution of tert-butyl (5-cyano-6-ethylpyridin-2-yl)carbamate (370 mg, 1.5 mmol; synthesized according to U.S. Pat. No. 5,668,289) in MeOH (5 mL) was added 7 M $NH_3$-MeOH (25 mL). The solution was briefly degassed then Raney nickel (~0.3 g) was added. The reaction was put under $H_2$ atm and stirred 5.5 h. After reduction was complete, part of the mixture was filtered through diatomaceous earth. The remainder was filtered through paper. The combined filtrates were conc in vacuo. The residue was dissolved in 5% $H_2O$-MeOH and filtered (0.2 μm syringe filter) then conc in vacuo to give tert-butyl (5-(aminomethyl)-6-ethylpyridin-2-yl)carbamate as a white solid (323 mg, 86% yield).

-continued

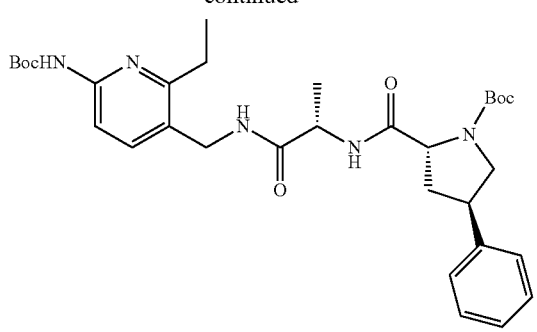

Step 2: ((2R,4R)-1-(tert-Butoxycarbonyl)-4-phenylpyrrolidine-2-carbonyl)-L-alanine was coupled to tert-butyl (5-(aminomethyl)-6-ethylpyridin-2-yl)carbamate according to the procedure for compound (1265), step 1 to give tert-butyl (2R,4R)-2-(((S)-1-(((6-amino-2-ethylpyridin-3-yl)methyl)amino)-1-oxopropan-2-yl)carbamoyl)-4-phenylpyrrolidine-1-carboxylate (134 mg, 77% yield).

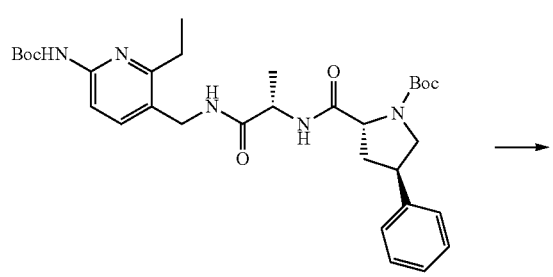

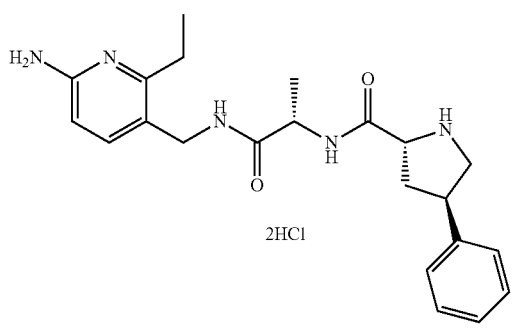

Step 3: tert-Butyl (2R,4R)-2-(((S)-1-(((6-amino-2-ethylpyridin-3-yl)methyl)amino)-1-oxopropan-2-yl)carbamoyl)-4-phenylpyrrolidine-1-carboxylate was deprotected according to the procedure given for compound (1243), except that the product was not extracted with $CH_2Cl_2$. The aqueous solution was filtered (0.2 µm syringe filter) then lyophilized to give (2R,4R)—N—((S)-1-(((6-amino-2-ethylpyridin-3-yl)methyl)amino)-1-oxopropan-2-yl)-4-phenylpyrrolidine-2-carboxamide dihydrochloride (114.9 mg, quant. yield).

Example 127. Preparation of (2R,4S)—N—((S)-1-(((6-Amino-2-methylpyridin-3-yl)methyl)amino)-1-oxopropan-2-yl)-4-(naphthalen-1-ylmethyl)pyrrolidine-2-carboxamide Di-trifluoroacetate salt (1324)

(1324)

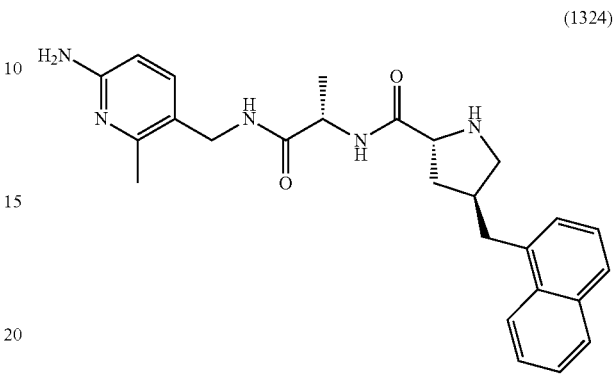

(2R,4S)—N—((S)-1-(((6-Amino-2-methylpyridin-3-yl)methyl)amino)-1-oxopropan-2-yl)-4-(naphthalen-1-ylmethyl)pyrrolidine-2-carboxamide di-trifluoroacetate salt was synthesized according to the procedures for compound (1304), except that the final product was purified using reverse-phase HPLC.

Example 128. Preparation of (R)-2-amino-N—((S)-1-((5-chloro-2-(1H-tetrazol-1-yl)benzyl)amino)-1-oxopropan-2-yl)-4-phenylbutanamide (1325)

(1325)

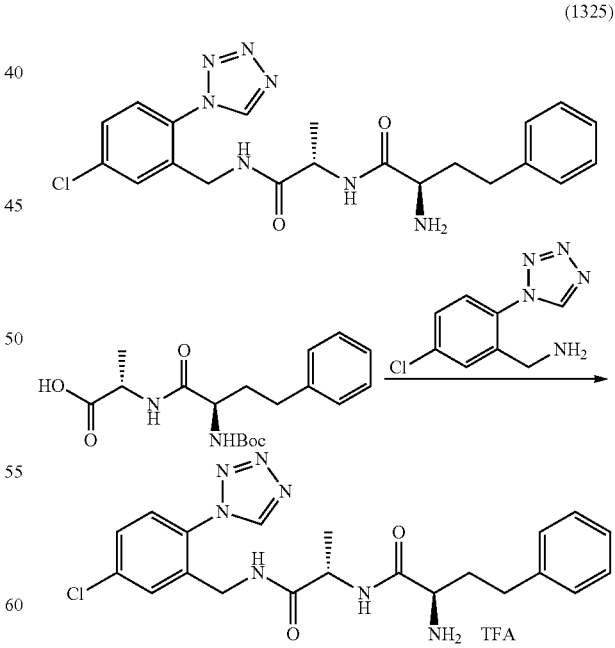

Steps 1-2: The title compound was synthesized as a white solid according to steps 3-4 of the procedure for compound (1313) using the appropriate starting materials (42 mg, 38% yield over two steps).

Example 129. Preparation of (R)-2-Amino-N—((S)-1-((4-carbamimidoylbenzyl)amino)-3-(4-hydroxyphenyl)-1-oxopropan-2-yl)-4-phenylbutanamide Di-trifluoroacetate salt (1326)

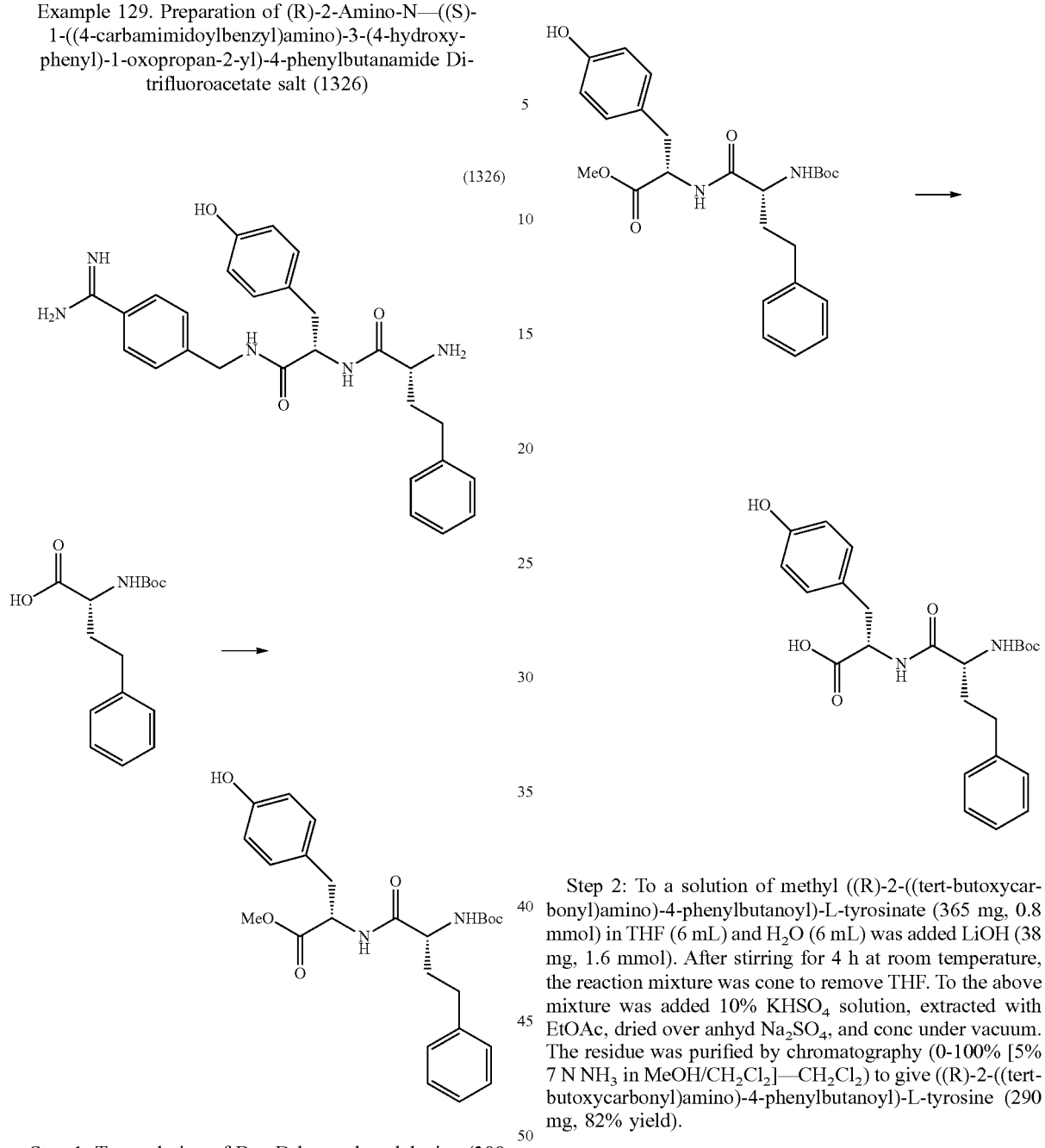

Step 1: To a solution of Boc-D-homophenylalanine (300 mg, 1.07 mmol) in anhyd DMF (6 mL, 0.18 M) was added HOBt (214 mg, 1.4 mmol), DIEA (0.75 mL, 4.3 mmol), and EDC (208 mg, 1.34 mmol). After stirring for 30 min at room temperature, L-tyrosine methyl ester hydrochloride (354 mg, 1.29 mmol) was added and stirred for 16 h. The reaction mixture was conc and the residue was partitioned with EtOAc and 10% $KHSO_4$ solution. The organic layer was separated and washed with $H_2O$ and sat. aq $NaHCO_3$. The organic layer was dried over anhyd $Na_2SO_4$ and concd. The residue was purified by chromatography (0-100% EtOAc-hexanes) to give methyl ((R)-2-((tert-butoxycarbonyl)amino)-4-phenylbutanoyl)-L-tyrosinate (365 mg, 74% yield).

Step 2: To a solution of methyl ((R)-2-((tert-butoxycarbonyl)amino)-4-phenylbutanoyl)-L-tyrosinate (365 mg, 0.8 mmol) in THF (6 mL) and $H_2O$ (6 mL) was added LiOH (38 mg, 1.6 mmol). After stirring for 4 h at room temperature, the reaction mixture was conc to remove THF. To the above mixture was added 10% $KHSO_4$ solution, extracted with EtOAc, dried over anhyd $Na_2SO_4$, and conc under vacuum. The residue was purified by chromatography (0-100% [5% 7 N $NH_3$ in MeOH/$CH_2Cl_2$]—$CH_2Cl_2$) to give ((R)-2-((tert-butoxycarbonyl)amino)-4-phenylbutanoyl)-L-tyrosine (290 mg, 82% yield).

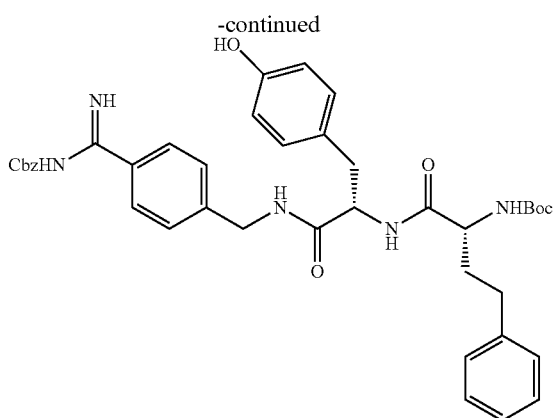

Step 3: To a solution of ((R)-2-((tert-butoxycarbonyl)amino)-4-phenylbutanoyl)-L-tyrosine (290 mg, 0.65 mmol) in CH$_2$Cl$_2$ (18 mL, 0.04 M) was added NHS (83 mg, 0.72 mmol) with stirring at room temp until dissolved. DCC (148 mg, 0.72 mmol) was added and stirred for 1 h. Benzyl ((4-(aminomethyl)phenyl)(imino)methyl)carbamate (222 mg, 0.78 mmol) was added to the above mixture and stirred for 1 h. The reaction was quenched by addition of H$_2$O and the resulting mixture was extracted with CH$_2$Cl$_2$, dried over anhyd Na$_2$SO$_4$, and conc under vacuum. The residue was purified by chromatography (0-100% EtOAc-hexanes) to give tert-butyl ((R)-1-(((S)-1-((4-(N-((benzyloxy)carbonyl)carbamimidoyl)benzyl)amino)-3-(4-hydroxyphenyl)-1-oxopropan-2-yl)amino)-1-oxo-4-phenylbutan-2-yl)carbamate (244 mg, 52% yield).

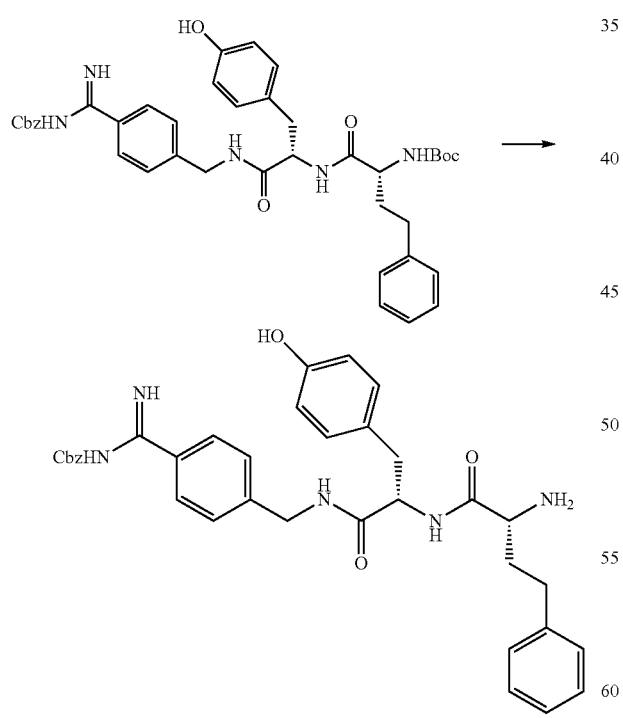

Step 4: Deprotection of tert-butyl ((R)-1-(((S)-1-((4-(N-((benzyloxy)carbonyl)carbamimidoyl)benzyl)amino)-3-(4-hydroxyphenyl)-1-oxopropan-2-yl)amino)-1-oxo-4-phenylbutan-2-yl)carbamate (244 mg, 0.34 mmol) was conducted according to the procedure for compound (1260), step 4 to give benzyl ((4-(((S)-2-((R)-2-amino-4-phenylbutanamido)-3-(4-hydroxyphenyl)propanamido)methyl)phenyl)(imino)methyl)carbamate (126 mg, 61% yield).

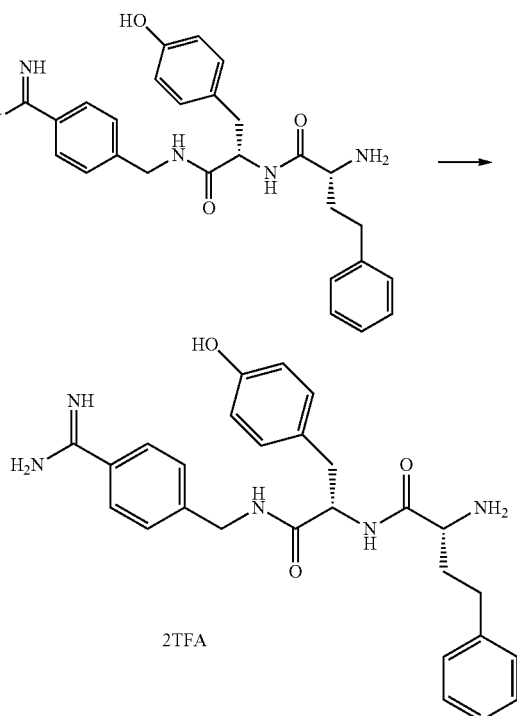

Step 5: Deprotection of benzyl ((4-(((S)-2-((R)-2-amino-4-phenylbutanamido)-3-(4-hydroxyphenyl)propanamido)methyl)phenyl)(imino)methyl)carbamate (126 mg, 0.21 mmol) was conducted according to the procedure for compound (1264), step 2 except that the crude material was purified using reverse-phase HPLC.

Example 130. Preparation of (R)—N—((S)-1-((4-Carbamimidoylbenzyl)amino)-1-oxopropan-2-yl)-2-((4-hydroxyphenethyl)amino)-4-phenylbutanamide dihydrochloride (1327)

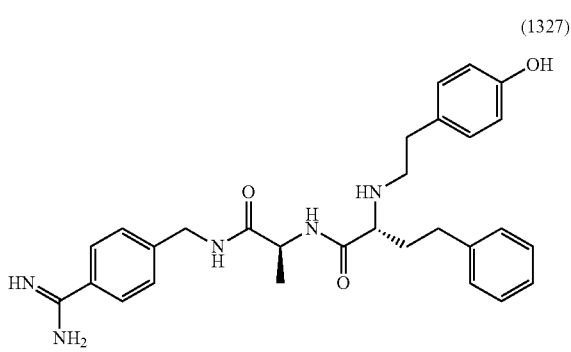 [SMILES: C[C@H](NC(=O)[C@@H](CCc1ccccc1)NCCc1ccc(O)cc1)C(=O)NCc1ccc(C(=N)N)cc1]

Step 1: Benzyl ((4-(((S)-2-((R)-2-amino-4-phenylbutanamido)propanamido)methyl)phenyl)(imino)methyl)carbamate (1.9 g, 41% yield in 4 steps) was synthesized by a method similar to that used for compound 1119, except the crude product was purified by chromatography (10% MeOH—CH$_2$Cl$_2$ and then 5% 7 N NH$_3$ in MeOH—CH$_2$Cl$_2$).

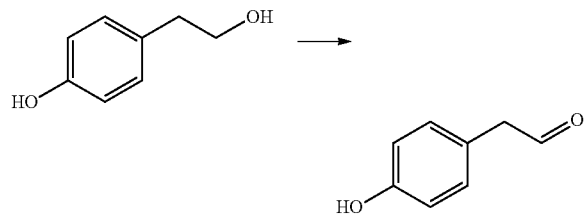

Step 2: To a 25-mL round bottom flask, 4-(2-hydroxyethyl)phenol (1 g, 7.24 mmol) was added and followed by DMSO (8 mL). After purging with N₂, the reaction was treated with TEA (2.2 mL) and followed by the addition of a solution of sulfur trioxide pyridine complex (2.50 g, 15.7 mmol) in DMSO (9 mL) by cannulation. The reaction was stirred at room temp for 1 h and quenched with ice water. The reaction mixture was diluted with CH₂Cl₂ and washed with ice water (3 times). The organic layer was collected, washed with brine, dried (Na₂SO₄), vacuum filtered, and evaporated under vacuum. The crude product was dissolved in CH₂Cl₂ and adsorbed on silica gel. Purification by chromatography (0-100% EtOAc-hexanes) afforded 2-(4-hydroxyphenyl)acetaldehyde (227.4 mg, 23% yield).

Step 3: Benzyl ((4-(((S)-2-((R)-2-((4-hydroxyphenethyl)amino)-4 phenylbutanamido)propanamido)methyl)phenyl)(imino)methyl)carbamate was synthesized according to the procedure for compound 1130, step 2.

Step 4: Deprotection of benzyl ((4-(((S)-2-((R)-2-((4-hydroxyphenethyl)amino)-4 phenylbutanamido)propanamido)methyl)phenyl)(imino)methyl) according to the procedure for compound 1130, step 3 afforded (R)—N—((S)-1-((4-carbamimidoylbenzyl)amino)-1-oxopropan-2-yl)-2-((4-hydroxyphenethyl)amino)-4-phenylbutanamide.

Step 5: (R)—N—((S)-1-((4-Carbamimidoylbenzyl)amino)-1-oxopropan-2-yl)-2-((4-hydroxyphenethyl)amino)-4-phenylbutanamide dihydrochloride was formed according to the procedure for compound (1319), step 6.

Example 131. Preparation of (2R,4S)—N—((S)-1-(((6-amino-2-methylpyridin-3-yl)methyl)amino)-1-oxopropan-2-yl)-4-(3-chlorobenzyl)pyrrolidine-2-carboxamide Dihydrochloride (1328)

(1328)

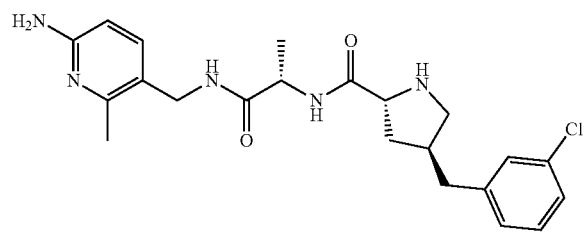

(2R,4S)—N—((S)-1-(((6-Amino-2-methylpyridin-3-yl)methyl)amino)-1-oxopropan-2-yl)-4-(3-chlorobenzyl)pyrrolidine-2-carboxamide dihydrochloride was synthesized according to the procedures for compound (1304), except that the benzyl deprotection was done by following LiOH conditions as shown below.

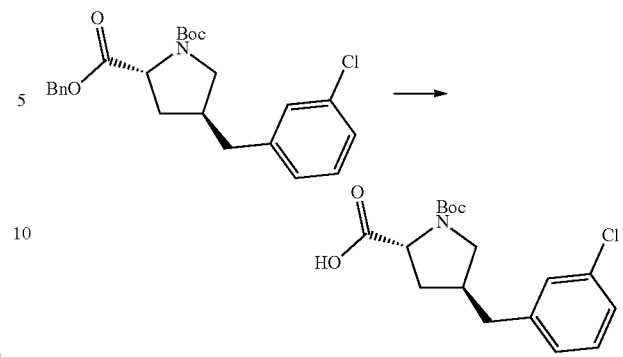

Step 1: To a stirred solution of 2-benzyl 1-(tert-butyl) (2R,4S)-4-(3-chlorobenzyl)pyrrolidine-1,2-dicarboxylate (329 mg, 1 mmol) in THF (24 mL), MeOH (12 mL), and water (12 mL) was added LiOH (360 mg, 15 mmol) at ambient temperature. The resulting reaction mixture was stirred at ambient temperature overnight. Aqueous HCl (12 mL, 1 M) was added to the reaction mixture and organic volatiles were removed under vacuum. The aqueous layer was extracted with EtOAc (3×20 mL). The combined organic extracts were thoroughly dried using Na₂SO₄, filtered, and concentrated to afford (2R,4S)-1-(tert-butoxycarbonyl)-4-(3-chlorobenzyl)pyrrolidine-2-carboxylic acid (320 mg crude, 0.96 mmol) that was directly used in the next step without further purification.

Example 132. Preparation of (2R,4R)—N—((S)-1-(((3-chloro-1H-pyrrolo[2,3-b]pyridin-5-yl)methyl)amino)-1-oxopropan-2-yl)-4-phenylpyrrolidine-2-carboxamide Dihydrochloride (1329)

(1329)

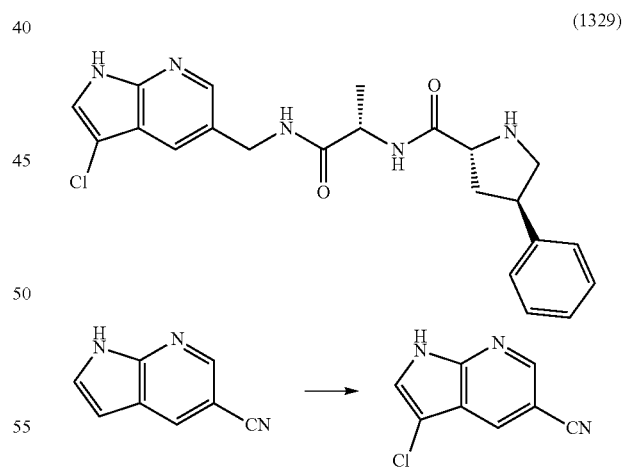

Step 1: To a solution of 1H-pyrrolo[2,3-b]pyridine-5-carbonitrile (1.04 g, 7.24 mmol) in anhyd DMF (14 mL) under Ar was added NCS (1.06 g, 6.9 mmol). The mixture was heated at 55° C. for 2.5 h, cooled to ambient temperature, then diluted with H₂O until the final volume was ~90 mL. The mixture was cooled and the solid was isolated by filtration, rinsed with H₂O and dried in a vac oven (at ambient temperature) to give 3-chloro-1H-pyrrolo[2,3-b]pyridine-5-carbonitrile (1.2 g, 93% yield).

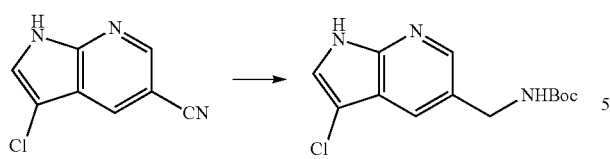

Step 2: To a suspension of 3-chloro-1H-pyrrolo[2,3-b]pyridine-5-carbonitrile (0.50 g, 2.8 mmol) in MeOH (75 mL) was added di-tert-butyl dicarbonate (1.29 g, 5.9 mmol) and CoCl$_2$-6H$_2$O (0.36 g, 1.5 mmol). NaBH$_4$ (0.37 g, 9.8 mmol) was added in 4 aliquots over 20 min. The mixture was stirred for 2 h then additional NaBH$_4$ (0.21 g, 5.6 mmol) was added and stirred overnight. The reaction was acidified with 0.5 M KHSO$_4$ until the pH was neutral. Volatiles were removed in vacuo then the aqueous mixture was extracted with 10% MeOH—CH$_2$Cl$_2$ twice. The aqueous layer was re-adjusted to neutral pH and extracted with 10% MeOH—CH$_2$Cl$_2$. The combined organics were conc in vacuo to remove all volatiles and H$_2$O. Purification by chromatography (two runs: with 0-5% MeOH—CH$_2$Cl$_2$ then 0-25% acetone-CH$_2$Cl$_2$) gave tert-butyl ((3-chloro-1H-pyrrolo[2,3-b]pyridin-5-yl)methyl)carbamate (307 mg, 39% yield).

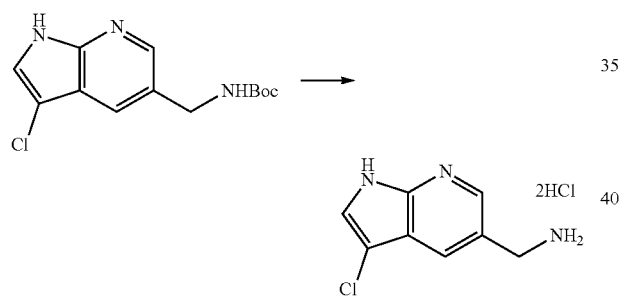

Step 3: To a suspension of tert-butyl ((3-chloro-1H-pyrrolo[2,3-b]pyridin-5-yl)methyl)carbamate (305 mg, 1.08 mmol) in MeOH (6 mL) was added 3 M HCl-CPME (9 mL). The resulting solution was stirred for 2.5 h then additional 3 M HCl-CPME (5 mL) was added. After stirring for 45 min, the solution was conc in vacuo. The residue was dissolved in MeOH and conc in vacuo. The solid was suspended in MeOH-Et$_2$O and the solid was collected by filtration and air dried to give (3-chloro-1H-pyrrolo[2,3-b]pyridin-5-yl)methanamine hydrochloride (285 mg, quant. yield).

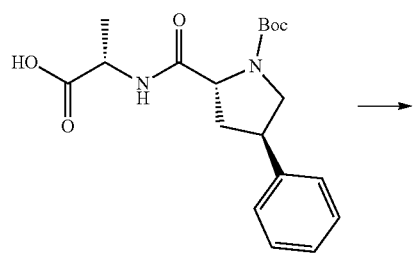

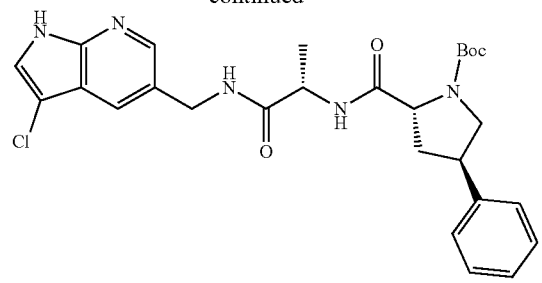

Step 4: ((2R,4R)-1-(tert-Butoxycarbonyl)-4-phenylpyrrolidine-2-carbonyl)-L-alanine was coupled to (3-chloro-1H-pyrrolo[2,3-b]pyridin-5-yl)methanamine according to the procedure for compound (1265) to give tert-butyl (2R,4R)-2-(((S)-1-(((3-chloro-1H-pyrrolo[2,3-b]pyridin-5-yl)methyl)amino)-1-oxopropan-2-yl)carbamoyl)-4-phenylpyrrolidine-1-carboxylate (71.7 mg, 62% yield).

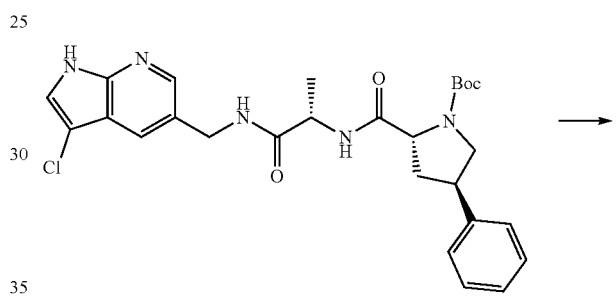

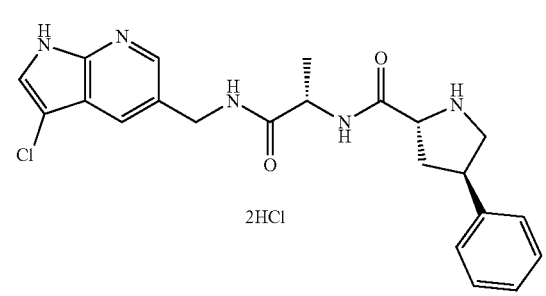

Step 5: tert-Butyl (2R,4R)-2-(((S)-1-(((3-chloro-1H-pyrrolo[2,3-b]pyridin-5-yl)methyl)amino)-1-oxopropan-2-yl)carbamoyl)-4-phenylpyrrolidine-1-carboxylate was deprotected according to the procedure for compound (1243), except that the reaction mixture was diluted with Et$_2$O. The solid was collected by filtration, rinsed with 2% MeOH-Et$_2$O and dried in a vac oven overnight to give (2R,4R)—N—((S)-1-(((3-chloro-1H-pyrrolo[2,3-b]pyridin-5-yl)methyl)amino)-1-oxopropan-2-yl)-4-phenylpyrrolidine-2-carboxamide dihydrochloride (64 mg, 96% yield).

Example 133. Preparation of (R)—N—((S)-1-((4-Carbamimidoylbenzyl)amino)-1-oxopropan-2-yl)-2-((3-hydroxyphenethyl)amino)-4-phenylbutanamide Di-trifluoroacetate salt (1330)

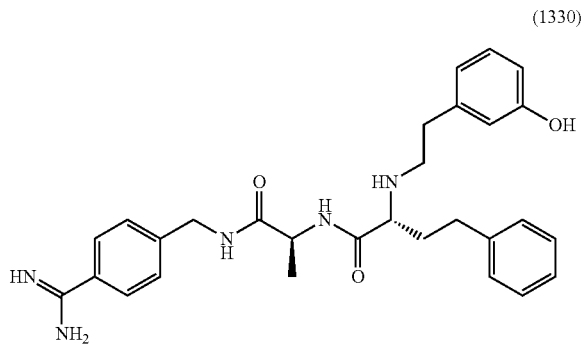 [SMILES: C[C@H](NC(=O)[C@@H](CCc1ccccc1)NCCc1cccc(O)c1)C(=O)NCc1ccc(C(=N)N)cc1]

(1330)

Step 1: 2-(3-Hydroxyphenyl)acetaldehyde was synthesized according to the procedure for compound (1327), step 2.

Step 2: Benzyl ((4-(((S)-2-((R)-2-((3-hydroxyphenethyl)amino)-4-phenylbutanamido)propanamido)methyl)phenyl)(imino)methyl)carbamate was synthesized according to the procedure for compound 1130, step 2.

Step 3: Deprotection of benzyl ((4-(((S)-2-((R)-2-((3-hydroxyphenethyl)amino)-4-phenylbutanamido)propanamido)methyl)phenyl)(imino)methyl)carbamate was done according to the procedure for compound 1130, step 3. Purification by reverse phase HPLC (5-75% MeCN—H₂O) afforded (R)—N—((S)-1-((4-carbamimidoylbenzyl)amino)-1-oxopropan-2-yl)-2-((3-hydroxyphenethyl)amino)-4-phenylbutanamide di-trifluoroacetate salt.

Example 134. Preparation of (2R,4S)—N—((S)-1-(((6-amino-2-methylpyridin-3-yl)methyl)amino)-1-oxopropan-2-yl)-4-(3,5-dimethylbenzyl)pyrrolidine-2-carboxamide Dihydrochloride (1331)

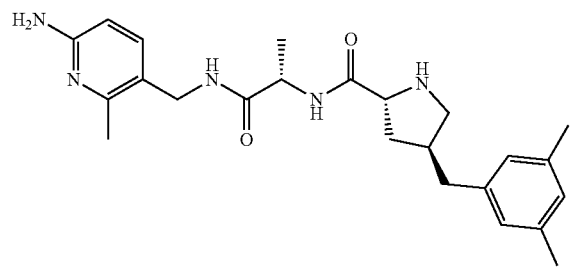

(1331)

(2R,4S)—N—((S)-1-(((6-Amino-2-methylpyridin-3-yl)methyl)amino)-1-oxopropan-2-yl)-4-(3,5-dimethylbenzyl)pyrrolidine-2-carboxamide dihydrochloride was synthesized according to the procedures for compound (1304).

Example 135. Preparation of (R)-2-Amino-N—((S)-1-((4-carbamimidoylbenzyl)amino)-3-(1H-imidazol-5-yl)-1-oxopropan-2-yl)-4-phenylbutanamide Di-trifluoroacetate (1332)

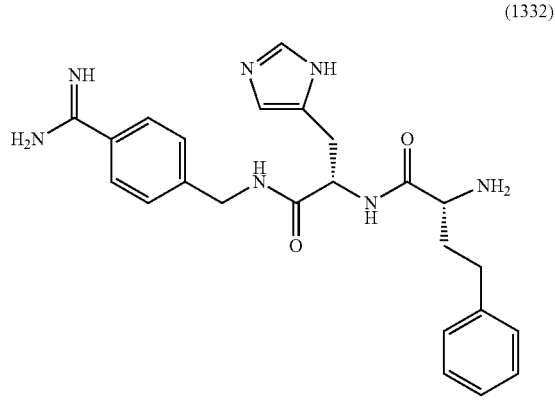

(1332)

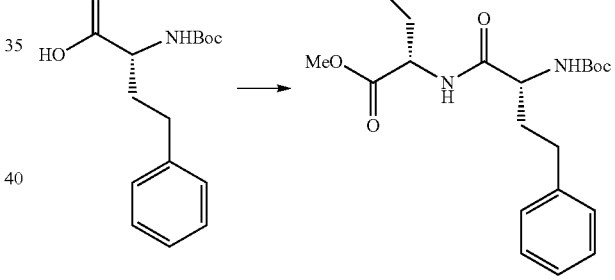

Step 1: Methyl ((R)-2-((tert-butoxycarbonyl)amino)-4-phenylbutanoyl)-L-histidinate (500 mg, 65% yield) was synthesized from Boc-D-homophenylalanine (500 mg, 1.79 mmol) and L-histidine methyl ester dihydrochloride according to the procedure for compound (1326), step 1.

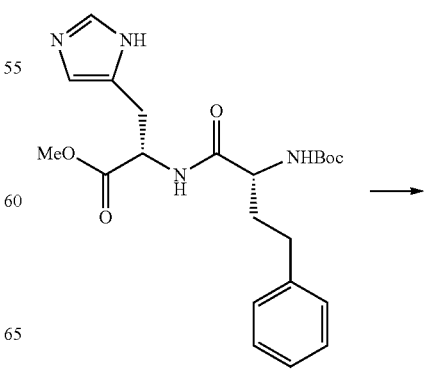

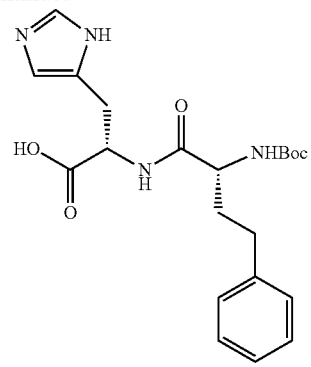

Step 2: ((R)-2-((tert-Butoxycarbonyl)amino)-4-phenylbutanoyl)-L-histidine (320 mg, 66% yield) was synthesized from methyl ((R)-2-((tert-butoxycarbonyl)amino)-4-phenylbutanoyl)-L-histidinate (500 mg, 1.16 mmol) according to the procedure for compound (1326), step 2.

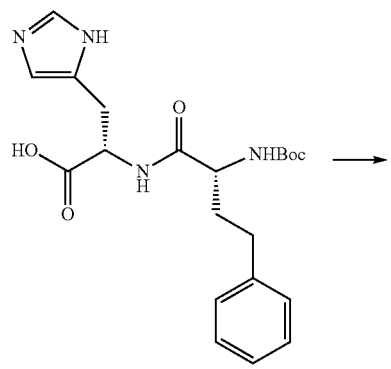

Step 3: tert-Butyl ((R)-1-(((S)-1-((4-(N-((benzyloxy)carbonyl)carbamimidoyl)benzyl)amino)-3-(1H-imidazol-5-yl)-1-oxopropan-2-yl)amino)-1-oxo-4-phenylbutan-2-yl)carbamate (160 mg, 30% yield) was synthesized from ((R)-2-((tert-butoxycarbonyl)amino)-4-phenylbutanoyl)-L-histidine (320 mg, 0.77 mmol) according to the procedure for compound (1326), step 3.

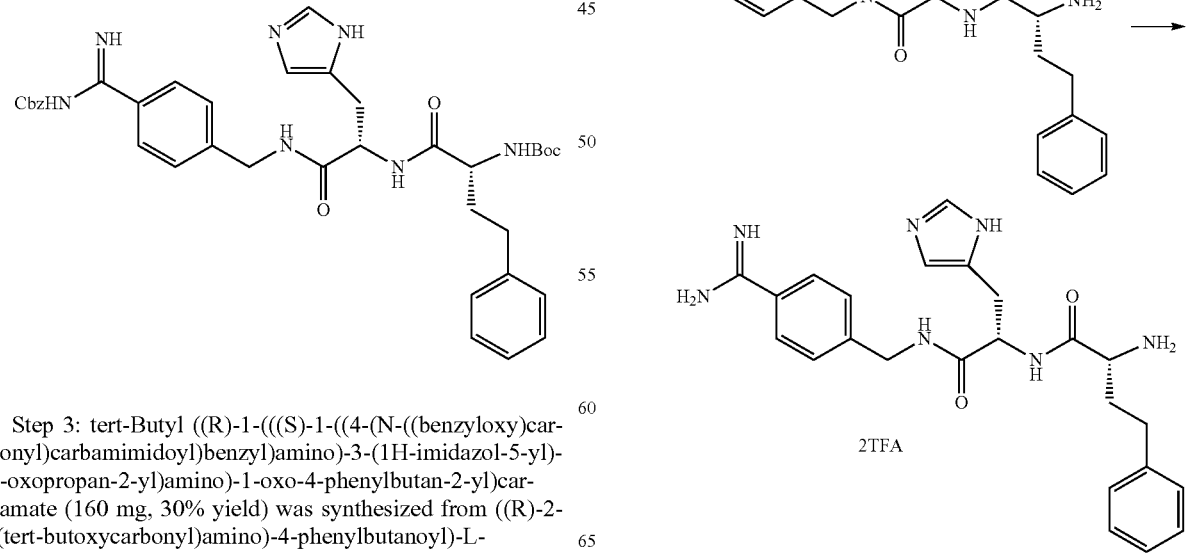

Step 4: Deprotection of tert-butyl ((R)-1-(((S)-1-((4-(N-((benzyloxy)carbonyl)carbamimidoyl)benzyl)amino)-3-(1H-imidazol-5-yl)-1-oxopropan-2-yl)amino)-1-oxo-4-phenylbutan-2-yl)carbamate (160 mg, 0.23 mmol) was conducted according to the procedure for compound (1260), step 4 to give benzyl ((4-(((S)-2-((R)-2-amino-4-phenylbutanamido)-3-(1H-imidazol-5-yl)propanamido)methyl)phenyl)(imino)methyl)carbamate (49 mg, 36% yield).

Step 5: Deprotection of benzyl ((4-(((S)-2-((R)-2-amino-4-phenylbutanamido)-3-(1H-imidazol-5-yl)propanamido)methyl)phenyl)(imino)methyl)carbamate (49 mg, 0.08 mmol) was conducted according to the procedure for compound (1264), step 2 except that the crude material was purified using reverse-phase HPLC.

Example 136. Preparation of (2R,4R)—N—((S)-1-((3-Chloro-5-methylbenzyl)amino)-1-oxopropan-2-yl)-4-phenylpyrrolidine-2-carboxamide Hydrochloride (1333)

(1333)

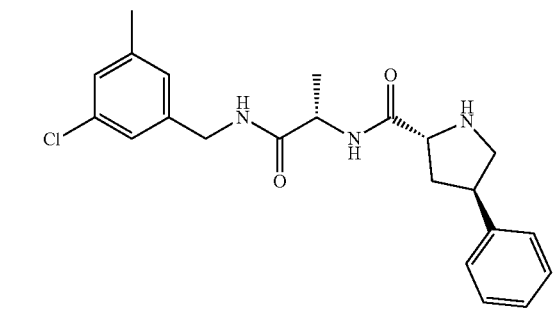

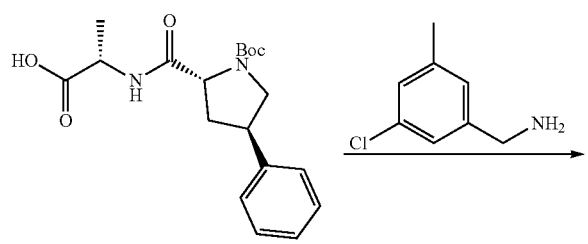

Steps 1-2: The title compound was synthesized as a white powder according to steps 1-2 of the procedure for compound (1246) using the appropriate starting materials (46 mg, 53% yield over two steps).

Example 137. Preparation of (2R,4S)-4-Benzyl-N—((S)-1-(((3-chloro-1H-pyrrolo[2,3-b]pyridin-5-yl)methyl)amino)-1-oxopropan-2-yl)pyrrolidine-2-carboxamide Di-hydrochloride (1334)

(1334)

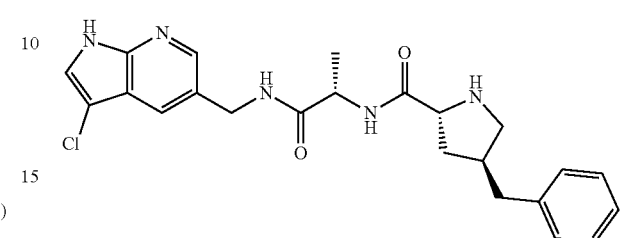

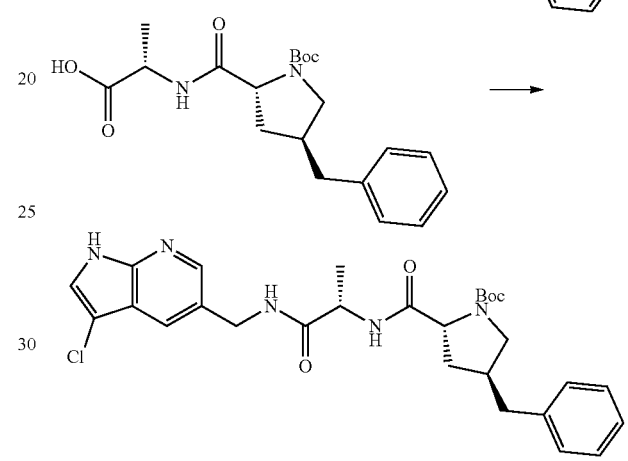

Step 1: tert-butyl (2R,4S)-4-benzyl-2-(((S)-1-(((3-chloro-1H-pyrrolo[2,3-b]pyridin-5-yl)methyl)amino)-1-oxopropan-2-yl)carbamoyl)pyrrolidine-1-carboxylate (46 mg, 80% yield) was synthesized from ((2R,4S)-4-benzyl-1-(tert-butoxycarbonyl)pyrrolidine-2-carbonyl)-L-alanine (40 mg, 0.11 mmol) according to the procedure for compound (1234), step 3.

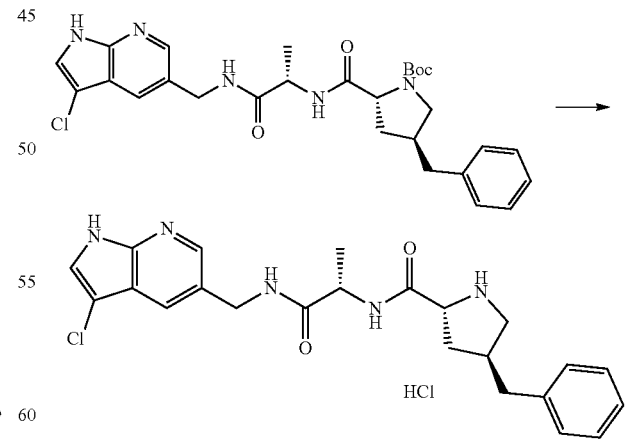

Step 2: (2R,4S)-4-Benzyl-N—((S)-1-(((3-chloro-1H-pyrrolo[2,3-b]pyridin-5-yl)methyl)amino)-1-oxopropan-2-yl) pyrrolidine-2-carboxamide di-hydrochloride (38.2 mg, 80% yield) was synthesized from tert-butyl (2R,4S)-4-benzyl-2-(((S)-1-(((3-chloro-1H-pyrrolo[2,3-b]pyridin-5-yl)methyl)

amino)-1-oxopropan-2-yl)carbamoyl)pyrrolidine-1-carboxylate (46 mg, 0.85 mmol) according to the procedure for compound (1234), step 3.

Example 138. Preparation of (S)-2-((R)-2-Amino-4-phenylbutanamido)-N'-(4-carbamimidoylbenzyl)pentanediamide Di-trifluoroacetate (1335)

(1335)

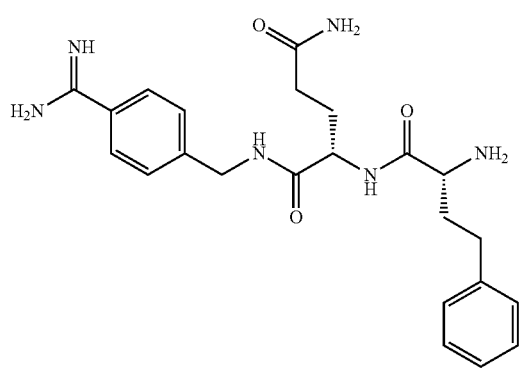

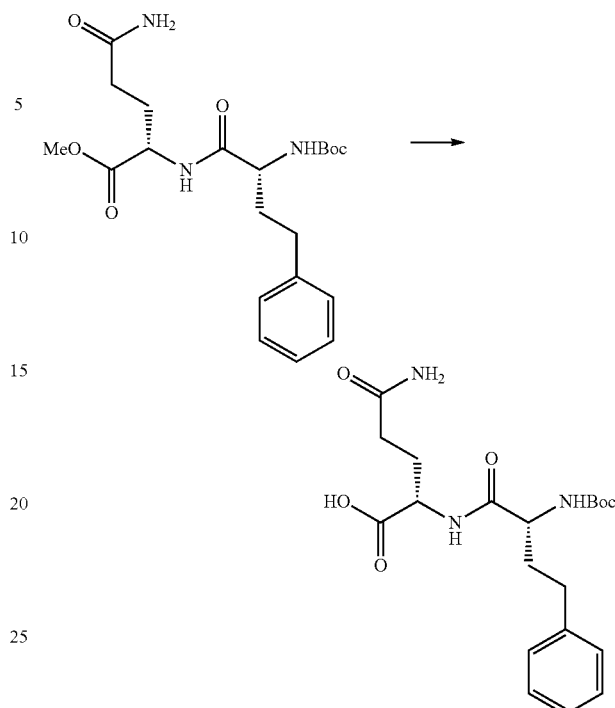

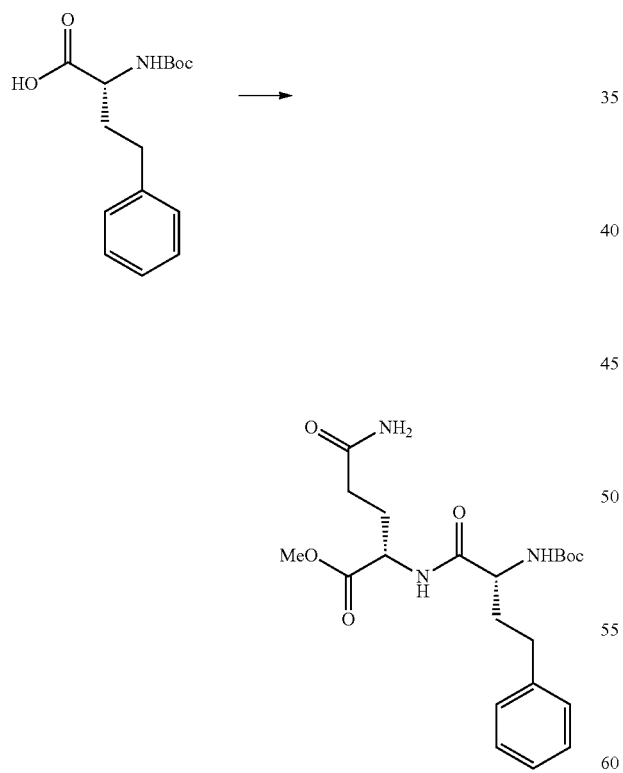

Step 1: Methyl ((R)-2-((tert-butoxycarbonyl)amino)-4-phenylbutanoyl)-L-glutaminate (149 mg, 41% yield) was synthesized from Boc-D-homophenylalanine (241 mg, 0.86 mmol) and L-glutamine methyl ester hydrochloride according to the procedure for compound (1326), step 1.

Step 2: ((R)-2-Amino-4-phenylbutanoyl)-L-glutamine (112 mg, 78% yield) was synthesized from methyl ((R)-2-((tert-butoxycarbonyl)amino)-4-phenylbutanoyl)-L-glutaminate (149 mg, 0.35 mmol) according to the procedure for compound (1326), step 2 except that the crude material was applied to the next step without further purification.

Step 3: tert-Butyl ((R)-1-(((S)-5-amino-1-((4-(N-((benzyloxy)carbonyl)carbamimidoyl)benzyl)amino)-1,5-dioxopentan-2-yl)amino)-1-oxo-4-phenylbutan-2-yl)carbamate (156 mg, 84% yield) was synthesized from ((R)-2-amino-4-phenylbutanoyl)-L-glutamine (112 mg, 0.28 mmol) according to the procedure for compound (1326), step 3.

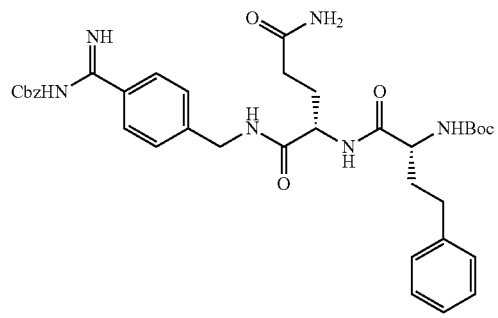

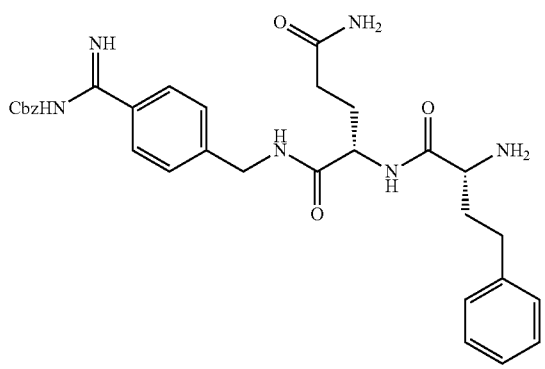

Step 4: Deprotection of tert-butyl ((R)-1-(((S)-5-amino-1-((4-(N-((benzyloxy)carbonyl)carbamimidoyl)benzyl)amino)-1,5-dioxopentan-2-yl)amino)-1-oxo-4-phenylbutan-2-yl)carbamate (156 mg, 0.23 mmol) was conducted according to the procedure for compound (1260), step 4 to give benzyl ((4-(((S)-5-amino-2-((R)-2-amino-4-phenylbutanamido)-5-oxopentanamido)methyl)phenyl)(imino)methyl)carbamate (47 mg, 36% yield).

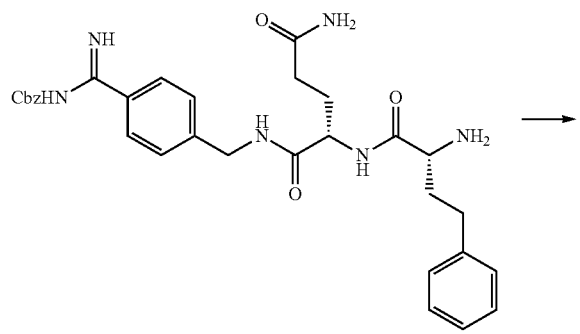

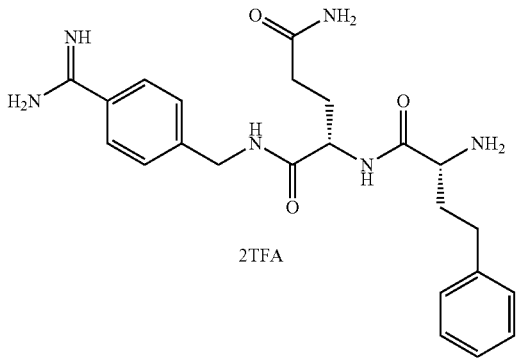

Step 5: Deprotection of benzyl ((4-(((S)-5-amino-2-((R)-2-amino-4-phenylbutanamido)-5-oxopentanamido)methyl)phenyl)(imino)methyl)carbamate (47 mg, 0.08 mmol) was conducted according to the procedure for compound (1264), step 2 except that the crude material was purified using reverse-phase HPLC.

Example 139. Preparation of (2R,4R)—N—((S)-1-(((3-Amino-1H-pyrazol-5-yl)methyl)amino)-1-oxopropan-2-yl)-4-phenylpyrrolidine-2-carboxamide Dihydrochloride (1336)

(1336)

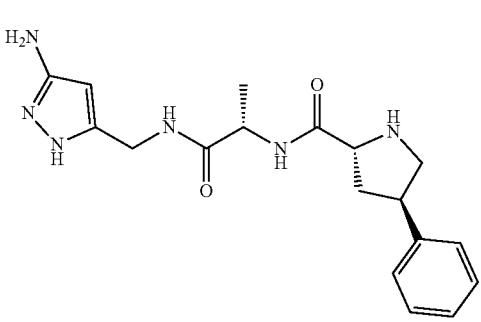

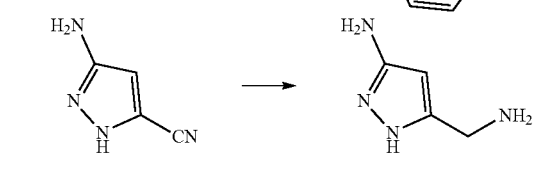

Step 1: 3-Amino-1H-pyrazole-5-carbonitrile was reduced according to the procedure for compound (1311), step 1 to give 5-(aminomethyl)-1H-pyrazol-3-amine which was used in the next step without further purification.

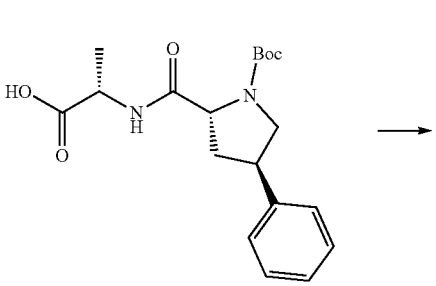

-continued

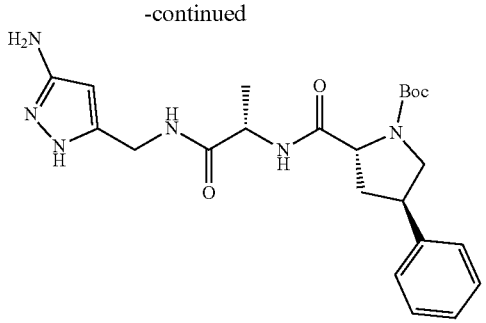

Step 2: ((2R,4R)-1-(tert-butoxycarbonyl)-4-phenylpyrrolidine-2-carbonyl)-L-alanine was coupled with 5-(aminomethyl)-1H-pyrazol-3-amine following the procedure given for compound (1265), step 1 except that the amine was added to the reaction mixture as a solution in DMF. After the reaction was complete, the mixture was diluted with 5% MeOH—$CH_2Cl_2$ and washed with sat. $NaHCO_3$ and brine, dried ($Na_2SO_4$) and conc in vacuo. Purification by chromatography (0-10% MeOH—$CH_2Cl_2$) provided tert-butyl (2R,4R)-2-(((S)-1-(((3-amino-1H-pyrazol-5-yl)methyl)amino)-1-oxopropan-2-yl)carbamoyl)-4-phenylpyrrolidine-1-carboxylate (64 mg, 47% yield).

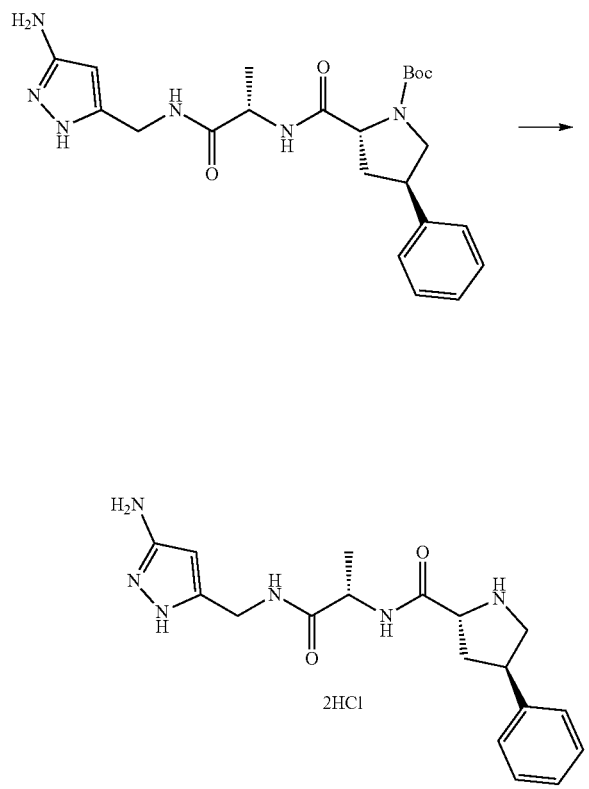

Step 3: tert-Butyl (2R,4R)-2-(((S)-1-(((3-amino-1H-pyrazol-5-yl)methyl)amino)-1-oxopropan-2-yl)carbamoyl)-4-phenylpyrrolidine-1-carboxylate was deprotected according to the procedure given for compound (1323), step 3 to give (2R,4R)—N—((S)-1-(((3-amino-1H-pyrazol-5-yl)methyl)amino)-1-oxopropan-2-yl)-4-phenylpyrrolidine-2-carboxamide dihydrochloride (60 mg, quant. yield).

Example 140. Preparation of (2R,4S)—N—((S)-1-(((6-amino-2-methylpyridin-3-yl)methyl)amino)-1-oxopropan-2-yl)-4-(3-methylbenzyl)pyrrolidine-2-carboxamide dihydrochloride (1337)

(1337)

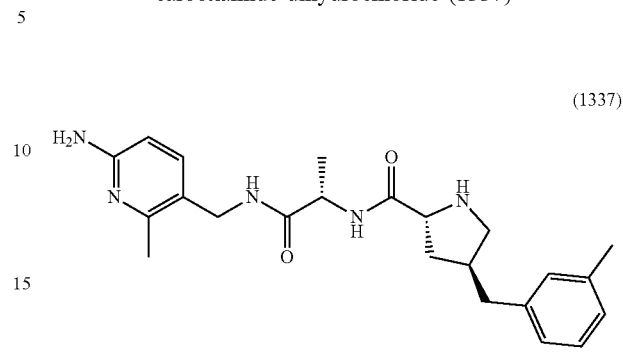

(2R,4S)—N—((S)-1-(((6-amino-2-methylpyridin-3-yl)methyl)amino)-1-oxopropan-2-yl)-4-(3-methylbenzyl)pyrrolidine-2-carboxamide dihydrochloride was synthesized according to the procedures for compound (1304).

Example 141. Preparation of (2R,4S)—N—((S)-1-(((6-Amino-2-methylpyridin-3-yl)methyl)amino)-1-oxopropan-2-yl)-4-(naphthalen-2-ylmethyl)pyrrolidine-2-carboxamide Dihydrochloride (1338)

(1338)

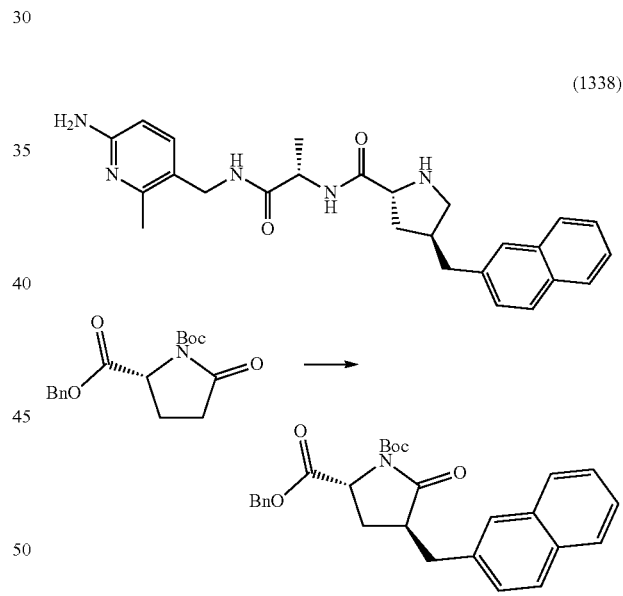

Step 1: To a stirred solution of 2-benzyl 1-(tert-butyl) (R)-5-oxopyrrolidine-1,2-dicarboxylate (600 g, 1.88 mmol) in THF (12.5 mL) at −78° C. was slowly added lithium bis(trimethylsilyl)amide (2.06 mL, 2.06 mmol, 1 M in THF) under Ar atmosphere. After stirring for 1 h at −78° C., 2-(bromomethyl)naphthalene (500 mg, 2.26 mmol) in 1 mL THF was added and the stirring continued for an additional 2 h. The reaction mixture was quenched with sat. $NH_4Cl$ solution and extracted with diethyl ether (3×20 mL). The combined extracts were dried over $Na_2SO_4$ filtered and concentrated under vacuum. The residue was purified by chromatography (EtOAc-hexanes) gave 2-benzyl 1-(tert-butyl) (2R,4S)-4-(naphthalen-2-ylmethyl)-5-oxopyrrolidine-1,2-dicarboxylate (600 mg, 70% yield).

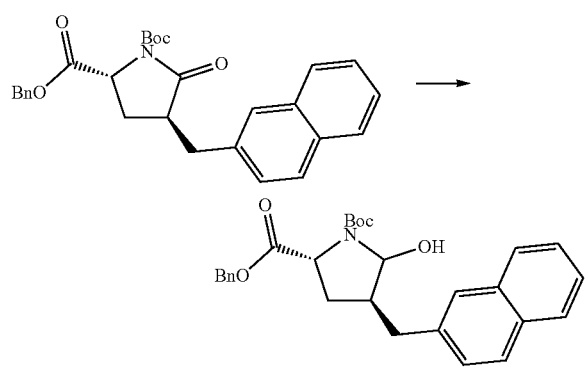

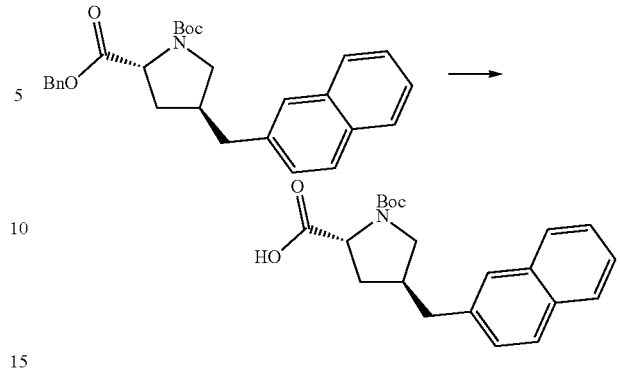

Step 2: To a solution of 2-benzyl 1-(tert-butyl) (2R,4S)-4-(naphthalen-2-ylmethyl)-5-oxopyrrolidine-1,2-dicarboxylate (600 mg, 3.91 mmol) in THF (8.6 mL) at −78° C. was added lithium triethylborohydride solution (1.56 mL, 1.56 mmol, 1 M in THF) under Ar atmosphere. After 30 min, the reaction mixture was quenched with sat. NaHCO₃ solution (3 mL) and warmed to 0° C. At 0° C., 30% H₂O₂ (about 10 drops) was added and the reaction mixture was stirred at same temperature for 30 min. The organic volatiles were removed under vacuum and the aqueous layer was extracted with CH₂Cl₂ (3×10 mL). The combined organic extracts were thoroughly dried using Na₂SO₄, filtered, concentrated to 2-benzyl 1-(tert-butyl) (2R,4S)-5-hydroxy-4-(naphthalen-2-ylmethyl)pyrrolidine-1,2-dicarboxylate (550 mg crude) that was directly used in the next step without further purification.

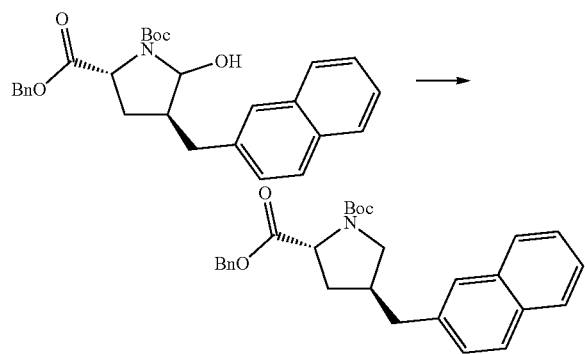

Step 3: To a stirred solution of 2-benzyl 1-(tert-butyl) (2R,4S)-5-hydroxy-4-(naphthalen-2-ylmethyl)pyrrolidine-1,2-dicarboxylate (550 mg crude) and triethylsilane (0.25 mL, 1.56 mmol) in CH₂Cl₂ (5.5 mL) at −78° C. was drop wise added boron trifluoride diethyl etherate (0.19 mL, 1.56 mmol) under Ar. After 30 min at same temperature additional triethylsilane (0.25 mL, 1.56 mmol) and boron trifluoride diethyl etherate (0.19 mL, 1.56 mmol) were added. After stirring for 2 h at −78° C., the reaction mixture was quenched with sat. aqueous NaHCO₃ solution (5 mL) and extracted with CH₂Cl₂ (3×15 mL). The combined extracts were dried over Na₂SO₄ filtered and conc under vacuum. The residue was purified by chromatography (EtOAc-hexanes) to afford 2-benzyl 1-(tert-butyl) (2R,4S)-4-(naphthalen-2-ylmethyl)pyrrolidine-1,2-dicarboxylate (350 mg, 60% yield in two steps).

Step 4: A solution of 2-benzyl 1-(tert-butyl) (2R,4S)-4-(naphthalen-2-ylmethyl)pyrrolidine-1,2-dicarboxylate (350 mg, 0.78 mmol) in MeOH (8 mL) was bubbled with Ar gas for 5 minutes. 10% Pd/C (35 mg) was added to the reaction mixture and stirred under 1 atm of H₂ for 3 h. The reaction mixture was filtered (0.2 µM syringe filter) and the filtrate was concentrated under vacuum to give (2R,4S)-1-(tert-butoxycarbonyl)-4-(naphthalen-2-ylmethyl)pyrrolidine-2-carboxylic acid (250 mg, 90% yield).

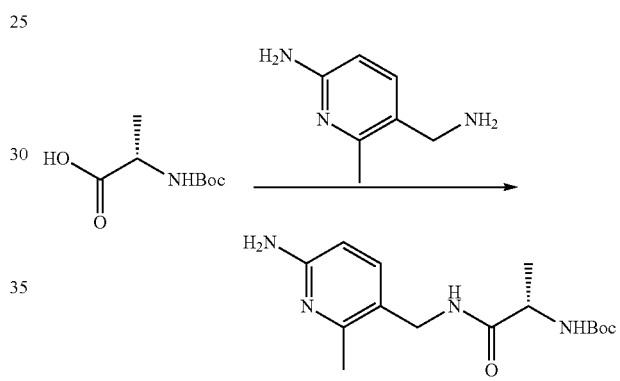

Step 5: To a stirred solution of (tert-butoxycarbonyl)-L-alanine (1.96 g, 10.38 mmol) in CH₂Cl₂ (55 mL) was added NHS (1.25 g, 10.89 mmol) at room temperature. To the reaction mixture DCC (2.25 g 10.9 mmol) was added and the reaction mixture stirred for 1.0 h. 5-(Aminomethyl)-6-methylpyridin-2-amine was added to the reaction mixture and sonicated for 5 min. The 5-(aminomethyl)-6-methylpyridin-2-amine was completely dissolved and stirred the reaction mixture at ambient temperature for 1 h. The crude reaction mixture was filtered and conc under reduced pressure. Purification by chromatography using MeOH—CH₂Cl₂ afforded tert-butyl (S)-(1-(((6-amino-2-methylpyridin-3-yl)methyl)amino)-1-oxopropan-2-yl)carbamate (2.35 g, 70% yield) as a white solid.

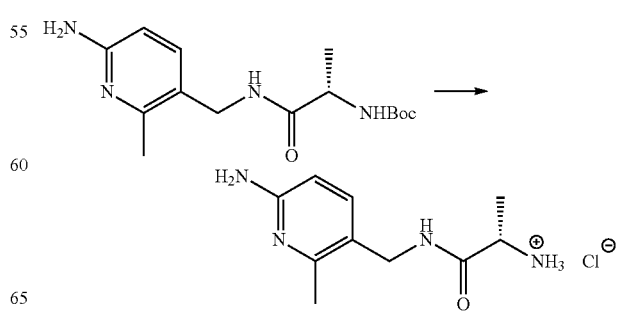

Step 6: To tert-butyl (S)-(1-(((6-amino-2-methylpyridin-3-yl)methyl)amino)-1-oxopropan-2-yl)carbamate (2.35 g, 7.62 mmol) was added a solution of MeOH—HCl (19 mL, 2 M) with stirring at ambient temperature while monitoring for the consumption of starting material (typically 1 h). The solution was evaporated to dryness and MeOH (50 mL) was added and evaporated to dryness to remove residual HCl gas to give (S)-2-amino-N-((6-amino-2-methylpyridin-3-yl)methyl)propanamide hydrochloride (1.60 g, 90% yield) as an off white solid (Hygroscopic).

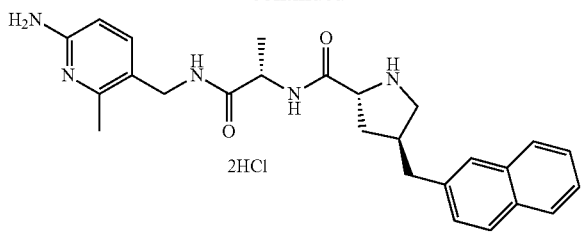

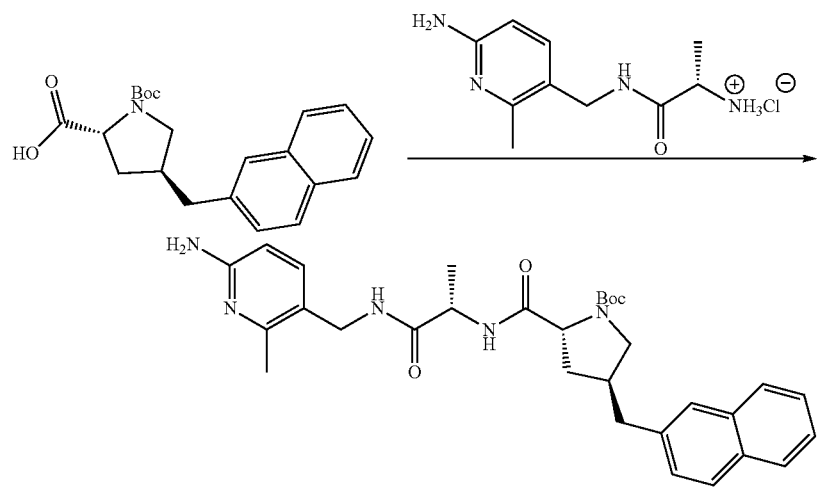

Step 7: To a stirred solution of (2R,4S)-1-(tert-butoxycarbonyl)-4-(naphthalen-2-ylmethyl)pyrrolidine-2-carboxylic acid (75 mg, 0.21 mmol) in anhydrous DMF (1.4 mL) was added HOBt (32 mg, 0.23 mmol), DIEA (0.15 mL, 0.84 mmol) and EDC (45 mg, 0.23 mmol) at ambient temperature. The reaction mixture was stirred for 30 min at ambient temperature. (S)-2-amino-N-((6-amino-2-methylpyridin-3-yl)methyl)propanamide hydrochloride (61 mg, 0.32 mmol) was added to the reaction mixture and stirred overnight. The solution was evaporated to dryness and the residue was partitioned with EtOAc (15 mL) and 10% KHSO$_4$ (10 mL). The organic layer was separated and washed with sat. NaHCO$_3$ solution (10 mL), dried over anhydrous Na$_2$SO$_4$ and conc under vacuum. The crude reaction mixture was purified by chromatography using MeOH—CH$_2$Cl$_2$ to afford tert-butyl (2R,4S)-2-(((S)-1-(((6-amino-2-methylpyridin-3-yl)methyl)amino)-1-oxopropan-2-yl)carbamoyl)-4-(naphthalen-2-ylmethyl)pyrrolidine-1-carboxylate (52 mg, 45% yield) as a white solid.

Step 8: To tert-butyl (2R,4S)-2-(((S)-1-(((6-amino-2-methylpyridin-3-yl)methyl)amino)-1-oxopropan-2-yl)carbamoyl)-4-(naphthalen-2-ylmethyl)pyrrolidine-1-carboxylate (52 mg, 0.095 mmol) was added a solution of MeOH—HCl (2.0 mL, 2 M) with stirring at ambient temperature while monitoring for the consumption of starting material (30 min to 1 h). The solution was evaporated to dryness and MeOH (10 mL) was added and evaporated to dryness to remove residual HCl gas to yield (2R,4S)—N—((S)-1-(((6-amino-2-methylpyridin-3-yl)methyl)amino)-1-oxopropan-2-yl)-4-(naphthalen-2-ylmethyl)pyrrolidine-2-carboxamide dihydrochloride (29 mg, 74% yield) as a white solid.

Example 142. Preparation of (R)—N—((S)-1-((4-Carbamimidoylbenzyl)amino)-1-oxopropan-2-yl)-2-((4-chlorophenethyl)amino)-4-phenylbutanamide Di-trifluoroacetate salt (1339)

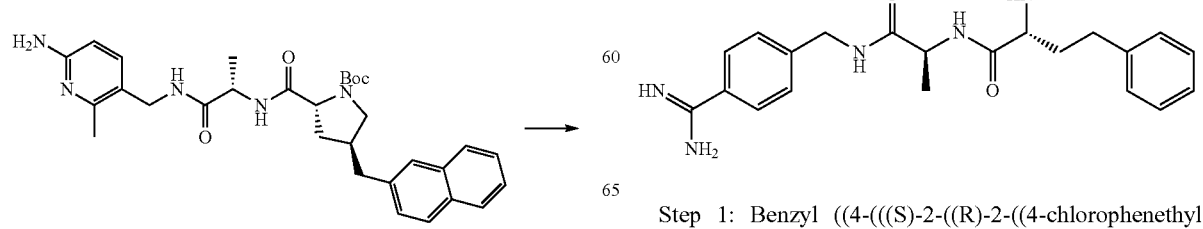

(1339)

Step 1: Benzyl ((4-(((S)-2-((R)-2-((4-chlorophenethyl)amino)-4-phenylbutanamido)propanamido)methyl)phenyl)

(imino)methyl)carbamate was synthesized according to the procedure for compound 1130, step 2.

Step 2: Deprotection of benzyl ((4-(((S)-2-((R)-2-((4-chlorophenethyl)amino)-4-phenylbutanamido)propanamido)methyl)phenyl)(imino)methyl)carbamate carbamate according to the procedure for compound 1130, step 3. Purification by reverse phase HPLC (5-75% MeCN—H₂O) to afford (R)—N—((S)-1-((4-carbamimidoylbenzyl)amino)-1-oxopropan-2-yl)-2-((4-chlorophenethyl)amino)-4-phenylbutanamide di-trifluoroacetate salt.

Example 143. Preparation of (R)—N—((S)-1-((4-Carbamimidoylbenzyl)amino)-1-oxopropan-2-yl)-2-(phenethylamino)-4-phenylbutanamide Dihydrochloride (1340)

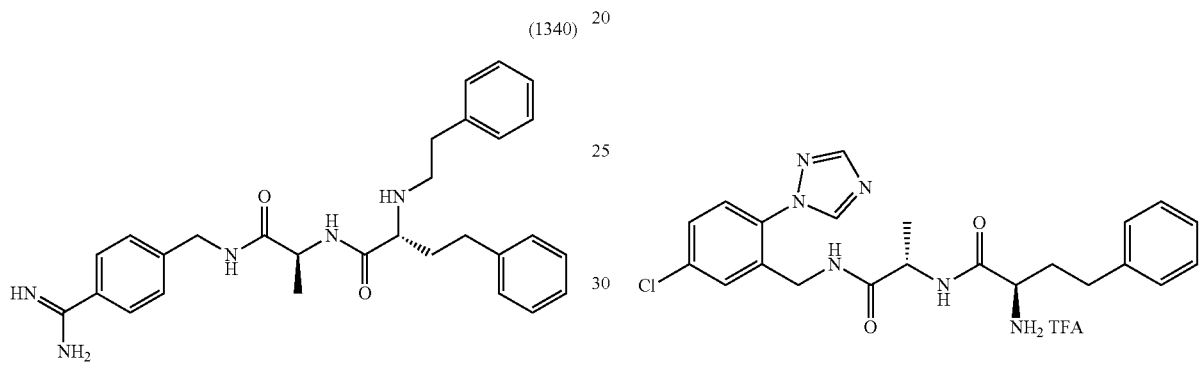

(1340)

Step 1: Benzyl (imino(4-(((S)-2-((R)-2-(phenethylamino)-4-phenylbutanamido)propanamido)methyl)phenyl)methyl)carbamate was synthesized according to the procedure for compound 1130, step 2.

Step 2: Deprotection of benzyl (imino(4-(((S)-2-((R)-2-(phenethylamino)-4-phenylbutanamido)propanamido)methyl)phenyl)methyl)carbamate according to the procedure for compound 1130, step 3 afforded (R)—N—((S)-1-((4-carbamimidoylbenzyl)amino)-1-oxopropan-2-yl)-2-(phenethylamino)-4-phenylbutanamide.

Step 3: (R)—N—((S)-1-((4-Carbamimidoylbenzyl)amino)-1-oxopropan-2-yl)-2-(phenethylamino)-4-phenylbutanamide dihydrochloride was formed according to the procedure for compound (1319), step 6.

Example 144. Preparation of (R)-2-amino-N—((S)-1-((5-chloro-2-(1H-1,2,4-triazol-1-yl)benzyl)amino)-1-oxopropan-2-yl)-4-phenylbutanamide (1341)

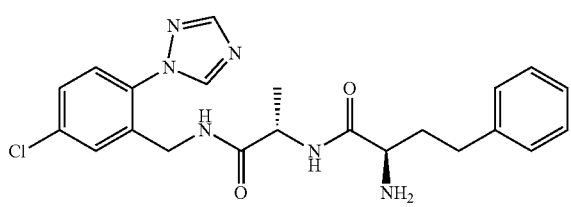

(1341)

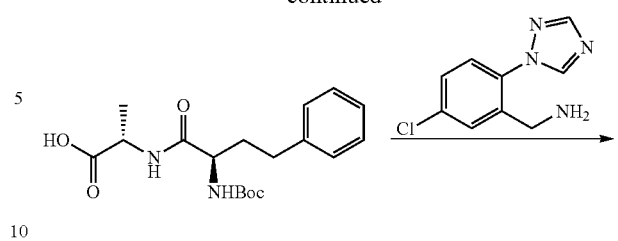

Steps 1-2: The title compound was synthesized as a white solid according to steps 3-4 of the procedure for compound (1313) using the appropriate starting materials (36 mg, 32% yield over two steps).

Example 145. Preparation of (2R,4R)—N—((S)-1-(((6-Amino-2-methylpyridin-3-yl)methyl)amino)-1-oxopropan-2-yl)-4-(naphthalen-1-yl)piperidine-2-carboxamide Dihydrochloride (1342)

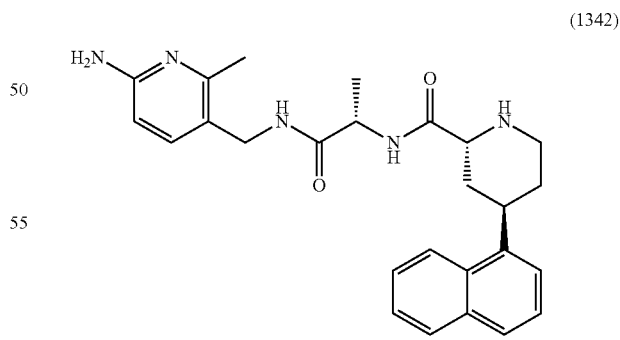

(1342)

(2R,4R)—N—((S)-1-(((6-Amino-2-methylpyridin-3-yl)methyl)amino)-1-oxopropan-2-yl)-4-(naphthalen-1-yl)piperidine-2-carboxamide dihydrochloride was synthesized according to the procedures for compound (1231) (the first UVActive material eluting from the column in step 6 was carried forward) and compound (1253), steps 1 and 2.

Example 146. Preparation of (2R,4S)—N—((S)-1-(((6-Amino-2-methylpyridin-3-yl)methyl)amino)-1-oxopropan-2-yl)-4-(isoquinolin-5-ylmethyl)pyrrolidine-2-carboxamide Di-trifluoroacetate salt (1343)

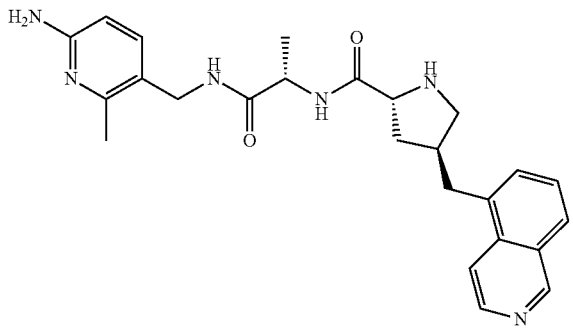

(2R,4S)—N—((S)-1-(((6-amino-2-methylpyridin-3-yl)methyl)amino)-1-oxopropan-2-yl)-4-(isoquinolin-5-ylmethyl)pyrrolidine-2-carboxamide di-trifluoroacetate salt was synthesized according to the procedures for compound (1304), except that the final product was purified using reverse-phase HPLC.

Example 147. Preparation of (2R,4S)—N—((S)-1-(((6-Amino-2-methylpyridin-3-yl)methyl)amino)-1-oxopropan-2-yl)-4-((±)-1-phenylethyl)pyrrolidine-2-carboxamide Dihydrochloride (1344)

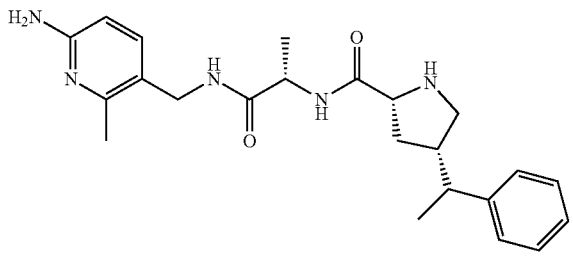

(2R,4S)—N—((S)-1-(((6-Amino-2-methylpyridin-3-yl)methyl)amino)-1-oxopropan-2-yl)-4-((±)-1-phenylethyl)pyrrolidine-2-carboxamide dihydrochloride was followed according to the procedures for compound (1257).

Example 148. Preparation of (R)-2-((4-acetamidophenethyl)amino)-N—((S)-1-((4-carbamimidoylbenzyl)amino)-1-oxopropan-2-yl)-4-phenylbutanamide dihydrochloride (1345)

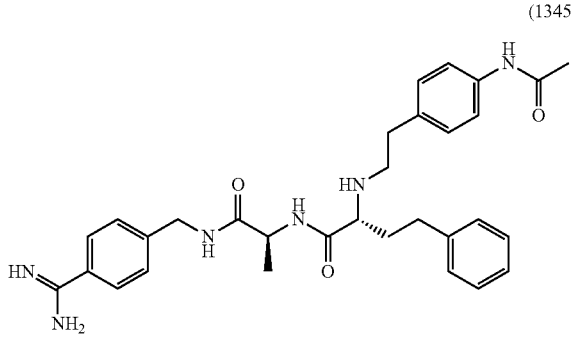

Step 1: Benzyl ((4-(((S)-2-((R)-2-((4-acetamidophenethyl)amino)-4-phenylbutanamido)propanamido)methyl)phenyl)(imino)methyl)carbamate was synthesized according to the procedure for compound 1130, step 2.

Step 2: Deprotection of benzyl ((4-(((S)-2-((R)-2-((4-acetamidophenethyl)amino)-4-phenylbutanamido)propanamido)methyl)phenyl)(imino)methyl) according to the procedure for compound 1130, step 3 afforded (R)-2-((4-acetamidophenethyl)amino)-N—((S)-1-((4-carbamimidoylbenzyl)amino)-1-oxopropan-2-yl)-4-phenylbutanamide.

Step 3: (R)-2-((4-Acetamidophenethyl)amino)-N—((S)-1-((4-carbamimidoylbenzyl)amino)-1-oxopropan-2-yl)-4-phenylbutanamide dihydrochloride was formed according to the procedure for compound (1319), step 6.

Example 149. Preparation of (R)-2-Amino-N—((S)-1-(((2-aminopyridin-3-yl)methyl)amino)-1-oxopropan-2-yl)-4-phenylbutanamide Dihydrochloride (1346)

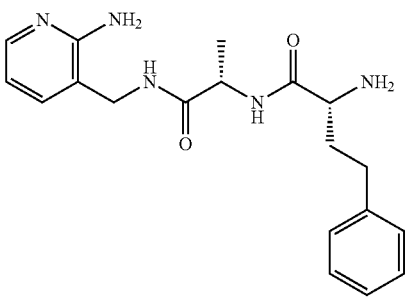

(R)-2-Amino-N—((S)-1-(((2-aminopyridin-3-yl)methyl)amino)-1-oxopropan-2-yl)-4-phenylbutanamide dihydrochloride was synthesized according to the procedures given for compound (1323), steps 2 and 3.

Example 150. Preparation of (R)—N—((S)-1-(((6-Amino-2-methylpyridin-3-yl)methyl)amino)-1-oxopropan-2-yl)-4-benzylpiperazine-2-carboxamide Dihydrochloride (1347)

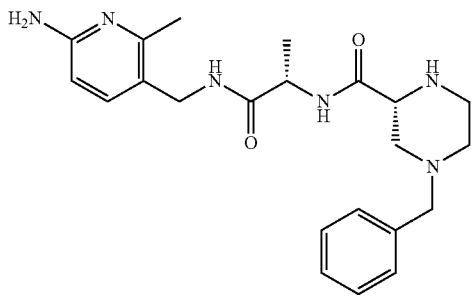

(R)—N—((S)-1-(((6-Amino-2-methylpyridin-3-yl)methyl)amino)-1-oxopropan-2-yl)-4-benzylpiperazine-2-carboxamide dihydrochloride was synthesized according to the procedures for compound (1253).

Example 151. Preparation of (R)—N—((S)-1-(((6-Amino-2-methylpyridin-3-yl)methyl)amino)-1-oxo-propan-2-yl)-4-(2-methylbenzyl)piperazine-2-carboxamide Dihydrochloride (1348)

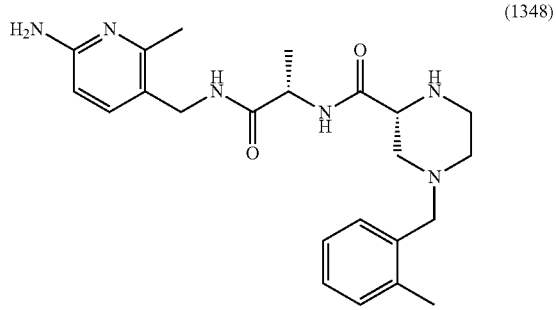 [SMILES: Cc1ccccc1CN1CCN[C@@H](C(=O)N[C@@H](C)C(=O)NCc2ccc(N)nc2C)C1]

(R)—N—((S)-1-(((6-Amino-2-methylpyridin-3-yl)methyl)amino)-1-oxopropan-2-yl)-4-(2-methylbenzyl)piperazine-2-carboxamide dihydrochloride was synthesized according to the procedures for compound (1230), except using (R)-1-(tert-butoxycarbonyl)-4-(2-methylbenzyl)piperazine-2-carboxylic acid in step 1 and 5-(aminomethyl)-6-methylpyridin-2-amine in step 3.

Example 152. Preparation of (R)—N—((S)-1-(((6-Amino-2-methylpyridin-3-yl)methyl)amino)-1-oxo-propan-2-yl)-2-((3-hydroxyphenethyl)amino)-4-phenylbutanamide Dihydrochloride (1349)

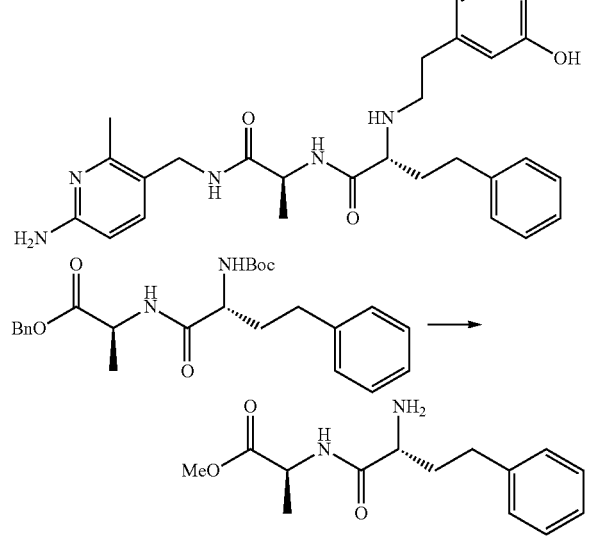

Step 1: Deprotection of benzyl ((R)-2-((tert-butoxycarbonyl)amino)-4-phenylbutanoyl)-L-alaninate (789.3 mg, 1.79 mmol) was done according to the procedure for compound 1119, step 2. The crude product was dissolved in $CH_2Cl_2$ and adsorbed on silica gel. Purification by chromatography (0-15% MeOH—$CH_2Cl_2$) afforded methyl ((R)-2-amino-4-phenylbutanoyl)-L-alaninate (335.0 mg, 71% yield).

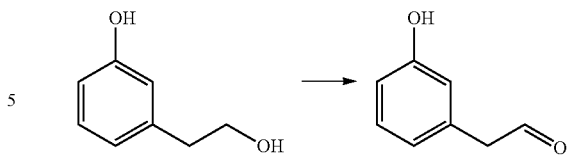

Step 2: 3-(2-Hydroxyethyl)phenol (2.1 g, 15.2 mmol) was dissolved in DMSO (8 mL) under $N_2$. The solution was treated dropwise with a solution of sulfur trioxide pyridine complex (2.5 g, 15.7 mmol) in DMSO (9 mL). The reaction was stirred at room temp for 1 h, quenched with ice water, and diluted with $CH_2Cl_2$. The organic layer was washed with ice water (3 times), washed with brine, dried ($Na_2SO_4$), vacuum filtered, and evaporated under vacuum. The crude product was dissolved in $CH_2Cl_2$ and adsorbed on silica gel. Purification by chromatography (0-100% EtOAc-hexanes) afforded the crude 2-(3-hydroxyphenyl)acetaldehyde (1.83 g, 88% yield).

Step 3: Methyl ((R)-2-amino-4-phenylbutanoyl)-L-alaninate (335.0 mg, 1.27 mmol) was coupled with crude 2-(3-hydroxyphenyl)acetaldehyde (417 mg, 3.06 mmol) according to the procedure for compound 1130, step 2. The crude product was dissolved in $CH_2Cl_2$ and adsorbed on silica gel. Purification by chromatography (0-5% MeOH—$CH_2Cl_2$) afforded methyl ((R)-2-((3-hydroxyphenethyl)amino)-4-phenylbutanoyl)-L-alaninate (270 mg, 61% yield).

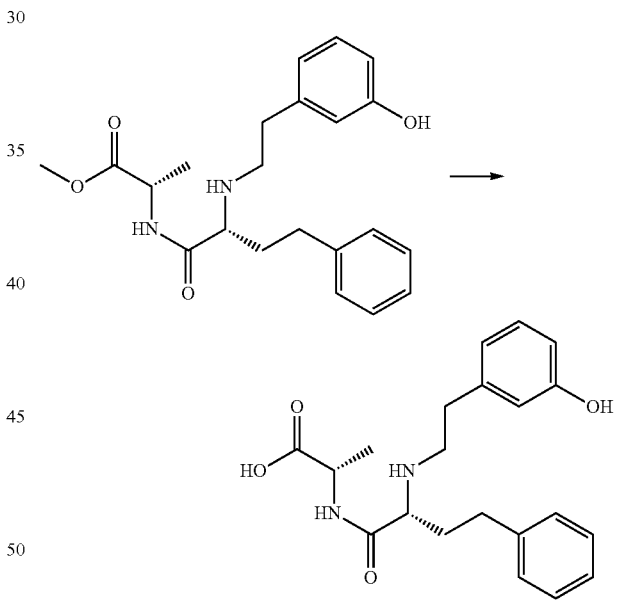

Step 4: A mixture of ((R)-2-((3-hydroxyphenethyl)amino)-4-phenylbutanoyl)-L-alaninate (270.3 mg, 0.703 mmol) in THF (3.4 mL) and water (3.4 mL) was treated with LiOH (84 mg, 3.51 mmol). The reaction was stirred for 16 h at room temp, adjusted to pH 3 with the slow addition of 10% $KHSO_4$ solution, extracted with EtOAc (3 times). The organic layers were combined, washed with 5% $NaHCO_3$ solution, washed with brine, dried ($Na_2SO_4$), vacuum filtered, and evaporated under vacuum to afford the crude ((R)-2-((3-hydroxyphenethyl)amino)-4-phenylbutanoyl)-L-alanine (213.6 mg, 82% yield).

Step 5: ((R)-2-((3-Hydroxyphenethyl)amino)-4-phenylbutanoyl)-L-alanine (110.6 mg, 0.299 mmol) was coupled with 5-(aminomethyl)-6-methylpyridin-2-amine (66 mg, 0.481 mmol) according to the procedure for compound 1088, step 2 except HBTU was added to the reaction at 0° C. to afford (R)—N—((S)-1-(((6-amino-2-methylpyridin-3-yl)methyl)amino)-1-oxopropan-2-yl)-2-((3-hydroxyphenethyl)amino)-4-phenylbutanamide (97.6 mg, 67% yield).

Step 6: (R)—N—((S)-1-(((6-Amino-2-methylpyridin-3-yl)methyl)amino)-1-oxopropan-2-yl)-2-((3-hydroxyphenethyl)amino)-4-phenylbutanamide dihydrochloride was formed according to the procedure for compound (1319), step 6.

Example 153. Preparation of (2R,4S)—N—((S)-1-(((6-Amino-2-methylpyridin-3-yl)methyl)amino)-1-oxopropan-2-yl)-4-(4-bromobenzyl)pyrrolidine-2-carboxamide Dihydrochloride (1350)

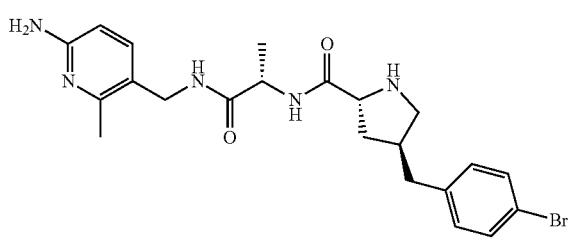

(1350)

(2R,4S)—N—((S)-1-(((6-amino-2-methylpyridin-3-yl)methyl)amino)-1-oxopropan-2-yl)-4-(4-bromobenzyl)pyrrolidine-2-carboxamide dihydrochloride was synthesized according to the procedures for compound (1328).

Example 154. Preparation of (2R,4S)-4-([1,1'-Biphenyl]-4-ylmethyl)-N—((S)-1-(((6-amino-2-methylpyridin-3-yl)methyl)amino)-1-oxopropan-2-yl)pyrrolidine-2-carboxamide Dihydrochloride (1351)

Step 1: 2-benzyl 1-(tert-butyl) (2R,4S)-4-(4-bromobenzyl)pyrrolidine-1,2-dicarboxylate was synthesized according to the procedures for compound (1304), step 1 to step 3.

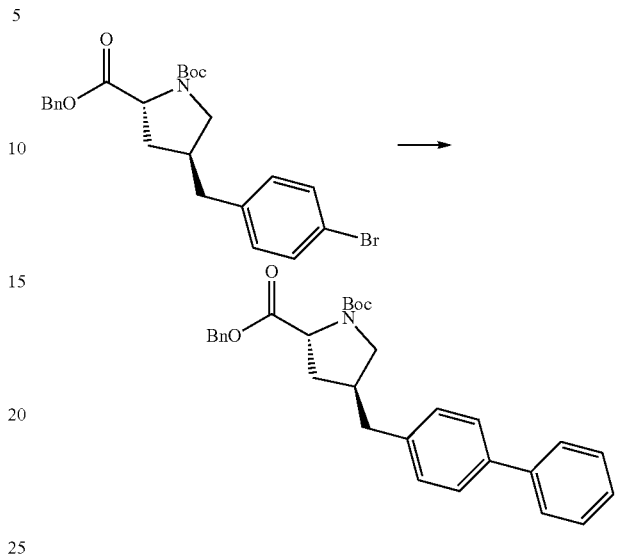

Step 2: In a 50 mL round bottom flask equipped with a stir bar and septum was added 2-benzyl 1-(tert-butyl) (2R,4S)-4-(4-bromobenzyl)pyrrolidine-1,2-dicarboxylate (143 mg, 0.30 mmol), phenyl boronic acid (44 mg, 0.36), Pd(dppf)Cl$_2$ (22 mg, 0.03 mmol), cesium carbonate (293 mg, 0.90 mmol), THF (3 mL) and water (0.3 mL). The resulting mixture was degassed by bubbling N$_2$ through the solution for 10 min. The reaction was then heated to 90° C. for 4 h. Upon cooling to room temperature, the reaction solution was filtered through diatomaceous earth, eluting with EtOAc, concentrated and purified by chromatography using EtOAc-hexanes to afford 2-benzyl 1-(tert-butyl) (2R,4S)-4-([1,1'-biphenyl]-4-ylmethyl)pyrrolidine-1,2-dicarboxylate (110 mg, 78% yield) as a colorless sticky liquid.

(1351)

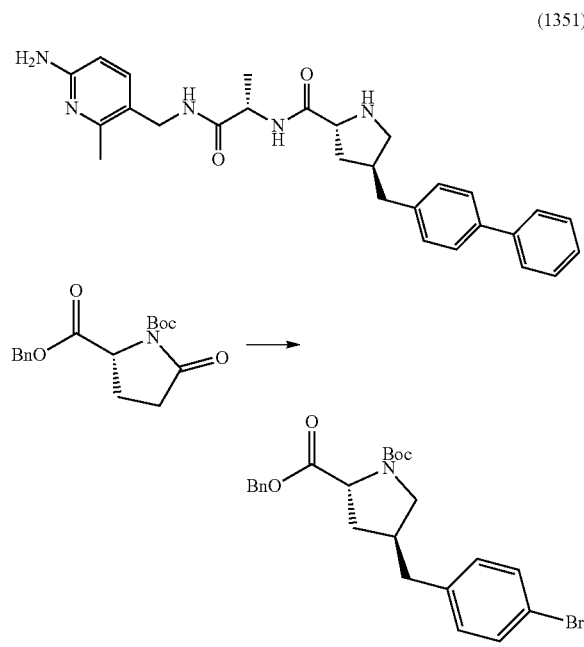

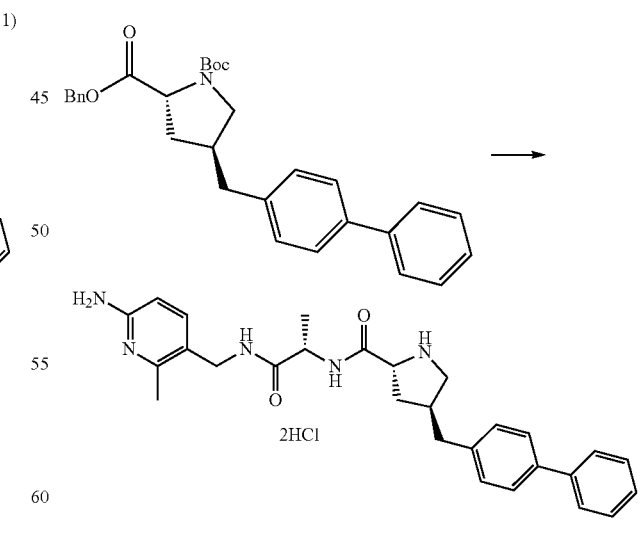

Step 3: (2R,4S)-4-([1,1'-Biphenyl]-4-ylmethyl)-N—((S)-1-(((6-amino-2-methylpyridin-3-yl)methyl)amino)-1-oxopropan-2-yl)pyrrolidine-2-carboxamide dihydrochloride was synthesized according to the procedures for compound (1304), step 4 to step 8.

Example 155. Preparation of (R)—N—((S)-1-((4-Carbamimidoylbenzyl)amino)-1-oxopropan-2-yl)-4-phenyl-2-((3-(trifluoromethoxy)phenethyl)amino)butanamide Di-trifluoroacetate salt (1352)

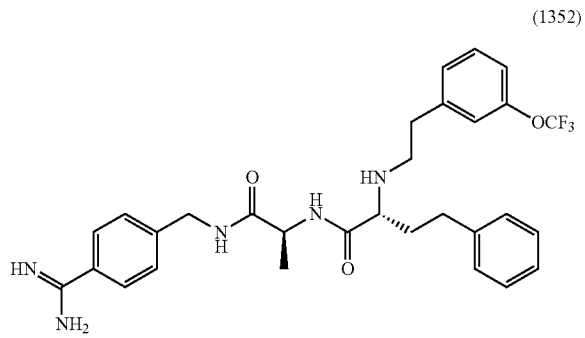 [SMILES: C[C@H](NC(=O)[C@@H](CCc1ccccc1)NCCc1cccc(OC(F)(F)F)c1)C(=O)NCc1ccc(C(=N)N)cc1]

(1352)

Step 1: Benzyl (imino(4-(((S)-2-((R)-4-phenyl-2-((3-(trifluoromethoxy)phenethyl)amino)butanamido)propanamido)methyl)phenyl)methyl)carbamate was synthesized according to the procedure for compound 1130, step 2.

Step 2: Deprotection of benzyl (imino(4-(((S)-2-((R)-4-phenyl-2-((3-(trifluoromethoxy)phenethyl)amino)butanamido)propanamido)methyl)phenyl)methyl)carbamate according to the procedure for compound 1130, step 3. Purification by reverse phase HPLC (5-75% MeCN—H₂O) to afford (R)—N—((S)-1-((4-carbamimidoylbenzyl)amino)-1-oxopropan-2-yl)-4-phenyl-2-((3-(trifluoromethoxy)phenethyl)amino)butanamide di-trifluoroacetate salt.

Example 156. Preparation of (2R,4S)—N—((S)-1-(((6-Amino-2-methylpyridin-3-yl)methyl)amino)-1-oxopropan-2-yl)-4-benzylpiperidine-2-carboxamide Dihydrochloride (1353)

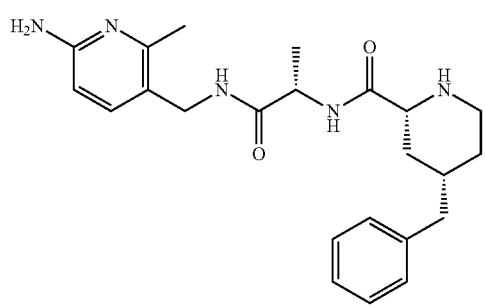

(1353)

(2R,4S)—N—((S)-1-(((6-Amino-2-methylpyridin-3-yl)methyl)amino)-1-oxopropan-2-yl)-4-benzylpiperidine-2-carboxamide dihydrochloride was synthesized according to the procedures for compound (1253).

Example 157. Preparation of (2S,4R)—N—((S)-1-(((6-Amino-2-methylpyridin-3-yl)methyl)amino)-1-oxopropan-2-yl)-4-benzylpiperidine-2-carboxamide Dihydrochloride (1354)

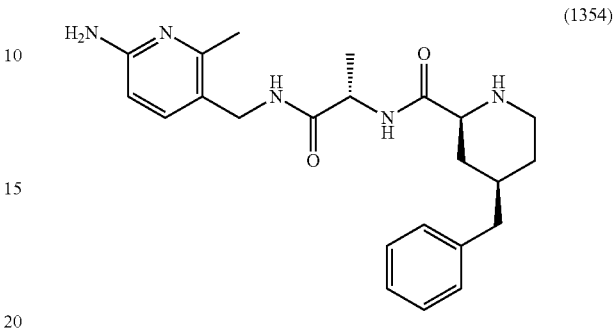

(1354)

(2S,4R)—N—((S)-1-(((6-Amino-2-methylpyridin-3-yl)methyl)amino)-1-oxopropan-2-yl)-4-benzylpiperidine-2-carboxamide was synthesized according to the procedures for compound (1230), except using 4-benzyl-1-(tert-butoxycarbonyl)piperidine-2-carboxylic acid in step 1 and 5-(aminomethyl)-6-methylpyridin-2-amine in step 3.

Example 158. Preparation of (R)-2-amino-N—((S)-1-((5-bromo-2-hydroxy-3-methylbenzyl)amino)-1-oxopropan-2-yl)-4-phenylbutanamide Trifluoroacetate salt (1355)

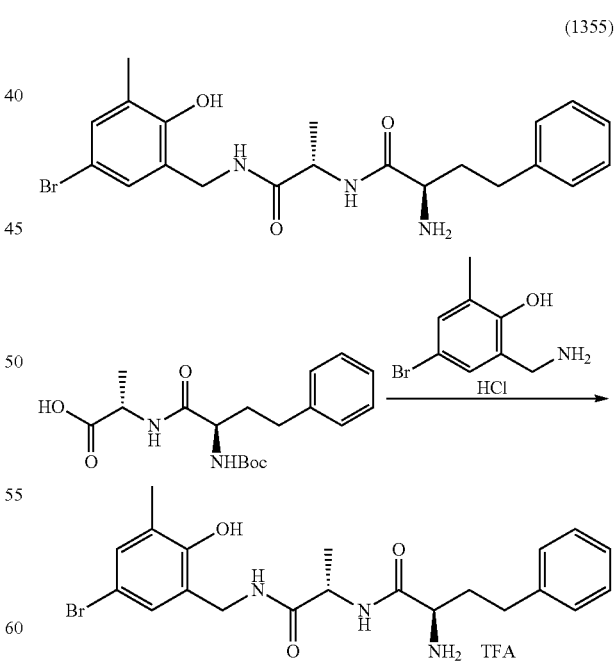

(1355)

Steps 1-2: The title compound was synthesized as a white hygroscopic solid according to steps 3-4 of the procedure for compound (1313) using the appropriate starting materials (8.3 mg, 17% yield over two steps).

Example 159. Preparation of (2R,4S)-4-([1,1'-Biphenyl]-4-ylmethyl)-N—((S)-1-(((3-chloro-1H-pyrrolo[2,3-b]pyridin-5-yl)methyl)amino)-1-oxopropan-2-yl)pyrrolidine-2-carboxamide Di-trifluoroacetate salt (1356)

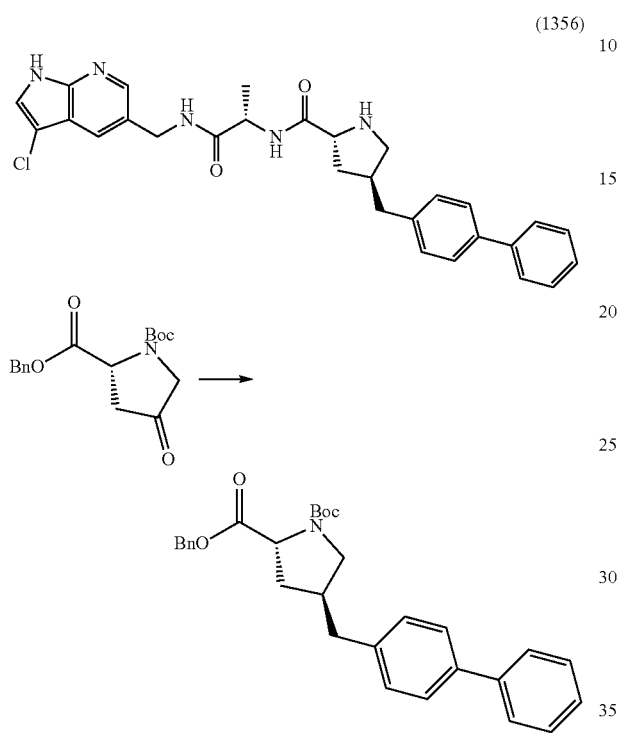

(1356)

Step 1: 2-Benzyl 1-(tert-butyl) (2R,4S)-4-([1,1'-biphenyl]-4-ylmethyl)pyrrolidine-1,2-dicarboxylate was synthesized according to the procedures for compound (1351) step 1 and step 2.

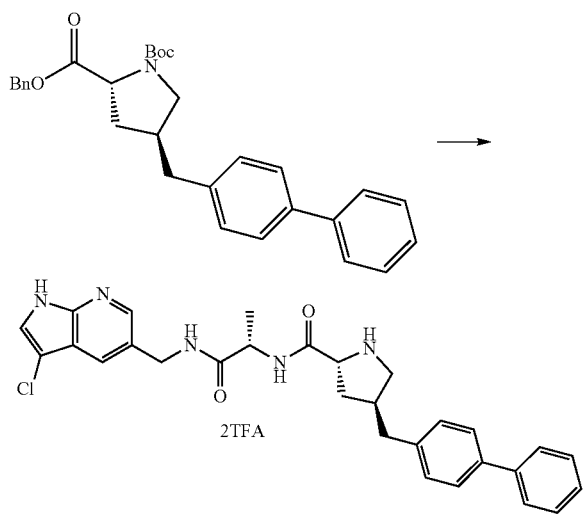

Step 2: (2R,4S)-4-([1,1'-Biphenyl]-4-ylmethyl)-N—((S)-1-(((3-chloro-1H-pyrrolo[2,3-b]pyridin-5-yl)methyl)amino)-1-oxopropan-2-yl)pyrrolidine-2-carboxamide di-trifluoroacetate salt was synthesized according to the procedures for compound (1307), step 1 to step 5, followed by purification by reverse-phase HPLC.

Example 160. Preparation of (2R,4S)—N—((S)-1-(((6-Amino-2-methylpyridin-3-yl)methyl)amino)-1-oxopropan-2-yl)-4-(4-(pyridin-3-yl)benzyl)pyrrolidine-2-carboxamide Di-trifluoroacetate salt (1357)

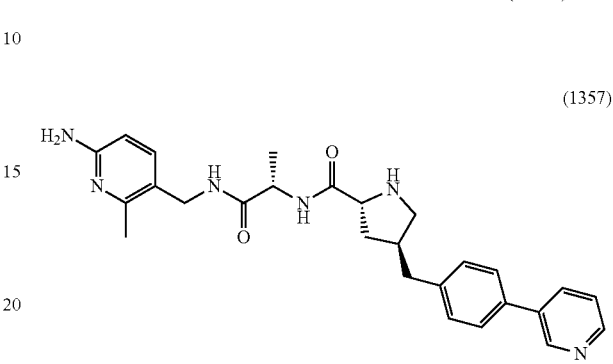

(1357)

(2R,4S)—N—((S)-1-(((6-amino-2-methylpyridin-3-yl)methyl)amino)-1-oxopropan-2-yl)-4-(4-(pyridin-3-yl)benzyl)pyrrolidine-2-carboxamide di-trifluoroacetate salt was synthesized according to the procedures for compound (1351), except that the final product was purified by chromatography using reverse-phase HPLC.

Example 161. Preparation of (2R,4R)—N—((S)-1-(((2-Amino-5-chloropyridin-3-yl)methyl)amino)-1-oxopropan-2-yl)-4-phenylpyrrolidine-2-carboxamide Di-trifluoroacetate salt (1358)

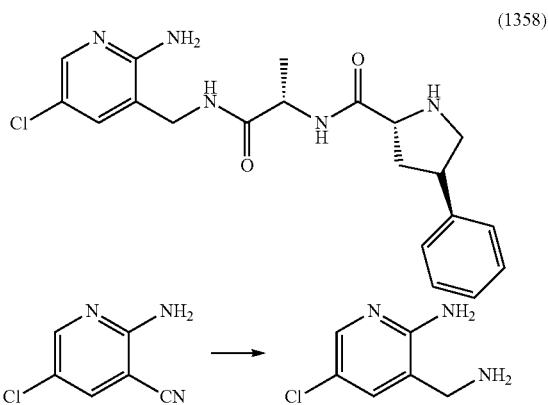

(1358)

Step 1: A solution of 2-amino-5-chloropyridine-3-carbonitrile (250 mg, 1.62 mmol) in MeOH (5 mL) and 7 N $NH_3$ in MeOH (25 mL) was degassed with a stream of Ar 2 times. Raney nickel (300 mg) was added and a vacuum was pulled for 1 min. A balloon of $H_2$ was added and the reaction mixture was stirred for 16 h at room temperature. Upon completion, the reaction mixture was degassed with a stream of Ar 2 times. The catalyst was removed by diatomaceous earth filtration and the solution was conc. The residue was taken up in 5% $H_2O$ in MeOH, filtered (0.2 µm syringe filter), and the filtrate was conc under vacuum to give 3-(aminomethyl)-5-chloropyridin-2-amine (189 mg, 74% yield).

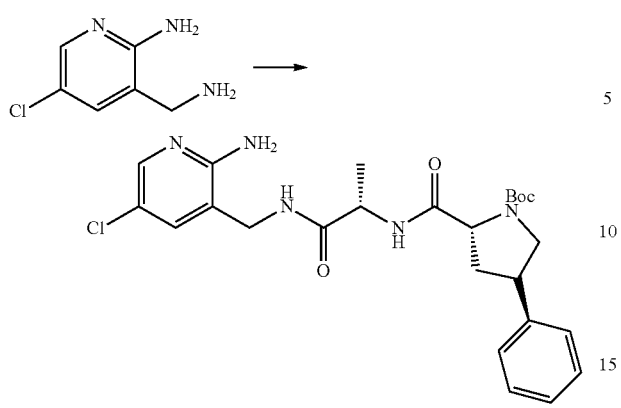

Step 2: To a solution of 3-(aminomethyl)-5-chloropyridin-2-amine (47 mg, 0.3 mmol) in DMF (5 mL, 0.06 mmol) was added ((2R,4R)-1-(tert-butoxycarbonyl)-4-phenylpyrrolidine-2-carbonyl)-L-alanine (84 mg, 0.23 mmol). The resulting mixture was cooled to 0° C. HBTU (114 mg, 0.3 mmol) and DIEA (0.16 mL) were added to the above mixture. After stirring for 30 min at the same temperature, the reaction was warmed to room temperature. The reaction was stirred for 90 min then conc under vacuum. The residue was dissolved in EtOAc-CH$_2$Cl$_2$ then washed with 10% KHSO$_4$, H$_2$O, sat. aq NaHCO$_3$, and brine. The organic layer was dried over anhyd Na$_2$SO$_4$ and conc under vacuum. The residue was purified by chromatography (0-100% [5% 7 N NH$_3$ in MeOH/CH$_2$Cl$_2$]—CH$_2$Cl$_2$) to give tert-butyl (2R,4R)-2-(((S)-1-(((2-amino-5-chloropyridin-3-yl)methyl)amino)-1-oxopropan-2-yl)carbamoyl)-4-phenylpyrrolidine-1-carboxylate (104 mg, 90% yield).

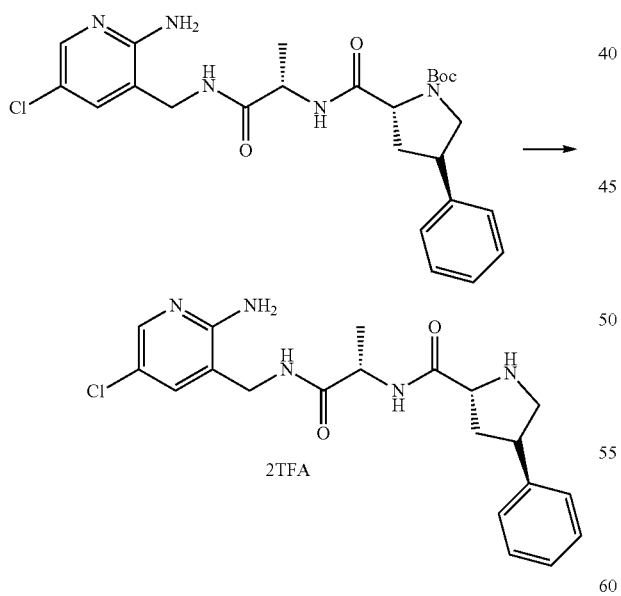

Step 3: Deprotection of tert-butyl (2R,4R)-2-(((S)-1-(((2-amino-5-chloropyridin-3-yl)methyl)amino)-1-oxopropan-2-yl)carbamoyl)-4-phenylpyrrolidine-1-carboxylate (104 mg, 0.21 mmol) was conducted according to the procedure for compound (1260), step 4 except that the final product was purified using reverse-phase HPLC.

Example 162. Preparation of (2R,4R)-4-([1,1'-Biphenyl]-3-yl)-N—((S)-1-(((6-amino-2-methylpyridin-3-yl)methyl)amino)-1-oxopropan-2-yl)pyrrolidine-2-carboxamide Di-trifluoroacetate salt (1359)

(1359)

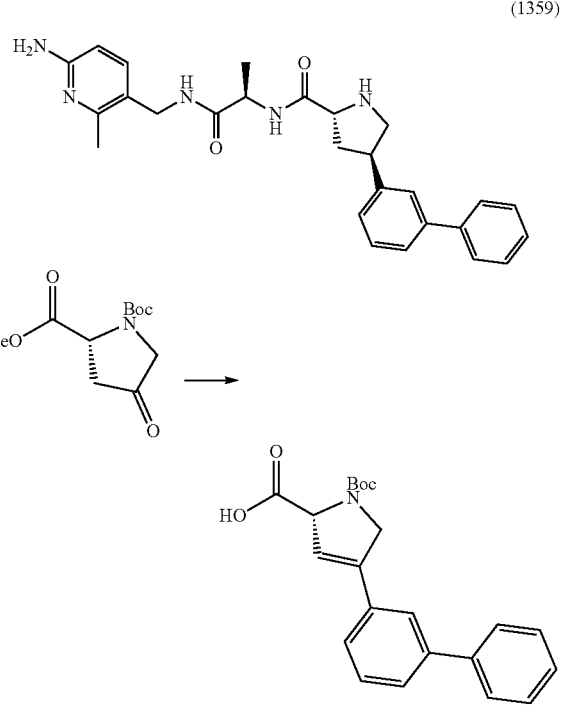

Step 1: (R)-4-([1,1'-Biphenyl]-3-yl)-1-(tert-butoxycarbonyl)-2,5-dihydro-1H-pyrrole-2-carboxylic acid was synthesized from 1-(tert-butyl) 2-methyl (R)-4-oxopyrrolidine-1,2-dicarboxylate according to the procedures for compound (1247), step 1 to step 3.

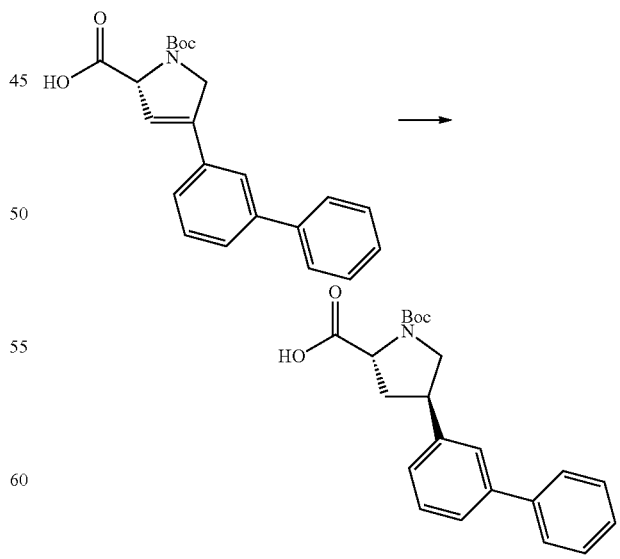

Step 2: Under Ar, (R)-4-([1,1'-biphenyl]-3-yl)-1-(tert-butoxycarbonyl)-2,5-dihydro-1H-pyrrole-2-carboxylic acid (347 mg, 0.95 mmol) and chlorotris(triphenylphosphine)

rhodium (88 mg, 0.095 mmol) were dissolved in anhydrous THF (15 mL), MeOH (15 mL), and Et₃N (0.13 mL, 0.95 mmol). The atmosphere in the flask was then changed to H₂ and a slight positive pressure maintained while the solution was stirred 36 h. The volatiles were evaporated, the residue suspended in NaHCO₃ (60 mL) and the pH adjusted to approximately 10 with 1 M aq. NaOH. EtOAc (60 mL) was added and the mixture was partitioned. The organic layer was washed with another 30 mL of NaHCO₃ and the combined aqueous layers were brought to pH 3-4 using 1 M aq. HCl; the product subsequently back-extracted with EtOAc (3×60 mL). The combined organic layers were dried over Na₂SO₄ and evaporated to furnish (2R,4R)-4-([1,1'-biphenyl]-3-yl)-1-(tert-butoxycarbonyl)pyrrolidine-2-carboxylic acid (175 mg, 50% yield) as an orange colored sticky liquid.

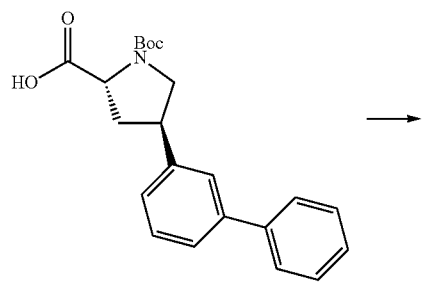

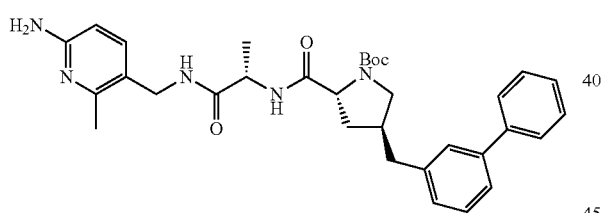

Step 3: (2R,4R)-4-([1,1'-biphenyl]-3-yl)-1-(tert-butoxycarbonyl)pyrrolidine-2-carboxylic acid was coupled to (S)-2-amino-N-((6-amino-2-methylpyridin-3-yl)methyl)propanamide hydrochloride according to the procedure for compound (1304), step 7 to give tert-butyl (2R,4S)-4-([1,1'-biphenyl]-3-ylmethyl)-2-(((S)-1-(((6-amino-2-methylpyridin-3-yl)methyl)amino)-1-oxopropan-2-yl)carbamoyl)pyrrolidine-1-carboxylate.

Step 4: Deprotection of tert-butyl (2R,4S)-4-([1,1'-biphenyl]-3-ylmethyl)-2-(((S)-1-(((6-amino-2-methylpyridin-3-yl)methyl)amino)-1-oxopropan-2-yl)carbamoyl)pyrrolidine-1-carboxylate according to the procedure for compound (1304), step 8, gave (2R,4R)-4-([1,1'-biphenyl]-3-yl)-N—((S)-1-(((6-amino-2-methylpyridin-3-yl)methyl)amino)-1-oxopropan-2-yl)pyrrolidine-2-carboxamide which was purified using reverse-phase HPLC and isolated as the di-trifluoroacetate salt.

Example 163. Preparation of (2R,4R)-4-([1,1'-Biphenyl]-3-yl)-N—((R)-1-(((6-amino-2-methylpyridin-3-yl)methyl)amino)-1-oxopropan-2-yl)pyrrolidine-2-carboxamide Di-trifluoroacetate salt (1360)

(1360)

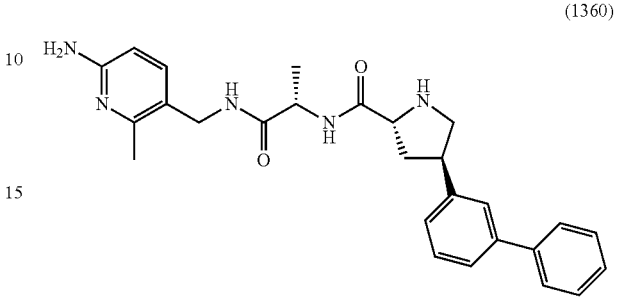

tert-Butyl (2R,4R)-4-([1,1'-biphenyl]-3-ylmethyl)-2-(((S)-1-(((6-amino-2-methylpyridin-3-yl)methyl)amino)-1-oxopropan-2-yl)carbamoyl)pyrrolidine-1-carboxylate, isolated from the preparation of tert-butyl (2R,4S)-4-([1,1'-biphenyl]-3-ylmethyl)-2-(((S)-1-(((6-amino-2-methylpyridin-3-yl)methyl)amino)-1-oxopropan-2-yl) carbamoyl)pyrrolidine-1-carboxylate (compound (1359), step 3) was deprotected according to the procedure for compound (1304), step 8 to give (2R,4R)-4-([1,1'-biphenyl]-3-yl)-N—((R)-1-(((6-amino-2-methylpyridin-3-yl)methyl) amino)-1-oxopropan-2-yl)pyrrolidine-2-carboxamide di-trifluoroacetate salt after purification using reverse-phase HPLC.

Example 164. Preparation of (2R,4S)—N—((S)-1-(((6-Amino-2-methylpyridin-3-yl)methyl)amino)-1-oxopropan-2-yl)-4-(4-(thiazol-2-yl)benzyl)pyrrolidine-2-carboxamide Di-trifluoroacetate salt (1361)

(1361)

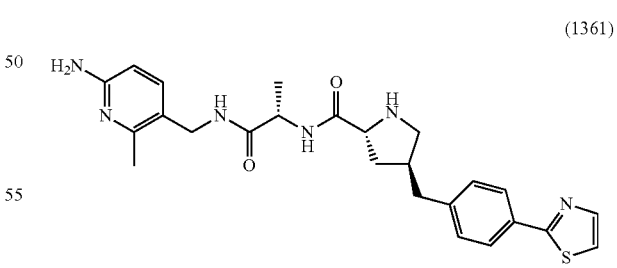

(2R,4S)—N—((S)-1-(((6-amino-2-methylpyridin-3-yl) methyl)amino)-1-oxopropan-2-yl)-4-(4-(thiazol-2-yl)benzyl)pyrrolidine-2-carboxamide di-trifluoroacetate salt was synthesized according to the procedures for compound (1304), except that the final product was purified using reverse-phase HPLC.

Example 165. Preparation of (2R,4R)—N—((S)-1-(((3-Chloro-1H-indol-5-yl)methyl)amino)-1-oxopropan-2-yl)-4-phenylpyrrolidine-2-carboxamide (1362)

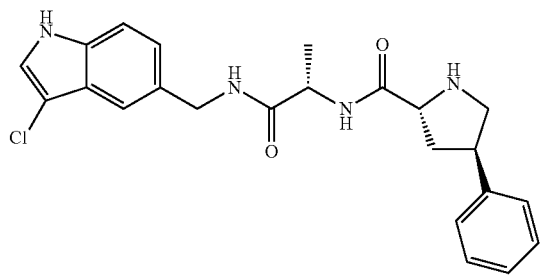

(1362)

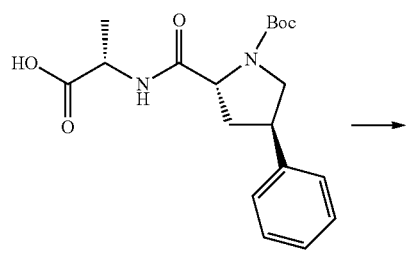

→

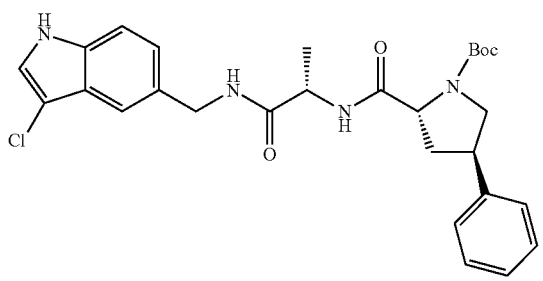

Step 1: ((2R,4R)-1-(tert-Butoxycarbonyl)-4-phenylpyrrolidine-2-carbonyl)-L-alanine was coupled with (3-chloro-1H-indol-5-yl)methanamine (synthesized according to the procedures reported in WO200002611) according to the procedure for compound (1265), step 1 to give tert-butyl (2R,4R)-2-(((S)-1-(((3-chloro-1H-indol-5-yl)methyl)amino)-1-oxopropan-2-yl)carbamoyl)-4-phenylpyrrolidine-1-carboxylate (71.7 mg, 62% yield).

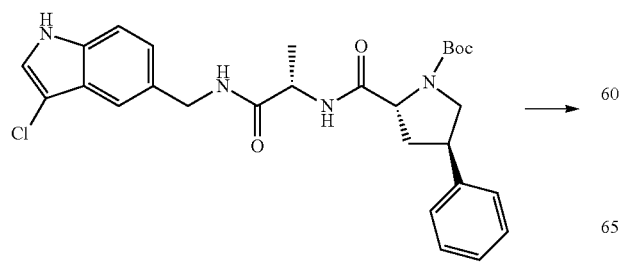

→

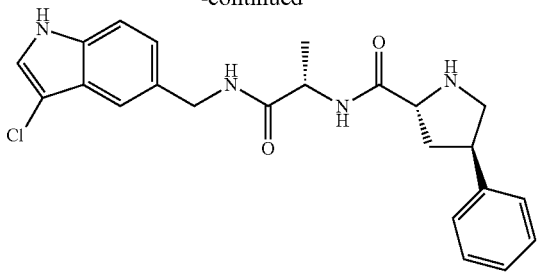

Step 2: To a solution of tert-butyl (2R,4R)-2-(((S)-1-(((3-chloro-1H-indol-5-yl)methyl)amino)-1-oxopropan-2-yl)carbamoyl)-4-phenylpyrrolidine-1-carboxylate (28.7 mg, 0.055 mmol) in anhyd $CH_2Cl_2$ (5 mL) over an ice bath was added TFA (6 µL), triethylsilane (2 drops). Additional TFA (6 µL) was added. After stirring for 15 min the ice bath was removed and stirring continued for 1 h. Additional TFA (0.25 mL) was added and the mixture was stirred for 75 min. The reaction was quenched with slow addition of 1 M NaOH (3 mL). After stirring for 5 min the mixture was cooled over an ice bath. Sat. $NaHCO_3$ was added until the pH was neutral. The mixture was saturated with NaCl and extracted with 10% MeOH—$CH_2Cl_2$. The combined organics were dried ($Na_2SO_4$) and conc in vacuo. Purification by chromatography (0-7.5% MeOH—$CH_2Cl_2$) gave (2R,4R)—N—((S)-1-(((3-chloro-1H-indol-5-yl)methyl)amino)-1-oxopropan-2-yl)-4-phenylpyrrolidine-2-carboxamide (12.8 mg, 55% yield).

Example 166. Preparation of (2R,4S)-4-Benzyl-N—((S)-1-((5-chloro-2-hydroxy-3-methylbenzyl)amino)-1-oxopropan-2-yl)piperidine-2-carboxamide Hydrochloride (1363)

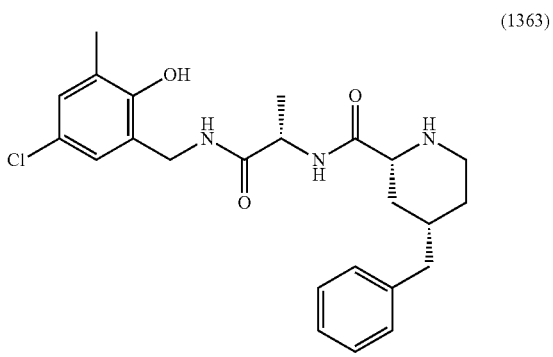 [SMILES: Cc1cc(Cl)cc(CNC(=O)[C@H](C)NC(=O)[C@H]2C[C@@H](Cc3ccccc3)CCN2)c1O]

(1363)

(2R,4S)-4-Benzyl-N—((S)-1-((5-chloro-2-hydroxy-3-methylbenzyl)amino)-1-oxopropan-2-yl)piperidine-2-carboxamide hydrochloride was synthesized according to the procedures for compound (1230), except using ((2R,4S)-4-benzyl-1-(tert-butoxycarbonyl)piperidine-2-carbonyl)-L-alanine in step 3.

Example 167. Preparation of (2R,4R)—N—((S)-1-((3-Chloro-5-hydroxybenzyl)amino)-1-oxopropan-2-yl)-4-phenylpyrrolidine-2-carboxamide Hydrochloride (1364)

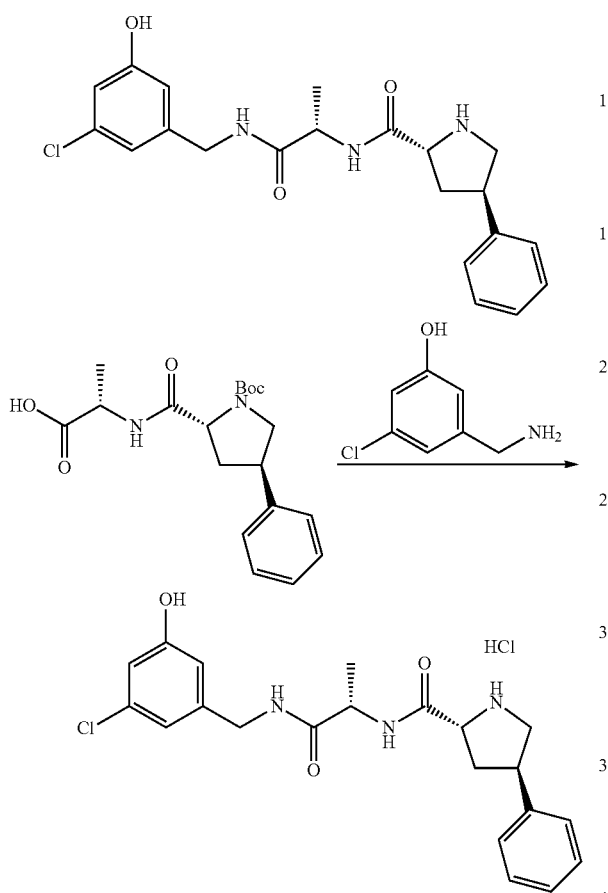

Steps 1-2: The title compound was synthesized as a white powder according to steps 3-4 of the procedure for compound 1119 using the appropriate starting materials (8.5 mg, 11% yield over two steps).

Example 168. Preparation of (2R,4S)—N—((S)-1-((5-Chloro-2-hydroxy-3-methylbenzyl)amino)-1-oxopropan-2-yl)-4-phenylpiperidine-2-carboxamide Hydrochloride (1365)

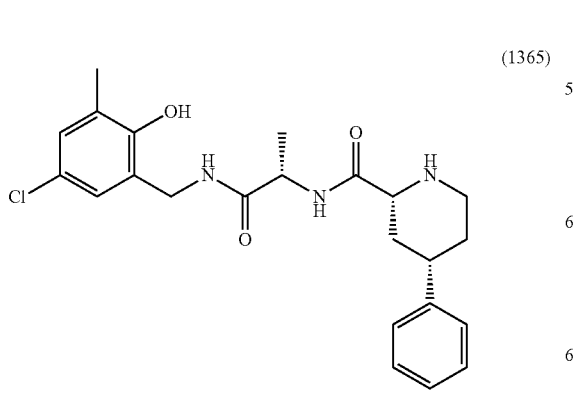

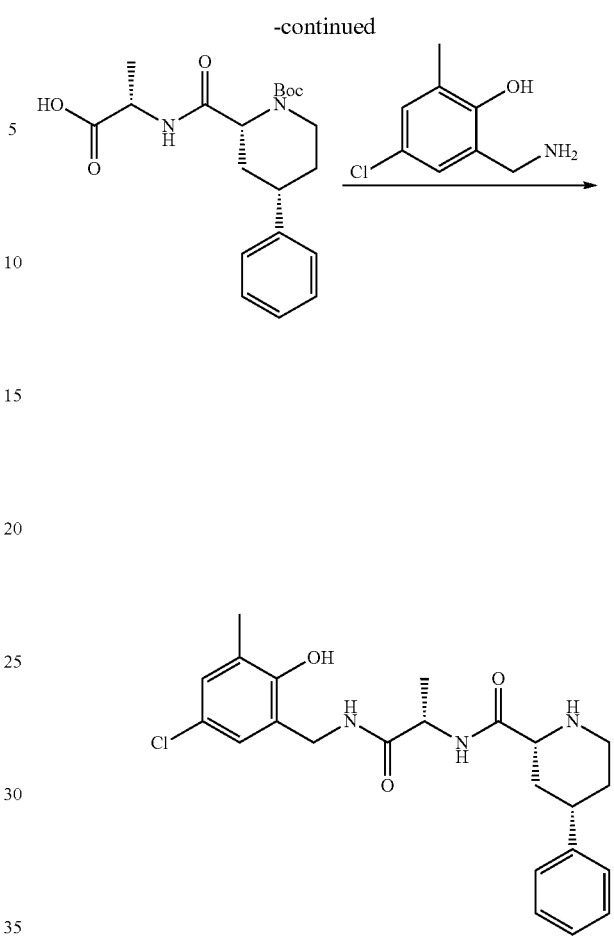

Steps 1-2: The title compound was synthesized as a white powder according to steps 1-2 of the procedure for compound (1246) using the appropriate starting materials (33 mg, 35% yield over two steps).

Example 169. Preparation of (2R,4R)—N—((S)-1-((Imidazo[1,2-a]pyridin-7-ylmethyl)amino)-1-oxopropan-2-yl)-4-phenylpyrrolidine-2-carboxamide Dihydrochloride (1366)

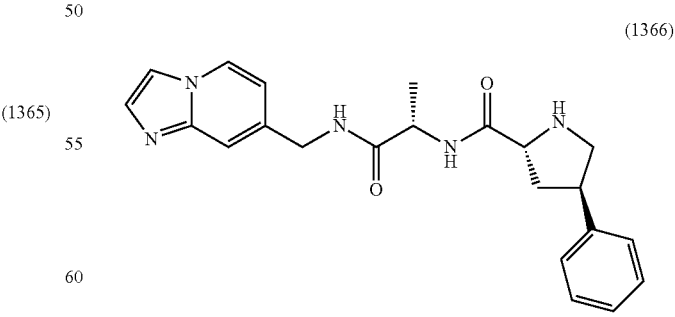

(2R,4R)—N—((S)-1-((Imidazo[1,2-a]pyridin-7-ylmethyl)amino)-1-oxopropan-2-yl)-4-phenylpyrrolidine-2-carboxamide dihydrochloride was synthesized according to the procedure given for compound (1323), steps 2 and 3.

Example 170. Preparation of (S)—N-(1-(((6-Amino-2-methylpyridin-3-yl)methyl)amino)-1-oxopropan-2-yl)-3-benzyl-1H-pyrazole-5-carboxamide (1367)

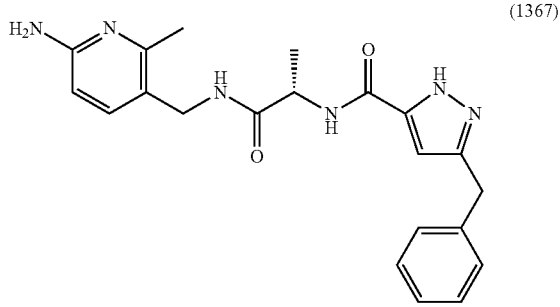 [SMILES: Cc1nc(N)ccc1CNC(=O)[C@H](C)NC(=O)c1cc(Cc2ccccc2)n[nH]1]

(1367)

(S)—N-(1-(((6-Amino-2-methylpyridin-3-yl)methyl)amino)-1-oxopropan-2-yl)-3-benzyl-1H-pyrazole-5-carboxamide was synthesized according to the procedures for compound (1230), except using 3-benzyl-1H-pyrazole-5-carboxylic acid in step 1 and 5-(aminomethyl)-6-methylpyridin-2-amine in step 3.

Example 171. Preparation of (R)-2-((4-Acetamidophenethyl)amino)-N—((S)-1-(((6-amino-2-methylpyridin-3-yl)methyl)amino)-1-oxopropan-2-yl)-4-phenylbutanamide Dihydrochloride (1368)

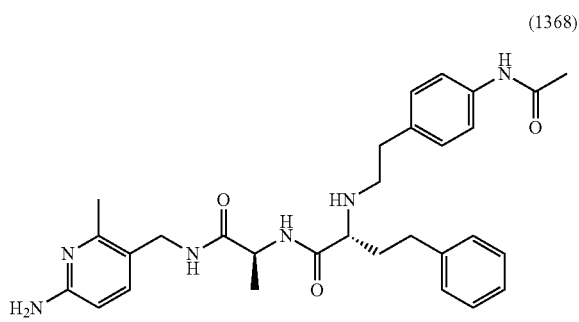 [SMILES: CC(=O)Nc1ccc(CCN[C@H](CCc2ccccc2)C(=O)N[C@@H](C)C(=O)NCc2ccc(N)nc2C)cc1]

(1368)

Step 1: Benzyl ((R)-2-amino-4-phenylbutanoyl)-L-alaninate (403.0 mg, 1.18 mmol) was coupled with N-(4-(2-oxoethyl)phenyl)acetamide (251.0 mg, 1.42 mmol) according to the procedure for compound 1130, step 2. The crude product was dissolved in CH₂Cl₂ and adsorbed on silica gel. Purification by chromatography (0-10% MeOH—CH₂Cl₂) afforded benzyl ((R)-2-((4-acetamidophenethyl)amino)-4-phenylbutanoyl)-L-alaninate (500.1 mg, 84% yield).

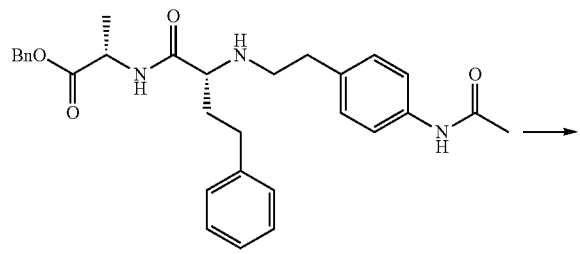

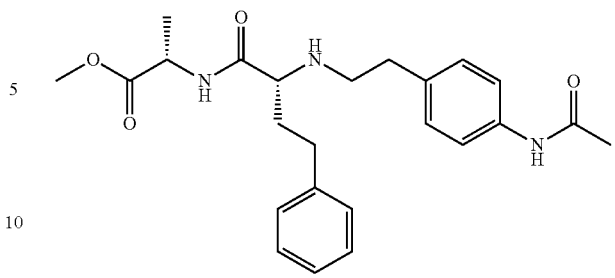

Step 2: Deprotection of benzyl ((R)-2-((4-acetamidophenethyl)amino)-4-phenylbutanoyl)-L-alaninate (500.1 mg, 0.997 mmol)) according to the procedure for compound 1119, step 2 afforded methyl ((R)-2-((4-acetamidophenethyl)amino)-4-phenylbutanoyl)-L-alaninate (122.0 mg, 29% yield).

Step 3: Hydrolysis of methyl ((R)-2-((4-acetamidophenethyl)amino)-4-phenylbutanoyl)-L-alaninate (122.0 mg, 0.287 mmol) according to the procedure for compound (1349), step 4 afforded the crude ((R)-2-((4-acetamidophenethyl)amino)-4-phenylbutanoyl)-L-alanine (37.5 mg, 32% yield).

Step 4: ((R)-2-((4-Acetamidophenethyl)amino)-4-phenylbutanoyl)-L-alanine (37.5 mg, 0.091 mmol) was coupled with 5-(aminomethyl)-6-methylpyridin-2-amine (21.0 mg, 0.15 mmol) according to the procedure for compound 1088, step 2 except HBTU was added to the reaction at 0° C. The crude product was dissolved in CH₂Cl₂ and adsorbed on silica gel. Purification by chromatography (0-15% MeOH—CH₂Cl₂) afforded (R)-2-((4-acetamidophenethyl)amino)-N—((S)-1-(((6-amino-2-methylpyridin-3-yl)methyl)amino)-1-oxopropan-2-yl)-4-phenylbutanamide (31.1 mg, 64% yield).

Step 5: (R)-2-((4-Acetamidophenethyl)amino)-N—((S)-1-(((6-amino-2-methylpyridin-3-yl)methyl)amino)-1-oxopropan-2-yl)-4-phenylbutanamide dihydrochloride was formed according to the procedure for compound (1319), step 6.

Example 172. Preparation of (2R,4S)—N—((S)-1-((5-Chloro-2-hydroxy-3-methylbenzyl)amino)-1-oxopropan-2-yl)-4-(3-methylbenzyl)pyrrolidine-2-carboxamide Hydrochloride (1369)

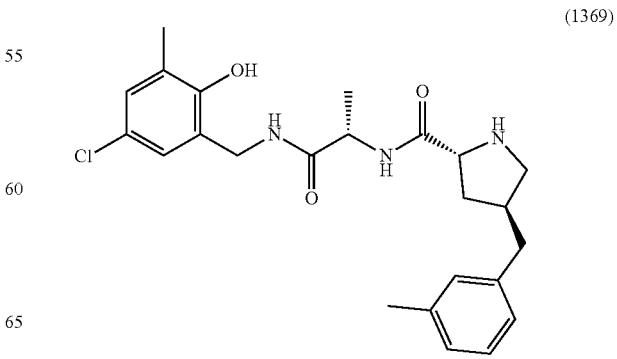

(1369)

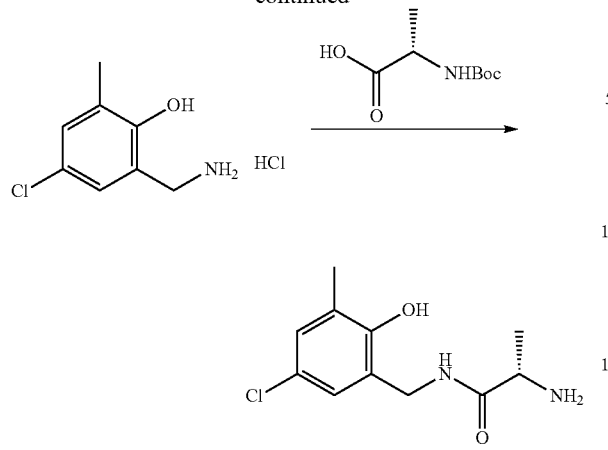

Steps 1-2: A 250 mL round bottom flask was charged with N-(tert-butoxycarbonyl)-L-alanine (503 mg, 2.66 mmol) and ACN (13 mL) then cooled to 0° C. Oxyma (435 mg, 3.06 mmol) and EDC (560 mg, 2.92 mmol) were added portionwise and allowed to stir for 10 min. 2-(Aminomethyl)-4-chloro-6-methylphenol (500 mg, 2.92 mmol) and DIEA (695 μL, 4 mmol) were then added, respectively, and the reaction allowed to slowly warm to ambient temperature overnight. The solvent was removed under reduced pressure and the residue re-dissolved in EtOAc before being washed with 10% aq. KHSO$_4$ and brine, dried over Na$_2$SO$_4$ and concentrated in vacuo. The crude product was purified by chromatography (60-70% EtOAc/hexanes). tert-Butyl (S)-(1-((5-chloro-2-hydroxy-3-methylbenzyl)amino)-1-oxopropan-2-yl)carbamate was dissolved in conc. HCl in MeOH (10 mL) and stirred at ambient temperature overnight. The reaction mixture was then concentrated and purified by chromatography (MeOH/CH$_2$Cl$_2$ containing 2.5% 7 N NH$_3$-MeOH) to yield (S)-2-amino-N-(5-chloro-2-hydroxy-3-methylbenzyl)propenamide as a yellow powder (469 mg, 73% yield over two steps).

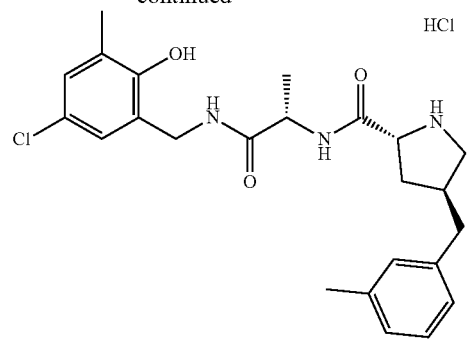

Steps 3-4: The title compound was synthesized as a white solid according to steps 1-2 of the procedure for compound (1246) using the appropriate starting materials (11 mg, 15% yield over two steps).

Example 173. Preparation of (2R,4S)—N—((S)-1-((5-Chloro-2-hydroxy-3-methylbenzyl)amino)-1-oxopropan-2-yl)-4-(naphthalen-2-ylmethyl)pyrrolidine-2-carboxamide (1370)

(1370)

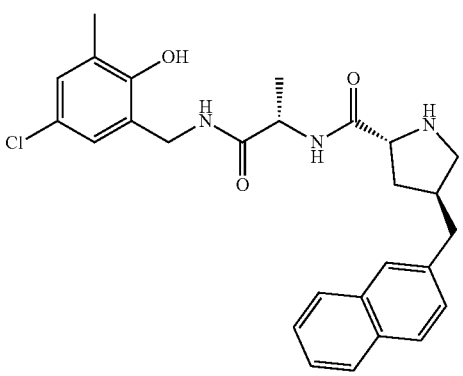

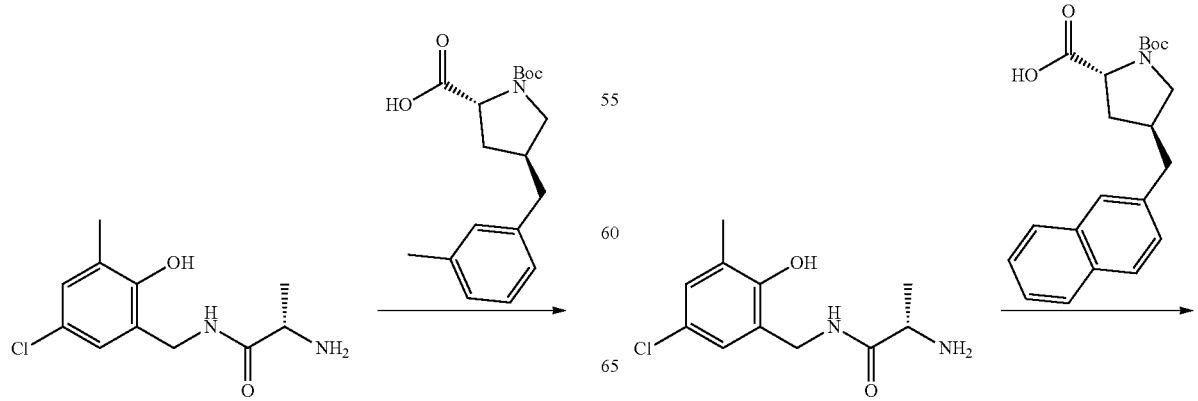

-continued

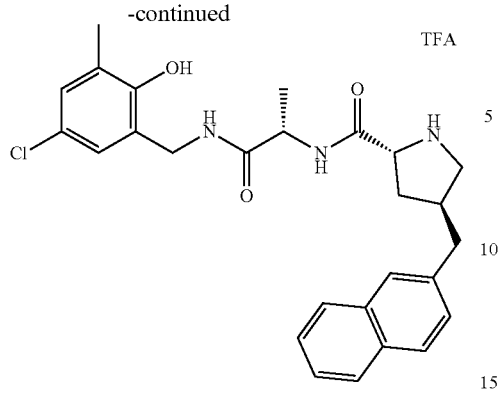

Steps 1-2: The title compound was synthesized as a white solid according to steps 3-4 of the procedure for compound (1313) using the appropriate starting materials (17.4 mg, 36% yield over two steps).

Example 174. Preparation of (2R,4S)-4-Benzyl-N—((S)-1-((5-chloro-2-(1H-tetrazol-1-yl)benzyl)amino)-1-oxopropan-2-yl)pyrrolidine-2-carboxamide Hydrochloride (1371)

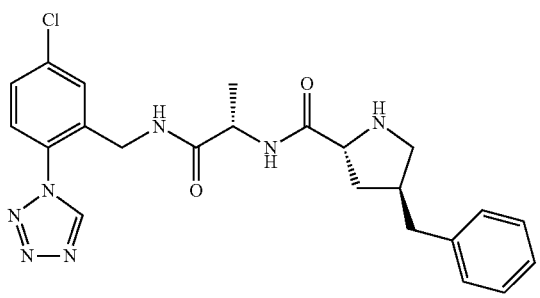

(2R,4S)-4-Benzyl-N—((S)-1-((5-chloro-2-(1H-tetrazol-1-yl)benzyl)amino)-1-oxopropan-2-yl)pyrrolidine-2-carboxamide hydrochloride was synthesized according to the procedures for compound (1307).

Example 175. Preparation of (2R,4S)—N—((S)-1-(((6-Amino-2-methylpyridin-3-yl)methyl)amino)-1-oxopropan-2-yl)-4-(2-bromobenzyl)pyrrolidine-2-carboxamide Di-trifluoroacetate salt (1372)

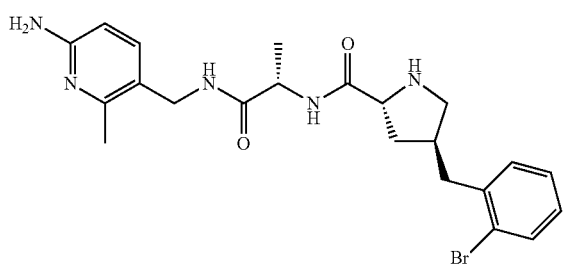

(2R,4S)—N—((S)-1-(((6-Amino-2-methylpyridin-3-yl)methyl)amino)-1-oxopropan-2-yl)-4-(2-bromobenzyl)pyrrolidine-2-carboxamide di-trifluoroacetate salt was synthesized according to the procedures for compound (1328), except that the final product was purified using reverse-phase HPLC.

Example 176. Preparation of (2R,4S)-4-([1,1'-Biphenyl]-2-ylmethyl)-N—((S)-1-(((6-amino-2-methylpyridin-3-yl)methyl)amino)-1-oxopropan-2-yl)pyrrolidine-2-carboxamide Di-trifluoroacetate salt (1373)

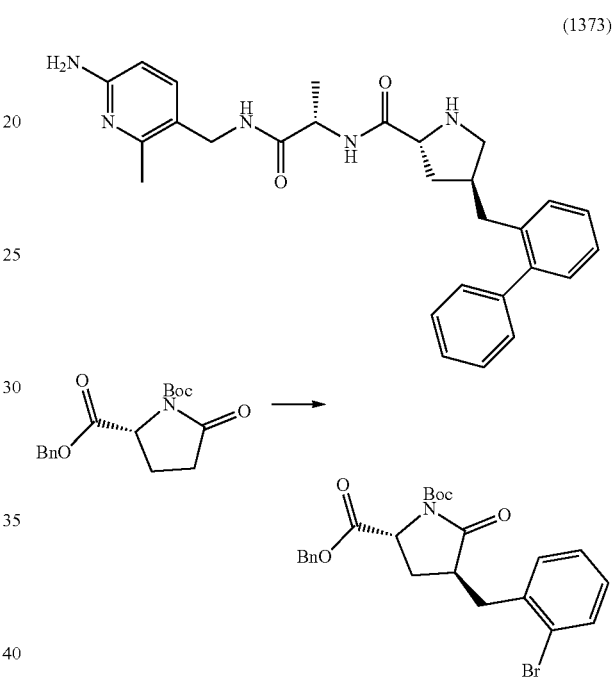

Step 1: To a stirred solution of 2-benzyl 1-(tert-butyl) (R)-5-oxopyrrolidine-1,2-dicarboxylate (2.0 g, 6.28 mmol) in THF (40 mL) at −78° C. was slowly added lithium bis(trimethylsilyl)amide (6.90 mL, 6.90 mmol, 1 M in THF) under Ar. After stirring for 1 h at −78° C., 2-bromobenzyl bromide (1.88 g, 7.53 mmol) was added and the stirring continued for an additional 2 h. The reaction mixture was quenched with sat. NH$_4$Cl solution and extracted with diethyl ether (3×60 mL). The combined extracts were dried over Na$_2$SO$_4$, filtered and concentrated under vacuum. The residue was purified by chromatography (EtOAc-hexanes) gave 2-benzyl 1-(tert-butyl) (2R,4S)-4-(2-bromobenzyl)-5-oxopyrrolidine-1,2-dicarboxylate (2.63 g, 86% yield).

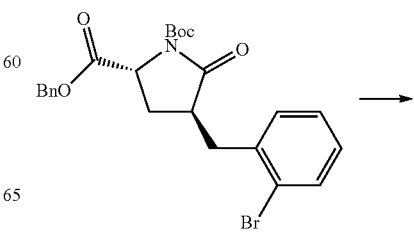

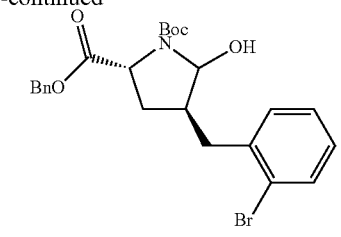

Step 2: To a solution of 2-benzyl 1-(tert-butyl) (2R,4S)-4-(2-bromobenzyl)-5-oxopyrrolidine-1,2-dicarboxylate (1.60 g, 3.91 mmol) in THF (22 mL) at −78° C. was added lithium triethylborohydride solution (3.94 mL, 3.94 mmol, 1 M in THF) under Ar atmosphere. After 30 min, the reaction mixture was quenched with sat. NaHCO$_3$ solution (8.60 mL) and warmed to 0° C. At 0° C., 30% H$_2$O$_2$ (about 25 drops) was added and the reaction mixture was stirred at same temperature for 30 min. The organic volatiles were removed under vacuum and the aqueous layer was extracted with CH$_2$Cl$_2$ (3×40 mL). The combined organic extracts were thoroughly dried using Na$_2$SO$_4$, filtered, concentrated to afford 2-benzyl 1-(tert-butyl) (2R,4S)-4-(2-bromobenzyl)-5-hydroxypyrrolidine-1,2-dicarboxylate (1.60 g crude) that was directly used in the next step without further purification.

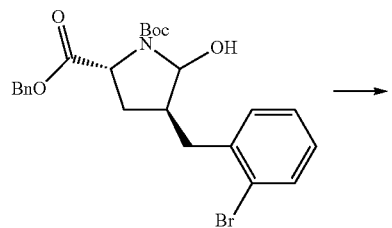

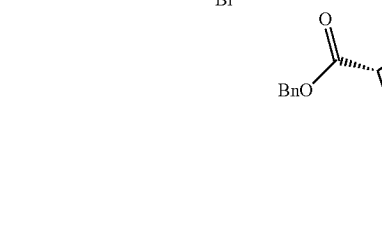

Step 3: To a stirred solution of 2-benzyl 1-(tert-butyl) (2R,4S)-4-(2-bromobenzyl)-5-hydroxypyrrolidine-1,2-dicarboxylate (1.60 g crude) and triethylsilane (0.63 mL, 3.94 mmol) in CH$_2$Cl$_2$ at −78° C. was dropwise added boron trifluoride diethyl etherate (0.49 mL, 3.94 mmol) under Ar atmosphere. After 30 min at same temperature additional triethylsilane (0.63 mL, 3.94 mmol) and boron trifluoride diethyl etherate (0.49 mL, 3.94 mmol) were added. After stirring for 2 h at −78° C., the reaction mixture was quenched with sat. aqueous NaHCO$_3$ solution (10 mL) and extracted with CH$_2$Cl$_2$ (3×40 mL). The combined extracts were dried over Na$_2$SO$_4$, filtered and conc under vacuum. The residue was purified by chromatography (EtOAc-hexanes) to afford 2-benzyl 1-(tert-butyl) (2R,4S)-4-(2-bromobenzyl)pyrrolidine-1,2-dicarboxylate (931 mg, 60% yield in two steps).

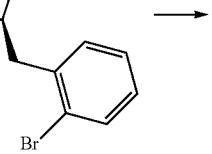

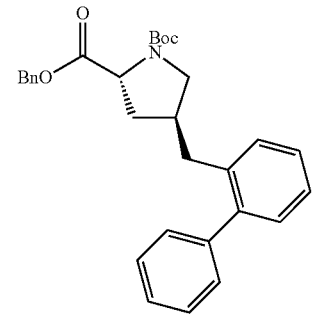

Step 4: In a 50 mL round bottom flask equipped with a stir bar and septum was added 2-benzyl 1-(tert-butyl) (2R,4S)-4-(2-bromobenzyl)pyrrolidine-1,2-dicarboxylate (200 mg, 0.42 mmol), phenyl boronic acid (62 mg, 0.51), Pd(dppf)Cl$_2$ (31 mg, 0.042 mmol), cesium carbonate (413 mg, 1.26 mmol), THF (4.2 mL) and water (0.42 mL). The resulting mixture was degassed by bubbling N$_2$ through the solution for 10 min. The reaction was then heated to 90° C. for 4 h. Upon cooling to room temperature, the reaction solution was filtered through diatomaceous earth, eluted with EtOAc, concentrated and purified by chromatography using EtOAc-hexanes to afford 2-benzyl 1-(tert-butyl) (2R,4S)-4-([1,1'-biphenyl]-2-ylmethyl)pyrrolidine-1,2-dicarboxylate (200 mg, 99% yield) as a colorless sticky liquid.

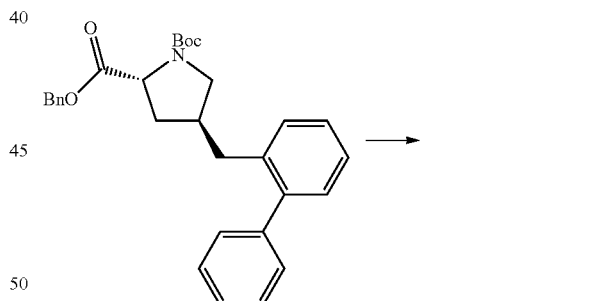

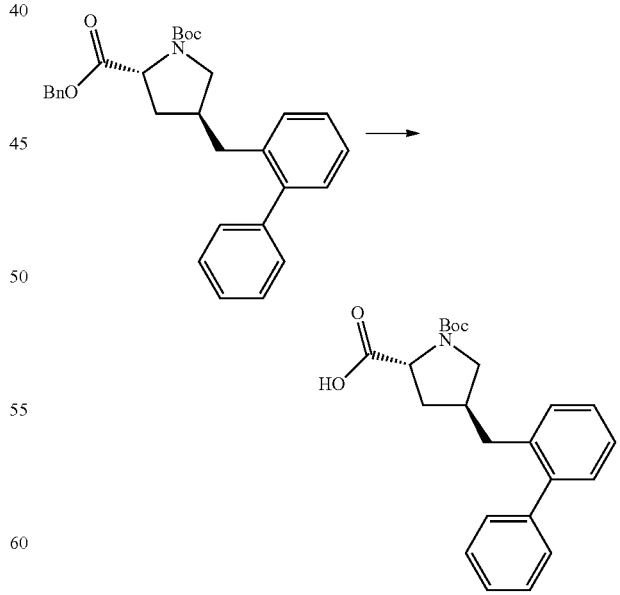

Step 4: A solution of 2-benzyl 1-(tert-butyl) (2R,4S)-4-([1,1'-biphenyl]-2-ylmethyl)pyrrolidine-1,2-dicarboxylate (200 mg, 0.42 mmol) in MeOH (4.2 mL) was bubbled with Ar gas for 5 minutes. 10% Pd/C (20 mg) was added to the reaction mixture and that was stirred under 1 atm of H₂ for 3 h. The reaction mixture was filtered (0.2 μm syringe filter) and the filtrate was concentrated under vacuum to give (2R,4S)-4-([1,1'-biphenyl]-2-ylmethyl)-1-(tert-butoxycarbonyl)pyrrolidine-2-carboxylic acid (150 mg, 93% yield).

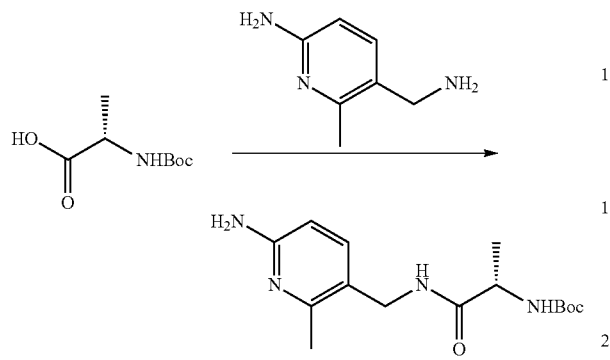

Step 5: To a stirred solution of (tert-butoxycarbonyl)-L-alanine (1.96 g, 10.38 mmol) in CH₂Cl₂ (55 mL) was added NHS (1.25 g, 10.89 mmol) at room temperature. To the reaction mixture DCC (2.25 g 10.9 mmol) was added and the reaction mixture stirred for 1.0 h. 5-(Aminomethyl)-6-methylpyridin-2-amine was added to the reaction mixture and sonicated for 5 min. The 5-(aminomethyl)-6-methylpyridin-2-amine was completely dissolved and the reaction mixture was stirred at ambient temperature for 1 h. The crude reaction mixture was filtered and conc under reduced pressure. Purified the crude reaction mixture by chromatography using MeOH—CH₂Cl₂ to afford tert-butyl (S)-(1-(((6-amino-2-methylpyridin-3-yl)methyl)amino)-1-oxopropan-2-yl)carbamate (2.35 g, 70% yield) as a white solid.

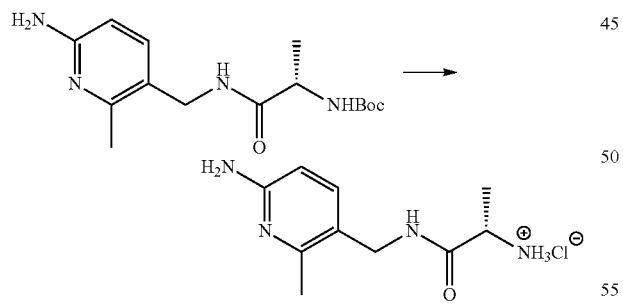

Step 6: To tert-butyl (S)-(1-(((6-amino-2-methylpyridin-3-yl)methyl)amino)-1-oxopropan-2-yl)carbamate (2.35 g, 7.62 mmol) was added a solution of MeOH—HCl (19 mL, 2 M) with stirring at ambient temperature while monitoring for the consumption of starting material (typically 1 h). The solution was evaporated to dryness and MeOH (50 mL) was added and evaporated to dryness to remove residual HCl gas to give (S)-2-amino-N-((6-amino-2-methylpyridin-3-yl)methyl)propanamide hydrochloride (1.60 g, 90% yield) as an off white solid (hygroscopic).

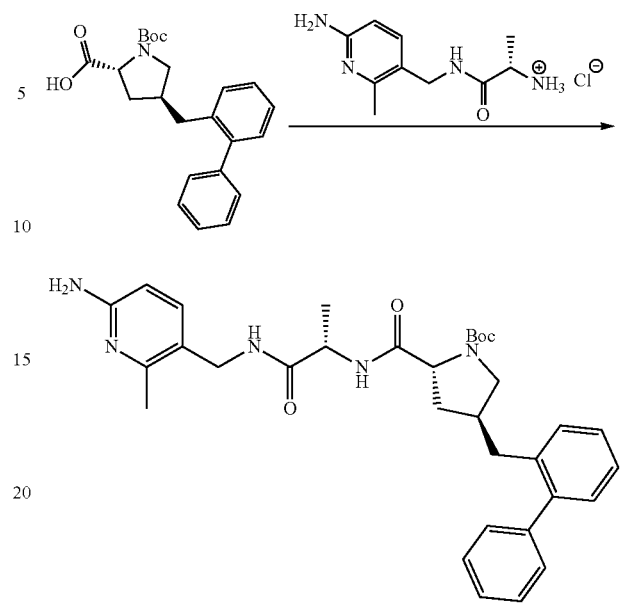

Step 7: To a stirred solution of (2R,4S)-4-([1,1'-biphenyl]-2-ylmethyl)-1-(tert-butoxycarbonyl)pyrrolidine-2-carboxylic acid (38 mg, 0.1 mmol) in anhydrous DMF (1 mL) was added HOBt (24 mg, 0.11 mmol), DIEA (0.1 mL, 0.52 mmol) and EDC (28 mg, 0.11 mmol) at ambient temperature. The reaction mixture was stirred for 30 min at ambient temperature. (S)-2-amino-N-((6-amino-2-methylpyridin-3-yl)methyl)propanamide hydrochloride (23 mg, 0.12 mmol) was added to the reaction mixture and stirred overnight. The solution was evaporated to dryness and the residue was partitioned with EtOAc (10 mL) and 10% KHSO₄ (5 mL). The organic layer was separated and washed with sat. NaHCO₃ solution (10 ml), dried over anhydrous Na₂SO₄ and conc under vacuum. The crude reaction mixture was purified by chromatography using MeOH—CH₂Cl₂ to afford tert-butyl (2R,4S)-4-([1,1'-biphenyl]-2-ylmethyl)-2-(((S)-1-(((6-amino-2-methylpyridin-3-yl)methyl)amino)-1-oxopropan-2-yl)carbamoyl)pyrrolidine-1-carboxylate (40 mg, 70% yield) as a white solid.

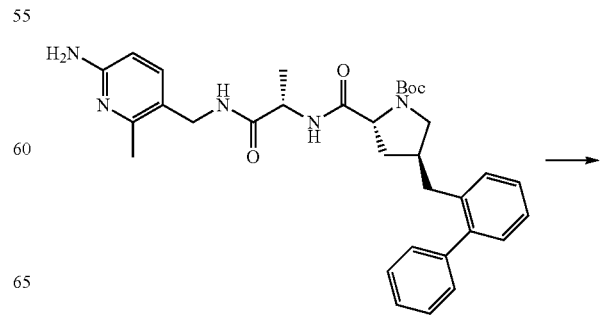

529

-continued

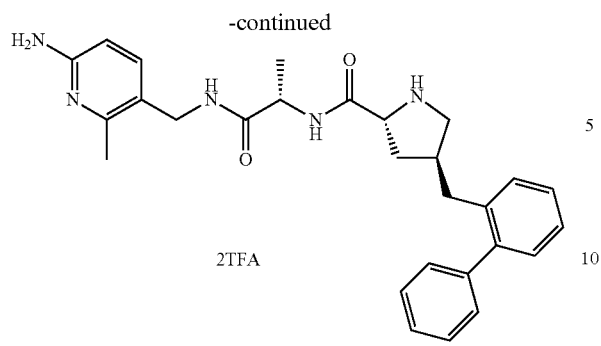

2TFA

Step 8: To tert-butyl (2R,4S)-4-([1,1'-biphenyl]-2-ylmethyl)-2-(((S)-1-(((6-amino-2-methylpyridin-3-yl)methyl)amino)-1-oxopropan-2-yl)carbamoyl)pyrrolidine-1-carboxylate (40 mg, 0.07 mmol) in 1 mL CH$_2$Cl$_2$ was added TFA (0.11 mL, 1.39 mmol) with stirring at ambient temperature while monitoring for the consumption of starting material (30 min to 1 h). The solution was evaporated to dryness and MeOH (10 mL) was added and evaporated to dryness to remove residual TFA. The resulting crude reaction mixture was purified using reverse-phase HPLC to afford (2R,4S)-4-([1,1'-biphenyl]-2-ylmethyl)-N—((S)-1-(((6-amino-2-methylpyridin-3-yl)methyl)amino)-1-oxopropan-2-yl)pyrrolidine-2-carboxamide di-trifluoroacetate salt (22.2 mg, 67% yield) as a white solid.

Example 177. Preparation of (2R,4S)-4-(4-bromobenzyl)-N—((S)-1-((5-chloro-2-hydroxy-3-methylbenzyl)amino)-1-oxopropan-2-yl)pyrrolidine-2-carboxamide Hydrochloride (1374)

530

-continued

Steps 1-2: tert-Butyl (2R,4S)-4-(4-bromobenzyl)-2-(((S)-1-((5-chloro-2-hydroxy-3-methylbenzyl)amino)-1-oxopropan-2-yl)carbamoyl)pyrrolidine-1-carboxylate was synthesized according to step 3 of the procedure for compound 1119 using the appropriate starting materials. Removal of the Boc group was achieved using the procedure from step 4 for compound (1313). The crude product was purified by chromatography (MeOH/CH$_2$Cl$_2$ containing 2.5% 7 N NH$_3$-MeOH), then the collected fractions were concentrated, treated with 1 N HCl and lyophilized to yield the title compound as a white powder (28 mg, 47% yield over 2 steps).

Example 178. Preparation of (R)—N—((S)-1-(((6-Amino-2-methylpyridin-3-yl)methyl)amino)-1-oxopropan-2-yl)-2-((4-chlorobenzyl)amino)-4-phenylbutanamide (1375)

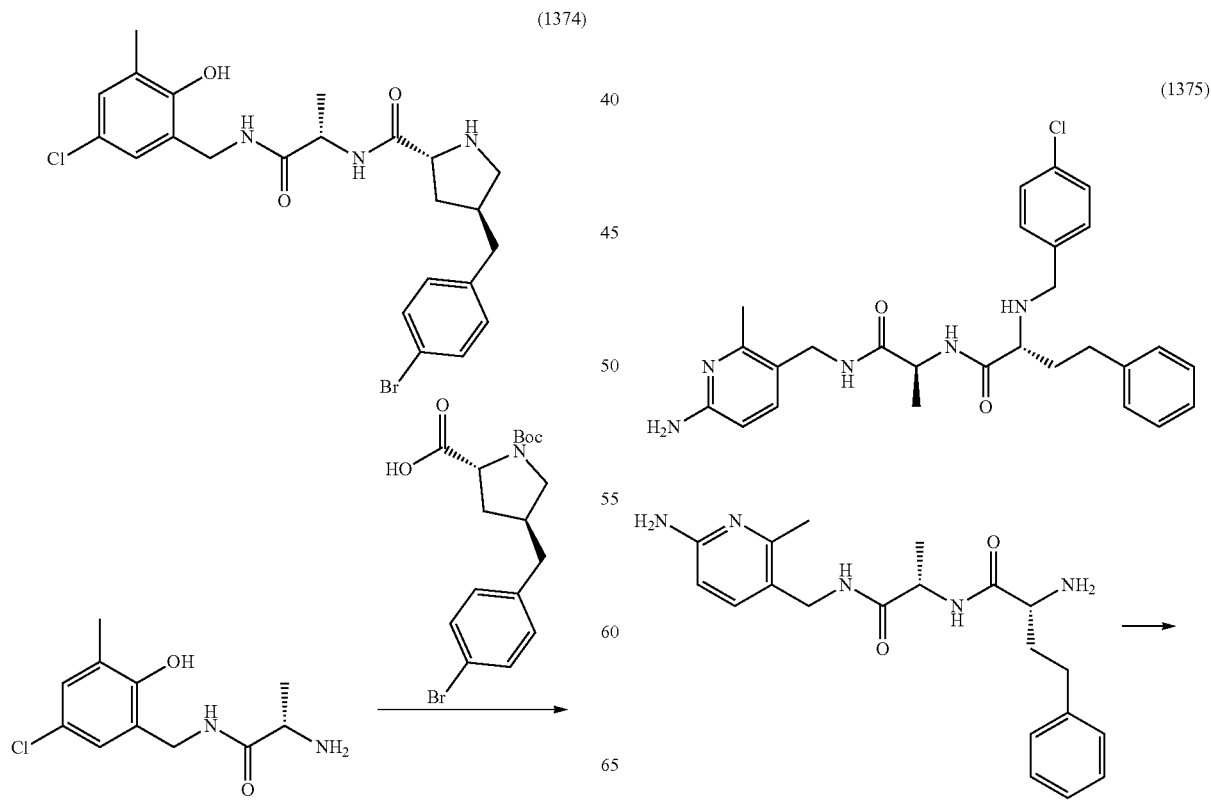

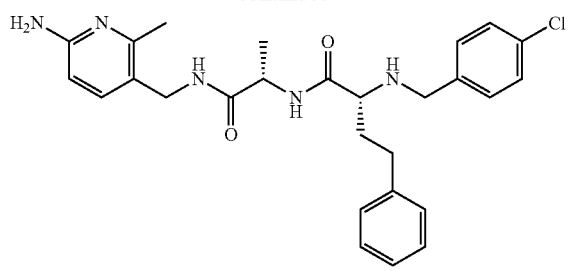

(R)-2-Amino-N—((S)-1-(((6-amino-2-methylpyridin-3-yl)methyl)amino)-1-oxopropan-2-yl)-4-phenylbutanamide (148.5 mg, 0.246 mmol) was coupled with 4-chlorobenzaldehyde (45 mg, 0.320 mmol) according to the procedure for compound 1130, step 2. The crude product was dissolved in CH₂Cl₂ and adsorbed on silica gel. Purification by chromatography (0-5% MeOH—CH₂Cl₂) afforded (R)—N—((S)-1-(((6-amino-2-methylpyridin-3-yl)methyl)amino)-1-oxopropan-2-yl)-2-((4-chlorobenzyl)amino)-4-phenylbutanamide (57.3 mg, 44% yield).

Example 179. Preparation of (S)—N'-((6-Amino-2-methylpyridin-3-yl)methyl)-2-((R)-2-amino-4-phenylbutanamido)pentanediamide Di-trifluoroacetate (1376)

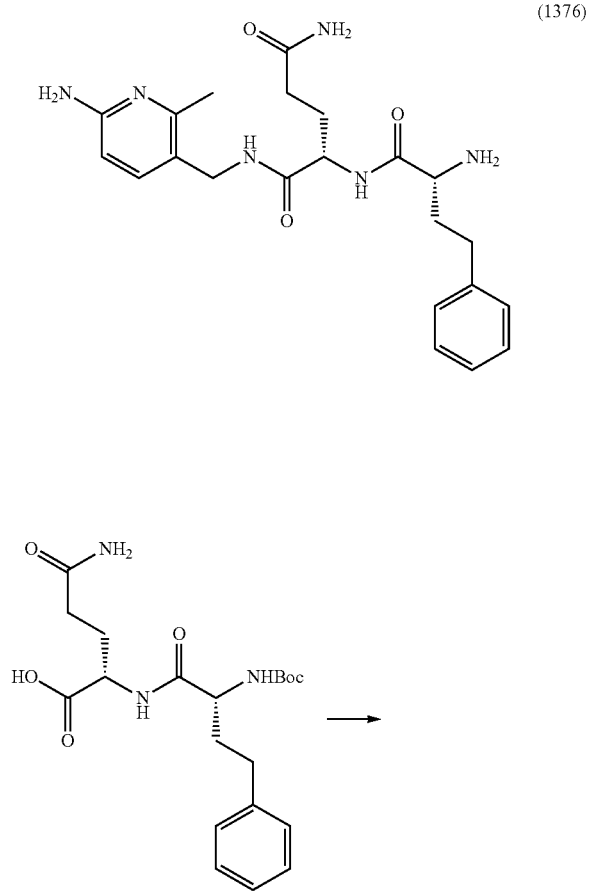

Step 1: tert-Butyl ((R)-1-(((S)-5-amino-1-(((6-amino-2-methylpyridin-3-yl)methyl)amino)-1,5-dioxopentan-2-yl)amino)-1-oxo-4-phenylbutan-2-yl)carbamate (49 mg, 17% yield) was synthesized from ((R)-2-amino-4-phenylbutanoyl)-L-glutamine (230 mg, 0.56 mmol, prepared according to the procedure for compound (1335), step 1-2 and 5-(aminomethyl)-6-methylpyridine-2-amine according to the procedure for compound (1326), step 3.

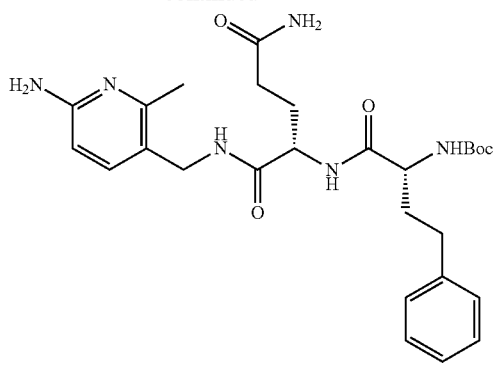

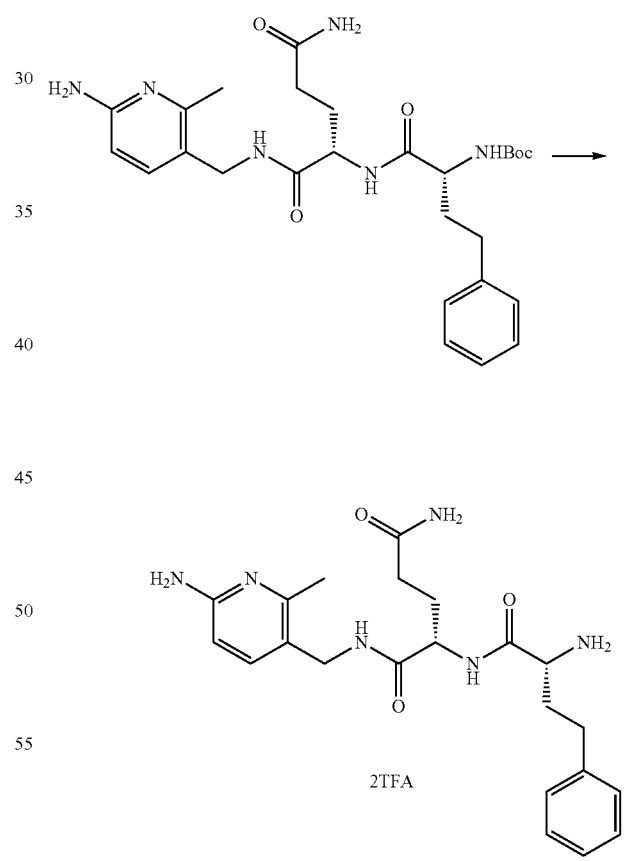

Step 2: Deprotection of tert-butyl ((R)-1-(((S)-5-amino-1-(((6-amino-2-methylpyridin-3-yl)methyl)amino)-1,5-dioxopentan-2-yl)amino)-1-oxo-4-phenylbutan-2-yl)carbamate (49 mg, 0.09 mmol) was conducted according to the procedure for compound (1260), step 4 except that the final product was purified using reverse-phase HPLC.

Example 180. Preparation of (R)—N—((S)-1-(((6-Amino-2-methylpyridin-3-yl)methyl)amino)-1-oxopropan-2-yl)-2-(pentylamino)-4-phenylbutanamide Di-trifluoroacetate salt (1377)

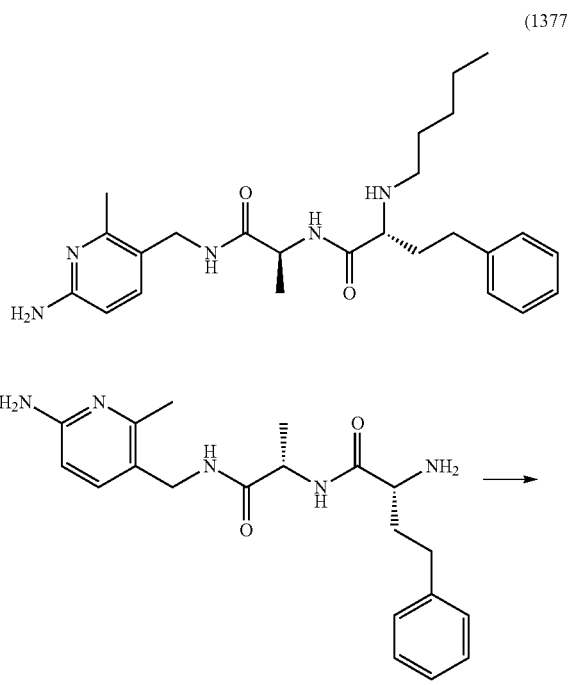

(1377)

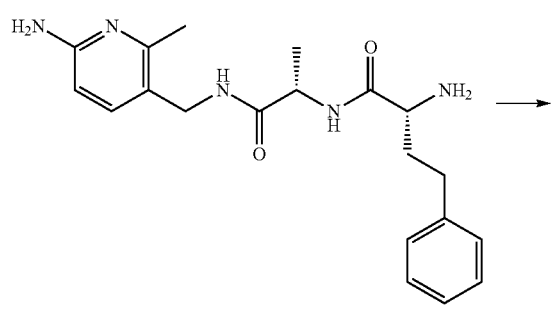

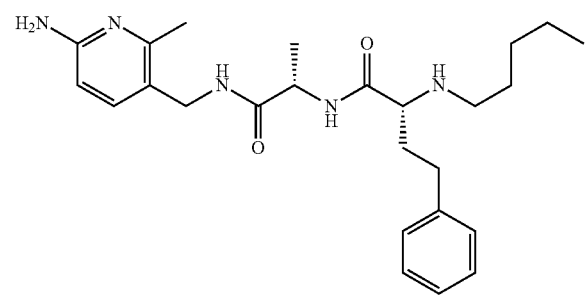

Step 1: (R)-2-Amino-N—((S)-1-(((6-amino-2-methylpyridin-3-yl)methyl)amino)-1-oxopropan-2-yl)-4-phenylbutanamide (99.0 mg, 0.224 mmol) was coupled with pentanal (30 μL, 0.282 mmol) according to the procedure for compound 1130, step 2. The crude product was dissolved in $CH_2Cl_2$ and adsorbed on silica gel. Purification by chromatography (0-5% MeOH—$CH_2Cl_2$) afforded (R)—N—((S)-1-(((6-amino-2-methylpyridin-3-yl)methyl)amino)-1-oxopropan-2-yl)-2-(pentylamino)-4-phenylbutanamide (12.5 mg, 13% yield).

Step 2: To a solution of (R)—N—((S)-1-(((6-amino-2-methylpyridin-3-yl)methyl)amino)-1-oxopropan-2-yl)-2-(pentylamino)-4-phenylbutanamide in $CH_2Cl_2$ (1 mL) was added TFA (0.5 mL). Volatile was evaporated under vacuum to afford of (R)—N—((S)-1-(((6-amino-2-methylpyridin-3-yl)methyl)amino)-1-oxopropan-2-yl)-2-(pentylamino)-4-phenylbutanamide di-trifluoroacetate salt.

Example 181. Preparation of (2R,4S)—N—((S)-1-(((3-Chloro-1H-pyrrolo[2,3-b]pyridin-5-yl)methyl)amino)-1-oxopropan-2-yl)-4-(4-cyclobutylbenzyl)pyrrolidine-2-carboxamide Di-trifluoroacetate salt (1378)

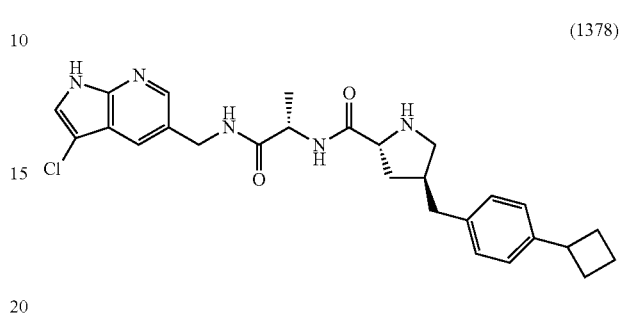

(1378)

(2R,4S)—N—((S)-1-(((3-Chloro-1H-pyrrolo[2,3-b]pyridin-5-yl)methyl)amino)-1-oxopropan-2-yl)-4-(4-cyclobutylbenzyl)pyrrolidine-2-carboxamide di-trifluoroacetate salt was synthesized according to the procedures for compound (1356).

Example 182. Preparation of (2R,4S)—N—((S)-1-(((6-Amino-2-methylpyridin-3-yl)methyl)amino)-1-oxopropan-2-yl)-4-(4-cyclobutylbenzyl)pyrrolidine-2-carboxamide Di-trifluoroacetate salt (1379)

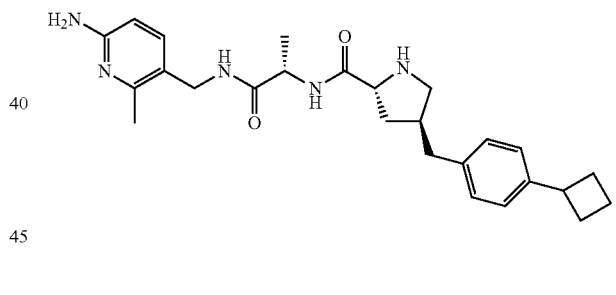

(1379)

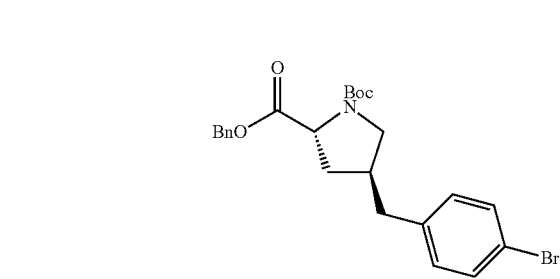

Step 1: 2-Benzyl 1-(tert-butyl) (2R,4S)-4-(4-bromobenzyl)pyrrolidine-1,2-dicarboxylate was synthesized according to the procedures for compound (1304), step 1 to step 3.

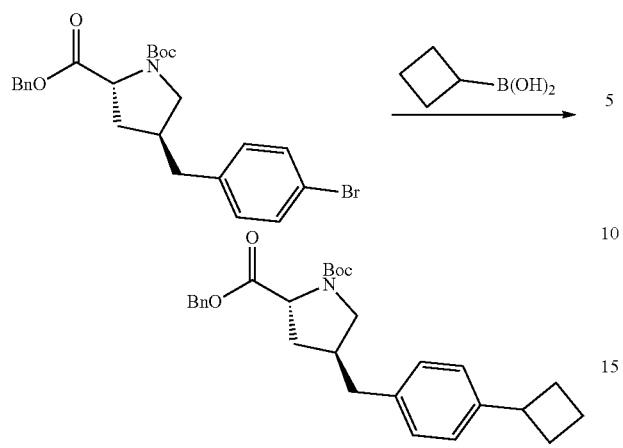

Step 2: In a 50 mL round bottom flask equipped with a stir bar and septum was added 2-benzyl 1-(tert-butyl) (2R,4S)-4-(4-bromobenzyl)pyrrolidine-1,2-dicarboxylate (200 mg, 0.42 mmol), cyclobutyl boronic acid (84 mg, 0.84), Pd(dppf)Cl$_2$ (31 mg, 0.042 mmol), K$_3$PO$_4$ (180 mg, 0.84 mmol), Toluene (3 mL) and water (0.3 mL). The resulting mixture was degassed by bubbling N$_2$ through the solution for 10 min. The reaction was then heated to 90° C. for 16 h. Upon cooling to room temperature, the reaction solution was filtered through diatomaceous earth, eluting with EtOAc, concentrated and purified by chromatography using EtOAc/hexanes to afford 2-benzyl 1-(tert-butyl) (2R,4S)-4-(4-cyclobutylbenzyl)pyrrolidine-1,2-dicarboxylate (30 mg, 16% yield) as a colorless sticky liquid.

Step 3: (2R,4S)—N—((S)-1-(((6-Amino-2-methylpyridin-3-yl)methyl)amino)-1-oxopropan-2-yl)-4-(4-cyclobutylbenzyl)pyrrolidine-2-carboxamide di-trifluoroacetate salt was synthesized according to the procedures for compound (1304), step 4 to step 8, except that the final product was purified using reverse-phase HPLC.

Example 183. Preparation of (2R,4S)—N—((S)-1-(((6-Amino-2-methylpyridin-3-yl)methyl)amino)-1-oxopropan-2-yl)-4-(4-(tert-butyl)benzyl)pyrrolidine-2-carboxamide Dihydrochloride (1380)

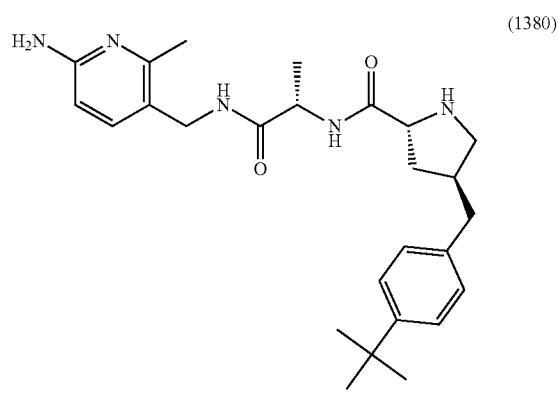 [SMILES: Cc1nc(N)ccc1CNC(=O)[C@H](C)NC(=O)[C@H]1C[C@H](Cc2ccc(C(C)(C)C)cc2)CN1]

(1380)

(2R,4S)—N—((S)-1-(((6-Amino-2-methylpyridin-3-yl)methyl)amino)-1-oxopropan-2-yl)-4-(4-(tert-butyl)benzyl)pyrrolidine-2-carboxamide dihydrochloride was synthesized according to the procedures for compound (1304).

Example 184. Preparation of (R)—N—((S)-1-(((6-Amino-2-methylpyridin-3-yl)methyl)amino)-1-oxopropan-2-yl)-2-((4-(morpholine-4-carbonyl)benzyl)amino)-4-phenylbutanamide Di-trifluoroacetate salt (1381)

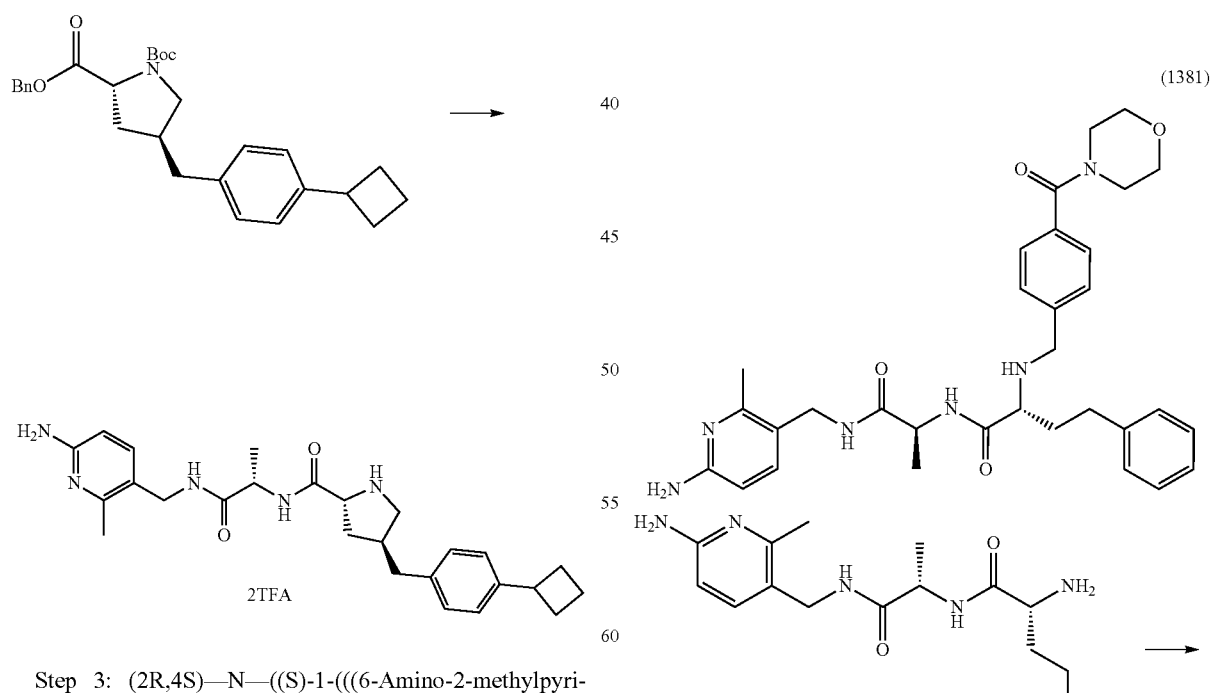

(1381)

537
-continued

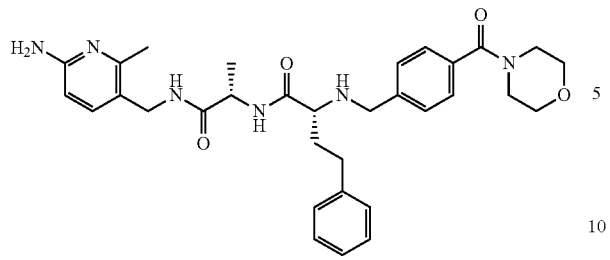

Step 1: (R)-2-Amino-N—((S)-1-(((6-amino-2-methylpyridin-3-yl)methyl)amino)-1-oxopropan-2-yl)-4-phenylbutanamide (42.5 mg, 0.115 mmol) was coupled with 4-(morpholine-4-carbonyl)benzaldehyde (37.5 mg, 0.171 mmol) according to the procedure for compound 1130, step 2. The crude product was dissolved in CH$_2$Cl$_2$ and adsorbed on silica gel. Purification by chromatography (0-10% MeOH—CH$_2$Cl$_2$) afforded (R)—N—((S)-1-(((6-amino-2-methylpyridin-3-yl)methyl)amino)-1-oxopropan-2-yl)-2-((4-(morpholine-4-carbonyl)benzyl)amino)-4-phenylbutanamide (21.4 mg, 32% yield).

Step 2: (R)—N—((S)-1-(((6-Amino-2-methylpyridin-3-yl)methyl)amino)-1-oxopropan-2-yl)-2-((4-(morpholine-4-carbonyl)benzyl)amino)-4-phenylbutanamide di-trifluoroacetate salt was formed according to the procedure for compound (1368), step 2.

Example 185. Preparation of (S)—N'-((6-Amino-2-methylpyridin-3-yl)methyl)-2-((2R,4S)-4-benzylpyrrolidine-2-carboxamido)pentanediamide Di-trifluoroacetate salt (1382)

(1382)

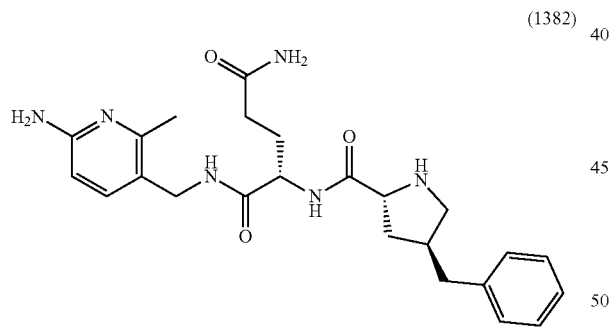

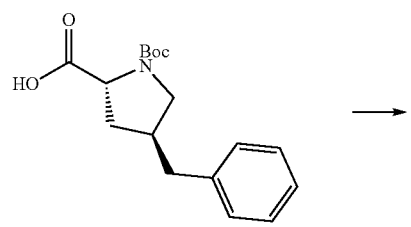

538
-continued

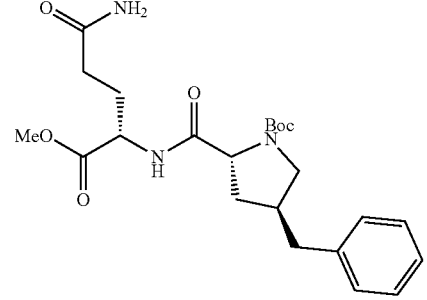

Step 1: Methyl ((2R,4S)-4-benzylpyrrolidine-2-carbonyl)-L-glutaminate (130 mg, 84% yield) was synthesized from (2R,4S)-4-benzyl-1-(tert-butoxycarbonyl)pyrrolidine-2-carboxylic acid (106 mg, 0.35 mmol) and L-glutamine methyl ester hydrochloride according to the procedure for compound (1326), step 1.

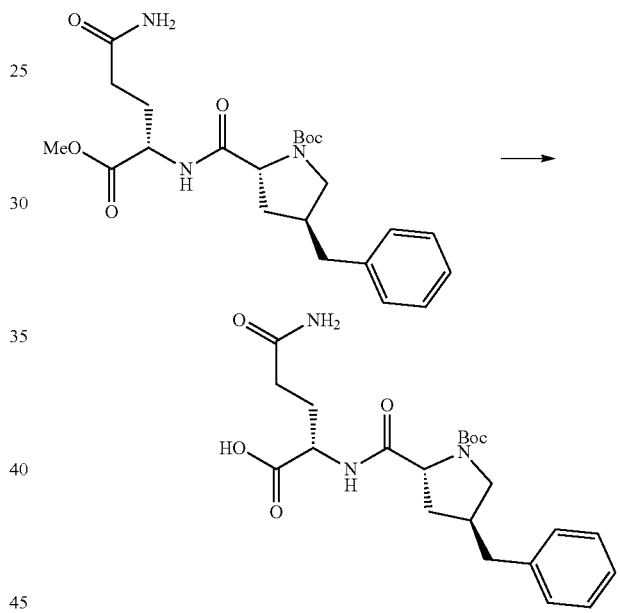

Step 2: ((2R,4S)-4-Benzylpyrrolidine-2-carbonyl)-L-glutamine (123 mg, 96% yield) was synthesized from methyl ((2R,4S)-4-benzylpyrrolidine-2-carbonyl)-L-glutaminate (130 mg, 0.29 mmol) according to the procedure for compound (1326), step 2 except that the crude material was applied to the next step without further purification.

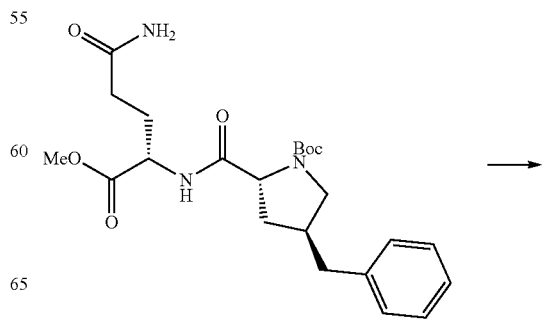

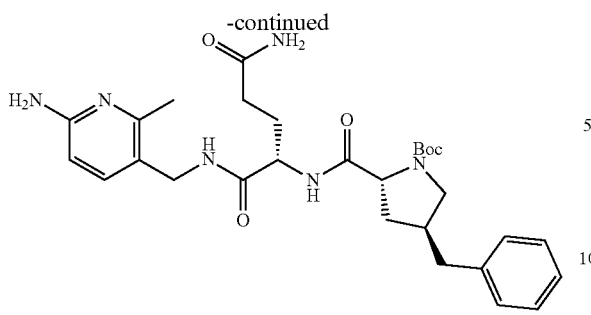

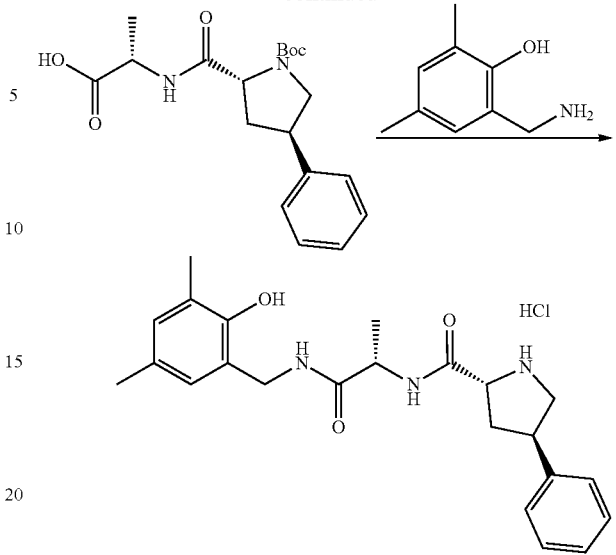

Step 3: tert-Butyl (2R,4S)-2-(((S)-5-amino-1-(((6-amino-2-methylpyridin-3-yl)methyl)amino)-1,5-dioxopentan-2-yl)carbamoyl)-4-benzylpyrrolidine-1-carboxylate (125 mg, 81% yield) was synthesized from ((2R,4S)-4-benzylpyrrolidine-2-carbonyl)-L-glutamine (123 mg, 0.28 mmol) and 5-(aminomethyl)-6-methylpyridine-2-amine according to the procedure for compound (1326), step 3.

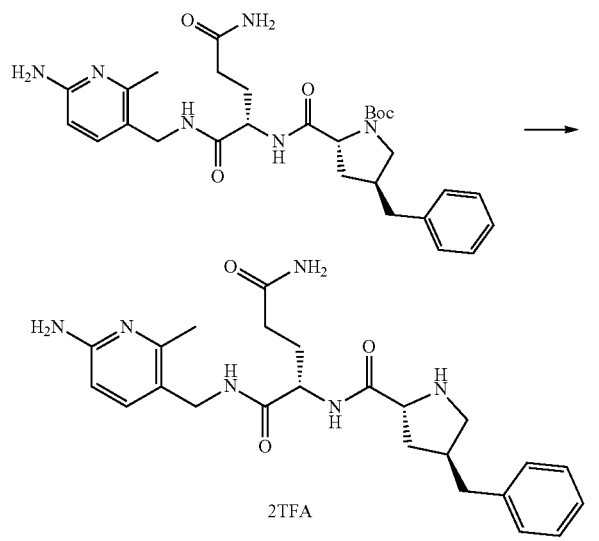

Step 4: Deprotection of tert-butyl (2R,4S)-2-(((S)-5-amino-1-(((6-amino-2-methylpyridin-3-yl)methyl)amino)-1,5-dioxopentan-2-yl)carbamoyl)-4-benzylpyrrolidine-1-carboxylate (125 mg, 0.23 mmol) was conducted according to the procedure for compound (1260), step 4 except that the final product was purified using reverse-phase HPLC.

Example 186. Preparation of (2R,4R)—N—((S)-1-((2-Hydroxy-3,5-dimethylbenzyl)amino)-1-oxopropan-2-yl)-4-phenylpyrrolidine-2-carboxamide Hydrochloride (1383)

(1383)

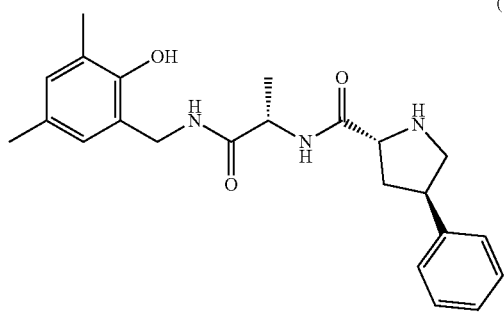

Steps 1-2: tert-Butyl (2R,4S)-4-(4-bromobenzyl)-2-(((S)-1-((5-chloro-2-hydroxy-3-methylbenzyl)amino)-1-oxopropan-2-yl)carbamoyl)pyrrolidine-1-carboxylate was synthesized according to step 3 of the procedure for compound 1119 using the appropriate starting materials. Removal of the Boc group was achieved using the procedure from step 4 for compound (1313) to yield the title compound as a beige solid (17.4 mg, 39% over two steps).

Example 187. Preparation of (2R,4R)—N—((S)-1-(((3-Chloro-1H-pyrazolo[3,4-b]pyridin-5-yl)methyl)amino)-1-oxopropan-2-yl)-4-phenylpyrrolidine-2-carboxamide Dihydrochloride (1384)

(1384)

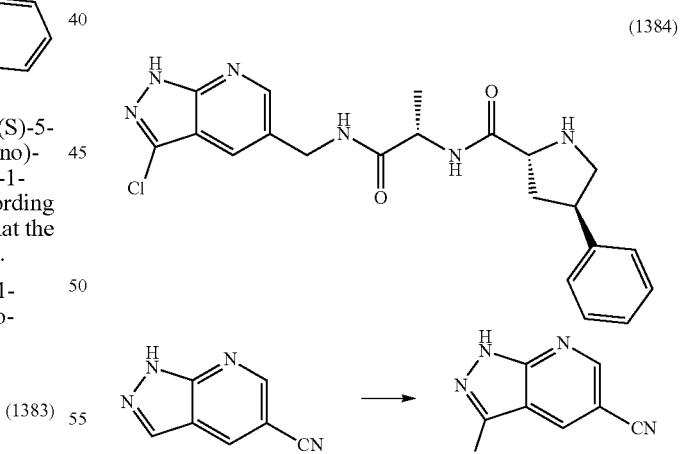

Step 1: To a solution of 1H-pyrazolo[3,4-b]pyridine-5-carbonitrile (303 mg, 2.1 mmol) in anhyd DMF (5 mL) under Ar was added NCS (280 mg, 2.1 mmol). The mixture was heated at 40° C. for 18 h after which the heat was increased to 55° C. After heating for 5 h, additional NCS (134 mg, 1.0 mmol) was added and heating continued for 30 min. The mixture was slowly cooled to ambient temperature then H$_2$O was added. The mixture was extracted with EtOAc and the combined organics were washed with H$_2$O, sat.

NaHCO₃ and brine then dried (Na₂SO₄) and conc in vacuo. The solid was chromatographed (0-40% EtOAc-hexanes) to give 3-chloro-1H-pyrazolo[3,4-b]pyridine-5-carbonitrile (216 mg, 58% yield).

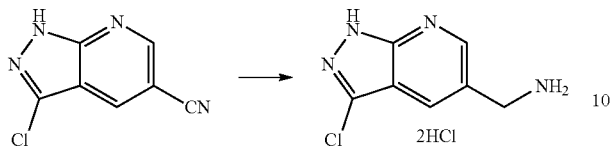

Step 2: 3-Chloro-1H-pyrazolo[3,4-b]pyridine-5-carbonitrile was reduced according to the procedure given for compound (1323), step 1. Following filtration of the reaction mixture through diatomaceous earth and conc in vacuo, the solid was dissolved in 1 M HCl and washed with EtOAc 3×. The aq layer was conc in vacuo to give (3-chloro-1H-pyrazolo[3,4-b]pyridin-5-yl)methanamine as a tan solid (184 mg, 60% yield).

Step 3: ((2R,4R)-1-(tert-Butoxycarbonyl)-4-phenylpyrrolidine-2-carbonyl)-L-alanine was coupled to (3-chloro-1H-pyrazolo[3,4-b]pyridin-5-yl)methanamine according to the procedure given for (1280). Purification by chromatography (0-5% MeOH—CH₂Cl₂) gave the product contaminated with acid starting material. The product was dissolved in EtOAc, washed with sat. NaHCO₃ 3×, brine then dried over Na₂SO₄ and conc in vacuo to give tert-butyl (2R,4R)-2-(((S)-1-(((3-chloro-1H-pyrazolo[3,4-b]pyridin-5-yl)methyl)amino)-1-oxopropan-2-yl)carbamoyl)-4-phenylpyrrolidine-1-carboxylate (81 mg, 61% yield).

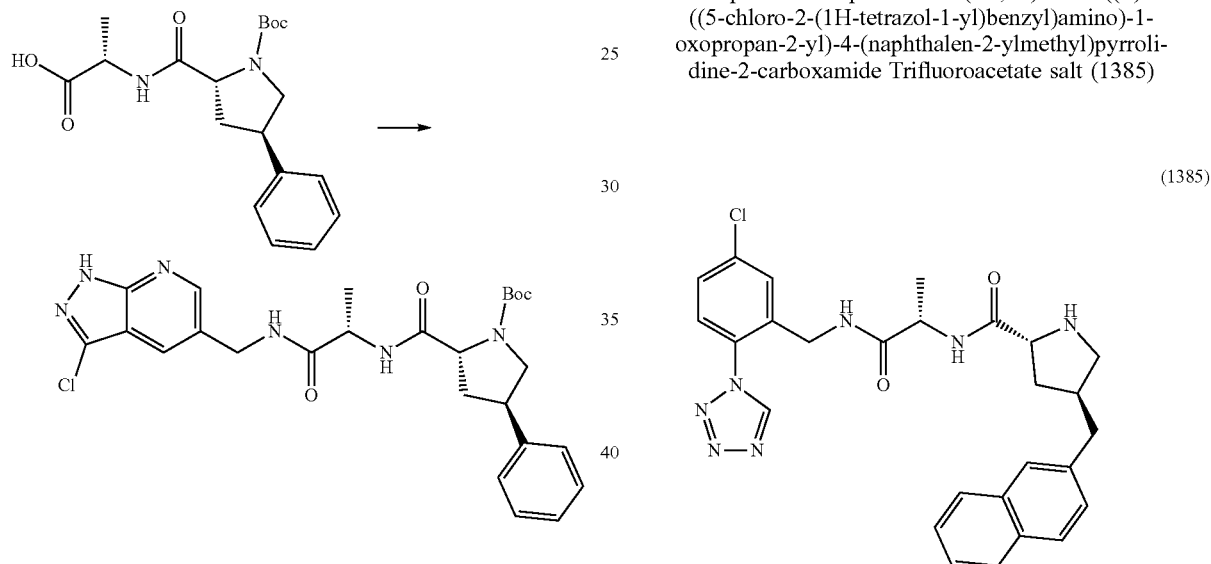

Step 4: tert-Butyl (2R,4R)-2-(((S)-1-(((3-chloro-1H-pyrazolo[3,4-b]pyridin-5-yl)methyl)amino)-1-oxopropan-2-yl)carbamoyl)-4-phenylpyrrolidine-1-carboxylate was deprotected according to the procedure given for compound (1311), step 3 to give (2R,4R)—N—((S)-1-(((3-chloro-1H-pyrazolo[3,4-b]pyridin-5-yl)methyl)amino)-1-oxopropan-2-yl)-4-phenylpyrrolidine-2-carboxamide dihydrochloride (67.6 mg, 88% yield).

Example 188. Preparation of (2R,4S)—N—((S)-1-((5-chloro-2-(1H-tetrazol-1-yl)benzyl)amino)-1-oxopropan-2-yl)-4-(naphthalen-2-ylmethyl)pyrrolidine-2-carboxamide Trifluoroacetate salt (1385)

(1385)

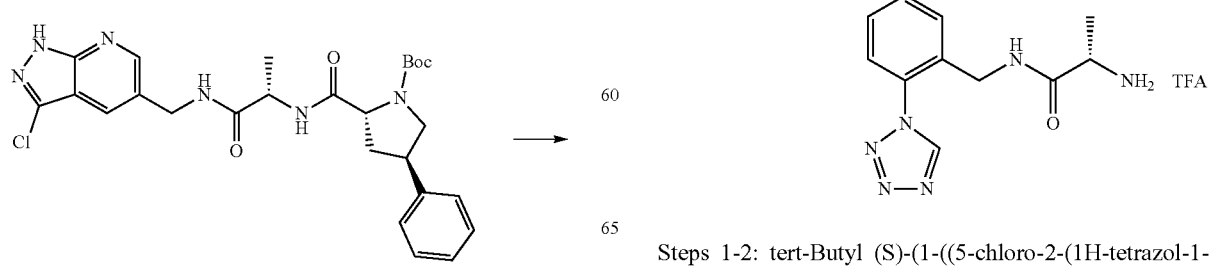

Steps 1-2: tert-Butyl (S)-(1-((5-chloro-2-(1H-tetrazol-1-yl)benzyl)amino)-1-oxopropan-2-yl)carbamate was synthesized according to steps 3-4 of the procedure for compound (1313) using the appropriate starting materials (3.54 g, 76% yield over two steps).

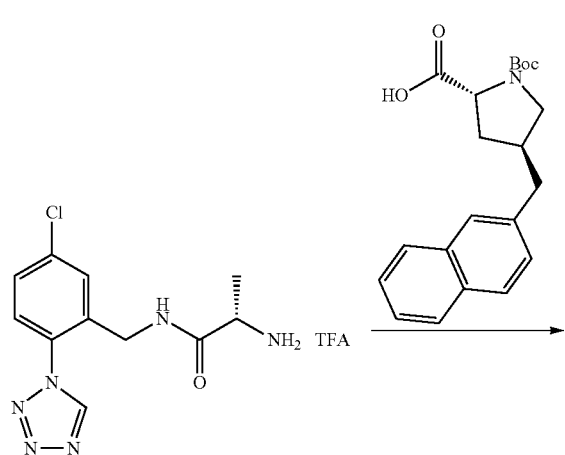

Steps 3-4: The title compound was synthesized as a white powder according to steps 3-4 of the procedure for compound (1313) using the appropriate starting materials (15 mg, 40% yield over two steps).

Example 189. Preparation of (2R,4R)—N—((S)-1-((3-Chloro-5-cyanobenzyl)amino)-1-oxopropan-2-yl)-4-phenylpyrrolidine-2-carboxamide Trifluoroacetate salt (1386)

(1386)

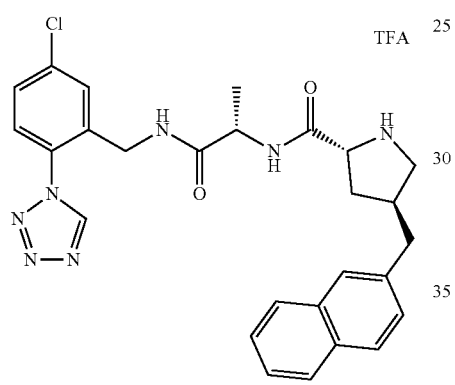

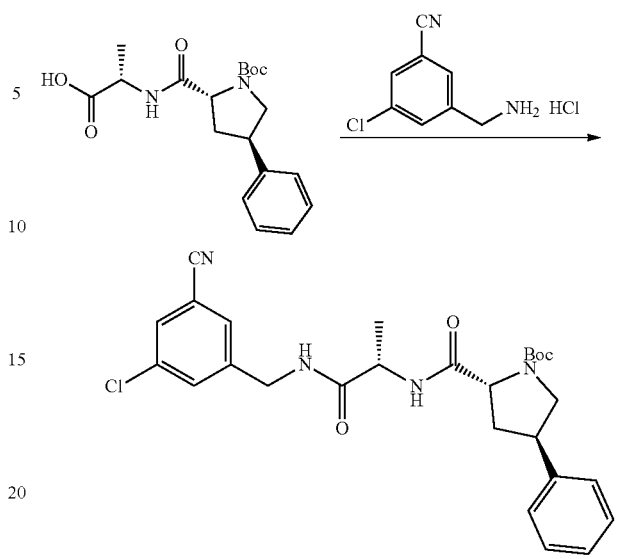

Step 1: tert-Butyl ((R)-1-(((S)-1-((3-chloro-5-cyanobenzyl)amino)-1-oxopropan-2-yl)amino)-1-oxo-4-phenylbutan-2-yl)carbamate was synthesized as a colorless oil (95 mg, 62% yield) according to step 1 of the procedure for compound (1246) using the appropriate starting materials.

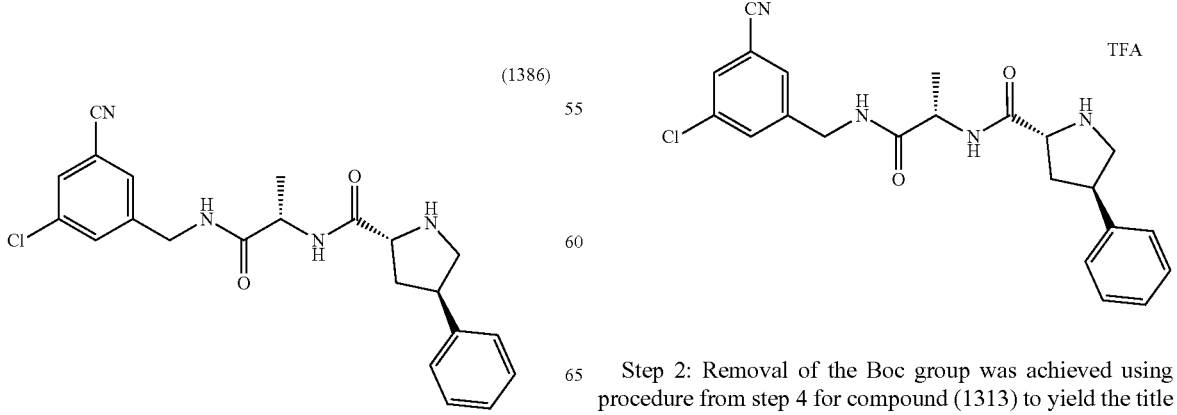

Step 2: Removal of the Boc group was achieved using procedure from step 4 for compound (1313) to yield the title compound as a white powder (21 mg, 67% yield).

Example 190. Preparation of (2R,4R)—N—((S)-1-((3-Carbamoyl-5-chlorobenzyl)amino)-1-oxopropan-2-yl)-4-phenylpyrrolidine-2-carboxamide Trifluoroacetate salt (1387)

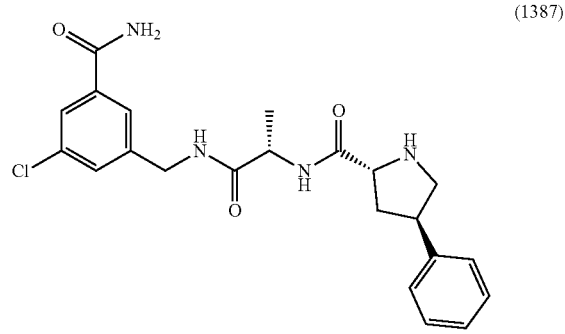

(1387)

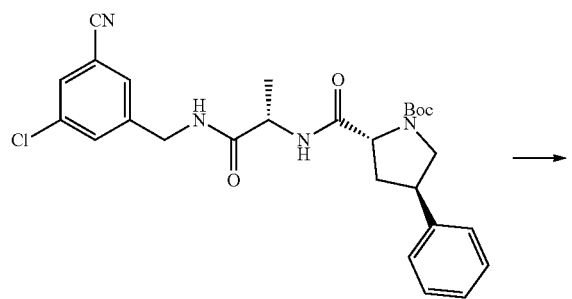

Step 1: tert-Butyl (2R,4R)-2-(((S)-1-((3-chloro-5-cyanobenzyl)amino)-1-oxopropan-2-yl)carbamoyl)-4-phenylpyrrolidine-1-carboxylate (65 mg, 0.13 mmol) was dissolved in EtOH (0.5 mL) and added dropwise to a stirring mixture of urea hydrogen peroxide (72 mg, 0.76 mmol) and NaOH (18 mg, 0.46 mmol) in H$_2$O (1.2 mL) at 0° C., then allowed to warm to ambient temperature over 2 h. Upon completion, the reaction mixture was diluted in EtOAc, washed with 10% aq. KHSO$_4$ and brine. The organic layer was dried over Na$_2$SO$_4$, concentrated and purified by chromatography. The intermediate was then dissolved in CH$_2$Cl$_2$ (2 mL) and treated with TFA (0.5 mL) at ambient temperature for 2 h, before being concentrated to furnish the title compound as a white powder (28 mg, 40% yield over two steps).

Example 191. Preparation of N—((S)-1-(((6-Amino-2-methylpyridin-3-yl)methyl)amino)-1-oxopropan-2-yl)-7,7-dimethyl-5-oxo-4-phenyl-1,4,5,6,7,8-hexahydroquinoline-2-carboxamide (1388)

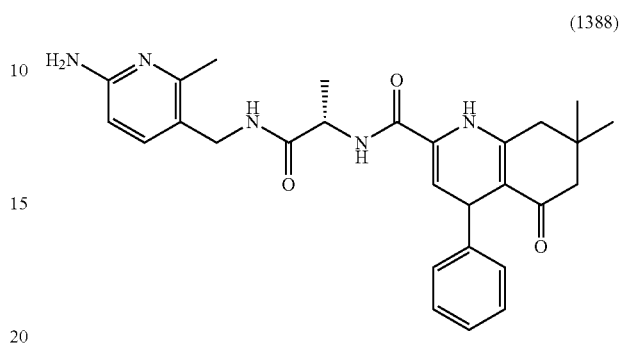

(1388)

N—((S)-1-(((6-amino-2-methylpyridin-3-yl)methyl)amino)-1-oxopropan-2-yl)-7,7-dimethyl-5-oxo-4-phenyl-1,4,5,6,7,8-hexahydroquinoline-2-carboxamide was synthesized according to the procedure for compound (1304), step 7 using 7,7-dimethyl-5-oxo-4-phenyl-1,4,5,6,7,8-hexahydroquinoline-2-carboxylic acid.

Example 192. Preparation of (R)—N—((S)-1-(((6-Amino-2-methylpyridin-3-yl)methyl)amino)-1-oxopropan-2-yl)-2,3,4,9-tetrahydro-1H-pyrido[3,4-b]indole-3-carboxamide Hydrochloride (1389)

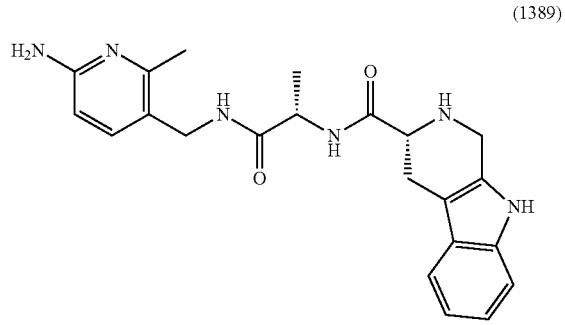 [SMILES: Cc1nc(N)ccc1CNC(=O)[C@H](C)NC(=O)[C@H]1Cc2c([nH]c3ccccc23)CN1]

(1389)

(R)—N—((S)-1-(((6-Amino-2-methylpyridin-3-yl)methyl)amino)-1-oxopropan-2-yl)-2,3,4,9-tetrahydro-1H-pyrido[3,4-b]indole-3-carboxamide hydrochloride was synthesized according to the procedures for compound (1304), steps 7 and 8 using (3R)-2-(tert-butoxycarbonyl)-2,3,4,4a,9,9a-hexahydro-1H-pyrido[3,4-b]indole-3-carboxylic acid.

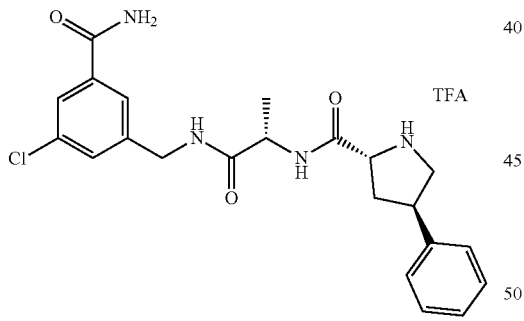

Example 193. Preparation of (2R,4R)—N—((S)-1-(((3-Aminobenzo[d]isoxazol-6-yl)methyl)amino)-1-oxopropan-2-yl)-4-phenylpyrrolidine-2-carboxamide Di-trifluoroacetate salt (1390)

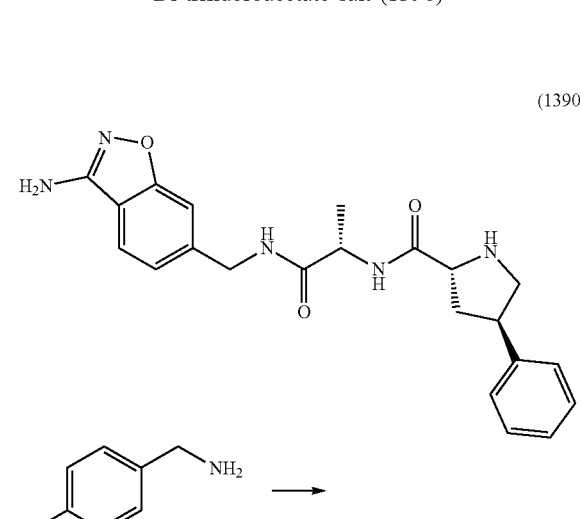

(1390)

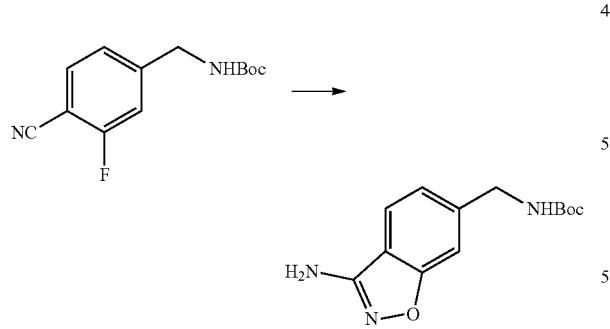

Step 1: To a solution of 4-aminomethyl-2-fluoro-benzonitrile hydrochloride (1.0 g, 5.35 mmol) in MeOH (10 mL) and MeCN (10 mL) was added Et₃N (2.2 mL, 16.05 mmol), di-tert-butyl dicarbonate (1.4 g, 6.43 mmol) and DMAP (653 mg, 5.35 mmol). After stirring for 16 h, the reaction mixture was conc and the residue was partitioned with EtOAc and H₂O. The organic layer was separated, washed with brine, dried over anhyd Na₂SO₄, and conc under vacuum. The residue was purified by chromatography (0-100% EtOAc-hexanes) to give tert-butyl (4-cyano-3-fluorobenzyl)carbamate (1.13 g, 88% yield).

Step 2: To a solution of acetohydroxamic acid in anhyd DMF was added KO$^t$Bu (1 M in THF, 7.1 mL, 7.1 mmol). After stirring for 30 min at ambient temperature, tert-butyl (4-cyano-3-fluorobenzyl)carbamate (1.13 g, 4.73 mmol) was added to the above mixture. After stirring for 19 h at the same temperature, the reaction was quenched by addition of H₂O and extracted with EtOAc. The organic layer was washed with brine, dried over anhyd Na₂SO₄, and conc under vacuum. The residue was purified by chromatography (0-100% EtOAc-hexanes) to give tert-butyl ((3-aminobenzo[d]isoxazol-6-yl)methyl)carbamate (925 mg, 74% yield).

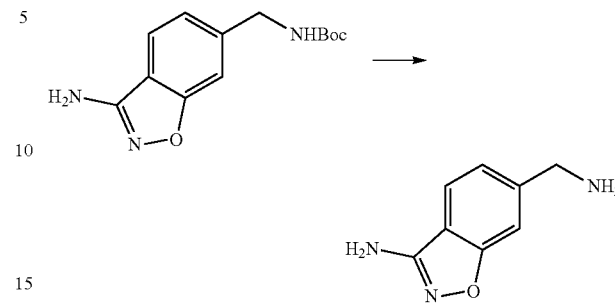

Step 3: Deprotection of tert-butyl ((3-aminobenzo[d]isoxazol-6-yl)methyl)carbamate (125 mg, 0.48 mmol) was conducted according to the procedure for compound (1259), step 2 to give 6-(aminomethyl)benzo[d]isoxazol-3-amine di-trifluoroacetate salt (186 mg, 100% yield).

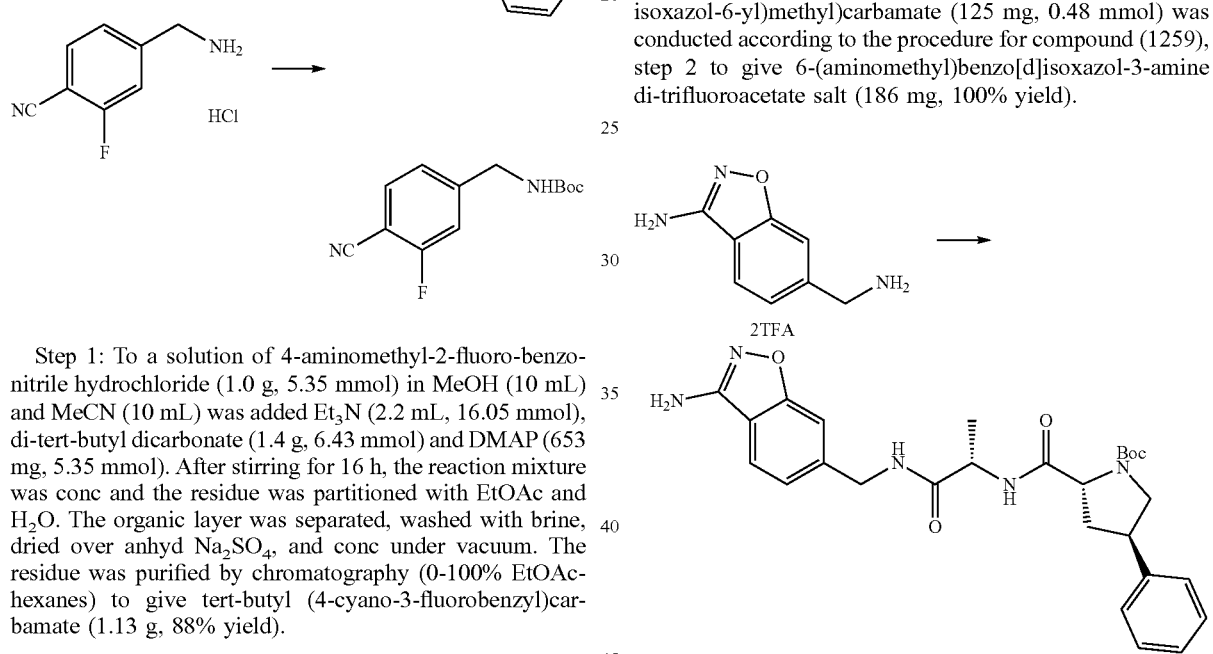

Step 4: tert-Butyl (2R,4R)-2-(((S)-1-(((3-aminobenzo[d]isoxazol-6-yl)methyl)amino)-1-oxopropan-2-yl)carbamoyl)-4-phenylpyrrolidine-1-carboxylate (153 mg, 84% yield) was synthesized from 6-(aminomethyl)benzo[d]isoxazol-3-amine di-trifluoroacetate salt (130 mg, 0.47 mmol) according to the procedure for compound (1358), step 2.

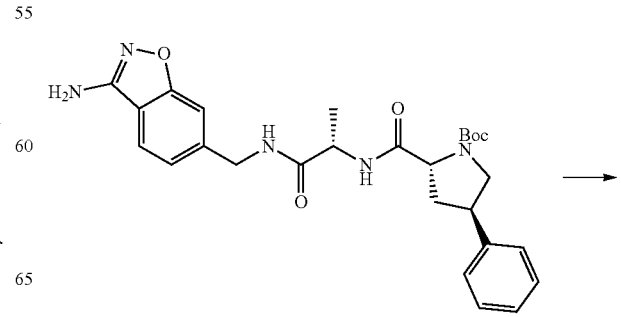

-continued

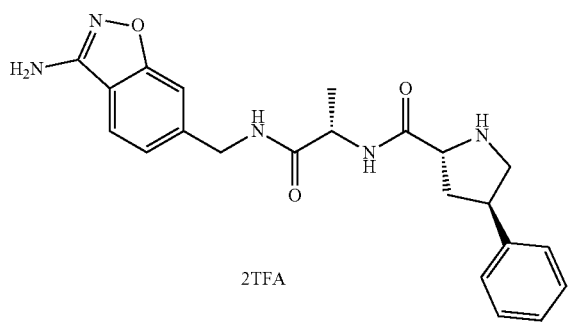

2TFA

Step 5: Deprotection of tert-butyl (2R,4R)-2-(((S)-1-(((3-aminobenzo[d]isoxazol-6-yl)methyl)amino)-1-oxopropan-2-yl)carbamoyl)-4-phenylpyrrolidine-1-carboxylate (153 mg, 0.3 mmol) was conducted according to the procedure for compound (1260), step 4 except that the final product was purified using reverse-phase HPLC.

Example 194. Preparation of (2R,4S)—N—((S)-1-(((6-Amino-2-methylpyridin-3-yl)methyl)amino)-1-oxopropan-2-yl)-4-(4-(2-oxopyrrolidin-1-yl)benzyl)pyrrolidine-2-carboxamide Di-trifluoroacetate salt (1391)

(1391)

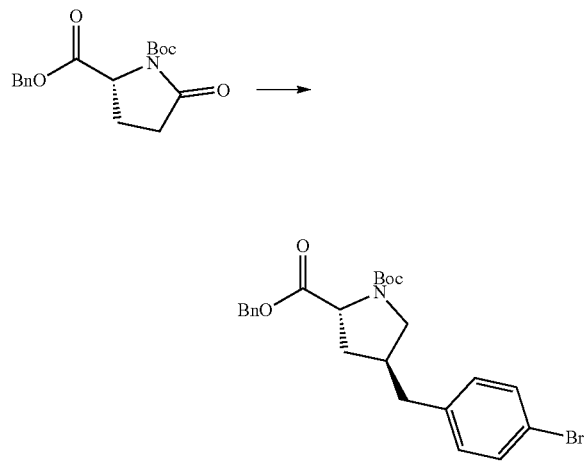

2TFA

Step 1: 2-Benzyl 1-(tert-butyl) (2R,4S)-4-(4-bromobenzyl)pyrrolidine-1,2-dicarboxylate was synthesized according to the procedures for compound (1304), step 1 to step 3.

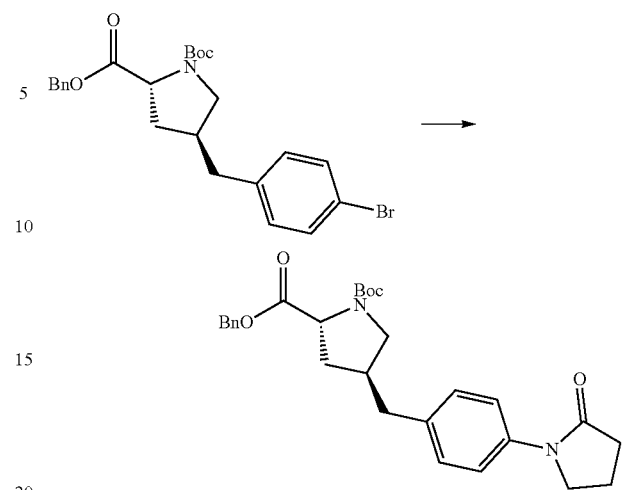

Step 2: In a 50 mL round bottom flask equipped with a stir bar and septum was added 2-benzyl 1-(tert-butyl) (2R,4S)-4-(4-bromobenzyl)pyrrolidine-1,2-dicarboxylate (120 mg, 0.25 mmol), 2-pyridone (43 mg, 0.51), BrettPhos palladacycle (4.2 mg, 0.005 mmol), $K_3PO_4$ (108 mg, 0.51 mmol), tert-butanol (1.2 mL). The resulting mixture was degassed by bubbling $N_2$ through the solution for 5 min. The reaction was then heated to 100° C. for 12 h. Upon cooling to room temperature, the reaction solution was filtered through diatomaceous earth, eluting with EtOAc, concentrated and purified by chromatography using EtOAc-hexanes to afford 2-benzyl 1-(tert-butyl) (2R,4S)-4-(4-(2-oxopyrrolidin-1-yl)benzyl)pyrrolidine-1,2-dicarboxylate (30 mg, 25% yield) as a colorless oil.

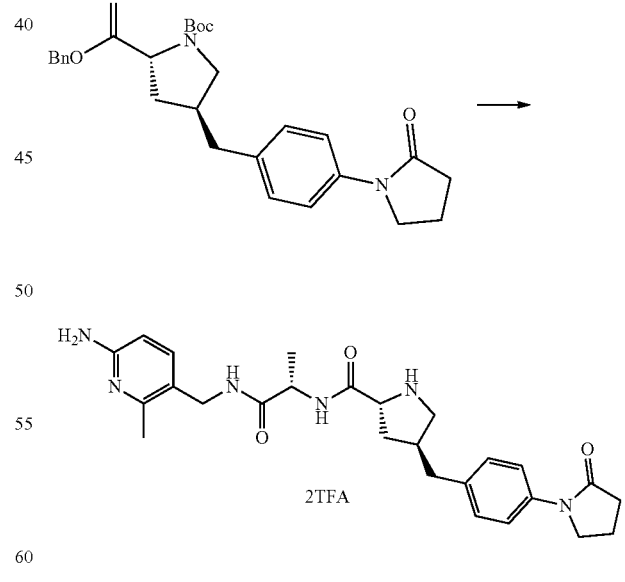

2TFA

Step 3: (2R,4S)—N—((S)-1-(((6-Amino-2-methylpyridin-3-yl)methyl)amino)-1-oxopropan-2-yl)-4-(4-(2-oxopyrrolidin-1-yl)benzyl)pyrrolidine-2-carboxamide di-trifluoroacetate salt was synthesized according to the procedures for compound (1304), step 4 to step 8, except that the final product was purified using reverse-phase HPLC.

Example 195. Preparation of (2R,4S)—N—((S)-1-(((3-Chloro-1H-pyrrolo[2,3-b]pyridin-5-yl)methyl)amino)-1-oxopropan-2-yl)-4-(naphthalen-2-ylmethyl)pyrrolidine-2-carboxamide Di-Trifluoroacetate salt (1392)

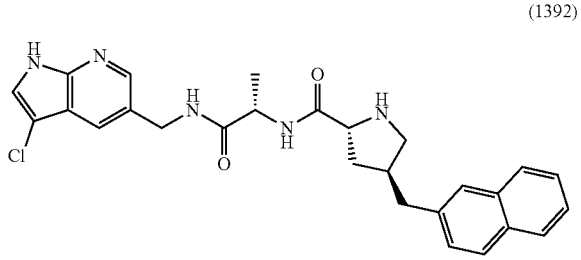 [SMILES: C[C@H](NC(=O)[C@H]1C[C@H](Cc2ccc3ccccc3c2)CN1)C(=O)NCc1cnc2[nH]cc(Cl)c2c1]

(1392)

(2R,4S)—N—((S)-1-(((3-Chloro-1H-pyrrolo[2,3-b]pyridin-5-yl)methyl)amino)-1-oxopropan-2-yl)-4-(naphthalen-2-ylmethyl)pyrrolidine-2-carboxamide di-trifluoroacetate salt was synthesized according to the procedures for compound (1334).

Example 196. Preparation of (2R,4S)-4-([1,1'-Biphenyl]-2-ylmethyl)-N—((S)-1-(((3-chloro-1H-pyrrolo[2,3-b]pyridin-5-yl)methyl)amino)-1-oxopropan-2-yl)pyrrolidine-2-carboxamide Di-trifluoroacetate salt (1393)

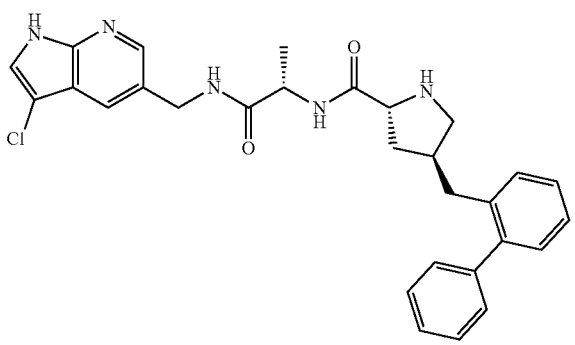

(1393)

(2R,4S)-4-([1,1'-Biphenyl]-2-ylmethyl)-N—((S)-1-(((3-Chloro-1H-pyrrolo[2,3-b]pyridin-5-yl)methyl)amino)-1-oxopropan-2-yl)pyrrolidine-2-carboxamide di-trifluoroacetate salt was synthesized according to the procedures for compound (1356).

Example 197. Preparation of (2R,4R)—N—((S)-1-((5-chloro-2-(2H-tetrazol-2-yl)benzyl)amino)-1-oxopropan-2-yl)-4-phenylpyrrolidine-2-carboxamide Trifluoroacetate (1394)

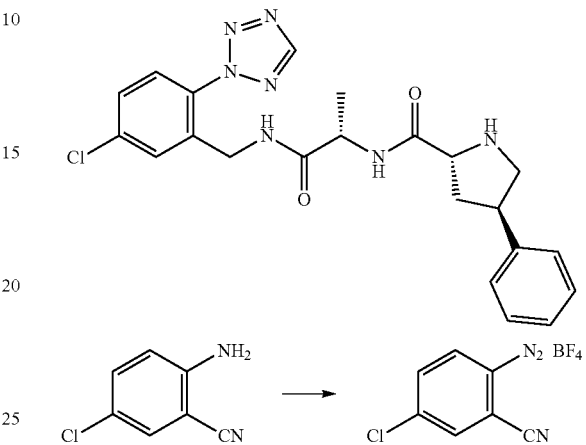

(1394)

Step 1: 2-Amino-5-chlorobenzonitrile (1 g, 6.55 mmol) was dissolved in EtOH (5 mL) and $H_2O$ (10 mL), then treated with tetrafluoroboric acid (48% in $H_2O$; 1.7 mL, 13.1 mmol) and cooled to 0° C. Sodium nitrite (497 mg, 7.2 mmol) in $H_2O$ (10 mL) was added dropwise to the stirring mixture. After 1 h, the suspension was filtered using cold $Et_2O$ and $H_2O$ then dried under vacuum to yield the diazonium tetrafluoroborate salt as a yellow solid (502 mg, 31% yield).

Step 2: The diazonium salt (502 mg, 2 mmol) and $CF_3CO_2Ag$ (530 mg, 2.4 mmol) were suspended in dry THF (20 mL) and cooled to −78° C. under Ar. $Et_3N$ (418 μL, 3 mmol) was added dropwise followed by $TMSCHN_2$ (2 M in hexanes; 1.1 mL, 2.2 mmol) after 10 minutes. The reaction mixture was allowed to stir for 1 h before slowly warming to ambient temperature and quenched with CsF (304 mg, 2 mmol) in MeOH. After 30 minutes, EtOAc and brine were added, then the organic layer separated and dried over $Na_2SO_4$ and concentrated. Purification by chromatography (30-40% EtOAc/hexanes) furnished 5-chloro-2-(2H-tetrazol-2-yl)benzonitrile as a brown solid (86 mg, 21% yield).

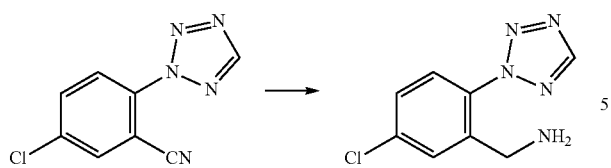

Step 3: A solution of 5-chloro-2-(2H-tetrazol-2-yl)benzonitrile (86 mg, 0.42 mmol) in 7 N NH₃ in MeOH (5 mL) was degassed with an Ar balloon. Raney nickel (~40 mg) was added and a vacuum was pulled for 0.5 min prior to backfilling with a balloon of H₂. The reaction mixture was stirred for 16 h at ambient temperature. Upon completion, the catalyst was removed by filtration through diatomaceous earth and the solution concentrated in vacuo to give (5-chloro-2-(2H-tetrazol-2-yl)phenyl)methanamine (78 mg, 89% yield) as a brown oil.

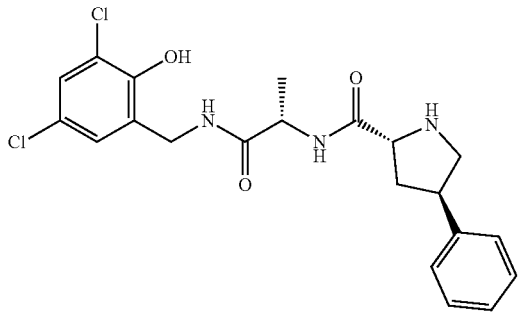

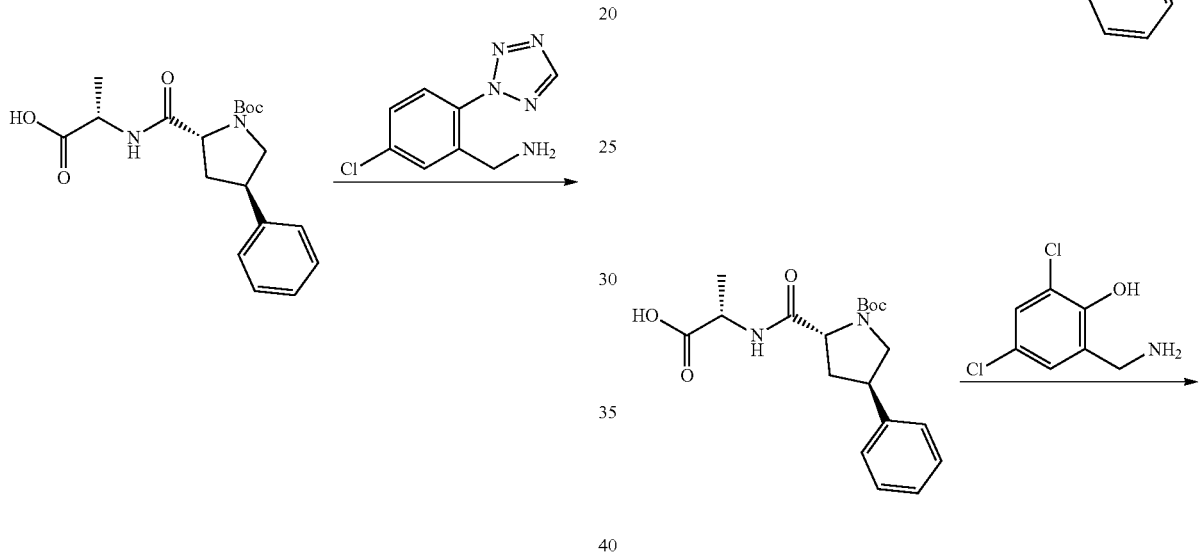

Steps 4-5: The title compound was synthesized as a white powder according to steps 3-4 of the procedure for compound (1313) using the appropriate starting materials, except with purification by prep HPLC (2.3 mg, 3% yield over two steps).

Example 198. Preparation of (2R,4R)—N—((S)-1-((3,5-dichloro-2-hydroxybenzyl)amino)-1-oxopropan-2-yl)-4-phenylpyrrolidine-2-carboxamide Trifluoroacetate (1395)

(1395)

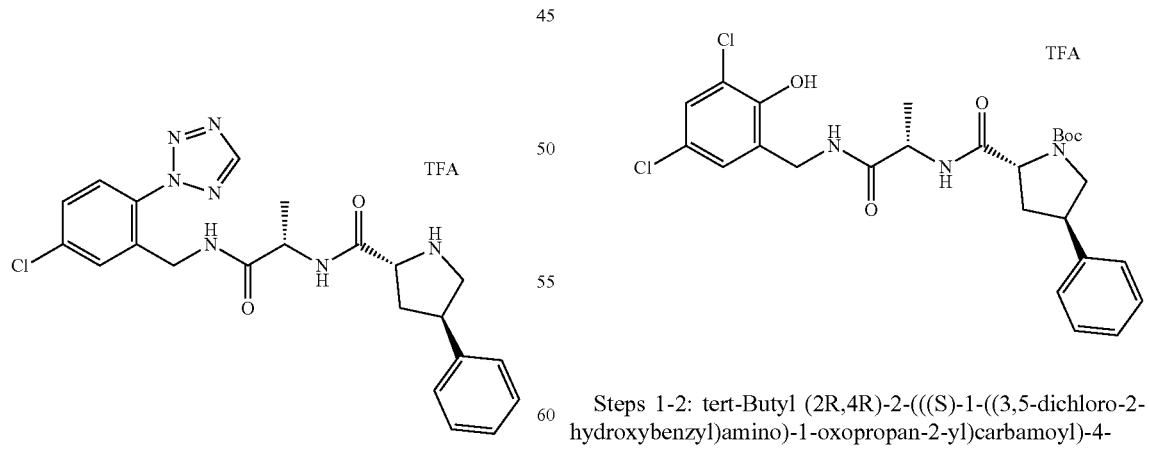

Steps 1-2: tert-Butyl (2R,4R)-2-(((S)-1-((3,5-dichloro-2-hydroxybenzyl)amino)-1-oxopropan-2-yl)carbamoyl)-4-phenylpyrrolidine-1-carboxylate synthesized according to step 1 of the procedure for compound (1242) using the appropriate starting materials. Removal of the Boc group was achieved according to step 4 of compound (1313) to yield the title compound as a white crystalline solid (23 mg, 35% yield over two steps).

Example 199. Preparation of (2R,4S)—N—((S)-1-(((6-Amino-2-methylpyridin-3-yl)methyl)amino)-1-oxopropan-2-yl)-4-((2'-cyano-4'-fluoro-[1,1'-biphenyl]-4-yl)methyl)pyrrolidine-2-carboxamide (1396)

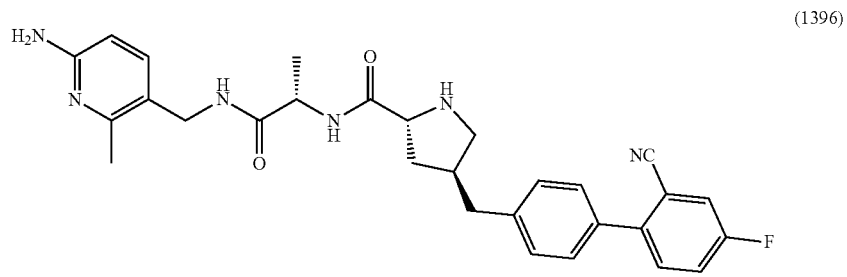 [SMILES: Cc1nc(N)ccc1CNC(=O)[C@H](C)NC(=O)[C@H]1C[C@H](Cc2ccc(-c3ccc(F)cc3C#N)cc2)CN1]

(1396)

(2R,4S)—N—((S)-1-(((6-Amino-2-methylpyridin-3-yl)methyl)amino)-1-oxopropan-2-yl)-4-((2'-cyano-4'-fluoro-[1,1'-biphenyl]-4-yl)methyl)pyrrolidine-2-carboxamide was synthesized according to the procedures for compound (1351), except that the free base was isolated after purification by column chromatography (0-10% [7 N NH$_3$-MeOH]—CH$_2$Cl$_2$).

Example 200. Preparation of (2R,4S)—N—((S)-1-(((6-amino-2-methylpyridin-3-yl)methyl)amino)-1-oxopropan-2-yl)-4-((2'-carbamoyl-4'-fluoro-[1,1'-biphenyl]-4-yl)methyl)pyrrolidine-2-carboxamide Di-trifluoroacetate salt (1397)

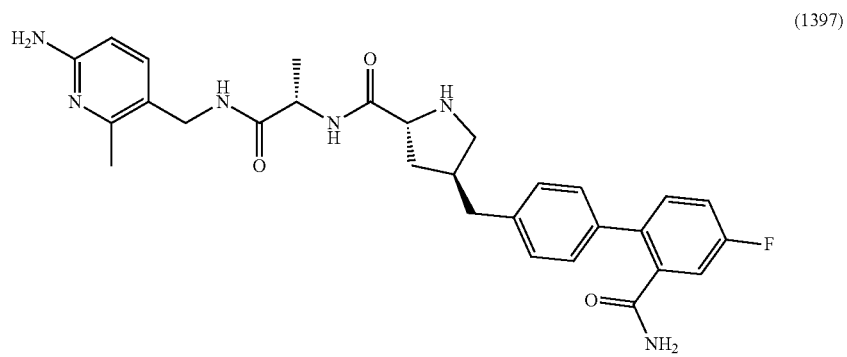 [SMILES: Cc1nc(N)ccc1CNC(=O)[C@H](C)NC(=O)[C@H]1C[C@H](Cc2ccc(-c3ccc(F)cc3C(N)=O)cc2)CN1]

(1397)

(2R,4S)—N—((S)-1-(((6-Amino-2-methylpyridin-3-yl)methyl)amino)-1-oxopropan-2-yl)-4-((2'-carbamoyl-4'-fluoro-[1,1'-biphenyl]-4-yl)methyl)pyrrolidine-2-carboxamide di-trifluoroacetate salt was synthesized according to the procedures for compound (1351), except that the final product was purified using reverse-phase HPLC.

Example 201. Preparation of 2-((2R,4S)-2-(((S)-1-(((6-Amino-2-methylpyridin-3-yl)methyl)amino)-1-oxopropan-2-yl)carbamoyl)-4-phenylpiperidin-1-yl) acetic acid Trifluoroacetate salt (1398)

Example 202. Preparation of (2R,4R)—N—((S)-1-(((6-Amino-2-methylpyridin-3-yl)methyl)amino)-1-oxopropan-2-yl)-4-((4-phenylthiophen-2-yl)methyl) pyrrolidine-2-carboxamide Dihydrochloride (1399)

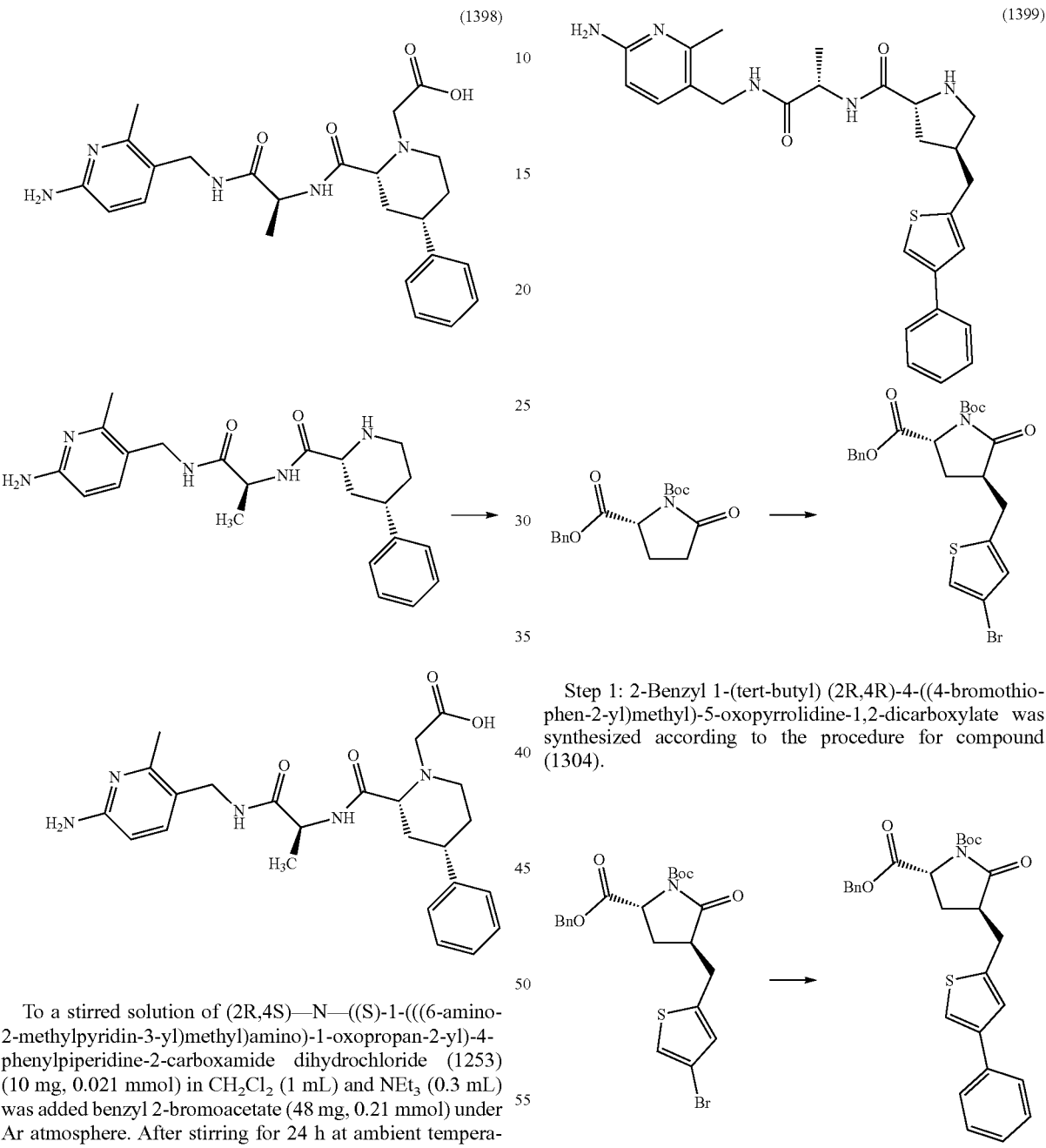

To a stirred solution of (2R,4S)—N—((S)-1-(((6-amino-2-methylpyridin-3-yl)methyl)amino)-1-oxopropan-2-yl)-4-phenylpiperidine-2-carboxamide dihydrochloride (1253) (10 mg, 0.021 mmol) in CH$_2$Cl$_2$ (1 mL) and NEt$_3$ (0.3 mL) was added benzyl 2-bromoacetate (48 mg, 0.21 mmol) under Ar atmosphere. After stirring for 24 h at ambient temperature the reaction mixture was concentrated and dissolved in MeOH. To the solution was added 10% Pd/C (50 mg) and stirred under H$_2$ atmosphere at room temperature for 18 h. The reaction mixture was filtered over diatomaceous earth and washed with MeOH. The organic washes were concentrated and purified by reverse-phase HPLC to yield 2-((2R,4S)-2-(((S)-1-(((6-amino-2-methylpyridin-3-yl)methyl)amino)-1-oxopropan-2-yl)carbamoyl)-4-phenylpiperidin-1-yl)acetic acid trifluoroacetate salt (6.2 mg, 52% yield over 2 steps).

Step 1: 2-Benzyl 1-(tert-butyl) (2R,4R)-4-((4-bromothiophen-2-yl)methyl)-5-oxopyrrolidine-1,2-dicarboxylate was synthesized according to the procedure for compound (1304).

Step 2: A solution of 2-benzyl 1-(tert-butyl) (2R,4R)-4-((4-bromothiophen-2-yl)methyl)-5-oxopyrrolidine-1,2-dicarboxylate (270 mg, 0.55 mmol) and phenylboronic acid (0.66 mmol, 1.2 equiv.) in THF/2M K$_2$CO$_3$ (1:1) was degassed with a stream of Ar for 5 min. Pd(PPh$_3$)$_4$ (0.05 equiv.) was added and the solution was heated at 60° C. overnight. THF was removed by evaporation and the solution was extracted with EtOAc. The organic layer was dried over Na$_2$SO$_4$ and evaporated. Column chromatography (10% EtOAc-hexanes) gave 2-benzyl 1-(tert-butyl) (2R,4R)-5-oxo-4-((4-phenylthiophen-2-yl)methyl)pyrrolidine-1,2-dicarboxylate (141 mg, 53% yield) as an oil.

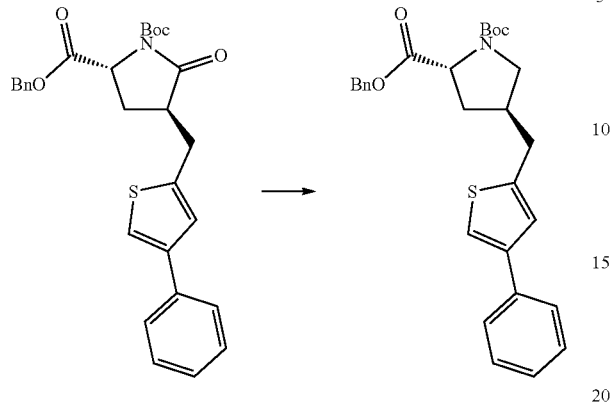

Step 3: 2-Benzyl 1-(tert-butyl) (2R,4R)-4-((4-phenylthiophen-2-yl)methyl)pyrrolidine-1,2-dicarboxylate was synthesized according to the procedure for compound (1304).

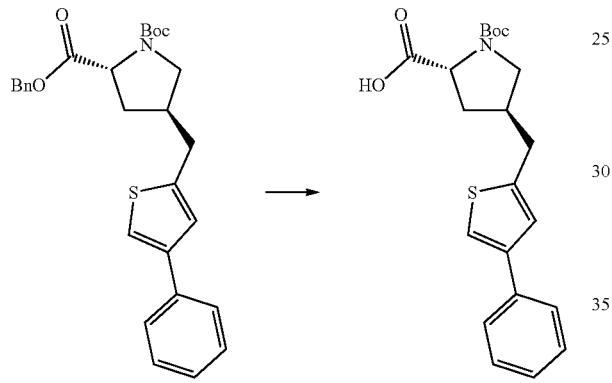

Step 4: To a solution of 2-benzyl 1-(tert-butyl) (2R,4R)-4-((4-phenylthiophen-2-yl)methyl)pyrrolidine-1,2-dicarboxylate (100 mg, 0.21 mmol) in THF (2.0 ml) and MeOH (1.0 ml) was added LiOH (3.14 mmol, 15.0 equiv.) in $H_2O$ (1.0 ml) with stirring at room temp. overnight. The solution was evaporated to dryness and $H_2O$ (5.0 ml) was added to the residue with swirling. The aqueous layer was extracted with ether, separated, pH adjusted to 5 with 10% $KHSO_4$ and extracted with $CH_2Cl_2$. The organic layer was dried over $Na_2SO_4$ and evaporated giving (2R,4R)-1-(tert-butoxycarbonyl)-4-((4-phenylthiophen-2-yl)methyl)pyrrolidine-2-carboxylic acid (75 mg, 93% yield) as a foamy white solid.

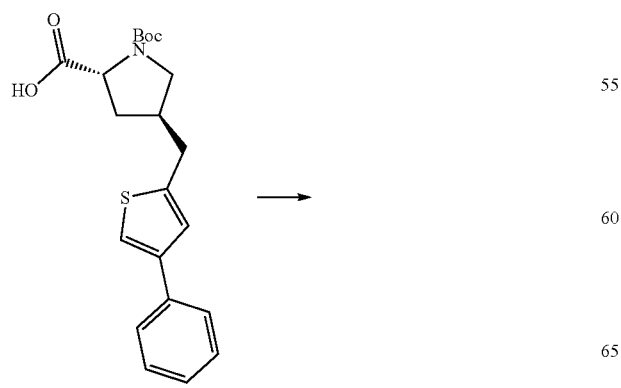

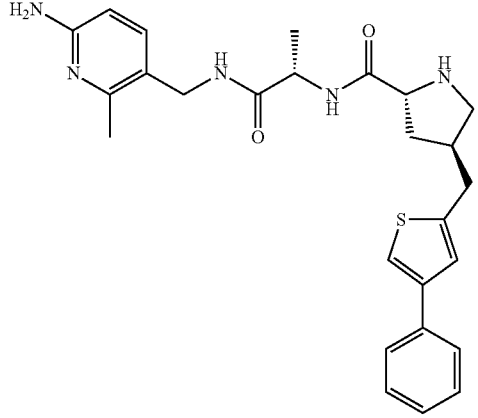

Steps 5-6: (2R,4R)—N—((S)-1-(((6-Amino-2-methylpyridin-3-yl)methyl)amino)-1-oxopropan-2-yl)-4-((4-phenylthiophen-2-yl)methyl)pyrrolidine-2-carboxamide dihydrochloride was synthesized according to the procedures for compound (1304).

Example 203. Preparation of (R)—N—((S)-1-(((6-Amino-2-methylpyridin-3-yl)methyl)amino)-1-oxopropan-2-yl)-1,2,3,4-tetrahydrobenzo[4,5]thieno[2,3-c]pyridine-3-carboxamide Hydrochloride (1400)

(1400)

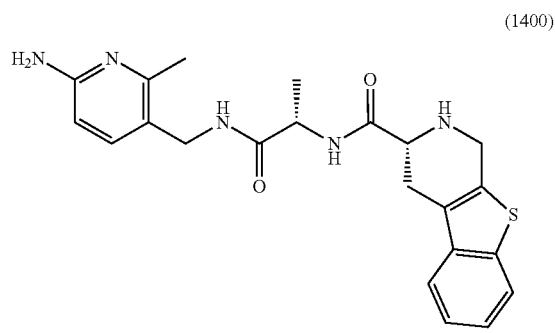 [SMILES: Cc1nc(N)ccc1CNC(=O)[C@H](C)NC(=O)[C@H]1Cc2c(sc3ccccc23)CN1]

(R)—N—((S)-1-(((6-Amino-2-methylpyridin-3-yl)methyl)amino)-1-oxopropan-2-yl)-1,2,3,4-tetrahydrobenzo[4,5]thieno[2,3-c]pyridine-3-carboxamide hydrochloride was synthesized according to the procedures for compound (1304), steps 7 and 8 using (R)-2-(tert-butoxycarbonyl)-1,2,3,4-tetrahydrobenzo[4,5]thieno[2,3-c]pyridine-3-carboxylic acid.

561

Example 204. Preparation of (2R,4S)-4-([1,1'-Biphenyl]-2-ylmethyl)-N—((S)-1-((5-chloro-2-hydroxy-3-methylbenzyl)amino)-1-oxopropan-2-yl)pyrrolidine-2-carboxamide Hydrochloride (1401)

562

Example 205. Preparation of (2R,4S)-4-([1,1'-Biphenyl]-2-ylmethyl)-N—((S)-1-((5-chloro-2-(1H-tetrazol-1-yl)benzyl)amino)-1-oxopropan-2-yl)pyrrolidine-2-carboxamide Trifluoroacetate (1402)

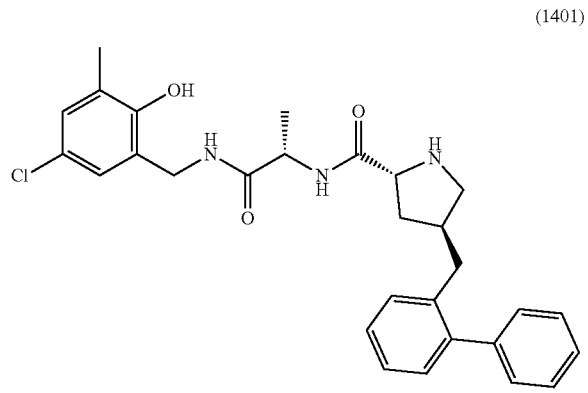

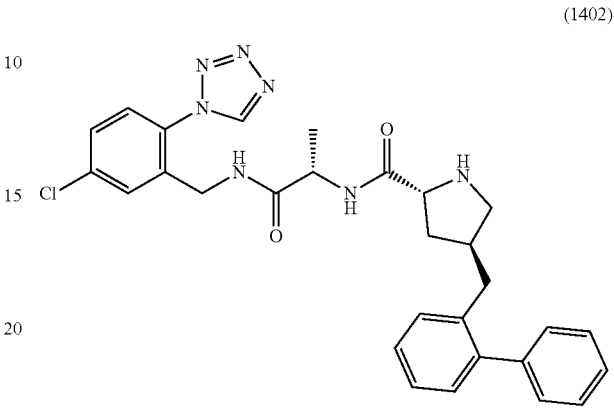

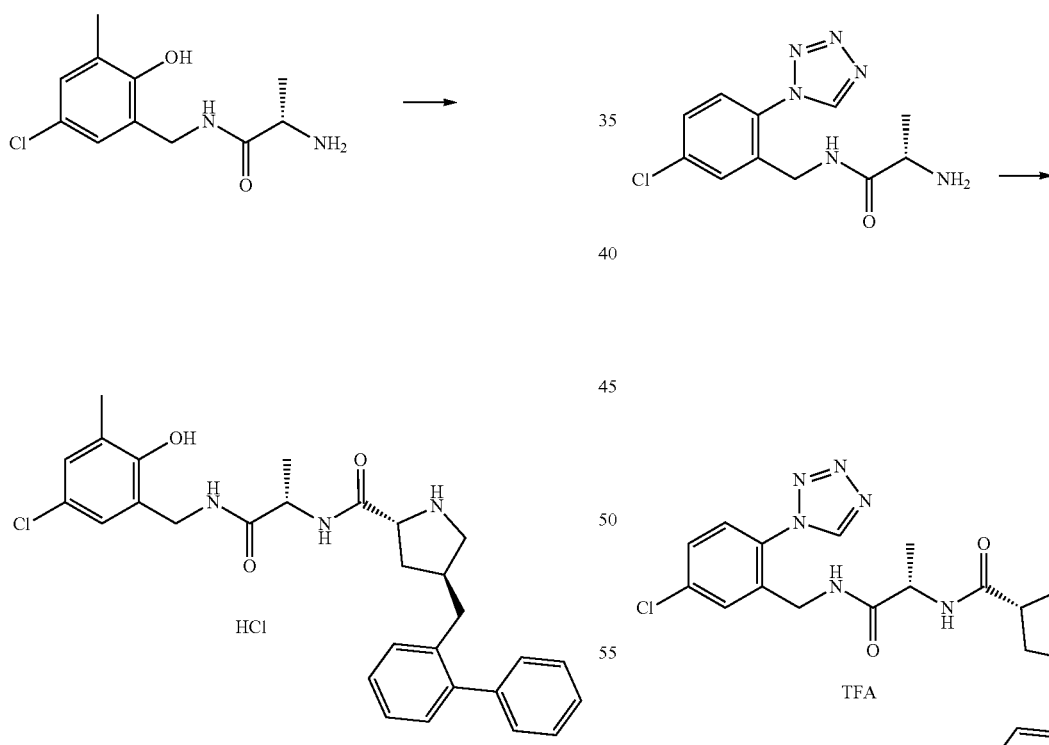

Step 1-2: The title compound was synthesized as a white powder (7.4 mg, 27% yield) according to steps 3-4 of the procedure for compound (1313) using the appropriate starting materials, except with purification of the crude product by chromatography (MeOH/CH$_2$Cl$_2$ containing 2.5% 7 N NH$_3$-MeOH), followed by treatment with 1 N HCl and lyophilization overnight.

Steps 1-2: The title compound was synthesized as a white solid according to steps 3-4 of the procedure for compound (1313) using the appropriate starting materials (11 mg, 33% yield over two steps).

Example 206. Preparation of (2R,4S)—N—((S)-1-(((6-Amino-2-methylpyridin-3-yl)methyl)amino)-1-oxopropan-2-yl)-4-((2'-(aminomethyl)-4'-fluoro-[1,1'-biphenyl]-4-yl)methyl)pyrrolidine-2-carboxamide (1403)

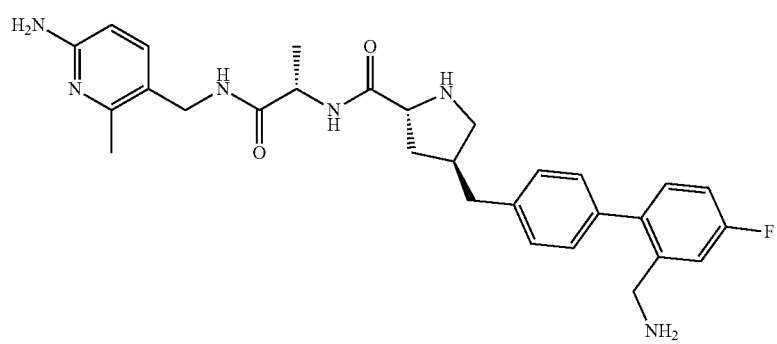

(1403)

(2R,4S)—N—((S)-1-(((6-Amino-2-methylpyridin-3-yl)methyl)amino)-1-oxopropan-2-yl)-4-((2'-(aminomethyl)-4'-fluoro-[1,1'-biphenyl]-4-yl)methyl)pyrrolidine-2-carboxamide was synthesized from (1396) according the procedure given for compound (1304), step 4.

Example 207. Preparation of (2R,4S)—N—((S)-1-((5-Chloro-2-(1H-tetrazol-1-yl)benzyl)amino)-1-oxopropan-2-yl)-4-(4-(pyridin-3-yl)benzyl)pyrrolidine-2-carboxamide Hydrochloride (1404)

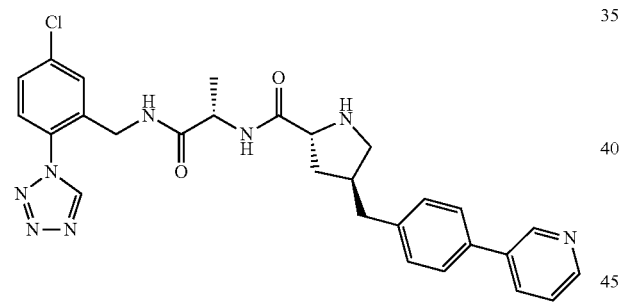

(1404)

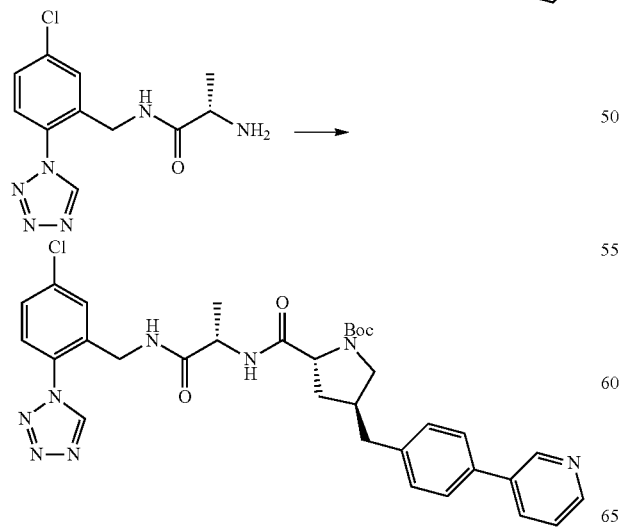

Step 1: tert-Butyl (2R,4S)-2-(((S)-1-((5-chloro-2-(1H-tetrazol-1-yl)benzyl)amino)-1-oxopropan-2-yl)carbamoyl)-4-(4-(pyridin-3-yl)benzyl)pyrrolidine-1-carboxylate (47 mg, 80% yield) was synthesized from (S)-2-amino-N-(5-chloro-2-(1H-tetrazol-1-yl)benzyl)propanamide trifluoroacetate (28 mg, 0.10 mmol) according to the procedure for compound (1304), step 7.

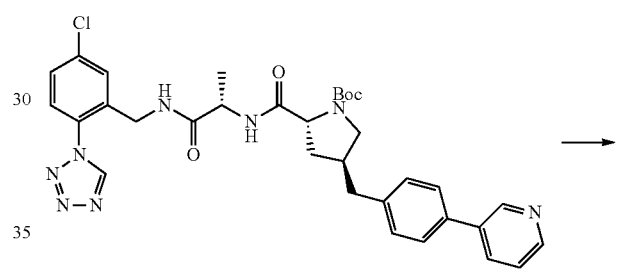

Step 2: (2R,4S)—N—((S)-1-((5-Chloro-2-(1H-tetrazol-1-yl)benzyl)amino)-1-oxopropan-2-yl)-4-(4-(pyridin-3-yl)benzyl)pyrrolidine-2-carboxamide hydrochloride (43 mg, 90% yield) was synthesized from tert-butyl (2R,4S)-2-(((S)-1-((5-chloro-2-(1H-tetrazol-1-yl)benzyl)amino)-1-oxopropan-2-yl)carbamoyl)-4-(4-(pyridin-3-yl)benzyl)pyrrolidine-1-carboxylate (47 mg, 0.07 mmol) according to the procedure for compound (1304), step 8.

Example 208. Preparation of (2R,4S)-4-((2'-Carbamoyl-4'-fluoro-[1,1'-biphenyl]-4-yl)methyl)-N—((S)-1-((5-chloro-2-(1H-tetrazol-1-yl)benzyl)amino)-1-oxopropan-2-yl)pyrrolidine-2-carboxamide Hydrochloride (1405)

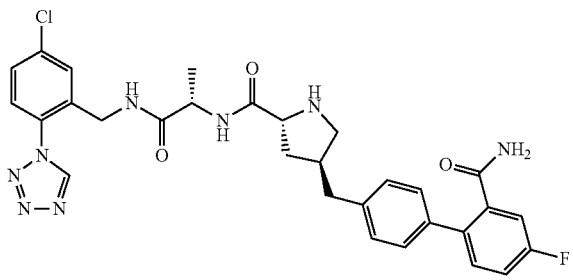

(1405)

(2R,4S)-4-((2'-Carbamoyl-4'-fluoro-[1,1'-biphenyl]-4-yl)methyl)-N—((S)-1-((5-chloro-2-(1H-tetrazol-1-yl)benzyl)amino)-1-oxopropan-2-yl)pyrrolidine-2-carboxamide hydrochloride was synthesized according to the procedures for compound (1404).

Example 209. Preparation of (2R,4S)-4-([1,1'-Biphenyl]-3-ylmethyl)-N—((S)-1-(((6-amino-2-methylpyridin-3-yl)methyl)amino)-1-oxopropan-2-yl)pyrrolidine-2-carboxamide Dihydrochloric acid (1406)

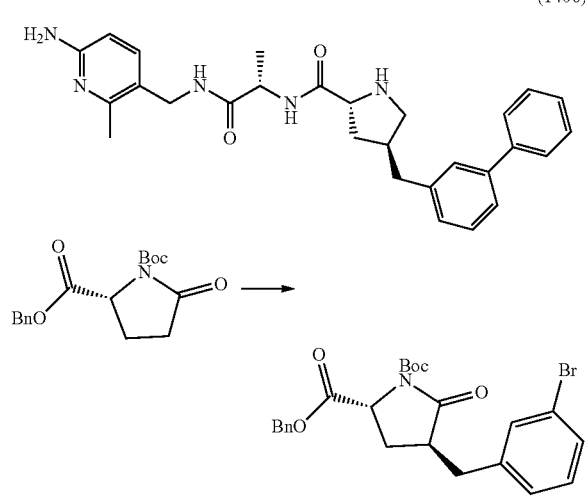

(1406)

Step 1: To a stirred solution of 2-benzyl 1-(tert-butyl) (R)-5-oxopyrrolidine-1,2-dicarboxylate (3.25 g, 10.2 mmol) in THF (60 mL) at −78° C. was slowly added lithium bis(trimethylsilyl)amide (11.25 mL, 11.25 mmol, 1 M in THF) under Ar atmosphere. After stirring for 1 h at −78° C., 3-bromobenzyl bromide (2.80 g, 11.25 mmol) was added and the stirring continued for an additional 2 h. The reaction mixture was quenched with sat. NH₄Cl solution and extracted with diethyl ether (3×100 mL). The combined extracts were dried over Na₂SO₄, filtered and concentrated under vacuum. The residue was purified by chromatography (EtOAc-hexanes) gave 2-benzyl 1-(tert-butyl) (2R,4S)-4-(3-bromobenzyl)-5-oxopyrrolidine-1,2-dicarboxylate (3.47 g, 70% yield).

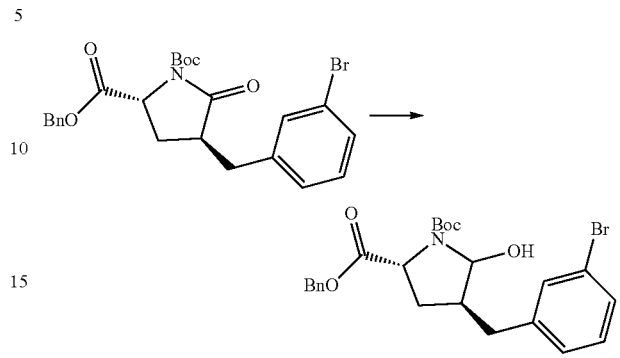

Step 2: To a solution of 2-benzyl 1-(tert-butyl) (2R,4S)-4-(3-bromobenzyl)-5-oxopyrrolidine-1,2-dicarboxylate (3.47 g, 7.12 mmol) in THF (47 mL) at −78° C. was added lithium triethylborohydride solution (7.83 mL, 7.83 mmol, 1 M in THF) under Ar atm. After 30 min, the reaction mixture was quenched with sat. NaHCO₃ solution (20 mL) and warmed to 0° C. At 0° C., 30% H₂O₂ (about 60 drops) was added and the reaction mixture was stirred at same temperature for 30 min. The volatiles were removed under vacuum and the aqueous layer was extracted with CH₂Cl₂ (3×60 mL). The combined organic extracts were thoroughly dried using Na₂SO₄, filtered, concentrated to afford 2-benzyl 1-(tert-butyl) (2R,4S)-4-(3-bromobenzyl)-5-hydroxypyrrolidine-1,2-dicarboxylate (3.30 g crude) that was directly used in the next step without further purification.

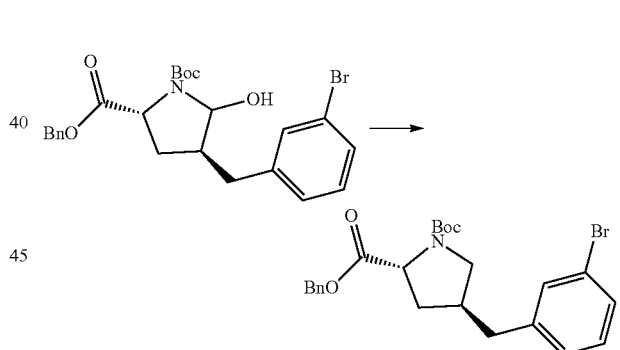

Step 3: To a stirred solution of 2-benzyl 1-(tert-butyl) (2R,4S)-4-(3-bromobenzyl)-5-hydroxypyrrolidine-1,2-dicarboxylate (3.30 g crude) and triethylsilane (1.25 mL, 7.80 mmol) in CH₂Cl₂ (36 mL) at −78° C. was drop wise added boron trifluoride diethyl etherate (0.95 mL, 7.80 mmol) under Ar atm. After 30 min at same temperature additional triethylsilane (1.25 mL, 7.80 mmol) and boron trifluoride diethyl etherate (0.95 mL, 7.80 mmol) were added. After stirring for 2 h at −78° C., the reaction mixture was quenched with sat. aqueous NaHCO₃ solution (20 mL) and extracted with CH₂Cl₂ (3×60 mL). The combined extracts were dried over Na₂SO₄, filtered and conc under vacuum. The residue was purified by chromatography (EtOAc-hexanes) to afford 2-benzyl 1-(tert-butyl) (2R,4S)-4-(3-bromobenzyl)pyrrolidine-1,2-dicarboxylate (1.60 g, 47% yield in two steps).

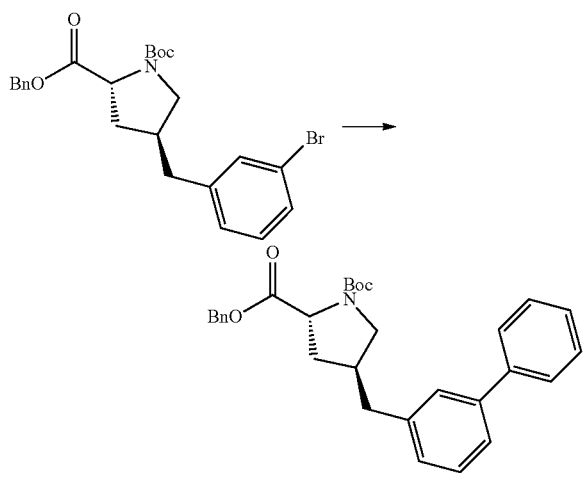

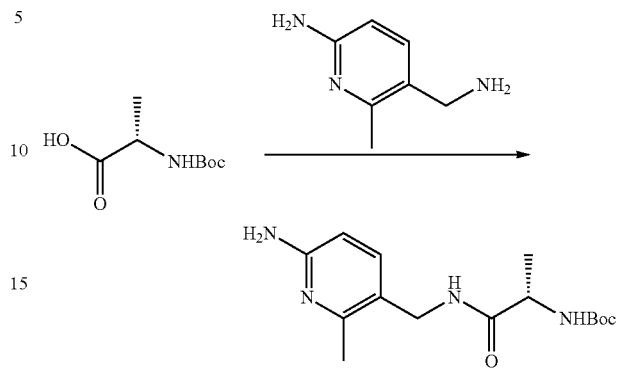

Step 4: In a 50 mL round bottom flask equipped with a stir bar and septum was added 2-benzyl 1-(tert-butyl) (2R,4S)-4-(3-bromobenzyl)pyrrolidine-1,2-dicarboxylate (200 mg, 0.42 mmol), phenyl boronic acid (62 mg, 0.51), Pd(dppf)Cl$_2$ (31 mg, 0.042 mmol), cesium carbonate (413 mg, 1.26 mmol), THF (4.2 mL) and water (0.42 mL). The resulting mixture was degassed by bubbling N$_2$ through the solution for 10 min. The reaction was then heated to 90° C. for 4 h. Upon cooling to ambient temperature, the reaction solution was filtered through diatomaceous earth, eluting with EtOAc, concentrated and purified by chromatography using EtOAc-hexanes to afford 2-benzyl 1-(tert-butyl) (2R,4S)-4-([1,1'-biphenyl]-3-ylmethyl)pyrrolidine-1,2-dicarboxylate (167 mg, 83% yield) as a colorless sticky liquid.

(2R,4S)-4-([1,1'-biphenyl]-3-ylmethyl)-1-(tert-butoxycarbonyl)pyrrolidine-2-carboxylic acid (130 mg, 96% yield).

Step 5: To a stirred solution of (tert-butoxycarbonyl)-L-alanine (1.96 g, 10.38 mmol) in CH$_2$Cl$_2$ (55 mL) was added NHS (1.25 g, 10.89 mmol) at room temperature. To the reaction mixture DCC (2.25 g 10.9 mmol) was added and the reaction mixture stirred for 1.0 h. 5-(Aminomethyl)-6-methylpyridin-2-amine was added to the reaction mixture and sonicated for 5 min. The 5-(aminomethyl)-6-methylpyridin-2-amine was completely dissolved and stirred the reaction mixture at ambient temperature for 1 h. The crude reaction mixture was filtered and conc under reduced pressure. The crude reaction mixture was purified by chromatography using MeOH—CH$_2$Cl$_2$ to afford tert-butyl (S)-(1-(((6-amino-2-methylpyridin-3-yl)methyl)amino)-1-oxopropan-2-yl)carbamate (2.35 g, 70% yield) as a white solid.

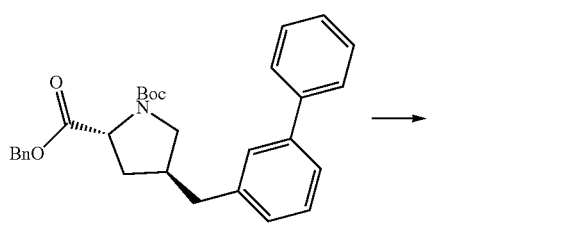

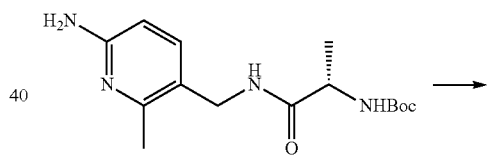

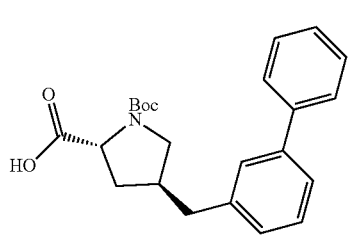

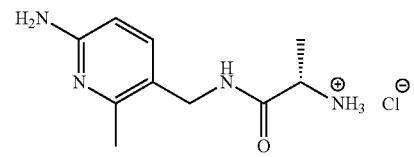

Step 4: A solution of 2-benzyl 1-(tert-butyl) (2R,4S)-4-([1,1'-biphenyl]-3-ylmethyl)pyrrolidine-1,2-dicarboxylate (167 mg, 0.35 mmol) in MeOH (3 mL) was bubbled with Ar gas for 5 minutes. 10% Pd/C (17 mg) was added to the reaction mixture and that was stirred under 1 atm of H$_2$ for 3 h. The reaction mixture was filtered (0.2 μm syringe filter) and the filtrate was concentrated under vacuum to give Step 6: To tert-butyl (S)-(1-(((6-amino-2-methylpyridin-3-yl)methyl)amino)-1-oxopropan-2-yl)carbamate (2.35 g, 7.62 mmol) was added a solution of MeOH—HCl (19 mL, 2 M) with stirring at ambient temperature while monitoring for the consumption of starting material (typically 1 h). The solution was evaporated to dryness and MeOH (50 mL) was added and evaporated to dryness to remove residual HCl gas to give (S)-2-amino-N-((6-amino-2-methylpyridin-3-yl)methyl)propanamide hydrochloride (1.60 g, 90% yield) as an off white solid (hygroscopic).

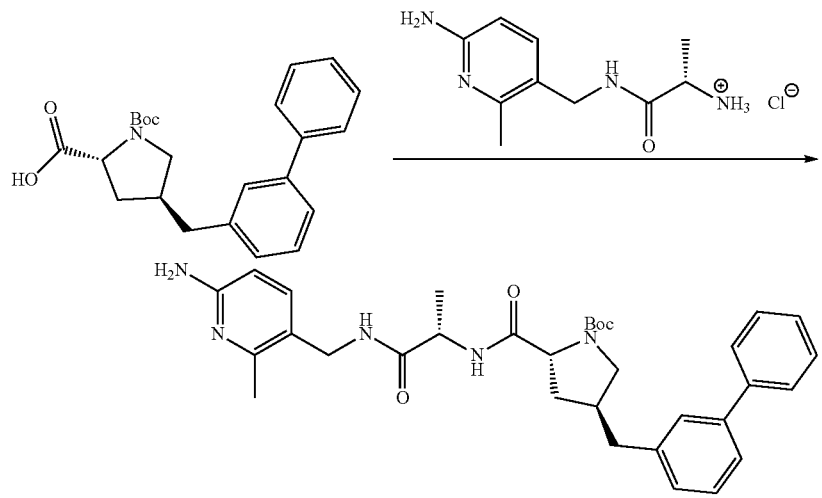

Step 7: To a stirred solution of (2R,4S)-4-([1,1'-biphenyl]-3-ylmethyl)-1-(tert-butoxycarbonyl)pyrrolidine-2-carboxylic acid (40 mg, 0.10 mmol) in anhydrous DMF (1 mL) was added HOBt (16 mg, 0.11 mmol), DIEA (0.07 mL, 0.42 mmol) and EDC (22 mg, 0.11 mmol) at ambient temperature. The reaction mixture was stirred for 30 min at ambient temperature. (S)-2-amino-N-((6-amino-2-methylpyridin-3-yl)methyl)propanamide hydrochloride (26 mg, 0.12 mmol) was added to the reaction mixture and stirred overnight. The solution was evaporated to dryness and the residue was partitioned with EtOAc (10 mL) and 10% $KHSO_4$ (5 mL). The organic layer was separated and washed with sat. $NaHCO_3$ solution (10 ml), dried over anhydrous $Na_2SO_4$ and conc under vacuum. The crude reaction mixture was purified by chromatography using MeOH—$CH_2Cl_2$ to afford tert-butyl (2R,4S)-4-([1,1'-biphenyl]-3-ylmethyl)-2-(((S)-1-(((6-amino-2-methylpyridin-3-yl)methyl)amino)-1-oxopropan-2-yl)carbamoyl)pyrrolidine-1-carboxylate (48 mg, 80% yield) as a white solid.

Step 8: To tert-butyl (2R,4S)-4-([1,1'-biphenyl]-3-ylmethyl)-2-(((S)-1-(((6-amino-2-methylpyridin-3-yl)methyl)amino)-1-oxopropan-2-yl)carbamoyl)pyrrolidine-1-carboxylate (48 mg, 0.08 mmol) was added a solution of MeOH—HCl (2.0 mL, 2 M) with stirring at ambient temperature while monitoring for the consumption of starting material (30 min to 1 h). The solution was evaporated to dryness and MeOH (10 mL) was added and evaporated to dryness to remove residual HCl gas to yield (2R,4S)-4-([1,1'-biphenyl]-3-ylmethyl)-N—((S)-1-(((6-amino-2-methylpyridin-3-yl)methyl)amino)-1-oxopropan-2-yl)pyrrolidine-2-carboxamide dihydrochloride (48 mg, 95%) as a white solid.

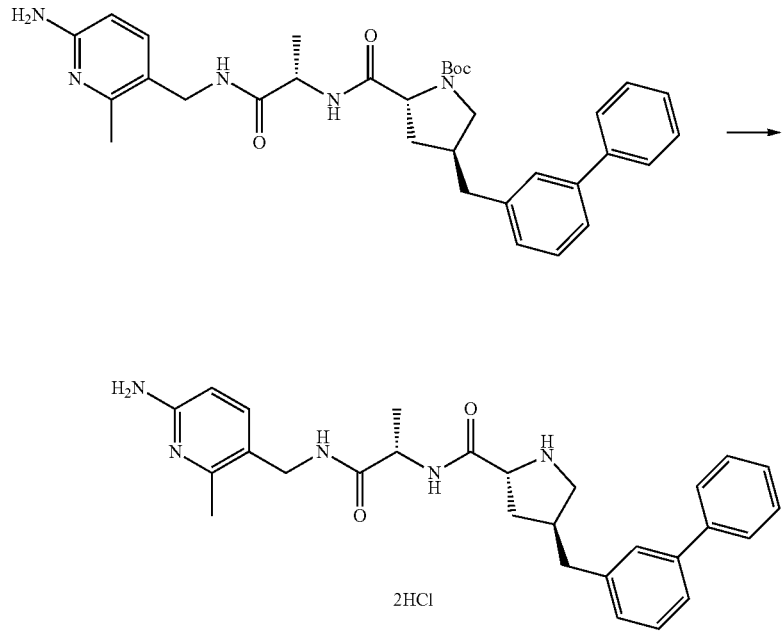 [SMILES: Cc1nc(N)ccc1CNC(=O)[C@H](C)NC(=O)[C@H]1C[C@H](Cc2cccc(-c3ccccc3)c2)CN1C(=O)OC(C)(C)C ; Cc1nc(N)ccc1CNC(=O)[C@H](C)NC(=O)[C@H]1C[C@H](Cc2cccc(-c3ccccc3)c2)CN1]

Example 210. Preparation of (2R,4S)—N—((S)-1-(((6-Amino-2-methylpyridin-3-yl)methyl)amino)-1-oxopropan-2-yl)-4-(3,5-dimethoxybenzyl)pyrrolidine-2-carboxamide Di-trifluoroacetate salt (1407)

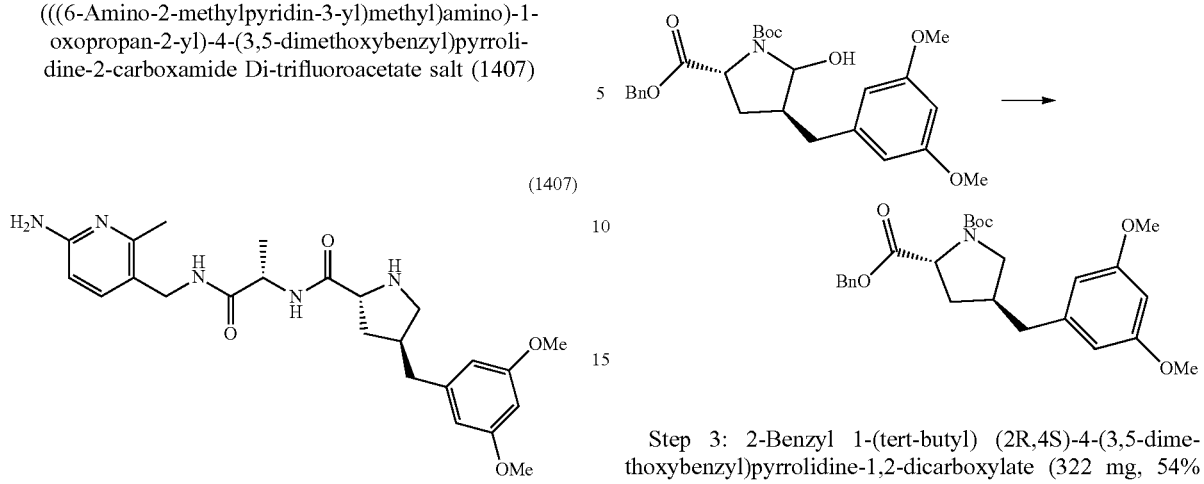

(1407)

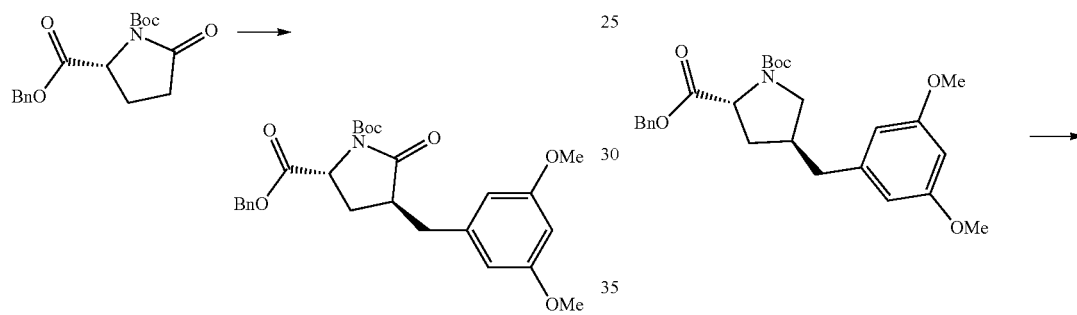

Step 1: 2-Benzyl 1-(tert-butyl) (2R,4S)-4-(3,5-dimethoxybenzyl)-5-oxopyrrolidine-1,2-dicarboxylate (619 mg, 85% yield) was synthesized from 2-benzyl 1-(tert-butyl) (R)-5-oxopyrrolidine-1,2-dicarboxylate (500 mg, 1.56 mmol) and 3,5-dimethoxybenzyl bromide according to the procedure for compound (1304), step 1.

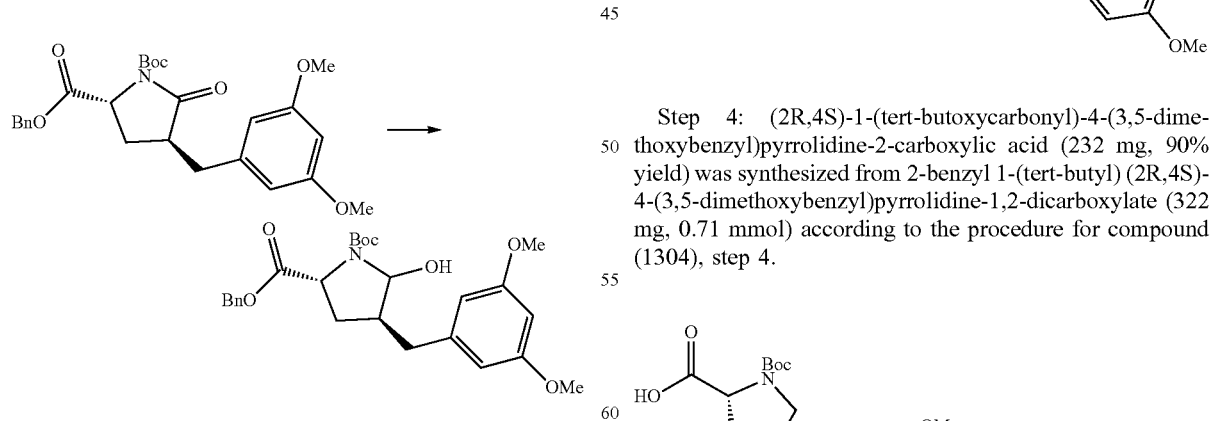

Step 2: 2-Benzyl 1-(tert-butyl) (2R,4S)-4-(3,5-dimethoxybenzyl)-5-hydroxypyrrolidine-1,2-dicarboxylate was synthesized from 2-benzyl 1-(tert-butyl) (2R,4S)-4-(3,5-dimethoxybenzyl)-5-oxopyrrolidine-1,2-dicarboxylate (619 mg, 1.32 mmol) according to the procedure for compound (1304), step 2.

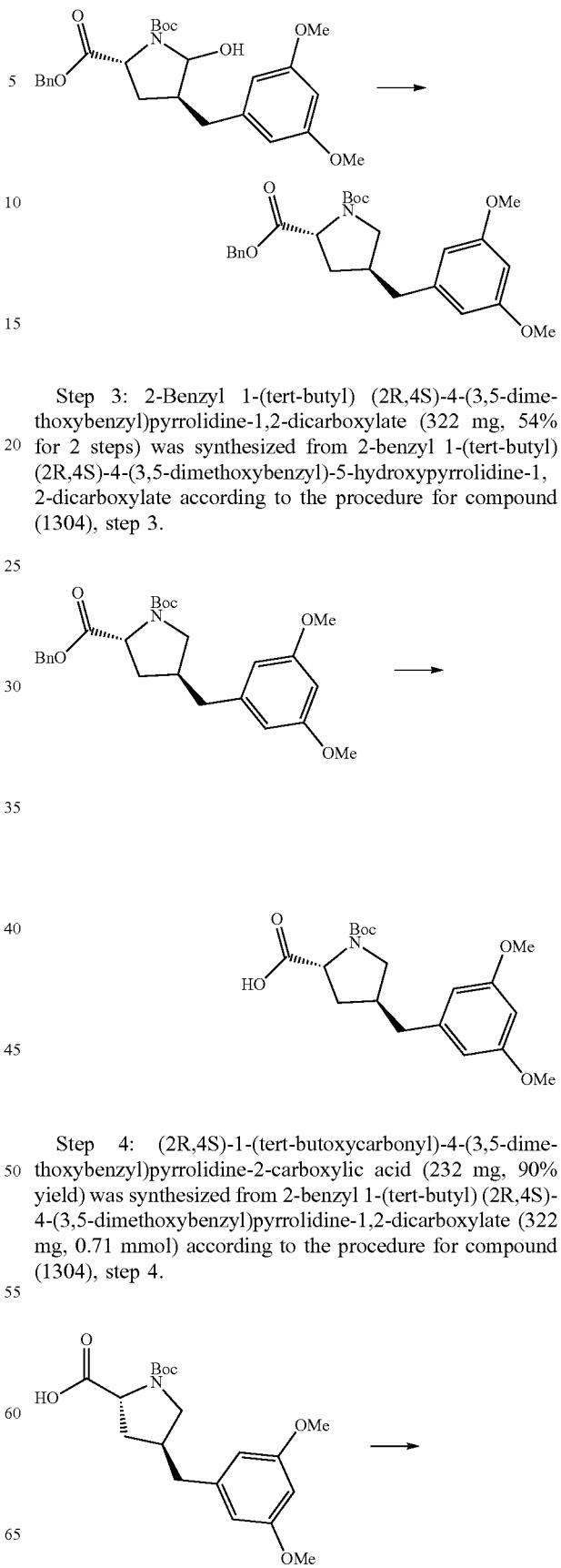

Step 3: 2-Benzyl 1-(tert-butyl) (2R,4S)-4-(3,5-dimethoxybenzyl)pyrrolidine-1,2-dicarboxylate (322 mg, 54% for 2 steps) was synthesized from 2-benzyl 1-(tert-butyl) (2R,4S)-4-(3,5-dimethoxybenzyl)-5-hydroxypyrrolidine-1,2-dicarboxylate according to the procedure for compound (1304), step 3.

Step 4: (2R,4S)-1-(tert-butoxycarbonyl)-4-(3,5-dimethoxybenzyl)pyrrolidine-2-carboxylic acid (232 mg, 90% yield) was synthesized from 2-benzyl 1-(tert-butyl) (2R,4S)-4-(3,5-dimethoxybenzyl)pyrrolidine-1,2-dicarboxylate (322 mg, 0.71 mmol) according to the procedure for compound (1304), step 4.

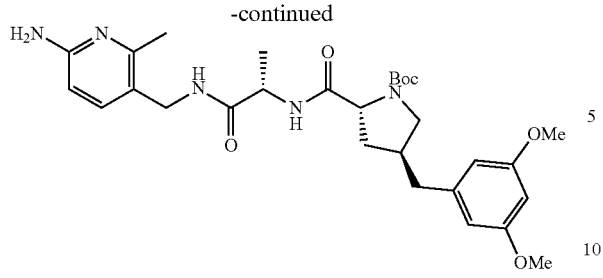

Step 5: tert-Butyl (2R,4S)-2-(((S)-1-(((6-amino-2-methylpyridin-3-yl)methyl)amino)-1-oxopropan-2-yl)carbamoyl)-4-(3,5-dimethoxybenzyl)pyrrolidine-1-carboxylate (61 mg, 76% yield) was synthesized from (2R,4S)-1-(tert-butoxycarbonyl)-4-(3,5-dimethoxybenzyl)pyrrolidine-2-carboxylic acid (53 mg, 0.15 mmol) according to the procedure for compound (1304), step 5.

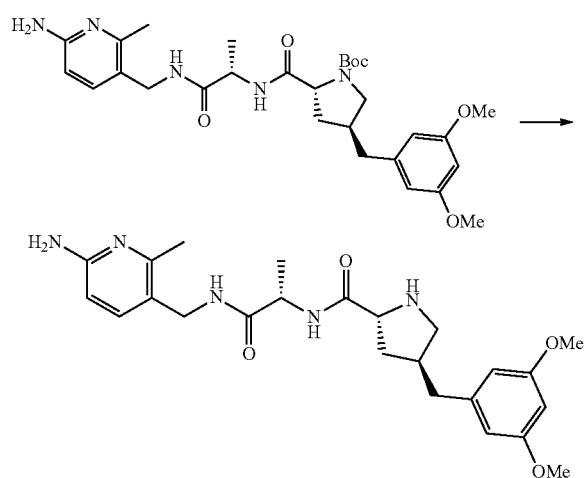

Step 6: Deprotection of tert-butyl (2R,4S)-2-(((S)-1-(((6-amino-2-methylpyridin-3-yl)methyl)amino)-1-oxopropan-2-yl)carbamoyl)-4-(3,5-dimethoxybenzyl)pyrrolidine-1-carboxylate (61 mg, 0.11 mmol) was conducted according to the procedure for compound (1260), step 4 except that the final product was purified using reverse-phase HPLC.

Example 211. Preparation of (2R,4S)—N—((S)-1-((5-Chloro-2-hydroxy-3-methylbenzyl)amino)-1-oxopropan-2-yl)-4-(2-(5-chlorothiophen-2-yl)benzyl)pyrrolidine-2-carboxamide Hydrochloride (1408)

(1408)

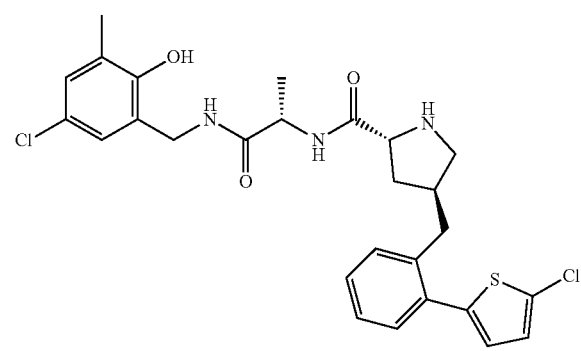

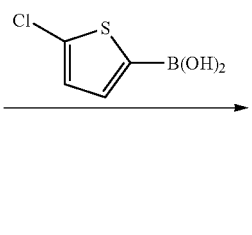

Step 1: A 20 mL pressure vial was charged with 2-benzyl 1-(tert-butyl) (2R,4S)-4-(2-bromobenzyl)pyrrolidine-1,2-dicarboxylate (121 mg, 0.26 mmol), (5-chlorothiophen-2-yl)boronic acid (83 mg, 0.51 mmol), Pd(dppf)Cl$_2$ (19 mg, 0.026 mmol) and K$_2$CO$_3$ (108 mg, 0.78 mmol) before being sparged with Ar. Dioxane (3 mL) and H$_2$O (0.3 mL) were added by syringe, and the reaction mixture was sealed and allowed to stir at 90° C. for 18 h. Upon completion, the reaction mixture was concentrated and purified by chromatography (0-30% EtOAc/hexanes) to yield 2-benzyl 1-(tert-butyl) (2R,4S)-4-(2-(5-chlorothiophen-2-yl)benzyl)pyrrolidine-1,2-dicarboxylate (82 mg, 62% yield) as a yellow oil.

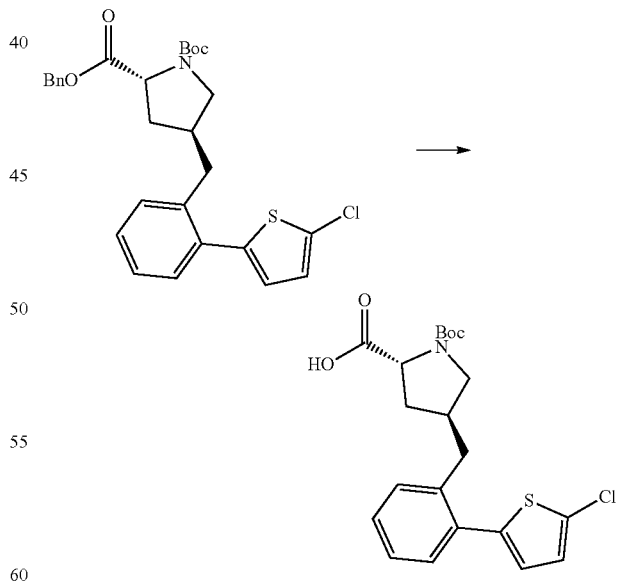

Step 2: A 50 mL round bottom flask was charged with 2-benzyl 1-(tert-butyl) (2R,4S)-4-(2-(5-chlorothiophen-2-yl)benzyl)pyrrolidine-1,2-dicarboxylate (82 mg, 0.16 mmol), LiOH (58 mg, 2.4 mmol) and a mixture of THF/MeOH/H$_2$O (2:1:1). Upon completion, the reaction mixture was concentrated, acidified to pH ~3 with 1 M HCl and extracted with EtOAc 2×. Concentration in vacuo gave (2R,4S)-1-(tert-butoxycarbonyl)-4-(2-(5-chlorothiophen-2-yl)benzyl)pyrrolidine-2-carboxylic acid as a yellow oil.

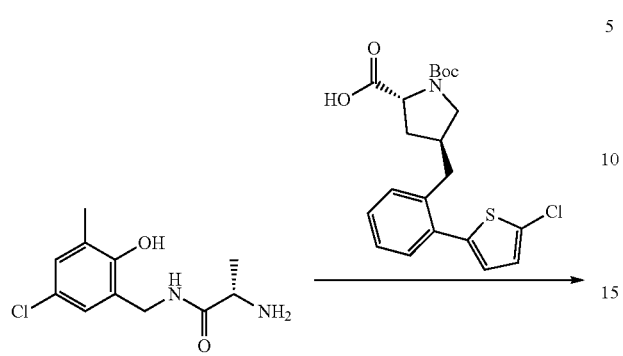

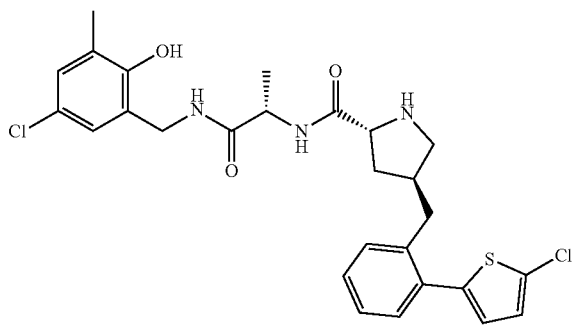

Step 4: The title compound was synthesized as an off-white powder (10 mg, 46% yield over two steps) according to step 4 of the procedure for compound (1313), except with purification by chromatography (5% MeOH/CH$_2$Cl$_2$ containing 2.5% 7 N NH$_3$-MeOH) followed by treatment with 1 N HCl and lyophilization overnight.

Example 212. Preparation of (2R,4S)—N—((S)-1-((5-Chloro-2-(1H-tetrazol-1-yl)benzyl)amino)-1-oxopropan-2-yl)-4-(2-(5-chlorothiophen-2-yl)benzyl)pyrrolidine-2-carboxamide Trifluoroacetate (1409)

(1409)

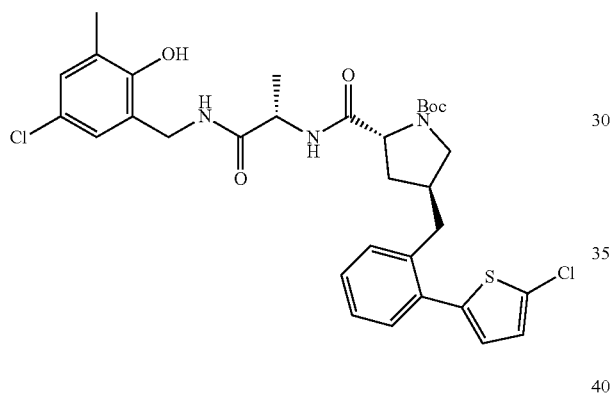

Step 3: (2R,4S)-1-(tert-Butoxycarbonyl)-4-(2-(5-chlorothiophen-2-yl)benzyl)pyrrolidine-2-carboxylic (17 mg, 0.04 mmol) and HOBt (5.9 mg, 0.044 mmol) were dissolved in DMF (1 mL). EDC (8.4 mg, 0.044 mmol) was then added in a single portion, followed by ethylamine (2 M in THF, 150 µL) and DIEA (21 µL, 0.12 mmol). The resulting solution was allowed to stir at room temp for 16 h. The reaction mixture was then diluted with EtOAc, washed with 10% aqueous KHSO$_4$ and brine. Purification by chromatography (70-80% EtOAc/hexanes) gave tert-butyl (2R,4S)-2-(((S)-1-((5-chloro-2-hydroxy-3-methylbenzyl)amino)-1-oxopropan-2-yl)carbamoyl)-4-(2-(5-chlorothiophen-2-yl)benzyl)pyrrolidine-1-carboxylate as a colorless oil.

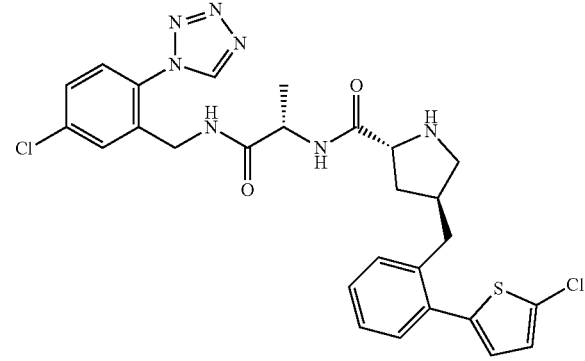

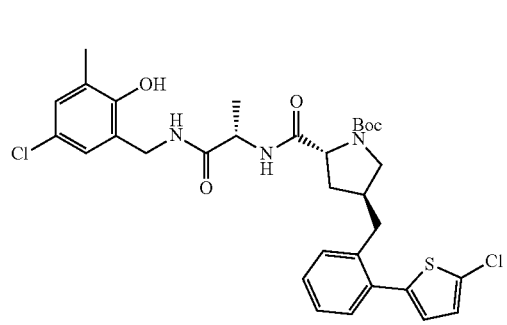

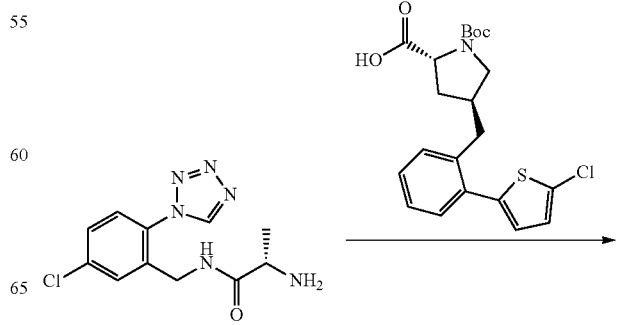

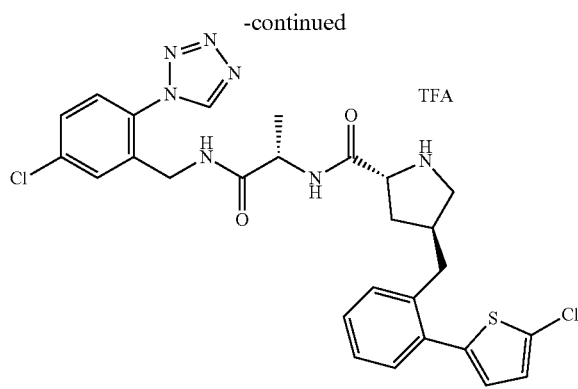

Steps 1-2: The title compound was synthesized as a beige powder (10 mg, 43% yield over two steps) according to steps 3-4 of the procedure for compound (1408) except with purification by prep-HPLC (ACN/H₂O+TFA).

Example 213. Preparation of (2R,4S)—N—((S)-1-(((6-Amino-2-methylpyridin-3-yl)methyl)amino)-1-oxopropan-2-yl)-4-(2-(5-chlorothiophen-2-yl)benzyl)pyrrolidine-2-carboxamide Trifluoroacetate (1410)

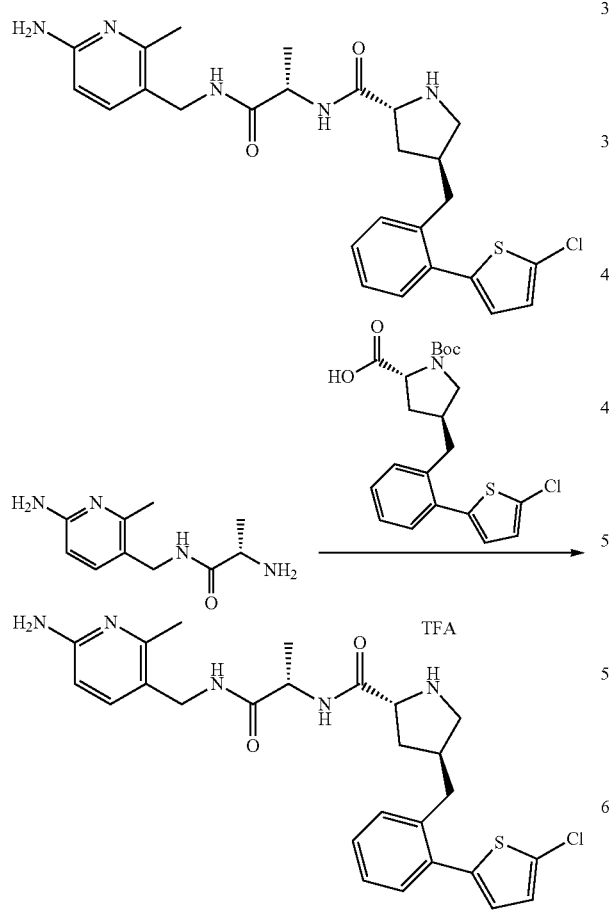

Steps 1-2: The title compound was synthesized as a beige powder (7.6 mg, 37% yield over two steps) according to steps 3-4 of the procedure for compound (1408) except with purification by prep-HPLC (ACN/H₂O+TFA).

Example 214. Preparation of 3-((2R,4S)-2-(((S)-1-(((6-Amino-2-methylpyridin-3-yl)methyl)amino)-1-oxopropan-2-yl)carbamoyl)-4-phenylpiperidin-1-yl)propanoic acid Trifluoroacetate salt (1411)

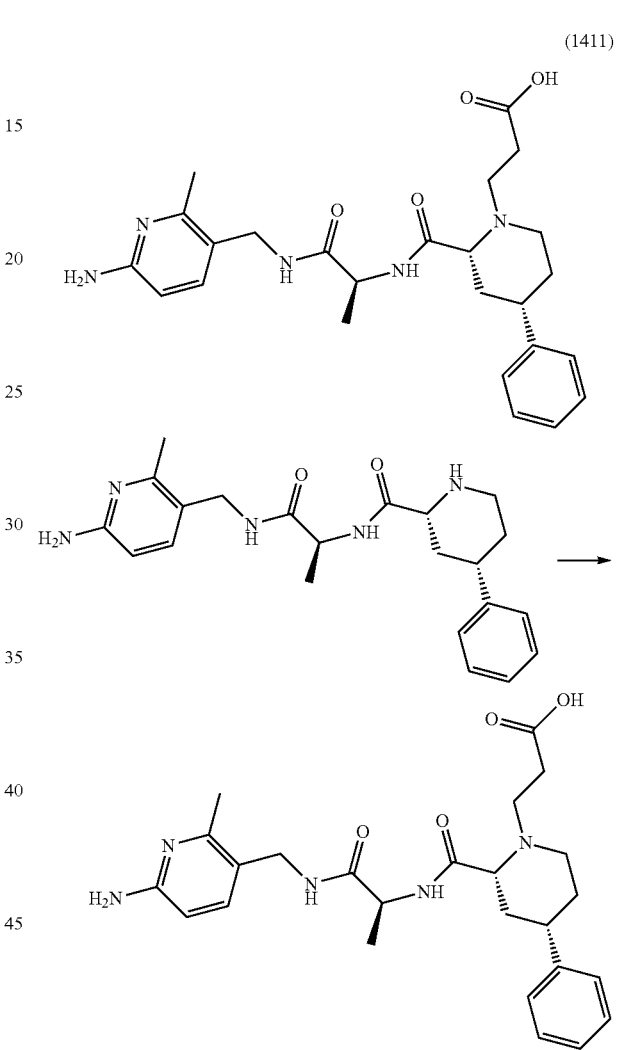

Steps 1 and 2: To a stirred solution of (2R,4S)—N—((S)-1-(((6-amino-2-methylpyridin-3-yl)methyl)amino)-1-oxopropan-2-yl)-4-phenylpiperidine-2-carboxamide dihydrochloride (10 mg, 0.021 mmol) in CH₂Cl₂ (2 mL) and NEt₃ (0.1 mL) was added ethyl 3-bromopropanoate (0.026 ml, 0.21 mmol) under Ar atmosphere. After stirring for 24 h at ambient temperature the reaction mixture was concentrated and dissolved in THF (2 mL). To the solution was added LiOH (10 mg, 0.21 mmol) dissolved in 2 ml of water at room temperature and stirred at ambient temperature for 18 h. The reaction mixture was acidified with TFA and purified by reverse-phase HPLC to yield 3-((2R,4S)-2-(((S)-1-(((6-amino-2-methylpyridin-3-yl)methyl)amino)-1-oxopropan-2-yl)carbamoyl)-4-phenylpiperidin-1-yl)propanoic acid trifluoroacetate salt (8.0 mg, 81% yield over two steps).

Example 215. Preparation of 6-((2R,4S)-2-(((S)-1-(((6-Amino-2-methylpyridin-3-yl)methyl)amino)-1-oxopropan-2-yl)carbamoyl)-4-phenylpiperidin-1-yl) hexanoic acid Trifluoroacetate salt (1412)

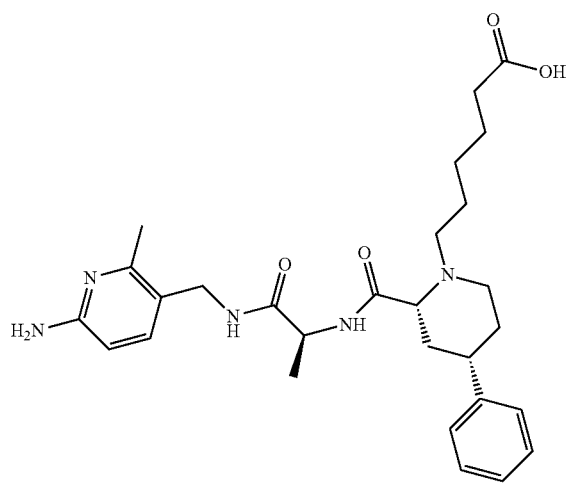

(1412)

6-((2R,4S)-2-(((S)-1-(((6-Amino-2-methylpyridin-3-yl)methyl)amino)-1-oxopropan-2-yl)carbamoyl)-4-phenylpiperidin-1-yl)hexanoic acid trifluoroacetate salt was synthesized according to the procedures for compound (1411) using the corresponding bromoester.

Example 216. Preparation of (2R,4S,5R)—N—((S)-1-(((6-Amino-2-methylpyridin-3-yl)methyl)amino)-1-oxopropan-2-yl)-4-benzyl-5-ethylpyrrolidine-2-carboxamide Di-trifluoroacetate salt (1413)

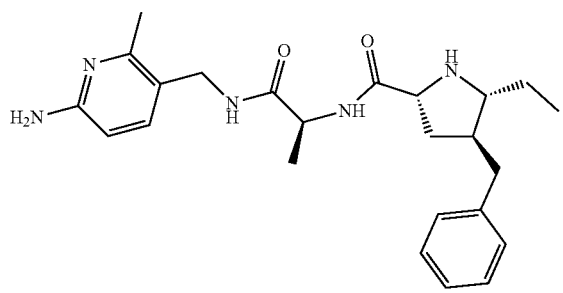

(1413)

To a solution of 2-benzyl 1-(tert-butyl) (2R,4S)-4-benzyl-5-oxopyrrolidine-1,2-dicarboxylate (0.2 g, 0.49 mmol) in THF (20 mL) at −78° C. was added ethyl magnesium bromide solution (0.53 mL, 0.53 mmol, 1 M in THF) under Ar atmosphere. After 30 min, the reaction mixture was quenched with saturated NaHCO$_3$ solution (5 mL) and warmed to 0° C. The organic volatiles were removed under vacuum and the aqueous layer was extracted with CH$_2$Cl$_2$ (3×10 mL). The combined organic extracts were thoroughly dried using Na$_2$SO$_4$, filtered, and concentrated to afford 2-benzyl 1-(tert-butyl) (2R,4S)-4-benzyl-5-ethyl-5-hydroxypyrrolidine-1,2-dicarboxylate (220 mg crude). This material was directly used in the next step without further purification. Subsequent steps were followed according to the procedures for compound (1304).

Example 217. Preparation of (2R,4S)—N—((S)-1-((5-Chloro-2-(1H-tetrazol-1-yl)benzyl)amino)-1-oxopropan-2-yl)-4-(naphthalen-1-ylmethyl)pyrrolidine-2-carboxamide Hydrochloride (1414)

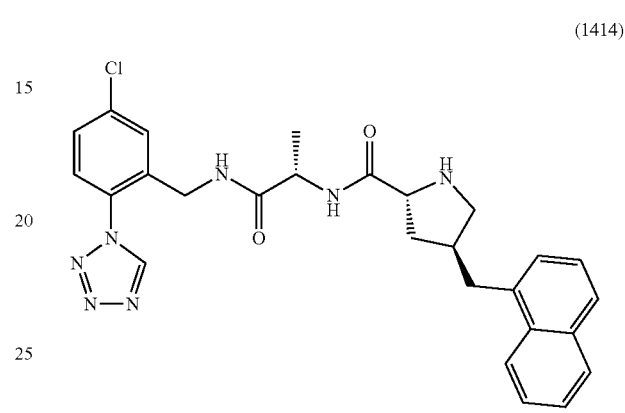

(1414)

(2R,4S)—N—((S)-1-((5-Chloro-2-(1H-tetrazol-1-yl)benzyl)amino)-1-oxopropan-2-yl)-4-(naphthalen-1-ylmethyl)pyrrolidine-2-carboxamide hydrochloride was synthesized according to the procedures for compound (1404).

Example 218. Preparation of (2R,4S)—N—((S)-1-(((3-Chloro-1H-pyrrolo[2,3-b]pyridin-5-yl)methyl)amino)-1-oxopropan-2-yl)-4-(naphthalen-1-ylmethyl)pyrrolidine-2-carboxamide Hydrochloride (1415)

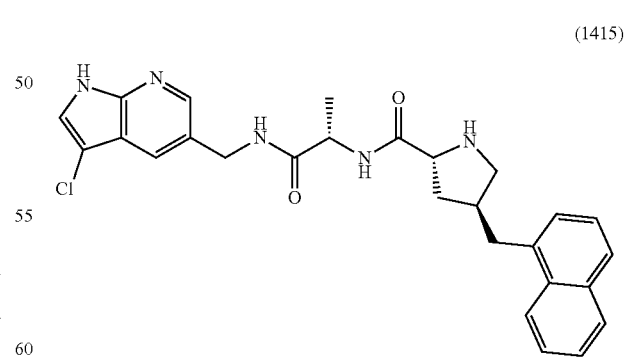

(1415)

(2R,4S)—N—((S)-1-(((3-Chloro-1H-pyrrolo[2,3-b]pyridin-5-yl)methyl)amino)-1-oxopropan-2-yl)-4-(naphthalen-1-ylmethyl)pyrrolidine-2-carboxamide hydrochloride was synthesized according to the procedures for compound (1334).

Example 219. Preparation of (2R,4S)—N—((S)-1-((5-Chloro-2-(1H-tetrazol-1-yl)benzyl)amino)-1-oxopropan-2-yl)-4-(3,5-dimethylbenzyl)pyrrolidine-2-carboxamide Hydrochloride (1416)

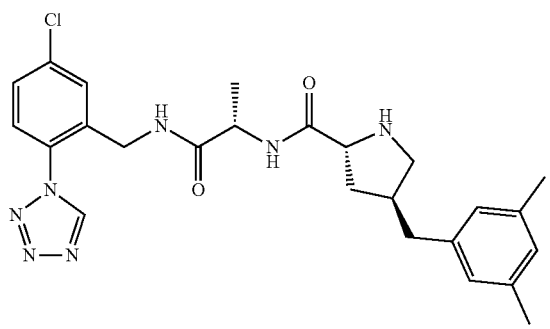

(1416)

(2R,4S)—N—((S)-1-((5-Chloro-2-(1H-tetrazol-1-yl)benzyl)amino)-1-oxopropan-2-yl)-4-(3,5-dimethylbenzyl)pyrrolidine-2-carboxamide hydrochloride was synthesized according to the procedures for compound (1404).

Example 220. Preparation of (2R,4R)—N—((S)-1-(((7-Chloro-1H-benzo[d]imidazol-5-yl)methyl)amino)-1-oxopropan-2-yl)-4-phenylpyrrolidine-2-carboxamide Trifluoroacetate salt (1417)

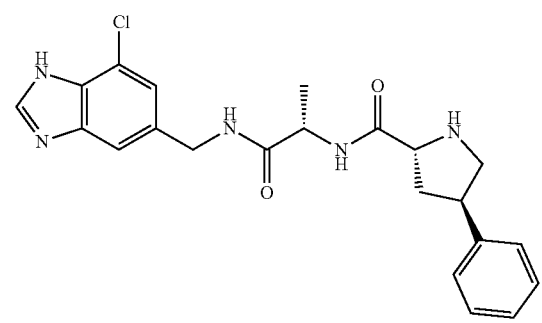

(1417)

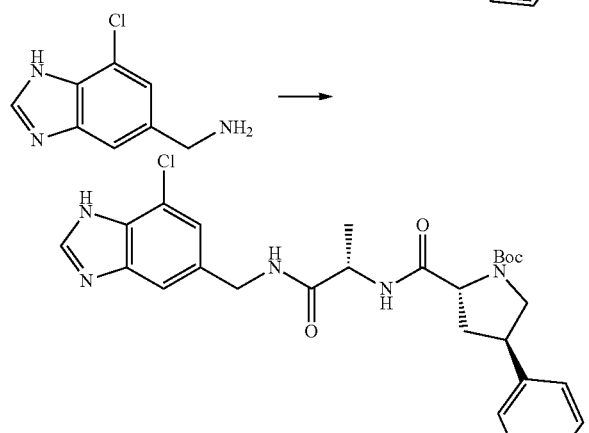

Step 1: tert-Butyl (2R,4R)-2-(((S)-1-(((7-chloro-1H-benzo[d]imidazol-5-yl)methyl)amino)-1-oxopropan-2-yl)carbamoyl)-4-phenylpyrrolidine-1-carboxylate (102 mg, 92% yield) was synthesized from 1-(7-chloro-1H-benzimidazole-5-yl)methanamine (50 mg, 0.28 mmol) according to the procedure for compound (1358), step 2.

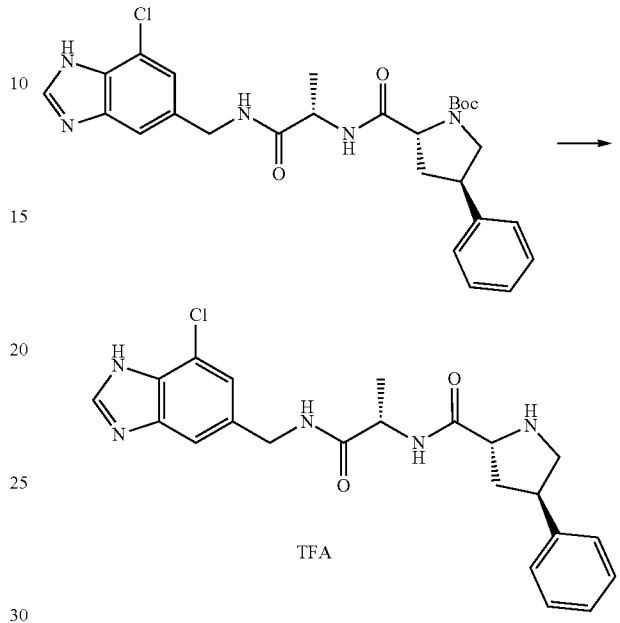

Step 2: Deprotection of tert-butyl (2R,4R)-2-(((S)-1-(((7-chloro-1H-benzo[d]imidazol-5-yl)methyl)amino)-1-oxopropan-2-yl)carbamoyl)-4-phenylpyrrolidine-1-carboxylate (102 mg, 0.19 mmol) was conducted according to the procedure for compound (1260), step 4 except that the final product was purified using reverse-phase HPLC.

Example 221. Preparation of (2R,4R)—N—((S)-1-(((7-Chloro-2-methyl-1H-benzo[d]imidazol-5-yl)methyl)amino)-1-oxopropan-2-yl)-4-phenylpyrrolidine-2-carboxamide Trifluoroacetate salt (1418)

(1418)

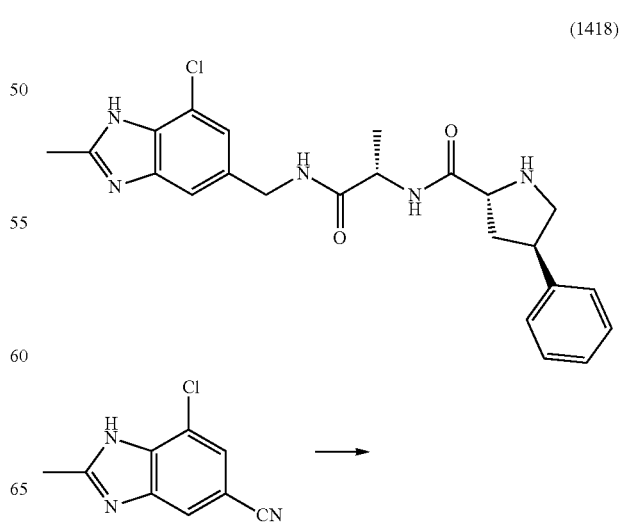

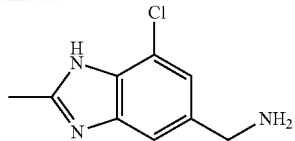

Step 1: (7-Chloro-2-methyl-1H-benzo[d]imidazol-5-yl)methanamine was synthesized from 7-chloro-2-methyl-1H-benzo[d]imidazole-5-carbonitrile (100 mg, 0.52 mmol) according to the procedure for compound (1358), step 1.

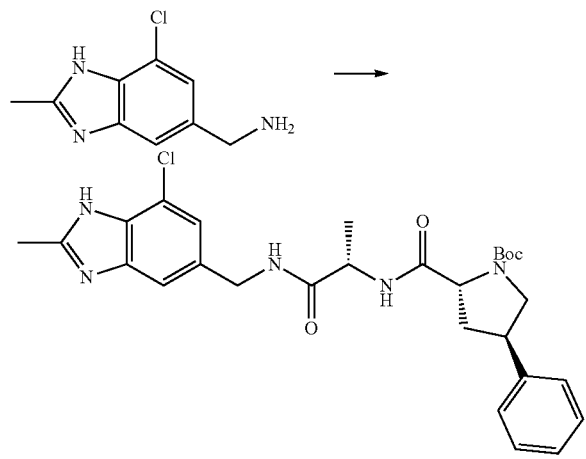

Step 2: tert-Butyl (2R,4R)-2-(((S)-1-(((7-chloro-2-methyl-1H-benzo[d]imidazol-5-yl)methyl)amino)-1-oxopropan-2-yl)carbamoyl)-4-phenylpyrrolidine-1-carboxylate (98 mg, 35% for 2 steps) was synthesized from (7-Chloro-2-methyl-1H-benzo[d]imidazol-5-yl)methanamine (102 mg, 0.52 mmol) according to the procedure for compound (1358), step 2.

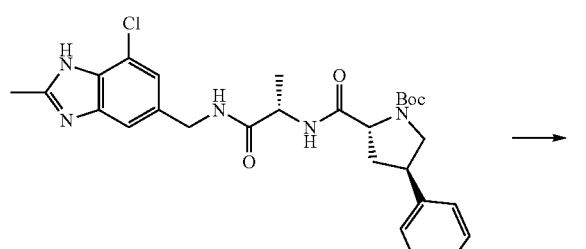

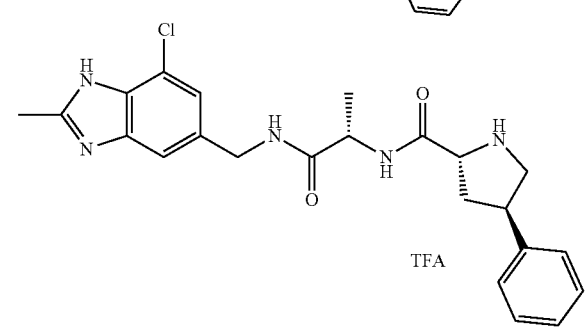

Step 3: Deprotection of tert-butyl (2R,4R)-2-(((S)-1-(((7-chloro-2-methyl-1H-benzo[d]imidazol-5-yl)methyl)amino)-1-oxopropan-2-yl)carbamoyl)-4-phenylpyrrolidine-1-carboxylate (98 mg, 0.18 mmol) was conducted according to the procedure for compound (1260), step 4 except that the final product was purified using reverse-phase HPLC.

Example 222. Preparation of (2R,4S)—N—((S)-1-((5-Chloro-2-(1H-tetrazol-1-yl)benzyl)amino)-1-oxopropan-2-yl)-4-(3,5-dimethoxybenzyl)pyrrolidine-2-carboxamide Trifluoroacetate salt (1419)

(1419)

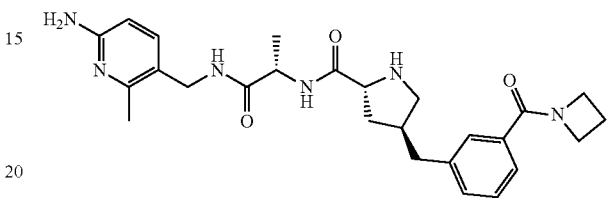

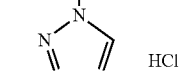

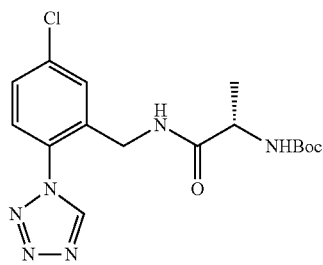

Step 1: tert-Butyl (S)-(1-((5-chloro-2-(1H-tetrazol-1-yl)benzyl)amino)-1-oxopropan-2-yl)carbamate (3.54 g, 76% yield) was synthesized from 5-chloro-2-(1H-tetrazole-1-yl)benzenemethamine (3.0 g, 12.2 mmol) according to the procedure for compound (1259), step 3.

585
-continued

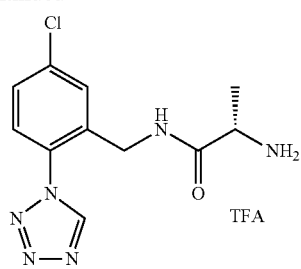

Step 2: Deprotection of tert-butyl (S)-(1-((5-chloro-2-(1H-tetrazol-1-yl)benzyl)amino)-1-oxopropan-2-yl)carbamate (3.54 g, 9.3 mmol) was conducted according to the procedure for compound (1259), step 2.

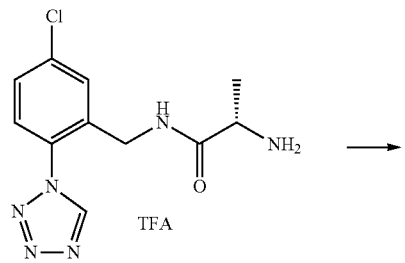

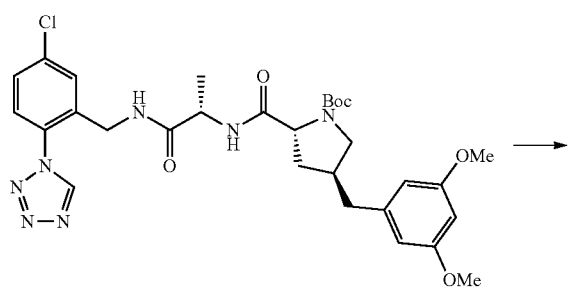

Step 3: tert-Butyl (2R,4S)-2-(((S)-1-((5-chloro-2-(1H-tetrazol-1-yl)benzyl)amino)-1-oxopropan-2-yl)carbamoyl)-4-(3,5-dimethoxybenzyl)pyrrolidine-1-carboxylate (85 mg, 76% yield) was synthesized from (S)-2-amino-N-(5-chloro-2-(1H-tetrazol-1-yl)benzyl)propenamide trifluoroacetate salt (99 mg, 0.23 mmol) according to the procedure for compound (1358), step 2.

586
-continued

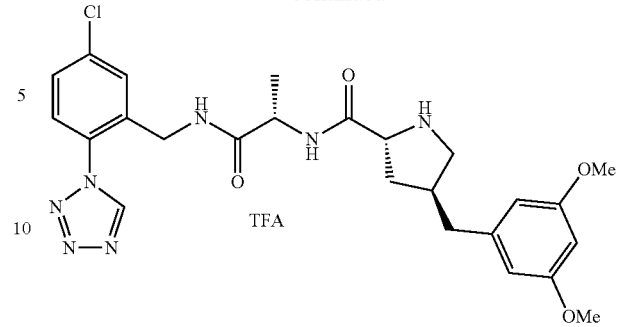

Step 4: Deprotection of tert-butyl (2R,4S)-2-(((S)-1-((5-chloro-2-(1H-tetrazol-1-yl)benzyl)amino)-1-oxopropan-2-yl)carbamoyl)-4-(3,5-dimethoxybenzyl)pyrrolidine-1-carboxylate (85 mg, 0.14 mmol) was conducted according to the procedure for compound (1260), step 4 except that the final product was purified using reverse-phase HPLC.

Example 223. Preparation of (2R,4S)—N—((S)-1-(((6-Amino-2-methylpyridin-3-yl)methyl)amino)-1-oxopropan-2-yl)-4-(3-(azetidine-1-carbonyl)benzyl)pyrrolidine-2-carboxamide Di-trifluoroacetate salt (1420)

(1420)

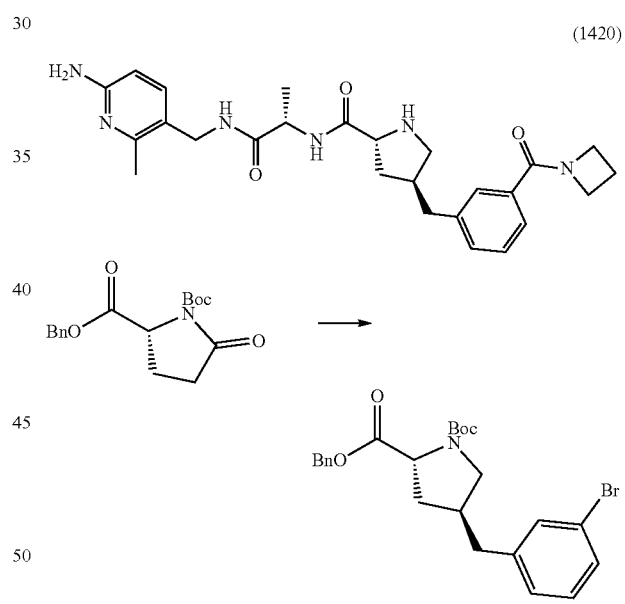

Step 1: 2-Benzyl 1-(tert-butyl) (2R,4S)-4-(3-bromobenzyl)pyrrolidine-1,2-dicarboxylate was synthesized according to the procedures for compound (1304), step 1 to step 3.

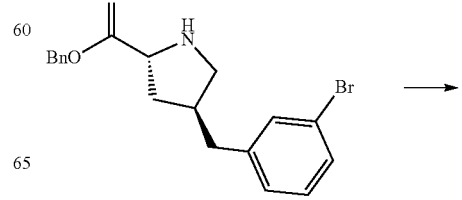

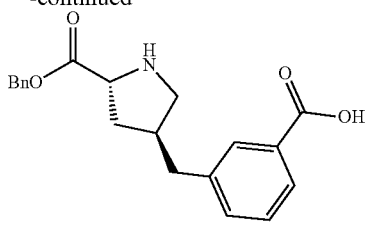

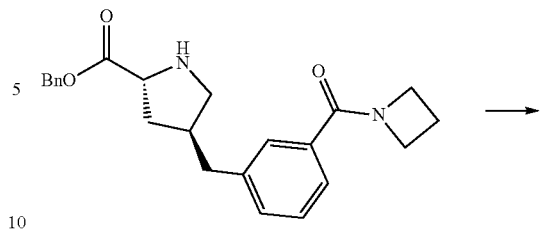

Step 2: A 25 mL vial equipped with a stir bar was charged with (CO$_2$H·H$_2$O)$_2$ (80 mg, 0.63 mmol), Pd(OAc)$_2$ (1 mg, 0.0042), xantphos (2.5 mg, 0.0042), benzyl (2R,4S)-4-(3-bromobenzyl)pyrrolidine-2-carboxylate (200 mg, 0.42 mmol), Ac$_2$O (60 µL, 0.633 mmol), DIEA (0.11 mL, 0.63 mmol), and DMF (2.0 mL) in air. The tube was quickly sealed with a Teflon® high pressure valve, frozen in liquid nitrogen, evacuated and backfilled with N$_2$ (5 times). After the reaction mixture was stirred in a preheated oil bath (100° C.) for 6 h, it was allowed to cool down to ambient temperature. The reaction mixture was diluted with EtOAc (10 mL), acidified with 2 M HCl (5 mL, once), and washed with brine (5 mL, twice). The organic phase was dried over anhydrous Na$_2$SO$_4$ and concentrated in vacuo to afford 3-(((3S,5R)-5-((benzyloxy)carbonyl)pyrrolidin-3-yl)methyl)benzoic acid (45 mg, 25% yield) that was directly used in the next step without further purification.

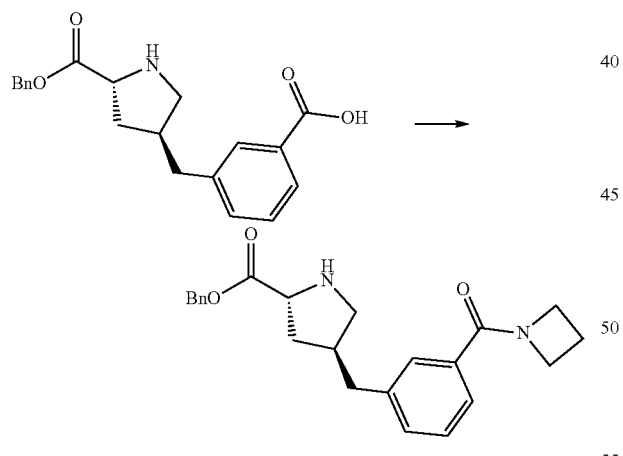

Step 3: To a stirred solution of 3-(((3S,5R)-5-((benzyloxy)carbonyl)pyrrolidin-3-yl)methyl)benzoic acid (45 mg, 0.10 mmol) and triethylamine (0.10 mL, 0.70 mmol) in CH$_2$Cl$_2$ (1 mL) at 0° C. was added oxalyl chloride (0.34 µL, 0.40 mmol), azetidine (30 mg, 0.50 mmol) followed by DMF (2 drops) under Ar atm. The reaction mixture was stirred at ambient temperature overnight and the solvents were removed under reduced pressure. The residue was purified by chromatography (EtOAc-hexanes) to afford benzyl (2R,4S)-4-(3-(azetidine-1-carbonyl)benzyl)pyrrolidine-2-carboxylate (31 mg, 61% yield).

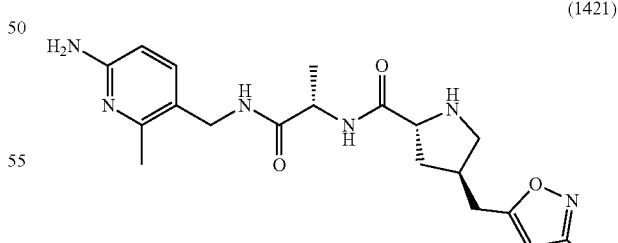

Step 4: (2R,4S)—N—((S)-1-(((6-Amino-2-methylpyridin-3-yl)methyl)amino)-1-oxopropan-2-yl)-4-(3-(azetidine-1-carbonyl)benzyl)pyrrolidine-2-carboxamide di-trifluoroacetate salt was synthesized according to the procedures for compound (1304), step 4 to step 8, except that the final product was purified using reverse-phase HPLC.

Example 224. Preparation of (2R,4R)—N—((S)-1-(((6-Amino-2-methylpyridin-3-yl)methyl)amino)-1-oxopropan-2-yl)-4-((3-bromoisoxazol-5-yl)methyl)pyrrolidine-2-carboxamide Di-trifluoroacetate salt (1421)

(1421)

(2R,4R)—N—((S)-1-(((6-Amino-2-methylpyridin-3-yl)methyl)amino)-1-oxopropan-2-yl)-4-((3-bromoisoxazol-5-yl)methyl)pyrrolidine-2-carboxamide di-trifluoroacetate salt was synthesized according to the procedures for compound (1328), except that the final product was purified using reverse-phase HPLC.

Example 225. Preparation of (2R,4S)—N—((S)-1-(((6-Amino-2-methylpyridin-3-yl)methyl)amino)-1-oxopropan-2-yl)-4-(3,4-dichlorobenzyl)pyrrolidine-2-carboxamide Dihydrochloride (1422)

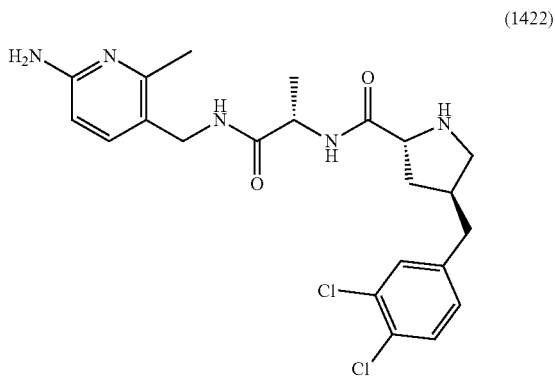 [SMILES: Cc1nc(N)ccc1CNC(=O)[C@H](C)NC(=O)[C@H]1C[C@H](Cc2ccc(Cl)c(Cl)c2)CN1]

(1422)

(2R,4S)—N—((S)-1-(((6-Amino-2-methylpyridin-3-yl)methyl)amino)-1-oxopropan-2-yl)-4-(3,4-dichlorobenzyl)pyrrolidine-2-carboxamide dihydrochloride was synthesized according to the procedures for compound (1304), except that the benzyl deprotection (Step 4) was done by following LiOH conditions as described for compound (1399).

Example 226. Preparation of (2R,4S)—N—((S)-1-(((6-Amino-2-methylpyridin-3-yl)methyl)amino)-1-oxopropan-2-yl)-4-((4-fluoronaphthalen-1-yl)methyl)pyrrolidine-2-carboxamide Dihydrochloride (1423)

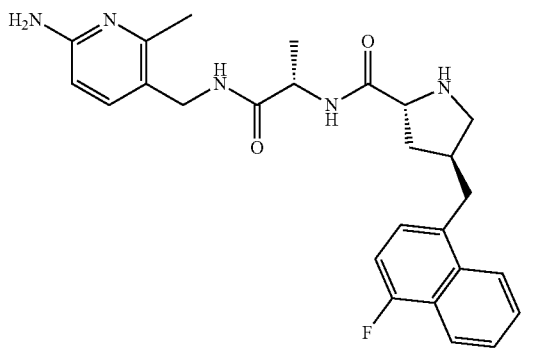

(1423)

(2R,4S)—N—((S)-1-(((6-Amino-2-methylpyridin-3-yl)methyl)amino)-1-oxopropan-2-yl)-4-((4-fluoronaphthalen-1-yl)methyl)pyrrolidine-2-carboxamide dihydrochloride was synthesized according to the procedures for compound (1304).

Example 227. Preparation of (2R,4S)—N—((S)-1-(((6-Amino-2-methylpyridin-3-yl)methyl)amino)-1-oxopropan-2-yl)-4-(3,5-bis(trifluoromethyl)benzyl)pyrrolidine-2-carboxamide Di-trifluoroacetate salt (1424)

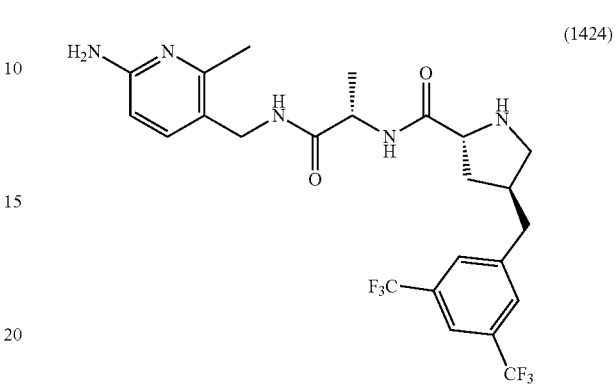

(1424)

(2R,4S)—N—((S)-1-(((6-Amino-2-methylpyridin-3-yl)methyl)amino)-1-oxopropan-2-yl)-4-(3,5-bis(trifluoromethyl)benzyl)pyrrolidine-2-carboxamide di-trifluoroacetate salt was synthesized according to the procedures for compound (1304), except for the final Boc deprotection:

To tert-butyl (2R,4S)-2-(((S)-1-(((6-amino-2-methylpyridin-3-yl)methyl)amino)-1-oxopropan-2-yl)carbamoyl)-4-(3,5-bis(trifluoromethyl)benzyl)pyrrolidine-1-carboxylate (27.7 mg, 0.04 mmol) in $CH_2Cl_2$ (200 µL, 0.2 M) was added TFA (67 µL, 0.88 mmol) with stirring at ambient temperature while monitoring for the consumption of starting material (1-2 h). The solution was evaporated to dryness and was purified using reverse-phase HPLC to yield (2R,4S)—N—((S)-1-(((6-amino-2-methylpyridin-3-yl)methyl)amino)-1-oxopropan-2-yl)-4-(3,5-bis(trifluoromethyl)benzyl)pyrrolidine-2-carboxamide di-trifluoroacetate salt (12.8 mg, 39% yield) as a white solid.

Example 228. Preparation of (2R,4R)—N—((S)-1-(((3-Amino-1H-indazol-6-yl)methyl)amino)-1-oxopropan-2-yl)-4-phenylpyrrolidine-2-carboxamide Trifluoroacetate salt (1425)

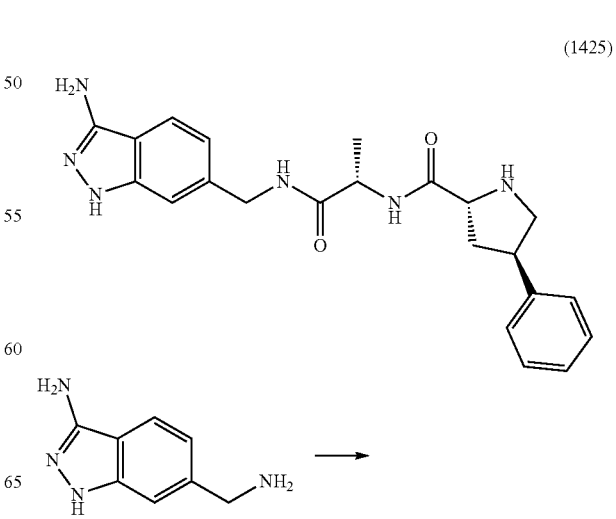

(1425)

-continued

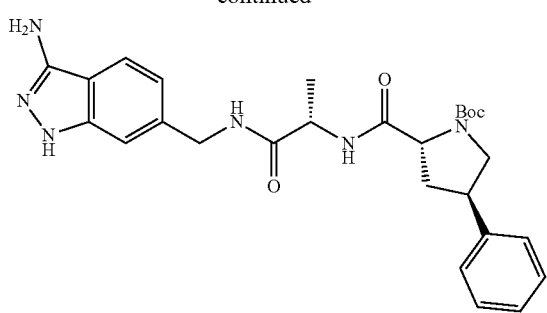

Step 1: tert-Butyl (2R,4R)-2-(((S)-1-(((3-amino-1H-indazol-6-yl)methyl)amino)-1-oxopropan-2-yl)carbamoyl)-4-phenylpyrrolidine-1-carboxylate (147 mg, 88% yield) was synthesized from 6-(aminomethyl)-1H-indazol-3-amine (70 mg, 0.43 mmol) according to the procedure for compound (1358), step 2.

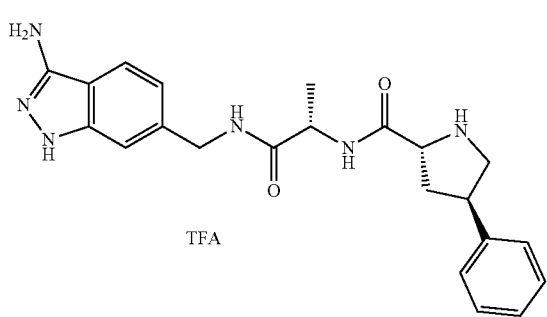

Step 2: Deprotection of tert-butyl (2R,4R)-2-(((S)-1-(((3-amino-1H-indazol-6-yl)methyl)amino)-1-oxopropan-2-yl)carbamoyl)-4-phenylpyrrolidine-1-carboxylate (147 mg, 0.29 mmol) was conducted according to the procedure for compound (1260), step 4 except that the final product was purified using reverse-phase HPLC.

Example 229. Preparation of (2R,4S)—N—((S)-1-(((5-Chloro-2-(1H-tetrazol-1-yl)benzyl)amino)-1-oxopropan-2-yl)-4-phenylpiperidine-2-carboxamide Trifluoroacetate (1426)

(1426)

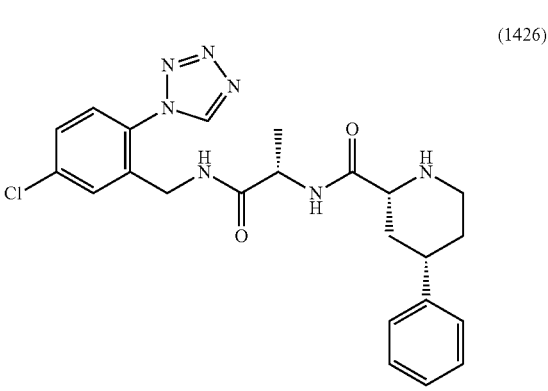

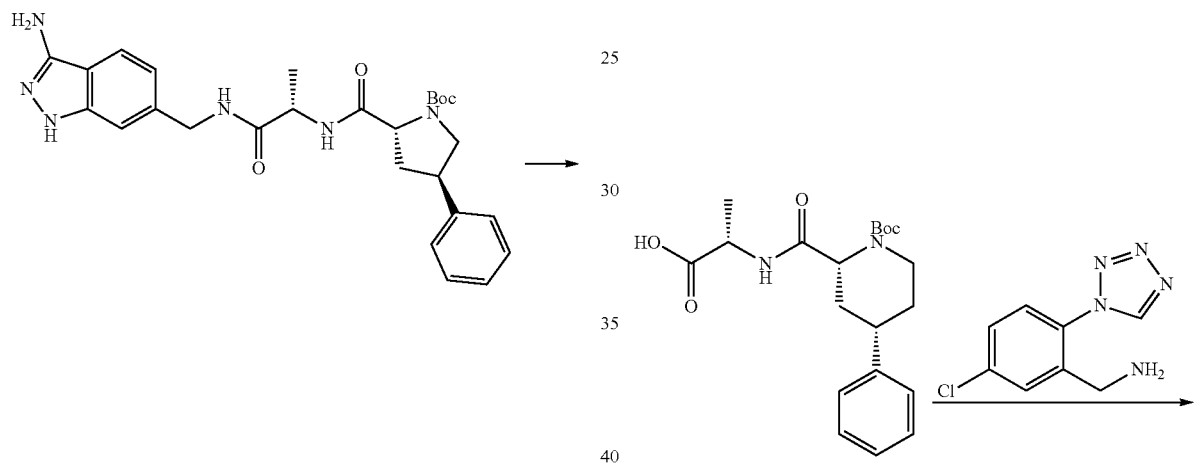

Steps 1-2: The title compound was synthesized as a white powder (11 mg, 16% yield over two steps) according to steps 1-2 of the procedure for compound (1246) using the appropriate starting materials, except with purification by prep-HPLC (ACN/H$_2$O+TFA).

Example 230. Preparation of (2R,4S)—N—((S)-1-(((6-Amino-2-methylpyridin-3-yl)methyl)amino)-1-oxopropan-2-yl)-4-(4-bromobenzyl)pyrrolidine-2-carboxamide Di-trifluoroacetate salt (1427)

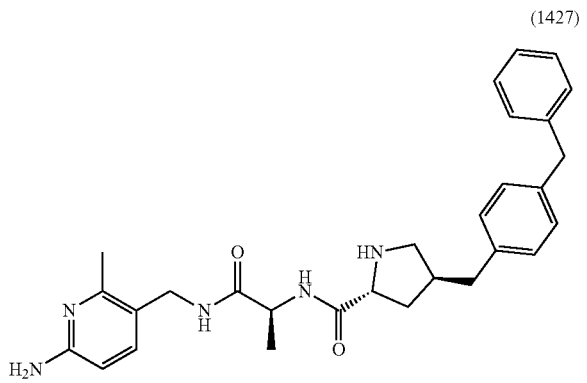 [SMILES: Cc1nc(N)ccc1CNC(=O)[C@H](C)NC(=O)[C@H]1C[C@H](Cc2ccc(Cc3ccccc3)cc2)CN1]

Step 1: (2R,4S)—N—((S)-1-(((6-Amino-2-methylpyridin-3-yl)methyl)amino)-1-oxopropan-2-yl)-4-(4-bromobenzyl)pyrrolidine-2-carboxamide was synthesized according to the procedure for compound (1304) (30% yield in 3 steps).

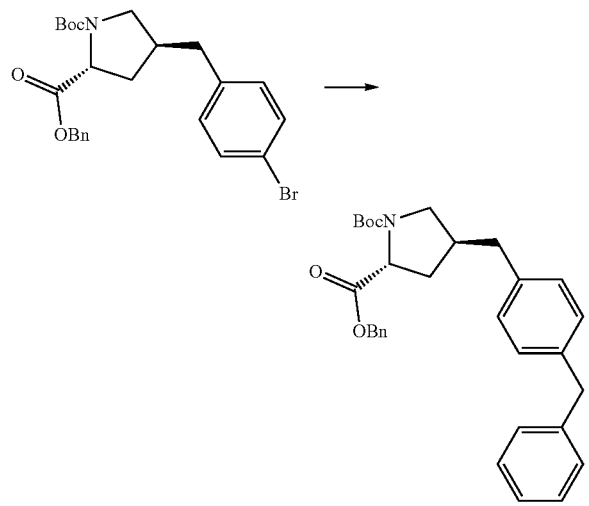

Step 2: A solution of (2R,4S)—N—((S)-1-(((6-amino-2-methylpyridin-3-yl)methyl)amino)-1-oxopropan-2-yl)-4-(4-bromobenzyl)pyrrolidine-2-carboxamide (503.3 mg, 1.06 mmol) in THF (11 mL) and water (1.1 mL) was treated with potassium benzyltrifluoroborate (287.0 mg, 1.45 mmol), CsCO₃ (1.05 g, 3.22 mmol), and PdCl₂(pddf) (78 mg, 0.11 mmol). After purging with N₂, the reaction was heated at 90° C. for 16 h and quenched with water. The reaction mixture was extracted with EtOAc (3 times). The organic layers were combined, washed with brine, dried (Na₂SO₄), vacuum filtered, and evaporated under vacuum. The crude product was dissolved in CH₂Cl₂ and adsorbed on silica gel. Purification by chromatography (0-100% EtOAc-hexanes) afforded 2-benzyl 1-(tert-butyl) (2R,4S)-4-(4-benzylbenzyl)pyrrolidine-1,2-dicarboxylate (425.8 mg, 83% yield).

Step 3: Deprotection of 2-benzyl 1-(tert-butyl) (2R,4S)-4-(4-benzylbenzyl)pyrrolidine-1,2-dicarboxylate according to the procedure for compound (1304), step 4 afforded the crude (2R,4S)-4-(4-benzylbenzyl)-1-(tert-butoxycarbonyl)pyrrolidine-2-carboxylic acid.

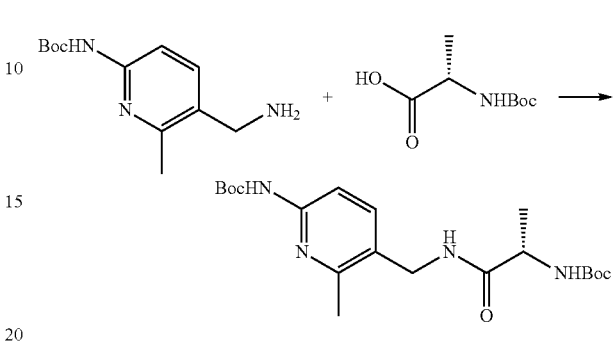

Step 4: tert-Butyl (S)-(1-(((6-((tert-butoxycarbonyl)amino)-2-methylpyridin-3-yl)methyl)amino)-1-oxopropan-2-yl)carbamate was obtained according to the procedure for compound (1304), step 5 (87% yield).

Step 5: Deprotection of tert-butyl (S)-(1-(((6-((tert-butoxycarbonyl)amino)-2-methylpyridin-3-yl)methyl)amino)-1-oxopropan-2-yl)carbamate was done according to the procedure for compound (1304), step 6 except the crude product was purified by chromatography (0-10% 7 N NH₃ in MeOH—CH₂Cl₂) afforded (S)-2-amino-N-((6-amino-2-methylpyridin-3-yl)methyl)propanamide (92% yield).

Step 6: (S)-2-Amino-N-((6-amino-2-methylpyridin-3-yl)methyl)propanamide was coupled with the crude (2R,4S)-4-(4-benzylbenzyl)-1-(tert-butoxycarbonyl)pyrrolidine-2-carboxylic acid according to the procedure for compound 1119, step 1 to afford tert-butyl (2R,4S)-2-(((S)-1-(((6-amino-2-methylpyridin-3-yl)methyl)amino)-1-oxopropan-2-yl)carbamoyl)-4-(4-benzylbenzyl)pyrrolidine-1-carboxylate.

Step 7: A solution of tert-butyl (2R,4S)-2-(((S)-1-(((6-amino-2-methylpyridin-3-yl)methyl)amino)-1-oxopropan-2-yl)carbamoyl)-4-(4-benzylbenzyl)pyrrolidine-1-carboxylate (45.0 mg, 0.0768 mmol) in CH₂Cl₂ (1.0 mL) and TES (50 µL) was treated with TFA (500 µL) at 0° C. The reaction was stirred at room temp for 2 h and concentrated under reduced pressure. The crude product was dissolved in CH₂Cl₂ and adsorbed on silica gel. Purification by chromatography (0-5% 7 N NH₃ in MeOH—CH₂Cl₂) afforded (2R,4S)—N—((S)-1-(((6-amino-2-methylpyridin-3-yl)methyl)amino)-1-oxopropan-2-yl)-4-(4-benzylbenzyl)pyrrolidine-2-carboxamide (33.0 mg, 88% yield).

Step 8: (2R,4S)—N—((S)-1-(((6-Amino-2-methylpyridin-3-yl)methyl)amino)-1-oxopropan-2-yl)-4-(4-benzylbenzyl)pyrrolidine-2-carboxamide di-trifluoroacetate salt was formed according to the procedure for compound (1368), step 2.

Example 231. Preparation of (2R,4S)—N—((S)-1-(((6-Amino-2-methylpyridin-3-yl)methyl)amino)-1-oxopropan-2-yl)-4-(4-cyanobenzyl)pyrrolidine-2-carboxamide Di-trifluoroacetate salt (1428)

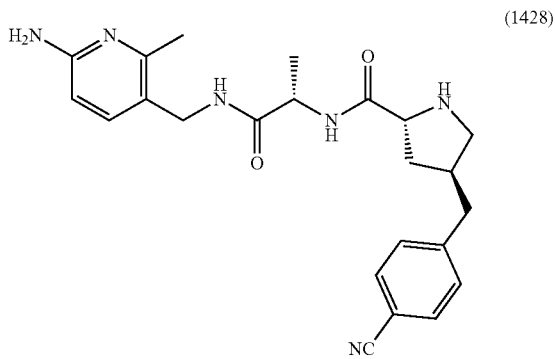 [SMILES: Cc1nc(N)ccc1CNC(=O)[C@H](C)NC(=O)[C@H]1C[C@H](Cc2ccc(C#N)cc2)CN1]

(2R,4S)—N—((S)-1-(((6-Amino-2-methylpyridin-3-yl)methyl)amino)-1-oxopropan-2-yl)-4-(4-cyanobenzyl)pyrrolidine-2-carboxamide di-trifluoroacetate salt was synthesized according to the procedures for compound (1424).

Example 232. Preparation of (2R,4S)—N—((S)-1-(((6-Amino-2-methylpyridin-3-yl)methyl)amino)-1-oxopropan-2-yl)-4-(3-cyanobenzyl)pyrrolidine-2-carboxamide Di-trifluoroacetate salt (1429)

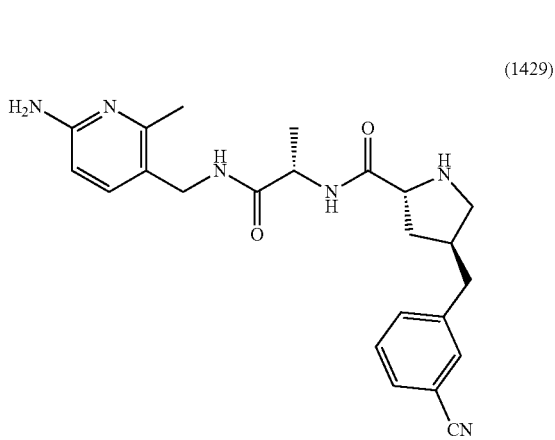 [SMILES: Cc1nc(N)ccc1CNC(=O)[C@H](C)NC(=O)[C@H]1C[C@H](Cc2cccc(C#N)c2)CN1]

(2R,4S)—N—((S)-1-(((6-Amino-2-methylpyridin-3-yl)methyl)amino)-1-oxopropan-2-yl)-4-(3-cyanobenzyl)pyrrolidine-2-carboxamide di-trifluoroacetate salt was synthesized according to the procedures for compound (1424).

Example 233. Preparation of (2R,4S)—N—((S)-1-(((6-Amino-2-methylpyridin-3-yl)methyl)amino)-1-oxopropan-2-yl)-4-(4-phenoxybenzyl)pyrrolidine-2-carboxamide Di-trifluoroacetate salt (1430)

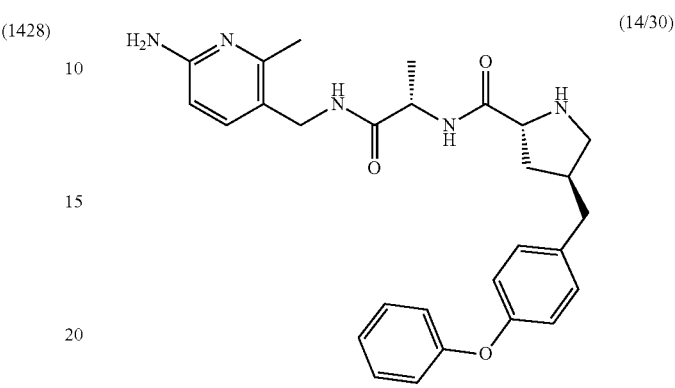

(2R,4S)—N—((S)-1-(((6-amino-2-methylpyridin-3-yl)methyl)amino)-1-oxopropan-2-yl)-4-(4-phenoxybenzyl)pyrrolidine-2-carboxamide di-trifluoroacetate salt was synthesized according to the procedures for compound (1424).

Example 234. Preparation of (2R,4S)—N—((S)-1-(((6-Amino-2-methylpyridin-3-yl)methyl)amino)-1-oxopropan-2-yl)-4-((4-cyanonaphthalen-1-yl)methyl)pyrrolidine-2-carboxamide Dihydrochloride (1431)

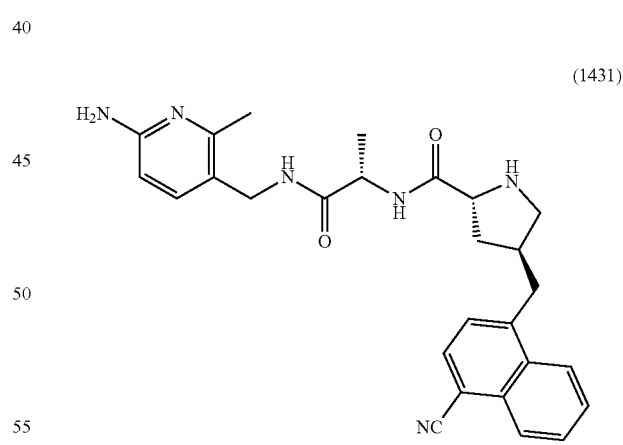

(2R,4S)—N—((S)-1-(((6-Amino-2-methylpyridin-3-yl)methyl)amino)-1-oxopropan-2-yl)-4-((4-cyanonaphthalen-1-yl)methyl)pyrrolidine-2-carboxamide dihydrochloride was synthesized according to the procedures for compound (1304).

597

Example 235. Preparation of (2R,4S)—N—((S)-1-(((6-Amino-2-methylpyridin-3-yl)methyl)amino)-1-oxopropan-2-yl)-4-((3-chloronaphthalen-1-yl)methyl)pyrrolidine-2-carboxamide Dihydrochloride (1432)

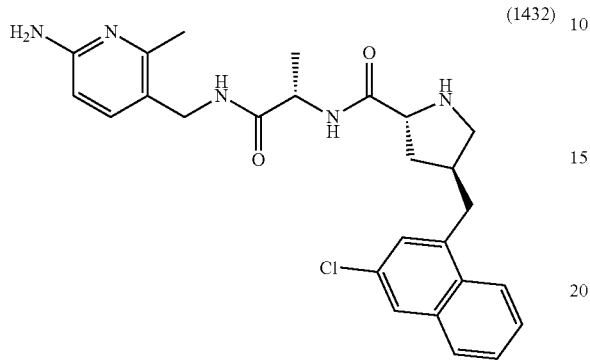
(1432)

(2R,4S)—N—((S)-1-(((6-Amino-2-methylpyridin-3-yl)methyl)amino)-1-oxopropan-2-yl)-4-((3-chloronaphthalen-1-yl)methyl)pyrrolidine-2-carboxamide dihydrochloride was synthesized according to the procedures for compound (1304), except that the benzyl deprotection (Step 4) was done by following LiOH conditions as described in compound (1399).

Example 236. Preparation of (2R,4S)—N—((S)-1-(((3-Chloro-1H-pyrrolo[2,3-b]pyridin-5-yl)methyl)amino)-1-oxopropan-2-yl)-4-phenylpiperidine-2-carboxamide (1433)

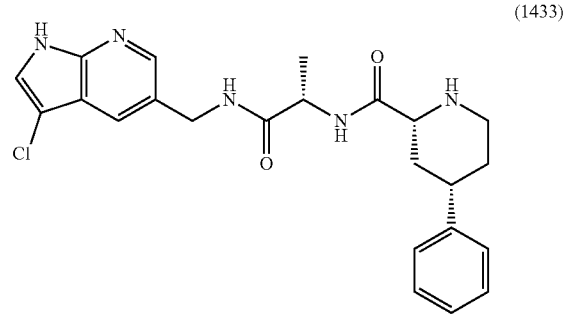
(1433)

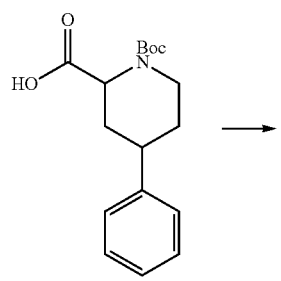

598

-continued

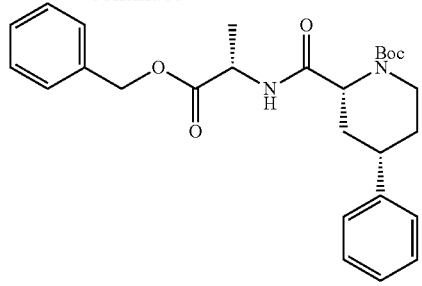

Step 1: To a solution of (2R,4S)-1-(tert-butoxycarbonyl)-4-phenylpiperidine-2-carboxylic acid (5.0 g, 16.4 mmol) in MeCN (300 mL, 0.05 M) was added HOBt (2.g, 3.77 mmol), DIEA (11.4 mL, 13.7 mmol), and EDC (2.8 g, 3.77 mmol). After stirring for 30 min at ambient temperature, benzyl L-alanine hydrochloride (814 mg, 18 mmol) was added and stirred for 16 h. The reaction mixture was conc and the residue was partitioned with EtOAc and 10% KHSO$_4$ solution. The organic layer was separated and washed with H$_2$O and sat. aq NaHCO$_3$. The organic layer was dried over anhyd Na$_2$SO$_4$ and conc under vacuum. The residue was purified by chromatography (0-20% EtOAc-hexanes) to give tert-butyl (2R,4S)-2-(((S)-1-(benzyloxy)-1-oxopropan-2-yl)carbamoyl)-4-phenylpiperidine-1-carboxylate (2.59 mg, 34% yield).

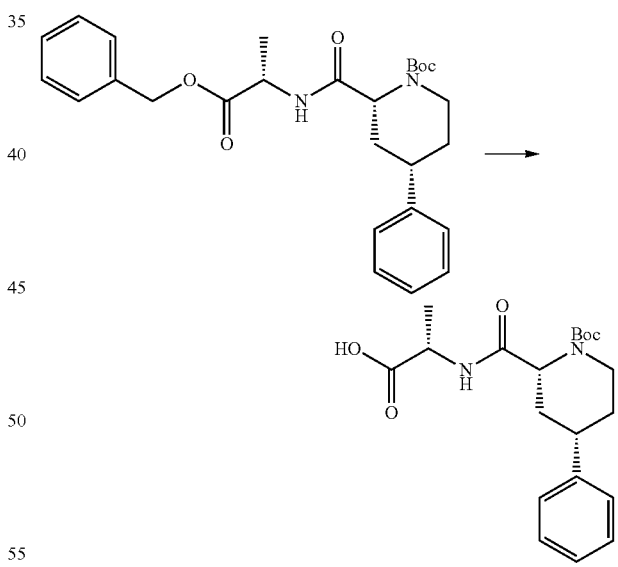

Step 2: A solution of tert-butyl (2R,4S)-2-(((S)-1-(benzyloxy)-1-oxopropan-2-yl)carbamoyl)-4-phenylpiperidine-1-carboxylate (2.59 mg, 5.54 mmol) was degassed with a stream of argon for 2 min. 10% Pd/C (130 mg) was added and a vacuum was pulled for 1 min. A balloon of H$_2$ was added and the reaction was monitored for the consumption of starting material for 1.5 h. The catalyst was removed by filtration and the solution was evaporated to give ((2R,4S)-1-(tert-butoxycarbonyl)-4-phenylpiperidine-2-carbonyl)-L-alanine (1.8 g, 86% yield).

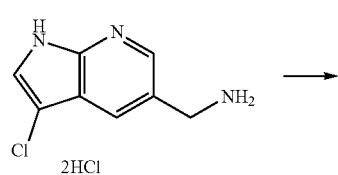

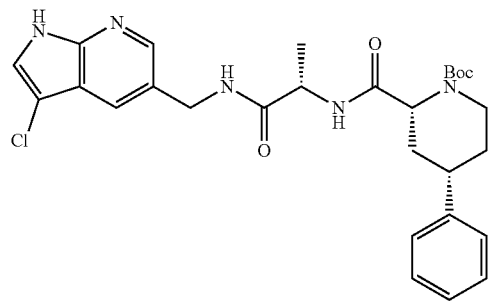

Step 3: tert-Butyl (2R,4S)-2-(((S)-1-(((3-chloro-1H-pyrrolo[2,3-b]pyridin-5-yl)methyl)amino)-1-oxopropan-2-yl)carbamoyl)-4-phenylpiperidine-1-carboxylate (75 mg, 93% yield) was synthesized from (3-chloro-1H-pyrrolo[2,3-b]pyridin-5-yl)methanamine dihydrochloride (50 mg, 0.2 mmol) and ((2R,4S)-1-(tert-butoxycarbonyl)-4-phenylpiperidine-2-carbonyl)-L-alanine (57 mg, 0.15 mmol) according to the procedure for compound (1358), step 2

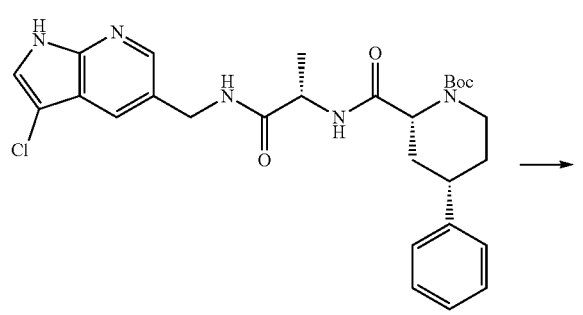

TFA

Step 4: Deprotection of tert-butyl (2R,4S)-2-(((S)-1-(((3-chloro-1H-pyrrolo[2,3-b]pyridin-5-yl)methyl)amino)-1-oxopropan-2-yl)carbamoyl)-4-phenylpiperidine-1-carboxylate (75 mg, 0.14 mmol) was conducted according to the procedure for compound (1260), step 4 except that the final product was purified using reverse-phase HPLC.

Example 237. Preparation of (2R,4R)—N—((S)-1-((Imidazo[1,2-a]pyridin-6-ylmethyl)amino)-1-oxopropan-2-yl)-4-phenylpyrrolidine-2-carboxamide Dihydrochloride (1434)

(1434)

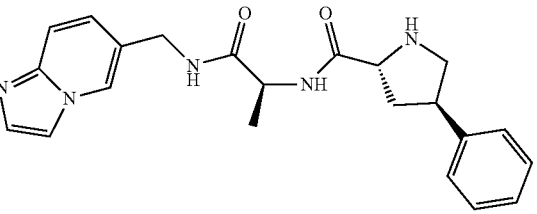

Step 1: ((2R,4R)-1-(tert-Butoxycarbonyl)-4-phenylpyrrolidine-2-carbonyl)-L-alanine was coupled to imidazo[1,2-a]pyridin-6-ylmethanamine dihydrochloride according to the procedure for (1280), step 4 to give tert-butyl (2R,4R)-2-(((S)-1-((imidazo[1,2-a]pyridin-6-ylmethyl)amino)-1-oxopropan-2-yl)carbamoyl)-4-phenylpyrrolidine-1-carboxylate (80 mg, 74% yield).

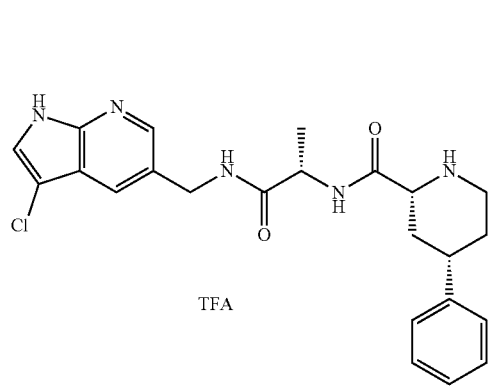

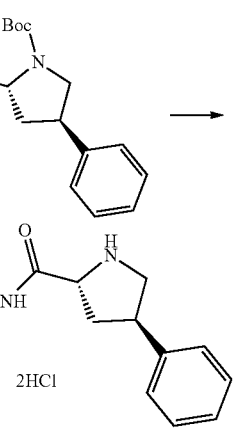

2HCl

Step 2: tert-Butyl (2R,4R)-2-(((S)-1-((imidazo[1,2-a]pyridin-6-ylmethyl)amino)-1-oxopropan-2-yl)carbamoyl)-4-phenylpyrrolidine-1-carboxylate was deprotected according to the procedure for compound (1323), step 3 to give (2R,4R)—N—((S)-1-((imidazo[1,2-a]pyridin-6-ylmethyl)

amino)-1-oxopropan-2-yl)-4-phenylpyrrolidine-2-carboxamide dihydrochloride (86 mg, quant. yield).

Example 238. Preparation of (2R,4S)—N—((S)-1-(((6-Amino-2-methylpyridin-3-yl)methyl)amino)-1-oxopropan-2-yl)-4-(3,5-dichlorobenzyl)pyrrolidine-2-carboxamide Dihydrochloride (1435)

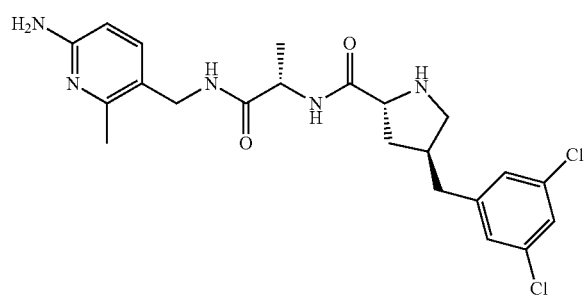

(1435)

(2R,4S)—N—((S)-1-(((6-Amino-2-methylpyridin-3-yl)methyl)amino)-1-oxopropan-2-yl)-4-(3,5-dichlorobenzyl)pyrrolidine-2-carboxamide dihydrochloride was synthesized according to the procedures for compound (1328).

Example 239. Preparation of (2R,4S)-4-Benzyl-N—((S)-1-((5-bromo-3-methyl-2-(1H-tetrazol-1-yl)benzyl)amino)-1-oxopropan-2-yl)pyrrolidine-2-carboxamide Trifluoroacetate (1436) and (2R,4S)-4-Benzyl-N—((S)-1-((3-methyl-2-(2H-tetrazol-2-yl)benzyl)amino)-1-oxopropan-2-yl)pyrrolidine-2-carboxamide (1437)

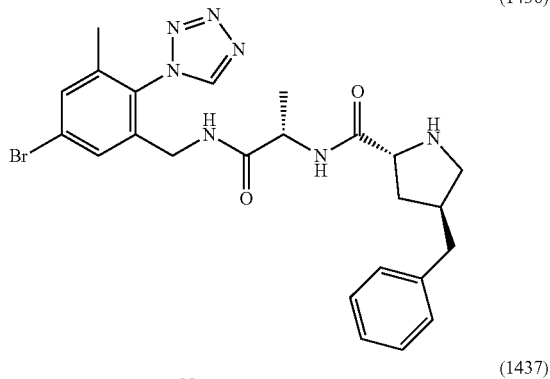

(1436)

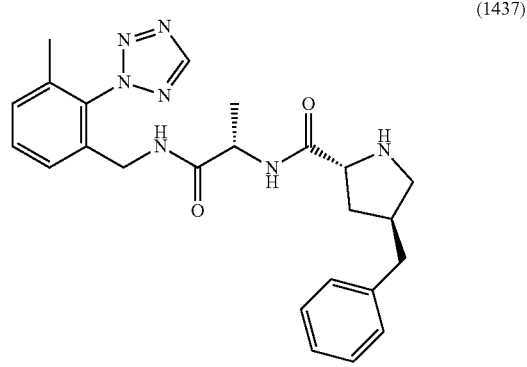

(1437)

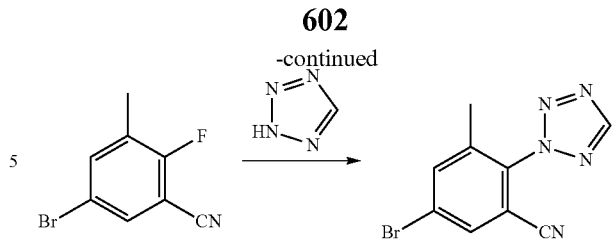

Step 1: A 100 mL round bottom flask was charged with 5-bromo-2-fluoro-3-methylbenzonitrile (428 mg, 2 mmol), 1H-tetrazole (0.45 M in CAN; 5 mL), $K_2CO_3$ (318 mg, 2.3 mmol), and DMF (15 mL), then sealed under Ar and stirred at 80° C. for 72 h. Reaction mixture was then diluted with EtOAc, washed with $H_2O$, 5% aq. LiCl and brine. The organic layer was dried over $Na_2SO_4$, concentrated and purified by chromatography (20-60% EtOAc/hexanes) to give 5-bromo-3-methyl-2-(2H-tetrazol-2-yl)benzonitrile as a white solid (78 mg, 80% yield based on recovered starting material).

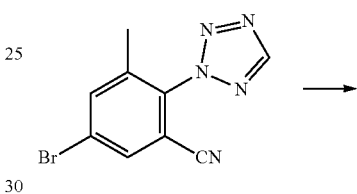

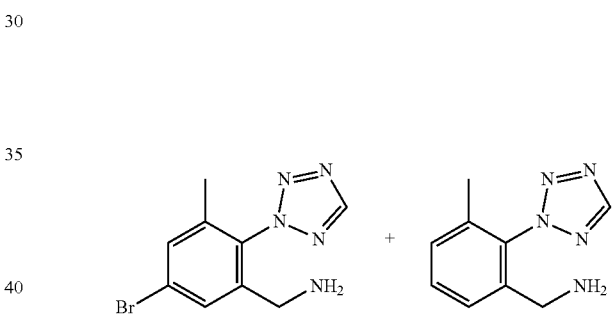

Step 2: A solution of 5-bromo-3-methyl-2-(2H-tetrazol-2-yl)benzonitrile (49 mg, 0.19 mmol) in 7 M $NH_3$ in MeOH (5 mL) was degassed with an Ar balloon. Raney nickel (~40 mg) was added and a vacuum was pulled for 0.5 min prior to backfilling with a balloon of $H_2$. The reaction mixture was stirred for 16 h at ambient temperature. Upon completion, the catalyst was removed by filtration through diatomaceous earth and the solution concentrated in vacuo to give an inseparable mixture of (5-bromo-3-methyl-2-(2H-tetrazol-2-yl)phenyl)methanamine and (3-methyl-2-(2H-tetrazol-2-yl)phenyl)methanamine.

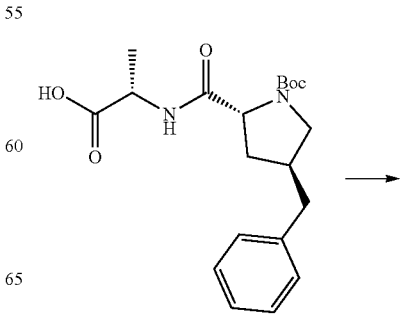

603
-continued

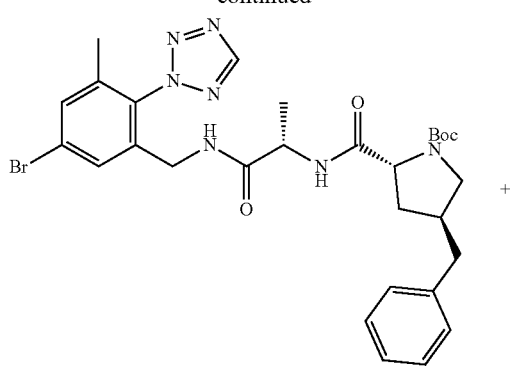

+

Step 3: DCC-mediated coupling was accomplished according to step 3 of the procedure for compound (1313) using the appropriate starting materials. Purification by chromatography (EtOAc/hexanes) furnished both tert-butyl (2R,4S)-4-benzyl-2-(((S)-1-((5-bromo-3-methyl-2-(2H-tetrazol-2-yl)benzyl)amino)-1-oxopropan-2-yl)carbamoyl)pyrrolidine-1-carboxylate (44 mg, 35% yield) and tert-butyl (2R,4S)-4-benzyl-2-(((S)-1-((3-methyl-2-(2H-tetrazol-2-yl)benzyl)amino)-1-oxopropan-2-yl)carbamoyl)pyrrolidine-1-carboxylate (66 mg, 60% yield).

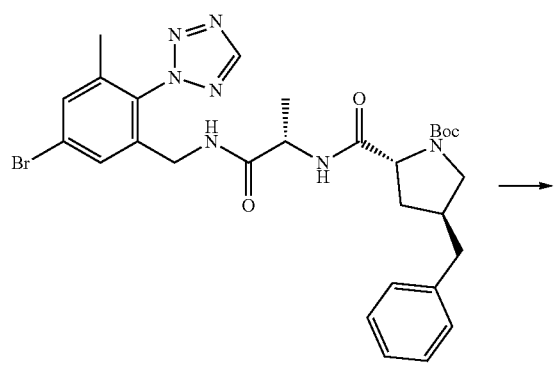

604
-continued

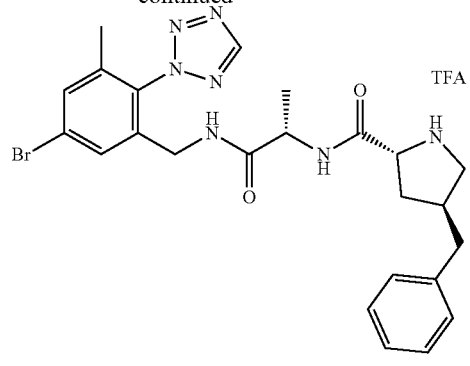

Step 4: Removal of the Boc group from tert-butyl (2R,4S)-4-benzyl-2-(((S)-1-((5-bromo-3-methyl-2-(2H-tetrazol-2-yl)benzyl)amino)-1-oxopropan-2-yl)carbamoyl)pyrrolidine-1-carboxylate was achieved using procedure from step 4 for compound (1313) except with purification by prep-HPLC (ACN/H$_2$O+TFA) to yield the title compound as a beige powder (7 mg, 19% yield).

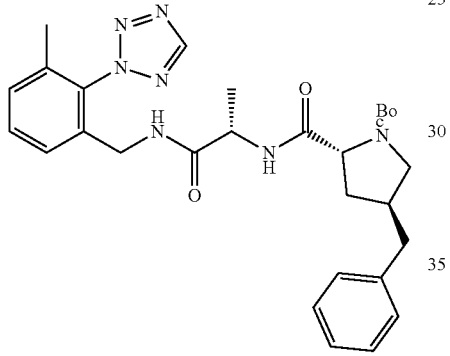

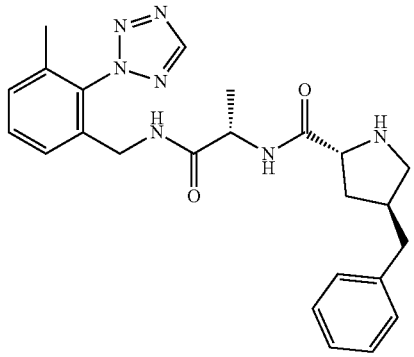

Step 4: Removal of the Boc group from tert-butyl (2R,4S)-4-benzyl-2-(((S)-1-((3-methyl-2-(2H-tetrazol-2-yl)benzyl)amino)-1-oxopropan-2-yl)carbamoyl)pyrrolidine-1-carboxylate was achieved using procedure from step 4 for compound (1313) except with purification by prep HPLC (ACN/H$_2$O+TFA) to yield the title compound as a white powder (7 mg, 13% yield).

Example 240. Preparation of (S)—N-((6-Amino-2-methylpyridin-3-yl)methyl)-1-((2R,4S)-4-(4-bromobenzyl)pyrrolidine-2-carbonyl)azetidine-2-carboxamide Di-trifluoroacetate salt (1438)

(1438)

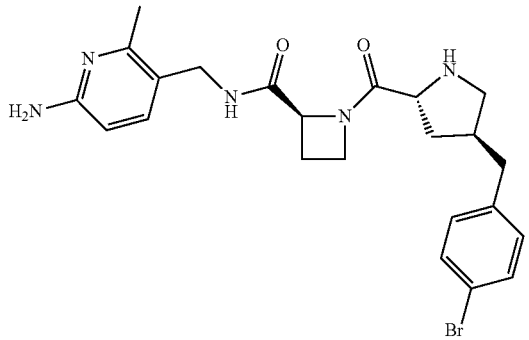

(S)—N-((6-Amino-2-methylpyridin-3-yl)methyl)-1-((2R,4S)-4-(4-bromobenzyl)pyrrolidine-2-carbonyl)azetidine-2-carboxamide di-trifluoroacetate salt was synthesized according to the procedures for compound (1451), except that in step 5, a solution of 6 N HCl in iPrOH was used to deprotect the Boc group and the amide coupling was performed using HATU.

To (S)—N-((6-amino-2-methylpyridin-3-yl)methyl)azetidine-2-carboxamide hydrochloride (27 mg, 0.11 mmol), (2R,4S)-4-(4-bromobenzyl)-1-(tert-butoxycarbonyl)pyrrolidine-2-carboxylic acid (0.11 mmol), DIEA (100 μL, 0.55 mmol) in DMF (370 μL, 0.3 M) was added a HATU (63 mg, 0.17 mmol) with stirring at ambient temperature while monitoring for the consumption of starting material (16 h). The solution was diluted with EtOAc, extracted with sat. aq NH$_4$C$_1$. The aqueous layer was extracted 2 additional times, then the organic layer was washed with H$_2$O, then brine, dried over Na$_2$SO$_4$ and evaporated to dryness. The resulting residue was purified on an amine column using EtOAc, then MeOH/CH$_2$Cl$_2$ to yield tert-butyl (2R,4S)-2-((S)-2-(((6-amino-2-methylpyridin-3-yl)methyl)carbamoyl)azetidine-1-carbonyl)-4-(4-bromobenzyl)pyrrolidine-1-carboxylate (33 mg, 54% yield) as an off-white film.

Example 241. Preparation of 4-((2R,4S)-2-(((S)-1-(((6-Amino-2-methylpyridin-3-yl)methyl)amino)-1-oxopropan-2-yl)carbamoyl)-4-phenylpiperidin-1-yl)butanoic acid Trifluoroacetate salt (1439)

(1439)

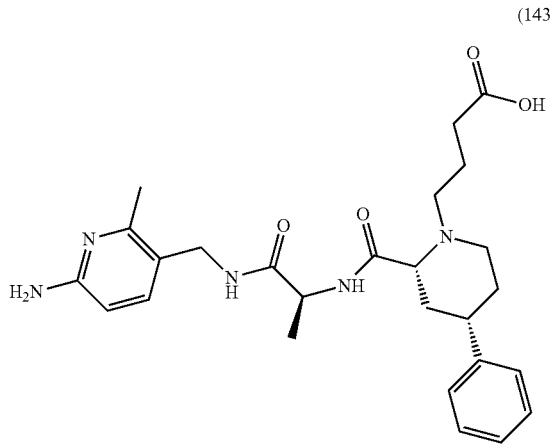

4-((2R,4S)-2-(((S)-1-(((6-Amino-2-methylpyridin-3-yl)methyl)amino)-1-oxopropan-2-yl)carbamoyl)-4-phenylpiperidin-1-yl)butanoic acid trifluoroacetate salt was synthesized according to the procedures for compound (1411) using the corresponding bromoester.

Example 242. Preparation of Ethyl 4-((2R,4S)-2-(((S)-1-(((6-amino-2-methylpyridin-3-yl)methyl)amino)-1-oxopropan-2-yl)carbamoyl)-4-phenylpiperidin-1-yl)butanoate (1439)

(1440)

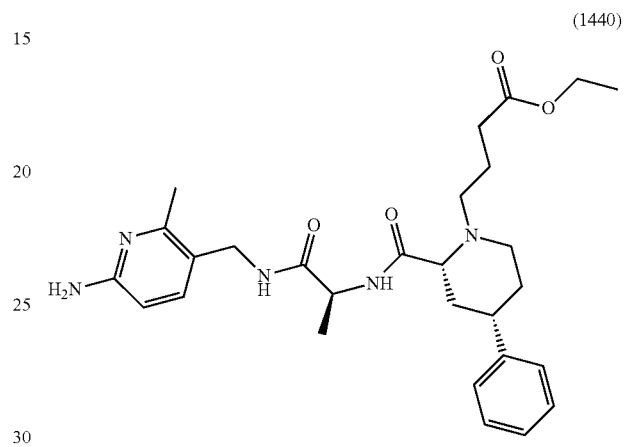

Ethyl 4-((2R,4S)-2-(((S)-1-(((6-amino-2-methylpyridin-3-yl)methyl)amino)-1-oxopropan-2-yl)carbamoyl)-4-phenylpiperidin-1-yl)butanoate was synthesized according to the procedures for compound (1411), step 1, using the corresponding bromoester except that the final product was purified on an amine column (100% EtOAc).

Example 243. Preparation of (2R,4S)—N—((S)-1-(((6-Amino-2-methylpyridin-3-yl)methyl)amino)-1-oxopropan-2-yl)-1-methyl-4-phenylpiperidine-2-carboxamide (1441)

(1441)

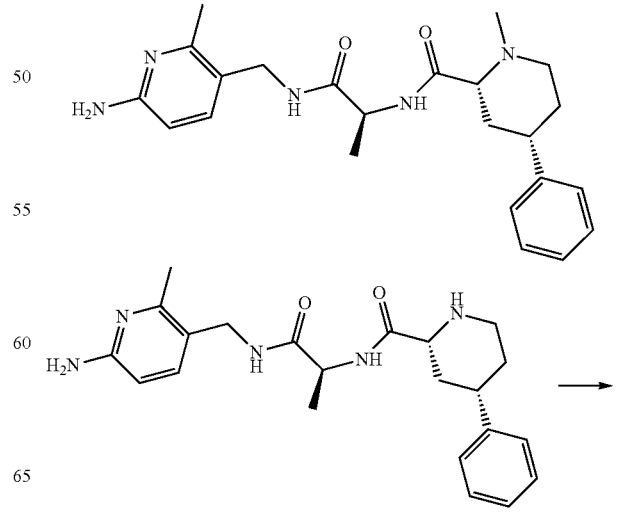

-continued

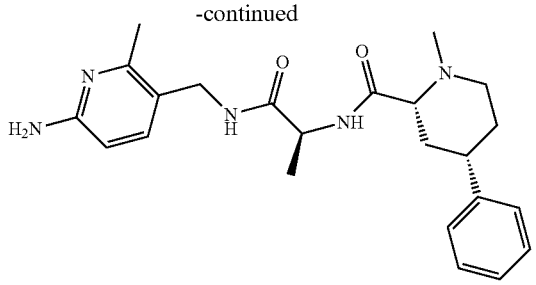

To a stirred solution of (2R,4S)—N—((S)-1-(((6-amino-2-methylpyridin-3-yl)methyl)amino)-1-oxopropan-2-yl)-4-phenylpiperidine-2-carboxamide di-trifluoroacetate salt (100 mg, 0.16 mmol) in CH$_2$Cl$_2$ (2 mL) and NEt$_3$ (0.1 mL) was added methyl iodide (0.048 ml, 0.8 mmol) under Ar atmosphere. After stirring for 18 h at ambient temperature the reaction mixture was concentrated and purified on an amine column (100% EtOAc) to yield (2R,4S)—N—((S)-1-(((6-amino-2-methylpyridin-3-yl)methyl)amino)-1-oxopropan-2-yl)-1-methyl-4-phenylpiperidine-2-carboxamide (22 mg, 34% yield).

Example 244. Preparation of (2R,4R)—N—((S)-1-(((3-Chloro-1-methyl-1H-pyrrolo[2,3-b]pyridin-5-yl)methyl)amino)-1-oxopropan-2-yl)-4-phenylpyrrolidine-2-carboxamide Dihydrochloride (1441)

(1442)

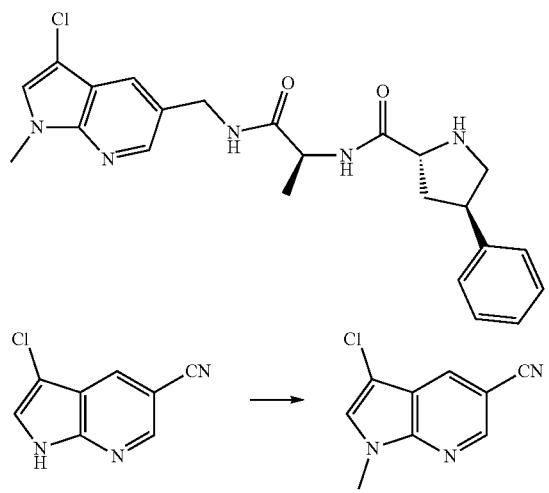

Step 1: A solution of 3-chloro-1H-pyrrolo[2,3-b]pyridine-5-carbonitrile (215 mg, 1.21 mmol; described for compound (1329)) in anhyd DMF (7 mL) was added to an ice-cold suspension of NaH (60% in oil; 538 mg, 13.4 mmol) in anhyd DMF (2 mL) under Ar. The mixture was allowed to warm to ambient temperature. After stirring for 30 min, the mixture was cooled over an ice bath and iodomethane (0.22 µl, 3.5 mmol) was added over 5 min. The mixture was slowly warmed to ambient temperature, stirred 3 h, then cooled over an ice bath. The reaction was quenched with H$_2$O then EtOAc was added. The layers were separated. The aq layer was extracted with EtOAc and the combined organics were washed with brine, dried (Na$_2$SO$_4$) and conc in vacuo. Purification by chromatography (10-35% EtOAc-hexanes) gave 3-chloro-1-methyl-1H-pyrrolo[2,3-b]pyridine-5-carbonitrile (226 mg, 97% yield).

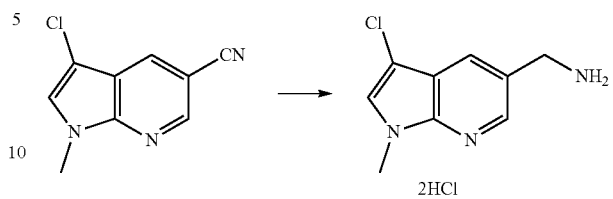

Steps 2-3: 3-Chloro-1-methyl-1H-pyrrolo[2,3-b]pyridine-5-carbonitrile was reduced using the two-step procedure described for compound (1329)) to give (3-chloro-1-methyl-1H-pyrrolo[2,3-b]pyridin-5-yl)methanamine dihydrochloride (75 mg, 54% for two steps).

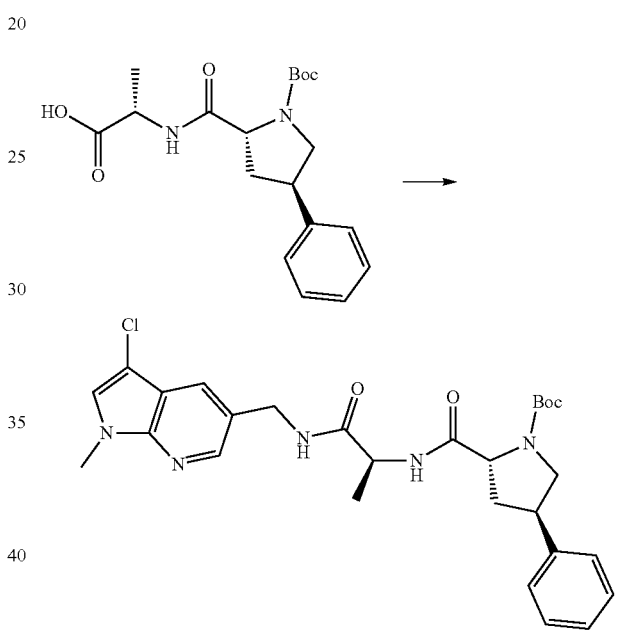

Step 4: ((2R,4R)-1-(tert-Butoxycarbonyl)-4-phenylpyrrolidine-2-carbonyl)-L-alanine was coupled to (3-chloro-1-methyl-1H-pyrrolo[2,3-b]pyridin-5-yl)methanamine dihydrochloride following the procedure given for (1280), step 4 to give tert-butyl (2R,4R)-2-(((S)-1-(((3-chloro-1-methyl-1H-pyrrolo[2,3-b]pyridin-5-yl)methyl)amino)-1-oxopropan-2-yl)carbamoyl)-4-phenylpyrrolidine-1-carboxylate (35 mg, 64% yield).

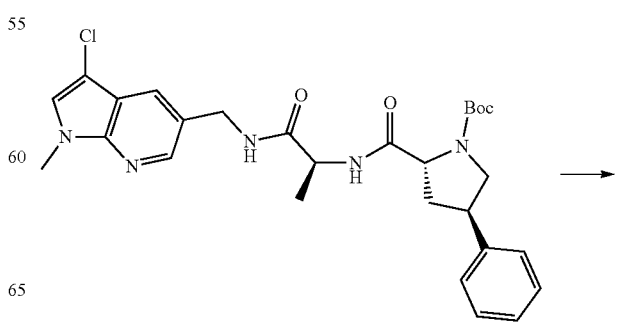

609
-continued

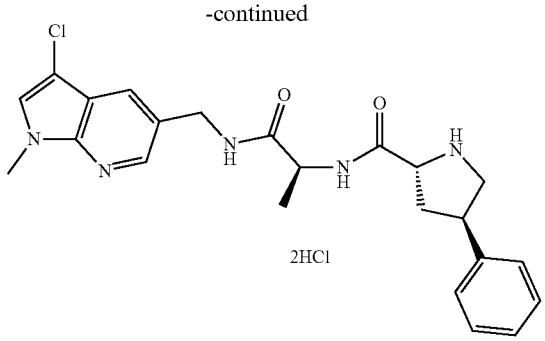

Step 5: tert-Butyl (2R,4R)-2-(((S)-1-(((3-chloro-1-methyl-1H-pyrrolo[2,3-b]pyridin-5-yl)methyl)amino)-1-oxopropan-2-yl)carbamoyl)-4-phenylpyrrolidine-1-carboxylate was deprotected according to the procedure given for compound (1323), step 3 to give (2R,4R)—N—((S)-1-(((3-chloro-1-methyl-1H-pyrrolo[2,3-b]pyridin-5-yl)methyl)amino)-1-oxopropan-2-yl)-4-phenylpyrrolidine-2-carboxamide dihydrochloride (30.9 mg, 93% yield).

Example 245. Preparation of (2R,4S)—N—((S)-1-(((6-Amino-2-methylpyridin-3-yl)methyl)amino)-1-oxopropan-2-yl)-4-(2,4-dichlorobenzyl)pyrrolidine-2-carboxamide Dihydrochloride (1443)

(1443)

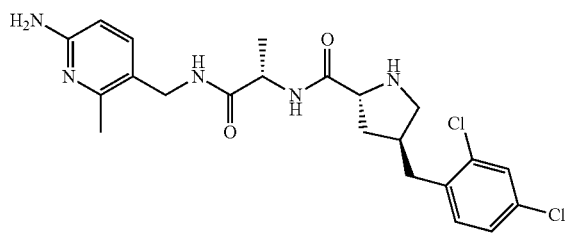

(2R,4S)—N—((S)-1-(((6-Amino-2-methylpyridin-3-yl)methyl)amino)-1-oxopropan-2-yl)-4-(2,4-dichlorobenzyl)pyrrolidine-2-carboxamide dihydrochloride was synthesized according to the procedures for compound (1328).

Example 246. Preparation of (2R,4S)—N—((S)-1-(((6-Amino-2-methylpyridin-3-yl)methyl)amino)-1-oxopropan-2-yl)-4-(2,5-dichlorobenzyl)pyrrolidine-2-carboxamide Dihydrochloride (1444)

(1444)

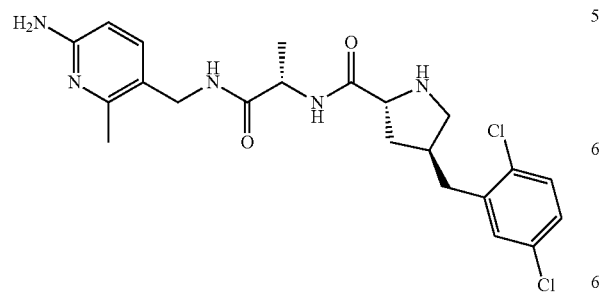

610

(2R,4S)—N—((S)-1-(((6-Amino-2-methylpyridin-3-yl)methyl)amino)-1-oxopropan-2-yl)-4-(2,5-dichlorobenzyl)pyrrolidine-2-carboxamide dihydrochloride was synthesized according to the procedures for compound (1328).

Example 247. Preparation of (2R,4S)—N—((S)-1-(((6-Amino-2-methylpyridin-3-yl)methyl)amino)-1-oxopropan-2-yl)-4-(4-bromophenoxy)pyrrolidine-2-carboxamide Dihydrochloride (1445)

(1445)

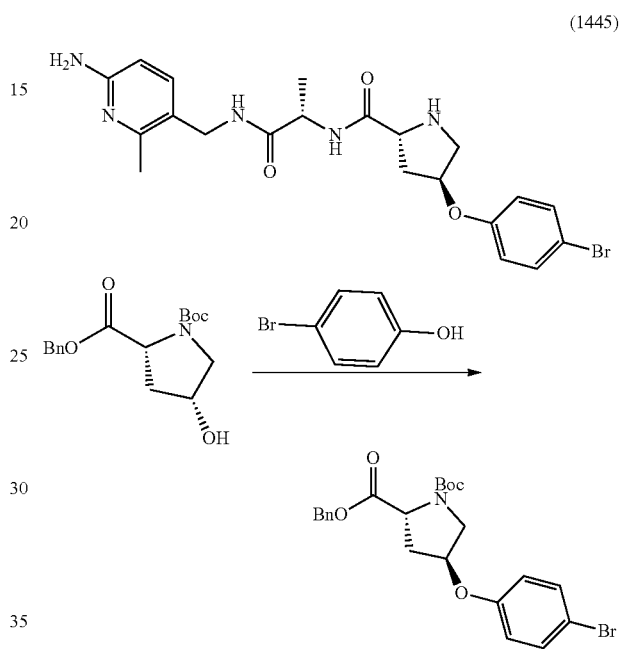

Step 1: To a stirred solution of 2-benzyl 1-(tert-butyl) (2R,4R)-4-hydroxypyrrolidine-1,2-dicarboxylate (410 mg, 1.27 mmol), 4-bromophenol (242 mg, 1.39 mmol) and TPP (367 mg, 1.39 mmol) in THF (6.35 mL) was added DIAD (0.27 mL, 1.39 mmol) at ambient temperature under Ar. The mixture was stirred at ambient temperature overnight. After removal of the solvent, the resulting residue was purified by chromatography using EtOAc-hexanes to afford 2-benzyl 1-(tert-butyl) (2R,4S)-4-(4-bromophenoxy)pyrrolidine-1,2-dicarboxylate (533 mg, 88% yield) as a colorless solid.

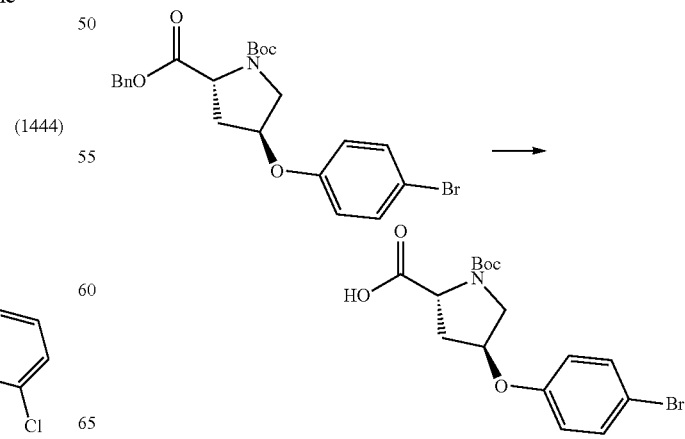

Step 2: (2R,4S)-4-(4-Bromophenoxy)-1-(tert-butoxycarbonyl)pyrrolidine-2-carboxylic acid was synthesized from 2-benzyl 1-(tert-butyl) (2R,4S)-4-(4-bromophenoxy)pyrrolidine-1,2-dicarboxylate according to the procedures for compound (1328), step 1.

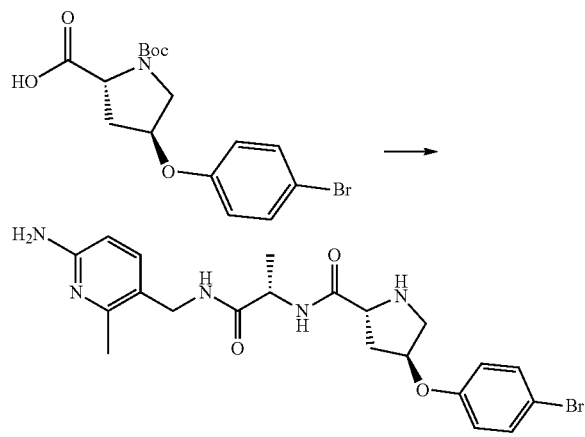

Step 3: (2R,4S)—N—((S)-1-(((6-Amino-2-methylpyridin-3-yl)methyl)amino)-1-oxopropan-2-yl)-4-(4-bromophenoxy)pyrrolidine-2-carboxamide dihydrochloride was synthesized from (2R,4S)-4-(4-bromophenoxy)-1-(tert-butoxycarbonyl)pyrrolidine-2-carboxylic acid according to the procedures for compound (1304), step 7 and step 8.

Example 248. Preparation of (2R,4S)—N—((S)-1-(((6-Amino-2-methylpyridin-3-yl)methyl)amino)-1-oxopropan-2-yl)-4-phenoxypyrrolidine-2-carboxamide Dihydrochloride (1446)

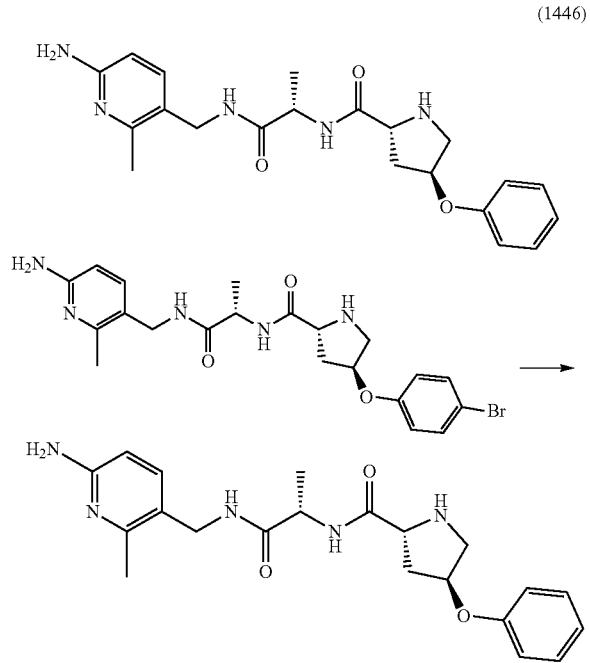

(2R,4S)—N—((S)-1-(((6-Amino-2-methylpyridin-3-yl)methyl)amino)-1-oxopropan-2-yl)-4-phenoxypyrrolidine-2-carboxamide dihydrochloride was synthesized from (2R,4S)—N—((S)-1-(((6-amino-2-methylpyridin-3-yl)methyl)amino)-1-oxopropan-2-yl)-4-(4-bromophenoxy)pyrrolidine-2-carboxamide dihydrochloride according to the procedures for compound (1304), step 4.

Example 249. Preparation of (2R,4S)—N—((S)-1-(((6-Amino-2-methylpyridin-3-yl)methyl)amino)-1-oxopropan-2-yl)-4-(4-fluorobenzyl)pyrrolidine-2-carboxamide Di-trifluoroacetate salt (1447)

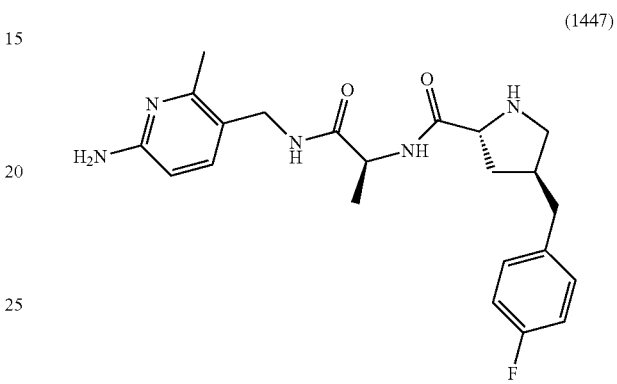

(2R,4S)—N—((S)-1-(((6-Amino-2-methylpyridin-3-yl)methyl)amino)-1-oxopropan-2-yl)-4-(4-fluorobenzyl)pyrrolidine-2-carboxamide di-trifluoroacetate salt was synthesized according to the procedures for compound (1304).

Example 250. Preparation of (2R,4S)-4-benzyl-N—((S)-1-((3,5-dichloro-2-hydroxybenzyl)amino)-1-oxopropan-2-yl)pyrrolidine-2-carboxamide, hydrochloride (1448)

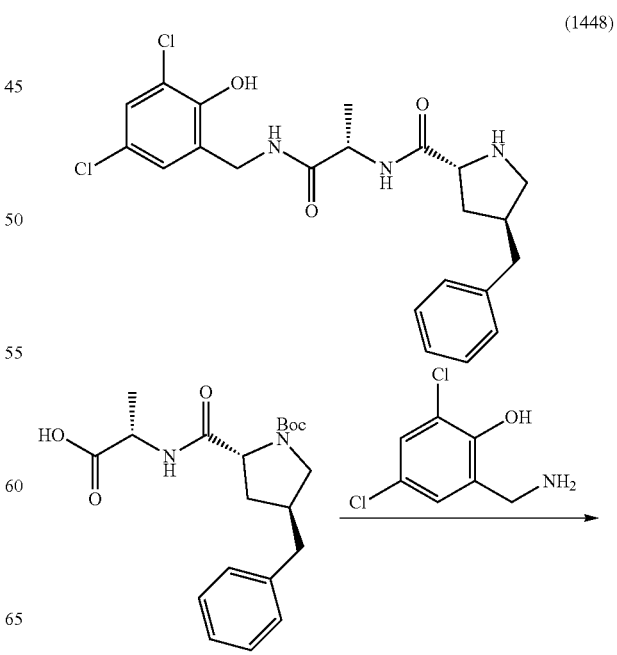

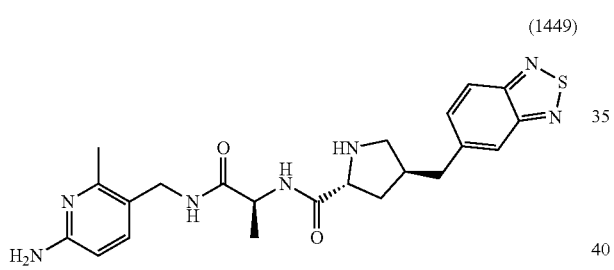

Steps 1-2: The title compound was synthesized according to steps 1-2 of the procedure for compound (1246) using the appropriate starting materials, except with purification by column (MeOH/CH$_2$Cl$_2$ containing 2.5% 7 N NH$_3$-MeOH), then treatment with 1 M HCl and lyophilization (10 mg, 19% yield over two steps).

Example 251. Preparation of (2R,4S)—N—((S)-1-(((6-Amino-2-methylpyridin-3-yl)methyl)amino)-1-oxopropan-2-yl)-4-(benzo[c][1,2,5]thiadiazol-5-ylmethyl)pyrrolidine-2-carboxamide Di-trifluoroacetate salt (1449)

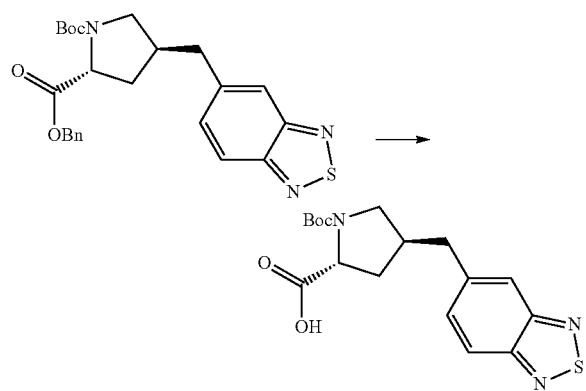

(1449)

Step 1: 2-Benzyl 1-(tert-butyl) (2R,4S)-4-(benzo[c][1,2,5]thiadiazol-5-ylmethyl)pyrrolidine-1,2-dicarboxylate was synthesized according to the procedure for compound (1304).

Step 2: To a solution of 2-benzyl 1-(tert-butyl) (2R,4S)-4-(benzo[c][1,2,5]thiadiazol-5-ylmethyl)pyrrolidine-1,2-dicarboxylate (141.4 mg, 0.311 mmol) in THF (7.2 mL) and MeOH (3.6 mL) was added water (3.6 mL) followed by the addition of LiOH (117.0 mg, 4.89 mmol). After purging with N$_2$, the reaction was stirred at room temp for 16 h, diluted with water, and washed with EtOAc. The organic layer was discarded. The aqueous layer was adjusted to pH 3 with the slow addition of 1 M KHSO$_4$ solution and extracted with EtOAc (3 times). The organic layers were combined, washed with 5% NaHCO$_3$ solution, washed with brine, dried (Na$_2$SO$_4$), vacuum filtered, and evaporated under vacuum to afford the crude (2R,4S)-4-(benzo[c][1,2,5]thiadiazol-5-ylmethyl)-1-(tert-butoxycarbonyl)pyrrolidine-2-carboxylic acid.

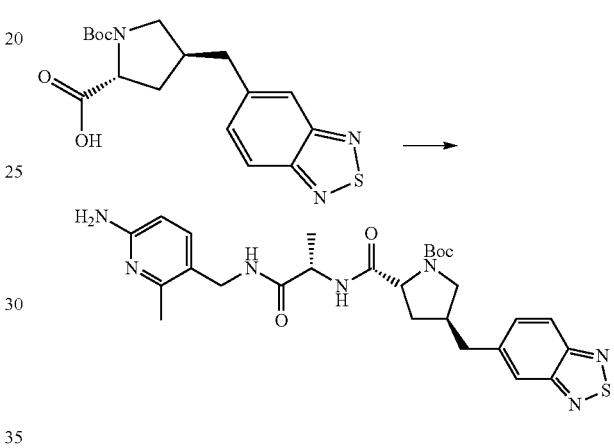

Step 3: To the crude (2R,4S)-4-(benzo[c][1,2,5]thiadiazol-5-ylmethyl)-1-(tert-butoxycarbonyl)pyrrolidine-2-carboxylic acid in DMF (5.2 mL) was added NHS (45.0 mg, 0.391 mmol) and DCC (72.0 mg, 0.349 mmol). After purging with N$_2$, the reaction was stirred at room temp for 45 min and (S)-2-amino-N-((6-amino-2-methylpyridin-3-yl)methyl)propanamide (81.0 mg, 0.389 mmol) was added. The reaction was stirred at room temp for 16 h and evaporated under reduced pressure to dryness. The crude product was dissolved in CH$_2$Cl$_2$ and adsorbed onto silica gel. Purification by chromatography (0-10% MeOH—CH$_2$Cl$_2$) afforded tert-butyl (2R,4S)-2-(((S)-1-(((6-amino-2-methylpyridin-3-yl)methyl)amino)-1-oxopropan-2-yl)carbamoyl)-4-(benzo[c][1,2,5]thiadiazol-5-ylmethyl)pyrrolidine-1-carboxylate.

Step 4: Deprotection of tert-butyl (2R,4S)-2-(((S)-1-(((6-amino-2-methylpyridin-3-yl)methyl)amino)-1-oxopropan-2-yl)carbamoyl)-4-(benzo[c][1,2,5]thiadiazol-5-ylmethyl)pyrrolidine-1-carboxylate according to the procedure for compound (1427), step 7 except purification by reverse phase HPLC (5-75% MeCN—H$_2$O) afforded (2R,4S)—N—((S)-1-(((6-amino-2-methylpyridin-3-yl)methyl)amino)-1-oxopropan-2-yl)-4-(benzo[c][1,2,5]thiadiazol-5-ylmethyl)pyrrolidine-2-carboxamide di-trifluoroacetate salt.

Example 252. Preparation of (2R,4S)-4-Benzyl-N—((S)-1-(((3-chloro-1-methyl-1H-pyrrolo[2,3-b]pyridin-5-yl)methyl)amino)-1-oxopropan-2-yl)pyrrolidine-2-carboxamide Dihydrochloride (1450)

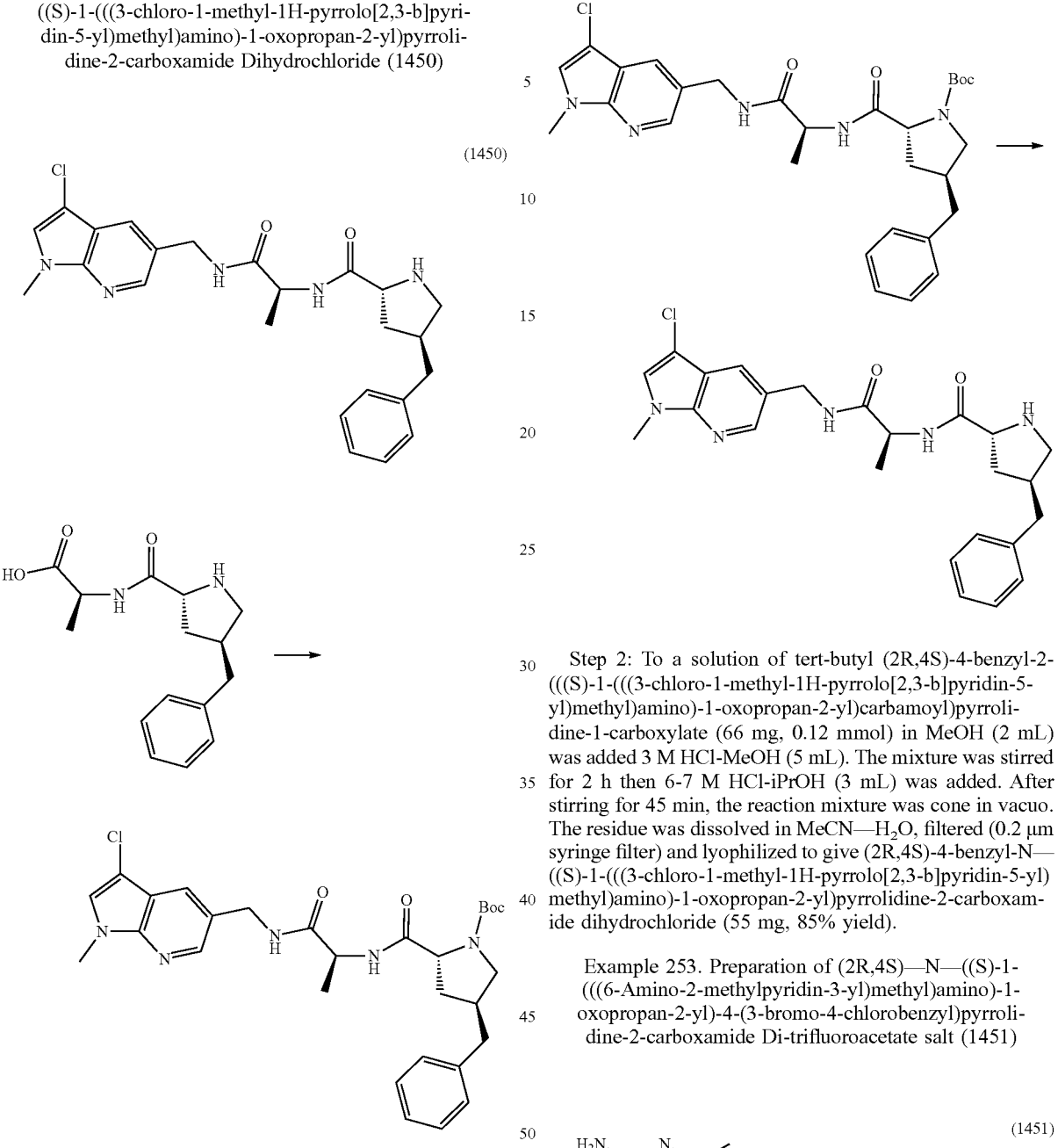

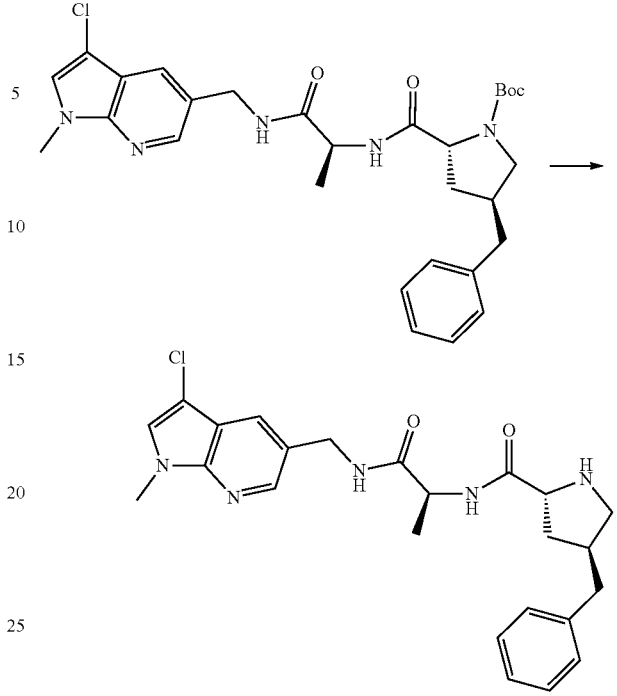

Step 1: To a solution of ((2R,4S)-4-benzylpyrrolidine-2-carbonyl)-L-alanine (70.2 mg, 0.187 mmol) and NHS (25 mg, 0.22 mmol) in CH$_2$Cl$_2$ (3.5 mL) was added DCC (24 mg, 0.12 mmol). After stirring for 30 min, a mixture of (3-chloro-1-methyl-1H-pyrrolo[2,3-b]pyridin-5-yl)methanamine dihydrochloride (55 mg, 0.24 mmol) in CH$_2$Cl$_2$ (2 mL) and sat. NaHCO$_3$ (3 mL) was added to the reaction mixture. After stirring for 30 min, the reaction was diluted with 5% MeOH—CH$_2$Cl$_2$ and washed with sat. NaHCO$_3$ 3×, dried (Na$_2$SO$_4$) and conc in vacuo. Purification (0-10% MeOH—CH$_2$Cl$_2$; then 50-100% EtOAc-hexanes) gave tert-butyl (2R,4S)-4-benzyl-2-(((S)-1-(((3-chloro-1-methyl-1H-pyrrolo[2,3-b]pyridin-5-yl)methyl)amino)-1-oxopropan-2-yl)carbamoyl)pyrrolidine-1-carboxylate (67.8 mg, 66% yield).

Step 2: To a solution of tert-butyl (2R,4S)-4-benzyl-2-(((S)-1-(((3-chloro-1-methyl-1H-pyrrolo[2,3-b]pyridin-5-yl)methyl)amino)-1-oxopropan-2-yl)carbamoyl)pyrrolidine-1-carboxylate (66 mg, 0.12 mmol) in MeOH (2 mL) was added 3 M HCl-MeOH (5 mL). The mixture was stirred for 2 h then 6-7 M HCl-iPrOH (3 mL) was added. After stirring for 45 min, the reaction mixture was conc in vacuo. The residue was dissolved in MeCN—H$_2$O, filtered (0.2 μm syringe filter) and lyophilized to give (2R,4S)-4-benzyl-N—((S)-1-(((3-chloro-1-methyl-1H-pyrrolo[2,3-b]pyridin-5-yl)methyl)amino)-1-oxopropan-2-yl)pyrrolidine-2-carboxamide dihydrochloride (55 mg, 85% yield).

Example 253. Preparation of (2R,4S)—N—((S)-1-(((6-Amino-2-methylpyridin-3-yl)methyl)amino)-1-oxopropan-2-yl)-4-(3-bromo-4-chlorobenzyl)pyrrolidine-2-carboxamide Di-trifluoroacetate salt (1451)

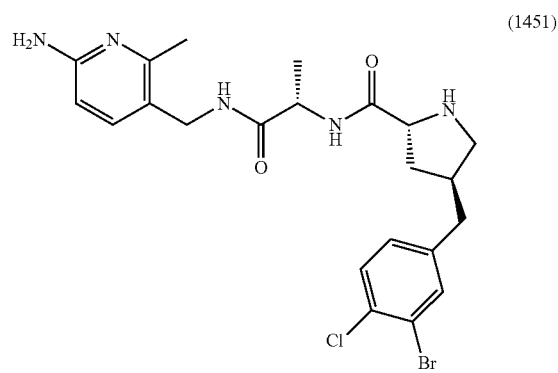 [SMILES: Cc1nc(N)ccc1CNC(=O)[C@H](C)NC(=O)[C@H]1C[C@H](Cc2ccc(Cl)c(Br)c2)CN1]

(2R,4S)—N—((S)-1-(((6-Amino-2-methylpyridin-3-yl)methyl)amino)-1-oxopropan-2-yl)-4-(3-bromo-4-chlorobenzyl)pyrrolidine-2-carboxamide di-trifluoroacetate salt was synthesized according to the procedures for compound (1424), except that in step 4, the ester was deprotected following the procedure below. Additionally, the title compound was not purified by prep HPLC.

To 2-benzyl 1-(tert-butyl) (2R,4S)-4-(3-bromo-4-chlorobenzyl)pyrrolidine-1,2-dicarboxylate (50 mg, 0.1 mmol) in THF (2 mL, 0.05 M), MeOH (1 mL, 0.1 M), H₂O (1 mL, 0.1 M) was added a LiOH—H₂O (66 mg, 1.5 mmol) with stirring at ambient temperature while monitoring for the consumption of starting material (16 h). The solution was brought to pH 3 with 1 N HCl, extracted 3× with EtOAc then dried over Na₂SO₄ and evaporated to dryness. The resulting residue was carried forward without further purification.

Example 254. Preparation of (2R,4S)—N—((S)-1-(((6-Amino-2-methylpyridin-3-yl)methyl)amino)-1-oxopropan-2-yl)-4-(3-bromobenzyl)pyrrolidine-2-carboxamide Dihydrochloride (1452)

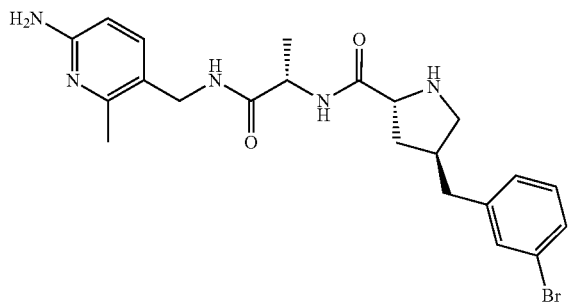

(1452)

(2R,4S)—N—((S)-1-(((6-Amino-2-methylpyridin-3-yl)methyl)amino)-1-oxopropan-2-yl)-4-(3-bromobenzyl)pyrrolidine-2-carboxamide dihydrochloride was synthesized according to the procedures for compound (1328).

Example 255. Preparation of (2R,4S)—N—((S)-1-(((6-Amino-2-methylpyridin-3-yl)methyl)amino)-1-oxopropan-2-yl)-4-((6-methoxynaphthalen-2-yl)methyl)pyrrolidine-2-carboxamide Dihydrochloride (1453)

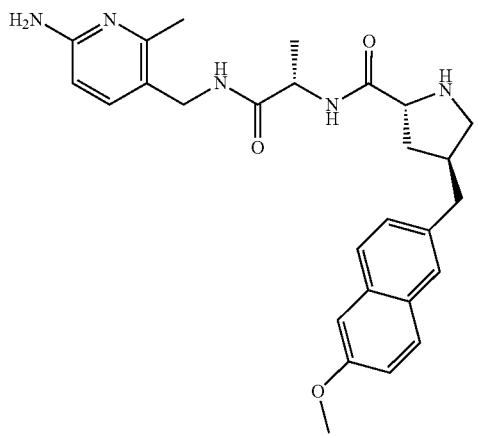

(1453)

(2R,4S)—N—((S)-1-(((6-Amino-2-methylpyridin-3-yl)methyl)amino)-1-oxopropan-2-yl)-4-((6-methoxynaphthalen-2-yl)methyl)pyrrolidine-2-carboxamide dihydrochloride was synthesized according to the procedures for compound (1304).

Example 256. Preparation of (2R,4R)—N—((S)-1-(((6-Amino-2-methylpyridin-3-yl)methyl)amino)-1-oxopropan-2-yl)-4-((5-chlorothiophen-2-yl)methyl)pyrrolidine-2-carboxamide Dihydrochloride (1454)

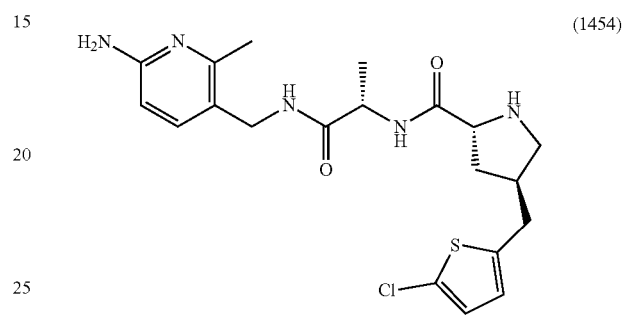

(1454)

(2R,4R)—N—((S)-1-(((6-Amino-2-methylpyridin-3-yl)methyl)amino)-1-oxopropan-2-yl)-4-((5-chlorothiophen-2-yl)methyl)pyrrolidine-2-carboxamide dihydrochloride was synthesized according to the procedures for compound (1304), except that the benzyl deprotection (Step 4) was done by following LiOH conditions as described for compound (1399).

Example 257. Preparation of (2R,4S)—N—((S)-1-(((6-Amino-2-methylpyridin-3-yl)methyl)amino)-1-oxopropan-2-yl)-4-(3-chloro-4-(trifluoromethoxy)benzyl)pyrrolidine-2-carboxamide Di-trifluoroacetate salt (1455)

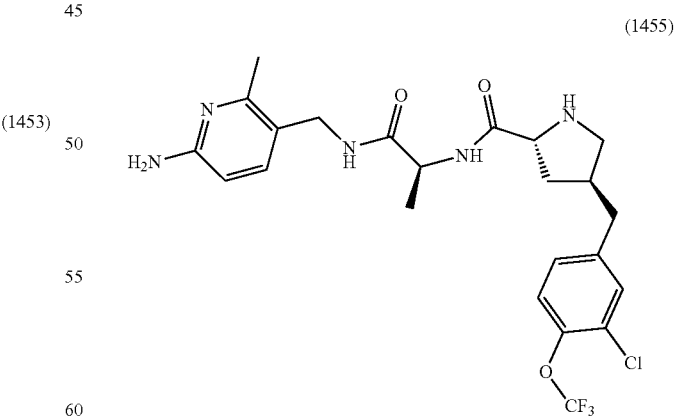

(1455)

(2R,4S)—N—((S)-1-(((6-Amino-2-methylpyridin-3-yl)methyl)amino)-1-oxopropan-2-yl)-4-(3-chloro-4-(trifluoromethoxy)benzyl)pyrrolidine-2-carboxamide di-trifluoroacetate salt was synthesized according to the procedures for compound (1328).

Example 258. Preparation of (2R,4R)—N—((S)-1-((5-Chloro-2-hydroxy-3-methylbenzyl)amino)-1-oxopropan-2-yl)-4-((5-chlorothiophen-2-yl)methyl)pyrrolidine-2-carboxamide Dihydrochloride (1456)

(1456)

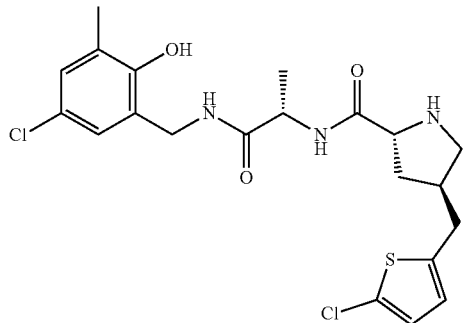

(2R,4R)—N—((S)-1-((5-Chloro-2-hydroxy-3-methylbenzyl)amino)-1-oxopropan-2-yl)-4-((5-chlorothiophen-2-yl)methyl)pyrrolidine-2-carboxamide dihydrochloride was synthesized according to the procedures for compound (1304), except (S)-2-amino-N-(5-chloro-2-hydroxy-3-methylbenzyl)propenamide was used in step 7 and the benzyl deprotection (Step 4) was done by following LiOH conditions as described for compound (1399).

Example 259. Preparation of (2R,4R)—N—((S)-1-(((5-chloroquinolin-3-yl)methyl)amino)-1-oxopropan-2-yl)-4-phenylpyrrolidine-2-carboxamide (1457)

(1457)

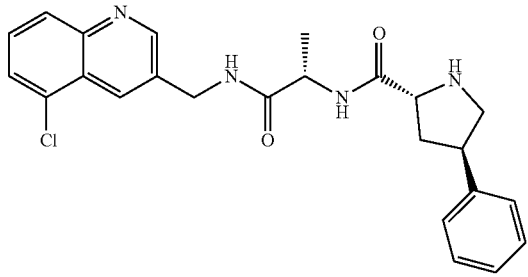

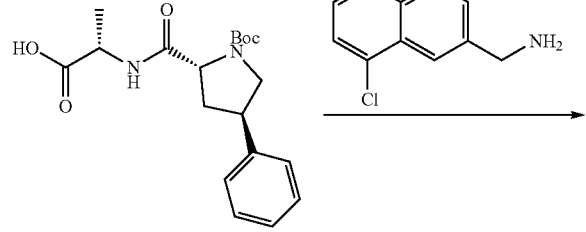

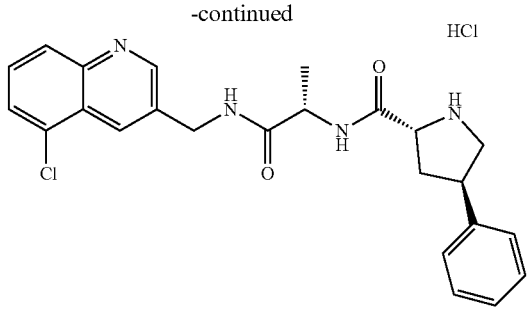

Steps 1-2: The title compound was synthesized as a beige powder according to steps 3-4 of the procedure for compound 1119 using the appropriate starting materials (8.1 mg, 12% yield over two steps).

Example 260. Preparation of (2R,4R)—N—((S)-1-(((6-Amino-2-methylpyridin-3-yl)methyl)amino)-1-oxopropan-2-yl)-4-(benzo[b]thiophen-2-ylmethyl)pyrrolidine-2-carboxamide Di-trifluoroacetate salt (1458)

(1458)

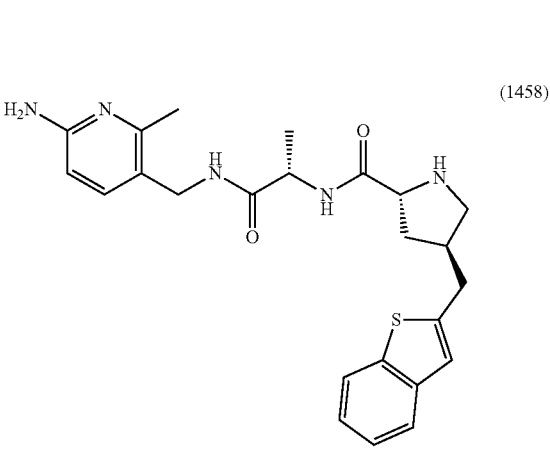 [SMILES: Cc1nc(N)ccc1CNC(=O)[C@H](C)NC(=O)[C@H]1C[C@H](Cc2cc3ccccc3s2)CN1]

(2R,4R)—N—((S)-1-(((6-Amino-2-methylpyridin-3-yl)methyl)amino)-1-oxopropan-2-yl)-4-(benzo[b]thiophen-2-ylmethyl)pyrrolidine-2-carboxamide di-trifluoroacetate salt was synthesized according to the procedures for compound (1451).

Example 261. Preparation of (2R,4S)—N—((S)-1-(((6-Amino-2-methylpyridin-3-yl)methyl)amino)-1-oxopropan-2-yl)-4-(3-chloro-4-fluorobenzyl)pyrrolidine-2-carboxamide Di-trifluoroacetate salt (1459)

(1459)

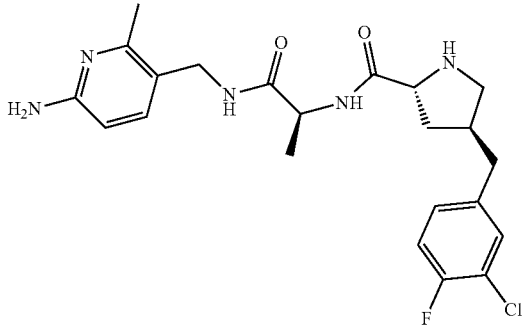

(2R,4S)—N—((S)-1-(((6-Amino-2-methylpyridin-3-yl)methyl)amino)-1-oxopropan-2-yl)-4-(3-chloro-4-fluorobenzyl)pyrrolidine-2-carboxamide di-trifluoroacetate salt was synthesized according to the procedures for compound (1328).

Example 262. Preparation of (2R,4R)—N—((S)-1-(((6-Amino-2-methylpyridin-3-yl)methyl)amino)-1-oxopropan-2-yl)-4-((5-chlorobenzo[d]thiazol-2-yl)methyl)pyrrolidine-2-carboxamide Di-trifluoroacetate salt (1460)

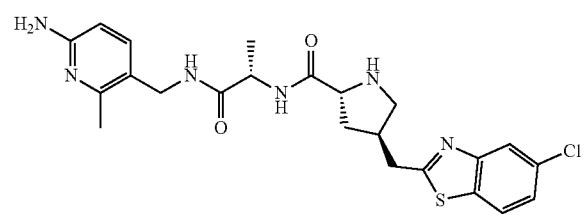

(1460)

(2R,4R)—N—((S)-1-(((6-Amino-2-methylpyridin-3-yl)methyl)amino)-1-oxopropan-2-yl)-4-((5-chlorobenzo[d]thiazol-2-yl)methyl)pyrrolidine-2-carboxamide di-trifluoroacetate salt was synthesized according to the procedures for compound (1328), except that the final product was purified using reverse-phase HPLC.

Example 263. Preparation of (2R,4S)—N—((S)-1-(((6-Amino-2-methylpyridin-3-yl)methyl)amino)-1-oxopropan-2-yl)-4-((5-chlorothiophen-3-yl)methyl)pyrrolidine-2-carboxamide Dihydrochloride (1461)

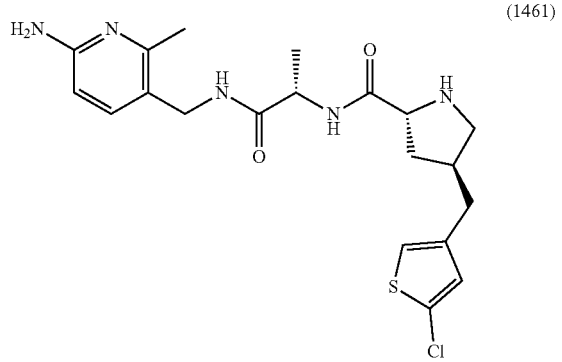 [SMILES: Cc1nc(N)ccc1CNC(=O)[C@H](C)NC(=O)[C@H]1C[C@H](Cc2csc(Cl)c2)CN1]

(1461)

(2R,4S)—N—((S)-1-(((6-Amino-2-methylpyridin-3-yl)methyl)amino)-1-oxopropan-2-yl)-4-((5-chlorothiophen-3-yl)methyl)pyrrolidine-2-carboxamide dihydrochloride was synthesized according to the procedures for compound (1304), except that the benzyl deprotection (Step 4) was done by following LiOH conditions as described for compound (1399).

Example 264. Preparation of (2R,4R)—N—((S)-1-(((5-bromo-1H-indazol-7-yl)methyl)amino)-1-oxopropan-2-yl)-4-phenylpyrrolidine-2-carboxamide (1462)

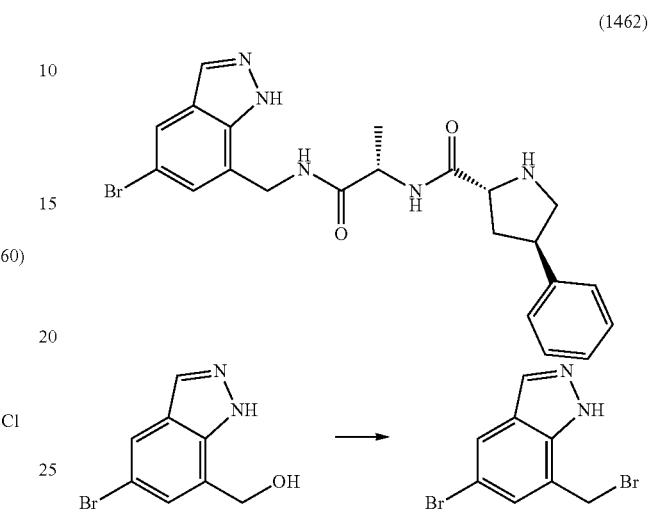

(1462)

Step 1: (5-Bromo-1H-indazol-7-yl)methanol (62 mg, 0.2 mmol) was dissolved in CH$_2$Cl$_2$ (2 mL) and treated with PBr$_3$ (20 µL, 0.21 mmol), then stirred at ambient temperature overnight. The reaction mixture was diluted with CH$_2$Cl$_2$ and washed with H$_2$O and brine, then dried over Na$_2$SO$_4$ and concentrated to furnish 5-bromo-7-(bromomethyl)-1H-indazole as a white solid (58 mg, quant. yield).

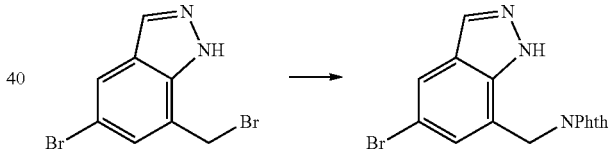

Step 2: A 50 mL round bottom flask was charged with 5-bromo-7-(bromomethyl)-1H-indazole (58 mg, 0.2 mmol), potassium phthalimide (37 mg, 0.2 mmol) and DMF (2 mL), then stirred at ambient temperature overnight. Upon completion, the reaction mixture was concentrated and purified by chromatography to give 2-((5-bromo-1H-indazol-7-yl)methyl)isoindoline-1,3-dione as a white solid (13 mg, 18% yield).

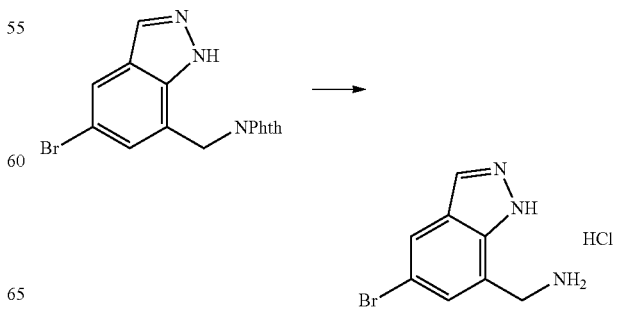

Step 3: 2-((5-Bromo-1H-indazol-7-yl)methyl)isoindoline-1,3-dione (13 mg, 0.04 mmol) was dissolved in EtOH (1 mL) and treated with hydrazine hydrate. After 4 h at ambient temperature, the reaction mixture was concentrated, dissolved in 3 N HCl and filtered through a syringe filter (0.2 μm) and concentrated in vacuo to give (5-bromo-1H-indazol-7-yl)methanamine, hydrochloride as a white solid (10 mg, quant. yield).

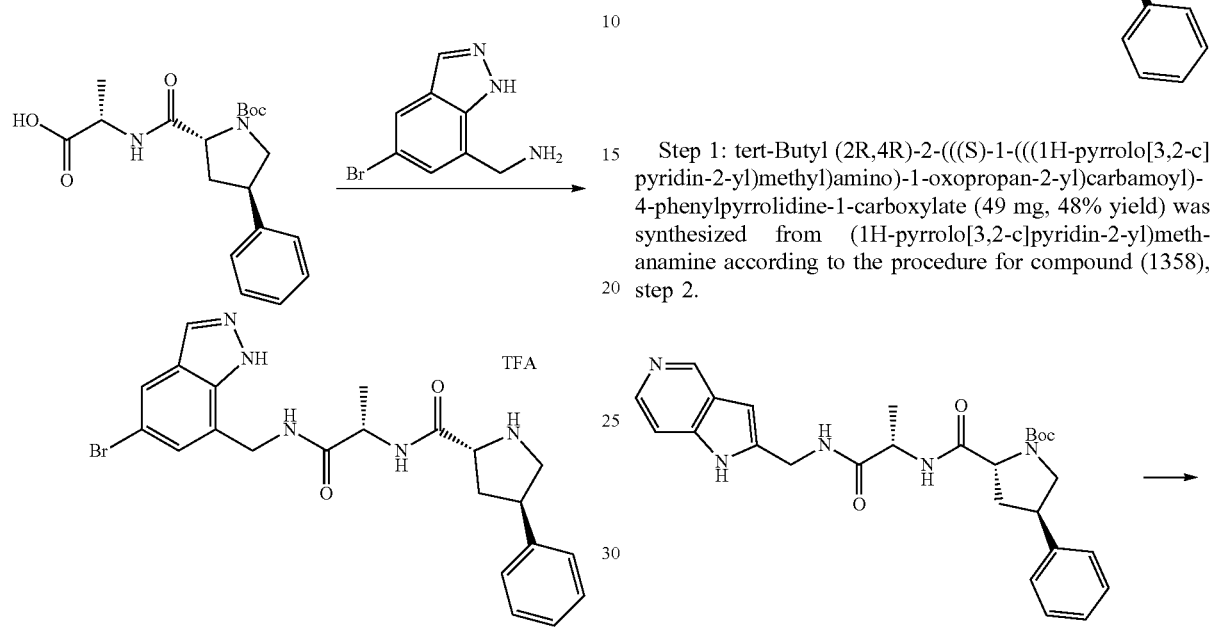

Step 4: The title compound was synthesized as a white solid (6.2 mg, 35% yield over two steps) according to steps 1-2 of the procedure for compound (1246) using the appropriate starting materials, except with purification by prep HPLC (ACN/H₂O+TFA).

Example 265. Preparation of (2R,4R)—N—((S)-1-(((1H-Pyrrolo[3,2-c]pyridin-2-yl)methyl)amino)-1-oxopropan-2-yl)-4-phenylpyrrolidine-2-carboxamide Di-trifluoroacetate salt (1463)

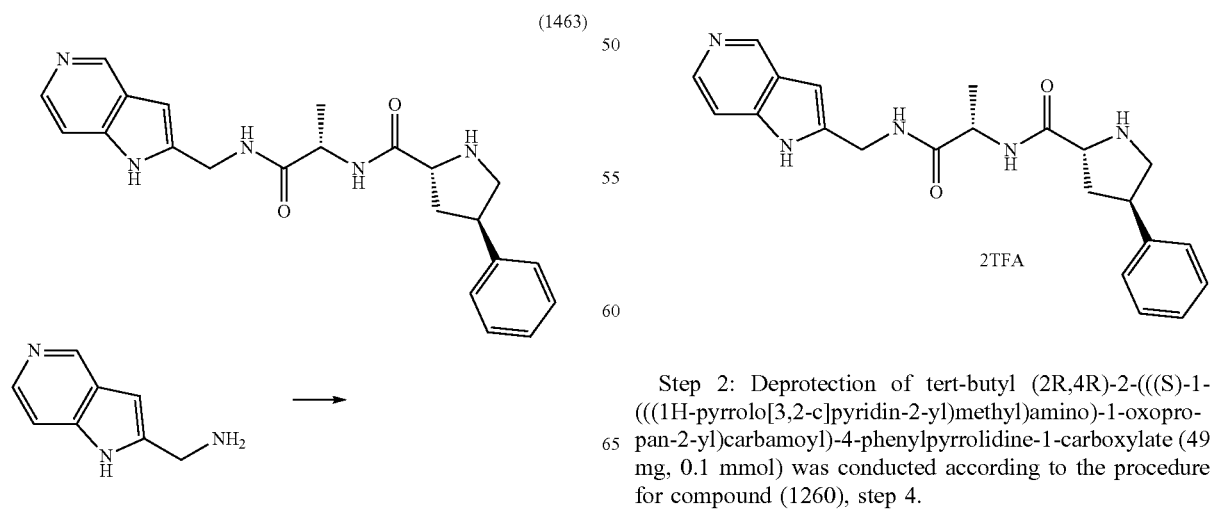

Step 1: tert-Butyl (2R,4R)-2-(((S)-1-(((1H-pyrrolo[3,2-c]pyridin-2-yl)methyl)amino)-1-oxopropan-2-yl)carbamoyl)-4-phenylpyrrolidine-1-carboxylate (49 mg, 48% yield) was synthesized from (1H-pyrrolo[3,2-c]pyridin-2-yl)methanamine according to the procedure for compound (1358), step 2.

Step 2: Deprotection of tert-butyl (2R,4R)-2-(((S)-1-(((1H-pyrrolo[3,2-c]pyridin-2-yl)methyl)amino)-1-oxopropan-2-yl)carbamoyl)-4-phenylpyrrolidine-1-carboxylate (49 mg, 0.1 mmol) was conducted according to the procedure for compound (1260), step 4.

Example 266. Preparation of (2R,4S)—N—((S)-1-(((6-Amino-2-methylpyridin-3-yl)methyl)amino)-1-oxopropan-2-yl)-4-(3-bromo-4-chlorobenzyl)-1-ethylpyrrolidine-2-carboxamide (1464)

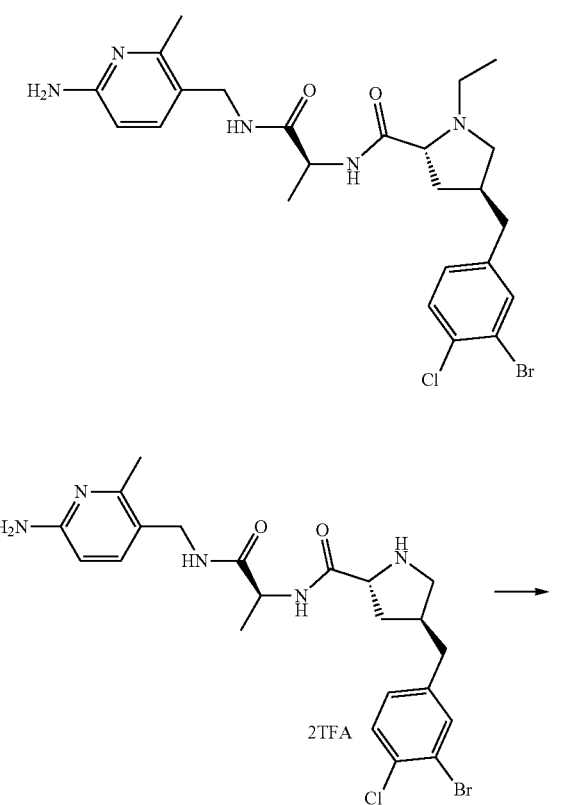

To (2R,4S)—N—((S)-1-(((6-amino-2-methylpyridin-3-yl)methyl)amino)-1-oxopropan-2-yl)-4-(3-bromo-4-chlorobenzyl)pyrrolidine-2-carboxamide ditrifluoroacetate (20 mg, 0.027 mmol) in NEt$_3$ (20 μL, 1.6 M) and CH$_2$Cl$_2$ (340 μL, 0.08 M) was added ethyl bromide (10 μL, 0.135 mmol) with stirring at ambient temperature while monitoring for the consumption of starting material (3 d). The solution was concentrated and evaporated to dryness. The resulting residue was purified on an amine column using EtOAc, then MeOH/CH$_2$Cl$_2$ to yield (2R,4S)—N—((S)-1-(((6-amino-2-methylpyridin-3-yl)methyl)amino)-1-oxopropan-2-yl)-4-(3-bromo-4-chlorobenzyl)-1-ethylpyrrolidine-2-carboxamide (4.6 mg, 32% yield) as an off-white solid.

Example 267. Preparation of (S)—N-((6-Amino-2-methylpyridin-3-yl)methyl)-1-((2R,4S)-4-(4-bromobenzyl)pyrrolidine-2-carbonyl)pyrrolidine-2-carboxamide Di-trifluoroacetate salt (1465)

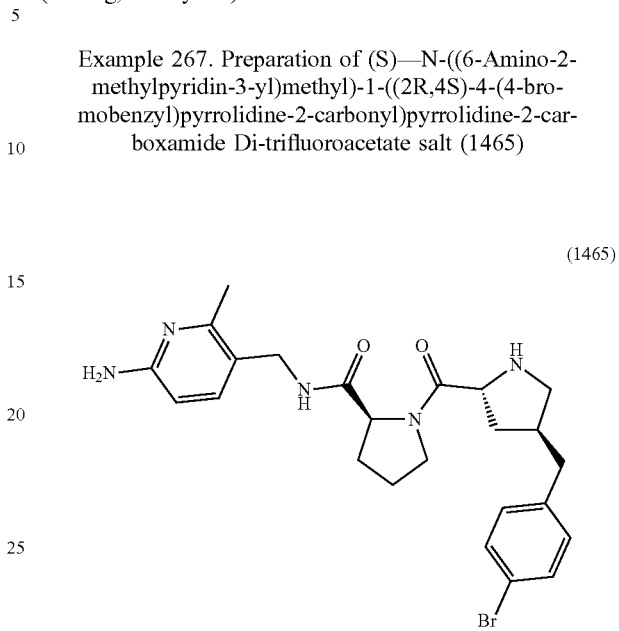

(S)—N-((6-Amino-2-methylpyridin-3-yl)methyl)-1-((2R,4S)-4-(4-bromobenzyl)pyrrolidine-2-carbonyl)pyrrolidine-2-carboxamide ditrifluoroacetate was synthesized according to the procedures for compound (1438) except that in step 5, DMF was used as the solvent in place of CH$_2$Cl$_2$ for the DCC coupling and TFA (20 eq.) in CH$_2$Cl$_2$ (0.2 M) was used to deprotect the Boc group.

Example 268. Preparation of (2R,4S)—N—((S)-1-(((6-Amino-2-methylpyridin-3-yl)methyl)amino)-1-oxopropan-2-yl)-4-(4-bromo-3-chlorobenzyl)pyrrolidine-2-carboxamide Di-trifluoroacetate salt (1466)

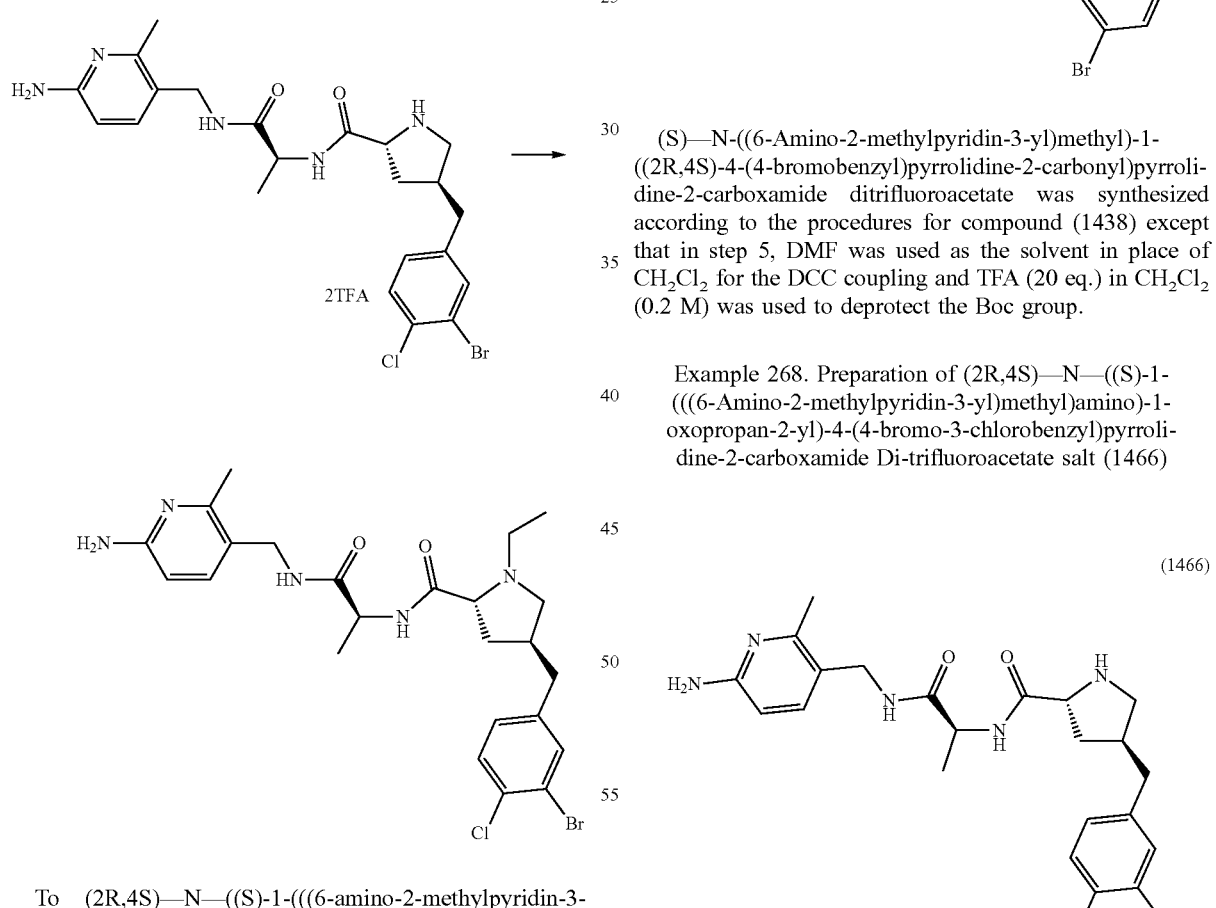

(2R,4S)—N—((S)-1-(((6-Amino-2-methylpyridin-3-yl)methyl)amino)-1-oxopropan-2-yl)-4-(4-bromo-3-chlorobenzyl)pyrrolidine-2-carboxamide di-trifluoroacetate salt was synthesized according to the procedures for compound (1451).

Example 269. Preparation of (S)—N-(1-(((6-Amino-2-methylpyridin-3-yl)methyl)amino)-1-oxopropan-2-yl)-4-benzyl-1H-pyrrole-2-carboxamide trifluoroacetic acid (1467)

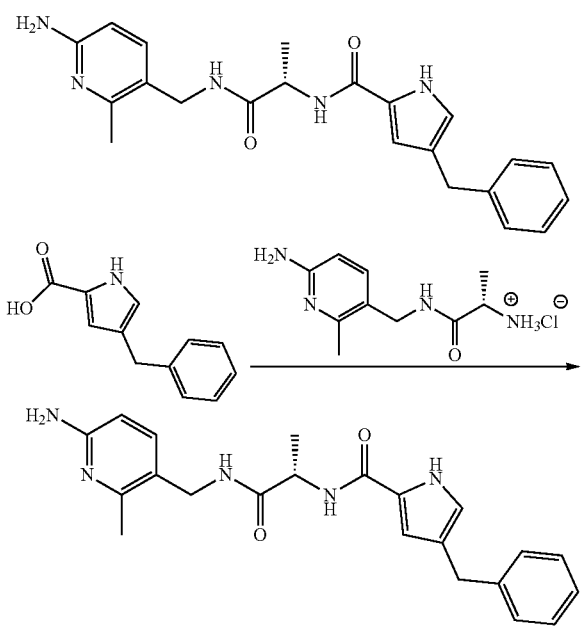

(1467)

To a solution consisting of 4-benzyl-1H-pyrrole-2-carboxylic acid (25 mg, 0.13 mmol) and HATU (53 mg, 0.14 mmol) in anhydrous DMF (1 mL) was added DIEA (60 μL, 0.34 mmol). The reaction mixture was stirred for 30 min at ambient temperature before (S)-2-amino-N-((6-amino-2-methylpyridin-3-yl)methyl)propanamide hydrochloride (28 mg, 0.11 mmol) was added to the reaction mixture and stirred overnight. The reaction mixture was made acidic by adding TFA (100 μL) and the crude reaction mixture purified by reverse-phase HPLC to afford (S)—N-(1-(((6-amino-2-methylpyridin-3-yl)methyl)amino)-1-oxopropan-2-yl)-4-benzyl-1H-pyrrole-2-carboxamide trifluoroacetic acid (17.2 mg, 30%) as a light tan solid.

Example 270. Preparation of (2R,4S)—N—((S)-1-(((3-Chloro-1H-pyrrolo[2,3-b]pyridin-5-yl)methyl)amino)-1-oxopropan-2-yl)-4-((2-methylpyridin-4-yl)methyl)pyrrolidine-2-carboxamide Trifluoroacetate (1468)

(1468)

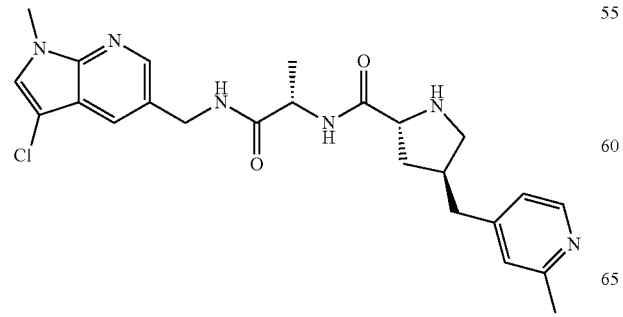

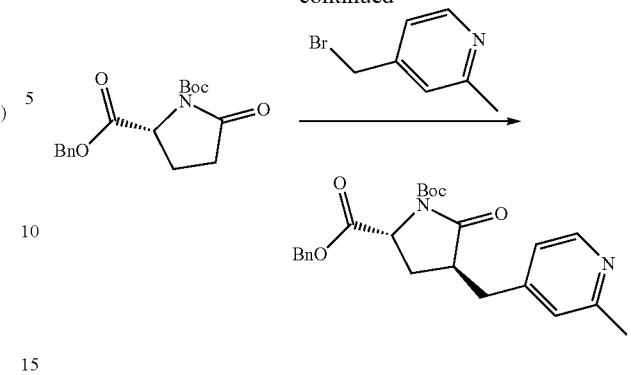

Step 1: 2-Benzyl 1-(tert-butyl) (2R,4S)-4-((2-methylpyridin-4-yl)methyl)-5-oxopyrrolidine-1,2-dicarboxylate was synthesized according step 1 of the procedure for compound (1304) using the appropriate starting materials (113 mg, 24% yield).

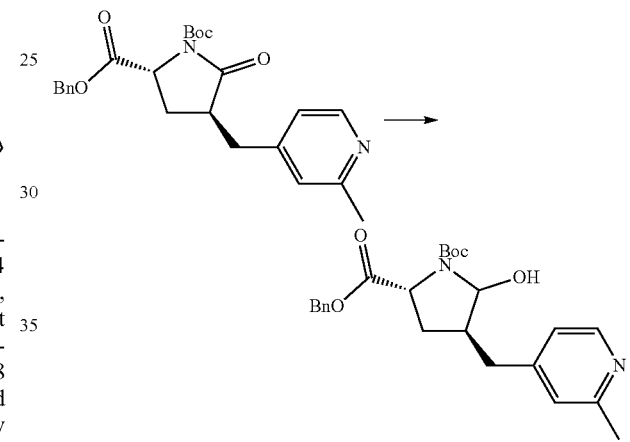

Step 2: 2-Benzyl 1-(tert-butyl) (2R,4S)-5-hydroxy-4-((2-methylpyridin-4-yl)methyl)pyrrolidine-1,2-dicarboxylate was synthesized as a colorless oil according to step 2 of the procedure for compound (1304), except the crude product was filtered through diatomaceous earth (101 mg, 87% yield).

Step 3: 2-Benzyl 1-(tert-butyl) (2R,4S)-4-((2-methylpyridin-4-yl)methyl)pyrrolidine-1,2-dicarboxylate was synthesized as a colorless oil according step 3 of the procedure for compound (1304) (52 mg, 62% yield).

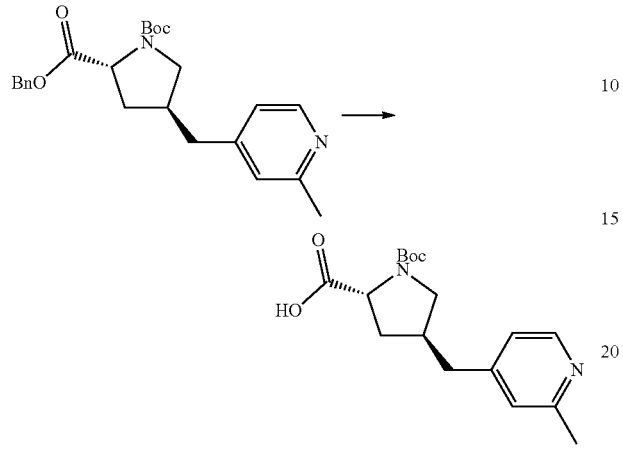

Step 4: (2R,4S)-1-(tert-butoxycarbonyl)-4-((2-methylpyridin-4-yl)methyl)pyrrolidine-2-carboxylic acid was synthesized as a colorless oil according to step 4 of the procedure for compound (1304) (41 mg, 98% yield).

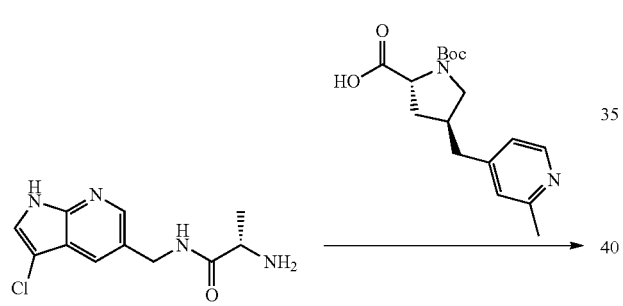

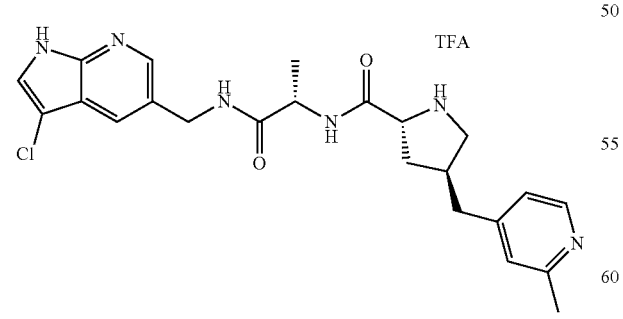

Steps 5-6: The title compound was synthesized as a light pink solid according to steps 5-6 of the procedure for compound (1304), except for purification by prep HPLC (ACN/H₂O+TFA) (16.8 mg, 40% yield over two steps).

Example 271. Preparation of (2R,4S)—N—((S)-1-(((6-Amino-2-methylpyridin-3-yl)methyl)amino)-1-oxopropan-2-yl)-4-((2-methylpyridin-4-yl)methyl)pyrrolidine-2-carboxamide Dihydrochloride (1469)

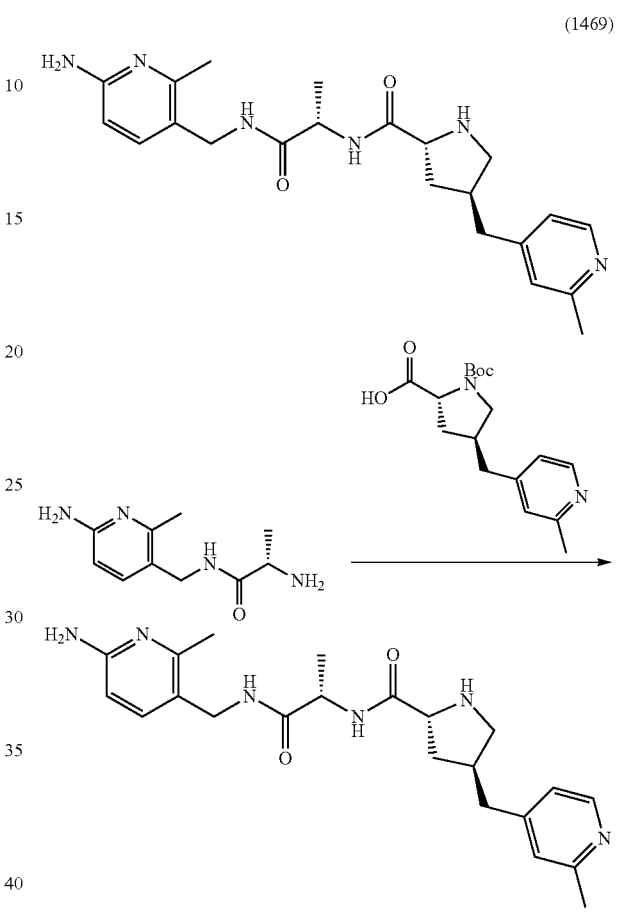

Steps 1-2: The title compound was synthesized as a beige powder according to steps 5-6 of the procedure for compound (1304) (15.4 mg, 75% yield over two steps).

Example 272. Preparation of (2R,4S)—N—((S)-1-(((6-Amino-2-methylpyridin-3-yl)methyl)amino)-1-oxopropan-2-yl)-4-(benzo[c][1,2,5]oxadiazol-5-ylmethyl)pyrrolidine-2-carboxamide Di-trifluoroacetate salt (1470)

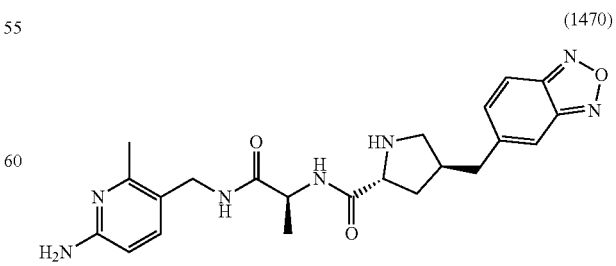

(2R,4S)—N—((S)-1-(((6-Amino-2-methylpyridin-3-yl)methyl)amino)-1-oxopropan-2-yl)-4-(benzo[c][1,2,5]oxadiazol-5-ylmethyl)pyrrolidine-2-carboxamide di-trifluoroacetate salt was synthesized according to the procedure for compound (1449), step 1-4.

Example 273. Preparation of (2R,4R)—N—((S)-1-oxo-1-((Thieno[2,3-b]pyridin-5-ylmethyl)amino)propan-2-yl)-4-phenylpyrrolidine-2-carboxamide Trifluoroacetate salt (1471) (69)

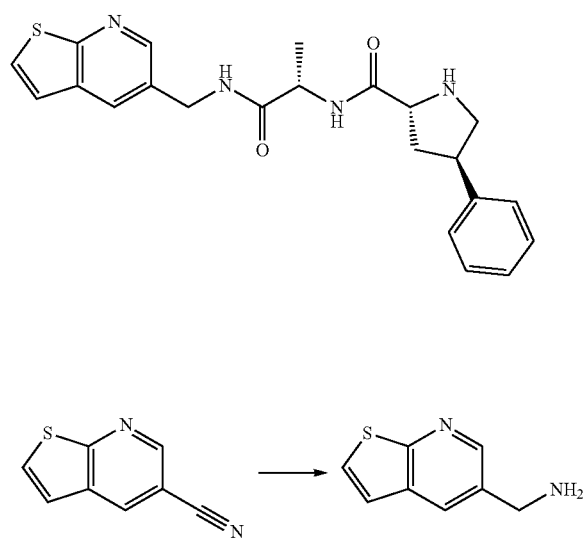
(1471)

Step 1: Thieno[2,3-b]pyridin-5-ylmethanamine (97 mg, 95% yield) was synthesized from thieno[2,3-b]pyridine-5-carbonitrile (100 mg, 0.62 mmol) according to the procedure for compound (1358), step 1.

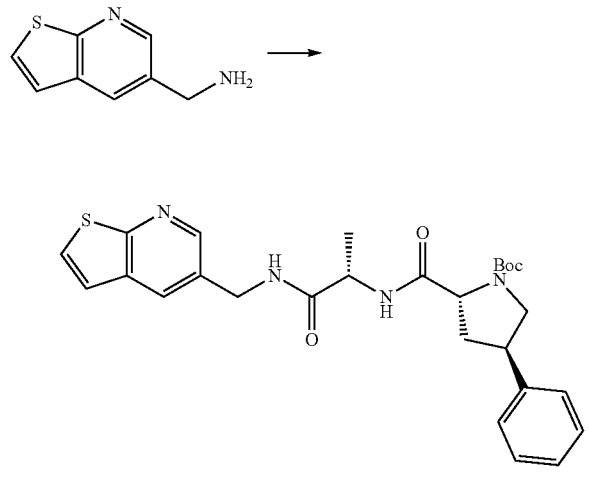

Step 2: tert-Butyl (2R,4R)-2-(((S)-1-oxo-1-((thieno[2,3-b]pyridin-5-ylmethyl)amino)propan-2-yl)carbamoyl)-4-phenylpyrrolidine-1-carboxylate (120 mg, 91% yield) was synthesized from thieno[2,3-b]pyridin-5-ylmethanamine (50 mg, 0.34 mmol) according to the procedure for compound (1358), step 2.

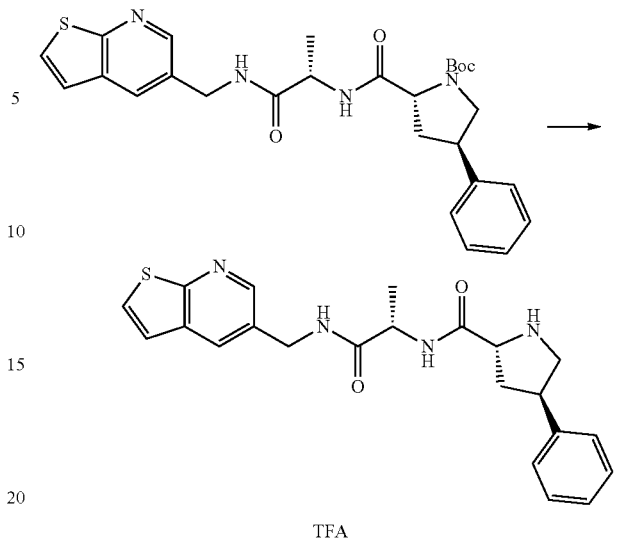

TFA

Step 3: Deprotection of tert-butyl (2R,4R)-2-(((S)-1-oxo-1-((thieno[2,3-b]pyridin-5-ylmethyl)amino)propan-2-yl)carbamoyl)-4-phenylpyrrolidine-1-carboxylate (120 mg, 0.29 mmol) was conducted according to the procedure for compound (1260), step 4 except that the final product was purified using reverse-phase HPLC.

Example 274. Preparation of (2R,4S)—N—((S)-1-(((1H-Pyrrolo[3,2-c]pyridin-2-yl)methyl)amino)-1-oxopropan-2-yl)-4-benzylpyrrolidine-2-carboxamide Di-trifluoroacetate salt (1472)

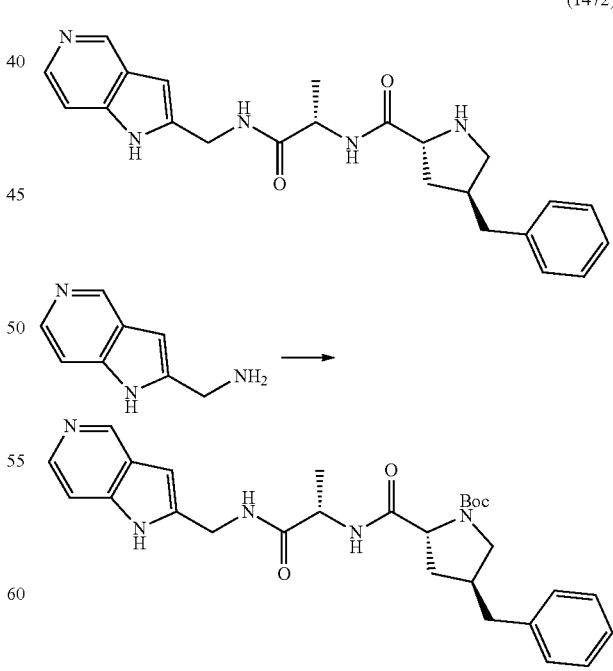
(1472)

Step 1: tert-Butyl (2R,4S)-2-(((S)-1-(((1H-pyrrolo[3,2-c]pyridin-2-yl)methyl)amino)-1-oxopropan-2-yl)carbamoyl)-4-benzylpyrrolidine-1-carboxylate (36 mg, 33% yield) was synthesized from (1H-pyrrolo[3,2-c]pyridin-2-yl)methanamine and (2R,4S)-4-benzyl-1-(tert-butoxycarbonyl)pyrrolidine-2-carboxylic acid (80 mg, 0.21 mmol, prepared according to the procedure for compound (1304), step 1-4 according to the procedure for compound (1358), step 2.

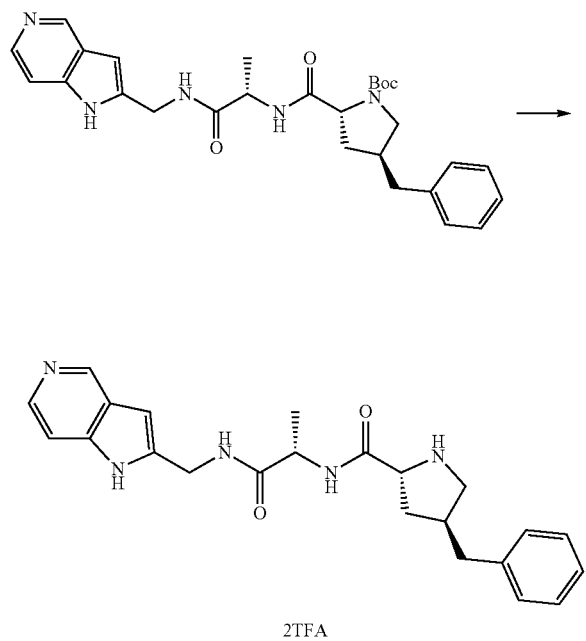

2TFA

Step 2: Deprotection of tert-butyl (2R,4S)-2-(((S)-1-(((1H-pyrrolo[3,2-c]pyridin-2-yl)methyl)amino)-1-oxopropan-2-yl)carbamoyl)-4-benzylpyrrolidine-1-carboxylate (36 mg, 0.07 mmol) was conducted according to the procedure for compound (1260), step 4 except that the final product was purified using reverse-phase HPLC.

Example 275. Preparation of 3-((2R,4S)-2-(((S)-1-(((6-Amino-2-methylpyridin-3-yl)methyl)amino)-1-oxopropan-2-yl)carbamoyl)-4-(3-chloro-4-fluorobenzyl)pyrrolidin-1-yl)propanoic acid Trifluoroacetate salt (1473)

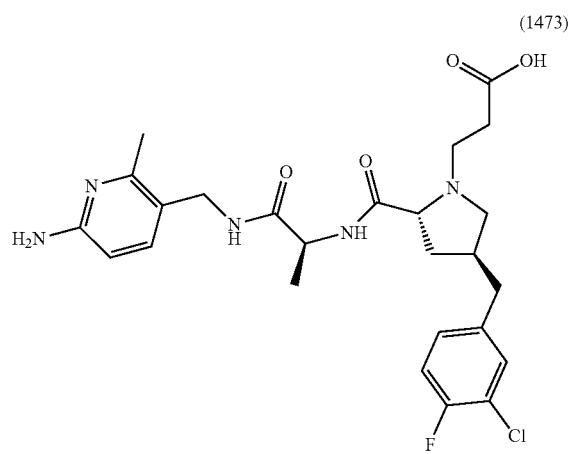 [SMILES: Cc1nc(N)ccc1CNC(=O)[C@H](C)NC(=O)[C@H]1C[C@H](Cc2ccc(F)c(Cl)c2)CN1CCC(=O)O]

3-((2R,4S)-2-(((S)-1-(((6-Amino-2-methylpyridin-3-yl)methyl)amino)-1-oxopropan-2-yl)carbamoyl)-4-(3-chloro-4-fluorobenzyl)pyrrolidin-1-yl)propanoic acid was synthesized according to the procedures for compound (1411) using the corresponding bromoester.

Example 276. Preparation of (2R,4S)—N—((S)-1-(((3-Chloro-1-methyl-1H-pyrrolo[2,3-b]pyridin-5-yl)methyl)amino)-1-oxopropan-2-yl)-4-(3-chloro-4-fluorobenzyl)pyrrolidine-2-carboxamide Trifluoroacetate salt (1474)

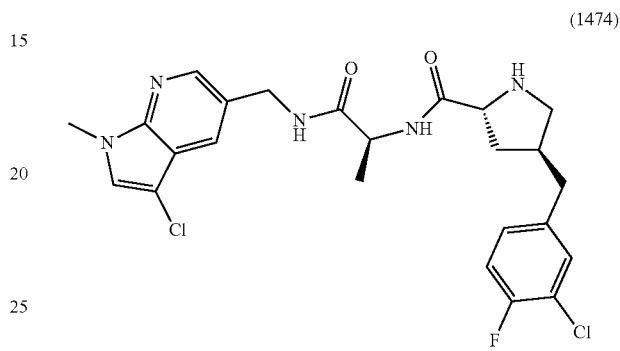

(2R,4S)—N—((S)-1-(((3-chloro-1-methyl-1H-pyrrolo[2,3-b]pyridin-5-yl)methyl)amino)-1-oxopropan-2-yl)-4-(3-chloro-4-fluorobenzyl)pyrrolidine-2-carboxamide trifluoroacetate salt was synthesized according to the procedures for compound (1476).

Example 277. Preparation of (2R,4S)—N—((S)-1-(((6-Amino-2-methylpyridin-3-yl)methyl)amino)-1-oxopropan-2-yl)-4-(3-chloro-4-methoxybenzyl)pyrrolidine-2-carboxamide Di-trifluoroacetate salt (1475)

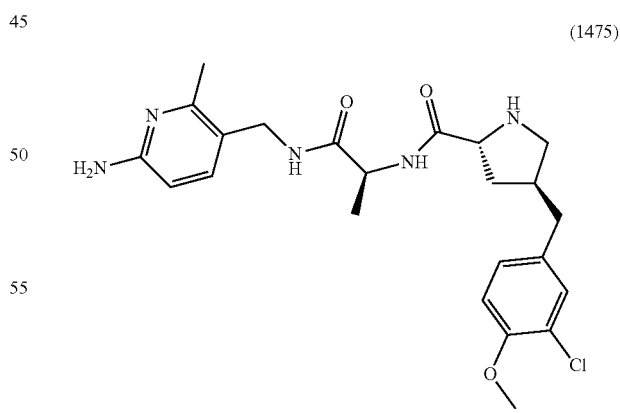

(2R,4S)—N—((S)-1-(((6-Amino-2-methylpyridin-3-yl)methyl)amino)-1-oxopropan-2-yl)-4-(3-chloro-4-methoxybenzyl)pyrrolidine-2-carboxamide di-trifluoroacetate salt was synthesized according to the procedures for compound (1328).

Example 278. Preparation of (2R,4S)—N—((S)-1-(((3-Chloro-1-methyl-1H-pyrrolo[2,3-b]pyridin-5-yl)methyl)amino)-1-oxopropan-2-yl)-4-(3-methylbenzyl)pyrrolidine-2-carboxamide Hydrochloride (1476)

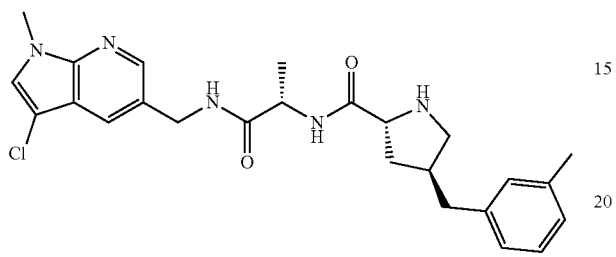

(2R,4S)—N—((S)-1-(((3-Chloro-1-methyl-1H-pyrrolo[2,3-b]pyridin-5-yl)methyl)amino)-1-oxopropan-2-yl)-4-(3-methylbenzyl)pyrrolidine-2-carboxamide hydrochloride was synthesized according to the procedures for compound (1450).

Example 279. Preparation of (2R,4S)—N—((S)-1-(((3-Chloro-1-methyl-1H-pyrrolo[2,3-b]pyridin-5-yl)methyl)amino)-1-oxopropan-2-yl)-4-(3-chlorobenzyl)pyrrolidine-2-carboxamide Trifluoroacetate salt (1477)

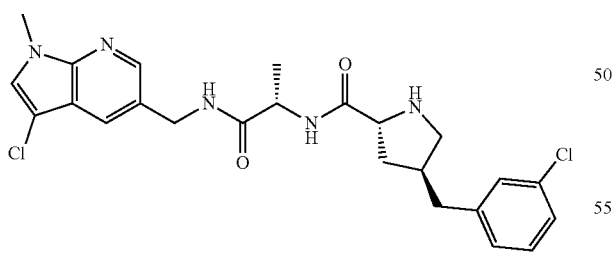

(2R,4S)—N—((S)-1-(((3-chloro-1-methyl-1H-pyrrolo[2,3-b]pyridin-5-yl)methyl)amino)-1-oxopropan-2-yl)-4-(3-chlorobenzyl)pyrrolidine-2-carboxamide trifluoroacetate salt was synthesized according to the procedures for compound (1450).

Example 280. Preparation of (2R,4S)—N—((S)-1-(((6-Amino-2-methylpyridin-3-yl)methyl)amino)-1-oxopropan-2-yl)-4-((3-methoxynaphthalen-2-yl)methyl)pyrrolidine-2-carboxamide Dihydrochloride (1478)

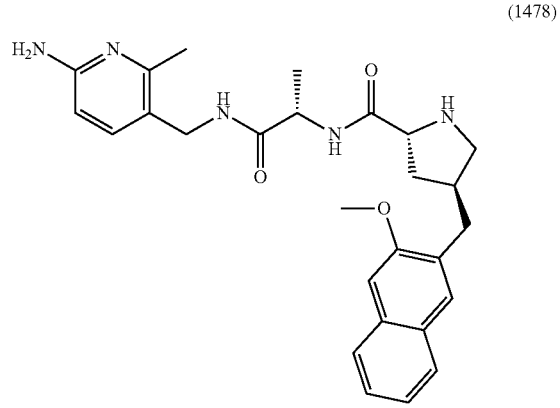 [SMILES: COc1cc2ccccc2cc1C[C@@H]1CN[C@@H](C(=O)N[C@@H](C)C(=O)NCc2ccc(N)nc2C)C1]

(2R,4S)—N—((S)-1-(((6-Amino-2-methylpyridin-3-yl)methyl)amino)-1-oxopropan-2-yl)-4-((3-methoxynaphthalen-2-yl)methyl)pyrrolidine-2-carboxamide dihydrochloride was synthesized according to the procedures for compound (1304).

Example 281. Preparation of (2R,4S)—N—((S)-1-(((6-Amino-2-methylpyridin-3-yl)methyl)amino)-1-oxopropan-2-yl)-4-((4-methylnaphthalen-1-yl)methyl)pyrrolidine-2-carboxamide Dihydrochloride (1479)

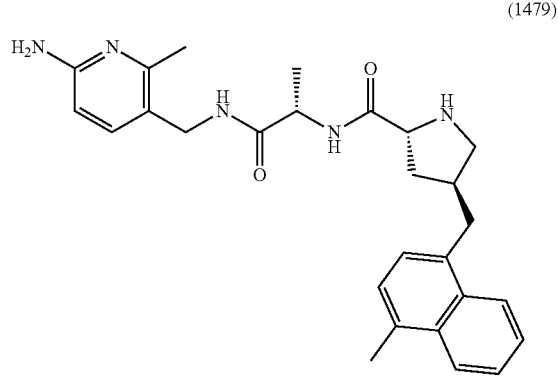 [SMILES: Cc1nc(N)ccc1CNC(=O)[C@H](C)NC(=O)[C@H]1C[C@H](Cc2ccc(C)c3ccccc23)CN1]

(2R,4S)—N—((S)-1-(((6-Amino-2-methylpyridin-3-yl)methyl)amino)-1-oxopropan-2-yl)-4-((4-methylnaphthalen-1-yl)methyl)pyrrolidine-2-carboxamide dihydrochloride was synthesized according to the procedures for compound (1304).

Example 282. Preparation of (R)—N—((S)-1-(((6-Amino-2-methylpyridin-3-yl)methyl)amino)-1-oxo-propan-2-yl)-4,4-bis(4-fluorobenzyl)pyrrolidine-2-carboxamide Di-trifluoroacetate salt (1480)

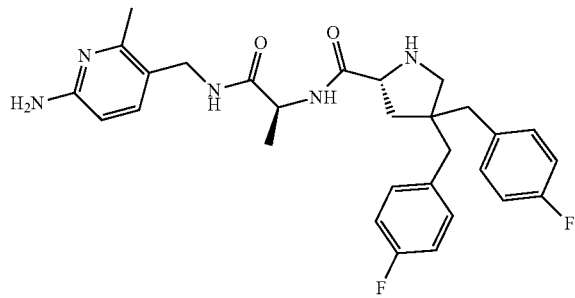

(1480)

(R)—N—((S)-1-(((6-Amino-2-methylpyridin-3-yl)methyl)amino)-1-oxopropan-2-yl)-4,4-bis(4-fluorobenzyl)pyrrolidine-2-carboxamide di-trifluoroacetate salt was synthesized according to the procedures for compound (1304).

Example 283. Preparation of (2R,4R)—N—((S)-1-(((6-Amino-2-methylpyridin-3-yl)methyl)amino)-1-oxopropan-2-yl)-4-(1-phenylcyclopropyl)pyrrolidine-2-carboxamide Di-trifluoroacetate salt (1481)

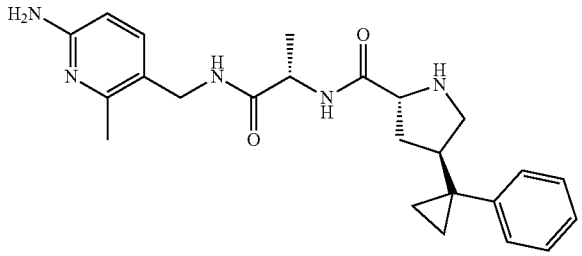

(1481)

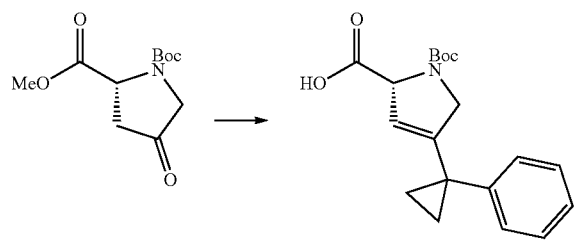

Step 1: (R)-1-(tert-Butoxycarbonyl)-4-(1-phenylcyclopropyl)-2,5-dihydro-1H-pyrrole-2-carboxylic acid was synthesized from 1-(tert-butyl) 2-methyl (R)-4-oxopyrrolidine-1,2-dicarboxylate according to the procedures for compound (1247), steps 1 to 3, utilizing potassium trifluoro(1-phenylcyclopropyl)borate as the coupling partner in the first step.

Steps 2-4: (2R,4R)—N—((S)-1-(((6-Amino-2-methylpyridin-3-yl)methyl)amino)-1-oxopropan-2-yl)-4-(1-phenylcyclopropyl)pyrrolidine-2-carboxamide di-trifluoroacetate salt was synthesized according to the procedures for compound (1359), steps 2-4.

Example 284. Preparation of (2R,4S)-4-(2-bromobenzyl)-N—((S)-1-(((3-chloro-1-methyl-1H-pyrrolo[2,3-b]pyridin-5-yl)methyl)amino)-1-oxopropan-2-yl)pyrrolidine-2-carboxamide Hydrochloride (1482)

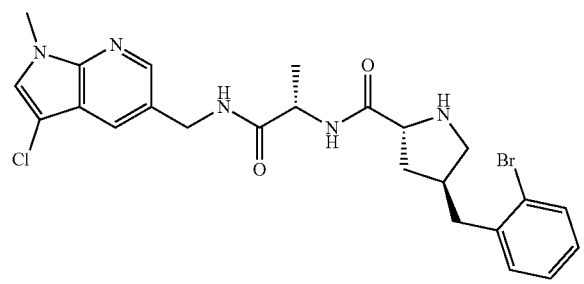

(1482)

(2R,4S)-4-(2-bromobenzyl)-N—((S)-1-(((3-chloro-1-methyl-1H-pyrrolo[2,3-b]pyridin-5-yl)methyl)amino)-1-oxopropan-2-yl)pyrrolidine-2-carboxamide Hydrochloride was synthesized according to the procedures for compound (1450).

Example 285. Preparation of (2R,4R)—N—((S)-1-(((6-Amino-2-methylpyridin-3-yl)methyl)amino)-1-oxopropan-2-yl)-4-((4-bromo-5-chlorothiophen-2-yl)methyl)pyrrolidine-2-carboxamide Di-trifluoroacetate salt (1483)

(1483)

(2R,4R)—N—((S)-1-(((6-Amino-2-methylpyridin-3-yl)methyl)amino)-1-oxopropan-2-yl)-4-((4-bromo-5-chlorothiophen-2-yl)methyl)pyrrolidine-2-carboxamide di-trifluoroacetate salt was synthesized according to the procedure for compound (1449).

Example 286. Preparation of 2-((2R,4S)-2-(((S)-1-(((3-Chloro-1-methyl-1H-pyrrolo[2,3-b]pyridin-5-yl)methyl)amino)-1-oxopropan-2-yl)carbamoyl)-4-(3-chloro-4-fluorobenzyl)pyrrolidin-1-yl)acetic acid Trifluoroacetate salt (1484)

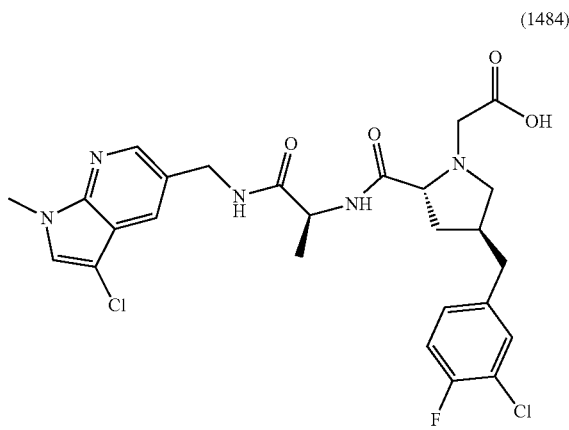 [SMILES: C[C@H](NC(=O)[C@H]1C[C@H](Cc2ccc(F)c(Cl)c2)CN1CC(=O)O)C(=O)NCc1cnc2c(c1)c(Cl)cn2C]

(1484)

2-((2R,4S)-2-(((S)-1-(((3-Chloro-1-methyl-1H-pyrrolo[2,3-b]pyridin-5-yl)methyl)amino)-1-oxopropan-2-yl)carbamoyl)-4-(3-chloro-4-fluorobenzyl)pyrrolidin-1-yl)acetic acid trifluoroacetate salt was synthesized according to the procedures for compound (1411).

Example 287. Preparation of (2R,4R)—N—((S)-1-((4-carbamimidoylbenzyl)amino)-1-oxopropan-2-yl)-4-phenylpiperidine-2-carboxamide Dihydrochloride (1485)

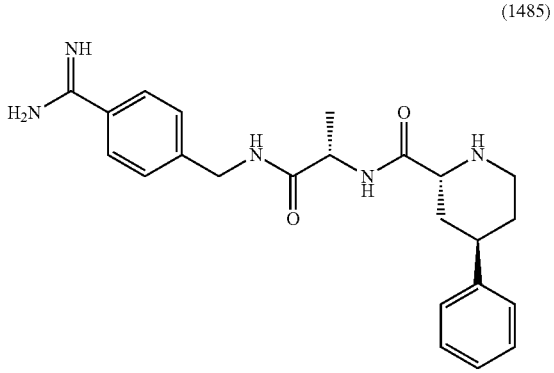 [SMILES: C[C@H](NC(=O)[C@H]1C[C@H](c2ccccc2)CCN1)C(=O)NCc1ccc(C(=N)N)cc1]

(1485)

(2R,4R)—N—((S)-1-((4-Carbamimidoylbenzyl)amino)-1-oxopropan-2-yl)-4-(m-tolyl)piperidine-2-carboxamide was synthesized according to the procedures for compound 6. The first UVActive material eluting from the column in step 1.

Example 288. Preparation of (2S,4S)—N—((S)-1-((4-carbamimidoylbenzyl)amino)-1-oxopropan-2-yl)-4-phenylpiperidine-2-carboxamide Dihydrochloride (1486)

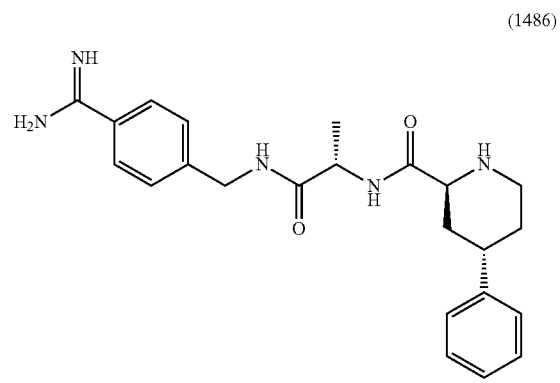 [SMILES: C[C@H](NC(=O)[C@@H]1C[C@@H](c2ccccc2)CCN1)C(=O)NCc1ccc(C(=N)N)cc1]

(1486)

(2R,4R)—N—((S)-1-((4-Carbamimidoylbenzyl)amino)-1-oxopropan-2-yl)-4-(m-tolyl)piperidine-2-carboxamide was synthesized according to the procedures for compound 6. The second UVActive material eluting from the column in step 1.

Example 289. Preparation of (2S,4R)—N—((S)-1-((4-carbamimidoylbenzyl)amino)-1-oxopropan-2-yl)-4-phenylpiperidine-2-carboxamide Dihydrochloride (1487)

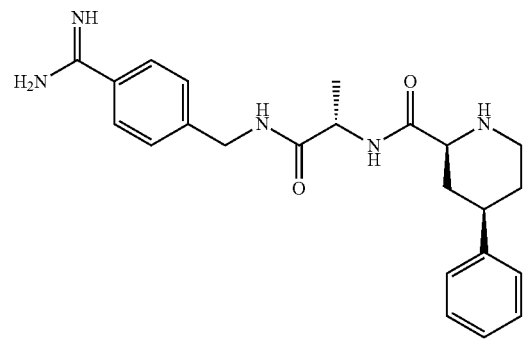

(1487)

(2R,4R)—N—((S)-1-((4-Carbamimidoylbenzyl)amino)-1-oxopropan-2-yl)-4-(m-tolyl)piperidine-2-carboxamide was synthesized according to the procedures for compound 6. The fourth UVActive material eluting from the column in step 1.

Example 290. Preparation of N-(5-Chloro-2-(1H-tetrazol-1-yl)benzyl)-2-(6-methyl-2-oxo-3-(phenethylamino)pyrazin-1(2H)-yl)acetamide (1489)

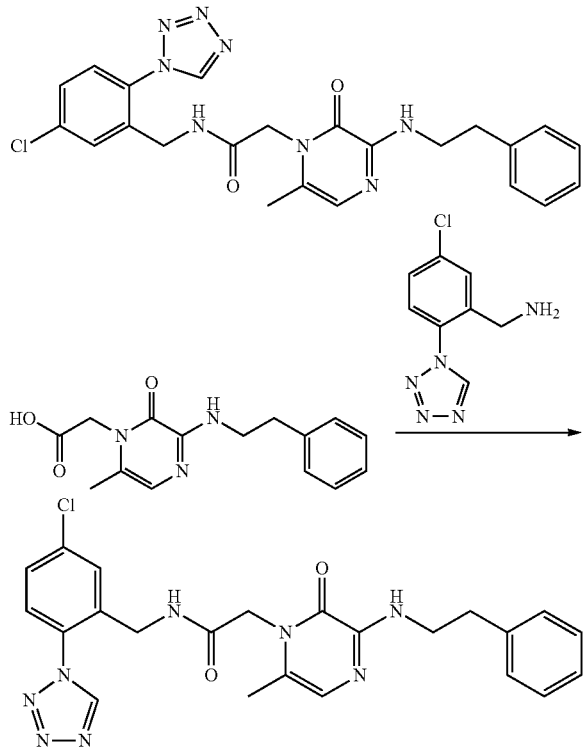

Step 1: The title compound was prepared according to step 3 of the procedure for compound (1365), using the appropriate starting materials except with purification by chromatography (95% EtOAc/hexanes; 42 mg, 88% yield).

Example 291. Preparation of N-((3-Chloro-1H-pyrrolo[2,3-b]pyridin-5-yl)methyl)-2-(6-methyl-2-oxo-3-(phenethylamino)pyrazin-1(2H)-yl)acetamide Acetate salt (1490)

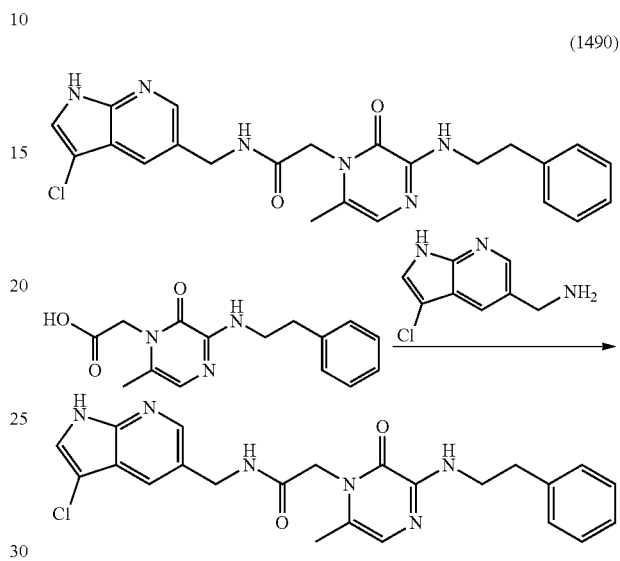

Step 1: The title compound was prepare according to step 3 of the procedure or compound (1365), using the appropriate starting materials except with purification by chromatography (MeOH/CH$_2$Cl$_2$+AcOH; 10 mg, 22% yield).

Example 292. Preparation of N-((1-Aminoisoquinolin-6-yl)methyl)-2-(6-methyl-2-oxo-3-(phenethylamino)pyrazin-1(2H)-yl)acetamide Trifluoroacetamide salt (1491)

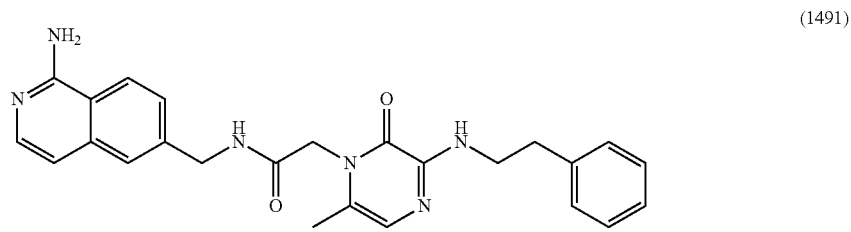

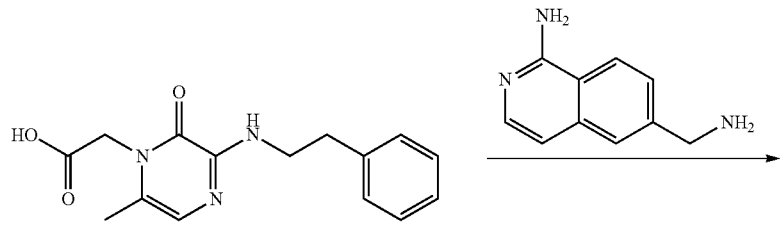

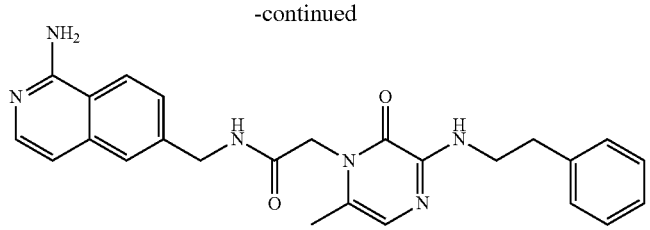

Step 1: The title compound was prepared according to step 3 of the procedure for compound (1365), using the appropriate starting materials (9 mg, 20% yield).

Example 293. Preparation of N-((2-Amino-1H-benzo[d]imidazol-6-yl)methyl)-2-(6-methyl-2-oxo-3-(phenethylamino)pyrazin-1(2H)-yl)acetamide Trifluoroacetamide salt (1492)

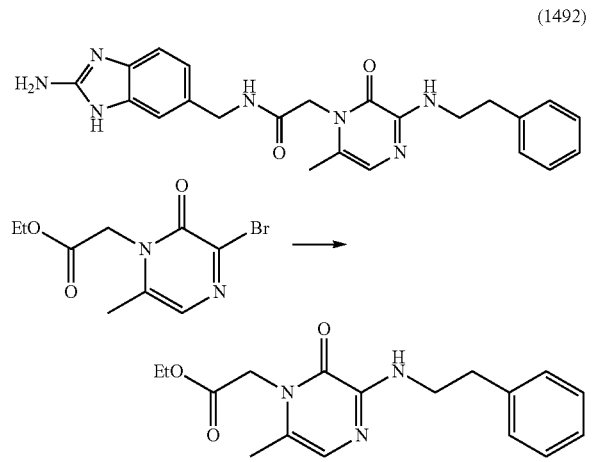

Step 1: A solution of ethyl 2-(3-bromo-6-methyl-2-oxopyrazin-1(2H)-yl)acetate (411 mg, 1.5 mmol) and phenethylamine (189 µL, 1.5 mmol) in 1:1 toluene/EtOH (10 mL) was heated at 125° C. for 18 h in a sealed flask. Upon cooling, the reaction mixture was concentrated then taken up in EtOAc and washed with sat. aq. NaHCO₃, brine and dried over Na₂SO₄ then concentrated. The crude product was purified by chromatography (60% EtOAc/hexanes) to furnish ethyl 2-(6-methyl-2-oxo-3-(phenethylamino)pyrazin-1(2H)-yl)acetate as a beige solid (390 mg, 82% yield).

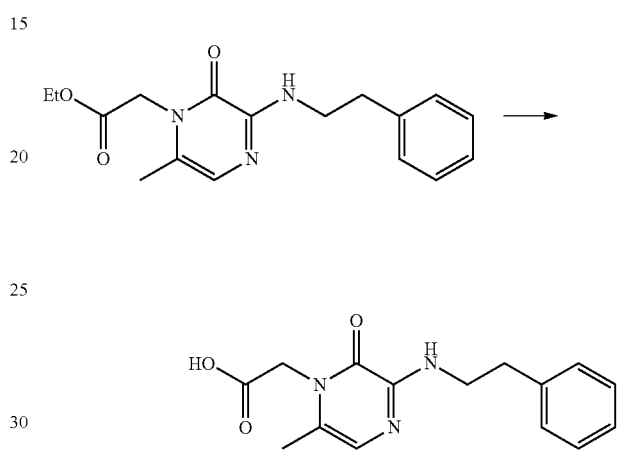

Step 2: Ethyl 2-(6-methyl-2-oxo-3-(phenethylamino)pyrazin-1(2H)-yl)acetate (390 mg, 1.24 mmol) was dissolved in 1:1 THF/MeOH (6 mL) and treated with 1 N aq. NaOH (3 mL). After 2 h, the organic solvents were removed in vacuo and cooled to 0° C. before being acidified with 1 N HCl. The precipitated product was collected by filtration to give 2-(6-methyl-2-oxo-3-(phenethylamino)pyrazin-1(2H)-yl)acetic acid as a pale yellow powder (285 mg, 81% yield).

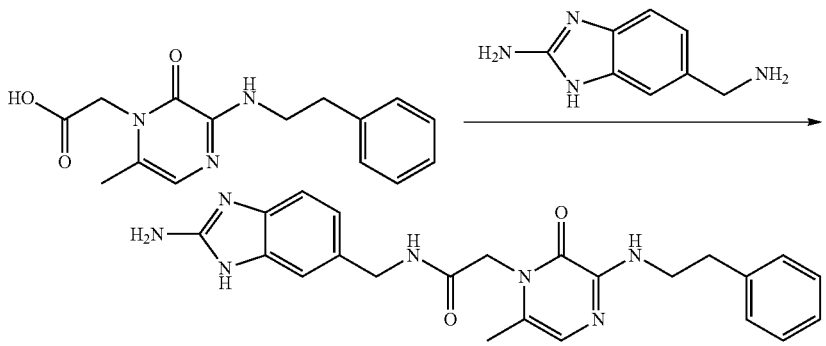

Step 3: A 50 mL round bottom flask was charged with 2-(6-methyl-2-oxo-3-(phenethylamino)pyrazin-1(2H)-yl) acetic acid (29 mg, 0.1 mmol), EDC (21 mg, 0.11 mmol), HOBt (16 mg, 0.12 mmol) and DMF (1 mL). After 5 min, 6-(aminomethyl)-1H-benzo[d]imidazol-2-amine dihydrochloride (26 mg, 0.11 mmol) and DIEA (52 µL, 0.3 mmol) were added and the reaction stirred for 16 h at ambient temperature. Upon completion, the reaction mixture was diluted with EtOAc and washed with sat. NaHCO₃ and Example 294. Preparation of (2R,4R)—N—((S)-1-(((4-Bromo-1H-pyrrolo[2,3-c]pyridin-2-yl)methyl)amino)-1-oxopropan-2-yl)-4-phenylpyrrolidine-2-carboxamide Di-trifluoroacetate salt (1493)

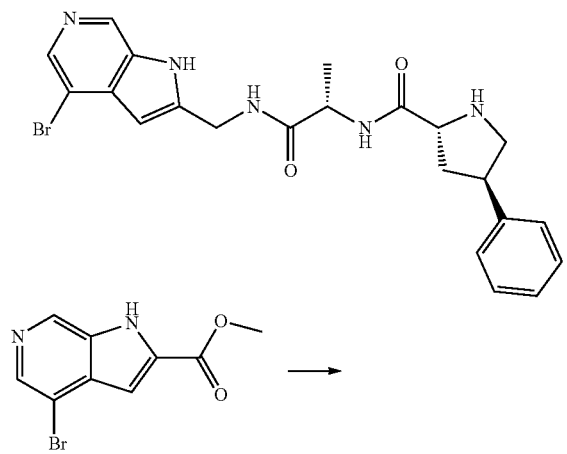

(1493)

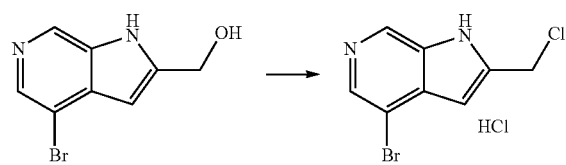 [SMILES: OCc1cc2c(Br)cncc2[nH]1 ; ClCc1cc2c(Br)cncc2[nH]1 ; Cl]

Step 1: To a 0° C. solution of methyl 4-bromo-1H-pyrrolo[2,3-c]pyridine-2-carboxylate (1.0 g, 3.92 mmol) in THF (20 mL, 5.1 M) was added lithium aluminum hydride (1 M in THF, 6.3 mL, 6.3 mmol). After stirring for 1 h at the same temperature, the reaction was quenched by addition of H₂O. The resulting mixture was extracted with EtOAc, dried over anhyd Na₂SO₄, and conc under vacuum. The residue was purified by chromatography (0-100% EtOAc-hexanes) to give (4-bromo-1H-pyrrolo[2,3-c]pyridin-2-yl)methanol (206 mg, 23% yield).

Step 2: To a solution of (4-bromo-1H-pyrrolo[2,3-c]pyridin-2-yl)methanol (206 mg, 0.91 mmol) in CH₂Cl₂ (1.5 mL, 0.6 M) was added 4.0 M HCl in dioxane (2.2 mL). After stirring for 15 min, the reaction mixture was conc under vacuum. To this residue was added thionyl chloride (1 mL) at 0° C. After stirring for 2 min at reflux, the reaction mixture was concentrated to give the crude 4-bromo-2-(chloromethyl)-1H-pyrrolo[2,3-c]pyridine hydrochloride salt (256 mg, 99% yield).

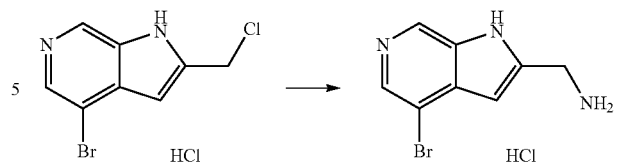

Step 3: To a solution of di-tert-butyl iminodicarboxylate (295 mg, 1.36 mmol) in DMF (5 mL, 0.27 M) was added sodium hydride (60% dispersion in mineral oil). After stirring for 30 min, the crude 4-bromo-2-(chloromethyl)-1H-pyrrolo[2,3-c]pyridine hydrochloride salt (256 mg, 0.9 mmol) in DMF (1.0 mL, 0.9 M) was added drop-wise. After stirring for 2 h at room temperature, another 0.5 eq of sodium hydride was added. After stirring for 16 h at the same temperature, the reaction was quenched by addition of H₂O. The resulting mixture was extracted with EtOAc, dried over anhyd Na₂SO₄, and conc under vacuum. The residue was dissolved in CH₂Cl₂ (5 mL) and 4.0 M HCl in dioxane was added. After stirring for 22 h, the reaction mixture was concentrated to the crude (4-bromo-1H-pyrrolo[2,3-c]pyridin-2-yl)methanamine hydrochloride salt (233 mg, 86% yield).

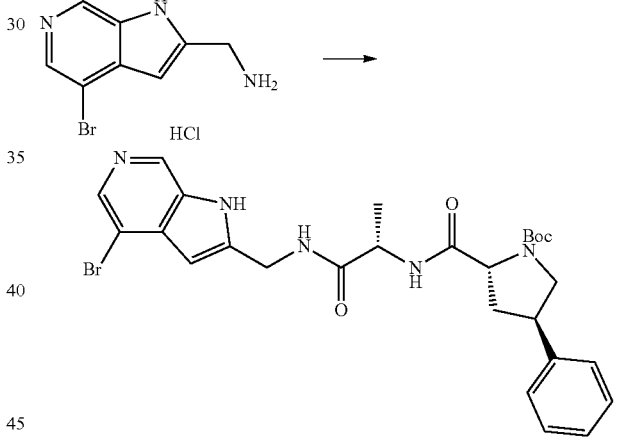

Step 4: tert-Butyl (2R,4R)-2-(((S)-1-(((4-bromo-1H-pyrrolo[2,3-c]pyridin-2-yl)methyl)amino)-1-oxopropan-2-yl)carbamoyl)-4-phenylpyrrolidine-1-carboxylate (13 mg, 4% yield) was synthesized from the crude (4-bromo-1H-pyrrolo[2,3-c]pyridin-2-yl)methanamine hydrochloride salt (217 mg, 0.6 mmol) according to the procedure for compound, step 2.

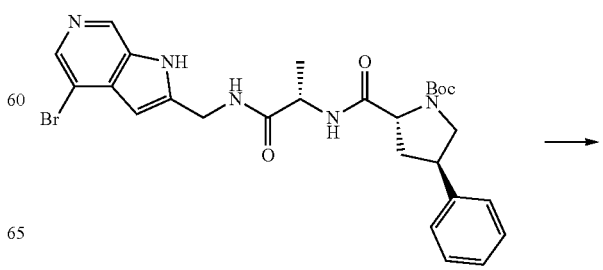

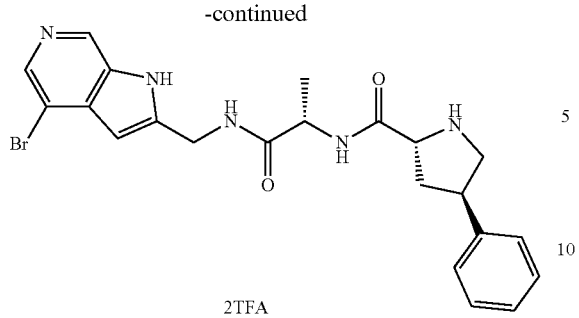

2TFA

Step 5: Deprotection of tert-butyl (2R,4R)-2-(((S)-1-(((4-bromo-1H-pyrrolo[2,3-c]pyridin-2-yl)methyl)amino)-1-oxopropan-2-yl)carbamoyl)-4-phenylpyrrolidine-1-carboxylate (13 mg, 0.02 mmol) was conducted according to the procedure for compound, step 4 except that the final product was purified using reverse-phase HPLC.

Example 295. Preparation of (2R,4S)—N—((S)-1-(((1H-Pyrrolo[3,2-c]pyridin-2-yl)methyl)amino)-1-oxopropan-2-yl)-4-(3-chloro-4-fluorobenzyl)pyrrolidine-2-carboxamide Di-trifluoroacetate salt (1494)

(1494)

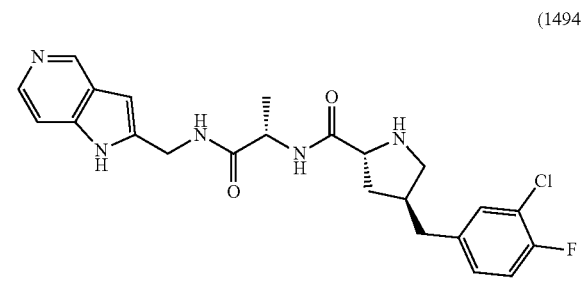

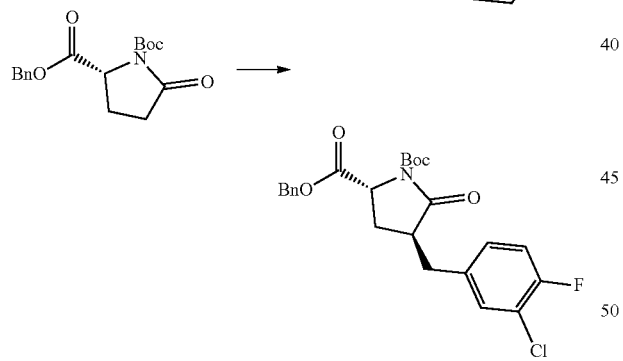

Step 1: To a −78° C. solution of 2-benzyl 1-(tert-butyl) (R)-5-oxopyrrolidine-1,2-dicarboxylate (500 mg, 1.57 mmol) in THF (10 mL, 0.16 M) was slowly added lithium bis(trimethylsilyl)amide (1 M in THF, 1.72 mL, 1.72 mmol). After stirring for 1 h at the same temperature, 4-(bromomethyl)-2-chloro-1-fluorobenzene (420 mg, 1.88 mmol) in THF (2 mL) was added. After stirring for 2 h at the same temperature, the reaction was quenched by addition of sat. aq NH$_4$C$_1$. The resulting mixture was extracted with EtOAc, dried over anhyd Na$_2$SO$_4$, and conc under vacuum. The residue was purified by chromatography (0-100% EtOAc-hexanes) to give 2-benzyl 1-(tert-butyl) (2R,4S)-4-(3-chloro-4-fluorobenzyl)-5-oxopyrrolidine-1,2-dicarboxylate (450 mg, 62% yield).

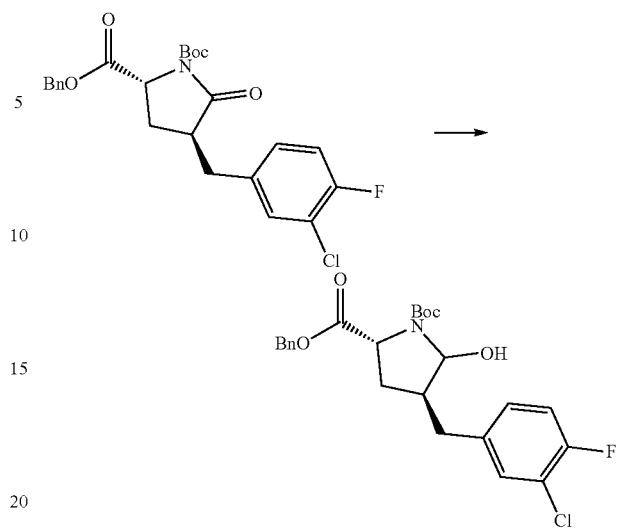

Step 2: To a −78° C. solution of 2-benzyl 1-(tert-butyl) (2R,4S)-4-(3-chloro-4-fluorobenzyl)-5-oxopyrrolidine-1,2-dicarboxylate (450 mg, 0.97 mmol) in THF (7 mL, 0.14 M) was added lithium triethylborohydride (1 M in THF, 1.07 mL, 1.07 mmol). After stirring for 30 min, the reaction was quenched by addition of sat. aq NaHCO$_3$ and warmed to 0° C. 30% H$_2$O$_2$ (about 8 drops) was added and the reaction mixture was stirred for 30 min at same temperature. The organic volatiles were removed under vacuum and the aqueous layer was extracted with CH$_2$Cl$_2$. The combined extracts were dried over anhyd Na$_2$SO$_4$, and conc under vacuum to give 2-benzyl 1-(tert-butyl) (2R,4S)-4-(3-chloro-4-fluorobenzyl)-5-hydroxypyrrolidine-1,2-dicarboxylate (450 mg, 100%) which was used in the next step without further purification.

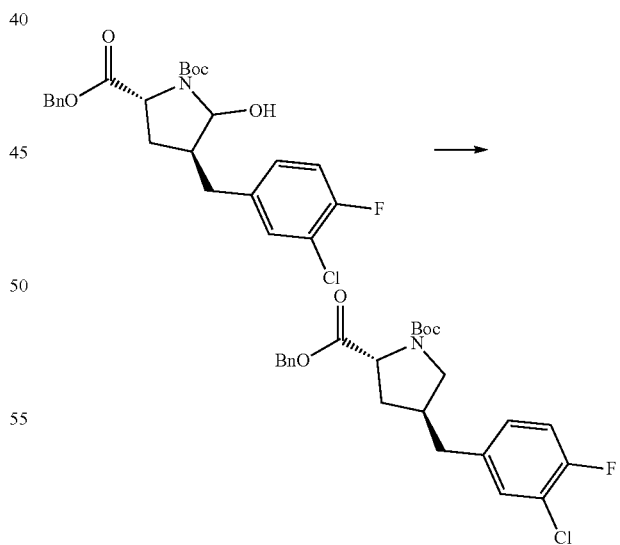

Step 3: To a −78° C. solution of 2-benzyl 1-(tert-butyl) (2R,4S)-4-(3-chloro-4-fluorobenzyl)-5-hydroxypyrrolidine-1,2-dicarboxylate (450 mg, 0.97 mmol) in CH$_2$Cl$_2$ (6 mL, 0.16 M) was added triethylsilane (0.38 mL, 2.13 mmol) and boron trifluoride diethyl etherate (0.65 mL, 2.13 mmol). After stirring for 2 h at the same temperature, the reaction was quenched by addition of sat. aq NaHCO₃ solution. The resulting mixture was extracted with CH₂Cl₂, dried over anhyd Na₂SO₄, and conc under vacuum. The residue was purified by chromatography (0-100% EtOAc-hexanes) to give 2-benzyl 1-(tert-butyl) (2R,4S)-4-(3-chloro-4-fluorobenzyl)pyrrolidine-1,2-dicarboxylate (220 mg, 51% yield for two steps).

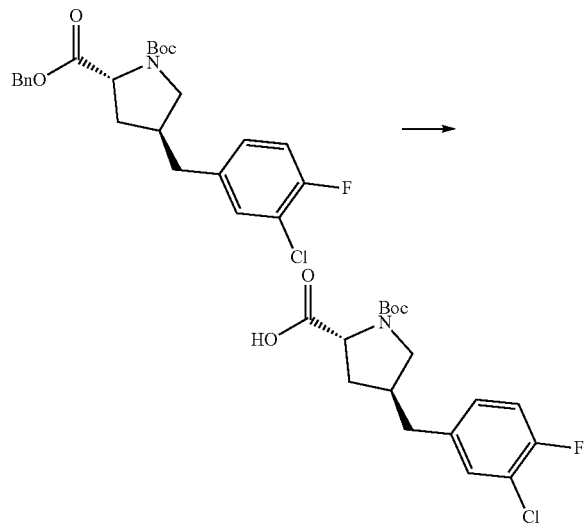

Step 4: A solution of 2-benzyl 1-(tert-butyl) (2R,4S)-4-(3-chloro-4-fluorobenzyl)pyrrolidine-1,2-dicarboxylate (220 mg, 0.49 mmol) was degassed with a stream of Ar for 2 min. 10% Pd/C (10 mg) was added and a vacuum was pulled for 1 min. A balloon of H₂ was added and the reaction was monitored for the consumption of starting material for 1.5 h. The catalyst was removed by filtration and the solution was evaporated to give (2R,4S)-1-(tert-butoxycarbonyl)-4-(3-chloro-4-fluorobenzyl)pyrrolidine-2-carboxylic acid (175 mg, 100% yield).

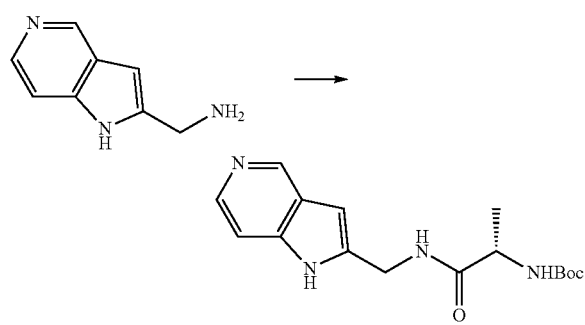

Step 5: To a solution of (tert-butoxycarbonyl)-L-alanine (467 mg, 2.47 mmol) in CH₂Cl₂ (15 mL) and MeOH (5 mL) was added NHS (313 mg, 2.72 mmol) with stirring at room temp until dissolved. DCC (561 mg, 2.72 mmol) was added and stirred for 1 h. (1H-pyrrolo[3,2-c]pyridin-2-yl)methanamine (400 mg, 2.72 mmol) was added to the above mixture and stirred for 1 h. The reaction was quenched by addition of H₂O and the resulting mixture was extracted with CH₂Cl₂, dried over anhyd Na₂SO₄, and conc under vacuum. The residue was purified by chromatography (0-100% EtOAc-hexanes) to give tert-butyl (S)-(1-(((1H-pyrrolo[3,2-c]pyridin-2-yl)methyl)amino)-1-oxopropan-2-yl)carbamate (129 mg, 15% yield).

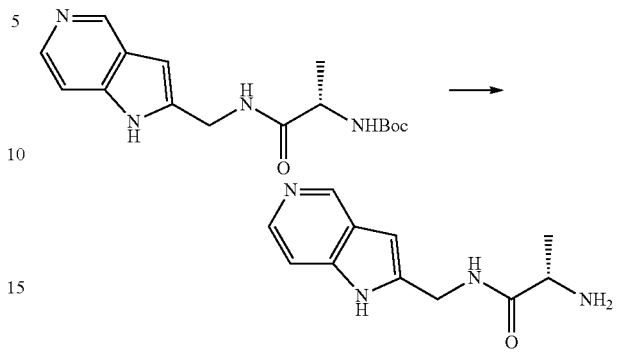

Step 6: To a 0° C. solution of tert-butyl (S)-(1-(((1H-pyrrolo[3,2-c]pyridin-2-yl)methyl)amino)-1-oxopropan-2-yl)carbamate (129 mg, 0.4 mmol) in CH₂Cl₂ (10 mL, 0.04 M) was added 20% TFA in CH₂Cl₂ (10 mL). After stirring for 3 h at room temperature, the reaction mixture was concentrated to give (S)—N-((1H-pyrrolo[3,2-c]pyridin-2-yl)methyl)-2-aminopropanamide di-trifluoroacetate salt (180 mg, 100% yield).

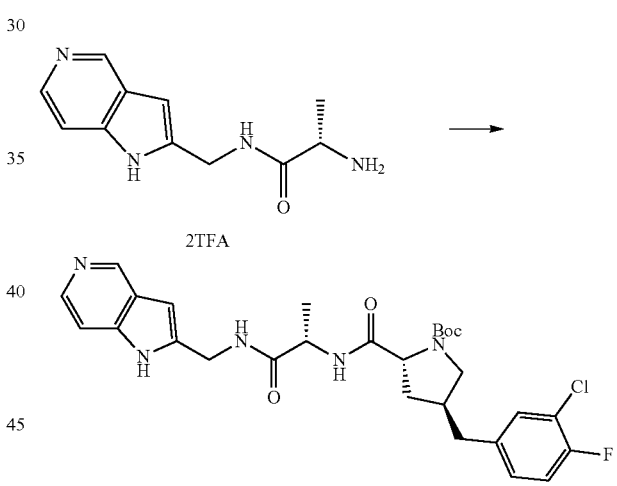

Step 7: To a solution of 2-benzyl 1-(tert-butyl) (2R,4S)-4-(3-chloro-4-fluorobenzyl)pyrrolidine-1,2-dicarboxylate (25 mg, 0.07 mmol) in anhyd DMF (2 mL, 0.04 M) was added HOBt (14 mg, 0.09 mmol), DIEA (0.05 mL, 0.28 mmol), and EDC (14 mg, 0.09 mmol). After stirring for 30 min at ambient temperature, (S)—N-((1H-pyrrolo[3,2-c]pyridin-2-yl)methyl)-2-aminopropanamide di-trifluoroacetate salt (38 mg, 0.08 mmol) was added and stirred for 16 h. The reaction mixture was conc and the residue was partitioned with EtOAc and 10% KHSO₄ solution. The organic layer was separated and washed with H₂O and sat. aq NaHCO₃. The organic layer was dried over anhyd Na₂SO₄ and concd. The residue was purified by chromatography (0-100% [5% 7 N NH₃ in MeOH/CH₂Cl₂]—CH₂Cl₂) to give tert-butyl (2R,4S)-2-(((S)-1-(((1H-pyrrolo[3,2-c]pyridin-2-yl)methyl)amino)-1-oxopropan-2-yl)carbamoyl)-4-(3-chloro-4-fluorobenzyl)pyrrolidine-1-carboxylate (27 mg, 68% yield).

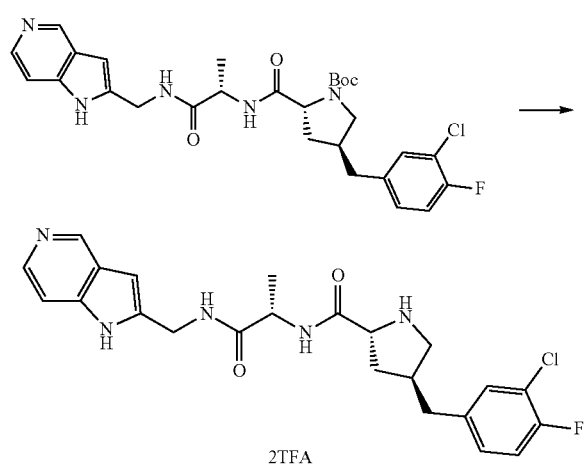

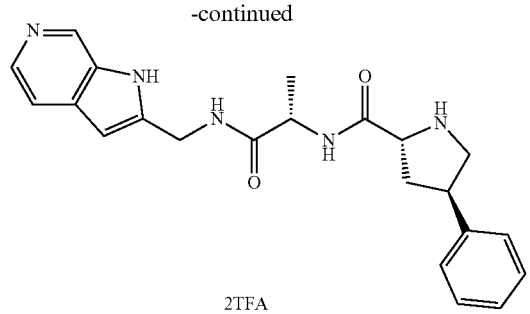

Step 8: To a 0° C. solution of tert-butyl (2R,4S)-2-(((S)-1-((((1H-pyrrolo[3,2-c]pyridin-2-yl)methyl)amino)-1-oxopropan-2-yl)carbamoyl)-4-(3-chloro-4-fluorobenzyl)pyrrolidine-1-carboxylate (27 mg, 0.05 mmol) in CH₂Cl₂ (1 mL, 0.05 M) was added 20% TFA in CH₂Cl₂ (1 mL). After stirring for 3 h at room temperature, the reaction mixture was concentrated to give (2R,4S)—N—((S)-1-(((1H-pyrrolo[3,2-c]pyridin-2-yl)methyl)amino)-1-oxopropan-2-yl)-4-(3-chloro-4-fluorobenzyl)pyrrolidine-2-carboxamide di-trifluoroacetate salt (33 mg, 100% yield).

Example 296. Preparation of (2R,4R)—N—((S)-1-((((1H-Pyrrolo[2,3-c]pyridin-2-yl)methyl)amino)-1-oxopropan-2-yl)-4-phenylpyrrolidine-2-carboxamide Di-trifluoroacetate salt (1495)

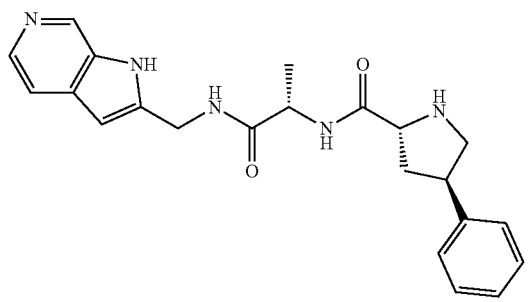

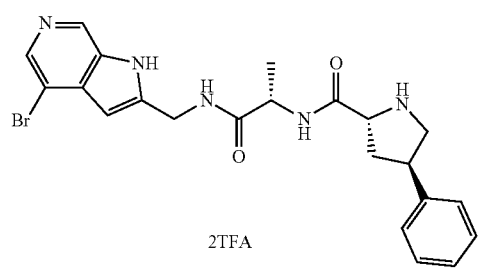

Step 1: (2R,4R)—N—((S)-1-((((1H-Pyrrolo[2,3-c]pyridin-2-yl)methyl)amino)-1-oxopropan-2-yl)-4-phenylpyrrolidine-2-carboxamide di-trifluoroacetate salt (2.0 mg, 80% yield) was synthesized from (2R,4R)—N—((S)-1-((((4-Bromo-1H-pyrrolo[2,3-c]pyridin-2-yl)methyl)amino)-1-oxopropan-2-yl)-4-phenylpyrrolidine-2-carboxamide di-trifluoroacetate salt (prepared according to the procedure for compound (1493), step 1-5) according to the procedure for compound (1264), step 2.

Example 297. Preparation of (2R,4S)—N—((S)-1-(((6-Amino-2-methylpyridin-3-yl)methyl)amino)-1-oxopropan-2-yl)-1-ethyl-4-phenylpiperidine-2-carboxamide (1496)

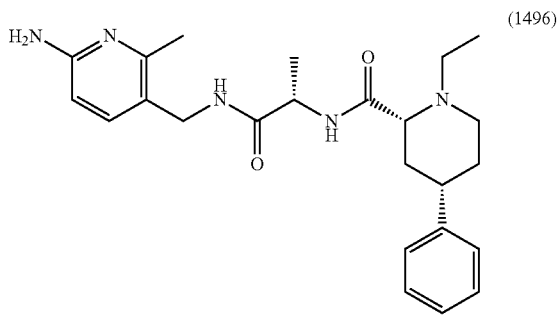 [SMILES: CCN1CC[C@H](c2ccccc2)C[C@@H]1C(=O)N[C@@H](C)C(=O)NCc1ccc(N)nc1C]

(2R,4S)—N—((S)-1-(((6-Amino-2-methylpyridin-3-yl)methyl)amino)-1-oxopropan-2-yl)-1-ethyl-4-phenylpiperidine-2-carboxamide was synthesized according to the procedures for compound (1464).

Example 298. Preparation of (2R,4S)—N—((S)-1-(((6-Amino-2-methylpyridin-3-yl)methyl)amino)-1-oxopropan-2-yl)-4-(4-bromobenzyl)-N-methylpyrrolidine-2-carboxamide Di-trifluoroacetate salt (1497)

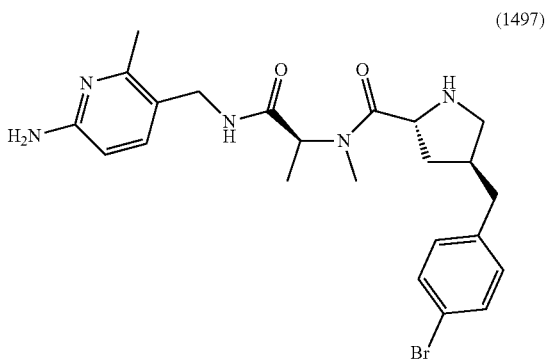 [SMILES: Cc1nc(N)ccc1CNC(=O)[C@H](C)N(C)C(=O)[C@H]1C[C@H](Cc2ccc(Br)cc2)CN1]

(2R,4S)—N—((S)-1-(((6-Amino-2-methylpyridin-3-yl)methyl)amino)-1-oxopropan-2-yl)-4-(4-bromobenzyl)-N-methylpyrrolidine-2-carboxamide di-trifluoroacetate salt was synthesized according to the procedures for compound (1438), except that the title compound was not purified by prep HPLC.

Example 299. Preparation of 2-(Pyridin-2-yl)-1H-benzo[d]imidazole-5-carboximidamide Dihydrochloride (2001)

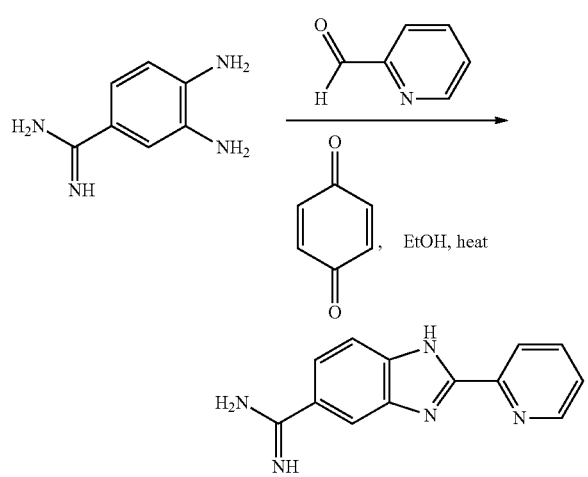

This method is a modification of the general procedure of W. B. Young et al., Bioorg. Med. Chem. Lett. 16 (2006) 710-713. A mixture of 3,4-diaminobenzimidamide HCl (0.5 g, 2.6 mmol), picolinaldehyde (0.22 mL, 2.3 mmol), benzoquinone (0.28 g, 2.6 mmol) and ethanol (15 mL) was heated at reflux. After stirring for 3 h, the mixture was allowed to warm to room temp and the volatiles removed under reduced pressure. The residue was dissolved in methanol (5 mL) then added to cold MeCN (100 mL) while stirring to yield a precipitate that was isolated by filtration. The precipitate was dissolved in 6 N HCl (20 mL) and poured into stirring acetone (150 mL) to give a precipitate. The precipitate was isolated by filtration, washed with acetone and dried under reduced pressure to provide 2-(pyridin-2-yl)-1H-benzo[d]imidazole-5-carboximidamide, dihydrochloride salt (0.53 g, 65%).

Proceeding similarly to the procedure for compound 2001, but with the appropriate starting materials, the following compounds were made: 2-(1H-imidazol-4-yl)-1H-benzo[d]imidazole-5-carboximidamide dihydrochloride (2000); 2-(6-methylpyridin-2-yl)-1H-benzo[d]imidazole-5-carboximidamide; 2-(6-methylpyridin-2-yl)-1H-benzo[d]imidazole-5-carboximidamide (2003); 2-(3-methylpyridin-2-yl)-1H-benzo[d]imidazole-5-carboximidamide dihydrochloride (2004); 2-(4-methylpyridin-2-yl)-1H-benzo[d]imidazole-5-carboximidamide dihydrochloride (2005); 2-(5-ethylpyridin-2-yl)-1H-benzo[d]imidazole-5-carboximidamide dihydrochloride (2007); 2-(6-ethylpyridin-2-yl)-1H-benzo[d]imidazole-5-carboximidamide dihydrochloride (2008); 1H,1'H-[2,2'-bibenzo[d]imidazole-5-carboximidamide dihydrochloride (2009); 2-(5-methylpyridin-2-yl)-1H-benzo[d]imidazole-5-carboximidamide dihydrochloride (2010); 2-(6-(methoxymethyl)pyridin-2-yl)-1H-benzo[d]imidazole-5-carboximidamide dihydrochloride (2011); 2-(4-ethoxypyridin-2-yl)-1H-benzo[d]imidazole-5-carboximidamide dihydrochloride (2012); 2-(quinolin-2-yl)-1H-benzo[d]imidazole-5-carboximidamide dihydrochloride (2013); 2-(isoquinolin-3-yl)-1H-benzo[d]imidazole-5-carboximidamide dihydrochloride (2014); and 2-(6-(4-fluorophenyl)pyridin-2-yl)-benzo[d]imidazole-5-carboximidamide dihydrochloride (2016).

Example 300. Preparation of 2-(Pyridin-2-ylmethyl)-1H-benzo[d]imidazole-5-carboximidamide Dihydrochloride (2002)

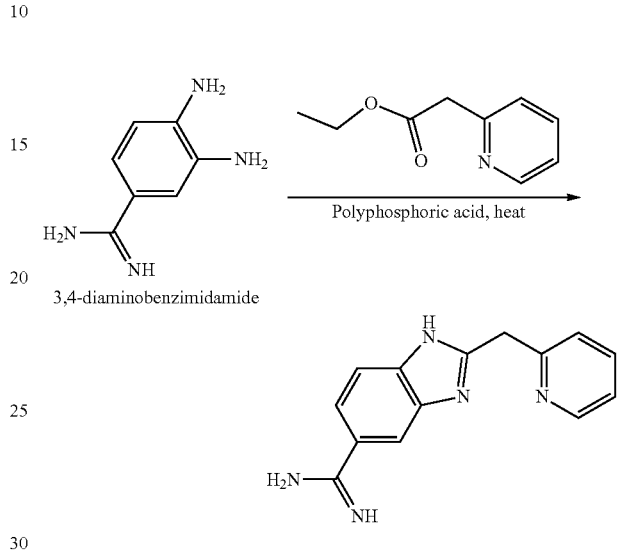

This method is a modification of the general procedure of W. B. Young et al., Bioorg. Med. Chem. Lett. 16 (2006) 710-713. An oven-dried flask was charged with 3,4-diaminobenzimidamide HCl (0.99 g, 5.3 mmol), ethyl 2-(pyridin-2-yl)acetate (0.9 mL, 5.9 mmol) and polyphosphoric acid (8 mL). The mixture was heated to 180° C. After stirring for 2 h, the mixture was allowed to warm to room temp. The mixture was diluted with $H_2O$ (50 mL) and then cooled over an ice bath. After the mixture was cooled, an aq solution of 50% NaOH was added to adjust the pH to 8, and the mixture was allowed to warm to room temp. To the gummy mixture was added MeOH (10 mL); the volatiles were removed under reduced pressure. Aqueous saturated $NaHCO_3$ was added with vigorous stirring until a precipitate was obtained. The precipitate was then isolated by filtration and rinsed with $H_2O$. The precipitate was dissolved in 6 N HCl (15 mL). The solution was poured into stirring acetone (150 mL) to give a precipitate, which was isolated by filtration, washed with acetone, and dried to provide 2-(pyridin-2-ylmethyl)-1H-benzo[d]imidazole-5-carboximidamide, dihydrochloride salt (0.24 g, 14%).

Example 301. Preparation of 2-((1H-Benzo[d]imidazol-2-yl)methyl)-1H-benzo[d]imidazole-5-carboximidamide Dihydrochloride (2015)

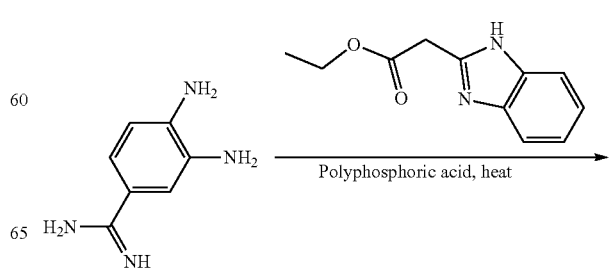

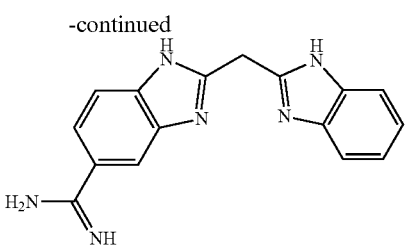

This method is a modification of the general procedure of W. B. Young et al., Bioorg. Med. Chem. Lett. 16 (2006) 710-713. An oven-dried flask was charged with 3,4-diaminobenzimidamide HCl (0.98 g, 5.2 mmol), ethyl 2-(1H-benzo[d]imidazol-2-yl)acetate (1.2 g, 5.8 mmol) and polyphosphoric acid (8 mL). The mixture was heated to 185° C. After stirring for 2 h, the mixture was allowed to cool to room temp. After 8 h, the mixture was diluted with H$_2$O (50 mL) and then cooled over an ice bath. After the mixture was cooled, a solution of 50% NaOH was added to adjust the pH to 9. The mixture was vigorously stirred and gradually warmed to room temp; the solids were isolated by vacuum filtration and rinsed with H$_2$O. The solids were then stirred for 30 min with saturated aq NaHCO$_3$, filtered, and rinsed with H$_2$O. The precipitate was collected and dissolved in 6 N HCl (15 mL). The solution was poured into stirring acetone (150 mL) to give a precipitate. The precipitate was isolated by filtration, washed with acetone and dried to provide 2-((1H-benzo[d]imidazol-2-yl)methyl)-1H-benzo[d]imidazole-5-carboximidamide, dihydrochloride salt (1.6 g, 85%).

Example 302. Preparation of ((4-((2-(3-Benzyl-7-carbamoyl-2,4-dioxo-3,4-dihydroquinazolin-1(2H)-yl)acetamido)methyl)phenyl)(imino)methyl)-λ$^5$-azaneyl Acetate (2017)

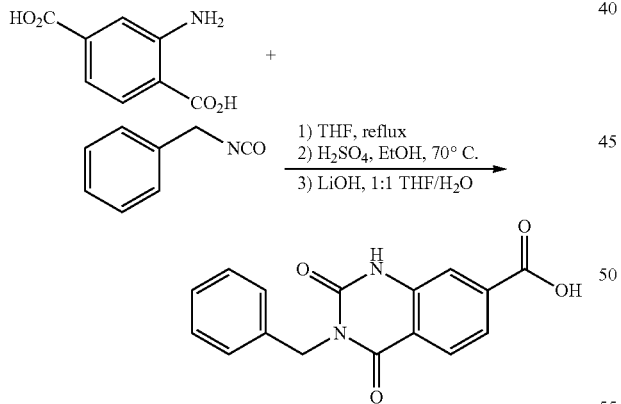

Step 1: A reaction vessel was charged with 2-aminoterephthalic acid (600 mg, 3.31 mmol) and THF (10 mL). To this was added benzyl isocyanate (485 mg, 3.64 mmol), and the mixture was refluxed at 70° C. for 4 h. The reaction mixture was then cooled, and the solvent was evaporated under vacuum and replaced with EtOH (10 mL). The reaction was treated with H$_2$SO$_4$ (2 mL) and stirred at 70° C. for 2 h. Upon completion, the reaction was cooled to 5° C. and treated with water, whereupon a slurry was formed. The precipitate was filtered and washed with H$_2$O and hexanes, then collected as an off-white solid that was then re-suspended in THF (10 mL) and H$_2$O (10 mL). LiOH (2 equiv, 159 mg) was added in one portion and the reaction stirred at ambient temperature for 2 h. After completion, THF was removed under vacuum and the reaction then acidified with 1 N HCl. The resulting slurry was filtered to yield 3-benzyl-2,4-dioxo-1,2,3,4-tetrahydroquinazoline-7-carboxylic acid as a white powder (650 mg, 66% yield over 3 steps).

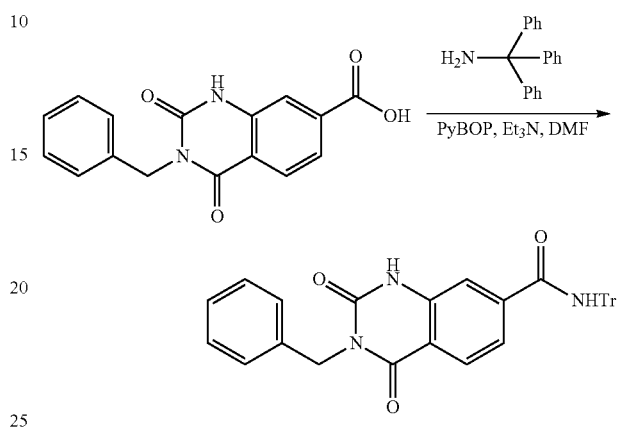

Step 2: A mixture of 3-benzyl-2,4-dioxo-1,2,3,4-tetrahydroquinazoline-7-carboxylic acid (297 mg, 1 mmol), tritylamine (285 mg, 1.1 mmol), Et$_3$N (418 µL, 3 mmol) in DMF (10 mL) was treated with PyBOP (513 mg, 1.1 mmol). The reaction mixture was allowed to stir at ambient temperature overnight, then diluted with EtOAc and washed with 10% aq KHSO$_4$, brine, and saturated aq NaHCO$_3$. The organic layer was dried over Na$_2$SO$_4$, filtered, concentrated under vacuum, and then purified by chromatography (10-30% EtOAc-hexanes) to yield 3-benzyl-2,4-dioxo-N-trityl-1,2,3,4-tetrahydroquinazoline-7-carboxamide as a white crystalline solid (126 mg, 23% yield).

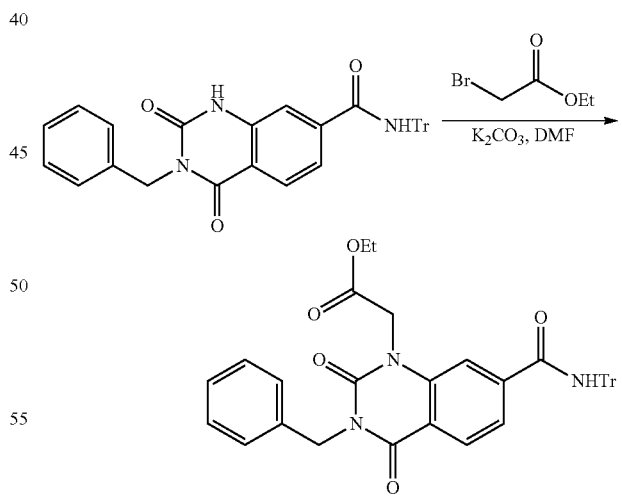

Step 3: A reaction vessel was charged with 3-benzyl-2,4-dioxo-N-trityl-1,2,3,4-tetrahydroquinazoline-7-carboxamide (120 mg, 0.22 mmol), K$_2$CO$_3$ (76 mg, 0.55 mmol) and DMF (2 mL). To this stirring solution was added ethyl bromoacetate (28 µL, 0.25 mmol) and the mixture was allowed to stir at room temp overnight. Upon completion, the reaction mixture was treated with H$_2$O, whereupon ethyl 2-(3-benzyl-2,4-dioxo-7-(tritylcarbamoyl)-3,4-dihydroquinazolin-1(2H)-yl)acetate precipitated as a white solid (62 mg, quant. yield) which was collected by filtration.

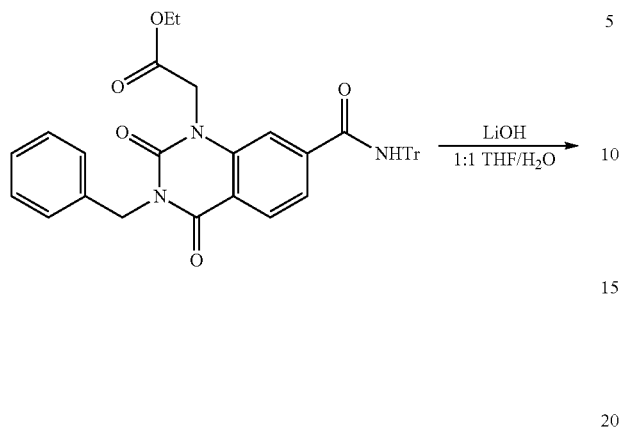

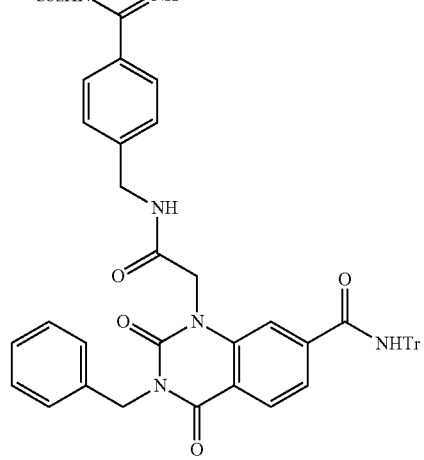
-continued

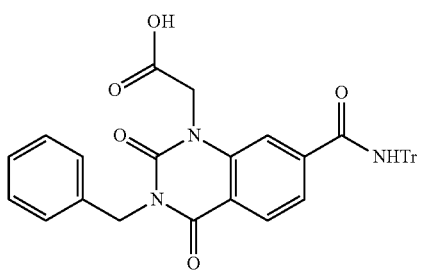

Step 4: To a stirring suspension of ethyl 2-(3-benzyl-2,4-dioxo-7-(tritylcarbamoyl)-3,4-dihydroquinazolin-1(2H)-yl) acetate (137 mg, 0.22 mmol) in THF (2.5 mL) and H₂O (2.5 mL) was added LiOH (11 mg, 0.44 mmol) in one portion. The reaction mixture was stirred at ambient temp overnight. After completion, the reaction mixture was neutralized with 10% aq KHSO₄, and extracted with EtOAc (10 mL×3). The combined organics were washed with brine, dried (Na₂SO₄), filtered and concentrated under vacuum to provide 2-(3-benzyl-2,4-dioxo-7-(tritylcarbamoyl)-3,4-dihydroquinazolin-1(2H)-yl)acetic acid as a white powder (59 mg, 45% yield).

Step 5: To the reaction vessel was added 2-(3-benzyl-2,4-dioxo-7-(tritylcarbamoyl)-3,4-dihydroquinazolin-1(2H)-yl)acetic acid (59 mg, 0.1 mmol), DMAP (24.4 mg, 0.2 mmol) and CH₂Cl₂ (1 mL). To this stirring mixture was added EDC (23 mg, 0.12 mmol) followed by benzyl ((4-(aminomethyl)phenyl)(imino)methyl)carbamate (35.2 mg, 0.11 mmol). The reaction mixture was stirred at ambient temp overnight, after which time it was washed successively with 10% aq KHSO₄, H₂O, saturated aq NaHCO₃, and brine. The organic layer was dried (Na₂SO₄) and concentrated under vacuum to provide benzyl ((4-((2-(3-benzyl-2,4-dioxo-7-(tritylcarbamoyl)-3,4-dihydroquinazolin-1(2H)-yl)acetamido)methyl)phenyl)(imino)methyl)carbamate as a white solid (86 mg, quant. yield).

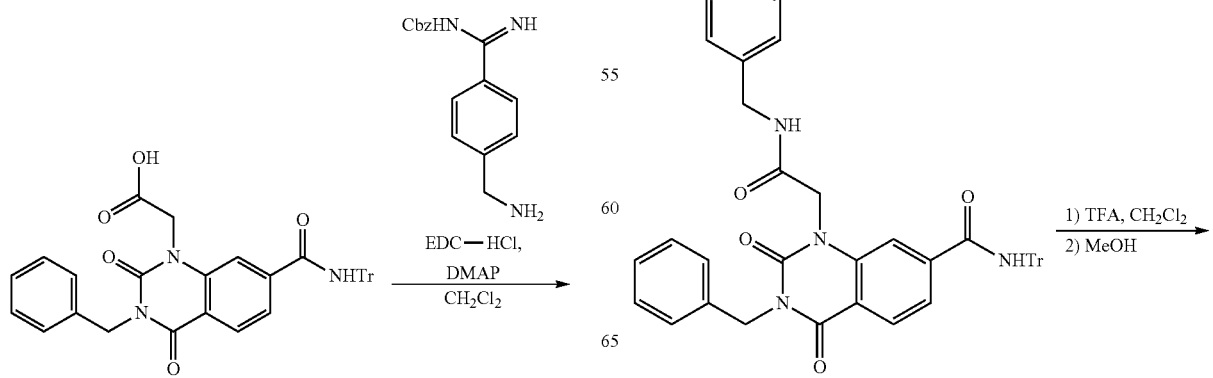

659

-continued

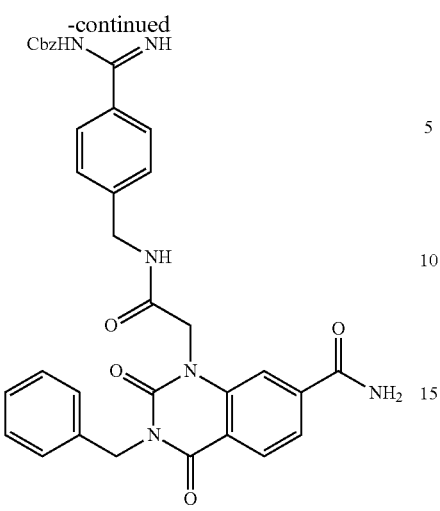

Step 6: Benzyl ((4-((2-(3-benzyl-2,4-dioxo-7-(tritylcarbamoyl)-3,4-dihydroquinazolin-1(2H)-yl)acetamido)methyl)phenyl)(imino)methyl)carbamate (86 mg, 0.1 mmol) was dissolved in $CH_2Cl_2$ (1 mL) and treated with TFA (600 μL). The resulting yellow solution was stirred for 3 h and then treated with MeOH (150 μL), whereupon the solution immediately became colorless. The reaction mixture was evaporated to dryness and purified by chromatography (10% MeOH-$CH_2Cl_2$+1% 7 M $NH_3$-MeOH to yield benzyl ((4-((2-(3-benzyl-7-carbamoyl-2,4-dioxo-3,4-dihydroquinazolin-1(2H)-yl)acetamido)methyl)phenyl)(imino)methyl)carbamate as a white solid (42 mg, 68% yield).

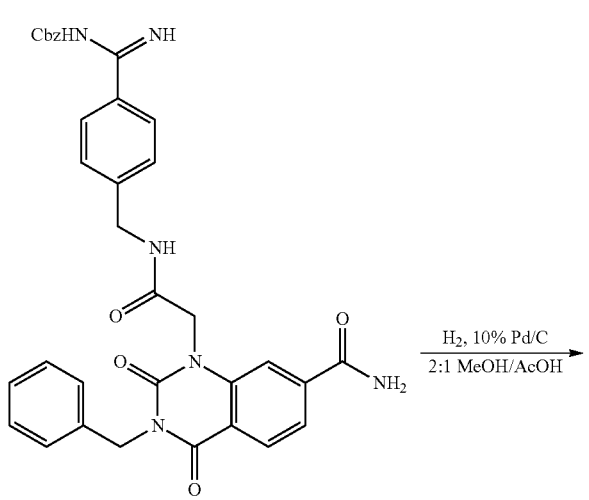

660

-continued

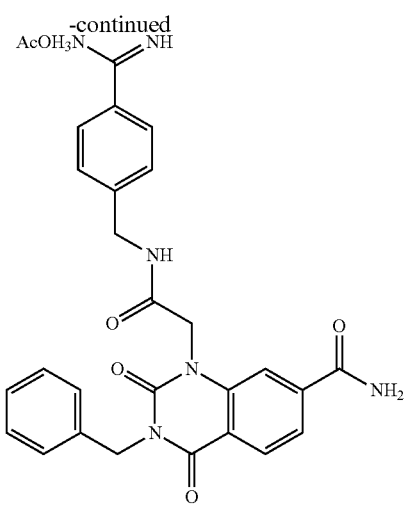

Step 7: Benzyl ((4-((2-(3-benzyl-7-carbamoyl-2,4-dioxo-3,4-dihydroquinazolin-1(2H)-yl)acetamido)methyl)phenyl)(imino)methyl)carbamate (14 mg, 0.023 mmol) was dissolved in a mixture of MeOH (6 ml) and HOAc (3 mL). The resulting solution was degassed with a stream of nitrogen for 2-3 min. 10% Pd/C (5 mg) was added, and the mixture was put under vacuum for approximately 1 minute. A balloon of hydrogen was applied, and the reaction was monitored for the consumption of starting material. The reaction mixture was filtered through a 0.2 m syringe filter and evaporated to dryness to give compound 2017 as a white solid (11 mg, 99% yield).

Example 303. Preparation of 3-Benzyl-1-(2-((4-carbamimidoylbenzyl)amino)-2-oxoethyl)-N-methyl-2,4-dioxo-1,2,3,4-tetrahydroquinazoline-7-carboxamide (2018)

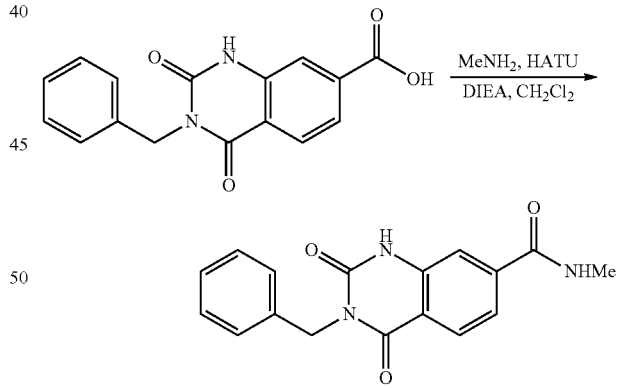

Step 1: 3-Benzyl-2,4-dioxo-1,2,3,4-tetrahydroquinazoline-7-carboxylic acid (330 mg, 1.1 mmol) was suspended in $CH_2Cl_2$ (15 mL). To the stirred mixture was added methylamine (2 M in THF, 660 μL, 1.32 mmol) and DIEA (570 μL, 3.3 mmol). After 5 min at ambient temp, the reaction mixture became a clear solution. To this solution was added HATU (550 mg, 1.32 mmol). Upon completion of reaction after 4 h, the reaction mixture was washed with 1 M HCl, $H_2O$, and saturated aq $NaHCO_3$, then filtered through a glass fritted funnel to yield 3-benzyl-N-methyl-2,4-dioxo-1,2,3,4-tetrahydroquinazoline-7-carboxamide as a white solid (340 mg, quant).

Steps 2-5: 3-Benzyl-1-(2-((4-carbamimidoylbenzyl)amino)-2-oxoethyl)-N-methyl-2,4-dioxo-1,2,3,4-tetrahydroquinazoline-7-carboxamide was prepared from 3-benzyl-N-methyl-2,4-dioxo-1,2,3,4-tetrahydroquinazoline-7-carboxamide following similar protocols as described in steps 3-5, and 7 in Example 4 (i.e., for compound 2017).

Example 304. Preparation of 3-Benzyl-1-(2-((4-carbamimidoylbenzyl)amino)-2-oxoethyl)-N-cyclohexyl-2,4-dioxo-1,2,3,4-tetrahydoroquinazoline-7-carboxamide (2021)

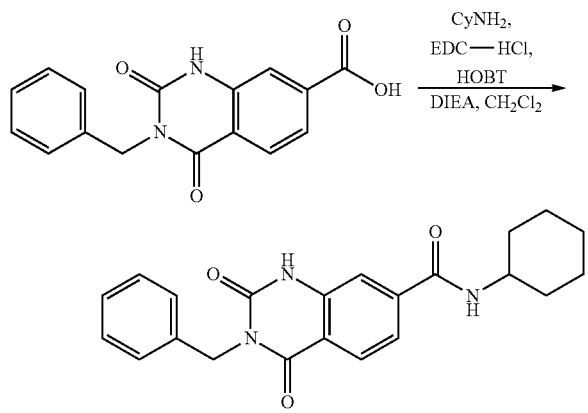

Step 1: 3-Benzyl-2,4-dioxo-1,2,3,4-tetrahydroquinazoline-7-carboxylic acid (300 mg, 1.0 mmol) was suspended in $CH_2Cl_2$ (10 mL). To this stirring mixture was added cyclohexylamine (140 µL, 1.2 mmol), DIEA (529 µL, 3 mmol), HOBt (165 mg, 1.2 mmol) and EDC (234 mg, 1.2 mmol) in sequential order. The mixture was stirred for 24 h. Upon completion, the reaction mixture was washed with 1 N HCl, and saturated aq $NaHCO_3$. The organic layer was dried over $Na_2SO_4$ and concentrated under vacuum to provide 3-benzyl-N-cyclohexyl-2,4-dioxo-1,2,3,4-tetrahydroquinazoline-7-carboxamide as a white solid (200 mg, 52% yield).

Steps 2-5: 3-Benzyl-1-(2-((4-carbamimidoylbenzyl)amino)-2-oxoethyl)-n-cyclohexyl-2,4-dioxo-1,2,3,4-tetrahydroquinazoline-7-carboxamide was prepared from 3-benzyl-N-cyclohexyl-2,4-dioxo-1,2,3,4-tetrahydroquinazoline-7-carboxamide following similar protocols to those described in steps 3-5, and 7 in Example 4 (i.e., for compound 2017).

Table 31 lists compounds of the Examples described above, as well as additional compounds that may be prepared according to methods analogous to those described for the compounds above and other methods known to a person having skill in the art.

TABLE 31

Compound List

| Compound No. | Structure | Salt | Exact Mass (ES+; M + H, Obsd) | Exact Mass (Calc) |
| --- | --- | --- | --- | --- |
| 1000 | 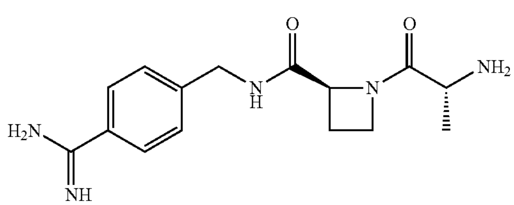 [SMILES: C[C@@H](N)C(=O)N1CC[C@H]1C(=O)NCc1ccc(C(=N)N)cc1] | NA | 304.20 | 303.17 |
| 1001 | 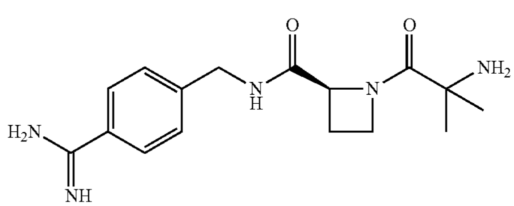 [SMILES: CC(C)(N)C(=O)N1CC[C@H]1C(=O)NCc1ccc(C(=N)N)cc1] | NA | 318.15 | 317.19 |
| 1002 | 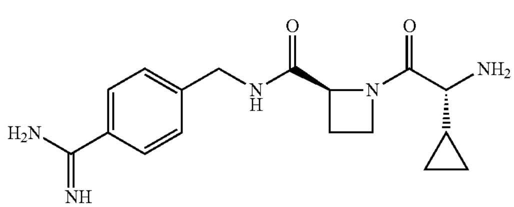 [SMILES: N=C(N)c1ccc(CNC(=O)[C@@H]2CCN2C(=O)[C@H](N)C2CC2)cc1] | NA | 330.20 | 329.19 |

TABLE 31-continued

Compound List

| Compound No. | Structure | Salt | Exact Mass (ES+; M + H, Obsd) | Exact Mass (Calc) |
|---|---|---|---|---|
| 1003 | 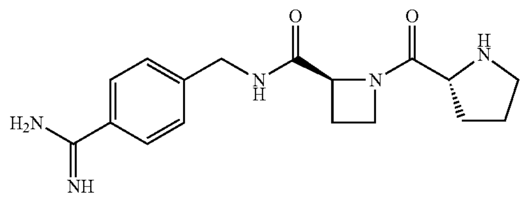 [SMILES: N=C(N)c1ccc(CNC(=O)[C@@H]2CCN2C(=O)[C@H]2CCCN2)cc1] | NA | 330.12 | 329.19 |
| 1004 | 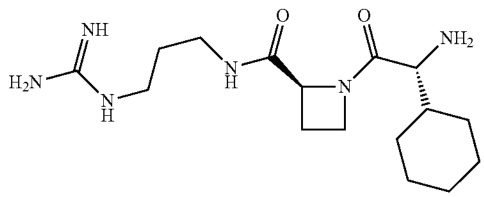 [SMILES: N=C(N)NCCCNC(=O)[C@@H]1CCN1C(=O)[C@H](N)C1CCCCC1] | 2HCl | 339.26 | 338.24 |
| 1005 | 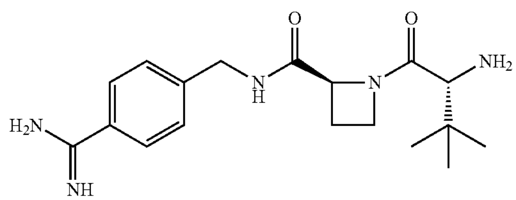 [SMILES: CC(C)(C)[C@@H](N)C(=O)N1CC[C@H]1C(=O)NCc1ccc(C(=N)N)cc1] | NA | 346.13 | 345.22 |
| 1006 | 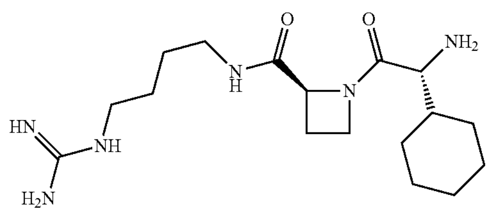 [SMILES: N=C(N)NCCCCNC(=O)[C@@H]1CCN1C(=O)[C@H](N)C1CCCCC1] | 2HCl | 353.28 | 352.26 |
| 1007 | 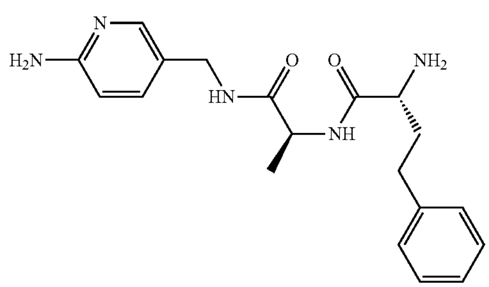 [SMILES: C[C@H](NC(=O)[C@H](N)CCc1ccccc1)C(=O)NCc1ccc(N)nc1] | 2HCl | 356.00 | 355.20 |
| 1008 | 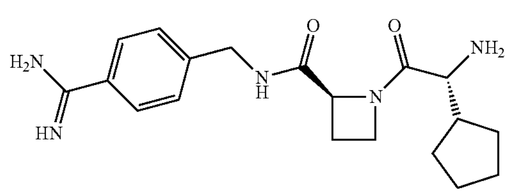 [SMILES: N=C(N)c1ccc(CNC(=O)[C@@H]2CCN2C(=O)[C@H](N)C2CCCC2)cc1] | NA | 358.20 | 357.22 |
| 1009 | 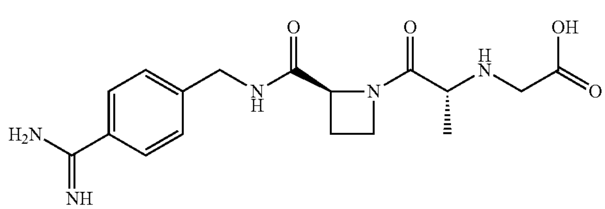 [SMILES: C[C@@H](NCC(=O)O)C(=O)N1CC[C@H]1C(=O)NCc1ccc(C(=N)N)cc1] | NA | 362.16 | 361.18 |

TABLE 31-continued

Compound List

| Compound No. | Structure | Salt | Exact Mass (ES+; M + H, Obsd) | Exact Mass (Calc) |
|---|---|---|---|---|
| 1010 | 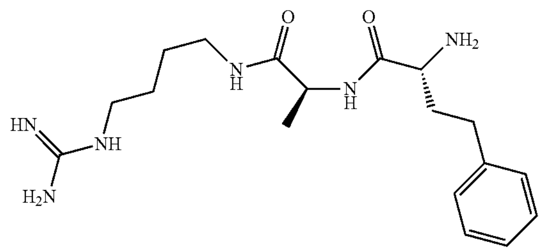 [SMILES: C[C@H](NC(=O)[C@H](N)CCc1ccccc1)C(=O)NCCCCNC(=N)N] | 2HCl | 363.28 | 362.24 |
| 1011 | 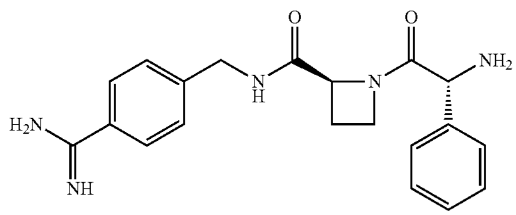 [SMILES: N=C(N)c1ccc(CNC(=O)[C@@H]2CCN2C(=O)[C@H](N)c2ccccc2)cc1] | NA | 366.12 | 365.19 |
| 1012 | 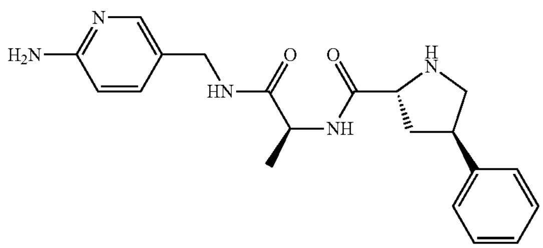 [SMILES: C[C@H](NC(=O)[C@H]1C[C@H](c2ccccc2)CN1)C(=O)NCc1ccc(N)nc1] | 2HCl | 368.26 | 367.20 |
| 1013 | 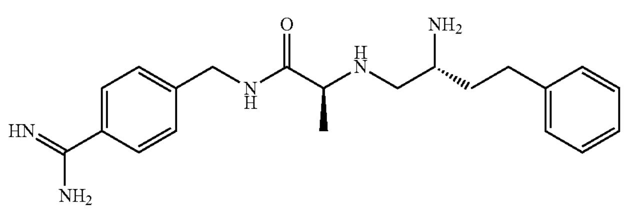 [SMILES: C[C@H](NC[C@H](N)CCc1ccccc1)C(=O)NCc1ccc(C(=N)N)cc1] | 2HCl | 368.25 | 367.24 |
| 1014 | 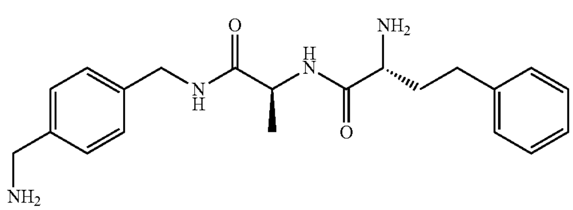 [SMILES: C[C@H](NC(=O)[C@H](N)CCc1ccccc1)C(=O)NCc1ccc(CN)cc1] | 2HCl | 369.25 | 368.22 |
| 1015 | 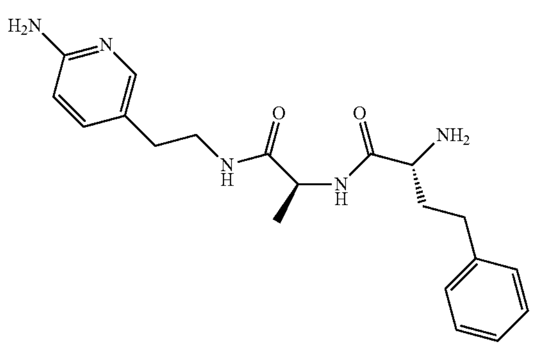 [SMILES: C[C@H](NC(=O)[C@H](N)CCc1ccccc1)C(=O)NCCc1ccc(N)nc1] | 2HCl | 370.16 | 369.22 |

TABLE 31-continued

Compound List

| Compound No. | Structure | Salt | Exact Mass (ES+; M + H, Obsd) | Exact Mass (Calc) |
|---|---|---|---|---|
| 1016 | 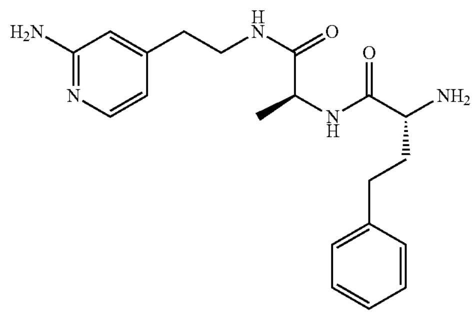 [SMILES: C[C@H](NC(=O)[C@H](N)CCc1ccccc1)C(=O)NCCc1ccnc(N)c1] | 2HCl | 370.17 | 369.22 |
| 1017 | 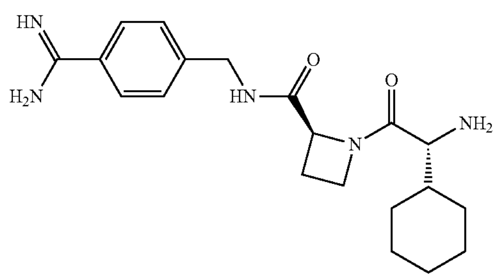 [SMILES: N=C(N)c1ccc(CNC(=O)[C@@H]2CCN2C(=O)[C@H](N)C2CCCCC2)cc1] | NA | 372.23 | 371.23 |
| 1018 | 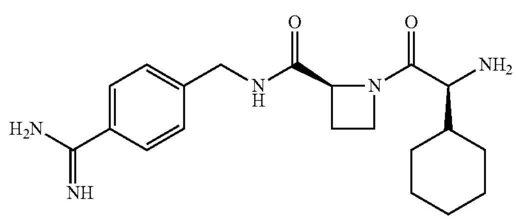 [SMILES: N=C(N)c1ccc(CNC(=O)[C@@H]2CCN2C(=O)[C@@H](N)C2CCCCC2)cc1] | NA | 372.23 | 371.23 |
| 1019 | 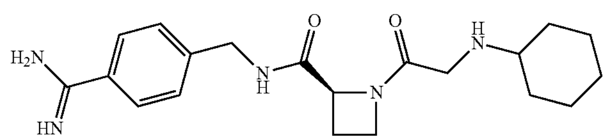 [SMILES: N=C(N)c1ccc(CNC(=O)[C@@H]2CCN2C(=O)CNC2CCCCC2)cc1] | NA | 372.18 | 371.23 |
| 1020 | 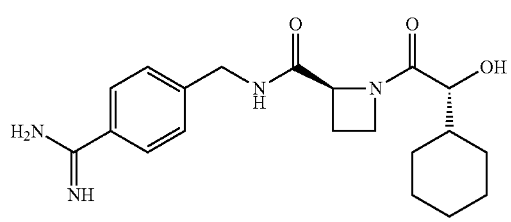 [SMILES: N=C(N)c1ccc(CNC(=O)[C@@H]2CCN2C(=O)[C@H](O)C2CCCCC2)cc1] | NA | 373.16 | 372.22 |
| 1021 | 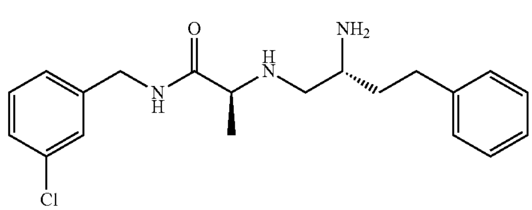 [SMILES: C[C@H](NC[C@H](N)CCc1ccccc1)C(=O)NCc1cccc(Cl)c1] | HCl | 374.17 | 373.16 |

TABLE 31-continued

Compound List

| Compound No. | Structure | Salt | Exact Mass (ES+; M + H, Obsd) | Exact Mass (Calc) |
|---|---|---|---|---|
| 1022 | 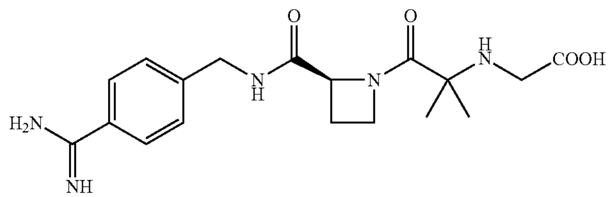 [SMILES: CC(C)(NCC(=O)O)C(=O)N1CC[C@H]1C(=O)NCc1ccc(C(=N)N)cc1] | NA | 376.13 | 375.19 |
| 1023 | 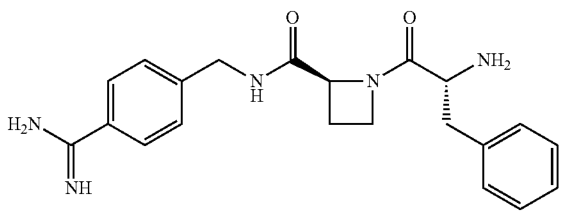 [SMILES: N=C(N)c1ccc(CNC(=O)[C@@H]2CCN2C(=O)[C@H](N)Cc2ccccc2)cc1] | NA | 380.13 | 379.20 |
| 1024 | 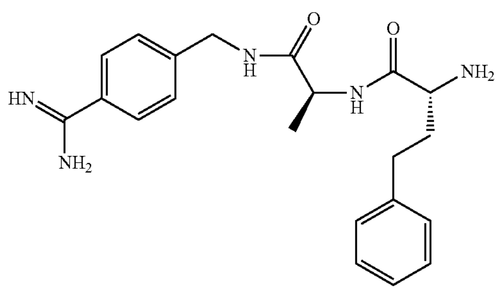 [SMILES: C[C@H](NC(=O)[C@H](N)CCc1ccccc1)C(=O)NCc1ccc(C(=N)N)cc1] | 2HCl | 382.26 | 381.22 |
| 1025 | isomer 3 | 2HCl | 382.25 | 381.22 |
| 1026 | 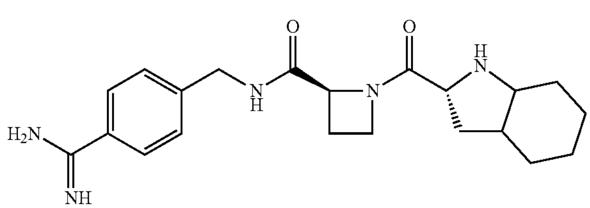 | NA | 384.14 | 383.23 |

TABLE 31-continued

Compound List

| Compound No. | Structure | Salt | Exact Mass (ES+; M + H, Obsd) | Exact Mass (Calc) |
|---|---|---|---|---|
| 1027 | 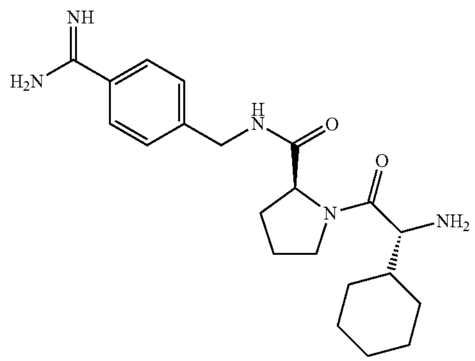 [SMILES: N=C(N)c1ccc(CNC(=O)[C@@H]2CCCN2C(=O)[C@H](N)C2CCCCC2)cc1] | 2HCl | 386.28 | 385.25 |
| 1028 | 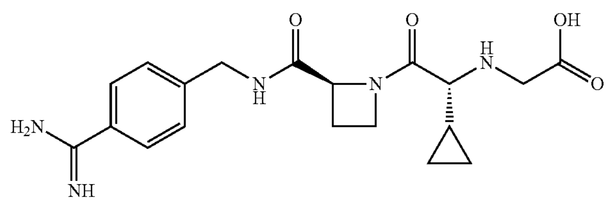 [SMILES: N=C(N)c1ccc(CNC(=O)[C@@H]2CCN2C(=O)[C@H](NCC(=O)O)C2CC2)cc1] | NA | 388.24 | 387.19 |
| 1029 | 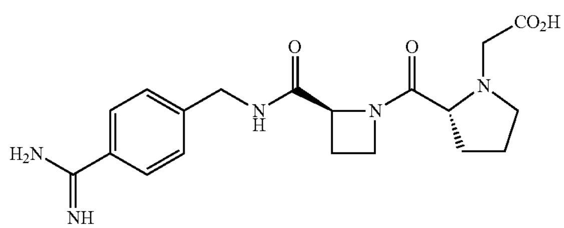 [SMILES: N=C(N)c1ccc(CNC(=O)[C@@H]2CCN2C(=O)[C@H]2CCCN2CC(=O)O)cc1] | NA | 388.11 | 387.19 |
| 1030 | 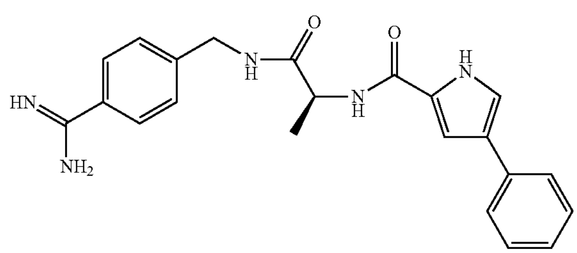 [SMILES: C[C@H](NC(=O)c1cc(-c2ccccc2)c[nH]1)C(=O)NCc1ccc(C(=N)N)cc1] | NA | 390.11 | 389.19 |
| 1031 | 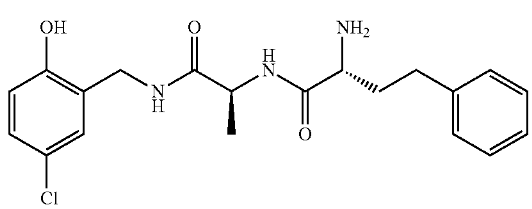 [SMILES: C[C@H](NC(=O)[C@H](N)CCc1ccccc1)C(=O)NCc1cc(Cl)ccc1O] | HCl | 390.17 | 389.15 |
| 1032 | 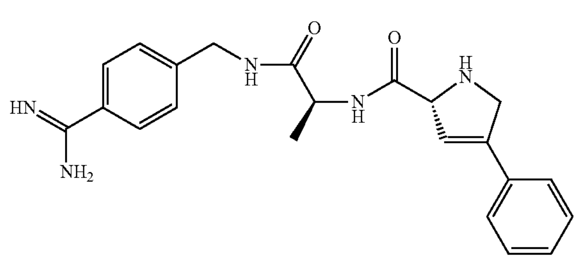 [SMILES: C[C@H](NC(=O)[C@H]1C=C(c2ccccc2)CN1)C(=O)NCc1ccc(C(=N)N)cc1] | 2HCl | 392.22 | 391.20 |

TABLE 31-continued

Compound List

| Compound No. | Structure | Salt | Exact Mass (ES+; M + H, Obsd) | Exact Mass (Calc) |
|---|---|---|---|---|
| 1033 | 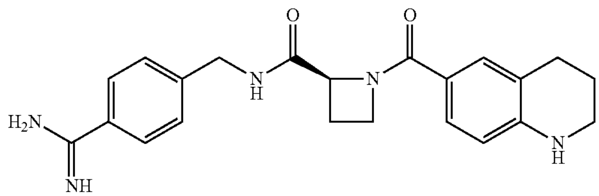 [SMILES: N=C(N)c1ccc(CNC(=O)[C@@H]2CCN2C(=O)c2ccc3c(c2)CCCN3)cc1] | NA | 392.10 | 391.20 |
| 1034 | 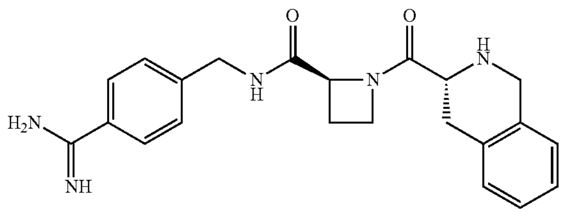 [SMILES: N=C(N)c1ccc(CNC(=O)[C@@H]2CCN2C(=O)[C@H]2Cc3ccccc3CN2)cc1] | NA | 392.12 | 391.20 |
| 1035 | 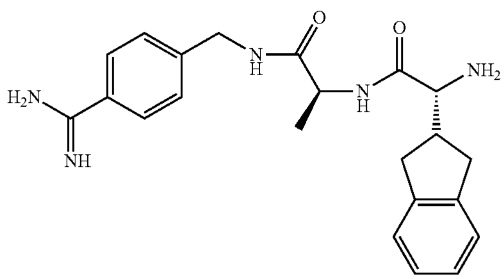 [SMILES: C[C@H](NC(=O)[C@H](N)C1Cc2ccccc2C1)C(=O)NCc1ccc(C(=N)N)cc1] | 2HCl | 394.25 | 393.22 |
| 1036 | 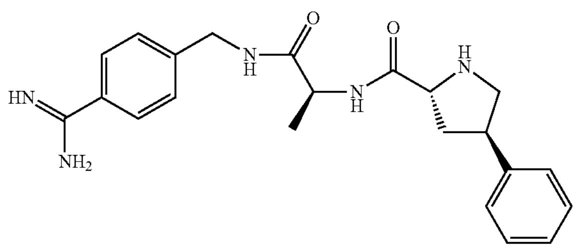 [SMILES: C[C@H](NC(=O)[C@H]1C[C@H](c2ccccc2)CN1)C(=O)NCc1ccc(C(=N)N)cc1] | 2HCl | 394.23 | 393.22 |
| 1037 | 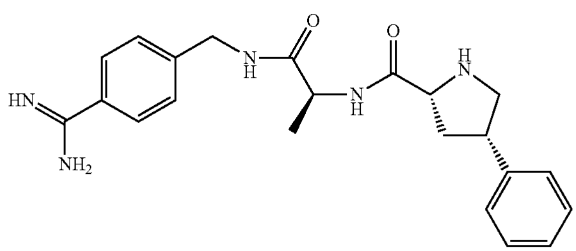 [SMILES: C[C@H](NC(=O)[C@H]1C[C@@H](c2ccccc2)CN1)C(=O)NCc1ccc(C(=N)N)cc1] | 2HCl | 394.23 | 393.22 |
| 1038 | 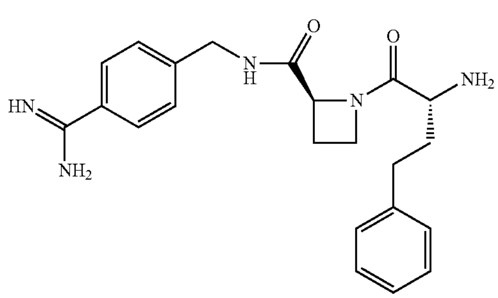 [SMILES: N=C(N)c1ccc(CNC(=O)[C@@H]2CCN2C(=O)[C@H](N)CCc2ccccc2)cc1] | 2HCl | 394.22 | 393.48 |

TABLE 31-continued

Compound List

| Compound No. | Structure | Salt | Exact Mass (ES+; M + H, Obsd) | Exact Mass (Calc) |
|---|---|---|---|---|
| 1039 | 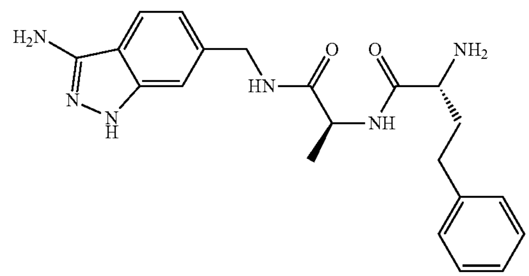 [SMILES: C[C@H](NC(=O)[C@H](N)CCc1ccccc1)C(=O)NCc1ccc2c(N)n[nH]c2c1] | 2HCl | 393.12 (ES−) | 394.21 |
| 1040 | 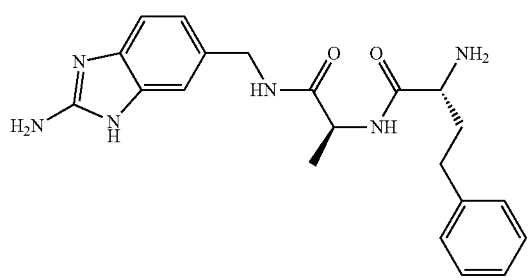 [SMILES: C[C@H](NC(=O)[C@H](N)CCc1ccccc1)C(=O)NCc1ccc2nc(N)[nH]c2c1] | 2HCl | 395.12 | 394.21 |
| 1041 | 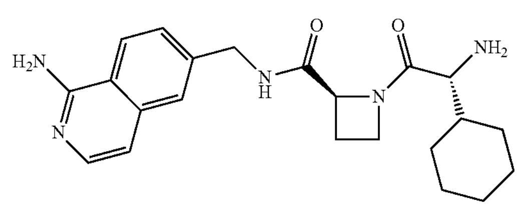 [SMILES: Nc1nccc2cc(CNC(=O)[C@@H]3CCN3C(=O)[C@H](N)C3CCCCC3)ccc12] | 2HCl | 396.13 | 395.23 |
| 1042 | 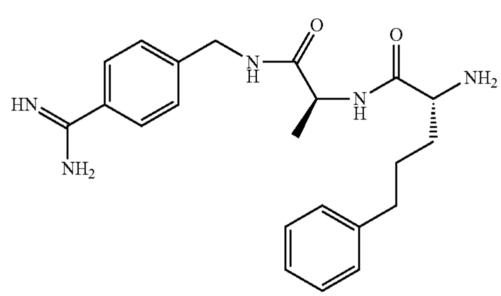 [SMILES: C[C@H](NC(=O)[C@H](N)CCCc1ccccc1)C(=O)NCc1ccc(C(=N)N)cc1] | 2HCl | 396.27 | 395.23 |
| 1043 | 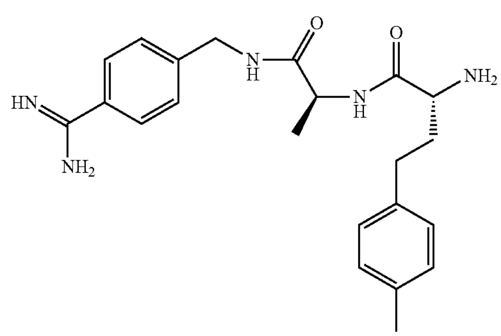 [SMILES: Cc1ccc(CC[C@@H](N)C(=O)N[C@@H](C)C(=O)NCc2ccc(C(=N)N)cc2)cc1] | 2HCl | 396.28 | 395.23 |

TABLE 31-continued
Compound List
| Compound No. | Structure | Salt | Exact Mass (ES+; M + H, Obsd) | Exact Mass (Calc) |
|---|---|---|---|---|
| 1044 | 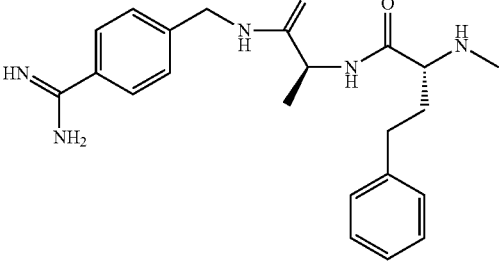 | 2HCl | 396.15 | 395.23 |
| 1045 | 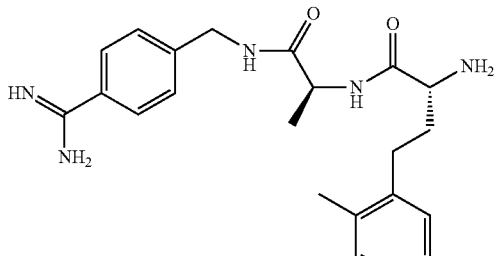 | 2HCl | 396.18 | 395.23 |
| 1046 | 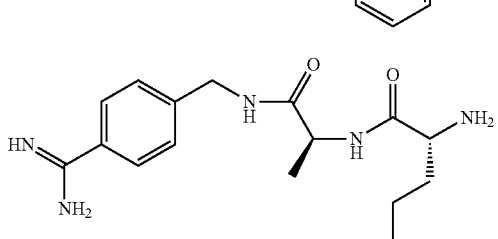 | 2HCl | 396.17 | 395.23 |
| 1047 | 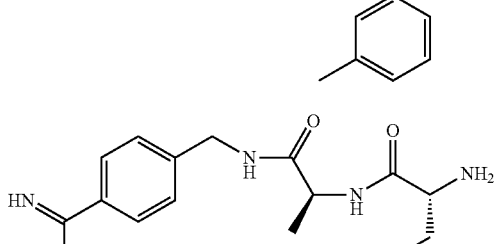 | 2HCl | 400.24 | 399.21 |
| 1048 | 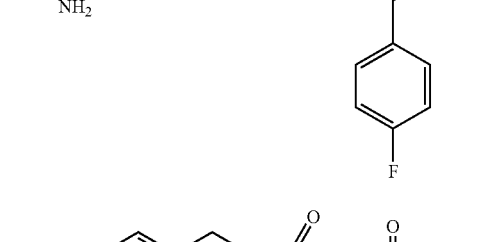 | 2HCl | 400.24 | 399.21 |

TABLE 31-continued

Compound List

| Compound No. | Structure | Salt | Exact Mass (ES+; M + H, Obsd) | Exact Mass (Calc) |
|---|---|---|---|---|
| 1049 | 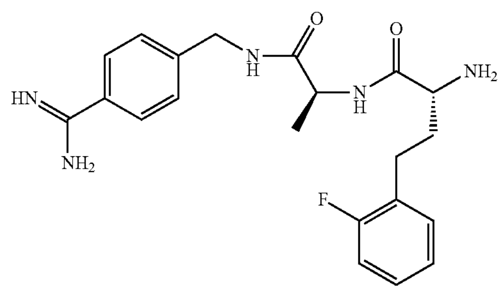 [SMILES: C[C@H](NC(=O)[C@H](N)CCc1ccccc1F)C(=O)NCc1ccc(C(=N)N)cc1] | 2HCl | 400.14 | 399.21 |
| 1050 | 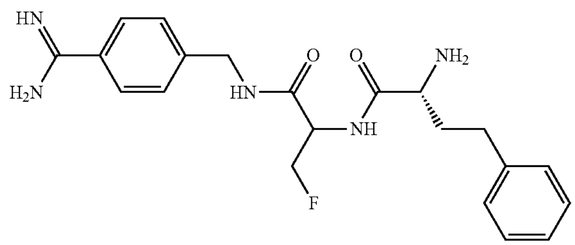 [SMILES: N=C(N)c1ccc(CNC(=O)C(CF)NC(=O)[C@H](N)CCc2ccccc2)cc1] | 2HCl | 400.24 | 399.21 |
| 1051 | 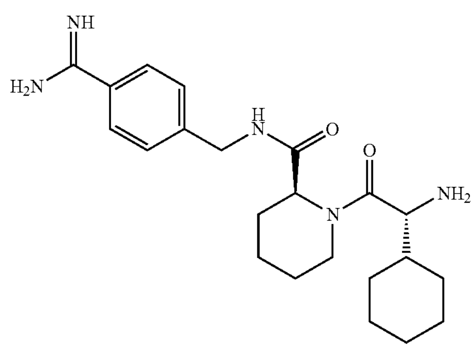 [SMILES: N=C(N)c1ccc(CNC(=O)[C@@H]2CCCCN2C(=O)[C@H](N)C2CCCCC2)cc1] | 2HCl | 400.30 | 399.26 |
| 1052 | 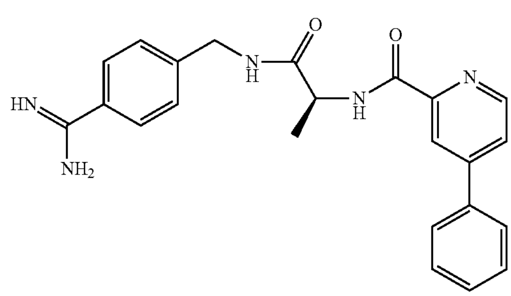 [SMILES: C[C@H](NC(=O)c1cc(-c2ccccc2)ccn1)C(=O)NCc1ccc(C(=N)N)cc1] | 2HCl | 402.20 | 401.19 |
| 1053 | 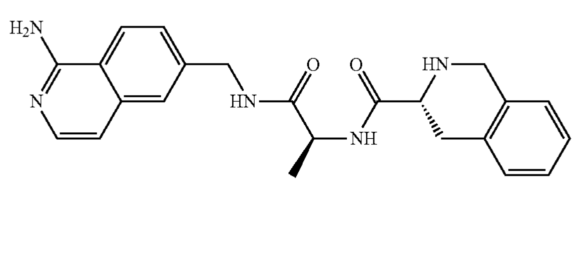 [SMILES: C[C@H](NC(=O)[C@H]1Cc2ccccc2CN1)C(=O)NCc1ccc2c(N)nccc2c1] | 2 TFA | 404.20 | 403.20 |

TABLE 31-continued
Compound List
| Compound No. | Structure | Salt | Exact Mass (ES+; M + H, Obsd) | Exact Mass (Calc) |
|---|---|---|---|---|
| 1054 | 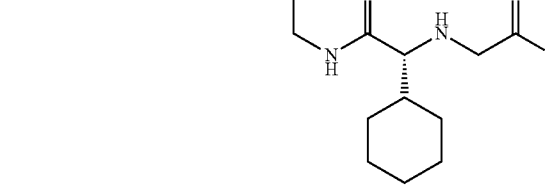 | 2HCl | 404.25 | 403.22 |
| 1055 | 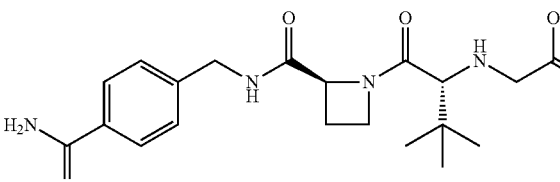 | NA | 404.25 | 403.22 |
| 1056 | 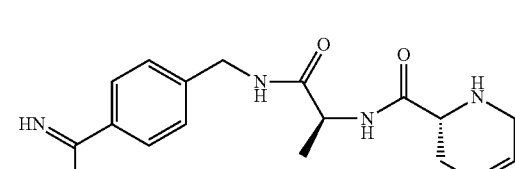 | 2HCl | 406.20 | 405.22 |
| 1057 | 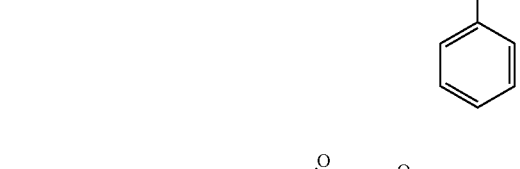 | 2HCl | 406.21 | 405.22 |
| 1058 | 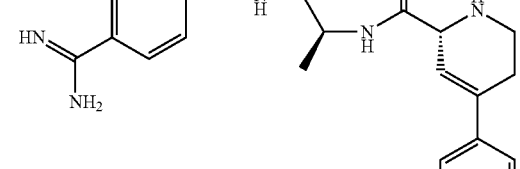 | NA | 406.06 | 405.22 |

TABLE 31-continued

Compound List

| Compound No. | Structure | Salt | Exact Mass (ES+; M + H, Obsd) | Exact Mass (Calc) |
|---|---|---|---|---|
| 1059 | 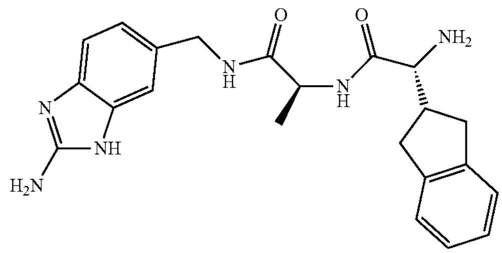 [SMILES: C[C@H](NC(=O)[C@H](N)C1Cc2ccccc2C1)C(=O)NCc1ccc2nc(N)[nH]c2c1] | 2HCl | 407.16 | 406.21 |
| 1060 | 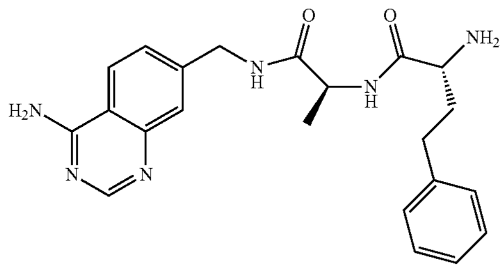 [SMILES: C[C@H](NC(=O)[C@H](N)CCc1ccccc1)C(=O)NCc1ccc2c(N)ncnc2c1] | 2HCl | 407.20 | 406.21 |
| 1061 | 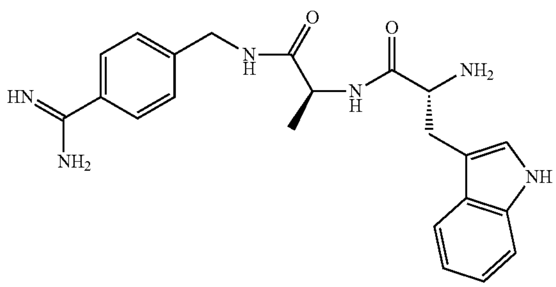 [SMILES: C[C@H](NC(=O)[C@H](N)Cc1c[nH]c2ccccc12)C(=O)NCc1ccc(C(=N)N)cc1] | 2HCl | 407.16 | 406.21 |
| 1062 | 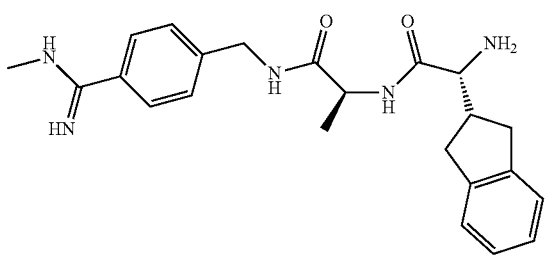 [SMILES: CNC(=N)c1ccc(CNC(=O)[C@H](C)NC(=O)[C@H](N)C2Cc3ccccc3C2)cc1] | 2HCl | 408.14 | 407.23 |
| 1063 | isomer 1 | 2HCl | 408.23 | 407.23 |

TABLE 31-continued
Compound List
| Compound No. | Structure | Salt | Exact Mass (ES+; M + H, Obsd) | Exact Mass (Calc) |
|---|---|---|---|---|
| 1064 | 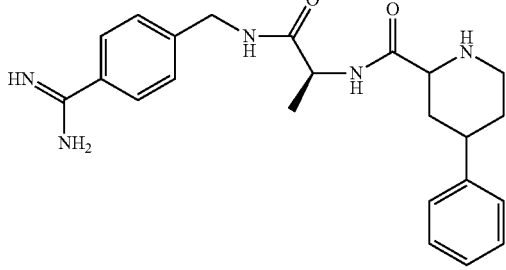 isomer 2 | 2HCl | 408.21 | 407.23 |
| 1065 | 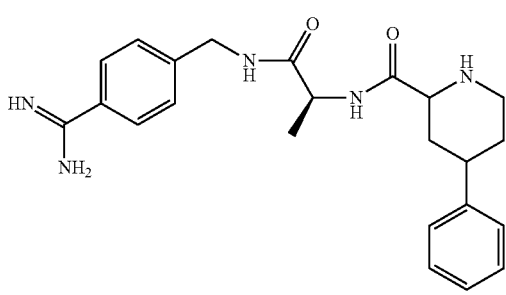 isomer 3 | 2HCl | 408.21 | 407.23 |
| 1066 | 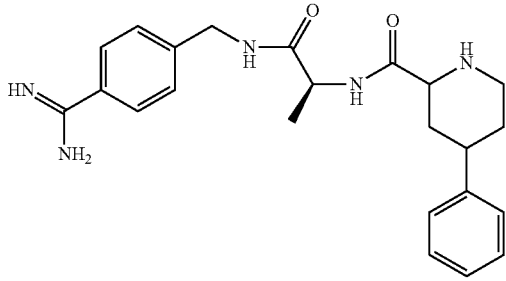 isomer 4 | 2HCl | 408.22 | 407.23 |
| 1067 | 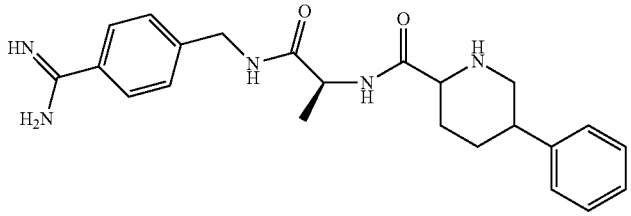 isomer 1 | 2HCl | 408.17 | 407.23 |
| 1068 | 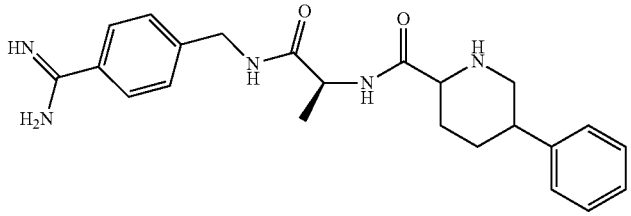 isomer 2 | 2HCl | 408.26 | 407.23 |

TABLE 31-continued
Compound List
| Compound No. | Structure | Salt | Exact Mass (ES+; M + H, Obsd) | Exact Mass (Calc) |
|---|---|---|---|---|
| 1069 | 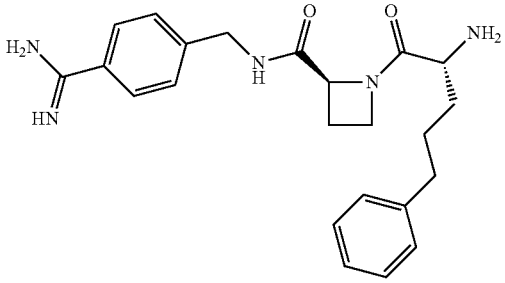 [SMILES: N=C(N)c1ccc(CNC(=O)[C@@H]2CCN2C(=O)[C@H](N)CCCc2ccccc2)cc1] | NA | 408.17 | 407.23 |
| 1070 | 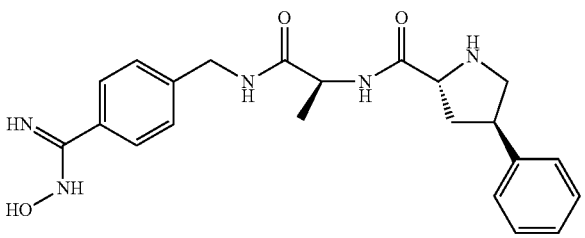 [SMILES: C[C@H](NC(=O)[C@H]1C[C@H](c2ccccc2)CN1)C(=O)NCc1ccc(C(=N)NO)cc1] | 2HCl | 410.22 | 409.21 |
| 1071 | 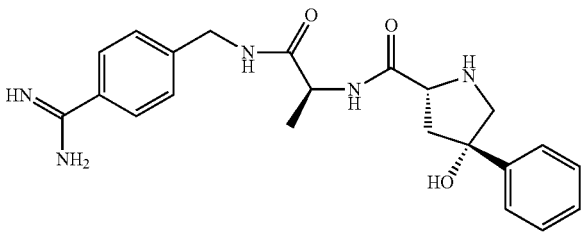 [SMILES: C[C@H](NC(=O)[C@H]1C[C@](O)(c2ccccc2)CN1)C(=O)NCc1ccc(C(=N)N)cc1] | 2HCl | 410.17 | 409.21 |
| 1072 | 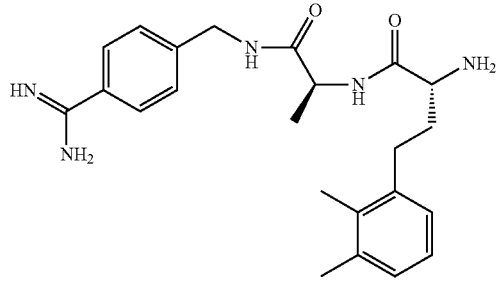 [SMILES: Cc1cccc(CC[C@@H](N)C(=O)N[C@@H](C)C(=O)NCc2ccc(C(=N)N)cc2)c1C] | 2HCl | 410.20 | 409.25 |
| 1073 | 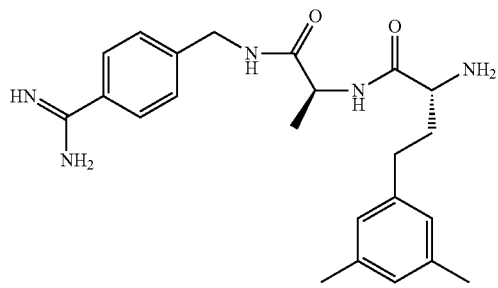 [SMILES: Cc1cc(C)cc(CC[C@@H](N)C(=O)N[C@@H](C)C(=O)NCc2ccc(C(=N)N)cc2)c1] | 2HCl | 410.19 | 409.25 |

TABLE 31-continued

Compound List

| Compound No. | Structure | Salt | Exact Mass (ES+; M + H, Obsd) | Exact Mass (Calc) |
|---|---|---|---|---|
| 1074 | 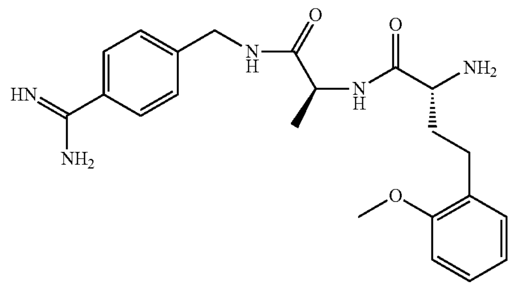 [SMILES: COc1ccccc1CC[C@@H](N)C(=O)N[C@@H](C)C(=O)NCc1ccc(C(=N)N)cc1] | 2HCl | 412.13 | 411.23 |
| 1075 | 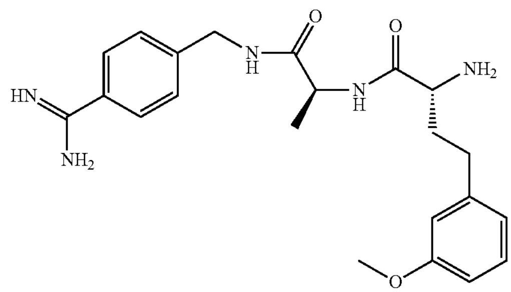 [SMILES: COc1cccc(CC[C@@H](N)C(=O)N[C@@H](C)C(=O)NCc2ccc(C(=N)N)cc2)c1] | 2HCl | 412.12 | 411.23 |
| 1076 | 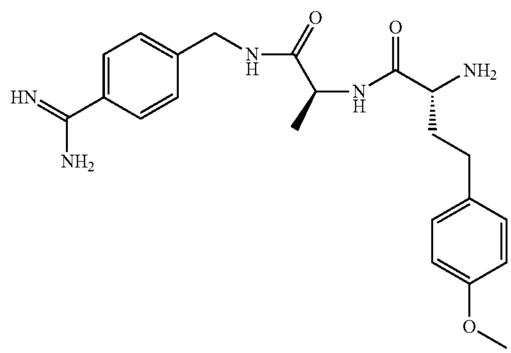 [SMILES: COc1ccc(CC[C@@H](N)C(=O)N[C@@H](C)C(=O)NCc2ccc(C(=N)N)cc2)cc1] | 2HCl | 412.12 | 411.23 |
| 1077 | 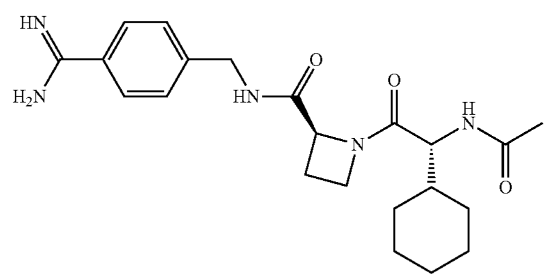 [SMILES: CC(=O)N[C@@H](C(=O)N1CC[C@H]1C(=O)NCc1ccc(C(=N)N)cc1)C1CCCCC1] | NA | 414.18 | 413.24 |
| 1078 | 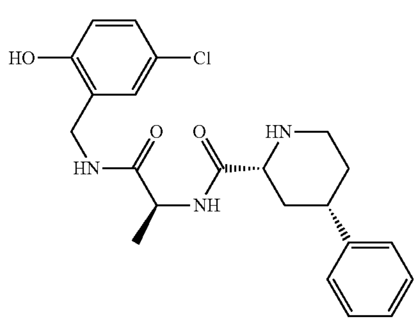 [SMILES: C[C@H](NC(=O)[C@H]1C[C@@H](c2ccccc2)CCN1)C(=O)NCc1cc(Cl)ccc1O] | HCl | 416.16 | 415.17 |

TABLE 31-continued

Compound List

| Compound No. | Structure | Salt | Exact Mass (ES+; M + H, Obsd) | Exact Mass (Calc) |
|---|---|---|---|---|
| 1079 | 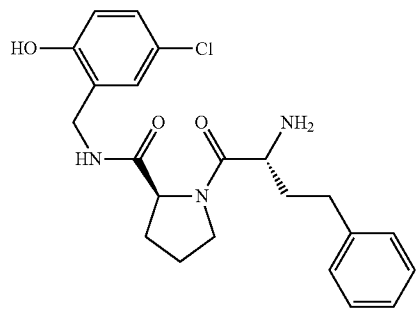 [SMILES: N[C@H](CCc1ccccc1)C(=O)N1CCC[C@H]1C(=O)NCc1cc(Cl)ccc1O] | HCl | 416.18 | 415.17 |
| 1080 | 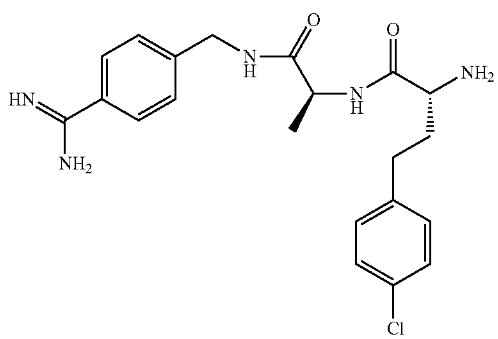 [SMILES: C[C@H](NC(=O)[C@H](N)CCc1ccc(Cl)cc1)C(=O)NCc1ccc(C(=N)N)cc1] | 2HCl | 416.18 | 415.18 |
| 1081 | 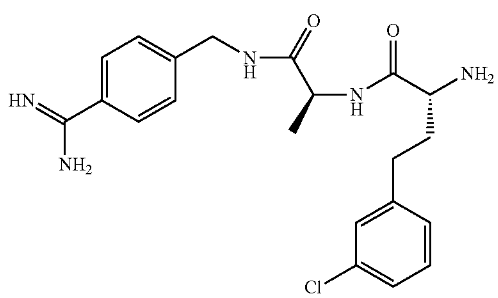 [SMILES: C[C@H](NC(=O)[C@H](N)CCc1cccc(Cl)c1)C(=O)NCc1ccc(C(=N)N)cc1] | 2HCl | 416.18 | 415.18 |
| 1082 | 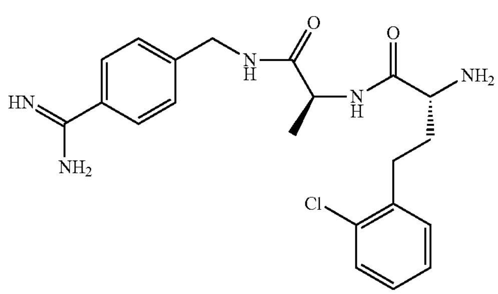 [SMILES: C[C@H](NC(=O)[C@H](N)CCc1ccccc1Cl)C(=O)NCc1ccc(C(=N)N)cc1] | 2HCl | 416.07 | 415.18 |
| 1083 | 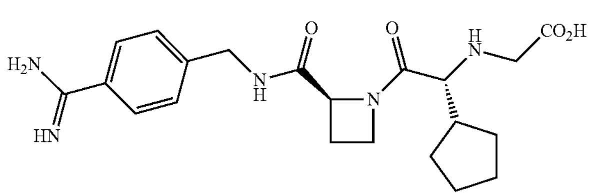 [SMILES: N=C(N)c1ccc(CNC(=O)[C@@H]2CCN2C(=O)[C@H](NCC(=O)O)C2CCCC2)cc1] | NA | 416.14 | 415.22 |

TABLE 31-continued

Compound List

| Compound No. | Structure | Salt | Exact Mass (ES+; M + H, Obsd) | Exact Mass (Calc) |
|---|---|---|---|---|
| 1084 | 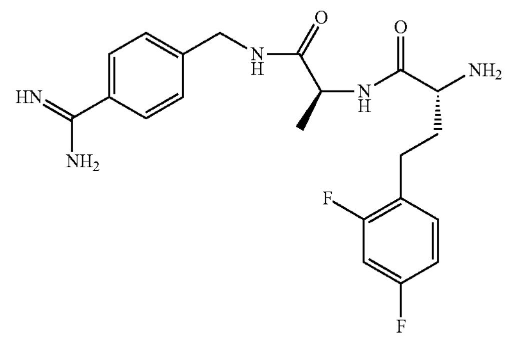 [SMILES: C[C@H](NC(=O)[C@H](N)CCc1ccc(F)cc1F)C(=O)NCc1ccc(C(=N)N)cc1] | 2HCl | 418.20 | 417.20 |
| 1085 | 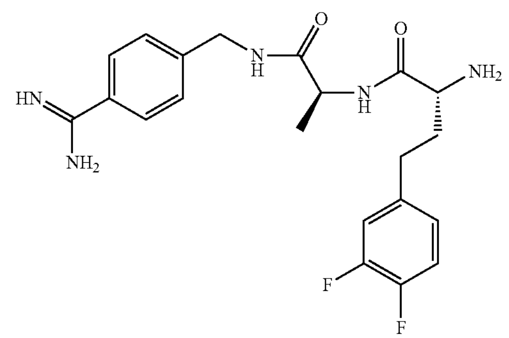 [SMILES: C[C@H](NC(=O)[C@H](N)CCc1ccc(F)c(F)c1)C(=O)NCc1ccc(C(=N)N)cc1] | 2HCl | 418.20 | 417.20 |
| 1086 | 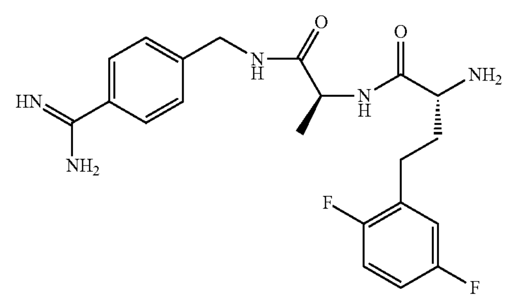 [SMILES: C[C@H](NC(=O)[C@H](N)CCc1cc(F)ccc1F)C(=O)NCc1ccc(C(=N)N)cc1] | 2HCl | 418.19 | 417.20 |
| 1087 | 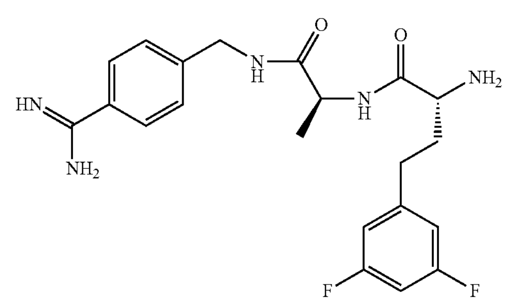 [SMILES: C[C@H](NC(=O)[C@H](N)CCc1cc(F)cc(F)c1)C(=O)NCc1ccc(C(=N)N)cc1] | 2HCl | 418.19 | 417.20 |
| 1088 | 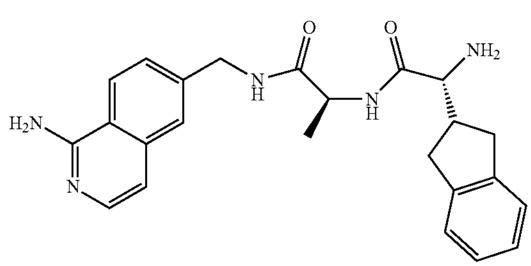 [SMILES: C[C@H](NC(=O)[C@H](N)C1Cc2ccccc2C1)C(=O)NCc1ccc2c(N)nccc2c1] | 2HCl | 418.12 | 417.22 |

TABLE 31-continued

Compound List

| Compound No. | Structure | Salt | Exact Mass (ES+; M + H, Obsd) | Exact Mass (Calc) |
|---|---|---|---|---|
| 1089 | 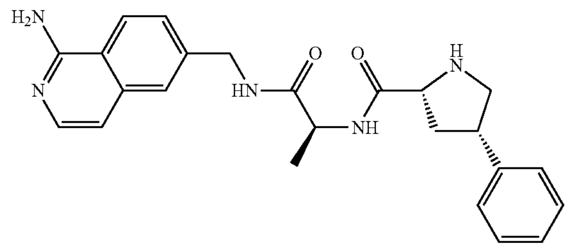 [SMILES: C[C@H](NC(=O)[C@H]1C[C@@H](c2ccccc2)CN1)C(=O)NCc1ccc2c(N)nccc2c1] | 2HCl | 418.19 | 417.22 |
| 1090 | 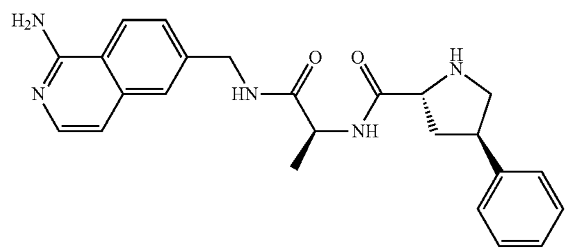 [SMILES: C[C@H](NC(=O)[C@H]1C[C@H](c2ccccc2)CN1)C(=O)NCc1ccc2c(N)nccc2c1] | 2HCl | 418.01 | 417.22 |
| 1091 | 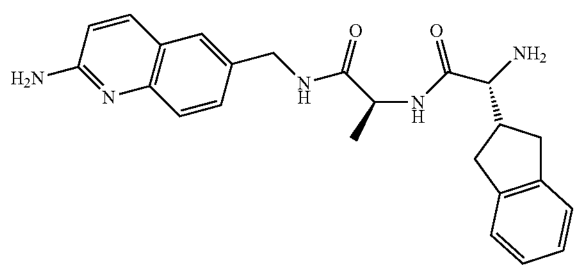 [SMILES: C[C@H](NC(=O)[C@H](N)C1Cc2ccccc2C1)C(=O)NCc1ccc2nc(N)ccc2c1] | 2HCl | 416.13 (ES−) | 417.22 |
| 1092 | 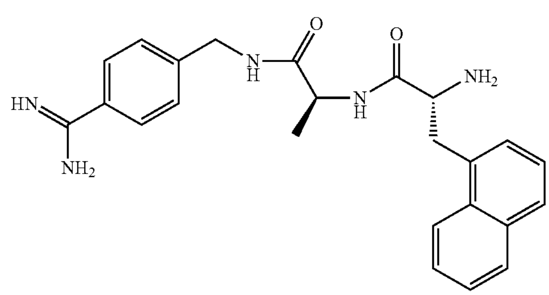 [SMILES: C[C@H](NC(=O)[C@H](N)Cc1cccc2ccccc12)C(=O)NCc1ccc(C(=N)N)cc1] | 2HCl | 418.10 | 417.22 |
| 1093 | 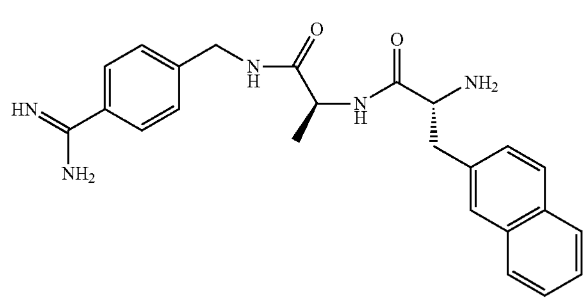 [SMILES: C[C@H](NC(=O)[C@H](N)Cc1ccc2ccccc2c1)C(=O)NCc1ccc(C(=N)N)cc1] | 2HCl | 418.05 | 417.22 |

TABLE 31-continued

Compound List

| Compound No. | Structure | Salt | Exact Mass (ES+; M + H, Obsd) | Exact Mass (Calc) |
|---|---|---|---|---|
| 1094 | 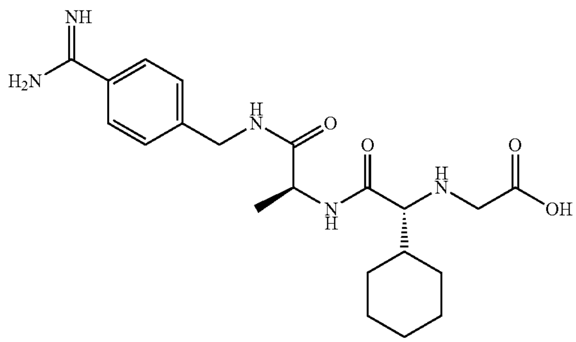 [SMILES: C[C@H](NC(=O)[C@H](NCC(=O)O)C1CCCCC1)C(=O)NCc1ccc(C(=N)N)cc1] | 2HCl | 418.23 | 417.24 |
| 1095 | 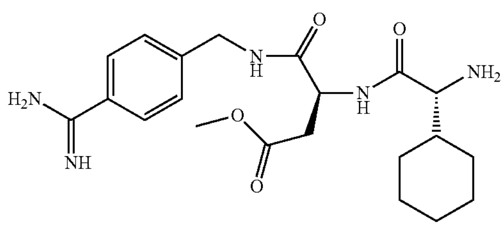 [SMILES: COC(=O)C[C@H](NC(=O)[C@H](N)C1CCCCC1)C(=O)NCc1ccc(C(=N)N)cc1] | 2HCl | 418.08 | 417.24 |
| 1096 | 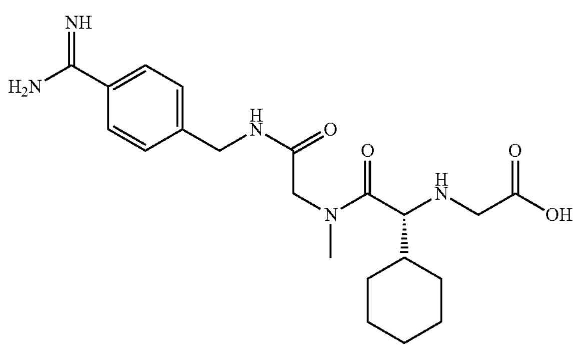 [SMILES: CN(CC(=O)NCc1ccc(C(=N)N)cc1)C(=O)[C@H](NCC(=O)O)C1CCCCC1] | NA | 418.26 | 417.24 |
| 1097 | 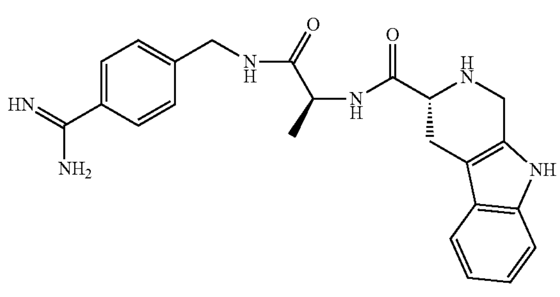 [SMILES: C[C@H](NC(=O)[C@H]1Cc2c([nH]c3ccccc23)CN1)C(=O)NCc1ccc(C(=N)N)cc1] | 2HCl | 419.17 | 418.21 |
| 1098 | isomer 3 | 2HCl | 422.25 | 421.25 |

TABLE 31-continued

Compound List

| Compound No. | Structure | Salt | Exact Mass (ES+; M + H, Obsd) | Exact Mass (Calc) |
|---|---|---|---|---|
| 1099 | 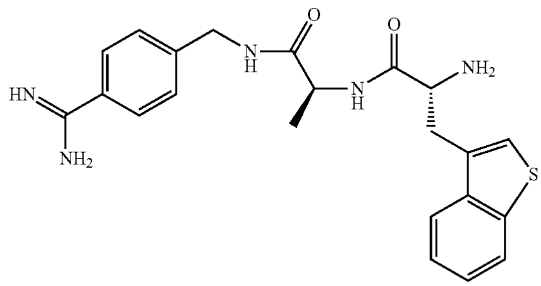 [SMILES: C[C@H](NC(=O)[C@H](N)Cc1csc2ccccc12)C(=O)NCc1ccc(C(=N)N)cc1] | 2HCl | 424.17 | 423.17 |
| 1100 | 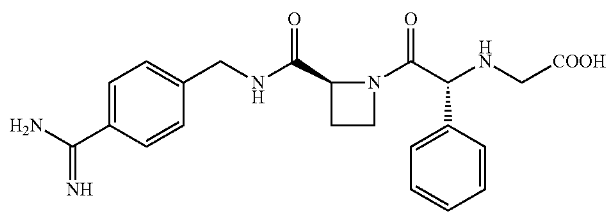 [SMILES: N=C(N)c1ccc(CNC(=O)[C@@H]2CCN2C(=O)[C@H](NCC(=O)O)c2ccccc2)cc1] | NA | 423.99 | 423.19 |
| 1101 | 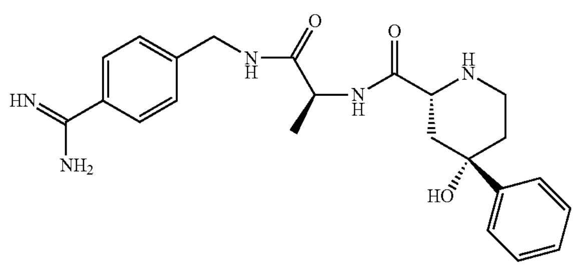 [SMILES: C[C@H](NC(=O)[C@H]1C[C@](O)(c2ccccc2)CCN1)C(=O)NCc1ccc(C(=N)N)cc1] | 2HCl | 424.18 | 423.23 |
| 1102 | 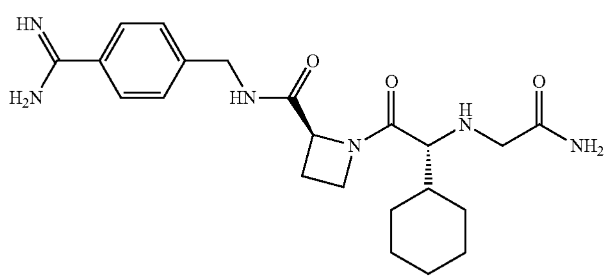 [SMILES: N=C(N)c1ccc(CNC(=O)[C@@H]2CCN2C(=O)[C@H](NCC(N)=O)C2CCCCC2)cc1] | NA | 429.24 | 428.25 |
| 1103 | 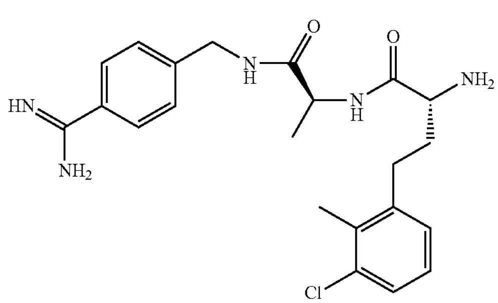 [SMILES: Cc1c(Cl)cccc1CC[C@@H](N)C(=O)N[C@@H](C)C(=O)NCc1ccc(C(=N)N)cc1] | 2HCl | 430.19 | 429.19 |

TABLE 31-continued

Compound List

| Compound No. | Structure | Salt | Exact Mass (ES+; M + H, Obsd) | Exact Mass (Calc) |
|---|---|---|---|---|
| 1104 | 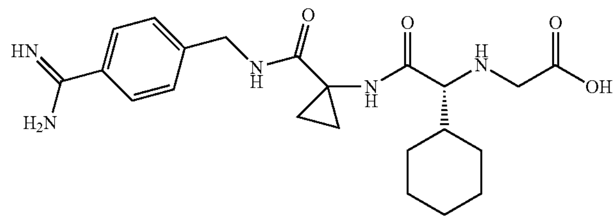 [SMILES: N=C(N)c1ccc(CNC(=O)C2(NC(=O)[C@H](NCC(=O)O)C3CCCCC3)CC2)cc1] | 2HCl | 430.21 | 429.24 |
| 1105 | 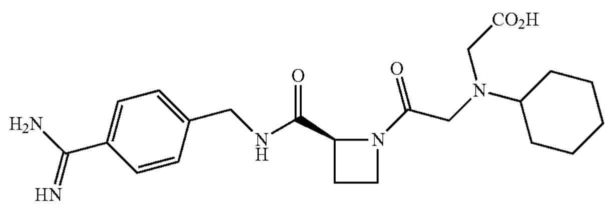 [SMILES: N=C(N)c1ccc(CNC(=O)[C@@H]2CCN2C(=O)CN(CC(=O)O)C2CCCCC2)cc1] | NA | 430.16 | 429.24 |
| 1106 | 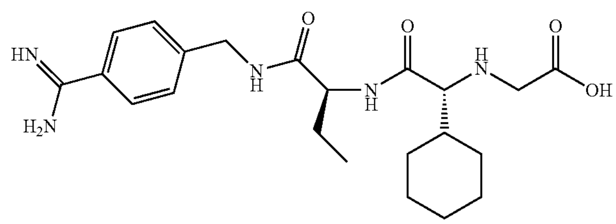 [SMILES: CC[C@H](NC(=O)[C@H](NCC(=O)O)C1CCCCC1)C(=O)NCc1ccc(C(=N)N)cc1] | 2HCl | 432.24 | 431.25 |
| 1107 | 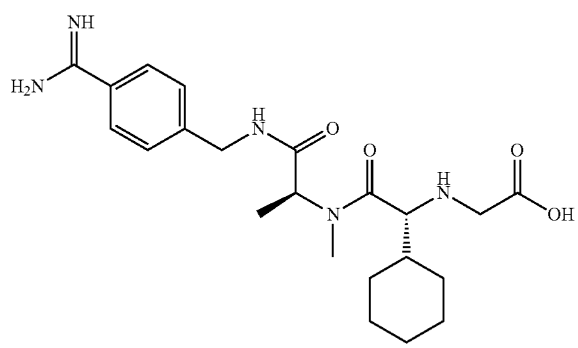 [SMILES: C[C@@H](C(=O)NCc1ccc(C(=N)N)cc1)N(C)C(=O)[C@H](NCC(=O)O)C1CCCCC1] | NA | 432.25 | 431.25 |
| 1108 | 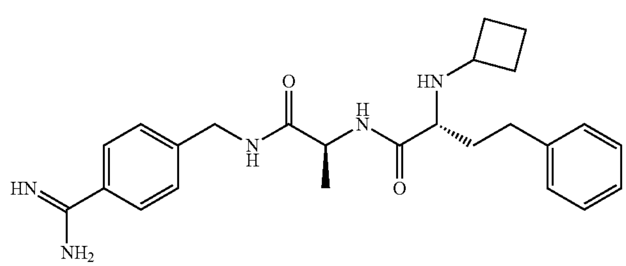 [SMILES: C[C@H](NC(=O)[C@@H](CCc1ccccc1)NC1CCC1)C(=O)NCc1ccc(C(=N)N)cc1] | 2HCl | 436.16 | 435.26 |
| 1109 | 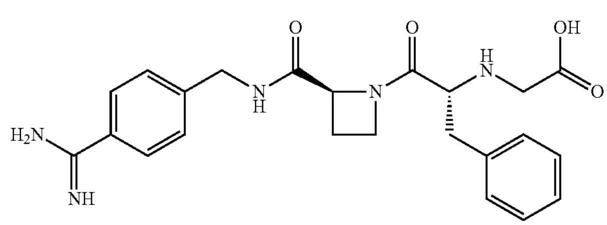 [SMILES: N=C(N)c1ccc(CNC(=O)[C@@H]2CCN2C(=O)[C@@H](Cc2ccccc2)NCC(=O)O)cc1] | NA | 438.02 | 437.21 |

TABLE 31-continued

Compound List

| Compound No. | Structure | Salt | Exact Mass (ES+; M + H, Obsd) | Exact Mass (Calc) |
|---|---|---|---|---|
| 1110 | 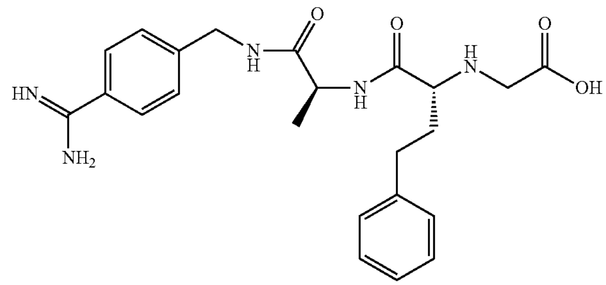 [SMILES: C[C@H](NC(=O)[C@@H](CCc1ccccc1)NCC(=O)O)C(=O)NCc1ccc(C(=N)N)cc1] | 2HCl | 440.19 | 439.22 |
| 1111 | 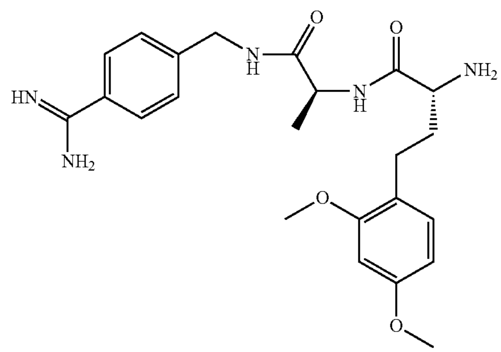 [SMILES: COc1ccc(CC[C@@H](N)C(=O)N[C@@H](C)C(=O)NCc2ccc(C(=N)N)cc2)c(OC)c1] | 2HCl | 442.22 | 441.24 |
| 1112 | 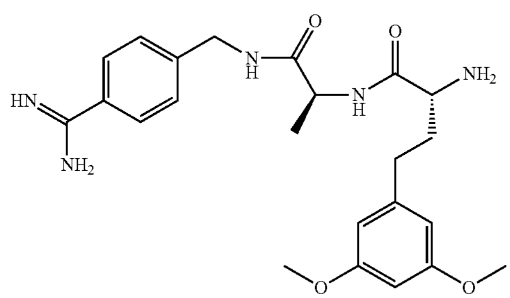 [SMILES: COc1cc(CC[C@@H](N)C(=O)N[C@@H](C)C(=O)NCc2ccc(C(=N)N)cc2)cc(OC)c1] | 2HCl | 442.21 | 441.24 |
| 1113 | 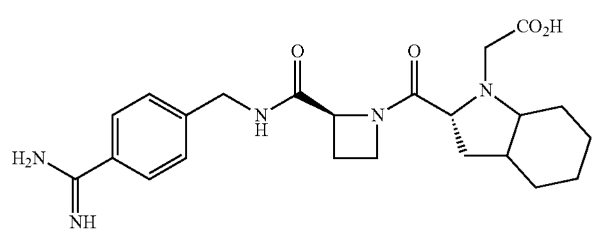 | NA | 441.99 | 441.24 |
| 1114 | 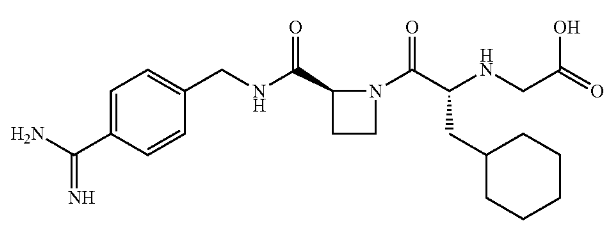 [SMILES: N=C(N)c1ccc(CNC(=O)[C@@H]2CCN2C(=O)[C@@H](CC2CCCCC2)NCC(=O)O)cc1] | NA | 444.10 | 443.25 |

TABLE 31-continued

Compound List

| Compound No. | Structure | Salt | Exact Mass (ES+; M + H, Obsd) | Exact Mass (Calc) |
|---|---|---|---|---|
| 1115 | 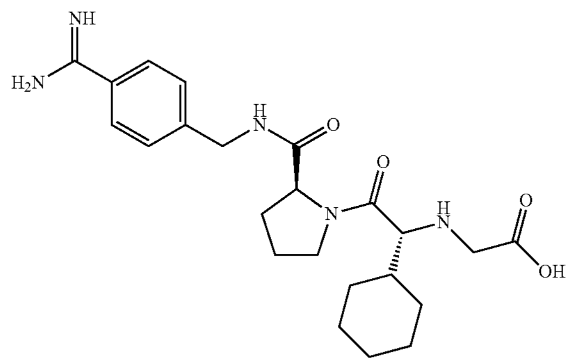 [SMILES: N=C(N)c1ccc(CNC(=O)[C@@H]2CCCN2C(=O)[C@H](NCC(=O)O)C2CCCCC2)cc1] | NA | 444.25 | 443.25 |
| 1116 | 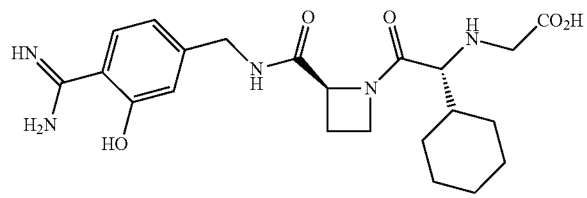 [SMILES: N=C(N)c1ccc(CNC(=O)[C@@H]2CCN2C(=O)[C@H](NCC(=O)O)C2CCCCC2)cc1O] | NA | 445.99 | 445.23 |
| 1117 | 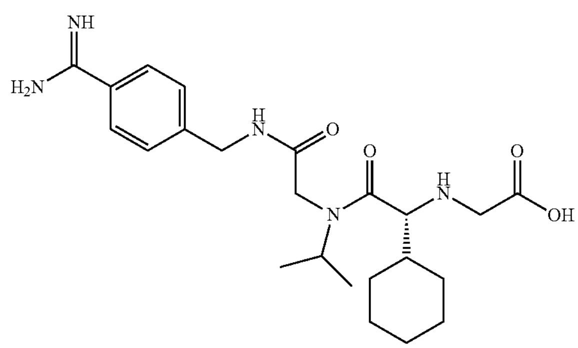 [SMILES: CC(C)N(CC(=O)NCc1ccc(C(=N)N)cc1)C(=O)[C@H](NCC(=O)O)C1CCCCC1] | NA | 446.25 | 445.27 |
| 1118 | 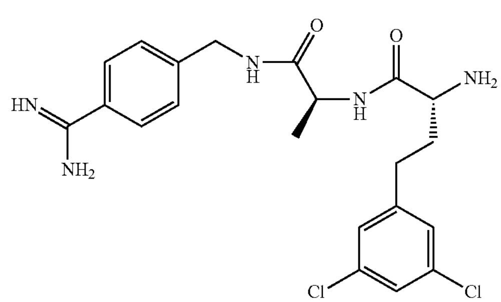 [SMILES: C[C@H](NC(=O)[C@H](N)CCc1cc(Cl)cc(Cl)c1)C(=O)NCc1ccc(C(=N)N)cc1] | 2HCl | 449.90 | 449.14 |

TABLE 31-continued

Compound List

| Compound No. | Structure | Salt | Exact Mass (ES+; M + H, Obsd) | Exact Mass (Calc) |
|---|---|---|---|---|
| 1119 | 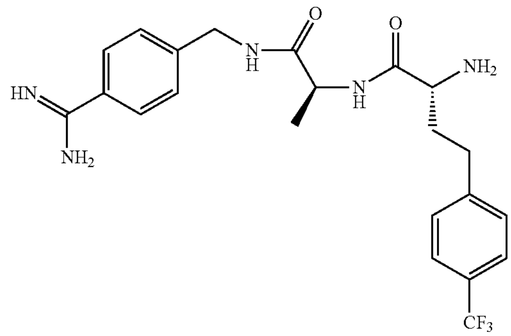 [SMILES: C[C@H](NC(=O)[C@H](N)CCc1ccc(C(F)(F)F)cc1)C(=O)NCc1ccc(C(=N)N)cc1] | 2HCl | 450.15 | 449.20 |
| 1120 | 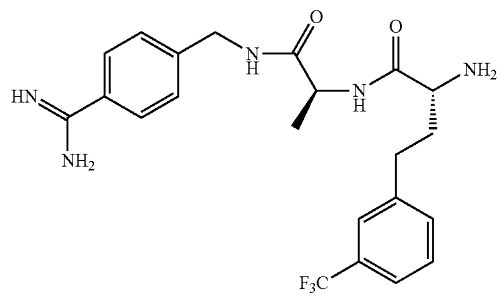 [SMILES: C[C@H](NC(=O)[C@H](N)CCc1cccc(C(F)(F)F)c1)C(=O)NCc1ccc(C(=N)N)cc1] | 2HCl | 450.16 | 449.20 |
| 1121 | 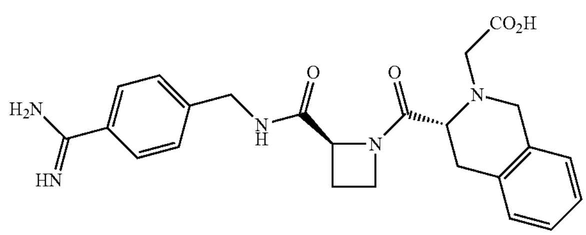 [SMILES: N=C(N)c1ccc(CNC(=O)[C@@H]2CCN2C(=O)[C@H]2Cc3ccccc3CN2CC(=O)O)cc1] | NA | 449.94 | 449.21 |
| 1122 | 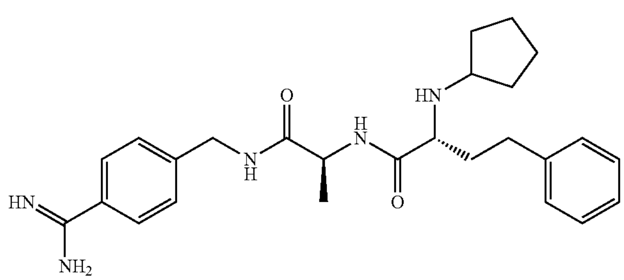 [SMILES: C[C@H](NC(=O)[C@@H](CCc1ccccc1)NC1CCCC1)C(=O)NCc1ccc(C(=N)N)cc1] | 2HCl | 450.25 | 449.28 |
| 1123 | 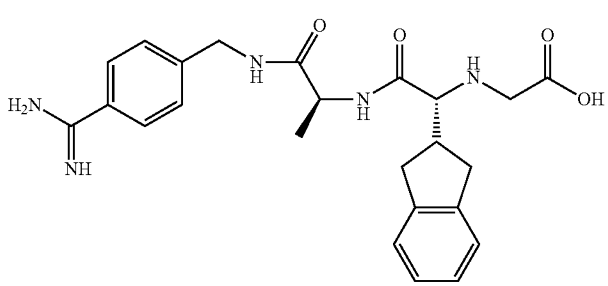 [SMILES: C[C@H](NC(=O)[C@H](NCC(=O)O)C1Cc2ccccc2C1)C(=O)NCc1ccc(C(=N)N)cc1] | 2HCl | 452.10 | 451.22 |

TABLE 31-continued

Compound List

| Compound No. | Structure | Salt | Exact Mass (ES+; M + H, Obsd) | Exact Mass (Calc) |
|---|---|---|---|---|
| 1124 | 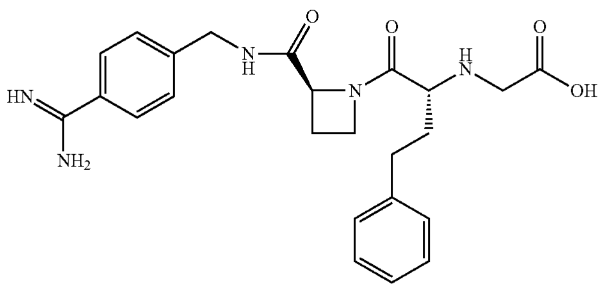 [SMILES: N=C(N)c1ccc(CNC(=O)[C@@H]2CCN2C(=O)[C@@H](CCc2ccccc2)NCC(=O)O)cc1] | 2HCl | 452.20 | 451.22 |
| 1125 | 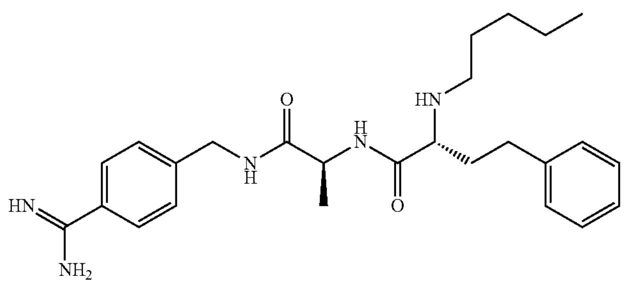 [SMILES: CCCCCN[C@H](CCc1ccccc1)C(=O)N[C@@H](C)C(=O)NCc1ccc(C(=N)N)cc1] | 2HCl | 452.30 | 451.29 |
| 1126 | 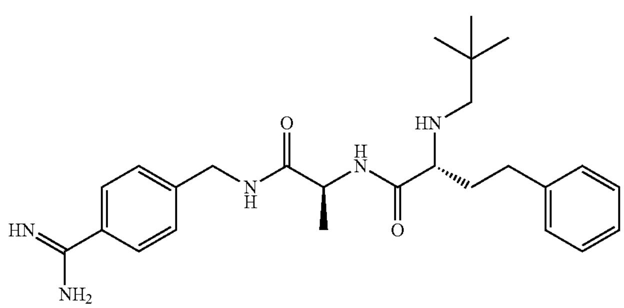 [SMILES: C[C@H](NC(=O)[C@@H](CCc1ccccc1)NCC(C)(C)C)C(=O)NCc1ccc(C(=N)N)cc1] | 2HCl | 452.29 | 451.29 |
| 1127 | 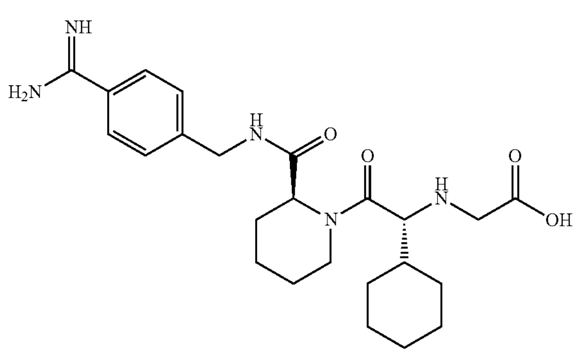 [SMILES: N=C(N)c1ccc(CNC(=O)[C@@H]2CCCCN2C(=O)[C@H](NCC(=O)O)C2CCCCC2)cc1] | NA | 458.24 | 457.27 |

TABLE 31-continued
Compound List
| Compound No. | Structure | Salt | Exact Mass (ES+; M + H, Obsd) | Exact Mass (Calc) |
|---|---|---|---|---|
| 1128 | 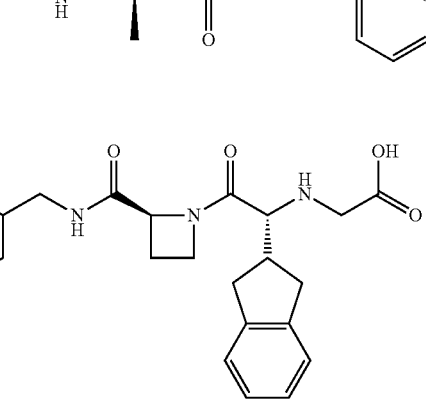 | 2HCl | 459.19 (ES−) | 460.26 |
| 1129 | 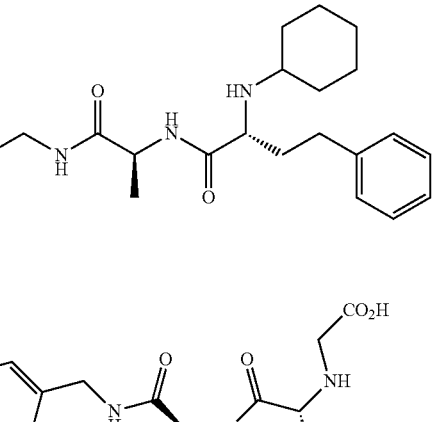 | NA | 463.98 | 463.22 |
| 1130 | 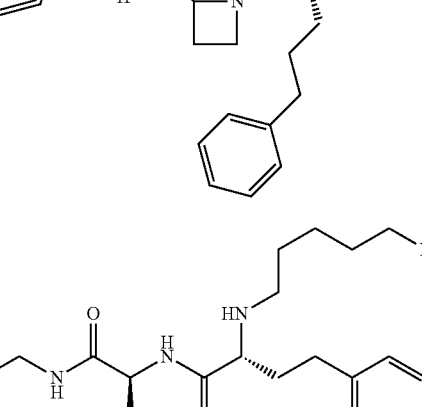 | 2 HCl | 464.32 | 463.29 |
| 1131 | 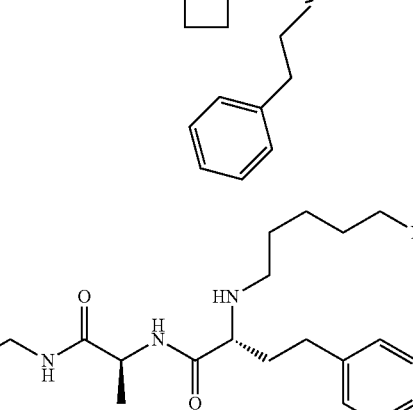 | NA | 466.09 | 465.24 |
| 1132 | 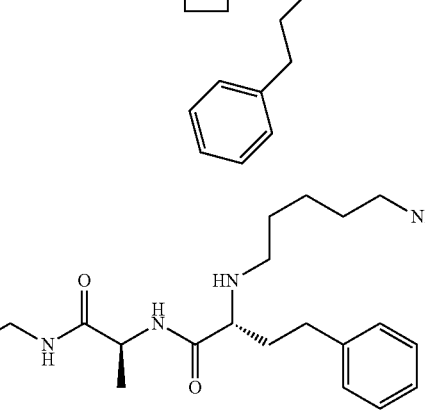 | 3HCl | 467.30 | 466.31 |

TABLE 31-continued
Compound List
| Compound No. | Structure | Salt | Exact Mass (ES+; M + H, Obsd) | Exact Mass (Calc) |
|---|---|---|---|---|
| 1133 | 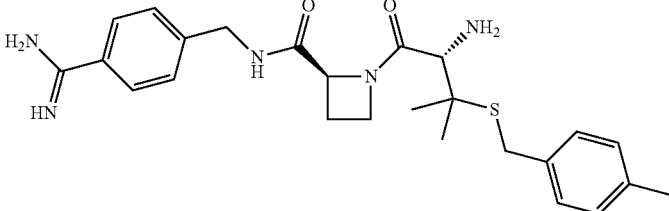 [SMILES: Cc1ccc(CSC(C)(C)[C@@H](N)C(=O)N2CC[C@H]2C(=O)NCc2ccc(C(=N)N)cc2)cc1] | NA | 468.07 | 467.24 |
| 1134 | 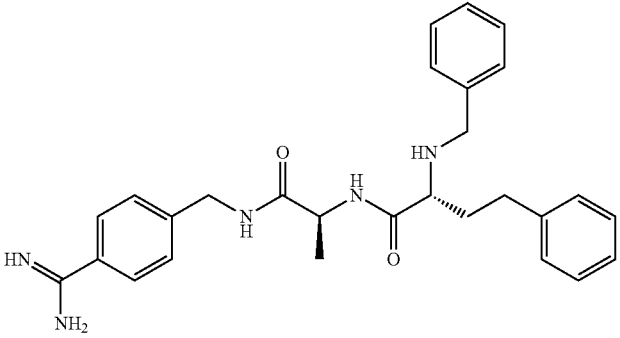 [SMILES: C[C@H](NC(=O)[C@@H](CCc1ccccc1)NCc1ccccc1)C(=O)NCc1ccc(C(=N)N)cc1] | 2HCl | 472.25 | 471.26 |
| 1135 | 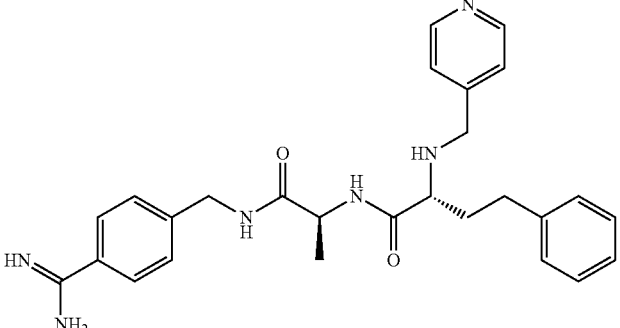 | 3HCl | 473.15 | 472.26 |
| 1136 | 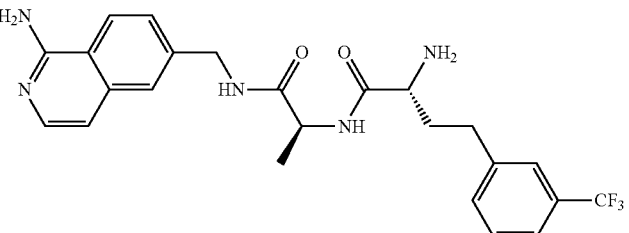 | 2HCl | 474.19 | 473.20 |
| 1137 | 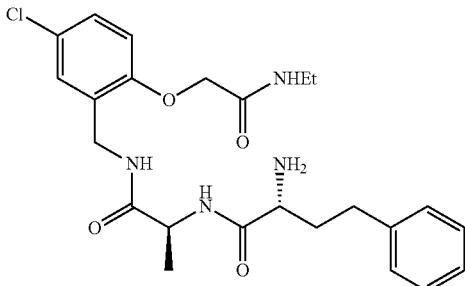 | TFA | 475.20 | 474.20 |

TABLE 31-continued

Compound List

| Compound No. | Structure | Salt | Exact Mass (ES+; M + H, Obsd) | Exact Mass (Calc) |
|---|---|---|---|---|
| 1138 | 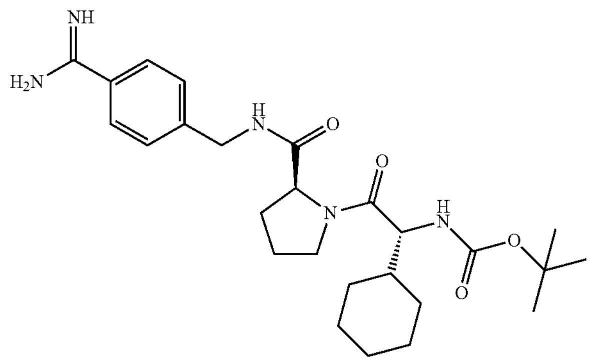 [SMILES: CC(C)(C)OC(=O)N[C@@H](C(=O)N1CCC[C@H]1C(=O)NCc1ccc(C(=N)N)cc1)C1CCCCC1] | NA | 486.31 | 485.30 |
| 1139 | 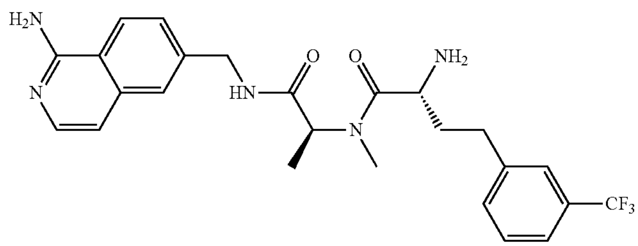 [SMILES: C[C@@H](C(=O)NCc1ccc2c(N)nccc2c1)N(C)C(=O)[C@H](N)CCc1cccc(C(F)(F)F)c1] | 2HCl | 488.20 | 487.22 |
| 1140 | 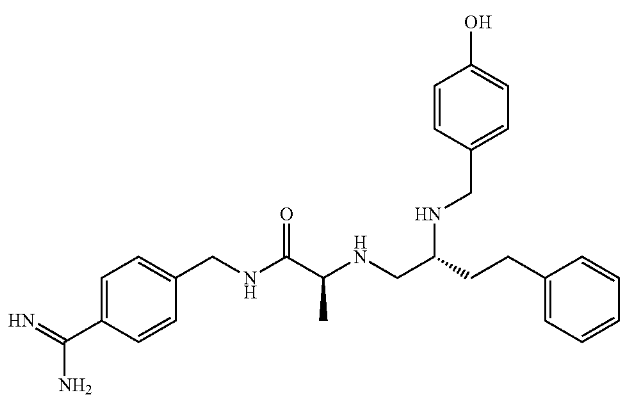 [SMILES: C[C@H](NC[C@@H](CCc1ccccc1)NCc1ccc(O)cc1)C(=O)NCc1ccc(C(=N)N)cc1] | 2HCl | 487.98 | 487.26 |
| 1141 | 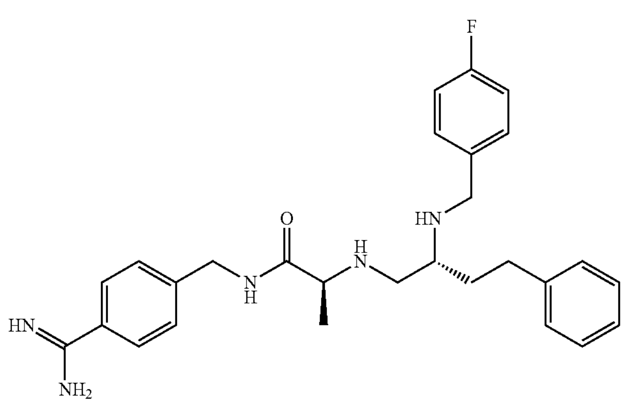 [SMILES: C[C@H](NC[C@@H](CCc1ccccc1)NCc1ccc(F)cc1)C(=O)NCc1ccc(C(=N)N)cc1] | 2HCl | 490.27 | 489.25 |

TABLE 31-continued

Compound List

| Compound No. | Structure | Salt | Exact Mass (ES+; M + H, Obsd) | Exact Mass (Calc) |
|---|---|---|---|---|
| 1142 | 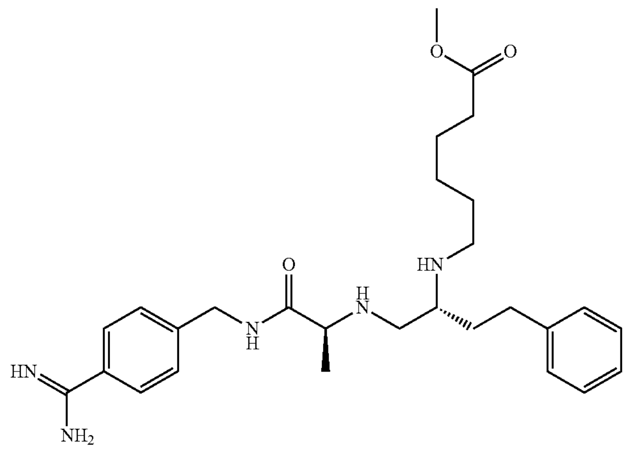 [SMILES: COC(=O)CCCCCN[C@H](CCc1ccccc1)CN[C@@H](C)C(=O)NCc1ccc(C(=N)N)cc1] | 2HCl | 510.26 | 509.30 |
| 1143 | 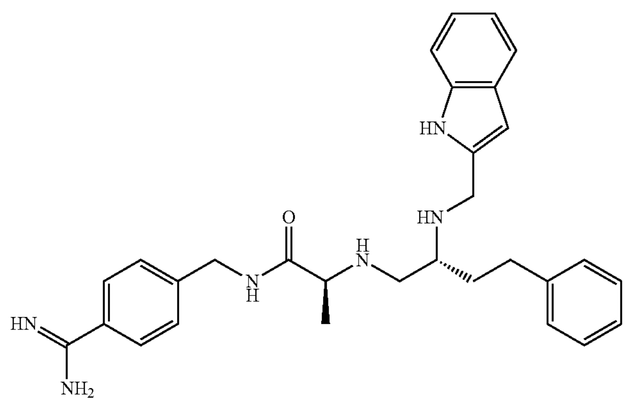 [SMILES: C[C@H](NC[C@@H](CCc1ccccc1)NCc1cc2ccccc2[nH]1)C(=O)NCc1ccc(C(=N)N)cc1] | 2HCl | 509.23 (ES−) | 510.27 |
| 1144 | 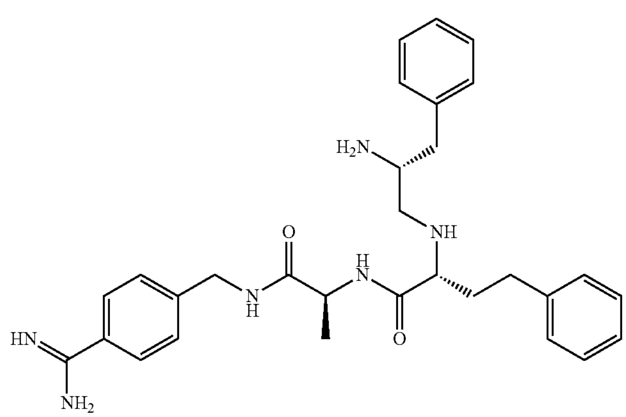 [SMILES: C[C@H](NC(=O)[C@@H](CCc1ccccc1)NC[C@H](N)Cc1ccccc1)C(=O)NCc1ccc(C(=N)N)cc1] | 3TFA | 515.33 | 514.31 |

TABLE 31-continued

Compound List

| Compound No. | Structure | Salt | Exact Mass (ES+; M + H, Obsd) | Exact Mass (Calc) |
|---|---|---|---|---|
| 1145 | 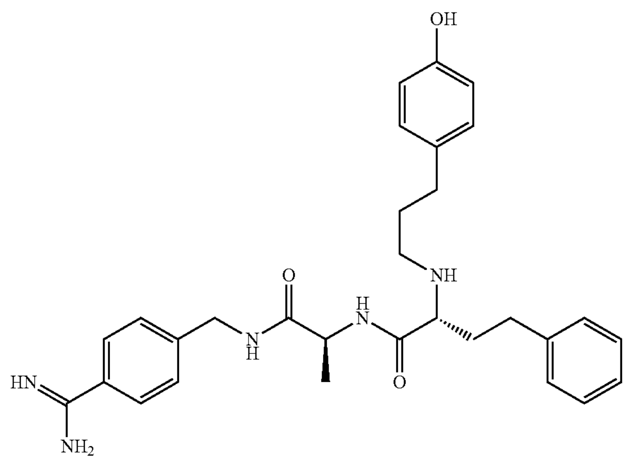 [SMILES: C[C@H](NC(=O)[C@@H](CCc1ccccc1)NCCCc1ccc(O)cc1)C(=O)NCc1ccc(C(=N)N)cc1] | 2HCl | 516.35 | 515.29 |
| 1146 | 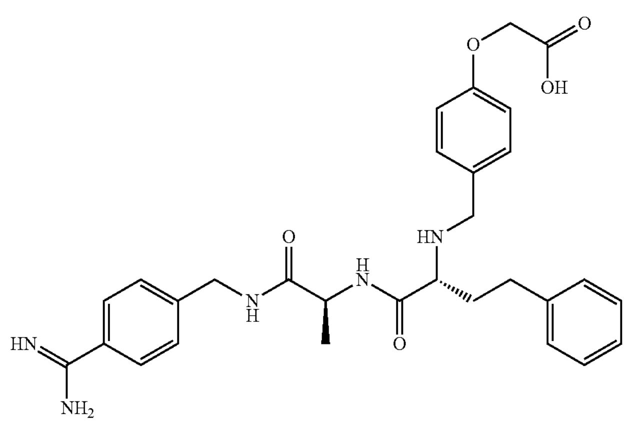 [SMILES: C[C@H](NC(=O)[C@@H](CCc1ccccc1)NCc1ccc(OCC(=O)O)cc1)C(=O)NCc1ccc(C(=N)N)cc1] | NA | 546.32 | 545.26 |
| 1147 | 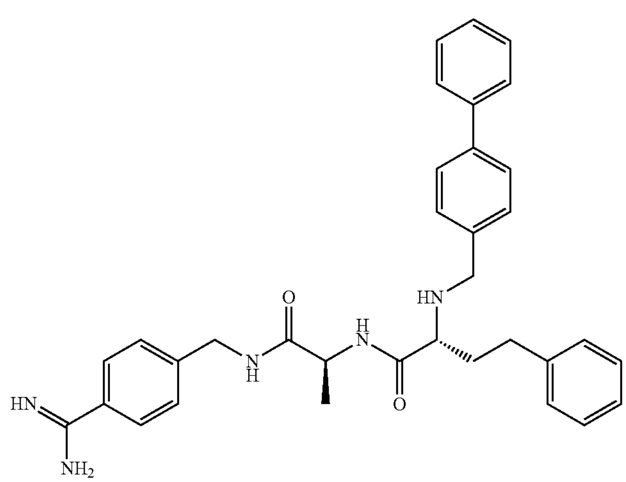 [SMILES: C[C@H](NC(=O)[C@@H](CCc1ccccc1)NCc1ccc(-c2ccccc2)cc1)C(=O)NCc1ccc(C(=N)N)cc1] | 2HCl | 548.33 | 547.29 |

TABLE 31-continued

Compound List

| Compound No. | Structure | Salt | Exact Mass (ES+; M + H, Obsd) | Exact Mass (Calc) |
|---|---|---|---|---|
| 1148 | 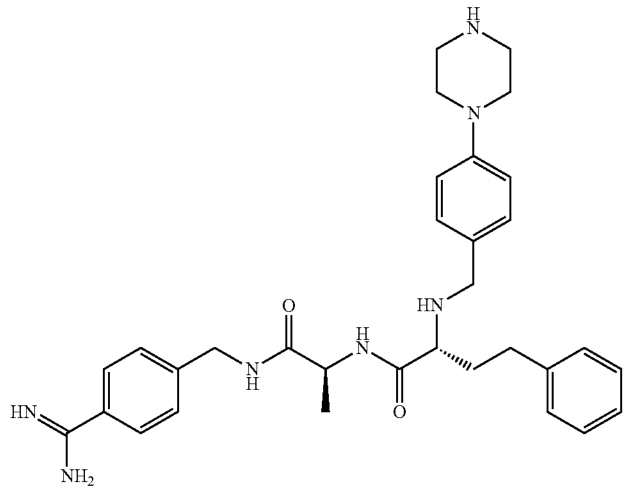 [SMILES: C[C@H](NC(=O)[C@@H](CCc1ccccc1)NCc1ccc(N2CCNCC2)cc1)C(=O)NCc1ccc(C(=N)N)cc1] | 3TFA | 556.39 | 555.33 |
| 1149 | 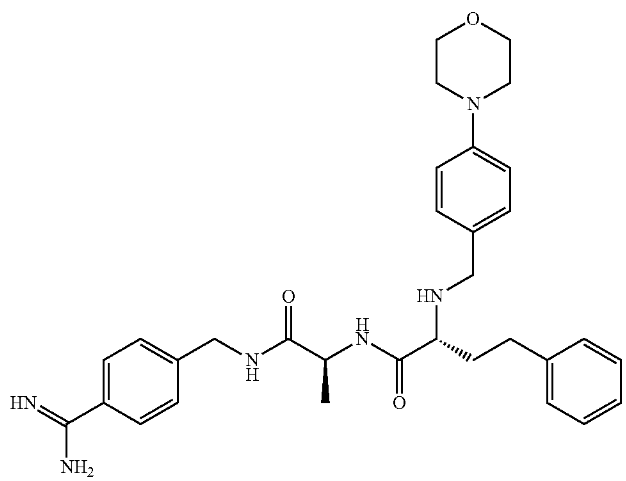 [SMILES: C[C@H](NC(=O)[C@@H](CCc1ccccc1)NCc1ccc(N2CCOCC2)cc1)C(=O)NCc1ccc(C(=N)N)cc1] | 2HCl | 557.28 | 556.32 |
| 1150 | 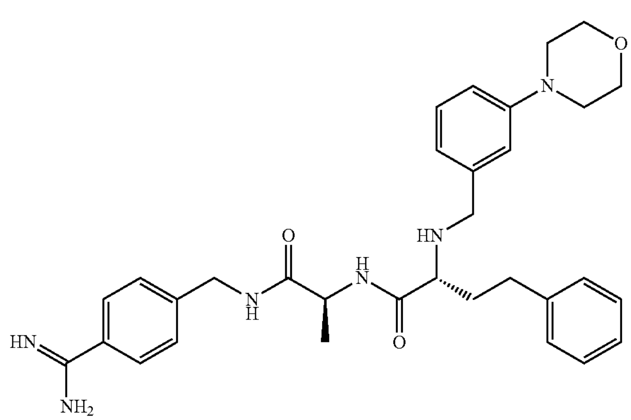 [SMILES: C[C@H](NC(=O)[C@@H](CCc1ccccc1)NCc1cccc(N2CCOCC2)c1)C(=O)NCc1ccc(C(=N)N)cc1] | 2HCl | 557.34 | 556.32 |

TABLE 31-continued
| Compound No. | Structure | Salt | Exact Mass (ES+; M + H, Obsd) | Exact Mass (Calc) |
|---|---|---|---|---|
| 1151 | 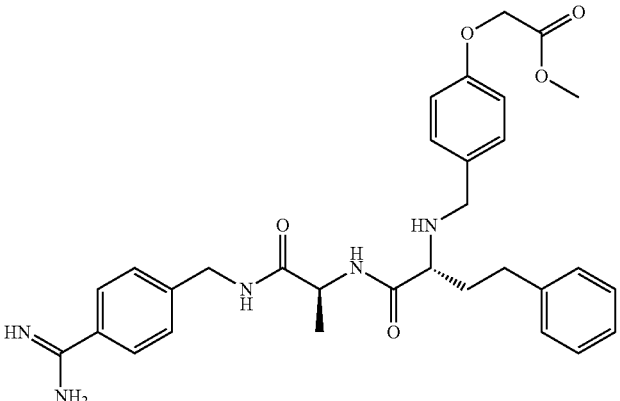 | 2HCl | 558.17 | 559.28 |
| 1152 | 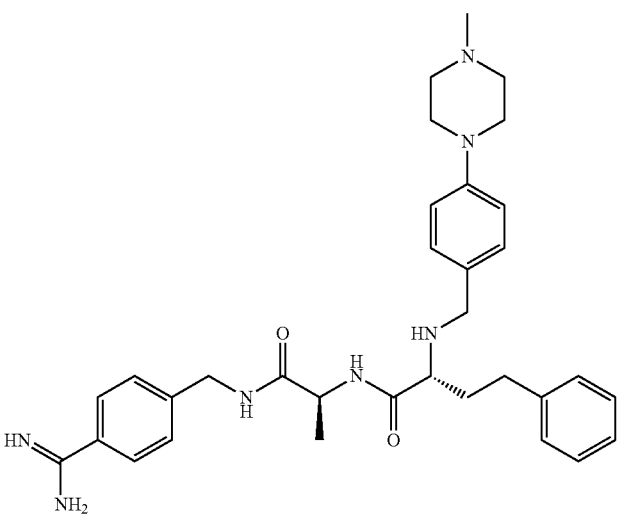 [SMILES: C[C@H](NC(=O)[C@@H](CCc1ccccc1)NCc1ccc(N2CCN(C)CC2)cc1)C(=O)NCc1ccc(C(=N)N)cc1] | 2HCl | 570.33 | 569.35 |
| 1153 | 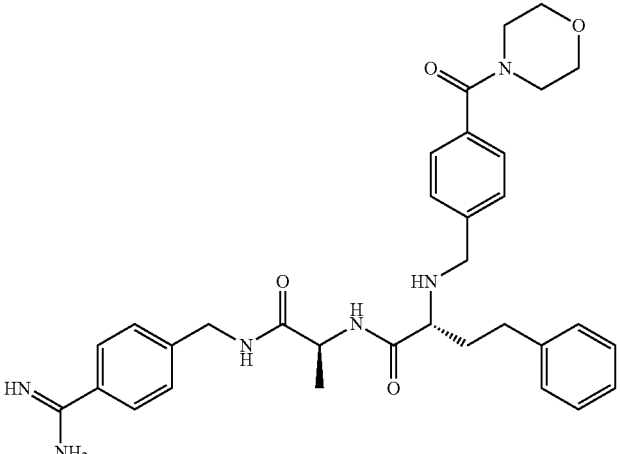 | 2HCl | 585.32 | 584.31 |

TABLE 31-continued

Compound List

| Compound No. | Structure | Salt | Exact Mass (ES+; M + H, Obsd) | Exact Mass (Calc) |
| --- | --- | --- | --- | --- |
| 1154 | 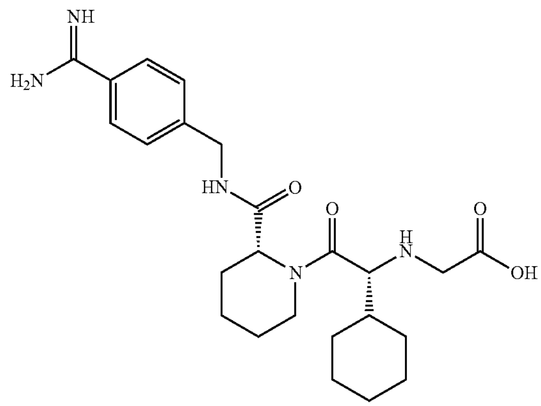 [SMILES: N=C(N)c1ccc(CNC(=O)[C@H]2CCCCN2C(=O)[C@H](NCC(=O)O)C2CCCCC2)cc1] | NA | 458.22 | 457.27 |
| 1156 | 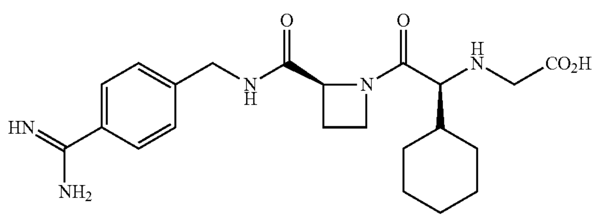 [SMILES: N=C(N)c1ccc(CNC(=O)[C@@H]2CCN2C(=O)[C@@H](NCC(=O)O)C2CCCCC2)cc1] | NA | 430.22 | 429.24 |
| 1157 | 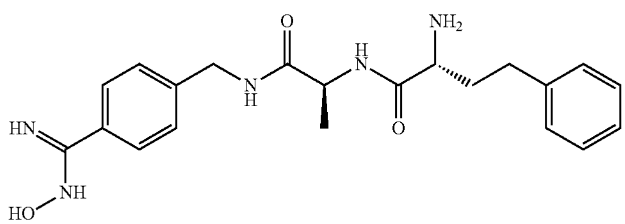 [SMILES: C[C@H](NC(=O)[C@H](N)CCc1ccccc1)C(=O)NCc1ccc(C(=N)NO)cc1] | 2HCl | 398.15 | 397.21 |
| 1158 | 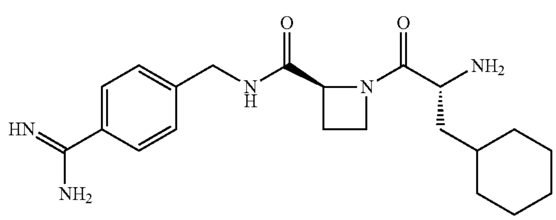 [SMILES: N=C(N)c1ccc(CNC(=O)[C@@H]2CCN2C(=O)[C@H](N)CC2CCCCC2)cc1] | 2HCl | 386.17 | 385.25 |
| 1170 | 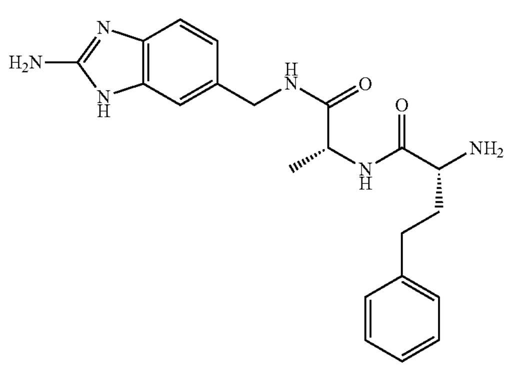 [SMILES: C[C@@H](NC(=O)[C@H](N)CCc1ccccc1)C(=O)NCc1ccc2nc(N)[nH]c2c1] | | | |

TABLE 31-continued

Compound List

| Compound No. | Structure | Salt | Exact Mass (ES+; M + H, Obsd) | Exact Mass (Calc) |
|---|---|---|---|---|
| 1171 | 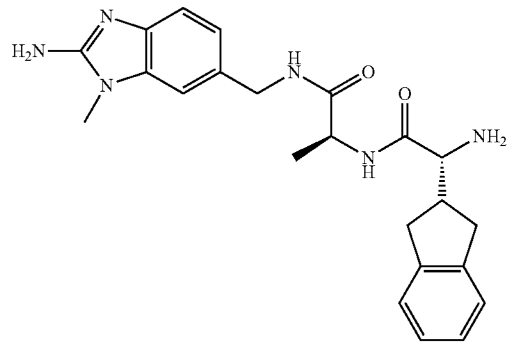 [SMILES: C[C@H](NC(=O)[C@H](N)C1Cc2ccccc2C1)C(=O)NCc1ccc2nc(N)n(C)c2c1] | 2HCl | 421.14 | 420.23 |
| 1192 | 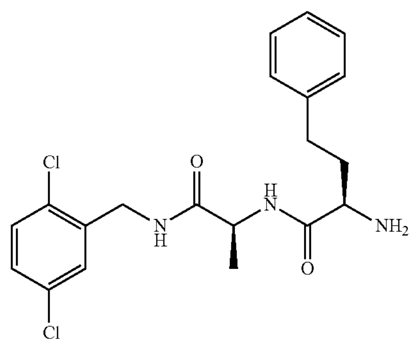 [SMILES: C[C@H](NC(=O)[C@H](N)CCc1ccccc1)C(=O)NCc1cc(Cl)ccc1Cl] | 1HCl | 408.12 | 407.12 |
| 1194 | 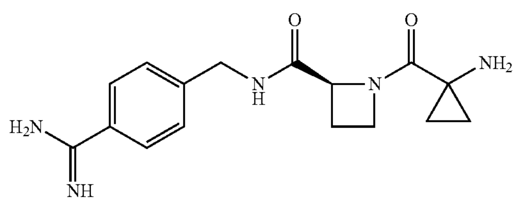 [SMILES: N=C(N)c1ccc(CNC(=O)[C@@H]2CCN2C(=O)C2(N)CC2)cc1] | NA | 316.11 | 315.17 |
| 1195 | 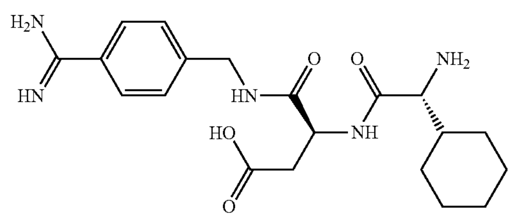 [SMILES: N=C(N)c1ccc(CNC(=O)[C@H](CC(=O)O)NC(=O)[C@H](N)C2CCCCC2)cc1] | 2HCl | 404.17 | 403.22 |
| 1207 | 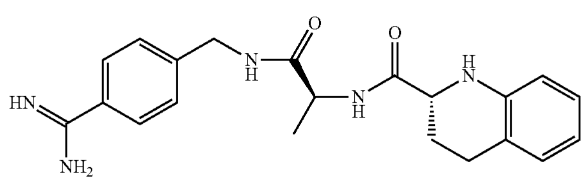 [SMILES: C[C@H](NC(=O)[C@H]1CCc2ccccc2N1)C(=O)NCc1ccc(C(=N)N)cc1] | 2HCl | 380.25 | 379.20 |
| 1211 | 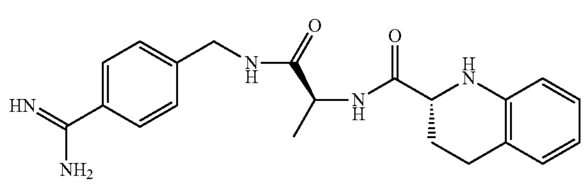 [SMILES: C[C@H](NC(=O)[C@H]1CCc2ccccc2N1)C(=O)NCc1ccc(C(=N)N)cc1] | 2HCl | 557.34 | 536.32 |

TABLE 31-continued

Compound List

| Compound No. | Structure | Salt | Exact Mass (ES+; M + H, Obsd) | Exact Mass (Calc) |
|---|---|---|---|---|
| 1213 | 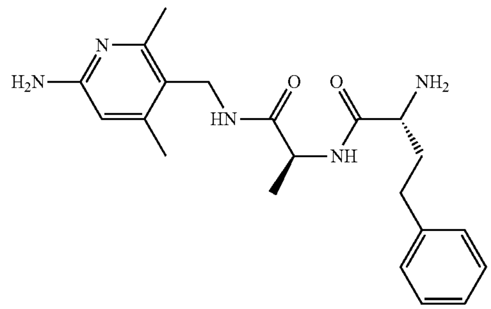 [SMILES: Cc1cc(N)nc(C)c1CNC(=O)[C@H](C)NC(=O)[C@H](N)CCc1ccccc1] | 2HCl | 384.27 | 383.23 |
| 1215 | 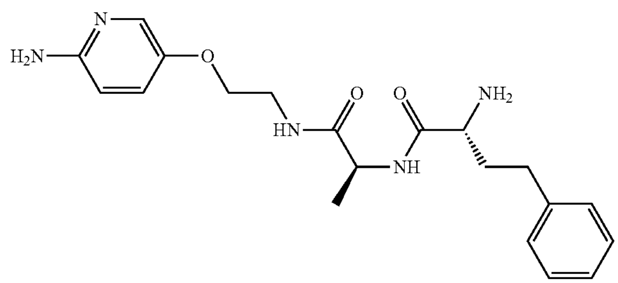 [SMILES: C[C@H](NC(=O)[C@H](N)CCc1ccccc1)C(=O)NCCOc1ccc(N)nc1] | 2HCl | 386.15 | 385.21 |
| 1218 | 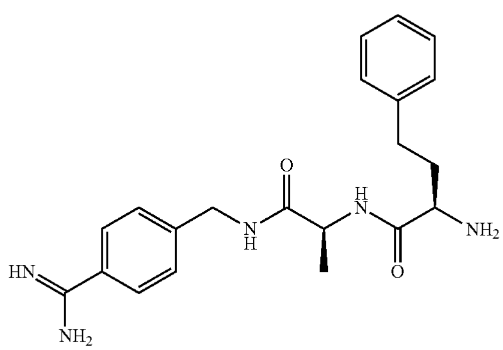 [SMILES: C[C@H](NC(=O)[C@H](N)CCc1ccccc1)C(=O)NCc1ccc(C(=N)N)cc1] | 2HCl | 388.28 | 387.26 |
| 1223 | 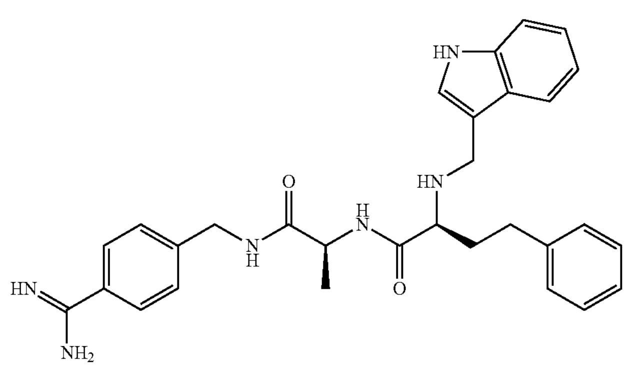 [SMILES: C[C@H](NC(=O)[C@H](CCc1ccccc1)NCc1c[nH]c2ccccc12)C(=O)NCc1ccc(C(=N)N)cc1] | 2HCl | 509.22 | 510.27 |

TABLE 31-continued

Compound List

| Compound No. | Structure | Salt | Exact Mass (ES+; M + H, Obsd) | Exact Mass (Calc) |
| --- | --- | --- | --- | --- |
| 1229 | 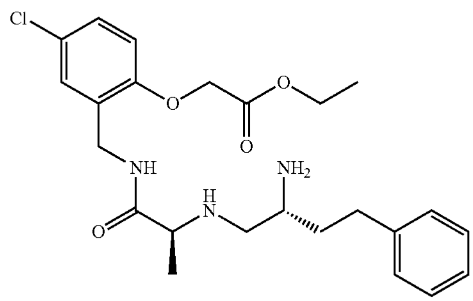 [SMILES: CCOC(=O)COc1ccc(Cl)cc1CNC(=O)[C@H](C)NC[C@H](N)CCc1ccccc1] | 1 HCl | 476.18 | 475.19 |
| 999 (melagatran control) | 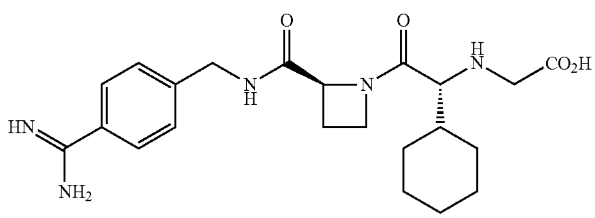 [SMILES: N=C(N)c1ccc(CNC(=O)[C@@H]2CCN2C(=O)[C@H](NCC(=O)O)C2CCCCC2)cc1] | | | 429.24 |
| 1230 | 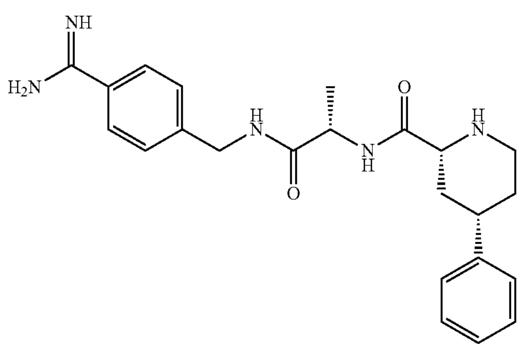 [SMILES: C[C@H](NC(=O)[C@H]1C[C@@H](c2ccccc2)CCN1)C(=O)NCc1ccc(C(=N)N)cc1] | 2 HCl | 408.21 | 407.23 |
| 1231 | 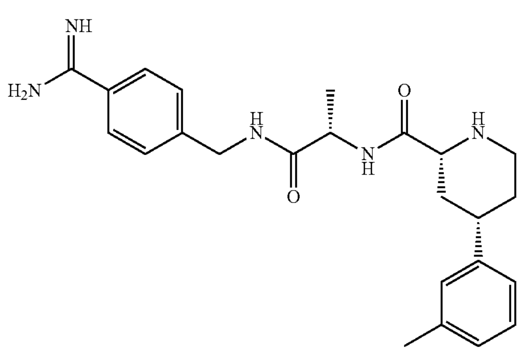 [SMILES: Cc1cccc([C@H]2CCN[C@@H](C(=O)N[C@@H](C)C(=O)NCc3ccc(C(=N)N)cc3)C2)c1] | 2 HCl | 422.25 | 421.25 |

TABLE 31-continued

Compound List

| Compound No. | Structure | Salt | Exact Mass (ES+; M + H, Obsd) | Exact Mass (Calc) |
|---|---|---|---|---|
| 1232 | 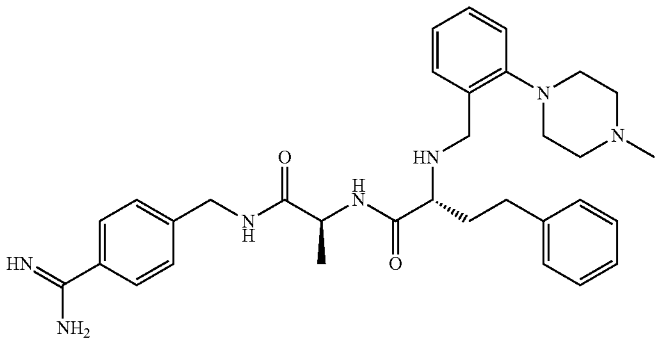 [SMILES: C[C@H](NC(=O)[C@@H](CCc1ccccc1)NCc1ccccc1N1CCN(C)CC1)C(=O)NCc1ccc(C(=N)N)cc1] | 2TFA | 570.38 | 569.35 |
| 1233 | 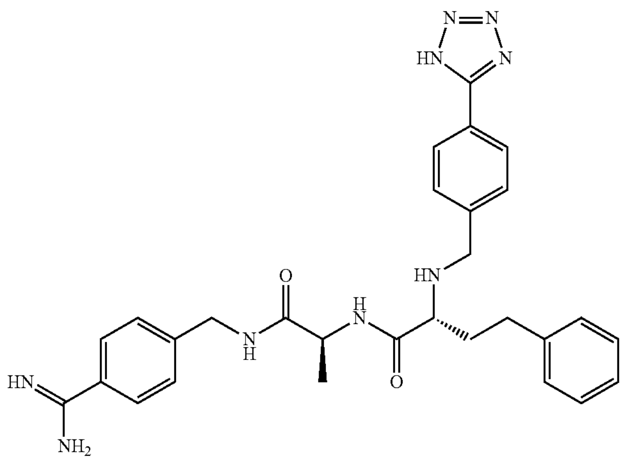 [SMILES: C[C@H](NC(=O)[C@@H](CCc1ccccc1)NCc1ccc(-c2nnn[nH]2)cc1)C(=O)NCc1ccc(C(=N)N)cc1] | 2TFA | 540.33 | 539.28 |
| 1234 | 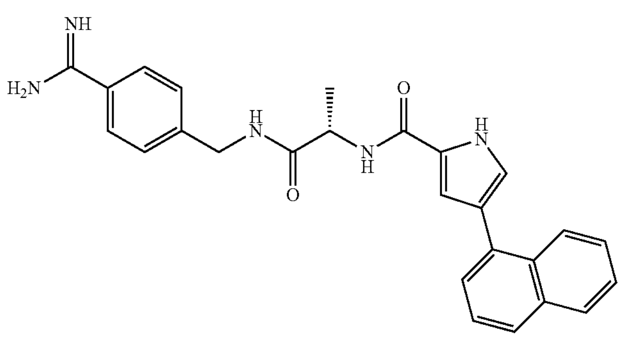 [SMILES: C[C@H](NC(=O)c1cc(-c2cccc3ccccc23)c[nH]1)C(=O)NCc1ccc(C(=N)N)cc1] | NA | 440.18 | 439.2 |
| 1235 | 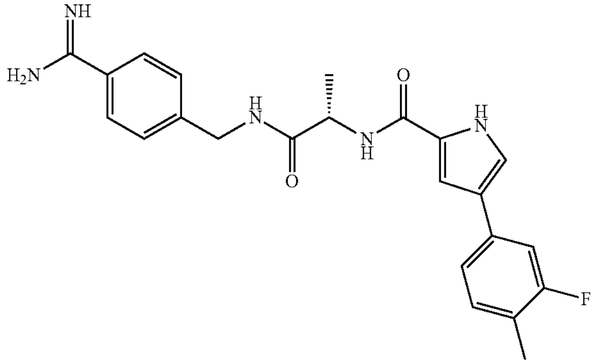 [SMILES: Cc1ccc(-c2c[nH]c(C(=O)N[C@@H](C)C(=O)NCc3ccc(C(=N)N)cc3)c2)cc1F] | NA | 422.2 | 421.19 |

TABLE 31-continued

Compound List

| Compound No. | Structure | Salt | Exact Mass (ES+; M + H, Obsd) | Exact Mass (Calc) |
|---|---|---|---|---|
| 1236 | 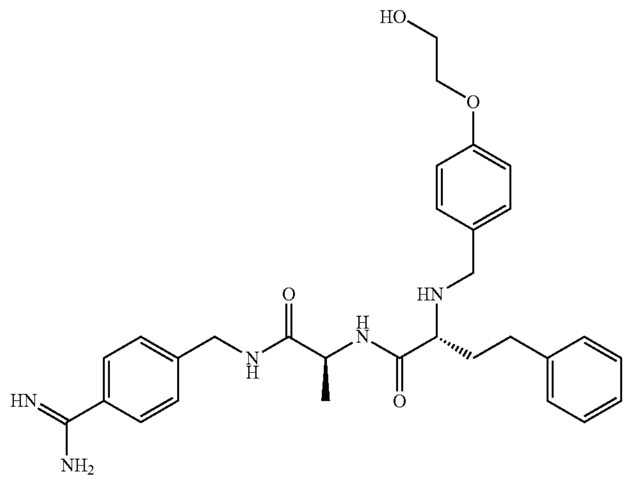 [SMILES: C[C@H](NC(=O)[C@@H](CCc1ccccc1)NCc1ccc(OCCO)cc1)C(=O)NCc1ccc(C(=N)N)cc1] | 2TFA | 532.34 | 531.28 |
| 1237 | 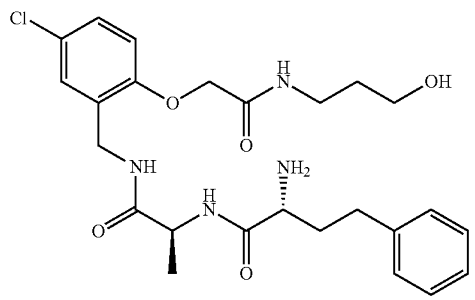 [SMILES: C[C@H](NC(=O)[C@H](N)CCc1ccccc1)C(=O)NCc1cc(Cl)ccc1OCC(=O)NCCCO] | HCl | 504.21 (ES−) | 505.01 |
| 1238 | 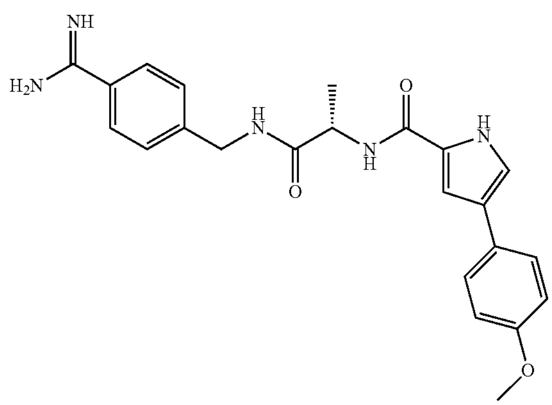 [SMILES: COc1ccc(-c2c[nH]c(C(=O)N[C@@H](C)C(=O)NCc3ccc(C(=N)N)cc3)c2)cc1] | TFA | 420.2 | 419.2 |
| 1239 | 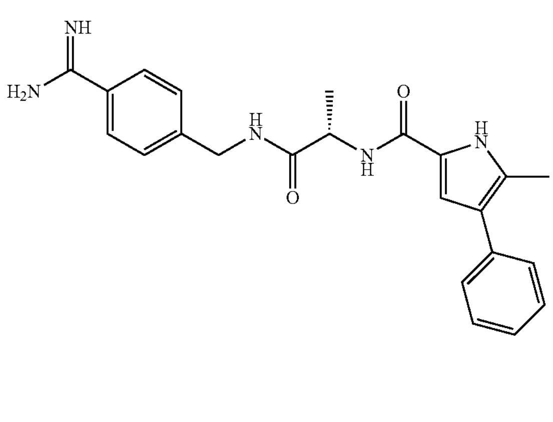 [SMILES: Cc1[nH]c(C(=O)N[C@@H](C)C(=O)NCc2ccc(C(=N)N)cc2)cc1-c1ccccc1] | TFA | 404.16 | 403.2 |

TABLE 31-continued

Compound List

| Compound No. | Structure | Salt | Exact Mass (ES+; M + H, Obsd) | Exact Mass (Calc) |
|---|---|---|---|---|
| 1240 | 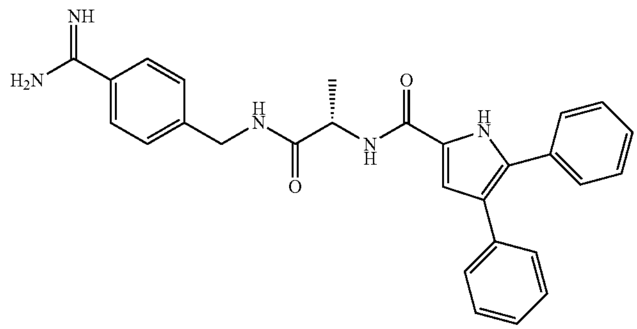 [SMILES: C[C@H](NC(=O)c1cc(-c2ccccc2)c(-c2ccccc2)[nH]1)C(=O)NCc1ccc(C(=N)N)cc1] | NA | 466.21 | 465.22 |
| 1241 | 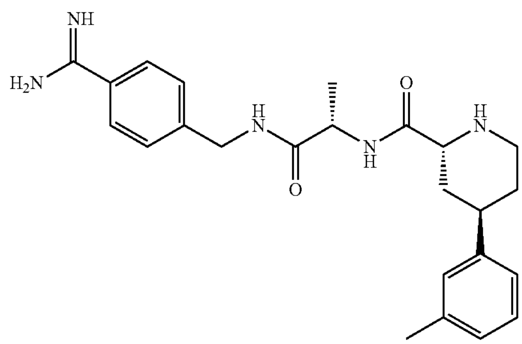 [SMILES: Cc1cccc([C@@H]2CCN[C@@H](C(=O)N[C@@H](C)C(=O)NCc3ccc(C(=N)N)cc3)C2)c1] | HCl | 422.26 | 421.25 |
| 1242 | 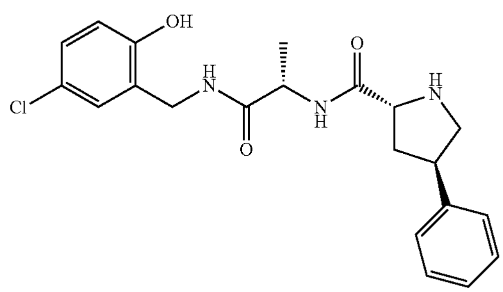 [SMILES: C[C@H](NC(=O)[C@H]1C[C@H](c2ccccc2)CN1)C(=O)NCc1cc(Cl)ccc1O] | N/A | 402.15 | 401.15 |
| 1243 | 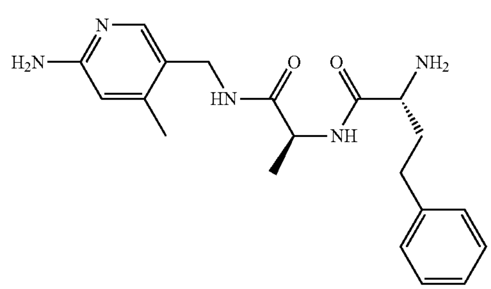 [SMILES: Cc1cc(N)ncc1CNC(=O)[C@H](C)NC(=O)[C@H](N)CCc1ccccc1] | 2HCl | 370.23 | 369.22 |
| 1244 | 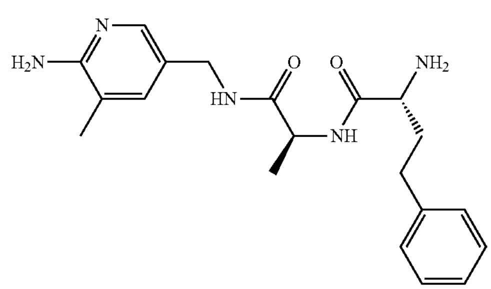 [SMILES: Cc1cc(CNC(=O)[C@H](C)NC(=O)[C@H](N)CCc2ccccc2)cnc1N] | 2HCl | 370.23 | 369.22 |

TABLE 31-continued

Compound List

| Compound No. | Structure | Salt | Exact Mass (ES+; M + H, Obsd) | Exact Mass (Calc) |
|---|---|---|---|---|
| 1245 | 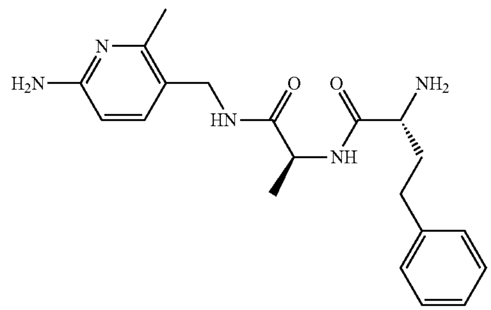 [SMILES: Cc1nc(N)ccc1CNC(=O)[C@H](C)NC(=O)[C@H](N)CCc1ccccc1] | 2HCl | 370.22 | 369.22 |
| 1246 | 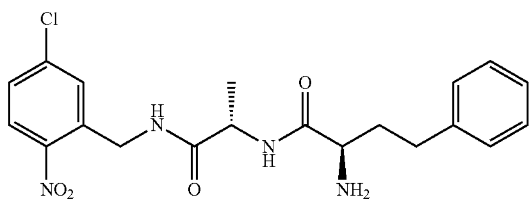 [SMILES: C[C@H](NC(=O)[C@H](N)CCc1ccccc1)C(=O)NCc1cc(Cl)ccc1[N+](=O)[O-]] | HCl | 419.13 | 418.14 |
| 1247 | 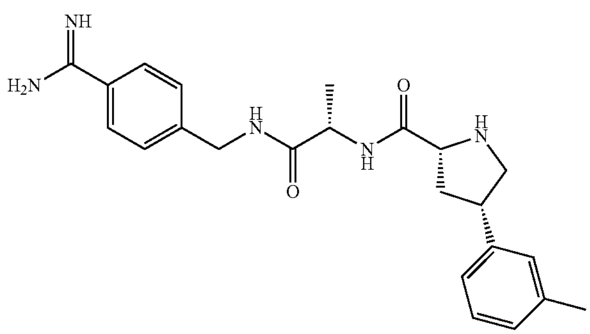 [SMILES: Cc1cccc([C@H]2CN[C@@H](C(=O)N[C@@H](C)C(=O)NCc3ccc(C(=N)N)cc3)C2)c1] | 2HCl | 408.22 | 407.23 |
| 1248 | 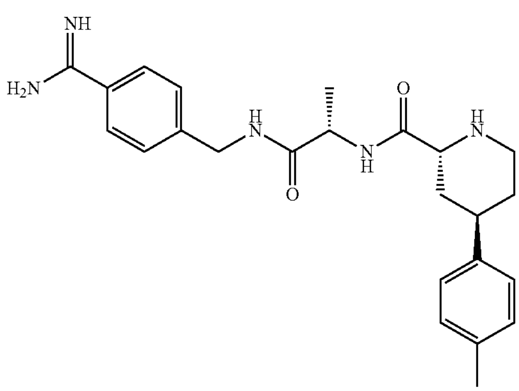 [SMILES: Cc1ccc([C@@H]2CCN[C@@H](C(=O)N[C@@H](C)C(=O)NCc3ccc(C(=N)N)cc3)C2)cc1] | 2 HCl | 422.23 | 421.25 |

TABLE 31-continued

Compound List

| Compound No. | Structure | Salt | Exact Mass (ES+; M + H, Obsd) | Exact Mass (Calc) |
|---|---|---|---|---|
| 1249 | 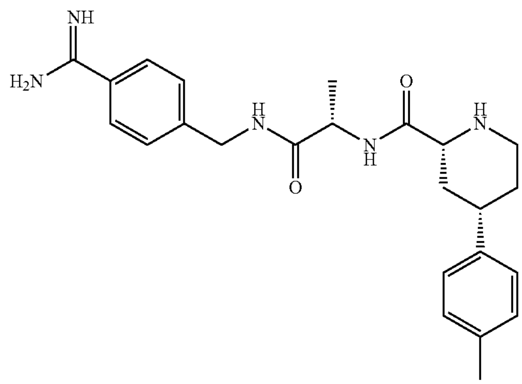 [SMILES: Cc1ccc([C@H]2CCN[C@@H](C(=O)N[C@@H](C)C(=O)NCc3ccc(C(=N)N)cc3)C2)cc1] | 2 HCl | 422.24 | 421.25 |
| 1250 | 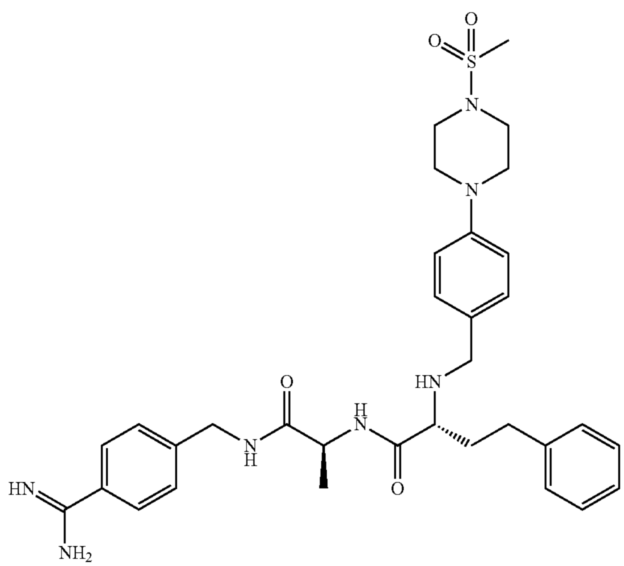 [SMILES: C[C@H](NC(=O)[C@@H](CCc1ccccc1)NCc1ccc(N2CCN(S(C)(=O)=O)CC2)cc1)C(=O)NCc1ccc(C(=N)N)cc1] | 2 TFA | 634.31 | 633.31 |
| 1251 | 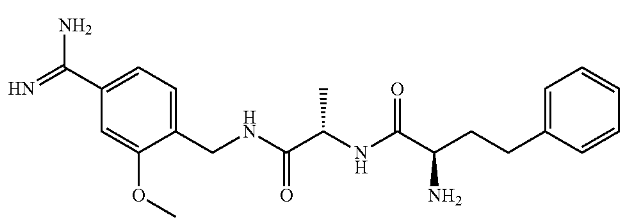 [SMILES: COc1cc(C(=N)N)ccc1CNC(=O)[C@H](C)NC(=O)[C@H](N)CCc1ccccc1] | TFA | 412.22 | 411.23 |
| 1252 | 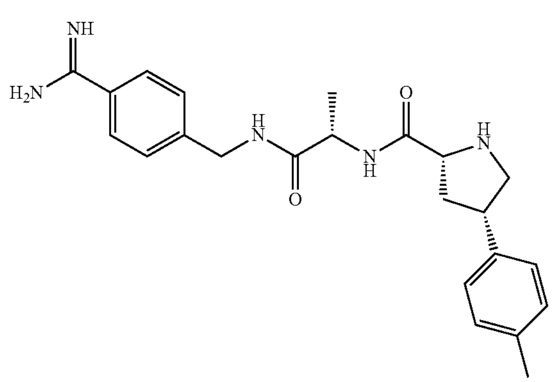 [SMILES: Cc1ccc([C@H]2CN[C@@H](C(=O)N[C@@H](C)C(=O)NCc3ccc(C(=N)N)cc3)C2)cc1] | 2 HCl | 408.24 | 407.23 |

TABLE 31-continued

Compound List

| Compound No. | Structure | Salt | Exact Mass (ES+; M + H, Obsd) | Exact Mass (Calc) |
|---|---|---|---|---|
| 1253 | 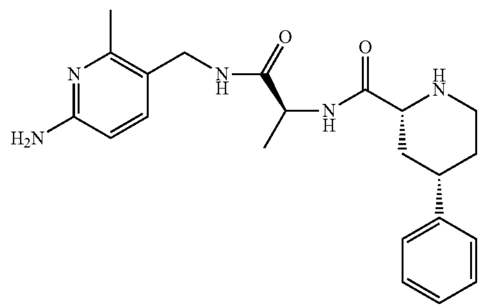 [SMILES: Cc1nc(N)ccc1CNC(=O)[C@H](C)NC(=O)[C@H]1C[C@@H](c2ccccc2)CCN1] | HCl | 396.27 | 395.23 |
| 1254 | 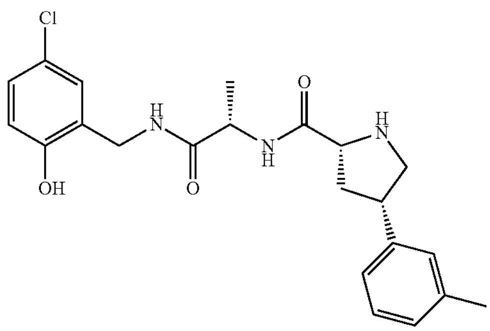 [SMILES: Cc1cccc([C@H]2CN[C@@H](C(=O)N[C@@H](C)C(=O)NCc3cc(Cl)ccc3O)C2)c1] | HCl | 416.16 | 415.17 |
| 1255 | 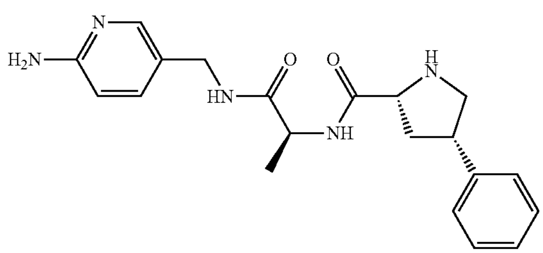 [SMILES: C[C@H](NC(=O)[C@H]1C[C@@H](c2ccccc2)CN1)C(=O)NCc1ccc(N)nc1] | 2HCl | 368.23 | 367.2 |
| 1256 | 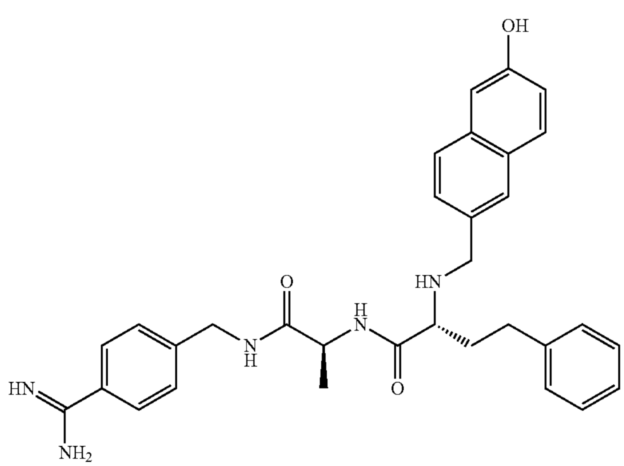 [SMILES: C[C@H](NC(=O)[C@@H](CCc1ccccc1)NCc1ccc2cc(O)ccc2c1)C(=O)NCc1ccc(C(=N)N)cc1] | 2TFA | 538.28 | 537.27 |

TABLE 31-continued

Compound List

| Compound No. | Structure | Salt | Exact Mass (ES+; M + H, Obsd) | Exact Mass (Calc) |
|---|---|---|---|---|
| 1257 | 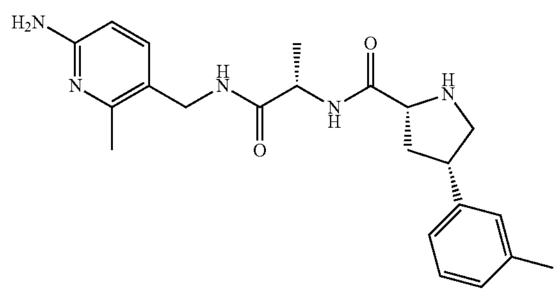 [SMILES: Cc1cccc([C@H]2CN[C@@H](C(=O)N[C@@H](C)C(=O)NCc3ccc(N)nc3C)C2)c1] | 2HCl | 396.26 | 395.23 |
| 1258 | 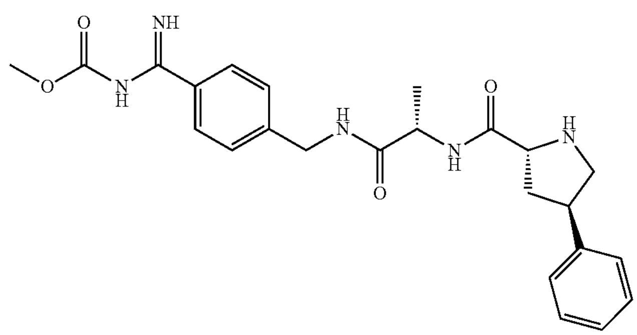 [SMILES: COC(=O)NC(=N)c1ccc(CNC(=O)[C@H](C)NC(=O)[C@H]2C[C@H](c3ccccc3)CN2)cc1] | NA | 452.18 | 451.22 |
| 1259 | 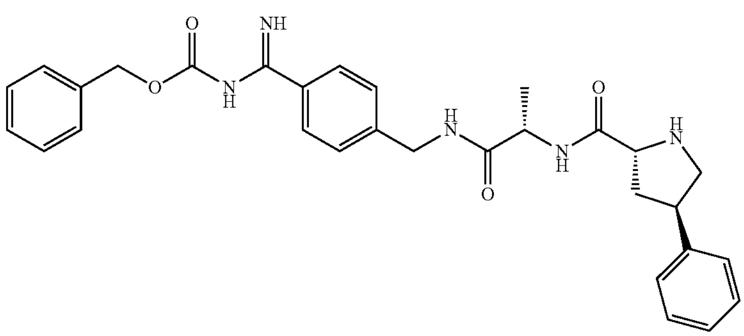 [SMILES: C[C@H](NC(=O)[C@H]1C[C@H](c2ccccc2)CN1)C(=O)NCc1ccc(C(=N)NC(=O)OCc2ccccc2)cc1] | NA | 528.27 | 527.25 |
| 1260 | (n = 3) | NA | 522.32 | 521.3 |

TABLE 31-continued
Compound List
| Compound No. | Structure | Salt | Exact Mass (ES+; M + H, Obsd) | Exact Mass (Calc) |
|---|---|---|---|---|
| 1261 | 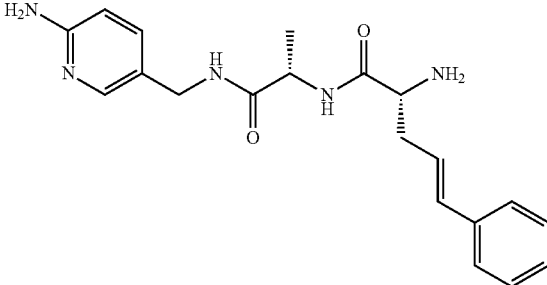 | 2HCl | 368.24 | 367.2 |
| 1262 | 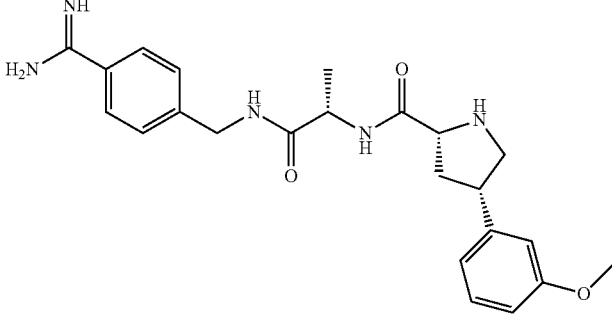 | 2HCl | 424.20 | 423.23 |
| 1263 | 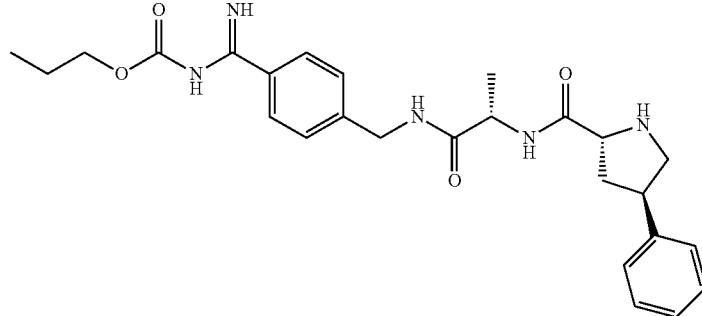 | NA | 480.23 | 479.25 |
| 1264 | 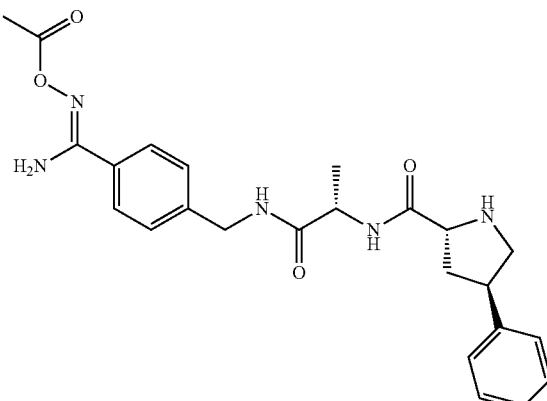 | NA | 452.19 | 451.22 |

TABLE 31-continued

Compound List

| Compound No. | Structure | Salt | Exact Mass (ES+; M + H, Obsd) | Exact Mass (Calc) |
|---|---|---|---|---|
| 1265 | 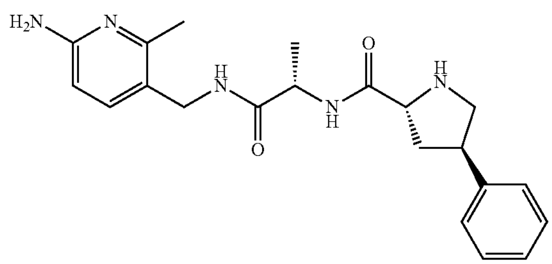 [SMILES: Cc1nc(N)ccc1CNC(=O)[C@H](C)NC(=O)[C@H]1C[C@H](c2ccccc2)CN1] | N/A | 382.25 | 381.22 |
| 1266 | 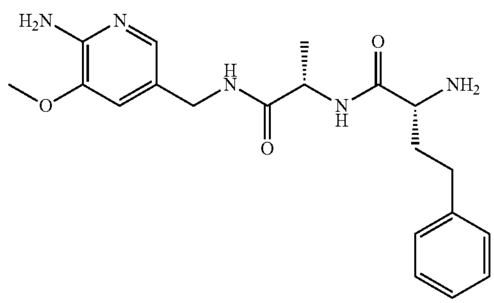 [SMILES: COc1cc(CNC(=O)[C@H](C)NC(=O)[C@H](N)CCc2ccccc2)cnc1N] | 2HCl | 386.22 | 385.21 |
| 1267 | 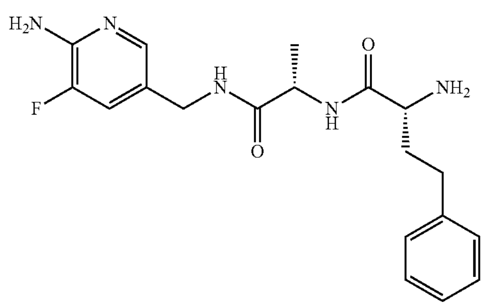 [SMILES: C[C@H](NC(=O)[C@H](N)CCc1ccccc1)C(=O)NCc1cnc(N)c(F)c1] | 2HCl | 374.24 | 373.19 |
| 1268 | 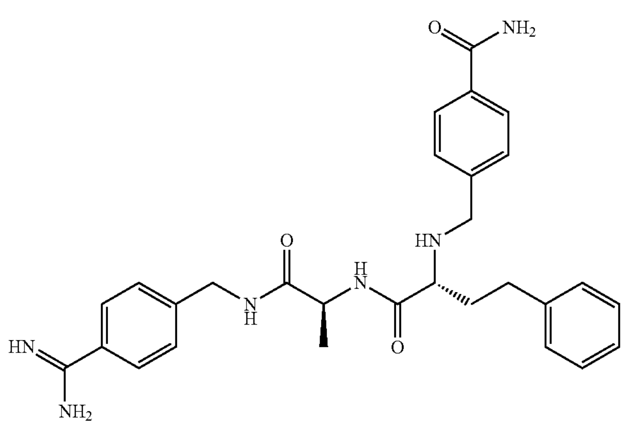 [SMILES: C[C@H](NC(=O)[C@@H](CCc1ccccc1)NCc1ccc(C(N)=O)cc1)C(=O)NCc1ccc(C(=N)N)cc1] | 2TFA | 515.27 | 514.27 |

TABLE 31-continued

Compound List

| Compound No. | Structure | Salt | Exact Mass (ES+; M + H, Obsd) | Exact Mass (Calc) |
|---|---|---|---|---|
| 1269 | 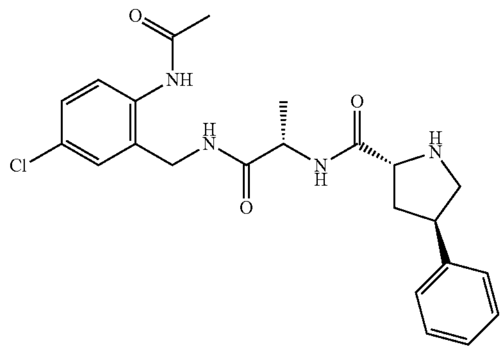 [SMILES: CC(=O)Nc1ccc(Cl)cc1CNC(=O)[C@H](C)NC(=O)[C@H]1C[C@H](c2ccccc2)CN1] | HCl | 443.13 | 442.18 |
| 1270 | 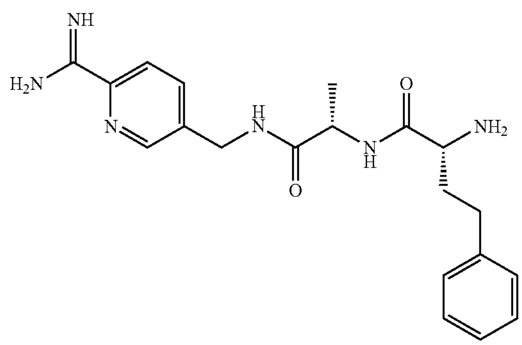 [SMILES: C[C@H](NC(=O)[C@H](N)CCc1ccccc1)C(=O)NCc1ccc(C(=N)N)nc1] | 2 HCl | 383.25 | 382.21 |
| 1271 | 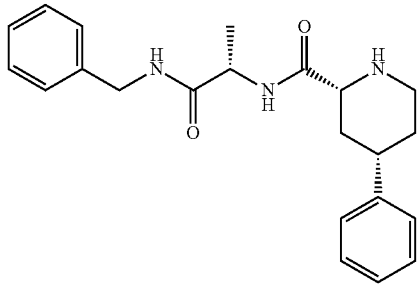 [SMILES: C[C@H](NC(=O)[C@H]1C[C@@H](c2ccccc2)CCN1)C(=O)NCc1ccccc1] | HCl | 366.25 | 365.21 |
| 1272 | 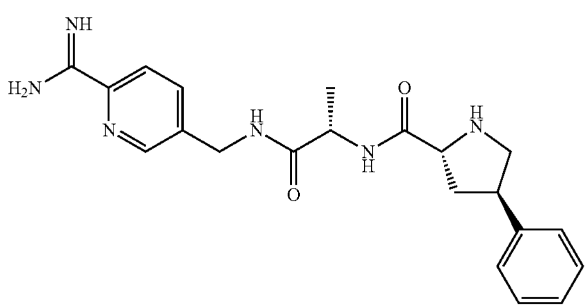 [SMILES: C[C@H](NC(=O)[C@H]1C[C@H](c2ccccc2)CN1)C(=O)NCc1ccc(C(=N)N)nc1] | 2 HCl | 395.22 | 394.21 |

TABLE 31-continued

Compound List

| Compound No. | Structure | Salt | Exact Mass (ES+; M + H, Obsd) | Exact Mass (Calc) |
|---|---|---|---|---|
| 1273 | 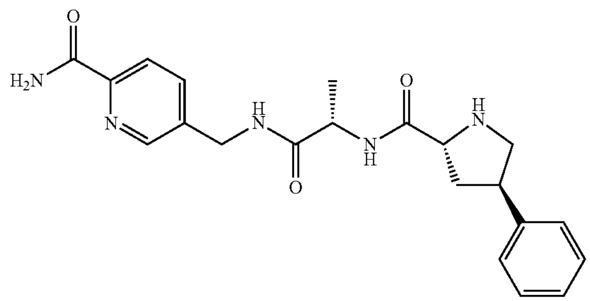 [SMILES: C[C@H](NC(=O)[C@H]1C[C@H](c2ccccc2)CN1)C(=O)NCc1ccc(C(N)=O)nc1] | HCl | 395.2 | 394.21 |
| 1274 | 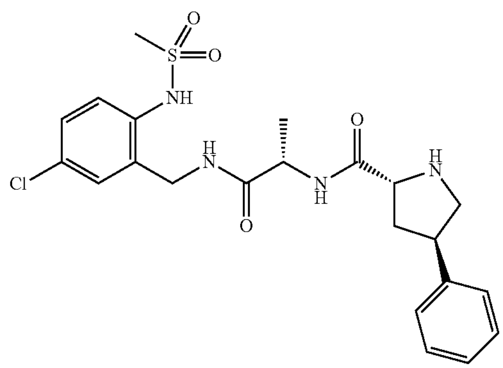 [SMILES: C[C@H](NC(=O)[C@H]1C[C@H](c2ccccc2)CN1)C(=O)NCc1cc(Cl)ccc1NS(C)(=O)=O] | HCl | 479.12 | 478.14 |
| 1275 | 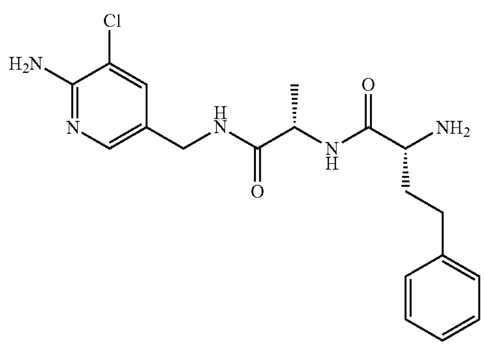 [SMILES: C[C@H](NC(=O)[C@H](N)CCc1ccccc1)C(=O)NCc1cnc(N)c(Cl)c1] | 2HCl | 390.17 | 389.16 |
| 1276 | 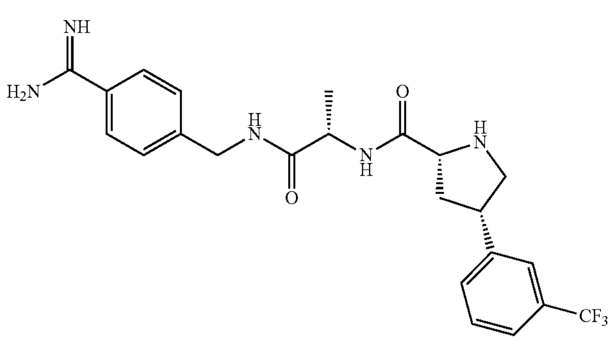 [SMILES: C[C@H](NC(=O)[C@H]1C[C@@H](c2cccc(C(F)(F)F)c2)CN1)C(=O)NCc1ccc(C(=N)N)cc1] | 2HCl | 462.16 | 461.20 |

TABLE 31-continued
Compound List
| Compound No. | Structure | Salt | Exact Mass (ES+; M + H, Obsd) | Exact Mass (Calc) |
|---|---|---|---|---|
| 1277 | 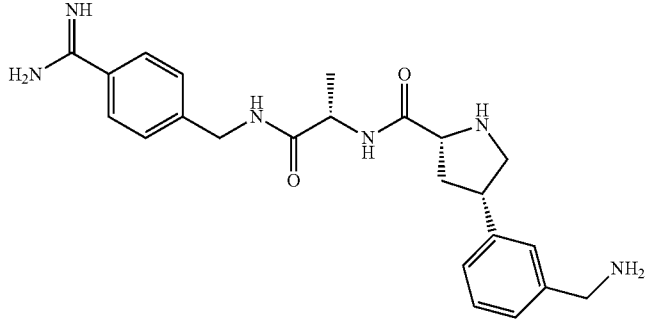 [SMILES: C[C@H](NC(=O)[C@H]1C[C@@H](c2cccc(CN)c2)CN1)C(=O)NCc1ccc(C(=N)N)cc1] | 3HCl | 423.20 | 422.24 |
| 1278 | 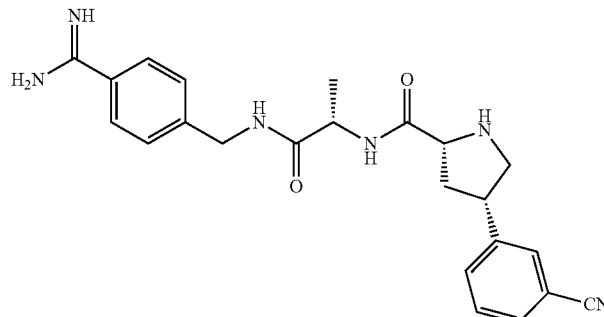 | 2HCl | 419.19 | 418.21 |
| 1279 | 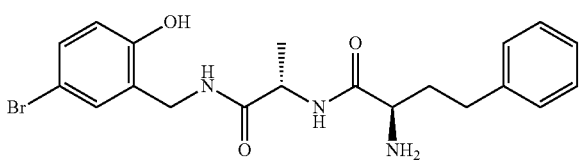 | HCl | 432.05 (ES−) | 433.1 |
| 1280 | 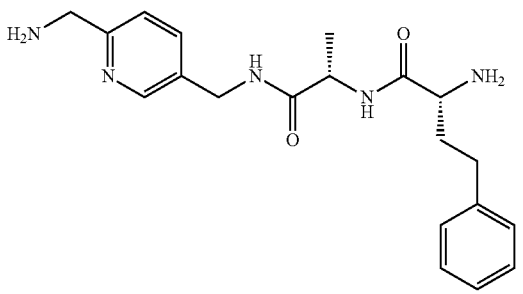 [SMILES: C[C@H](NC(=O)[C@H](N)CCc1ccccc1)C(=O)NCc1ccc(CN)nc1] | 2HCl | 370.23 | 369.22 |
| 1281 | 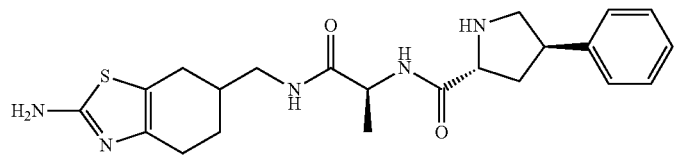 [SMILES: C[C@H](NC(=O)[C@H]1C[C@H](c2ccccc2)CN1)C(=O)NCC1CCc2nc(N)sc2C1] | 2TFA | 428.17 | 427.2 |

TABLE 31-continued

Compound List

| Compound No. | Structure | Salt | Exact Mass (ES+; M + H, Obsd) | Exact Mass (Calc) |
|---|---|---|---|---|
| 1282 | 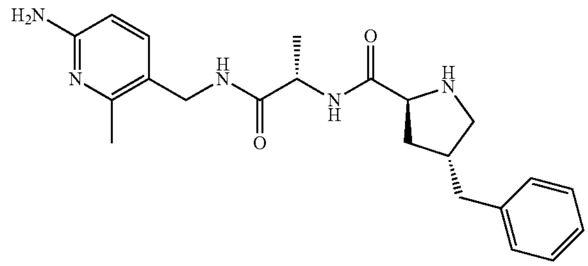 [SMILES: Cc1nc(N)ccc1CNC(=O)[C@H](C)NC(=O)[C@@H]1C[C@@H](Cc2ccccc2)CN1] | 2HCl | 396.27 | 395.23 |
| 1283 | 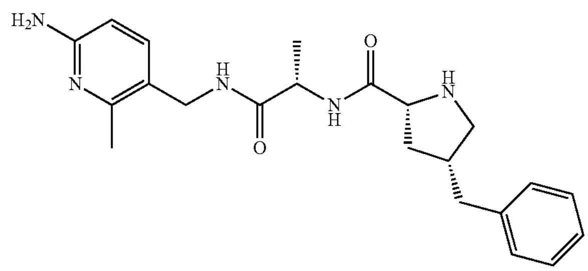 [SMILES: Cc1nc(N)ccc1CNC(=O)[C@H](C)NC(=O)[C@H]1C[C@@H](Cc2ccccc2)CN1] | 2HCl | 396.25 | 395.23 |
| 1284 | 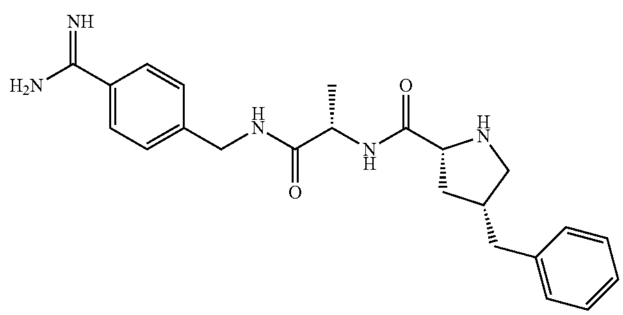 [SMILES: C[C@H](NC(=O)[C@H]1C[C@@H](Cc2ccccc2)CN1)C(=O)NCc1ccc(C(=N)N)cc1] | 2TFA | 408.24 | 407.23 |
| 1285 | 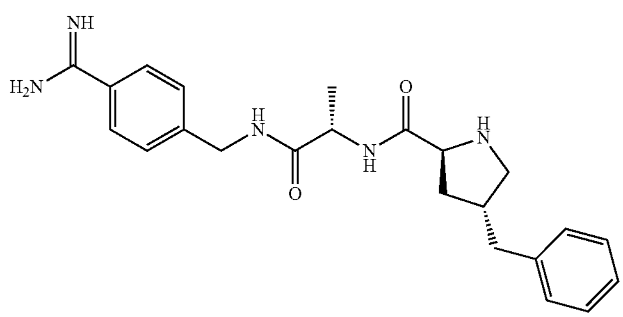 [SMILES: C[C@H](NC(=O)[C@@H]1C[C@@H](Cc2ccccc2)CN1)C(=O)NCc1ccc(C(=N)N)cc1] | 2HCl | 408.23 | 407.23 |
| 1286 | 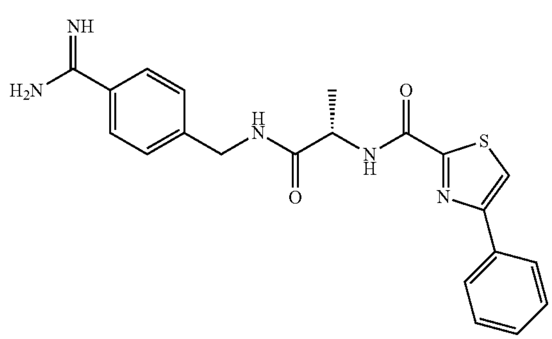 [SMILES: C[C@H](NC(=O)c1nc(-c2ccccc2)cs1)C(=O)NCc1ccc(C(=N)N)cc1] | HCl | 408.14 | 407.14 |

TABLE 31-continued

Compound List

| Compound No. | Structure | Salt | Exact Mass (ES+; M + H, Obsd) | Exact Mass (Calc) |
|---|---|---|---|---|
| 1287 | 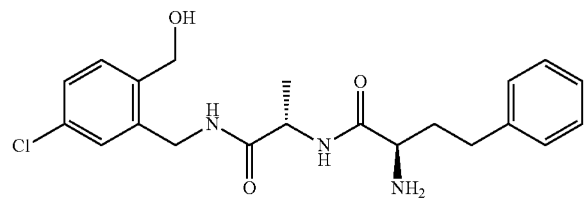 [SMILES: C[C@H](NC(=O)[C@H](N)CCc1ccccc1)C(=O)NCc1cc(Cl)ccc1CO] | HCl | 404.17 | 403.17 |
| 1288 | 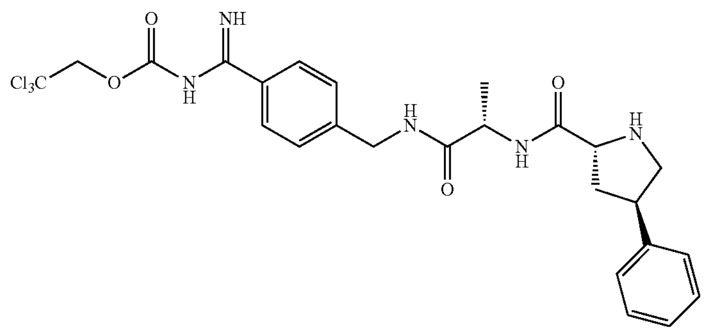 | NA | 568.13 | 567.12 |
| 1289 | 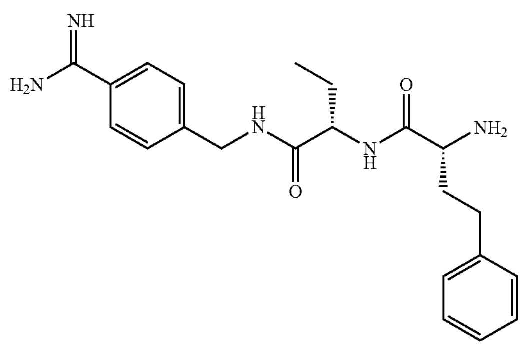 [SMILES: CC[C@H](NC(=O)[C@H](N)CCc1ccccc1)C(=O)NCc1ccc(C(=N)N)cc1] | HCl | 396.24 | 395.23 |
| 1290 | 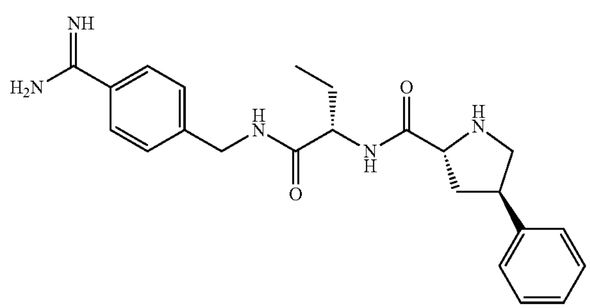 [SMILES: CC[C@H](NC(=O)[C@H]1C[C@H](c2ccccc2)CN1)C(=O)NCc1ccc(C(=N)N)cc1] | HCl | 408.21 | 407.23 |
| 1291 | 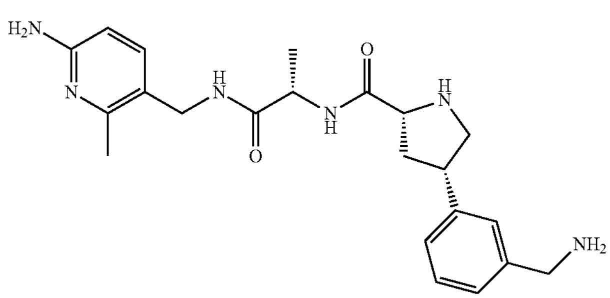 [SMILES: Cc1nc(N)ccc1CNC(=O)[C@H](C)NC(=O)[C@H]1C[C@@H](c2cccc(CN)c2)CN1] | 2HCl | 411.2 | 410.24 |

TABLE 31-continued
Compound List
| Compound No. | Structure | Salt | Exact Mass (ES+; M + H, Obsd) | Exact Mass (Calc) |
|---|---|---|---|---|
| 1292 | 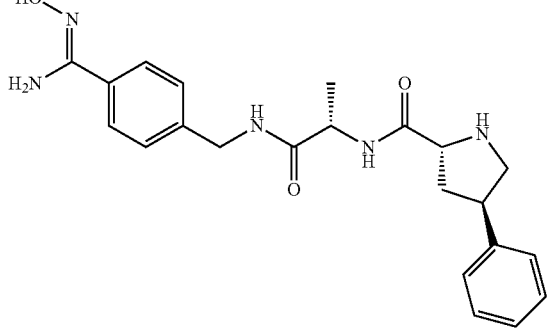 | NA | 410.18 | 409.21 |
| 1293 | 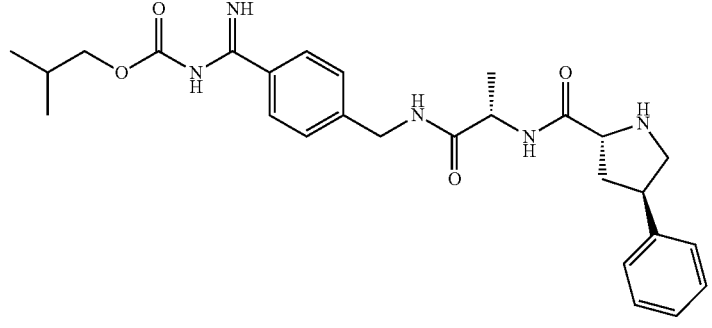 [SMILES: CC(C)COC(=O)NC(=N)c1ccc(CNC(=O)[C@H](C)NC(=O)[C@H]2C[C@H](c3ccccc3)CN2)cc1] | NA | 494.25 | 493.27 |
| 1294 | 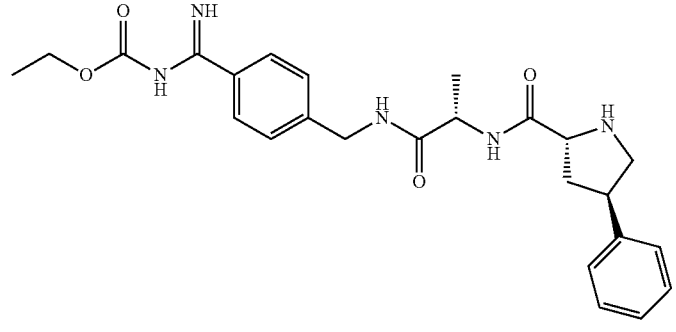 [SMILES: CCOC(=O)NC(=N)c1ccc(CNC(=O)[C@H](C)NC(=O)[C@H]2C[C@H](c3ccccc3)CN2)cc1] | NA | 466.11 | 465.24 |
| 1295 | 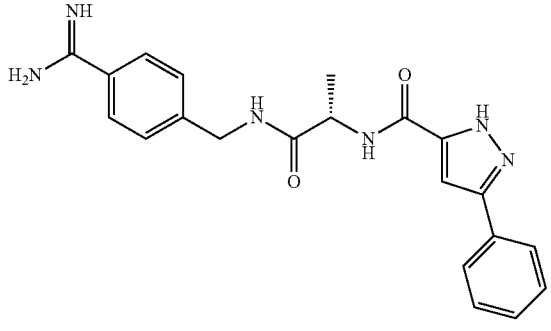 [SMILES: C[C@H](NC(=O)c1cc(-c2ccccc2)n[nH]1)C(=O)NCc1ccc(C(=N)N)cc1] | NA | 391.19 | 390.18 |

TABLE 31-continued

Compound List

| Compound No. | Structure | Salt | Exact Mass (ES+; M + H, Obsd) | Exact Mass (Calc) |
|---|---|---|---|---|
| 1296 | 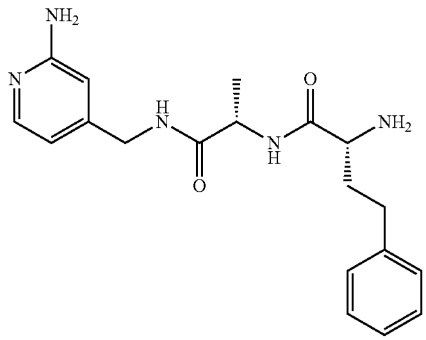 [SMILES: C[C@H](NC(=O)[C@H](N)CCc1ccccc1)C(=O)NCc1ccnc(N)c1] | 2HCl | 356.21 | 355.2 |
| 1297 | 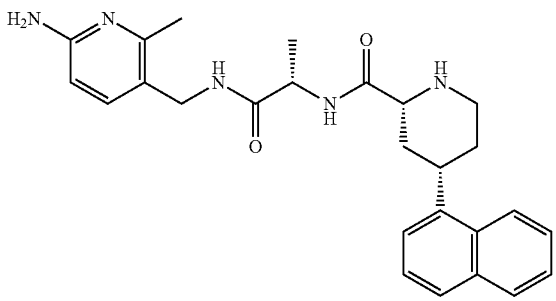 | 2 HCl | 446.1 | 445.25 |
| 1298 | 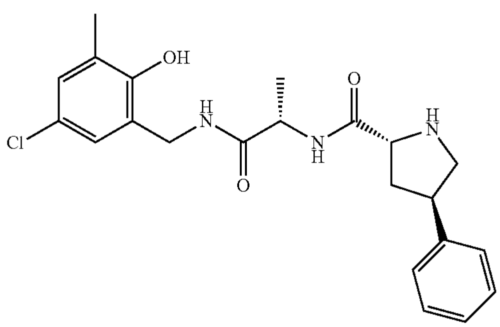 [SMILES: Cc1cc(Cl)cc(CNC(=O)[C@H](C)NC(=O)[C@H]2C[C@H](c3ccccc3)CN2)c1O] | HCl | 416.13 | 415.17 |
| 1299 | 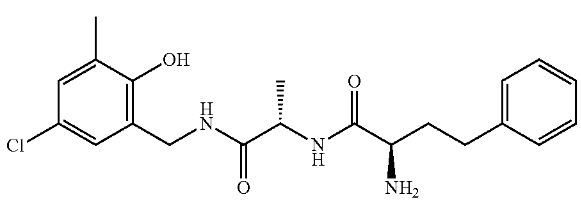 [SMILES: Cc1cc(Cl)cc(CNC(=O)[C@H](C)NC(=O)[C@H](N)CCc2ccccc2)c1O] | HCl | 404.15 | 403.17 |
| 1300 | 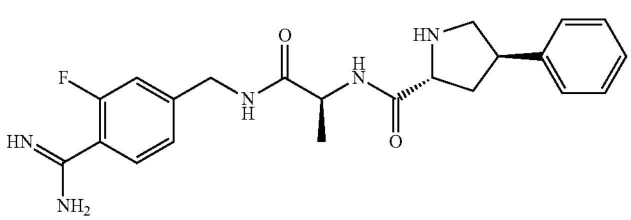 [SMILES: C[C@H](NC(=O)[C@H]1C[C@H](c2ccccc2)CN1)C(=O)NCc1ccc(C(=N)N)c(F)c1] | 2TFA | 412.19 | 411.21 |

TABLE 31-continued

Compound List

| Compound No. | Structure | Salt | Exact Mass (ES+; M + H, Obsd) | Exact Mass (Calc) |
|---|---|---|---|---|
| 1301 | 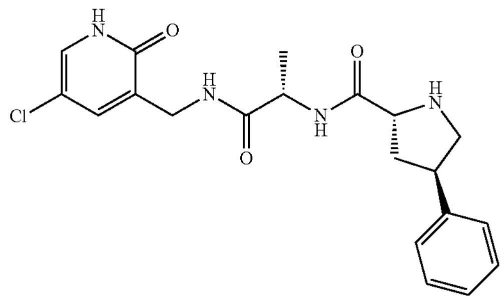 [SMILES: C[C@H](NC(=O)[C@H]1C[C@H](c2ccccc2)CN1)C(=O)NCc1cc(Cl)c[nH]c1=O] | N/A | 403.13 | 402.15 |
| 1302 | 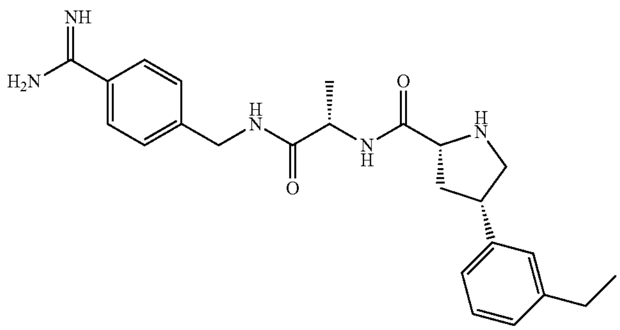 [SMILES: CCc1cccc([C@H]2CN[C@@H](C(=O)N[C@@H](C)C(=O)NCc3ccc(C(=N)N)cc3)C2)c1] | 2HCl | 422.22 | 421.25 |
| 1303 | 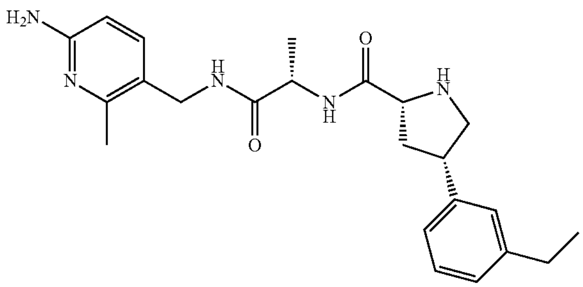 [SMILES: CCc1cccc([C@H]2CN[C@@H](C(=O)N[C@@H](C)C(=O)NCc3ccc(N)nc3C)C2)c1] | 2HCl | 410.21 | 409.25 |
| 1304 | 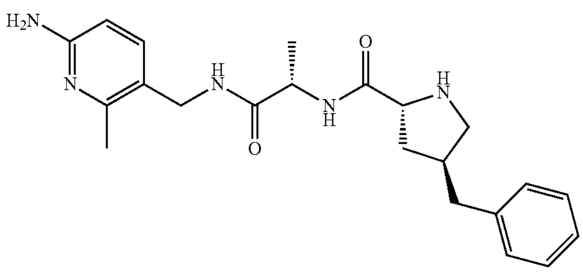 [SMILES: Cc1nc(N)ccc1CNC(=O)[C@H](C)NC(=O)[C@H]1C[C@H](Cc2ccccc2)CN1] | 2HCl | 396.24 | 395.23 |
| 1305 | 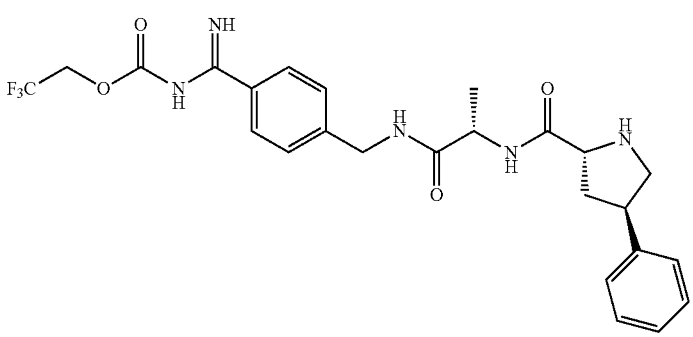 [SMILES: C[C@H](NC(=O)[C@H]1C[C@H](c2ccccc2)CN1)C(=O)NCc1ccc(C(=N)NC(=O)OCC(F)(F)F)cc1] | NA | 520.19 | 519.21 |

TABLE 31-continued

Compound List

| Compound No. | Structure | Salt | Exact Mass (ES+; M + H, Obsd) | Exact Mass (Calc) |
|---|---|---|---|---|
| 1306 | 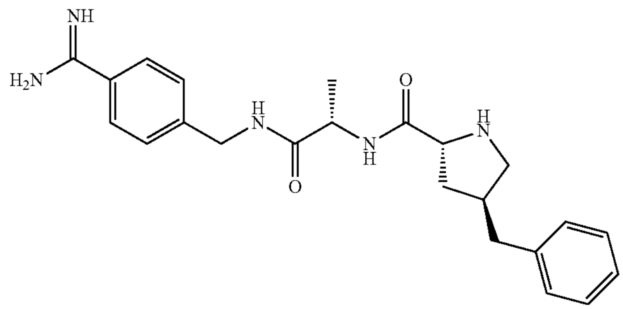 [SMILES: C[C@H](NC(=O)[C@H]1C[C@H](Cc2ccccc2)CN1)C(=O)NCc1ccc(C(=N)N)cc1] | 2HCl | 408.21 | 407.23 |
| 1307 | 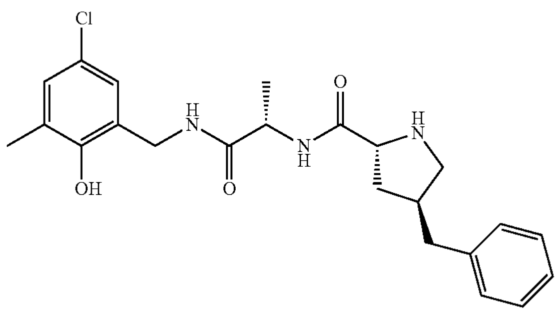 [SMILES: Cc1cc(Cl)cc(CNC(=O)[C@H](C)NC(=O)[C@H]2C[C@H](Cc3ccccc3)CN2)c1O] | HCl | 430.12 | 429.18 |
| 1308 | 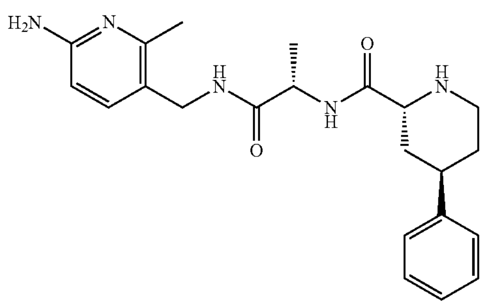 [SMILES: Cc1nc(N)ccc1CNC(=O)[C@H](C)NC(=O)[C@H]1C[C@H](c2ccccc2)CCN1] | 2 HCl | 396.22 | 395.23 |
| 1309 | 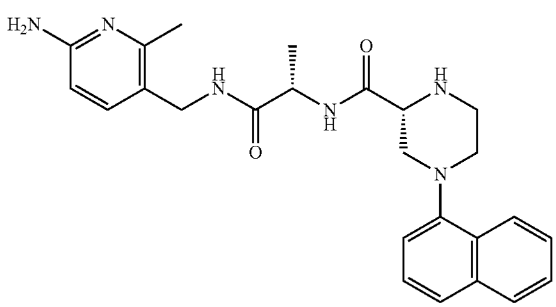 [SMILES: Cc1nc(N)ccc1CNC(=O)[C@H](C)NC(=O)[C@H]1CN(c2cccc3ccccc23)CCN1] | 2 HCl | 447.13 | 446.24 |
| 1310 | 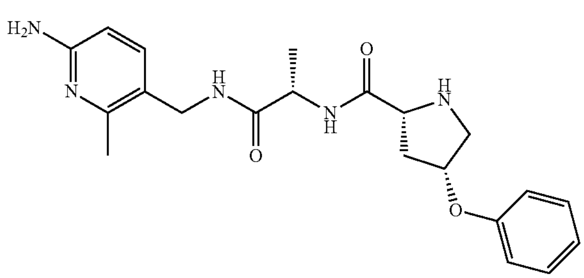 [SMILES: Cc1nc(N)ccc1CNC(=O)[C@H](C)NC(=O)[C@H]1C[C@@H](Oc2ccccc2)CN1] | 2HCl | 398.19 | 397.21 |

TABLE 31-continued

Compound List

| Compound No. | Structure | Salt | Exact Mass (ES+; M + H, Obsd) | Exact Mass (Calc) |
|---|---|---|---|---|
| 1311 | 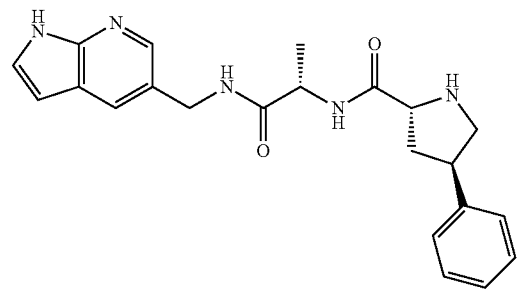 [SMILES: C[C@H](NC(=O)[C@H]1C[C@H](c2ccccc2)CN1)C(=O)NCc1cnc2[nH]ccc2c1] | 2HCl | 392.2 | 391.2 |
| 1312 | 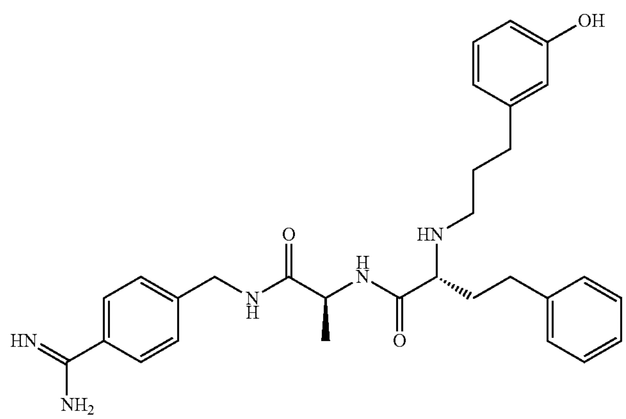 [SMILES: C[C@H](NC(=O)[C@@H](CCc1ccccc1)NCCCc1cccc(O)c1)C(=O)NCc1ccc(C(=N)N)cc1] | 2TFA | 516.24 | 515.29 |
| 1313 | 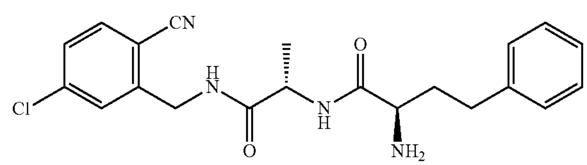 [SMILES: C[C@H](NC(=O)[C@H](N)CCc1ccccc1)C(=O)NCc1cc(Cl)ccc1C#N] | TFA | 399.13 | 398.15 |
| 1314 | 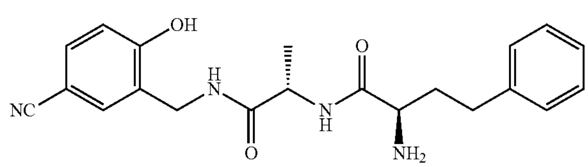 [SMILES: C[C@H](NC(=O)[C@H](N)CCc1ccccc1)C(=O)NCc1cc(C#N)ccc1O] | TFA | 379.11 (ES−) | 380.18 |
| 1315 | 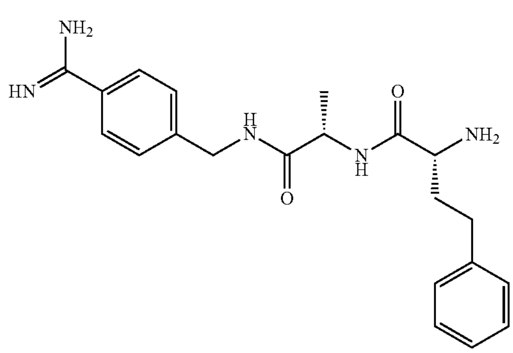 [SMILES: C[C@H](NC(=O)[C@H](N)CCc1ccccc1)C(=O)NCc1ccc(C(=N)N)cc1] | HCl | 383.19 | 382.2 |

TABLE 31-continued

Compound List

| Compound No. | Structure | Salt | Exact Mass (ES+; M + H, Obsd) | Exact Mass (Calc) |
|---|---|---|---|---|
| 1316 | 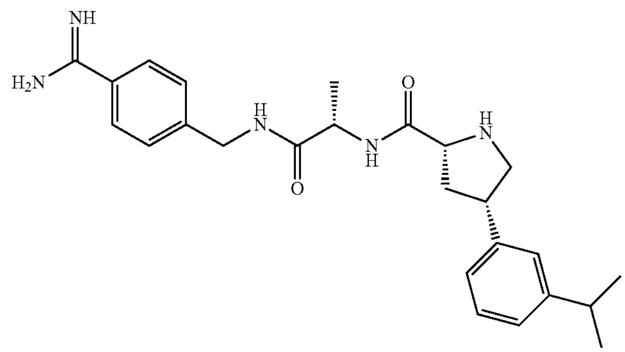 [SMILES: CC(C)c1cccc([C@H]2CN[C@@H](C(=O)N[C@@H](C)C(=O)NCc3ccc(C(=N)N)cc3)C2)c1] | 2HCl | 436.19 | 435.26 |
| 1317 | 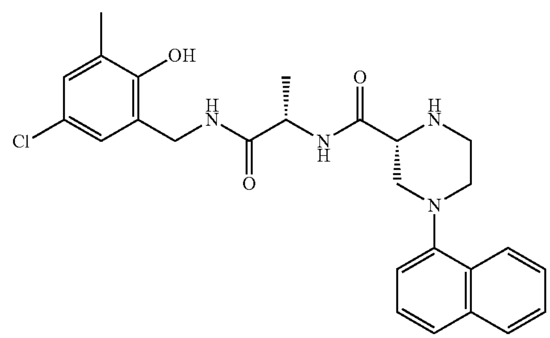 [SMILES: Cc1cc(Cl)cc(CNC(=O)[C@H](C)NC(=O)[C@H]2CN(c3cccc4ccccc34)CCN2)c1O] | HCl | 481.06 | 480.19 |
| 1318 | 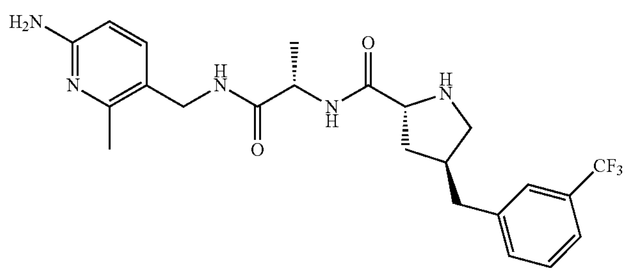 [SMILES: Cc1nc(N)ccc1CNC(=O)[C@H](C)NC(=O)[C@H]1C[C@H](Cc2cccc(C(F)(F)F)c2)CN1] | 2HCl | 464.12 | 463.22 |
| 1319 | 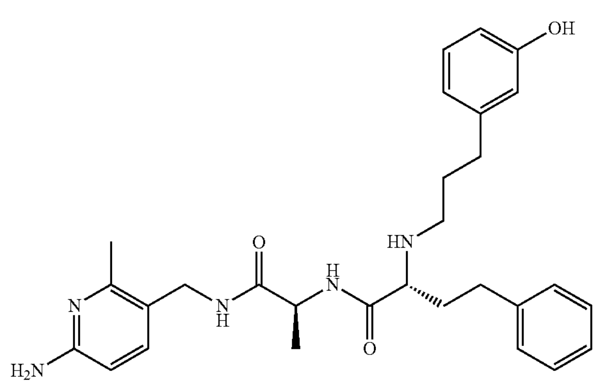 [SMILES: Cc1nc(N)ccc1CNC(=O)[C@H](C)NC(=O)[C@@H](CCc1ccccc1)NCCCc1cccc(O)c1] | 2HCl | 504.24 | 503.29 |

TABLE 31-continued

Compound List

| Compound No. | Structure | Salt | Exact Mass (ES+; M + H, Obsd) | Exact Mass (Calc) |
|---|---|---|---|---|
| 1320 | 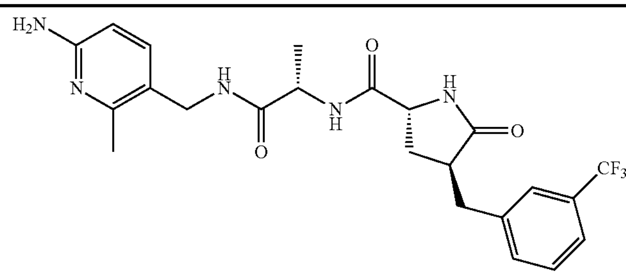 | 2TFA | 478.09 | 477.2 |
| 1321 | 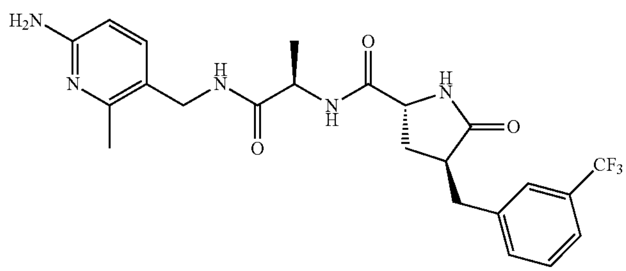 [SMILES: Cc1nc(N)ccc1CNC(=O)[C@@H](C)NC(=O)[C@H]1C[C@H](Cc2cccc(C(F)(F)F)c2)C(=O)N1] | 2TFA | 478.14 | 477.2 |
| 1322 | 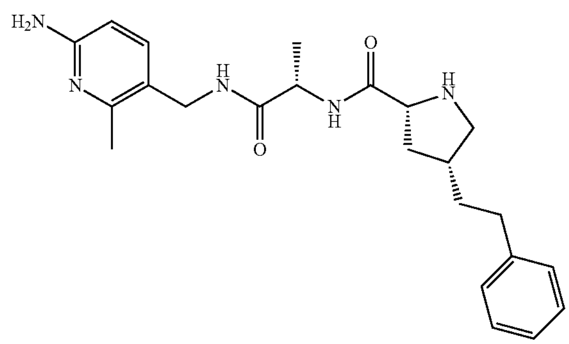 [SMILES: Cc1nc(N)ccc1CNC(=O)[C@H](C)NC(=O)[C@H]1C[C@@H](CCc2ccccc2)CN1] | 2HCl | 410.2 | 409.25 |
| 1323 | 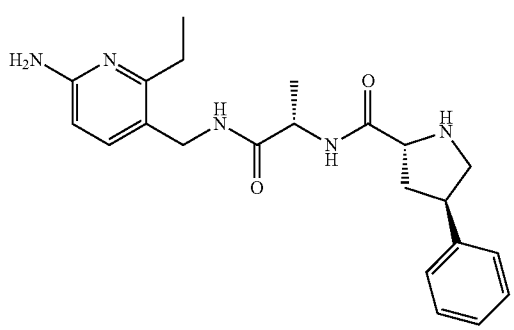 [SMILES: CCc1nc(N)ccc1CNC(=O)[C@H](C)NC(=O)[C@H]1C[C@H](c2ccccc2)CN1] | 2HCl | 396.2 | 395.23 |
| 1324 | 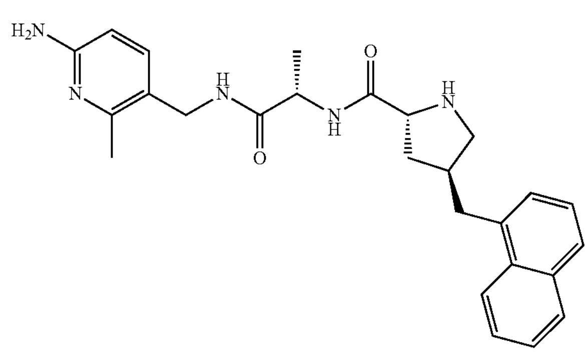 [SMILES: Cc1nc(N)ccc1CNC(=O)[C@H](C)NC(=O)[C@H]1C[C@H](Cc2cccc3ccccc23)CN1] | 2TFA | 446.16 | 445.25 |

TABLE 31-continued
Compound List
| Compound No. | Structure | Salt | Exact Mass (ES+; M + H, Obsd) | Exact Mass (Calc) |
|---|---|---|---|---|
| 1325 | 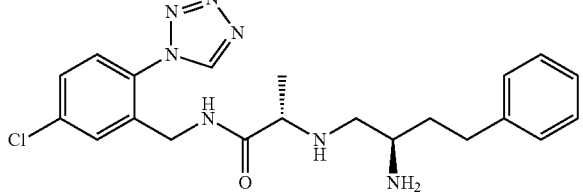 | TFA | 442.01 | 441.17 |
| 1326 | 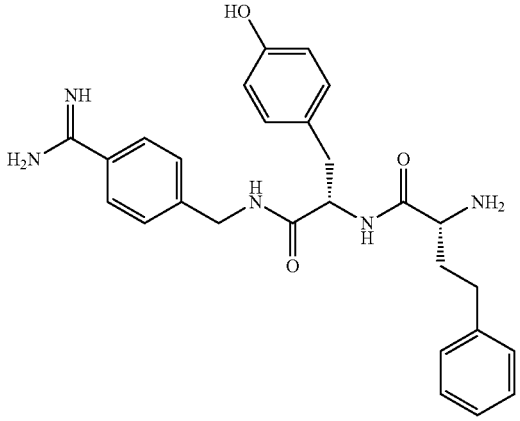 [SMILES: N=C(N)c1ccc(CNC(=O)[C@H](Cc2ccc(O)cc2)NC(=O)[C@H](N)CCc2ccccc2)cc1] | 2TFA | 474.09 | 473.24 |
| 1327 | 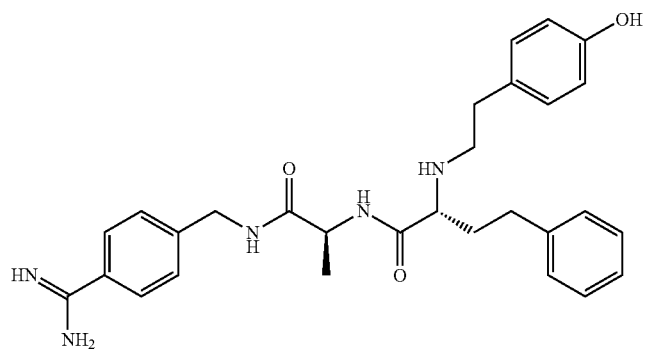 [SMILES: C[C@H](NC(=O)[C@@H](CCc1ccccc1)NCCc1ccc(O)cc1)C(=O)NCc1ccc(C(=N)N)cc1] | 2HCl | 502.19 | 501.27 |
| 1328 | 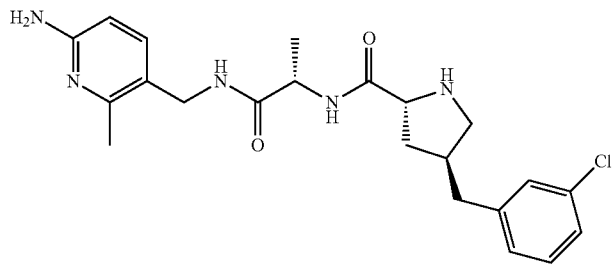 [SMILES: Cc1nc(N)ccc1CNC(=O)[C@H](C)NC(=O)[C@H]1C[C@H](Cc2cccc(Cl)c2)CN1] | 2HCl | 430.12 | 429.19 |

TABLE 31-continued

Compound List

| Compound No. | Structure | Salt | Exact Mass (ES+; M + H, Obsd) | Exact Mass (Calc) |
|---|---|---|---|---|
| 1329 | 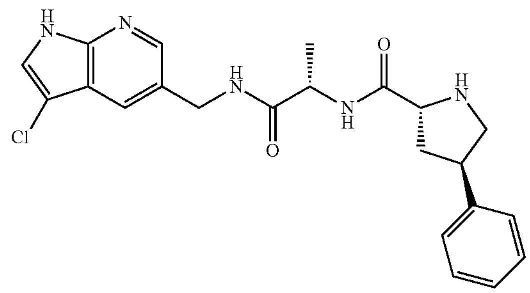 [SMILES: C[C@H](NC(=O)[C@H]1C[C@H](c2ccccc2)CN1)C(=O)NCc1cnc2[nH]cc(Cl)c2c1] | 2HCl | 426.07 | 425.16 |
| 1330 | 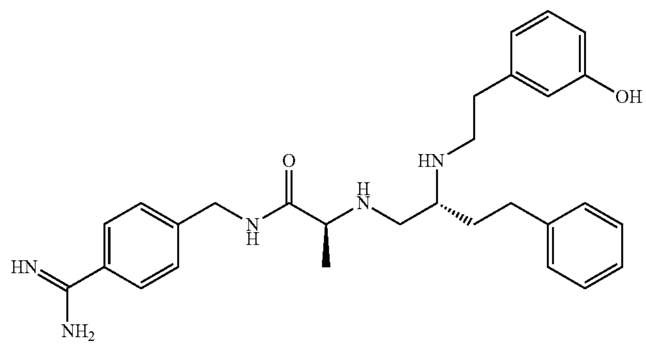 [SMILES: C[C@H](NC[C@@H](CCc1ccccc1)NCCc1cccc(O)c1)C(=O)NCc1ccc(C(=N)N)cc1] | 2TFA | 502.21 | 501.27 |
| 1331 | 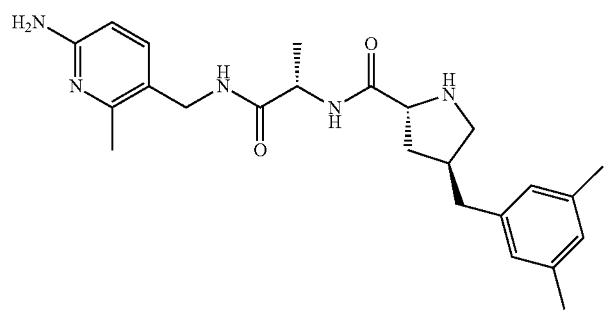 [SMILES: Cc1cc(C)cc(C[C@@H]2CN[C@@H](C(=O)N[C@@H](C)C(=O)NCc3ccc(N)nc3C)C2)c1] | 2HCl | 424.18 | 423.26 |
| 1332 | 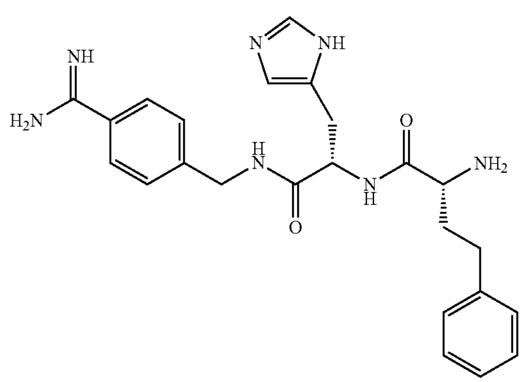 [SMILES: N=C(N)c1ccc(CNC(=O)[C@H](Cc2cnc[nH]2)NC(=O)[C@H](N)CCc2ccccc2)cc1] | 2TFA | 448.1 | 447.24 |

TABLE 31-continued

Compound List

| Compound No. | Structure | Salt | Exact Mass (ES+; M + H, Obsd) | Exact Mass (Calc) |
|---|---|---|---|---|
| 1333 | 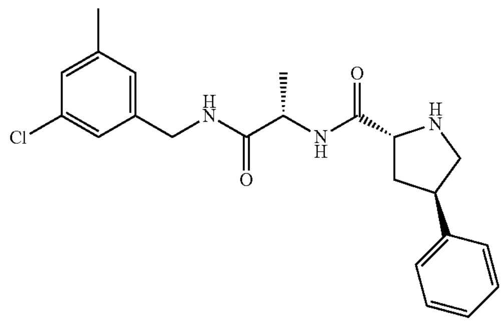 [SMILES: Cc1cc(Cl)cc(CNC(=O)[C@H](C)NC(=O)[C@H]2C[C@H](c3ccccc3)CN2)c1] | HCl | 400.12 | 399.17 |
| 1334 | 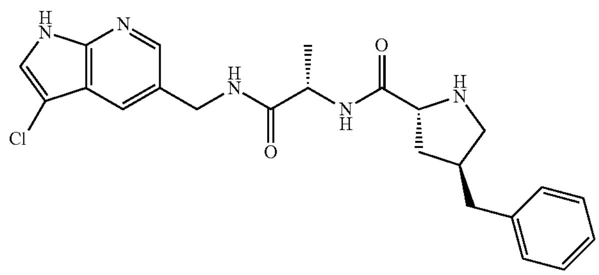 [SMILES: C[C@H](NC(=O)[C@H]1C[C@H](Cc2ccccc2)CN1)C(=O)NCc1cnc2[nH]cc(Cl)c2c1] | 2HCl | 440.04 | 439.18 |
| 1335 | 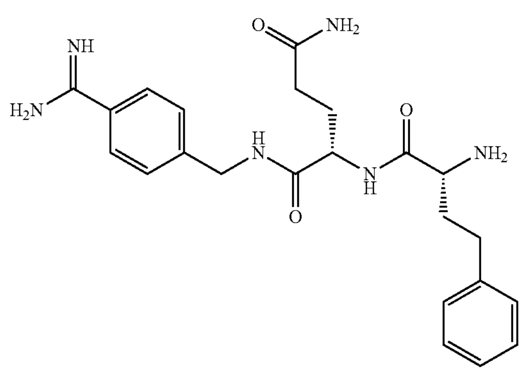 [SMILES: N=C(N)c1ccc(CNC(=O)[C@H](CCC(N)=O)NC(=O)[C@H](N)CCc2ccccc2)cc1] | 2TFA | 439.15 | 438.24 |
| 1336 | 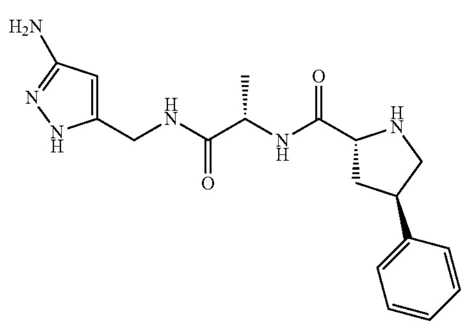 [SMILES: C[C@H](NC(=O)[C@H]1C[C@H](c2ccccc2)CN1)C(=O)NCc1cc(N)n[nH]1] | 2HCl | 357.16 | 356.2 |

TABLE 31-continued

Compound List

| Compound No. | Structure | Salt | Exact Mass (ES+; M + H, Obsd) | Exact Mass (Calc) |
|---|---|---|---|---|
| 1337 | 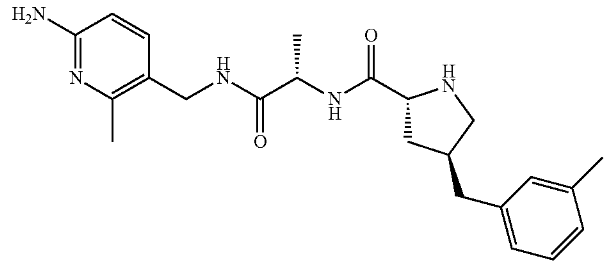 [SMILES: Cc1cccc(C[C@@H]2CN[C@@H](C(=O)N[C@@H](C)C(=O)NCc3ccc(N)nc3C)C2)c1] | 2HCl | 410.15 | 409.25 |
| 1338 | 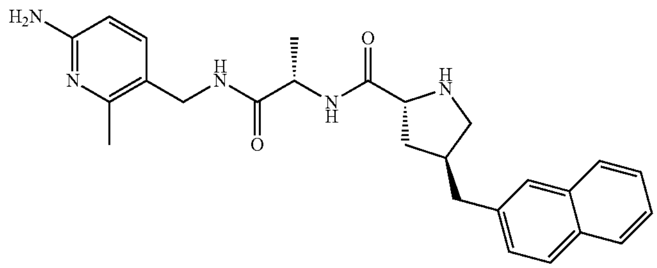 [SMILES: Cc1nc(N)ccc1CNC(=O)[C@H](C)NC(=O)[C@H]1C[C@H](Cc2ccc3ccccc3c2)CN1] | 2HCl | 446.1 | 445.25 |
| 1339 | 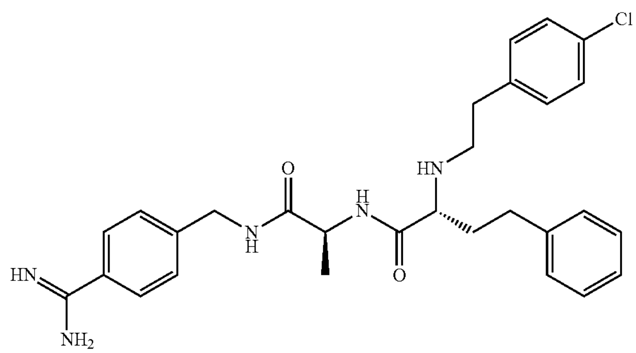 [SMILES: C[C@H](NC(=O)[C@@H](CCc1ccccc1)NCCc1ccc(Cl)cc1)C(=O)NCc1ccc(C(=N)N)cc1] | 2TFA | 520.17 | 519.24 |
| 1340 | 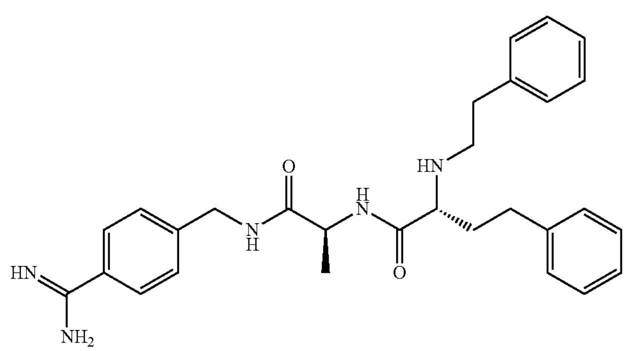 [SMILES: C[C@H](NC(=O)[C@@H](CCc1ccccc1)NCCc1ccccc1)C(=O)NCc1ccc(C(=N)N)cc1] | 2HCl | 486.21 | 485.28 |
| 1341 | 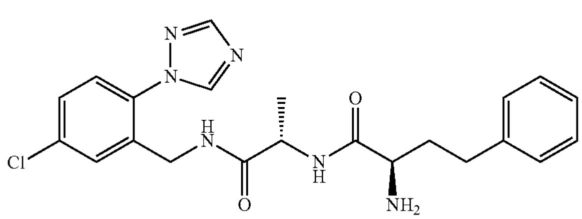 [SMILES: C[C@H](NC(=O)[C@H](N)CCc1ccccc1)C(=O)NCc1cc(Cl)ccc1-n1cncn1] | TFA | 441.1 | 440.17 |

TABLE 31-continued

Compound List

| Compound No. | Structure | Salt | Exact Mass (ES+; M + H, Obsd) | Exact Mass (Calc) |
|---|---|---|---|---|
| 1342 | 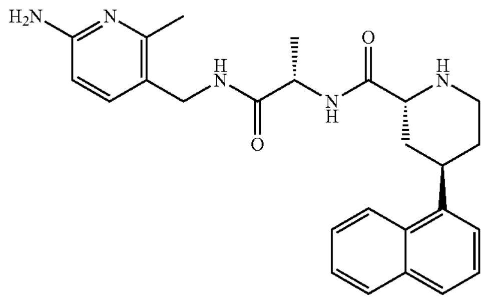 [SMILES: Cc1nc(N)ccc1CNC(=O)[C@H](C)NC(=O)[C@H]1C[C@H](c2cccc3ccccc23)CCN1] | 2 HCl | 446.07 | 445.25 |
| 1343 | 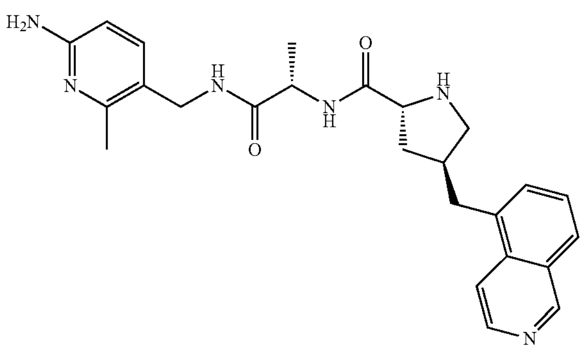 [SMILES: Cc1nc(N)ccc1CNC(=O)[C@H](C)NC(=O)[C@H]1C[C@H](Cc2cccc3cnccc23)CN1] | 2TFA | 447.12 | 446.24 |
| 1344 | 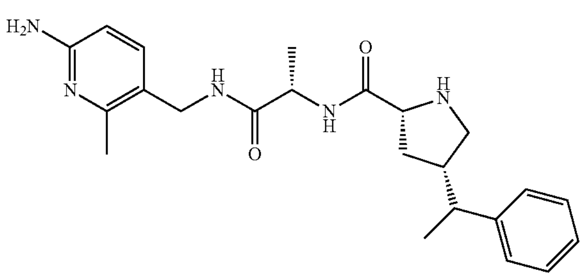 [SMILES: Cc1nc(N)ccc1CNC(=O)[C@H](C)NC(=O)[C@H]1C[C@@H](C(C)c2ccccc2)CN1] | 2HCl | 410.17 | 409.25 |
| 1345 | 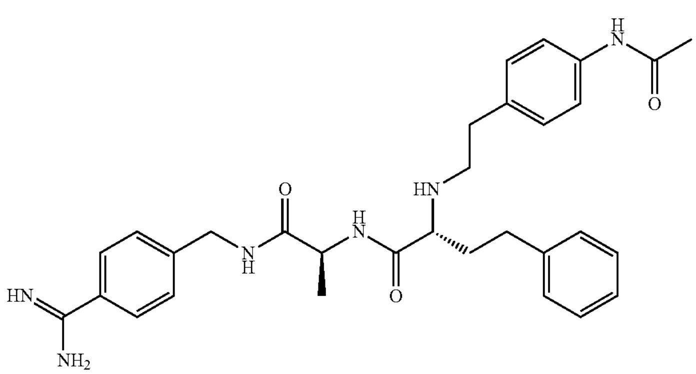 [SMILES: CC(=O)Nc1ccc(CCN[C@H](CCc2ccccc2)C(=O)N[C@@H](C)C(=O)NCc2ccc(C(=N)N)cc2)cc1] | 2HCl | 543.23 | 542.3 |

TABLE 31-continued

Compound List

| Compound No. | Structure | Salt | Exact Mass (ES+; M + H, Obsd) | Exact Mass (Calc) |
|---|---|---|---|---|
| 1346 | 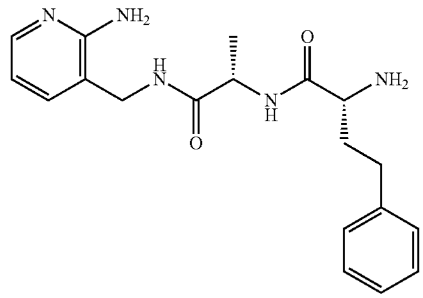 [SMILES: C[C@H](NC(=O)[C@H](N)CCc1ccccc1)C(=O)NCc1cccnc1N] | 2HCl | 356.18 | 355.2 |
| 1347 | 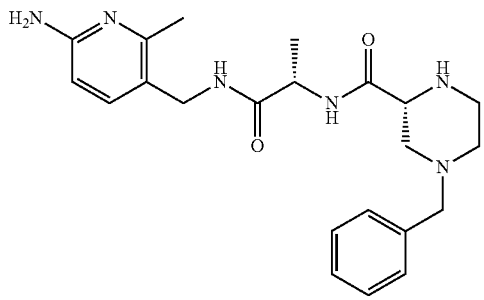 [SMILES: Cc1nc(N)ccc1CNC(=O)[C@H](C)NC(=O)[C@H]1CN(Cc2ccccc2)CCN1] | 2 HCl | 411.17 | 410.24 |
| 1348 | 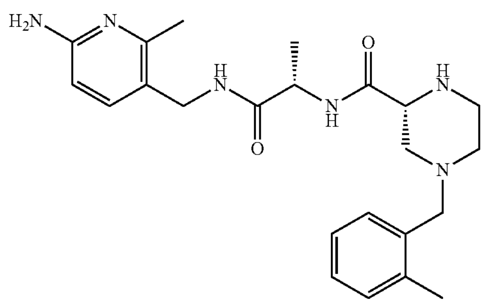 [SMILES: Cc1ccccc1CN1CCN[C@@H](C(=O)N[C@@H](C)C(=O)NCc2ccc(N)nc2C)C1] | 2 HCl | 425.18 | 424.26 |
| 1349 | 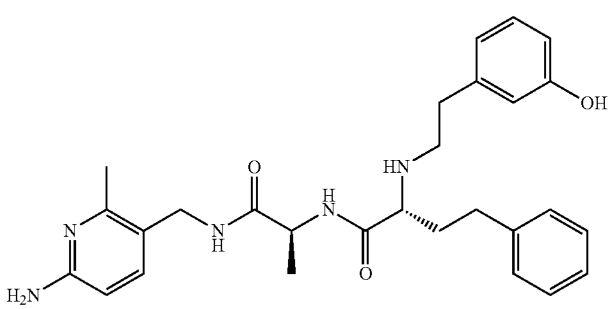 [SMILES: Cc1nc(N)ccc1CNC(=O)[C@H](C)NC(=O)[C@@H](CCc1ccccc1)NCCc1cccc(O)c1] | 2HCl | 489.27 | 490.14 |
| 1350 | 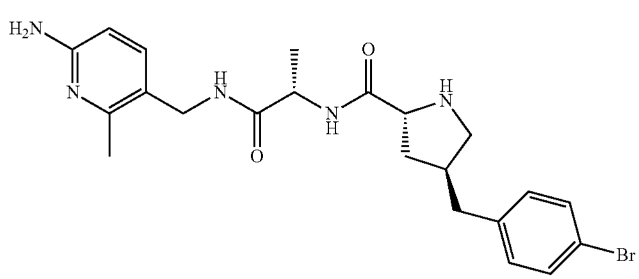 [SMILES: Cc1nc(N)ccc1CNC(=O)[C@H](C)NC(=O)[C@H]1C[C@H](Cc2ccc(Br)cc2)CN1] | 2HCl | 474.02 | 473.14 |

TABLE 31-continued

Compound List

| Compound No. | Structure | Salt | Exact Mass (ES+; M + H, Obsd) | Exact Mass (Calc) |
|---|---|---|---|---|
| 1351 | 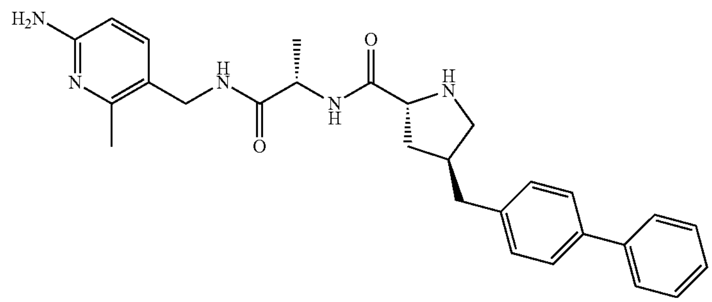 [SMILES: Cc1nc(N)ccc1CNC(=O)[C@H](C)NC(=O)[C@H]1C[C@H](Cc2ccc(-c3ccccc3)cc2)CN1] | 2HCl | 472.12 | 471.26 |
| 1352 | 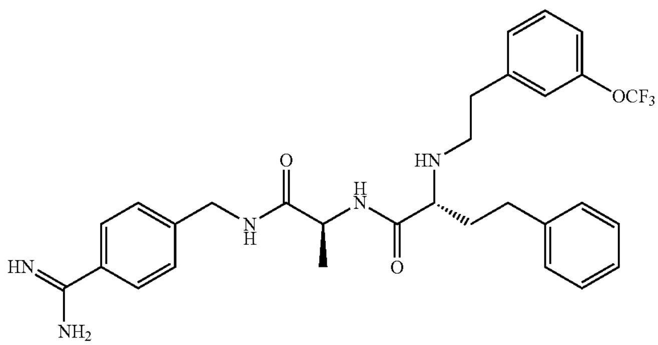 [SMILES: C[C@H](NC(=O)[C@@H](CCc1ccccc1)NCCc1cccc(OC(F)(F)F)c1)C(=O)NCc1ccc(C(=N)N)cc1] | 2TFA | 570.21 | 569.26 |
| 1353 | 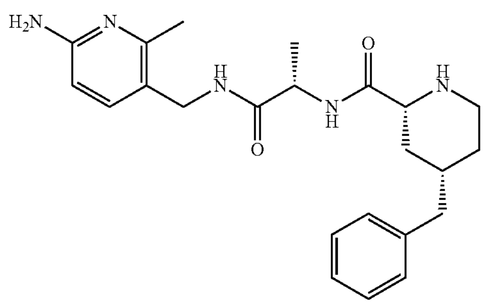 [SMILES: Cc1nc(N)ccc1CNC(=O)[C@H](C)NC(=O)[C@H]1C[C@@H](Cc2ccccc2)CCN1] | 2 HCl | 410.17 | 409.25 |
| 1354 | 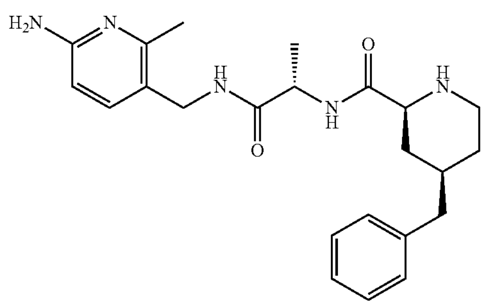 [SMILES: Cc1nc(N)ccc1CNC(=O)[C@H](C)NC(=O)[C@@H]1C[C@H](Cc2ccccc2)CCN1] | 2 HCl | 410.24 | 409.25 |
| 1355 | 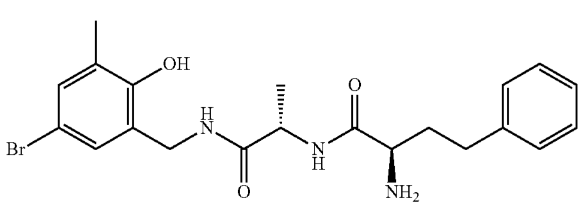 | TFA | 448.03 | 447.12 |

TABLE 31-continued

Compound List

| Compound No. | Structure | Salt | Exact Mass (ES+; M + H, Obsd) | Exact Mass (Calc) |
|---|---|---|---|---|
| 1356 | 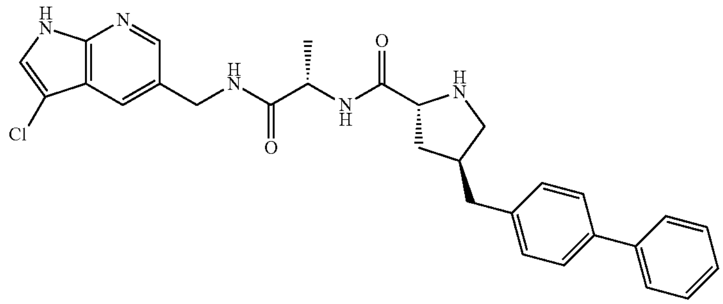 [SMILES: C[C@H](NC(=O)[C@H]1C[C@H](Cc2ccc(-c3ccccc3)cc2)CN1)C(=O)NCc1cnc2[nH]cc(Cl)c2c1] | TFA | 516.16 | 515.21 |
| 1357 | 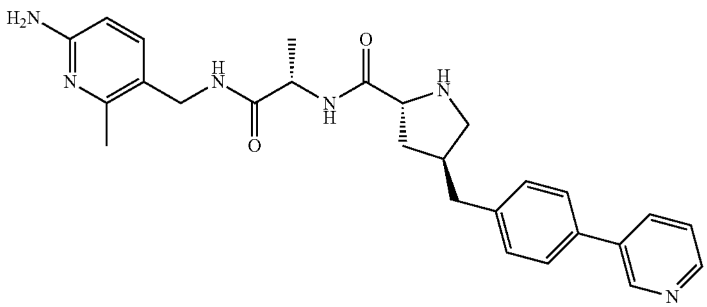 [SMILES: Cc1nc(N)ccc1CNC(=O)[C@H](C)NC(=O)[C@H]1C[C@H](Cc2ccc(-c3cccnc3)cc2)CN1] | 2TFA | 473.13 | 472.26 |
| 1358 | 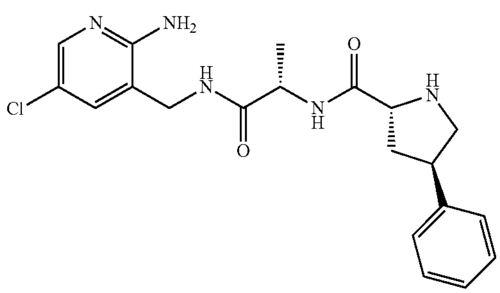 [SMILES: C[C@H](NC(=O)[C@H]1C[C@H](c2ccccc2)CN1)C(=O)NCc1cc(Cl)cnc1N] | 2TFA | 402.1 | 401.16 |
| 1359 | 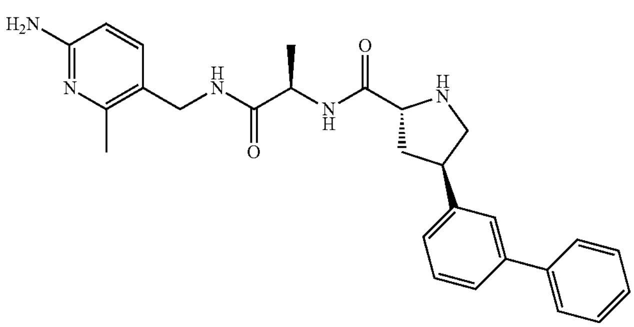 [SMILES: Cc1nc(N)ccc1CNC(=O)[C@@H](C)NC(=O)[C@H]1C[C@H](c2cccc(-c3ccccc3)c2)CN1] | 2TFA | 458.04 | 457.25 |

TABLE 31-continued

Compound List

| Compound No. | Structure | Salt | Exact Mass (ES+; M + H, Obsd) | Exact Mass (Calc) |
|---|---|---|---|---|
| 1360 | 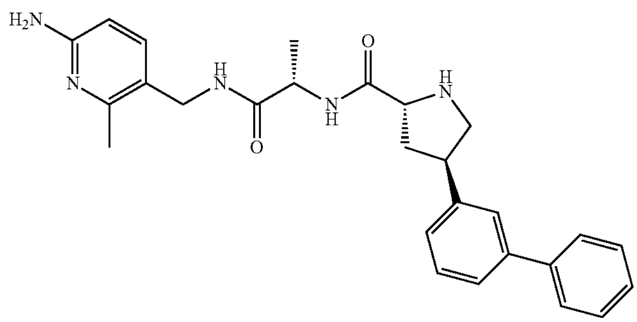 [SMILES: Cc1nc(N)ccc1CNC(=O)[C@H](C)NC(=O)[C@H]1C[C@H](c2cccc(-c3ccccc3)c2)CN1] | 2TFA | 458.12 | 457.25 |
| 1361 | 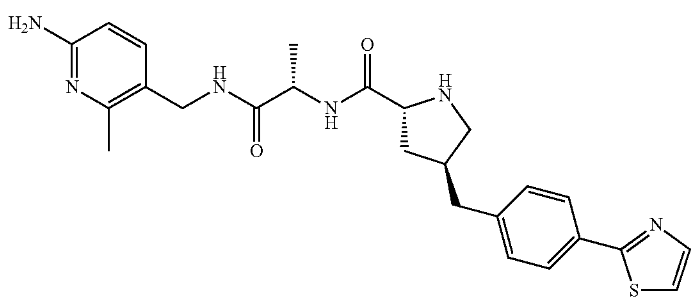 [SMILES: Cc1nc(N)ccc1CNC(=O)[C@H](C)NC(=O)[C@H]1C[C@H](Cc2ccc(-c3nccs3)cc2)CN1] | 2TFA | 479.10 | 478.22 |
| 1362 | 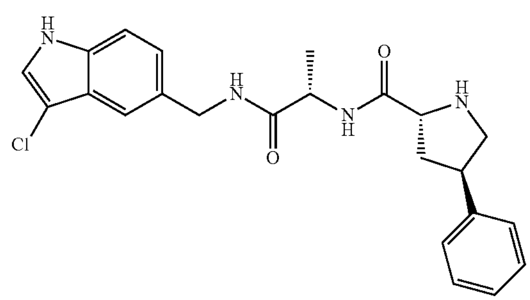 [SMILES: C[C@H](NC(=O)[C@H]1C[C@H](c2ccccc2)CN1)C(=O)NCc1ccc2[nH]cc(Cl)c2c1] | N/A | 425.09 | 424.17 |
| 1363 | 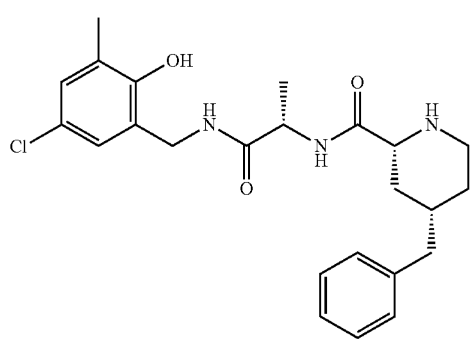 [SMILES: Cc1cc(Cl)cc(CNC(=O)[C@H](C)NC(=O)[C@H]2C[C@@H](Cc3ccccc3)CCN2)c1O] | HCl | 444.08 | 443.2 |

TABLE 31-continued

Compound List

| Compound No. | Structure | Salt | Exact Mass (ES+; M + H, Obsd) | Exact Mass (Calc) |
|---|---|---|---|---|
| 1364 | 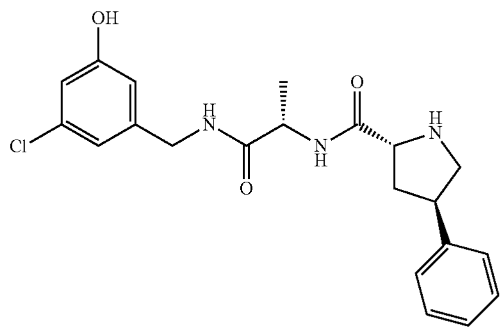 [SMILES: C[C@H](NC(=O)[C@H]1C[C@H](c2ccccc2)CN1)C(=O)NCc1cc(O)cc(Cl)c1] | HCl | 402.09 | 401.15 |
| 1365 | 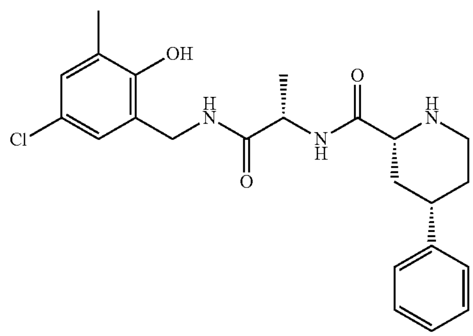 [SMILES: Cc1cc(Cl)cc(CNC(=O)[C@H](C)NC(=O)[C@H]2C[C@@H](c3ccccc3)CCN2)c1O] | HCl | 430.1 | 429.18 |
| 1366 | 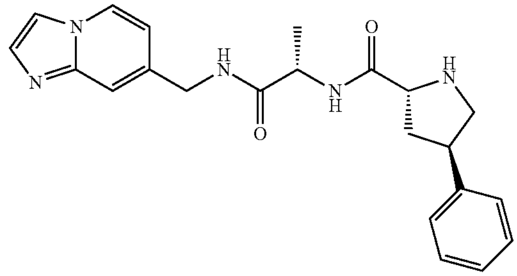 [SMILES: C[C@H](NC(=O)[C@H]1C[C@H](c2ccccc2)CN1)C(=O)NCc1ccn2ccnc2c1] | 2HCl | 392.2 | 391.2 |
| 1367 | 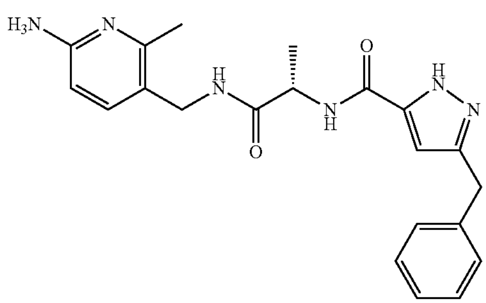 [SMILES: Cc1nc(N)ccc1CNC(=O)[C@H](C)NC(=O)c1cc(Cc2ccccc2)n[nH]1] | NA | 393.19 | 392.2 |

TABLE 31-continued

Compound List

| Compound No. | Structure | Salt | Exact Mass (ES+; M + H, Obsd) | Exact Mass (Calc) |
|---|---|---|---|---|
| 1368 | 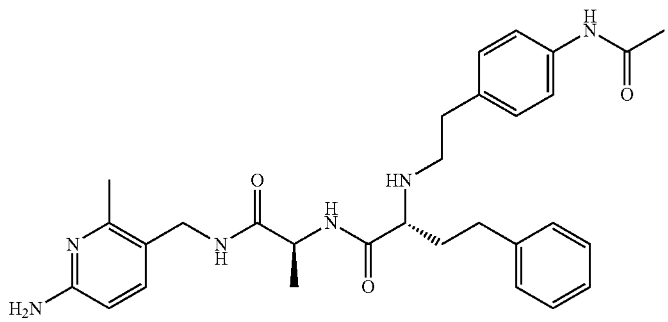 [SMILES: CC(=O)Nc1ccc(CCN[C@H](CCc2ccccc2)C(=O)N[C@@H](C)C(=O)NCc2ccc(N)nc2C)cc1] | 2HCl | 531.26 | 530.3 |
| 1369 | 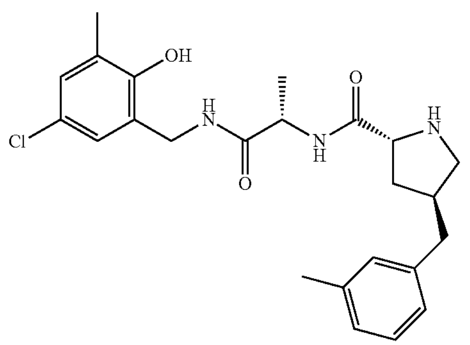 [SMILES: Cc1cccc(C[C@@H]2CN[C@@H](C(=O)N[C@@H](C)C(=O)NCc3cc(Cl)cc(C)c3O)C2)c1] | HCl | 444.12 | 443.2 |
| 1370 | 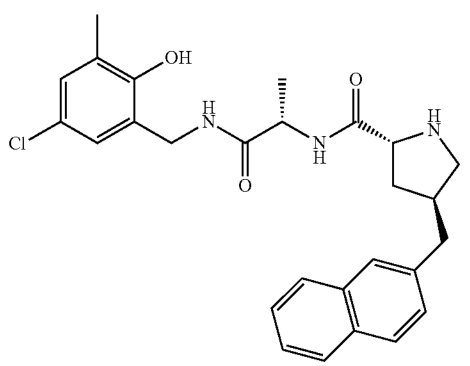 [SMILES: Cc1cc(Cl)cc(CNC(=O)[C@H](C)NC(=O)[C@H]2C[C@H](Cc3ccc4ccccc4c3)CN2)c1O] | TFA | 480.13 | 479.2 |
| 1371 | 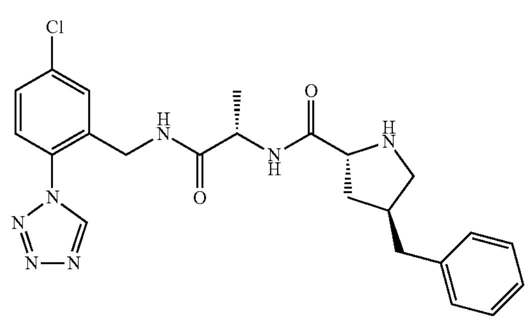 [SMILES: C[C@H](NC(=O)[C@H]1C[C@H](Cc2ccccc2)CN1)C(=O)NCc1cc(Cl)ccc1-n1cnnn1] | HCl | 468.07 | 467.18 |

TABLE 31-continued

Compound List

| Compound No. | Structure | Salt | Exact Mass (ES+; M + H, Obsd) | Exact Mass (Calc) |
| --- | --- | --- | --- | --- |
| 1372 | 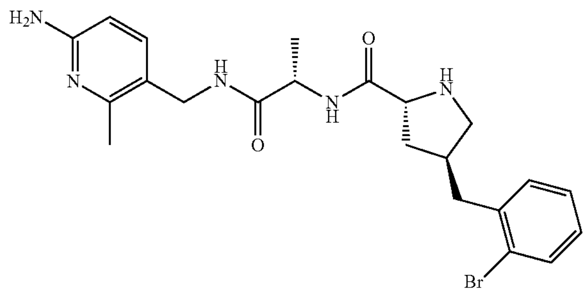 [SMILES: Cc1nc(N)ccc1CNC(=O)[C@H](C)NC(=O)[C@H]1C[C@H](Cc2ccccc2Br)CN1] | 2TFA | 474.08 | 473.14 |
| 1373 | 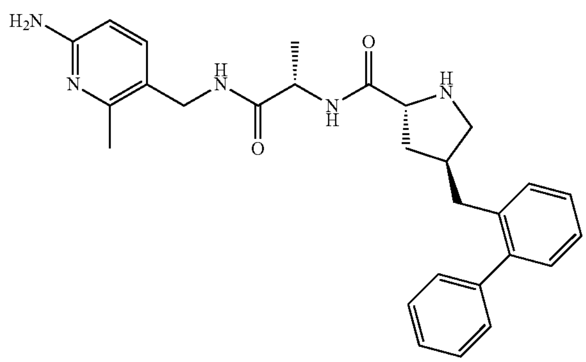 [SMILES: Cc1nc(N)ccc1CNC(=O)[C@H](C)NC(=O)[C@H]1C[C@H](Cc2ccccc2-c2ccccc2)CN1] | 2TFA | 472.23 | 471.26 |
| 1374 | 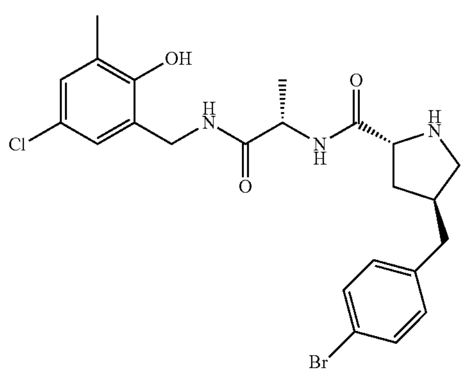 [SMILES: Cc1cc(Cl)cc(CNC(=O)[C@H](C)NC(=O)[C@H]2C[C@H](Cc3ccc(Br)cc3)CN2)c1O] | HCl | 508.08 | 507.09 |
| 1375 | 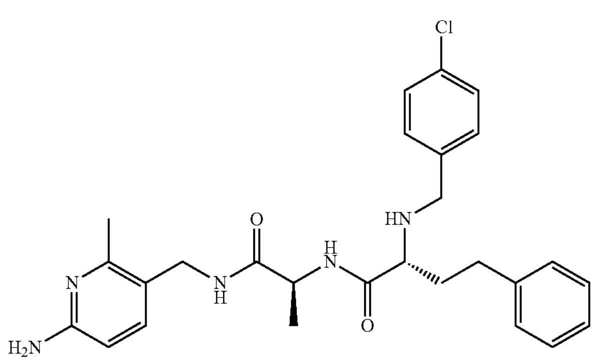 [SMILES: Cc1nc(N)ccc1CNC(=O)[C@H](C)NC(=O)[C@@H](CCc1ccccc1)NCc1ccc(Cl)cc1] | NA | 494.18 | 493.22 |

TABLE 31-continued

Compound List

| Compound No. | Structure | Salt | Exact Mass (ES+; M + H, Obsd) | Exact Mass (Calc) |
|---|---|---|---|---|
| 1376 | 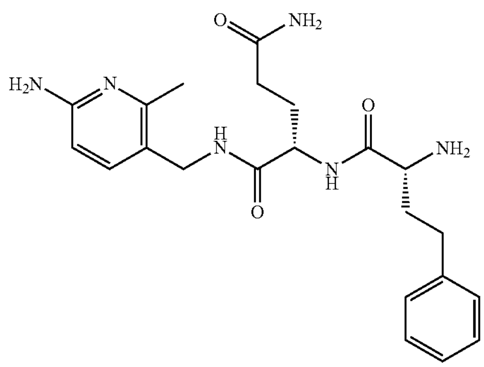 [SMILES: Cc1nc(N)ccc1CNC(=O)[C@H](CCC(N)=O)NC(=O)[C@H](N)CCc1ccccc1] | 2TFA | 427.16 | 426.24 |
| 1377 | 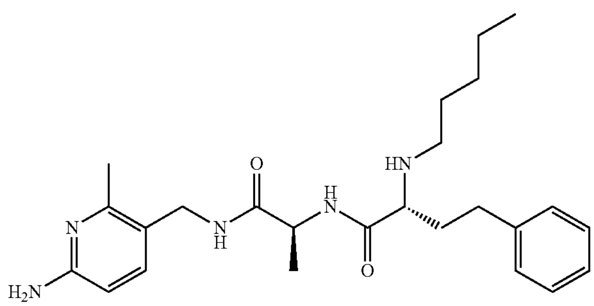 [SMILES: CCCCCN[C@H](CCc1ccccc1)C(=O)N[C@@H](C)C(=O)NCc1ccc(N)nc1C] | 2TFA | 440.21 | 439.29 |
| 1378 | 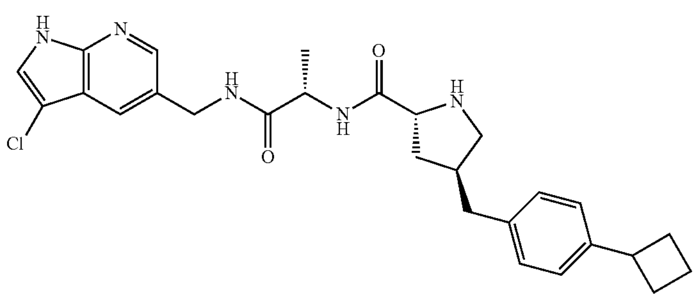 [SMILES: C[C@H](NC(=O)[C@H]1C[C@H](Cc2ccc(C3CCC3)cc2)CN1)C(=O)NCc1cnc2[nH]cc(Cl)c2c1] | 2TFA | 494.21 | 493.22 |
| 1379 | 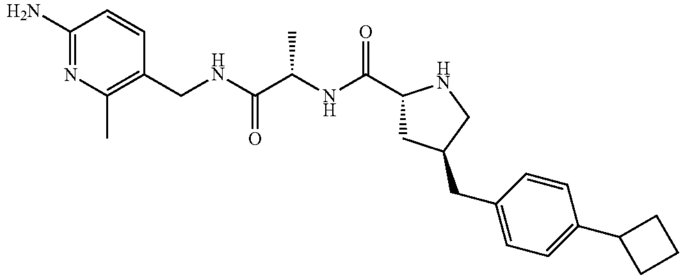 [SMILES: Cc1nc(N)ccc1CNC(=O)[C@H](C)NC(=O)[C@H]1C[C@H](Cc2ccc(C3CCC3)cc2)CN1] | 2TFA | 450.14 | 449.28 |

TABLE 31-continued

Compound List

| Compound No. | Structure | Salt | Exact Mass (ES+; M + H, Obsd) | Exact Mass (Calc) |
|---|---|---|---|---|
| 1380 | 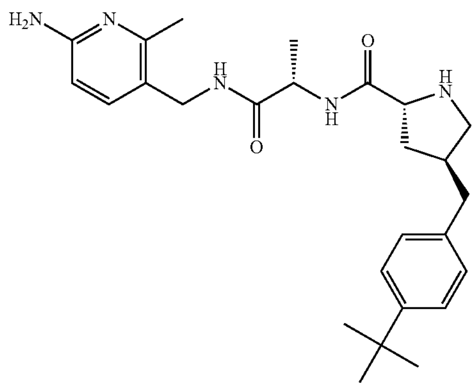 [SMILES: Cc1nc(N)ccc1CNC(=O)[C@H](C)NC(=O)[C@H]1C[C@H](Cc2ccc(C(C)(C)C)cc2)CN1] | 2 HCl | 452.24 | 451.29 |
| 1381 | 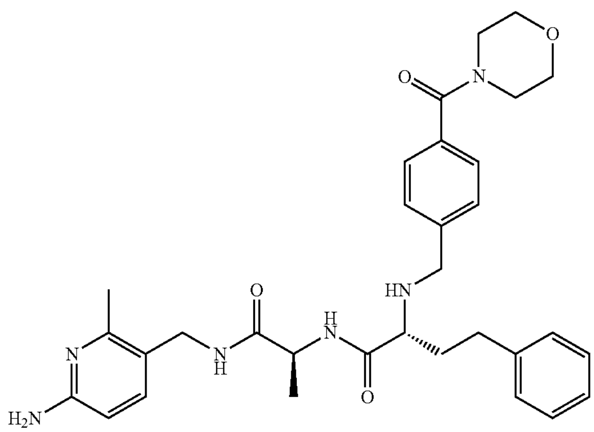 [SMILES: Cc1nc(N)ccc1CNC(=O)[C@H](C)NC(=O)[C@@H](CCc1ccccc1)NCc1ccc(C(=O)N2CCOCC2)cc1] | 2TFA | 573.32 | 572.31 |
| 1382 | 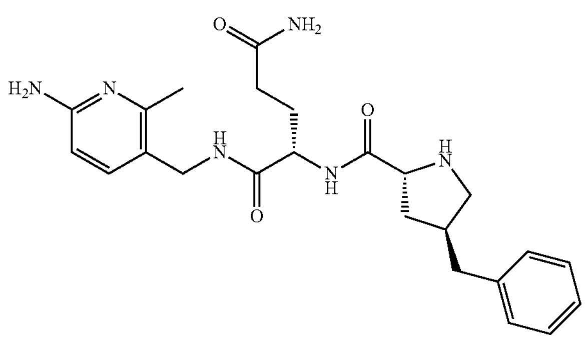 [SMILES: Cc1nc(N)ccc1CNC(=O)[C@H](CCC(N)=O)NC(=O)[C@H]1C[C@H](Cc2ccccc2)CN1] | 2TFA | 453.2 | 452.25 |
| 1383 | 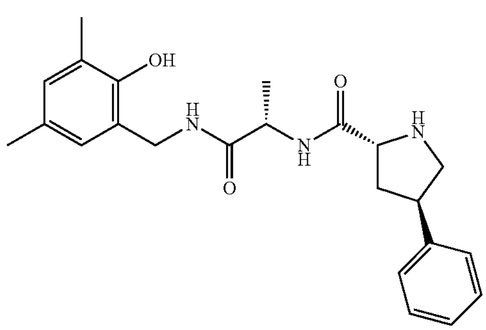 [SMILES: Cc1cc(C)c(O)c(CNC(=O)[C@H](C)NC(=O)[C@H]2C[C@H](c3ccccc3)CN2)c1] | TFA | 396.24 | 395.22 |

TABLE 31-continued

Compound List

| Compound No. | Structure | Salt | Exact Mass (ES+; M + H, Obsd) | Exact Mass (Calc) |
|---|---|---|---|---|
| 1384 | 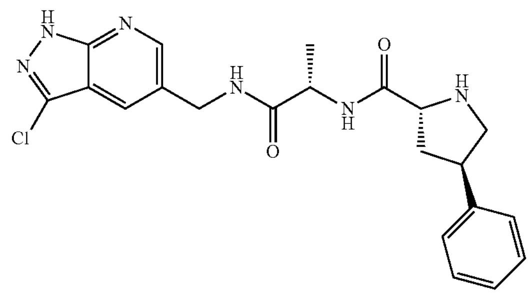 [SMILES: C[C@H](NC(=O)[C@H]1C[C@H](c2ccccc2)CN1)C(=O)NCc1cnc2[nH]nc(Cl)c2c1] | 2HCl | 427.12 | 426.16 |
| 1385 | 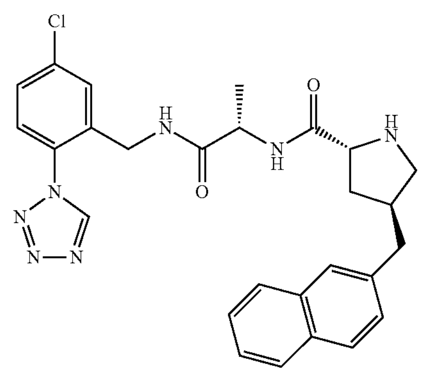 [SMILES: C[C@H](NC(=O)[C@H]1C[C@H](Cc2ccc3ccccc3c2)CN1)C(=O)NCc1cc(Cl)ccc1-n1cnnn1] | TFA | 518.23 | 517.2 |
| 1386 | 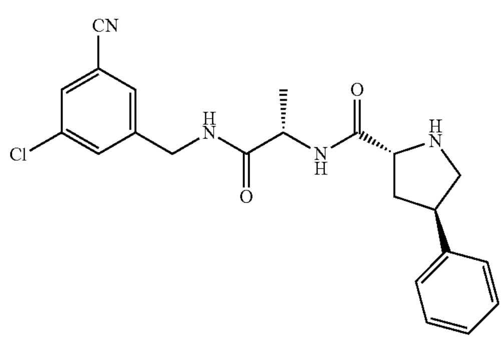 [SMILES: C[C@H](NC(=O)[C@H]1C[C@H](c2ccccc2)CN1)C(=O)NCc1cc(Cl)cc(C#N)c1] | TFA | 411.16 | 410.15 |
| 1387 | 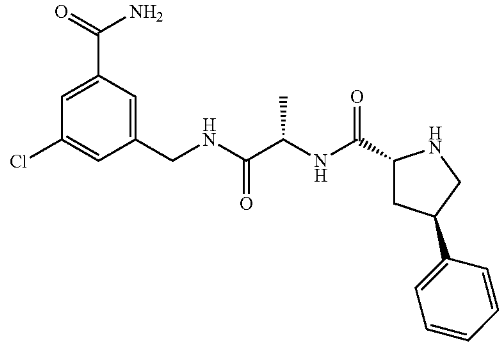 [SMILES: C[C@H](NC(=O)[C@H]1C[C@H](c2ccccc2)CN1)C(=O)NCc1cc(Cl)cc(C(N)=O)c1] | TFA | 429.12 | 428.16 |

TABLE 31-continued

Compound List

| Compound No. | Structure | Salt | Exact Mass (ES+; M + H, Obsd) | Exact Mass (Calc) |
|---|---|---|---|---|
| 1388 | 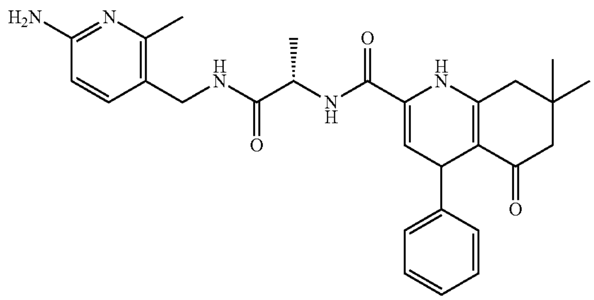 [SMILES: Cc1nc(N)ccc1CNC(=O)[C@H](C)NC(=O)C1=CC(c2ccccc2)C2=C(CC(C)(C)CC2=O)N1] | NA | 488.28 | 487.26 |
| 1389 | 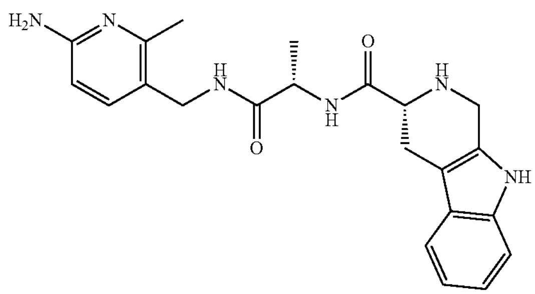 [SMILES: Cc1nc(N)ccc1CNC(=O)[C@H](C)NC(=O)[C@H]1Cc2c([nH]c3ccccc23)CN1] | 2 HCl | 407.21 | 406.21 |
| 1390 | 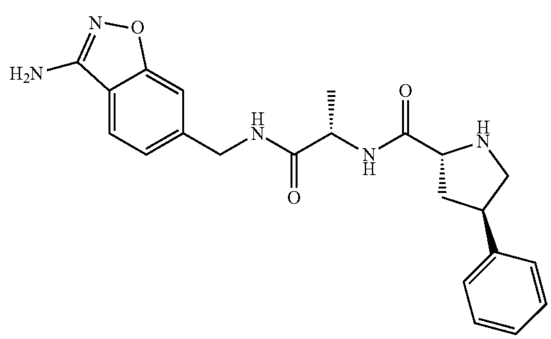 [SMILES: C[C@H](NC(=O)[C@H]1C[C@H](c2ccccc2)CN1)C(=O)NCc1ccc2c(N)noc2c1] | 2TFA | 408.19 | 407.2 |
| 1391 | 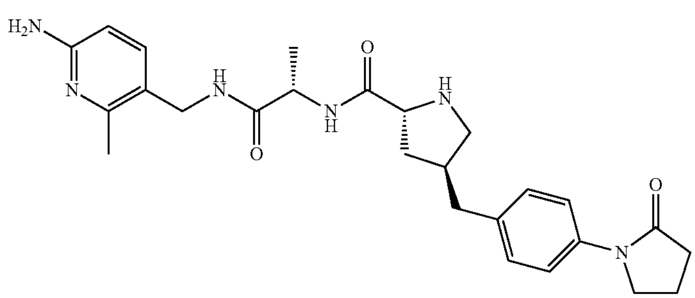 [SMILES: Cc1nc(N)ccc1CNC(=O)[C@H](C)NC(=O)[C@H]1C[C@H](Cc2ccc(N3CCCC3=O)cc2)CN1] | 2TFA | 479.29 | 478.27 |
| 1392 | 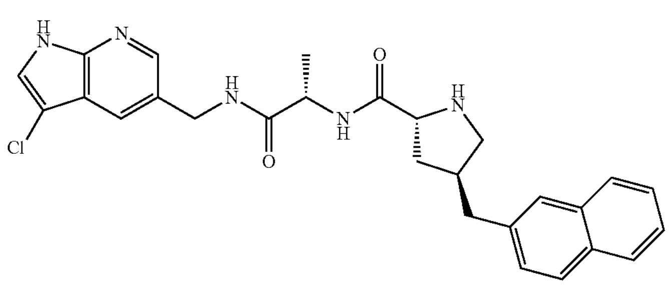 [SMILES: C[C@H](NC(=O)[C@H]1C[C@H](Cc2ccc3ccccc3c2)CN1)C(=O)NCc1cnc2[nH]cc(Cl)c2c1] | 2TFA | 490.19 | 489.19 |

TABLE 31-continued

Compound List

| Compound No. | Structure | Salt | Exact Mass (ES+; M + H, Obsd) | Exact Mass (Calc) |
|---|---|---|---|---|
| 1393 | 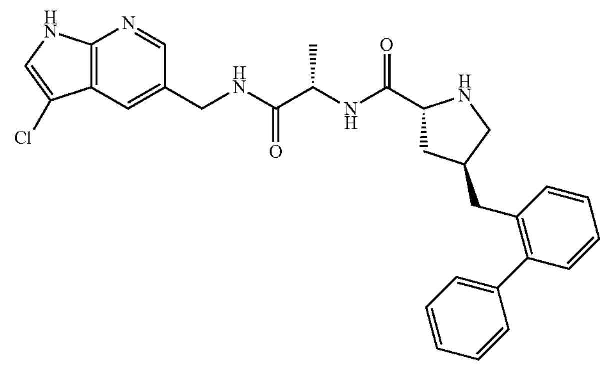 [SMILES: C[C@H](NC(=O)[C@H]1C[C@H](Cc2ccccc2-c2ccccc2)CN1)C(=O)NCc1cnc2[nH]cc(Cl)c2c1] | 2TFA | 516.25 | 515.21 |
| 1394 | 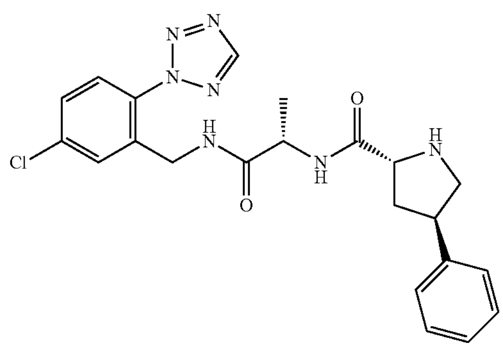 [SMILES: C[C@H](NC(=O)[C@H]1C[C@H](c2ccccc2)CN1)C(=O)NCc1cc(Cl)ccc1-n1ncnn1] | TFA | 454.14 | 453.17 |
| 1395 | 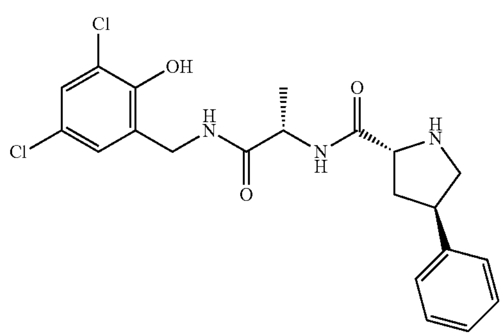 [SMILES: C[C@H](NC(=O)[C@H]1C[C@H](c2ccccc2)CN1)C(=O)NCc1cc(Cl)cc(Cl)c1O] | TFA | 436.16 | 435.11 |
| 1396 | 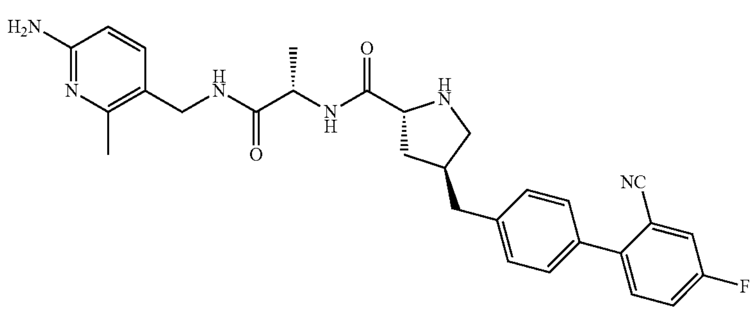 [SMILES: Cc1nc(N)ccc1CNC(=O)[C@H](C)NC(=O)[C@H]1C[C@H](Cc2ccc(-c3ccc(F)cc3C#N)cc2)CN1] | NA | 515.29 | 514.25 |

TABLE 31-continued
Compound List
| Compound No. | Structure | Salt | Exact Mass (ES+; M + H, Obsd) | Exact Mass (Calc) |
|---|---|---|---|---|
| 1397 | 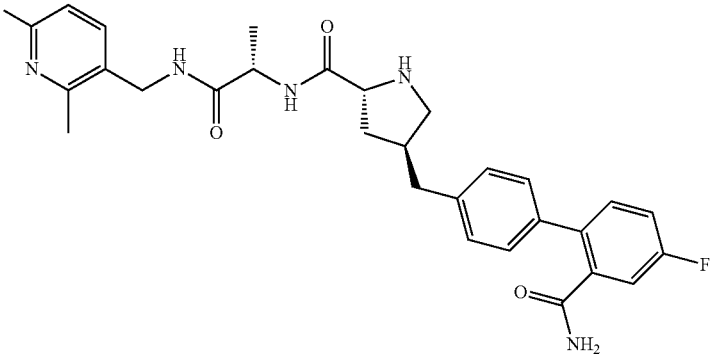 | 2TFA | 533.24 | 532.26 |
| 1398 | 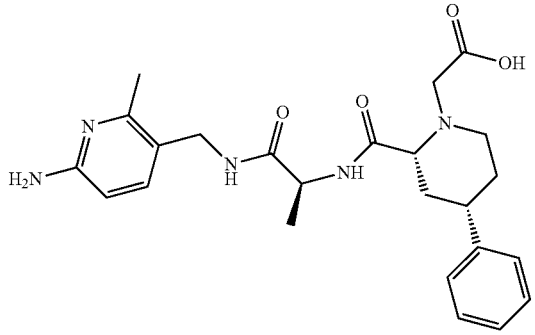 [SMILES: Cc1nc(N)ccc1CNC(=O)[C@H](C)NC(=O)[C@H]1C[C@@H](c2ccccc2)CCN1CC(=O)O] | TFA | 454.28 | 453.24 |
| 1399 | 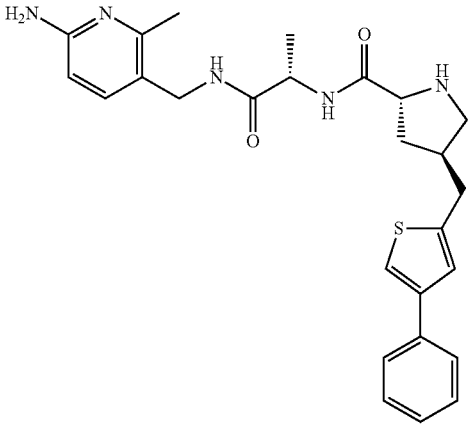 [SMILES: Cc1nc(N)ccc1CNC(=O)[C@H](C)NC(=O)[C@H]1C[C@H](Cc2cc(-c3ccccc3)cs2)CN1] | 2 HCl | 478.29 | 477.22 |
| 1400 | 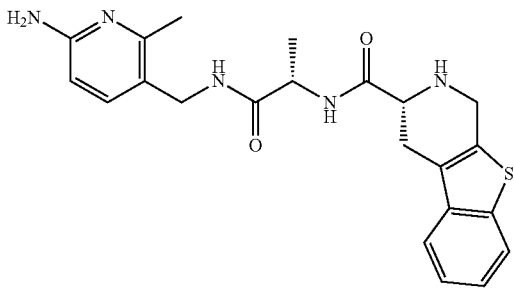 [SMILES: Cc1nc(N)ccc1CNC(=O)[C@H](C)NC(=O)[C@H]1Cc2c(sc3ccccc23)CN1] | 2 HCl | 424.24 | 423.17 |

TABLE 31-continued

Compound List

| Compound No. | Structure | Salt | Exact Mass (ES+; M + H, Obsd) | Exact Mass (Calc) |
|---|---|---|---|---|
| 1401 | 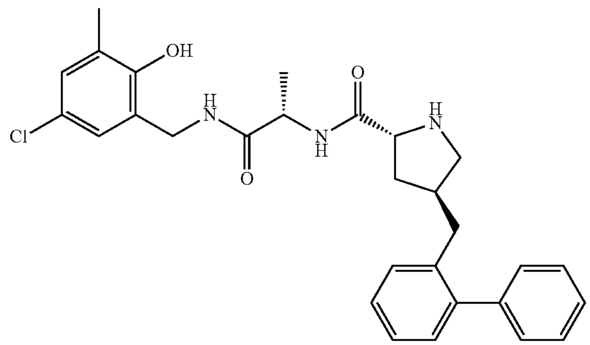 [SMILES: Cc1cc(Cl)cc(CNC(=O)[C@H](C)NC(=O)[C@H]2C[C@H](Cc3ccccc3-c3ccccc3)CN2)c1O] | HCl | 506.27 | 505.21 |
| 1402 | 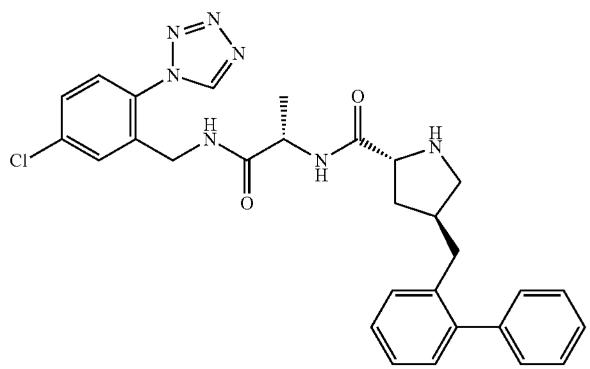 [SMILES: C[C@H](NC(=O)[C@H]1C[C@H](Cc2ccccc2-c2ccccc2)CN1)C(=O)NCc1cc(Cl)ccc1-n1cnnn1] | TFA | 544.29 | 543.21 |
| 1403 | 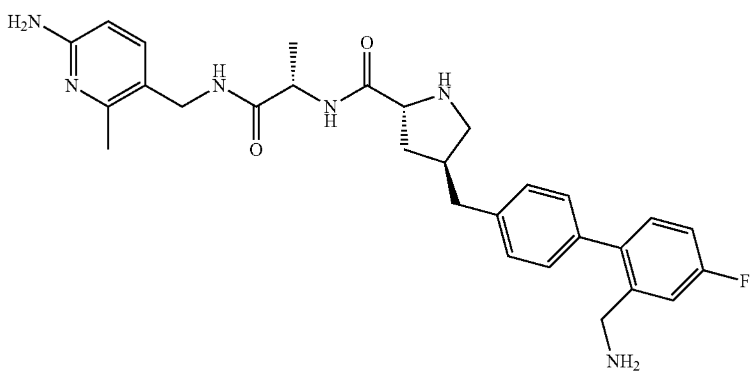 [SMILES: Cc1nc(N)ccc1CNC(=O)[C@H](C)NC(=O)[C@H]1C[C@H](Cc2ccc(-c3ccc(F)cc3CN)cc2)CN1] | NA | 519.34 | 518.28 |
| 1404 | 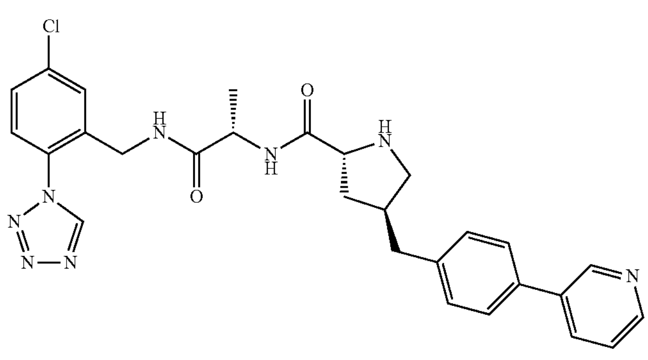 [SMILES: C[C@H](NC(=O)[C@H]1C[C@H](Cc2ccc(-c3cccnc3)cc2)CN1)C(=O)NCc1cc(Cl)ccc1-n1cnnn1] | HCl | 545.29 | 544.21 |

TABLE 31-continued

Compound List

| Compound No. | Structure | Salt | Exact Mass (ES+; M + H, Obsd) | Exact Mass (Calc) |
|---|---|---|---|---|
| 1405 | 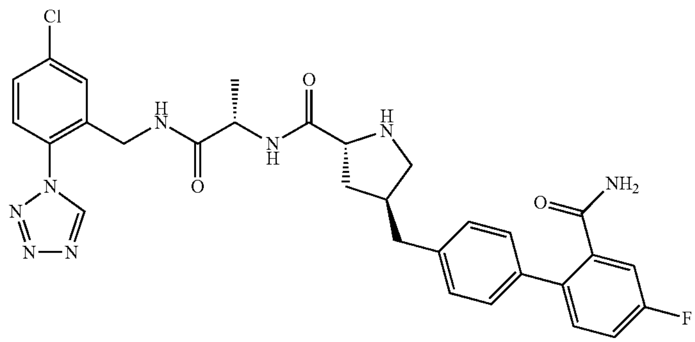 [SMILES: C[C@H](NC(=O)[C@H]1C[C@H](Cc2ccc(-c3ccc(F)cc3C(N)=O)cc2)CN1)C(=O)NCc1cc(Cl)ccc1-n1cnnn1] | HCl | 605.3 | 604.21 |
| 1406 | 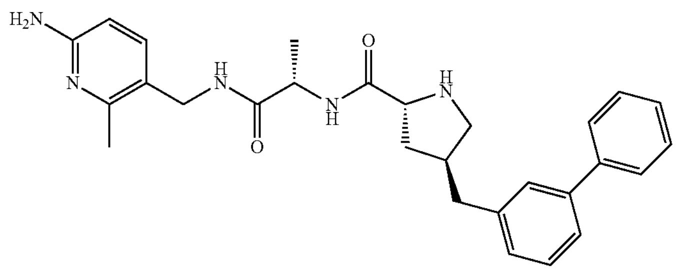 [SMILES: Cc1nc(N)ccc1CNC(=O)[C@H](C)NC(=O)[C@H]1C[C@H](Cc2cccc(-c3ccccc3)c2)CN1] | 2HCl | 472.33 | 471.26 |
| 1407 | 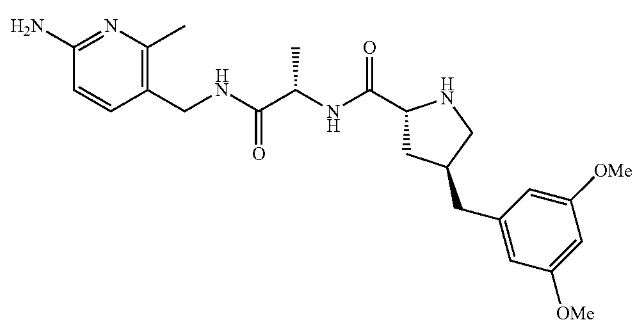 [SMILES: COc1cc(C[C@@H]2CN[C@@H](C(=O)N[C@@H](C)C(=O)NCc3ccc(N)nc3C)C2)cc(OC)c1] | 2TFA | 456.35 | 455.25 |
| 1408 | 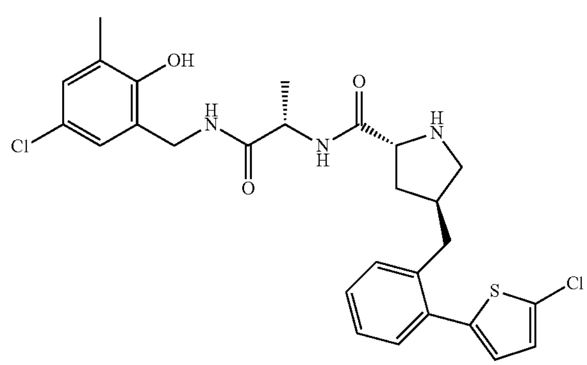 [SMILES: Cc1cc(Cl)cc(CNC(=O)[C@H](C)NC(=O)[C@H]2C[C@H](Cc3ccccc3-c3ccc(Cl)s3)CN2)c1O] | HCl | 546.2 | 545.13 |

TABLE 31-continued

Compound List

| Compound No. | Structure | Salt | Exact Mass (ES+; M + H, Obsd) | Exact Mass (Calc) |
|---|---|---|---|---|
| 1409 | 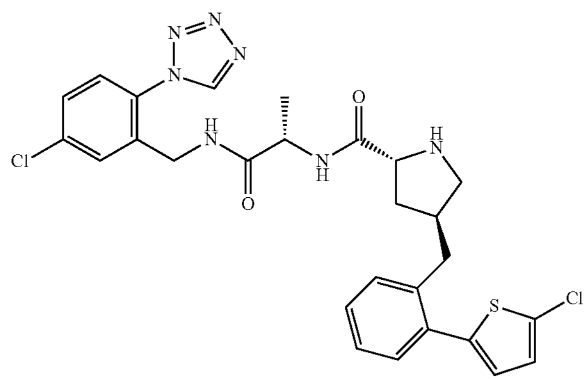 [SMILES: C[C@H](NC(=O)[C@H]1C[C@H](Cc2ccccc2-c2ccc(Cl)s2)CN1)C(=O)NCc1cc(Cl)ccc1-n1cnnn1] | TFA | 584.23 | 583.13 |
| 1410 | 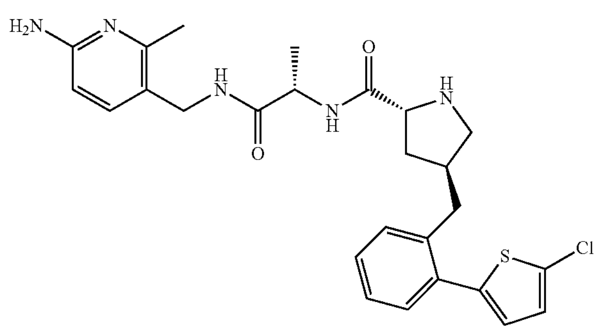 [SMILES: Cc1nc(N)ccc1CNC(=O)[C@H](C)NC(=O)[C@H]1C[C@H](Cc2ccccc2-c2ccc(Cl)s2)CN1] | TFA | 512.27 | 511.18 |
| 1411 | 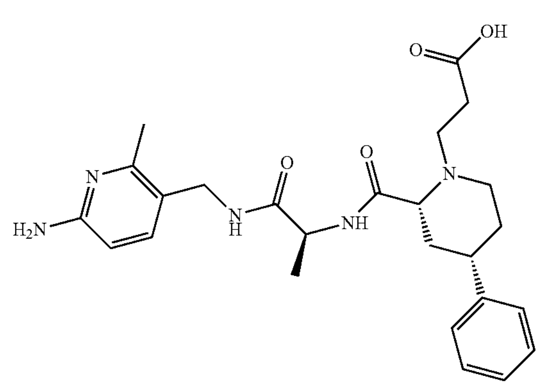 [SMILES: Cc1nc(N)ccc1CNC(=O)[C@H](C)NC(=O)[C@H]1C[C@@H](c2ccccc2)CCN1CCC(=O)O] | TFA | 468.33 | 467.25 |

TABLE 31-continued

Compound List

| Compound No. | Structure | Salt | Exact Mass (ES+; M + H, Obsd) | Exact Mass (Calc) |
|---|---|---|---|---|
| 1412 | 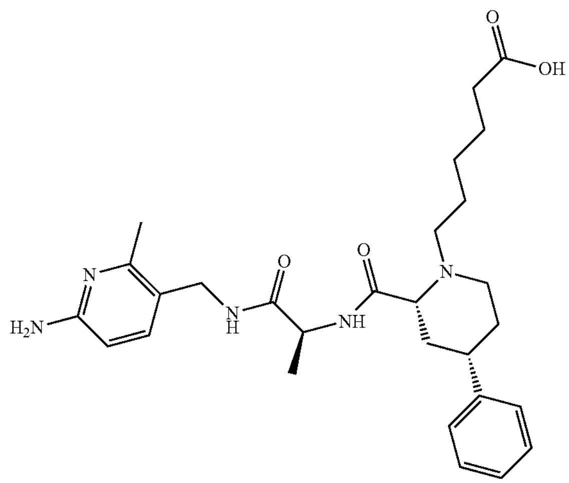 [SMILES: Cc1nc(N)ccc1CNC(=O)[C@H](C)NC(=O)[C@H]1C[C@@H](c2ccccc2)CCN1CCCCCC(=O)O] | TFA | 510.38 | 509.3 |
| 1413 | 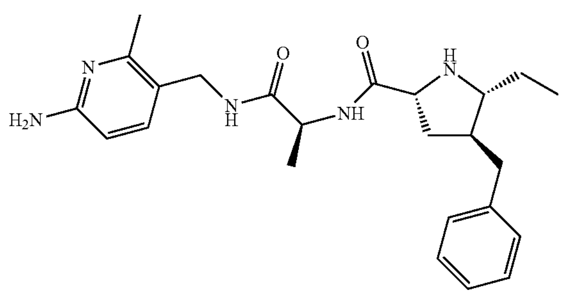 [SMILES: CC[C@H]1N[C@@H](C(=O)N[C@@H](C)C(=O)NCc2ccc(N)nc2C)C[C@@H]1Cc1ccccc1] | 2TFA | 424.36 | 423.26 |
| 1414 | 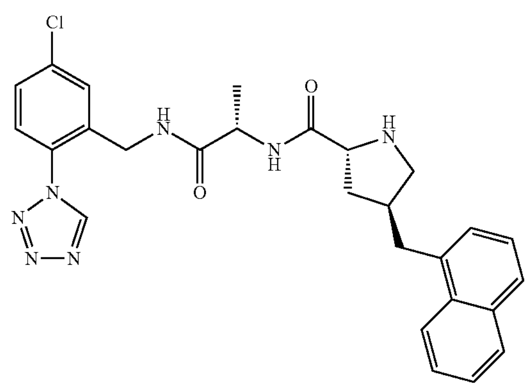 [SMILES: C[C@H](NC(=O)[C@H]1C[C@H](Cc2cccc3ccccc23)CN1)C(=O)NCc1cc(Cl)ccc1-n1cnnn1] | HCl | 518.27 | 517.2 |
| 1415 | 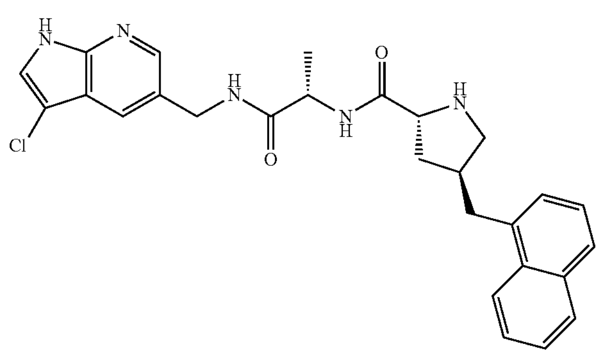 [SMILES: C[C@H](NC(=O)[C@H]1C[C@H](Cc2cccc3ccccc23)CN1)C(=O)NCc1cnc2[nH]cc(Cl)c2c1] | HCl | 490.26 | 489.19 |

TABLE 31-continued

Compound List

| Compound No. | Structure | Salt | Exact Mass (ES+; M + H, Obsd) | Exact Mass (Calc) |
|---|---|---|---|---|
| 1416 | 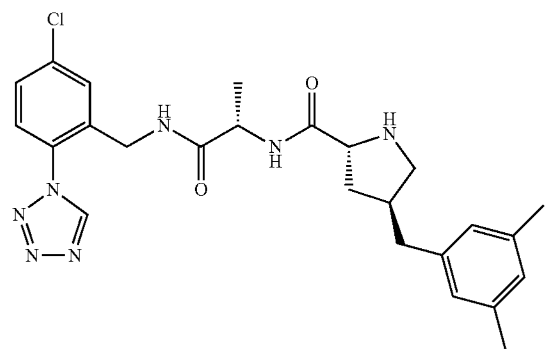 [SMILES: Cc1cc(C)cc(C[C@@H]2CN[C@@H](C(=O)N[C@@H](C)C(=O)NCc3cc(Cl)ccc3-n3cnnn3)C2)c1] | HCl | 496.30 | 495.21 |
| 1417 | 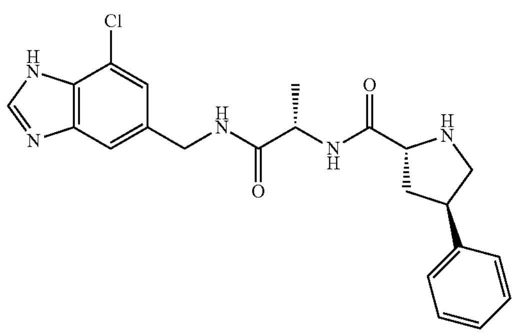 [SMILES: C[C@H](NC(=O)[C@H]1C[C@H](c2ccccc2)CN1)C(=O)NCc1cc(Cl)c2[nH]cnc2c1] | TFA | 426.23 | 425.16 |
| 1418 | 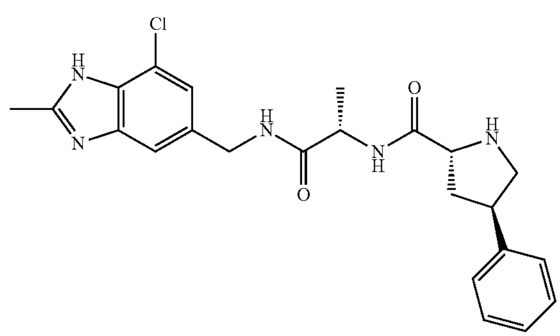 [SMILES: Cc1nc2cc(CNC(=O)[C@H](C)NC(=O)[C@H]3C[C@H](c4ccccc4)CN3)cc(Cl)c2[nH]1] | TFA | 440.26 | 439.18 |
| 1419 | 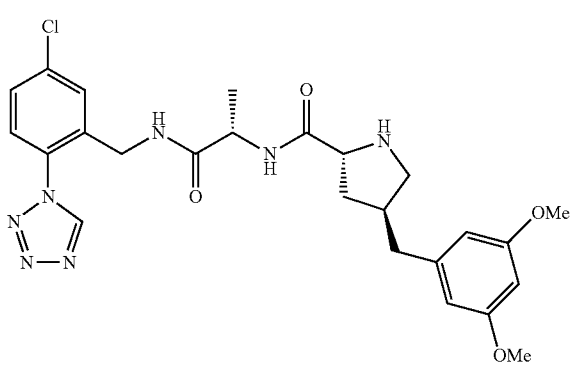 [SMILES: COc1cc(C[C@@H]2CN[C@@H](C(=O)N[C@@H](C)C(=O)NCc3cc(Cl)ccc3-n3cnnn3)C2)cc(OC)c1] | TFA | 528.28 | 527.2 |

TABLE 31-continued

Compound List

| Compound No. | Structure | Salt | Exact Mass (ES+; M + H, Obsd) | Exact Mass (Calc) |
|---|---|---|---|---|
| 1420 | 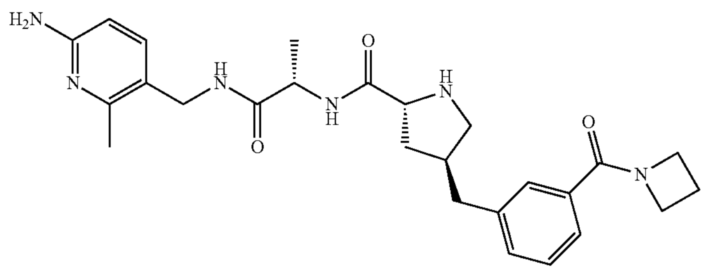 [SMILES: Cc1nc(N)ccc1CNC(=O)[C@H](C)NC(=O)[C@H]1C[C@H](Cc2cccc(C(=O)N3CCC3)c2)CN1] | 2TFA | 479.36 | 478.27 |
| 1421 | 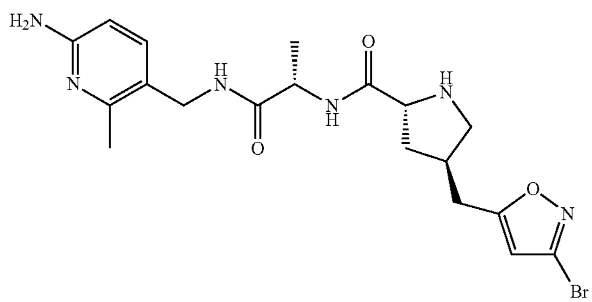 [SMILES: Cc1nc(N)ccc1CNC(=O)[C@H](C)NC(=O)[C@H]1C[C@H](Cc2cc(Br)no2)CN1] | 2TFA | 465.19 | 464.12 |
| 1422 | 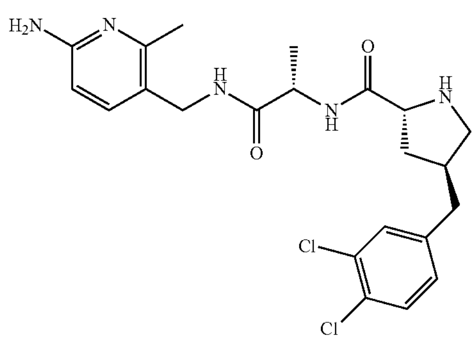 [SMILES: Cc1nc(N)ccc1CNC(=O)[C@H](C)NC(=O)[C@H]1C[C@H](Cc2ccc(Cl)c(Cl)c2)CN1] | HCl | 464.24 | 463.15 |
| 1423 | 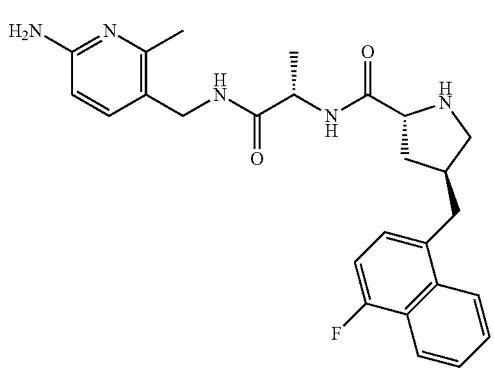 | HCl | 464.32 | 463.24 |

TABLE 31-continued

Compound List

| Compound No. | Structure | Salt | Exact Mass (ES+; M + H, Obsd) | Exact Mass (Calc) |
|---|---|---|---|---|
| 1424 | 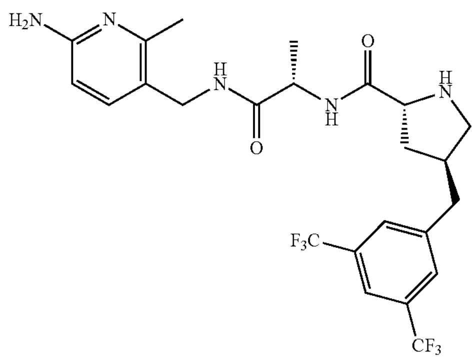 [SMILES: Cc1nc(N)ccc1CNC(=O)[C@H](C)NC(=O)[C@H]1C[C@H](Cc2cc(C(F)(F)F)cc(C(F)(F)F)c2)CN1] | 2TFA | 532.29 | 531.21 |
| 1425 | 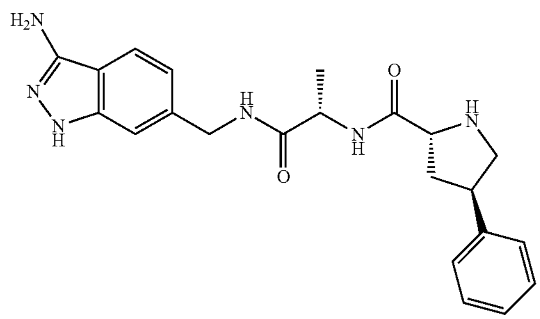 [SMILES: C[C@H](NC(=O)[C@H]1C[C@H](c2ccccc2)CN1)C(=O)NCc1ccc2c(N)n[nH]c2c1] | TFA | 407.34 | 406.21 |
| 1426 | 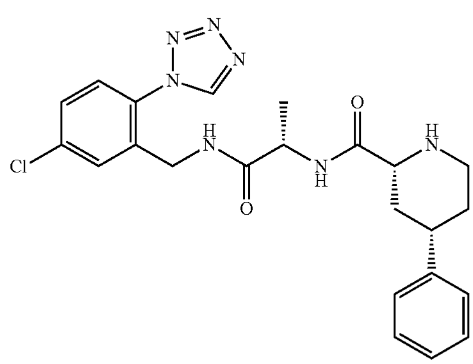 [SMILES: C[C@H](NC(=O)[C@H]1C[C@@H](c2ccccc2)CCN1)C(=O)NCc1cc(Cl)ccc1-n1cnnn1] | TFA | 468.26 | 467.18 |
| 1427 | 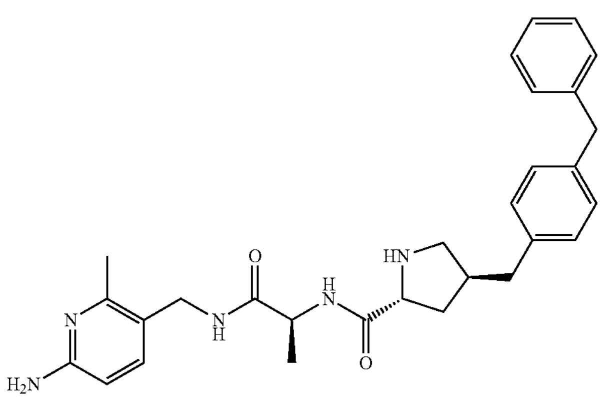 [SMILES: Cc1nc(N)ccc1CNC(=O)[C@H](C)NC(=O)[C@H]1C[C@H](Cc2ccc(Cc3ccccc3)cc2)CN1] | 2TFA | 486.35 | 485.28 |

TABLE 31-continued

Compound List

| Compound No. | Structure | Salt | Exact Mass (ES+; M + H, Obsd) | Exact Mass (Calc) |
|---|---|---|---|---|
| 1428 | 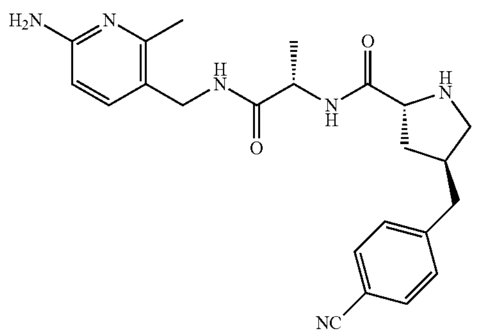 | 2TFA | 421.35 | 420.23 |
| 1429 | 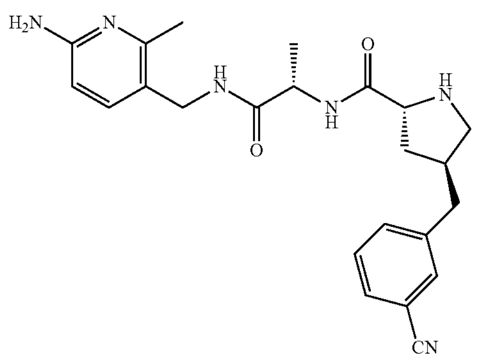 [SMILES: Cc1nc(N)ccc1CNC(=O)[C@H](C)NC(=O)[C@H]1C[C@H](Cc2cccc(C#N)c2)CN1] | 2TFA | 421.35 | 420.23 |
| 1430 | 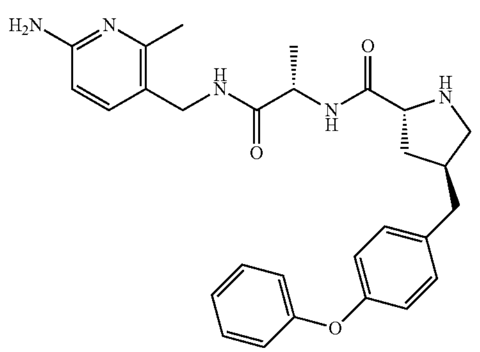 [SMILES: Cc1nc(N)ccc1CNC(=O)[C@H](C)NC(=O)[C@H]1C[C@H](Cc2ccc(Oc3ccccc3)cc2)CN1] | 2TFA | 488.38 | 487.26 |
| 1431 | 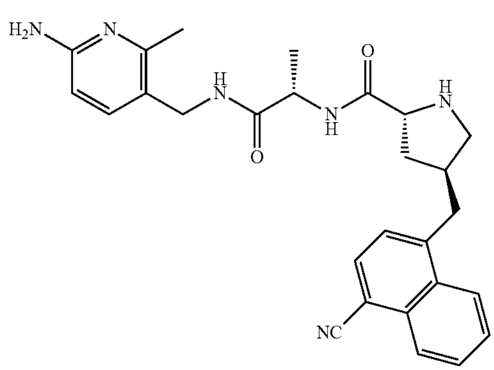 [SMILES: Cc1nc(N)ccc1CNC(=O)[C@H](C)NC(=O)[C@H]1C[C@H](Cc2ccc(C#N)c3ccccc23)CN1] | HCl | 471.33 | 470.24 |

TABLE 31-continued

Compound List

| Compound No. | Structure | Salt | Exact Mass (ES+; M + H, Obsd) | Exact Mass (Calc) |
|---|---|---|---|---|
| 1432 | 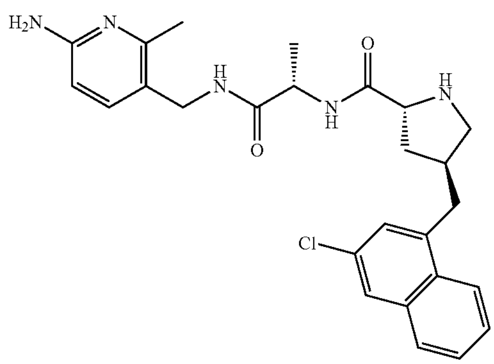 [SMILES: Cc1nc(N)ccc1CNC(=O)[C@H](C)NC(=O)[C@H]1C[C@H](Cc2cc(Cl)cc3ccccc23)CN1] | HCl | 480.30 | 479.21 |
| 1433 | 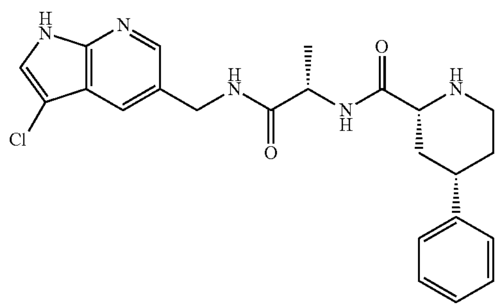 [SMILES: C[C@H](NC(=O)[C@H]1C[C@@H](c2ccccc2)CCN1)C(=O)NCc1cnc2[nH]cc(Cl)c2c1] | TFA | 440.28 | 439.18 |
| 1434 | 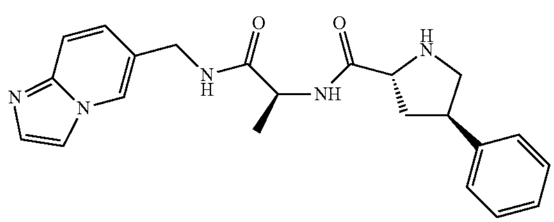 [SMILES: C[C@H](NC(=O)[C@H]1C[C@H](c2ccccc2)CN1)C(=O)NCc1ccc2nccn2c1] | 2HCl | 392.35 | 391.2 |
| 1435 | 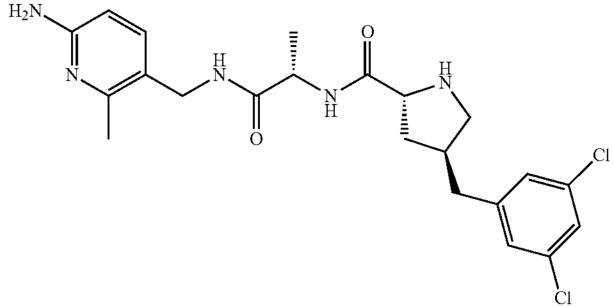 [SMILES: Cc1nc(N)ccc1CNC(=O)[C@H](C)NC(=O)[C@H]1C[C@H](Cc2cc(Cl)cc(Cl)c2)CN1] | 2HCl | 464.24 | 463.15 |

TABLE 31-continued

Compound List

| Compound No. | Structure | Salt | Exact Mass (ES+; M + H, Obsd) | Exact Mass (Calc) |
|---|---|---|---|---|
| 1436 | 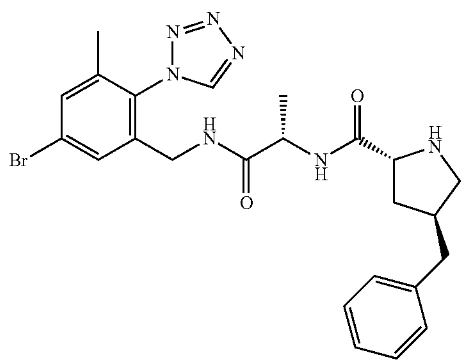 [SMILES: Cc1cc(Br)cc(CNC(=O)[C@H](C)NC(=O)[C@H]2C[C@H](Cc3ccccc3)CN2)c1-n1cnnn1] | TFA | 526.3 | 525.15 |
| 1437 | 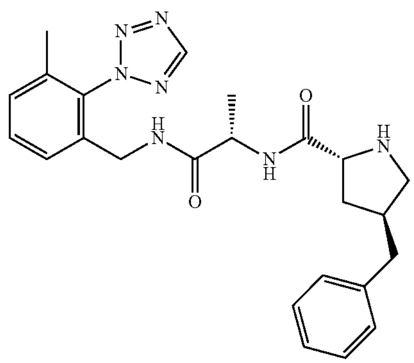 [SMILES: Cc1cccc(CNC(=O)[C@H](C)NC(=O)[C@H]2C[C@H](Cc3ccccc3)CN2)c1-n1ncnn1] | TFA | 448.35 | 447.24 |
| 1438 | 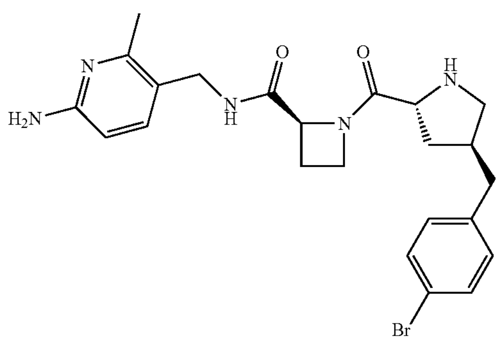 [SMILES: Cc1nc(N)ccc1CNC(=O)[C@@H]1CCN1C(=O)[C@H]1C[C@H](Cc2ccc(Br)cc2)CN1] | 2TFA | 486.26 | 485.14 |
| 1439 | 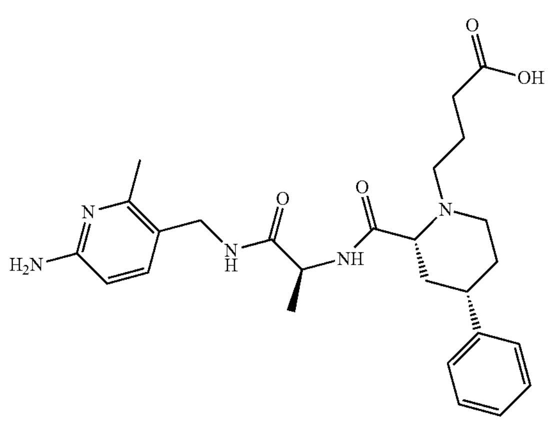 [SMILES: Cc1nc(N)ccc1CNC(=O)[C@H](C)NC(=O)[C@H]1C[C@@H](c2ccccc2)CCN1CCCC(=O)O] | TFA | 482.39 | 481.27 |

TABLE 31-continued

Compound List

| Compound No. | Structure | Salt | Exact Mass (ES+; M + H, Obsd) | Exact Mass (Calc) |
| --- | --- | --- | --- | --- |
| 1440 | 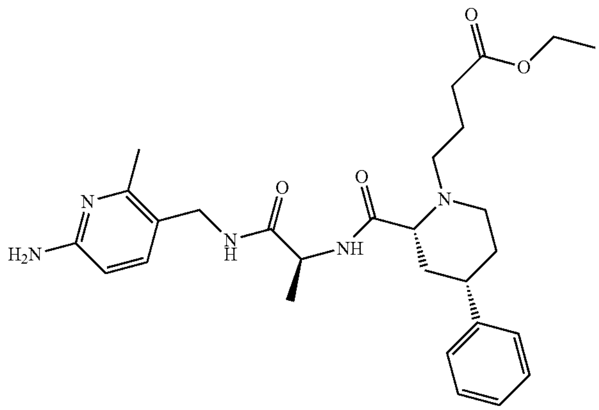 [SMILES: CCOC(=O)CCCN1CC[C@H](c2ccccc2)C[C@@H]1C(=O)N[C@@H](C)C(=O)NCc1ccc(N)nc1C] | NA | 510.43 | 509.3 |
| 1441 | 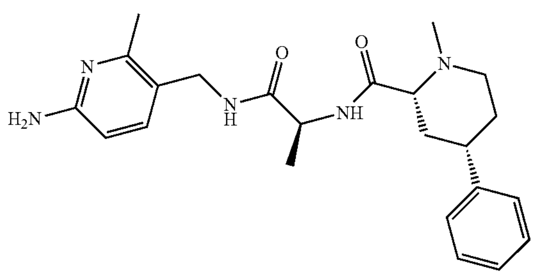 [SMILES: Cc1nc(N)ccc1CNC(=O)[C@H](C)NC(=O)[C@H]1C[C@@H](c2ccccc2)CCN1C] | NA | 410.36 | 409.25 |
| 1442 | 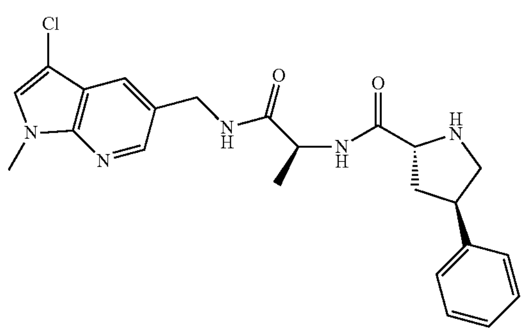 [SMILES: C[C@H](NC(=O)[C@H]1C[C@H](c2ccccc2)CN1)C(=O)NCc1cnc2c(c1)c(Cl)cn2C] | 2HCl | 440.3 | 439.18 |
| 1443 | 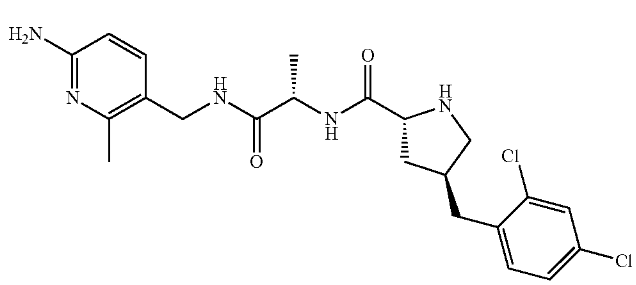 [SMILES: Cc1nc(N)ccc1CNC(=O)[C@H](C)NC(=O)[C@H]1C[C@H](Cc2ccc(Cl)cc2Cl)CN1] | 2HCl | 464.26 | 463.15 |

TABLE 31-continued

Compound List

| Compound No. | Structure | Salt | Exact Mass (ES+; M + H, Obsd) | Exact Mass (Calc) |
|---|---|---|---|---|
| 1444 | 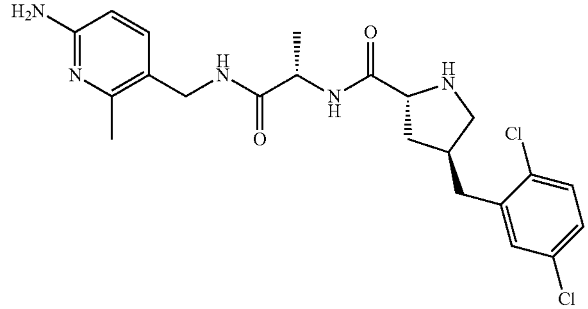 [SMILES: Cc1nc(N)ccc1CNC(=O)[C@H](C)NC(=O)[C@H]1C[C@H](Cc2cc(Cl)ccc2Cl)CN1] | 2HCl | 464.28 | 463.15 |
| 1445 | 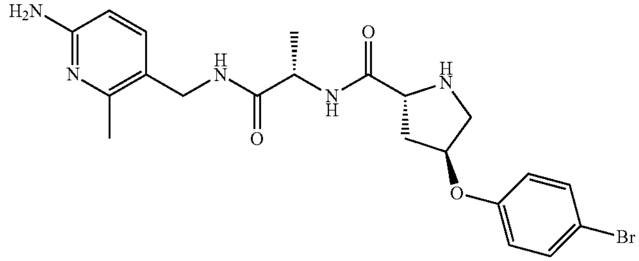 [SMILES: Cc1nc(N)ccc1CNC(=O)[C@H](C)NC(=O)[C@H]1C[C@H](Oc2ccc(Br)cc2)CN1] | 2HCl | 476.18 | 475.12 |
| 1446 | 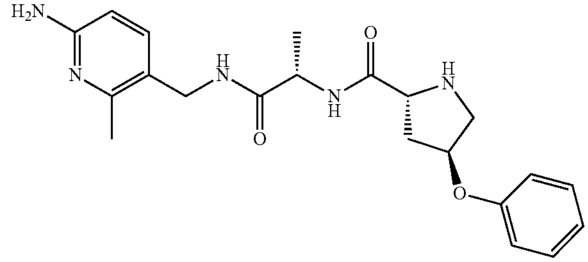 [SMILES: Cc1nc(N)ccc1CNC(=O)[C@H](C)NC(=O)[C@H]1C[C@H](Oc2ccccc2)CN1] | 2HCl | 398.37 | 397.21 |
| 1447 | 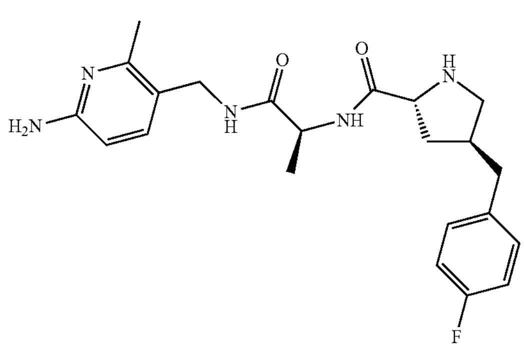 [SMILES: Cc1nc(N)ccc1CNC(=O)[C@H](C)NC(=O)[C@H]1C[C@H](Cc2ccc(F)cc2)CN1] | 2TFA | 414.46 | 413.22 |

TABLE 31-continued

Compound List

| Compound No. | Structure | Salt | Exact Mass (ES+; M + H, Obsd) | Exact Mass (Calc) |
|---|---|---|---|---|
| 1448 | 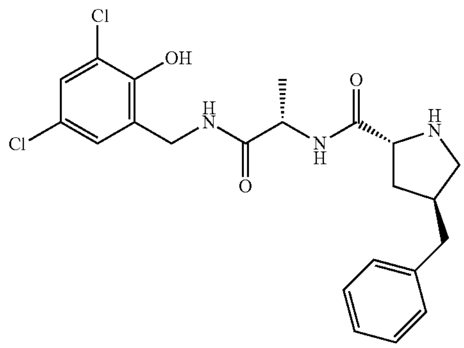 [SMILES: C[C@H](NC(=O)[C@H]1C[C@H](Cc2ccccc2)CN1)C(=O)NCc1cc(Cl)cc(Cl)c1O] | HCl | 450.2 | 449.13 |
| 1449 | 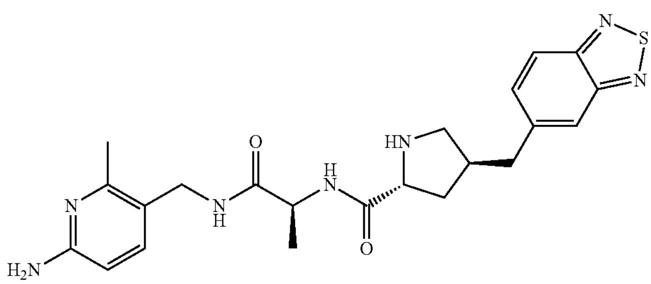 [SMILES: Cc1nc(N)ccc1CNC(=O)[C@H](C)NC(=O)[C@H]1C[C@H](Cc2ccc3nsnc3c2)CN1] | 2TFA | 454.12 | 453.19 |
| 1450 | 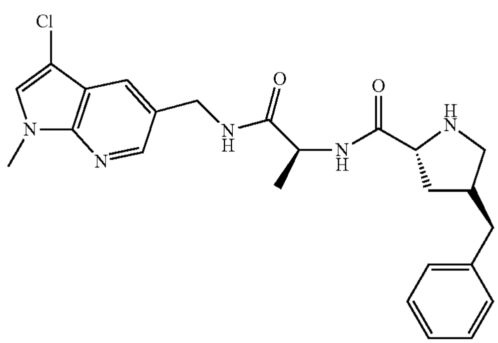 | 2HCl | 454.11 | 453.19 |
| 1451 | 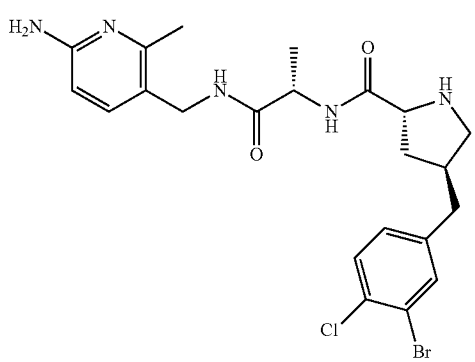 [SMILES: Cc1nc(N)ccc1CNC(=O)[C@H](C)NC(=O)[C@H]1C[C@H](Cc2ccc(Cl)c(Br)c2)CN1] | 2TFA | 508.32 | 507.1 |

TABLE 31-continued

Compound List

| Compound No. | Structure | Salt | Exact Mass (ES+; M + H, Obsd) | Exact Mass (Calc) |
|---|---|---|---|---|
| 1452 | 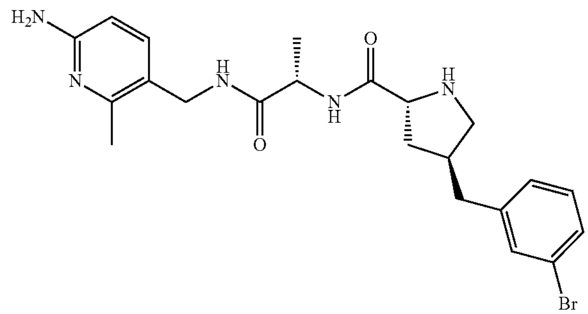 [SMILES: Cc1nc(N)ccc1CNC(=O)[C@H](C)NC(=O)[C@H]1C[C@H](Cc2cccc(Br)c2)CN1] | 2HCl | 474.24 | 473.14 |
| 1453 | 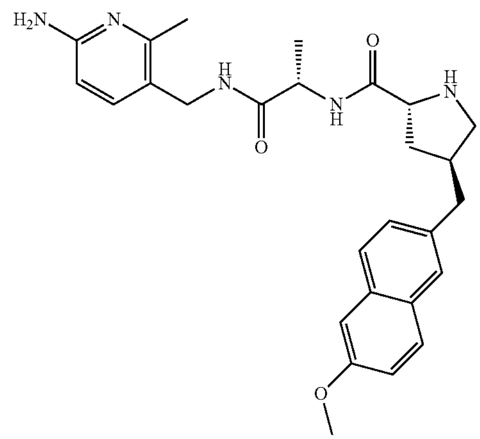 [SMILES: COc1ccc2cc(C[C@@H]3CN[C@@H](C(=O)N[C@@H](C)C(=O)NCc4ccc(N)nc4C)C3)ccc2c1] | HCl | 476.20 | 475.26 |
| 1454 | 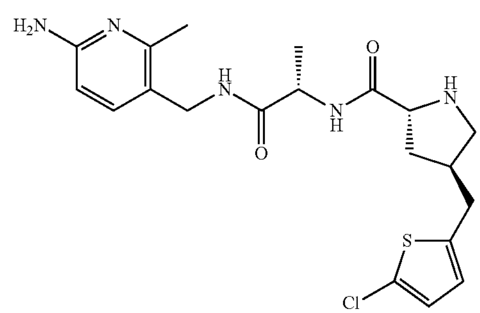 [SMILES: Cc1nc(N)ccc1CNC(=O)[C@H](C)NC(=O)[C@H]1C[C@H](Cc2ccc(Cl)s2)CN1] | HCl | 436.08 | 435.15 |
| 1455 | 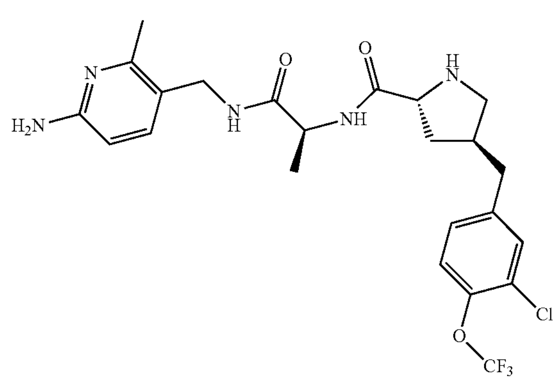 [SMILES: Cc1nc(N)ccc1CNC(=O)[C@H](C)NC(=O)[C@H]1C[C@H](Cc2ccc(OC(F)(F)F)c(Cl)c2)CN1] | 2TFA | 514.41 | 513.18 |

TABLE 31-continued

Compound List

| Compound No. | Structure | Salt | Exact Mass (ES+; M + H, Obsd) | Exact Mass (Calc) |
|---|---|---|---|---|
| 1456 | 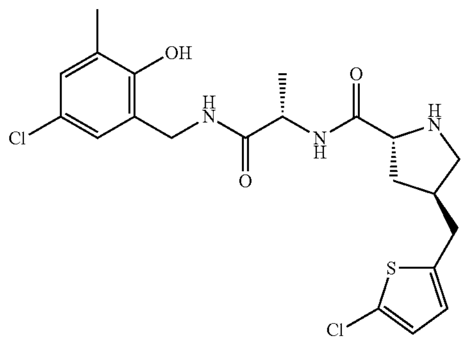 [SMILES: Cc1cc(Cl)cc(CNC(=O)[C@H](C)NC(=O)[C@H]2C[C@H](Cc3ccc(Cl)s3)CN2)c1O] | HCl | 470.01 | 469.1 |
| 1457 | 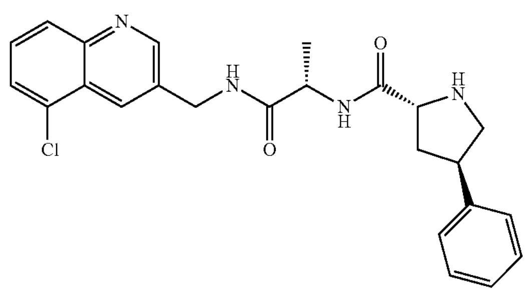 [SMILES: C[C@H](NC(=O)[C@H]1C[C@H](c2ccccc2)CN1)C(=O)NCc1cnc2cccc(Cl)c2c1] | HCl | 437.1 | 436.17 |
| 1458 | 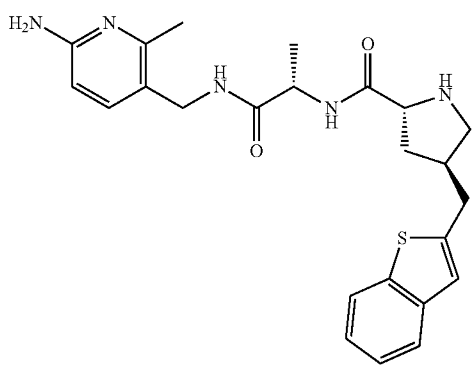 [SMILES: Cc1nc(N)ccc1CNC(=O)[C@H](C)NC(=O)[C@H]1C[C@H](Cc2cc3ccccc3s2)CN1] | 2TFA | 452.41 | 451.2 |
| 1459 | 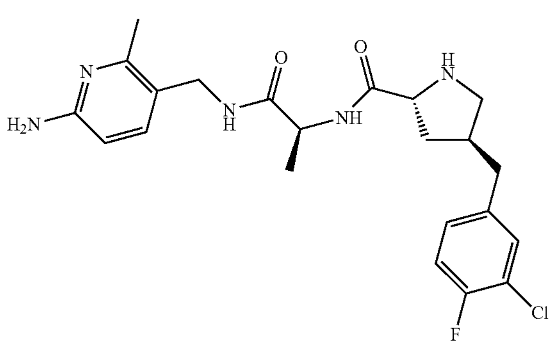 [SMILES: Cc1nc(N)ccc1CNC(=O)[C@H](C)NC(=O)[C@H]1C[C@H](Cc2ccc(F)c(Cl)c2)CN1] | 2TFA | 448.36 | 447.18 |

TABLE 31-continued
Compound List
| Compound No. | Structure | Salt | Exact Mass (ES+; M + H, Obsd) | Exact Mass (Calc) |
|---|---|---|---|---|
| 1460 | 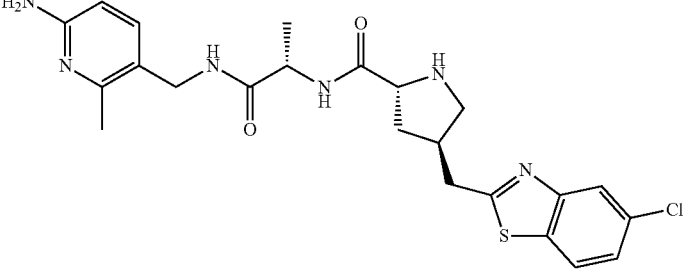 | 2TFA | 487.10 | 486.16 |
| 1461 | 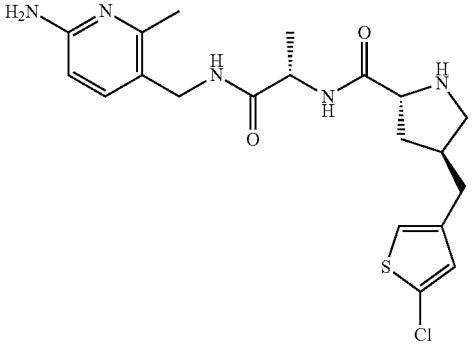 [SMILES: Cc1nc(N)ccc1CNC(=O)[C@H](C)NC(=O)[C@H]1C[C@H](Cc2csc(Cl)c2)CN1] | HCl | 436.08 | 435.15 |
| 1462 | 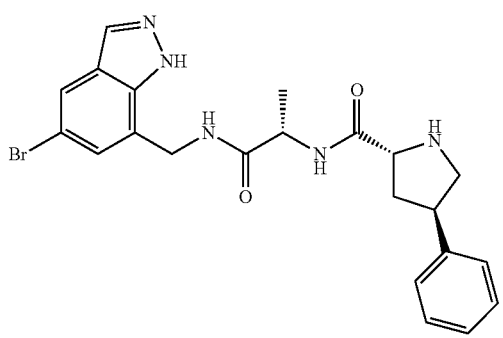 [SMILES: C[C@H](NC(=O)[C@H]1C[C@H](c2ccccc2)CN1)C(=O)NCc1cc(Br)cc2cn[nH]c12] | TFA | 470.05 | 469.11 |
| 1463 | 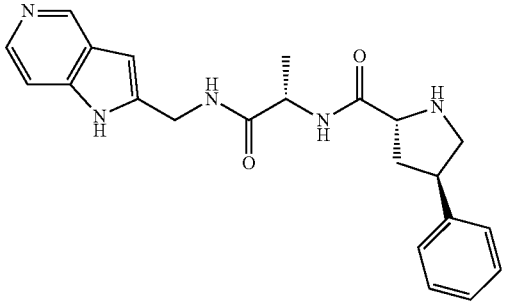 [SMILES: C[C@H](NC(=O)[C@H]1C[C@H](c2ccccc2)CN1)C(=O)NCc1cc2cnccc2[nH]1] | 2TFA | 392.16 | 391.2 |

TABLE 31-continued

Compound List

| Compound No. | Structure | Salt | Exact Mass (ES+; M + H, Obsd) | Exact Mass (Calc) |
|---|---|---|---|---|
| 1464 | 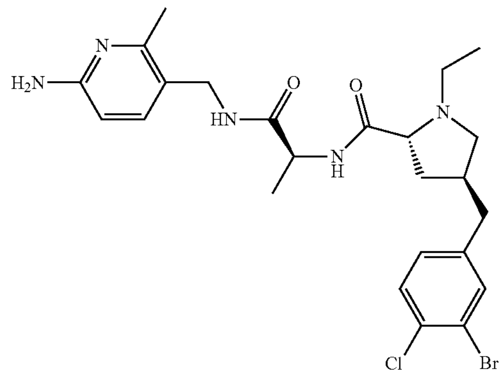 [SMILES: CCN1C[C@@H](Cc2ccc(Cl)c(Br)c2)C[C@@H]1C(=O)N[C@@H](C)C(=O)NCc1ccc(N)nc1C] | NA | 536.23 | 535.13 |
| 1465 | 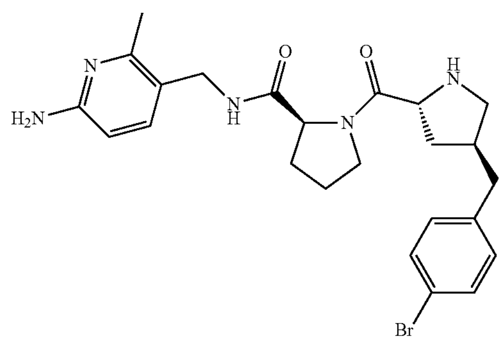 [SMILES: Cc1nc(N)ccc1CNC(=O)[C@@H]1CCCN1C(=O)[C@H]1C[C@H](Cc2ccc(Br)cc2)CN1] | 2TFA | 500.28 | 499.16 |
| 1466 | 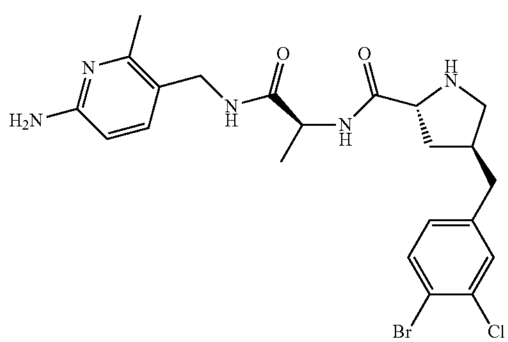 [SMILES: Cc1nc(N)ccc1CNC(=O)[C@H](C)NC(=O)[C@H]1C[C@H](Cc2ccc(Br)c(Cl)c2)CN1] | 2TFA | 508.37 | 507.1 |
| 1467 | 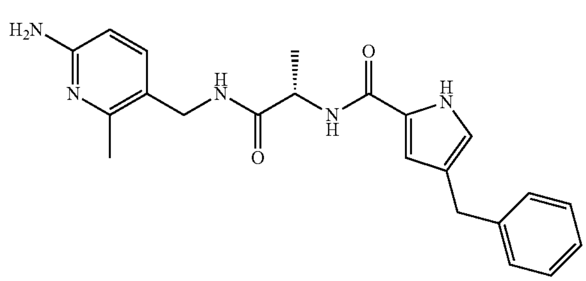 [SMILES: Cc1nc(N)ccc1CNC(=O)[C@H](C)NC(=O)c1cc(Cc2ccccc2)c[nH]1] | TFA | 392.19 | 391.2 |

TABLE 31-continued
Compound List
| Compound No. | Structure | Salt | Exact Mass (ES+; M + H, Obsd) | Exact Mass (Calc) |
|---|---|---|---|---|
| 1468 | 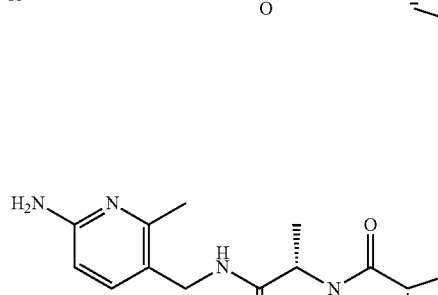 | TFA | 469.15 | 468.2 |
| 1469 | 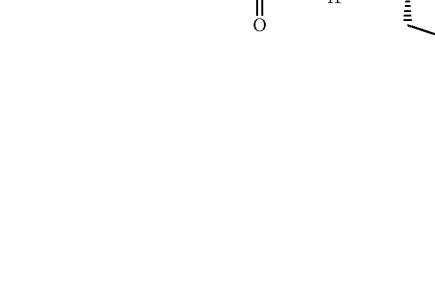 | HCl | 411.21 | 410.24 |
| 1470 | 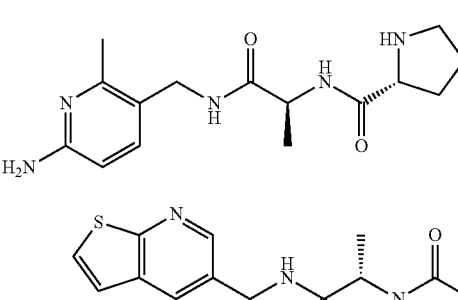 | 2TFA | 438.16 | 437.22 |
| 1471 | 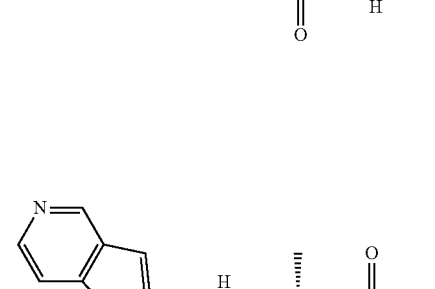 | 1TFA | 409.1 | 408.16 |
| 1472 | 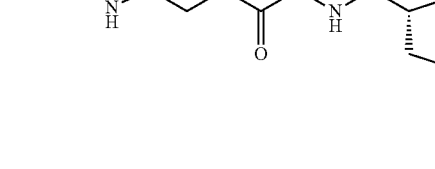 | 2TFA | 406.18 | 405.22 |

TABLE 31-continued

Compound List

| Compound No. | Structure | Salt | Exact Mass (ES+; M + H, Obsd) | Exact Mass (Calc) |
|---|---|---|---|---|
| 1473 | 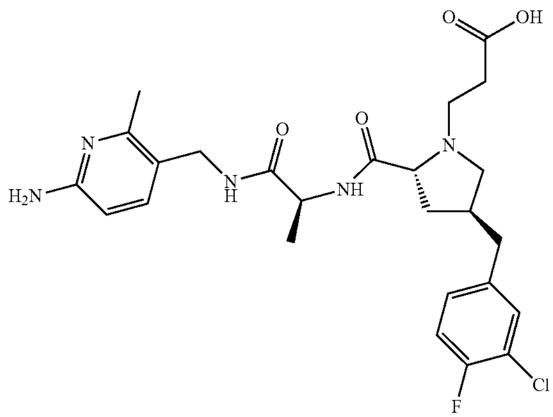 [SMILES: Cc1nc(N)ccc1CNC(=O)[C@H](C)NC(=O)[C@H]1C[C@H](Cc2ccc(F)c(Cl)c2)CN1CCC(=O)O] | 1TFA | 520.48 | 519.2 |
| 1474 | 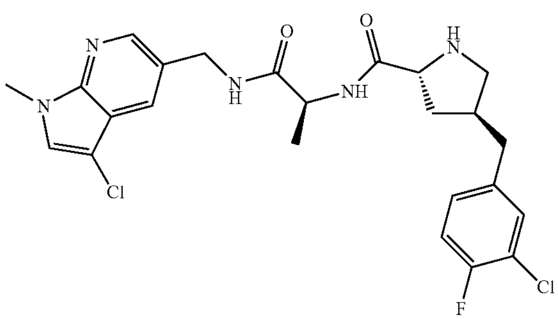 [SMILES: C[C@H](NC(=O)[C@H]1C[C@H](Cc2ccc(F)c(Cl)c2)CN1)C(=O)NCc1cnc2c(c1)c(Cl)cn2C] | TFA | 506.46 | 505.14 |
| 1475 | 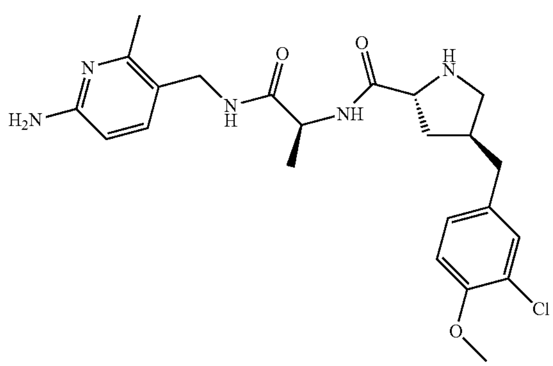 [SMILES: COc1ccc(C[C@@H]2CN[C@@H](C(=O)N[C@@H](C)C(=O)NCc3ccc(N)nc3C)C2)cc1Cl] | 2TFA | 460.55 | 459.2 |
| 1476 | 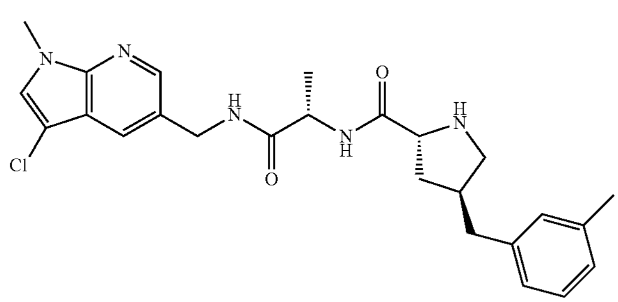 [SMILES: Cc1cccc(C[C@@H]2CN[C@@H](C(=O)N[C@@H](C)C(=O)NCc3cnc4c(c3)c(Cl)cn4C)C2)c1] | HCl | 468.16 | 467.21 |

TABLE 31-continued

Compound List

| Compound No. | Structure | Salt | Exact Mass (ES+; M + H, Obsd) | Exact Mass (Calc) |
|---|---|---|---|---|
| 1477 | 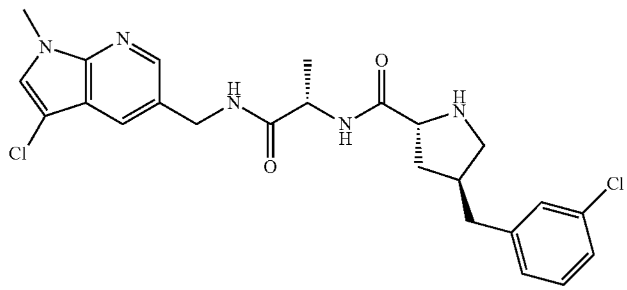 [SMILES: C[C@H](NC(=O)[C@H]1C[C@H](Cc2cccc(Cl)c2)CN1)C(=O)NCc1cnc2c(c1)c(Cl)cn2C] | TFA | 488.09 | 487.15 |
| 1478 | 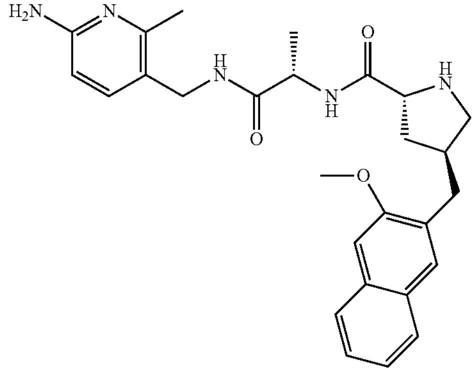 [SMILES: COc1cc2ccccc2cc1C[C@@H]1CN[C@@H](C(=O)N[C@@H](C)C(=O)NCc2ccc(N)nc2C)C1] | HCl | 476.18 | 475.26 |
| 1479 | 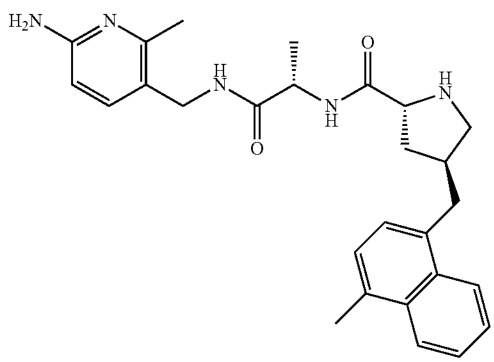 [SMILES: Cc1nc(N)ccc1CNC(=O)[C@H](C)NC(=O)[C@H]1C[C@H](Cc2ccc(C)c3ccccc23)CN1] | HCl | 460.19 | 459.26 |
| 1480 | 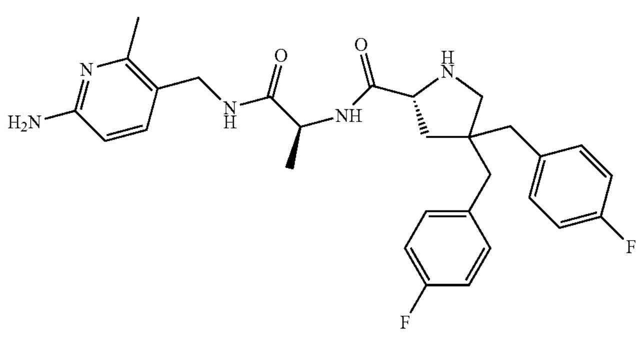 [SMILES: Cc1nc(N)ccc1CNC(=O)[C@H](C)NC(=O)[C@H]1CC(Cc2ccc(F)cc2)(Cc2ccc(F)cc2)CN1] | 2TFA | 522.45 | 521.26 |

TABLE 31-continued

Compound List

| Compound No. | Structure | Salt | Exact Mass (ES+; M + H, Obsd) | Exact Mass (Calc) |
|---|---|---|---|---|
| 1481 | 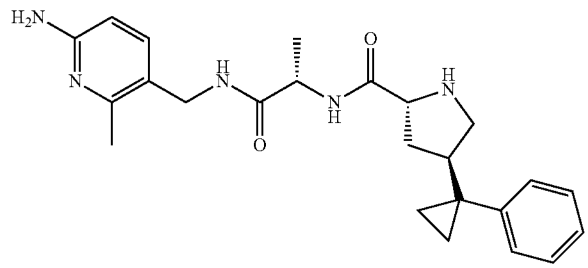 [SMILES: Cc1nc(N)ccc1CNC(=O)[C@H](C)NC(=O)[C@H]1C[C@H](C2(c3ccccc3)CC2)CN1] | 2TFA | 422.2 | 421.25 |
| 1482 | 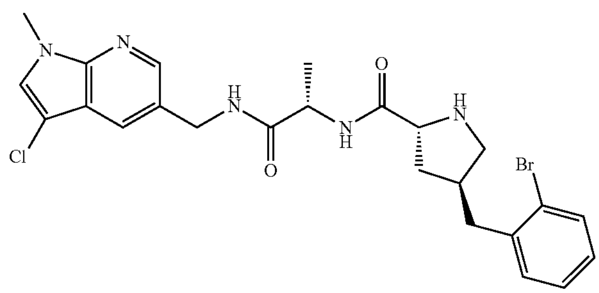 [SMILES: C[C@H](NC(=O)[C@H]1C[C@H](Cc2ccccc2Br)CN1)C(=O)NCc1cnc2c(c1)c(Cl)cn2C] | HCl | 532.05 | 531.1 |
| 1483 | 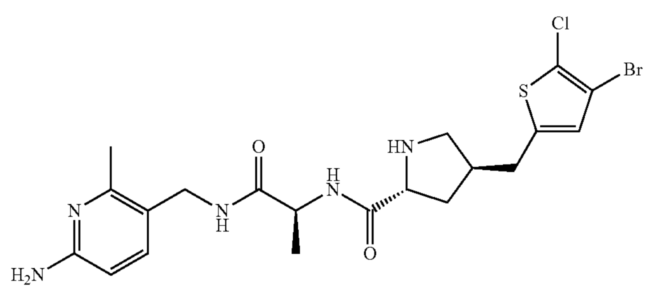 [SMILES: Cc1nc(N)ccc1CNC(=O)[C@H](C)NC(=O)[C@H]1C[C@H](Cc2cc(Br)c(Cl)s2)CN1] | 2TFA | 513.97 | 513.06 |
| 1484 | 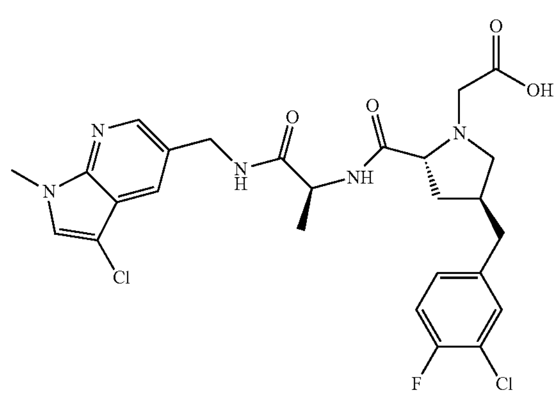 [SMILES: C[C@H](NC(=O)[C@H]1C[C@H](Cc2ccc(F)c(Cl)c2)CN1CC(=O)O)C(=O)NCc1cnc2c(c1)c(Cl)cn2C] | 1TFA | 564.28 | 563.15 |

TABLE 31-continued

Compound List

| Compound No. | Structure | Salt | Exact Mass (ES+; M + H, Obsd) | Exact Mass (Calc) |
|---|---|---|---|---|
| 1485 | 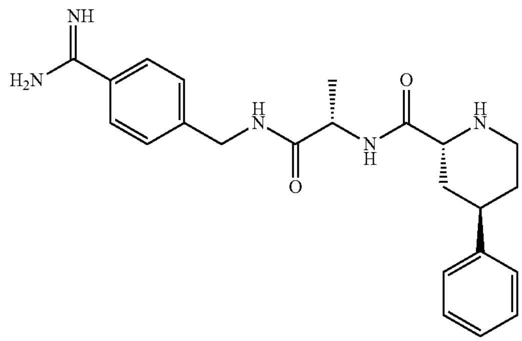 [SMILES: C[C@H](NC(=O)[C@H]1C[C@H](c2ccccc2)CCN1)C(=O)NCc1ccc(C(=N)N)cc1] | 2 HCl | 408.23 | 407.23 |
| 1486 | 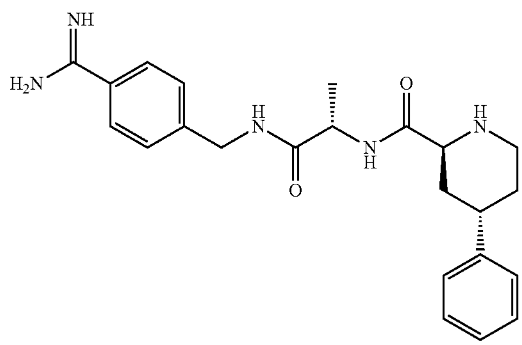 [SMILES: C[C@H](NC(=O)[C@@H]1C[C@@H](c2ccccc2)CCN1)C(=O)NCc1ccc(C(=N)N)cc1] | 2 HCl | 408.21 | 407.23 |
| 1487 | 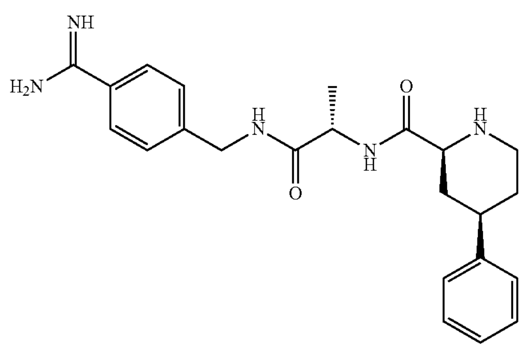 [SMILES: C[C@H](NC(=O)[C@@H]1C[C@H](c2ccccc2)CCN1)C(=O)NCc1ccc(C(=N)N)cc1] | 2HCl | 408.22 | 407.23 |
| 1488* Purchased | 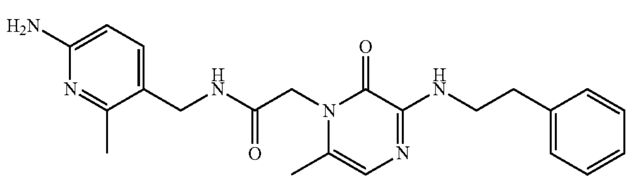 [SMILES: Cc1nc(N)ccc1CNC(=O)Cn1c(C)cnc(NCCc2ccccc2)c1=O] | NA | 407.17 | 406.21 |
| 1489 | 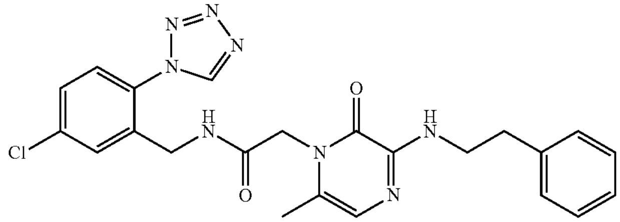 [SMILES: Cc1cnc(NCCc2ccccc2)c(=O)n1CC(=O)NCc1cc(Cl)ccc1-n1cnnn1] | NA | 479.09 | 478.16 |

TABLE 31-continued

Compound List

| Compound No. | Structure | Salt | Exact Mass (ES+; M + H, Obsd) | Exact Mass (Calc) |
| --- | --- | --- | --- | --- |
| 1490 | 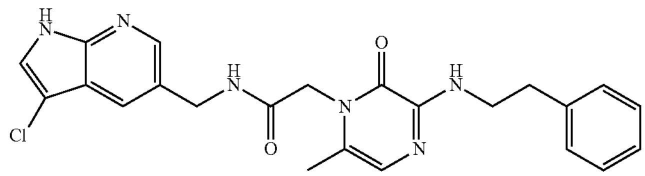 [SMILES: Cc1cnc(NCCc2ccccc2)c(=O)n1CC(=O)NCc1cnc2[nH]cc(Cl)c2c1] | AcOH | 451.05 | 450.16 |
| 1491 | 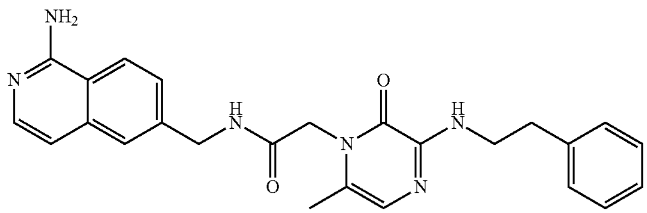 [SMILES: Cc1cnc(NCCc2ccccc2)c(=O)n1CC(=O)NCc1ccc2c(N)nccc2c1] | TFA | 443.17 | 442.21 |
| 1492 | 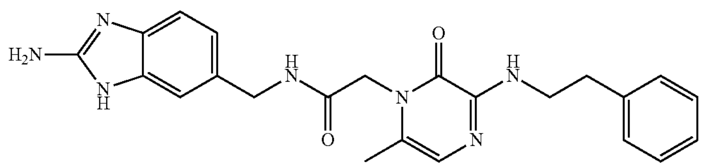 [SMILES: Cc1cnc(NCCc2ccccc2)c(=O)n1CC(=O)NCc1ccc2nc(N)[nH]c2c1] | TFA | 432.19 | 431.21 |
| 1493 | 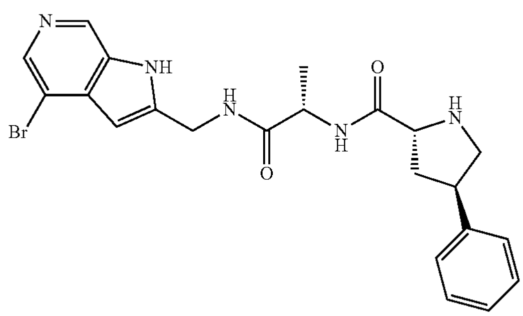 [SMILES: C[C@H](NC(=O)[C@H]1C[C@H](c2ccccc2)CN1)C(=O)NCc1cc2c(Br)cncc2[nH]1] | 2TFA | 470.03 | 469.11 |
| 1494 | 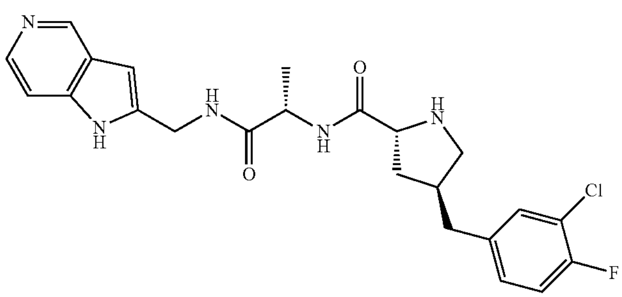 [SMILES: C[C@H](NC(=O)[C@H]1C[C@H](Cc2ccc(F)c(Cl)c2)CN1)C(=O)NCc1cc2cnccc2[nH]1] | 2TFA | 458.08 | 457.17 |
| 1495 | 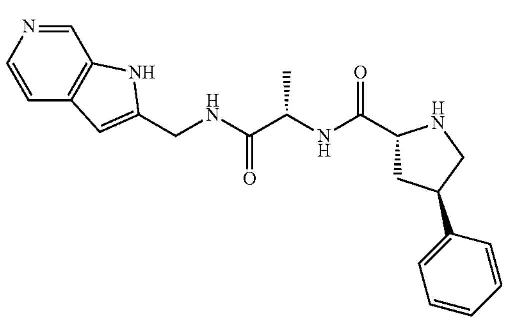 [SMILES: C[C@H](NC(=O)[C@H]1C[C@H](c2ccccc2)CN1)C(=O)NCc1cc2ccncc2[nH]1] | 2TFA | 392.16 | 391.20 |

TABLE 31-continued

Compound List

| Compound No. | Structure | Salt | Exact Mass (ES+; M + H, Obsd) | Exact Mass (Calc) |
|---|---|---|---|---|
| 1496 | 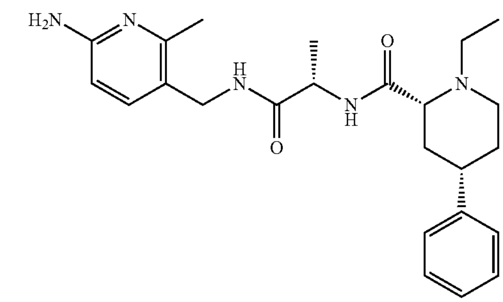 [SMILES: CCN1CC[C@H](c2ccccc2)C[C@@H]1C(=O)N[C@@H](C)C(=O)NCc1ccc(N)nc1C] | NA | 424.50 | 423.26 |
| 1497 | 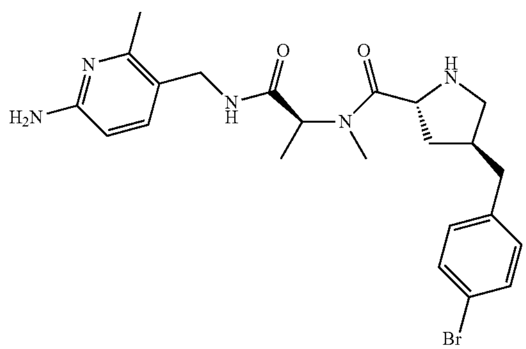 [SMILES: Cc1nc(N)ccc1CNC(=O)[C@H](C)N(C)C(=O)[C@H]1C[C@H](Cc2ccc(Br)cc2)CN1] | 2TFA | 488.25 | 487.16 |
| 2000 | 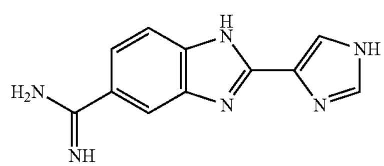 [SMILES: N=C(N)c1ccc2[nH]c(-c3c[nH]cn3)nc2c1] | 2 HCl | 227.11 | 226.10 |
| 2001 | 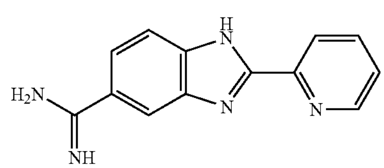 | 2 HCl | 238.11 | 237.10 |
| 2002 | 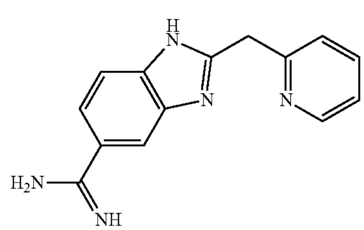 [SMILES: N=C(N)c1ccc2[nH]c(Cc3ccccn3)nc2c1] | 2 HCl | 252.07 | 251.12 |
| 2003 | 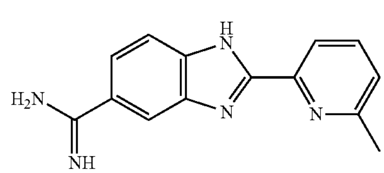 [SMILES: Cc1cccc(-c2nc3cc(C(=N)N)ccc3[nH]2)n1] | 2 HCl | 252.12 | 251.12 |

TABLE 31-continued

Compound List

| Compound No. | Structure | Salt | Exact Mass (ES+; M + H, Obsd) | Exact Mass (Calc) |
|---|---|---|---|---|
| 2004 | 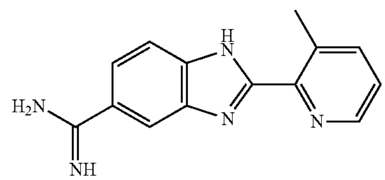 [SMILES: Cc1cccnc1-c1nc2cc(C(=N)N)ccc2[nH]1] | 2 HCl | 252.11 | 251.12 |
| 2005 | 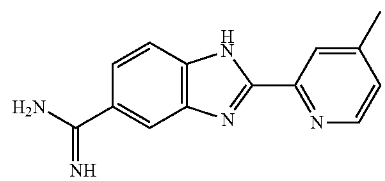 [SMILES: Cc1ccnc(-c2nc3cc(C(=N)N)ccc3[nH]2)c1] | 2 HCl | 252.13 | 251.12 |
| 2006* Purchased | 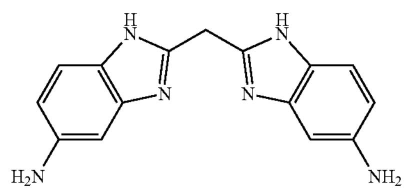 [SMILES: Nc1ccc2[nH]c(Cc3nc4cc(N)ccc4[nH]3)nc2c1] | | | 278.13 |
| 2007 | 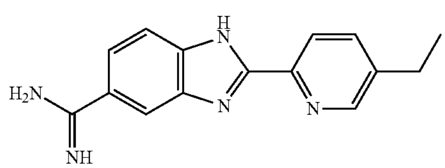 [SMILES: CCc1ccc(-c2nc3cc(C(=N)N)ccc3[nH]2)nc1] | 2 HCl | 266.11 | 265.13 |
| 2008 | 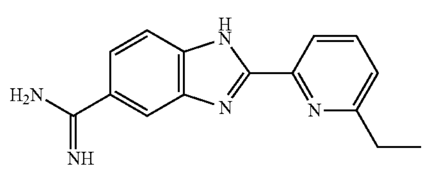 [SMILES: CCc1cccc(-c2nc3cc(C(=N)N)ccc3[nH]2)n1] | 2 HCl | 266.10 | 265.13 |
| 2009 | 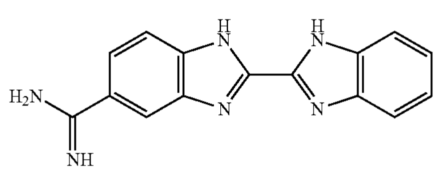 [SMILES: N=C(N)c1ccc2[nH]c(-c3nc4ccccc4[nH]3)nc2c1] | 2 HCl | 277.09 | 276.11 |
| 2010 | 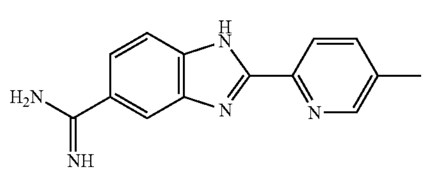 [SMILES: Cc1ccc(-c2nc3cc(C(=N)N)ccc3[nH]2)nc1] | 2 HCl | 252.11 | 251.12 |
| 2011 | 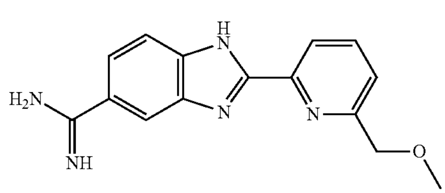 [SMILES: COCc1cccc(-c2nc3cc(C(=N)N)ccc3[nH]2)n1] | 2 HCl | 282.13 | 281.13 |

TABLE 31-continued

Compound List

| Compound No. | Structure | Salt | Exact Mass (ES+; M + H, Obsd) | Exact Mass (Calc) |
|---|---|---|---|---|
| 2012 | 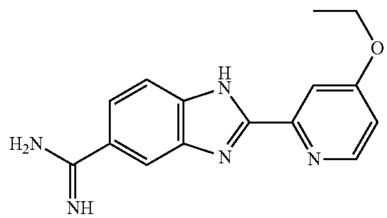 [SMILES: CCOc1ccnc(-c2nc3cc(C(=N)N)ccc3[nH]2)c1] | 2 HCl | 282.12 | 281.13 |
| 2013 | 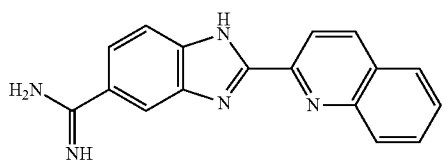 [SMILES: N=C(N)c1ccc2[nH]c(-c3ccc4ccccc4n3)nc2c1] | 2 HCl | 288.13 | 287.12 |
| 2014 | 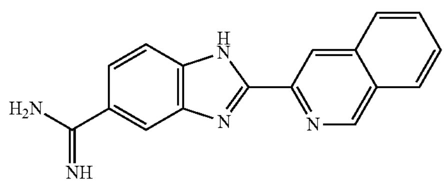 [SMILES: N=C(N)c1ccc2[nH]c(-c3cc4ccccc4cn3)nc2c1] | 2 HCl | 288.12 | 287.12 |
| 2015 | 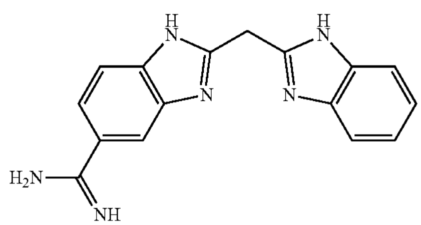 [SMILES: N=C(N)c1ccc2[nH]c(Cc3nc4ccccc4[nH]3)nc2c1] | 2 HCl | 291.07 | 290.13 |
| 2016 | 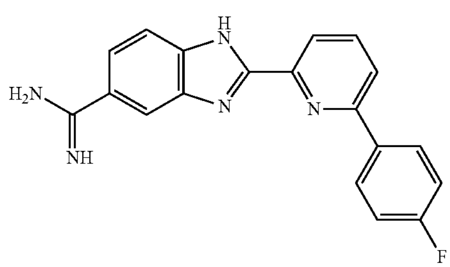 [SMILES: N=C(N)c1ccc2[nH]c(-c3cccc(-c4ccc(F)cc4)n3)nc2c1] | 2 HCl | 332.15 | 331.12 |
| 2017 | 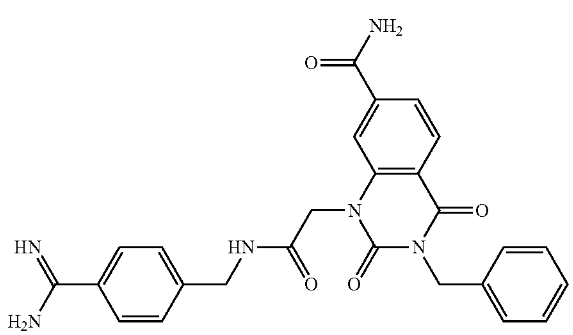 [SMILES: N=C(N)c1ccc(CNC(=O)Cn2c(=O)n(Cc3ccccc3)c(=O)c3ccc(C(N)=O)cc32)cc1] | HOAc | 485.16 | 484.19 |

TABLE 31-continued

Compound List

| Compound No. | Structure | Salt | Exact Mass (ES+; M + H, Obsd) | Exact Mass (Calc) |
|---|---|---|---|---|
| 2018 | 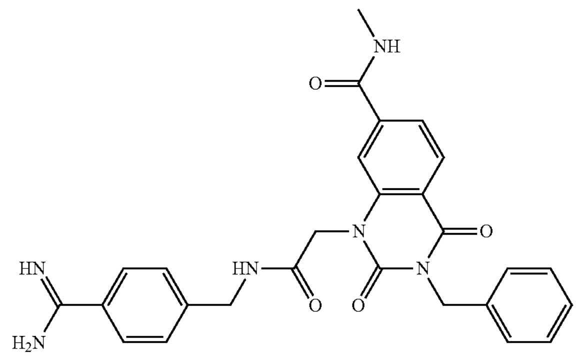 [SMILES: CNC(=O)c1ccc2c(=O)n(Cc3ccccc3)c(=O)n(CC(=O)NCc3ccc(C(=N)N)cc3)c2c1] | HOAc | 499.17 | 498.20 |
| 2019* Purchased | 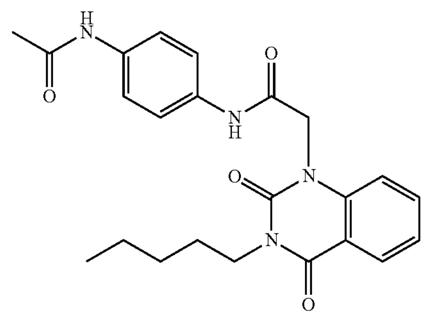 [SMILES: CCCCCn1c(=O)c2ccccc2n(CC(=O)Nc2ccc(NC(C)=O)cc2)c1=O] | N/A | N/A | 422.20 |
| 2020* Purchased | 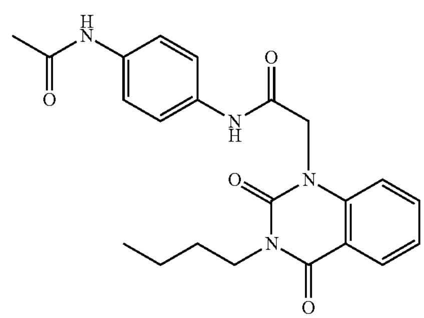 [SMILES: CCCCn1c(=O)c2ccccc2n(CC(=O)Nc2ccc(NC(C)=O)cc2)c1=O] | N/A | N/A | 408.45 |
| 2021 | 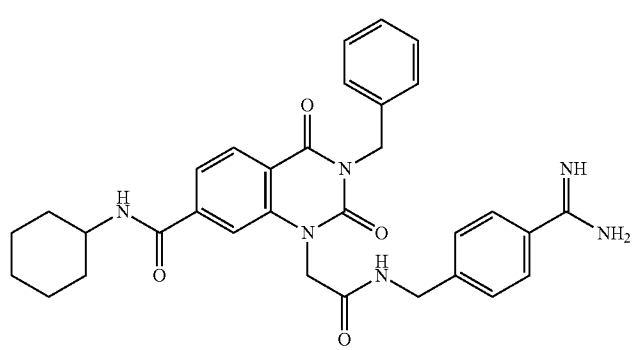 [SMILES: N=C(N)c1ccc(CNC(=O)Cn2c(=O)n(Cc3ccccc3)c(=O)c3ccc(C(=O)NC4CCCCC4)cc32)cc1] | N/A | 567.15 | 566.26 |

Example 305. Enzymatic Assay for MASP-2

The MASP-2 assay utilizes a fluorogenic substrate, based on the cleavage site for its natural substrate C2. The assay was run at room temperature in an assay buffer containing 20 mM Hepes, pH 7.4, 140 mM NaCl and 0.1% Tween 20. Assay parameters were adjusted such that the assay was linear with respect to time, enzyme and substrate concentrations. Under these optimized assays conditions, $IC_{50}$ values were equivalent to Ki values, except in a few cases of "tight binding" inhibitors. Cases of 'tight binding' or possible 'slow binding' inhibitors were handled by the methods described in Copeland R. A. (2013) Evaluation of Enzyme Inhibitors in Drug Discovery. 2nd Ed., John Wiley and Sons, Inc., Chapters 5-7.

The MASP-2 assay protocol was carried out as follows. Test compounds were serially diluted in DMSO and then 100 nL of each dilution was transferred to the assay plate(s). 10 µL of Assay Buffer was added, followed by 15 µL of Enzyme (MASP-2 (CCP1-CCP2-SP) in Assay Buffer. 15 µL of Substrate in Assay Buffer was then added and mixed to start the reactions. After 20 min at room temperature, 15 µL of a stop solution (0.1 M acetic acid) was added, mixed and the plates were read on a SpectraMax i3x Microplate Reader and exported as Excel files. Each assay plate included a "no inhibitor" (DMSO Only) control, a "no enzyme" control and a reference inhibitor control. % Activity values=100*(ave. test comp. fluorescence−ave. "no enz" fluorescence)/(ave. "DMSO only" fluorescence−ave. "no enz" fluorescence). $IC_{50}$ and Ki values were very reproducible, falling well within ±2-fold.

Example 306. Lectin Pathway Activation Assay in Human Serum Treated with Small Compounds Microtiter ELISA plate was coated with mannan from *Saccharomyces cerevisiae* (Sigma-Aldrich, M7504) for overnight at 4° C. in coating buffer [15 mM $Na_2CO_3$, 35 mM $NaHCO_3$]. Plate was blocked with 1% bovine serum albumin (BSA) (Sigma-Aldrich, A3294) in Tris-buffered Saline (TBS) [10 mM Tris-HCl, 140 mM NaCl] for 2 hours at room temperature. 1% human serum was incubated with serial dilutions of small compounds in GVB++ [4 mM Barbital, 145 mM NaCl, 0.2 mM $MgCl_2$, 0.2 mM $CaCl_2$, 1% Gelatin] and incubated for 15 minutes at room temperature. 100 µL of this mixture were then added to the plate and plate was incubated at 37° C. for up to an hour with gentle shaking, 200 rpm. After that, plate was washed thrice in wash buffer [TBS containing 5 mM $CaCl_2$ and 0.05% Tween-20] and 100 µL of rabbit anti human C3c (Dako, A0062) diluted 1:5000 in wash buffer were added and incubated at 37° C. for 30 minutes. Plate was washed and 100 µL of HRP goat anti rabbit IgG (Southern Biotech, 4050-05) diluted 1:8000 in wash buffer were added and incubated at room temperature for 30 minutes. After that, plate was washed three times and 100 µL/well of TMB Colorimetric substrate (Thermo Scientific, 34029) were added and incubated at room temperature for 5 minutes and the reaction was stop by adding 100 µL/well of 0.1 N sulfuric acid (BDH7230) and the absorbance was measured at 450 nm.

Example 307. Enzymatic Assay for Thrombin

The thrombin assay utilizes a fluorogenic peptide substrate (Boc-VPR-AMC (R&D Systems) and was run at room temperature in an assay buffer containing 20 mM Hepes, pH 7.4, 140 mM NaCl and 0.1% Tween 20. Assay parameters were adjusted such that the assay was linear with respect to time, enzyme and substrate concentrations. Under these optimized assays conditions, $IC_{50}$ values were equivalent to Ki values, except in a few cases of "tight binding" inhibitors. Cases of "tight binding" or possible "slow binding" inhibitors were handled by the methods described in Copeland R. A. (2013) Evaluation of Enzyme Inhibitors in Drug Discovery. 2nd Ed. John Wiley and Sons, Inc., Chapters 5-7.

The thrombin assay protocol was carried out as follows. Test compounds were serially diluted in DMSO and then 100 nl of each dilution was transferred to the assay plate(s). 10 µL of Assay Buffer was added, followed by 15 µL of enzyme (human α-thrombin (BioPharm Lab.)) in assay buffer. 15 µL of substrate in assay buffer were then added and mixed to start the reactions. After 20 min at room temperature, 15 µL of a stop solution (0.1 M acetic acid) was added, mixed and the plates were read on a SpectraMax i3x Microplate Reader and exported as Excel files. Each assay plate included a "no inhibitor" (DMSO Only) control, a "no enzyme" control and a reference inhibitor control. % Activity values=100*(ave. test comp. fluorescence−ave. "no enz" fluorescence)/(ave. "DMSO only" fluorescence−ave. "no enz" fluorescence). $IC_{50}$ and Ki values were very reproducible, falling well within ±2-fold.

The results of biological assays for the compounds listed in Table 31 are listed in Tables 32, 33 and 34 below.

TABLE 32

MASP-2/Thrombin/Lectin Pathway Inhibition for Compounds 1000-1229

| Compound | MASP-2 $K_i$ (µM) | mMASP-2 $K_i$ (µM) | Thrombin $K_i$ (µM) | Lectin Pathway $IC_{50}$ (µM) | MASP-2 vs. thrombin selectivity |
|---|---|---|---|---|---|
| 1000 | *** | ND | *** | ND | + |
| 1001 | ** | ND | *** | ND | -- |
| 1002 | ** | ND | **** | ND | ND |
| 1003 | *** | ND | **** | ND | -- |
| 1004 | *** | ND | **** | ND | -- |
| 1005 | ** | ND | **** | ND | -- |
| 1006 | **** | **** | **** | ND | -- |
| 1007 | **** | ** | * | ND | *** |
| 1008 | *** | ND | **** | + | -- |
| 1009 | ** | ND | *** | ND | -- |
| 1010 | **** | ND | -- | ND | **** |
| 1011 | **** | ND | **** | ++ | -- |
| 1012 | *** | ND | -- | ND | *** |
| 1013 | ** | ND | * | ND | ** |
| 1014 | ** | ND | -- | ND | ** |
| 1015 | *** | * | -- | + | * |
| 1016 | *** | * | -- | + | ** |
| 1017 | **** | ND | **** | ND | -- |
| 1018 |  | ND | /*** | -- | -- |
| 1019 | *** | ND | *** | ND | -- |
| 1020 | **** | ND | **** | ND | -- |
| 1021 | ** | -- | -- | -- | *** |
| 1022 | * | ND | *** | ND | -- |
| 1023 | *** | ND | **** | + | -- |

TABLE 32-continued

MASP-2/Thrombin/Lectin Pathway Inhibition for Compounds 1000-1229

| Compound | MASP-2 $K_i$ (µM) | mMASP-2 $K_i$ (µM) | Thrombin $K_i$ (µM) | Lectin Pathway $IC_{50}$ (µM) | MASP-2 vs. thrombin selectivity |
|---|---|---|---|---|---|
| 1024 | **** | ND | **** | +++/++++ | ** |
| 1025 | **** | ND | -- | ++ | **** |
| 1026 | *** | ND | **** | ND | ** |
| 1027 | **** | ND | **** | ++/+++ | -- |
| 1028 | ** | ND | **** | ND | -- |
| 1029 | ** | ND | *** | ND | -- |
| 1030 | **** | **** | ** | ++ | *** |
| 1031 | *** | ND | * | ND | ** |
| 1032 | **** | ND | ** | ND | **** |
| 1033 | ** | ND | ** | ND | -- |
| 1034 | **** | ND | *** | +/++ | * |
| 1035 | **** | ND | **** | ++++ | ** |
| 1036 | ** |  | */ | +++/++++ | ** |
| 1037 | **** | ND | *** | ND | *** |
| 1038 | **** | ND | **** | +++/++++ | * |
| 1039 | ** | * | -- | ND | *** |
| 1040 | **** | **** | -- | ++ | **** |
| 1041 | *** | ND | **** | + | -- |
| 1042 | **** | ND | **** | ++++ | ** |
| 1043 | **** | **** | *** | ++/+++ | ** |
| 1044 | **** | **** | **** | ND | ** |
| 1045 | **** | **** | **** | ND | ** |
| 1046 | **** | **** | **** | ND | ** |
| 1047 | **** | **** | **** | ++/+++ | ** |
| 1048 | **** | **** | **** | ++/+++ | ** |
| 1049 | **** | ND | **** | ND | ** |
| 1050 | **** | ND | ** | ND | ND |
| 1051 | ** | ND | **** | + | -- |
| 1053 | **** | ND | ** | ++ | ** |
| 1054 | *** | ND | ** | + | * |
| 1055 | *** | ND | **** | + | -- |
| 1056 | **** | ND | *** | ND | **** |
| 1057 | **** | ND | *** | ND | **** |
| 1058 | **** | ND | **** | ++/+++ | -- |
| 1059 | **** | **** | -- | ++/+++ | **** |
| 1060 | **/* | -- | -- | -- | *** |
| 1061 | **** | ND | *** | ND | * |
| 1062 | *** | ND | * | ND | *** |
| 1063 | **** | ND | *** | ND | ** |
| 1064 | *** | ND | ** | ND | ** |
| 1065 | **** | **** | * | ++++ | **** |
| 1066 | **** | ND | -- | ND | *** |
| 1067 | **** | **** | ** | ND | **** |
| 1068 | *** | ND | * | ND | ** |
| 1069 | **** | ND | **** | ++ | -- |
| 1070 | ** | ND | -- | ND | * |
| 1071 | **** | **** | ** | ND | *** |
| 1072 | **** | **** | **** | ND | ** |
| 1073 | **** | **** | **** | ND | ** |
| 1074 | **** | **** | **** | ND | ** |
| 1075 | **** | **** | **** | ND | ** |
| 1076 | **** | ND | **** | ND | ** |
| 1077 | ** | ND | **** | ND | -- |
| 1078 | **** | ND | ND | ++ | ND |
| 1079 | **** | ND | ND | + | ND |
| 1080 | **** | **** | **** | ++/+++ | ** |
| 1081 | **** | **** | **** | ++/+++ | ** |
| 1082 | **** | ND | **** | ND | * |
| 1083 | **** | ND | **** | + | -- |
| 1084 | **** | ND | **** | ND | ** |
| 1085 | **** | ND | **** | ND | ** |
| 1086 | **** | ND | **** | ND | ** |
| 1087 | **** | ND | **** | ND | ** |
| 1088 | **** | **** | *** | +++ | ** |
| 1089 | **** | ND | ** | ND | *** |
| 1090 | **** | **** | **/* | ++ | *** |
| 1091 | *** | **** | -- | + | *** |
| 1092 | **** | **** | **** | ++/+++ | -- |
| 1093 | **** | ND | **** | ND | -- |
| 1094 | **** | ND | **** | + | -- |
| 1095 | ** | ND | ** | ND | * |
| 1096 | *** | ND | **** | +/++ | -- |
| 1097 | **** | **** | **** | ND | *** |
| 1098 | **** | ND | ND | ++++ | ND |
| 1099 | **** | ND | **** | +++ | -- |

TABLE 32-continued

MASP-2/Thrombin/Lectin Pathway Inhibition for Compounds 1000-1229

| Compound | MASP-2 $K_i$ (μM) | mMASP-2 $K_i$ (μM) | Thrombin $K_i$ (μM) | Lectin Pathway $IC_{50}$ (μM) | MASP-2 vs. thrombin selectivity |
|---|---|---|---|---|---|
| 1100 | *** | ND | **** | ND | -- |
| 1101 | **** | **** | *** | ND | * |
| 1102 | *** | ND | **** | ND | -- |
| 1103 | **** | **** | **** | +++ | ** |
| 1104 | * | ND | *** | ND | -- |
| 1105 | ** | ND | *** | ND | -- |
| 1106 | *** | ND | **** | ND | -- |
| 1107 | **** | ND | **** | ++/+ | -- |
| 1108 | **** | **** | **** | ND | * |
| 1109 | ** | ND | **** | -- | -- |
| 1110 | **** | ND | **** | +++/++++ | * |
| 1111 | **** | ND | **** | ND | * |
| 1112 | **** | ND | **** | ND | ** |
| 1113 | ** | ND | *** | ND | -- |
| 1114 | **** | ND | **** | ++ | -- |
| 1115 | **** | ND | **** | ++ | -- |
| 1116 | *** | ND | **** | + | -- |
| 1117 | ** | ND | **** | ND | -- |
| 1118 | **** | **** | **** | ND | ** |
| 1119 | **** | ND | *** | ND | ** |
| 1120 | **** | ND | **** | ND | ** |
| 1121 | ** | ND | *** | ND | -- |
| 1122 | **** | ND | **** | ND | -- |
| 1123 | **** | ND | *** | ++ | ** |
| 1124 | **** | ND | **** | +++/++++ | -- |
| 1125 | **** | **** | **** | ND | -- |
| 1126 | **** | ND | **** | ND | -- |
| 1127 | *** | ND | **** | + | -- |
| 1128 | **** | **** | **** | ND | * |
| 1129 | **** | ND | **** | ++ | -- |
| 1130 | **** | ND | **** | ND | -- |
| 1131 | **** | ND | **** | ++ | -- |
| 1132 | *** | ND | ND | ND | ND |
| 1133 | **** | ND | **** | + | -- |
| 1134 | **** | **** | **** | ND | -- |
| 1135 | **** | ND | *** | ND | * |
| 1136 | **** | ND | *** | ND | *** |
| 1137 | *** | ND | ND | -- | ND |
| 1138 | ** | ND | **** | ND | -- |
| 1139 | **** | ** | *** | + | * |
| 1140 | **** | ND | **** | ND | -- |
| 1141 | **** | ND | **** | ND | -- |
| 1142 | **** | ND | **** | ND | * |
| 1143 | **** | **** | **** | ND | -- |
| 1144 | *** | ND | ND | ND | ND |
| 1145 | **** | ND | ND | +++ | ND |
| 1146 | **** | ND | *** | ND | * |
| 1147 | *** | ND | *** | ND | * |
| 1148 | **** | ND | ND | ND | ND |
| 1149 | **** | **** | **** | ND | ** |
| 1151 | **** | ND | **** | ND | -- |
| 1152 | **** | ND | **** | ND | * |
| 1153 | **** | ND | **** | ND | **** |
| 1154 | **** | ND | **** | ND | -- |
| 1156 | * | ND | */** | ND | -- |
| 1157 | * | ND | -- | ND | * |
| 1158 | * | ND | **** | ND | -- |
| 1170 | **** | * | -- | ND | **** |
| 1171 | * | * | -- | -- | * |
| 1192 | * | ND | -- | ND | * |
| 1194 | * | ND | ** | ND | -- |
| 1195 | * | ND | * | ND | -- |
| 1207 | ** | ND | *** | ND | -- |
| 1211 | **** | ND | **** | ND | -- |
| 1213 | * | ND | -- | ND | * |
| 1215 | ** | * | -- | ND | * |
| 1218 | **** | ND | **** | ND | -- |
| 1223 | **** | **** | **** | ND | *** |

TABLE 32-continued

MASP-2/Thrombin/Lectin Pathway Inhibition for Compounds 1000-1229

| Compound | MASP-2 K$_i$ (μM) | mMASP-2 K$_i$ (μM) | Thrombin K$_i$ (μM) | Lectin Pathway IC$_{50}$ (μM) | MASP-2 vs. thrombin selectivity |
|---|---|---|---|---|---|
| 1229 | ** | ND | ** | ND | * |
| 999 (melagatran control) | **** | **** | **** | +/++ | -- |

MASP-2 Inhibition and Thrombin Inhibition Ki Values:
* K$_i$ of less than 25 μM
** K$_i$ of less than 10 μM
*** K$_i$ of less than 2.5 μM
**** K$_i$ of less than 0.5 μM
-- K$_i$ of >25 μM
Lectin Pathway Inhibition
-- IC$_{50}$ value >50 μM
+ IC$_{50}$ value in the range of 5 μM to 50 μM
++ IC$_{50}$ value in the range of 0.5 μM to 5 μM
+++ IC$_{50}$ value in the range of 0.05 μM to 0.5 μM
++++ IC$_{50}$ value <0.05 μM
Selectivity of compound for MASP-2 inhibition versus thrombin:
-- less than 1.0-fold
* 1.0 to 5.0-fold
** 5.0 to 25-fold
*** 25 to 100-fold
**** >100-fold
ND Not determined

TABLE 33

MASP-2/Thrombin/Lectin Pathway Inhibition for Compounds 1230-1497

| Compound | MASP-2 K$_i$ (μM) | mMASP-2 K$_i$ (μM) | Thrombin K$_i$ (μM) | Lectin Pathway IC$_{50}$ (μM) | MASP-2 vs. thrombin selectivity |
|---|---|---|---|---|---|
| 1230 | **** | **** | * | ++++ | **** |
| 1231 | **** | **** | ** | ND | **** |
| 1232 | *** | ND | **** | ND | -- |
| 1233 | **** | **** | *** | ND | * |
| 1234 | **** | **** | * | ND | *** |
| 1235 | **** | ND | * | ND | *** |
| 1236 | **** | **** | **** | ND | * |
| 1237 | * | ND | *** | ND | -- |
| 1238(:02 | **** | **** | ** | ND | *** |
| 1239 | **** | **** | ** | ++ | ** |
| 1240 | *** | ND | * | ++ | ** |
| 1241 | **** | **** | **** | ND | * |
| 1242 | *** | ** | ** | ND | ** |
| 1243 | * | ND | -- | ND | ND |
| 1244 | *** | ND | -- | ND | ** |
| 1245 | **** | * | * | ND | **** |
| 1246 | * | ND | * | ND | * |
| 1247 | **** | **** | *** | ND | *** |
| 1248 | **** | **** | *** | ND | ** |
| 1249 | **** | **** | * | ND | **** |
| 1250 | **** | **** | **** | ND | * |
| 1251 | *** | ND | **** | ND | -- |
| 1252 | **** | ND | ** | ND | *** |
| 1253 | **** | *** | -- | +++ | ND |
| 1254 | **** | ND | * | ND | *** |
| 1255 | *** | ND | -- | ND | ND |
| 1256 | **** | ND | **** | ND | * |
| 1257 | **** | * | -- | ND | *** |
| 1258 | ** | ND | -- | ND | ND |
| 1259 | ** | ND | -- | ND | ND |
| 1260 | ** | ND | -- | ND | ND |
| 1261 | * | * | -- | ND | * |
| 1262 | **** | ND | *** | ND | *** |
| 1263 | ** | ** | -- | ND | ND |
| 1264 | ** | * | -- | ND | ND |
| 1265 | **** | ** | -- | ND | **** |
| 1266 | *** | -- | -- | ND | ** |
| 1267 | ** | -- | -- | ND | ND |
| 1268 | **** | **** | **** | ND | * |
| 1269 | *** | * | -- | ND | ** |
| 1270 | **** | **** | **** | ND | ** |

TABLE 33-continued

MASP-2/Thrombin/Lectin Pathway Inhibition for Compounds 1230-1497

| Compound | MASP-2 $K_i$ (μM) | mMASP-2 $K_i$ (μM) | Thrombin $K_i$ (μM) | Lectin Pathway $IC_{50}$ (μM) | MASP-2 vs. thrombin selectivity |
|---|---|---|---|---|---|
| 1271 | ** | -- | -- | ND | ND |
| 1272 | **** | **** | *** | ND | *** |
| 1273 | * | * | -- | ND | ND |
| 1274 | ** | * | -- | ND | ** |
| 1275 | *** | -- | -- | ND | *** |
| 1276 | **** | **** | *** | ND | *** |
| 1277 | **** | **** | **** | ND | ** |
| 1278 | **** | **** | ** | ND | *** |
| 1279 | *** | -- | ** | ND | ** |
| 1280 | ** | * | -- | ND | ND |
| 1281 | ** | -- | -- | ND | ND |
| 1282 | * | -- | -- | ND | ND |
| 1283 | **** | *** | ** | ND | *** |
| 1284 | **** | **** | **** | ND | * |
| 1285 | *** | *** | ** | ND | ** |
| 1286 | ** | **** | *** | ND | -- |
| 1287 | * | -- | -- | ND | ND |
| 1288 | ** | ** | -- | ND | ND |
| 1289 | **** | **** | **** | ND | -- |
| 1290 | **** | **** | *** | ND | ** |
| 1291 | *** | * | -- | ND | ND |
| 1292 | ** | * | -- | ND | ND |
| 1293 | ** | ** | -- | ND | * |
| 1294 | ** | ** | -- | ND | ND |
| 1295 | **** | **** | ** | ND | *** |
| 1296 | ** | -- | -- | ND | ** |
| 1297 | **** | **** | * | ND | **** |
| 1298 | **** | ** | -- | ND | ND |
| 1299 | **** | * | -- | ND | **** |
| 1300 | **** | **** | ** | ND | *** |
| 1301 | ** | -- | -- | ND | ND |
| 1302 | **** | **** | *** | ND | *** |
| 1303 | **** | ** | -- | ND | *** |
| 1304 | **** | *** | *** | +++ | *** |
| 1305 | *** | **** | -- | ND | ** |
| 1306 | **** | **** | **** | ND | * |
| 1307 | **** | **** | -- | +++ | **** |
| 1308 | *** | *** | * | ND | ** |
| 1309 | **** | **** | -- | ND | **** |
| 1310 | *** | -- | -- | ND | *** |
| 1311 | ** | ** | -- | ND | * |
| 1312 | **** | **** | **** | ND | * |
| 1313 | ** | -- | * | ND | * |
| 1314 | * | -- | -- | ND | * |
| 1315 | *** | **** | ** | ND | * |
| 1316 | **** | **** | *** | ND | *** |
| 1317 | **** | *** | -- | ND | ND |
| 1318 | **** | **** | ** | ND | **** |
| 1319 | **** | * | ** | ND | ** |
| 1320 | **** | *** | *** | ND | ** |
| 1321 | * | -- | -- | ND | ND |
| 1322 | **** | *** | * | ND | *** |
| 1323 | -- | * | -- | ND | ND |
| 1324 | **** | **** | *** | +++ | *** |
| 1325 | *** | * | **** | ND | -- |
| 1326 | **** | **** | * | ND | *** |
| 1327 | **** | **** | **** | ND | *** |
| 1328 | **** | **** | *** | +++ | **** |
| 1329 | **** | **** | *** | ND | * |
| 1330 | **** | **** | **** | ND | *** |
| 1331 | **** | **** | -- | +++ | **** |
| 1332 | * | ** | -- | ND | ND |
| 1333 | ** | * | -- | ND | ND |
| 1334 | **** | **** | **** | +++ | -- |
| 1335 | **** | **** | ** | ND | *** |
| 1336 | * | -- | -- | ND | ND |
| 1337 | **** | **** | *** | ++ | **** |
| 1338 | **** | **** | -- | +++ | **** |
| 1339 | **** | **** | **** | ++++ | ** |
| 1340 | **** | **** | **** | ND | ** |
| 1341 | * | -- | *** | ND | -- |
| 1342 | **** | *** | * | ND | **** |
| 1343 | **** | **** | ** | +++ | **** |
| 1344 | **** | **** | ** | ND | **** |
| 1345 | **** | **** | **** | ++++ | **** |

TABLE 33-continued

MASP-2/Thrombin/Lectin Pathway Inhibition for Compounds 1230-1497

| Compound | MASP-2 K$_i$ (μM) | mMASP-2 K$_i$ (μM) | Thrombin K$_i$ (μM) | Lectin Pathway IC$_{50}$ (μM) | MASP-2 vs. thrombin selectivity |
|---|---|---|---|---|---|
| 1346 | * | -- | -- | ND | ND |
| 1347 | **** | **** | *** | ++++ | *** |
| 1348 | **** | **** | **** | ++++ | *** |
| 1349 | *** | ** | -- | ND | ** |
| 1350 | **** | **** | ** | ++ | **** |
| 1351 | **** | **** | -- | ++++ | **** |
| 1352 | **** | **** | *** | +++ | *** |
| 1353 | **** | **** | **** | ++++ | *** |
| 1354 | **** | *** | ** | ND | *** |
| 1355 | **** | * | -- | ND | ND |
| 1356 | **** | **** | -- | +++ | **** |
| 1357 | **** | **** | -- | ++++ | **** |
| 1358 | *** | -- | -- | ND | ND |
| 1359 | *** | * | -- | ND | ** |
| 1360 | **** | **** | -- | +++ | **** |
| 1361 | **** | **** | -- | ++++ | **** |
| 1362 | *** | *** | *** | ND | * |
| 1363 | **** | **** | ** | +++ | **** |
| 1364 | *** | * | -- | ND | ND |
| 1365 | **** | **** | -- | ++++ | **** |
| 1366 | ** | ** | -- | ND | ND |
| 1367 | **** | * | -- | ND | ND |
| 1368 | *** | * | -- | +++ | ** |
| 1369 | **** | **** | -- | ND | **** |
| 1370 | **** | *** | -- | +++ | ND |
| 1371 | **** | *** | **** | +++ | -- |
| 1372 | **** | **** | **** | +++ | ** |
| 1373 | **** | **** | *** | +++ | *** |
| 1374 | **** | **** | -- | ND | ND |
| 1375 | *** | * | * | ++ | ** |
| 1376 | *** | -- | -- | ND | ND |
| 1377 | *** | -- | * | +++ | ** |
| 1378 | **** | **** | *** | ++ | * |
| 1379 | **** | **** | -- | ++ | **** |
| 1380 | *** | **** | -- | -- | *** |
| 1381 | *** | * | * | ++ | ** |
| 1382 | **** | ** | -- | + | *** |
| 1383 | *** | ** | -- | + | ND |
| 1384 | * | -- | -- | ND | * |
| 1385 | **** | **** | **** | +++ | ** |
| 1386 | * | -- | -- | ND | ND |
| 1387 | ** | * | -- | ND | ND |
| 1388 | **** | **** | -- | ++++ | **** |
| 1389 | **** | ** | -- | ++ | **** |
| 1390 | ** | -- | -- | ND | ND |
| 1391 | **** | **** | -- | ++ | **** |
| 1392 | **** | **** | *** | ++ | *** |
| 1393 | **** | **** | **** | +++ | * |
| 1394 | ** | -- | * | ND | * |
| 1395 | *** | ** | -- | + | ND |
| 1396 | **** | **** | -- | ++ | **** |
| 1397 | **** | **** | -- | +++ | **** |
| 1398 | **** | *** | -- | +++ | ND |
| 1399 | **** | **** | * | +++ | **** |
| 1400 | **** | ** | -- | ++ | ND |
| 1401 | **** | *** | -- | ND | ND |
| 1402 | **** | *** | **** | ND | * |
| 1403 | **** | *** | -- | ND | ND |
| 1404 | **** | **** | **** | ND | ** |
| 1405 | **** | *** | *** | ND | ** |
| 1406 | **** | **** | ** | +++ | **** |
| 1407 | **** | **** | ** | +++ | **** |
| 1408 | **** | ** | ** | ND | ** |
| 1409 | **** | ** | **** | ++ | * |
| 1410 | **** | *** | *** | ++ | *** |
| 1411 | **** | **** | -- | +++ | ND |
| 1412 | **** | ** | -- | ND | ND |
| 1413 | *** | ** | -- | ND | *** |
| 1414 | **** | **** | **** | +++ | -- |
| 1415 | **** | **** | **** | +++ | * |
| 1416 | **** | **** | **** | +++ | ** |
| 1417 | *** | ** | -- | ND | ND |
| 1418 | ** | * | -- | ND | ND |
| 1419 | **** | **** | **** | ++++ | * |
| 1420 | **** | **** | ** | +++ | **** |

TABLE 33-continued

MASP-2/Thrombin/Lectin Pathway Inhibition for Compounds 1230-1497

| Compound | MASP-2 $K_i$ (μM) | mMASP-2 $K_i$ (μM) | Thrombin $K_i$ (μM) | Lectin Pathway $IC_{50}$ (μM) | MASP-2 vs. thrombin selectivity |
|---|---|---|---|---|---|
| 1421 | **** | *** | * | ND | **** |
| 1422 | **** | **** | ** | ++ | **** |
| 1423 | **** | **** | ** | +++ | **** |
| 1424 | *** | *** | **** | ND | ND |
| 1425 | ** | *** | -- | ND | ND |
| 1426 | **** | *** | *** | ++++ | *** |
| 1427 | **** | **** | -- | ND | **** |
| 1428 | **** | *** | * | ++ | **** |
| 1429 | **** | **** | ** | ++ | **** |
| 1430 | **** | **** | -- | ++ | **** |
| 1431 | **** | **** | * | +++ | **** |
| 1432 | **** | **** | * | ++ | **** |
| 1433 | **** | **** | *** | +++ | **** |
| 1434 | * | * | -- | ND | ND |
| 1435 | **** | **** | * | ++ | **** |
| 1436 | *** | -- | * | ND | ** |
| 1437 | *** | ** | -- | ND | ** |
| 1438 | **** | *** | **** | ++ | ** |
| 1439 | **** | ** | -- | ND | ND |
| 1440 | **** | ** | -- | ND | ND |
| 1441 | **** | **** | -- | +++ | ND |
| 1442 | **** | **** | -- | ++ | ND |
| 1443 | **** | **** | *** | ++ | *** |
| 1444 | **** | **** | **** | ++ | ** |
| 1445 | **** | *** | -- | + | **** |
| 1446 | **** | *** | -- | + | **** |
| 1447 | **** | **** | ** | ++ | **** |
| 1448 | **** | ** | -- | ND | **** |
| 1449 | **** | **** | ** | ++ | **** |
| 1450 | **** | **** | ** | +++ | **** |
| 1451 | **** | **** | * | ++ | **** |
| 1452 | **** | **** | *** | ++ | **** |
| 1453 | **** | **** | * | ++++ | **** |
| 1454 | **** | **** | *** | ++ | *** |
| 1455 | **** | **** | -- | ND | **** |
| 1456 | **** | *** | -- | + | ND |
| 1457 | * | ** | -- | ND | ND |
| 1458 | **** | **** | -- | ND | **** |
| 1459 | **** | **** | ** | ND | **** |
| 1460 | **** | **** | -- | ND | **** |
| 1461 | **** | **** | *** | ND | **** |
| 1462 | *** | ** | * | ND | ** |
| 1463 | **** | **** | -- | ND | ND |
| 1464 | **** | **** | -- | ND | ND |
| 1465 | **** | *** | **** | ND | * |
| 1466 | **** | **** | * | ND | **** |
| 1467 | **** | *** | -- | ND | **** |
| 1468 | **** | **** | -- | ND | **** |
| 1469 | **** | **** | ** | ND | **** |
| 1470 | **** | **** | ** | ND | **** |
| 1471 | ** | ** | -- | ND | ND |
| 1472 | **** | **** | ** | ND | **** |
| 1473 | **** | **** | -- | ND | ND |
| 1474 | **** | **** | -- | ND | **** |
| 1475 | **** | **** | * | ND | **** |
| 1476 | **** | **** | ** | ND | **** |
| 1477 | **** | **** | * | ND | **** |
| 1478 | **** | **** | * | ND | **** |
| 1479 | **** | **** | * | ND | **** |
| 1480 | **** | *** | -- | ND | **** |
| 1481 | **** | **** | ** | ND | **** |
| 1482 | **** | **** | *** | ND | *** |
| 1483 | **** | **** | * | ND | **** |
| 1484 | *** | *** | -- | ND | ND |
| 1485 | **** | **** | *** | ND | ** |
| 1486 | *** | **** | ** | ND | ** |
| 1487 | **** | ND | -- | ND | *** |
| 1488*Purchased | **** | ** | **** | ++ | -- |
| 1489 | **** | *** | **** | ND | -- |
| 1490 | **** | ** | **** | + | -- |
| 1491 | *** | **** | **** | + | -- |
| 1492 | **** | **** | **** | +++ | ** |

TABLE 33-continued

MASP-2/Thrombin/Lectin Pathway Inhibition for Compounds 1230-1497

| Compound | MASP-2 $K_i$ (µM) | mMASP-2 $K_i$ (µM) | Thrombin $K_i$ (µM) | Lectin Pathway $IC_{50}$ (µM) | MASP-2 vs. thrombin selectivity |
|---|---|---|---|---|---|
| 1493 | * | -- | * | ND | * |
| 1494 | **** | **** | ** | ND | **** |
| 1495 | ** | *** | -- | ND | ** |
| 1496 | **** | *** | -- | ND | ND |
| 1497 | **** | ** | ** | ND | ** |

MASP-2 Inhibition and Thrombin Inhibition Ki Values:
* 10 µM < $K_i$ ≤ 25 µM
** 2.5 µM ≤ $K_i$ < 10 µM
*** 0.5 µM ≤ $K_i$ < 2.5 µM
**** $K_i$ <0.5 µM
-- $K_i$ of >25 µM
ND Not determined
Lectin Pathway Inhibition
+ 5 µM < $IC_{50}$ ≤ 50 µM
++ 0.5 µM ≤ $IC_{50}$ < 5 µM
+++ 0.05 µM ≤ $K_i$ < 0.5 µM
++++ $K_i$ <0.05 µM
-- $IC_{50}$ >50 µM
Selectivity of compound for MASP-2 inhibition versus thrombin:
-- <1.0-fold
* ≥1.0 to <5.0-fold
** ≥5.0 to <25-fold
*** ≥25 to <100-fold
**** ≥100-fold
ND Not determined

TABLE 34

MASP-2/Thrombin/Lectin Pathway Inhibition

| Compound No. | MASP-2 $K_i$ (µM) | Thrombin $K_i$ (µM) | Lectin $K_i$ | MASP-2 versus thrombin selectivity |
|---|---|---|---|---|
| 2000 | **** (+Zn) | ** (+Zn) | ND | ++ (+Zn) |
|  | -- (+EDTA) | -- (+EDTA) |  |  |
| 2001 | **** (+Zn) | *** (+Zn) | ND | ++ (+Zn) |
|  | -- (+EDTA) | -- (+EDTA) |  |  |
| 2002 | *** (+Zn) | * (+Zn) | ND | ++ (+Zn) |
|  | -- (+EDTA) | -- (+EDTA) |  |  |
| 2003 | ***** (+Zn) | *** (+Zn) | ND | +++ (+Zn) |
|  | -- (+EDTA) | -- (+EDTA) |  |  |
| 2004 | **** (+Zn) | **** (+Zn) | ND | + (+Zn) |
|  | -- (+EDTA) | -- (+EDTA) |  |  |
| 2005 | ***** (+Zn) | ***** (+Zn) | ND | + (+Zn) |
|  | -- (+EDTA) | -- (+EDTA) |  |  |
| 2006 | ** (+Zn) | -- (+Zn) | ND | + (+Zn) |
|  | -- (+EDTA) | -- (+EDTA) |  |  |
| 2007 | **** (+Zn) | *** (+Zn) | ND | ++ (+Zn) |
|  | -- (+EDTA) | -- (+EDTA) |  |  |
| 2008 | **** (+Zn) | ** (+Zn) | ND | +++ (+Zn) |
|  | -- (+EDTA) | -- (+EDTA) |  |  |
| 2009 | **** (+Zn) | *** (+Zn) | ND | ++ (+Zn) |
|  | -- (+EDTA) | * (+EDTA) |  |  |
| 2010 | ***** (+Zn) | *** (+Zn) | ND | ++ (+Zn) |
|  | -- (+EDTA) | * (+EDTA) |  |  |
| 2011 | **** (+Zn) | *** (+Zn) | ND | ++ (+Zn) |
|  | -- (+EDTA) | -- (+EDTA) |  |  |
| 2012 | ***** (+Zn) | **** (+Zn) | ND | + (+Zn) |
|  | -- (+EDTA) | -- (+EDTA) |  |  |
| 2013 | **** (+Zn) | ** (+Zn) | ND | ++++ (+Zn) |
|  | -- (+EDTA) | -- (+EDTA) |  |  |
| 2014 | **** (+Zn) | *** (+Zn) | ND | +++ (+Zn) |
|  | -- (+EDTA) | * (+EDTA) |  |  |
| 2015 | *** (−Zn) | *** (−Zn) | ND | + (+Zn) |
|  | ***** (+Zn) | **** (+Zn) |  |  |
|  | -- (+EDTA)] | -- (+EDTA)] |  |  |
| 2016 | **** (+Zn) | * (+Zn) | ND | +++ (+Zn) |
|  | -- (+EDTA) | * (+EDTA) |  |  |
| 2017 | *** | -- | ND | >++ |
| 2018 | *** | -- | ND | >++ |
| 2019 | ** | -- | ND | >+ |
| 2020 | * | -- | ND | >+ |
| 2021 | ** | -- | + | >++ |

MASP-2 Inhibition and Thrombin Inhibition Ki values:
* $K_i$ of less than 25 µM
** $K_i$ of less than 10 µM
*** $K_i$ of less than 2.5 µM
**** $K_i$ of less than 0.5 µM
***** $K_i$ of less than 0.05 µM
-- $K_i$ of >25 µM
Lectin Pathway Inhibition:
-- $IC_{50}$ value >50 µM
+ $IC_{50}$ value in the range of 5 µM to 50 µM
Selectivity of compound for MASP-2 versus thrombin:
-- less than 1.0-fold
+ 1.0 to 5.0-fold
++ 5.0 to 25-fold
+++ 25 to 100-fold
++++ >100-fold
ND Not determined Example 308. MASP-2 Protein Preparation This example illustrates the preparation of recombinant MASP-2 protein, based on UniProt O00187, human mannan-binding lectin serine protease 2. Expression constructs for human MASP-2 CCP2-SP and CCP2-SP-6HIS were generated for recombinant expression in *E. coli* cells.

Recombinant expression of MASP-2 in *E. coli* as inclusion bodies and protein purification was carried out according to methods described in Ambrus G. et al., 2003, with minor modifications. For the HIS tagged version, the MASP-2 protein (CCP2-SP-6HIS) was purified under denaturing conditions according to the methods described in Ni-NTA Superflow Cartridge Handbook, Qiagen, March 2007.

Purification of MASP-2 included extraction, unfolding, refolding and chromatography using standard methods as described by Harmat et al., J. Mol. Biol. 2004; 342:1533-1546; and Gal et al., J. Biol. Chem. 2005; 280:33435-33444; and Ambrus et al. J Immunol. 2003 Feb. 1; 170(3):1374-82. After size exclusion chromatography, the recombinant MASP-2 protein was concentrated from 5 mg/mL to 20 mg/mL with spin concentrator (Amicon NMWL 10 kDa). Concentrated MASP-2 protein samples were flash-frozen and stored until thawing for complex formation. Purification and cleavage were monitored by SDS-PAGE stained by Commassie Blue Simply Blue™ Safe Stain (Invitrogen).

Example 309. MASP-2 Co-Crystallization

To prepare co-crystallization solutions of MASP-2 with inhibitory compounds, the compounds were dissolved in aqueous solution at a concentration of 100 mM to 10 mM. Such stock solutions were diluted 1:10 into MASP-2 protein samples at a protein concentration of 5 to 20 mg/mL.

Crystallization trials were setup as sitting drop, vapor diffusion experiments by combining equal volumes of MASP-2 compound complex solution with commercially available crystallization formulations. Typically, crystallization hits were obtained by screening against two 96-well crystallization reagent kits (GRAS6, GRAS2, Hampton Research; MORPHEUS, Molecular Dimensions; Wizard 1&2 Cryo, Rigaku Reagents) and crystal growth was inspected by optical microscopy. Crystals were used directly or further optimized for X-ray diffraction. Crystals were captured with cryogenic loops and dipped into liquid nitrogen directly or cryoprotected with a 20% glycerol in crystallization formulation before flash-cooling in liquid nitrogen.

Listing of compound-MASP-2 crystallographic structures with their respective construct employed, as well as resulting space group and dimensions are provided for each co-crystal structure in Table A3 (Appendix).

In cases where multiple ligand poses within a single or multiple crystallographic units were observed, and in cases where crystal structures of multiple space groups were obtained, the most representative pose was selected for hydrogen bonding and van der Waals contacts analysis.

Example 310. MASP-2 Crystal Soaking

To prepare crystals that contain complexes of MASP-2 bound with inhibitory compounds, crystals grown with weakly bound compounds can be washed and soaked. At first MASP-2 compound complex crystals are grown, for instance with compound 43 and individual crystals are washed twice, for a minimum of 4 h with the crystallization solution lacking any inhibitor compounds. Thereafter crystals are transferred once or twice for soaking within the crystallization solution containing the MASP-2 inhibitor. Further crystal handling and data processing is carried out as described in the immediately preceding Example 307.

Example 311. X-ray Crystallography

X-Ray Diffraction and Structure Determination

Crystals were diffracted with synchrotron X-rays of 1.0 wavelength and X-ray diffraction datasets were collected at beamlines SSRL BL9-2, BL14-1, BL12-2 as well as ALS sector 5 using Dectris Pilatus and Eiger detectors. Structures were determined by molecular replacement using portions of the structure 1Q3X as search models and partially refined with Buster 2.10.2 or Refmac 5.8. Electron densities were inspected with Coot (Emsley et al., 2010) and subjected to iterative refinement cycles until the density of ligand in the binding pocket was clearly visible and R-factors sufficient; at this point the partial refinement was deemed completed and models for ligand, solvent and protein were inspected. When multiple ligand poses were observed, for instance arising from multiple molecules in the asymmetric unit or refined dual poses within the same molecule, only one pose was selected and analyzed.

Example 312. Structure Analysis

Partially refined structures were analyzed for ligand-protein and -solvent interaction types and distances, using LigPlot+(Laskowski and Swindells, 2011) and ICM-Pro (Molsoft, LLC) software with parameters set for 3.35 Å for the maximum distance between hydrogen bond donor and acceptor; and non-bonded contact parameters between hydrophobic to any contacts, such as van der Waals interactions with maximum contact distance of 3.90 Å. Table A2 (Appendix) shows van der Waals interactions of MASP-2 atoms with compound atoms that result by LigPlot-based analysis of the crystallographic structures. LigPlot+ calls these 'nonbonded contacts' or 'hydrophobic contacts'. Despite the name, there are atom pairings that include possible H-bonds. Thus, in some instances, the Table A2 also contains H-bond interactions.

In certain aspects, MASP-2 CCP2-SP amino acids interact with (1129) through van der Waals interactions. van der Waals interactions include weak, short-range electrostatic attractive forces between uncharged molecules, arising from the interaction of permanent or transient electric dipole moments.

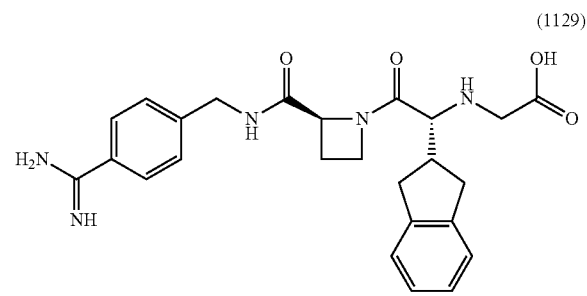 [SMILES: N=C(N)c1ccc(CNC(=O)[C@@H]2CCN2C(=O)[C@H](NCC(=O)O)C2Cc3ccccc3C2)cc1]

(1129)

As shown in Table A2, 1129 Compound atom CO2 interacts with atom CD2 in HIS483. C30 interacts with CE1 of PHE 529, and atoms NO4, CO3 and CO1 interact with CZ of PHE529. PRO 606 carbon atom C of MASP-2 CCP2-SP amino acid interacts with (1129) through C28. In addition, amidine nitrogen N19 interacts with carbon CG of ASP 627. Carbon C14 of (1129) interacts with C of SER 628. Carbons C18, C15 and C14 of (1129) interacts with an oxygen on SER 628. C14 of (1129) also interacts with oxygen OG on SER 628. C17 and C12 of (1129) interacts with carbon CA of CYS 629. Carbons C13, C12 and C11 of (1129) interacts with oxygen O of CYS 629. Oxygen O25 of (1129) interacts with carbon CD and CG of ARG 630. Oxygen O8 interacts with carbon CG of ARG 630. Carbon C17 interacts with the nitrogen of ARG 630. Carbon C11 and carbon 06 interact with oxygen OG of SER 633. Carbon C13 interacts with carbon CG1 of VAL 653. Nitrogen N10 interacts with carbon C of SER 654. Carbon C11, C06 and C 01 interact with carbon C of SER 654. Carbons C14 and C13 and oxygen O07 interact with carbon C of TRP 655. Nitrogen N10 and oxygen O07 interact with carbon CA of TRP 655. Oxygen O7 interacts with carbon CB of TRP 655. Carbons C14 and C13 interact with oxygen O of TRP 655. Nitrogen N20 of (1129) interacts with carbon C of GLY 656. Nitrogen N20 and carbons C18 and C15 all interact with carbon CA of GLY 656. Carbons C16 and 15 interact with nitrogen N of GLY 656. Carbons C23, C09 and C05 interact with oxygen O of GLY 656. Carbon C23 and nitrogen N20 interact with carbon C of SER 657. Carbons C24, C23 and C16 interact with oxygen O of SER 657. Oxygen O25 and carbon C24 interact with carbon CA of MET 658. Oxygen O26 interacts with carbon CG of MET 658. Nitrogen N19 interacts with carbons CA and CB of CYS 660. Carbon C18 interacts with carbon CB of CYS 660. Nitrogen N20 and carbons C18, C16 and C15 interact with sulfur SG of CYS 660. Carbon C18 interacts with oxygen OE1 of GLN 665. Nitrogen N19 interacts with carbon CA of GLY 667.

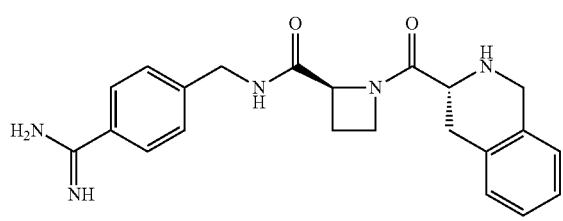

(1034)

In certain aspects, MASP-2 CCP2-SP amino acids interact with (1034) through van der Waals interactions. As shown in Table A2, carbon C28 of (1034) interacts with carbon CG of PRO 606. Nitrogen atom O4, CO3, CO2 and CO1 of (1034) interact with CZ of PHE 529. Carbons C28 and C27 interact with oxygen O of PRO 606. Nitrogen N20 interacts with carbon CG of ASP 627. Carbon C16 interacts with carbon C of SER 628. Carbons C18, C16 and C15 interact with oxygen O of SER 628. Carbon C16 of (1034) interacts with oxygen OG of SER 628. Carbons C17, C13, C12, C11, C17, C14, C13 and C12 interact with carbon CA of CYS 629. Carbon C12 and C11 interact with oxygen O of CYS 629. Carbon C11 of (1034) interacts with carbon CA of ARG 630. Carbons C13, C12, C11 interact with nitrogen N of ARG 630. Carbon C11 interacts with oxygen OG of SER 633. Carbon C11 of (1034) interacts with carbon C of SER 654. Carbons C17 and C16 and oxygen O07 interact with carbon C of TRP 655. Oxygen O07 interact with carbon CA of TRP 655. Oxygen O7 and carbon 05 interacts with carbon CB of TRP 655. Carbon C16 interacts with oxygen O of TRP 655. Nitrogen N19 and oxygen O7 of (1129) interacts with carbon C of GLY 656. Nitrogen N19 and carbon C18 and oxygen O07 all interact with carbon CA of GLY 656. Carbons C24, C09 and C05 interact with oxygen O of GLY 656. Nitrogen N19 interacts with carbon C of SER 657. Nitrogen N19 interacts with carbon CA of SER 657. Carbons C18, C14 interact with oxygen O of SER 657. Nitrogen N19 interacts with carbon CD of GLN 665. Carbon C18 interacts with oxygen OE1 of GLN 665. Nitrogen N20 interacts with carbon CA of GLY 667.

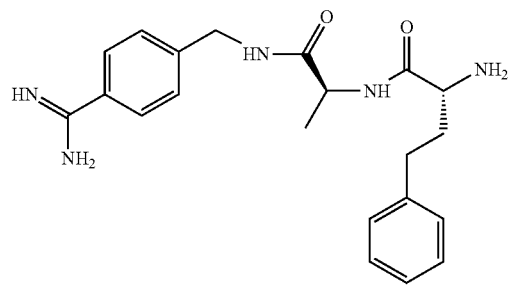

(1024)

In certain aspects, MASP-2 CCP2-SP amino acids interact with (1024) through van der Waals interactions. As shown in Table A2, specific atoms of (1024) interact with specific atoms of TYR 607, PRO 608, SER 611, ASP 627, SER 628, CYS 629, ARG 630, SER 633, SER 654, TRP 655, GLY 656, SER 657, and GLY 667 in a manner similar to the entries 1 and 2 of Table 9 and above.

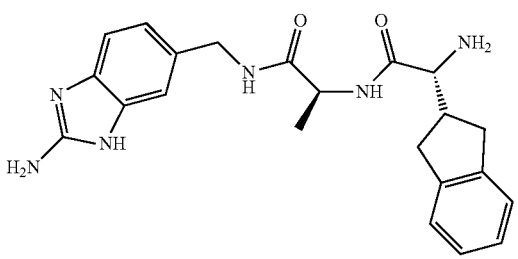

(1059)

In certain aspects, MASP-2 CCP2-SP amino acids interact with (1059) through van der Waals interactions. As shown in Table A2, specific atoms of (1059) interact with specific atoms of TYR 607, PRO 608, ASP 627, SER 628, CYS 629, ARG 630, SER 633, VAL 653, SER 654, TRP 655, GLY 656, SER 657, CYS 660, and GLY 667.

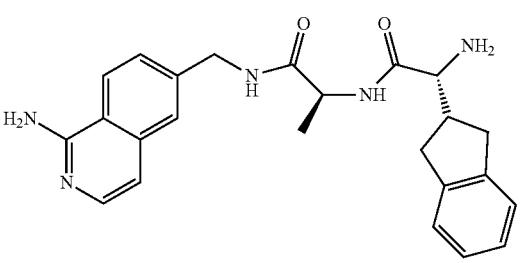

(1088)

In certain aspects, MASP-2 CCP2-SP amino acids interact with (1088) through van der Waals interactions. As shown in Table A2, specific atoms of (1088) interact with specific atoms of PRO 606, TYR 607, PRO 608, ASP 627, SER 628, ARG 630, SER 633, VAL 653, SER 654, TRP 655, GLY 656, SER 657, CYS 660, and GLY 667.

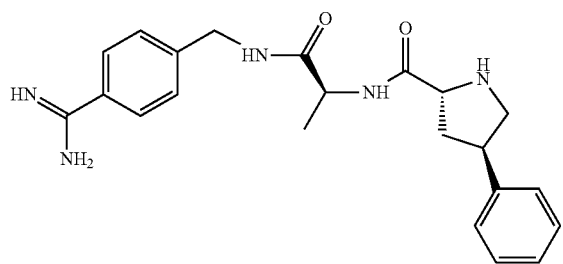

(1036)

In certain aspects, MASP-2 CCP2-SP amino acids interact with (1036) through van der Waals interactions. As shown in Table A2, specific atoms of (1088) interact with specific atoms of ASP 627, SER 628, CYS 629, ARG 630, SER 633, SER 654, TRP 655, GLY 656, SER 657, ASN 659, CYS 660, and GLY 667.

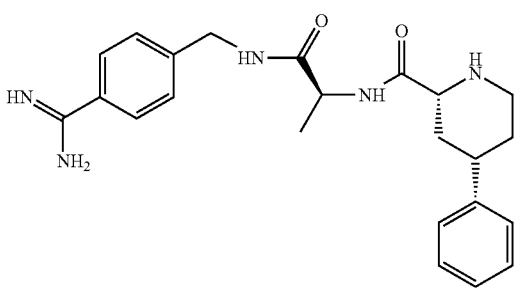

(1065)

In certain aspects, MASP-2 CCP2-SP amino acids interact with (1065) through van der Waals interactions. As shown in Table A2, specific atoms of (1065) interact with specific atoms of TYR 607, PRO 608, SER 611, ASP 627, SER 628, CYS 629, ARG 630, SER 633, VAL 653, SER 654, TRP 655, GLY 656, SER 657, MET 658, CYS 660, and GLY 667.

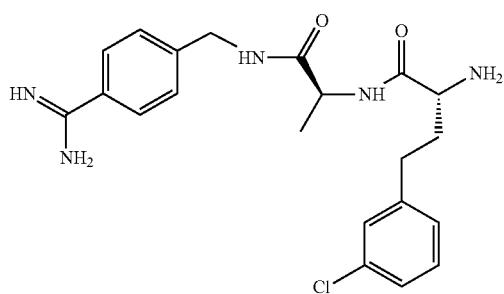

(1081)

In certain aspects, MASP-2 CCP2-SP amino acids interact with (1081) through van der Waals interactions. As shown in Table A2, specific atoms of (1081) interact with specific atoms of SER 611, ASP 627, SER 628, CYS 629, ARG 630, SER 633, VAL 653, SER 654, TRP 655, GLY 656, SER 657, and GLY 667.

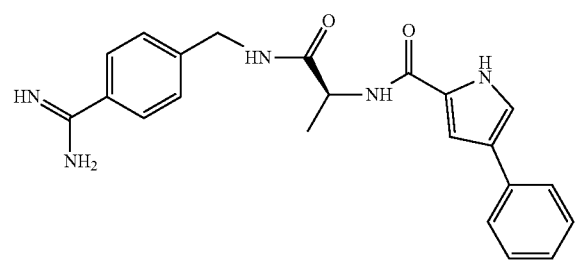

(1030)

In certain aspects, MASP-2 CCP2-SP amino acids interact with (1030) through van der Waals interactions. As shown in Table A2, specific atoms of (1030) interact with specific atoms of ASP 627, SER 628, ARG 630, SER 633, SER 654, TRP 655, GLY 656, SER 657, CYS 660, and GLY 667.

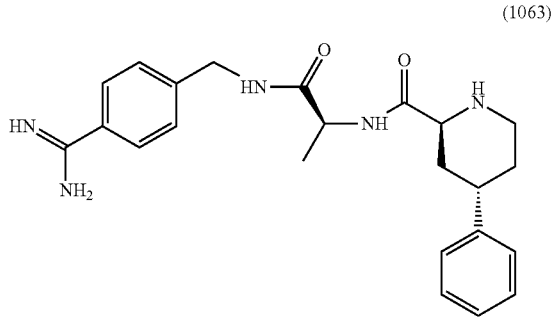 [SMILES: C[C@H](NC(=O)[C@@H]1C[C@@H](c2ccccc2)CCN1)C(=O)NCc1ccc(C(=N)N)cc1]

(1063)

In certain aspects, MASP-2 CCP2-SP amino acids interact with (1063) through van der Waals interactions. As shown in Table A2, specific atoms of (1063) interact with specific atoms of SER 611, ASP 627, SER 628, CYS 629, ARG 630, SER 633, VAL 653, SER 654, TRP 655, GLY 656, SER 657, and GLY 667.

(1037)

In certain aspects, MASP-2 CCP2-SP amino acids interact with (1037) through van der Waals interactions. As shown in Table A2, specific atoms of (1037) interact with specific atoms of PRO 606, ASP 627, SER 628, CYS 629, ARG 630, SER 633, VAL 653, SER 654, TRP 655, GLY 656, SER 657, MET 658, CYS 660, and GLY 667.

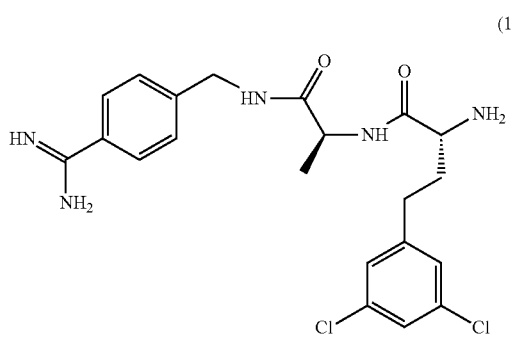
(1118)

In certain aspects, MASP-2 CCP2-SP amino acids interact with (1118) through van der Waals interactions. As shown in Table A2, specific atoms of (1118) interact with specific atoms of TYR 607, PRO 608, SER 611, ASP 627, SER 628, CYS 629, ARG 630, SER 633, VAL 653, SER 654, TRP 655, GLY 656, SER 657, CYS 660, and GLY 667.

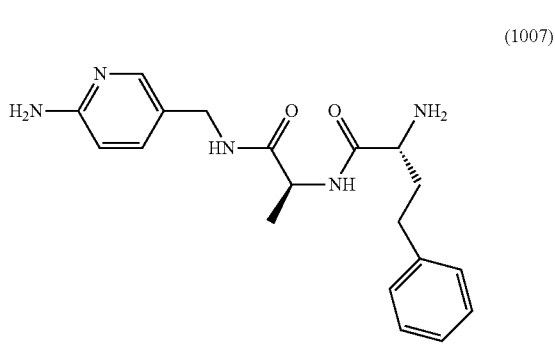 [SMILES: C[C@H](NC(=O)[C@H](N)CCc1ccccc1)C(=O)NCc1ccc(N)nc1]
(1007)

In certain aspects, MASP-2 CCP2-SP amino acids interact with (1007) through van der Waals interactions. As shown in Table A2, specific atoms of (1007) interact with specific atoms of TYR 607, SER 611, ASP 627, SER 628, CYS 629, ARG 630, SER 633, SER 654, TRP 655, GLY 656, SER 656, and MET 658.

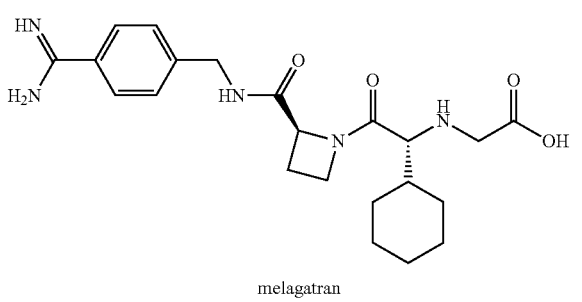 [SMILES: N=C(N)c1ccc(CNC(=O)[C@@H]2CCN2C(=O)[C@H](NCC(=O)O)C2CCCCC2)cc1]
melagatran

In certain aspects, MASP-2 CCP2-SP amino acids interact with (melagatran) through van der Waals interactions. As shown in Table A2, specific atoms of (melagatran) interact with specific atoms of TYR 607, ASP 627, SER 628, CYS 629, ARG 630, SER 633, SER 654, TRP 655, GLY 656, SER 657, MET 658, and GLY 667.

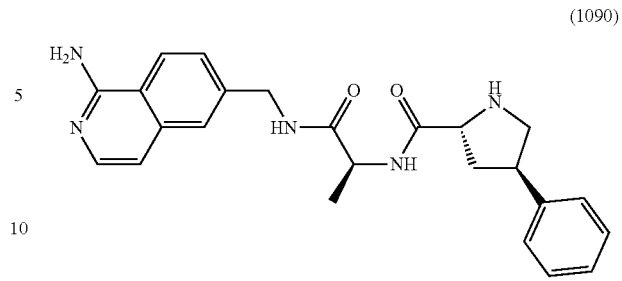
(1090)

In certain aspects, MASP-2 CCP2-SP amino acids interact with (1090) through van der Waals interactions. As shown in Table A2, specific atoms of (1090) interact with specific atoms of PRO 606, TYR 607, PRO 608, ASP 627, SER 628, CYS 629, ARG 630, SER 633, TRP 655, GLY 656, and SER 657.

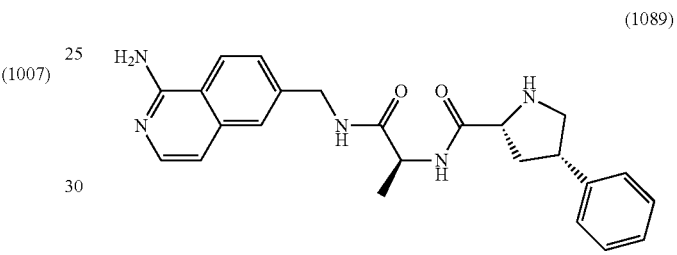
(1089)

In certain aspects, MASP-2 CCP2-SP amino acids interact with (1089) through van der Waals interactions. As shown in Table A2, specific atoms of (1089) interact with specific atoms of PRO 606, ASP 627, SER 628, ARG 630, SER 633, SER 654, TRP 655, GLY 656, SER 657, CYS 660, and GLY 667.

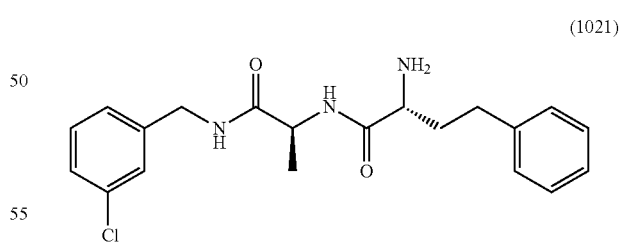
(1021)

In certain aspects, MASP-2 CCP2-SP amino acids interact with (1021) through van der Waals interactions. As shown in Table A2, specific atoms of (1021) interact with specific atoms of ASP 627, SER 628, CYS 629, ARG 630, SER 633, VAL 653, SER 654, TRP 655, GLY 656, SER 657, MET 658, GLY 667 and TYR 669.

(1097)

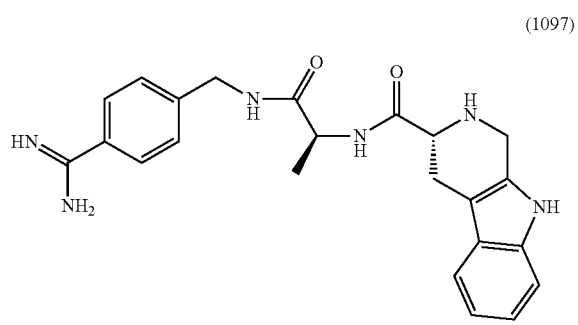 [SMILES: C[C@H](NC(=O)[C@H]1Cc2c([nH]c3ccccc23)CN1)C(=O)NCc1ccc(C(=N)N)cc1]

(1042)

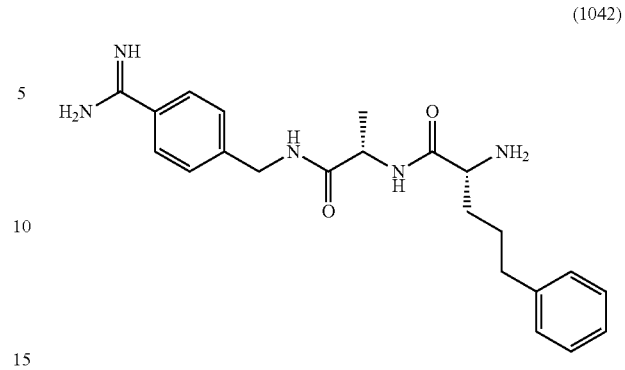

In certain aspects, MASP-2 CCP2-SP amino acids interact with (1097) through van der Waals interactions. As shown in Table A2, specific atoms of (1118) interact with specific atoms of PRO 606, TYR 607, PRO 608, ASP 627, SER 628, CYS 629, ARG 630, SER 633, SER 654, TRP 655, GLY 656, SER 657, MET 658, CYS 660, and GLY 667.

The crystal structure showed that MASP-2 CCP2-SP amino acids interact with compound (54) through van der Waals interactions. As shown in Table A2, specific atoms of compound (54) interact with specific atoms of HIS 483, PHE 529, PRO 608, SER 611, ASP 627, SER 628, CYS 629, SER 633, SER 654, TRP 655, GLY656, SER 657, and GLY 667.

(14)

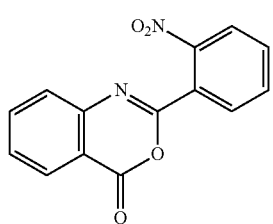

(2018)

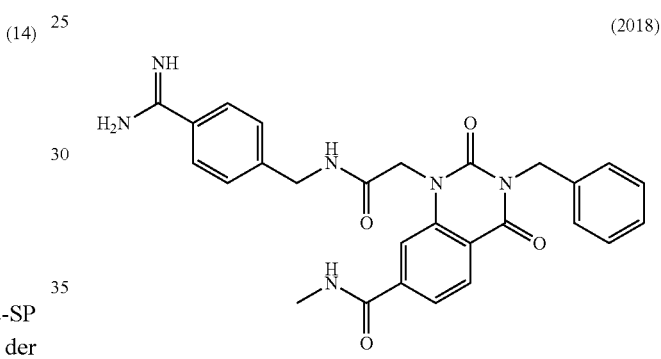

The crystal structure showed that MASP-2 CCP2-SP amino acids interact with compound (54) through van der Waals interactions. As shown in Table A2, specific atoms of compound (54) interact with specific atoms of ALA 468, ALA 469, PHE 529, SER 628, CYS 629, ARG 630, GLY 631, ASP 632, GLY 634, GLY 635, VAL 653, SER 654, TRP 655, GLY656, SER 657, and MET 658.

The crystal structure showed that MASP-2 CCP2-SP amino acids interact with compound (2018) through van der Waals interactions. As shown in Table A2, specific atoms of compound (2018) interact with specific atoms of HIS 483, PHE 529, TYR 607, ASP 627, SER 628, CYS 629, ARG 630, SER 633, SER 654, TRP 655, GLY656, SER 657, CYS 660, GLN 665, and GLY 667.

(54)

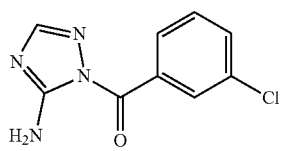

(1149)

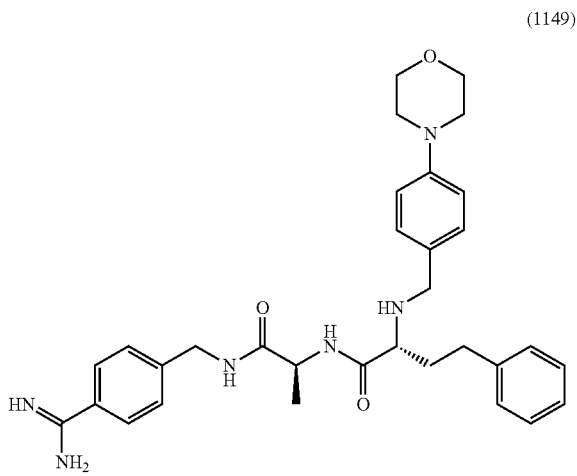 [SMILES: C[C@H](NC(=O)[C@@H](CCc1ccccc1)NCc1ccc(N2CCOCC2)cc1)C(=O)NCc1ccc(C(=N)N)cc1]

The crystal structure showed that MASP-2 CCP2-SP amino acids interact with compound (54) through van der Waals interactions. As shown in Table A2, specific atoms of compound (54) interact with specific atoms of GLY 528, ASP627, SER628, CYS 629, ARG 630, SER 633, VAL653, SER 654, TRP 655, GLY 656, SER 657, CYS 660, and GLY 667.

The crystal structure showed that MASP-2 CCP2-SP amino acids interact with compound (1149) through van der Waals interactions. As shown in Table A2, specific atoms of compound (1149) interact with specific atoms of HIS 483, ASP 526, GLY 528, PHE 529, PRO 608, SER 611, ASP 627, SER 628, CYS 629, SER 633, SER 654, TRP 655, GLY656, SER 657, MET 658, CYS 660, and GLY 667.

The crystal structure showed that MASP-2 CCP2-SP amino acids interact with compound (1025) through van der Waals interactions. As shown in Table A2, specific atoms of compound (1025) interact with specific atoms of HIS 483, PHE 529, TYR 607, ASP 627, SER 628, CYS 629, SER 633, SER 654, TRP 655, GLY656, SER 657, MET 658, and CYS 660.

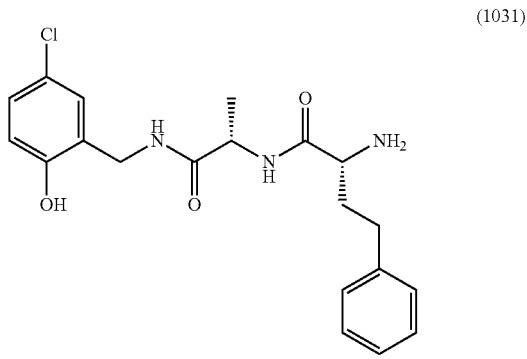 [SMILES: C[C@H](NC(=O)[C@H](N)CCc1ccccc1)C(=O)NCc1cc(Cl)ccc1O]
(1031)

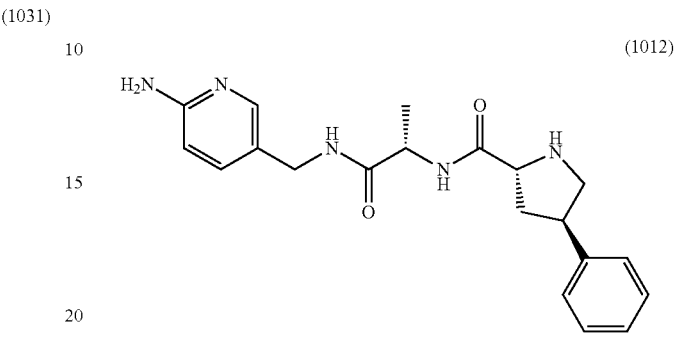
(1012)

The crystal structure showed that MASP-2 CCP2-SP amino acids interact with compound (1031) through van der Waals interactions. As shown in Table A2, specific atoms of compound (1031) interact with specific atoms of HIS 483, PHE 529, TYR 607, SER 611, ASP 627, SER 628, CYS 629, ARG 630, SER 633, VAL 653, SER 654, TRP 655, GLY656, SER 657, and CYS 660.

The crystal structure showed that MASP-2 CCP2-SP amino acids interact with compound (1012) through van der Waals interactions. As shown in Table A2, specific atoms of compound (1012) interact with specific atoms of HIS 483, PHE 529, PRO 606, TYR 607, PRO 608, SER 628, CYS 629, ARG 630, SER 633, SER 654, TRP 655, GLY656, SER 657, MET 658, and CYS 660.

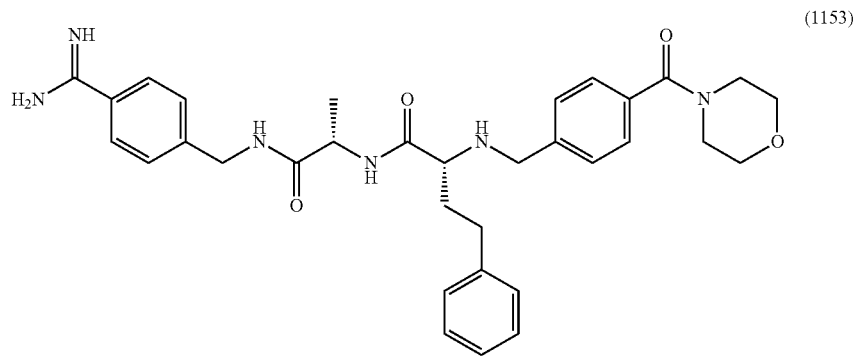 [SMILES: C[C@H](NC(=O)[C@@H](CCc1ccccc1)NCc1ccc(C(=O)N2CCOCC2)cc1)C(=O)NCc1ccc(C(=N)N)cc1]
(1153)

The crystal structure showed that MASP-2 CCP2-SP amino acids interact with compound (1153) through van der Waals interactions. As shown in Table A2, specific atoms of compound (1153) interact with specific atoms of HIS 483, PHE 529, ASP 627, SER 628, CYS 629, ARG 630, SER 633, VAL 653, SER 654, TRP 655, GLY656, SER 657, MET 658, CYS 660, and GLY 667.

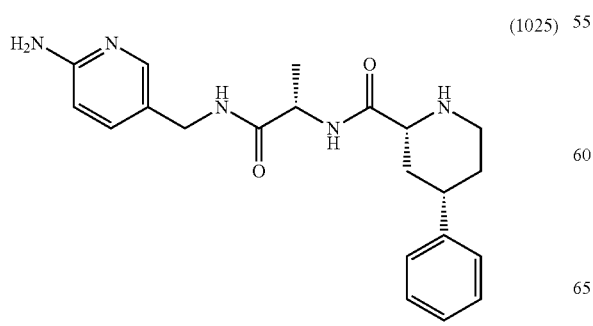
(1025)

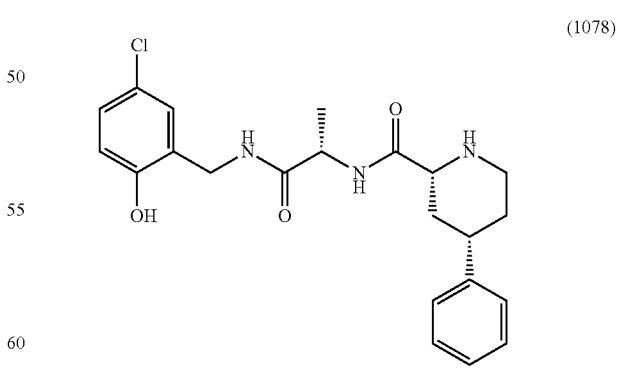
(1078)

The crystal structure showed that MASP-2 CCP2-SP amino acids interact with compound (1078) through van der Waals interactions. As shown in Table A2, specific atoms of compound (1078) interact with specific atoms of HIS 483, PHE 529, PRO 608, SER 611, ASP 627, SER 628, CYS 629, ARG 630, SER 633, VAL 653, SER 654, TRP 655, GLY656, MET 658, GLY 667, and TYR 669

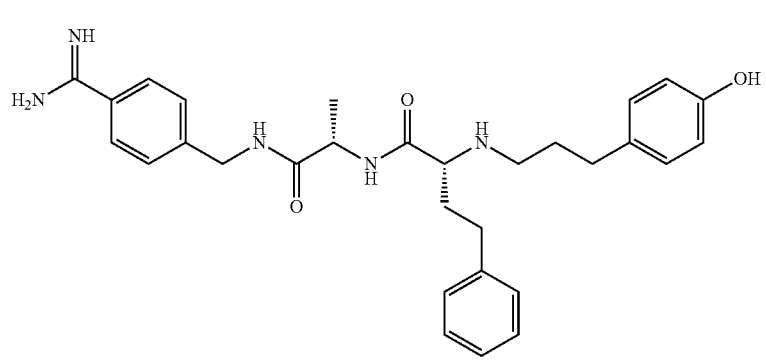

(1145)

The crystal structure showed that MASP-2 CCP2-SP amino acids interact with compound (1145) through van der Waals interactions. As shown in Table A2, specific atoms of compound (1145) interact with specific atoms of HIS 483, PHE 529, TYR 607, SER 611, ASP 627, SER 628, CYS 629, ARG 630, SER 633, VAL 653, SER 654, TRP 655, GLY656, SER 657, MET 658, CYS 660, and GLY 667.

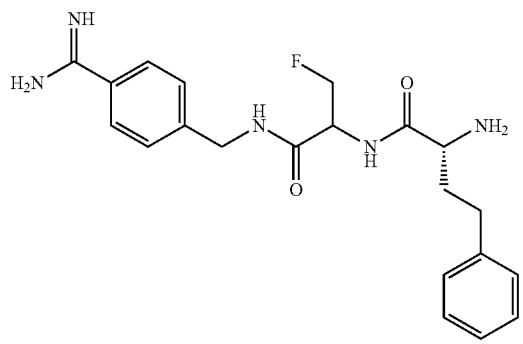

(1050)

The crystal structure showed that MASP-2 CCP2-SP amino acids interact with compound (1050) through van der Waals interactions. As shown in Table A2, specific atoms of compound (1050) interact with specific atoms of PHE 529, TYR 607, PRO 608, ASP 627, SER 628, CYS 629, ARG 630, SER 633, VAL 653, SER 654, TRP 655, GLY656, SER 657, CYS 660, and GLY 667.

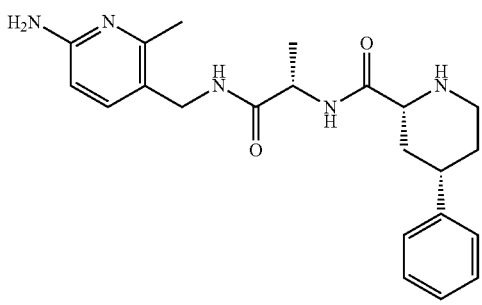

(1253)

The crystal structure showed that MASP-2 CCP2-SP amino acids interact with compound (1253) through van der Waals interactions. As shown in Table A2, specific atoms of compound (1253) interact with specific atoms of HIS 483, PHE 529, TYR 607, SER 611, SER 628, CYS 629, ARG 630, SER 633, VAL 653, SER 654, TRP 655, GLY656, SER 657, and CYS 660.

(1257)

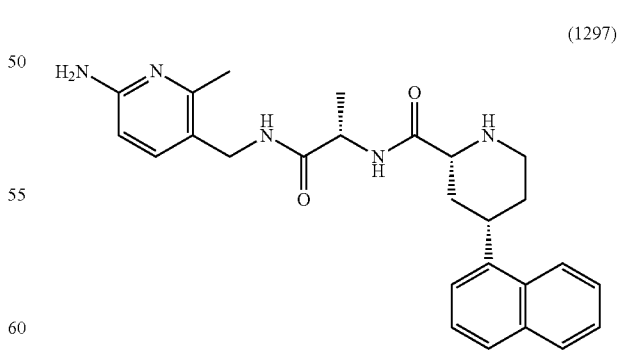

The crystal structure showed that MASP-2 CCP2-SP amino acids interact with compound (1257) through van der Waals interactions. As shown in Table A2, specific atoms of compound (1257) interact with specific atoms of HIS 483, PHE 529, PRO 606, TYR 607, PRO 608, SER 611, SER 628, CYS 629, ARG 630, SER 633, VAL 653, SER 654, TRP 655, GLY656, SER 657, and CYS 660.

(1297)

The crystal structure showed that MASP-2 CCP2-SP amino acids interact with compound (1297) through van der Waals interactions. As shown in Table A2, specific atoms of compound (1297) interact with specific atoms of HIS 483, GLY 528, PHE 529, TYR 607, PRO 608, SER 611, SER 628, CYS 629, ARG 630, SER 633, VAL 653, SER 654, TRP 655, GLY656, and SER 657.

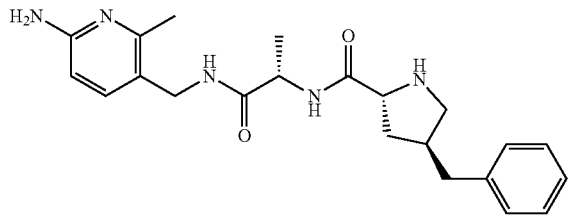
(1304)

The crystal structure showed that MASP-2 CCP2-SP amino acids interact with compound (1304) through van der Waals interactions. As shown in Table A2, specific atoms of compound (1304) interact with specific atoms of HIS 483, GLY 528, PHE 529, TYR 607, PRO 608, SER 611, SER 628, CYS 629, ARG 630, SER 633, VAL 653, SER 654, TRP 655, GLY656, SER 657, and CYS 660.

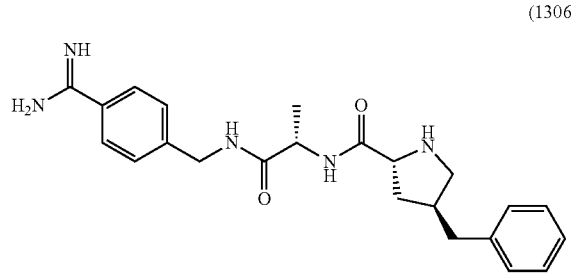
(1306)

The crystal structure showed that MASP-2 CCP2-SP amino acids interact with compound (1306) through van der Waals interactions. As shown in Table A2, specific atoms of compound (1306) interact with specific atoms of HIS 483, PHE 529, TYR 607, PRO 608, SER 611, ASP 627, SER 628, ARG 630, SER 633, SER 654, TRP 655, GLY656, SER 657, CYS 660.

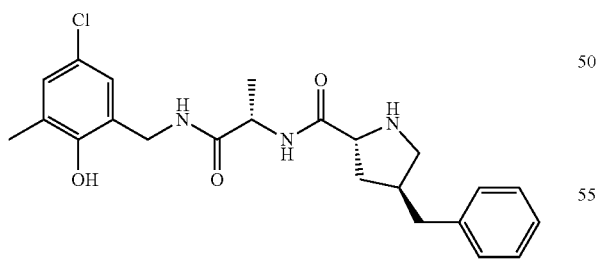
(1307)

The crystal structure showed that MASP-2 CCP2-SP amino acids interact with compound (1307) through van der Waals interactions. As shown in Table A2, specific atoms of compound (1307) interact with specific atoms of HIS 483, GLY 528, PHE 529, TYR 607, PRO 608, SER 611, ASP 627, SER 628, CYS 629, ARG 630, SER 633, VAL 653, SER 654, TRP 655, GLY656, SER 657, MET 658, CYS 660, GLY 667, and TYR 669

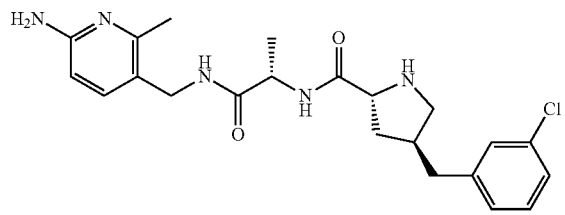
(1328)

The crystal structure showed that MASP-2 CCP2-SP amino acids interact with compound (1328) through van der Waals interactions. As shown in Table A2, specific atoms of compound (1328) interact with specific atoms of HIS 483, PHE 529, TYR 607, PRO 608, SER 611, SER 628, CYS 629, ARG 630, SER 633, VAL 653, SER 654, TRP 655, GLY656, SER 657, MET 658, and CYS 660.

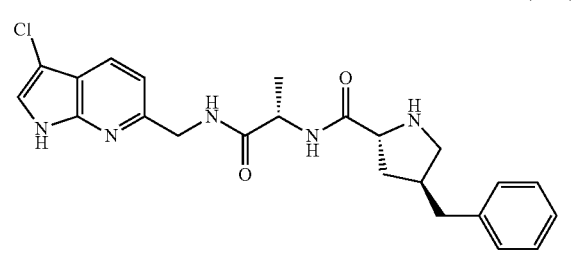
(1334)

The crystal structure showed that MASP-2 CCP2-SP amino acids interact with compound (1334) through van der Waals interactions. As shown in Table A2, specific atoms of compound (1334) interact with specific atoms of HIS 483, PHE 529, TYR 607, PRO 608, SER 611, ASP 627, SER 628, CYS 629, ARG 630, SER 633, VAL 653, SER 654, TRP 655, GLY656, CYS 660, GLY 667, and TYR 669.

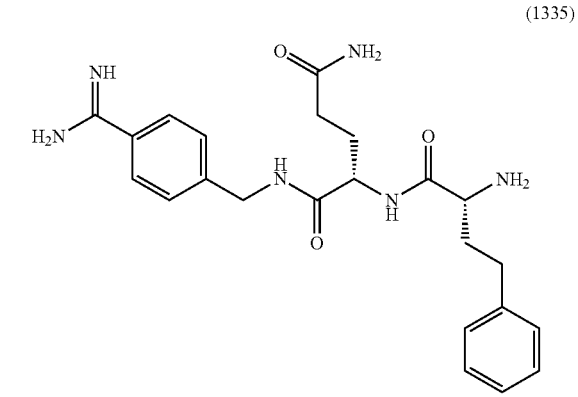 [SMILES: N=C(N)c1ccc(CNC(=O)[C@H](CCC(N)=O)NC(=O)[C@H](N)CCc2ccccc2)cc1]
(1335)

The crystal structure showed that MASP-2 CCP2-SP amino acids interact with compound (1335) through van der Waals interactions. As shown in Table A2, specific atoms of compound (1335) interact with specific atoms of HIS 483, PHE 529, TYR 607, PRO 608, ASP 627, SER 628, CYS 629, ARG 630, SER 633, VAL 653, SER 654, TRP 655, GLY656, SER 657, CYS 660, GLN 665, and GLY 667.

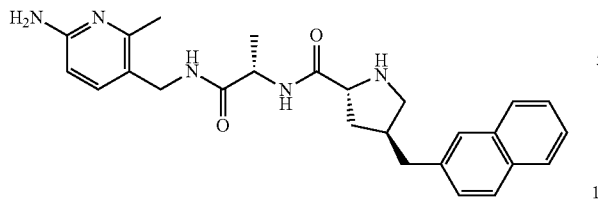
(1338)

The crystal structure showed that MASP-2 CCP2-SP amino acids interact with compound (1338) through van der Waals interactions. As shown in Table A2, specific atoms of compound (1338) interact with specific atoms of HIS 483, ALA 527, GLY 528, PHE 529, PRO 608, SER 611, SER 628, CYS 629, ARG 630, SER 633, VAL 653, SER 654, TRP 655, GLY656, SER 657, MET 658, and CYS 660.

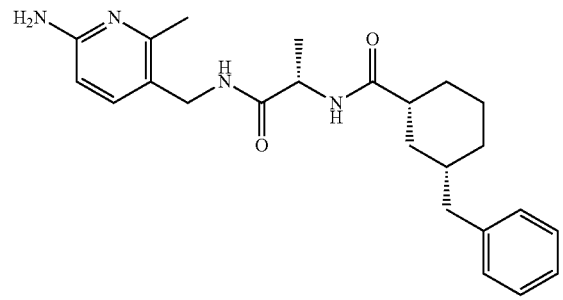
(1353)

The crystal structure showed that MASP-2 CCP2-SP amino acids interact with compound (1353) through van der Waals interactions. As shown in Table A2, specific atoms of compound (1353) interact with specific atoms of HIS 483, GLY 528, PHE 529, TYR 607, PRO 608, SER 611, SER 628, CYS 629, ARG 630, SER 633, VAL 653, SER 654, TRP 655, GLY656, SER 657, and MET 658.

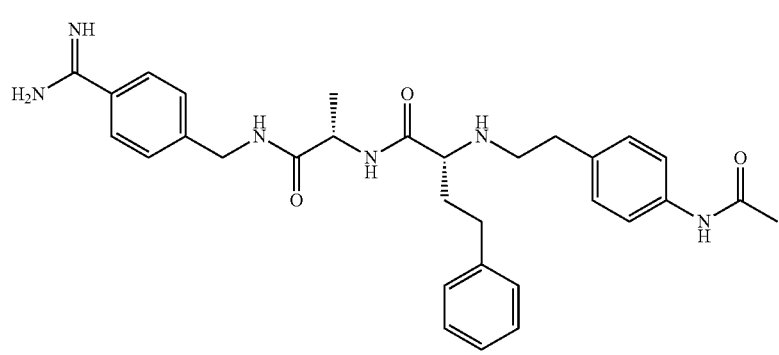
(1345)

The crystal structure showed that MASP-2 CCP2-SP amino acids interact with compound (1345) through van der Waals interactions. As shown in Table A2, specific atoms of compound (1345) interact with specific atoms of HIS 483, PHE 529, LEU 575, SER 611, ASP 627, SER 628, CYS 629, ARG 630, SER 633, SER 654, TRP 655, GLY656, SER 657, MET 658, CYS 660, GLN 665, and GLY 667.

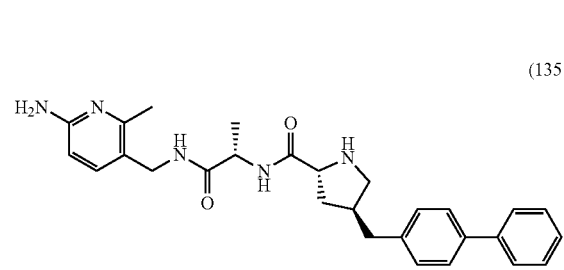
(1351)

The crystal structure showed that MASP-2 CCP2-SP amino acids interact with compound (1351) through van der Waals interactions. As shown in Table A2, specific atoms of compound (1351) interact with specific atoms of HIS 483, ALA 527, GLY 528, PHE 529, TYR 607, PRO 608, SER 611, SER 628, CYS 629, ARG 630, SER 633, VAL 653, SER 654, TRP 655, GLY656, SER 657, and CYS 660.

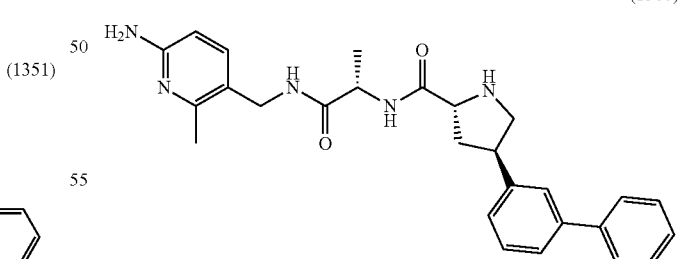
(1360)

The crystal structure showed that MASP-2 CCP2-SP amino acids interact with compound (1360) through van der Waals interactions. As shown in Table A2, specific atoms of compound (1360) interact with specific atoms of HIS 483, GLY 528, GLY 528, PHE 529, PRO 606, TYR 607, PRO 608, SER 611, SER 628, CYS 629, ARG 630, SER 654, TRP 655, GLY656, and SER 657.

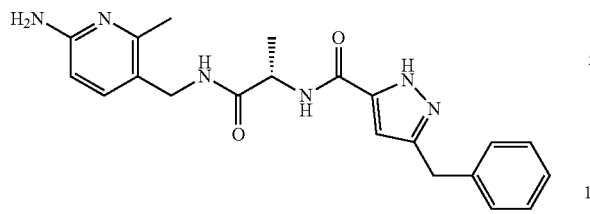

(1367)

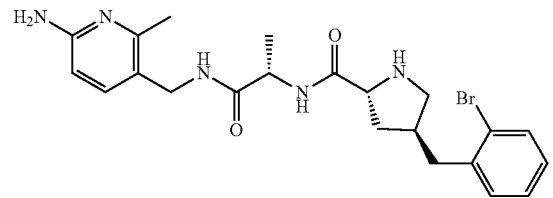

(1372)

The crystal structure showed that MASP-2 CCP2-SP amino acids interact with compound (1367) through van der Waals interactions. As shown in Table A2, specific atoms of compound (1367) interact with specific atoms of HIS 483, GLY 528, PHE 529, TYR 607, PRO 608, SER 628, CYS 629, ARG 630, SER 633, VAL 653, SER 654, TRP 655, GLY656, and SER 657.

The crystal structure showed that MASP-2 CCP2-SP amino acids interact with compound (1372) through van der Waals interactions. As shown in Table A2, specific atoms of compound (1372) interact with specific atoms of HIS 483, GLY 528, PHE 529, TYR 607, PRO 608, SER 611, SER 628, CYS 629, ARG 630, SER 633, VAL 653, SER 654, TRP 655, GLY656, SER 657, and CYS 660.

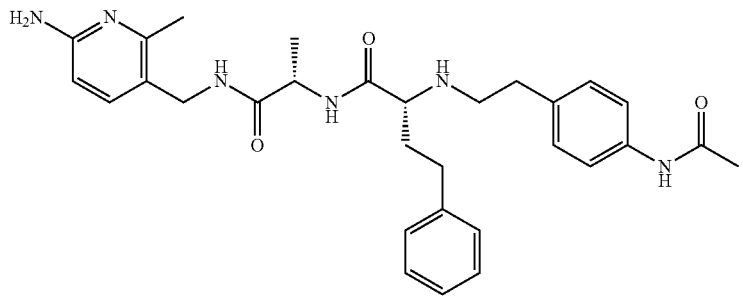

(1368)

The crystal structure showed that MASP-2 CCP2-SP amino acids interact with compound (1368) through van der Waals interactions. As shown in Table A2, specific atoms of compound (1368) interact with specific atoms of HIS 483, PHE 529, PRO 606, TYR 607, SER 611, SER 628, CYS 629, ARG 630, SER 633, VAL 653, SER 654, TRP 655, GLY656, SER 657, MET 658, and CYS 660.

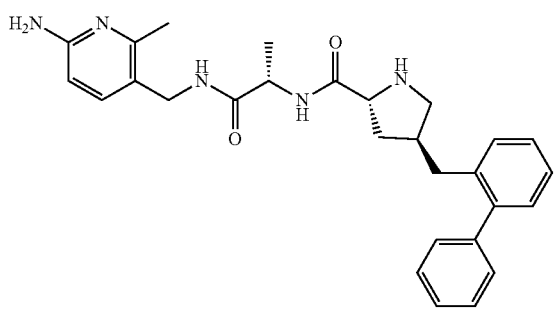

(1373)

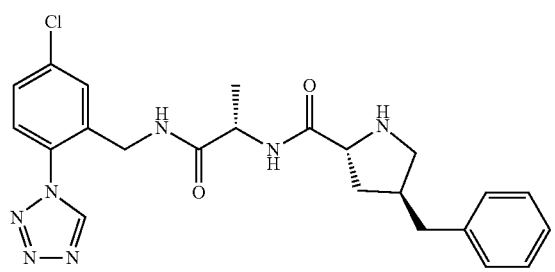

(1371)

The crystal structure showed that MASP-2 CCP2-SP amino acids interact with compound (1373) through van der Waals interactions. As shown in Table A2, specific atoms of compound (1373) interact with specific atoms of HIS 483, GLY 528, PHE 529, TYR 607, PRO 608, SER 611, SER 628, CYS 629, ARG 630, SER 633, VAL 653, SER 654, TRP 655, GLY656, SER 657, and CYS 660.

The crystal structure showed that MASP-2 CCP2-SP amino acids interact with compound (1371) through van der Waals interactions. As shown in Table A2, specific atoms of compound (1371) interact with specific atoms of HIS 483, GLY 528, PHE 529, TYR 607, PRO 608, SER 611, ASP 627, SER 628, CYS 629, ARG 630, SER 633, VAL 653, SER 654, TRP 655, GLY656, SER 657, MET 658, CYS 660, GLY 667, and TYR 669.

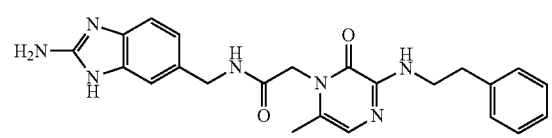

(1492)

The crystal structure showed that MASP-2 CCP2-SP amino acids interact with compound (1492) through van der Waals interactions. As shown in Table A2, specific atoms of compound (1492) interact with specific atoms of HIS 483, PHE 529, PRO 606, ASP 627, SER 628, CYS 629, ARG 630, SER 633, VAL 653, SER 654, TRP 655, GLY656, SER 657, CYS 660, and GLY 667.

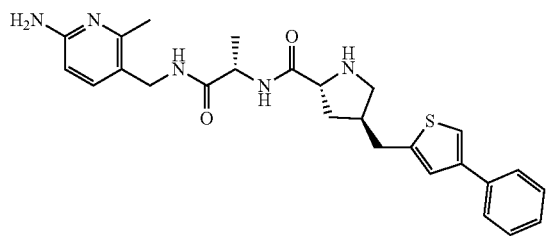

(1399)

The crystal structure showed that MASP-2 CCP2-SP amino acids interact with compound (1399) through van der Waals interactions. As shown in Table A2, specific atoms of compound (1399) interact with specific atoms of HIS 483, ALA 527, GLY 528, PHE 529, TYR 607, PRO 608, SER 628, CYS 629, ARG 630, SER 633, VAL 653, SER 654, TRP 655, GLY656, and SER 657.

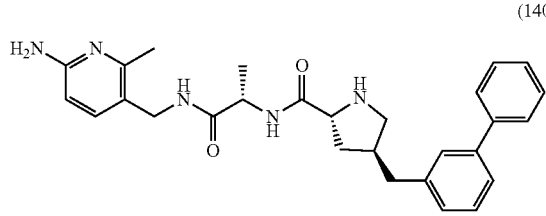

(1406)

The crystal structure showed that MASP-2 CCP2-SP amino acids interact with compound (1406) through van der Waals interactions. As shown in Table A2, specific atoms of compound (1406) interact with specific atoms of HIS 483, ASP 526, ALA 527, GLY 528, PHE 529, TYR 607, PRO 608, SER 628, CYS 629, ARG 630, SER 633, VAL 653, SER 654, TRP 655, GLY656, SER 657, and CYS 660.

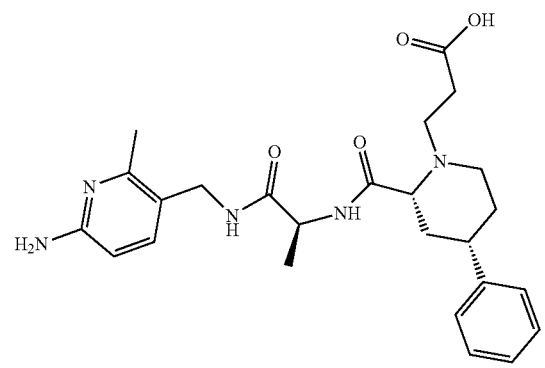

(1411)

The crystal structure showed that MASP-2 CCP2-SP amino acids interact with compound (1411) through van der Waals interactions. As shown in Table A2, specific atoms of compound (1411) interact with specific atoms of HIS 483, GLY 528, PHE 529, TYR 607, PRO 608, SER 611, SER 628, CYS 629, ARG 630, SER 633, VAL 653, SER 654, TRP 655, GLY656, SER 657, MET 658, and CYS 660.

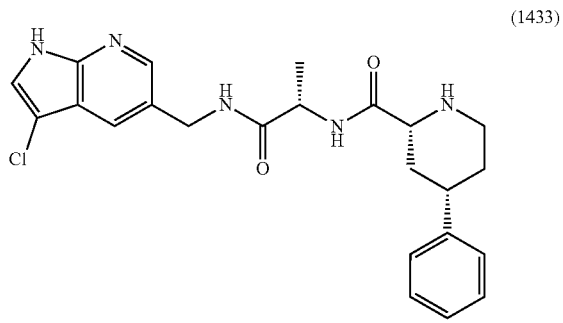 [SMILES: C[C@H](NC(=O)[C@H]1C[C@@H](c2ccccc2)CCN1)C(=O)NCc1cnc2[nH]cc(Cl)c2c1]

(1433)

The crystal structure showed that MASP-2 CCP2-SP amino acids interact with compound (1433) through van der Waals interactions. As shown in Table A2, specific atoms of compound (1433) interact with specific atoms of HIS 483, PHE 529, TYR 607, ASP 627, SER 628, CYS 629, ARG 630, SER 633, VAL 653, SER 654, TRP 655, GLY656, MET 658, GLY 667, and TYR 669.

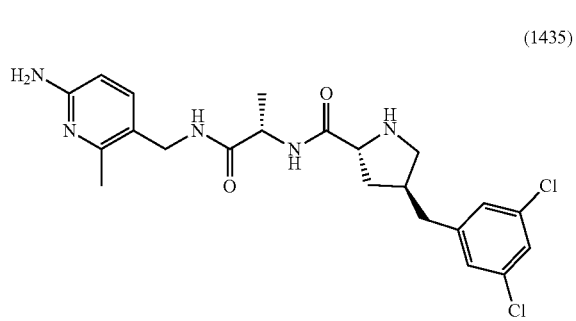 [SMILES: Cc1nc(N)ccc1CNC(=O)[C@H](C)NC(=O)[C@H]1C[C@H](Cc2cc(Cl)cc(Cl)c2)CN1]

(1435)

The crystal structure showed that MASP-2 CCP2-SP amino acids interact with compound (1435) through van der Waals interactions. As shown in Table A2, specific atoms of compound (1435) interact with specific atoms of HIS 483, PHE 529, TYR 607, ASP 627, SER 628, CYS 629, ARG 630, SER 633, VAL 653, SER 654, TRP 655, GLY656, GLY 667, and TYR 669.

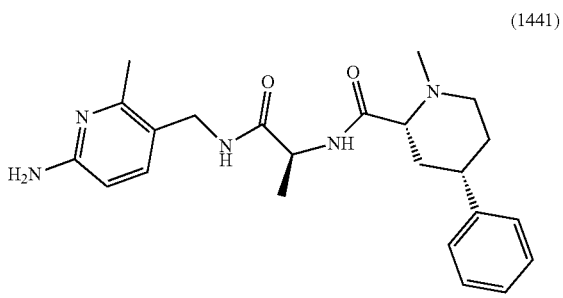 [SMILES: Cc1nc(N)ccc1CNC(=O)[C@H](C)NC(=O)[C@H]1C[C@@H](c2ccccc2)CCN1C]

(1441)

The crystal structure showed that MASP-2 CCP2-SP amino acids interact with compound (1441) through van der Waals interactions. As shown in Table A2, specific atoms of compound (1441) interact with specific atoms of HIS 483, GLY 528, PHE 529, TYR 607, PRO 608, SER 611, SER 628, CYS 629, ARG 630, SER 633, VAL 653, SER 654, TRP 655, GLY656, SER 657, MET 658, and CYS 660.

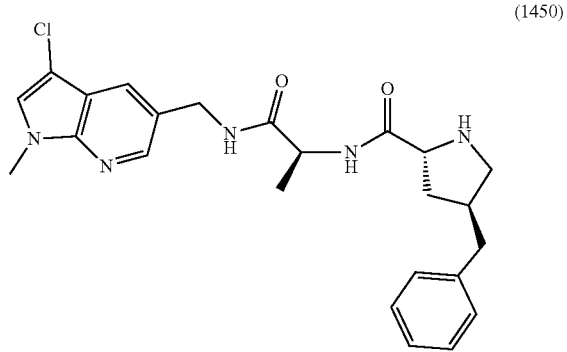 [SMILES: C[C@H](NC(=O)[C@H]1C[C@H](Cc2ccccc2)CN1)C(=O)NCc1cnc2c(c1)c(Cl)cn2C]

(1450)

The crystal structure showed that MASP-2 CCP2-SP amino acids interact with compound (1450) through van der Waals interactions. As shown in Table A2, specific atoms of compound (1450) interact with specific atoms of HIS 483, GLY 528, PHE 529, TYR 607, ASP 627, SER 628, CYS 629, SER 654, TRP 655, GLY656, SER 657, CYS 660, GLY 667, and TYR 669.

Example 313. MASP-2 Specificity Over Thrombin

The crystallographic structure of thrombin in complex with melagatran (Protein Data Bank accession code 4BAH) was compared to the crystallographic structure of MASP-2 in complex with melagatran and to that with other compounds.

The X-ray crystallographic structure of human alpha-thrombin in complex with compound (1334) was also determined as described by Biela et al., J. Med. Chem 2012, 55, 6094-6110, to a resolution of 1.8 A in space group C 1 2 1 and compared to the crystallographic structure of MASP-2 co-crystallized with compound (1334).

Overlays were created with MatchMaker functionality in Chimera software (Pettersen et al., 2004), using the respective serine protease domains for iterative matching.

Thrombin melagatran co-structure (4BAH) overlaid with the co-structure of compound 1065 with MASP-2.

The thrombin co-structure with compound (1334) (using numbering according to PDB Protein Data Bank accession code 1K22) was overlaid with the co-structure of a compound of this disclosure with MASP-2 (see, FIG. 61-63). FIG. 63 clearly shows that the elongated and bulky M4 of the MASP-2 inhibitor not being accommodated and reversing the orientation of the pyrrolidine and benzyl moiety of compound (1334).

It was found that thrombin possesses a ridge, made up of residues GLU 130 and ILE 209 (ASN98, LEU99 and ILE 174), creating a barrier for large bulky residues to occupy this site (see, FIG. 61-63). In the corresponding region in MASP-2 however, a crevice exists that is lined by amino acids PHE 529, GLY 528, TRP 655, SER 611, PRO 608, TYR 607, and PRO 606. FIG. 61, FIG. 65. Crucially, there is no corresponding barrier to large bulky residues in MASP-2, hence allowing large bulky residues to bind and, providing a means to design specificity for MASP-2 over thrombin and other similar proteases.

As discussed, compounds of the disclosure may have specificity for MASP-2 over that of thrombin. MASP-2 has a V-shaped crevice that extends out of the S3 and S4 binding pocket. Compounds can reach into this crevice and form productive van der Waals interactions with bulky aromatic residues in the M4 region. The corresponding area in thrombin is blocked however, by ridge-forming residues GLU 130 and ILE 209 (GLU 259, ASN98, LEU99 and ILE 209). FIG. 61, FIG. 65.

As discussed, compounds of the disclosure may have specificity for MASP-2 over that of thrombin. MASP-2 has a S1 indentation extending inside the S1 binding pocket. Compounds can reach into this crevice and form productive van der Waals interactions with CYS629, CYS660 residues that interact with the $M_1$ region. The corresponding area in thrombin is blocked however, by ridge-forming residues CYS220 and GLY219 (1 k22).

As discussed, compounds of the disclosure may have specificity for MASP-2 over that of thrombin. MASP-2 has a S2 shelf extending the S1 binding pocket. Compounds can reach into this crevice and form productive van der Waals interactions with LEU99, SER654, HIS483, residues in the $M_3$ region. The corresponding area in thrombin is blocked however, by ridge-forming residues TYR60A and LYS60F (1 k22).

As discussed, compounds of the disclosure may have specificity for MASP-2 over that of thrombin. MASP-2 has a S3 entry indentation the S3 binding area. Compounds can reach into this crevice and form productive hydrogen bond interactions with GLY656, a residue in the $M_3$ region. The corresponding area by residue GLY 216 (1 k22) in thrombin is displaced as compared to the corresponding residue GLY656 in MASP-2.

Based on the experimentally determined interactions of compounds with MASP-2, it is evident that H-bonds are preferentially formed with residues ASP627, SER628, SER654, GLY656, GLN 665, ARG630, PRO606, SER 633, CYS660 and SER 657, ionic/electrostatic interactions with ASP627 or ARG 630, via a water molecule as well as additional van der Waals contacts with ALA 468, ALA469, HIS 483, ASP526, ALA527, GLY528, PHE 529, LEU575, PRO 606, TYR 607, PRO608, SER 611, ASP627, SER 628, CYS 629, ARG 630, GLY 631, ASP 632, SER 633, GLY634, GLY 635, VAL 653, SER 654, TRP 655, GLY656, SER 657, MET 658, ASN 659, CYS 660, GLN 665, GLY 667, TYR 669.

REFERENCES

Ambrus, G., Gál, P., Kojima, M., Szilágyi, K., Balczer, J., Antal, J., Gráf, L., Laich, A., Moffat, B. E., Schwaeble, W., Sim, R. B., and Závodszky, P. Natural Substrates and Inhibitors of Mannan-Binding Lectin-Associated Serine Protease-1 and -2: A Study on Recombinant Catalytic Fragments J. Immunol. 170, 1374-1382 (2003).

Harmat V, Gál P, Kardos J, Szilágyi K, Ambrus G, Végh B, Náray-Szabó G, Závodszky P. The structure of MBL-associated serine protease-2 reveals that identical substrate specificities of $C_1$s and MASP-2 are realized through different sets of enzyme-substrate interactions. J Mol Biol. 2004 Oct. 1; 342(5):1533-46.

Gál P, Harmat V, Kocsis A, Bián T, Barna L, Ambrus G, Végh B, Balczer J, Sim R B, Náray-Szabó G, Závodszky P. J Biol Chem. 2005 Sep. 30; 280(39):33435-44. Epub 2005 Jul. 21. A true autoactivating enzyme. Structural insight into mannose-binding lectin-associated serine protease-2 activations.

Laskowski R A, Swindells M B (2011). LigPlot+: multiple ligand-protein interaction diagrams for drug discovery. J. Chem. Inf. Model., 51, 2778-2786.

Paul Emsley, Bernhard Lohkamp, William G. Scott, Kevin Cowtan Features and Development of Coot. Acta Crystallographica Section D—Biological Crystallography (2010) 66, 486-501.

UCSF Chimera—a visualization system for exploratory research and analysis. Pettersen E F, Goddard T D, Huang C C, Couch G S, Greenblatt D M, Meng E C, Ferrin T E. J Comput Chem. 2004 October; 25(13):1605-12.

Example 314. Testing the Virtual Binding Site Identification Method

To evaluate the utility of the crystallographically determined MASP-2-CCP2-SP small molecule inhibitor compound co-structures for the identification of virtual binding sites of HTS hit compounds, a preliminary control experiment was carried out according to the virtual binding site identification process of the invention.

The crystallographically determined MASP-2 structure with bound 1030 (FIG. 10) was prepared for docking by producing an initial MASP-2 model according to Step 1 (FIG. 76). As such, the CCP2 chain, sulfate ions, the polyethylene glycol molecule, the 307 water molecules, and the bound 1030 molecule were removed from the experimental crystallographic structure parameters in the PDB file, followed by reproducing the modified crystal structure as an initial MASP-2 model using ICM Pro software (Abagyan & Totrov, 1994 and Abagyan et al., 1994).

In accordance with Step 2 of the inventive method, during the conversion from PDB filetype to an ICM object, the MASP-2 model is optimized by adding hydrogens and optimizing the following amino acids: His, Pro, Asn, Gln, Cys. As a next step, a portion of the surface area (ca. ⅓ of the molecular surface of the MASP-2 SP domain) around the S1 binding site is defined, and internal surfaces are excluded using the ICM pocket finder tool, using a tolerance setting of 1. This procedure yields a surface area of approx. 2,300 square Angstrom. Then, a MASP-2 receptor map is calculated for a box that confines the docking calculation to only ⅓$^{rd}$ of the protein surface.

Step 3 involves converting digital representations for small molecule 1030 (FIG. 10) and small molecule (1024) (FIG. 3) as energy minimized three dimensional digital representations. The digital representations for 1030 and 1024 are reproduced below:

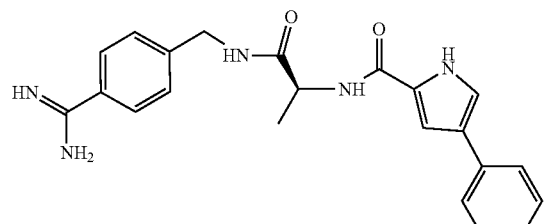

Small molecule 1030

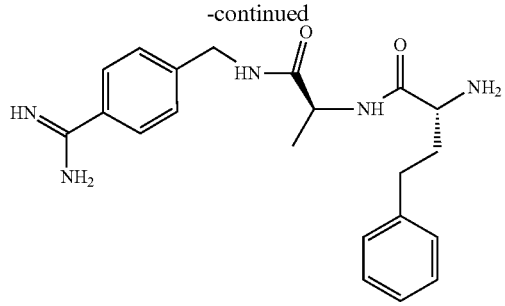

Small molecule 1024

The 3D representations for 1030 and 1024 were prepared by loading the structure-data file (SDF) format representations for each compound, followed by computationally building the hydrogens for each compound, assigning charges, and, finally, converting the compounds into 3D molecules and subsequently used in virtual docking calculations (Step 4). Virtual docking calculations using ICM Pro software were performed with effort settings of 1 or 2 and resulting location, orientation and poses were compared with crystallographically determined to those of the same molecule.

Re-docking of 1030 into the crystal structure of MASP-2 bound to 1030 re-produces the pose with a score of −38.46 and an RMSD of 1.75 Å. The cross-docking of 1024 into the crystal structure of MASP-2 bound to 1030 was performed and compared to the overlayed crystallographically determined 1024 molecule in MASP-2 re-produces the pose with a score of −35.41 and an RMSD of 0.577 Å.

The MASP-2 contacts with hydrogen bonding residues and atoms of ASP 627 (OD2), Ser 628 (O), SER 654 (O), GLY 656 (N) and SER 657 (O) were reproduced for the cross-docked compound 1024, confirming that the interaction of small molecules from Table A1 with affinity and inhibitory capacity can also be predicted computationally with high accuracy.

Example 315. Interaction of MASP-2 with Peptide SGMI-2

Heja et al. (2012) describe the interaction of a 38-mer peptide (SGMI-2) with the serine protease domain of MASP-2. In their reported high-resolution crystallographic structure of SGMI-2 bound to MASP-2 (Protein Data Bank accession code 3TJV), H-bonding analysis herein (using distance cutoff as defined above) depicts hydrogen bonding residues and respective atoms for MASP-2 amino acids GLY 464 (O-atom), GLY 465 (O atom), Thr (N, O and OG1 atom), PRO 606 (O atom), ARG 609 (OG atom), ASP 627 (O atom), SER 628 (O and OG atoms), GLY 631 (N atom), SER 633 (N and OG atom), GLY 656 (N and O atom) and the N atom of MET 657 binding via H-bonds to SGMI-2. Notably, hydrogen bonds are not established between the SGMI-2 peptide and MASP-2 oxygen atom O of SER 654, the oxygen atoms O and OG of SER 657, the sulfur atom of CYS 660 nor with the oxygen atoms O and OE1 of GLN 665.

Furthermore, in their reported high-resolution crystallographic structure (Protein Data Bank accession code 3TJV), van der Waals bonding analysis herein (using distance cutoff as defined above) reveals the binding of MASP-2 amino acid atoms to certain atoms of SGMI-2, utilizing MASP-2 Carbon atom C and oxygen atom O of Gly 464, Carbon atoms C, CA, CB, CG2 and Nitrogen atom N and oxygen atoms O and OG1 of Thr 467, Carbon atom CB of Alanine 468, Carbon atoms CE1 and CG and Nitrogen atom ND1 of His 483, Carbon atoms CA and CB of Ala 484, Oxygen atom O of His 525, Carbon atom O and Oxygen atom O of Asp 526, Carbon atom CA of Ala 527, Nitrogen atom N of Gly 528, Carbon atom CD1 of Leu 575, Carbon atoms CD1, CD2, CG and Nitrogen atom of Leu 581, Carbon atom CE2 of Tyr 601, Carbon atom CA of PRO 606, Carbon atom C and Oxygen atom O of Arg 609, Carbon atom C of Gly 610, Carbon atom CA and Nitrogen atom N of Ser 611, Carbon atom C and CB and Oxygene atom O of ARG 630, Carbon atoms C and CA and Nitrogen atom N of Gly 631, Nitrogen atom N and Carbon atoms CA and CB of Asp 632, Carbon atoms CB and CE of Met 658, as well as Carbon atom CD2 and Nitrogen atom NE2 of Histidine 483, Carbon atoms CE1, CD2 and CZ of Phe 529, Carbon atoms C, CB, CG and oxygen atom of PRO 606, Carbon atom CD2 of Tyr 607, Carbon atoms CB and CG of PRO 608, oxygen atom OG of Ser 611, Oxygen atom OD1 of ASP 627, Carbon atom C oxygen atoms O and OG of Ser 628, Carbon atoms CA, CD, CG of ARG 630, oxygen atom OG and Carbon atom CG1 of Ser 633, Carbon atom CG1 of Val 653, Oxygen atom O of Ser 654, Carbon atoms C, CA, CB, CE3, CZ3 and Oxygen atom O of Trp 655, Nitrogen atom N and Oxygen atom O of Gly 656, Nitrogen atom of Met 658 and Carbon atom CA of Gly 667. Notably, van der Waals interactions are not established between the SGMI-2 peptide and MASP-2 Carbon atoms C and CA of ALA 468, carbon atom CA of ALA 469, carbon atom CA of ASP 526, Carbon atom C and Oxygen atom O of ALA 527, nitrogen atom N and carbon atom CA of GLY528, Carbon atoms CD2 and CE1 of PHE 529, OH atom of TYR 607, carbon atom CB of SER 611, Carbon atom CG and oxygen atom OD2 of SER 628, Carbon atoms C, CA, CB and nitrogen atom N of CYS 629, Carbon atom CZ and nitrogen atom NE2 of ARG 630, C atom of GLY 631, Carbon atoms C, CA and CB as well as oxygen atom O of ASP 632, Carbon atoms C and CA as well as nitrogen atom N of GLY634, Nitrogen atom N of GLY 635, carbon atom CB and oxygen atom O of VAL 653, carbon atom CH2 of TRP 655, Carbon atom CB and oxygen atom OG of SER 657, Carbon atom CA, C and CE as well as oxygen atom O of MET658, Carbon atom C and nitrogen atom N of GLY 667, carbon atom CE2 of TYR669, C and CA, Nitrogen and oxygen atom of SER657, Carbon atom C of Asparagine 659, Carbon atom CA, CB and Sulphur atom SG of Cysteine 660, Carbon atom CD and Oxygen atom OE1 of Glutamine 665, Tyrosine 669 carbon atoms CZ2 and CE1.

It is understood that the examples and embodiments described herein are for illustrative purposes only and that various modifications or changes in light thereof will be suggested to persons skilled in the art and are to be included within the spirit and purview of this application and scope of the appended claims. Each reference, including without limitation all patent, patent applications, and publications, cited in the present application is incorporated herein by reference in its entirety for all purposes.

TABLE A1

(H-Bonds)

| | | Amino Acid | | | | | | | | | | | |
|---|---|---|---|---|---|---|---|---|---|---|---|---|---|
| | | ASP | | SER | | | | ARG | | | SER | GLY | |
| | | MASP-2 AA# | | | | | | | | | | | |
| | | 627 | | 628 | | | | 630 | | | 654 | 656 | |
| | | AA atom | | | | | | | | | | | |
| | | OD1 | OD2 | O | O | OG | OG | NE | NH1 | NH1 | O | O | N |
| 1 | 1097 | | 2.74<br>N5<br>D | 3.03<br>N5<br>D | | | | | | | 2.81<br>N4<br>D | 2.98<br>N1<br>D | 3.12<br>O2<br>A |
| 2 | 1024 | 2.74<br>N4<br>D | | 2.79<br>N4<br>D | | | | | | | 2.86<br>N3<br>D | | 3.06<br>O2<br>A |
| 3 | 1036 | | 2.96<br>N27<br>D | 2.9<br>N27<br>D | | | | | | | 2.8<br>N17<br>D | | 3.22<br>029<br>D |
| 4 | 1081 | | | 2.86<br>N27<br>D | | | | | | | 2.81<br>N17<br>D | 2.92<br>N03<br>D | |
| 5 | 1063 | | | 2.93<br>N4<br>D | | | | | | | 2.94<br>N3<br>D | | 3.25<br>O1<br>A |
| 6 | 1065 | 3.14<br>N29<br>D | 3.08<br>N28<br>D | | | | | | | | 2.92<br>N14<br>D | | 3.31<br>O09<br>A |
| 7 | 1030 | | | | | 3.17<br>N5<br>D | | | | | 2.82<br>N3<br>D | 2.82<br>N1<br>D | 3.12<br>O2<br>A |
| 8 | 1037 | | 2.91<br>N19<br>D | | | | | | | | 2.89<br>N09<br>D | | 3.35<br>O04<br>A |
| 9 | 1118 | | | | | 3.18<br>N5<br>D | | | | | 2.88<br>N3<br>D | 2.77<br>N1<br>D | 3.07<br>O1<br>A |

TABLE A1-continued

| | | | | | | | | |
|---|---|---|---|---|---|---|---|---|
| 10 | Melagatran 999 | | | | 2.75 N24 D | | | |
| 11 | 1129 | 2.79 N19 D | | | 2.86 N19 D | | 2.84 N10 D | 2.93 O07 A |
| 12 | 1034 | 2.9 N20 D | | 2.91 N20 D | | | 2.99 N10 D | 2.91 O07 A |
| 13 | 1088 | 2.91 N31 D | 3.16 N29 D | | 3.16 N31 D | | 2.89 N01 D | 3.22 O07 A |
| 14 | 1059 | 2.99 N4 D | 2.95 N6 | | | | 2.95 N1 D | 2.94 N3 D | 3.13 O2 A |
| 15 | 1007 | | 3.27 N5 D | 2.59 N1 D | | | 2.94 N2 D | | |
| 16 | 1090 | 2.8 N4 D | | | | | 2.96 N2 D | 2.78 N1 D | 3.3 O2 A |
| 17 | 1089 | 2.8 N4 D | | | | | 2.93 N3 D | 2.82 N1 D | 3.3 O2 A |
| 18 | 1021 | | | | | | 2.99 N1 D | | 3.08 O1 A |
| 19 | 1297 | | 3.13 N5 D | 2.96 N4 D | | | 2.88 N3 D | 2.67 N1 D | 3.33 O1 A |
| 20 | 1304 | | 3.17 N5 D | 3.18 N4 D | | | 2.97 N3 D | 2.81 N2 D | 3.2 O1 A |
| 21 | 1306 | | 2.6 N4 D | 2.24 N4 D | | | | 2.69 N2 D | 3.05 O1 A |
| 22 | 1307 | | | | | | 2.91 N3 D | 2.86 N2 D | 2.95 O1 A |
| 23 | 1328 | | | 3.06 N4 D | | | 2.67 N3 D | 2.82 N2 D | 3.33 O1 A |
| 24 | 1334 | | | | | | 2.81 N3 D | 2.83 N2 D | 3.16 O1 A |
| 25 | 1335 | | | | 3.21 N5 D | | 2.99 N1 D | 2.77 N3 D | 3.08 O1 A |
| 26 | 1338 | | 3.2 N5 D | 3.04 N4 D | | | 2.99 N3 D | 2.78 N2 D | 3.23 O1 A |
| 27 | 1345 | | | 2.64 N5 D | | 2.37 O1 A | 3.02 N1 D | 3.13 N3 D | 3.05 O2 A |
| 28 | 1351 | | 3.22 N5 D | | | | 2.98 N3 D | 2.76 N2 D | 3.25 O1 A |
| 29 | 1353 | | 3.17 N5 D | | | | 3 N3 D | 2.85 N1 D | 3.15 O1 A |
| 30 | 1367 | | 3.15 N4 D | 3.15 N3 D | | | 3.08 N2 D | 2.77 N6 D | 3.15 O2 A |
| 31 | 1368 | | 3.24 N38 D | 3.16 N34 D | | | 3.04 NO1 D | | 3.07 O29 A |
| 32 | 1371 | | | | | | 2.86 N3 D | 2.75 N2 D | 3.18 O1 A |
| 33 | 1372 | | 3.17 N4 D | 3.18 N3 D | | | 2.97 N2 D | 2.81 N5 D | 3.23 O2 A |
| 34 | 1373 | | 3.21 N5 D | 3.18 N4 D | | | 3.04 N3 D | 2.76 N2 D | 3.2 O1 A |
| 35 | 1492 | | 3.32 N7 D | | | | 2.78 N4 D | 2.7 N3 D | 3.06 O1 A |

TABLE A1-continued

| # | Cmpd | SER 657 O | SER 657 OG | GLN 665 O | GLN 665 OE1 | GLN 665 OE1 | SER 633 OG | PRO 606 O | HIS 483 NE2 | ALA 469 N | CYS 660 SG |
|---|------|-----------|------------|-----------|-------------|-------------|------------|-----------|-------------|-----------|------------|
| 36 | 1399 | 3.26 N5 D | 3.15 N4 D | | | | | | 3.04 N3 D | 2.75 N1 D | 3.21 O2 A |
| 37 | 1406 | 3.22 N5 D | | | | | | | 2.96 N3 D | 2.76 N2 D | 3.28 O1 A |
| 38 | 54 | | | | 2.81 N11 A | 2.74 O09 A | | | | | |
| 39 | 2018 | | 3.01 N5 D | | | | | | 2.94 N3 D | | 3.26 O2 A |
| 40 | 1031 | | | | | | 2.18 O04 A | 2.83 O09 A | 2.67 N11 D | | |
| 41 | 1153 | 3.27 N1 D | | | 2.96 N2 D | | | 2.3 O1 A | | 2.84 N5 D | 2.96 O2 A |
| 42 | 1025 | 3.11 N09 D | 2.38 N05 D | 3.17 N09 D | | | | | | | |
| 43 | 1012 | 3.18 N5 D | | | | | | | 2.93 N3 D | 2.77 N1 D | 3.18 O2 A |
| 44 | 1078 | | | | | | 2.92 O2 A | 3.25 N2 D | 2.66 N1 D | | 3.14 O1 A |
| 45 | 1145 | | | 2.84 N4 D | | | | | 2.84 N1 D | 2.58 N3 D | 3.09 O2 A |
| 46 | 1050 | | | | | | | | 3.03 N2 D | 2.58 N5 D | 3.18 O2 A |
| 47 | 1253 | 3.33 N07 D | 3.12 N01 D | | | | | | 2.99 N10 D | 2.83 N22 D | 3.23 O17 A |
| 48 | 1257 | | 3.12 N01 D | | | | | | 3.02 N10 D | 2.82 N18 D | |
| 49 | 14 | | | | | | | | | | |
| 50 | 1042 | 3.32 N22 D | 2.74 N22 D | | | | | | | 2.34 N03 D | |
| 51 | 1433 | | | | | | | | 2.89 N3 D | 2.75 N5 D | 3.13 O2 A |
| 52 | 1360 | 3.15 N5 D | 3.18 N3 D | | | | | | 3.04 N4 D | 2.9 N2 D | 3.21 O1 A |
| 53 | 1450 | | | | | | | | 2.97 N3 D | 2.78 N2 D | 3.04 O1 A |
| 54 | 1435 | 3.32 N5 D | | | | | | | 3.01 N3 D | 2.79 N2 D | 3.26 O1 A |
| 55 | 1441 | 3.23 N5 D | 3.06 N4 D | | | | | | 3.07 N1 D | | 3.2 O1 A |
| 56 | 1411 | 3.17 N5 D | 3.2 N4 D | | | 2.66 O3 A | | | 3.06 N1 D | | 3.07 O2 A |
| 57 | 1149 | 3.09 N1 D | | | | | | | 2.7 N3 D | | 3.24 O2 A |

| Amino Acid | SER | | GLN | | | SER | PRO | HIS | ALA | CYS |
|------------|-----|-----|-----|-----|-----|-----|-----|-----|-----|-----|
| MASP-2 AA# | 657 | | 665 | | | 633 | 606 | 483 | 469 | 660 |
| AA atom | O | OG | O | OE1 | OE1 | OG | O | NE2 | N | SG |
| 1  1097 | 2.74 N6 D | | | | | | | | | |

TABLE A1-continued

| # | Compound | | | | | |
|---|---|---|---|---|---|---|
| 2 | 1024 | 2.94 N5 D | | | | |
| 3 | 1036 | 2.93 N26 D | | | | |
| 4 | 1081 | 2.69 N26 D | | | | |
| 5 | 1063 | 2.83 N5 D | | | | |
| 6 | 1065 | | | | | |
| 7 | 1030 | 2.91 N4 D | | | | |
| 8 | 1037 | 2.85 N18 D | | | | |
| 9 | 1118 | 2.93 N4 D | | | | |
| 10 | Melagatran 999 | 2.84 N25 D | | | | |
| 11 | 1129 | 2.92 N20 D | | | 2.76 N20 D | | |
| 12 | 1034 | 2.75 N19 D | | | 3.26 N20 D | 2.8 N19 D | |
| 13 | 1088 | | | | | | |
| 14 | 1059 | 2.77 N5 D | 2.94 N6 D | 3.31 N6 D | | | |
| 15 | 1007 | 2.88 N5 D | | | | | |
| 16 | 1090 | | 2.73 N5 D | | | | |
| 17 | 1089 | 2.93 N5 D | | | | | |
| 18 | 1021 | | | | | | |
| 19 | 1297 | 3.06 N5 D | | | | | |
| 20 | 1304 | 2.96 N5 D | | | | | |
| 21 | 1306 | 2.87 N5 D | | | | | |
| 22 | 1307 | | | | | | |
| 23 | 1328 | 2.44 N5 D | | | | | |
| 24 | 1334 | | | | | | |
| 25 | 1335 | 2.85 N6 D | | | 2.73 N6 D | | |
| 26 | 1338 | 2.93 N5 D | | | | | |
| 27 | 1345 | 3.01 N6 D | | | 2.63 N6 D | | |
| 28 | 1351 | 2.8 N5 D | | | | | |
| 29 | 1353 | 2.91 N5 D | | | | | |
| 30 | 1367 | 2.88 N4 D | | | | | |
| 31 | 1368 | 2.94 N38 D | | | | | 3.21 N17 D |

TABLE A1-continued

| | | | | | | | |
|---|---|---|---|---|---|---|---|
| 32 | 1371 | 2.96 C23 D | | | | | |
| 33 | 1372 | 2.87 N4 D | | | | | |
| 34 | 1373 | 2.89 N5 D | | | | | |
| 35 | 1492 | 2.72 N5 D | 2.62 N7 D | | | | |
| 36 | 1399 | 2.86 N5 D | | | | | |
| 37 | 1406 | 2.78 N5 D | | | | | |
| 38 | 54 | | 2.57 N15 D | | | | |
| 39 | 2018 | 2.84 N4 D | | 2.56 N4 D | 3.08 N3 A | | |
| 40 | 1031 | | | | | | |
| 41 | 1153 | 2.98 N1 D | | | | | |
| 42 | 1025 | | | | | | |
| 43 | 1012 | 2.89 N5 D | | | | | |
| 44 | 1078 | | | | | | |
| 45 | 1145 | 2.81 N5 D | | | | | |
| 46 | 1050 | 2.86 N4 D | | | | | |
| 47 | 1253 | 2.85 N07 D | | | | | |
| 48 | 1257 | 2.86 N08 D | | | | | |
| 49 | 14 | | | | | 2.89 O2 D | 3 O7 D |
| 50 | 1042 | 2.65 N21 D | | | | | |
| 51 | 1433 | | | | | | |
| 52 | 1360 | 2.96 N5 D | | | | | |
| 53 | 1450 | | | | | | |
| 54 | 1435 | 2.84 N5 D | | | | | |
| 55 | 1441 | 2.91 N5 D | | | | | |
| 56 | 1411 | 2.61 N5 D | | | | | |
| 57 | 1149 | 2.75 N2 D | 3.19 N2 D | | | | 3.16 N2 D |

TABLE A2

TABLE A2-1: van der Waals

| Amino Acid MASP-2 AA# | ALA 468 C | ALA 468 CA | ALA 468 CB | ALA 469 CA | HIS 483 CD2 | HIS 483 CE1 | HIS 483 NE2 | ASP 526 C | ASP 526 CA | ASP 526 O |
|---|---|---|---|---|---|---|---|---|---|---|
| AA atom | | | | | | | | | | |
| 1 1129 | | | | | 3.75 C02 | | | | | |
| 2 1034 | | | | | 3.39 C21 | | | | | |
| 3 1024 | | | | | 3.69 C14 | | | | | |
| 4 1059 | | | | | | | | | | |
| 5 1088 | | | | | 3.81 C28 | | | | | |
| 6 1036 | | | | | 3.74 C29 | | | | | |
| 7 1081 | | | | | | | | | | |
| 8 1063 | | | | | 3.67 C30 | | | | | |
| 9 1065 | | | | | 3.61 C22 | | | | | |
| 10 1030 | | | | | | | | | | |
| 11 1037 | | | | | 3.64 C8 | | | | | |
| 12 1118 | | | | | 3.38 C8 | | | | | |
| 13 1007 | | | | | | | | | | |
| 14 Melagatran 999 | | | | | 3.74 C19 | | | | | |
| 15 1090 | | | | | 3.71 C24 | | | | | |
| 16 1089 | | | | | 3.51 C20 | | | | | |
| 17 1021 | | | | | 3.63 C23 | | | | | |
| 18 1097 | | | | | | | 3.83 C24 | | | |
| | | | | | | | 3.58 C20 | | | |
| | | | | | | | 3.53 C23 | | | |
| 19 54 | | | | | 3.7 N6 | | | | | |
| 20 1042 | | | | | 3.57 C07 | | | | | |
| 21 2018 | | | | | | | 3.56 C29 | | | |
| | | | | | | | 3.87 C16 | | | |
| 22 1031 | | | | | | 3.62 C07 | 3.17 C07 | | | |
| 23 1153 | | | | | | | 3.83 C11 | | | |
| 24 1025 | | | | | 3.68 O28 | 3.81 O28 | | | | |

TABLE A2-continued

| # | ID | | | | | | | | | | | | |
|---|---|---|---|---|---|---|---|---|---|---|---|---|---|
| 25 | 1012 | | | | | | 3.63 C20, 3.35 C15, 3.75 C22 | | | 3.57 C20, 3.28 C15 | | | |
| 26 | 1078 | | | | | | | | | | | | |
| 27 | 1145 | | | | | | | | | | | | |
| 28 | 1050 | | | | | | | | | | | | |
| 29 | 1253 | | | | | | | | | | | | |
| 30 | 1257 | | | | | | 3.74 C29, 3.7 C29, 3.74 C29 | | | 3.66 C29, 3.72 C29, 3.84 C20 | | | |
| 31 | 1297 | | | | | | 3.18 C18, 3.71 C14 | | | 3.65 C14 | | | |
| 32 | 1304 | | | | | | 3.47 C14 | | | 3.32 C14 | | | |
| 33 | 1306 | | | | | | | | | 3.5 C14 | | | |
| 34 | 1307 | | | | | | | | | 3.73 C14 | | | |
| 35 | 1328 | | | | | | 3.79 C14, 3.66 C14 | | | | | | |
| 36 | 1334 | | | | | | 3.72 C20, 3.58 C18, 3.69 C3 | 3.84 N3 | | 3.84 C20, 3.82 C18, 3.37 C3 | | | |
| 37 | 1335 | | | | | | | 3.7 C22 | | 3.9 C20, 3.67 C23 | | | |
| 38 | 1338 | | | | | | 3.66 C20, 3.77 C23 | 3.58 N4 | | 3.59 C12, 3.67 C04 | | | |
| 39 | 1345 | | | | | | 3.71 C12, 3.86 C04 | | | 3.61 C14, 3.67 C2 | | | |
| 40 | 1351 | | | | | | 3.55 C14, 3.77 C2 | | | | | | |
| 41 | 1353 | | | | | | 3.71 C14, 3.78 C13 | | | 3.62 C14 | | | |
| 42 | 1367 | | | | | | 3.72 C26 | | | 3.84 C13, 3.6 C26 | | | |
| 43 | 1368 | | | | | | 3.7 C15, 3.73 C23 | | | 3.67 C15, 3.76 C23 | | | |
| 44 | 1371 | | | | | | 3.72 O5 | | | | | | |
| 45 | 1372 | | | | | | | | | | | | |
| 46 | 1373 | | | | | | | | | | | | |
| 47 | 1492 | | | | | | | | | | 3.68 C14 | | | |
| 48 | 1399 | | | | | | | | | | | | | |
| 49 | 1406 | | | | | | | | | | | 3.55 C26 | 3.89 C26 | 3.69 C26 |
| 50 | 1433 | | | | | | | | | | | | |
| 51 | 14 | 3.69 O7 | 3.52 O7 | 3.52 O7 | 3.89 O7 | 3.84 C15 | 3.78 C8 | 3 O2 | 3.59 O5 | | | | |

TABLE A2-continued

| | | | |
|---|---|---|---|
| 52 | 1360 | 3.76 C19 | 3.69 C19 |
| 53 | 1450 | 3.9 C14 | 3.88 C14 |
| 54 | 1435 | 3.7 C14 | 3.6 C14 |
| 55 | 1441 | 3.74 C18 | 3.61 C18 |
| 56 | 1411 | 3.51 C2 | 3.46 C2 |
| 57 | 1149 | 3.81 C11 | | 3.29 C27 | 3.87 C28 |

TABLE A2-2: van der Waals

| | Amino Acid MASP-2 AA# | ALA 527 | | GLY 528 | | | |
|---|---|---|---|---|---|---|---|
| | AA atom | C | CA | CA | O | CA | N |
| 1 | 1129 | | | | | | |
| 2 | 1034 | | | | | | |
| 3 | 1024 | | | | | | |
| 4 | 1059 | | | | | | |
| 5 | 1088 | | | | | | |
| 6 | 1036 | | | | | | |
| 7 | 1081 | | | | | | |
| 8 | 1063 | | | | | | |
| 9 | 1065 | | | | | | |
| 10 | 1030 | | | | | | |
| 11 | 1037 | | | | | | |
| 12 | 1118 | | | | | | |
| 13 | 1007 | | | | | | |
| 14 | Melagatran 999 | | | | | | |
| 15 | 1090 | | | | | | |
| 16 | 1089 | | | | | | |
| 17 | 1021 | | | | | | |
| 18 | 1097 | | | | | | |
| 19 | 54 | | | | 3.87 C17 | | |
| 20 | 1042 | | | | | | |
| 21 | 2018 | | | | | | |
| 22 | 1031 | | | | | | |
| 23 | 1153 | | | | | | |
| 24 | 1025 | | | | | | |
| 25 | 1012 | | | | | | |
| 26 | 1078 | | | | | | |
| 27 | 1145 | | | | | | |
| 28 | 1050 | | | | | | |
| 29 | 1253 | | | | | | |
| 30 | 1257 | | | | | | |

TABLE A2-continued

| # | ID | | | | | | | | | | | | | | |
|---|----|---|---|---|---|---|---|---|---|---|---|---|---|---|---|
| 31 | 1297 | | | | 3.76 C15<br>3.79 C11 | | | | | 3.61 C14 | 3.39 C15 | | | | |
| 32 | 1304 | | | | | | | | | | | | | | |
| 33 | 1306 | | | | | | | | | | | | | | |
| 34 | 1307 | | | | 3.75 C11 | | | | | | | | | | |
| 35 | 1328 | | | | | | | | | | | | | | |
| 36 | 1334 | | | | | | | | | | | | | | |
| 37 | 1335 | | | | | | | | | | | | | | |
| 38 | 1338 | 3.67 C16 | | | 3.33 C16 | 3.32 C17 | | | 3.81 C16 | 3.72 C15 | 3.32 C16 | | 3.84 C17 | | |
| 39 | 1345 | | | | | | | | | | | | | | |
| 40 | 1351 | 3.59 C17 | 3.35 C18 | | 3.66 C14<br>3.52 C10<br>3.78 C18 | 3.68 C15<br>3.81 C9<br>3.52 C19 | | 3.9 C18 | | 3.8 C17 | 3.42 C18 | | 3.5 C19 | | |
| 41 | 1353 | | | 3.72 C18 | | | 3.79 C19 | | | | | | | | |
| 42 | 1367 | | | | 3.75 C11 | | | | | | | | | | |
| 43 | 1368 | | | | | | | | | | | | | | |
| 44 | 1371 | | | | 3.8 C11<br>3.83 C19<br>3.79 C11 | | | | | | | | | | |
| 45 | 1372 | | | | | | | | | | | | | | |
| 46 | 1373 | | | | | | | | | | | | | | |
| 47 | 1492 | 3.73 C12<br>3.68 C25 | 3.49 C13 | 3.71 C13 | 3.45 C10<br>3.71 C12 | 3.84 C11<br>3.75 C24 | | 3.87 C14 | 3.49 C15 | 3.75 C10<br>3.56 C24 | 3.61 C11<br>3.51 C25 | 3.53 C12 | 3.67 C13 | 3.81 C14 | 3.86 C15 |
| 48 | 1399 | | 3.72 C14 | 3.69 C14 | | | | | | | | | | | |
| 49 | 1406 | | | 3.8 C12<br>3.83 C25 | | | | | | | | | | | |
| 50 | 1433 | | | | | | | | | | | | | | |
| 51 | 1434 | | | | | | | | | | | | | | |
| 52 | 1360 | | | | 3.79 C12<br>3.89 C10 | 3.31 C13 | | 3.82 C14 | | | | | | | |
| 53 | 1450 | | | | | | | | | | | | | | |
| 54 | 1435 | | | | | | | | | | | | | | |
| 55 | 1441 | | | | 3.71 C15<br>3.85 C13 | | | | | | | | | | |
| 56 | 1411 | | | | 3.61 C29 | 3.49 C31 | | C3.72 N6 | 3.76 O3 | 3.4 C29 | | | | | |
| 57 | 1149 | | | | | | | | | | | | | | |

TABLE A2-continued

TABLE A2-3: van der Waals

| | Amino Acid MASP-2 AA# | CD1 | CD2 | CE1 | PHE 529 CE2 | CZ | |
|---|---|---|---|---|---|---|---|
| | AA atom | | | | | | |
| 1 | 1129 | | | 3.52 C30 | | 3.68 N04 3.86 C03 3.84 C01 | |
| 2 | 1034 | | | | | 3.7 N04 3.41 C03 3.71 C02 3.87 C21 3.79 C11 3.74 N2 | |
| 3 | 1024 | 3.85 C7 | 3.58 C6 | 3.46 C6 | 3.7 C5 | 3.8 C4 | 3.9 C13 3.61 C8 | 3.8 C14 3.76 N2 3.71 C2 3.83 C13 3.71 N05 3.59 C04 | |
| 4 | 1059 | | | | | | 3.64 C19 3.86 C04 | 3.45 N13 3.84 C06 | |
| 5 | 1088 | | | 3.62 C13 | 3.66 C12 | 3.52 C06 | | 3.58 C09 3.7 | |
| 6 | 1036 | | | | | | | 3.44 N04 | |
| 7 | 1081 | 3.38 C16 3.71 C15 | | 3.4 C16 3.51 C15 3.69 C30 3.56 C22 3.27 C20 | 3.58 C08 3.63 C2 3.85 C11 3.7 C12 3.49 C13 | 3.49 C07 | 3.64 C29 3.66 C10 3.86 C19 3.86 N2 | 3.72 C7 3.54 C19 3.72 C14 3.62 C29 3.54 C10 3.72 C30 3.51 C22 3.73 C20 3.79 C8 3.62 N3 | 3.34 N2 3.56 N10 3.3 N2 3.37 N03 3.63 N2 | |
| 8 | 1063 | | | | | | | | |
| 9 | 1065 | | | | | | | | |
| 10 | 1030 | | | | | | | | |
| 11 | 1037 | | | | | | | | |
| 12 | 1118 | 3.52 C13 3.83 C16 | | 3.58 C18 | 3.6 C17 | 3.75 C16 3.89 C15 3.88 C14 3.74 C13 | 3.76 C8 3.85 C8 | | 3.85 C01 | |
| 13 | 1007 | | | | | | 3.8 C6 3.81 C7 | | | |
| 14 | Melagatran 999 | | | 3.87 C18 3.83 C12 | 3.81 C24 | | 3.56 C10 | | 3.8 C26 3.61 N3 3.66 N3 3.85 C19 3.85 C24 | 3.87 C12 3.84 C19 3.85 C24 3.73 N11 |
| 15 | 1090 | | | | | | | | | |
| 16 | 1089 | | | | | | | | 3.68 C12 3.66 N2 | |
| 17 | 1021 | | | | | | | | | |
| 18 | 1097 | | | | | | | | 3.79 N3 3.88 C13 | |
| 19 | 54 | | | | | | | | | |
| 20 | 1042 | | | | | | 3.24 C29 | | 3.57 C29 | |
| 21 | 2018 | | | | | | 3.64 C09 3.68 C11 3.75 C07 2.93 C11 | | 3.74 C16 3.85 C7 3.55 N1 | |
| 22 | 1031 | | | | | | | | | |
| 23 | 1153 | 3.36 C17 | 3.48 C18 | | 3.58 C16 | 3.57 C18 | 3.05 C17 | 3.55 C15 | 3.67 C20 3.25 C21 | 3.87 C10 3.08 C11 |
| 24 | 1025 | | | 3.74 C21 | 3.8 C22 | | | | 3.56 C22 | 3.88 C15 |

TABLE A2-continued

| # | ID | | | | | | | | | |
|---|---|---|---|---|---|---|---|---|---|---|
| 25 | 1012 | | | | 3.75 C20 / 3.85 C14 / 3.69 C12 / 3.56 C17 / 3.7 C18 | 3.61 C8 / 3.51 C6 | 3.87 C9 / 3.67 C7 | 3.78 C4 / 3.87 C15 / 3.78 C15 | 3.85 C2 / 3.88 C2 | 3.72 C12 / 3.88 C2 / 3.75 C2 / 3.88 N1 | 3.79 C20 / 3.8 C8 / 3.88 C22 | 3.54 N2 / 3.82 N2 / 3.69 N2 |
| 26 | 1078 | | | | | | | | | | |
| 27 | 1145 | | 3.54 C12 / 3.61 C17 | | | | | | | | |
| 28 | 1050 | | | | | | | | | | |
| 29 | 1253 | | 3.89 C28 | | 3.86 C24 | | | 3.77 C29 | | | |
| 30 | 1257 | | | | | | | | | | |
| 31 | 1297 | | | | | | | | | 3.82 C12 / 3.79 C12 / 3.67 C12 | 3.81 C29 / 3.88 C29 / 3.82 N2 | 3.65 N14 / 3.82 N14 / 3.69 N14 |
| 32 | 1304 | | | 3.79 C12 | 3.85 C1 | 3.75 C14 | | | 3.67 C11 / 3.84 C11 | 3.5 C2 / 3.84 C12 | 3.77 C6 / 3.84 C4 | 3.71 C1 / 3.81 C1 | 3.55 N1 |
| 33 | 1306 | | 3.88 C10 | 3.69 C10 | | | | | 3.63 N1 / 3.86 N1 | 3.9 C4 / 3.61 C14 / 3.88 C13 | | 3.65 C1 / 3.7 C1 | 3.75 N1 / 3.69 N1 |
| 34 | 1307 | | 3.78 C12 | | 3.8 C4 / 3.84 C14 / 3.76 C11 / 3.58 C12 / 3.84 C1 | 3.76 C12 / 3.6 C14 | | 3.74 C10 / 3.81 C1 / 3.7 C12 / 3.8 C20 | | | 3.85 C20 / 3.76 C1 / 3.88 N2 | 3.69 C14 / 3.81 C14 | |
| 35 | 1328 | | | 3.73 C12 | | 3.72 C18 | | | 3.77 C6 / 3.84 C4 | 3.7 C19 / 3.59 C20 / 3.71 C1 | 3.71 C23 | 3.7 C1 / 3.88 C12 / 3.84 C1 | 3.51 N1 |
| 36 | 1334 | | 3.75 C15 | | 3.8 C4 | 3.7 C23 / 3.87 C3 / 3.51 C23 | 3.7 C28 | 3.89 C04 / 3.88 C12 / 3.84 C1 | | | | |
| 37 | 1335 | | | 3.43 C28 | | | | | | | | |
| 38 | 1338 | | | 3.86 C10 / 3.74 C18 / 3.79 C11 | 3.84 C1 / 3.88 C1 | 3.69 C2 / 3.75 C14 | | 3.82 C8 / 3.64 C13 | 3.88 C19 / 3.82 C11 | 3.88 C12 / 3.71 C04 / 3.84 N2 | 3.61 C1 / 3.68 C2 / 3.77 C14 / 3.89 C13 | 3.45 N1 / 3.54 N2 / 3.39 N1 |
| 39 | 1345 | | | 3.81 C19 / 3.84 C12 | | | | 3.89 C4 | | | | |
| 40 | 1351 | | | | | | | | | | | |
| 41 | 1353 | | | 3.68 C9 / 3.8 C20 | 3.84 C14 / 3.76 C11 | | | 3.61 C1 / 3.7 C | | | | |
| 42 | 1367 | | | | | | | | 3.88 C19 / 3.82 C11 | 3.81 C4 | 3.68 C2 / 3.77 C14 | 3.45 N1 / 3.47 N1 |
| 43 | 1368 | | 3.76 C23 | 3.86 C10 / 3.74 C18 / 3.79 C11 | | | | | | | | |
| 44 | 1371 | | | | | | | | | | | |
| 45 | 1372 | | | 3.85 C7 / 3.63 C11 | | | | | | | | |
| 46 | 1373 | | | | | | | | | | | |
| 47 | 1492 | | | | | | | | | | | |
| 48 | 1399 | | | | | | | | 3.7 C2 / 3.8 C11 / 3.82 C13 | 3.73 C12 | 3.82 C5 | 3.71 C17 / 3.73 C15 / 3.76 C10 | 3.47 N2 / 3.45 N1 / 3.73 N4 |
| 49 | 1406 | | | | | | | | | | | |
| 50 | 1433 | | 3.74 C12 | | 3.7 C26 / 3.84 C2 | | | | | | 3.76 C26 / 3.69 C2 / 3.78 C23 | |

TABLE A2-continued

| | | | | | | | | | | | | |
|---|---|---|---|---|---|---|---|---|---|---|---|---|
| 51 | 14 | | | | | 3.21 O5 | | | 3.47 N2 | 3.86 O4 | 3.1 O5 | |
| 52 | 1360 | | | | | 3.78 C19 | | | 3.72 C1 | 3.75 C19 | 3.59 N1 | |
| 53 | 1450 | | | | | 3.86 C13 | 3.58 C14 | 3.76 C10 | 3.6 C13 | 3.47 C14 | 3.63 N1 | |
| 54 | 1435 | | | 3.61 C12 | | 3.88 C1 | 3.7 C14 | | 3.66 C1 | 3.71 C14 | 3.51 N1 | |
| 55 | 1441 | | | | | 3.85 C18 | | 3.87 C12 | 3.89 C18 | 3.7 N2 | | |
|  | | | | | | | | | | 3.61 C7 | | |
| 56 | 1411 | | | | | 3.69 C2 | | 3.71 C11 | 3.83 C2 | 3.63 N2 | | |
|  | | | | | | | | | | 3.59 C6 | | |
| 57 | 1149 | | | | | 3.68 C11 | | 3.78 C27 | 3.8 C10 | 3.34 C11 | | |
|  | | | | | | | | | | 3.53 C28 | | |

TABLE A2-4: van der Waals

| | Amino Acid MASP-2 AA# | LEU 575 | PRO 606 | | | | | TYR 607 | | |
|---|---|---|---|---|---|---|---|---|---|---|
| | AA atom | CD1 | C | CB | CG | CD | O | CA | CD1 | CD2 |
| 1 | 1129 | | 3.86 C28 | | | | | | | |
| 2 | 1034 | | | | 3.71 C28 | | 3.41 C27 | | | |
| | | | | | | | 3.33 C28 | | | |
| 3 | 1024 | | | | | 3.62 C8 | | | | |
| 4 | 1059 | | | | | 3.85 C7 | | | | |
| 5 | 1088 | | 3.89 C16 | | | | 2.97 C16 | 3.9 C8 | | |
| | | | | | | | 3.88 C17 | 3.89 C13 | | |
| | | | | | | | | 3.82 C16 | | |
| 6 | 1036 | | | | | | | | | |
| 7 | 1081 | | | | | | | | | |
| 8 | 1063 | | | | | | | | | |
| 9 | 1065 | | | | | | | | | |
| 10 | 1030 | | | | | | | | | |
| 11 | 1037 | | | | | | | | | |
| 12 | 1118 | | | | | | 3.73 C27 | 3.79 C27 | | |
| | | | | | | | 3.49 C28 | | | |
| 13 | 1007 | | | | | | | | | |
| 14 | Melagatran 999 | | | | | | | 3.84 C14 | | |
| 15 | 1090 | | | | | | 3.3 C8 | | | |
| | | | | | | | 3.4 C7 | | | |
| | | | | | | | 3.36 C7 | | | |
| 16 | 1089 | | | | | | | | | 3.72 C5 |
| 17 | 1021 | 3.61 C12 | | 3.84 C9 | 3.82 C9 | | 3.33 C10 | 3.79 C10 | 3.61 C9 | |
| 18 | 1097 | | 3.74 C10 | | | | | 3.8 C8 | 3.73 C10 | |

TABLE A2-continued

| # | Cmpd | | | | | | | |
|---|---|---|---|---|---|---|---|---|
| 19 | 54 | | | | | | | |
| 20 | 1042 | | | | | | | |
| 21 | 2018 | | | | | | | |
| 22 | 1031 | | | | | | | |
| 23 | 1153 | | | | 3.85 C9 | | | |
| 24 | 1025 | | | | | | | |
| 25 | 1012 | | | | | | 3.9 C12; 3.85 C15 | 3.56 C13 | 3.77 C14 |
| 26 | 1078 | | | | | | | |
| 27 | 1145 | | | | | | | |
| 28 | 1050 | | | 3.33 C8 | | 3.86 C9 | | | |
| 29 | 1253 | | | | | | 3.82 C20 | 3.74 C21 | |
| 30 | 1257 | | | 3.38 C26 | | | 3.83 C24; 3.81 C7 | 3.72 C25 | 3.82 C26 |
| 31 | 1297 | | | | | | 3.78 C7 | | |
| 32 | 1304 | | | | | | 3.85 C7 | | |
| 33 | 1306 | | | | | | 3.83 C7 | | |
| 34 | 1307 | | | | | | | | 3.89 C9 |
| 35 | 1328 | | | | | | 3.81 C7 | | |
| 36 | 1334 | | | | | | 3.84 C18 | 3.84 C19 | |
| 37 | 1335 | | 3.6 C15 | 3.44 C15 | 3.74 C16 | | | | |
| 38 | 1338 | 3.59 C14 | 3.66 N4 | 3.8 O1 | | | | | |
| 39 | 1345 | | | | | | | | |
| 40 | 1351 | | | | | | | | |
| 41 | 1353 | | | | | | | | |
| 42 | 1367 | | | 3.75 C18 | | | 3.75 C6 | | |
| 43 | 1368 | | | | | | | | |
| 44 | 1371 | | | 3.81 C9 | | | 3.79 C7; 3.77 C16; 3.82 C13 | 3.81 C8; 3.77 C17; 3.81 C7 | 3.6 C9 |
| 45 | 1372 | | | | | | | | 3.86 C13 |
| 46 | 1373 | | | | | | | | 3.68 C7 |
| 47 | 1492 | | | | | | 3.7 C5; 3.74 C8 | | |
| 48 | 1399 | | | | | | | | |
| 49 | 1406 | | | | | | | | |

TABLE A2-continued

| | MASP-2 AA# | | |
|---|---|---|---|
| 50 | 1433 | | |
| 51 | 14 | | |
| 52 | 1360 | | |
| 53 | 1450 | 3.83 C16 | 3.75 C17 |
| 54 | 1435 | | 3.44 C12 |
| 55 | 1441 | | 3.83 C7 |
| 56 | 1411 | | 3.8 C9 |
| 57 | 1149 | | 3.8 C8 |

TABLE A2-5: van der Waals

| | Amino Acid MASP-2 AA# | TYR 607 | | | | PRO 608 | | SER 611 |
|---|---|---|---|---|---|---|---|---|
| | AA atom | CE1 | CE2 | OH | CD | CD | CG | CA |
| 1 | 1129 | | | | | | | |
| 2 | 1034 | | | | | | | |
| 3 | 1024 | | | | | | | |
| 4 | 1059 | | | | 3.69 C8 | | | |
| 5 | 1088 | | | | | | | |
| 6 | 1036 | | | | | | | |
| 7 | 1081 | | | | | | | |
| 8 | 1063 | | | | 3.85 C12 | | | |
| 9 | 1065 | 3.84 C04 | | | 3.54 C9 / 3.89 C12 / 3.73 C15 | 3.86 C16 | 3.81 C16 | |
| 10 | 1030 | 3.67 C4 | | | | | | |
| 11 | 1037 | 3.82 C5 | | | | | | |
| 12 | 1118 | 3.8 N2 | | | 3.58 C17 | 3.74 C11 / 3.81 C15 | 3.43 C17 | |
| 13 | 1007 | | | | 3.64 C27 / 3.58 C16 | | 3.83 C17 | |
| 14 | Melagatran 999 | | | | | | | |
| 15 | 1090 | 3.76 C6 | | | 3.63 C8 | | | |
| 16 | 1089 | | | | | | | |
| 17 | 1021 | 3.61 C8 | | | 3.84 C10 | 3.62 C11 | | |
| 18 | 1097 | | 3.78 C9 | | | | | |
| 19 | 54 | | | | | | | |
| 20 | 1042 | | | | 3.79 C26 | 3.69 C27 | 3.65 C26 / 3.55 C27 | |
| 21 | 2018 | | | | | | | |

TABLE A2-continued

| | | | | | | | | | | |
|---|---|---|---|---|---|---|---|---|---|---|
| 22 | 1031 | | | | | | | | | |
| 23 | 1153 | | | | | | | | | |
| 24 | 1025 | | | | | | | | | |
| 25 | 1012 | 3.64 C17 | | | | | | | | |
| | | 3.88 C5 | | | | | | | | |
| 26 | 1078 | | | 3.79 C7 | 3.84 C12 | | 3.68 C11 | 3.78 C12 | | |
| | | | | 3.66 C11 | | | | | | |
| 27 | 1145 | | | | | | | | | |
| 28 | 1050 | | | 3.68 C19 | | | | | | |
| 29 | 1253 | 3.73 C20 | | | | | | | | |
| 30 | 1257 | | | 3.8 C25 | | | | | | |
| | | | | 3.54 C9 | | | | | | |
| | | | | 3.65 C10 | 3.69 C11 | | | | | |
| 31 | 1297 | 3.66 C4 | | | | | 3.89 C15 | 3.67 C9 | | |
| | | 3.83 C7 | | | | | 3.73 C10 | 3.86 C11 | | |
| | | | | | | | 3.5 C11 | 3.58 C12 | | |
| 32 | 1304 | | | | 3.88 C12 | | | | | |
| | | | | | 3.78 C11 | | | | | |
| 33 | 1306 | | | | | | | | | |
| 34 | 1307 | 3.83 C7 | | 3.81 C11 | 3.88 C12 | 3.75 C14 | 3.72 C10 | 3.87 C11 | 3.55 C11 | |
| | | | | 3.64 C10 | | | 3.6 C10 | 3.6 C11 | | |
| | | | | 3.7 C10 | | | | | | |
| | | | | 3.82 C17 | | | | | | |
| 35 | 1328 | | 3.78 C7 | | | | | | | |
| 36 | 1334 | 3.78 C7 | | | | | | | | |
| 37 | 1335 | | | 3.79 C11 | | | | 3.9 C15 | 3.63 C16 | |
| 38 | 1338 | | | | 3.88 C12 | | 3.88 C11 | 3.58 C15 | 3.79 C16 | |
| | | | | | | | | 3.89 C11 | | |
| 39 | 1345 | 3.71 C7 | | 3.86 C10 | 3.79 C11 | 3.87 C13 | 3.63 C14 | | | |
| 40 | 1351 | 3.81 C4 | | 3.89 C7 | | 3.76 C21 | 3.86 C10 | | | |
| | | | | | | 3.86 C9 | | | | |
| 41 | 1353 | | | 3.79 C18 | 3.88 C19 | | | | | |
| 42 | 1367 | 3.69 N5 | | | | 3.86 C15 | | | | |
| 43 | 1368 | | | 3.36 C09 | 3.72 C16 | | | | | |
| 44 | 1371 | 3.74 C5 | 3.74 C7 | | | | | | | |
| | | 3.81 C16 | | | | | | | | |
| 45 | 1372 | | | 3.8 C11 | 3.42 C12 | | 3.8 C12 | | | |
| | | | | 3.8 C19 | 3.53 C20 | | 3.71 C20 | | | |
| | | | | 3.66 C10 | 3.76 C11 | | 3.82 C10 | | | |
| 46 | 1373 | | | | | | | | | |
| 47 | 1492 | | | | | | | | | |
| 48 | 1399 | 3.84 C5 | | 3.82 C10 | 3.84 C8 | | 3.77 C10 | 3.78 C14 | 3.61 C15 | |
| | | | | | | | 3.6 C24 | | | |
| 49 | 1406 | 3.86 C8 | | | | | | | | 3.6 C17 | 3.85 C17 |
| 50 | 1433 | 3.73 C15 | | | | | | | | |

TABLE A2-continued

| | | CB | | SER 611 | | | | | |
|---|---|---|---|---|---|---|---|---|---|
| 51 | 14 | | | | | | | | |
| 52 | 1360 | 3.88 C18 | 3.88 C7 | | | | | 3.87 C14 | 3.43 C15 | 3.37 C14 | 3.47 C15 | 3.83 C12 |
| 53 | 1450 | 3.54 C12 | 3.38 C4 | 3.7 C6 | | | | | |
| 54 | 1435 | 3.73 C7 | | | 3.69 C4 | 3.6 C5 | 3.65 C11 | | |
| 55 | 1441 | 3.59 C9 | | 3.54 C8 | | | 3.66 C15 | 3.72 C16 | 3.85 C15 | 3.78 C16 |
| 56 | 1411 | 3.6 C8 | | | | | 3.81 C12 | 3.56 C13 | 3.62 C12 | 3.25 C13 |
| 57 | 1149 | | | | | | | | 3.58 C30 | |
| | | | | | | | | | | 3.71 C31 | 3.89 C32 |

TABLE A2-6: van der Waals

| | Amino Acid MASP-2 AA# | | | ASP 627 | | | SER 628 | | |
|---|---|---|---|---|---|---|---|---|---|
| | AA atom | CG | OD1 | OD2 | C | CA |
| 1 | 1129 | 3.07 N19 / 3.18 N20 / 3.04 N4 | | | | | | |
| 2 | 1034 | 3.36 N4 | | | | | | |
| 3 | 1024 | | | 3.62 C20 / 3.34 C22 | 3.88 C14 / 3.75 C16 | | |
| 4 | 1059 | 3.54 N31 | | 3.76 C30 / 3.89 C25 | | | |
| 5 | 1088 | 3.83 N29 | 3.84 C30 | | 3.87 C19 / 3.66 N31 | 3.44 C18 / 3.81 C30 | |
| 6 | 1036 | 3.4 N27 | | | | | |
| 7 | 1081 | 3.19 N27 | | | | | |
| 8 | 1063 | 3.09 N4 | | 3.89 C23 | 3.85 N4 | | |
| 9 | 1065 | 3.76 N28 | 3.84 C27 | 3.85 C27 | 3.8 N29 | 3.8 C27 | 3.85 C23 |
| 10 | 1030 | 3.79 N29 | | 3.62 C21 | 3.74 N5 | | |
| 11 | 1037 | 3.11 N5 | | 3.68 C17 / 3.79 C21 | | 3.8 C13 | |
| 12 | 1118 | 3.31 N19 | | | | | |
| 13 | 1007 | 3.15 N5 | | | | | |
| 14 | Melagatran 999 | 3.88 N5 / 3.02 N24 | | 3.61 C23 / 3.75 C22 | | 3.36 N1 / 3.85 N24 | 3.82 C2 / 3.69 C21 |
| 15 | 1090 | 3.33 N4 | 3.09 C23 / 2.93 C22 | 3.45 C23 / 3.62 C22 | | | 3.54 C24 |
| 16 | 1089 | 3.56 C22 / 3.22 N4 | | 3.51 C23 | 3.54 C21 | 3.54 C22 | |

TABLE A2-continued

| # | ID | | | | | | | | | | | | |
|---|---|---|---|---|---|---|---|---|---|---|---|---|---|
| 17 | 1021 | | | | | | | | | | | | |
| 18 | 1097 | | | | | | | | | 3.83 C2 | 3.78 C1 | 3.77 C2 | |
| 19 | 54 | | 3.64 C26 | | | | | | 3.78 C22 3.37 C12 | | | | |
| 20 | 1042 | 3.62 C25 | | | | | | 3.35 C12 | | | 3.76 C08 3.84 N22 | 3.64 C12 | 3.77 C14 |
| 21 | 2018 | | | | | 3.63 C25 | | | | | | | 3.36 N10 |
| 22 | 1031 | | | 3.89 C16 | | | | | | | | 3.48 C23 | 3.28 N11 |
| 23 | 1153 | | | | | 3.87 C8 3.84 N09 | 2.95 N2 | 3.65 C23 3.72 C8 | 3.83 C23 3.54 C8 | | 3.5 C22 3.32 N2 3.41 N05 3.6 N4 | | 3.9 N11 |
| 24 | 1025 | | | | | | | | | | | | |
| 25 | 1012 | | | | | | | | | | | | |
| 26 | 1078 | | | 3.36 C12 3.54 C10 | | | | 3.62 C20 | 3.82 C20 3.67 C30 3.89 C10 | | 3.82 C19 3.75 N4 3.8 N3 | 3.81 C20 | |
| 27 | 1145 | | | | | 3.04 N4 3.17 N3 | | | | | 3.71 N01 | | |
| 28 | 1050 | | | | | | | | | | 3.82 N01 | | |
| 29 | 1253 | | | 3.8 C25 3.75 C28 | | | | | | | 3.57 N4 | | |
| 30 | 1257 | | | 3.28 C8 3.74 C11 3.47 C10 3.27 C10 3.83 C12 | 3.33 C9 3.38 C12 | | | | | | | | |
| 31 | 1297 | 3.78 C8 3.79 C12 3.84 C10 3.83 C10 | | | | | | | | | | | |
| 32 | 1304 | | | | | | | | | | | | |
| 33 | 1306 | | | | 3.63 C11 | 3.01 N4 | 3.72 C20 | | 3.49 C23 3.75 C23 | | 3.38 N4 3.73 N4 | | |
| 34 | 1307 | | | | | | | | | | 3.88 C19 | | |
| 35 | 1328 | | | | 3.69 C17 | | | | | | 3.57 C19 | | |
| 36 | 1334 | | | 3.46 C10 3.89 C21 3.79 C15 | 3.78 C11 | 3.73 N23 3.09 N5 | 3.18 C23 | | 3.82 C23 3.71 C23 | | 3.22 C22 3.76 C23 3.8 N5 | | |
| 37 | 1335 | | | | | | | | | | 3.68 N4 | | |
| 38 | 1338 | | | | | | | | | | 3.69 N5 3.73 N4 | | |
| 39 | 1345 | | | 3.61 C8 | 3.43 C9 | 3.88 C31 | 2.7 N5 | | 3.37 C31 | | 3.76 N4 3.71 N3 | 3.61 N4 3.81 N5 | |
| 40 | 1351 | | | | | | | | | | | | |
| 41 | 1353 | | | | | | | | | | | | |
| 42 | 1367 | | | | | | | | | | | | |

TABLE A2-continued

| # | | | | | | | | | | | |
|---|---|---|---|---|---|---|---|---|---|---|---|
| 43 | 1368 | 3.88 C26 | | | | | | | | | |
| 44 | 1371 | | | | | | | 3.49 C20 | | | |
| 45 | 1372 | 3.68 C18 | | 3.35 C18 | 3.4 C19 | | | | | 3.72 N3 / 3.73 N4 | |
| 46 | 1373 | 3.63 C12 | | 3.39 C7 | 3.88 S1 | | | | | | |
| 47 | 1492 | | | | | 3.24 N6 | | | 3.45 C19 | 3.45 C20 | 3.44 C23 | 3.75 C18 / 3.71 N4 |
| 48 | 1399 | 3.85 C7 | | | | | | | | | |
| 49 | 1406 | 3.78 C11 | 3.68 C10 | 3.11 C11 | | | | | | | 3.79 N4 |
| 50 | 1433 | | | | | 3.7 C6 | | | 3.14 C6 | | 3.79 C6 | 3.7 C6 / 3.53 C19 |
| 51, 52 | 14, 1360 | 3.68 C12 | | | | | | | | | |
| 53 | 1450 | | | C11 3.74 | C12 3.63 | 3.51 C22 | | 3.82 N5 | 2.86 C22 | 3.84 C24 | 3.61 C22 | 3.79 C20 / 3.77 N4 / 3.74 N2 |
| 54 | 1435 | 3.78 C12 | | | 3.66 C12 | 3.82 C13 | | | | | | 3.63 C22 |
| 55 | 1441 | 3.87 C14 | 3.5 C14 | 3.71 C15 | | | | | | | | 3.77 N4 |
| 56 | 1411 | 3.73 C14 | 3.66 C13 | 3.38 C14 | | | | | | | 2.89 C24 | 3.82 C22 / 3.54 C1 |
| 57 | 1149 | | 3.78 C32 | | | 3.67 N1 | | | | | 3.38 C8 | |

TABLE A2-7: van der Waals

| Amino Acid MASP-2 AA# | AA atom | CB | O | | SER 628 OG | |
|---|---|---|---|---|---|---|
| 1 | 1129 | 3.47 C18 | 3.46 C15 | 3.34 C14 | 3.22 C15 | 3.71 C14 |
| 2 | 1034 | | 3.29 C18 | 3.13 C16 | 3.42 C17 | 3.82 C16 |
| 3 | 1024 | | 3.34 C20 | 3.43 C18 | | 3.66 C18 |
| 4 | 1059 | | 3.35 C19 | 3.37 C18 | | 3.4 C18 |
| 5 | 1088 | | 3.11 C30 | 3.81 C24 | | 3.64 C21 |
| 6 | 1036 | | 3.35 C25 | 3.24 C22 | 3.25 C21 | |
| 7 | 1081 | | 3.37 C25 | 3.42 C22 | 3.42 C21 | |
| 8 | 1063 | | 3.57 C23 | 3.82 C20 | | |

TABLE A2-continued

| # | ID | | | | | | | |
|---|---|---|---|---|---|---|---|---|
| 9 | 1065 | | | | 2.89 C27 | 3.46 C24, 3.79 C18 | 3.66 C23 | | 3.59 C23, 3.38 C19 |
| 10 | 1030 | | | | 3.43 C21 | | | | 3.26 C17 |
| 11 | 1037 | | | | 3.34 C17 | 3.1 C14 | 2.92 C13 | | |
| 12 | 1118 | | | | 3.34 C17 | 3.1 C14 | 2.92 C13 | 3.57 C12 | |
| 13 | 1007 | | | | 3.13 C3 | 3.44 C2 | | | |
| 14 | Melagatran 999 | | | 3.87 C20 | 3.06 C23 | 3.27 C21 | 3.1 C20 | 3.89 C19 | 3.63 C21 |
| 15 | 1090 | | | 3.64 C23 | 3.77 C15 | 3.77 C22 | 2.93 C23 | 3.21 C24 | 3.46 C23 |
| 16 | 1089 | | | | 3.79 C19 | 3.32 C21 | 2.97 C22 | 3.23 C23 | 3.26 C23 |
| 17 | 1021 | | | | 3.05 C1 | 3.05 C2 | 3.78 C3 | 3.48 | 3.26 C22 |
| 18 | 1097 | | | 3.79 C6 | 3.39 C18 | 3.46 C19 | 3.54 C22 | | |
| 19 | 54 | 3.86 N11 | 3.58 O09 | | 2.56 C12 | 2.88 C14 | | | 3.18 C24, 3.11 C21 |
| 20 | 1042 | | | 3.61 C08, 3.55 C16 | 3.58 C17 | 3.26 C20 | | | 3.71 C18, 3.38 C08 |
| 21 | 2018 | | | 3.48 C21 | 3.33 C22 | 3.36 C25 | | | 3.78 C12 |
| 22 | 1031 | 3.64 C23 | 3.62 C24 | 3.18 C22 | 3.28 C23 | | | | 3.77 C20 |
| 23 | 1153 | | | 3.7 C2 | 3.16 C8 | | | | 3.14 C21 |
| 24 | 1025 | | | 3.3 C3 | 3.06 C4 | | | | 3.35 C3 |
| 25 | 1012 | | | 3.04 C53, 3.17 | | | | | |
| 26 | 1078 | | | 3.85 C18 | 3.07 C19 | 3.1 C20 | 3.89 C21 | | 3.86 C20, 3.36 C28, 3.39 C6 | 3.34 C21 | 3.86 C22 |
| 27 | 1145 | | | 3.59 C27 | 3.27 C30 | | | | |
| 28 | 1050 | | | 3.34 C10 | 3.58 C7 | | | | |
| 29 | 1253 | | | 3.58 C02 | | | | | |
| 30 | 1257 | | | 3.68 C02 | 3.84 C06 | | | | 3.85 C07, 3.61 C26 |
| 31 | 1297 | | | 3.79 C22 | 3.51 C23 | | | | |
| 32 | 1304 | | | 3.65 C19 | | | | | |
| 33 | 1306 | | | 3.65 C19 | 3.63 C20 | 3.33 C23 | | | 3.89 C18 |
| 34 | 1307 | 3.67 C21 | 3.76 C11 | 3.45 C19 | 3.63 C20 | 3.4 C23 | | | 3.51 C19 |

TABLE A2-continued

| No. | ID | | | | | | | |
|---|---|---|---|---|---|---|---|---|
| 35 | 1328 | 3.67 C22; 3.83 C11 | | 3.76 C18; 3.73 C19; 3.65 C1; 3.81 C22; 3.66 C27 | 3.76 C19; 3.25 C23 | 3.79 C22 | | 3.51 C22 | |
| 36 | 1334 | | | 3.7 C25; 3.66 C19 | 3.42 C23; 3.52 C23 | | | 3.28 C2 | |
| 37 | 1335 | | | 3.56 C8 | | | | | |
| 38 | 1338 | | | 3.63 C35 | 3.33 C28 | 3.12 C31 | | 3.33 C27 | |
| 39 | 1345 | | | | | | | | |
| 40 | 1351 | 3.89 C28 | | | | | | | |
| 41 | 1353 | | | | | | | | |
| 42 | 1367 | | | | | | | | |
| 43 | 1368 | | | | | | | | |
| 44 | 1371 | 3.87 C11 | | 3.41 C19 | 3.36 C20 | | | 3.75 C20 | 3.15 C21 |
| 45 | 1372 | | 3.64 C11 | 3.68 C9 | | | | | |
| 46 | 1373 | | | 3.64 C19 | | | | | |
| 47 | 1492 | 3.82 C19 | 3.71 C11 | 3.81 C18 | 3.24 C19 | 3.38 C20 | | 3.16 C18 | 2.8 C19 |
| 48 | 1399 | | | 3.61 C22 | | | | | |
| 49 | 1406 | | | 3.76 C20 | | | | | |
| 50 | 1433 | 3.67 C7 | | 3.71 C5 | 3.22 C6 | 3.89 C7 | | 3.65 C14 | |
| 51 | 14 | | | | | | | | |
| 52 | 1360 | | | C24; 3.61 | | | | | |
| 53 | 1450 | 3.65 C23 | | 3.19 C19; 3.88 C19 | C20; 3.33 | C22; 3.01 | C23 3.71 | | |
| 54 | 1435 | | | 3.67 | | | C24 2.95 | | |
| 55 | 1441 | | | 3.85 C19 | 3.53 C20 | | | | |
| 56 | 1411 | 3.82 C22 | | 3.76 C20 | | | | | |
| 57 | 1149 | | | 3.41 C1 | 3.69 C2 | 3.44 C8 | | | 3.78 C22 |

TABLE A2-continued

| | Amino Acid MASP-2 AA# | AA atom | | | | | CYS 629 | | |
|---|---|---|---|---|---|---|---|---|---|
| | | | | | | | CA | | |
| 1 | 1129 | 3.75 C17 | 3.66 C12 | | | | | | |
| 2 | 1034 | 3.89 C17 | 3.69 C13 | 3.48 C12 | | 3.86 C17 | 3.89 C14 | 3.85 C13 | 3.83 C12 |
| 3 | 1024 | 3.75 C15 | 3.75 C14 | | | | | | 3.67 C17 |
| 4 | 1059 | 3.72 C17 | 3.76 C16 | | 3.69 C11 | 3.86 C17 | | | |
| 5 | 1088 | 3.49 C24 | 3.75 C19 | | | | | | |
| 6 | 1036 | | | | | | 3.82 C23 | | |
| 7 | 1081 | 3.8 C19 | | | | | | | |
| 8 | 1063 | 3.78 C22 | 3.76 C21 | | | | | | |
| 9 | 1065 | | | | | | | | |
| 10 | 1030 | 3.61 C16 | 3.56 C11 | 3.85 C10 | | | | | |
| 11 | 1037 | 3.76 C20 | 3.89 C15 | | | | | | |
| 12 | 1118 | 3.89 C15 | | | | | | | |
| 13 | 1007 | 3.8 C19 | 3.8 C5 | 3.53 C2 | 3.41 C1 | 3.76 C3 | 3.55 N1 | 3.61 C2 | 3.48 C18 |
| 14 | Melagatran 999 | 3.68 C18 | 3.64 C17 | 3.8 C16 | | 3.84 C22 | 3.88 C21 | 3.74 C20 | 3.55 C19 |
| 15 | 1090 | 3.89 C15 | | | 3.74 N15 | | | | |
| 16 | 1089 | 3.84 C1 | 3.58 C6 | | | | | | |
| 17 | 1021 | | | | | | | | |
| 18 | 1097 | 3.88 C08 | 3.73 C14 | 3.79 N10 | | | | | |
| 19 | 54 | | | | | | | | |
| 20 | 1042 | 3.87 C24 | | 3.67 O26 | | | | | |
| 21 | 2018 | | | | | | | | |
| 22 | 1031 | 3.76 C21 | 3.62 C22 | | | 3.82 C24 | | | |
| 23 | 1153 | 3.85 C2 | | | | | | | |
| 24 | 1025 | 3.83 C04 | 3.84 C06 | 3.48 N05 | | | | | |
| 25 | 1012 | 3.71 C16 | 3.72 N4 | | | | | | |
| 26 | 1078 | 3.74 C18 | 3.63 O3 | | | | | | |
| 27 | 1145 | 3.85 C26 | | | | | | | |

TABLE A2-continued

| | | | | |
|---|---|---|---|---|
| 28 | 1050 | 3.75/C06 | | |
| 29 | 1253 | 3.86/C06 | 3.68/N01 | |
| 30 | 1257 | 3.6/C22 | 3.86/N01 | |
| 31 | 1297 | 3.81/N4 | 3.89/C23 | 3.55/N4 |
| 32 | 1304 | 3.8/C18 | | |
| 33 | 1306 | 3.59/C18 | 3.7/O3 | |
| 34 | 1307 | 3.77/C19 | 3.86/C22 | 3.6/N4 |
| 35 | 1328 | 3.84/C6 | 3.66/N4 | |
| 36 | 1334 | 3.75/C22 | | |
| 37 | 1335 | 3.62/C29 | 3.74/N4 | |
| 38 | 1338 | 3.85/C24 | 3.71/C30 | |
| 39 | 1345 | 3.76/C18 | 3.82/N4 | |
| 40 | 1351 | 3.89/C7 | 3.65/N4 | |
| 41 | 1353 | 3.86/C33 | 3.79/N3 | |
| 42 | 1367 | 3.76/N5 | 3.76/N4 | |
| 43 | 1368 | 3.9/C6 | | |
| 44 | 1371 | 3.83/N4 | 3.78/N3 | |
| 45 | 1372 | 3.86/C17 | | |
| 46 | 1373 | 3.81/N4 | | |
| 47 | 1492 | 3.86/C14 | 3.78/N4 | |
| 48 | 1399 | 3.81/N4 | 3.66/N1 | |
| 49 | 1406 | 3.89/C14 | | |
| 50 | 1433 | 3.86/C23 | 3.75/N4 | |
| 51 | 14 | 3.78/C20 | 3.57/N4 | |
| 52 | 1360 | 3.88/C18 | 3.85/N4 | |
| 53 | 1450 | | | |
| 54 | 1435 | | | |

TABLE A2-continued

| | | | | |
|---|---|---|---|---|
| 55 | 1441 | | 3.87 C19 | 3.83 N4 |
| 56 | 1411 | | 3.68 C21 | 3.72 N4 |
| 57 | 1149 | | 3.68 C1 | 3.82 C6 |

TABLE A2-8: van der Waals

| | Amino Acid MASP-2 AA# | | | CYS 629 | | | | ARG 630 | | |
|---|---|---|---|---|---|---|---|---|---|---|
| | AA atom | CB | N | C | O | O | CA | CB | CD |
| 1 | 1129 | | | | 3.88 C13 | 3.66 C12 | 3.6 C11 | | 3.67 O25 | |
| 2 | 1034 | | | | 3.74 C12 | 3.6 C11 | | | | |
| 3 | 1024 | | 3.65 C18 | | | | | | | |
| 4 | 1059 | | 3.83 C17 | | 3.73 C17 | | | | 3.8 O1 | |
| 5 | 1088 | | | | 3.84 C24 | 3.66 C19 | 3.58 C18 | | | |
| 6 | 1036 | | | | 3.8 C19 | 3.86 C18 | | | | |
| 7 | 1081 | | | | 3.73 C19 | | | | | |
| 8 | 1063 | | | | 3.65 C22 | 3.82 C21 | | | | |
| 9 | 1065 | | | | | | | | | |
| 10 | 1030 | | | | 3.8 C12 | 3.44 C11 | 3.38 C10 | 3.86 C10 | | |
| 11 | 1037 | | | | | | | | | |
| 12 | 1118 | | | | 3.41 C19 | 3.4 C2 | 3.39 C1 | | 3.86 O31 | |
| 13 | 1007 | | | | 3.76 C16 | | | | | |
| 14 | Melagatran | 3.84 C19 | | | | | | | | |
| 15 | 999 | | | 3.9 C16 | | | | | | |
| | 1090 | | | | | | | | | |
| 16 | 1089 | | | 3.78 C5 | 3.66 C5 | 3.86 C6 | 3.47 C7 | | | |
| 17 | 1021 | | | 3.83 C16 | 3.81 C15 | 3.89 C16 | | | | |
| 18 | 1097 | | | 3.71 C01 | 3.52 C6 | | | | | |
| | | | | 3.68 C14 | 3.88 C21 | | | | | |
| | | | | 3.78 C18 | 3.62 C02 | | | | | |
| | | | | 3.84 C21 | 3.76 C15 | | | | | |
| 19 | 54 | | | 3.77 C02 | 3.6 C19 | | | 3.68 C06 | | |
| | | | | 3.54 C13 | 3.53 O26 | | | | | |
| | | | | 3.64 C18 | | | | | | |
| 20 | 1042 | | | | 3.27 C14 | 3.2 C15 | 3.79 C05 | 3.86 C06 | | |
| | | | | | 3.81 C19 | | | | | |
| 21 | 2018 | | | 3.58 C24 | | 3.82 C16 | | | 3.39 O3 | |
| 22 | 1031 | | 3.72 C22 | | | | | | 2.94 O04 | |

TABLE A2-continued

| # | ID | | | | | | | | | | | |
|---|---|---|---|---|---|---|---|---|---|---|---|---|
| 23 | 1153 | 3.85 C3 | | 3.8 C4 | | | | | 3.8 C7 | 3.52 C9 | 3.43 N3 | 2.94 O1 |
| 24 | 1025 | | | 3.53 C04 / 3.55 C15 | 3.74 N05 / 3.7 | 3.17 C04 / 3.69 C03 / 3.72 C14 | | | | | | |
| 25 | 1012 | 3.88 C16 | | 3.86 C18 | 3.51 C16 | 3.83 C16 | | | | | | |
| 26 | 1078 | | | 3.84 C24 / 3.78 C9 | 3.69 C25 | | | | | | | |
| 27 | 1145 | | | | | 3.83 C24 / 3.88 C4 | | | 3.43 C15 | | | |
| 28 | 1050 | | | 3.62 C05 / 3.68 C05 | 3.66 C06 / 3.73 C06 | 3.85 C05 / 3.8 C07 / 3.79 C09 / 3.9 C16 | 3.73 C08 / 3.89 C09 | 3.82 C09 | 3.86 C09 | | | |
| 29 | 1253 | | | 3.58 C21 / 3.71 C17 | 3.54 C22 / 3.75 C18 | 3.81 C20 / 3.85 C18 | 3.69 C22 / 3.71 C22 | 3.57 C26 | 3.89 C16 | | | |
| 30 | 1257 | 3.87 C26 | | | | | | | | | | |
| 31 | 1297 | | | 3.77 C18 / 3.74 C17 | 3.48 O3 / 3.68 C18 | 3.54 C16 / 3.85 C18 | 3.87 C17 | | | | | |
| 32 | 1304 | 3.81 C18 | 3.55 C22 | 3.71 C18 | 3.78 | | | | | | | |
| 33/34 | 1306/1307 | | | 3.82 C4 / 3.9 C20 | 3.7 / 3.61 C5 | 3.86 C4 / 3.71 C20 | | 3.37 C30 | | | | |
| 35 | 1328 | | | 3.89 C24 / 3.62 C23 | 3.55 C25 / 3.68 C24 | 3.45 C24 / 3.85 C22 | 3.71 C22 / 3.85 C29 | | | | | |
| 36 | 1334 | | | 3.72 C17 / 3.74 C6 | 3.68 C18 / 3.78 C7 | 3.85 C23 / 3.87 C17 | 3.69 C22 / 3.77 C26 | 3.76 C22 / 3.83 C24 / 3.75 C18 | 3.76 C21 / 3.85 C25 / 3.87 C17 | 3.75 C26 / 3.68 C30 / 3.73 C28 / 3.69 C22 | 3.86 C22 | | |
| 37 | 1335 | | | 3.66 C32 / 3.52 N5 | 3.69 C33 | | | 3.8 C33 | 3.74 C39 | | 3.83 N6 | |
| 38 | 1338 | | | 3.73 C5 / 3.68 C17 | 3.72 C6 / 3.77 C18 | 3.69 C22 / 3.87 C17 | | 3.83 C6 / 3.86 C18 | 3.72 C22 | | 3.75 N5 | 3.72 O1 |
| 39 | 1345 | 3.8 C18 | | 3.51 C16 / 3.69 C20 | 3.66 C17 / 3.73 C21 | 3.84 C21 / 3.87 C17 | | 3.73 C25 / 3.87 C19 | | | | 3.49 C16 / 3.62 C17 |
| 40 | 1351 | | | 3.69 C18 | 3.74 C19 | 3.71 C23 | | | | | | |

TABLE A2-continued

| | | | | | | | | |
|---|---|---|---|---|---|---|---|---|
| 50 | 1433 | 3.88 C3 3.83 C13 | 3.55 C4 3.58 C14 | | 3.77 C3 3.51 C13 3.81 C21 3.77 C17 | 3.63 C14 3.82 C22 3.88 C21 | | 3.89 C4 |
| 51 | 14 | 3.68 C22 | 3.77 C23 | | | | | 3.78 C1 |
| 52 | 1360 | 3.86 C21 3.71 C17 | 3.51 C21 3.78 C18 | 3.62 N4 | 3.84 C22 | | 3.75 C27 | |
| 53 | 1450 | 3.6 C1 3.81 C16 | 3.75 C19 3.59 C17 | 3.67 C21 | 3.85 C1 3.62 C16 | 3.89 C19 3.76 C17 | 3.83 C23 3.51 C22 | 3.85 C2 3.85 C16 |
| 54 | 1435 | | | | | | | |
| 55 | 1441 | | | | | | | |
| 56 | 1411 | 3.72 C22 | | | | | | 3.47 O3 3.72 O4 |
| 57 | 1149 | 3.64 C1 3.66 C6 | | | 3.54 C6 | | | |

TABLE A2-9 van der Waals

| | Amino Acid MASP-2 AA# | CG | | ARG 630 | CZ |
|---|---|---|---|---|---|
| | AA atom | | | | |
| 1 | 1129 | 3.41 O25 | | | |
| 2 | 1034 | | | | |
| 3 | 1024 | 3.14 O1 | | | |
| 4 | 1059 | 3.79 O03 | | | |
| 5 | 1088 | | | | |
| 6 | 1036 | 3.76 O11 | | | |
| 7 | 1081 | | | | |
| 8 | 1063 | 3.55 O13 | | | |
| 9 | 1065 | | | | |
| 10 | 1030 | 3.85 O2 | | | |
| 11 | 1037 | 3.61 O1 | | | |
| 12 | 1118 | | | | |
| 13 | 1007 | 3.8 O31 | | | |
| 14 | Melagatran | | | | |
| 15 | 999 1090 | | 3.64 O1 | | |
| 16 | 1089 | | 3.31 C05 | 2.93 C06 | |
| 17 | 1021 | 3.89 C01 | | | |
| 18 | 1097 | | | | |
| 19 | 54 | | | | |

TABLE A2-continued

| | | | | | | | | |
|---|---|---|---|---|---|---|---|---|
| 20 21 22 | 1042 2018 1031 | 3.05 O04 3.89 C6 | | | | | | |
| 23 | 1153 | 3.51 C7 | 3.86 C9 | 3.25 N3 | 3.76 O1 | 3.17 O04 3.78 C7 | 3.86 O09 3.87 C9 | 3.03 O1 |
| 24 25 | 1025 1012 | 3.83 O1 3.78 O2 | | | | | | |
| 26 | 1078 | | | | | 3.77 C15 | 3.6 C16 | 2.85 C17 | 3.57 C18 |
| 27 | 1145 | 3.44 C15 | | | | | | |
| 28 | 1050 | 3.66 O1 | | | | | | |
| 29 | 1253 | 3.77 C04 3.53 O13 | | | | | | |
| 30 | 1257 | 3.63 O13 | | | | | | |
| 31 | 1297 | 3.47 O2 3.71 C21 | | | | | | |
| 32 | 1304 | | 3.7 O2 | | | | | |
| 33 34 | 1306 1307 | 3.57 O2 3.9 C21 | 3.85 O3 3.79 O2 | | | | | |
| 35 | 1328 | 3.89 C18 3.48 O3 3.75 O2 | | | | | | |
| 36 | 1334 | | | | | | | |
| 37 | 1335 | 3.81 C27 3.74 C21 | 3.78 O30 | | | | | |
| 38 | 1338 | 3.86 O1 3.67 C37 | | | | | | |
| 39 | 1345 | | | | | 3.52 O1 | | |
| 40 | 1351 | 3.68 C7 3.7 C21 | 3.69 O1 3.66 O2 | | | | | |
| 41 | 1353 | | | | | | | |
| 42 | 1367 | 3.73 C24 | 3.74 O1 | | | | | |
| 43 | 1368 | | | | | | | |
| 44 45 | 1371 1372 | | | | | | | |
| 46 | 1373 | | | | | | | |
| 47 48 | 1492 1399 | | | | | | | |
| 49 | 1406 | | | | | | | |

TABLE A2-continued

| | MASP-2 AA# | | | | | |
|---|---|---|---|---|---|---|
| 50 | 1433 | | 3.73 C10 | | 3.8 N1 | |
| 51 | 14 | | | | | |
| 52 | 1360 | | | | | |
| 53 | 1450 | | | | | |
| 54 | 1435 | | | | | |
| 55 | 1441 | | 3.87 O2 | | | |
| 56 | 1411 | | 3.7 C18 | 3.57 O3 | | 3.71 O3 |
| 57 | 1149 | | | | | |

| | Amino Acid MASP-2 AA# | | ARG 630 | |
|---|---|---|---|---|
| | AA atom | | N | NE | NH1 |
| 1 | 1129 | 3.69 C17 | | | |
| 2 | 1034 | 3.45 C13 | 3.63 C12 | | |
| 3 | 1024 | 3.48 C15 | 3.83 C14 | | |
| 4 | 1059 | | | | |
| 5 | 1088 | 3.9 C26 | | | |
| 6 | 1036 | 3.5 C24 | | | |
| 7 | 1081 | 3.81 C24 | | | |
| 8 | 1063 | 3.71 C18 | 3.88 C17 | | |
| 9 | 1065 | 3.77 C26 | 3.82 C21 | | |
| 10 | 1030 | 3.83 C16 | | | |
| 11 | 1037 | 3.54 C16 | 3.86 C11 | | |
| 12 | 1118 | 3.67 C20 | | | |
| 13 | 1007 | 3.77 C5 | 3.74 C1 | | |
| 14 | Melagatran 999 | 3.64 C18 | 3.89 C16 | | 3.83 C27 |
| 15 | 1090 | | 3.85 C11 | | |
| 16 | 1089 | 3.88 C15 | 3.86 C16 | | |
| 17 | 1021 | | 3.89 C6 | | |
| 18 | 1097 | | 3.71 C21 | | |

TABLE A2-continued

| | | | | | | | | | | |
|---|---|---|---|---|---|---|---|---|---|---|
| 19 | 54 | 3.5 C01 | 3.86 C02 | 3.63 C06 | | | | | | |
| 20 21 | 1042 2018 | 3.89 C18 | 3.82 C19 | 3.43 C24 | | | | | | |
| 22 | 1031 | | | | 3.34 C03 | | | | | |
| 23 | 1153 | 3.86 C6 | | | | | | | | |
| 24 25 | 1025 1012 | 3.74 C15 | 3.73 C19 | | | | | | | |
| 26 27 | 1078 1145 | 3.58 C25 | | | 3.69 C15 | 3.37 C16 | 2.93 C17 | 3.28 C1 3.81 C08 | 3.34 C2 | 3.33 C26 |
| 28 | 1050 | 3.66 C9 | | | | | | | | |
| 29 | 1253 | 3.78 C04 | 3.69 C05 3.72 C05 | | | | | | | |
| 30 | 1257 | 3.81 C04 | 3.61 C21 | | | | | | | |
| 31 | 1297 | 3.87 C20 3.76 C17 | 3.88 C21 | 3.76 C25 | | | | | | |
| 32 | 1304 | 3.76 C22 | | | | | | | | |
| 33 | 1306 | | | | | | | | | |
| 34 35 36 | 1307 1328 1334 | 3.59 C18 3.57 C5 | | | | | | | | |
| 37 | 1335 | | | | | | | | | |
| 38 | 1338 | 3.88 C20 3.44 C30 | 3.7 C21 | 3.71 C25 | | | | | | |
| 39 | 1345 | | | | | | | | 3.55 C17 | |
| 40 | 1351 | 3.89 C22 3.81 C17 | 3.69 C23 3.89 C21 | 3.76 C27 | | | | 3.72 C15 | | |
| 41 | 1353 | | | | | | | | | |
| 42 | 1367 | 3.8 C6 | | | | | | | | |
| 43 | 1368 | 3.71 C32 | 3.81 C37 | | | | | | | |
| 44 | 1371 | 3.44 N5 | | | | | | | | |
| 45 | 1372 | 3.79 C5 | 3.86 C7 | | | | | | | |
| 46 | 1373 | 3.76 C17 | 3.86 C21 | | | | | 3.31 C14 | | |
| 47 | 1492 | 3.71 C16 | | | | | | | | |

TABLE A2-continued

| # | MASP-2 AA# | | | | |
|---|---|---|---|---|---|
| 48 | 1399 | 3.75 C20 | 3.81 C24 | | |
| 49 | 1406 | 3.7 C18 | 3.81 C22 | | |
| 50 | 1433 | 3.49 C4 | | | |
| 51 | 14 | | | | |
| 52 | 1360 | | | | |
| 53 | 1450 | | | | |
| 54 | 1435 | | | | |
| 55 | 1441 | 3.68 C1 | 3.89 C2 | 3.72 C22 | |
| 56 | 1411 | 3.88 C16 | 3.76 C17 | 3.87 C18 | |
| 57 | 1149 | | | | 3.82 C23 |

TABLE A2-10 van der Waals

| | Amino Acid MASP-2 AA# | ARG 630 | GLY 631 | ASP 632 | | | SER 633 | |
|---|---|---|---|---|---|---|---|---|
| | AA atom | NH2 | C | CA | CB | O | OG | O |
| 1 | 1129 | | | | | | 3.11 C11 | |
| 2 | 1034 | | | | | | 3.11 C11 | 3.9 C06 |
| 3 | 1024 | | | | | | 3.41 C13 | |
| 4 | 1059 | | | | | | 3.51 C15 | |
| 5 | 1088 | | | | | | 3.7 C20 | |
| 6 | 1036 | | | | | | 3.53 C18 | 3.8 C15 |
| 7 | 1081 | | | | | | 3.36 C18 | |
| 8 | 1063 | | | | | | 3.67 C16 | |
| 9 | 1065 | | | | | | 3.14 C20 | |
| 10 | 1030 | | | | | | 3.31 C14 | |
| 11 | 1037 | | | | | | 3.31 C10 | |
| 12 | 1118 | | | | | | 3.4 C14 | |
| 13 | 1007 | | | | | | 3.2 C19 | |
| 14 | Melagatran 999 | | | | | | 2.98 C16 | |
| 15 | 1090 | | | | | | 3.2 C21 | 3.61 C21 |

TABLE A2-continued

| | | | | | | | |
|---|---|---|---|---|---|---|---|
| 16 | 1089 | | | | | | |
| 17 | 1021 | | | | | | |
| 18 | 1097 | | | | | | |
| 19 | 54 | | | | | | |
| 20 | 1042 | | | | | | |
| 21 | 2018 | | | | | | |
| 22 | 1031 | | | | | | |
| 23 | 1153 | 3.36 C9 | | | | | |
| 24 | 1025 | | | | | | |
| 25 | 1012 | | | | | | |
| 26 | 1078 | 3.71 C1 | 3.75 C15 | 3.75 C2 | 3.85 C3 | | |
| 27 | 1145 | 2.92 C17 | 3.23 C18 | | | | |
| 28 | 1050 | | | | | | |
| 29 | 1253 | 3.82 C03 | | | | | |
| 30 | 1257 | | | | | | |
| 31 | 1297 | | | | | | |
| 32 | 1304 | | | | | | |
| 33 | 1306 | | | | | | |
| 34 | 1307 | | | | | | |
| 35 | 1328 | | | | | | |
| 36 | 1334 | | | | | | |
| 37 | 1335 | | | | | | |
| 38 | 1338 | | | | | | |
| 39 | 1345 | | | | | | |
| 40 | 1351 | | | | | | |
| 41 | 1353 | | | | | | |
| 42 | 1367 | | | | | | |

| | | | |
|---|---|---|---|
| | 3.29 C7 | | |
| | 3.45 C15 | | |
| | 2.86 C03 | 2.68 C04 | |
| | 3.28 C13 | | |
| | 3.17 C18 | | |
| | 3.7 C01 | | |
| | 3.32 C7 | | |
| | 3.82 C02 | | |
| | 3.47 C14 | | |
| | 3.5 C3 | | |
| | 3.22 C16 | | |
| | 3.23 C23 | | |
| | 3.17 C3 | | |
| | 3.22 C09 | | |
| | 3.24 C09 | 3.8 C8 | |
| | 3.19 C20 | | |
| | 3.29 C16 | | |
| | 3.39 C16 | | |
| | 3.18 C16 | | |
| | 3.14 C16 | | |
| | 3.35 C16 | | |
| | 3.44 C7 | | |
| | 3.47 C20 | | |
| | 3.31 C24 | | |
| | 3.53 C22 | | |
| | 3.31 C26 | | |
| | 3.37 | 3.17 C14 | |

TABLE A2-continued

| # | MASP-2 AA# | | | | | | | | | | | | |
|---|---|---|---|---|---|---|---|---|---|---|---|---|
| 43 | 1368 | 3.75 C36 | | | | | | | | | | 3.32 C5 |
| 44 | 1371 | | | | | | | | | | | 3.68 C31 |
| 45 | 1372 | 3.88 C8 | | | | | | | | | | 3.3 C16 |
| 46 | 1373 | | | | | | | | | | | 3.27 C4 |
| 47 | 1492 | | | | | | | | | | | 3.49 C16 |
| 48 | 1399 | | | | | | | | | | | 3.31 C16 |
| 49 | 1406 | | | | | | | | | | | 3.25 C19 |
| 50 | 1433 | | | | | | | | | | | 3.17 C17 C8 |
| 51 | 14 | 3.25 N3 | 3.61 C15 | 2.34 C16 | 3.08 C17 | 3.89 O3 | 3.14 O7 | 3.69 C16 | 2.4 N3 | 3.37 N3 | 2.66 C16 | 3.09 C17 |
| 52 | 1360 | | | | | | | | | | | |
| 53 | 1450 | | | | | | | | | | | |
| 54 | 1435 | | | | | | | | | | | |
| 55 | 1441 | 3.88 C21 | | | | | | | | | | 3.38 C2 |
| 56 | 1411 | 3.62 C25 | | | | | | | | | | 3.47 C16 |
| 57 | 1149 | | | | | | | | | | | 3.45 C7 |

TABLE A2-11 van der Waals

| Amino Acid MASP-2 AA# | | GLY 634 | | GLY 635 |
|---|---|---|---|---|
| AA atom | C | CA | N | N |
| 1 | 1129 | | | |
| 2 | 1034 | | | |
| 3 | 1024 | | | |
| 4 | 1059 | | | |
| 5 | 1088 | | | |
| 6 | 1036 | | | |
| 7 | 1081 | | | |
| 8 | 1063 | | | |
| 9 | 1065 | | | |
| 10 | 1030 | | | |
| 11 | 1037 | | | |
| 12 | 1118 | | | |
| 13 | 1007 | | | |
| 14 | Melagatran999 | | | |
| 15 | 1090 | | | |
| 16 | 1089 | | | |
| 17 | 1021 | | | |

TABLE A2-continued

| AA# | | | | | | | |
|---|---|---|---|---|---|---|---|
| 18 | 1097 | | | | | | |
| 19 | 54 | | | | | | |
| 20 | 1042 | | | | | | |
| 21 | 2018 | | | | | | |
| 22 | 1031 | | | | | | |
| 23 | 1153 | | | | | | |
| 24 | 1025 | | | | | | |
| 25 | 1012 | | | | | | |
| 26 | 1078 | | | | | | |
| 27 | 1145 | | | | | | |
| 28 | 1050 | | | | | | |
| 29 | 1253 | | | | | | |
| 30 | 1257 | | | | | | |
| 31 | 1297 | | | | | | |
| 32 | 1304 | | | | | | |
| 33 | 1306 | | | | | | |
| 34 | 1307 | | | | | | |
| 35 | 1328 | | | | | | |
| 36 | 1334 | | | | | | |
| 37 | 1335 | | | | | | |
| 38 | 1338 | | | | | | |
| 39 | 1345 | | | | | | |
| 40 | 1351 | | | | | | |
| 41 | 1353 | | | | | | |
| 42 | 1367 | | | | | | |
| 43 | 1368 | | | | | | |
| 44 | 1371 | | | | | | |
| 45 | 1372 | | | | | | |
| 46 | 1373 | | | | | | |
| 47 | 1492 | | | | | | |
| 48 | 1399 | | | | | | |
| 49 | 1406 | | | | | | |
| 50 | 1433 | | | | | 2.57 C17 | |
| 51 | 14 | 3.52 C17 | 3.74 O7 | 3.81 C16 | 3 O7 | 3.12 C15 | 2.33 C16 | 3.52 C17 |
| 52 | 1360 | | | | | | |
| 53 | 1450 | | | | | | |
| 54 | 1435 | | | | | | |
| 55 | 1441 | | | | | | |
| 56 | 1411 | | | | | | |
| 57 | 1149 | | | | | | |

| Amino Acid | VAL 653 | | | | SER 654 |
|---|---|---|---|---|---|
| MASP-2 AA# | | | | | |
| AA atom | CB | CG1 | C | O | C |
| 1 | 1129 | 3.9 C13 | | 3.65 N10 | | 3.8 C11 / 3.74 C06 / 3.71 C01 |
| 2 | 1034 | | | | | 3.83 C11 / 3.7 C12 |
| 3 | 1024 | | | 3.75 N3 | | 3.72 C13 / 3.62 C11 |

TABLE A2-continued

| # | ID | | | | | | |
|---|---|---|---|---|---|---|---|
| 4 | 1059 | | 3.81 C17, 3.62 C23 | | 3.87 N1, 3.68 C22, 3.52 N17, 3.78 N17 | 3.73 C15, 3.55 C22, 3.52 C18, 3.74 C18, 3.87 C16, 3.78 C20 | 3.74 C21, 3.75 C15, 3.72 C10, 3.76 C9 | 3.5 C20, 3.71 C14, 3.71 C09, 3.65 C8 |
| 5 | 1088 | | | 3.55 C22 | | | | |
| 6 | 1036 | | | | | | | |
| 7 | 1081 | | 3.84 C20 | | | | | |
| 8 | 1063 | | | | | | | |
| 9 | 1065 | | 3.6 C22 | | | | | |
| 10 | 1030 | | | | 3.79 N3 | 3.62 C20, 3.79 C14, 3.79 C10 | 3.77 C13, 3.85 C06 | 3.81 C12 |
| 11 | 1037 | | 3.9 C12, 3.86 C16 | | | | | |
| 12 | 1118 | | | | 3.84 N09 | 3.76 C14, 3.76 C19 | 3.73 C7, 3.85 C7 | 3.7 C6, 3.85 C6 |
| 13 | 1007 | | | | | 3.66 C16 | | |
| 14 | Melagatran999 | | | | | | | |
| 15 | 1090 | | | | | | | |
| 16 | 1089 | | | | | | | |
| 17 | 1021 | | 3.43 C4 | | | 3.84 C4, 3.73 N4 | | |
| 18 | 1097 | | | | | | | |
| 19 | 54 | | 3.75 O09 | 3.79 N3 | | | | |
| 20 | 1042 | | | | 3.36 O11, 3.79 N3 | | | |
| 21 | 2018 | | | | 3.77 C01 | | | |
| 22 | 1031 | | 3.58 C25 | | | | 3.56 C25 | |
| 23 | 1153 | | 3.9 C4 | | | | | |
| 24 | 1025 | | 3.49 C22 | | | | | |
| 25 | 1012 | | 3.9 C29 | | | | | |
| 26 | 1078 | | 3.74 C5 | | 3.66 C22 | 3.48 N1 | | |
| 27 | 1145 | | 3.31 C08 | | | | | |
| 28 | 1050 | | 3.36 C07 | | | | | |
| 29 | 1253 | | 3.22 C26 | | | | | |
| 30 | 1257 | | | | | | | |
| 31 | 1297 | | | | | | | |

TABLE A2-continued

| # | No. | | | | | | | | | |
|---|-----|---|---|---|---|---|---|---|---|---|
| 32 | 1304 | 3.27 C22 | | | | | | | | |
| 33 | 1306 | | | | | | | | | |
| 34 | 1307 | | | | | | | | | |
| 35 | 1328 | 3.47 C22 / 3.23 C22 | | | | | | | | |
| 36 | 1334 | 3.55 C21 | 3.81 C11 | | | | 3.79 N1 / 3.62 C16 / 3.72 C22 / 3.71 N3 | | | 3.79 N3 |
| 37 | 1335 | 3.83 C3 | | | | | | | | |
| 38 | 1338 | 3.33 C26 | | | | | 3.89 C21 / 3.84 N1 | | | 3.76 N3 |
| 39 | 1345 | | | | | | | | | |
| 40 | 1351 | 3.3 C28 / 3.3 C22 / 3.35 C11 | | | | | | | | |
| 41 | 1353 | | | | | | | | | |
| 42 | 1367 | 3.32 C39 | | | | | | | | |
| 43 | 1368 | 3.43 C22 | 3.87 C11 | | | | | | | |
| 44 | 1371 | 3.32 C25 / 3.34 C22 | | | | | | | | |
| 45 | 1372 | | | | | | | | | |
| 46 | 1373 | | | | | | | | | |
| 47 | 1492 | 3.61 C18 / 3.32 C25 | | | | | 3.9 C26 | | | |
| 48 | 1399 | 3.27 C23 | | | | | 3.88 N1 / 3.89 C22 / 3.59 N4 | | | 3.62 N3 |
| 49 | 1406 | 3.71 C2 | | | | | 3.88 C2 | | | |
| 50 | 1433 | | | | | | | | | 3.89 N3 |
| 51 | 14 | 3.77 C16 | | 3.44 C16 | 3.77 N3 | 3.45 O3 | 3.71 C15 | 3.57 C16 | 3.67 C17 | |
| 52 | 1360 | | | | | | | | | |
| 53 | 1450 | | | | | | | | | |
| 54 | 1435 | 3.38 C23 | | | | | 3.81 C18 | | | |
| 55 | 1441 | 3.52 C22 | | | | | | | | |
| 56 | 1411 | | | | | | | | | |
| 57 | 1149 | | | | | | 3.68 N3 | | | |

TABLE A2-continued

TABLE A2-12: van der Waals

| | Amino Acid MASP-2 AA# | AA atom | SER 654 | TRP 655 | | |
|---|---|---|---|---|---|---|
| | | | O | | C | CA |
| 1 | 1129 | | | 3.7 N10<br>3.42 O07<br>3.28 O2<br>3.49 O2<br>3.82 C23<br>3.4 C20<br>3.88 C21<br>3.62 C22<br>3.46 O09<br>3.4 O2<br>3.85 C12<br>3.61 C16<br>3.31 O2 | 3.64 C14<br>3.88 C17<br>3.71 O2<br>3.85 C21<br>3.62 C24<br>3.84 C22<br>3.83 C22<br>3.75 C23<br>3.61 C24<br>3.77 O2<br>3.5 C13<br>3.34 C17 | 3.75 C13<br>3.71 C16<br>3.66 C19<br>3.76 C20<br>3.72 C23<br>3.19 C21<br>3.49 C21<br>3.48 C21<br>3.73 C23<br>3.57 C20<br>3.68 C12<br>3.57 C16 | 3.56 O07<br>3.64 O07<br>3.5 C18<br>3.82 O2<br>3.89 O07<br>3.21 C20<br>3.84 C20<br>3.77 O1<br>3.89 C19<br>3.44 C19<br>3.8 C04<br>3.73 O1 | 3.76 N3<br>3.47 O07<br>3.63 C19<br>3.5 O05<br>3.89 C7<br>3.68 N3<br>3.32 O1 | 3.89 N01<br>3.85 C18 |
| 2 | 1034 | | | | | | |
| 3 | 1024 | | | | | | |
| 4 | 1059 | | | | | | |
| 5 | 1088 | | | | | | |
| 6 | 1036 | | | | 3.83 C19 | | |
| 7 | 1081 | | | | | | |
| 8 | 1063 | | | | | | |
| 9 | 1065 | | | | | | |
| 10 | 1030 | | | | | | |
| 11 | 1037 | | | | | | |
| 12 | 1118 | | | | | | |
| 13 | 1007 | | | | | | |
| 14 | Melagatran999 | | | 3.79 C22 | 3.73 C22<br>3.79 C14<br>3.82 C20 | 3.57 C21<br>3.65 C15<br>3.61 C19 | 3.89 C20<br>3.87 C16<br>3.77 C18 | 3.85 O14<br>3.59 O2 | 3.83 C16 |
| 15 | 1090 | 3.57 C14 | 3.84 C7<br>3.75 C8<br>3.59 C15 | 3.9 C4 | | 3.74 O1 | 3.72 C4 | 3.38 C3 | 3.76 N2<br>3.84 C15<br>3.87 C3 | 3.84 N3 |
| 16 | 1089 | 3.73 C9 | 3.83 C8 | | | | | | 3.68 C4 | |
| 17 | 1021 | 3.76 C13 | 3.75 C14 | | | 3.82 C11<br>3.67 C17 | 3.59 C18 | 3.76 C4 | 3.8 C17 | |
| 18 | 1097 | 3.69 C03 | 3.58 C04 | | | 3.81 C02 | 3.57 C08 | 3.41 O09 | 3.34 O2 | |
| 19 | 54 | | | | | 3.57 C16 | | | 3.61 C03 | |
| 20 | 1042 | 3.84 C10 | 3.85 C13 | 3.17 C15 | | 3.53 C20 | 3.48 C21 | 3.88 C16 | 3.67 C15 | 3.89 O05 | 3.23 O11 |
| 21 | 2018 | 3.46 C16 | 3.68 C17 | 3.88 C18 | | 3.67 C20 | 3.4 C24 | 3.88 O2<br>3.26 C25 | 3.73 C20 | 3.45 N3 |
| 22 | 1031 | 3 C01 | 3.17 C07 | 3.76 C20 | 3.59 C25 | | | | 3.64 C01 | 3.25 C25 |
| 23 | 1153 | 3.77 C10 | 3.76 C7 | | | 3.86 C3 | 3.58 O2 | | 3.19 O2 | 3.68 N06 |

TABLE A2-continued

| | | | | | | | | | | |
|---|---|---|---|---|---|---|---|---|---|---|
| 24 | 1025 | 3.51 C02 | 3.68 C12 | 3.76 C13 | 3.87 C14 | | 3.8 O2 | | | 3.68 O26 | 3.36 O2 |
| 25 | 1012 | 3.59 C1 | 3.48 C16 | 3.62 C2 | | | 3.67 C20 | 3.39 C21 | | 3.71 C17 | |
| 26 | 1078 | 3.81 C1 | 3.89 C16 | 3.61 C23 | | | 3.45 C28 | 3.57 C29 | 3.5 C22 | 3.59 C29 | 3.88 C21 | 3.42 C22 |
| 27 | 1145 | 3.72 C3 | 3.89 C2 | | | | 3.47 C5 | 3.31 C6 | 3.71 O2 | 3.77 C4 | 3.74 N1 | 3.28 O2 |
| 28 | 1050 | | | | | | 3.82 C6 | 3.82 O17 | 3.74 C7 | 3.85 O2 | | 3.41 C4 | 3.48 C5 | 3.89 C6 |
| 29 | 1253 | 3.82 C09 | 3.83 C12 | | | | 3.8 N01 | | | | | |
| 30 | 1257 | 3.73 C09 | | | | | 3.86 C06 | 3.76 N01 | | 3.57 O37 | 3.66 N2 | 3.47 O2 |
| 31 | 1297 | 3.51 C20 | | | | | 3.89 N4 | | | 3.49 O1 | | |
| 32 | 1304 | 3.87 C1 | 3.88 C15 | 3.79 C16 | | | 3.82 C18 | 3.76 N4 | 3.83 O1 | 3.42 O1 | | |
| 33 | 1306 | 3.71 C1 | 3.08 C16 | | | | 3.58 C18 | 3.72 C19 | 3.71 O1 | 3.69 C16 | 3.68 C17 | 3.35 O1 3.3 O1 |
| 34 | 1307 | 3.74 C1 | 3.79 C15 | 3.73 C16 | | | 3.56 C20 | 3.4 C21 | 3.61 O1 | 3.84 C17 | 3.59 C18 | |
| 35 | 1328 | 3.79 C1 | 3.65 C15 | 3.44 C16 | 3.84 C26 | | | | 3.61 C22 | 3.73 N3 | 3.45 O1 | |
| 36 | 1334 | 3.82 C1 | 3.77 C15 | 3.58 C16 | 3.86 C28 | | 3.51 C20 | 3.74 C21 | 3.69 C22 | 3.6 O1 | 3.88 N3 | 3.42 O1 |
| 37 | 1335 | 3.79 C1 | 3.9 C15 | 3.87 C16 | | | 3.48 C2 | 3.68 C3 | 3.73 O1 | 3.21 C26 | 3.87 N1 | 3.36 O1 |
| 38 | 1338 | 3.86 C7 | 3.9 C8 | 3.81 C9 | | | 3.82 C2 | 3.84 C3 | | 3.4 C3 | | |
| 39 | 1345 | 3.88 C1 | 3.88 C19 | 3.81 C20 | | | 3.61 N4 | 3.84 O1 | 3.66 O2 | 3.81 O1 | 3.7 N1 | 3.25 O2 |
| 40 | 1351 | 3.75 C24 | | | | | 3.61 C26 | 3.61 C27 | | 3.26 C26 | | |
| 41 | 1353 | 3.89 C1 | 3.9 C21 | 3.81 C22 | | | 3.8 N4 | 3.81 O1 | | 3.34 O1 | | |
| 42 | 1367 | 3.86 C14 | 3.89 C22 | 3.82 C16 | | | 3.8 N4 | 3.72 O1 | | 3.3 O1 | | 3.81 O1 |
| 43 | 1368 | 3.87 C5 | 3.85 C15 | 3.77 C4 | | | 3.81 N3 | 3.73 O2 | | 3.29 O2 | | |
| 44 | 1371 | 3.53 C03 | 3.66 C15 | | | | 3.89 N34 | 3.63 O29 | 3.56 C21 | 3.72 C22 | 3.68 C17 | 3.4 O1 |
| 45 | 1372 | 3.9 C1 | 3.89 C19 | 3.77 C4 | | | 3.85 N3 | 3.88 O2 | 3.84 O1 | 3.48 O2 | 3.59 C18 | |
| 46 | 1373 | 3.87 C5 | | | | | 3.84 C18 | 3.77 N4 | | 3.44 O1 | 3.45 O1 | |
| 47 | 1492 | 3.25 C16 | 3.47 C15 | 3.82 C16 | | | 3.7 O1 | 3.82 O29 | | 3.87 C15 | 3.58 N4 | 3.33 O1 |
| 48 | 1399 | 3.88 C17 | 3.85 C19 | | | | 3.83 C21 | 3.75 C28 | 3.84 O2 | 3.43 O2 | | 3.89 N3 | 3.38 O1 |
| 49 | 1406 | 3.88 C16 | 3.76 C17 | 3.88 C2 | | | 3.81 C19 | 3.81 N4 | 3.87 O1 | 3.84 C19 | | |

TABLE A2-continued

| | | | | | | | | | | | | | |
|---|---|---|---|---|---|---|---|---|---|---|---|---|---|
| 50 | 1433 | 3.89 C10 | 3.89 C2 | 3.57 C8 | 3.87 C9 | 3.5 C1 | 3.74 C2 | 3.75 O2 | 3.67 C7 | | 3.62 C2 3.69 O1 3.44 O1 | 3.37 O2 | | |
| 51 | 14 | 3.54 C12 | 3.21 C8 | | | 3.72 C9 | | | | | | | | |
| 52 | 1360 | 3.89 C1 | 3.85 C21 | | | 3.9 C23 | 3.85 N4 | | | | | | | |
| 53 | 1450 | 3.68 C16 | 3.79 C18 | | | 3.65 C18 | 3.39 C19 | | 3.82 O1 3.54 C23 | 3.67 O1 | 3.53 C18 3.41 O1 | 3.85 C19 | 3.9 N3 | 3.31 O1 |
| 54 | 1435 | 3.88 C1 | 3.9 C15 | 3.85 C16 | | 3.87 C18 | 3.75 C19 | | 3.87 O1 | | | | | |
| 55 | 1441 | 3.85 C4 | | | | 3.88 C19 | 3.77 N4 | | 3.77 O1 | | 3.34 O1 | | | |
| 56 | 1411 | 3.77 C1 | 3.88 C3 | | | 3.86 N4 | 3.61 O2 | | | | 3.14 O2 | | | |
| 57 | 1149 | 3.77 C7 3.34 C9 | 3.88 C9 3.69 | | | 3.82 C1 | 3.83 C2 | | 3.87 C3 | | 3.73 C5 | 3.51 N3 | 3.61 O2 | |

| | Amino Acid MASP-2 AA# | | | | TRP 655 | | | |
|---|---|---|---|---|---|---|---|---|
| | AA atom | | | | CB | | CD | CE2 |
| 1 | 1129 | 3.26 O07 | | | | | | |
| 2 | 1034 | 3.4 O07 | 3.87 C05 | | | | | |
| 3 | 1024 | 3.23 O2 | 3.89 C1 | | | | | |
| 4 | 1059 | 3.3 O2 | | | | | | |
| 5 | 1088 | 3.34 O07 | | | | | | |
| 6 | 1036 | 3.22 O29 | | | | | | |
| 7 | 1081 | 3.31 O05 | | | | | | |
| 8 | 1063 | 3.25 O1 | 3.42 C7 | 3.65 C2 | | 3.84 C1 | 3.84 C6 | |
| 9 | 1065 | 3.35 O09 | | | | | | |
| 10 | 1030 | 3.24 O2 | | | | | | |
| 11 | 1037 | 3.2 O04 | 3.69 C01 | | | | 3.48 C16 | |
| 12 | 1118 | | 3.89 C9 | | | | | |
| 13 | 1007 | 3.13 O2 | | | | | 3.68 C13 | |
| 14 15 | Melagatran 999 1090 | 3.31 O2 | | | | | | |
| 16 | 1089 | | 3.39 O2 | | | | | |

TABLE A2-continued

| # | ID | Col A | Col B |
|---|---|---|---|
| 17 | 1021 | | 3.59 / O1 |
| 18 | 1097 | | 3.27 / O2 |
| 19 | 54 | | |
| 20 | 1042 | 3.64 / O05 | 3.33 / O11 |
| 21 | 2018 | 3.15 / O2 | |
| 22 | 1031 | 3.53 / N06 | |
| 23 | 1153 | 3.87 / C12 | 3.05 / O2 |
| 24 | 1025 | 3.84 / O26 | |
| 25 | 1012 | 3.89 / C11 | 3.32 / O2 |
| 26 | 1078 | 3.52 / O1 | |
| 27 | 1145 | 3.88 / C3 | 3.08 / O2 |
| 28 | 1050 | 3.23 / O2 | |
| 29 | 1253 | 3.31 / O17 | |
| 30 | 1257 | 3.36 / O17 | |
| 31 | 1297 | 3.38 / O1 | |
| 32 | 1304 | 3.89 / C2 | |
| 33 | 1306 | 3.33 / O1 | |
| 34 | 1307 | 3.33 / O1 | 3.3 / O1 |
| 35 | 1328 | 3.4 / O1 | |
| 36 | 1334 | 3.31 / O1 | |
| 37 | 1335 | 3.38 / O1 | |
| 38 | 1338 | 3.9 / C2 | 3.32 / O1 | 3.67 / C12, 3.9 / C17 |
| 39 | 1345 | 3.23 / O2 | |
| 40 | 1351 | 3.8 / C2 | 3.24 / O1 |
| 41 | 1353 | 3.77 / C13 | 3.22 / O1 |
| 42 | 1367 | 3.71 / C2 | 3.22 / O2 | 3.84 / C15 |
| 43 | 1368 | 3.81 / C06 | 3.27 / O29 | 3.52 / C28 |

TABLE A2-continued

| | | CE3 | CH2 | CZ2 | | |
|---|---|---|---|---|---|---|
| 44 | 1371 | | | 3.45 O1 | | |
| | | | | 3.35 O2 | | |
| 45 | 1372 | | | 3.87 C2 | 3.34 O1 | |
| 46 | 1373 | | | 3.44 O1 | | |
| 47 | 1492 | | | 3.85 C16 | 3.31 O2 | |
| 48 | 1399 | | | 3.84 C3 | 3.13 O1 | |
| 49 | 1406 | | | 3.32 O2 | | |
| 50 | 1433 | | | 3.68 O1 | | |
| 51 | 14 | | | 3.36 O1 | | |
| 52 | 1360 | | | 3.83 C1 | 3.28 O1 | |
| 53 | 1450 | | | 3.3 O1 | | |
| 54 | 1435 | | | 3.8 C5 | 3.25 O1 | 3.76 S1 |
| 55 | 1441 | 3.23 C16 | | 3.63 C4 | 3.02 O2 | |
| 56 | 1411 | 3.9 C08 | | 3.88 C12 | 3.24 O2 | |
| 57 | 1149 | | | | | |

TABLE A2-13: van der Waals

| | Amino Acid MASP-2 AA# | AA atom | CE3 | CZ3 | TRP 655 N | | O |
|---|---|---|---|---|---|---|---|
| 1 | 1129 | | | | | | 3.9 C13 |
| 2 | 1034 | | | | | | |
| 3 | 1024 | | 3.9 C7 | 3.86 C7 | 3.86 C6 | | |
| 4 | 1059 | | 3.5 C6 | 3.84 C13 | | | |
| | | | 3.57 C9 | | | | |
| | | | 3.66 C13 | | | | |
| 5 | 1088 | | | | 3.78 C19 | | |
| 6 | 1036 | | | | 3.78 C23 | 3.7 C22 | 3.72 C24 |
| | | | | | 3.58 C20 | | 3.48 C20 |
| 7 | 1081 | | 3.86 C15 | 3.67 C16 | 3.83 C20 | | |
| | | | 3.81 C2 | | | | |
| 8 | 1063 | | 3.23 C16 | 3.82 C15 | | | 3.75 C23 |
| | | | 3.83 C15 | | | | |

TABLE A2-continued

| | ID | | | | | | | | | | |
|---|---|---|---|---|---|---|---|---|---|---|---|
| 9 | 1065 | 3.6 C19 | | | | | | | | | |
| 10 | 1030 | | | | | | | | | | |
| 11 | 1037 | 3.4 C13, 3.69 C14, 3.75 C6 | | | | | | | | | |
| 12 | 1118 | | 3.8 C5 | | 3.66 C4 | | | | 3.81 C20 | 3.8 C20, 3.25 C13, 3.4 C17 | 3.39 C19, 3.64 C12, 3.88 C16 | |
| 13 | 1007 | | | | | | | 3.87 C12 | 3.76 C16 | | | |
| 14 | Melagatran | | | | | | | | | | | |
| 15 | 999 | | | | | | | | | | | |
| 16 | 1090 | | 3.59 C10 | | | | | | | | | |
| 17 | 1089 | | | | | | | | | | | |
| 18 | 1021 | | | | | | | | | | | |
| 19 | 1097 | | | | | | | | | | | |
| 20 | 54 | | | | | | | | | | | |
| 21 | 1042 | 3.42 C24, 3.76 C11 | 3.65 C25 | 3.88 C25 | | 3.38 C24 | 3.45 C25 | | 3.88 C3 | 3.79 C22, 3.81 C15, 3.77 C21, 3.31 C3, 3.87 C17, 3.7 C08 | 3.39 C21, 3.79 C24, 3.71 C19, 3.6 C2, 3.56 C18 | |
| 22 | 2018 | 3.49 C15 | | | | 3.68 C15 | | | | | | |
| 23 | 1031 | 3.61 C17 | 3.78 C18 | | | | | 3.61 C4 | | | | |
| 24 | 1153 | | | | | | | | | | | |
| 25 | 1012 | 3.71 C13, 3.49 C12 | 3.28 C14 | | | 3.62 C13 | | | 3.89 C20, 3.28 C25 | 3.74 C20, 3.31 C24, 3.85 C3 | 3.42 C21, 3.54 C25 | |
| 26 | 1078 | | | | | | | | | | | |
| 27 | 1145 | 3.84 C15, 3.61 C24 | 3.5 C17 | | | 3.81 C17, 3.71 C24, 3.77 C28, 3.38 C7, 3.68 C13 | 3.47 C14 | 3.29 C22 | 3.85 C23, 3.79 C29, 3.74 C5 | 3.77 C20, 3.47 C28, 3.56 C5 | 3.39 C21, 3.84 C29, 3.09 C6 | 3.83 C22 |
| 28 | 1050 | 3.87 C23, 3.54 C7, 3.78 C13 | | 3.74 C28, 3.86 C8 | | | | | | | | 3.72 C7 |
| 29 | 1253 | 3.87 C10, 3.75 C9 | 3.44 C9 | 3.84 C10 | | 3.66 C10, 3.76 C9, 3.53 C13 | 3.27 C9 | 3.7 C8 | | | | |
| 30 | 1257 | | | | | | | | | | | |
| 31 | 1297 | | | | | | | | | | | |
| 32 | 1304 | | | | | | | | | | | |
| 33 | 1306 | 3.49 C13 | | | | | | 3.78 C18, 3.48 C22 | 3.85 C16, 3.87 C21 | 3.79 C18, 3.57 C20 | 3.75 C19, 3.3 C21 | 3.85 C22 |
| 34 | 1307 | | | | | | | | | | | |
| 35 | 1328 | | | | | | | | | | | |

TABLE A2-continued

| 36 | 3.66 C13 3.84 C13 3.83 C9 | | 3.67 C13 3.7 C15 3.74 C9 | 3.68 C21 3.82 C3 3.9 C26 | 3.68 C20 3.44 C2 | 3.38 C22 3.9 C3 |
| --- | --- | --- | --- | --- | --- | --- |
| 37 | 3.39 C15 | | | | | |
| 38 | 3.89 C21 3.52 C28 | | | | | 3.52 C27 |
| 39 | | | | | 3.77 C26 | |
| 40 41 42 | | | 3.86 C21 3.87 C28 | | | |
| 43 | 3.78 C10 3.54 C17 3.65 C13 | 3.63 C9 | 3.7 C10 3.48 C17 3.57 C13 | 3.86 C21 | 3.56 C20 | 3.42 C21 |
| 44 | | | | 3.54 C22 | | |
| 45 | | | 3.68 C9 | | | |
| 46 | 3.74 C12 | | | | | |
| 47 | 3.89 C3 3.7 C10 3.59 C22 | 3.49 S1 | 3.42 S1 3.51 C10 3.73 C22 | 3.85 C23 3.68 C2 | 3.75 C1 | 3.44 C7 |
| 48 | | | | | | |
| 49 | | | | | | |
| 50 | | | | 3.66 C18 | 3.63 C19 | 3.79 C22 |
| 51 52 53 | | 3.7 O07 | | | | |
| 54 55 | 3.65 C13 3.6 C15 | | 3.75 C13 3.57 C15 | | | |
| 56 | | | | | | 3.26 C23 |
| 57 | 3.28 N5 | 3.83 C22 | | | 3.6 C1 | 3.85 C2 3.88 C6 |

| Amino Acid MASP-2 AA# | AA atom | | | GLY 656 | | |
| --- | --- | --- | --- | --- | --- | --- |
| | | C | | | CA | |
| 1 | 1129 | 3.54 N20 | | 3.47 N20 | 3.66 C18 | 3.66 C15 |
| 2 | 1034 | 3.63 N19 | | 3.84 N19 | 3.83 C18 | 3.86 O07 |
| 3 | 1024 | 3.53 N5 | | 3.54 N5 | 3.57 C20 | 3.58 C17 |
| 4 | 1059 | 3.28 N5 | | 3.4 N5 | 3.69 C22 | 3.85 C20 |

TABLE A2-continued

| # | ID | | | | | | |
|---|---|---|---|---|---|---|---|
| 5 | 1088 | 3.75 C28 / 3.48 N26 / 3.27 | 3.56 N18 / 3.83 C25 | | | 3.75 N29 / 3.82 N26 / 3.28 N26 | 3.67 C28 / 3.64 C25 / 3.54 C25 / 3.46 C23 / 3.74 C27 | 3.89 C27 / 3.56 C22 / 3.83 C22 / 3.64 C20 |
| 6 | 1036 | 3.63 N26 / 3.36 N5 | 3.88 C22 | | | 3.24 N26 / 3.88 N28 / 3.86 N28 | | |
| 7 | 1081 | 3.73 N4 / 3.7 N18 | | | | 3.4 | | |
| 8 | 1063 | 3.63 N4 / 3.74 N5 | | | | 3.69 C17 / 3.7 N4 | 3.79 C14 / 3.78 C21 / 3.86 C3 | 3.88 C18 |
| 9 | 1065 | 3.42 N25 | | | | 3.63 N5 | | |
| 10 | 1030 | 3.82 C13 / 3.84 C17 | 3.86 C22 / 3.59 N5 | | | 3.42 N25 / 3.74 C13 / 3.83 C17 / 3.72 C1 | 3.59 C23 / 3.5 C34 / 3.66 C18 / 3.55 C2 | 3.69 C20 / 3.37 C22 / 3.67 C22 / 3.64 C23 |
| 11 | 1037 | 3.76 N3 / 3.46 N6 | | | | 3.81 C19 / 3.86 N28 | 3.78 C22 / 3.66 N10 | 3.65 N6 |
| 12 | 1118 | | | | | 3.85 C17 | 3.53 C20 | 3.76 N21 / 3.81 N4 |
| 13 | 1007 | 3.86 C17 / 3.64 N4 / 3.61 N11 | 3.57 C20 | 3.45 N03 | 3.29 M21 | 3.82 C22 | 3.85 C25 | 3.44 N5 / 3.67 N5 |
| 14 | Melagatran 999 | | | | 3.85 O05 | | | |
| 15 | 1090 | 3.88 C18 / 3.86 C17 / 3.87 C5 | 3.89 N19 / 3.53 N5 / 3.89 O1 | | | 3.88 N1 | | |
| 16 | 1089 | 3.78 N3 / 3.54 N4 | 3.54 N5 / 3.6 N5 | | | 3.73 C17 / 3.76 C19 | 3.57 N5 / 3.66 C20 | 3.61 N5 / 3.46 N4 |
| 17 | 1021 | 3.85 C02 | 3.52 N07 | | | 3.82 C27 / 3.7 C10 | 3.79 C30 / 3.77 C7 | 3.45 N08 |
| 18 | 1097 | 3.72 C02 | 3.39 N08 | | | 3.67 C02 / 3.63 C02 | 3.52 N07 / 3.88 N01 | 3.76 N22 |
| 19 | 54 | | | | | | | |
| 20 | 1042 | | | | | | | |
| 21 | 2018 | | | | | | | |
| 22 | 1031 | | | | | | | |
| 23 | 1153 | | | | | | | |
| 24 | 1025 | | | | | | | |
| 25 | 1012 | | | | | | | |
| 26 | 1078 | | | | | | | |
| 27 | 1145 | | | | | | | |
| 28 | 1050 | | | | | | | |
| 29 | 1253 | | | | | | | |
| 30 | 1257 | | | | | | | |

TABLE A2-continued

| # | ID | Col1 | Col2 | Col3 | Col4 | Col5 | Col6 |
|---|---|---|---|---|---|---|---|
| 31 | 1297 | 3.88 N1 | 3.65 N5 | | 3.59 C23 | 3.44 N5 | |
| 32 | 1304 | 3.82 C19 | 3.56 N5 | | 3.61 C19 | 3.49 N5 | |
| 33 | 1306 | 3.54 N5 | | | 3.61 N5 | | |
| 34 | 1307 | | | | 3.7 C19 | 3.64 C20 | 3.78 C23 |
| 35 | 1328 | 3.67 C19 | 3.31 N5 | | 3.53 C19 | 3.76 N4 | 3.41 N5 |
| 36 | 1334 | | | | 3.78 C19 | 3.85 C23 | 3.58 N5 |
| 37 | 1335 | 3.51 N6 | | | 3.86 C23 | 3.6 N6 | |
| 38 | 1338 | 3.86 C23 | 3.56 N5 | | 3.75 C23 | 3.57 N5 | 3.63 C33 |
| 39 | 1345 | 3.74 N6 | | | 3.83 C27 | 3.52 C28 | |
| 40 | 1351 | 3.84 C25 | 3.45 N5 | | 3.62 C25 | 3.37 N5 | |
| 41 | 1353 | 3.77 C19 | 3.44 N5 | | 3.68 C19 | 3.5 N5 | |
| 42 | 1367 | 3.8 C8 | 3.49 N5 | | 3.78 C8 | 3.61 N4 | |
| 43 | 1368 | 3.72 C35 | 3.46 N38 | | 3.67 C35 | 3.55 N38 | |
| 44 | 1371 | 3.84 N2 | | | 3.52 C19 | 3.69 N2 | |
| 45 | 1372 | 3.73 C9 | 3.47 N4 | | 3.6 C9 | 3.49 N4 | 3.47 N5 |
| 46 | 1373 | 3.82 C19 | 3.52 N5 | | 3.68 C19 | 3.53 N5 | |
| 47 | 1492 | 3.72 C23 | 3.31 N5 | | 3.72 C21 | 3.65 C23 | |
| 48 | 1399 | 3.73 C22 | 3.41 N5 | | 3.61 C22 | 3.44 N5 | |
| 49 | 1406 | 3.84 C20 | 3.54 N5 | | 3.62 C20 | 3.46 N5 | |
| 50 | 1433 | | | | 3.88 C5 | 3.67 N2 | |
| 51 | 34 | 3.73 C9 | | 3.6 N5 | 3.72 C9 | | 3.51 N6 |
| 52 | 1360 | 3.8 C24 | 3.47 N5 | | 3.68 C24 | 3.5 N5 | |
| 53 | 1450 | | | | 3.75 N5 | | |
| 54 | 1435 | 3.82 C19 | 3.49 N5 | | 3.72 C19 | 3.55 N5 | |
| 55 | 1441 | 3.85 C20 | 3.55 N5 | | 3.75 C20 | 3.6 N5 | |
| 56 | 1411 | 3.86 C20 | 3.89 N3 | | 3.82 C20 | 3.7 N5 | |

TABLE A2-continued

| | Amino Acid MASP-2 AA# | 3.89 C2 | 3.54 C3 | 3.72 C8 | 3.89 N1 | 3.66 C2 | 3.67 C3 | 3.63 C8 | 3.47 N1 |
|---|---|---|---|---|---|---|---|---|---|
| | AA atom | | | | | | | | |
| | | | | N | | | O | | |
| 57 | 1149 | | | | | | | | |

TABLE A2-14: van der Waals

| | Amino Acid MASP-2 AA# | 3.89 C2 | 3.54 C3 | 3.72 C8 | 3.89 N1 | GLY 656 | | 3.66 C2 | 3.67 C3 | 3.63 C8 | SER 657 | | 3.47 N1 |
|---|---|---|---|---|---|---|---|---|---|---|---|---|---|
| | AA atom | | | | | | O | | | | | C | |
| 1 | 1129 | 3.87 C16 | 3.77 C15 | | | 3.3 C23 | 3.79 C05 | | | 3.8 C23 | | 3.75 N20 |
| 2 | 1034 | | | | | 3.69 C24 3.49 C3 | 3.51 C05 | | | 3.51 N19 3.77 N5 | | |
| 3 | 1024 | 3.66 C18 | 3.59 C17 | | | 3.41 C9 | | | | 3.78 N5 | | |
| 4 | 1059 | 3.68 C21 | 3.5 C20 | | | 3.35 C08 | 3.83 C3 | | | 3.64 N18 | | 3.74 N3 |
| 5 | 1088 | 3.77 C27 | 3.6 C25 | | | 3.29 C04 | | | | 3.57 N18 | | |
| 6 | 1036 | 3.75 C23 | 3.41 C22 | 3.53 C20 | 3.86 C19 | 3.55 C02 | | | | 3.62 N26 | | |
| 7 | 1081 | 3.71 C25 | 3.79 C23 | 3.58 C21 | | 3.81 C02 | | | | 3.75 N5 | | |
| 8 | 1063 | 3.81 C23 | 3.88 C22 | 3.4 C20 | 3.79 C19 | 3.46 C4 | 3.69 C2 | 3.07 C1 | | | | |
| 9 | 1065 | 3.82 C27 | 3.61 C25 | | | 3.06 C05 | 3.64 C01 | | | | | |
| 10 | 1030 | 3.77 C19 | 3.78 C18 | | | 3.65 C3 | | | | 3.82 N4 | | |
| 11 | 1037 | 3.86 C14 | 3.86 C13 | | | 3.66 C22 | 3.86 C01 | | | 3.73 N18 | | |
| 12 | 1118 | 3.67 C18 | 3.58 C17 | | | 3.62 C4 | | | | 3.8 N4 | | |
| 13 | 1007 | 3.71 C3 | | | | 3.85 C11 | | | | 3.87 N5 | | |
| 14 | Melagatran 999 | 3.9 C21 | 3.72 C20 | 3.41 C13 | 3.38 C14 | 3.25 C28 | 3.16 C4 | 3.87 C13 | | 3.68 C28 | | 3.77 N25 |
| 15 | 1090 | 3.83 C22 | 3.74 C15 | | | 3.88 C1 | | | | 3.7 N5 | | |
| 16 | 1089 | 3.47 C17 | 3.48 C18 | | | 2.95 C2 | | | | 3.86 N5 | | |
| 17 | 1021 | 3.58 C1 | 3.47 C2 | | | 3.85 C11 | 3.79 C12 | | | 3.55 N3 | | |
| 18 | 1097 | 3.76 C18 | 3.8 C19 | | | 3.84 C1 | 3.64 C3 | 3.84 C6 | | 3.52 N6 | | 3.74 N3 |
| 19 | 54 | 3.78 C02 | 3.64 C08 | | | | | | | 3.68 N15 | | |
| 20 | 1042 | 3.67 C16 | 3.76 C17 | | | 3.47 C01 | 3.85 C17 | 3.7 C18 | | 3.53 N03 | | 3.49 N21 |
| 21 | 2018 | 3.74 C21 | 3.78 C22 | | | 3.3 C9 | | | | 3.7 N4 | | |

TABLE A2-continued

| | | | | | | | | | |
|---|---|---|---|---|---|---|---|---|---|
| 22 | 1031 | 3.76<br>C20<br>3.75<br>C1 | 3.82<br>C21<br>3.82<br>C2 | 3.83<br>C24 | 3.76<br>C25 | 3.3<br>C10<br>3.79<br>C12<br>3.46<br>C14<br>3.85<br>C1 | | | 3.7<br>N11 |
| 23 | 1153 | | | | | | | | |
| 24 | 1025 | | | | | | | | |
| 25 | 1012 | 3.64<br>C17 | | | | | | | |
| 26 | 1078 | 3.87<br>C18 | 3.63<br>C19 | 3.59<br>C20 | 3.79<br>C21 | 2.71<br>C5 | | | 3.81<br>N5 |
| 27 | 1145 | 3.61<br>C27 | 3.62<br>C28 | 3.89<br>C8 | | 3.47<br>C13<br>3.89<br>C12 | 3.8<br>C3<br>3.65<br>C13 | 3.59<br>C4<br>3.53<br>C15 | 3.83<br>C13<br>3.79<br>N4 | 3.75<br>N5<br>3.76<br>N5 |
| 28 | 1050 | 3.74<br>C6 | 3.68<br>C7 | | | 3.79<br>C16 | 3.79<br>C20 | 3.15<br>C21 | 3.82<br>N07 | |
| 29 | 1253 | 3.55<br>C02 | | | | | | | 3.85<br>N08 | |
| 30 | 1257 | 3.53<br>C02 | 3.88<br>C03 | 3.9<br>C06 | | 3.8<br>C03<br>3.79<br>C1 | 3.04<br>C19<br>3.66<br>C4 | 3.29<br>C5 | | |
| 31 | 1297 | 3.65<br>C23 | 3.78<br>C24 | | | | 3.14<br>C6 | | | |
| 32 | 1304 | 3.9<br>C18 | 3.53<br>C19 | | | 3.64<br>C5 | | | | |
| 33 | 1306 | 3.86<br>C19 | | | | 3.83<br>C2 | 3.78<br>C3 | 3.62<br>C5 | 3.86<br>N5 | |
| 34 | 1307 | 3.8<br>C18 | 3.54<br>C19 | 3.54<br>C20 | 3.85<br>C21 | 3.87<br>C3 | 3.49<br>C5 | 3.11<br>C6 | | 3.14<br>C6 |
| 35 | 1328 | 3.78<br>C18 | 3.48<br>C19 | 3.76<br>C20 | | 3.8<br>C20 | 3.8<br>C3 | 3.4<br>C5 | 3.5<br>N5 | 3.16<br>C6 |
| 36 | 1334 | 3.7<br>C19 | 3.72<br>C20 | | | 3.58<br>C5 | 3.21<br>C6 | | | |
| 37 | 1335 | 3.74<br>C1 | 3.7<br>C2 | | | 3.75<br>C11 | 3.72<br>C13 | | 3.83<br>N3 | 3.74<br>N6 |
| 38 | 1338 | 3.57<br>C23 | | | | 3.85<br>C3 | 3.64<br>C5 | | 3.89<br>N5 | |
| 39 | 1345 | 3.89<br>C26 | 3.7<br>C27 | 3.76<br>C28 | | 3.62<br>C16 | 3.78<br>C5 | 3.21<br>C6 | | |
| 40 | 1351 | 3.49<br>C25 | | | | 3.84<br>C3 | 3.61<br>C5 | | 3.83<br>N5 | |
| 41 | 1353 | 3.55<br>C9 | 3.87<br>C20 | | | 3.81<br>C1 | 3.44<br>C4 | 3.18<br>C6 | 3.87<br>N5 | |
| 42 | 1367 | 3.54<br>C8 | 3.87<br>C9 | | | 3.78<br>C1 | 3.71<br>C9 | 3.33<br>C5 | 3.82<br>N4 | |
| 43 | 1368 | 3.66<br>C35 | | 3.88<br>C20 | | 3.55<br>C07 | 3.18<br>C09 | 3.82<br>C21 | 3.88<br>N38 | |
| 44 | 1371 | 3.64<br>C19 | 3.79<br>C20 | | | 3.89<br>C2 | 3.78<br>C3 | 3.77<br>C5 | 3.85<br>N2 | |
| 45 | 1372 | 3.52<br>C9 | | | | 3.78<br>C13 | 3.14<br>C14 | | 3.84<br>N4 | |
| 46 | 1373 | 3.86<br>C18 | 3.51<br>C19 | | | 3.88<br>C5 | 3.75<br>C5 | 3.2<br>C6 | 3.84<br>N5 | 3.87<br>C23 |
| 47 | 1492 | 3.56<br>C21 | 3.73<br>C22 | | | 3.69<br>C3 | 3.79<br>C4 | 3.37<br>C5 | 3.79<br>N5 | 3.38<br>C6 |

TABLE A2-continued

| # | AA# | | | | | | | | |
|---|---|---|---|---|---|---|---|---|---|
| 48 | 1399 | | | 3.83 C21; 3.56 C20 | | 3.88 C23 | | | 3.82 N5; 3.84 N5 |
| 49 | 1406 | | 3.68 N19 | 3.5 C22 | | | | 3.65 C7; 3.13 C7 | |
| 50 | 1433 | | | 3.69 C20 | 3.61 C5; 3.47 C9 | | 3.65 C7; 3.75 C15 | 3.16 C4; 3.13 C7 | 3.32 C16 |
| 51 | 14 | | | 3.59 C10 | C1 | | | | |
| 52 | 1360 | | | 3.66 C24 | | | 3.13 C6 | | |
| 53 | 1450 | | | 3.61 C19 | 3.62 C20 | | 3.65 C2; 3.55 C5 | 3.89 C1; 3.1 C3 | 3.78 C4 |
| 54 | 1435 | | | 3.58 C19 | | | | 3.88 C3 | 3.28 C5 |
| 55 | 1441 | | | 3.61 C20 | | | 3.08 C11; 3.76 C5 | 3.24 C10; 2.92 C23 | 3.79 C9; 3.37 C9 |
| 56 | 1411 | | | 3.66 C20 | 3.73 N26; 3.86 N26 | | 3.66 C3 | 3.89 C6; 3.88 C8 | |
| 57 | 1149 | 3.8 C4 | | 3.72 C2 | 3.5 C3 | | 3.78 C23; 3.14 C14 | | 3.85 N5; 3.88 C11; 3.88 C23; 3.68 N2 |

| | | SER 657 | | | | |
|---|---|---|---|---|---|---|
| Amino Acid MASP-2 AA# | AA atom | CA | CB | N | O | OG |
| 1 | 1129 | | | 3.84 C24 | 3.56 C23 | |
| 2 | 1034 | 3.68 N19 | | 3.9 C18 | 3.56 C14 | |
| 3 | 1024 | | | 3.86 C20 | 3.44 C16 | |
| 4 | 1059 | | | 3.67 C22 | 3.79 C20 | |
| 5 | 1088 | | | 3.1 C28 | 3.19 C27 | |
| 6 | 1036 | 3.73 N26 | | 3.77 C25 | 3.41 C23 | |
| 7 | 1081 | 3.86 N26 | | 3.85 C23 | | |
| 8 | 1063 | | | 3.8 C23 | 3.5 C39 | |
| 9 | 1065 | | | 3.59 C17 | | |
| 10 | 1030 | | | 3.84 C17 | 3.47 C15 | |
| 11 | 1037 | | | 3.77 C19 | | |
| 12 | 1118 | | | 3.51 C3 | | |
| 13 | 1007 | | | 3.8 C23 | | 3.63 C16 |
| 14 | Melagatran 999 | | | 3.8 C23 | 3.55 C19 | |

TABLE A2-continued

| | | | | | | | | |
|---|---|---|---|---|---|---|---|---|
| 15 | 1090 | 3.57 N5 | 3.77 N4 | 3.41 C23 | | | 3.46 C13 3.58 C17 | 3.78 C22 |
| 16 | 1089 | | | | | | | 3.28 C20 |
| 17 18 | 1021 1097 | 3.68 N6 | | | | | 3.85 C19 | |
| 19 | 54 | | | | 3.6 C14 3.79 C20 | 3.66 C22 3.57 C14 | 3.69 C20 3.79 C25 | |
| 20 | 1042 | 3.75 N03 | | | | 3.3 C18 3.36 C23 | | |
| 21 | 2018 | 3.89 N4 | | | | | | |
| 22 23 | 1031 1153 | | | | | 3.39 C1 3.58 C07 3.55 C17 | 3.41 C18 | |
| 24 | 1025 | | | | | | | |
| 25 | 1012 | | | | | | | |
| 26 27 | 1078 1145 | | | | | 3.74 C26 3.62 C8 | | |
| 28 | 1050 | | | | | 3.5 C02 | | |
| 29 | 1253 | | | | | 3.52 C02 | 3.29 C03 3.39 C03 | |
| 30 | 1257 | | | | | 3.64 C23 3.52 C19 | 3.37 C24 3.31 C20 | |
| 31 | 1297 | | | | | 3.61 C21 | 3.64 C23 | |
| 32 | 1304 | | | | | 3.55 C23 | | |
| 33 | 1306 | | | | | | | |
| 34 | 1307 | | | | 3.73 C23 | 3.28 C19 | | |
| 35 | 1328 | | | | | 3.85 C23 | 3.34 C20 | |
| 36 37 | 1334 1335 | 3.89 N6 | | | | 3.48 C23 | 3.54 C6 3.26 C24 | |
| 38 | 1338 | | | | | 3.85 C29 | 3.75 C7 3.31 C26 | |
| 39 | 1345 | | | | | 3.47 C25 | | |
| 40 | 1351 | | | | | 3.52 C19 | 3.28 C20 | |
| 41 | 1353 | | | | | 3.52 C8 | 3.32 C9 | 3.86 C9 |
| 42 | 1367 | | | | | | | |

TABLE A2-continued

| # | MASP-2 AA# | | | | | |
|---|---|---|---|---|---|---|
| 43 | 1368 | | | | | 3.54 C35 / 3.32 C36 |
| 44 | 1371 | | | | | |
| 45 | 1372 | | | | | 3.3 C8 / 3.5 C9 |
| 46 | 1373 | | | | | 3.5 C19 / 3.31 C20 |
| 47 | 1492 | 3.82 N7 | | 3.69 N7 | 3.53 C23 | 3.84 C21 / 3.51 C23 |
| 48 | 1399 | | | | | 3.46 C22 / 3.24 C23 |
| 49 | 1406 | | | | | 3.4 C20 / 3.21 C23 |
| 50 | 1433 | | | | | |
| 51 | 14 | | | | | |
| 52 | 1360 | | | | | 3.82 C10 / 3.82 C9 / 3.53 C24 / 3.32 C25 |
| 53 | 1450 | | | | 3.89 C24 | 3.58 C24 |
| 54 | 1435 | | | | | 3.46 C19 / 3.29 C20 |
| 55 | 1441 | | | | | 3.49 C20 / 3.28 C21 |
| 56 | 1411 | | | | | 3.23 C19 / 3.28 C20 |
| 57 | 1149 | | | | 3.51 C8 | 3.75 C2 / 3.15 C3 / 3.44 C8 |

TABLE A2-15: van der Waals

| | Amino Acid | MET 658 | | | | | |
|---|---|---|---|---|---|---|---|
| | MASP-2 AA# | | | | | | |
| | AA atom | C | CA | CB | CE | CG |
| 1 | 1129 | | | | | |
| 2 | 1034 | O25 3.72 | C24 3.76 | | | |
| 3 | 1024 | | | | | |
| 4 | 1059 | | | | | |
| 5 | 1088 | | | | | |
| 6 | 1036 | | | | | |
| 7 | 1081 | | | | | |
| 8 | 1063 | | | | | |
| 9 | 1065 | | | | | |
| 10 | 1030 | | | | | |
| 11 | 1037 | | | | | |
| 12 | 1118 | | | | | |
| 13 | 1007 | | | | | |
| 14 | Melagatran 999 | 3.83 C28 | | | | 3.89 O26 |
| 15 | 1090 | | | | | 3.84 O30 |

TABLE A2-continued

| # | ID | | | | | | | | | | | | | | | | | |
|---|----|---|---|---|---|---|---|---|---|---|---|---|---|---|---|---|---|---|
| 16 | 1089 | | | | | | | | | | | | | | | | | |
| 17 | 1021 | 3.74 N3 | | | | | | | | | | | | | | | | |
| 18 | 1097 | | | | | | | | | | | | | | | | | |
| 19 | 54 | | | | | | | | | | | | | | | | | |
| 20 | 1042 | | | | | | | | | | | | | | | | | |
| 21 | 2018 | | | | | | | | | | | | | | | | | |
| 22 | 1031 | | | | | | | | | | | | | | | | | |
| 23 | 1153 | | | | | | | | | | | | | | | | | |
| 24 | 1025 | | | | | | | | | | | | | | | | | |
| 25 | 1012 | | | | | | | | | | | | | | | | | |
| 26 | 1078 | | | | | | | | | | | | | | | | | |
| 27 | 1145 | 3.81 C17 | 3.81 C13 | 3.87 C15 | 3.58 C16 | 3.28 C17 | 3.84 C18 | 3.46 C16 | 3.2 C17 | 3.28 C18 | 3.59 C19 | 3.8 C20 | 3.74 C21 | 3.86 C28 | 3.3 C19 | 3.23 C20 | 3.33 O1 | 3.79 C28 |
| 28 | 1050 | | | | | | | | | | | | | | | | | |
| 29 | 1253 | | | | | | | | | | | | | | | | | |
| 30 | 1257 | | | | | | | | | | | | | | | | | |
| 31 | 1297 | | | | | | | | | | | | | | | | | |
| 32 | 1304 | | | | | | | | | | | | | | | | | |
| 33 | 1306 | | | | | | | | | | | | | 3.64 C6 | | | | |
| 34 | 1307 | | | | | | | | | | | | | | | | | |
| 35 | 1328 | | | | | | | | | | | | | | | | | |
| 36 | 1334 | | | | | | | | | | | | | | | | | |
| 37 | 1335 | | | | | | | | | | | | | | | | | |
| 38 | 1338 | | | | | | | | | | | | | | | | | |
| 39 | 1345 | 3.77 C9 | 3.79 C6 | 3.83 C8 | 3.75 C9 | | | | | | | | | | | | | |
| 40 | 1351 | | | | | | | | | | | | | | | | | |
| 41 | 1353 | | | | | | | | | | | | | | | | | |
| 42 | 1367 | | | | | | | | | | | | | | | | | |
| 43 | 1368 | | | | | | | | | | | | | | | | | |
| 44 | 1371 | | | | | | | | | | | | | | | | | |
| 45 | 1372 | | | | | | | | | | | | | | | | | |
| 46 | 1373 | | | | | | | | | | | | | | | | | |
| 47 | 1492 | | | | | | | | | | | | | | | | | |
| 48 | 1399 | | | | | | | | | | | | | | | | | |
| 49 | 1406 | | | | | | | | | | | | | | | | | |
| 50 | 1433 | | | | | | | | | | | | | | | | | |
| 51 | 14 | | | | | | | | | | | | | | | | | |
| 52 | 1360 | | | | | | | | | | | | | | | | | |
| 53 | 1450 | | | | | | | | | | | | | | | | | |
| 54 | 1435 | | | | | | | | | | | | | | | | | |
| 55 | 1441 | 3.71 C11 | 3.8 C23 | 3.79 C25 | 3.47 O3 | | | | | | | | | | | | | |
| 56 | 1411 | | | | | | | | | | | | | | | 3.37 C2 | | |
| 57 | 1149 | | | | | | | | | | | | | | | 3.69 C15 | | 3.58 C16 |

TABLE A2-continued

| Amino Acid | | | MET 658 | |
|---|---|---|---|---|
| MASP-2 AA# | | | | |
| AA atom | | CG | N | O |
| 1 | 1129 | | | |
| 2 | 1034 | | | |
| 3 | 1024 | | | |
| 4 | 1059 | | | |
| 5 | 1088 | | | |
| 6 | 1036 | | | |
| 7 | 1081 | | | |
| 8 | 1063 | | 3.85 C05 | |
| 9 | 1065 | | | |
| 10 | 1030 | | | |
| 11 | 1037 | | | |
| 12 | 1118 | | | |
| 13 | 1007 | | | |
| 14 | Melagatran 999 | | 3.52 C28 | |
| 15 | 1090 | | | |
| 16 | 1089 | | | |
| 17 | 1021 | | 3.69 C3 | |
| 18 | 1097 | | | |
| 19 | 54 | | 3.41 C18 | |
| 20 | 1042 | | 3.86 C2 | |
| 21 | 2018 | | 3.72 C5 | |
| 22 | 1031 | | 3.68 C13 | |
| 23 | 1153 | | | |
| 24 | 1025 | | | |
| 25 | 1012 | | | |
| 26 | 1078 | | | |
| 27 | 1145 | | | 3.44 C17 | 3.56 C18 |
| 28 | 1050 | | | |
| 29 | 1253 | | | |
| 30 | 1257 | | | |
| 31 | 1297 | | | |
| 32 | 1304 | | | |
| 33 | 1306 | | | |
| 34 | 1307 | | | |
| 35 | 1328 | | 3.76 C6 | |
| 36 | 1334 | | | |
| 37 | 1335 | | | |
| 38 | 1338 | | 3.89 C6 | |

TABLE A2-continued

| | | | |
|---|---|---|---|
| 39 | 1345 | 3.32 C10 | 3.48 C9 |
| 40 | 1351 | | |
| 41 | 1353 | | |
| 42 | 1367 | 3.74 C5 | |
| 43 | 1368 | 3.65 C09 | |
| | | 3.83 C6 | |
| 44 | 1371 | | |
| 45 | 1372 | | |
| 46 | 1373 | | |
| 47 | 1492 | | |
| 48 | 1399 | | |
| 49 | 1406 | | |
| 50 | 1433 | | |
| 51 | 14 | | |
| 52 | 1360 | | |
| 53 | 1450 | | |
| 54 | 1435 | 3.89 C6 | |
| | | 3.61 C11 | |
| | | 3.56 C23 | |
| 55 | 1441 | | |
| 56 | 1411 | | |
| 57 | 1149 | 3.74 C21 | |

TABLE A2-16: van der Waals

| | Amino Acid MASP-2 AA# | Met 658 | ASN 659 | | CA | CB | CYS 660 | | SG | |
|---|---|---|---|---|---|---|---|---|---|---|
| | AA atom | SD | C | | | | | | | |
| 1 | 1129 | | | | | 3.54 N19 | 3.71 C18 | 3.43 N20 | 3.45 C18 | |
| 2 | 1034 | | | | | | | | | |
| 3 | 1024 | | | | | | | | | |
| 4 | 1059 | | | | | | | | | |
| 5 | 1088 | | 3.72 N6 | | | | | | | |
| | | | 3.86 C28 | | | 3.84 N29 | 3.78 C28 | | | |
| 6 | 1036 | | 3.7 N26 | | | | | | | |
| | | | 3.63 N26 | | | | | | | |
| 7 | 1081 | | | | | | | | | |
| 8 | 1063 | | | | | | | 3.78 N28 | | |
| 9 | 1065 | | | | | | | 3.76 N4 | | |
| 10 | 1030 | 3.64 C05 | 3.74 N4 | | | | | | | 3.5 C17 |
| 11 | 1037 | 3.51 | 3.6 N18 | | | | | 3.63 C15 | 3.35 C16 | |

TABLE A2-continued

| | | | | | | | | | | |
|---|---|---|---|---|---|---|---|---|---|---|
| 12 | 1118 | N1 | 3.84 N4 | | | | | | | |
| 13 14 | 1007 Melagatran 999 | | | | | | | | | |
| 15 16 | 1090 1089 | | 3.49 N5 | 3.66 N5 | | | | | | |
| 17 18 | 1021 1097 | | 3.85 N6 | | | | | | | |
| 19 | 54 | | 3.84 N4 | | 3.75 N15 | 3.53 C14 | 3.22 N13 | 3.67 N15 | | |
| 20 21 | 1042 2018 | | | | | | | | | |
| 22 23 | 1031 1153 | | 3.78 N09 | | | 3.8 C8 | 3.62 N1 | | | |
| 24 | 1025 | | | | | | | | | |
| 25 | 1012 | | | | | 3.7 C17 | 3.68 C18 | 3.53 N5 | | |
| 26 27 | 1078 1145 | | | | | 3.83 C30 3.78 C8 | 3.83 N4 | | | |
| 28 | 1050 | | | | | 3.55 C02 | 3.6 C03 | 3.33 N07 | | |
| 29 | 1253 | | 3.83 N08 | | | | | | | |
| 30 | 1257 | | | | | | | | | |
| 31 32 | 1297 1304 | | | 3.21 N4 | | | | | | |
| 33 | 1306 | | 3.65 C23 | | 3.63 N5 | 3.86 N5 3.42 N4 3.66 C23 | | | | |
| 34 | 1307 | | | | | | | | | |
| 35 | 1328 | | 3.42 N5 | | 3.61 C19 | | | | | |
| 36 | 1334 | | | | | 3.75 N4 3.64 C6 3.83 N5 | | | | | |
| 37 | 1335 | | | | | | | | | |
| 38 | 1338 | | | | | | | | | |
| 39 | 1345 | | 3.69 N6 | | | 3.8 C10 3.68 C25 | 3.34 C29 3.66 C26 | 3.87 C31 3.55 N5 | 3.6 C9 | 3.7 N6 |
| 40 | 1351 | | | | | | | | | |
| 41 42 | 1353 1367 | | | | | | | | | |
| | | | | | | 3.02 N4 | 2.92 N5 | | | |

TABLE A2-continued

| # | Amino Acid MASP-2 AA# / AA atom | GLN 665 CD | GLN 665 OE1 | C | GLY 667 CA | GLY 667 N | CZ | TYR 669 CE1 | TYR 669 CE2 |
|---|---|---|---|---|---|---|---|---|---|
| 43 | 1368 | | | 3.36 N38 | | | | | 3.8 N6 |
| 44 | 1371 | 3.78 N19 | | | | 3.55 N5 | 3.78 N4 | | |
| 45 | 1372 | | | | | 3.82 N5 | | | |
| 46 | 1373 | | | 3.54 N4 | | | | | |
| 47 | 1492 | | | | | | | | |
| 48 | 1399 | | | | | | | | |
| 49 | 1406 | | | | | | | | |
| 50 | 1433 | | | | | | | | |
| 51 | 14 | | | | | | | | |
| 52 | 1360 | | | | | 3.39 C24 | | | |
| 53 | 1450 | | | | | 3.88 N5 | | | |
| 54 | 1435 | | | | | 3.78 N5 | | | |
| 55 | 1441 | | | | | | | | |
| 56 | 1411 | | | | | 3.56 N5 | | | |
| 57 | 1149 | | | 3.76 N2 | | | | | |
| 1 | 1129 | | | | 3.36 N19 | | | | |
| 2 | 1034 | 3.78 N19 | 3.68 C18 | | 3.32 N20 | | | | |
| 3 | 1024 | | 3.47 C18 | | 3.47 N4 | | | | |
| 4 | 1059 | | | | 3.68 N4 | | | | |
| 5 | 1088 | | | | 3.35 N31 | | | | |
| 6 | 1036 | | | | 3.44 N27 | | | | |
| 7 | 1081 | | | | 3.86 N27 | | | | |
| 8 | 1063 | | | | 3.76 N4 | | | | |
| 9 | 1065 | | | | 3.48 N29 | | | | |
| 10 | 1030 | | | | 3.44 N5 | | | | |

TABLE A2-continued

| | ID | | | | | | | | | |
|---|---|---|---|---|---|---|---|---|---|---|
| 11 | 1037 | | | | 3.46 N19 / 3.53 N5 | | | | | |
| 12 | 1118 | | | | | | | | | |
| 13 | 1007 | | | | | | | | | |
| 14 | Melagatran / 999 | | | | 3.49 N24 | | | | | |
| 15 | 1090 | | | | | | | | | |
| 16 | 1089 | | | | 3.35 C22 / 3.7 C11 / 3.5 N5 | | | 3.82 C11 | 3.89 C11 | |
| 17 | 1021 | | | | | 3.73 N4 | | | | |
| 18 | 1097 | | | | | | | | | |
| 19 | 54 | | | | 3.84 C12 / 3.87 N22 / 3.4 N5 | | | | | |
| 20 | 1042 | | | | | 3.42 N11 | 3.87 C12 | | | |
| 21 | 2018 | 3.66 N4 | 3.47 C25 | | 3.31 N2 | | | | | |
| 22 | 1031 | | | | | | | | | |
| 23 | 1153 | | | | | | | | | |
| 24 | 1025 | | | 3.67 C11 | | | | | | |
| 25 | 1012 | | | | 3.46 C11 / 3.33 N4 / 3.27 N3 | | | | | |
| 26 | 1078 | | | | | | | 3.47 C11 | 3.49 C11 | |
| 27 | 1145 | | | | | | | | | |
| 28 | 1050 | | | 3.89 C11 | | | | | | |
| 29 | 1253 | | | | | | | | | |
| 30 | 1257 | | | | | | | | | |
| 31 | 1297 | | | | | | | | | |
| 32 | 1304 | | | | | | | | | |
| 33 | 1306 | | | | | | | | | |
| 34 | 1307 | | | 3.89 C11 | 3.63 C11 | 3.65 C11 | | 3.44 C11 | 3.67 C11 | |
| 35 | 1328 | 3.9 N6 | 3.72 C23 | | 3.65 C23 / 3.45 N5 | | | | | |
| 36 | 1334 | | | | | | | 3.69 C11 | | |
| 37 | 1335 | | | | 3.68 N5 | | | | | |
| 38 | 1338 | 3.85 N6 | 3.56 C31 | | | | | | | |
| 39 | 1345 | | | | | | | | | |
| 40 | 1351 | | | | | | | | | |
| 41 | 1353 | | | | | | | | | |
| 42 | 1367 | | | | | | | | | |
| 43 | 1368 | | | | | | | | | 3.8 C11 |
| 44 | 1371 | | | | 3.67 C11 | | | 3.34 C11 | 3.64 C11 | |
| 45 | 1372 | | | | | | | | | 3.71 C11 |

TABLE A2-continued

| | | | | | | |
|---|---|---|---|---|---|---|
| 46 | 1373 | | | | | |
| 47 | 1492 | 3.65 N6 | | | | |
| 48 | 1399 | | | | | |
| 49 | 1406 | | 3.7 C6 | | | |
| 50 | 1433 | | 3.72 C11 | 3.69 C11 | | |
| 51 | 14 | | | | | |
| 52 | 1360 | | | | | |
| 53 | 1450 | 3.6 C22 | | | | |
| 54 | 1435 | | | | | |
| 55 | 1441 | | | | | |
| 56 | 1411 | 3.19 N1 | | | 3.58 C11 | 3.83 C11 |
| 57 | 1149 | | | | 3.56 C11 | 3.77 C11 | 3.9 C11 |

TABLE A3

| # | Compound | Construct | Resolution [Å] | Space Group | Unit Cell parameters |
|---|---|---|---|---|---|
| 1 | Melagatran 999 | CCP2-SP | 2.31 | C121 | a = 72.6, b = 40.8, c = 103.4, beta = 98.45 |
| 2 | 1129 | CCP2-SP | 1.90 | C2221 | a = 41.1, b = 72.5, c = 267.1 |
| 3 | 1088 | CCP2-SP-HIS | 1.17 | P1211 | a = 40.82, b = 76.72, c = 50.53, b = 105.09 |
| 4 | 1036 | CCP2-SP-HIS | 1.69 | P1211 | a = 40.59, b = 75.96, c = 50.87, a = 90, b = 105.21, c = 90.0 |
| 5 | 1024 | CCP2-SP | 2 | C121 | a = 72.34, b = 41.26, c = 110.59, a = 90.0, b = 106.2, g = 90.0 |
| 6 | 1037 | CCP2-SP | 1.88 | P65 | a = 41.61, b = 41.61, c = 326.15, a = 90, b = 90, g = 120 |
| 7 | 1081 | CCP2-SP | 2.5 | P1 | a = 39.62, b = 41.69, c = 51.34, a = 78.25, b = 86.48, g = 64.20 |
| 8 | 1065 | CCP2-SP-HIS | 1.70 | P212121 | a = 40.64, b = 50.83, c = 137.20, a = 90, b = 90, g = 90 |
| 9 | 1034 | CCP2-SP-HIS | 2.7 | P6122 | a = 83.29, b = 83.29, c = 150.80, a = 90, b = 90, g = 120 |
| 10 | 1059 | CCP2-SP-HIS | 1.90 | I222 | a = 73.62, b = 99.42, c = 105.36, a = 90, b = 90, g = 90 |
| 11 | 1030 | CCP2-SP-HIS | 1.8 | I222 | a = 74.04, b = 99.58, c = 106.24, a = 90, b = 90, g = 90 |
| 12 | 1118 | CCP2-SP-HIS | 1.20 | P1 | a = 39.64, b = 42.06, c = 51.38, a = 78.45, b = 86.21, g = 63.56 |
| 13 | 1063 | CCP2-SP-HIS | 2.5 | P1 | a = 39.34, b = 41.65, c = 51.18, a = 77.87, b = 85.71, g = 63.57 |
| 14 | 1007 | CCP2-SP-HIS | 2.50 | P1 | a = 41.13, b = 41.23, c = 119.53, a = 87.46, b = 82.51, g = 61.13 |
| 15 | 1090 | CCP2-SP-HIS | 2.3 | P21 | a = 40.50, b = 76.50, c = 50.64, a = 90, b = 105.24, g = 90 |
| 16 | 1089 | CCP2-SP-HIS | 1.10 | P21 | a = 40.64, b = 76.04, c = 50.67, a = 90, b = 105.31, g = 90 |
| 17 | 1021 | CCP2-SP-HIS | 2.3 | C2221 | a = 72.14, b = 40.68, c = 102.91, a = 90, b = 98.14, g = 90 |
| 18 | 1097 | CCP2-SP-HIS | 1.90 | P21 | a = 55.54, b = 75.63, c = 71.86, a = 90, b = 102.69, g = 90 |
| 19 | 1297 | CCP2-SP-HIS | 2 | P1 | a = 50.63, b = 99.39, c = 138.7, a = 90.17, b = 90.24, g = 90.16 |
| 20 | 1304 | CCP2-SP-HIS | 1.30 | P212121 | a = 51.70, b = 71.61, c = 79.83, a = 90, b = 90, g = 90 |
| 21 | 1306 | CCP2-SP-HIS | 2 | P61 | a = 84.11, b = 84.11, c = 156.08, a = 90.00, b = 90.00, g = 90.00 |
| 22 | 1307 | CCP2-SP-HIS | 1.54 | P212121 | a = 51.24, b = 71.10, c = 79.16, a = 90, b = 90, g = 90 |
| 23 | 1328 | CCP2-SP-HIS | 2.71 | P1211 | a = 75.44, b = 128.52, c = 84.66, a = 90, b = 108.58, g = 90 |
| 24 | 1334 | CCP2-SP-HIS | 1.67 | P1 | a = 39.52, b = 41.90, c = 51.02, a = 78.01, b = 85.84, g = 63.92 |
| 25 | 1335 | CCP2-SP-HIS | 1.5 | P212121 | a = 38.06, b = 68.48, c = 117.67, a = 90, b = 90, g = 90 |
| 26 | 1338 | CCP2-SP-HIS | 1.49 | P1 | a = 40.54, b = 41.78, c = 53.96, a = 86.44, b = 81.35, g = 61.04 |
| 27 | 1345 | CCP2-SP-HIS | 2 | P61 | a = 84.12, b = 84.12, c = 156.10, a = 90.00, b = 90, g = 120 |
| 28 | 1351 | CCP2-SP-HIS | 2.00 | P212121 | a = 60.80, b = 62.80, c = 93.87, a = 90.00, b = 90.00, g = 90.00 |
| 29 | 1353 | CCP2-SP-HIS | 1.2 | P212121 | a = 51.36, b = 71.52, c = 81.32, a = 90, b = 90, g = 90 |
| 30 | 1367 | CCP2-SP-HIS | 1.54 | P212121 | a = 51.60, b = 71.42, c = 79.38, a = 90, b = 90, g = 90 |
| 31 | 1368 | CCP2-SP-HIS | 1.38 | P212121 | a = 51.63, b = 71.60, c = 79.19, a = 90, b = 90, g = 90 |
| 32 | 1371 | CCP2-SP-HIS | 2.30 | C121 | a = 73.03, b = 41.12, c = 108.70, a = 90, b = 106.51, g = 90 |
| 33 | 1372 | CCP2-SP-HIS | 1.3 | P212121 | a = 51.71, b = 71.71, c = 79.67, a = 90, b = 90, g = 90 |
| 34 | 1373 | CCP2-SP-HIS | 1.40 | P212121 | a = 51.65, b = 71.58, c = 79.78, a = 90, b = 90, g = 90 |
| 35 | 1492 | CCP2-SP-HIS | 2.2 | P61 | a = 83.60, b = 83.60, c = 154.39, a = 90, b = 90, g = 120 |
| 36 | 1399 | CCP2-SP-HIS | 1.50 | P212121 | a = 51.64, b = 71.47, c = 79.62, a = 90, b = 90, g = 90 |
| 37 | 1406 | CCP2-SP-HIS | 1.84 | P212121 | a = 51.55, b = 71.49, c = 79.77, a = 90, b = 90, g = 90 |
| 38 | 54 | CCP2-SP-HIS | 1.85 | P212121 | a = 37.76, b = 68.38, c = 118.06, a = 90, b = 90, g = 90 |
| 39 | 2018 | CCP2-SP | 1.48 | P212121 | a = 51.43, b = 71.49, c = 79.01, a = 90, b = 90, g = 90 |
| 40 | 1031 | CCP2-SP-HIS | 3.00 | P4212 | a = 142.10, b = 142.10, c = 174.33, a = 90, b = 90, g = 90 |
| 41 | 1153 | CCP2-SP-HIS | 2.3 | P6122 | a = 83.05, b = 83.05, c = 149.46, a = 90, b = 90, g = 120 |
| 42 | 1025 | CCP2-SP-HIS | 2.45 | P1 | a = 50.279, b = 99.140, c = 138.454, a = 90.01, b = 90.01, g = 90.00 |
| 43 | 1012 | CCP2-SP-HIS | 1.8 | P212121 | a = 50.71, b = 102.21, c = 137.53, a = 90, b = 90, g = 90 |
| 44 | 1078 | CCP2-SP-HIS | 2.90 | P1211 | a = 92.20, b = 180.97, c = 196.95, a = 90, b = 92.5, g = 90 |
| 45 | 1145 | CCP2-SP-HIS | 1.9 | P212121 | a = 38.23, b = 68.15, c = 117.16, a = 90, b = 90, g = 90 |
| 46 | 1050 | CCP2-SP-HIS | 2.50 | P212121 | a = 37.80, b = 67.96, c = 116.92, a = 90, b = 90, g = 90 |
| 47 | 1253 | CCP2-SP | 1.3 | P212121 | a = 51.30, b = 71.56, c = 79.40, a = 90, b = 90, g = 90 |
| 48 | 1257 | CCP2-SP | 1.10 | P1211 | a = 40.86, b = 75.91, c = 51.05, a = 90, b = 105.47, g = 90 |
| 49 | 14 | CCP2-SP-HIS | 1.8 | P212121 | a = 37.94, b = 69.14, c = 117.53, a = 90, b = 90, g = 90 |
| 50 | 1042 | CCP2-SP-HIS | 2.25 | P31 | a = 83.758, b = 83.758, c = 153.239, a = 90.00, b = 90.00, g = 120.00 |
| 51 | 1433 | CCP2-SP-HIS | 1.4 | P212121 | a = 51.62, b = 71.81, c = 79.86, a = 90, b = 90, g = 90 |
| 52 | 1360 | CCP2-SP-HIS | 1.40 | P212121 | a = 51.71, b = 71.95, c = 82.20, a = 90, b = 90, g = 90 |
| 53 | 1450 | CCP2-SP-HIS | 1.4 | P212121 | a = 51.73, b = 71.79, c = 79.73, a = 90, b = 90, g = 90 |
| 54 | 1435 | CCP2-SP-HIS | 1.50 | P212121 | a = 51.66, b = 71.54, c = 79.96, a = 90, b = 90, g = 90 |
| 55 | 1441 | CCP2-SP-HIS | 1.40 | P212121 | a = 51.48, b = 71.24, c = 79.57, a = 90, b = 90, g = 90 |
| 56 | 1411 | CCP2-SP-HIS | 1.60 | P212121 | a = 51.51, b = 71.35, c = 79.80, a = 90, b = 90, g = 90 |
| 57 | 1149 | CCP2-SP-HIS | 2.8 | P 61 2 2 | a = 80.11, b = 80.11, c = 150.17, a = 90, b = 90, c = 120 |

TABLE A4

Table A4-1: Ligand-pharmacophore element distances

| | | Pharmacophore element | | | | | | | | | | |
|---|---|---|---|---|---|---|---|---|---|---|---|---|
| | compounds | C2 | C3 | C4 | C5 | C6 | C7 | CA1 | CA2 | CA3 | CA4 | CA5 | CA6 |
| 1 | 14 | 0 | 0 | 0 | 0 | 0 | 0 | 1.47 | 0 | 0 | 0 | 0 | 1.68 |
| 2 | 999_1 | 2.69 | 0 | 0 | 0 | 0 | 0 | 0.48 | 0 | 0 | 0 | 0 | 0 |
| 3 | 999_2_A | 2.87 | 0 | 0 | 0 | 0 | 0 | 0.6 | 0 | 0 | 0 | 0 | 0 |
| 4 | 999_2_B | 2.86 | 0 | 0 | 0 | 0 | 0 | 0.57 | 0 | 0 | 0 | 0 | 0 |
| 5 | 54_A | 0 | 4.06 | 0 | 0 | 0 | 0 | 0.6 | 0 | 0 | 0 | 0 | 0 |
| 6 | 54_B | 4 | 0 | 0 | 0 | 0 | 0 | 0.49 | 0 | 0 | 0 | 0 | 0 |
| 7 | 1129 | 3.15 | 0 | 0 | 0 | 0 | 0 | 0.35 | 0 | 0 | 0 | 0.67 | 0 |

TABLE A4-continued

| | | | | | | | | | | | | | |
|---|---|---|---|---|---|---|---|---|---|---|---|---|---|
| 8 | 1034 | 2.4 | 0 | 0 | 0 | 0 | 0 | 0.28 | 0 | 0 | 0 | 0.98 | 0 |
| 9 | 1024 | 0 | 0 | 0 | 0 | 0 | 0 | 0.4 | 0.33 | 0 | 0 | 0 | 0 |
| 10 | 1042_1 | 1.81 | 0 | 0 | 0 | 0 | 0 | 0.87 | 0.48 | 0 | 0 | 0 | 0 |
| 11 | 1042_2 | 1.33 | 0 | 0 | 0 | 0 | 0 | 0.5 | 0.72 | 0 | 0 | 0 | 0 |
| 12 | 1042_3 | 2.05 | 0 | 0 | 0 | 0 | 0 | 0.5 | 1.65 | 0 | 0 | 0 | 0 |
| 13 | 2018 | 0 | 9.61 | 0 | 0 | 0 | 0 | 0.54 | 0 | 0 | 0 | 1.25 | 1.35 |
| 14 | 1059 | 1.86 | 0 | 0 | 0 | 0 | 0 | 1.27 | 0.8 | 0 | 0 | 0 | 0 |
| 15 | 1088_A | 1.75 | 0 | 0 | 0 | 0 | 0 | 0.4 | 0 | 0 | 0 | 0.39 | 0 |
| 16 | 1088_B | 1.93 | 0 | 0 | 0 | 0 | 0 | 0.62 | 0.2 | 0 | 0 | 0 | 0 |
| 17 | 1036_1 | 0 | 0 | 0 | 0 | 0 | 0 | 0.35 | 0 | 0 | 0 | 1 | 0 |
| 18 | 1036_2_1 | 0 | 0 | 0 | 0 | 0 | 0 | 0.47 | 0 | 0 | 0 | 0.78 | 0 |
| 19 | 1036_2_2 | 0 | 0 | 0 | 0 | 0 | 0 | 0.54 | 0 | 0 | 0 | 1.25 | 0 |
| 20 | 1081 | 0 | 0 | 1.99 | 0 | 0 | 0 | 0.48 | 0.76 | 0 | 0 | 0 | 0 |
| 21 | 1063 | 0.48 | 0 | 0 | 0 | 0 | 0 | 0.3 | 0.85 | 0 | 0 | 0 | 0 |
| 22 | 1065 | 0.11 | 0 | 0 | 0 | 0 | 0 | 0.88 | 0.1 | 0 | 0 | 0 | 0 |
| 23 | 1030_A | 0 | 0 | 0 | 0 | 0 | 0 | 0.34 | 0 | 0 | 0 | 4.24 | 3.19 |
| 24 | 1030_B | 0 | 0 | 0 | 0 | 0 | 0 | 0.39 | 0 | 0 | 0 | 1.57 | 0 |
| 25 | 1037 | 0 | 0 | 0 | 0 | 0 | 0 | 0.27 | 0 | 0 | 0 | 1.21 | 0 |
| 26 | 1118 | 0 | 0 | 2.54 | 0 | 1.17 | 0 | 0.43 | 0.69 | 0 | 0 | 0 | 0 |
| 27 | 1090 | 0 | 0 | 0 | 0 | 0 | 0 | 0.98 | 0 | 0 | 0 | 0.91 | 0 |
| 28 | 1007_1 | 0 | 0 | 0 | 0 | 0 | 0 | 0.35 | 0.77 | 0 | 0 | 0 | 0 |
| 29 | 1007_2 | 0 | 0 | 0 | 0 | 0 | 0 | 0.59 | 0.86 | 0 | 0 | 0 | 0 |
| 30 | 1149 | 0 | 0 | 3.8 | 0 | 0 | 0 | 0.35 | 0 | 0 | 1.47 | 0 | 4.96 |
| 31 | 1021_A | 0 | 0 | 0 | 0.53 | 0 | 0 | 1.4 | 0 | 0 | 0 | 3.03 | 0 |
| 32 | 1021_B | 0 | 0 | 0 | 0.45 | 0 | 0 | 1.36 | 0.48 | 0 | 0 | 0 | 0 |
| 33 | 1097_1 | 0.69 | 0 | 0 | 0 | 0 | 0 | 0.29 | 0 | 0 | 0 | 0.98 | 0 |
| 34 | 1097_2 | 0.72 | 0 | 0 | 0 | 0 | 0 | 0.32 | 0 | 0 | 0 | 1.1 | 0 |
| 35 | 1031_1 | 0 | 0 | 0 | 0.34 | 0 | 0 | 1.42 | 0.36 | 0 | 0 | 0 | 0 |
| 36 | 1031_2 | 0 | 0 | 0 | 0.41 | 0 | 0 | 1.56 | 0.6 | 0 | 0 | 0 | 0 |
| 37 | 1031_3 | 0 | 0 | 0 | 0.48 | 0 | 0 | 1.56 | 0.44 | 0 | 0 | 0 | 0 |
| 38 | 1031_4 | 0 | 0 | 0 | 0.3 | 0 | 0 | 1.41 | 0.5 | 0 | 0 | 0 | 0 |
| 39 | 1153_A | 8.69 | 0 | 0 | 0 | 0 | 0 | 0.43 | 0.34 | 4.19 | 0 | 0 | 0 |
| 40 | 1153_B | 10.14 | 0 | 0 | 0 | 0 | 0 | 0.39 | 0.58 | 0 | 0 | 6.17 | 0 |
| 41 | 1025_1 | 0.84 | 0 | 0 | 0 | 0 | 0 | 0.49 | 0.53 | 0 | 0 | 0 | 0 |
| 42 | 1025_2 | 0.79 | 0 | 0 | 0 | 0 | 0 | 0.98 | 0.18 | 0 | 0 | 0 | 0 |
| 43 | 1025_3 | 0.49 | 0 | 0 | 0 | 0 | 0 | 0.81 | 0.86 | 0 | 0 | 0 | 0 |
| 44 | 1025_4 | 0.51 | 0 | 0 | 0 | 0 | 0 | 0.28 | 0.97 | 0 | 0 | 0 | 0 |
| 45 | 1025_5 | 0.67 | 0 | 0 | 0 | 0 | 0 | 0.62 | 0.37 | 0 | 0 | 0 | 0 |
| 46 | 1025_6 | 0.52 | 0 | 0 | 0 | 0 | 0 | 1.03 | 0.55 | 0 | 0 | 0 | 0 |
| 47 | 1089_A | 0 | 0 | 0 | 0 | 0 | 0 | 1 | 0.89 | 0 | 0 | 0 | 0 |
| 48 | 1089_B | 0 | 0 | 0 | 0 | 0 | 0 | 0.99 | 0 | 0 | 0 | 1.16 | 0 |
| 49 | 1012_1 | 0 | 0 | 0 | 0 | 0 | 0 | 0.4 | 0 | 0 | 0 | 1.27 | 0 |
| 50 | 1012_2 | 0 | 0 | 0 | 0 | 0 | 0 | 0.44 | 0 | 0 | 0 | 0.94 | 0 |
| 51 | 1078_1 | 0.69 | 0 | 0 | 0.4 | 0 | 0 | 1.58 | 0.48 | 0 | 0 | 0 | 0 |
| 52 | 1078_10 | 0.49 | 0 | 0 | 0.3 | 0 | 0 | 1.34 | 0.49 | 0 | 0 | 0 | 0 |
| 53 | 1078_11 | 0.6 | 0 | 0 | 0.41 | 0 | 0 | 1.64 | 0.64 | 0 | 0 | 0 | 0 |
| 54 | 1078_12 | 0.4 | 0 | 0 | 0.52 | 0 | 0 | 1.43 | 0.64 | 0 | 0 | 0 | 0 |
| 55 | 1078_13 | 0.58 | 0 | 0 | 0.47 | 0 | 0 | 1.62 | 0.73 | 0 | 0 | 0 | 0 |
| 56 | 1078_14 | 0.74 | 0 | 0 | 0.47 | 0 | 0 | 1.61 | 0.8 | 0 | 0 | 0 | 0 |
| 57 | 1078_15 | 0.81 | 0 | 0 | 0.43 | 0 | 0 | 1.56 | 0.65 | 0 | 0 | 0 | 0 |
| 58 | 1078_16 | 0.64 | 0 | 0 | 0.42 | 0 | 0 | 1.49 | 0.49 | 0 | 0 | 0 | 0 |
| 59 | 1078_2 | 0.61 | 0 | 0 | 0.46 | 0 | 0 | 1.55 | 0.61 | 0 | 0 | 0 | 0 |
| 60 | 1078_3 | 0.43 | 0 | 0 | 0.45 | 0 | 0 | 1.53 | 0.27 | 0 | 0 | 0 | 0 |
| 61 | 1078_4 | 0.67 | 0 | 0 | 0.52 | 0 | 0 | 1.62 | 0.59 | 0 | 0 | 0 | 0 |
| 62 | 1078_5 | 0.71 | 0 | 0 | 0.42 | 0 | 0 | 1.76 | 0.6 | 0 | 0 | 0 | 0 |
| 63 | 1078_6 | 1.09 | 0 | 0 | 0.48 | 0 | 0 | 1.31 | 0.65 | 0 | 0 | 0 | 0 |
| 64 | 1078_7 | 0.64 | 0 | 0 | 0.61 | 0 | 0 | 1.69 | 0.55 | 0 | 0 | 0 | 0 |
| 65 | 1078_8 | 0.85 | 0 | 0 | 0.78 | 0 | 0 | 1.67 | 0.92 | 0 | 0 | 0 | 0 |
| 66 | 1078_9 | 0.67 | 0 | 0 | 0.46 | 0 | 0 | 1.62 | 0.56 | 0 | 0 | 0 | 0 |
| 67 | 1145_A | 0 | 0 | 0 | 0 | 0 | 0 | 0.47 | 0.41 | 1.22 | 0 | 0 | 0 |
| 68 | 1145_B | 0 | 0 | 0 | 0 | 0 | 0 | 0.47 | 0.41 | 1.22 | 0 | 0 | 0 |
| 69 | 1050 | 6.95 | 0 | 0 | 0 | 0 | 0 | 0.57 | 0.33 | 0 | 0 | 0 | 0 |
| 70 | 1253 | 0.28 | 0.07 | 0 | 0 | 0 | 0 | 0.59 | 0.23 | 0 | 0 | 0 | 0 |
| 71 | 1257 | 0 | 0.1 | 0 | 0 | 0.53 | 0 | 0.65 | 0 | 0 | 0 | 1.2 | 0 |
| 72 | 1297_1 | 0.34 | 0.3 | 0 | 0 | 0 | 0 | 0.39 | 0.19 | 0 | 1.24 | 0 | 0 |
| 73 | 1297_2 | 0.34 | 0.17 | 0 | 0 | 0 | 0 | 0.47 | 0.22 | 0 | 1.25 | 0 | 0 |
| 74 | 1297_3 | 0.28 | 0.23 | 0 | 0 | 0 | 0 | 0.33 | 0.22 | 0 | 0.94 | 0 | 0 |
| 75 | 1297_4 | 0.31 | 0.18 | 0 | 0 | 0 | 0 | 0.48 | 0.24 | 0 | 0.98 | 0 | 0 |
| 76 | 1297_5 | 0.24 | 0.29 | 0 | 0 | 0 | 0 | 0.44 | 0.07 | 0 | 1.22 | 0 | 0 |
| 77 | 1297_6 | 0.33 | 0.4 | 0 | 0 | 0 | 0 | 0.36 | 0.24 | 0 | 1.14 | 0 | 0 |
| 78 | 1304 | 0 | 0.09 | 0 | 0 | 0 | 0 | 0.56 | 0.23 | 0 | 0 | 0 | 0 |
| 79 | 1306_1 | 0 | 0 | 0 | 0 | 0 | 0 | 0.05 | 0.6 | 0 | 0 | 0 | 0 |
| 80 | 1306_2 | 0 | 0 | 0 | 0 | 0 | 0 | 0.74 | 1.14 | 0 | 0 | 0 | 0 |
| 81 | 1307 | 0 | 0 | 0 | 0.37 | 0 | 0.76 | 1.55 | 0.17 | 0 | 0 | 0 | 0 |
| 82 | 1328_1 | 0 | 0.4 | 0.76 | 0 | 0 | 0 | 0.49 | 0.5 | 0 | 0 | 0 | 0 |
| 83 | 1328_2 | 0 | 0.15 | 1.28 | 0 | 0 | 0 | 0.41 | 0.43 | 0 | 0 | 0 | 0 |
| 84 | 1328_3 | 0 | 0.21 | 1.76 | 0 | 0 | 0 | 0.4 | 0.48 | 0 | 0 | 0 | 0 |
| 85 | 1328_4 | 0 | 0.18 | 1.86 | 0 | 0 | 0 | 0.5 | 0.3 | 0 | 0 | 0 | 0 |
| 86 | 1334 | 0 | 0 | 0 | 0.34 | 0 | 0 | 1.04 | 0.7 | 0 | 0 | 0 | 0 |
| 87 | 1335 | 0 | 0 | 0 | 0 | 0 | 0 | 0.38 | 0.56 | 0 | 0 | 0 | 0 |

TABLE A4-continued

| | | | | | | | | | | | | |
|---|---|---|---|---|---|---|---|---|---|---|---|---|
| 88 | 1338 | 0 | 0.12 | 0 | 0 | 0 | 0 | 0.55 | 0.59 | 0 | 1.21 | 0 | 0 |
| 89 | 1345_1 | 0 | 0 | 0 | 0 | 0 | 0 | 0.51 | 1.2 | 1.44 | 0 | 0 | 0 |
| 90 | 1345_2 | 0 | 0 | 0 | 0 | 0 | 0 | 0.45 | 0.89 | 1.13 | 0 | 0 | 0 |
| 91 | 1351 | 0 | 0.12 | 0 | 0 | 0 | 0 | 0.57 | 0.8 | 0 | 3.3 | 0 | 0 |
| 92 | 1353 | 0.58 | 0.13 | 0 | 0 | 0 | 0 | 0.61 | 0.5 | 0 | 0 | 0 | 0 |
| 93 | 1360 | 0 | 0.11 | 0 | 0 | 0 | 0 | 0.57 | 2.35 | 0 | 0 | 1.11 | 0 |
| 94 | 1367 | 0 | 0.13 | 0 | 0 | 0 | 0 | 0.5 | 0.57 | 0 | 0 | 3.27 | 0 |
| 95 | 1368 | 0 | 0.16 | 0 | 0 | 0 | 0 | 0.62 | 0.95 | 0 | 0 | 2.23 | 0 |
| 96 | 1371 | 0 | 0 | 0 | 0.48 | 0 | 0 | 0.58 | 0.46 | 0 | 0 | 0 | 0 |
| 97 | 1372_A | 0 | 0.09 | 1.91 | 0 | 0 | 0 | 0.55 | 0.47 | 0 | 0 | 0 | 0 |
| 98 | 1372_B | 0 | 0.1 | 0 | 0 | 1.46 | 0 | 0.57 | 1.41 | 0 | 0 | 0 | 0 |
| 99 | 1373 | 0 | 0.08 | 0 | 0 | 0 | 0 | 0.56 | 0.54 | 0 | 0 | 2.5 | 0 |
| 100 | 1492 | 2.91 | 0 | 0 | 0 | 0 | 0 | 1.7 | 0 | 0 | 0 | 0.84 | 0 |
| 101 | 1399 | 0 | 0.14 | 0 | 0 | 0 | 0 | 0.59 | 0.85 | 0 | 2.39 | 0 | 0 |
| 102 | 1406 | 0 | 0.12 | 0 | 0 | 0 | 0 | 0.56 | 0.42 | 0 | 1.59 | 0 | 0 |
| 103 | 1411 | 0.42 | 0.32 | 0 | 0 | 0 | 0 | 0.71 | 0.52 | 0 | 0 | 0 | 0 |
| 104 | 1433 | 0.26 | 0 | 0 | 0.2 | 0 | 0 | 0.98 | 0.18 | 0 | 0 | 0 | 0 |
| 105 | 1435 | 0 | 0.15 | 1.37 | 0 | 0.38 | 0 | 0.6 | 0.8 | 0 | 0 | 0 | 0 |
| 106 | 1441 | 0.54 | 0.17 | 0 | 0 | 0 | 0 | 0.64 | 0.64 | 0 | 0 | 0 | 0 |
| 107 | 1450_A | 0 | 0 | 0 | 0.34 | 0 | 0.72 | 1.03 | 0.4 | 0 | 0 | 0 | 0 |
| 108 | 1450_B | 0 | 0 | 0 | 1.67 | 0 | 1.3 | 0.94 | 1.24 | 0 | 0 | 0 | 0 |

Table A4-2: Ligand-pharmacophore element distances

| | | Pharmacophore element | | | | | | | | | |
|---|---|---|---|---|---|---|---|---|---|---|---|
| | compounds | H1 | H2 | H3 | H4 | N1 | N2 | O1 | O2 | O3 | O4 |
| 1 | 14 | 0 | 4.66 | 0 | 1.82 | 0 | 0 | 3.89 | 0.46 | 0 | 0 |
| 2 | 999_1 | 0 | 0 | 4.95 | 3.36 | 1.77 | 0.72 | 1.53 | 0.41 | 0 | 0 |
| 3 | 999_2_A | 0 | 0 | 4.85 | 3.24 | 1.71 | 0.89 | 1.86 | 0.53 | 0 | 0 |
| 4 | 999_2_B | 0 | 0 | 4.73 | 3.33 | 1.63 | 1.1 | 1.77 | 0.77 | 0 | 0 |
| 5 | 54_A | 0 | 0 | 5.03 | 0 | 0 | 0 | 0 | 0 | 0 | 3.96 |
| 6 | 54_B | 0 | 0 | 4.44 | 0 | 0 | 0 | 0 | 0 | 0 | 3.94 |
| 7 | 1129 | 0 | 0 | 1.34 | 3.79 | 1.8 | 1.8 | 0.39 | 0.58 | 0 | 0 |
| 8 | 1034 | 0 | 0 | 1.08 | 3.56 | 1.87 | 0.86 | 0.39 | 0.49 | 0 | 0 |
| 9 | 1024 | 0 | 0 | 4.93 | 3.21 | 1.74 | 0.59 | 0.4 | 0.4 | 0 | 0 |
| 10 | 1042_1 | 0 | 0 | 5.4 | 3.08 | 1.3 | 0.56 | 2.71 | 0.67 | 0 | 0 |
| 11 | 1042_2 | 0 | 0 | 5.3 | 3.52 | 1.61 | 1.72 | 3.1 | 0.75 | 0 | 0 |
| 12 | 1042_3 | 0 | 0 | 6.42 | 4.11 | 1.45 | 1.33 | 0 | 1.19 | 0 | 0 |
| 13 | 2018 | 0 | 0 | 7.09 | 1.03 | 2.16 | 0 | 2.54 | 2.38 | 0 | 0 |
| 14 | 1059 | 0 | 0 | 4.5 | 3.89 | 1.27 | 0.41 | 0.82 | 0.49 | 0 | 0 |
| 15 | 1088_A | 0 | 0 | 3.41 | 5 | 0.89 | 0.36 | 0.57 | 0.41 | 0 | 0 |
| 16 | 1088_B | 0 | 0 | 3.63 | 5.04 | 1.15 | 0.49 | 0.72 | 0.37 | 0 | 0 |
| 17 | 1036_1 | 0 | 0 | 5.87 | 3.25 | 1.78 | 0.45 | 0.38 | 0.34 | 0 | 0 |
| 18 | 1036_2_1 | 0 | 0 | 4.76 | 3.7 | 2.16 | 0.81 | 0.74 | 0.45 | 0 | 0 |
| 19 | 1036_2_2 | 0 | 0 | 5.81 | 3.32 | 2.08 | 0.66 | 0.8 | 0.68 | 0 | 0 |
| 20 | 1081 | 0 | 0 | 5.53 | 3.48 | 1.57 | 0.21 | 0.28 | 0.45 | 0 | 0 |
| 21 | 1063 | 0 | 0 | 4.66 | 3.47 | 1.56 | 1.21 | 0.6 | 0.68 | 0 | 0 |
| 22 | 1065 | 0 | 0 | 4.27 | 4.71 | 0.96 | 0.26 | 0.31 | 0.26 | 0 | 0 |
| 23 | 1030_A | 0 | 0 | 3.05 | 3.42 | 1.55 | 0 | 0.5 | 0.57 | 0 | 0 |
| 24 | 1030_B | 0 | 0 | 3.03 | 3.19 | 1.49 | 0 | 0.96 | 0.61 | 0 | 0 |
| 25 | 1037 | 0 | 0 | 3.03 | 3.2 | 1.98 | 0 | 0.66 | 0.53 | 0 | 0 |
| 26 | 1118 | 0 | 0 | 5.69 | 3.5 | 1.59 | 0.32 | 0.25 | 0.55 | 0 | 0 |
| 27 | 1090 | 0 | 0 | 5.6 | 0.54 | 1.59 | 0.46 | 0.53 | 0.47 | 0 | 0 |
| 28 | 1007_1 | 0 | 0 | 4.59 | 2.28 | 1.39 | 0.59 | 0.76 | 0.57 | 0 | 0 |
| 29 | 1007_2 | 0 | 0 | 4.59 | 2.16 | 1.55 | 1.03 | 0.89 | 0.77 | 0 | 0 |
| 30 | 1149 | 0 | 0 | 2.9 | 3.72 | 1.89 | 3.4 | 0.77 | 6.17 | 0 | 0 |
| 31 | 1021_A | 0 | 0 | 0.8 | 1.73 | 0 | 0.95 | 1 | 0.87 | 0 | 0 |
| 32 | 1021_B | 0 | 0 | 0.84 | 0.53 | 0 | 0.62 | 1.02 | 0.5 | 0 | 0 |
| 33 | 1097_1 | 0 | 0 | 2.07 | 3.33 | 1.92 | 0.61 | 0.51 | 0.44 | 0 | 0 |
| 34 | 1097_2 | 0 | 0 | 2.16 | 3.54 | 1.79 | 0.4 | 0.51 | 0.32 | 0 | 0 |
| 35 | 1031_1 | 0 | 1.6 | 1.16 | 2.79 | 0 | 0.64 | 0.91 | 0.63 | 0 | 0.92 |
| 36 | 1031_2 | 0 | 1.47 | 0.45 | 2.01 | 0 | 0.8 | 1.17 | 2.33 | 0 | 1.05 |
| 37 | 1031_3 | 0 | 1.36 | 1.16 | 2.79 | 0 | 0.3 | 1.05 | 0.83 | 0 | 0.97 |
| 38 | 1031_4 | 0 | 1.46 | 1.26 | 2.97 | 0 | 0.74 | 1.04 | 0.82 | 0 | 0.95 |
| 39 | 1153_A | 0 | 0 | 0.44 | 4.25 | 1.41 | 0.34 | 1.73 | 0.79 | 7.39 | 0 |
| 40 | 1153_B | 0 | 0 | 1.01 | 4.21 | 1.5 | 1.88 | 2.22 | 6.33 | 12.11 | 0 |
| 41 | 1025_1 | 0 | 0 | 2.07 | 3.53 | 1.74 | 0.97 | 2.51 | 2.94 | 0 | 0 |
| 42 | 1025_2 | 0 | 0 | 1.75 | 2.28 | 1.85 | 1.08 | 2.55 | 2.63 | 0 | 0 |
| 43 | 1025_3 | 0 | 0 | 1.7 | 3.95 | 1.06 | 0.59 | 1.27 | 3 | 0 | 0 |
| 44 | 1025_4 | 0 | 0 | 1.05 | 3.36 | 1.39 | 0.23 | 2.33 | 0.72 | 0 | 0 |
| 45 | 1025_5 | 0 | 0 | 2.04 | 3.68 | 0.4 | 0.91 | 1.12 | 2.96 | 0 | 0 |
| 46 | 1025_6 | 0 | 0 | 1.77 | 3.75 | 1.11 | 0.59 | 1.36 | 2.83 | 0 | 0 |
| 47 | 1089_A | 0 | 0 | 5.67 | 0.59 | 1.52 | 0.5 | 0.41 | 0.42 | 0 | 0 |
| 48 | 1089_B | 0 | 0 | 5.68 | 0.57 | 1.56 | 0.38 | 0.4 | 0.43 | 0 | 0 |
| 49 | 1012_1 | 0 | 0 | 4.44 | 2.79 | 1.21 | 0.32 | 0.39 | 0.42 | 0 | 0 |
| 50 | 1012_2 | 0 | 0 | 4.08 | 1.93 | 2.54 | 0.66 | 0.67 | 0.65 | 0 | 0 |
| 51 | 1078_1 | 0 | 0.54 | 0.94 | 1.67 | 0 | 0.64 | 1.05 | 0.43 | 0 | 1.26 |
| 52 | 1078_10 | 0 | 0.46 | 1.24 | 0.6 | 0 | 0.35 | 1.12 | 0.63 | 0 | 1.08 |

TABLE A4-continued

| | | | | | | | | | | | |
|---|---|---|---|---|---|---|---|---|---|---|---|
| 53 | 1078_11 | 0 | 0.5 | 0.5 | 1.68 | 0 | 0.3 | 1.35 | 0.7 | 0 | 1.19 |
| 54 | 1078_12 | 0 | 0.71 | 1 | 1.45 | 0 | 0.59 | 1.02 | 1 | 0 | 1.32 |
| 55 | 1078_13 | 0 | 0.71 | 1.11 | 0.63 | 0 | 0.2 | 1.24 | 0.51 | 0 | 1.38 |
| 56 | 1078_14 | 0 | 0.41 | 0.69 | 1.45 | 0 | 0.5 | 1.29 | 0.8 | 0 | 1.28 |
| 57 | 1078_15 | 0 | 0.41 | 0.85 | 1.59 | 0 | 0.61 | 1.2 | 0.69 | 0 | 1.34 |
| 58 | 1078_16 | 0 | 0.69 | 0.73 | 1.7 | 0 | 0.5 | 1.02 | 0.54 | 0 | 1.38 |
| 59 | 1078_2 | 0 | 0.34 | 0.59 | 1.74 | 0 | 0.35 | 1.19 | 0.55 | 0 | 0.98 |
| 60 | 1078_3 | 0 | 0.36 | 1.07 | 0.56 | 0 | 0.31 | 1.27 | 0.59 | 0 | 1.01 |
| 61 | 1078_4 | 0 | 0.67 | 0.39 | 1.67 | 0 | 0.33 | 1.17 | 0.51 | 0 | 1.28 |
| 62 | 1078_5 | 0 | 0.97 | 0.81 | 1.7 | 0 | 0.53 | 1.35 | 0.58 | 0 | 1.67 |
| 63 | 1078_6 | 0 | 0.61 | 1.78 | 1.01 | 0 | 1.38 | 1.26 | 0 | 0 | 1 |
| 64 | 1078_7 | 0 | 0.39 | 0.93 | 1.7 | 0 | 0.6 | 1.04 | 0.57 | 0 | 1.19 |
| 65 | 1078_8 | 0 | 0.46 | 0.74 | 1.57 | 0 | 0.58 | 1.21 | 0.73 | 0 | 1.36 |
| 66 | 1078_9 | 0 | 0.89 | 0.85 | 1.8 | 0 | 0.58 | 1.16 | 0.48 | 0 | 1.63 |
| 67 | 1145_A | 0.1 | 0 | 4.73 | 3.44 | 1.47 | 0.31 | 0.23 | 0.61 | 2.39 | 0 |
| 68 | 1145_B | 0.1 | 0 | 4.73 | 3.44 | 1.47 | 0.31 | 0.23 | 0.61 | 2.39 | 0 |
| 69 | 1050 | 0 | 0 | 0.65 | 3.44 | 1.43 | 0.26 | 0.59 | 0.42 | 0 | 0 |
| 70 | 1253 | 0 | 0 | 0.98 | 2.74 | 1.13 | 0.22 | 0.54 | 0.29 | 0 | 0 |
| 71 | 1257 | 0 | 0 | 0.74 | 2.6 | 1.22 | 0.23 | 0.61 | 0.29 | 0 | 0 |
| 72 | 1297_1 | 0 | 0 | 4.44 | 2.65 | 1.26 | 0.28 | 0.62 | 0.38 | 0 | 0 |
| 73 | 1297_2 | 0 | 0 | 4.23 | 2.77 | 1.12 | 0.14 | 0.6 | 0.37 | 0 | 0 |
| 74 | 1297_3 | 0 | 0 | 4.4 | 2.74 | 1.14 | 0.39 | 0.57 | 0.3 | 0 | 0 |
| 75 | 1297_4 | 0 | 0 | 4.27 | 2.72 | 1.17 | 0.19 | 0.57 | 0.38 | 0 | 0 |
| 76 | 1297_5 | 0 | 0 | 4.24 | 2.61 | 1.32 | 0.32 | 0.56 | 0.24 | 0 | 0 |
| 77 | 1297_6 | 0 | 0 | 4.25 | 2.58 | 1.39 | 0.88 | 0.6 | 0.28 | 0 | 0 |
| 78 | 1304 | 0 | 0 | 4.52 | 2.76 | 1.15 | 0.15 | 0.48 | 0.26 | 0 | 0 |
| 79 | 1306_1 | 0 | 0 | 4.93 | 4.21 | 2.05 | 0.66 | 1.07 | 0.19 | 0 | 0 |
| 80 | 1306_2 | 0 | 0 | 4.37 | 5.03 | 1.16 | 0.57 | 0.69 | 0.58 | 0 | 0 |
| 81 | 1307 | 0 | 0 | 0.82 | 0.55 | 0 | 0.56 | 1.43 | 0.73 | 0 | 0.83 |
| 82 | 1328_1 | 0 | 0 | 4.33 | 2.79 | 1.13 | 0.47 | 0.31 | 0.56 | 0 | 0 |
| 83 | 1328_2 | 0 | 0 | 4.58 | 2.68 | 1.16 | 0.17 | 0.48 | 0.39 | 0 | 0 |
| 84 | 1328_3 | 0 | 0 | 4.6 | 2.34 | 1.24 | 0.5 | 0.68 | 0.55 | 0 | 0 |
| 85 | 1328_4 | 0 | 0 | 4.56 | 2.55 | 1.1 | 0.61 | 1.12 | 0.58 | 0 | 0 |
| 86 | 1334 | 0 | 0 | 3.01 | 0.91 | 0 | 0.21 | 0.16 | 0.43 | 0 | 1.1 |
| 87 | 1335 | 0 | 0 | 4.98 | 1.46 | 1.65 | 0.36 | 2.14 | 0.29 | 0 | 0 |
| 88 | 1338 | 0 | 0 | 4.52 | 2.7 | 1.17 | 0.16 | 0.38 | 0.31 | 0 | 0 |
| 89 | 1345_1 | 0 | 0 | 5.45 | 3.64 | 1.98 | 1.06 | 1.1 | 0.38 | 2.93 | 0 |
| 90 | 1345_2 | 0 | 0 | 4.78 | 3.63 | 1.74 | 0.43 | 0.35 | 0.38 | 1.87 | 0 |
| 91 | 1351 | 0 | 0 | 4.36 | 2.69 | 1.21 | 0.31 | 0.43 | 0.39 | 0 | 0 |
| 92 | 1353 | 0 | 0 | 4.4 | 2.73 | 1.16 | 0.26 | 0.56 | 0.31 | 0 | 0 |
| 93 | 1360 | 0 | 0 | 4.55 | 2.82 | 1.1 | 0.18 | 0.59 | 0.27 | 0 | 0 |
| 94 | 1367 | 0 | 0 | 2.46 | 2.75 | 1.12 | 0 | 0.67 | 2 | 0 | 0 |
| 95 | 1368 | 0 | 0 | 3.8 | 2.77 | 1.11 | 0.24 | 0.6 | 5.09 | 0 | 0 |
| 96 | 1371 | 0 | 0 | 1.21 | 0.82 | 0 | 0.35 | 0.72 | 0.46 | 0 | 1.38 |
| 97 | 1372_A | 0 | 0 | 1.18 | 2.8 | 1.11 | 0.16 | 0.53 | 0.24 | 0 | 0 |
| 98 | 1372_B | 0 | 0 | 1.2 | 2.8 | 1.12 | 0.41 | 0.54 | 0.26 | 0 | 0 |
| 99 | 1373 | 0 | 0 | 4.46 | 2.77 | 1.11 | 0.22 | 0.51 | 0.26 | 0 | 0 |
| 100 | 1492 | 0 | 0 | 6 | 1.08 | 1.71 | 0 | 1.53 | 1.38 | 0 | 0 |
| 101 | 1399 | 0 | 0 | 4.29 | 2.79 | 1.08 | 0.52 | 0.59 | 0.3 | 0 | 0 |
| 102 | 1406 | 0 | 0 | 4.51 | 2.81 | 1.02 | 0.33 | 0.56 | 0.38 | 0 | 0 |
| 103 | 1411 | 0 | 0 | 4.01 | 2.9 | 1.03 | 0.54 | 0.46 | 0.47 | 0 | 0 |
| 104 | 1433 | 0 | 0 | 3.08 | 0.52 | 0 | 0.16 | 0.36 | 0.25 | 0 | 1.03 |
| 105 | 1435 | 0 | 0 | 4.44 | 2.75 | 1.1 | 0.18 | 0.49 | 0.23 | 0 | 0 |
| 106 | 1441 | 0 | 0 | 4.36 | 2.76 | 1.1 | 0.63 | 0.57 | 0.33 | 0 | 0 |
| 107 | 1450_A | 0 | 0 | 0.97 | 0.46 | 0 | 0.17 | 0.58 | 0.38 | 0 | 1.16 |
| 108 | 1450_B | 0 | 0 | 1.04 | 0.36 | 0 | 0.24 | 0.5 | 0.38 | 0 | 0.53 |

TABLE A5

Table A5-1: Pharmacophore: Distance between elements

| | | S2 Region | | | | Pharmacophore Region | | | S1 Region | | | | |
|---|---|---|---|---|---|---|---|---|---|---|---|---|---|
| | | | | | | Elements | | | | | | | |
| | | d(H4, O1) | d(H4, O2) | d(O1, O2) | d(CA6, O1) | d(CA6, O2) | d(CA1, O1) | d(CA1, O2) | d(CA1, N1) | d(C3, CA1) | d(CA1, N1)2 | d(CA1, O4) | d(CA1, C5) | d(O4, H2) |
| 1 | 14 | 3.02 | 3.13 | 5.28 | 7.02 | 3.51 | 3.49 | 3.51 | 3.61 | | | | | |
| 2 | 999_1 | 3.57 | 4.90 | 2.29 | | | 3.61 | 4.51 | 3.64 | | | | | |
| 3 | 999_2_A | 3.49 | 5.01 | 2.30 | | | 3.58 | 4.73 | 3.60 | | | | | |
| 4 | 999_2_B | 3.18 | 5.07 | 2.52 | | | 3.35 | 4.89 | 3.60 | | | | | |
| 5 | 1129 | 5.00 | 4.63 | 3.49 | | | 4.47 | 4.37 | 3.60 | | | | | |
| 6 | 1034 | 4.86 | 4.31 | 3.48 | | | 4.35 | 4.19 | 3.64 | | | | | |
| 7 | 1024 | 3.99 | 3.27 | 3.23 | | | 4.37 | 4.23 | 3.55 | | | | | |
| 8 | 1042_1 | 3.35 | 3.67 | 3.40 | | | 3.98 | 4.13 | 3.58 | | | | | |
| 9 | 1042_2 | 4.02 | 4.01 | 3.46 | | | 4.47 | 4.74 | 3.61 | | | | | |
| 10 | 1042_3 | | 4.90 | | | | | 4.54 | 3.63 | | | | | |
| 11 | 2018 | 3.89 | 5.39 | 4.92 | 2.73 | | 7.59 | 6.76 | 3.56 | | | | | |
| 12 | 1059 | 4.89 | 4.48 | 3.20 | | | 5.32 | 5.00 | 1.85 | | | | | |
| 13 | 1088_A | 6.97 | 5.89 | 3.49 | | | 5.33 | 4.61 | | | | | | |
| 14 | 1088_B | 6.73 | 6.06 | 3.02 | | | 5.22 | 4.78 | 3.60 | | | | | |
| 15 | 1036_1 | 4.04 | 3.64 | 3.31 | | | 4.41 | 4.55 | 3.66 | | | | | |
| 16 | 1036_2_1 | 4.42 | 3.44 | 3.17 | | | 4.62 | 4.33 | 3.61 | | | | | |
| 17 | 1036_2_2 | 4.14 | 3.26 | 3.29 | | | 4.55 | 4.34 | 3.62 | | | | | |
| 18 | 1081 | 5.10 | 4.46 | 3.45 | 5.19 | | 4.57 | 4.27 | 3.56 | | | | | |
| 19 | 1063 | 5.37 | 3.82 | 3.31 | | | 4.95 | 3.58 | 3.47 | | | | | |
| 20 | 1065 | 6.39 | 5.35 | 3.30 | | 3.40 | 4.32 | 4.20 | | | | | | |
| 21 | 1030_A | 5.04 | 4.57 | 3.20 | | | 4.56 | 4.46 | 3.64 | | | | | |
| 22 | 1030_B | 4.76 | 4.55 | 3.30 | | | 4.31 | 4.50 | 3.55 | | | | | |
| 23 | 1037 | 4.16 | 3.07 | 3.31 | | | 4.49 | 4.30 | | | | | | |
| 24 | 1118 | 4.85 | 4.52 | 3.25 | | | 4.35 | 4.33 | | | | | | |
| 25 | 1090 | 3.15 | 3.68 | 3.38 | 7.04 | 8.45 | 5.59 | 5.11 | | | | | | |
| 26 | 1007_1 | 3.59 | 2.73 | 3.55 | | | 4.39 | 3.86 | | | 1.38 | | | |
| 27 | 1007_2 | 3.69 | 2.76 | 3.63 | | | 4.52 | 4.00 | | | 1.38 | | | |
| 28 | 1149 | 5.59 | 8.32 | 8.70 | | | 5.15 | 9.42 | 3.57 | | | | | |
| 29 | 1021_A | 2.33 | 2.48 | 3.05 | | | 4.71 | 4.16 | | | | | | |
| 30 | 1021_B | 3.14 | 3.94 | 3.20 | | | 4.52 | 4.58 | 3.53 | | | | | |
| 31 | 1097_1 | 3.88 | 3.35 | 3.32 | | | 4.28 | 4.28 | 3.52 | | | | | |
| 32 | 1097_2 | 4.74 | 4.28 | 3.33 | | | 4.35 | 4.09 | | | | | | |
| 33 | 1031_1 | 2.48 | 3.90 | 3.55 | | | 5.66 | 4.45 | | | | 2.84 | 3.16 | 0.96 |
| 34 | 1031_2 | 2.45 | 3.99 | 3.45 | | | 5.53 | 7.12 | | | | 2.73 | 3.08 | 0.96 |
| 35 | 1031_3 | 2.45 | 3.87 | 3.43 | | | 5.37 | 4.35 | | | | 2.79 | 3.16 | 0.96 |
| 36 | 1031_4 | 2.53 | 3.54 | 3.29 | | | 5.59 | 4.22 | | | | 2.71 | 3.09 | 0.96 |
| 37 | 1153_A | 6.25 | 4.36 | 4.62 | | | 5.79 | 4.38 | 3.54 | | | | | |
| 38 | 1153_B | 5.77 | 7.90 | 9.57 | | | 5.51 | 8.18 | 3.54 | | | | | |
| 39 | 1025_1 | 5.36 | 5.79 | 5.16 | | | 5.54 | 5.58 | | | 1.36 | | 3.10 | |
| 40 | 1025_2 | 4.52 | 4.59 | 4.97 | | | 5.40 | 4.61 | | | 1.35 | | 3.11 | |

TABLE A5-continued

| | ID | C1 | C2 | C3 | C4 | C5 | C6 | C7 | C8 | C9 | C10 | C11 |
|---|---|---|---|---|---|---|---|---|---|---|---|---|
| 41 | 1025_3 | 4.84 | 4.68 | 4.91 | 5.60 | 4.57 | | | 1.36 | | | |
| 42 | 1025_4 | 4.83 | 3.57 | 2.98 | 5.48 | 3.79 | | | 1.36 | | | |
| 43 | 1025_5 | 4.66 | 5.13 | 4.84 | 5.62 | 5.31 | | | 1.37 | | | |
| 44 | 1025_6 | 4.98 | 4.26 | 5.71 | 6.05 | 4.12 | | | 1.36 | | | |
| 45 | 1089_A | 3.13 | 3.70 | 3.34 | 5.75 | 5.19 | | | | | | |
| 46 | 1089_B | 3.14 | 3.69 | 3.33 | 5.68 | 5.17 | | | | | | |
| 47 | 1012_1 | 4.36 | 3.79 | 3.51 | 4.38 | 3.84 | | | 1.39 | | | |
| 48 | 1012_2 | 2.36 | 2.42 | 3.35 | 4.38 | 3.81 | | | 1.39 | | | |
| 49 | 1078_1 | 2.29 | 2.61 | 3.05 | 4.56 | 4.72 | | | | 2.75 | 3.12 | 0.97 |
| 50 | 1078_10 | 3.11 | 3.46 | 2.72 | 4.35 | 4.37 | | | | 2.76 | 3.12 | 0.97 |
| 51 | 1078_11 | 2.26 | 2.51 | 3.42 | 4.69 | 4.58 | | | | 2.75 | 3.12 | 0.97 |
| 52 | 1078_12 | 3.08 | 3.40 | 2.81 | 4.34 | 4.51 | | | | 2.74 | 3.12 | 0.98 |
| 53 | 1078_13 | 3.14 | 3.66 | 3.25 | 4.37 | 4.66 | | | | 2.76 | 3.12 | 0.98 |
| 54 | 1078_14 | 2.48 | 2.59 | 2.91 | 4.46 | 4.47 | | | | 2.75 | 3.13 | 0.97 |
| 55 | 1078_15 | 2.66 | 2.49 | 2.93 | 4.59 | 4.59 | | | | 2.74 | 3.13 | 0.97 |
| 56 | 1078_16 | 2.20 | 2.69 | 3.11 | 4.42 | 4.54 | | | | 2.75 | 3.12 | 0.97 |
| 57 | 1078_2 | 2.19 | 2.44 | 3.25 | 4.69 | 4.62 | | | | 2.75 | 3.13 | 0.98 |
| 58 | 1078_3 | 3.13 | 3.61 | 3.17 | 4.44 | 4.54 | | | | 2.76 | 3.13 | 0.97 |
| 59 | 1078_4 | 2.27 | 2.64 | 3.39 | 4.56 | 4.61 | | | | 2.76 | 3.13 | 0.97 |
| 60 | 1078_5 | 2.40 | 2.46 | 3.41 | 4.48 | 4.88 | | | | 2.72 | 3.12 | 0.98 |
| 61 | 1078_6 | 2.75 | | | 5.90 | 4.83 | | | | 2.75 | 3.11 | 0.98 |
| 62 | 1078_7 | 2.08 | 2.49 | 3.35 | 4.83 | 4.59 | | | | 2.77 | 3.14 | 0.97 |
| 63 | 1078_8 | 2.28 | 2.53 | 2.73 | 4.33 | 4.59 | 3.54 | | | 2.75 | 3.10 | 0.98 |
| 64 | 1078_9 | 2.21 | 2.49 | 3.11 | 4.31 | 4.77 | 3.54 | | | 2.74 | 3.11 | 0.98 |
| 65 | 1145_A | 4.89 | 4.48 | 3.28 | 4.42 | 4.42 | 3.47 | | | | | |
| 66 | 1145_B | 4.89 | 4.48 | 3.28 | 4.42 | 4.42 | | | | | | |
| 67 | 1050 | 4.58 | 4.38 | 3.01 | 4.10 | 4.29 | | | | | | |
| 68 | 1253 | 4.38 | 3.69 | 3.39 | 4.36 | 3.83 | | | | | | |
| 69 | 1257 | 4.43 | 3.84 | 3.61 | 4.45 | 4.03 | | | | | | |
| 70 | 1297_1 | 4.31 | 3.81 | 3.46 | 4.35 | 3.86 | | | | | | |
| 71 | 1297_2 | 4.41 | 3.62 | 3.57 | 4.48 | 3.69 | | | | | | |
| 72 | 1297_3 | 4.37 | 3.85 | 3.55 | 4.43 | 3.92 | | | | | | |
| 73 | 1297_4 | 4.35 | 3.67 | 3.50 | 4.44 | 3.67 | | | | | | |
| 74 | 1297_5 | 4.56 | 3.82 | 3.43 | 4.59 | 3.88 | | 2.87 | 1.37 | | | |
| 75 | 1297_6 | 4.65 | 4.26 | 3.53 | 4.73 | 4.23 | | 2.87 | 1.35 | | | |
| 76 | 1304 | 4.40 | 3.85 | 3.37 | 4.39 | 3.89 | 3.54 | 2.87 | 1.39 | | | |
| 77 | 1306_1 | 4.25 | 5.09 | 3.06 | 4.38 | 4.22 | 3.60 | 2.88 | 1.37 | | | |
| 78 | 1306_2 | 6.07 | 5.71 | 2.68 | 3.99 | 4.29 | | 2.85 | 1.37 | | | |
| 79 | 1307 | 3.15 | 3.80 | 3.17 | 4.60 | 4.57 | | 2.87 | 1.38 | | | |
| 80 | 1328_1 | 4.21 | 3.54 | 3.13 | 4.24 | 3.54 | | 2.86 | 1.38 | 2.74 | 3.13 | 0.98 |
| 81 | 1328_2 | 4.38 | 3.84 | 3.08 | 4.43 | 4.01 | | 2.86 | 1.38 | | | |
| 82 | 1328_3 | 3.99 | 2.55 | 3.40 | 4.82 | 3.89 | | 2.84 | | | | |
| 83 | 1328_4 | 4.21 | 2.53 | 3.71 | 5.05 | 3.83 | | 2.85 | 1.37 | | | |
| 84 | 1334 | 3.14 | 3.74 | 3.24 | 5.33 | 4.84 | | 2.85 | 1.38 | | | |
| 85 | 1335 | 4.68 | 3.12 | 5.11 | 6.60 | 4.33 | 3.55 | 2.85 | 1.37 | 1.75 | 3.47 | |
| 86 | 1338 | 4.33 | 3.75 | 3.35 | 4.35 | 3.80 | | 2.85 | | | | |
| 87 | 1345_1 | 4.08 | 3.57 | 3.48 | 4.52 | 4.49 | | 2.88 | | | | |
| 88 | 1345_2 | 4.97 | 4.32 | 3.32 | 4.58 | 4.16 | | | 1.38 | | | |
| 89 | 1351 | 4.47 | 3.70 | 3.38 | 4.47 | 3.79 | | 2.85 | 1.36 | | | |
| 90 | 1353 | 4.38 | 3.72 | 3.27 | 4.38 | 3.85 | | 2.85 | 1.36 | | | |
| 91 | 1360 | 4.38 | 3.80 | 3.32 | 4.35 | 5.37 | | 2.85 | 1.39 | | | |
| 92 | 1367 | 4.37 | 5.63 | 4.72 | 4.35 | 8.92 | | 2.85 | 1.39 | | | |
| 93 | 1368 | 4.34 | 8.84 | 7.07 | 4.30 | | | 2.86 | | | | |

TABLE A5-continued

| | | | | | | | | | |
|---|---|---|---|---|---|---|---|---|---|
| 94 | 1371 | 3.13 | 3.66 | 3.25 | | 3.46 | 3.72 | | |
| 95 | 1372_A | 4.40 | 3.88 | 3.32 | | 4.38 | 3.94 | | |
| 96 | 1372_B | 4.39 | 3.91 | 3.35 | | 4.37 | 4.00 | | |
| 97 | 1373 | 4.40 | 3.78 | 3.38 | | 4.41 | 3.86 | | |
| 98 | 1492 | 3.14 | 5.11 | 3.18 | | 4.66 | 6.47 | | |
| 99 | 1399 | 4.40 | 3.82 | 3.33 | | 4.40 | 3.92 | | |
| 100 | 1406 | 4.35 | 3.89 | 3.29 | | 4.36 | 4.00 | | |
| 101 | 1411 | 4.34 | 3.90 | 3.50 | | 4.37 | 4.05 | | |
| 102 | 1433 | 3.16 | 3.59 | 3.46 | 3.43 | 5.49 | 4.76 | | |
| 103 | 1435 | 4.37 | 3.79 | 3.37 | | 4.36 | 3.86 | | |
| 104 | 1441 | 4.29 | 3.79 | 3.29 | | 4.27 | 3.96 | | |
| 105 | 1450_A | 3.16 | 3.57 | 3.11 | | 5.47 | 4.73 | | |
| 106 | 1450_B | 3.14 | 3.46 | 3.83 | | 5.49 | 4.57 | | |
| average distance | | 3.98 | 3.97 | 3.59 | 3.80 | 4.70 | 4.52 | | |
| standard deviation | | 1.07 | 1.13 | 1.03 | 2.48 | 0.65 | 0.95 | | |
| minimum value | | 2.08 | 2.42 | 2.29 | 1.13 | 3.35 | 3.51 | | |
| maximum value | | 6.97 | 8.84 | 9.57 | 8.45 | 7.59 | 9.42 | | |
| sample size | | 105 | 105 | 104 | 5 | 105 | 105 | | |

Table A5-2: Pharmacophore distance

Pharmacophore Region elements

| | | S3 Region | | | | S4 Region | | | |
|---|---|---|---|---|---|---|---|---|---|
| | | d(O2, H3) | d(O2, N2) | d(N2, C2) | d(N2, C4) | d(CA5, N2) | d(N2, CA2) | d(N2, C44) | d(N2, C6) | d(N2, CA3) | d(N2, O3) | d(N2, H1) |
| 1 | 14 | 5.38 | 2.64 | 2.93 | | | | | | | | |
| 2 | 999_1 | 5.47 | 2.40 | 3.23 | | | | | | | | |
| 3 | 999_2_A | 5.15 | 2.58 | 3.00 | | | | | | | | |
| 4 | 999_2_B | 2.83 | 3.19 | 2.76 | | | | | | | | |
| 5 | 1129 | 2.74 | 3.03 | 2.26 | | 5.54 | | | | | | |
| 6 | 1034 | 5.45 | 2.78 | | | 3.72 | | | | | | |
| 7 | 1024 | 5.43 | 2.64 | 3.42 | | | 6.19 | | | | | |
| 8 | 1042_1 | 5.89 | 2.86 | 4.38 | | | 6.20 | | | | | |
| 9 | 1042_2 | 6.75 | 4.11 | 3.55 | | | 7.44 | | | | | |
| 10 | 1042_3 | 9.00 | | | | | 6.60 | | | | | |
| 11 | 2018 | 4.97 | 2.67 | 3.70 | | | | | | | | |
| 12 | 1059 | 3.72 | 2.73 | 3.41 | | 5.30 | 5.88 | | | | | |
| 13 | 1088_A | 3.82 | 2.68 | 3.90 | | | 6.13 | | | | | |
| 14 | 1088_B | 6.25 | 2.67 | | | 5.05 | | | | | | |
| 15 | 1036_1 | 5.47 | 2.80 | | | 5.11 | | | | | | |
| 16 | 1036_2_1 | 6.42 | 2.84 | | | 5.14 | | | | | | |
| 17 | 1036_2_2 | 5.78 | 2.76 | | 7.56 | | 6.05 | 7.56 | | | | |
| 18 | 1081 | 4.92 | 3.36 | 1.38 | | | 5.62 | | | | | |
| 19 | 1063 | 4.40 | 2.83 | 1.40 | | | 5.75 | | | | | |
| 20 | 1065 | 3.36 | | | | | | | | | | |
| 21 | 1030_A | 3.28 | | | | | | | | | | |
| 22 | 1030_B | 3.99 | | | | | | | | | | |
| 23 | 1037 | | | | | | | | | | | |

TABLE A5-continued

| # | ID | | | | | | | | | | | |
|---|---|---|---|---|---|---|---|---|---|---|---|---|
| 24 | 1118 | 5.85 | 2.67 | | 7.40 | | 5.84 | 7.40 | 8.27 | | | |
| 25 | 1090 | 5.87 | 2.72 | | | 5.09 | | 7.94 | | | | |
| 26 | 1007_1 | 4.41 | 2.79 | | | | 6.02 | | | | | |
| 27 | 1007_2 | 4.67 | 2.86 | | | | 6.11 | | | | | |
| 28 | 1149 | 5.29 | 4.42 | | 7.94 | | | | | | | |
| 29 | 1021_A | 2.83 | 2.71 | | | | | | | | | |
| 30 | 1021_B | 2.30 | 2.65 | 1.42 | | 4.69 | | | | | | |
| 31 | 1097_1 | 4.58 | 2.81 | 1.42 | | | 5.22 | | | | | |
| 32 | 1097_2 | 4.29 | 2.81 | | | 4.50 | | | | | | |
| 33 | 1031_1 | 2.99 | 3.03 | | | 4.50 | | | | | | |
| 34 | 1031_2 | 3.09 | 3.00 | | | | 6.25 | | | | | |
| 35 | 1031_3 | 3.21 | 3.22 | | | | 5.86 | | | | | |
| 36 | 1031_4 | 3.10 | 3.13 | | | | 5.84 | | | | | |
| 37 | 1153_A | 2.71 | 2.88 | 8.34 | | | 6.23 | | | 3.78 | 7.78 | |
| 38 | 1153_B | 3.10 | 2.99 | 8.53 | | 3.75 | 6.18 | | | | 9.72 | |
| 39 | 1025_1 | 3.35 | 2.94 | 1.35 | | | 5.06 | | | | | |
| 40 | 1025_2 | 2.63 | 2.79 | 1.32 | | | 5.67 | | | | | |
| 41 | 1025_3 | 2.66 | 2.64 | 1.34 | | | 5.62 | | | | | |
| 42 | 1025_4 | 2.43 | 2.95 | 1.35 | | | 5.66 | | | | | |
| 43 | 1025_5 | 2.78 | 2.68 | 1.32 | | | 5.58 | | | | | |
| 44 | 1025_6 | 1.27 | 3.00 | 1.34 | | | 5.61 | | | | | |
| 45 | 1089_A | 5.94 | 2.66 | | | 5.10 | 5.64 | | | | | |
| 46 | 1089_B | 5.91 | 2.70 | | | 5.07 | 5.10 | | | | | |
| 47 | 1012_1 | 4.08 | 2.65 | | | 5.10 | | | | | | |
| 48 | 1012_2 | 4.07 | 2.78 | | | | | | | | | |
| 49 | 1078_1 | 2.93 | 2.77 | 1.48 | | | 5.74 | | | | | |
| 50 | 1078_10 | 1.97 | 2.74 | 1.48 | | | 5.72 | | | | | |
| 51 | 1078_11 | 3.05 | 2.97 | 1.47 | | | 5.75 | | | | | |
| 52 | 1078_12 | 2.85 | 2.84 | 1.45 | | | 5.74 | | | | | |
| 53 | 1078_13 | 2.11 | 2.79 | 1.47 | | | 5.61 | | | | | |
| 54 | 1078_14 | 2.58 | 2.77 | 1.45 | | | 5.66 | | | | | |
| 55 | 1078_15 | 2.97 | 2.84 | 1.45 | | | 5.69 | | | | | |
| 56 | 1078_16 | 2.96 | 2.90 | 1.49 | | | 5.80 | | | | | |
| 57 | 1078_2 | 2.53 | 2.72 | 1.44 | | | 5.72 | | | | | |
| 58 | 1078_3 | 2.05 | 2.79 | 1.45 | | | 5.70 | | | | | |
| 59 | 1078_4 | 2.72 | 2.70 | 1.51 | | | 5.66 | | | | | |
| 60 | 1078_5 | 3.24 | 2.95 | 1.45 | | | 5.65 | | | | | |
| 61 | 1078_6 | | | 1.49 | | | 5.49 | | | | | |
| 62 | 1078_7 | 3.26 | 3.04 | 1.47 | | | 5.74 | | | | | |
| 63 | 1078_8 | 2.69 | 2.85 | 1.44 | | | 5.66 | | | | | |
| 64 | 1078_9 | 3.06 | 2.89 | 1.46 | | | 5.71 | | | | | |
| 65 | 1145_A | 5.36 | 2.77 | | | | 5.91 | | | 5.59 | 7.97 | 8.64 |
| 66 | 1145_B | 5.36 | 2.77 | | | | 5.91 | | | 5.59 | 7.97 | 8.68 |
| 67 | 1050 | 2.72 | 2.76 | 6.69 | | | 5.73 | | | | | |
| 68 | 1253 | 2.04 | 2.70 | 1.46 | | 5.09 | 5.74 | | | | | |
| 69 | 1257 | 2.18 | 2.71 | | | | | | 6.64 | | | |
| 70 | 1297_1 | 4.23 | 2.71 | 1.44 | | | 5.68 | | | | | |
| 71 | 1297_2 | 3.98 | 2.84 | 1.47 | | | 5.78 | | | | | |
| 72 | 1297_3 | 4.22 | 2.72 | 1.43 | | | 5.64 | | | | | |
| 73 | 1297_4 | 4.02 | 2.76 | 1.47 | | | 5.72 | | | | | |
| 74 | 1297_5 | 4.06 | 2.67 | 1.43 | | | 5.69 | | | | | |
| 75 | 1297_6 | 4.15 | 2.83 | 1.44 | | | 5.72 | | | | | |
| 76 | 1304 | 4.37 | 2.62 | | | | 5.96 | | | | | |

TABLE A5-continued

| | | 1 | 2 | 3 | 4 | 5 | 6 | 7 | 8 | 9 | 10 | 11 |
|---|---|---|---|---|---|---|---|---|---|---|---|---|
| 77 | 1306_1 | 5.26 | 2.66 | | | | 6.06 | | | | | |
| 78 | 1306_2 | 4.46 | 2.71 | | | | 6.15 | | | | | |
| 79 | 1307 | 2.09 | 2.81 | | | | 6.14 | | | | | |
| 80 | 1328_1 | 4.20 | 2.79 | | 8.09 | | 5.88 | 8.09 | | | | |
| 81 | 1328_2 | 4.54 | 2.75 | | 7.87 | | 5.92 | 7.87 | | | | |
| 82 | 1328_3 | 4.77 | 2.77 | | 7.95 | | 6.00 | 7.95 | | | | |
| 83 | 1328_4 | 4.71 | 2.79 | | 7.92 | | 6.17 | 7.92 | | | | |
| 84 | 1334 | 2.99 | 2.77 | | | | 6.09 | | | | | |
| 85 | 1335 | 5.33 | 2.70 | | | | 5.83 | | | | | |
| 86 | 1338 | 4.29 | 2.74 | | | | 6.05 | | | | | |
| 87 | 1345_1 | 5.98 | 2.90 | | | | 6.14 | | | 5.17 | 8.75 | |
| 88 | 1345_2 | 5.51 | 2.87 | | | | 5.98 | | | 5.15 | 8.73 | |
| 89 | 1351 | 4.26 | 2.76 | | | | 6.12 | | | | | |
| 90 | 1353 | 4.10 | 2.69 | 1.45 | | | 6.50 | | | | | |
| 91 | 1360 | 4.32 | 2.66 | | | 5.07 | 8.32 | | | | | |
| 92 | 1367 | 2.68 | | | | | | | | | | |
| 93 | 1368 | 7.79 | 4.30 | | | 4.47 | 6.36 | | | | | |
| 94 | 1371 | 1.96 | 2.79 | | | | 5.90 | | | | | |
| 95 | 1372_A | 2.30 | 2.66 | | 6.06 | | 5.99 | 6.06 | 5.56 | | | |
| 96 | 1372_B | 2.23 | 2.63 | | | 6.60 | 6.02 | | | | | |
| 97 | 1373 | 4.31 | 2.65 | | | | 6.03 | | | | | |
| 98 | 1492 | 7.20 | | | 8.24 | | | 8.24 | 7.51 | | | |
| 99 | 1399 | 4.09 | 2.67 | | | | 5.96 | | | | | |
| 100 | 1406 | 4.44 | 2.64 | | | | 5.98 | | | | | |
| 101 | 1411 | 4.13 | 2.68 | 1.46 | | | 5.72 | | | | | |
| 102 | 1433 | 2.89 | 2.65 | 1.51 | | | 5.79 | | | | | |
| 103 | 1435 | 4.33 | 2.62 | | | | 6.00 | | | | | |
| 104 | 1441 | 4.15 | 2.72 | 1.45 | | | 5.75 | | | | | |
| 105 | 1450_A | 2.31 | 2.81 | | | | 5.88 | | | | | |
| 106 | 1450_B | 2.32 | 2.67 | | | | 6.07 | | | | | |
| | average distance | 3.99 | 2.83 | 2.22 | 7.67 | 4.94 | 5.91 | 7.67 | 6.99 | 5.06 | 8.49 | 8.66 |
| | standard deviation | 1.42 | 0.30 | 1.64 | 0.62 | 0.62 | 0.41 | 0.62 | 1.01 | 0.67 | 0.67 | 0.02 |
| | minimum value | 1.27 | 2.40 | 1.32 | 6.06 | 3.72 | 5.06 | 6.06 | 5.56 | 3.78 | 7.78 | 8.64 |
| | maximum value | 9.00 | 4.42 | 8.53 | 8.24 | 6.60 | 8.32 | 8.24 | 8.27 | 5.59 | 9.72 | 8.68 |
| | sample size | 104.00 | 98 | 51 | 9 | 18 | 81 | 9 | 4 | 5 | 6 | 2 |

TABLE A6

Table A6-1 Pharmacophore angles

| | | Pharmacophore Region | | | | | | | | |
|---|---|---|---|---|---|---|---|---|---|---|
| | | S1 Region | | | | | S2 Region | | | |
| | | Elements | | | | | | | | |
| | | a(O1, O2, H4) | a(O1, CA6, O2) | a(CA1, O1, O2) | A(N1, CA1, O1) a) | a(C3, CA1, O1) | a(N1, CA1, O1) b) | a(O1, CA1, O4) | a(C5, CA1, O1) | a(O1, CA1, C7) | a(CA1, O4, H2) |
| 1 | 14 | 61.95 | 75.74 | 139.05 | | | | | | | |
| 2 | 999_1 | 154.32 | | 127.44 | 159.37 | | | | | | |
| 3 | 999_2_A | 156.25 | | 133.11 | 156.55 | | | | | | |
| 4 | 999_2_B | 156.16 | | 140.65 | 153.11 | | | | | | |
| 5 | 1129 | 137.67 | | 111.77 | 164.78 | | | | | | |
| 6 | 1034 | 135.95 | | 111.64 | 160.69 | | | | | | |
| 7 | 1024 | 128.26 | | 109.78 | 163.32 | | | | | | |
| 8 | 1042_1 | 122.15 | | 117.21 | 158.11 | | | | | | |
| 9 | 1042_2 | 128.91 | | 116.12 | 164.17 | | | | | | |
| 10 | 1042_3 | | | | | | | | | | |
| 11 | 2018 | 118.45 | 159.18 | 100.76 | 169.37 | | | | | | |
| 12 | 1059 | 140.37 | | 102.43 | 176.16 | | | | | | |
| 13 | 1088_A | 149.95 | | 99.08 | | | | | | | |
| 14 | 1088_B | 153.40 | | 99.27 | | | | | | | |
| 15 | 1036_1 | 129.34 | | 113.86 | 162.74 | | | | | | |
| 16 | 1036_2_1 | 134.57 | | 105.64 | 163.26 | | | | | | |
| 17 | 1036_2_2 | 128.96 | | 108.40 | 164.16 | | | | | | |
| 18 | 1081 | 138.44 | | 108.25 | 163.55 | | | | | | |
| 19 | 1063 | 142.43 | | 88.32 | 167.99 | | | | | | |
| 20 | 1065 | 148.95 | | 110.77 | 165.45 | | | | | | |
| 21 | 1030_A | 141.50 | 76.43 | 109.09 | | | | | | | |
| 22 | 1030_B | 138.56 | | 115.15 | | | | | | | |
| 23 | 1037 | 128.21 | | 108.98 | 162.36 | | | | | | |
| 24 | 1118 | 139.63 | | 111.55 | 162.73 | | | | | | |
| 25 | 1090 | 121.29 | | 100.34 | | | | | | | |
| 26 | 1007_1 | 113.31 | | 107.37 | | | 174.46 | | | | |
| 27 | 1007_2 | 113.36 | | 107.55 | | | 174.22 | | | | |
| 28 | 1149 | 105.44 | 131.55 | 147.27 | 168.87 | | | | | | |
| 29 | 1021_A | 101.19 | 87.17 | 100.00 | | | | | 158.12 | | |
| 30 | 1021_B | 127.69 | | 111.61 | | | | | 159.75 | | |
| 31 | 1097_1 | 125.81 | | 112.80 | 162.99 | | | | | | |
| 32 | 1097_2 | 137.06 | | 109.11 | 163.92 | | | | | | |
| 33 | 1031_1 | 116.98 | | 90.53 | | | | 62.36 | 160.22 | | 123.26 |
| 34 | 1031_2 | 120.91 | | 130.70 | | | | 51.33 | 162.16 | | 126.02 |
| 35 | 1031_3 | 119.04 | | 93.66 | | | | 52.73 | 163.39 | | 122.20 |
| 36 | 1031_4 | 116.96 | | 84.57 | | | | 55.13 | 161.31 | | 122.41 |
| 37 | 1153_A | 132.39 | | 99.83 | 174.13 | | | | | | |
| 38 | 1153_B | 92.62 | | 144.91 | 171.50 | | | | | | |
| 39 | 1025_1 | 125.08 | | 118.04 | | | 171.14 | | | | |
| 40 | 1025_2 | 113.88 | | 111.48 | | | 171.54 | | | | |
| 41 | 1025_3 | 117.96 | | 107.75 | | | 174.66 | | | | |
| 42 | 1025_4 | 142.08 | | 72.65 | | | 171.39 | | | | |
| 43 | 1025_5 | 120.99 | | 112.95 | | | 174.47 | | | | |
| 44 | 1025_6 | 104.02 | | 106.08 | | | 170.14 | | | | |
| 45 | 1089_A | 122.16 | | 98.23 | | | | | | | |
| 46 | 1089_B | 122.31 | | 99.20 | | | | | | | |
| 47 | 1012_1 | 129.53 | | 107.17 | | | 173.56 | | | | |
| 48 | 1012_2 | 90.89 | | 105.03 | | | 161.82 | | | | |
| 49 | 1078_1 | 103.21 | | 111.94 | | | | 68.03 | 160.22 | | 126.79 |
| 50 | 1078_10 | 131.53 | | 108.49 | | | | 71.55 | 160.63 | | 127.01 |
| 51 | 1078_11 | 88.73 | | 109.94 | | | | 59.87 | 161.80 | | 130.34 |
| 52 | 1078_12 | 128.90 | | 111.74 | | | | 67.44 | 161.92 | | 127.55 |
| 53 | 1078_13 | 123.59 | | 115.77 | | | | 65.06 | 162.99 | | 129.33 |
| 54 | 1078_14 | 109.80 | | 109.29 | | | | 70.42 | 159.36 | | 126.58 |
| 55 | 1078_15 | 110.90 | | 108.62 | | | | 65.89 | 160.41 | | 127.31 |
| 56 | 1078_16 | 101.76 | | 112.44 | | | | 67.40 | 161.46 | | 126.68 |
| 57 | 1078_2 | 91.16 | | 109.26 | | | | 65.74 | 159.94 | | 128.74 |
| 58 | 1078_3 | 124.44 | | 112.44 | | | | 67.41 | 162.08 | | 128.44 |
| 59 | 1078_4 | 93.17 | | 112.48 | | | | 65.56 | 161.60 | | 128.57 |
| 60 | 1078_5 | 90.82 | | 117.54 | | | | 55.67 | 164.79 | | 131.80 |
| 61 | 1078_6 | | | | | | | 67.49 | 152.72 | | 126.69 |
| 62 | 1078_7 | 86.28 | | 110.36 | | | | 67.29 | 158.86 | | 126.10 |
| 63 | 1078_8 | 111.09 | | 112.99 | | | | 73.28 | 159.05 | | 125.48 |
| 64 | 1078_9 | 97.24 | | 117.85 | | | | 66.67 | 161.68 | | 128.05 |
| 65 | 1145_A | 139.31 | | 111.73 | 162.28 | | | | | | |
| 66 | 1145_B | 139.31 | | 111.73 | 162.28 | | | | | | |
| 67 | 1050 | 140.76 | | 114.34 | 160.78 | | | | | | |
| 68 | 1253 | 131.28 | | 105.84 | | 149.95 | 174.19 | | | | |
| 69 | 1257 | 128.83 | | 109.00 | | 150.46 | 174.64 | | | | |

TABLE A6-continued

| | | | | | | | | | | | |
|---|---|---|---|---|---|---|---|---|---|---|---|
| 70 | 1297_1 | 130.08 | | 107.14 | | 149.59 | 174.57 | | | | |
| 71 | 1297_2 | 128.26 | | 103.93 | | 150.01 | 174.54 | | | | |
| 72 | 1297_3 | 129.38 | | 107.42 | | 150.32 | 174.78 | | | | |
| 73 | 1297_4 | 129.06 | | 103.60 | | 149.60 | 174.41 | | | | |
| 74 | 1297_5 | 132.64 | | 102.43 | | 150.41 | 174.11 | | | | |
| 75 | 1297_6 | 133.61 | | 105.49 | | 150.35 | 173.49 | | | | |
| 76 | 1304 | 132.43 | | 105.87 | | 149.82 | 173.92 | | | | |
| 77 | 1306_1 | 143.05 | | 107.94 | 158.44 | | | | | | |
| 78 | 1306_2 | 153.92 | | 114.80 | 161.00 | | | | | | |
| 79 | 1307 | 126.83 | | 109.57 | | | | 66.49 | 161.35 | 121.00 | 127.11 |
| 80 | 1328_1 | 133.34 | | 101.20 | | 150.62 | 175.41 | | | | |
| 81 | 1328_2 | 136.71 | | 103.89 | | 150.10 | 173.89 | | | | |
| 82 | 1328_3 | 122.23 | | 97.62 | | 150.74 | 173.57 | | | | |
| 83 | 1328_4 | 119.12 | | 96.00 | | 151.05 | 173.49 | | | | |
| 84 | 1334 | 124.74 | | 100.10 | | | | 68.25 | 150.49 | | |
| 85 | 1335 | 100.88 | | 91.76 | 170.77 | | | | | | |
| 86 | 1338 | 131.78 | | 105.30 | | 148.99 | 173.72 | | | | |
| 87 | 1345_1 | 126.38 | | 112.39 | | | | | | | |
| 88 | 1345_2 | 138.87 | | 105.43 | | | | | | | |
| 89 | 1351 | 132.32 | | 103.11 | | 149.86 | 173.60 | | | | |
| 90 | 1353 | 133.22 | | 103.61 | | 149.99 | 173.73 | | | | |
| 91 | 1360 | 132.69 | | 105.67 | | 150.18 | 174.23 | | | | |
| 92 | 1367 | 125.36 | | 129.48 | | 149.67 | 173.97 | | | | |
| 93 | 1368 | 127.75 | | 151.69 | | 149.59 | 173.57 | | | | |
| 94 | 1371 | 123.31 | | 121.03 | | | | | | | |
| 95 | 1372_A | 133.23 | | 106.33 | | 149.88 | 174.16 | | | | |
| 96 | 1372_B | 132.88 | | 107.52 | | 149.88 | 174.13 | | | | |
| 97 | 1373 | 131.90 | | 105.28 | | 149.81 | 174.08 | | | | |
| 98 | 1492 | 143.64 | 87.17 | 137.45 | 173.84 | | | | | | |
| 99 | 1399 | 132.84 | | 105.80 | | 149.86 | 173.87 | | | | |
| 100 | 1406 | 133.28 | | 107.31 | | 149.47 | 173.92 | | | | |
| 101 | 1411 | 130.04 | | 109.85 | | 149.02 | 173.43 | | | | |
| 102 | 1433 | 118.66 | | 97.80 | | | | 65.77 | 151.25 | | |
| 103 | 1435 | 131.96 | | 106.19 | | 149.49 | 173.74 | | | | |
| 104 | 1441 | 132.47 | | 108.56 | | 148.89 | 173.13 | | | | |
| 105 | 1450_A | 125.38 | | 94.14 | | | | 68.80 | 150.97 | 136.18 | |
| 106 | 1450_B | 109.15 | | 98.92 | | | | 66.73 | 150.20 | 139.92 | |
| | average distance | 125.22 | 102.87 | 109.45 | 164.29 | 149.91 | 173.40 | 64.89 | 159.21 | 132.37 | 126.98 |
| | standard deviation | 16.57 | 31.42 | 12.06 | 5.24 | 0.51 | 2.19 | 5.55 | 4.12 | 8.18 | 2.30 |
| | minimum value | 61.95 | 75.74 | 72.65 | 153.11 | 148.89 | 161.82 | 51.33 | 150.20 | 121.00 | 122.20 |
| | maximum value | 156.25 | 159.18 | 151.69 | 176.16 | 151.05 | 175.41 | 73.28 | 164.79 | 139.92 | 131.80 |
| | sample size | 104 | 6 | 104 | 30 | 27 | 37 | 25 | 27 | 3 | 21 |

Table A6-2 Pharmacophore Angle

| | | Pharmacophore Region | | | | | | | | | |
|---|---|---|---|---|---|---|---|---|---|---|---|
| | | S3 Region | | | S4 Region | | | | RM Region | | |
| | | Elements | | | | | | | | | | |
| | | a(O1, O2, H3) | a(O1, O2, N2) | a(O2, N2, C2) | a(O2, N2, C4) | a(O2, N2, CA2) | a(O2, N2, C4) 2 | a(O2, N2, C6) | a(O2, N2, CA3) | a(O2, N2, O3) | a(O2, N2, H1) |
| 1 | 14 | | | | | | | | | | |
| 2 | 999_1 | 158.16 | 168.00 | 125.23 | | | | | | | |
| 3 | 999_2_A | 157.15 | 164.18 | 134.23 | | | | | | | |
| 4 | 999_2_B | 152.90 | 175.07 | 127.87 | | | | | | | |
| 5 | 1129 | 122.63 | 127.76 | 110.31 | | | | | | | |
| 6 | 1034 | 135.88 | 137.69 | 100.68 | | | | | | | |
| 7 | 1024 | 151.79 | 136.56 | | | 154.55 | | | | | |
| 8 | 1042_1 | 149.96 | 170.80 | 140.47 | | 155.50 | | | | | |
| 9 | 1042_2 | 152.56 | 148.96 | 139.99 | | 158.67 | | | | | |
| 10 | 1042_3 | | | 129.44 | | 145.75 | | | | | |
| 11 | 2018 | 154.86 | | | | | | | | | |
| 12 | 1059 | 148.70 | 132.46 | 139.14 | | 153.47 | | | | | |
| 13 | 1088_A | 144.04 | 141.09 | 141.58 | | | | | | | |
| 14 | 1088_B | 144.52 | 135.22 | 140.65 | | 154.54 | | | | | |
| 15 | 1036_1 | 153.49 | 143.79 | | | | | | | | |
| 16 | 1036_2_1 | 153.56 | 149.24 | | | | | | | | |
| 17 | 1036_2_2 | 154.60 | 146.84 | | | | | | | | |
| 18 | 1081 | 153.00 | 139.53 | | 161.57 | 153.98 | 119.80 | | | | |
| 19 | 1063 | 157.64 | 139.49 | 118.75 | | 154.05 | | | | | |
| 20 | 1065 | 145.76 | 144.81 | 124.85 | | 154.55 | | | | | |
| 21 | 1030_A | 146.48 | | | | | | | | | |
| 22 | 1030_B | 142.99 | | | | | | | | | |
| 23 | 1037 | 145.74 | | | | | | | | | |
| 24 | 1118 | 152.79 | 137.47 | | 162.84 | 154.60 | 125.21 | 88.59 | | | |
| 25 | 1090 | 152.05 | 140.84 | | | | | | | | |
| 26 | 1007_1 | 146.43 | 138.95 | | | 154.71 | | | | | |

TABLE A6-continued

| | | | | | | | | | |
|---|---|---|---|---|---|---|---|---|---|
| 27 | 1007_2 | 145.74 | 133.10 | | | 153.46 | | | |
| 28 | 1149 | 54.88 | 62.73 | | 154.82 | | 49.80 | | |
| 29 | 1021_A | 141.44 | 142.62 | | | | | | |
| 30 | 1021_B | 140.90 | 147.46 | | | 155.32 | | | |
| 31 | 1097_1 | 152.91 | 134.93 | 125.76 | | | | | |
| 32 | 1097_2 | 153.30 | 137.12 | 128.45 | | | | | |
| 33 | 1031_1 | 123.16 | 130.39 | | | 153.37 | | | |
| 34 | 1031_2 | 132.76 | 133.59 | | | 150.67 | | | |
| 35 | 1031_3 | 128.81 | 134.55 | | | 152.13 | | | |
| 36 | 1031_4 | 124.03 | 130.34 | | | 152.78 | | | |
| 37 | 1153_A | 138.79 | 132.96 | 168.69 | | 152.46 | | 157.3814094 | 167.70665 |
| 38 | 1153_B | 25.95 | 44.76 | 163.28 | | 150.51 | | | 165.2913429 |
| 39 | 1025_1 | 129.17 | 125.11 | 132.16 | | 158.42 | | | |
| 40 | 1025_2 | 137.62 | 130.51 | 139.00 | | 161.47 | | | |
| 41 | 1025_3 | 141.10 | 134.33 | 141.57 | | 163.85 | | | |
| 42 | 1025_4 | 170.92 | 162.26 | 126.70 | | 154.93 | | | |
| 43 | 1025_5 | 137.39 | 135.64 | 140.45 | | 163.61 | | | |
| 44 | 1025_6 | 108.29 | 105.09 | 124.73 | | 154.93 | | | |
| 45 | 1089_A | 153.00 | 141.72 | | | 154.37 | | | |
| 46 | 1089_B | 152.83 | 141.07 | | | | | | |
| 47 | 1012_1 | 144.24 | 141.07 | | | | | | |
| 48 | 1012_2 | 141.64 | 140.42 | | | | | | |
| 49 | 1078_1 | 141.96 | 145.93 | 121.70 | | 154.68 | | | |
| 50 | 1078_10 | 146.00 | 152.80 | 131.78 | | 156.19 | | | |
| 51 | 1078_11 | 137.81 | 142.32 | 120.15 | | 152.82 | | | |
| 52 | 1078_12 | 150.80 | 154.56 | 130.32 | | 157.60 | | | |
| 53 | 1078_13 | 135.66 | 146.15 | 127.57 | | 154.39 | | | |
| 54 | 1078_14 | 144.55 | 148.03 | 129.57 | | 155.65 | | | |
| 55 | 1078_15 | 143.22 | 147.42 | 124.17 | | 155.02 | | | |
| 56 | 1078_16 | 140.06 | 144.54 | 122.62 | | 154.31 | | | |
| 57 | 1078_2 | 141.98 | 146.00 | 128.07 | | 155.89 | | | |
| 58 | 1078_3 | 132.07 | 145.54 | 126.01 | | 154.83 | | | |
| 59 | 1078_4 | 141.42 | 146.07 | 126.96 | | 155.54 | | | |
| 60 | 1078_5 | 138.56 | 141.15 | 114.27 | | 151.79 | | | |
| 61 | 1078_6 | | | | | | | | |
| 62 | 1078_7 | 137.32 | 140.50 | 114.22 | | 151.33 | | | |
| 63 | 1078_8 | 140.66 | 145.13 | 125.44 | | 153.81 | | | |
| 64 | 1078_9 | 142.04 | 146.14 | 119.45 | | 153.36 | | | |
| 65 | 1145_A | 150.25 | 136.24 | | | 153.28 | | 161.48 | 168.41 | 168.81 |
| 66 | 1145_B | 150.25 | 136.24 | | | 153.28 | | 161.48 | 168.41 | 168.66 |
| 67 | 1050 | 137.51 | 140.97 | 159.29 | | 153.66 | | | |
| 68 | 1253 | 134.57 | 140.99 | 130.77 | | 155.92 | | | |
| 69 | 1257 | 132.63 | 141.45 | | | | 105.30 | | |
| 70 | 1297_1 | 144.22 | 143.88 | 130.88 | | 156.06 | | | |
| 71 | 1297_2 | 144.48 | 141.45 | 127.48 | | 154.79 | | | |
| 72 | 1297_3 | 143.41 | 144.44 | 132.31 | | 156.50 | | | |
| 73 | 1297_4 | 145.24 | 143.80 | 131.10 | | 156.08 | | | |
| 74 | 1297_5 | 146.79 | 147.10 | 132.77 | | 157.05 | | | |
| 75 | 1297_6 | 144.79 | 141.32 | 116.76 | | 154.05 | | | |
| 76 | 1304 | 147.16 | 139.74 | | | 156.83 | | | |
| 77 | 1306_1 | 152.11 | 135.46 | | | 155.89 | | | |
| 78 | 1306_2 | 151.24 | 153.80 | | | 158.08 | | | |
| 79 | 1307 | 129.22 | 142.81 | | | 155.37 | | | |
| 80 | 1328_1 | 150.01 | 145.32 | | 161.66 | 155.25 | 114.03 | | |
| 81 | 1328_2 | 149.68 | 139.05 | | 160.74 | 154.85 | 109.44 | | |
| 82 | 1328_3 | 151.35 | 139.67 | | 160.41 | 154.95 | 106.08 | | |
| 83 | 1328_4 | 150.66 | 142.82 | | 160.57 | 156.25 | 109.36 | | |
| 84 | 1334 | 136.63 | 143.82 | | | 155.99 | | | |
| 85 | 1335 | 152.03 | 130.91 | | | 154.21 | | | |
| 86 | 1338 | 148.03 | 141.48 | | | 157.11 | | | |
| 87 | 1345_1 | 149.79 | 134.33 | | | 153.15 | | 153.91 | 163.54 |
| 88 | 1345_2 | 152.27 | 142.63 | | | 153.90 | | 151.66 | 162.76 |
| 89 | 1351 | 148.60 | 141.59 | | | 158.04 | | | |
| 90 | 1353 | 146.74 | 137.66 | 130.69 | | 157.19 | | | |
| 91 | 1360 | 147.57 | 138.89 | | | 162.09 | | | |
| 92 | 1367 | 107.78 | | | | | | | |
| 93 | 1368 | 119.72 | 74.03 | | | 145.05 | | | |
| 94 | 1371 | 136.64 | 146.93 | | | 155.86 | | | |
| 95 | 1372_A | 137.15 | 140.15 | | 159.60 | 155.91 | 127.51 | | |
| 96 | 1372_B | 139.74 | 143.19 | | | 157.88 | 115.79 | | |
| 97 | 1373 | 147.32 | 141.07 | | | 156.78 | | | |
| 98 | 1492 | 153.97 | | | | | | | |
| 99 | 1399 | 145.77 | 143.45 | | | 157.06 | | | |
| 100 | 1406 | 147.38 | 140.17 | | | 156.30 | | | |
| 101 | 1411 | 142.75 | 140.47 | 130.32 | | 155.94 | | | |
| 102 | 1433 | 135.90 | 141.60 | 129.89 | | 155.75 | | | |
| 103 | 1435 | 147.24 | 139.75 | | 164.21 | 157.86 | 121.06 | 99.38 | |
| 104 | 1441 | 145.43 | 144.23 | 131.10 | | 156.32 | | | |
| 105 | 1450_A | 127.40 | 139.62 | | | 154.51 | | | |
| 106 | 1450_B | 123.50 | 138.89 | | | 155.81 | | | |

TABLE A6-continued

|  | | | | | | | | | | |
|---|---|---|---|---|---|---|---|---|---|---|
| average distance | 141.41 | 139.32 | 130.19 | 160.71 | 155.18 | 109.14 | 102.26 | 157.18 | 166.02 | 168.74 |
| standard deviation | 17.50 | 16.79 | 11.79 | 2.46 | 2.86 | 22.13 | 9.84 | 3.95 | 2.29 | 0.08 |
| minimum value | 25.95 | 44.76 | 100.68 | 154.82 | 145.05 | 49.80 | 88.59 | 151.66 | 162.76 | 168.66 |
| maximum value | 170.92 | 175.07 | 168.69 | 164.21 | 163.85 | 127.51 | 115.79 | 161.48 | 168.41 | 168.81 |
| sample size | 103 | 97 | 97 | 9 | 80 | 9 | 4 | 5 | 6 | 2 |

Footnote:
a) All compounds with protonatable center N1 except Methyl-amino-pyridine
b) Methyl-amino-pyridine compounds

TABLE A7

Table A7-1 Pharmacophore torsion Angles

| | | Pharmacophore Region | | | | | | | | |
|---|---|---|---|---|---|---|---|---|---|---|
| | | S2 Region | S1 Region | | | | | S3 Region | | | |
| | | | | | | elements | | | | | |
| | | a(CA6, O1, H4, O2) | a(O1, H4, O2, CA1) | a(N1, CA1, O2, H4) | a(C3, CA1, O1, H4) | a(N1, CA1, O1, H4) | a(C5, CA1, O1, H4) | a(C7, CA1, O1, H4) | a(H4, O1, O2, H3) | a(H4, O1, O2, N2) | a(O1, O2, N2, C2) | a(O1, O2, N2, C2)2 |
|---|---|---|---|---|---|---|---|---|---|---|---|---|
| 1 | 14 | 43.29 | 38.29 | | | | | | | | | |
| 2 | 999_1 | | −126.77 | −136.63 | | | | | 21.52 | 126.59 | 95.00 | 95.00 |
| 3 | 999_2_A | | −126.58 | −134.62 | | | | | 20.92 | 107.88 | 109.28 | 109.28 |
| 4 | 999_2_B | | −154.08 | −159.59 | | | | | 12.97 | 142.07 | 73.39 | 73.39 |
| 5 | 1129 | | −65.27 | −139.56 | | | | | 104.70 | 133.45 | 95.54 | 95.54 |
| 6 | 1034 | | −61.32 | −127.27 | | | | | 93.33 | 142.83 | 68.39 | 68.39 |
| 7 | 1024 | | −63.40 | −97.21 | | | | | 44.69 | 125.09 | | |
| 8 | 1042_1 | | −160.50 | 9.10 | | | | | −19.99 | 68.67 | 115.48 | 115.48 |
| 9 | 1042_2 | | 68.80 | 69.40 | | | | | −9.33 | 44.33 | 151.54 | 151.54 |
| 10 | 1042_3 | | | | | | | | | | | |
| 11 | 2018 | −9.94 | −146.71 | −154.72 | | | | | 30.27 | | | |
| 12 | 1059 | | −89.48 | −131.19 | | | | | 47.74 | 121.97 | 129.30 | 129.30 |
| 13 | 1088_A | | −54.60 | | | | | | 49.33 | 120.82 | 103.40 | 103.40 |
| 14 | 1088_B | | −63.34 | | | | | | 45.99 | 121.15 | 129.99 | 129.99 |
| 15 | 1036_1 | | −63.13 | −93.66 | | | | | 32.81 | 124.11 | | |
| 16 | 1036_2_1 | | −44.90 | −89.39 | | | | | 41.52 | 133.12 | | |
| 17 | 1036_2_2 | | −56.75 | −100.27 | | | | | 33.33 | 119.08 | | |
| 18 | 1081 | | −62.03 | −125.05 | | | | | 36.36 | 121.47 | | |
| 19 | 1063 | | −74.94 | −130.71 | | | | | 54.13 | 155.02 | 150.29 | 150.29 |
| 20 | 1065 | | −21.94 | −89.34 | | | | | 44.38 | 129.83 | 124.96 | 124.96 |
| 21 | 1030_A | 18.23 | −63.68 | | | | | | 52.95 | | | |
| 22 | 1030_B | | −59.93 | | | | | | 53.99 | | | |
| 23 | 1037 | | −51.12 | −92.49 | | | | | 57.29 | | | |
| 24 | 1118 | | −65.17 | −132.91 | | | | | 38.74 | 128.20 | | |
| 25 | 1090 | | −92.71 | | | | | | 91.31 | −177.46 | | |
| 26 | 1007_1 | | −94.99 | | | 39.07 | | | 50.93 | 137.94 | | |
| 27 | 1007_2 | | −94.30 | | | 48.80 | | | 47.32 | 126.25 | | |
| 28 | 1149 | 55.30 | −48.11 | −109.82 | | | | | 105.58 | 125.02 | | |
| 29 | 1021_A | | −66.24 | | | | 32.57 | | −132.46 | −124.87 | | |
| 30 | 1021_B | | −86.96 | | | | −13.44 | | −171.75 | −168.95 | | |
| 31 | 1097_1 | | −66.34 | −97.71 | | | | | 86.65 | 121.05 | 136.92 | 136.92 |
| 32 | 1097_2 | | −71.28 | −142.69 | | | | | 91.00 | 129.42 | 125.27 | 125.27 |
| 33 | 1031_1 | | −175.07 | | | | −101.95 | | 142.57 | 137.86 | | |
| 34 | 1031_2 | | −138.43 | | | | 36.72 | | 63.49 | 56.56 | | |
| 35 | 1031_3 | | −164.95 | | | | −92.95 | | 149.50 | 144.29 | | |
| 36 | 1031_4 | | −175.49 | | | | −110.81 | | 138.85 | 134.30 | | |
| 37 | 1153_A | | 15.20 | −11.60 | | | | | 86.11 | 97.90 | 30.40 | 30.40 |
| 38 | 1153_B | | 23.08 | 56.56 | | | | | 70.64 | 133.70 | −139.94 | −139.94 |
| 39 | 1025_1 | | −141.34 | | | 6.68 | | | −40.49 | −77.23 | −47.33 | −47.33 |
| 40 | 1025_2 | | −163.82 | | | −28.78 | | | −54.10 | −98.22 | −27.27 | −27.27 |
| 41 | 1025_3 | | 139.58 | | | −15.01 | | | −52.28 | −100.26 | −32.71 | −32.71 |
| 42 | 1025_4 | | 150.81 | | | −85.37 | | | 127.24 | 161.32 | 45.78 | 45.78 |
| 43 | 1025_5 | | −169.75 | | | −23.34 | | | −32.05 | −85.30 | −34.65 | −34.65 |
| 44 | 1025_6 | | −135.64 | | | −7.52 | | | 122.08 | 166.26 | 88.55 | 88.55 |
| 45 | 1089_A | | −95.88 | | | | | | 88.95 | −175.67 | | |
| 46 | 1089_B | | −94.63 | | | | | | 89.27 | −178.39 | | |
| 47 | 1012_1 | | −84.31 | | | 10.25 | | | 50.86 | 137.94 | | |
| 48 | 1012_2 | | −50.19 | | | −107.13 | | | 162.80 | −124.02 | | |
| 49 | 1078_1 | | −60.12 | | | | 25.08 | | −119.94 | −112.97 | 138.25 | 138.25 |
| 50 | 1078_10 | | −84.11 | | | | −9.97 | | −152.67 | −164.78 | 123.40 | 123.40 |
| 51 | 1078_11 | | −55.96 | | | | 37.14 | | −120.02 | −112.40 | 136.21 | 136.21 |
| 52 | 1078_12 | | −75.33 | | | | 11.21 | | −120.32 | −108.09 | 114.97 | 114.97 |
| 53 | 1078_13 | | −78.80 | | | | −7.66 | | −157.30 | −162.99 | 118.91 | 118.91 |
| 54 | 1078_14 | | −62.09 | | | | 20.44 | | −134.39 | −121.21 | 126.74 | 126.74 |

TABLE A7-continued

| | | | | | | | | | | |
|---|---|---|---|---|---|---|---|---|---|---|
| 55 | 1078_15 | | −64.96 | | | 19.98 | | −124.63 | −117.88 | 139.14 | 139.34 |
| 56 | 1078_16 | | −58.07 | | | 14.30 | | −119.50 | −111.94 | 136.30 | 136.30 |
| 57 | 1078_2 | | −57.88 | | | 38.04 | | −132.87 | −119.25 | 127.17 | 127.17 |
| 58 | 1078_3 | | −82.33 | | | −5.62 | | −160.53 | −166.69 | 132.95 | 132.95 |
| 59 | 1078_4 | | −58.33 | | | 32.90 | | −123.98 | −113.42 | 124.98 | 124.98 |
| 60 | 1078_5 | | −52.04 | | | 21.83 | | −119.72 | −115.76 | 148.01 | 148.01 |
| 61 | 1078_6 | | | | | −22.50 | | | | | |
| 62 | 1078_7 | | −57.85 | | | 30.48 | | −121.10 | −116.26 | 144.61 | 144.61 |
| 63 | 1078_8 | | −58.50 | | | 5.11 | | −134.33 | −122.87 | 135.84 | 135.84 |
| 64 | 1078_9 | | −50.72 | | | 14.92 | | −116.62 | −110.81 | 144.64 | 144.64 |
| 65 | 1145_A | | −59.90 | −128.41 | | | | 48.71 | 124.15 | | |
| 66 | 1145_B | | −59.90 | −128.41 | | | | 48.71 | 124.15 | | |
| 67 | 1050 | | −58.32 | −131.38 | | | | 102.21 | 123.45 | 66.94 | 66.94 |
| 68 | 1253 | | −82.09 | | 26.20 | 3.75 | | 115.64 | 140.24 | 120.69 | 120.69 |
| 69 | 1257 | | −83.51 | | 30.77 | 11.94 | | 108.60 | 132.94 | | |
| 70 | 1297_1 | | −85.98 | | 30.15 | 26.85 | | 50.42 | 137.09 | 117.40 | 117.40 |
| 71 | 1297_2 | | −87.24 | | 29.10 | 23.27 | | 51.75 | 141.21 | 116.16 | 116.16 |
| 72 | 1297_3 | | −86.03 | | 28.95 | 22.83 | | 50.29 | 141.16 | 114.36 | 114.36 |
| 73 | 1297_4 | | −89.51 | | 28.23 | 26.25 | | 51.40 | 142.36 | 110.29 | 110.29 |
| 74 | 1297_5 | | −86.41 | | 30.12 | 10.41 | | 47.86 | 144.38 | 111.81 | 111.81 |
| 75 | 1297_6 | | −89.84 | | 27.46 | 5.20 | | 43.22 | 150.19 | 132.97 | 132.97 |
| 76 | 1304 | | −84.58 | | 24.93 | 5.90 | | 49.79 | 138.09 | | |
| 77 | 1306_1 | | −170.32 | 106.51 | | | | 36.21 | 120.80 | | |
| 78 | 1306_2 | | −12.97 | −77.87 | | | | 40.51 | 134.08 | | |
| 79 | 1307 | | −88.47 | | | | −6.78 | −161.01 | −163.22 | −170.13 | |
| 80 | 1328_1 | | −88.07 | | 30.10 | 20.31 | | 55.62 | 136.65 | | |
| 81 | 1328_2 | | −83.32 | | 21.76 | −4.36 | | 51.26 | 134.72 | | |
| 82 | 1328_3 | | −87.28 | | 57.52 | 39.33 | | 47.98 | 130.71 | | |
| 83 | 1328_4 | | −91.48 | | 66.00 | 58.16 | | 44.95 | 135.08 | | |
| 84 | 1334 | | −93.67 | | | | 2.51 | 110.57 | −172.73 | | |
| 85 | 1335 | | −127.40 | −112.46 | | | | 55.79 | 140.77 | | |
| 86 | 1338 | | −85.13 | | 23.02 | −3.32 | | 52.11 | 140.39 | | |
| 87 | 1345_1 | | −62.84 | | | | | 39.71 | 114.36 | | |
| 88 | 1345_2 | | −68.67 | | | | | 49.59 | 128.64 | | |
| 89 | 1351 | | −83.97 | | 26.55 | −0.13 | | 51.88 | 138.69 | | |
| 90 | 1353 | | −84.72 | | 23.38 | 3.14 | | 51.34 | 136.30 | 126.15 | 126.15 |
| 91 | 1360 | | −83.81 | | 24.01 | 3.34 | | 51.00 | 138.89 | | |
| 92 | 1367 | | −85.54 | | 23.21 | 1.25 | | 42.45 | | | |
| 93 | 1368 | | −74.89 | | 22.95 | −2.26 | | 40.86 | 68.19 | | |
| 94 | 1371 | | −68.15 | | | | | −165.12 | −174.11 | | |
| 95 | 1372_A | | −83.68 | | 25.78 | 5.73 | | 99.84 | 136.36 | | |
| 96 | 1372_B | | −82.66 | | 25.77 | 4.96 | | 99.85 | 139.62 | | |
| 97 | 1373 | | −84.42 | | 25.67 | 4.28 | | 50.98 | 139.02 | | |
| 98 | 1492 | −19.90 | −60.21 | −132.36 | | | | 94.72 | | | |
| 99 | 1399 | | −83.35 | | 24.20 | 0.87 | | 50.25 | 142.63 | | |
| 100 | 1406 | | −83.05 | | 23.93 | −2.51 | | 50.99 | 135.75 | | |
| 101 | 1411 | | −82.11 | | 24.51 | −2.21 | | 55.16 | 137.13 | 117.46 | 117.46 |
| 102 | 1433 | | −96.26 | | | | 6.40 | 109.26 | −171.69 | 118.46 | 118.46 |
| 103 | 1435 | | −83.48 | | 24.44 | 1.43 | | 51.39 | 136.22 | | |
| 104 | 1441 | | −80.01 | | 21.88 | −6.82 | | 50.54 | 141.99 | 117.29 | 117.29 |
| 105 | 3450_A | | −99.46 | | | | −8.42 | −160.66 | −165.58 | −172.83 | |
| 106 | 1450_B | | −91.88 | | | | 13.21 | −150.35 | −176.95 | 177.59 | |
| average distance | | 17.40 | −76.06 | −92.19 | 28.54 | 2.57 | −0.88 | −157.34 | 17.93 | 47.94 | 99.05 | 99.05 |
| standard deviation | | 29.14 | 50.45 | 67.16 | 9.82 | 29.67 | 39.57 | 4.95 | 88.16 | 124.93 | 59.50 | 59.50 |
| minimum value | | −19.90 | −175.49 | −159.59 | 21.76 | −107.13 | −110.81 | −161.01 | −176.95 | −178.39 | −139.94 | −139.94 |
| maximum value | | 55.30 | 150.81 | 106.51 | 66.00 | 58.16 | 38.04 | −150.35 | 162.80 | 177.59 | 151.54 | 151.54 |
| sample size | | 5 | 104 | 30 | 27 | 37 | 27 | 3 | 103 | 97 | 49 | 49 |

Table A7-2 Pharmacophore torsion angles

| | | Pharmacophore Region | | | | | | | |
|---|---|---|---|---|---|---|---|---|---|
| | | S4 Region | | | | | RM Region | | |
| | | Elements | | | | | | | |
| | | a(O1, O2, N2, CA5) | a(O1, O2, N2, CA2) | a(O1, O2, N2, CA4) | a(O1, O2, N2, C6) | a(O2, N2, CA2) | a(O1, O2, N2, O3) | a(O1, O2, N2, H1) | a(O1, O2, N2, CA3) |
| 1 | 14 | | | | | | | | |
| 2 | 999_1 | | | | | | | | |
| 3 | 999_2_A | | | | | | | | |
| 4 | 999_2_B | | | | | | | | |
| 5 | 1129 | 145.95 | | | | | | | |
| 6 | 1034 | 137.68 | | | | | | | |
| 7 | 1024 | | 139.71 | | | | 154.55 | | |
| 8 | 1042_1 | | 136.01 | | | | 155.50 | | |
| 9 | 1042_2 | | 159.77 | | | | 158.67 | | |
| 10 | 1042_3 | | | | | | 145.75 | | |
| 11 | 2018 | | | | | | | | |

TABLE A7-continued

| | | | | | | | | |
|---|---|---|---|---|---|---|---|---|
| 12 | 1059 | | 134.69 | | | 153.47 | | |
| 13 | 1088_A | 116.27 | | | | | | |
| 14 | 1088_B | | 134.51 | | | 154.54 | | |
| 15 | 1036_1 | 142.62 | | | | | | |
| 16 | 1036_2_1 | 136.82 | | | | | | |
| 17 | 1036_2_2 | 137.32 | | | | | | |
| 18 | 1081 | | 142.86 | | | 153.98 | | |
| 19 | 3063 | | 133.32 | | | 154.05 | | |
| 20 | 1065 | | 129.88 | | | 154.55 | | |
| 21 | 1030_A | | | | | | | |
| 22 | 1030_B | | | | | | | |
| 23 | 1037 | | | | | | | |
| 24 | 1118 | | 145.00 | | 150.07 | 154.60 | | |
| 25 | 1090 | 134.91 | | | | | | |
| 26 | 1007_1 | | 128.23 | | | 154.71 | | |
| 27 | 1007_2 | | 131.44 | | | 153.46 | | |
| 28 | 1149 | | | 155.91 | | | | |
| 29 | 1021_A | 94.53 | | | | | | |
| 30 | 1021_B | | 136.58 | | | 155.32 | | |
| 31 | 1097_1 | 148.15 | | | | | | |
| 32 | 1097_2 | 137.08 | | | | | | |
| 33 | 1031_1 | | 124.94 | | | 153.37 | | |
| 34 | 1031_2 | | 457.89 | | | 150.67 | | |
| 35 | 1031_3 | | 133.88 | | | 152.13 | | |
| 36 | 1031_4 | | 127.07 | | | 152.78 | | |
| 37 | 1153_A | | 116.41 | | | 152.46 | 43.95 | 24.87 |
| 38 | 1153_B | −161.98 | 76.90 | | | 150.51 | −144.09 | |
| 39 | 1025_1 | | −46.36 | | | 158.42 | | |
| 40 | 1025_2 | | −25.28 | | | 161.47 | | |
| 41 | 1025_3 | | −34.46 | | | 163.85 | | |
| 42 | 1025_4 | | 44.29 | | | 154.93 | | |
| 43 | 1025_5 | | −36.22 | | | 163.61 | | |
| 44 | 1025_6 | | 87.30 | | | 154.93 | | |
| 45 | 1089_A | | 137.41 | | | 154.37 | | |
| 46 | 1089_B | 133.38 | | | | | | |
| 47 | 1012_1 | 127.02 | | | | | | |
| 48 | 1012_2 | 133.17 | | | | | | |
| 49 | 1078_1 | | 140.46 | | | 154.68 | | |
| 50 | 1078_10 | | 136.18 | | | 156.19 | | |
| 51 | 1078_11 | | 138.54 | | | 152.82 | | |
| 52 | 1078_12 | | 110.39 | | | 157.60 | | |
| 53 | 1078_13 | | 137.37 | | | 154.39 | | |
| 54 | 1078_14 | | 134.23 | | | 155.65 | | |
| 55 | 1078_15 | | 141.63 | | | 155.02 | | |
| 56 | 1078_16 | | 139 28 | | | 154.31 | | |
| 57 | 1078_2 | | 137.47 | | | 155.89 | | |
| 58 | 1078_3 | | 140.71 | | | 154.83 | | |
| 59 | 1078_4 | | 136.93 | | | 155.54 | | |
| 60 | 1078_5 | | 149.21 | | | 151.79 | | |
| 61 | 1078_6 | | | | | | | |
| 62 | 1078_7 | | 143.84 | | | 151.33 | | |
| 63 | 1078_8 | | 143.43 | | | 153.81 | | |
| 64 | 1078_9 | | 146.06 | | | 153.36 | | |
| 65 | 1145_A | | 140.87 | | | 153.28 | −10.98 | −17.10 | −15.65 |
| 66 | 1145_B | | 140.87 | | | 153.28 | −10.98 | −15.97 | −15.65 |
| 67 | 1050 | | 147.29 | | | 153.66 | | |
| 68 | 1253 | | 126.24 | | | 155.92 | | |
| 69 | 1257 | 134.25 | | | 146.13 | | | |
| 70 | 1297_1 | | 131.38 | 110.58 | | 156.06 | | |
| 71 | 1297_2 | | 126.84 | 106.20 | | 154.79 | | |
| 72 | 1297_3 | | 129.56 | 108.64 | | 156.50 | | |
| 73 | 1297_4 | | 126.11 | 105.94 | | 156.08 | | |
| 74 | 1297_5 | | 122.50 | 101.00 | | 157.05 | | |
| 75 | 1297_6 | | 131.04 | 109.63 | | 154.05 | | |
| 76 | 1304 | | 125.90 | | | 156.83 | | |
| 77 | 1306_1 | | 136.58 | | | 155.89 | | |
| 78 | 1306_2 | | 124.98 | | | 158.08 | | |
| 79 | 1307 | | 138.35 | | | 155.37 | | |
| 80 | 1328_1 | | 126.19 | | | 155.25 | | |
| 81 | 1328_2 | | 132.29 | | | 154.85 | | |
| 82 | 1328_3 | | 131.79 | | | 154.95 | | |
| 83 | 1328_4 | | 128.70 | | | 156.25 | | |
| 84 | 1334 | | 133.84 | | | 155.99 | | |
| 85 | 1335 | | 118.45 | | | 154.21 | | |
| 86 | 1338 | | 124.64 | 116.54 | | 157.11 | | |
| 87 | 1345_1 | | 138.94 | | | 153.15 | −11.99 | | −27.29 |
| 88 | 1345_2 | | 129.85 | | | 153.90 | −20.78 | | −34.52 |
| 89 | 1351 | | 121.52 | 119.61 | | 158.04 | | |
| 90 | 1353 | | 120.30 | | | 157.19 | | |
| 91 | 1360 | 129.35 | 130.24 | | | 162.09 | | |

TABLE A7-continued

| | | | | | | | | | |
|---|---|---|---|---|---|---|---|---|---|
| 92 | 1367 | | | | | | | | |
| 93 | 1368 | 124.36 | −100.57 | | | 145.05 | | | |
| 94 | 1371 | | 136.54 | | | 155.86 | | | |
| 95 | 1372_A | | 129.48 | | | 155.91 | | | |
| 96 | 1372_B | | 109.73 | | 141.41 | 157.88 | | | |
| 97 | 1373 | 91.76 | 127.58 | | | 156.78 | | | |
| 98 | 1492 | | | | | | | | |
| 99 | 1399 | | 126.87 | 113.10 | | 157.06 | | | |
| 100 | 1406 | | 127.54 | 102.90 | | 156.30 | | | |
| 101 | 1411 | | 127.52 | | | 155.94 | | | |
| 102 | 1433 | | 127.94 | | | 155.75 | | | |
| 103 | 1435 | | 123.48 | | 137.30 | 157.86 | | | |
| 104 | 1441 | | 126.16 | | | 156.32 | | | |
| 105 | 1450_A | | 120.74 | | | 154.51 | | | |
| 106 | 1450_B | | 137.59 | | | 155.81 | | | |
| | average distance | 113.48 | 114.59 | 113.64 | 143.73 | 155.18 | −25.81 | −16.54 | −13.65 |
| | standard deviation | 68.44 | 56.45 | 14.37 | 4.82 | 2.89 | 57.03 | 0.57 | 20.56 |
| | minimum value | −161.98 | −157.89 | 101.00 | 137.30 | 145.05 | −144.09 | −17.10 | −34.52 |
| | maximum value | 148.15 | 159.77 | 155.91 | 150.07 | 163.85 | 43.95 | −15.97 | 24.87 |
| | sample size | 18 | 79 | 11 | 4 | 80 | 6 | 2 | 5 |

TABLE A8

Table A8-1 Pharmacophore Protein distance

| | | | | | | | Pharmacophore element | | | | | | | | | | | |
|---|---|---|---|---|---|---|---|---|---|---|---|---|---|---|---|---|---|---|
| | | H4 | | | | | | | O2 | | | | | | CA6 | | C3 | |
| | | TRP_655 | | SER_633 | | HIS_483 | | SER_654 | | GLY_656 | | TRP_655 | | PHE_529 | | CYS_629 | SER_628 | VAL_653 | TRP_655 |
| 1 | 14 | HA | 2.47 | | | HE1 | 2.86 | O | 2.46 | H | 2.53 | HB2 | 2.82 | HZ | 2.99 | O 3.64 | HB2 3.26 | HG12 2.83 | HA 3.56 |
| 2 | 54_A | HA | 2.52 | HG | 2.62 | HE1 | 3.37 | O | 2.47 | H | 2.64 | HB2 | 2.67 | HZ | 3.05 | O 3.54 | HB2 3.40 | HG12 2.74 | HA 3.49 |
| 3 | 54_B | HA | 2.52 | OG | 2.71 | HE1 | 3.37 | O | 2.47 | H | 2.64 | HB2 | 2.67 | HZ | 3.05 | O 3.54 | HB2 3.40 | HG12 2.74 | HA 3.49 |
| 4 | 1129 | HA | 2.51 | HG | 2.83 | HE1 | 3.47 | O | 2.38 | H | 2.13 | HB2 | 2.99 | HZ | 3.41 | O 3.35 | HG 3.42 | HG13 2.71 | HA 3.97 |
| 5 | 1034 | HA | 2.65 | HG | 2.58 | HE1 | 3.42 | O | 2.47 | H | 2.36 | HA | 2.95 | HZ | 3.60 | O 3.14 | OG 3.64 | HG12 2.61 | HA 4.08 |
| 6 | 1024 | HA | 2.61 | HG | 3.11 | NE2 | 3.44 | O | 2.40 | H | 2.24 | HA | 2.82 | HZ | 3.53 | HA 3.55 | HG 3.21 | HG12 2.71 | HA 3.82 |
| 7 | 1042_1 | HA | 2.73 | HG | 2.65 | NE2 | 3.09 | O | 2.37 | H | 2.70 | HB2 | 3.15 | HZ | 3.24 | H 3.31 | HB2 2.80 | HG11 2.67 | HA 3.39 |
| 8 | 1042_2 | HA | 2.72 | HG | 3.71 | HE1 | 3.73 | O | 2.79 | H | 2.65 | HB2 | 3.10 | HZ | 4.53 | HA 3.29 | HB2 3.71 | HG11 3.04 | HA 3.67 |
| 9 | 1042_3 | HA | 3.26 | HG | 3.87 | HE1 | 2.63 | O | 2.57 | H | 2.94 | HA | 2.93 | HZ | 3.24 | HA 3.33 | HB2 2.73 | HG11 1.96 | HA 4.22 |
| 10 | 2018 | HA | 2.70 | HG | 2.70 | HE2 | 2.92 | O | 2.35 | H | 2.45 | HB2 | 2.92 | HZ | 3.22 | O 3.55 | HB2 3.40 | HG12 2.68 | HA 3.78 |
| 11 | 1059 | HA | 2.60 | HG | 2.80 | HE1 | 3.16 | O | 2.22 | H | 2.39 | HB2 | 2.82 | HZ | 2.96 | HA 3.59 | OG 3.91 | HG13 2.81 | HA 3.77 |
| 12 | 1088_A | HA | 2.57 | OG | 3.18 | HE2 | 3.59 | O | 2.31 | H | 2.29 | HB2 | 2.85 | HZ | 3.38 | O 3.66 | OG 3.94 | HG12 2.77 | HA 3.81 |
| 13 | 1088_B | HA | 2.50 | HG | 3.34 | NE2 | 3.59 | O | 2.31 | H | 2.29 | HB2 | 2.82 | HZ | 3.50 | O 3.66 | OG 3.94 | HG13 2.77 | HA 3.81 |
| 14 | 1036_1 | HA | 2.57 | HG | 3.31 | HE1 | 3.49 | O | 2.32 | H | 2.14 | HB2 | 2.82 | HZ | 3.24 | O 3.70 | HB2 3.21 | HG12 2.60 | HA 3.84 |
| 15 | 1036_2_1 | HA | 2.59 | OG | 3.07 | HE1 | 2.60 | O | 2.32 | H | 2.64 | HB2 | 2.82 | HZ | 3.00 | O 3.78 | HG 3.48 | HG13 2.72 | HA 3.81 |
| 16 | 1036_2_2 | HA | 2.50 | OG | 3.43 | HE2 | 3.86 | O | 2.50 | H | 2.23 | HB2 | 2.82 | HZ | 3.12 | O 3.28 | OG 3.72 | HG12 2.66 | HA 3.57 |
| 17 | 1081 | HA | 2.72 | OG | 3.12 | HE1 | 3.12 | O | 2.26 | H | 2.23 | HB2 | 2.88 | HZ | 3.32 | O 3.56 | OG 3.74 | HG13 2.61 | HA 3.77 |
| 18 | 1063 | HA | 2.65 | OG | 3.67 | HE2 | 3.09 | O | 2.30 | H | 2.47 | HB2 | 2.87 | HZ | 3.29 | O 3.73 | OG 3.56 | HG12 2.52 | HA 3.72 |
| 19 | 1065 | HA | 2.52 | HG | 3.27 | HE2 | 3.62 | O | 2.32 | H | 2.39 | HB2 | 2.74 | HZ | 3.17 | O 3.71 | HG 3.36 | HG13 2.57 | HA 3.67 |
| 20 | 1030_A | HA | 2.50 | HG | 3.30 | NE2 | 3.54 | O | 2.26 | H | 2.36 | HB2 | 2.73 | HZ | 3.32 | O 3.73 | OG 3.46 | HG13 2.58 | HA 3.87 |
| 21 | 1030_B | HA | 2.50 | OG | 3.23 | HE1 | 3.18 | O | 2.26 | H | 2.27 | HB2 | 2.88 | HZ | 3.32 | O 3.73 | HB2 3.19 | HG13 2.58 | HA 3.87 |
| 22 | 1037 | HA | 2.46 | OG | 3.23 | HE1 | 3.23 | O | 2.26 | H | 2.27 | HB2 | 2.88 | HZ | 3.17 | O 3.33 | HB2 3.70 | HG13 2.62 | HA 3.71 |
| 23 | 1118 | HA | 2.60 | HG | 2.93 | NE2 | 3.86 | O | 2.52 | H | 2.44 | HA | 2.94 | HZ | 3.57 | O 3.65 | HB3 3.03 | HG13 2.55 | HA 4.01 |
| 24 | 1090 | HA | 2.56 | HG | 3.29 | NE2 | 3.67 | O | 2.19 | H | 2.22 | HB2 | 2.67 | HZ | 3.06 | O 3.62 | OG 4.05 | HG12 2.57 | HA 3.71 |
| 25 | 1007_1 | HA | 2.35 | HG | 2.81 | NE2 | 3.32 | O | 2.45 | H | 2.26 | HB2 | 2.69 | HZ | 3.18 | O 3.43 | O 3.15 | HG13 2.77 | HA 3.46 |
| 26 | 1007_2 | HA | 2.41 | OG | 3.50 | NE2 | 3.77 | O | 2.30 | H | 2.30 | HB2 | 2.61 | HZ | 3.20 | O 3.63 | OG 3.65 | HG13 2.58 | HA 3.39 |
| 27 | 1149 | HA | 2.51 | HG | 3.77 | HE1 | 3.45 | O | 2.25 | H | 2.45 | HB2 | 2.71 | HZ | 3.69 | O 3.35 | OG 3.58 | HG12 2.76 | HA 3.65 |
| 28 | 1021_A | HA | 2.60 | HG | 3.42 | HE2 | 2.91 | O | 2.14 | H | 2.79 | HB2 | 2.82 | HZ | 2.97 | O 3.74 | HG 3.38 | HG12 2.84 | HA 3.64 |
| 29 | 1021_B | HA | 2.59 | OG | 3.35 | HE2 | 3.09 | O | 2.31 | H | 2.48 | HB2 | 2.82 | HZ | 2.97 | O 3.75 | HB2 3.38 | HG13 2.87 | HA 3.64 |
| 30 | 1097_1 | HA | 2.66 | OG | 3.35 | HE2 | 3.09 | O | 2.30 | H | 2.47 | HB2 | 2.82 | HZ | 3.38 | O 3.44 | HG 3.36 | HG12 2.87 | HA 3.91 |
| 31 | 1097_2 | HA | 2.63 | HG | 3.29 | HE2 | 3.33 | O | 2.34 | H | 2.32 | HB2 | 2.90 | HZ | 3.38 | O 3.55 | HG 3.34 | HG13 2.73 | HA 3.86 |
| 32 | 1031_1 | HA | 2.61 | HG | 3.22 | HE2 | 3.32 | O | 2.31 | H | 2.17 | HB2 | 2.81 | HZ | 3.24 | O 3.85 | HB3 3.29 | HG12 2.76 | HA 3.57 |
| 33 | 1031_2 | HA | 2.60 | HG | 3.13 | HE1 | 3.48 | O | 2.43 | H | 2.51 | HB2 | 2.73 | HZ | 3.17 | O 3.83 | HB3 3.34 | HG13 2.71 | HA 3.53 |
| 34 | 1031_3 | HA | 2.64 | HG | 3.14 | NE2 | 3.54 | O | 2.42 | H | 2.48 | HB2 | 2.71 | HZ | 3.25 | O 3.74 | HB3 3.30 | HG13 2.77 | HA 3.63 |
| 35 | 1031_4 | HA | 2.61 | HG | 3.56 | HE2 | 3.19 | O | 2.49 | H | 2.50 | HB2 | 2.81 | HZ | 3.28 | O 3.74 | HB2 3.31 | HG13 2.78 | HA 3.58 |
| 36 | 1153_A | HA | 2.62 | HG | 2.98 | HE1 | 3.46 | O | 2.47 | H | 2.49 | HB2 | 2.76 | HZ | 4.04 | O 3.49 | HG 3.30 | HG13 2.78 | HA 3.93 |
| 37 | 1153_B | HA | 2.62 | HG | 2.60 | NE2 | 3.31 | O | 2.43 | H | 2.29 | HB2 | 2.91 | HZ | 4.04 | O 3.70 | HG 3.24 | HG13 2.63 | HA 3.93 |
| 38 | 1025_1 | HA | 2.80 | HG | 2.59 | HE1 | 3.31 | O | 2.27 | H | 2.29 | HB2 | 2.95 | HZ | 3.38 | O 3.70 | HG 3.34 | HG11 2.52 | HA 3.77 |
| 39 | 1025_2 | HA | 2.89 | HG | 2.82 | HE2 | 3.29 | O | 2.47 | H | 2.57 | HB2 | 3.08 | HZ | 3.24 | O 3.85 | O 3.35 | HG12 2.74 | HA 3.71 |
| 40 | 1025_3 | HA | 2.61 | OG | 3.45 | HE2 | 3.46 | O | 2.46 | H | 2.79 | HB2 | 2.72 | HZ | 3.05 | O 3.79 | HG 2.70 | HG13 2.83 | HA 3.55 |
| 41 | 1025_4 | HA | 2.55 | HG | 3.33 | NE2 | 3.68 | O | 2.28 | H | 2.72 | HB2 | 2.86 | HZ | 3.28 | O 3.16 | O 3.36 | HG11 2.83 | HA 3.75 |

TABLE A8-continued

| | | | | | | | | | | | | | | | | |
|---|---|---|---|---|---|---|---|---|---|---|---|---|---|---|---|---|
| 42 | 1025_5 | HA | 2.72 | HG | 3.45 | NE2 | 3.51 | O | 2.13 | H | 2.53 | HB2 | 2.80 | HZ | 2.94 | HA | 3.46 | O | 2.97 | HG11 | 2.65 | HA | 3.63 |
| 43 | 1025_6 | HA | 2.78 | HG | 2.97 | HE1 | 3.10 | O | 2.22 | H | 2.91 | HB2 | 2.71 | HZ | 3.18 | O | 3.67 | HB2 | 3.35 | HG12 | 2.75 | HA | 3.37 |
| 44 | 1089_A | HA | 2.55 | HG | 2.97 | HE1 | 3.32 | O | 2.23 | H | 2.24 | HB2 | 2.73 | HZ | 3.35 | O | 3.61 | OG | 4.12 | HG12 | 2.72 | HA | 3.75 |
| 45 | 1089_B | HA | 2.55 | HG | 2.96 | HE1 | 3.32 | O | 2.23 | H | 2.24 | HB2 | 2.74 | HZ | 3.35 | O | 3.61 | OG | 4.12 | HG12 | 2.72 | HA | 3.75 |
| 46 | 1012_1 | HA | 2.64 | HG | 3.23 | HE1 | 3.40 | O | 2.35 | H | 2.49 | HB2 | 2.54 | HZ | 3.07 | O | 3.84 | OG | 3.35 | HG13 | 2.65 | HA | 3.62 |
| 47 | 1012_2 | HA | 2.37 | HG | 3.42 | HE1 | 3.75 | O | 2.23 | H | 2.27 | HB2 | 2.75 | HZ | 3.13 | O | 3.89 | OG | 3.25 | HG13 | 2.67 | HA | 3.58 |
| 48 | 1078_1 | HA | 2.51 | HG | 3.32 | HE1 | 3.69 | O | 2.43 | H | 2.41 | HB2 | 2.89 | HZ | 3.10 | HA | 3.89 | OG | 3.80 | HG13 | 2.88 | HA | 3.49 |
| 49 | 1078_10 | HA | 2.71 | OG | 3.15 | HE2 | 3.15 | O | 2.48 | H | 2.53 | HB2 | 2.76 | HZ | 3.20 | HA | 3.85 | OG | 2.94 | HG13 | 2.77 | HA | 3.60 |
| 50 | 1078_11 | HA | 2.50 | OG | 3.36 | HE2 | 3.45 | O | 2.42 | H | 2.40 | HB2 | 2.76 | HZ | 3.03 | HA | 3.82 | HG | 2.96 | HG13 | 2.88 | HA | 3.48 |
| 51 | 1078_12 | HA | 2.47 | HG | 3.42 | NE2 | 3.65 | O | 2.43 | H | 2.38 | HB2 | 2.76 | HZ | 3.08 | HA | 3.80 | HG | 2.87 | HG13 | 2.90 | HA | 3.49 |
| 52 | 1078_13 | HA | 2.50 | HG | 3.39 | NE2 | 3.42 | O | 2.42 | H | 2.37 | HB2 | 2.76 | HZ | 3.07 | HA | 3.83 | HG | 2.87 | HG13 | 2.87 | HA | 3.51 |
| 53 | 1078_14 | HA | 2.49 | OG | 3.29 | NE2 | 3.69 | O | 2.44 | H | 2.36 | HB2 | 2.77 | HZ | 3.15 | HA | 3.79 | HG | 2.89 | HG13 | 2.89 | HA | 3.51 |
| 54 | 1078_15 | HA | 2.49 | OG | 3.64 | HE2 | 3.73 | O | 2.45 | H | 2.39 | HB2 | 2.77 | HZ | 3.17 | HA | 3.80 | HG | 2.92 | HG13 | 2.91 | HA | 3.49 |
| 55 | 1078_16 | HA | 2.47 | HG | 3.70 | NE2 | 3.38 | O | 2.43 | H | 2.36 | HB2 | 2.78 | HZ | 3.12 | HA | 3.83 | HG | 2.91 | HG13 | 2.89 | HA | 3.50 |
| 56 | 1078_2 | HA | 2.47 | HG | 3.32 | HE2 | 3.43 | O | 2.45 | H | 2.35 | HB2 | 2.76 | HZ | 3.25 | HA | 3.80 | HG | 2.88 | HG13 | 2.87 | HA | 3.52 |
| 57 | 1078_3 | HA | 2.67 | HG | 3.18 | HE2 | 3.76 | O | 2.47 | H | 2.35 | HB2 | 2.76 | HZ | 3.16 | HA | 3.77 | HG | 2.76 | HG13 | 2.81 | HA | 3.59 |
| 58 | 1078_4 | HA | 2.45 | HG | 3.36 | HE2 | 3.59 | O | 2.44 | H | 2.51 | HB2 | 2.84 | HZ | 3.13 | HA | 3.80 | HG | 2.85 | HG13 | 2.89 | HA | 3.49 |
| 59 | 1078_5 | HA | 2.48 | HG | 3.36 | HE2 | 3.77 | O | 2.44 | H | 2.35 | HB2 | 2.75 | HZ | 3.12 | HA | 3.80 | HG | 2.90 | HG12 | 2.90 | HA | 3.56 |
| 60 | 1078_6 | HA | 2.50 | HG | 3.35 | NE2 | 3.72 | O | 2.46 | H | 2.38 | HB2 | 2.75 | HZ | 3.25 | HA | 3.82 | HG | 2.91 | HG13 | 2.93 | HA | 3.60 |
| 61 | 1078_7 | HA | 2.51 | HG | 3.34 | NE2 | 3.72 | O | 2.43 | H | 2.38 | HB2 | 2.78 | HZ | 3.14 | HA | 3.82 | HG | 2.91 | HG13 | 2.88 | HA | 3.51 |
| 62 | 1078_8 | HA | 2.49 | HG | 3.32 | HE2 | 3.70 | O | 2.42 | H | 2.40 | HB2 | 2.76 | HZ | 3.07 | HA | 3.84 | HG | 2.88 | HG12 | 2.87 | HA | 3.49 |
| 63 | 1078_9 | HA | 2.46 | HG | 3.41 | NE2 | 3.71 | O | 2.44 | H | 2.38 | HB2 | 2.74 | HZ | 3.07 | HA | 3.79 | HG | 2.86 | HG13 | 2.93 | HA | 3.48 |
| 64 | 1145_A | HA | 2.52 | HG | 3.11 | HE1 | 3.78 | O | 2.44 | H | 2.37 | HB2 | 2.77 | HZ | 3.11 | HA | 3.54 | HG | 2.84 | HG13 | 2.70 | HA | 3.83 |
| 65 | 1145_B | HA | 2.52 | HG | 3.11 | HE1 | 3.76 | O | 2.40 | H | 2.20 | HB2 | 2.83 | HZ | 3.75 | HA | 3.54 | HG | 3.09 | HG13 | 2.95 | HA | 3.83 |
| 66 | 1050 | HA | 2.50 | HG | 3.34 | NE2 | 3.60 | O | 2.57 | H | 2.30 | HB2 | 2.70 | HZ | 3.43 | O | 3.63 | HG | 3.08 | HG13 | 2.94 | HA | 3.60 |
| 67 | 1253 | HA | 2.59 | OG | 3.04 | HE1 | 3.01 | O | 2.09 | H | 2.47 | HB2 | 2.70 | HZ | 3.30 | O | 3.74 | HB2 | 3.34 | HG13 | 2.92 | HA | 3.50 |
| 68 | 1257 | HA | 2.49 | HG | 3.16 | HE1 | 3.21 | O | 2.15 | H | 2.28 | HB2 | 2.65 | HZ | 3.23 | O | 3.72 | HB3 | 3.45 | HG12 | 2.95 | HA | 3.42 |
| 69 | 999_1 | HA | 2.59 | HG | 2.76 | HE1 | 3.12 | O | 2.41 | H | 2.47 | HB2 | 2.85 | HZ | 3.08 | HA | 2.96 | HG | 3.45 | HG13 | 2.77 | HA | 3.46 |
| 70 | 999_2_A | HA | 2.50 | HG | 3.08 | NE2 | 3.53 | O | 2.51 | H | 2.48 | HB2 | 2.87 | HZ | 3.44 | HA | 3.32 | HB2 | 3.82 | HG13 | 2.65 | HA | 3.75 |
| 71 | 999_2_B | HA | 2.50 | HG | 3.03 | HE2 | 3.08 | O | 2.51 | H | 2.48 | HB2 | 2.87 | HZ | 3.44 | HA | 3.32 | HB3 | 3.58 | HG13 | 2.65 | HA | 3.92 |
| 72 | 1297_1 | HA | 2.50 | HG | 3.11 | HE1 | 2.82 | O | 2.07 | H | 2.42 | HB2 | 2.66 | HZ | 3.05 | HA | 3.74 | HB2 | 3.76 | HG13 | 2.95 | HA | 3.92 |
| 73 | 1297_2 | HA | 2.48 | HG | 2.85 | HE1 | 2.85 | O | 2.06 | H | 2.38 | HB2 | 2.63 | HZ | 3.01 | HA | 3.70 | HB2 | 3.69 | HG13 | 2.94 | HA | 3.42 |
| 74 | 1297_3 | HA | 2.55 | OG | 3.19 | HE2 | 3.19 | O | 2.11 | H | 2.30 | HB2 | 2.72 | HZ | 3.18 | O | 3.78 | HG | 3.12 | HG13 | 2.92 | HA | 3.50 |
| 75 | 1297_4 | HA | 2.46 | HG | 2.90 | HE1 | 3.63 | O | 2.06 | H | 2.36 | HB2 | 2.63 | HZ | 3.04 | O | 3.78 | HB2 | 3.46 | HG13 | 2.95 | HA | 3.42 |
| 76 | 1297_5 | HA | 2.52 | HG | 2.88 | HE1 | 3.62 | O | 2.09 | H | 2.41 | HB2 | 2.68 | HZ | 3.10 | O | 3.68 | HG | 3.46 | HG12 | 2.95 | HA | 3.46 |
| 77 | 1297_6 | HA | 2.59 | HG | 2.82 | NE2 | 3.62 | O | 2.15 | H | 2.47 | HB2 | 2.74 | HZ | 3.17 | O | 3.65 | HB2 | 3.41 | HG13 | 2.92 | HA | 3.52 |
| 78 | 1304 | HA | 2.72 | OG | 3.62 | HE2 | 3.01 | O | 2.04 | H | 2.46 | HB2 | 2.69 | HZ | 3.22 | O | 3.73 | OG | 3.29 | HG13 | 2.83 | HA | 3.59 |
| 79 | 1306_1 | HA | 2.48 | HG | 2.90 | HE2 | 3.08 | O | 2.16 | H | 2.08 | HA | 2.36 | HZ | 2.88 | O | 3.38 | HB2 | 3.49 | HG12 | 2.51 | HA | 3.80 |
| 80 | 1306_2 | HA | 2.51 | HG | 3.28 | HE1 | 3.23 | O | 2.17 | H | 2.22 | HB2 | 2.36 | HZ | 2.59 | O | 3.32 | OG | 3.41 | HG12 | 2.40 | HA | 3.76 |
| 81 | 1307 | HA | 2.43 | HG | 3.21 | HE1 | 3.22 | O | 2.19 | H | 2.55 | HA | 2.63 | HZ | 2.56 | O | 3.81 | HB2 | 3.37 | HG13 | 2.91 | HA | 3.54 |
| 82 | 1328_1 | HA | 2.48 | OG | 2.84 | HE1 | 3.27 | O | 2.23 | H | 2.58 | HB2 | 2.69 | HZ | 3.13 | O | 3.68 | HB2 | 3.33 | HG13 | 2.87 | HA | 3.38 |
| 83 | 1328_2 | HA | 2.51 | HG | 2.92 | HE1 | 3.23 | O | 2.19 | H | 2.43 | HB2 | 2.67 | HZ | 3.05 | O | 3.65 | HB2 | 3.10 | HG12 | 2.88 | HA | 3.40 |
| 84 | 1328_3 | HA | 2.43 | OG | 2.92 | HE1 | 3.22 | O | 2.19 | H | 2.47 | HB2 | 2.68 | HZ | 3.13 | O | 3.67 | HB2 | 3.09 | HG13 | 2.83 | HA | 3.49 |
| 85 | 1328_4 | HA | 2.49 | HG | 3.82 | HE1 | 3.29 | O | 2.59 | H | 2.43 | HB2 | 2.88 | HZ | 3.17 | O | 3.70 | HB2 | 3.03 | HG13 | 2.60 | HA | 3.52 |
| 86 | 1334 | HA | 2.70 | HG | 3.26 | HE2 | 3.62 | O | 2.38 | H | 2.25 | HA | 2.84 | HZ | 3.31 | O | 3.77 | HB2 | 3.52 | HG13 | 2.53 | HA | 3.85 |
| 87 | 1335 | HA | 2.61 | HG | 3.05 | HE1 | 3.38 | O | 2.13 | H | 2.52 | HB2 | 2.63 | HZ | 3.47 | O | 3.65 | HB3 | 3.30 | HG12 | 2.83 | HA | 3.95 |
| 88 | 1338 | HA | 2.65 | HG | 2.83 | HE1 | 3.25 | O | 2.13 | H | 2.22 | HA | 2.41 | HZ | 3.07 | O | 3.69 | HG | 3.40 | HG13 | 2.77 | HA | 3.54 |
| 89 | 1345_1 | HA | 2.32 | HG | 3.13 | HE1 | 3.59 | O | 2.43 | H | 2.03 | HB2 | 2.03 | HZ | 2.79 | O | 3.50 | OG | 3.31 | HG12 | 2.60 | HA | 3.57 |
| 90 | 1345_2 | HA | 2.56 | HG | 2.99 | HE1 | 3.25 | O | 2.19 | H | 2.24 | HA | 2.88 | HZ | 3.38 | O | 3.21 | HB2 | 2.96 | HG13 | 2.93 | HA | 3.86 |
| 91 | 1351 | HA | 2.59 | HG | 3.14 | HE1 | 3.61 | O | 2.06 | H | 2.50 | HB2 | 2.75 | HZ | 3.33 | O | 3.71 | HB2 | 3.25 | HG13 | 2.79 | HA | 3.60 |
| 92 | 1353 | HA | 2.66 | OG | 2.90 | HE1 | 2.98 | O | 2.06 | H | 2.47 | HB2 | 2.58 | HZ | 3.20 | O | 3.71 | HB3 | 3.41 | HG12 | 2.90 | HA | 3.54 |
| 93 | 1367 | HA | 2.59 | HG | 2.94 | HE1 | 2.96 | O | 2.06 | H | 2.55 | HB2 | 2.78 | HZ | 3.13 | O | 3.80 | HB2 | 3.43 | HG13 | 2.90 | HA | 3.64 |
| 94 | 1371 | HA | 2.90 | HG | 3.39 | HE2 | 3.12 | O | 2.49 | H | 2.74 | HA | 3.03 | HZ | 3.17 | O | 3.87 | HB2 | 3.27 | HG13 | 2.75 | HA | 3.83 |

TABLE A8-continued

| | | GLY_667 | | SER_628 | | TYR_669 | | TRP_655 | | VAL_668 | | SER_654 | | CYS_629 | | GLY_656 | | TRP_655 | | CYS_629 | | ASP_627 | |
|---|---|---|---|---|---|---|---|---|---|---|---|---|---|---|---|---|---|---|---|---|---|---|---|
| 95 | 1372_A | HA | 2.62 | OG | HG | 2.90 | HE1 | 3.08 | O | 2.07 | H | 2.46 | HB2 | 2.72 | HZ | 3.15 | O | 3.71 | HB2 | 3.30 | HG13 | 2.87 | HA | 3.60 |
| 96 | 1372_B | HA | 2.61 | OG | OG | 2.90 | HE1 | 3.08 | O | 2.07 | H | 2.46 | HB2 | 2.71 | HZ | 3.15 | O | 3.71 | HB2 | 3.30 | HG13 | 2.86 | HA | 3.60 |
| 97 | 1373 | HA | 2.61 | OG | OG | 2.89 | HE1 | 3.10 | O | 2.12 | H | 2.49 | HB2 | 2.71 | HZ | 3.12 | O | 3.73 | HB2 | 3.29 | HG13 | 2.89 | HA | 3.59 |
| 98 | 1492 | HA | 2.63 | OG | HG | 3.14 | HE1 | 3.15 | O | 2.36 | H | 2.35 | HB2 | 2.97 | HZ | 3.43 | O | 3.66 | HB2 | 3.81 | HG13 | 2.62 | HA | 3.75 |
| 99 | 1399 | HA | 2.64 | OG | OG | 2.86 | HE1 | 3.10 | O | 2.11 | H | 2.50 | HB2 | 2.71 | HZ | 3.25 | O | 3.68 | HB2 | 3.34 | HG13 | 2.83 | HA | 3.60 |
| 100 | 1360 | HA | 2.60 | OG | OG | 2.96 | HE1 | 3.12 | O | 2.07 | H | 2.47 | HB2 | 2.62 | HZ | 3.13 | O | 3.74 | HB2 | 3.38 | HG13 | 2.87 | HA | 3.56 |
| 101 | 1368 | HA | 2.65 | OG | OG | 2.88 | HE1 | 3.05 | O | 2.15 | H | 2.49 | HB2 | 2.82 | HZ | 3.82 | O | 3.69 | HB2 | 3.47 | HG12 | 2.82 | HA | 3.67 |
| 102 | 1406 | HA | 2.65 | OG | OG | 2.75 | HE1 | 3.16 | O | 2.09 | H | 2.63 | HB2 | 2.58 | HZ | 3.22 | O | 3.70 | HB2 | 3.19 | HG12 | 2.80 | HA | 3.42 |
| 103 | 1411 | HA | 2.57 | OG | OG | 2.92 | HE1 | 3.25 | O | 2.32 | H | 2.48 | HB2 | 2.62 | HZ | 3.48 | O | 3.71 | HB2 | 3.18 | HG12 | 2.92 | HA | 3.55 |
| 104 | 1433 | HA | 2.54 | OG | HG | 3.36 | HE2 | 3.53 | O | 2.28 | H | 2.28 | HB2 | 2.71 | HZ | 3.26 | O | 3.74 | HB2 | 3.50 | HG13 | 2.68 | HA | 3.71 |
| 105 | 1441 | HA | 2.62 | OG | OG | 2.94 | HE1 | 3.11 | O | 2.08 | H | 2.50 | HB2 | 2.75 | HZ | 3.51 | O | 3.79 | HB3 | 3.41 | HG12 | 2.87 | HA | 3.62 |
| 106 | 1435 | HA | 2.60 | OG | OG | 2.93 | HE1 | 3.07 | O | 2.09 | H | 2.50 | HB2 | 2.68 | HZ | 3.13 | O | 3.79 | HB2 | 3.30 | HG13 | 2.81 | HA | 3.60 |
| 107 | 1450_A | HA | 2.59 | OG | OG | 2.85 | HE2 | 3.15 | O | 2.27 | H | 2.42 | HB2 | 2.79 | HZ | 3.33 | O | 3.69 | HB3 | 3.44 | HG13 | 2.76 | HA | 3.70 |
| 108 | 1450_B | HA | 2.59 | OG | OG | 2.85 | HE2 | 3.15 | O | 2.27 | H | 2.42 | HB2 | 2.79 | HZ | 3.33 | O | 3.69 | HB3 | 3.44 | HG13 | 2.76 | HA | 3.70 |
| | average distance | | 2.58 | | | 3.13 | | 3.36 | | 2.31 | | 2.42 | | 2.77 | | 3.24 | | 3.64 | | 3.32 | | 2.76 | | 3.65 |
| | standard deviation | | 0.12 | | | 0.30 | | 0.27 | | 0.16 | | 0.16 | | 0.13 | | 0.26 | | 0.18 | | 0.31 | | 0.15 | | 0.17 |
| | minimum value | | 2.32 | | | 2.36 | | 2.60 | | 2.04 | | 2.03 | | 2.36 | | 2.56 | | 2.96 | | 2.70 | | 1.96 | | 3.37 |
| | maximum value | | 3.26 | | | 3.89 | | 3.86 | | 2.79 | | 2.94 | | 3.15 | | 4.53 | | 3.89 | | 4.12 | | 3.04 | | 4.22 |
| | sample size | | 108 | | | 107 | | 108 | | 108 | | 108 | | 108 | | 108 | | 108 | | 108 | | 108 | | 108 |

Table A8-2 Pharmacophore protein distances

| | | Pharmacophore element | | | | | | | | | | |
|---|---|---|---|---|---|---|---|---|---|---|---|---|
| | | C5 | | | | | | CA1 | | | | N1 | |
| | | protein | | | | | | | | | | | |
| | | GLY_667 | | SER_628 | | TYR_669 | | TRP_655 | VAL_668 | SER_654 | CYS_629 | GLY_656 | TRP_655 | CYS_629 | ASP_627 |

| | | GLY_667 | | SER_628 | | TYR_669 | | TRP_655 | | VAL_668 | | SER_654 | | CYS_629 | | GLY_656 | | TRP_655 | | CYS_629 | | ASP_627 | |
|---|---|---|---|---|---|---|---|---|---|---|---|---|---|---|---|---|---|---|---|---|---|---|---|
| 1 | 14 | HA3 | 2.61 | HG | 1.19 | CZ | 4.09 | O | 2.88 | H | 2.83 | H | 3.85 | HA | 3.35 | HA3 | 3.28 | HA | 3.62 | HA | 3.16 | OD1 | 5.08 |
| 2 | 54_A | HA3 | 2.66 | OG | 2.24 | HH | 3.99 | O | 2.89 | H | 2.77 | H | 3.76 | HA | 3.15 | H | 3.49 | HA | 3.53 | OD1 | 3.03 | OD1 | 5.27 |
| 3 | 54_B | HA3 | 2.66 | OG | 2.24 | HH | 4.00 | O | 2.89 | H | 2.77 | H | 3.76 | HA | 3.15 | H | 3.49 | HA | 3.53 | OD1 | 3.03 | OD1 | 5.27 |
| 4 | 1129 | HA3 | 2.59 | HG | 2.10 | CZ | 3.88 | O | 3.60 | H | 2.83 | H | 3.77 | HA | 3.03 | HA3 | 3.64 | HA | 3.91 | OD1 | 3.03 | OD1 | 4.45 |
| 5 | 1034 | HA2 | 2.60 | OG | 1.95 | CZ | 4.01 | O | 3.77 | H | 3.36 | H | 3.86 | HA | 2.41 | H | 4.05 | HA | 3.96 | OD1 | 2.78 | OD1 | 4.19 |
| 6 | 1024 | HA3 | 2.80 | OG | 2.14 | CE1 | 3.83 | O | 3.14 | H | 3.01 | H | 3.67 | HA | 3.01 | HA3 | 3.76 | HA | 3.50 | OD1 | 2.96 | OD2 | 4.38 |
| 7 | 1042_1 | HA2 | 2.94 | OG | 2.33 | CZ | 4.33 | O | 3.61 | H | 2.90 | H | 3.72 | HA | 3.01 | H | 3.73 | HA | 3.77 | OD1 | 3.20 | OD1 | 3.93 |
| 8 | 1042_2 | HA3 | 3.14 | OG | 2.48 | CZ | 3.92 | O | 3.38 | H | 3.01 | H | 4.11 | HA | 2.57 | H | 3.76 | HA | 3.87 | OD1 | 3.17 | OD1 | 4.16 |
| 9 | 1042_3 | HA2 | 3.12 | OG | 2.31 | HE1 | 1.82 | O | 3.94 | H | 3.39 | H | 3.65 | HA | 3.13 | H | 4.52 | HA | 3.65 | OD1 | 2.95 | OD2 | 4.55 |
| 10 | 2018 | HA3 | 2.96 | HG | 1.26 | CZ | 3.90 | O | 3.41 | H | 2.93 | H | 3.56 | HA | 2.83 | H | 3.87 | HA | 3.65 | OD1 | 3.02 | OD2 | 4.77 |
| 11 | 1059 | HA3 | 2.77 | OG | 2.80 | CZ | 3.71 | O | 3.47 | H | 2.91 | H | 3.60 | HA | 3.26 | H | 3.99 | HA | 3.58 | OD1 | 3.03 | OD1 | 3.99 |
| 12 | 1088_A | HA3 | 2.89 | OG | 2.65 | HH | 3.65 | O | 3.34 | H | 2.92 | H | 3.67 | HA | 3.26 | HA3 | 3.73 | HA | 3.63 | OD1 | 3.33 | OD1 | 3.80 |
| 13 | 1088_B | HA3 | 2.89 | OG | 2.75 | CZ | 3.73 | O | 3.34 | H | 2.91 | H | 3.67 | HA | 2.94 | H | 3.73 | HA | 3.63 | OD1 | 3.33 | OD2 | 3.80 |
| 14 | 1036_1 | HA3 | 2.84 | OG | 1.29 | CZ | 3.84 | O | 3.52 | H | 2.91 | H | 3.72 | HA | 2.94 | HA3 | 3.74 | HA | 3.69 | OD1 | 2.99 | OD2 | 4.61 |
| 15 | 1036_2_1 | HA3 | 2.72 | OG | 2.49 | CZ | 3.79 | O | 3.32 | H | 2.71 | H | 3.80 | HA | 2.32 | HA3 | 4.19 | HA | 3.74 | OD1 | 3.21 | OD1 | 4.47 |
| 16 | 1036_2_2 | HA2 | 3.00 | OG | 2.48 | HE1 | 3.77 | O | 3.51 | H | 2.95 | H | 3.77 | HA | 2.90 | H | 3.39 | HA | 3.65 | OD1 | 2.91 | OD2 | 4.76 |
| 17 | 1081 | HA2 | 2.92 | OG | 2.66 | CE1 | 3.70 | O | 3.53 | H | 3.33 | H | 3.86 | HA | 3.02 | H | 3.42 | HA | 3.53 | OD1 | 3.18 | OD1 | 4.39 |
| 18 | 1063 | HA3 | 3.05 | OG | 1.90 | CZ | 3.88 | O | 3.60 | H | 3.07 | H | 3.76 | HA | 3.24 | H | 3.57 | HA | 3.56 | OD1 | 3.35 | OD1 | 4.24 |
| 19 | 1065 | HA3 | 2.83 | HG | 2.33 | CZ | 3.80 | O | 3.31 | H | 2.85 | H | 3.86 | HA | 3.10 | H | 3.61 | HA | 3.57 | N | 3.27 | OD2 | 4.05 |
| 20 | 1030_A | HA3 | 2.83 | HG | 1.33 | CZ | 3.92 | O | 3.38 | H | 2.99 | H | 3.74 | HA | 2.96 | HA3 | 3.92 | HA | 3.76 | OD2 | 3.14 | OD2 | 4.34 |
| 21 | 1030_B | HA3 | 2.83 | HG | 1.33 | CZ | 3.92 | O | 3.38 | H | 2.99 | H | 3.74 | HA | 2.96 | HA3 | 3.92 | HA | 3.76 | OD1 | 3.14 | OD2 | 4.34 |
| 22 | 1037 | HA3 | 2.83 | HB2 | 2.42 | CE2 | 3.68 | O | 3.18 | H | 2.77 | H | 3.83 | HA | 3.32 | N | 3.85 | HA | 3.64 | OD2 | 3.28 | OD2 | 4.49 |
| 23 | 1118 | HA3 | 2.81 | HG | 1.21 | CZ | 3.89 | O | 3.55 | H | 2.94 | H | 3.76 | HA | 3.08 | H | 3.88 | HA | 3.85 | OD2 | 3.22 | OD2 | 4.36 |

TABLE A8-continued

| | | | | | | | | | | | | | | | | | | | |
|---|---|---|---|---|---|---|---|---|---|---|---|---|---|---|---|---|---|---|---|
| 24 | 1090 | HA3 | 3.12 | OG | 2.85 | CZ | 3.74 | O | 3.39 | H | 2.83 | H | 3.77 | H | 2.93 | H | 3.60 | HA | 3.55 | HA | 3.02 | OD2 | 4.20 |
| 25 | 1007_1 | HA3 | 3.06 | OG | 2.59 | HH | 3.62 | O | 3.06 | H | 3.12 | H | 4.19 | HA3 | 3.14 | H | 3.37 | HA | 3.63 | HA | 3.32 | OD2 | 3.20 |
| 26 | 1007_2 | HA3 | 2.89 | OG | 2.76 | CZ | 3.68 | O | 3.17 | H | 3.22 | H | 4.00 | H | 2.88 | H | 3.39 | HA | 3.43 | HA | 3.24 | OD2 | 3.37 |
| 27 | 1149 | HA3 | 2.71 | OG | 2.00 | HE1 | 3.74 | O | 2.99 | H | 3.22 | H | 3.78 | HA3 | 2.89 | H | 4.06 | HA | 3.57 | HA | 2.99 | OD2 | 3.98 |
| 28 | 1021_A | HA3 | 3.04 | OG | 3.61 | HH | 3.36 | O | 3.33 | H | 3.01 | H | 3.83 | H | 3.16 | H | 3.29 | HA | 3.60 | HA | 3.26 | OD2 | 3.84 |
| 29 | 1021_B | HA3 | 3.04 | HG | 2.76 | CZ | 3.35 | O | 3.34 | H | 3.01 | H | 3.83 | H | 3.16 | HA3 | 3.29 | HA | 3.60 | HA | 3.27 | OD2 | 3.83 |
| 30 | 1097_1 | HA3 | 2.76 | HG | 1.68 | CZ | 3.84 | O | 3.54 | H | 2.65 | H | 3.67 | N | 2.99 | H | 4.02 | HA | 3.76 | HA | 3.04 | OD2 | 4.46 |
| 31 | 1097_2 | HA2 | 2.88 | HB2 | 1.75 | CZ | 3.88 | O | 3.78 | H | 2.75 | H | 3.81 | H | 2.99 | H | 3.89 | HA | 3.72 | HA | 3.06 | OD2 | 4.47 |
| 32 | 1031_1 | HA3 | 3.13 | HB2 | 2.45 | CZ | 3.56 | O | 3.32 | H | 2.93 | H | 3.99 | H | 3.17 | H | 3.34 | HA | 3.57 | HA | 3.35 | OD2 | 3.00 |
| 33 | 1031_2 | HA3 | 3.12 | HB2 | 2.47 | CZ | 3.59 | O | 3.29 | H | 2.95 | H | 3.97 | HA3 | 3.21 | H | 3.30 | HA | 3.55 | HA | 3.39 | HD2 | 3.04 |
| 34 | 1031_3 | HA3 | 3.10 | HB2 | 2.39 | CZ | 3.63 | O | 3.36 | H | 2.98 | H | 4.01 | H | 3.11 | H | 3.36 | HA | 3.67 | HA | 3.23 | HD2 | 3.18 |
| 35 | 1031_4 | HA2 | 3.11 | HB2 | 2.42 | CZ | 3.62 | O | 3.31 | H | 2.92 | H | 4.02 | H | 3.16 | H | 3.27 | HA | 3.62 | HA | 3.21 | OD2 | 3.69 |
| 36 | 1153_A | HA2 | 2.70 | HG | 1.40 | CEI | 3.91 | O | 3.48 | H | 2.84 | H | 3.71 | H | 3.02 | HA3 | 3.80 | HA | 3.79 | HA | 3.02 | OD2 | 4.25 |
| 37 | 1153_B | HA3 | 3.07 | HG | 3.38 | CEI | 3.91 | O | 3.48 | H | 2.84 | H | 3.73 | H | 3.02 | H | 3.80 | HA | 3.79 | HA | 3.02 | OD2 | 4.25 |
| 38 | 1025_1 | HA3 | 3.13 | HG | 3.31 | CEI | 4.03 | O | 3.45 | H | 3.11 | H | 3.83 | H | 2.96 | H | 3.37 | HA | 3.66 | HA | 3.05 | ODI | 3.74 |
| 39 | 1025_2 | HA2 | 3.21 | OG | 2.29 | HH | 3.73 | O | 3.28 | H | 2.98 | H | 3.97 | H | 3.17 | HA3 | 4.13 | HA | 3.69 | HA | 3.24 | OD2 | 3.81 |
| 40 | 1025_3 | HA3 | 2.99 | HG | 2.86 | HH | 3.03 | O | 3.18 | H | 3.53 | H | 3.83 | H | 3.05 | H | 3.06 | HA | 3.54 | HA | 3.25 | OD2 | 3.71 |
| 41 | 1025_4 | HA3 | 3.19 | HG | 2.68 | HH | 3.68 | O | 3.19 | H | 3.20 | H | 4.07 | H | 3.11 | H | 3.52 | HA | 3.63 | HA | 3.17 | OD2 | 3.79 |
| 42 | 1025_5 | HA3 | 3.01 | HG | 2.24 | HH | 3.46 | O | 3.27 | H | 3.24 | H | 3.90 | H | 2.63 | H | 3.65 | HA | 3.55 | HA | 2.84 | ODI | 3.97 |
| 43 | 1025_6 | HA3 | 2.96 | HG | 2.87 | CZ | 3.95 | O | 3.13 | H | 3.34 | H | 3.94 | HA3 | 3.13 | H | 3.72 | HA | 3.34 | HA | 3.16 | OD2 | 3.53 |
| 44 | 1089_A | HA3 | 2.97 | HG | 2.85 | CZ | 3.82 | O | 3.43 | H | 2.90 | H | 3.57 | H | 3.21 | H | 3.74 | HA | 3.54 | HA | 3.23 | OD2 | 4.10 |
| 45 | 1089_B | HA3 | 2.97 | HG | 2.85 | CZ | 3.82 | O | 3.43 | H | 2.90 | H | 3.57 | H | 3.21 | H | 3.74 | HA | 3.54 | HA | 3.23 | OD2 | 4.10 |
| 46 | 1012_1 | HA3 | 3.13 | HG | 2.72 | CZ | 3.68 | O | 3.22 | H | 2.96 | H | 3.78 | H | 2.99 | H | 3.31 | HA | 3.53 | HA | 3.26 | OD2 | 3.43 |
| 47 | 1012_2 | HA3 | 3.10 | OG | 2.00 | CEI | 3.67 | O | 3.22 | H | 2.80 | H | 3.89 | H | 3.09 | HA3 | 3.33 | HA | 3.54 | HA | 3.29 | OD2 | 3.40 |
| 48 | 1078_1 | HA3 | 3.00 | OG | 2.96 | CZ | 3.64 | O | 3.45 | H | 2.92 | H | 3.73 | H | 3.15 | H | 3.21 | HA | 3.53 | HA | 3.39 | OD2 | 3.32 |
| 49 | 1078_10 | HA3 | 3.10 | HG | 2.45 | CZ | 3.65 | O | 3.50 | H | 2.99 | H | 3.60 | H | 3.08 | H | 3.37 | HA | 3.55 | HA | 3.30 | OD2 | 2.86 |
| 50 | 1078_11 | HA3 | 3.01 | HG | 2.47 | CZ | 3.63 | O | 3.45 | H | 2.93 | H | 3.73 | H | 3.13 | H | 3.21 | HA | 3.53 | HA | 3.38 | OD2 | 2.77 |
| 51 | 1078_12 | HA3 | 2.95 | HG | 2.54 | CZ | 3.64 | O | 3.46 | H | 2.92 | H | 3.75 | H | 3.14 | H | 3.22 | HA | 3.55 | HA | 3.40 | HD2 | 2.70 |
| 52 | 1078_13 | HA3 | 3.00 | HG | 2.51 | HH | 3.50 | O | 3.46 | H | 2.93 | H | 3.73 | H | 3.13 | H | 3.23 | HA | 3.54 | HA | 3.39 | HD2 | 2.71 |
| 53 | 1078_14 | HA3 | 2.97 | HG | 2.48 | CZ | 3.61 | O | 3.45 | H | 2.95 | H | 3.75 | H | 3.13 | H | 3.26 | HA | 3.57 | HA | 3.39 | HD2 | 2.70 |
| 54 | 1078_15 | HA3 | 2.98 | HG | 2.47 | CZ | 3.53 | O | 3.46 | H | 2.93 | H | 3.75 | H | 3.17 | H | 3.22 | HA | 3.55 | HA | 3.38 | HD2 | 2.73 |
| 55 | 1078_16 | HA3 | 2.97 | HG | 2.49 | CZ | 3.54 | O | 3.46 | H | 2.91 | H | 3.76 | H | 3.12 | H | 3.21 | HA | 3.57 | HA | 3.41 | HD2 | 2.70 |
| 56 | 1078_2 | HA3 | 2.96 | HG | 2.47 | CZ | 3.48 | O | 3.48 | H | 2.95 | H | 3.77 | H | 3.15 | H | 3.24 | HA | 3.58 | HA | 3.38 | HD2 | 2.79 |
| 57 | 1078_3 | HA3 | 3.07 | HG | 2.41 | CZ | 3.62 | O | 3.50 | H | 3.00 | H | 3.70 | H | 3.02 | H | 3.32 | HA | 3.56 | HA | 3.26 | HD2 | 2.70 |
| 58 | 1078_4 | HA3 | 2.95 | HG | 2.50 | CZ | 3.63 | O | 3.45 | H | 2.90 | H | 3.77 | H | 3.14 | H | 3.20 | HA | 3.55 | HA | 3.40 | HD2 | 2.72 |
| 59 | 1078_5 | HA3 | 3.00 | HG | 2.49 | CZ | 3.53 | O | 3.45 | H | 2.93 | H | 3.74 | H | 3.14 | H | 3.20 | HA | 3.54 | HA | 3.38 | HD2 | 2.72 |
| 60 | 1078_6 | HA3 | 2.98 | HG | 2.50 | CZ | 3.64 | O | 3.48 | H | 2.94 | H | 3.75 | H | 3.17 | H | 3.23 | HA | 3.57 | HA | 3.41 | HD2 | 2.73 |
| 61 | 1078_7 | HA3 | 3.00 | HG | 2.52 | CZ | 3.50 | O | 3.44 | H | 2.92 | H | 3.72 | H | 3.15 | H | 3.20 | HA | 3.53 | HA | 3.38 | HD2 | 2.73 |
| 62 | 1078_8 | HA3 | 2.97 | HG | 2.50 | CZ | 3.64 | O | 3.43 | H | 2.91 | H | 3.73 | H | 3.08 | H | 3.21 | HA | 3.53 | HA | 3.37 | HD2 | 2.77 |
| 63 | 1078_9 | HA3 | 2.96 | HG | 2.52 | HH | 3.51 | O | 3.46 | H | 2.89 | H | 3.75 | H | 3.13 | H | 3.18 | HA | 3.55 | HA | 3.42 | HD2 | 2.67 |
| 64 | 1145_A | HA3 | 2.49 | OG | 1.41 | CZ | 3.81 | O | 3.46 | H | 2.81 | H | 3.66 | H | 3.14 | H | 3.58 | HA | 3.75 | HA | 3.13 | OD2 | 4.31 |
| 65 | 1145_B | HA3 | 2.49 | OG | 1.41 | CZ | 3.81 | O | 3.46 | H | 2.81 | H | 3.66 | H | 3.04 | H | 3.58 | HA | 3.75 | HA | 3.13 | OD2 | 4.31 |
| 66 | 1050 | HA3 | 2.73 | OG | 1.60 | CZ | 3.82 | O | 3.17 | H | 3.10 | H | 3.83 | H | 3.07 | H | 3.83 | HA | 3.62 | HA | 3.09 | OD2 | 4.56 |
| 67 | 1253 | HA3 | 3.24 | HG | 2.53 | CZ | 3.71 | O | 3.19 | H | 2.92 | H | 3.50 | H | 2.98 | HA3 | 3.31 | HA | 3.43 | HA | 3.15 | OD2 | 3.62 |
| 68 | 1257 | HA3 | 3.08 | OG | 2.17 | CZ | 3.70 | O | 3.31 | H | 2.87 | H | 3.58 | H | 3.08 | H | 3.40 | HA | 3.49 | HA | 3.30 | OD2 | 3.82 |
| 69 | 999_1 | HA2 | 2.82 | HG | 2.54 | CZ | 3.93 | O | 3.27 | H | 2.80 | H | 3.92 | H | 2.20 | H | 3.86 | HA | 3.71 | HA | 2.75 | ODI | 4.47 |
| 70 | 999_2_A | HA3 | 2.79 | HG | 2.07 | CZ | 3.86 | O | 3.19 | H | 2.71 | H | 3.79 | H | 3.05 | H | 3.65 | HA | 3.83 | HA | 3.08 | OD2 | 4.44 |
| 71 | 999_2_B | HA3 | 3.02 | OG | 2.07 | CZ | 3.86 | O | 3.19 | H | 2.71 | H | 3.79 | H | 3.05 | H | 3.65 | HA | 3.83 | HA | 3.08 | OD2 | 4.44 |
| 72 | 1297_1 | HA3 | 2.99 | HB2 | 2.89 | CZ | 3.75 | O | 3.43 | H | 2.89 | H | 3.68 | HA3 | 2.88 | HA3 | 3.43 | HA | 3.36 | HA | 3.09 | ODI | 3.33 |
| 73 | 1297_2 | HA3 | 3.01 | OG | 3.24 | CZ | 3.67 | O | 3.21 | H | 2.88 | H | 3.70 | HA3 | 2.91 | HA3 | 3.47 | HA | 3.36 | HA | 3.12 | OD2 | 3.31 |
| 74 | 1297_3 | HA3 | 2.99 | HB2 | 2.86 | CZ | 3.71 | O | 3.22 | H | 2.90 | H | 3.66 | HA3 | 2.84 | HA3 | 3.44 | HA | 3.42 | HA | 3.11 | OD2 | 4.44 |
| 75 | 1297_4 | HA3 | 2.98 | OG | 3.25 | CZ | 3.65 | O | 3.20 | H | 2.87 | H | 3.70 | HA3 | 2.89 | HA3 | 3.45 | HA | 3.36 | HA | 3.13 | OD2 | 3.30 |
| 76 | 1297_5 | HA3 | 2.99 | HG | 2.38 | HH | 3.57 | O | 3.24 | H | 2.95 | H | 3.66 | HA3 | 2.80 | HA3 | 3.52 | HA | 3.40 | HA | 3.09 | OD2 | 3.25 |

TABLE A8-continued

| | | GLY_667 | | GLY_656 | | SER_628 | | CYS_660 | | CYS_629 | | GLY_661 | | ASP_627 | | SER_657 | | GLY_656 | | SER_628 | |
|---|---|---|---|---|---|---|---|---|---|---|---|---|---|---|---|---|---|---|---|---|---|
| 77 | 1297_6 | HA3 | 3.02 | HA3 | OG | 2.87 | CZ | 3.71 | O | 3.26 | H | 2.97 | H | 3.64 | HA | 3.53 | HA | 3.44 | HA | 3.08 | OD2 | 3.23 |
| 78 | 1304 | HA3 | 3.20 | HA3 | HB2 | 2.57 | CZ | 3.71 | O | 3.19 | H | 2.95 | H | 3.49 | HA | 3.39 | HA | 3.42 | HA | 3.20 | OD2 | 3.45 |
| 79 | 1306_1 | HA3 | 2.72 | HA3 | OG | 2.26 | CZ | 3.52 | O | 3.65 | H | 3.07 | N | 3.33 | HA | 3.71 | HA | 3.40 | HA | 3.64 | OD1 | 4.28 |
| 80 | 1306_2 | HA3 | 2.74 | HA3 | HG | 1.92 | CZ | 3.60 | O | 3.43 | H | 3.03 | HA3 | 3.49 | HA | 3.60 | HA | 3.43 | HA | 3.32 | OD1 | 4.34 |
| 81 | 1307 | HA3 | 3.20 | HA3 | HB2 | 2.60 | CZ | 3.70 | O | 3.32 | H | 3.11 | H | 3.42 | HA | 3.24 | HA | 3.39 | HA | 3.36 | OD1 | 4.13 |
| 82 | 1328_1 | HA3 | 3.12 | HA3 | OG | 2.56 | CZ | 3.77 | O | 3.22 | H | 2.87 | H | 3.76 | HA | 3.04 | HA | 3.38 | HA | 3.27 | OD2 | 3.14 |
| 83 | 1328_2 | HA3 | 3.15 | HA3 | HB2 | 2.59 | CZ | 3.73 | O | 3.22 | H | 2.87 | H | 3.75 | HA | 3.01 | HA | 3.39 | HA | 3.21 | OD2 | 3.17 |
| 84 | 1328_3 | HA3 | 3.06 | HA3 | HB2 | 2.51 | CZ | 3.71 | O | 3.32 | H | 2.91 | H | 3.83 | HA | 3.10 | HA | 3.46 | HA | 3.27 | OD2 | 3.24 |
| 85 | 1328_4 | HA3 | 3.12 | HA3 | HB2 | 2.59 | CZ | 3.63 | O | 3.36 | H | 2.93 | H | 3.74 | HA | 3.16 | HA | 3.49 | HA | 3.27 | OD1 | 3.16 |
| 86 | 1334 | HA3 | 3.01 | HA3 | HG | 2.69 | CZ | 3.83 | O | 3.46 | H | 2.88 | H | 3.85 | HA | 3.36 | HA | 3.46 | HA | 3.08 | OD2 | 4.09 |
| 87 | 1335 | HA3 | 2.77 | HA3 | HG | 1.38 | CZ | 3.89 | O | 3.50 | H | 2.95 | H | 3.72 | HA | 3.76 | HA | 3.74 | HA | 3.10 | OD2 | 4.50 |
| 88 | 1338 | HA3 | 3.27 | HA3 | HB2 | 2.50 | CZ | 3.83 | O | 3.22 | H | 2.87 | HA3 | 3.45 | HA | 3.26 | HA | 3.75 | HA | 3.26 | OD2 | 3.50 |
| 89 | 1345_1 | HA2 | 2.74 | HA2 | HG | 2.73 | CE1 | 3.85 | O | 3.27 | H | 2.48 | H | 3.57 | HA | 3.10 | HA | 3.36 | HA | 3.39 | OD2 | 4.56 |
| 90 | 1345_2 | HA2 | 2.50 | HA3 | OG | 2.17 | CZ | 3.88 | H | 3.66 | H | 2.79 | HA3 | 3.39 | HA | 3.85 | HA | 3.70 | HA | 2.93 | OD2 | 4.39 |
| 91 | 1351 | HA3 | 3.17 | HA3 | HB2 | 2.44 | CZ | 3.72 | O | 3.30 | H | 2.98 | H | 3.65 | HA | 3.28 | HA | 3.51 | HA | 3.24 | OD2 | 3.29 |
| 92 | 1353 | HA3 | 3.18 | HA3 | HB2 | 2.52 | CZ | 3.74 | O | 3.25 | H | 2.96 | H | 3.78 | HA | 3.31 | HA | 3.32 | HA | 3.21 | OD2 | 3.49 |
| 93 | 1367 | HA3 | 3.18 | HA3 | HB2 | 2.52 | CZ | 3.73 | O | 3.23 | H | 2.92 | H | 3.43 | HA | 3.23 | HA | 3.45 | HA | 3.18 | OD2 | 3.54 |
| 94 | 1371 | HA2 | 2.97 | HA2 | OG | 2.59 | CZ | 3.52 | O | 3.49 | H | 3.12 | H | 3.41 | HA | 3.61 | HA | 3.63 | HA | 3.42 | OD2 | 3.75 |
| 95 | 1372_A | HA3 | 3.20 | HA3 | HB2 | 2.60 | CZ | 3.74 | O | 3.19 | H | 2.89 | H | 3.59 | HA | 3.34 | HA | 3.41 | HA | 3.13 | OD2 | 3.46 |
| 96 | 1372_B | HA3 | 3.20 | HA3 | HB2 | 2.60 | CZ | 3.73 | O | 3.19 | H | 2.89 | H | 3.50 | HA | 3.34 | HA | 3.41 | HA | 3.13 | OD2 | 3.46 |
| 97 | 1373 | HA3 | 3.23 | HA3 | HB2 | 2.56 | CZ | 3.70 | O | 3.21 | H | 2.91 | H | 3.48 | HA | 3.24 | HA | 3.43 | HA | 3.14 | OD2 | 3.47 |
| 98 | 1492 | HA2 | 2.81 | HA3 | OG | 2.44 | CZ | 3.90 | O | 3.53 | H | 3.10 | H | 3.89 | HA | 3.70 | HA | 3.69 | HA | 3.13 | OD1 | 3.90 |
| 99 | 1399 | HA3 | 3.23 | HA3 | HB2 | 2.54 | CZ | 3.71 | O | 3.17 | H | 2.91 | H | 3.45 | HA | 3.26 | HA | 3.42 | HA | 3.13 | OD2 | 3.55 |
| 100 | 1360 | HA3 | 3.23 | HA3 | HB2 | 2.53 | CZ | 3.75 | O | 3.24 | H | 2.92 | H | 3.48 | HA | 3.47 | HA | 3.37 | HA | 3.16 | OD2 | 3.51 |
| 101 | 1368 | HA3 | 3.15 | HA3 | HB2 | 2.53 | CZ | 3.73 | O | 3.21 | H | 2.91 | H | 3.51 | HA | 3.40 | HA | 3.47 | HA | 3.23 | OD2 | 3.59 |
| 102 | 1406 | HA3 | 3.18 | HA3 | HB2 | 2.59 | CZ | 3.68 | O | 3.06 | H | 3.07 | H | 3.47 | HA | 3.44 | HA | 3.22 | HA | 3.28 | OD2 | 3.49 |
| 103 | 1411 | HA3 | 3.33 | HA3 | HB2 | 2.57 | CZ | 3.73 | O | 3.25 | H | 3.01 | H | 3.43 | HA | 3.35 | HA | 3.31 | HA | 3.23 | OD2 | 3.35 |
| 104 | 1433 | HA3 | 3.08 | HA3 | HB2 | 2.59 | CZ | 3.67 | O | 3.44 | H | 2.80 | H | 3.61 | HA | 3.36 | HA | 3.58 | HA | 3.28 | OD2 | 4.15 |
| 105 | 1441 | HA3 | 3.23 | HA3 | HB2 | 2.53 | CZ | 3.68 | O | 3.24 | H | 2.93 | H | 3.46 | HA | 3.30 | HA | 3.46 | HA | 3.12 | OD2 | 3.53 |
| 106 | 1435 | HA3 | 3.20 | HA3 | HB2 | 2.60 | CZ | 3.69 | O | 3.21 | H | 2.98 | H | 3.49 | HA | 3.36 | HA | 3.41 | HA | 3.21 | OD2 | 3.56 |
| 107 | 1450_A | HA3 | 3.10 | HA3 | HB2 | 2.53 | CZ | 3.69 | O | 3.32 | H | 2.89 | H | 3.58 | HA | 3.34 | HA | 3.55 | HA | 3.18 | OD2 | 3.94 |
| 108 | 1450_B | HA3 | 3.10 | HA3 | HB2 | 2.53 | CZ | 3.69 | O | 3.32 | H | 2.89 | H | 3.58 | HA | 3.34 | HA | 3.55 | HA | 3.22 | OD2 | 3.94 |
| | average distance | | 2.97 | | | 2.39 | | 3.71 | | 3.34 | | 2.94 | | 3.71 | | 3.49 | | 3.56 | | 3.20 | | 3.75 |
| | standard deviation | | 0.19 | | | 0.48 | | 0.25 | | 0.18 | | 0.15 | | 0.16 | | 0.28 | | 0.14 | | 0.15 | | 0.63 |
| | minimum value | | 2.49 | | | 1.19 | | 1.82 | | 2.88 | | 2.48 | | 3.33 | | 3.01 | | 3.22 | | 2.75 | | 2.67 |
| | maximum value | | 3.33 | | | 3.61 | | 4.33 | | 3.94 | | 3.53 | | 4.19 | | 4.52 | | 3.96 | | 3.64 | | 5.27 |
| | sample size | | 108 | | | 108 | | 108 | | 108 | | 108 | | 108 | | 108 | | 108 | | 108 | | 108 |

Table A8-3 Pharmacophore protein distances

| | | Pharmacophore element | | | | | | | | | | | | | | |
|---|---|---|---|---|---|---|---|---|---|---|---|---|---|---|---|---|
| | | N1 | | | | | | C7 | | | | | | O4 | | |
| | | protein | | | | | | | | | | | | | | |
| | | GLY_667 | | GLY_656 | | SER_628 | | CYS_660 | | CYS_629 | | GLY_661 | | ASP_627 | | SER_657 | | GLY_656 | | SER_628 | | CYS_660 | |
| 1 | 14 | HA2 | 3.80 | HA3 | 2.39 | O | 3.27 | HA | 3.82 | HA | 3.17 | H | 4.04 | HB3 | 5.20 | O | 2.68 | HA3 | 3.17 | O | 3.50 | HA | 5.32 |
| 2 | 54_A | HA2 | 3.78 | HA3 | 2.55 | O | 3.09 | HA | 3.39 | HA | 3.09 | H | 4.22 | HB3 | 5.19 | H | 2.75 | HA3 | 3.30 | O | 3.38 | HB2 | 4.19 |
| 3 | 54_B | HA2 | 3.78 | HA3 | 2.55 | O | 3.09 | HA | 3.39 | HA | 3.09 | H | 4.22 | HB3 | 5.19 | O | 2.75 | HA3 | 3.30 | O | 3.38 | HB2 | 4.19 |
| 4 | 1129 | HA2 | 3.57 | HA3 | 3.00 | O | 2.95 | HG | 1.07 | HA | 3.35 | H | 4.30 | OD2 | 4.25 | O | 3.25 | HA3 | 3.56 | O | 3.67 | HG | 3.37 |
| 5 | 1034 | HA2 | 3.67 | HA3 | 3.36 | O | 2.57 | HB3 | 1.55 | H | 3.46 | H | 4.11 | OD2 | 4.11 | O | 3.50 | HA3 | 3.90 | O | 3.43 | HB3 | 3.80 |

TABLE A8-continued

| | | HA2 | | HA3 | | | HA | | HA | | OD2/HD2 | | HA3 | | | HA3 | | HB2/SG/etc | |
|---|---|---|---|---|---|---|---|---|---|---|---|---|---|---|---|---|---|---|---|
| 6 | 1024 | HA2 | 3.79 | HA3 | 2.97 | O | 2.94 | HA | 2.63 | HA | 3.32 | H | 3.87 | OD2 | 3.08 | HA3 | 3.52 | O | 3.64 | HB2 | 5.18 |
| 7 | 1042_1 | HA2 | 3.84 | HA3 | 3.11 | O | 3.06 | HA | 2.49 | HA | 3.56 | H | 3.49 | OD2 | 3.06 | HA3 | 3.77 | O | 3.59 | SG | 4.30 |
| 8 | 1042_2 | HA2 | 4.12 | HA3 | 3.26 | O | 4.59 | HA | 2.46 | HA | 3.89 | H | 4.45 | OD2 | 2.74 | HA3 | 3.95 | O | 5.00 | SG | 4.34 |
| 9 | 1042_3 | HA2 | 4.11 | HA3 | 3.89 | OG | 3.18 | SG | 3.22 | HA | 2.61 | H | 4.07 | OD2 | 2.89 | HA3 | 4.36 | OG | 4.62 | SG | 4.32 |
| 10 | 2018 | HA2 | 3.93 | HA3 | 3.36 | O | 3.05 | HA | 2.22 | HA | 3.24 | H | 4.21 | OD2 | 2.85 | HA3 | 3.91 | O | 3.56 | HB3 | 4.02 |
| 11 | 1059 | HA2 | 3.82 | HA3 | 3.55 | O | 3.27 | HA | 2.40 | HA | 3.49 | H | 4.22 | OD2 | 3.26 | HA3 | 4.07 | O | 3.72 | SG | 3.37 |
| 12 | 1088_A | HA2 | 3.96 | HA3 | 2.90 | O | 3.26 | HB3 | 2.40 | HA | 3.60 | H | 4.02 | OD2 | 3.46 | HA3 | 3.40 | O | 3.78 | HB3 | 3.93 |
| 13 | 1088_B | HA2 | 3.76 | HA3 | 3.15 | O | 3.05 | HA | 2.40 | HA | 3.60 | H | 4.08 | OD2 | 3.46 | HA3 | 3.40 | O | 3.78 | HB3 | 3.82 |
| 14 | 1036_1 | HA2 | 3.69 | HA3 | 3.48 | O | 2.98 | HA | 2.64 | HA | 3.25 | H | 4.41 | OD2 | 3.18 | HA3 | 3.69 | O | 3.48 | SG | 5.28 |
| 15 | 1036_2_1 | HA2 | 3.74 | HA3 | 3.30 | O | 2.73 | HA | 2.71 | HA | 3.41 | H | 4.19 | OD2 | 3.09 | HA3 | 4.03 | O | 3.68 | H | 4.53 |
| 16 | 1036_2_2 | HA2 | 4.01 | HA3 | 3.25 | O | 3.06 | HA | 2.43 | HA | 3.23 | H | 4.34 | OD2 | 3.06 | HA3 | 3.82 | O | 3.55 | HB2 | 4.46 |
| 17 | 1081 | HA2 | 3.83 | HA3 | 2.94 | O | 2.87 | HA | 2.48 | HA | 3.59 | H | 3.74 | OD2 | 3.21 | HA3 | 3.73 | O | 3.64 | SG | 4.21 |
| 18 | 1063 | HA2 | 4.07 | HA3 | 3.00 | O | 3.28 | HA | 2.51 | HA | 3.65 | H | 4.01 | OD2 | 3.03 | HA3 | 3.42 | O | 3.70 | HB2 | 4.72 |
| 19 | 1065 | HA2 | 3.81 | HA3 | 3.29 | O | 2.95 | HA | 2.37 | HA | 3.59 | H | 3.79 | OD2 | 3.21 | HA3 | 3.57 | O | 3.55 | SG | 3.54 |
| 20 | 1030_A | HA2 | 3.81 | HA3 | 3.29 | O | 3.35 | HA | 2.46 | HA | 3.45 | H | 4.14 | OD2 | 2.96 | HA3 | 3.89 | O | 3.68 | HB2 | 3.54 |
| 21 | 1030_B | HA2 | 3.72 | HA3 | 3.08 | O | 3.35 | HA | 2.46 | HA | 3.45 | H | 4.34 | OD2 | 2.96 | HA3 | 3.89 | O | 3.68 | SG | 4.31 |
| 22 | 1037 | HA2 | 3.81 | HA3 | 3.28 | O | 2.71 | HA | 2.55 | HA | 3.54 | H | 3.82 | OD2 | 3.16 | HA3 | 3.65 | O | 3.61 | HB2 | 4.31 |
| 23 | 1118 | HA2 | 3.94 | HA3 | 2.83 | O | 3.18 | HA | 2.33 | HA | 3.46 | H | 4.00 | OD2 | 3.28 | HA3 | 3.80 | O | 3.53 | HB2 | 4.16 |
| 24 | 1090 | HA2 | 4.04 | HA3 | 2.51 | O | 3.36 | HA | 2.28 | HA | 3.50 | H | 3.98 | OD2 | 3.17 | HA3 | 3.31 | O | 3.87 | HB2 | 3.76 |
| 25 | 1007_1 | HA2 | 3.98 | HA3 | 2.63 | O | 2.88 | HA | 2.14 | HA | 3.64 | H | 2.89 | OD2 | 3.01 | HA3 | 3.31 | O | 4.02 | HB2 | 4.10 |
| 26 | 1007_2 | HA2 | 3.66 | HA3 | 3.20 | O | 2.70 | HA | 2.28 | HA | 3.64 | H | 3.39 | HD2 | 3.39 | HA3 | 3.38 | O | 3.55 | HB2 | 3.83 |
| 27 | 1149 | HA2 | 4.00 | HA3 | 2.53 | O | 3.03 | HA | 2.70 | HA | 3.20 | H | 3.83 | OD2 | 2.94 | HA3 | 3.88 | O | 3.30 | SG | 4.61 |
| 28 | 1021_A | HA2 | 3.99 | HA3 | 2.54 | O | 2.86 | HA | 2.61 | HA | 3.43 | H | 3.28 | OD2 | 2.96 | HA3 | 3.23 | O | 3.50 | HB2 | 4.61 |
| 29 | 1021_B | HA2 | 3.60 | HA3 | 3.31 | O | 2.90 | HA | 2.36 | HA | 3.44 | H | 3.82 | OD2 | 2.75 | HA3 | 3.23 | O | 3.50 | SG | 4.35 |
| 30 | 1097_1 | HA2 | 3.70 | HA3 | 3.16 | O | 2.89 | HA | 2.28 | HA | 3.37 | H | 4.09 | OD2 | 3.21 | HA3 | 3.84 | O | 3.56 | HB2 | 4.24 |
| 31 | 1097_2 | HA2 | 4.16 | HA3 | 2.38 | O | 3.36 | HA | 2.62 | HA | 3.33 | H | 4.07 | OD2 | 3.18 | HA3 | 3.70 | O | 3.48 | HB2 | 3.80 |
| 32 | 1031_1 | HA2 | 4.15 | HA3 | 2.35 | O | 3.39 | HA | 2.60 | HA | 3.61 | H | 3.17 | HD2 | 2.71 | HA3 | 3.10 | O | 3.70 | HB2 | 3.81 |
| 33 | 1031_2 | HA2 | 4.17 | HA3 | 2.39 | O | 3.37 | HB3 | 3.08 | HA | 3.68 | H | 3.05 | HD2 | 3.14 | HA3 | 3.06 | O | 3.75 | SG | 4.96 |
| 34 | 1031_3 | HA2 | 4.18 | HA3 | 2.27 | O | 3.42 | HB3 | 3.12 | HA | 3.53 | H | 3.10 | HD2 | 3.23 | HA3 | 3.14 | H | 3.71 | HA | 4.96 |
| 35 | 1031_4 | HA2 | 4.09 | HA3 | 3.17 | O | 3.35 | HA | 2.74 | HA | 3.47 | H | 3.03 | OD2 | 2.64 | HA3 | 3.02 | H | 3.75 | HA | 4.17 |
| 36 | 1153_A | HA2 | 3.57 | HA3 | 3.17 | O | 3.35 | SG | 2.27 | HA | 3.34 | H | 4.47 | OD2 | 2.56 | HA3 | 3.77 | O | 3.78 | SG | 4.17 |
| 37 | 1153_B | HA2 | 4.26 | HA3 | 2.47 | O | 2.67 | SG | 2.30 | HA | 3.42 | H | 3.52 | OD2 | 2.77 | HA3 | 3.14 | O | 3.62 | HB2 | 3.76 |
| 38 | 1025_1 | HA2 | 4.17 | HA3 | 3.43 | O | 2.66 | HA | 2.71 | HA | 3.48 | H | 3.62 | OD2 | 2.61 | HA3 | 3.99 | O | 3.70 | HB2 | 3.70 |
| 39 | 1025_2 | HA2 | 4.09 | HA3 | 2.17 | O | 2.63 | HA | 2.34 | HA | 3.60 | H | 3.23 | OD2 | 3.02 | HA3 | 2.80 | O | 3.74 | HB2 | 4.55 |
| 40 | 1025_3 | HA2 | 4.16 | HA3 | 2.69 | O | 2.70 | HA | 2.30 | HA | 3.51 | H | 3.27 | OD2 | 2.84 | HA3 | 3.34 | O | 3.76 | HB2 | 4.06 |
| 41 | 1025_4 | HA2 | 4.12 | HA3 | 3.07 | O | 2.73 | HA | 2.74 | HA | 3.35 | H | 3.76 | OD2 | 2.89 | HA3 | 3.67 | O | 3.96 | HA | 5.06 |
| 42 | 1025_5 | HA2 | 4.28 | HA3 | 3.11 | O | 3.07 | HA | 2.18 | HA | 3.37 | H | 3.69 | OD2 | 2.52 | HA3 | 3.77 | O | 3.37 | HB2 | 3.78 |
| 43 | 1025_6 | HA2 | 4.01 | HA3 | 3.03 | O | 3.06 | HA | 2.29 | HA | 3.51 | H | 4.12 | OD2 | 3.12 | HA3 | 3.54 | O | 3.76 | HB3 | 3.95 |
| 44 | 1089_A | HA2 | 4.01 | HA3 | 3.03 | O | 3.30 | HB3 | 2.29 | HA | 3.51 | H | 4.12 | OD2 | 3.12 | HA3 | 3.54 | O | 3.76 | HB3 | 3.95 |
| 45 | 1089_B | HA2 | 4.13 | HA3 | 2.71 | O | 3.01 | HB3 | 2.33 | HA | 3.54 | H | 3.03 | HD2 | 2.58 | HA3 | 3.36 | O | 3.51 | SG | 3.69 |
| 46 | 1912_1 | HA2 | 4.01 | HA3 | 2.56 | O | 2.99 | HA | 2.31 | HA | 3.57 | H | 3.56 | HD2 | 2.67 | HA3 | 3.25 | O | 3.54 | SG | 3.65 |
| 47 | 1012_2 | HA2 | 4.00 | HA3 | 2.47 | O | 3.07 | HA | 2.30 | HA | 3.77 | H | 3.50 | HD2 | 2.77 | HA3 | 3.16 | O | 3.70 | SG | 3.59 |
| 48 | 1078_0 | HA2 | 4.04 | HA3 | 2.62 | O | 3.03 | HA | 2.29 | HA | 3.64 | H | 3.55 | HD2 | 2.97 | HA3 | 3.22 | O | 3.61 | SG | 3.59 |
| 49 | 1078_11 | HA2 | 3.97 | HA3 | 2.47 | O | 3.07 | HA | 2.24 | HA | 3.76 | H | 3.27 | HD2 | 2.74 | HA3 | 3.16 | O | 3.70 | SG | 3.65 |
| 50 | 1078_12 | HA2 | 3.97 | HA3 | 2.49 | O | 3.07 | HA | 2.28 | HA | 3.80 | H | 3.52 | HD2 | 2.78 | HA3 | 3.20 | O | 3.72 | HA | 3.96 |
| 51 | 1078_13 | HA2 | 3.99 | HA3 | 2.47 | O | 3.06 | HA | 2.29 | HA | 3.77 | H | 3.47 | HD2 | 2.78 | HA3 | 3.15 | O | 3.69 | HB2 | 3.78 |
| 52 | 1078_14 | HA2 | 3.96 | HA3 | 2.50 | O | 3.08 | HB3 | 2.26 | HA | 3.79 | H | 3.50 | HD2 | 2.77 | HA3 | 3.20 | O | 3.73 | HB3 | 3.95 |
| 53 | 1078_15 | HA2 | 4.01 | HA3 | 2.45 | O | 3.30 | HB3 | 2.25 | HA | 3.77 | H | 3.45 | HD2 | 2.75 | HA3 | 3.15 | O | 3.70 | HB2 | 3.61 |
| 54 | 1078_16 | HA2 | 3.98 | HA3 | 2.48 | O | 3.05 | HA | 2.30 | HA | 3.80 | H | 3.49 | HD2 | 2.76 | HA3 | 3.19 | O | 3.73 | SG | 3.46 |
| 55 | 1078_2 | HA2 | 3.97 | HA3 | 2.47 | O | 3.05 | HA | 2.30 | HA | 3.77 | H | 3.54 | HD2 | 2.78 | HA3 | 3.18 | O | 3.63 | SG | 3.60 |
| 56 | 1078_3 | HA2 | 4.08 | HA3 | 2.57 | O | 2.99 | HA | 2.30 | HA | 3.64 | H | 3.47 | HD2 | 2.88 | HA3 | 3.21 | O | 3.63 | SG | 3.53 |
| 57 | 1078_4 | HA2 | 3.96 | HA3 | 2.43 | O | 3.06 | HA | 2.25 | HA | 3.79 | H | 3.47 | HD2 | 2.72 | HA3 | 3.15 | O | 3.70 | SG | 3.63 |

TABLE A8-continued

|  |  |  |  |  |  |  |  |  |  |  |  |  |  |  |  |  |  |
|---|---|---|---|---|---|---|---|---|---|---|---|---|---|---|---|---|---|
| 59 | 1078_5 | HA2 | 3.98 | HA3 | 2.46 | O | 3.07 | HA | 2.28 | HA | 3.78 | H | 3.48 | HD2 | 2.68 | H | 2.70 | HA3 | 3.17 | O | 3.71 | SG | 3.61 |
| 60 | 1078_6 | HA2 | 3.99 | HA3 | 2.49 | O | 3.08 | HA | 2.26 | HA | 3.80 | H | 3.49 | HD2 | 2.69 | H | 2.74 | HA3 | 3.20 | O | 3.72 | SG | 3.64 |
| 61 | 1078_7 | HA2 | 3.98 | HA3 | 2.47 | O | 3.06 | HA | 2.29 | HA | 3.77 | H | 3.50 | HD2 | 2.66 | H | 2.76 | HA3 | 3.15 | O | 3.70 | SG | 3.62 |
| 62 | 1078_8 | HA2 | 3.97 | HA3 | 2.44 | O | 3.07 | HA | 2.27 | HA | 3.74 | H | 3.52 | HD2 | 2.71 | H | 2.76 | HA3 | 3.13 | O | 3.69 | SG | 3.64 |
| 63 | 1078_9 | HA2 | 3.98 | HA3 | 2.45 | O | 3.05 | HA | 2.22 | HA | 3.83 | H | 3.42 | HD2 | 2.64 | H | 2.71 | HA3 | 3.17 | O | 3.71 | SG | 3.57 |
| 64 | 1145_A | HA2 | 3.55 | HA3 | 3.14 | O | 3.15 | HA | 2.66 | HA | 3.37 | H | 4.43 | OD2 | 3.80 | O | 2.98 | HA3 | 3.70 | O | 3.57 | HB2 | 4.52 |
| 65 | 1145_B | HA2 | 3.55 | HA3 | 3.14 | O | 3.15 | HA | 2.66 | HA | 3.37 | H | 4.43 | OD2 | 3.80 | O | 2.98 | HA3 | 3.70 | O | 3.57 | HB2 | 4.52 |
| 66 | 1050 | HA2 | 3.67 | HA3 | 3.07 | O | 3.15 | HA | 2.58 | HA | 3.29 | H | 4.25 | OD2 | 4.13 | O | 2.89 | HA3 | 3.61 | O | 3.54 | SG | 3.61 |
| 67 | 1253 | HA2 | 4.18 | HA3 | 2.67 | O | 2.85 | HA | 2.45 | HA | 3.45 | H | 3.82 | OD2 | 3.11 | O | 2.79 | HA3 | 3.25 | O | 3.42 | SG | 3.72 |
| 68 | 1257 | HA2 | 4.07 | HA3 | 2.72 | O | 2.73 | HA | 2.25 | HA | 3.59 | H | 3.98 | OD2 | 3.31 | O | 3.00 | HA3 | 3.30 | O | 3.44 | HB2 | 4.14 |
| 69 | 999_1 | HA2 | 3.85 | HA3 | 3.03 | O | 2.72 | HA | 2.47 | HB3 | 2.93 | H | 4.30 | OD2 | 3.98 | O | 2.72 | HA3 | 3.61 | O | 3.28 | HB2 | 4.12 |
| 70 | 999_2_A | HA2 | 3.67 | HA3 | 2.87 | O | 2.91 | HB2 | 2.39 | HA | 3.40 | H | 3.82 | OD2 | 4.09 | O | 3.09 | HA3 | 3.49 | O | 3.54 | HB2 | 4.00 |
| 71 | 999_2_B | HA2 | 3.67 | HA3 | 2.87 | O | 2.91 | HB2 | 2.39 | HA | 3.40 | H | 3.82 | OD2 | 4.09 | O | 3.09 | HA3 | 3.49 | O | 3.54 | HB2 | 4.00 |
| 72 | 1297_1 | HA2 | 4.11 | HA3 | 2.49 | O | 2.88 | HA | 2.23 | HA | 3.45 | H | 3.36 | OD2 | 2.99 | O | 2.75 | HA3 | 3.13 | O | 3.50 | HB2 | 4.37 |
| 73 | 1297_2 | HA2 | 4.10 | HA3 | 2.55 | O | 2.85 | HA | 2.25 | HA | 3.45 | H | 3.36 | OD2 | 2.96 | O | 2.76 | HA3 | 3.17 | O | 3.50 | HB2 | 4.41 |
| 74 | 1297_3 | HA2 | 4.08 | HA3 | 2.52 | O | 2.84 | HA | 2.18 | HA | 3.47 | H | 3.29 | OD2 | 2.93 | O | 2.83 | HA3 | 3.13 | O | 3.51 | HB2 | 4.28 |
| 75 | 1297_4 | HA2 | 4.09 | HA3 | 2.53 | O | 2.84 | HA | 2.26 | HA | 3.47 | H | 3.35 | OD2 | 2.94 | O | 2.77 | HA3 | 3.17 | O | 3.50 | HB2 | 4.29 |
| 76 | 1297_5 | HA2 | 4.11 | HA3 | 2.61 | O | 2.81 | HA | 2.17 | HA | 3.47 | H | 3.27 | OD2 | 2.92 | O | 2.86 | HA3 | 3.22 | O | 3.51 | HB2 | 4.17 |
| 77 | 1297_6 | HA2 | 4.10 | HA3 | 2.61 | O | 2.80 | HA | 2.17 | HA | 3.48 | H | 3.25 | OD2 | 2.88 | O | 2.88 | HA3 | 3.21 | O | 3.50 | HB2 | 4.12 |
| 78 | 1304 | HA2 | 4.17 | HA3 | 2.63 | O | 2.95 | HA | 2.44 | HA | 3.48 | H | 3.74 | OD2 | 3.01 | O | 2.78 | HA3 | 3.21 | O | 3.48 | SG | 3.73 |
| 79 | 1306_1 | HA2 | 3.21 | HA3 | 3.11 | O | 3.37 | HA | 2.51 | HA | 3.73 | H | 4.27 | OD2 | 3.70 | O | 3.12 | HA3 | 3.40 | O | 3.72 | HB2 | 3.84 |
| 80 | 1306_2 | HA2 | 3.35 | HA3 | 2.71 | O | 3.38 | HA | 2.76 | HA | 3.66 | H | 4.32 | OD2 | 3.75 | O | 2.86 | HA3 | 3.12 | O | 3.80 | HB2 | 4.28 |
| 81 | 1307 | HA2 | 4.13 | HA3 | 2.69 | O | 3.42 | HA | 2.56 | HA | 3.46 | H | 4.14 | OD2 | 3.57 | O | 3.04 | HA3 | 3.30 | O | 3.67 | SG | 4.18 |
| 82 | 1328_1 | HA2 | 4.16 | HA3 | 2.33 | O | 3.00 | HB3 | 2.07 | HA | 3.70 | H | 3.41 | OD2 | 3.04 | O | 2.52 | HA3 | 3.05 | O | 3.63 | HB3 | 3.28 |
| 83 | 1328_2 | HA2 | 4.18 | HA3 | 2.41 | O | 2.92 | HA | 2.10 | HA | 3.57 | H | 3.47 | OD2 | 2.99 | O | 2.57 | HA3 | 3.12 | O | 3.51 | SG | 3.61 |
| 84 | 1328_3 | HA2 | 4.14 | HA3 | 2.41 | O | 2.96 | HA | 2.08 | HA | 3.65 | H | 3.50 | OD2 | 3.08 | O | 2.51 | HA3 | 3.15 | O | 3.57 | SG | 3.63 |
| 85 | 1328_4 | HA2 | 4.11 | HA3 | 2.44 | O | 2.87 | HA | 2.08 | HA | 3.62 | H | 3.46 | OD2 | 2.96 | O | 2.63 | HA3 | 3.12 | O | 3.48 | SG | 3.62 |
| 86 | 1334 | HA2 | 4.04 | HA3 | 2.47 | O | 3.33 | SG | 2.65 | HA | 3.44 | H | 4.18 | OD2 | 3.53 | O | 2.93 | HA3 | 3.12 | O | 3.72 | SG | 3.64 |
| 87 | 1335 | HA2 | 3.79 | HA3 | 3.32 | O | 3.27 | HA | 2.68 | HA | 3.37 | H | 4.39 | OD2 | 3.96 | O | 2.92 | HA3 | 3.85 | O | 3.60 | SG | 3.75 |
| 88 | 1338 | HA2 | 4.26 | HA3 | 2.79 | O | 2.85 | HA | 2.32 | HA | 3.54 | H | 3.69 | OD2 | 3.02 | O | 2.74 | HA3 | 3.36 | O | 3.50 | HB2 | 4.64 |
| 89 | 1345_1 | HA2 | 3.45 | HA3 | 2.29 | O | 3.43 | HA | 2.91 | HA | 3.46 | H | 4.47 | OD2 | 3.95 | O | 3.08 | HA3 | 2.71 | O | 3.64 | SG | 3.92 |
| 90 | 1345_2 | HA2 | 3.63 | HA3 | 3.12 | O | 3.00 | HA | 2.72 | HA | 3.01 | H | 4.49 | OD2 | 3.68 | O | 3.48 | HA3 | 3.60 | O | 3.14 | SG | 3.73 |
| 91 | 1351 | HA2 | 4.12 | HA3 | 2.66 | O | 2.90 | HA | 2.21 | HA | 3.50 | H | 3.54 | OD2 | 2.87 | O | 2.67 | HA3 | 3.25 | O | 3.48 | SG | 3.62 |
| 92 | 1353 | HA2 | 4.18 | HA3 | 2.69 | O | 3.02 | HA | 2.46 | HA | 3.45 | H | 3.76 | OD2 | 3.02 | O | 2.72 | HA3 | 3.27 | O | 3.50 | SG | 3.86 |
| 93 | 1367 | HA2 | 4.19 | HA3 | 3.00 | O | 2.96 | HA | 2.48 | HA | 3.46 | H | 3.80 | OD2 | 3.09 | O | 2.58 | HA3 | 3.60 | O | 3.49 | SG | 3.77 |
| 94 | 1371 | HA2 | 3.95 | HA3 | 2.66 | O | 3.05 | HA | 2.38 | HA | 3.70 | H | 3.84 | OD2 | 3.21 | O | 3.05 | HA3 | 3.23 | O | 3.59 | SG | 3.47 |
| 95 | 1372_A | HA2 | 4.19 | HA3 | 2.70 | O | 2.96 | HA | 2.47 | HA | 3.41 | H | 3.89 | OD2 | 3.00 | O | 2.74 | HA3 | 3.28 | O | 3.48 | SG | 3.72 |
| 96 | 1372_B | HA2 | 4.18 | HA3 | 2.70 | O | 2.95 | HA | 2.47 | HA | 3.41 | H | 3.89 | OD2 | 3.01 | O | 2.75 | HA3 | 3.27 | O | 3.47 | SG | 3.72 |
| 97 | 1373 | HA2 | 4.18 | HA3 | 2.78 | O | 2.94 | HA | 2.42 | HA | 3.44 | H | 3.83 | OD2 | 3.01 | O | 2.76 | HA3 | 3.33 | O | 3.86 | SG | 3.74 |
| 98 | 1492 | HA2 | 3.81 | HA3 | 3.40 | O | 3.38 | HA | 2.22 | HA | 3.57 | H | 4.06 | OD2 | 3.99 | O | 3.30 | HA3 | 3.91 | O | 3.44 | HB2 | 3.95 |
| 99 | 1399 | HA2 | 4.16 | HA3 | 2.68 | O | 2.90 | HA | 2.41 | HA | 3.42 | H | 3.88 | OD2 | 3.06 | O | 2.76 | HA3 | 3.25 | O | 3.52 | SG | 3.79 |
| 100 | 1360 | HA2 | 4.20 | HA3 | 2.64 | O | 3.00 | HA | 2.47 | HA | 3.48 | H | 3.77 | OD2 | 3.05 | O | 2.77 | HA3 | 3.24 | O | 3.51 | SG | 3.78 |
| 101 | 1368 | HA2 | 4.14 | HA3 | 2.63 | O | 2.94 | HA | 2.48 | HA | 3.48 | H | 3.91 | OD2 | 3.12 | O | 2.79 | HA3 | 3.23 | O | 3.60 | SG | 3.83 |
| 102 | 1406 | HA2 | 4.12 | HA3 | 2.62 | O | 3.06 | HA | 2.37 | HA | 3.51 | H | 3.84 | OD2 | 3.12 | O | 2.71 | HA3 | 3.14 | O | 3.58 | HG | 3.02 |
| 103 | 1411 | HA2 | 4.23 | HA3 | 2.87 | O | 3.03 | HG | 1.74 | HA | 3.53 | H | 3.80 | OD2 | 3.00 | O | 2.64 | HA3 | 3.39 | O | 3.65 | SG | 3.89 |
| 104 | 1433 | HA2 | 4.03 | HA3 | 2.60 | O | 3.35 | HA | 2.82 | HA | 3.34 | H | 4.31 | OD2 | 3.58 | O | 2.94 | HA3 | 3.17 | O | 3.46 | SG | 3.79 |
| 105 | 1441 | HA2 | 4.16 | HA3 | 2.78 | O | 2.84 | HA | 2.47 | HA | 3.48 | H | 3.81 | OD2 | 3.04 | O | 2.82 | HA3 | 3.35 | O | 3.49 | SG | 3.79 |
| 106 | 1435 | HA2 | 4.13 | HA3 | 2.80 | O | 2.95 | HA | 2.40 | HA | 3.48 | H | 3.82 | OD2 | 3.07 | O | 2.77 | HA3 | 3.37 | O | 3.49 | SG | 3.67 |

TABLE A8-continued

| | | | | | | | | | | | | | | | | |
|---|---|---|---|---|---|---|---|---|---|---|---|---|---|---|---|---|
| 107 | 1450_A | HA2 | 4.06 | HA3 | 3.10 | O | 2.70 | HA | 2.73 | HA | 3.39 | OD2 | 4.06 | HA3 | 3.30 | O | 2.88 |
| 108 | 1450_B | HA2 | 4.06 | HA3 | 3.10 | O | 2.70 | HA | 2.73 | HA | 3.39 | OD2 | 4.06 | HA3 | 3.30 | O | 2.88 |
| | average distance | | 3.96 | | 3.05 | | 2.79 | | 2.44 | | 3.49 | | 3.82 | | 3.40 | | 2.87 |
| | standard deviation | | 0.21 | | 0.26 | | 0.34 | | 0.33 | | 0.20 | | 0.37 | | 0.30 | | 0.23 |
| | minimum value | | 3.21 | | 2.57 | | 2.17 | | 1.07 | | 2.61 | | 3.03 | | 2.71 | | 2.38 |
| | maximum value | | 4.28 | | 4.59 | | 3.89 | | 3.82 | | 3.89 | | 4.49 | | 4.36 | | 3.50 |
| | sample size | | 108 | | 108 | | 108 | | 108 | | 108 | | 108 | | 108 | | 108 |

Table A8-4 Pharmacophore Protein Distances

| | | Pharmacophore element | | | | | | | | | | | | | | |
|---|---|---|---|---|---|---|---|---|---|---|---|---|---|---|---|---|
| | | O4 | | | | N2 | | | | H3 | | | | CA2 | | |
| | | protein | | | | | | | | | | | | | | |
| | | CYS_629 | | ARG_630 | | SER_657 | | GLY_656 | | MET_658 | | SER_657 | | GLY_656 | | MET_658 | | SER_657 | | GLY_656 | | TYR_607 | |
| 1 | 14 | HA | 3.52 | HG3 | 2.07 | O | 2.87 | HA3 | 4.22 | HE2 | 2.43 | C | 3.76 | O | 2.85 | HE2 | 2.64 | C | 3.24 | O | 2.69 | HD1 | 3.03 |
| 2 | 54_A | HA | 3.33 | HG3 | 2.47 | O | 3.26 | H | 4.02 | HA | 3.15 | C | 3.88 | O | 3.02 | HA | 2.71 | C | 3.39 | O | 2.85 | HD2 | 3.18 |
| 3 | 54_B | HA | 3.33 | HG3 | 2.47 | O | 3.26 | H | 4.02 | HA | 3.15 | C | 3.88 | O | 3.02 | HA | 2.71 | C | 3.39 | O | 2.85 | HD2 | 3.18 |
| 4 | 1129 | HA | 3.34 | HG3 | 2.96 | O | 3.78 | HA3 | 4.37 | HA | 4.00 | HA | 3.69 | O | 2.29 | HA | 3.51 | O | 3.36 | O | 2.22 | HD1 | 3.07 |
| 5 | 1034 | HA | 2.96 | H | 3.08 | O | 3.77 | H | 4.61 | HA | 3.53 | O | 3.57 | O | 2.48 | HA | 3.08 | HA | 3.05 | O | 2.45 | HD1 | 3.62 |
| 6 | 1024 | HA | 3.41 | H | 2.89 | O | 3.50 | H | 4.14 | HA | 3.58 | HA | 3.63 | O | 2.60 | HA | 3.42 | O | 3.24 | O | 2.52 | HA | 2.64 |
| 7 | 1042_1 | HA | 3.29 | H | 3.78 | O | 3.35 | H | 4.33 | HA | 3.93 | C | 3.73 | O | 2.75 | HA | 2.76 | O | 3.22 | O | 2.63 | HA | 4.32 |
| 8 | 1042_2 | HA | 3.66 | H | 3.71 | O | 3.14 | H | 4.33 | HG3 | 3.08 | C | 3.73 | O | 2.82 | HG3 | 3.05 | O | 3.25 | O | 2.72 | HA | 4.49 |
| 9 | 1042_3 | HA | 2.98 | H | 3.09 | O | 4.14 | H | 4.91 | HG3 | 3.30 | HA | 4.26 | O | 3.19 | HG3 | 3.05 | HA | 4.01 | HA | 3.12 | HD1 | 4.90 |
| 10 | 2018 | HA | 3.45 | H | 3.08 | O | 3.75 | H | 4.25 | N | 3.81 | O | 3.93 | O | 2.66 | N | 3.29 | O | 3.47 | O | 2.50 | HD1 | 3.42 |
| 11 | 1059 | HA | 3.18 | HH11 | 2.69 | O | 3.68 | H | 4.34 | HA | 3.60 | O | 3.79 | O | 2.65 | HA | 3.11 | O | 3.27 | O | 2.57 | HD1 | 3.09 |
| 12 | 1088_A | HA | 3.52 | HG3 | 2.66 | O | 3.83 | H | 4.07 | HA | 3.94 | HA | 3.77 | O | 2.69 | HA | 3.48 | O | 3.25 | O | 2.61 | HD1 | 3.32 |
| 13 | 1088_B | HA | 3.52 | HG3 | 2.66 | O | 3.83 | H | 4.07 | HA | 3.94 | O | 3.77 | O | 2.69 | HA | 3.48 | O | 3.25 | O | 2.61 | HD1 | 3.32 |
| 14 | 1036_1 | HA | 3.20 | HG3 | 2.93 | O | 3.69 | H | 4.06 | HA | 3.87 | HA | 3.85 | O | 2.41 | HA | 3.38 | O | 3.44 | O | 2.28 | HD1 | 3.46 |
| 15 | 1036_2_1 | HA | 3.61 | H | 3.25 | O | 3.81 | O | 4.60 | HA | 3.61 | HA | 3.58 | O | 2.36 | HA | 3.11 | C | 3.26 | O | 2.25 | HA | 2.88 |
| 16 | 1036_2_2 | HA | 3.25 | H | 3.14 | O | 3.42 | H | 3.79 | N | 3.39 | O | 3.50 | O | 2.42 | N | 2.94 | O | 3.01 | O | 2.22 | HA | 2.83 |
| 17 | 1081 | HA | 3.37 | H | 3.54 | O | 3.93 | H | 3.86 | HA | 3.36 | C | 3.83 | O | 2.70 | HA | 2.91 | C | 3.40 | O | 2.61 | HD1 | 3.75 |
| 18 | 1063 | HA | 3.50 | HG3 | 2.82 | O | 3.73 | H | 3.80 | HA | 3.61 | C | 3.85 | O | 2.78 | HA | 3.10 | O | 3.39 | O | 2.69 | HD2 | 4.59 |
| 19 | 1065 | HA | 3.36 | HG3 | 3.38 | O | 3.75 | H | 3.98 | HA | 3.71 | O | 3.97 | O | 2.82 | HA | 3.26 | O | 3.50 | O | 2.68 | HD1 | 4.13 |
| 20 | 1030_A | HA | 3.20 | HG2 | 3.21 | O | 3.73 | H | 4.32 | HA | 3.69 | C | 3.87 | O | 2.63 | HA | 3.17 | C | 3.42 | O | 2.49 | HD1 | 3.30 |
| 21 | 1030_B | HA | 3.20 | HG2 | 3.21 | O | 3.73 | H | 4.32 | HA | 3.69 | C | 3.87 | O | 2.63 | HA | 3.17 | C | 3.42 | O | 2.49 | HD1 | 3.30 |
| 22 | 1037 | HA | 3.63 | HB2 | 3.59 | O | 3.50 | O | 4.20 | N | 3.54 | O | 3.53 | O | 2.37 | SD | 3.10 | HA | 3.05 | O | 2.21 | HD1 | 2.93 |
| 23 | 1118 | HA | 3.27 | HG3 | 2.89 | O | 3.70 | H | 4.20 | SD | 3.52 | O | 3.69 | O | 2.47 | H | 2.75 | O | 3.24 | O | 2.37 | HD1 | 4.09 |
| 24 | 1090 | HA | 3.37 | HG3 | 2.84 | O | 3.85 | H | 3.94 | HA | 3.83 | O | 3.80 | O | 2.53 | HA | 2.94 | C | 3.49 | O | 2.39 | HD1 | 3.48 |
| 25 | 1007_1 | HA | 3.39 | HG3 | 3.19 | O | 3.40 | H | 3.96 | H | 3.39 | HA | 3.87 | O | 2.69 | H | 2.95 | HA | 3.46 | O | 2.53 | HD1 | 3.35 |
| 26 | 1007_2 | HA | 3.31 | HB2 | 3.32 | O | 3.34 | H | 3.89 | HA | 3.29 | HA | 3.95 | O | 3.07 | HA | 2.90 | HA | 3.60 | O | 2.94 | HD1 | 3.22 |
| 27 | 1149 | HA | 3.10 | HH11 | 3.48 | O | 3.74 | O | 4.83 | HA | 3.24 | C | 4.09 | O | 2.91 | HA | 2.75 | C | 3.65 | O | 2.79 | HD1 | 3.48 |
| 28 | 1021_A | HA | 3.30 | HG3 | 3.51 | O | 3.51 | H | 3.81 | HA | 3.44 | C | 4.06 | O | 3.17 | HA | 2.94 | C | 3.59 | O | 3.07 | HD1 | 2.94 |
| 29 | 1021_B | HA | 3.30 | HG3 | 3.52 | O | 3.52 | H | 3.80 | HA | 3.45 | C | 4.06 | O | 3.15 | HA | 2.95 | C | 3.58 | O | 3.05 | HD1 | 2.94 |
| 30 | 1097_1 | HA | 3.31 | H | 3.31 | O | 3.53 | H | 4.39 | HA | 3.67 | O | 3.60 | O | 2.41 | HA | 3.19 | O | 3.14 | O | 2.30 | HD1 | 3.48 |
| 31 | 1097_2 | HA | 3.24 | H | 3.15 | O | 3.67 | H | 4.21 | HA | 3.56 | O | 3.72 | O | 2.48 | HA | 3.07 | O | 3.28 | O | 2.40 | HD1 | 3.29 |
| 32 | 1031_1 | HA | 3.36 | HD3 | 3.95 | O | 3.63 | H | 3.84 | HA | 3.47 | C | 4.09 | O | 3.13 | HA | 3.03 | C | 3.60 | O | 2.97 | HD2 | 3.66 |
| 33 | 1031_2 | HA | 3.42 | H | 4.08 | O | 3.62 | H | 3.80 | HA | 3.44 | C | 4.00 | O | 3.09 | HA | 3.03 | C | 3.52 | O | 2.94 | HD1 | 3.67 |
| 34 | 1031_3 | HA | 3.37 | H | 4.04 | O | 3.54 | H | 3.94 | HA | 3.33 | C | 3.89 | O | 3.05 | HA | 2.92 | C | 3.41 | O | 2.91 | HD1 | 3.37 |
| 35 | 1031_4 | HA | 3.42 | H | 3.89 | O | 3.55 | H | 3.84 | HA | 3.32 | C | 3.87 | O | 3.05 | HA | 2.92 | C | 3.39 | O | 2.91 | HD1 | 3.33 |

TABLE A8-continued

| | | | | | | | | | | | | | | | | |
|---|---|---|---|---|---|---|---|---|---|---|---|---|---|---|---|---|
| 36 | 1153_A | HA | 3.36 | HG2 | 3.01 | O | 3.58 | H | 4.16 | HA | 4.28 | O | 2.59 | HA | 3.76 | C | 3.64 | O | 2.47 | HD2 | 3.20 |
| 37 | 1153_B | HA | 3.36 | HG2 | 3.01 | O | 3.58 | H | 4.16 | HA | 4.28 | O | 2.59 | HA | 3.76 | HA | 3.64 | O | 2.47 | HD2 | 3.20 |
| 38 | 1025_1 | HA | 3.31 | H | 3.22 | O | 3.58 | HA3 | 4.23 | HA | 3.79 | O | 2.86 | HA | 3.28 | C | 3.60 | O | 2.68 | HD1 | 3.93 |
| 39 | 1025_2 | HA | 3.39 | H | 3.44 | O | 3.54 | H | 4.63 | C | 3.43 | O | 2.83 | HA | 2.88 | C | 3.65 | O | 2.72 | HD2 | 3.78 |
| 40 | 1025_3 | HA | 3.32 | HB3 | 3.39 | O | 4.38 | HA3 | 3.88 | HA | 2.96 | O | 3.00 | H | 2.63 | C | 3.77 | O | 2.86 | HD1 | 3.57 |
| 41 | 1025_4 | HA | 3.44 | H | 3.18 | O | 4.07 | H | 4.37 | C | 3.27 | O | 2.74 | HA | 2.77 | C | 3.77 | O | 2.55 | HD1 | 3.63 |
| 42 | 1025_5 | HA | 3.05 | H | 2.73 | O | 4.25 | H | 4.15 | C | 3.49 | O | 2.87 | HA | 3.00 | C | 3.85 | O | 2.62 | HD1 | 3.67 |
| 43 | 1025_6 | HA | 3.36 | H | 3.11 | O | 3.81 | H | 4.29 | HA | 3.40 | O | 3.70 | HA | 2.91 | C | 3.95 | O | 3.61 | HD1 | 3.84 |
| 44 | 1089_A | HA | 3.50 | H | 3.54 | O | 3.81 | H | 4.04 | HA | 3.94 | O | 2.49 | HA | 3.46 | C | 3.51 | O | 2.32 | HD1 | 3.59 |
| 45 | 1089_B | HA | 3.15 | H | 3.11 | O | 3.75 | H | 3.78 | HA | 3.94 | O | 2.49 | HA | 3.46 | C | 3.51 | O | 2.32 | HD1 | 3.59 |
| 46 | 1012_1 | HA | 3.28 | HG3 | 3.06 | O | 3.61 | H | 3.74 | HB2 | 3.60 | O | 2.92 | HA | 3.28 | C | 3.82 | O | 2.71 | HD1 | 4.05 |
| 47 | 1012_2 | HA | 3.42 | HG3 | 3.98 | O | 3.63 | H | 3.72 | H | 3.91 | O | 2.63 | N | 3.51 | HA | 3.69 | O | 2.41 | HD1 | 3.70 |
| 48 | 1078_1 | HA | 3.33 | H | 3.27 | O | 3.79 | H | 3.88 | C | 3.54 | O | 2.79 | HA | 3.22 | C | 3.43 | O | 2.65 | HD1 | 3.63 |
| 49 | 1078_10 | HA | 3.42 | HG2 | 3.97 | O | 3.62 | H | 3.72 | C | 3.63 | O | 2.94 | HA | 3.27 | C | 3.47 | O | 2.82 | HD1 | 3.77 |
| 50 | 1078_11 | HA | 3.43 | H | 3.48 | O | 3.59 | H | 3.74 | HA | 3.51 | O | 2.78 | HA | 3.18 | C | 3.42 | O | 2.63 | HD1 | 3.52 |
| 51 | 1078_12 | HA | 3.42 | HG2 | 3.52 | O | 3.63 | H | 3.73 | C | 3.47 | O | 2.73 | H | 3.15 | C | 3.36 | O | 2.59 | HD1 | 3.47 |
| 52 | 1078_13 | HA | 3.42 | HD3 | 3.33 | O | 3.59 | H | 3.76 | HA | 3.52 | O | 2.76 | H | 3.20 | C | 3.41 | O | 2.62 | HD1 | 3.55 |
| 53 | 1078_14 | HA | 3.42 | HG2 | 3.31 | O | 3.60 | H | 3.73 | C | 3.48 | O | 2.75 | H | 3.16 | C | 3.36 | O | 2.62 | HD1 | 3.50 |
| 54 | 1078_15 | HA | 3.42 | HD2 | 3.33 | O | 3.57 | H | 3.72 | HA | 3.47 | O | 2.75 | H | 3.15 | C | 3.37 | O | 2.61 | HD1 | 3.53 |
| 55 | 1078_16 | HA | 3.46 | HD2 | 3.28 | O | 3.56 | H | 3.74 | HA | 3.46 | O | 2.71 | H | 3.14 | C | 3.36 | O | 2.62 | HD1 | 3.53 |
| 56 | 1078_2 | HA | 3.40 | HD2 | 3.18 | O | 3.75 | H | 3.84 | HA | 3.49 | O | 2.94 | HA | 3.15 | C | 3.40 | O | 2.57 | HD2 | 3.56 |
| 57 | 1078_3 | HA | 3.30 | HD2 | 3.42 | O | 3.57 | H | 3.71 | C | 3.70 | O | 2.76 | H | 3.30 | C | 3.53 | O | 2.80 | HD2 | 3.89 |
| 58 | 1078_4 | HA | 3.42 | HD2 | 3.36 | O | 3.57 | H | 3.71 | C | 3.49 | O | 2.78 | H | 3.17 | C | 3.38 | O | 2.61 | HD1 | 3.52 |
| 59 | 1078_5 | HA | 3.43 | HD2 | 3.26 | O | 3.59 | H | 3.75 | HA | 3.48 | O | 2.76 | H | 3.16 | C | 3.40 | O | 2.62 | HD1 | 3.53 |
| 60 | 1078_6 | HA | 3.45 | HD2 | 3.23 | O | 3.57 | H | 3.72 | HA | 3.46 | O | 2.80 | H | 3.14 | C | 3.39 | O | 2.66 | HD1 | 3.58 |
| 61 | 1078_7 | HA | 3.42 | HD3 | 3.55 | O | 3.62 | H | 3.72 | HA | 3.54 | O | 2.78 | HA | 3.21 | C | 3.42 | O | 2.64 | HD1 | 3.59 |
| 62 | 1078_8 | HA | 3.43 | HD2 | 3.26 | O | 3.63 | H | 3.71 | C | 3.54 | O | 2.74 | H | 3.18 | C | 3.42 | O | 2.59 | HD1 | 3.59 |
| 63 | 1078_9 | HA | 3.42 | HD2 | 3.49 | O | 3.55 | H | 3.95 | HA | 3.42 | O | 2.77 | H | 3.10 | C | 3.35 | O | 2.63 | HD1 | 3.50 |
| 64 | 1145_A | HA | 3.25 | HG3 | 3.08 | O | 3.64 | H | 3.95 | N | 4.03 | O | 2.38 | HA | 3.59 | C | 3.38 | O | 2.25 | HD2 | 2.87 |
| 65 | 1145_B | HA | 3.25 | HG3 | 3.08 | O | 3.64 | H | 3.95 | N | 4.03 | O | 2.38 | HA | 3.59 | C | 3.38 | O | 2.25 | HD2 | 2.87 |
| 66 | 1050 | HA | 3.30 | HG3 | 3.06 | O | 3.53 | H | 4.34 | HA | 3.59 | O | 2.48 | HA | 3.23 | C | 3.21 | O | 2.43 | HD1 | 3.00 |
| 67 | 1253 | HA | 3.22 | HG3 | 3.03 | O | 3.84 | H | 3.74 | C | 3.69 | O | 2.96 | HA | 3.19 | HA | 3.83 | O | 2.78 | HD1 | 3.98 |
| 68 | 1257 | HA | 3.27 | HG3 | 3.28 | O | 3.83 | H | 3.78 | HA | 3.66 | O | 2.64 | HA | 3.19 | C | 3.61 | O | 2.43 | HD2 | 3.56 |
| 69 | 999_1 | HA | 2.76 | H | 3.12 | O | 3.70 | O | 4.44 | H | 4.15 | O | 2.51 | N | 3.68 | C | 3.22 | O | 2.36 | HD1 | 3.10 |
| 70 | 999_2_A | HA | 3.38 | HG3 | 2.63 | O | 3.77 | HA3 | 4.47 | HA | 3.98 | O | 2.54 | HA | 3.50 | C | 3.47 | O | 2.43 | HD1 | 2.81 |
| 71 | 999_2_B | HA | 3.38 | HG3 | 2.63 | O | 3.77 | HA3 | 4.47 | HA | 3.98 | O | 2.54 | HA | 3.50 | HA | 3.47 | O | 2.43 | HD1 | 2.81 |
| 72 | 1297_1 | HA | 3.14 | H | 3.20 | O | 3.77 | H | 4.09 | C | 3.86 | O | 2.79 | HA | 3.35 | C | 3.72 | O | 2.62 | HD1 | 3.77 |
| 73 | 1297_2 | HA | 3.14 | HG3 | 3.04 | O | 3.76 | H | 4.04 | HA | 3.90 | O | 2.76 | HA | 3.39 | O | 3.71 | O | 2.59 | HD1 | 3.79 |
| 74 | 1297_3 | HA | 3.07 | H | 3.01 | O | 3.75 | H | 4.15 | HA | 3.76 | O | 2.70 | HA | 3.26 | C | 3.65 | O | 2.61 | HD1 | 3.82 |
| 75 | 1297_4 | HA | 3.13 | HG3 | 3.05 | O | 3.76 | H | 4.05 | HA | 3.88 | O | 2.76 | HA | 3.37 | C | 3.68 | O | 2.54 | HD2 | 3.79 |
| 76 | 1297_5 | HA | 3.06 | H | 3.13 | O | 3.80 | H | 4.13 | HA | 3.78 | O | 2.75 | HA | 3.28 | C | 3.65 | O | 2.60 | HD1 | 3.80 |
| 77 | 1297_6 | HA | 3.01 | H | 3.12 | O | 3.79 | H | 4.19 | HA | 3.75 | O | 2.80 | HA | 3.26 | C | 3.65 | O | 2.65 | HD1 | 3.90 |
| 78 | 1304 | HA | 3.27 | H | 2.93 | O | 3.92 | H | 3.81 | HA | 3.83 | O | 2.95 | HA | 3.31 | C | 3.89 | O | 2.75 | HD1 | 4.00 |
| 79 | 1306_1 | HA | 3.75 | H | 3.46 | O | 3.79 | H | 3.89 | C | 3.82 | O | 2.18 | HA | 3.34 | C | 3.52 | O | 1.96 | HD2 | 4.12 |
| 80 | 1306_2 | HA | 3.37 | H | 3.17 | O | 3.88 | H | 4.08 | C | 4.20 | O | 2.46 | HA | 3.70 | C | 3.97 | O | 2.15 | HD1 | 4.64 |
| 81 | 1307 | HA | 3.52 | HG2 | 2.95 | O | 3.97 | H | 3.74 | HA | 4.06 | O | 3.25 | HA | 3.63 | O | 3.97 | O | 3.07 | HD1 | 4.00 |
| 82 | 1328_1 | HA | 3.26 | HG3 | 3.02 | O | 3.65 | H | 3.55 | HE2 | 3.70 | O | 2.97 | HA | 3.18 | C | 3.87 | O | 2.76 | HD2 | 3.99 |
| 83 | 1328_2 | HA | 3.19 | HG3 | 2.89 | O | 3.69 | H | 3.59 | HA | 3.57 | O | 3.02 | HA | 3.39 | C | 3.84 | O | 2.82 | HD1 | 4.05 |
| 84 | 1328_3 | HA | 3.30 | HG3 | 3.03 | O | 3.61 | H | 3.61 | HA | 3.76 | O | 2.89 | HA | 3.26 | C | 3.81 | O | 2.69 | HD2 | 3.90 |
| 85 | 1328_4 | HA | 3.19 | HG3 | 3.07 | O | 3.66 | H | 3.64 | HA | 3.72 | O | 2.86 | HA | 3.24 | C | 3.79 | O | 2.66 | HD2 | 3.90 |
| 86 | 1334 | HA | 3.27 | H | 2.93 | O | 3.85 | H | 4.11 | HA | 3.88 | O | 2.79 | HA | 3.21 | C | 3.74 | O | 2.61 | HD1 | 3.90 |
| 87 | 1335 | HA | 3.28 | HG3 | 2.85 | O | 3.55 | H | 4.09 | HA | 3.83 | O | 2.56 | HA | 3.40 | C | 3.40 | O | 2.44 | HD2 | 4.28 |
| 88 | 1338 | HA | 3.20 | HG3 | 3.33 | O | 3.77 | H | 3.71 | HA | 3.79 | O | 2.94 | HA | 3.28 | C | 3.71 | O | 2.74 | HD1 | 4.20 |

TABLE A8-continued

| | | PHE_529 | | CA2 | | PRO_608 | | | | PHE_529 | | CA4 | | PRO_608 | | | | |
|---|---|---|---|---|---|---|---|---|---|---|---|---|---|---|---|---|---|---|
| 89 | 1345_1 | HA | 3.49 | HE2 | 2.94 | HD2 | 4.26 | H | 3.80 | HE2 | 4.38 | HA2 | 3.16 | HE2 | 4.56 | N | 3.65 | HD1 | 3.52 | O | 2.41 | HD1 | 3.39 |
| 90 | 1345_2 | HA | 2.92 | HE1 | 3.38 | HD2 | 4.39 | H | 4.00 | HE1 | 4.32 | HA2 | 3.15 | HE1 | 4.90 | N | 4.19 | HA | 3.41 | O | 2.36 | HE1 | 3.03 |
| 91 | 1351 | HA | 3.14 | HE1 | 3.38 | HD2 | 4.39 | H | 3.78 | HE1 | 4.32 | HA2 | 3.15 | HE1 | 4.90 | HG3 | 3.76 | HA | 3.24 | O | 2.93 | HD1 | 3.83 |
| 92 | 1353 | HA | 3.28 | HE1 | 3.21 | HD2 | 4.10 | H | 3.95 | HE1 | 3.86 | H | 3.14 | HE1 | 4.02 | HA | 3.69 | HA | 3.60 | O | 3.00 | HD1 | 4.41 |
| 93 | 1367 | HA | 3.23 | HE2 | 3.60 | HD2 | 2.94 | H | 4.03 | HE2 | 4.03 | HA2 | 3.44 | HE2 | 2.99 | HG2 | 3.69 | HG2 | 2.06 | O | 3.03 | HD1 | 3.69 |
| 94 | 1371 | HA | 3.36 | HE2 | 3.52 | HD2 | 3.77 | HA3 | 4.57 | HD1 | 3.82 | H | 3.12 | HE1 | 2.99 | HA | 4.44 | HA | 3.14 | O | 2.95 | HE1 | 3.51 |
| 95 | 1372_A | HA | 3.20 | HD1 | 3.81 | HD3 | 3.44 | H | 2.85 | HE1 | 3.31 | HA2 | 3.24 | HE1 | 3.65 | HA | 3.76 | HA | 3.40 | O | 2.93 | HE1 | 3.48 |
| 96 | 1372_B | HA | 3.20 | HE1 | 3.48 | HD3 | 3.39 | H | 2.86 | HE1 | 3.82 | H | 3.09 | HE1 | 3.20 | HG3 | 3.91 | HA | 3.38 | O | 2.72 | HE1 | 3.92 |
| 97 | 1373 | HA | 3.18 | HE1 | 2.72 | HD3 | 3.82 | H | 2.92 | HE1 | 3.89 | HA2 | 2.24 | HE1 | 3.28 | HA | 3.90 | HA | 3.07 | O | 2.76 | HD1 | 4.03 |
| 98 | 1492 | HA | 3.48 | HE2 | 3.04 | HD2 | 4.05 | H | 3.65 | HE2 | 3.94 | H | 3.15 | HE2 | 3.61 | HA | 3.67 | HA | 2.40 | O | 2.27 | HD2 | 4.06 |
| 99 | 1399 | HA | 3.21 | HE1 | 3.22 | HD2 | 3.81 | HG3 | 3.16 | HE1 | 4.14 | HA2 | 3.31 | HE1 | 3.94 | HA | 4.12 | HA | 2.97 | O | 2.77 | HD1 | 4.09 |
| 100 | 1360 | HA | 3.26 | HE1 | 2.77 | HD2 | 3.66 | HG3 | 2.96 | HE1 | 3.63 | HA2 | 3.15 | HE1 | 3.10 | HG3 | 3.69 | HA | 3.35 | O | 2.40 | HD1 | 4.08 |
| 101 | 1368 | HA | 3.36 | HE2 | 3.22 | HD2 | 3.83 | HG3 | 3.03 | HE1 | 3.80 | H | 3.31 | HE1 | 3.79 | HA | 3.86 | HA | 3.40 | O | 2.99 | HD1 | 3.53 |
| 102 | 1406 | HA | 3.29 | HE1 | 3.40 | HD2 | 3.83 | H | 2.92 | HE2 | 3.93 | H | 3.25 | HE1 | 4.18 | HA | 3.82 | HA | 3.54 | O | 2.94 | HD1 | 4.28 |
| 103 | 1411 | HA | 3.28 | HE1 | 3.33 | HD2 | 3.33 | H | 3.40 | HE1 | 3.93 | H | 3.14 | HE1 | 3.86 | HA | 3.88 | HA | 3.03 | O | 3.03 | HE1 | 4.05 |
| 104 | 1433 | HA | 3.33 | HE2 | 3.28 | HD2 | 3.98 | HG3 | 3.33 | HE2 | 3.98 | HA2 | 3.25 | HE2 | 3.79 | HA | 3.73 | HA | 2.89 | O | 2.71 | HD1 | 3.65 |
| 105 | 1441 | HA | 3.22 | HE1 | 3.22 | HD2 | 3.00 | H | 2.84 | HE1 | 3.93 | H | 3.18 | HE1 | 3.86 | HA | 3.74 | HA | 3.48 | O | 2.55 | HD1 | 4.05 |
| 106 | 1435 | HA | 3.19 | HE1 | 3.00 | HD2 | 3.19 | HG3 | 3.22 | HE1 | 3.92 | HA2 | 3.24 | HE1 | 4.07 | HA | 3.73 | HA | 3.32 | O | 2.80 | HE1 | 4.02 |
| 107 | 1450_A | HA | 3.35 | HE1 | 3.34 | HD2 | 2.92 | HG3 | 3.00 | HE1 | 3.92 | HA2 | 3.15 | HE1 | 4.38 | HA | 3.74 | HA | 3.52 | O | 2.77 | HD2 | 3.48 |
| 108 | 1450_B | HA | 3.35 | HE1 | 3.42 | HD2 | 2.92 | HG3 | 2.92 | HE1 | 4.30 | H | 2.86 | HE1 | 4.48 | HA | 3.74 | HA | 3.52 | O | 2.66 | HD1 | 3.48 |
| | 1081 | HA | 3.31 | HE1 | 3.38 | HD2 | 3.19 | HA | 3.72 | HE1 | 3.76 | H | 3.04 | HE2 | 3.99 | HA | 3.99 | HA | 3.22 | O | 2.62 | HD1 | 3.62 |
| | average distance | | | | 0.16 | | 2.07 | | 0.21 | | | | | | 0.28 | | 0.29 | | 0.27 | | 0.24 | | 0.44 |
| | standard deviation | | 0.16 | | 0.37 | | 2.07 | | 0.21 | | | | | | 3.44 | | 3.55 | | 2.06 | | 2.18 | | 2.64 |
| | minimum value | | 2.76 | | | | | | 2.87 | | | | | | | | | | | | | | |
| | maximum value | | 3.75 | | 4.57 | | 4.75 | | 4.38 | | | | | | 4.58 | | 4.91 | | 3.76 | | 3.70 | | 4.90 |
| | sample size | | 108 | | 108 | | 108 | | 108 | | | | | | 108 | | 108 | | 108 | | 108 | | 108 |

Table A8-5 Pharmacophore protein distances

| | | Pharmacophore element | | | | | | | | | | | |
|---|---|---|---|---|---|---|---|---|---|---|---|---|---|
| | | CA2 | | C2 | | CA4 | | C4 | | CA5 | | | |
| | | PHE_529 | PRO_608 | GLY_528 | TYR_607 | PHE_529 | PRO_608 | GLY_656 | TRP_655 | PRO_608 | TYR_607 | | |
| 1 | 14 | HE2 2.94 | HD2 4.26 | HA2 3.16 | HE1 4.38 | HE2 4.56 | HD2 4.18 | O 3.61 | HE3 4.07 | HD2 4.18 | HD1 3.14 | | |
| 2 | 54_A | HE1 3.38 | HD2 4.39 | HA2 3.15 | HE2 2.87 | HE1 4.32 | HD3 4.49 | O 3.79 | HE3 4.07 | HD3 4.49 | HE2 3.00 | | |
| 3 | 54_B | HE1 3.38 | HD2 4.39 | HA2 3.15 | HE2 2.87 | HE1 4.32 | HD3 4.49 | O 3.79 | HE3 4.07 | HD3 4.49 | HE2 3.00 | | |
| 4 | 1129 | HE1 3.21 | HD2 4.10 | H 3.14 | HE1 3.29 | HE1 3.86 | HD3 3.42 | O 2.92 | HE3 3.65 | HD2 3.42 | HE1 3.36 | | |
| 5 | 1034 | HE2 3.60 | HD2 2.94 | HA2 3.44 | HE2 3.89 | HE2 4.03 | HD2 2.64 | O 3.18 | HE3 3.90 | HD2 2.64 | HE1 3.48 | | |
| 6 | 1024 | HE2 3.52 | HD2 3.77 | H 3.12 | HE1 2.95 | HE2 3.82 | HD2 3.31 | O 3.48 | HE3 4.01 | HD2 3.31 | HE1 2.98 | | |
| 7 | 1042_1 | HD1 3.81 | HD3 3.44 | HA2 3.24 | HE1 4.29 | HD1 3.31 | HD3 3.09 | O 3.46 | HE3 3.77 | HD3 3.09 | HE1 3.65 | | |
| 8 | 1042_2 | HE1 3.48 | HD3 3.39 | H 3.09 | HE1 4.35 | HE1 3.82 | HD3 3.24 | O 3.24 | HE3 3.94 | HD3 3.24 | HD1 3.63 | | |
| 9 | 1042_3 | HE1 2.72 | HD3 3.82 | HA2 2.24 | HE1 5.63 | HE1 3.89 | HG3 3.32 | O 3.58 | HE3 4.05 | HG3 3.32 | HA 4.32 | | |
| 10 | 2018 | HE2 3.04 | HD2 4.05 | H 3.15 | HE2 3.54 | HE2 3.94 | HG2 3.64 | O 3.43 | HE3 3.81 | HG2 3.64 | HD1 3.62 | | |
| 11 | 1059 | HE1 3.22 | HD2 3.81 | HA2 3.31 | HE1 3.27 | HE1 4.14 | HG2 3.03 | O 3.20 | HE3 4.05 | HG2 3.03 | HD1 3.27 | | |
| 12 | 1088_B | HE1 2.77 | HD2 3.66 | H 3.25 | HE1 3.54 | HE1 3.63 | HG2 3.53 | O 3.22 | HE3 4.01 | HG2 3.53 | HD1 3.51 | | |
| 13 | 1088_B | HE1 3.13 | HD2 3.83 | H 3.31 | HE1 3.64 | HE1 3.80 | HG2 3.85 | O 3.16 | HE3 3.75 | HG2 3.85 | HD1 3.68 | | |
| 14 | 1036_1 | HD1 3.34 | HD2 4.04 | H 3.18 | HE1 3.26 | HE1 4.10 | HD2 3.64 | O 3.07 | HE3 3.89 | HD2 3.64 | HD1 3.12 | | |
| 15 | 1036_2_1 | HE1 3.42 | HD2 4.28 | H 2.86 | HE1 3.11 | HE1 4.30 | HD2 3.81 | O 3.35 | HE3 3.66 | HD2 3.81 | HD1 2.74 | | |
| 16 | 1036_2_2 | HE1 3.38 | HD2 4.75 | H 3.04 | HE2 3.60 | HE1 3.76 | HG3 4.41 | O 3.27 | HE3 4.23 | HD2 4.41 | HE2 3.60 | | |
| 17 | 1081 | HE1 3.38 | HD2 4.75 | H 3.04 | HE2 3.60 | HE1 3.76 | HG3 4.41 | O 3.27 | HE3 4.23 | HD2 4.41 | HE2 3.60 | | |

TABLE A8-continued

| | | | | | | | | | | | | | | | | | |
|---|---|---|---|---|---|---|---|---|---|---|---|---|---|---|---|---|---|
| 18 | 1063 | HE1 | 3.14 | HD2 | 4.82 | HE1 | 3.65 | HG3 | 5.00 | H | 2.88 | HE1 | 4.25 | O | 3.33 | HE3 | 4.09 | HG3 | 4.68 | HD1 | 4.11 |
| 19 | 1065 | HE2 | 2.79 | HD2 | 3.59 | HE2 | 3.73 | HG3 | 3.28 | HA2 | 3.22 | HE1 | 3.99 | O | 3.46 | HE3 | 3.81 | HG3 | 3.07 | HD1 | 3.92 |
| 20 | 1030_A | HE2 | 3.07 | HD2 | 3.42 | HE2 | 3.88 | HG2 | 3.09 | HA2 | 3.11 | HE1 | 3.45 | O | 3.33 | HE3 | 3.79 | HD3 | 3.20 | HD1 | 3.32 |
| 21 | 1030_B | HE2 | 3.07 | HD2 | 4.28 | HE2 | 3.88 | HG2 | 3.09 | HA2 | 3.11 | HE1 | 3.45 | O | 3.33 | HE3 | 3.79 | HD3 | 3.20 | HD1 | 3.32 |
| 22 | 1037 | HE1 | 3.61 | HD2 | 4.98 | HE1 | 4.25 | HD2 | 4.28 | H | 3.32 | HE1 | 3.12 | O | 3.26 | HE3 | 3.58 | HD2 | 3.98 | HD1 | 3.14 |
| 23 | 1118 | HE1 | 3.15 | HD2 | 4.04 | HE1 | 3.49 | HG2 | 5.23 | HA2 | 3.39 | HE1 | 4.10 | O | 3.12 | HE3 | 4.09 | HD3 | 4.99 | HE1 | 4.06 |
| 24 | 1090 | HE2 | 2.91 | HD2 | 2.45 | HE1 | 3.93 | HG3 | 4.11 | HA2 | 3.24 | HE1 | 3.54 | O | 3.25 | HE3 | 3.71 | HD2 | 4.04 | HD1 | 3.67 |
| 25 | 1007_1 | HE1 | 3.36 | HD2 | 2.40 | HE1 | 4.14 | HG2 | 2.40 | H | 3.49 | HE1 | 3.19 | O | 3.49 | HE3 | 3.81 | HG2 | 2.21 | HD1 | 2.89 |
| 26 | 1007_2 | HE2 | 3.32 | HD2 | 4.16 | HE2 | 3.92 | HD2 | 2.08 | H | 3.40 | HE1 | 3.11 | O | 3.69 | HE3 | 3.85 | HD2 | 2.22 | HD1 | 3.09 |
| 27 | 1149 | HE2 | 3.05 | HD2 | 3.41 | HE2 | 4.04 | HG3 | 4.51 | H | 3.41 | HE1 | 3.01 | O | 3.52 | HE3 | 3.66 | HD2 | 4.06 | HD1 | 2.46 |
| 28 | 1021_A | HE1 | 3.11 | HD2 | 3.41 | HE1 | 4.06 | HG3 | 3.26 | H | 2.95 | HE1 | 2.90 | O | 3.70 | HE3 | 4.07 | HD3 | 2.84 | HD1 | 3.09 |
| 29 | 1021_B | HE1 | 3.10 | HD2 | 3.43 | HE1 | 4.05 | HG3 | 3.27 | H | 2.94 | HE1 | 2.90 | O | 3.68 | HE3 | 4.06 | HD3 | 2.86 | HD1 | 3.08 |
| 30 | 1097_1 | HE2 | 3.14 | HD3 | 3.88 | HE1 | 3.98 | HG2 | 3.91 | HA2 | 3.20 | HE1 | 3.53 | O | 3.12 | HE3 | 3.52 | HD3 | 3.72 | HD1 | 3.41 |
| 31 | 1097_2 | HE1 | 2.91 | HD2 | 3.71 | HE1 | 3.72 | HD3 | 3.71 | H | 3.06 | HE1 | 3.49 | O | 3.09 | HE3 | 3.42 | HD3 | 3.25 | HD1 | 3.08 |
| 32 | 1031_L1 | HE1 | 3.16 | HD2 | 3.05 | HE1 | 3.76 | HG3 | 3.31 | H | 3.19 | HE1 | 3.28 | O | 3.80 | HE3 | 3.94 | HD3 | 3.07 | HD1 | 3.50 |
| 33 | 1031_2 | HE1 | 3.22 | HD2 | 3.02 | HE1 | 3.82 | HG3 | 3.30 | H | 3.20 | HE1 | 3.26 | O | 3.77 | HE3 | 3.92 | HD3 | 3.06 | HD1 | 3.48 |
| 34 | 1031_3 | HE1 | 3.17 | HD2 | 3.00 | HE1 | 3.76 | HG3 | 3.40 | H | 3.26 | HE1 | 3.02 | O | 3.71 | HE3 | 3.96 | HD3 | 3.02 | HD1 | 3.19 |
| 35 | 1031_4 | HE1 | 3.17 | HD2 | 2.97 | HE1 | 3.73 | HG3 | 3.35 | H | 3.19 | HE1 | 2.99 | O | 3.73 | HE3 | 3.96 | HD2 | 2.96 | HD1 | 3.16 |
| 36 | 1153_A | HE1 | 3.32 | HD2 | 4.47 | HE1 | 3.44 | HD2 | 4.63 | H | 3.05 | HE2 | 3.20 | O | 3.28 | HE3 | 3.87 | HD3 | 4.25 | HE2 | 3.01 |
| 37 | 1153_B | HE1 | 3.32 | HD2 | 4.47 | HE1 | 3.44 | HD2 | 4.63 | H | 3.05 | HE2 | 3.20 | O | 3.28 | HE3 | 3.87 | HD3 | 4.25 | HE2 | 3.01 |
| 38 | 1025_1 | HE2 | 3.64 | HD3 | 3.34 | HE2 | 4.56 | HG2 | 2.96 | H | 2.73 | HE1 | 4.04 | O | 3.63 | HE3 | 3.88 | HG2 | 3.00 | HD1 | 3.74 |
| 39 | 1025_2 | HE1 | 2.81 | HD2 | 3.22 | HE1 | 3.42 | HG3 | 2.83 | H | 2.80 | HE1 | 4.15 | O | 3.46 | HE3 | 4.18 | HD2 | 2.95 | HD1 | 4.05 |
| 40 | 1025_3 | HE1 | 3.08 | HD2 | 3.55 | HE1 | 3.98 | HG3 | 3.68 | H | 2.83 | HE1 | 3.72 | O | 3.63 | HE3 | 3.87 | HG2 | 3.18 | HD2 | 3.20 |
| 41 | 1025_4 | HE2 | 2.85 | HD2 | 4.23 | HE2 | 4.08 | HD2 | 3.44 | H | 2.77 | HE1 | 3.56 | O | 3.54 | HE3 | 3.80 | HG2 | 2.54 | HD1 | 3.27 |
| 42 | 1025_5 | HE1 | 3.18 | HD2 | 3.65 | HE1 | 4.21 | HG3 | 3.37 | H | 3.01 | HE1 | 3.85 | O | 3.81 | HE3 | 4.00 | HG3 | 3.25 | HD1 | 3.62 |
| 43 | 1025_6 | HE1 | 3.04 | HD2 | 3.19 | HE1 | 4.13 | HG3 | 3.07 | H | 2.68 | HE1 | 3.43 | O | 4.09 | HE3 | 3.96 | HG3 | 2.97 | HD1 | 3.37 |
| 44 | 1089_A | HE1 | 2.87 | HD2 | 4.07 | HE1 | 3.84 | HG3 | 4.23 | H | 3.25 | HE1 | 3.73 | O | 3.27 | HE3 | 3.71 | HG3 | 3.81 | HD1 | 3.78 |
| 45 | 1089_B | HE1 | 2.87 | HD2 | 4.07 | HE1 | 3.84 | HG3 | 4.23 | H | 3.25 | HE1 | 3.73 | O | 3.27 | HE3 | 3.71 | HG3 | 3.81 | HD1 | 3.78 |
| 46 | 1012_1 | HE1 | 2.84 | HD2 | 3.82 | HE2 | 4.04 | HG3 | 3.88 | H | 3.04 | HE1 | 3.95 | O | 3.77 | HE3 | 3.91 | HG3 | 3.66 | HD1 | 3.92 |
| 47 | 1012_2 | HE2 | 3.02 | HD2 | 3.59 | HE2 | 3.93 | HG3 | 3.86 | HA2 | 3.24 | HE1 | 3.49 | O | 3.57 | HE3 | 3.67 | HG3 | 3.62 | HD1 | 3.49 |
| 48 | 1078_1 | HE1 | 3.36 | HD2 | 2.94 | HE2 | 4.01 | HG3 | 2.83 | HA2 | 3.32 | HE1 | 3.67 | O | 3.52 | HE3 | 3.86 | HG3 | 2.68 | HD1 | 3.41 |
| 49 | 1078_10 | HE2 | 3.14 | HD2 | 2.98 | HE1 | 3.87 | HD2 | 2.80 | H | 3.33 | HE2 | 3.93 | O | 3.57 | HE3 | 4.02 | HG3 | 2.70 | HD1 | 3.68 |
| 50 | 1078_11 | HE1 | 3.41 | HD3 | 2.72 | HE2 | 4.04 | HG3 | 2.52 | H | 3.33 | HE1 | 3.61 | O | 3.51 | HE3 | 3.91 | HG3 | 2.42 | HD1 | 3.35 |
| 51 | 1078_12 | HE1 | 3.50 | HD2 | 2.86 | HE1 | 4.08 | HG3 | 2.76 | H | 3.39 | HE1 | 3.56 | O | 3.46 | HE3 | 3.87 | HG3 | 2.65 | HD1 | 3.32 |
| 52 | 1078_13 | HE1 | 3.37 | HD2 | 2.83 | HE1 | 4.00 | HG3 | 2.64 | H | 3.35 | HE1 | 3.64 | O | 3.50 | HE3 | 3.90 | HG3 | 2.54 | HD1 | 3.38 |
| 53 | 1078_14 | HE1 | 3.45 | HD2 | 2.78 | HE1 | 4.03 | HG3 | 2.63 | H | 3.39 | HE1 | 3.56 | O | 3.46 | HE3 | 3.85 | HG3 | 2.54 | HD1 | 3.29 |
| 54 | 1078_15 | HE1 | 3.43 | HD2 | 2.76 | HE1 | 4.03 | HG3 | 2.55 | H | 3.40 | HE1 | 3.59 | O | 3.48 | HE3 | 3.90 | HG3 | 2.43 | HD1 | 3.32 |
| 55 | 1078_16 | HE1 | 3.44 | HD2 | 2.91 | HE1 | 4.05 | HG3 | 2.80 | H | 3.39 | HE1 | 3.59 | O | 3.47 | HE3 | 3.87 | HG3 | 2.68 | HD1 | 3.36 |
| 56 | 1078_2 | HE1 | 3.44 | HD2 | 2.86 | HE1 | 4.03 | HG3 | 2.75 | H | 3.37 | HE1 | 3.61 | O | 3.46 | HE3 | 3.85 | HG3 | 2.60 | HD1 | 3.36 |
| 57 | 1078_3 | HE1 | 3.16 | HD2 | 3.06 | HE1 | 3.88 | HD2 | 2.91 | H | 3.26 | HE2 | 3.96 | O | 3.60 | HE3 | 3.98 | HG3 | 2.67 | HD1 | 3.70 |
| 58 | 1078_4 | HE1 | 3.47 | HD2 | 2.84 | HE1 | 4.04 | HG3 | 2.79 | H | 3.42 | HE1 | 3.55 | O | 3.50 | HE3 | 3.86 | HG3 | 2.65 | HD1 | 3.33 |
| 59 | 1078_5 | HE1 | 3.44 | HD2 | 2.75 | HE1 | 4.06 | HG3 | 2.62 | H | 3.36 | HE1 | 3.58 | O | 3.51 | HE3 | 3.87 | HG3 | 2.50 | HD1 | 3.34 |
| 60 | 1078_6 | HE1 | 3.45 | HD2 | 2.81 | HE1 | 4.02 | HG3 | 2.70 | H | 3.40 | HE1 | 3.63 | O | 3.52 | HE3 | 3.86 | HG3 | 2.54 | HD1 | 3.37 |
| 61 | 1078_7 | HE1 | 3.39 | HD2 | 2.92 | HE1 | 4.03 | HG3 | 2.81 | H | 3.35 | HE1 | 3.65 | O | 3.49 | HE3 | 3.89 | HG3 | 2.68 | HD2 | 3.40 |
| 62 | 1078_8 | HE1 | 3.42 | HD2 | 2.78 | HE1 | 4.03 | HG3 | 2.66 | H | 3.35 | HE1 | 3.64 | O | 3.51 | HE3 | 3.84 | HG3 | 2.49 | HD1 | 3.38 |
| 63 | 1078_9 | HE1 | 3.49 | HD2 | 2.80 | HE1 | 4.07 | HG3 | 2.64 | H | 3.41 | HE1 | 3.56 | O | 3.51 | HE3 | 3.90 | HG3 | 2.53 | HD1 | 3.34 |
| 64 | 1145_A | HE1 | 3.84 | HD2 | 4.06 | HE1 | 3.74 | HD2 | 4.32 | H | 3.39 | HE1 | 2.78 | O | 3.15 | HE3 | 3.98 | HG3 | 2.68 | HD1 | 3.11 |
| 65 | 1145_B | HE1 | 3.84 | HD2 | 3.89 | HE1 | 3.59 | HD2 | 4.18 | HA2 | 2.83 | HE1 | 2.83 | O | 3.03 | HE3 | 3.86 | HG3 | 3.93 | HE2 | 3.11 |
| 66 | 1050 | HE1 | 3.44 | HD2 | 3.85 | HE1 | 3.65 | HG2 | 3.80 | HA2 | 3.20 | HE1 | 4.06 | O | 3.72 | HE3 | 4.09 | HG3 | 3.84 | HE2 | 3.17 |
| 67 | 1253 | HE1 | 2.82 | HD2 | 4.22 | HE1 | 3.94 | HD2 | 4.26 | HA2 | 3.22 | HE1 | 3.71 | O | 3.51 | HE3 | 3.82 | HG3 | 3.93 | HD2 | 4.14 |
| 68 | 1257 | HE1 | 3.01 | HD2 | 3.47 | HE1 | 4.36 | HG2 | 3.51 | HA2 | 3.53 | HE2 | 3.18 | O | 3.30 | HE3 | 3.73 | HG3 | 3.11 | HD1 | 3.91 |
| 69 | 999_1 | HE1 | 3.35 | HD2 | 3.47 | HE1 | 3.50 | HG2 | 3.50 | HA2 | 3.42 | HE2 | 2.82 | O | 3.22 | HE3 | 3.77 | HD3 | 3.21 | HD1 | 2.83 |
| 70 | 999_2_A | HE2 | 3.51 | HD2 | 3.50 | HE2 | 4.26 | HG3 | 3.50 | H | 3.42 | HE1 | 2.82 | O | 3.22 | HE3 | 3.77 | HD3 | 3.21 | HD1 | 2.69 |

TABLE A8-continued

| | | | | | | | | | | | | | | | | | | |
|---|---|---|---|---|---|---|---|---|---|---|---|---|---|---|---|---|---|---|
| 71 | 999_2_B | HE2 | 3.51 | HD2 | 3.50 | HE2 | 4.26 | HG3 | 3.50 | H | 3.42 | HE1 | 2.82 | O | 3.22 | HE3 | 3.77 | HG3 | 3.21 | HD1 | 2.69 |
| 72 | 1297_1 | HE2 | 2.80 | HD2 | 3.25 | HE2 | 3.89 | HG3 | 3.22 | H | 3.05 | HE1 | 3.78 | O | 3.55 | HE3 | 3.76 | HG3 | 3.10 | HD1 | 3.39 |
| 73 | 1297_2 | HE2 | 2.83 | HD2 | 3.33 | HE2 | 3.90 | HG3 | 3.36 | H | 3.11 | HE1 | 3.80 | O | 3.53 | HE3 | 3.69 | HG3 | 3.23 | HD1 | 3.41 |
| 74 | 1297_3 | HE2 | 2.73 | HD2 | 3.38 | HE2 | 3.84 | HG3 | 3.40 | H | 3.05 | HE1 | 3.83 | O | 3.50 | HE3 | 3.79 | HG3 | 3.29 | HD1 | 3.47 |
| 75 | 1297_4 | HE2 | 2.84 | HD2 | 3.35 | HE2 | 3.91 | HG3 | 3.38 | H | 3.11 | HE1 | 3.79 | O | 3.48 | HE3 | 3.66 | HG3 | 3.24 | HD1 | 3.41 |
| 76 | 1297_5 | HE2 | 2.84 | HD2 | 3.38 | HE2 | 3.90 | HG3 | 3.38 | H | 3.09 | HE1 | 3.86 | O | 3.47 | HE3 | 3.74 | HG3 | 3.23 | HD1 | 3.43 |
| 77 | 1297_6 | HE2 | 2.73 | HD2 | 3.48 | HE2 | 3.85 | HG3 | 3.55 | H | 3.03 | HE1 | 3.91 | O | 3.51 | HE3 | 3.79 | HG3 | 3.43 | HD1 | 3.53 |
| 78 | 1304 | HE2 | 2.73 | HD2 | 3.25 | HE2 | 3.87 | HG2 | 2.79 | HA2 | 3.20 | HE1 | 4.02 | O | 3.74 | HE3 | 3.98 | HG3 | 2.73 | HD1 | 4.07 |
| 79 | 1306_1 | HE1 | 3.11 | HG2 | 3.29 | HE1 | 3.94 | HG3 | 2.57 | HA2 | 2.95 | HE1 | 3.72 | O | 3.14 | HE3 | 3.09 | HG2 | 2.23 | HD1 | 3.02 |
| 80 | 1306_2 | HE2 | 3.44 | HD2 | 3.54 | HE2 | 4.76 | HG2 | 3.21 | HA2 | 2.72 | HE1 | 4.24 | O | 3.54 | HE3 | 3.30 | HG2 | 2.86 | HD1 | 3.57 |
| 81 | 1307 | HE2 | 2.96 | HD2 | 3.31 | HE2 | 4.24 | HG2 | 2.81 | HA2 | 3.07 | HE1 | 3.85 | O | 3.92 | HE3 | 4.14 | HG2 | 2.74 | HD1 | 4.09 |
| 82 | 1328_1 | HE2 | 3.00 | HD2 | 3.11 | HE1 | 4.14 | HG3 | 3.10 | H | 3.53 | HE2 | 3.81 | O | 3.82 | HE3 | 3.99 | HG3 | 2.66 | HD2 | 3.75 |
| 83 | 1328_2 | HE2 | 3.01 | HD2 | 3.23 | HE1 | 4.18 | HG3 | 3.19 | H | 3.51 | HE2 | 3.90 | O | 3.84 | HE3 | 4.05 | HG3 | 2.76 | HD2 | 3.84 |
| 84 | 1328_3 | HE1 | 2.93 | HD2 | 3.01 | HE1 | 4.03 | HG2 | 2.99 | H | 3.51 | HE2 | 3.78 | O | 3.75 | HE3 | 3.96 | HG3 | 2.65 | HD2 | 3.60 |
| 85 | 1328_4 | HE2 | 2.89 | HD2 | 3.12 | HE2 | 3.99 | HG2 | 3.11 | H | 3.54 | HE2 | 3.79 | O | 3.70 | HE3 | 3.94 | HG3 | 2.77 | HD2 | 3.63 |
| 86 | 1334 | HE2 | 2.49 | HD2 | 3.91 | HE1 | 3.69 | HG3 | 3.70 | HA2 | 3.42 | HE1 | 4.17 | O | 3.57 | HE3 | 4.13 | HG3 | 3.44 | HD1 | 4.06 |
| 87 | 1335 | HE1 | 3.17 | HD2 | 4.16 | HE1 | 3.69 | HD2 | 4.39 | HA2 | 3.18 | HE1 | 3.16 | O | 3.21 | HE3 | 3.88 | HD2 | 4.01 | HD1 | 3.33 |
| 88 | 1338 | HE2 | 2.66 | HD2 | 3.77 | HE2 | 4.01 | HG3 | 3.91 | HA2 | 3.20 | HE1 | 4.09 | O | 3.72 | HE3 | 3.88 | HG3 | 3.68 | HD1 | 4.08 |
| 89 | 1345_1 | HE2 | 3.45 | HE2 | 3.25 | HE2 | 4.32 | HG3 | 2.93 | HA2 | 2.86 | HE1 | 3.20 | O | 3.22 | HE3 | 3.72 | HG2 | 2.66 | HD2 | 2.73 |
| 90 | 1345_2 | HE1 | 3.30 | HE2 | 3.50 | HE2 | 3.92 | HG3 | 3.60 | HA2 | 3.53 | HE1 | 3.36 | O | 2.95 | HE3 | 3.74 | HG3 | 3.13 | HD1 | 3.06 |
| 91 | 1351 | HE2 | 2.79 | HD2 | 4.25 | HE2 | 3.82 | HG2 | 4.52 | HA2 | 3.32 | HE1 | 3.79 | O | 3.64 | HE3 | 3.90 | HD3 | 4.24 | HD1 | 4.03 |
| 92 | 1353 | HE2 | 2.90 | HD2 | 3.12 | HE2 | 3.96 | HG2 | 2.70 | HA2 | 3.25 | HE1 | 4.37 | O | 3.85 | HE3 | 3.93 | HG2 | 2.45 | HA | 4.28 |
| 93 | 1367 | HE2 | 2.76 | HD2 | 3.76 | HE2 | 3.91 | HG3 | 3.65 | HA2 | 3.09 | HE1 | 3.75 | O | 3.91 | HE3 | 4.02 | HG3 | 3.47 | HD1 | 3.78 |
| 94 | 1371 | HE2 | 2.97 | HD2 | 3.45 | HE2 | 3.91 | HG3 | 3.53 | H | 2.83 | HE1 | 3.48 | O | 3.59 | HE3 | 4.26 | HD3 | 3.22 | HD1 | 3.64 |
| 95 | 1372_A | HE2 | 2.79 | HD2 | 3.18 | HE2 | 3.94 | HG2 | 2.75 | HA2 | 3.15 | HE1 | 3.95 | O | 3.76 | HE3 | 4.00 | HG2 | 2.70 | HD1 | 4.04 |
| 96 | 1372_B | HE2 | 2.79 | HD2 | 3.18 | HE2 | 3.94 | HG2 | 2.75 | HA2 | 3.15 | HE1 | 3.94 | O | 3.75 | HE3 | 3.99 | HG2 | 2.70 | HD1 | 4.04 |
| 97 | 1373 | HE2 | 2.71 | HD2 | 3.39 | HE1 | 3.89 | HG2 | 2.98 | HA2 | 3.08 | HE1 | 4.02 | O | 3.77 | HE3 | 4.03 | HG2 | 2.98 | HD1 | 4.09 |
| 98 | 1492 | HD1 | 3.54 | HD2 | 3.74 | HE2 | 3.79 | HG2 | 3.93 | H | 2.98 | HE2 | 4.07 | O | 3.17 | HE3 | 3.52 | HD3 | 3.67 | HD2 | 4.11 |
| 99 | 1399 | HE2 | 2.74 | HE2 | 3.85 | HE1 | 3.77 | HG3 | 3.83 | HA2 | 3.17 | HE1 | 4.09 | O | 3.77 | HE3 | 4.14 | HG3 | 3.70 | HD1 | 4.30 |
| 100 | 1360 | HE2 | 2.83 | HD2 | 4.28 | HE2 | 3.87 | HG3 | 4.66 | HA2 | 3.14 | HE1 | 4.00 | O | 3.77 | HE3 | 3.84 | HG3 | 4.46 | HD2 | 4.18 |
| 101 | 1368 | HE1 | 3.40 | HD2 | 4.44 | HE1 | 3.45 | HD2 | 4.58 | HA2 | 3.26 | HE1 | 3.47 | O | 3.83 | HE3 | 4.32 | HG3 | 4.09 | HD1 | 3.74 |
| 102 | 1406 | HE2 | 2.66 | HD2 | 3.44 | HE1 | 3.81 | HG2 | 3.12 | HA2 | 3.08 | HE1 | 4.29 | O | 3.80 | HE3 | 4.00 | HG2 | 2.99 | HD1 | 4.37 |
| 103 | 1411 | HE2 | 3.01 | HD2 | 3.26 | HE1 | 3.59 | HG3 | 3.06 | H | 3.04 | HE1 | 4.13 | O | 3.66 | HE3 | 4.01 | HG3 | 3.01 | HD1 | 4.12 |
| 104 | 1433 | HE2 | 3.01 | HD2 | 4.25 | HE2 | 3.58 | HD2 | 4.45 | HA2 | 3.20 | HE1 | 3.81 | O | 3.57 | HE3 | 4.04 | HG3 | 4.14 | HD1 | 3.87 |
| 105 | 1441 | HE1 | 3.02 | HD2 | 3.61 | HE1 | 3.59 | HG2 | 3.23 | HA2 | 3.18 | HE1 | 4.16 | O | 3.74 | HE3 | 4.13 | HG3 | 3.24 | HD1 | 4.05 |
| 106 | 1435 | HE2 | 2.82 | HD2 | 3.90 | HE2 | 3.87 | HG2 | 3.87 | HA2 | 3.08 | HE1 | 4.06 | O | 3.73 | HE3 | 3.98 | HG3 | 3.60 | HD1 | 4.12 |
| 107 | 1450_A | HE2 | 2.97 | HD2 | 4.02 | HE2 | 3.67 | HG2 | 4.21 | HA2 | 3.20 | HE1 | 3.62 | O | 3.77 | HE3 | 4.10 | HG3 | 3.84 | HE1 | 4.03 |
| 108 | 1450_B | HE2 | 2.97 | HD2 | 4.02 | HE2 | 3.67 | HG2 | 4.21 | HA2 | 3.20 | HE1 | 3.62 | O | 3.77 | HE3 | 4.10 | HG3 | 3.84 | HE1 | 4.03 |
| average distance | | | 3.14 | | 3.56 | | 3.92 | | 3.51 | | 3.18 | | 3.62 | | 3.50 | | 3.89 | | 3.28 | | 3.52 |
| standard deviation | | | 0.30 | | 0.55 | | 0.24 | | 0.68 | | 0.21 | | 0.45 | | 0.25 | | 0.19 | | 0.61 | | 0.42 |
| minimum value | | | 2.49 | | 2.40 | | 3.31 | | 2.08 | | 2.24 | | 2.78 | | 2.92 | | 3.09 | | 2.21 | | 2.46 |
| maximum value | | | 3.84 | | 4.98 | | 4.76 | | 5.23 | | 3.54 | | 5.63 | | 4.09 | | 4.32 | | 4.99 | | 4.37 |
| sample size | | | 108 | | 108 | | 108 | | 108 | | 108 | | 108 | | 108 | | 108 | | 108 | | 108 |

TABLE A8-continued

Table A8-6 Pharmacophore protein distances

| | | C6 | | | | | | CA3 | | O3 | | H1 | |
|---|---|---|---|---|---|---|---|---|---|---|---|---|---|
| | | TRP_655 | | PHE_529 | | SER_611 | | PRO_608 | | GLY_528 | | MET_658 | | ARG_630 | | ARG_630 | | MET_658 | |
| 1 | 14 | CH2 | 3.76 | HD2 | 2.77 | HB3 | 2.64 | HD2 | 4.32 | HA2 | 3.51 | O | 2.13 | HH11 | 1.53 | HH12 | 2.47 | HG2 | 3.80 |
| 2 | 54_A | CH2 | 3.90 | HD1 | 2.99 | HB3 | 2.76 | HD2 | 4.34 | HA2 | 3.70 | O | 2.38 | HD3 | 1.88 | HH12 | 2.44 | HG2 | 3.80 |
| 3 | 54_B | CH2 | 3.90 | HD1 | 2.99 | HB3 | 2.76 | HD2 | 4.34 | HA2 | 3.70 | O | 2.38 | HD3 | 1.88 | HH12 | 2.44 | HG2 | 3.80 |
| 4 | 1129 | CZ3 | 3.31 | HD1 | 2.98 | HB3 | 2.58 | HD2 | 4.05 | HA2 | 3.51 | HG2 | 2.85 | HD2 | 2.14 | HD2 | 3.63 | HE3 | 3.11 |
| 5 | 1034 | CZ3 | 3.27 | HD1 | 3.09 | OG | 3.32 | HD2 | 2.97 | HA2 | 3.79 | HG2 | 2.86 | HD3 | 4.27 | HH11 | 3.41 | HG2 | 3.46 |
| 6 | 1024 | CH2 | 3.53 | HD1 | 3.20 | HB3 | 2.54 | HD2 | 3.95 | HA2 | 3.60 | HG2 | 1.94 | HD3 | 3.62 | HH11 | 3.35 | HG2 | 3.26 |
| 7 | 1042_1 | CZ3 | 3.28 | HD1 | 3.84 | HB3 | 2.14 | HD2 | 3.46 | HA2 | 4.67 | HG2 | 2.06 | HB2 | 4.52 | HD2 | 4.01 | SD | 3.40 |
| 8 | 1042_2 | CZ3 | 3.27 | HD1 | 3.09 | HB3 | 2.54 | HD2 | 3.74 | HA2 | 4.01 | HG2 | 1.07 | HB2 | 5.37 | HH11 | 5.65 | SD | 4.17 |
| 9 | 1042_3 | CZ3 | 3.21 | HD2 | 2.42 | HB3 | 2.32 | HD2 | 4.06 | HA2 | 2.99 | HG2 | 2.74 | HB2 | 4.10 | HD2 | 4.10 | HG2 | 4.20 |
| 10 | 2018 | CH2 | 3.77 | HD2 | 2.90 | HB3 | 2.86 | HD2 | 3.74 | HA2 | 3.65 | HG2 | 1.58 | HB2 | 4.11 | HH22 | 5.01 | SD | 2.86 |
| 11 | 1059 | CZ3 | 3.64 | HD2 | 2.97 | HB3 | 2.61 | HD2 | 3.70 | HA2 | 3.81 | SD | 1.94 | CZ | 2.01 | HH21 | 3.32 | HE2 | 0.74 |
| 12 | 1088_A | CH2 | 3.75 | HD2 | 2.75 | HB3 | 2.71 | HD2 | 3.74 | HA2 | 3.66 | HG3 | 3.04 | NH1 | 2.33 | HE | 3.72 | HE2 | 3.12 |
| 13 | 1088_B | CH2 | 3.75 | HD1 | 2.75 | HB3 | 2.71 | HD2 | 3.74 | HA2 | 3.66 | HG3 | 3.04 | NH1 | 2.33 | HE | 3.72 | HE2 | 3.12 |
| 14 | 1036_1 | CZ3 | 3.49 | HD1 | 2.97 | HB3 | 2.82 | HD2 | 4.17 | HA2 | 3.62 | HG2 | 2.89 | HH11 | 1.75 | HH22 | 2.82 | HE2 | 3.32 |
| 15 | 1036_2_1 | CZ3 | 3.43 | HD1 | 3.12 | HB3 | 2.69 | HD2 | 4.19 | HA2 | 3.51 | HG3 | 1.86 | HD3 | 3.64 | HD2 | 3.13 | HG2 | 2.42 |
| 16 | 1036_2_2 | CZ3 | 3.51 | HD1 | 3.09 | HB3 | 2.65 | HD2 | 4.42 | HA2 | 3.26 | HG2 | 2.14 | HB2 | 4.14 | HH11 | 3.90 | SD | 2.62 |
| 17 | 1081 | CZ3 | 3.69 | HD1 | 3.20 | HB3 | 2.66 | HD2 | 4.72 | HA2 | 3.22 | HG3 | 3.11 | HD3 | 4.09 | HH11 | 3.97 | SD | 3.70 |
| 18 | 1063 | CH2 | 3.73 | HD1 | 3.00 | HB3 | 3.00 | HD2 | 4.92 | HA2 | 3.37 | HG2 | 1.74 | HD2 | 2.08 | HH11 | 2.64 | SD | 2.75 |
| 19 | 1065 | CH2 | 3.87 | HD2 | 2.70 | HB3 | 2.57 | HD2 | 3.75 | HA2 | 3.56 | O | 3.34 | HD2 | 2.94 | HD3 | 4.01 | HE3 | 3.79 |
| 20 | 1030_A | CZ3 | 3.63 | HD1 | 2.90 | HB3 | 2.90 | HD2 | 3.66 | HA2 | 3.77 | HB2 | 3.11 | HD2 | 3.07 | HD3 | 4.19 | HG3 | 3.33 |
| 21 | 1030_B | CZ3 | 3.63 | HD1 | 2.90 | HB3 | 2.90 | HD2 | 3.66 | HA2 | 3.77 | HB2 | 3.11 | HD2 | 3.07 | HD3 | 4.19 | HG3 | 3.33 |
| 22 | 1037 | CH2 | 3.29 | HD1 | 3.25 | HB3 | 2.19 | HD2 | 4.17 | HA2 | 3.46 | HE3 | 2.38 | HD2 | 3.02 | HH12 | 2.95 | HG3 | 3.03 |
| 23 | 1118 | CZ3 | 3.71 | HD1 | 3.01 | HB3 | 3.12 | HD2 | 4.83 | HA2 | 3.82 | HG3 | 1.45 | HH11 | 2.14 | HD2 | 3.05 | HE2 | 3.28 |
| 24 | 1090 | CH2 | 3.50 | HD1 | 2.77 | HB3 | 2.87 | HD2 | 3.95 | HA2 | 3.61 | HG2 | 2.69 | HE | 1.87 | HH21 | 2.38 | HE2 | 2.71 |
| 25 | 1007_1 | CH2 | 3.70 | HD1 | 3.15 | HB3 | 2.06 | HD2 | 3.15 | HA2 | 3.76 | HA | 2.61 | NH1 | 2.01 | HH21 | 3.34 | HE2 | 3.25 |
| 26 | 1007_2 | CH2 | 3.60 | HD1 | 3.20 | HB3 | 2.21 | HD2 | 3.12 | HA2 | 3.72 | HA | 2.59 | NH1 | 2.20 | NE | 3.80 | HG3 | 3.37 |
| 27 | 1149 | CH2 | 3.27 | HD2 | 2.93 | HB3 | 2.96 | HD2 | 4.39 | HA2 | 3.92 | HG2 | 2.55 | HB2 | 4.48 | HH11 | 4.24 | HG2 | 3.25 |
| 28 | 1021_A | CZ3 | 3.96 | HD1 | 2.91 | HB3 | 2.27 | HD2 | 3.43 | HA2 | 3.58 | HG2 | 2.19 | HB2 | 4.48 | HD2 | 5.78 | SD | 3.50 |
| 29 | 1021_B | CZ3 | 3.95 | HD1 | 2.90 | HB3 | 2.27 | HD2 | 3.45 | HA2 | 3.59 | HG2 | 2.20 | HB2 | 4.47 | HD2 | 5.77 | SD | 3.50 |
| 30 | 1097_1 | CZ3 | 3.24 | HD1 | 2.89 | HB3 | 3.04 | HD2 | 3.89 | HA2 | 3.46 | HG2 | 2.40 | HH11 | 3.62 | HH11 | 2.96 | HG2 | 3.49 |
| 31 | 1097_2 | CH2 | 3.09 | HD2 | 3.02 | HB3 | 3.29 | HD2 | 3.56 | HA2 | 3.52 | HG2 | 2.55 | HD3 | 3.42 | HH12 | 3.06 | SD | 3.13 |
| 32 | 1031_1 | CH2 | 3.81 | HD1 | 3.12 | HB3 | 2.09 | HD2 | 3.68 | HA2 | 3.40 | O | 3.12 | HD3 | 3.31 | HH11 | 4.78 | HG2 | 4.43 |
| 33 | 1031_2 | CH2 | 3.80 | HD1 | 3.14 | HB3 | 2.00 | HD2 | 3.67 | HA2 | 3.46 | O | 3.02 | HD2 | 3.25 | HH21 | 4.71 | O | 4.44 |
| 34 | 1031_3 | CH2 | 3.77 | HD1 | 3.16 | HB3 | 2.21 | HD2 | 3.52 | HA2 | 3.51 | O | 2.96 | HD2 | 3.12 | HD2 | 4.69 | O | 4.41 |
| 35 | 1031_4 | CH2 | 3.78 | HD1 | 3.11 | HB3 | 2.18 | HD2 | 3.53 | HA2 | 3.41 | O | 2.96 | HD2 | 3.18 | HD2 | 4.47 | O | 4.40 |
| 36 | 1153_A | CH2 | 3.42 | HD1 | 3.23 | HB3 | 2.46 | HD2 | 4.41 | HA2 | 3.41 | HG3 | 2.53 | HG3 | 3.85 | HG3 | 5.84 | HG2 | 3.26 |
| 37 | 1153_B | CH2 | 3.42 | HD1 | 3.23 | HB3 | 2.46 | HD2 | 4.41 | HA2 | 3.41 | HG3 | 2.53 | HG3 | 3.85 | HG3 | 5.84 | HG2 | 3.26 |
| 38 | 1025_1 | CZ3 | 3.64 | HD1 | 3.33 | HB3 | 2.92 | HD2 | 3.34 | HA2 | 3.40 | HG2 | 2.13 | HG3 | 2.63 | HG3 | 3.92 | HG2 | 3.17 |
| 39 | 1025_2 | CZ3 | 3.94 | HD1 | 2.86 | HB3 | 2.92 | HD2 | 3.48 | HA2 | 3.65 | HG2 | 2.04 | HD2 | 2.22 | HH11 | 2.23 | HG2 | 3.76 |
| 40 | 1025_3 | CH2 | 3.77 | HD1 | 3.29 | HB3 | 3.99 | HG2 | 3.92 | HA2 | 3.28 | HG2 | 2.77 | HH22 | 0.15 | HH12 | 2.66 | HG2 | 3.75 |
| 41 | 1025_4 | CZ3 | 4.11 | HD2 | 2.69 | HB3 | 2.77 | HG2 | 4.73 | HA2 | 3.71 | HG2 | 2.30 | HD2 | 3.03 | HD2 | 1.74 | SD | 3.43 |
| 42 | 1025_5 | CZ3 | 3.83 | HD2 | 2.96 | HB3 | 3.26 | HG2 | 4.19 | HA2 | 3.45 | HG2 | 2.64 | HG3 | 3.76 | HH11 | 3.56 | HG2 | 3.27 |
| 43 | 1025_6 | CZ2 | 4.08 | HD1 | 2.99 | HB3 | 2.70 | HG2 | 3.50 | HA2 | 3.01 | O | 3.09 | HD2 | 3.57 | HD3 | 3.91 | HG2 | 3.64 |

TABLE A8-continued

| | | | | | | | | | | | | | | | | |
|---|---|---|---|---|---|---|---|---|---|---|---|---|---|---|---|---|
| 44 | 1089_A | CH2 | 3.57 | HD2 | 2.81 | HB3 | 2.79 | HD2 | 3.90 | HA2 | 3.59 | HG3 | 2.61 | HB3 | 4.55 | HD2 | 5.31 | HG3 | 3.31 |
| 45 | 1089_B | CH2 | 3.57 | HD2 | 2.81 | HB3 | 2.79 | HD2 | 3.90 | HA2 | 3.59 | HG3 | 2.61 | HB3 | 4.55 | HD2 | 5.31 | HG3 | 3.31 |
| 46 | 1012_1 | CZ2 | 3.91 | HD2 | 2.66 | HB3 | 3.15 | HD2 | 4.17 | HA2 | 3.39 | HG2 | 1.78 | HH11 | 2.09 | HE | 3.57 | HG2 | 3.32 |
| 47 | 1012_2 | CH2 | 3.61 | HD1 | 2.98 | HB3 | 2.57 | HD2 | 3.98 | HA2 | 3.69 | O | 1.87 | HH11 | 1.95 | NE | 3.50 | SD | 3.25 |
| 48 | 1078_1 | CH2 | 3.68 | HD1 | 3.30 | HB3 | 2.41 | HD2 | 3.85 | HA2 | 3.66 | O | 2.97 | HD2 | 3.27 | HD3 | 4.80 | HG2 | 3.50 |
| 49 | 1078_10 | CH2 | 3.89 | HD1 | 3.08 | HB3 | 2.78 | HD2 | 3.66 | HA2 | 3.40 | O | 3.04 | HD2 | 3.67 | HH12 | 4.55 | HG2 | 3.81 |
| 50 | 1078_11 | CH2 | 3.64 | HD1 | 3.33 | HB3 | 2.38 | HD2 | 3.69 | HA2 | 3.68 | HA | 3.00 | HG3 | 3.33 | HH12 | 4.87 | HG2 | 3.71 |
| 51 | 1078_12 | CH2 | 3.63 | HD1 | 3.41 | HB3 | 2.36 | HD2 | 3.77 | HA2 | 3.71 | O | 2.95 | HG3 | 3.99 | HH12 | 5.01 | HG2 | 3.50 |
| 52 | 1078_13 | CH2 | 3.66 | HD1 | 3.31 | HB3 | 2.46 | HD2 | 3.75 | HA2 | 3.63 | HA | 2.99 | HH22 | 3.72 | HH12 | 4.91 | HG2 | 3.66 |
| 53 | 1078_14 | CH2 | 3.60 | HD1 | 3.36 | HB3 | 2.33 | HD2 | 3.74 | HA2 | 3.68 | O | 2.94 | HG3 | 3.85 | HH12 | 4.50 | HG2 | 3.46 |
| 54 | 1078_15 | CH2 | 3.62 | HD1 | 3.35 | HB3 | 2.34 | HD2 | 3.75 | HA2 | 3.65 | O | 2.92 | HD3 | 3.82 | HH12 | 4.35 | HG2 | 3.44 |
| 55 | 1078_16 | CH2 | 3.62 | HD1 | 3.38 | HB3 | 2.38 | HD2 | 3.81 | HA2 | 3.72 | O | 2.91 | HD3 | 3.38 | HH12 | 4.49 | HG2 | 3.54 |
| 56 | 1078_2 | CH2 | 3.62 | HD1 | 3.35 | HB3 | 2.35 | HD2 | 3.80 | HA2 | 3.67 | HA | 2.86 | HD3 | 3.38 | HH12 | 4.58 | HE2 | 3.34 |
| 57 | 1078_3 | CH2 | 3.85 | HD1 | 3.07 | HB3 | 2.66 | HD2 | 3.81 | HA2 | 3.42 | O | 3.08 | NE | 3.18 | HE | 4.30 | HE2 | 3.79 |
| 58 | 1078_4 | CH2 | 3.63 | HD1 | 3.40 | HB3 | 2.27 | HD2 | 3.78 | HA2 | 3.71 | O | 2.91 | NE | 3.43 | HH21 | 4.75 | HE1 | 3.41 |
| 59 | 1078_5 | CH2 | 3.64 | HD1 | 3.36 | HB3 | 2.31 | HD2 | 3.70 | HA2 | 3.68 | O | 2.94 | CZ | 2.22 | HE | 4.35 | HG2 | 3.52 |
| 60 | 1078_6 | CH2 | 3.64 | HD1 | 3.36 | HB3 | 2.29 | HD2 | 3.75 | HA2 | 3.71 | O | 2.91 | NH2 | 3.42 | HH22 | 4.78 | HG3 | 3.53 |
| 61 | 1078_7 | CH2 | 3.70 | HD1 | 3.31 | HB3 | 2.46 | HD2 | 3.81 | HA2 | 3.67 | O | 2.92 | HD2 | 3.39 | HH12 | 4.89 | SD | 3.42 |
| 62 | 1078_8 | CH2 | 3.66 | HD1 | 3.34 | HB3 | 2.31 | HD2 | 3.76 | HA2 | 3.68 | O | 2.93 | HH12 | 3.06 | HH22 | 4.82 | HG2 | 3.11 |
| 63 | 1078_9 | CH2 | 3.64 | HD2 | 3.40 | HB3 | 2.41 | HD2 | 3.75 | HA2 | 3.70 | HA | 2.86 | HD3 | 3.32 | HH22 | 5.00 | HG2 | 3.29 |
| 64 | 1145_A | CH2 | 3.75 | HD1 | 3.57 | HB3 | 2.78 | HD2 | 4.21 | HA2 | 3.65 | HA | 2.98 | NE | 3.54 | HE | 5.17 | HG2 | 3.36 |
| 65 | 1145_B | CH2 | 3.75 | HD1 | 3.57 | HB3 | 2.78 | HD2 | 4.21 | HA2 | 3.65 | HA | 2.98 | NE | 2.66 | HE | 2.55 | HE2 | 3.20 |
| 66 | 1050 | CH2 | 3.63 | HD1 | 3.25 | HB3 | 2.37 | HD2 | 3.95 | HA2 | 3.29 | HE3 | 1.47 | CZ | 2.66 | HH21 | 2.55 | HE1 | 3.20 |
| 67 | 1253 | CZ2 | 3.95 | HD2 | 2.74 | HB2 | 2.80 | HG2 | 3.72 | HA2 | 3.46 | O | 2.41 | NH2 | 2.22 | HE | 2.49 | HE1 | 1.56 |
| 68 | 1257 | CH2 | 3.67 | HD2 | 2.93 | HB3 | 2.74 | HD2 | 4.08 | HA2 | 3.65 | HG3 | 2.77 | HD2 | 1.82 | HH11 | 3.25 | HE1 | 3.48 |
| 69 | 999_1 | CH2 | 3.48 | HD2 | 2.96 | HB3 | 2.66 | HD2 | 3.94 | HA2 | 3.99 | HG2 | 2.26 | HD3 | 2.81 | HD2 | 2.55 | HG3 | 3.40 |
| 70 | 999_2_A | CH2 | 3.40 | HD2 | 3.21 | HB3 | 2.27 | HD2 | 3.82 | HA2 | 3.73 | HG2 | 2.79 | HH11 | 3.21 | HH11 | 4.39 | SD | 3.11 |
| 71 | 999_2_B | CH2 | 3.40 | HD2 | 3.21 | HB3 | 2.27 | HD2 | 3.82 | HA2 | 3.73 | HG2 | 2.79 | HH11 | 1.60 | HD2 | 3.10 | HG2 | 3.29 |
| 72 | 1297_1 | CH2 | 3.63 | HD2 | 2.85 | HB3 | 2.48 | HD2 | 3.78 | HA2 | 3.45 | HG2 | 2.30 | HH21 | 1.91 | HH11 | 3.10 | HG2 | 3.36 |
| 73 | 1297_2 | CH2 | 3.59 | HD2 | 2.89 | HB3 | 2.43 | HD2 | 3.86 | HA2 | 3.52 | HG3 | 2.40 | HD3 | 2.03 | NE | 3.76 | HG2 | 3.16 |
| 74 | 1297_3 | CH2 | 3.70 | HD2 | 2.77 | HB3 | 2.59 | HD2 | 3.81 | HA2 | 3.38 | HG3 | 2.04 | HD3 | 2.04 | CZ | 2.94 | HG2 | 3.11 |
| 75 | 1297_4 | CH2 | 3.59 | HD2 | 2.91 | HB3 | 2.43 | HD2 | 3.87 | HA2 | 3.52 | HG3 | 2.14 | HD3 | 2.07 | CZ | 2.86 | HG2 | 3.14 |
| 76 | 1297_5 | CH2 | 3.59 | HD2 | 2.89 | HB3 | 2.45 | HD2 | 3.84 | HA2 | 3.48 | HG2 | 2.26 | HD3 | 2.88 | CZ | 2.94 | HG2 | 3.37 |
| 77 | 1297_6 | CH2 | 3.70 | HD2 | 2.77 | HB3 | 2.58 | HD2 | 3.89 | HA2 | 3.37 | HG2 | 2.76 | HH21 | 2.83 | HH11 | 2.37 | HG2 | 3.30 |
| 78 | 1304 | CH2 | 3.94 | HD2 | 2.67 | HB3 | 2.51 | HD2 | 3.39 | HA2 | 3.58 | HG3 | 2.95 | HD3 | 1.91 | NE | 2.30 | HG2 | 3.59 |
| 79 | 1306_1 | CH2 | 3.13 | HD1 | 2.73 | HB3 | 2.43 | HG2 | 3.86 | HA2 | 3.95 | HG2 | 2.32 | HB2 | 4.40 | HH11 | 3.62 | SD | 2.63 |
| 80 | 1306_2 | CZ2 | 3.55 | HD2 | 3.00 | HB2 | 2.50 | HG2 | 4.35 | HA2 | 3.56 | HG3 | 1.89 | HD3 | 4.30 | HH13 | 4.30 | O | 2.81 |
| 81 | 1307 | CH2 | 3.92 | HD2 | 2.83 | HB3 | 2.40 | HG2 | 3.30 | HA2 | 3.75 | HG3 | 2.31 | HD3 | 3.67 | HE | 3.19 | SD | 5.28 |
| 82 | 1328_1 | CH2 | 4.09 | HD1 | 2.89 | HB3 | 2.57 | HD2 | 3.34 | HA2 | 3.66 | O | 3.89 | HH11 | 1.72 | CZ | 3.05 | O | 3.33 |
| 83 | 1328_2 | CH2 | 4.11 | HD1 | 2.88 | HB3 | 2.57 | HD2 | 3.42 | HA2 | 3.60 | HG3 | 1.94 | HH11 | 2.13 | HE | 3.94 | HG2 | 3.33 |
| 84 | 1328_3 | CH2 | 3.95 | HD1 | 2.89 | HB3 | 2.40 | HD2 | 3.31 | HA2 | 3.68 | HG3 | 1.97 | NH1 | 1.93 | NE | 3.83 | HG2 | 3.35 |
| 85 | 1328_4 | CH2 | 3.99 | HD1 | 2.89 | HB3 | 2.60 | HG2 | 3.35 | HA2 | 3.67 | HG3 | 2.39 | HH11 | 1.88 | CZ | 3.91 | SD | 3.37 |
| 86 | 1334 | CZ3 | 3.67 | HD2 | 2.81 | HB3 | 3.19 | HG2 | 3.99 | HA2 | 3.61 | HA | 2.56 | HH11 | 1.79 | HH21 | 3.88 | HG2 | 3.30 |
| 87 | 1335 | CH2 | 3.94 | HD1 | 2.49 | HB3 | 2.61 | HG2 | 4.28 | HA2 | 3.22 | HG2 | 3.22 | HD2 | 2.39 | HE | 3.48 | HG3 | 3.59 |
| 88 | 1338 | CH2 | 3.13 | HD2 | 2.71 | HB3 | 2.70 | HD2 | 3.97 | HA2 | 3.41 | HA | 2.32 | HD3 | 2.36 | HE | 3.89 | SD | 3.52 |
| 89 | 1345_1 | CZ3 | 3.55 | HD1 | 3.08 | HB3 | 1.99 | HG2 | 4.30 | HA2 | 4.16 | HG2 | 2.23 | HB2 | 2.83 | HH11 | 4.40 | HG2 | 2.61 |
| 90 | 1345_2 | CH2 | 3.73 | HD1 | 3.19 | HB3 | 2.43 | HD2 | 3.65 | HA2 | 3.88 | HG3 | 2.28 | HD3 | 4.41 | NH1 | 3.53 | HG2 | 3.14 |
| 91 | 1351 | CH2 | 3.43 | HD2 | 2.76 | HB3 | 3.12 | HD2 | 4.09 | HA2 | 3.43 | HG3 | 2.44 | HB2 | 3.90 | HD3 | 3.59 | SD | 3.56 |
| 92 | 1353 | CH2 | 3.95 | HD2 | 2.80 | HB3 | 2.14 | HD2 | 3.40 | HA2 | 3.73 | HG2 | 2.00 | NH1 | 2.02 | HH11 | 3.51 | HG2 | 3.34 |
| 93 | 1367 | CZ3 | 3.88 | HD2 | 2.76 | HB3 | 2.49 | HD2 | 3.60 | HA2 | 3.45 | HG3 | 3.02 | HD3 | 1.94 | HE | 3.55 | HE3 | 3.97 |
| 94 | 1371 | CH2 | 3.76 | HD2 | 2.82 | HB2 | 2.49 | HD2 | 3.61 | HA2 | 3.24 | HG3 | 1.19 | O | 1.94 | NE | 4.34 | HE2 | 3.05 |
| 95 | 1372_A | CZ2 | 3.79 | HD2 | 2.69 | HB3 | 2.55 | HD2 | 3.39 | HA2 | 3.70 | HG3 | 2.76 | HH21 | 4.08 | HE | 3.50 | HG2 | 3.43 |
| 96 | 1372_B | CZ2 | 3.97 | HD2 | 2.69 | HB3 | 2.55 | HD2 | 3.39 | HA2 | 3.70 | HG3 | 2.31 | HH21 | 2.05 | HE | 3.49 | HG2 | 3.43 |

TABLE A8-continued

| | | | | | | | | | | | | | | | | | |
|---|---|---|---|---|---|---|---|---|---|---|---|---|---|---|---|---|---|
| 97 | 1373 | CZ2 | 4.01 | HD2 | HB3 | 2.70 | HD2 | 2.75 | HA2 | 3.33 | HG3 | 3.61 | HH11 | 2.29 | HE | 1.95 | HG2 | 3.49 |
| 98 | 1492 | CZ3 | 3.27 | HD1 | HB3 | 3.18 | HD2 | 2.95 | HA2 | 3.74 | HG3 | 3.82 | HD3 | 2.74 | HD3 | 2.94 | HG2 | 3.59 |
| 99 | 1399 | CZ2 | 4.00 | HD2 | HB3 | 2.77 | HD2 | 2.91 | HA2 | 3.78 | HG3 | 3.67 | NH1 | 2.32 | HE | 1.97 | HG2 | 3.51 |
| 100 | 1360 | CH2 | 3.66 | HD2 | HB3 | 2.63 | HD2 | 3.07 | HA2 | 4.29 | HG3 | 3.60 | HH21 | 2.20 | HE | 2.01 | HG3 | 3.56 |
| 101 | 1368 | CZ2 | 4.04 | HD1 | HB3 | 3.15 | HD2 | 2.97 | HA2 | 4.11 | HG3 | 3.92 | HE | 2.92 | HE | 1.93 | HG2 | 3.35 |
| 102 | 1406 | CH2 | 3.90 | HD2 | OG | 2.59 | HG2 | 2.95 | HA2 | 3.64 | HG3 | 3.81 | HH21 | 2.37 | HH11 | 3.85 | HG3 | 2.90 |
| 103 | 1411 | CH2 | 3.99 | HD2 | HB3 | 2.88 | HD2 | 2.94 | HA2 | 3.54 | HG3 | 3.39 | HD3 | 2.39 | HE | 2.01 | HG2 | 3.43 |
| 104 | 1433 | CZ2 | 3.84 | HD2 | HB3 | 2.89 | HG2 | 2.81 | HA2 | 4.16 | HG3 | 3.69 | NH2 | 2.51 | HE | 1.75 | HG2 | 3.17 |
| 105 | 1441 | CZ2 | 4.00 | HD2 | HB3 | 2.92 | HD2 | 2.98 | HA2 | 3.43 | HG3 | 3.56 | HD3 | 2.38 | HE | 1.86 | HG2 | 3.44 |
| 106 | 1435 | CH2 | 3.79 | HD2 | HB3 | 2.76 | HD2 | 2.95 | HA2 | 3.69 | HG3 | 3.54 | NH2 | 2.37 | HE | 1.91 | HG2 | 3.47 |
| 107 | 1450_A | CZ2 | 3.95 | HD2 | HB3 | 2.90 | HD2 | 2.76 | HA2 | 3.92 | HG3 | 3.75 | HH21 | 2.75 | HE | 1.92 | HG2 | 3.38 |
| 108 | 1450_B | CZ2 | 3.95 | HD2 | HB3 | 2.90 | HD2 | 2.76 | HA2 | 3.92 | HG3 | 3.75 | HH21 | 2.75 | HE | 1.92 | HG2 | 3.38 |
| average distance | | | 3.70 | | | 3.01 | | 2.60 | | 3.84 | | 3.61 | | 2.53 | | 2.86 | | 3.37 |
| standard deviation | | | 0.23 | | | 0.25 | | 0.30 | | 0.36 | | 0.21 | | 0.47 | | 0.96 | | 0.50 |
| minimum value | | | 3.09 | | | 2.42 | | 1.99 | | 2.97 | | 2.99 | | 1.07 | | 0.15 | | 0.74 |
| maximum value | | | 4.11 | | | 3.84 | | 3.32 | | 4.92 | | 4.67 | | 3.89 | | 5.37 | | 5.28 |
| sample size | | | 108 | | | 108 | | 108 | | 108 | | 108 | | 108 | | 108 | | 108 |

The invention claimed is:

1. A compound of Formula (I-4):

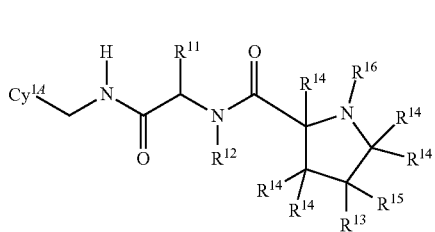

(I-4)

or a stereoisomer, tautomer, or pharmaceutically acceptable salt thereof, wherein:

$Cy^{1A}$ is unsubstituted or substituted 5-10 membered heteroaryl; wherein the ring atoms of the 5-10 membered heteroaryl forming $Cy^{1A}$ consist of carbon atoms and 1, 2, or 3 heteroatoms selected from O, N and S; wherein the substituted 5-10 membered heteroaryl forming $Cy^{1A}$ is substituted with 1, 2, 3, 4 or 5 substituents each independently selected from $R^{Cy1A}$, halogen, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $C(=NOR^{a11})NR^{c11}R^{d11}$, $C(=NOC(O)R^{b11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

each $R^{Cy1A}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10-membered heterocycloalkyl forming $R^{Cy1A}$ consist of carbon atoms and 1, 2, 3 or 4 heteroatoms selected from O, N and S, wherein each $C_{1-6}$ alkyl, $C_{2-6}$ alkenyl, or $C_{2-6}$ alkynyl forming $R^{Cy1A}$ is independently unsubstituted or substituted with 1, 2 or 3 substituents independently selected from halogen, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo, and wherein each $C_{6-10}$ aryl, 5-10 membered heteroaryl, $C_{3-10}$ cycloalkyl and 4-10 membered heterocycloalkyl forming $R^{Cy1A}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

$R^{11}$ is H or $C_{1-6}$ alkyl, $C_{6-10}$ aryl-$C_{1-6}$ alkyl or 5-10 membered heteroaryl-$C_{1-6}$ alkyl, wherein the $C_{1-6}$ alkyl forming $R^{11}$ is unsubstituted or substituted by 1, 2 or 3 substituents independently selected from halogen, CN, $OR^{a11}$, $SR^{a11}$, $C(O)R^{b11}$, $C(O)NR^{c11}R^{d11}$, $C(O)OR^{c11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo, and wherein the $C_{6-10}$ aryl-$C_{1-6}$ alkyl or 5-10 membered heteroaryl-$C_{1-6}$ alkyl forming $R^{11}$ is unsubstituted or substituted by 1, 2 or 3 substituents independently selected from $C_{1-6}$ alkyl, $C_{2-6}$ alkenyl, $C_{2-6}$ alkynyl, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$ $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

$R^{12}$ is H or $C_{1-6}$ alkyl;

each $R^{13}$ is independently $Cy^{1B}$, $(CR^{13A}R^{13B})_{n3}Cy^{1B}$, $(C_{1-6}$ alkylene)$Cy^{1B}$, $(C_{2-6}$ alkenylene) $Cy^{1B}$, $(C_{2-6}$ alkynylene) $Cy^{1B}$ or $OCy^{1B}$, wherein the $C_{1-6}$ alkylene, $C_{2-6}$ alkenylene, or $C_{2-6}$ alkynylene component of $R^{13}$ is unsubstituted or substituted by 1, 2, 3, 4 or 5 substituents each independently selected from the group consisting of halogen, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

each $R^{14}$ is independently selected from H and $C_{1-6}$ alkyl;

$R^{15}$ is selected from H, $R^{13}$, $C_{1-6}$ alkyl and OH;

n3 is 0, 1 or 2;

each $R^{13A}$ is independently H or $C_{1-6}$ alkyl, and each $R^{13B}$ is independently H or $C_{1-6}$ alkyl, or $R^{13A}$ and $R^{13B}$ attached to the same carbon atom, and independently of any other $R^{13A}$ and $R^{13B}$ groups, together may form $-(CH_2)_{2-5}-$, thereby forming a 3-6 membered cycloalkyl ring;

$Cy^{1B}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl; wherein the ring atoms of the 5-10 membered heteroaryl or 4-10 membered heterocycloalkyl forming $Cy^{1B}$ consist of carbon atoms and 1, 2 or 3 heteroatoms selected from O, N and S, wherein the substituted $C_{6-10}$ aryl, substituted 5-10 membered heteroaryl, substituted $C_{3-10}$ cycloalkyl or substituted 4-10 membered heterocycloalkyl forming $Cy^{1B}$ are substituted with 1, 2, 3, 4 or 5 substituents each independently selected from $R^{Cy1B}$, halogen, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $C(=NOR^{a11})NR^{c11}R^{d11}$, $C(=NOC(O)R^{b11})NR^{c11}R^{d11}$, $C(=NR^{e11})NR^{c11}C(O)OR^{a11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

each $R^{Cy1B}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10 membered heterocycloalkyl forming $R^{Cy1B}$ consist of carbon atoms and 1, 2 or 3 heteroatoms selected from O, N and S; wherein each $C_{1-6}$ alkyl, $C_{2-6}$ alkenyl, or $C_{2-6}$ alkynyl forming $R^{Cy1B}$ is independently unsubstituted or substituted with 1, 2 or 3 substituents independently selected from halogen, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$, oxo, and phenyl; and wherein each $C_{6-10}$ aryl, 5-10 membered heteroaryl, $C_{3-10}$ cycloalkyl and 4-10 membered heterocycloalkyl forming $R^{Cy1B}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

$R^{16}$ is H, $Cy^{1C}$, $C_{1-6}$ alkyl, $C_{2-6}$ alkenyl, or $C_{2-6}$ alkynyl, wherein the $C_{1-6}$ alkyl, $C_{2-6}$ alkenyl, or $C_{2-6}$ alkynyl forming $R^{16}$ is unsubstituted or substituted with 1, 2, 3, 4 or 5 substituents selected from the group consisting of $Cy^{1C}$, halogen, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo, provided that no more than one of the substituents of $R^{16}$ is $Cy^{1C}$;

$Cy^{1C}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl; wherein the ring atoms of the 5-10 membered heteroaryl or 4-10 membered heterocycloalkyl forming $Cy^{1C}$ consist of carbon atoms and 1, 2 or 3 heteroatoms selected from O, N and S, wherein the substituted $C_{6-10}$ aryl, substituted 5-10 membered heteroaryl, substituted $C_{3-10}$ cycloalkyl or substituted 4-10 membered heterocycloalkyl forming $Cy^{1C}$ are substituted with 1, 2, 3, 4 or 5 substituents each independently selected from $R^{Cy1C}$, halogen, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $C(=NR^{e11})NR^{c11}R^{d11}$, $C(=NOR^{a11})NR^{c11}R^{d11}$, $C(=NOC(O)R^{b11})NR^{c11}R^{d11}$, $C(=NR^{e11})NR^{c11}C(O)OR^{a11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

each $R^{Cy1C}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10 membered heterocycloalkyl forming $R^{Cy1C}$ consist of carbon atoms and 1, 2 or 3 heteroatoms selected from O, N and S; wherein each $C_{1-6}$ alkyl, $C_{2-6}$ alkenyl, or $C_{2-6}$ alkynyl forming $R_{Cy1C}$ is independently unsubstituted or substituted with 1, 2 or 3 substituents independently selected from halogen, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo; and wherein each $C_{6-10}$ aryl, 5-10 membered heteroaryl, $C_{3-10}$ cycloalkyl and 4-10 membered heterocycloalkyl forming $R^{Cy1C}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

$R^{a11}$ and $R^{b11}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a11}$ and $R^{b11}$ are each unsubstituted, or substituted with 1, 2, 3, 4 or 5 substituents independently selected from $C_{1-6}$ alkyl, halo, CN, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)NR^{c12}R^{d12}$, $NR^{c12}C(O)OR^{a12}$, $C(=NR^{e12})NR^{c12}R^{d12}$, $NR^{c12}C(=NR^{e12})NR^{c12}R^{d12}$, $S(O)R^{b12}$, $S(O)NR^{c12}R^{d12}$, $S(O)_2R^{b12}$, $NR^{c12}S(O)_2R^{b12}$, $S(O)_2NR^{c12}R^{d12}$ and oxo;

$R^{c11}$ and $R^{d11}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{c11}$ and $R^{b11}$ are each unsubstituted, or substituted with 1, 2, 3, 4 or 5 substituents independently selected from $C_{1-6}$ alkyl, halo, CN, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)NR^{c12}R^{d12}$, $NR^{c12}C(O)OR^{a12}$, $C(=NR^{e12})NR^{c12}R^{d12}$, $NR^{c12}C(=NR^{e12})NR^{c12}R^{d12}$, $S(O)R^{b12}$, $S(O)NR^{c12}R^{d12}$, $S(O)_2R^{b12}$, $NR^{c12}S(O)_2R^{b12}$, $S(O)_2NR^{c12}R^{d12}$ and oxo, or $R^{c11}$ and $R^{d11}$ attached to the same N atom, together with the N atom to which they are both attached, form a 4-, 5-, 6- or 7-membered heterocycloalkyl group or 5-membered heteroaryl group, each unsubstituted, or substituted with 1, 2 or 3 substituents independently selected from $C_{1-6}$ alkyl, halo, CN, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)NR^{c12}R^{d12}$, $NR^{c12}C(O)OR^{a12}$, $C(=NR^{e12})NR^{c12}R^{d12}$, $NR^{c12}C(=NR^{e12})NR^{c12}R^{d12}$, $S(O)R^{b12}$, $S(O)NR^{c12}R^{d12}$, $S(O)_2R^{b12}$, $NR^{c12}S(O)_2R^{b12}$, $S(O)_2NR^{c12}R^{d12}$ and oxo;

$R^{a12}$ and $R^{b12}$ are each independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl forming $R^{a12}$ and $R^{b12}$ are each unsubstituted, or substituted with 1, 2 or 3 substituents independently selected from OH, CN, amino, NH($C_{1-6}$ alkyl), N($C_{1-6}$ alkyl)2, halo, $C_{1-6}$ alkyl, $C_{1-6}$ alkoxy, $C_{1-6}$ haloalkyl, $C_{1-6}$ haloalkoxy and oxo;

$R^{c12}$ and $R^{d12}$ are each independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl forming $R^{c12}$ and $R^{d12}$ are each unsubstituted, or substituted with 1, 2 or 3 substituents independently selected from OH, CN, amino, NH($C_{1-6}$ alkyl), N($C_{1-6}$ alkyl) 2, halo, $C_{1-6}$ alkyl, $C_{1-6}$ alkoxy, $C_{1-6}$ haloalkyl, $C_{1-6}$ haloalkoxy and oxo, or $R^{c12}$ and $R^{d12}$ attached to the same N atom, together with the N atom to which they are both attached, form a 4-, 5-, 6- or 7-membered heterocycloalkyl group or 5-membered heteroaryl group, each of which is unsubstituted or substituted with 1, 2 or 3 substituents independently selected from OH, CN, amino, NH($C_{1-6}$ alkyl), N($C_{1-6}$ alkyl) 2, halo, $C_{1-6}$ alkyl, $C_{1-6}$ alkoxy, $C_{1-6}$ haloalkyl, $C_{1-6}$ haloalkoxy and oxo; and $R^{e11}$ and $R^{e12}$ are each, independently, H, CN or $NO_2$.

2. The compound or salt thereof of claim 1, wherein $Cy^{1A}$ is substituted with at least one $OR^{a11}$, $C(=NR^{e11})NR^{c11}R^{d11}$, $C(=NOR^{a11})NR^{c11}R^{d11}$, $C(=NOC(O)R^{b11})NR^{c11}R^{d11}$, or $C(=NR^{e11})NR^{c11}C(O)OR^{a11}$.

3. The compound or salt thereof of claim 1, wherein $Cy^{1A}$ is unsubstituted or substituted pyridin-3-yl, 1H-pyrrolo[2,3-b]pyridine-5-yl, or 1H-benzo[d]imidazol-6-yl.

4. The compound or salt thereof of claim 1, wherein $Cy^{1A}$ is of any one of the following formulae:

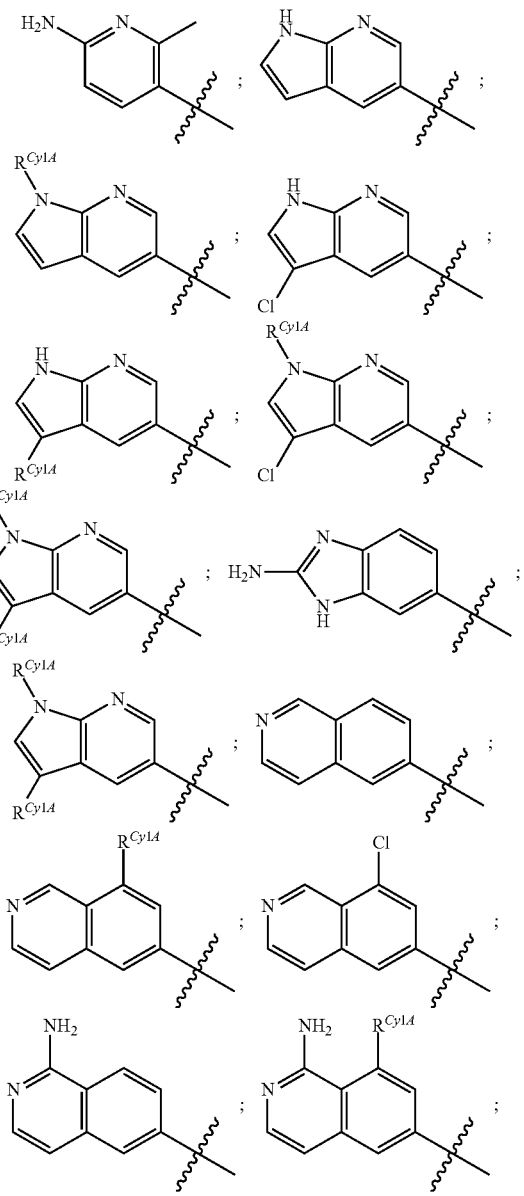

1085
-continued
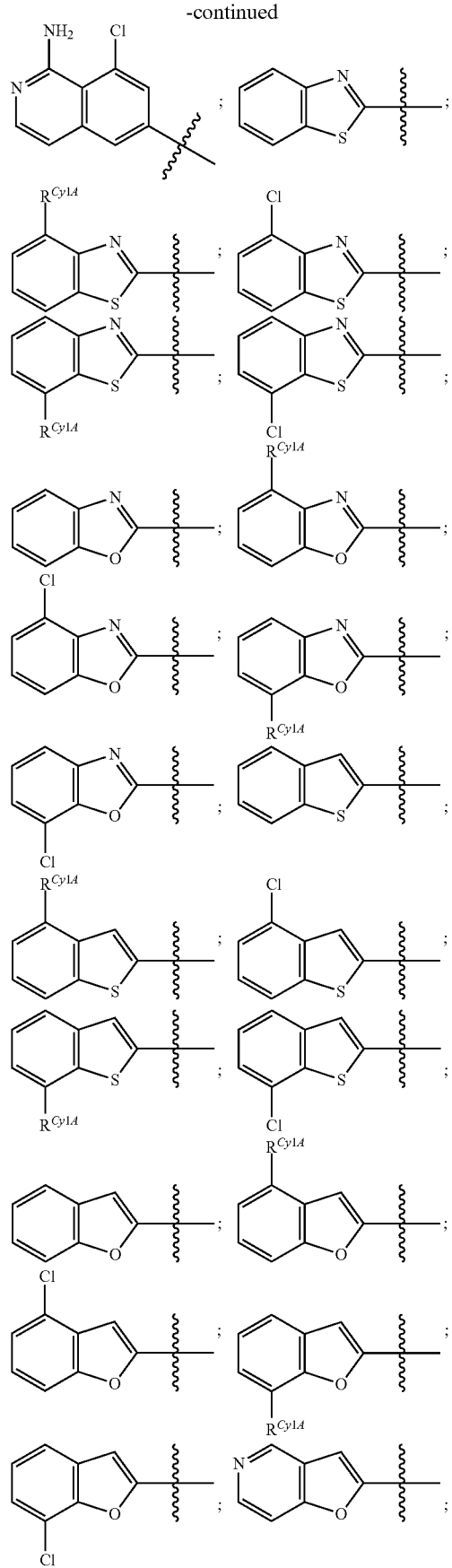
1086
-continued
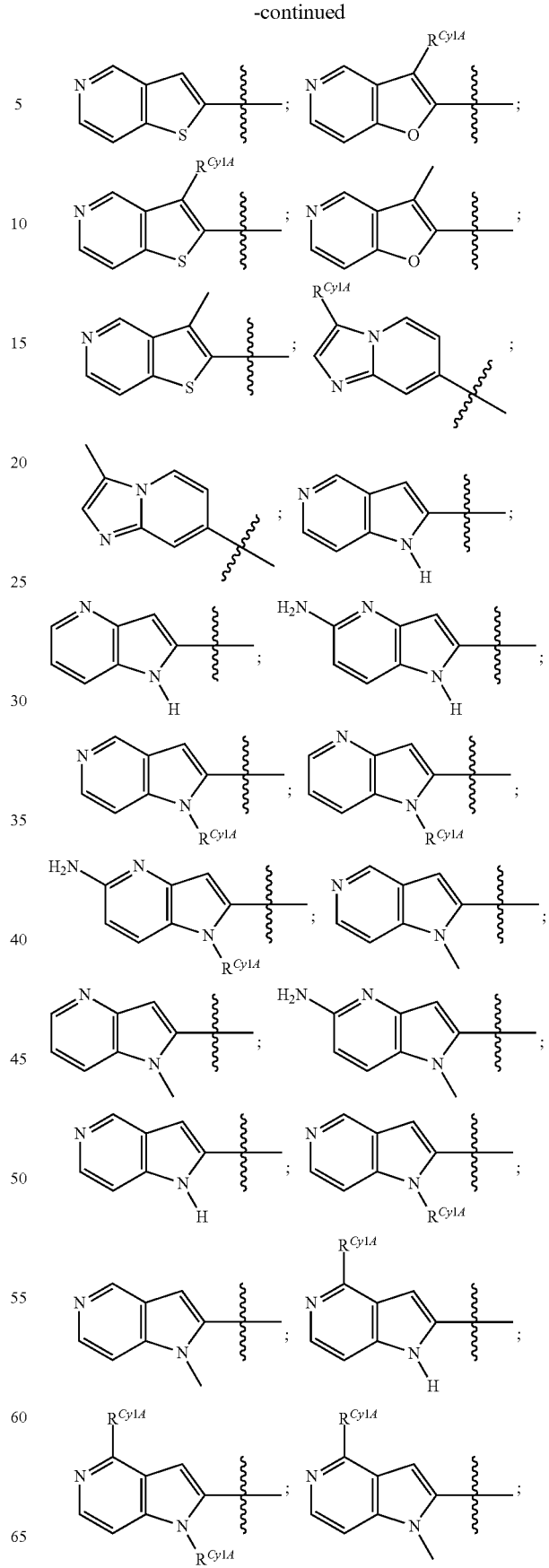

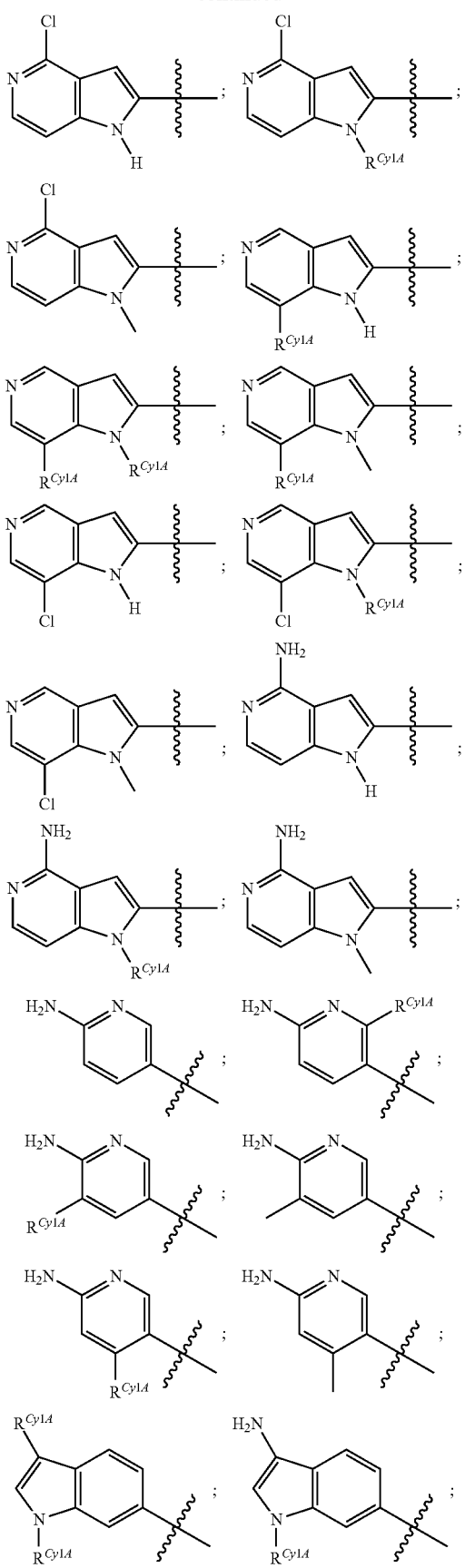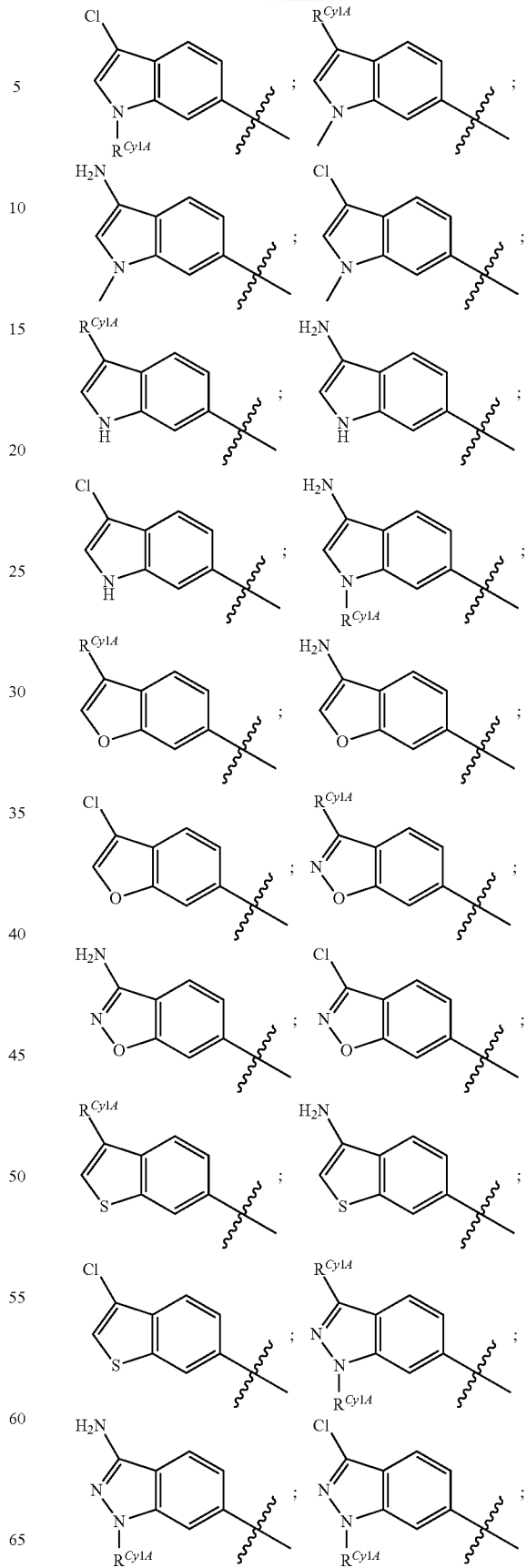

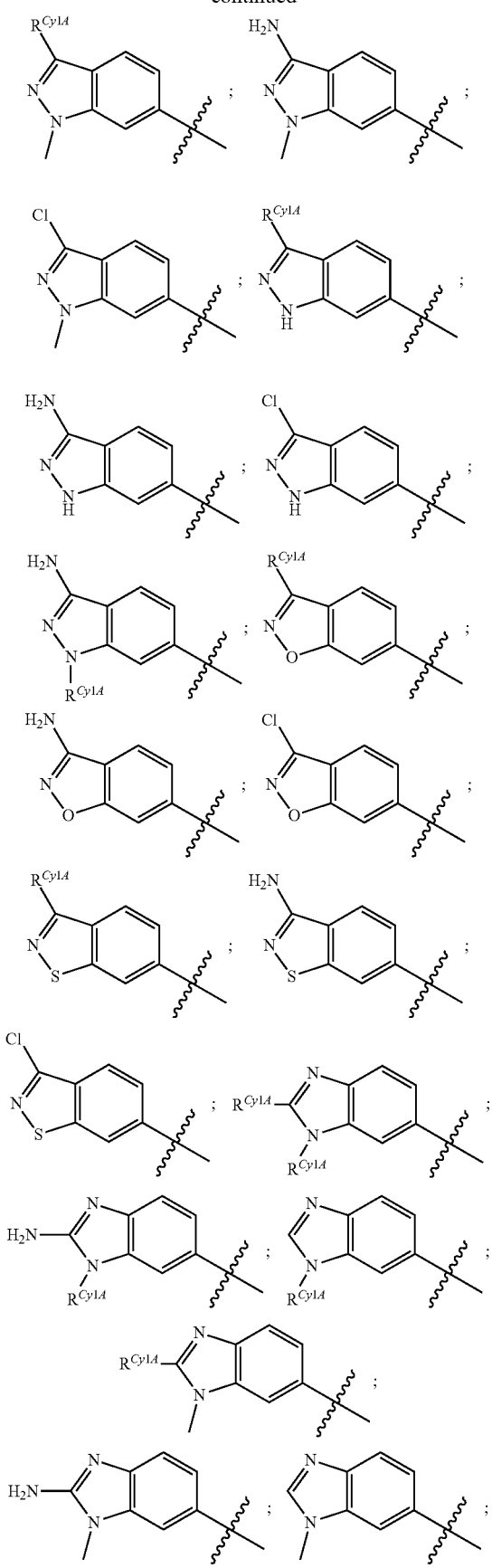
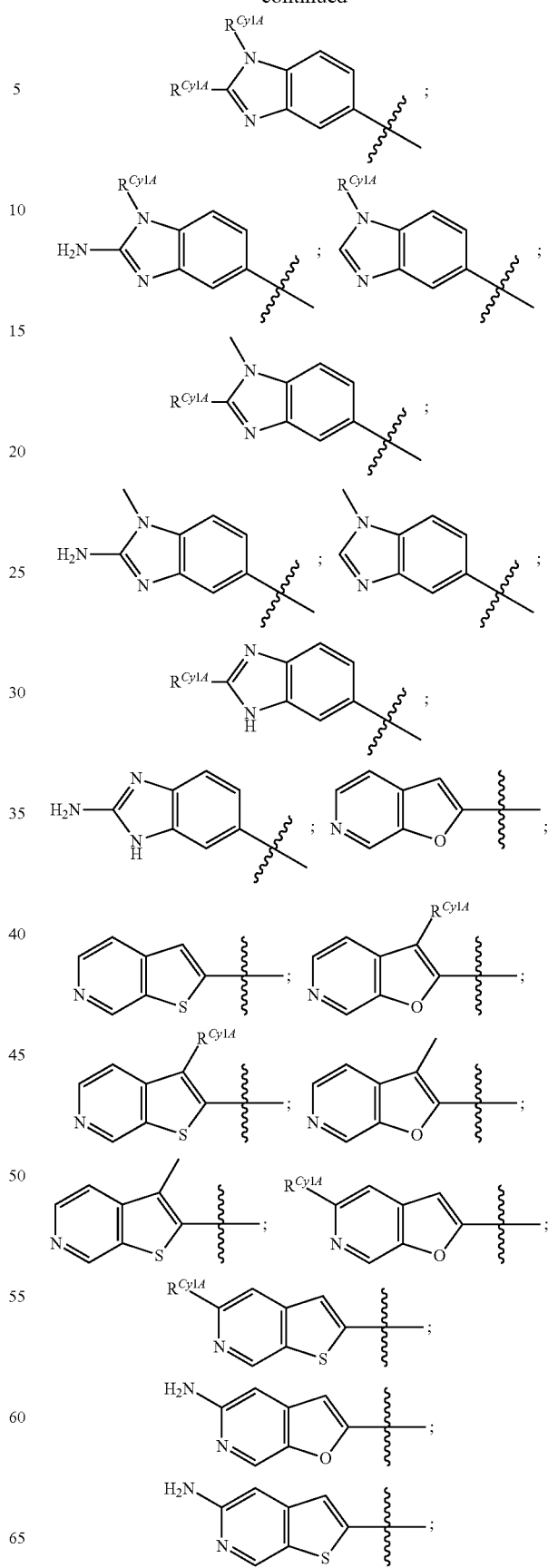

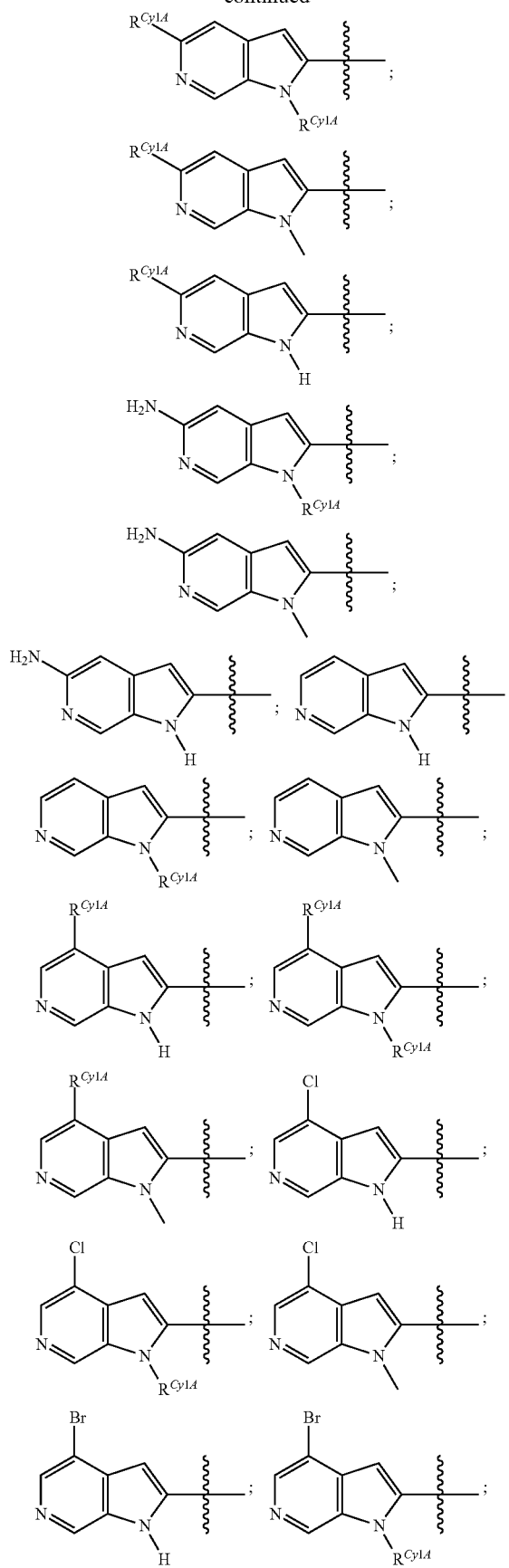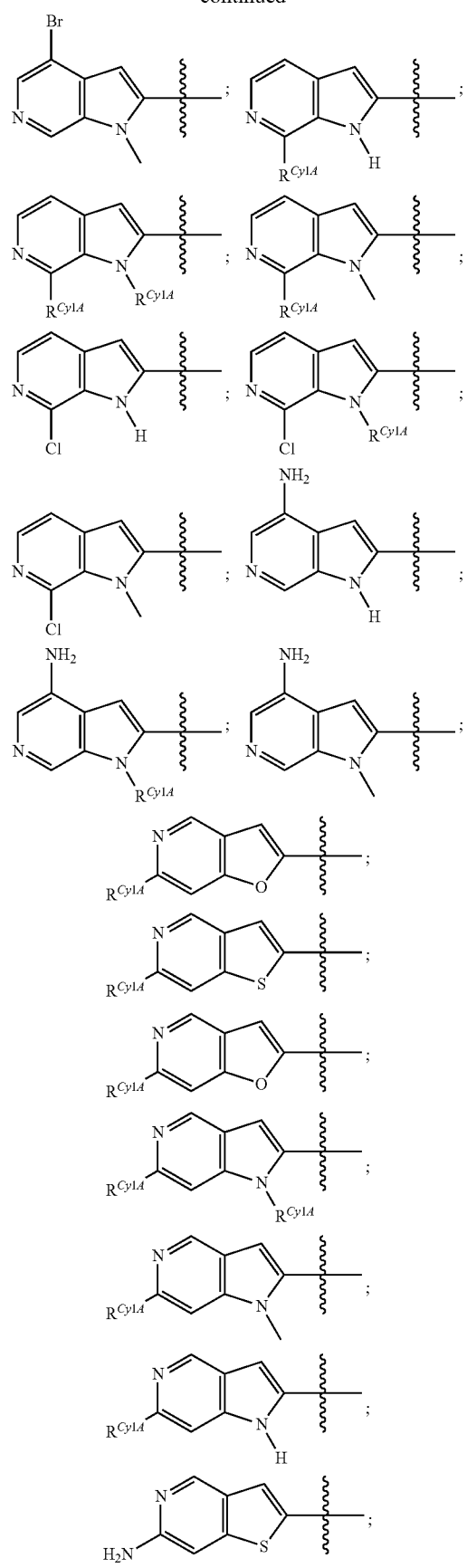

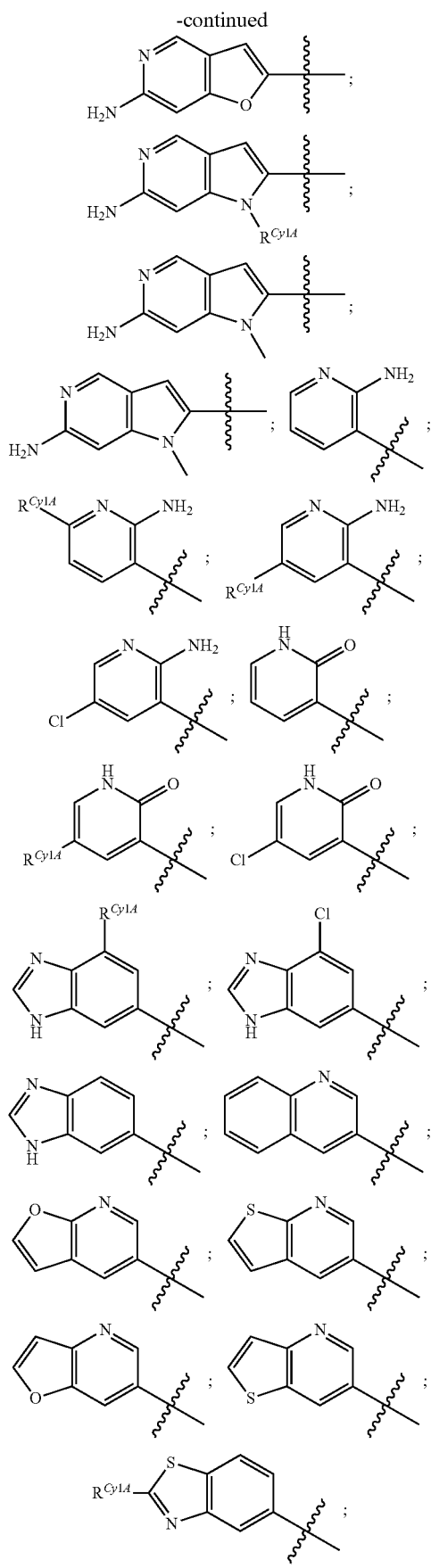

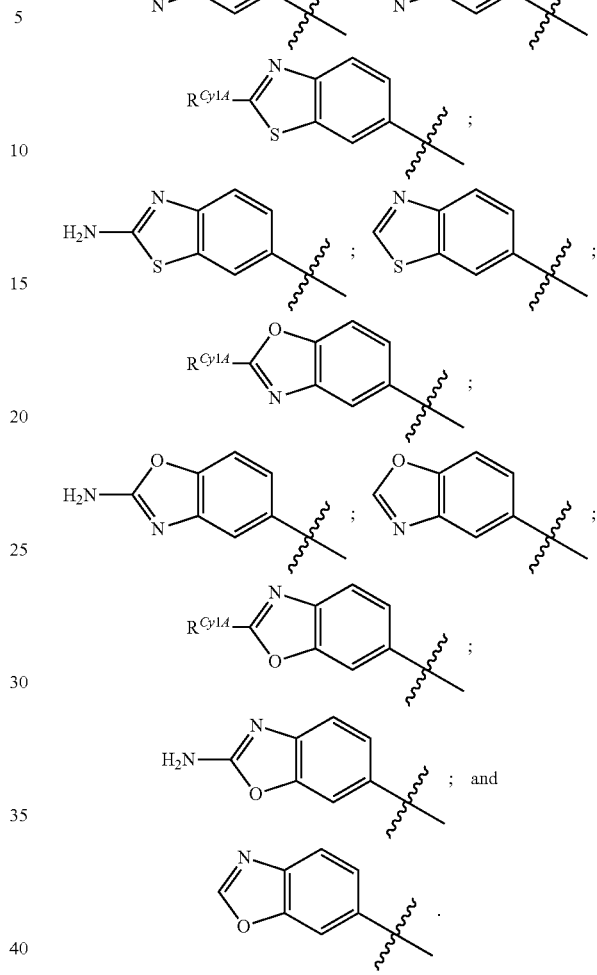

wherein each $R^{Cy1A}$ attached to a carbon atom is independently $C_{1-6}$ alkyl, halogen, or amino, and each $R^{Cy1A}$ attached to a nitrogen atom is H or $C_{1-6}$ alkyl.

5. The compound or salt thereof of claim 1, wherein $R^{11}$ is H or $C_{1-6}$ alkyl.

6. The compound or salt thereof of claim 1, wherein $R^{11}$ is methyl.

7. The compound or salt thereof of claim 1, wherein $R^{12}$ is H or $C_{1-6}$ alkyl.

8. The compound or salt thereof of claim 1, wherein the compound is according to Formula (I-8):

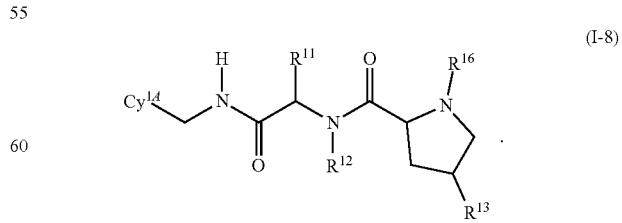

9. The compound or salt thereof of claim 1, wherein the compound is according to any one of the following Formulae (I-8a) to (I-8z):

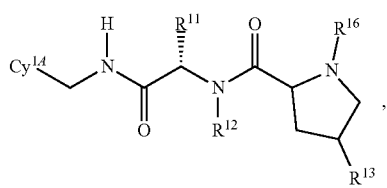
(I-8a)
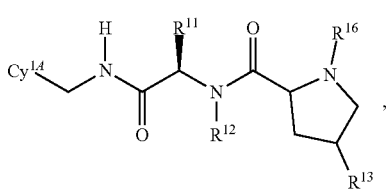
(I-8b)
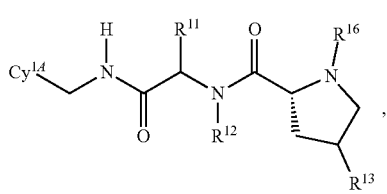
(I-8c)
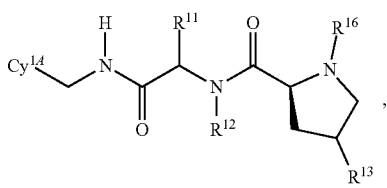
(I-8d)
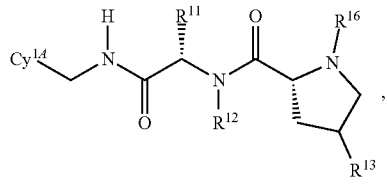
(I-8e)
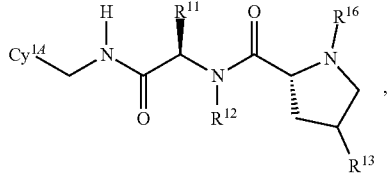
(I-8f)
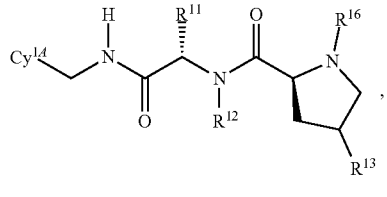
(I-8g)
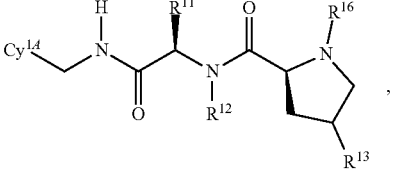
(I-8h)
-continued
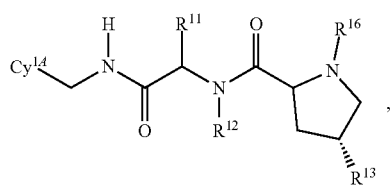
(I-8i)
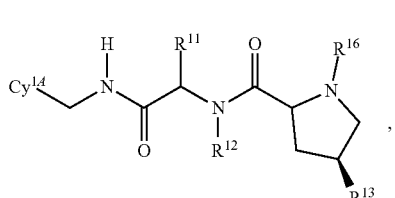
(I-8j)
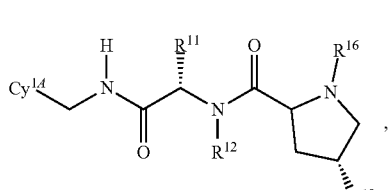
(I-8k)
(I-8l)
(I-8m)
(I-8n)
(I-8o)
(I-8p)

1097
-continued (I-8q) 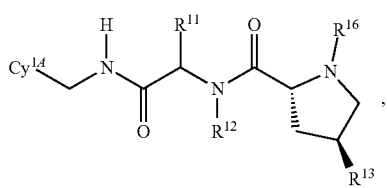

(I-8r) 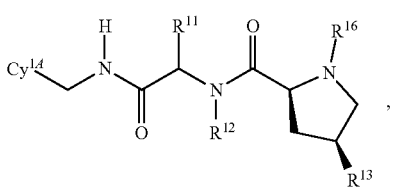

(I-8s) 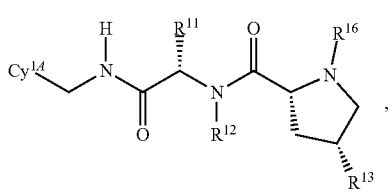

(I-8t) 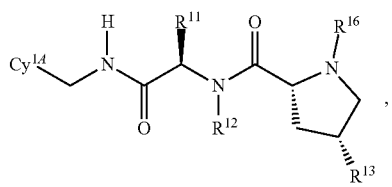

(I-8u) 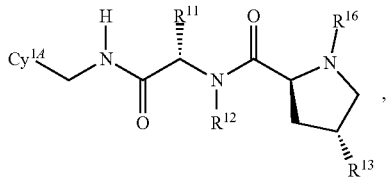

(I-8v) 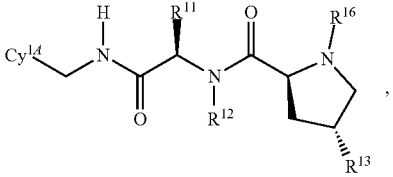

(I-8w) 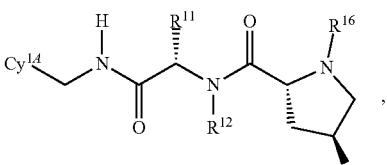

(I-8x) 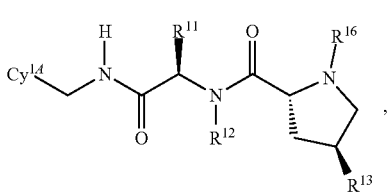

1098
-continued (I-8y) 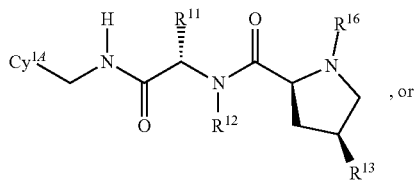, or (I-8z) 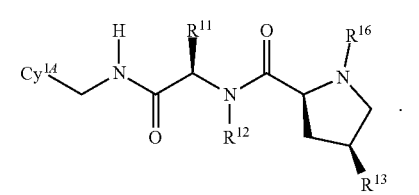.

10. The compound or salt thereof of claim 9, wherein $R^{13}$ is $Cy^{1B}$, $CH_2Cy^{1B}$, $CH_2CH_2Cy^{1B}$, or $OCy^{1B}$, and wherein $Cy^{1B}$ is substituted or unsubstituted $C_{6-10}$ aryl or substituted or unsubstituted 5-10 membered heteroaryl.

11. The compound or salt thereof of claim 10, wherein $Cy^{1B}$ is substituted with 1, 2, 3, 4 or 5 substituents each independently selected from $R^{Cy1B}$, halogen, $C_{1-6}$ haloalkyl, CN, $OR^{a11}$, $NR^{c11}C(O)R^{b11}$, $C(O)NR^{c11}R^{d11}$;

wherein each $R^{Cy1B}$ is independently selected from $C_{1-6}$ alkyl, $C_{2-6}$ alkenyl, $C_{2-6}$ alkynyl, $C_{3-10}$ cycloalkyl, and $C_{6-10}$ aryl or 5-10 membered heteroaryl, wherein each $C_{1-6}$ alkyl, $C_{6-10}$ aryl, or 5-10 membered heteroaryl forming $R^{Cy1B}$ is unsubstituted or substituted with 1, 2 or 3 substituents independently selected from halogen, $C_{1-6}$ alkyl, $C_{2-6}$ alkenyl, $C_{2-6}$ alkynyl, $NR^{c11}R^{d11}$, CN, $C(O)NR^{c11}R^{d11}$, $CH_2NR^{c11}R^{d11}$, and haloalkyl.

12. The compound or salt thereof of claim 1, wherein $R^{13}$ is a group selected from:

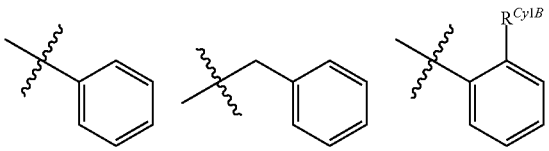

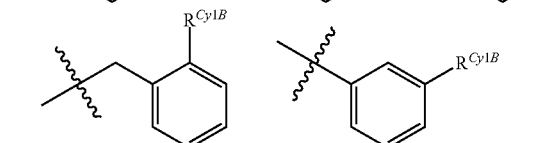

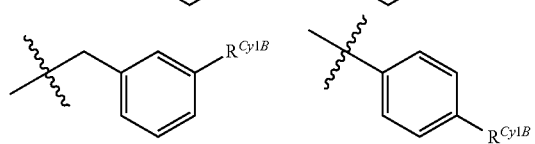

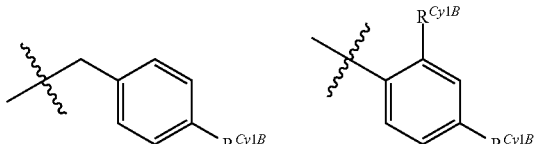

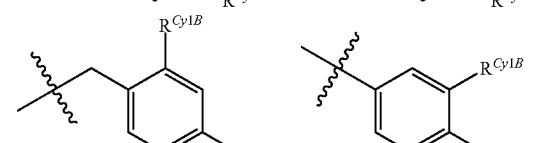

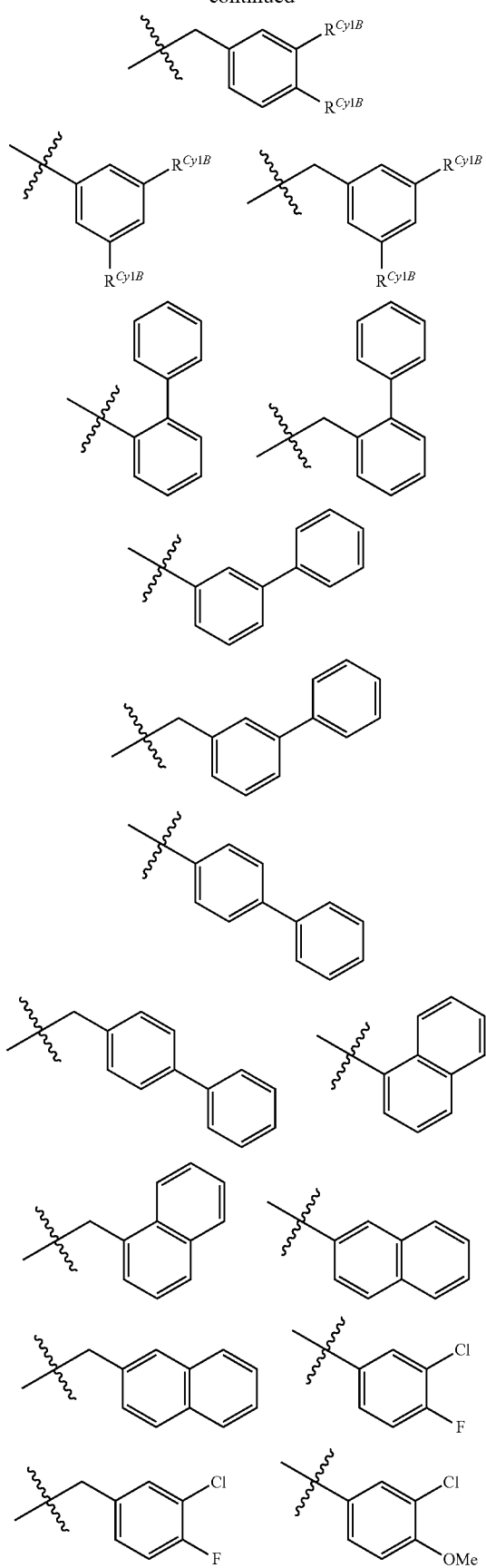
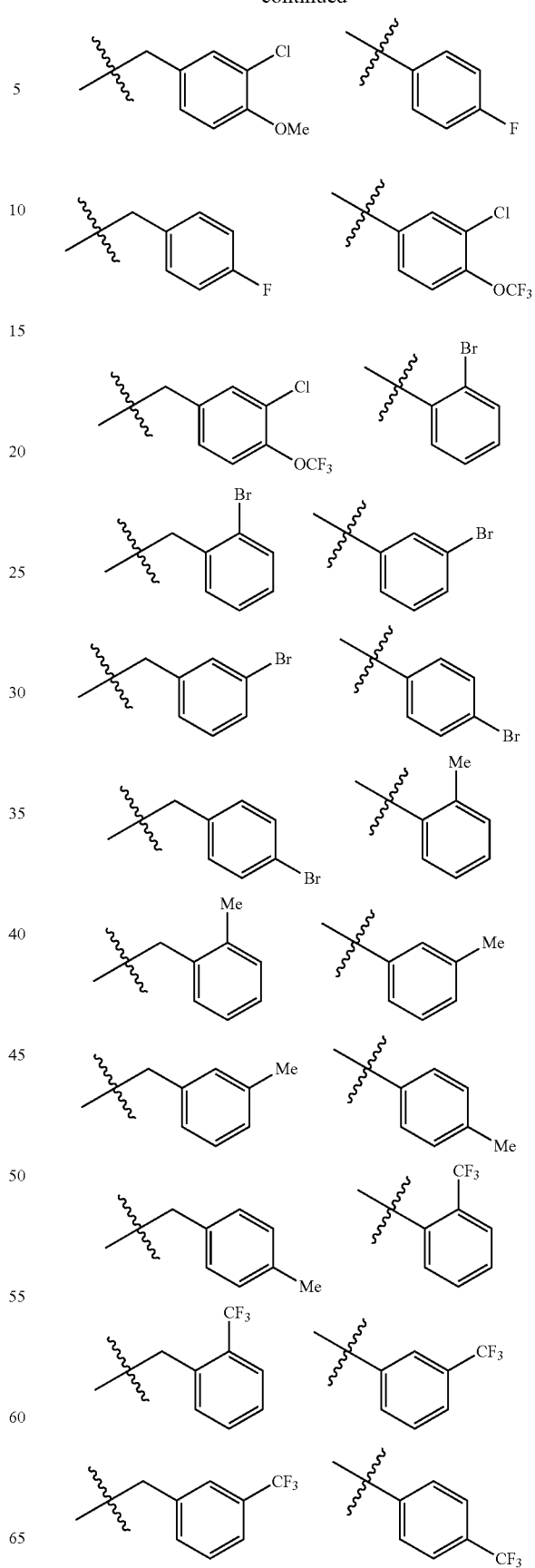

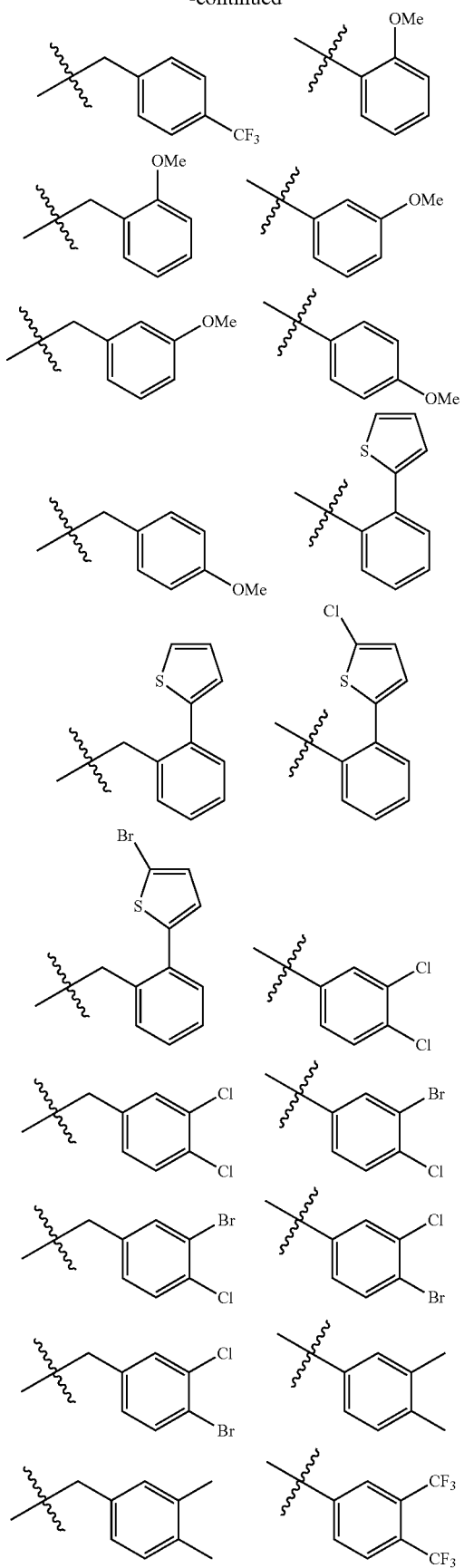
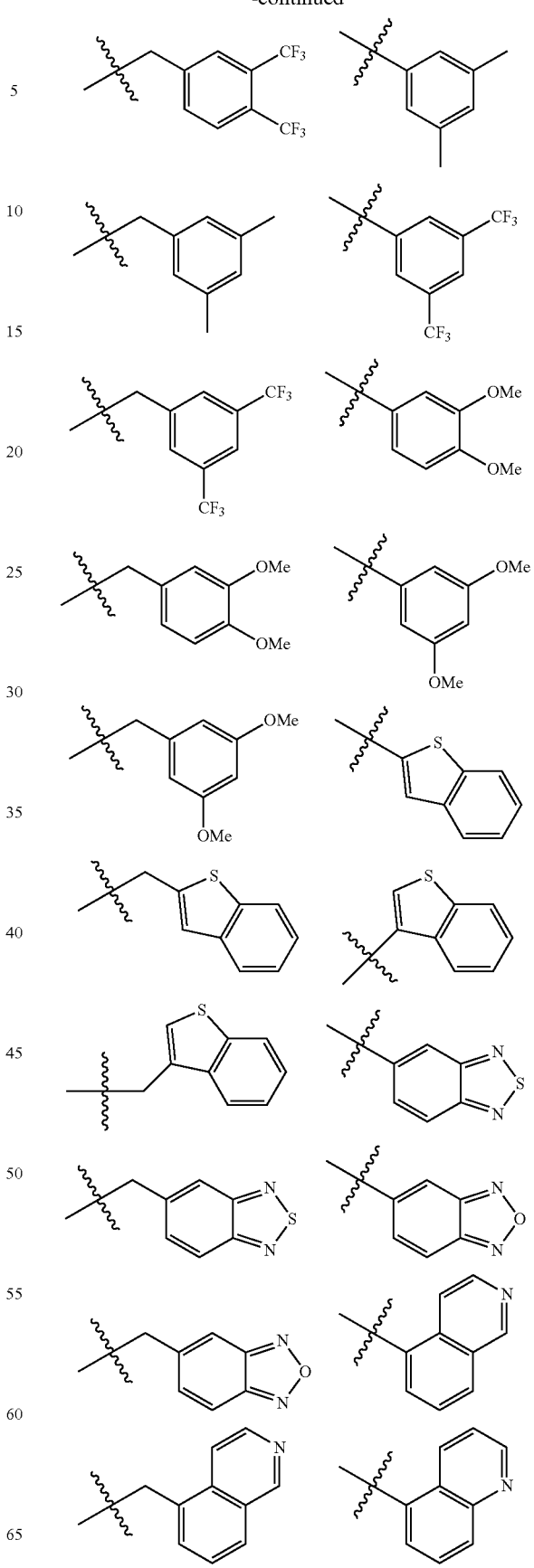

-continued

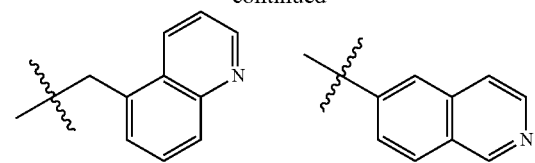

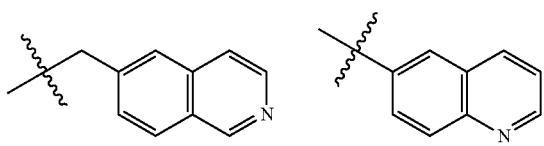

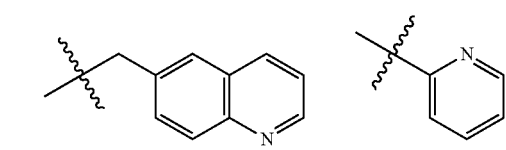

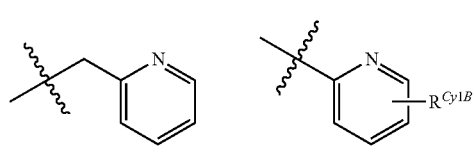

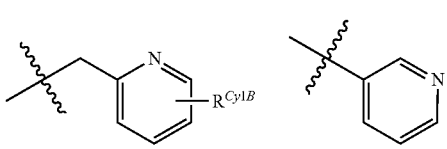

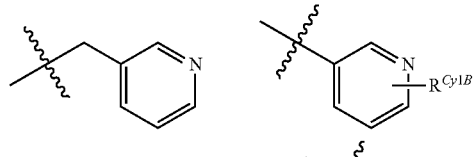

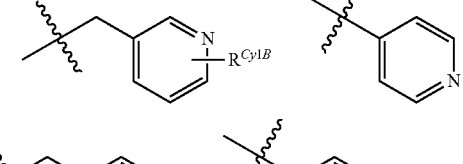
and

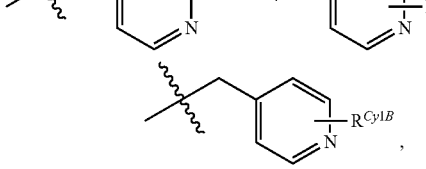

wherein $R^{Cy1B}$ is H, $C_{1-6}$ alkyl or halogen.

13. The compound or salt thereof of claim 1, wherein each $R^{14}$ is hydrogen.

14. The compound or salt thereof of claim 1, wherein $R^{15}$ is hydrogen.

15. The compound or salt thereof of claim 1, wherein $R^{16}$ is hydrogen, unsubstituted or substituted $C_{1-6}$ alkyl, unsubstituted or substituted $C_{2-6}$ alkenyl, or unsubstituted or substituted $C_{2-6}$ alkynyl.

16. The compound of claim 1, having a structure selected from the group consisting of:

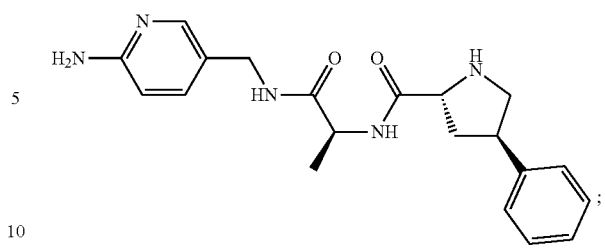
;

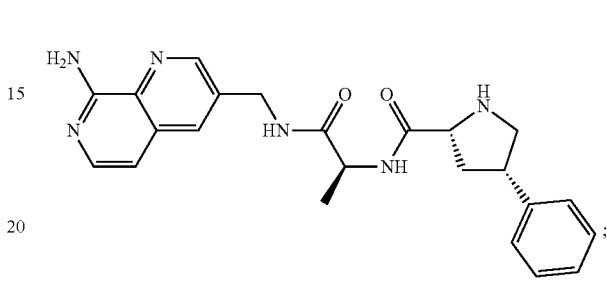
;

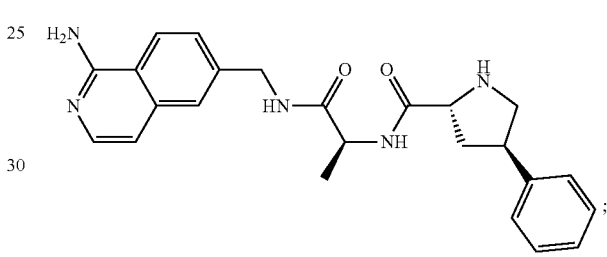
;

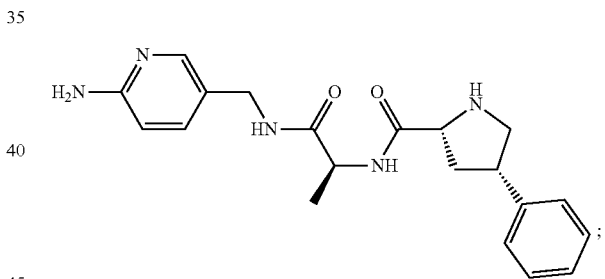
;

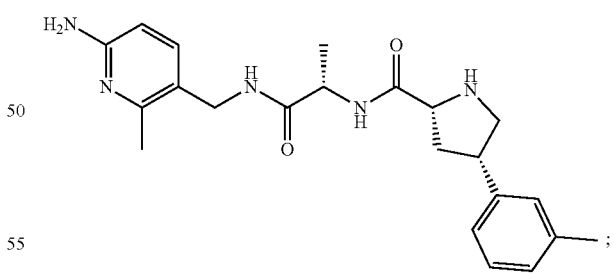
;

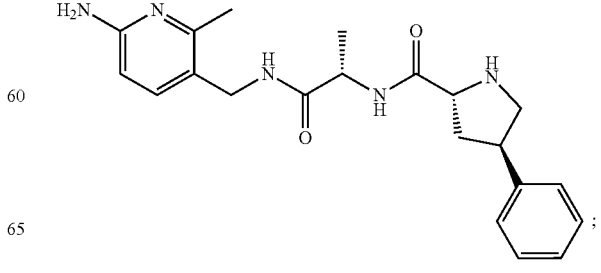
;

1105
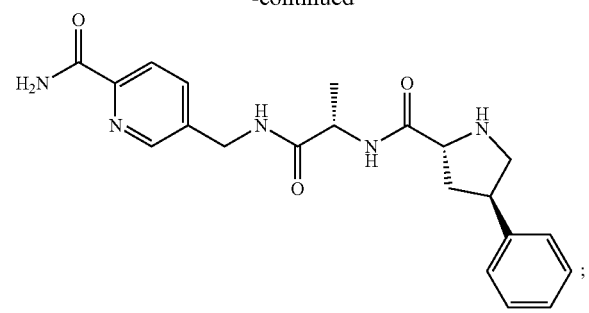
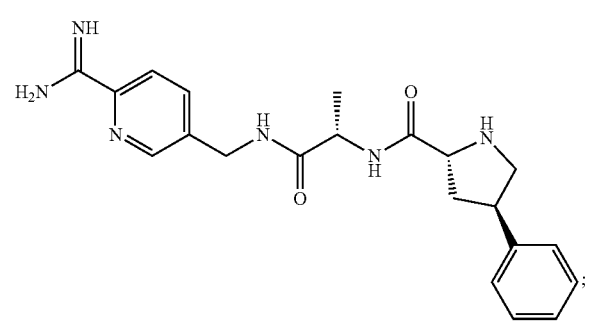
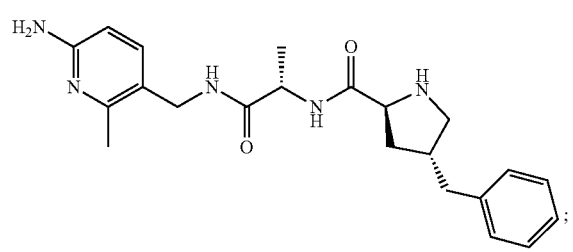
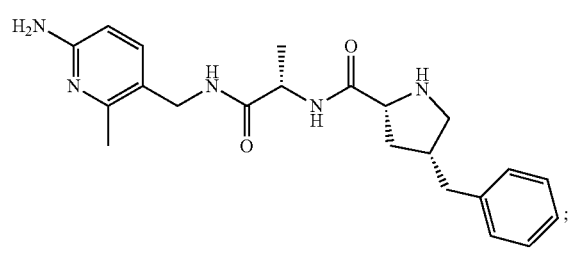
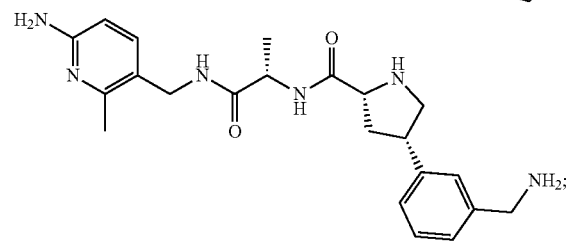
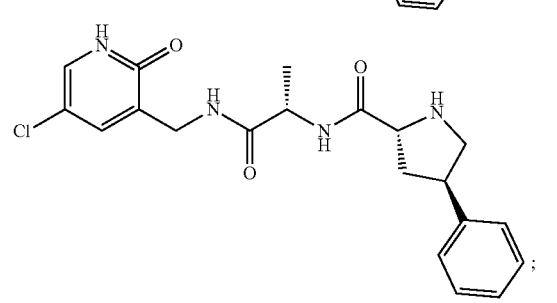
1106
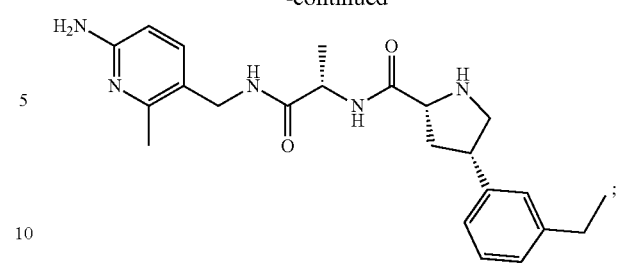
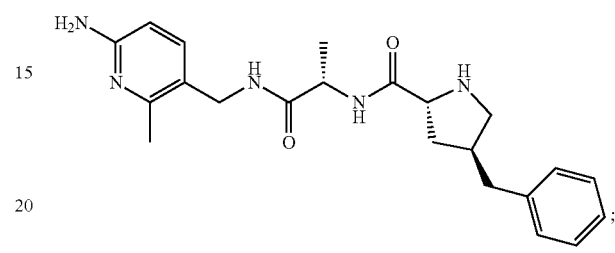
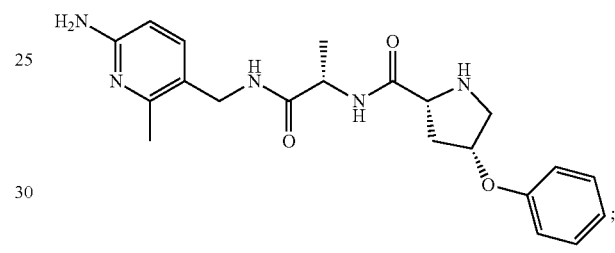
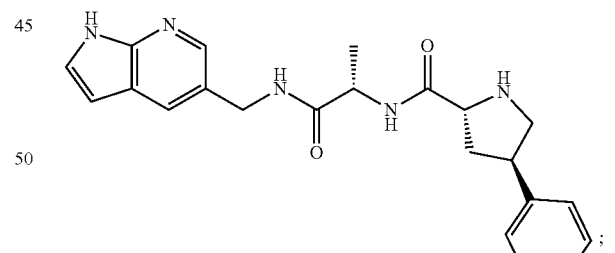
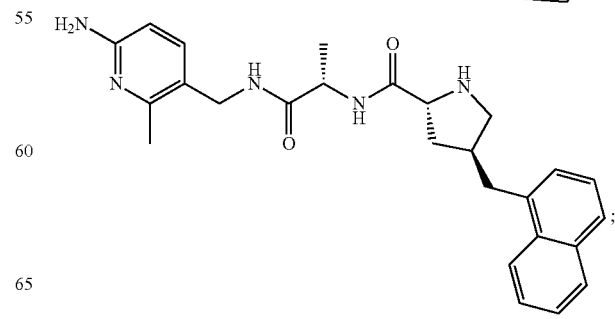

1107
-continued
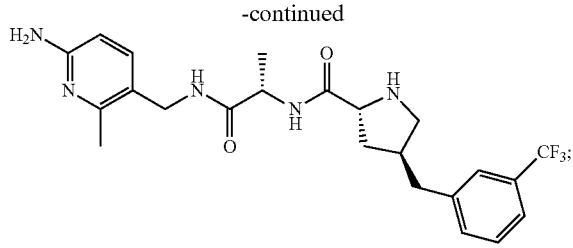
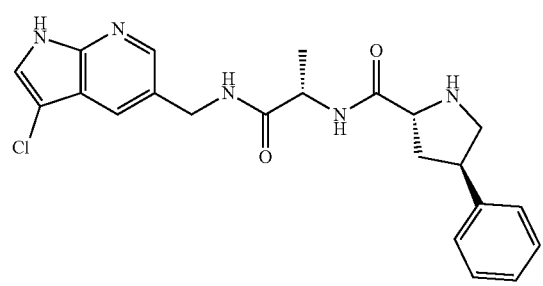
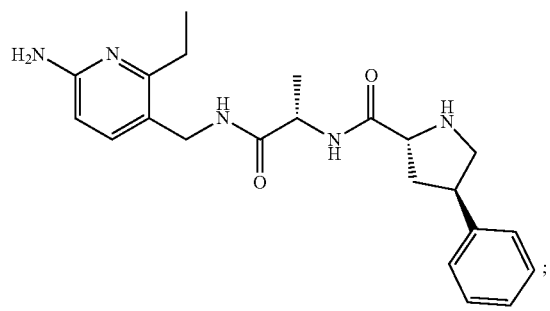
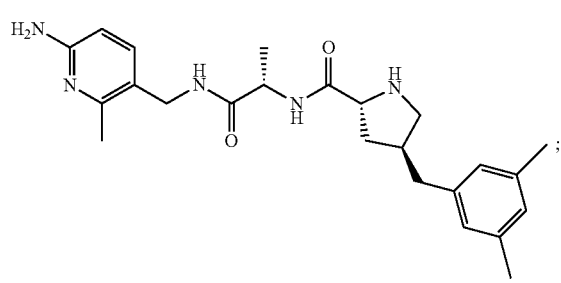
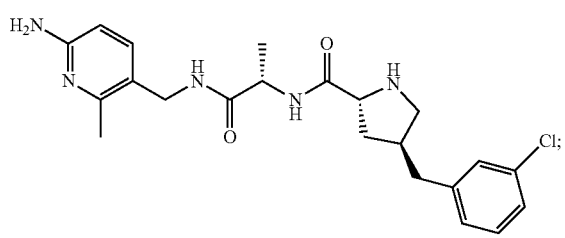
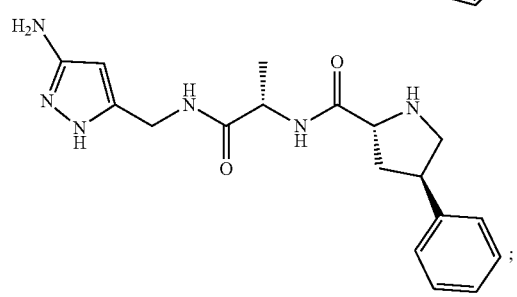
1108
-continued
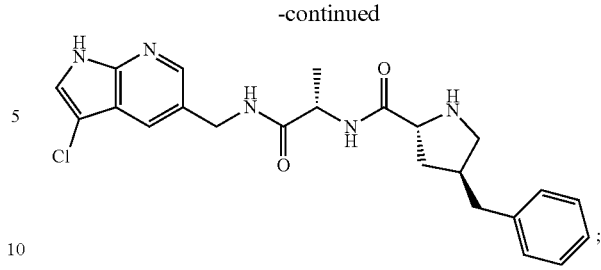
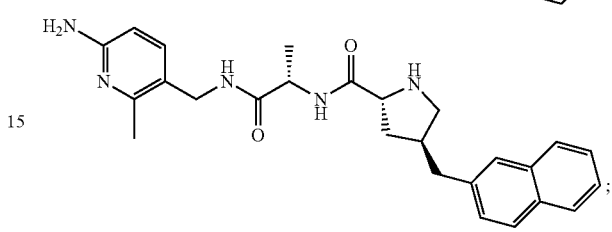
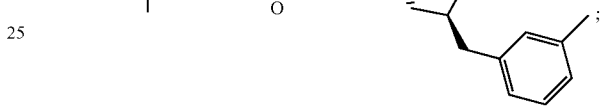
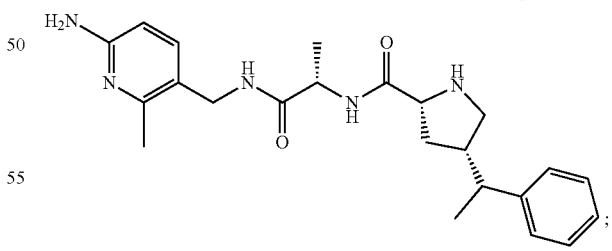
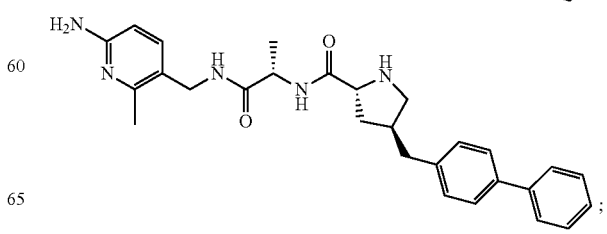

1109
-continued
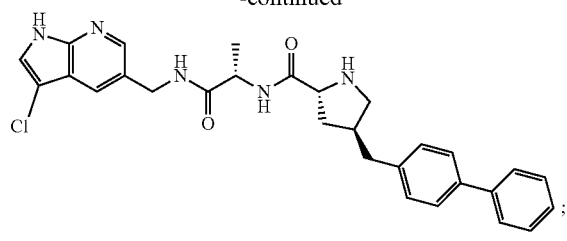
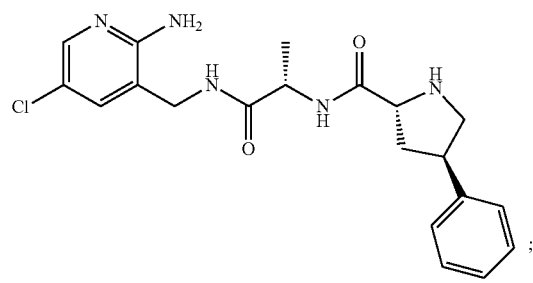
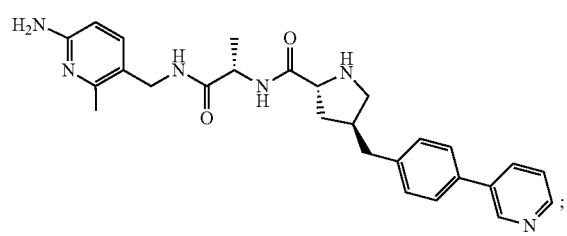
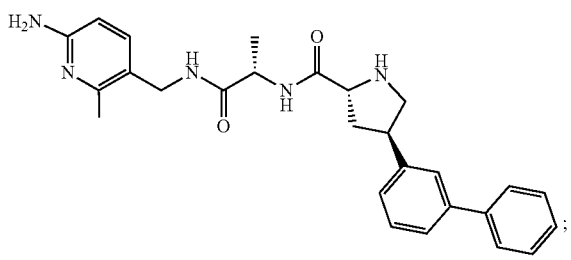
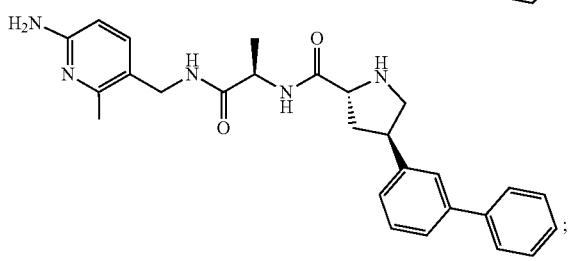
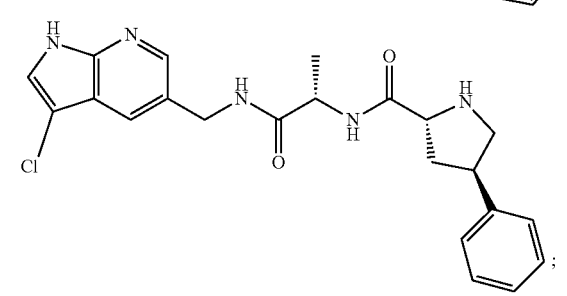
1110
-continued
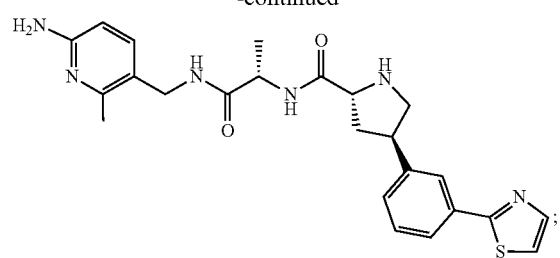
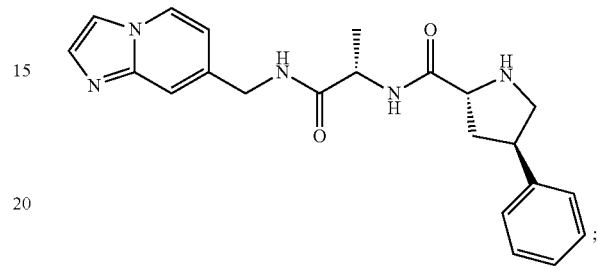
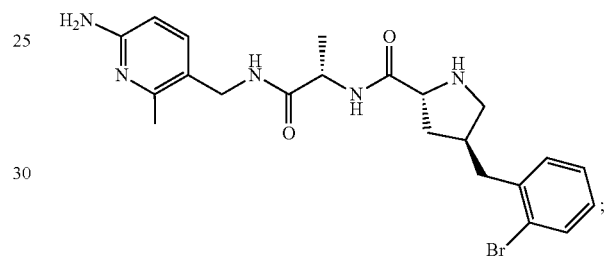
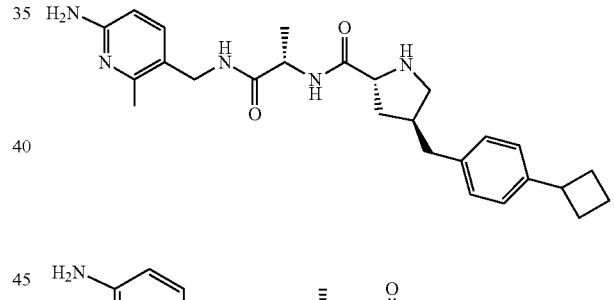
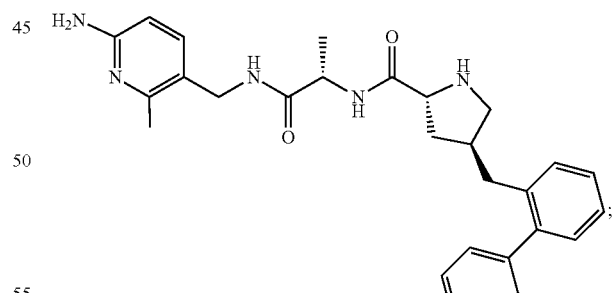
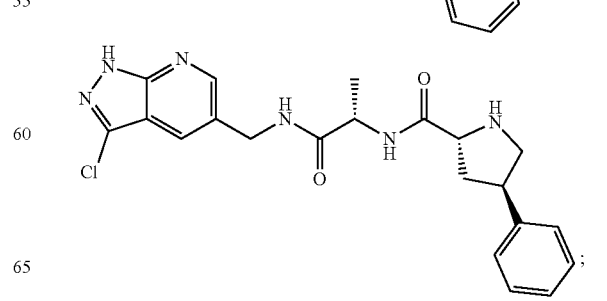

1111
-continued
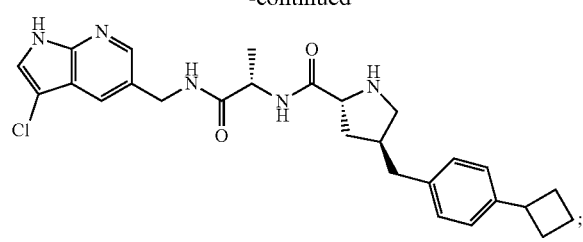
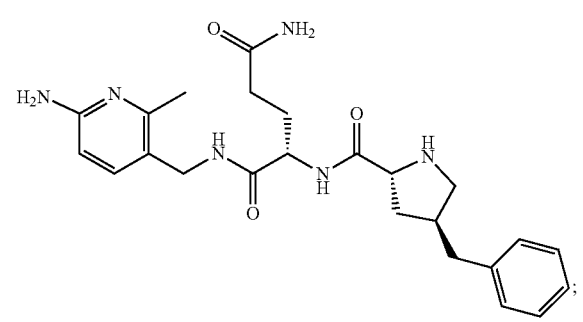
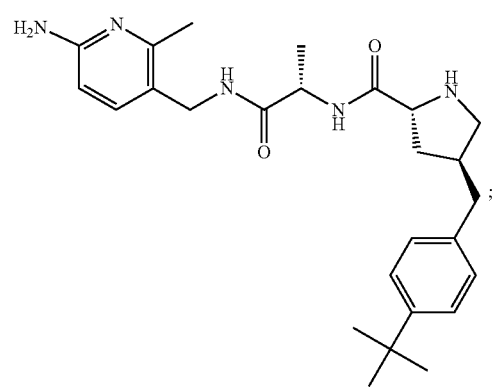
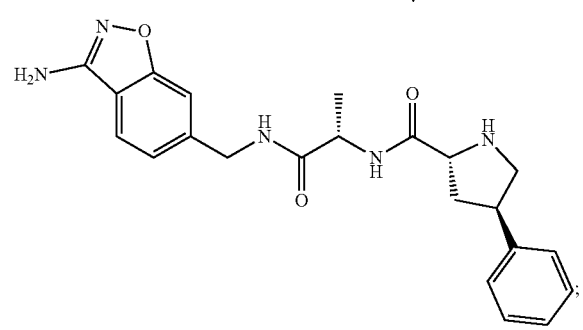
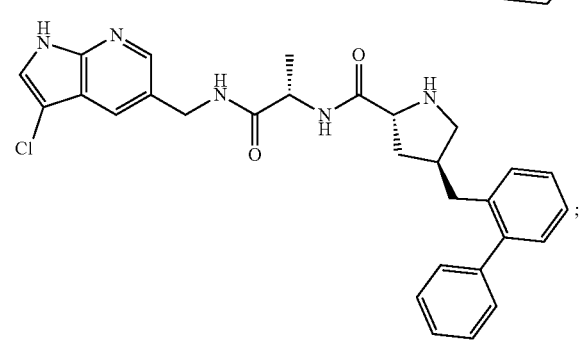
1112
-continued
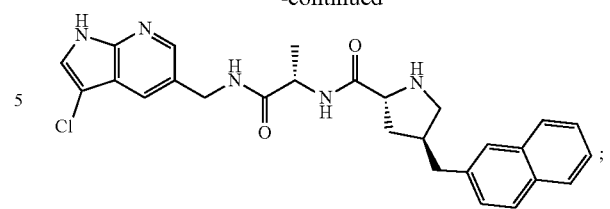
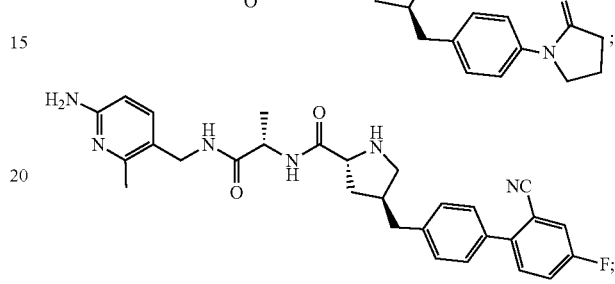
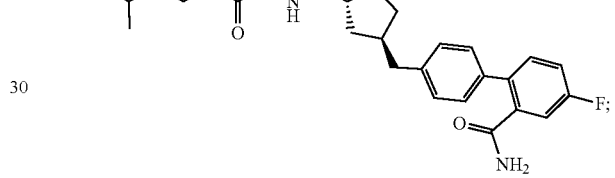
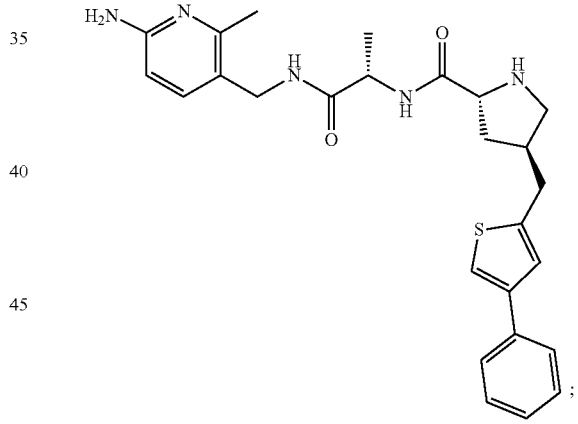
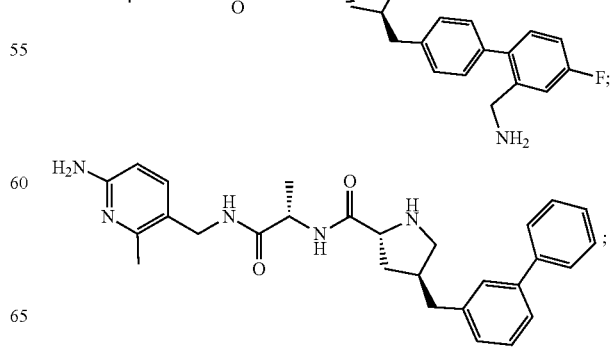

1113
-continued
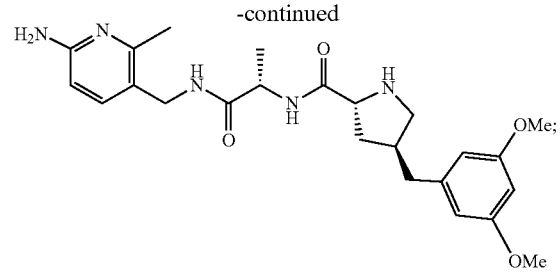
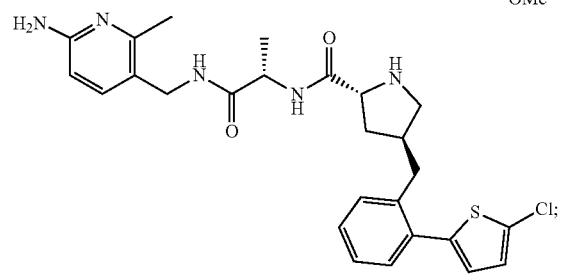
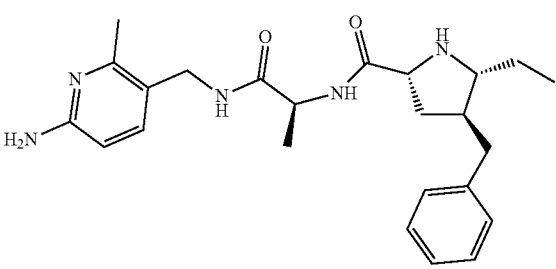
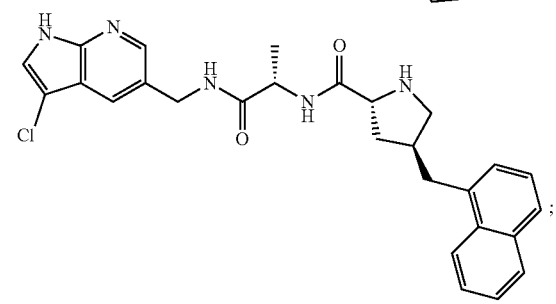
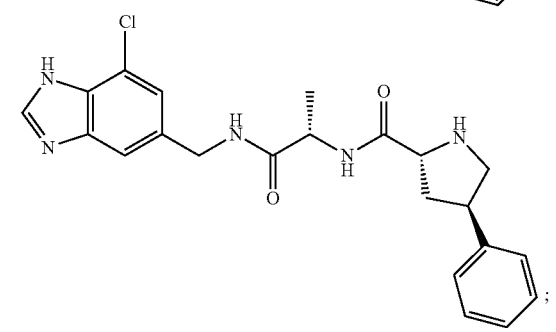
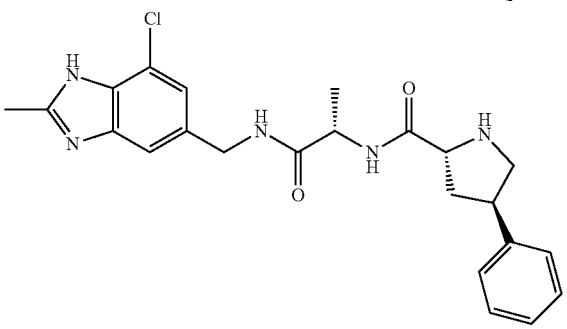
1114
-continued
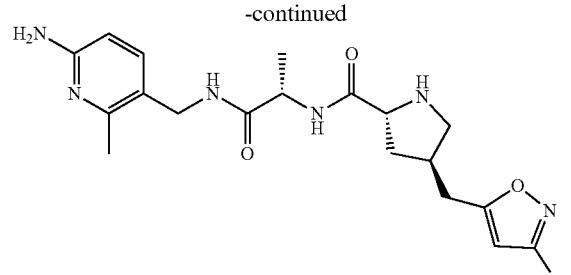
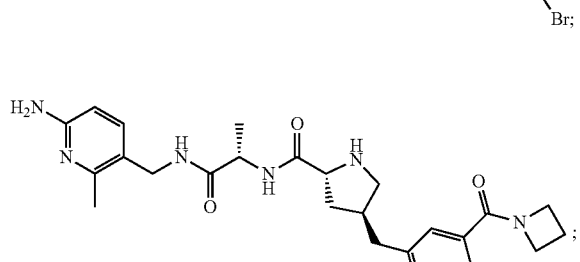
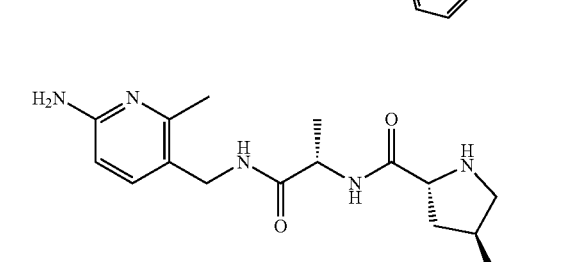
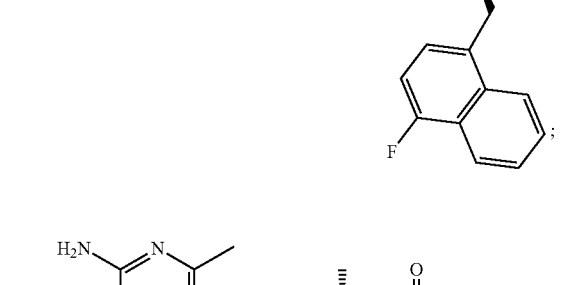
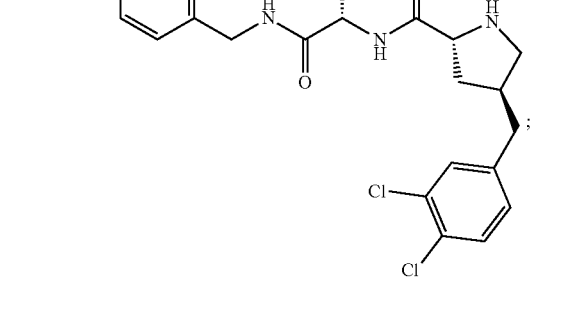
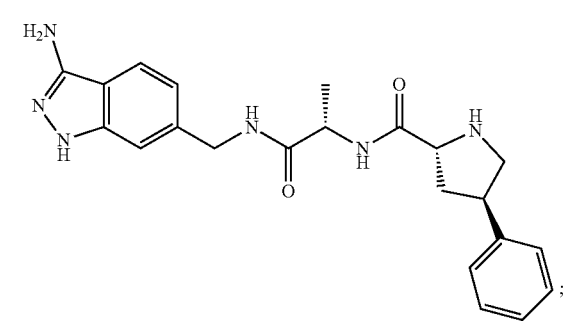

1115
-continued
1116
-continued
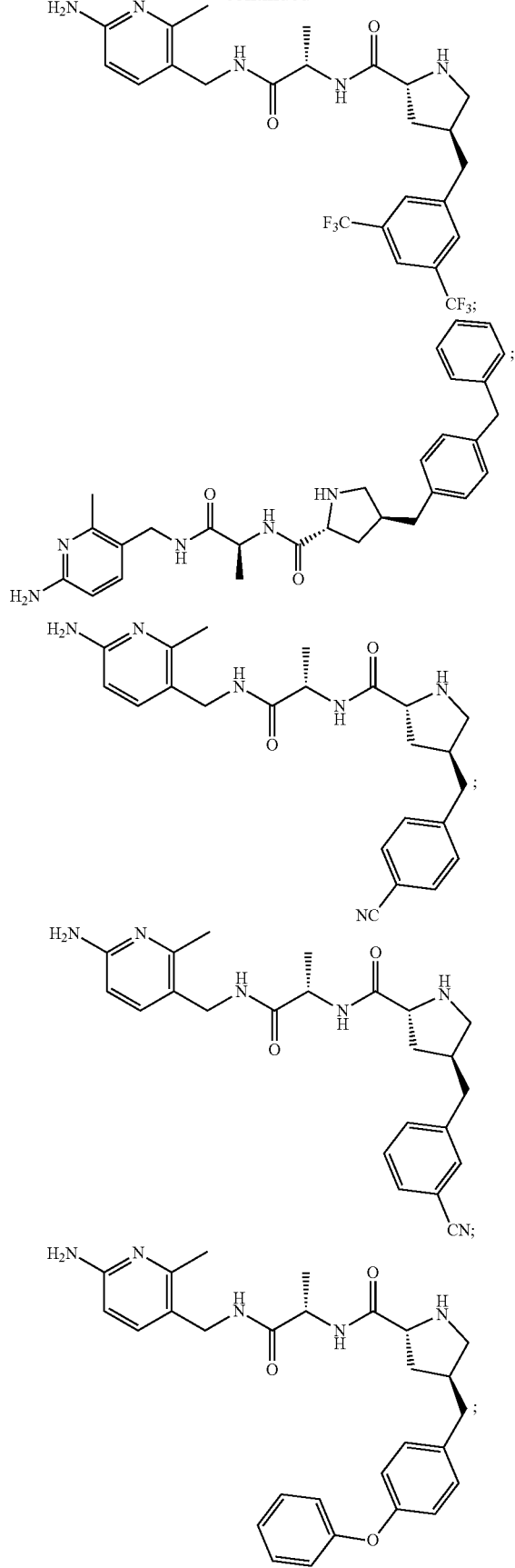
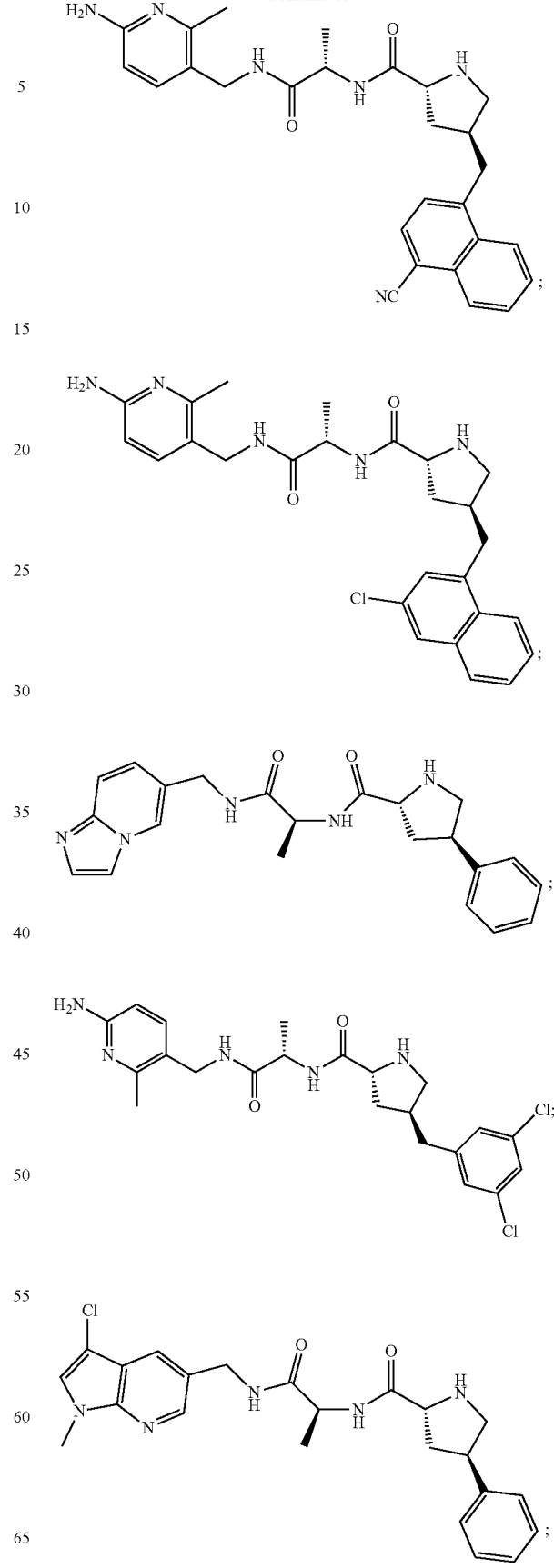

1117
-continued
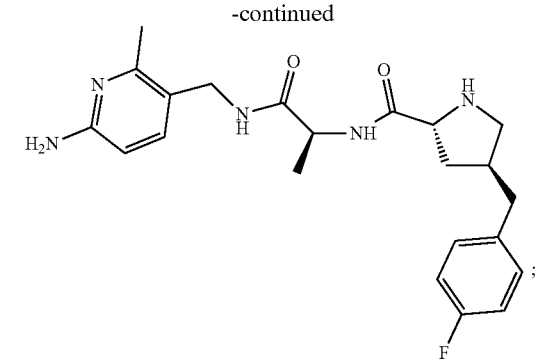
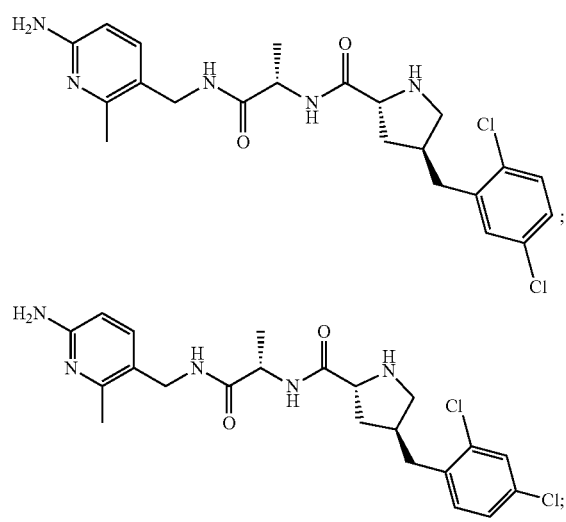
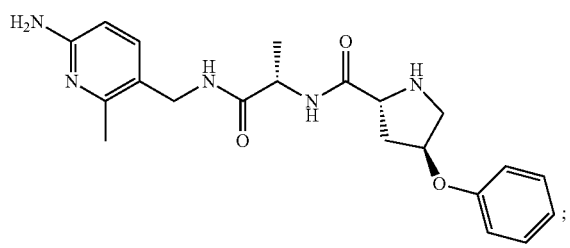
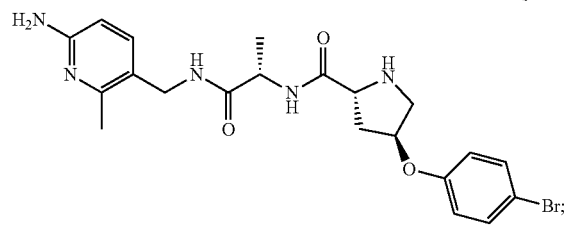
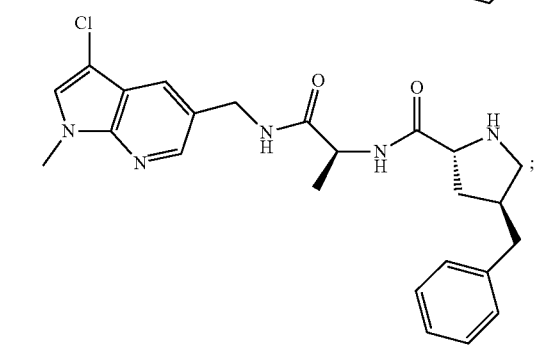
1118
-continued
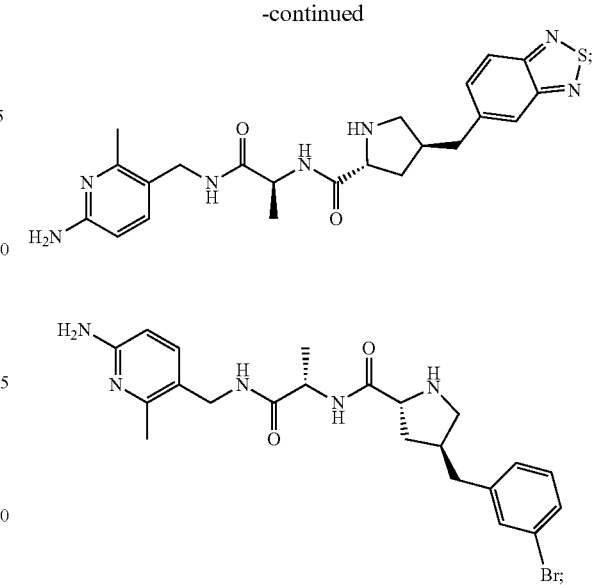
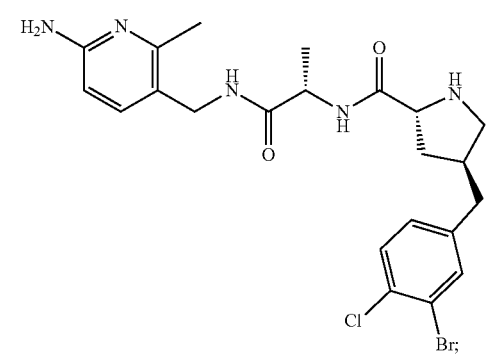
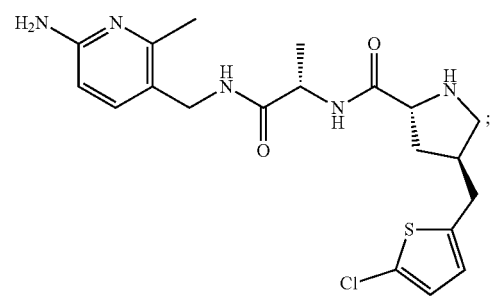
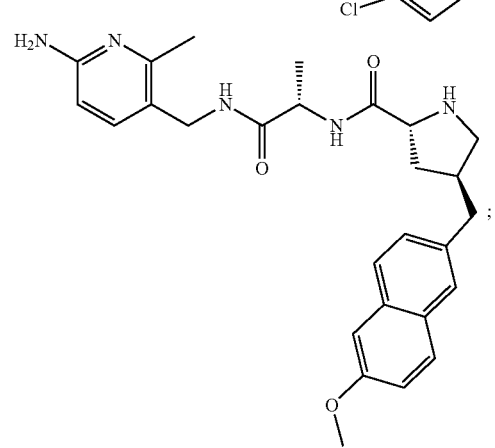

1119
-continued
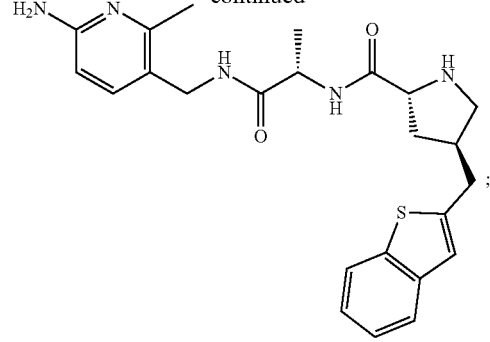
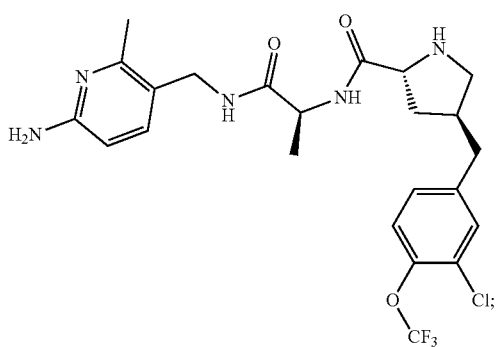
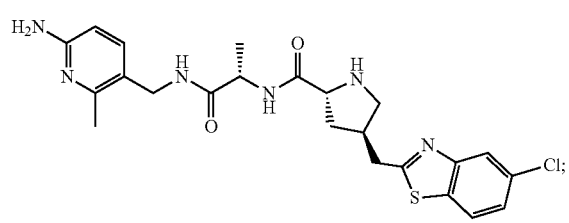
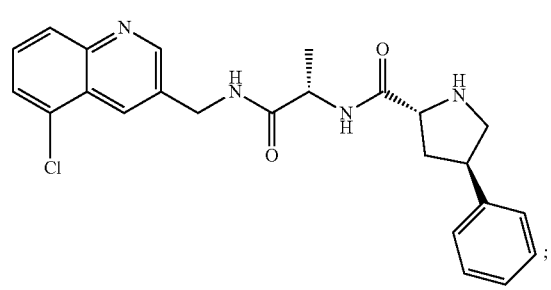
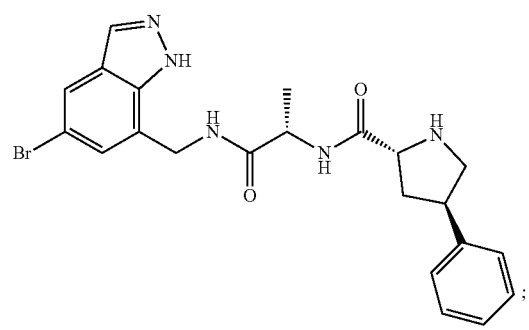
1120
-continued
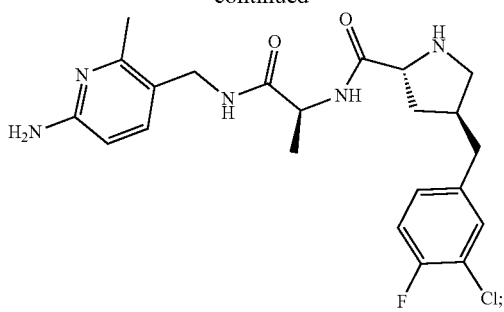
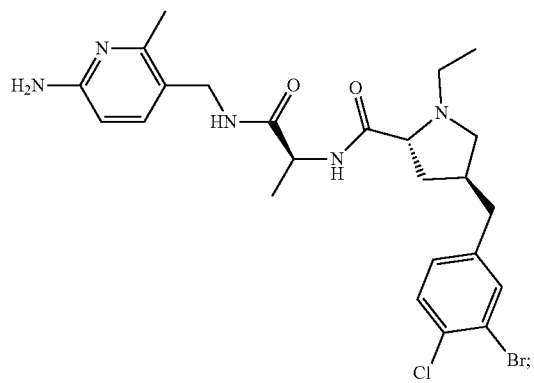
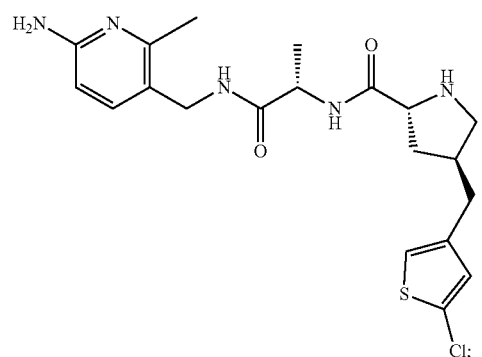
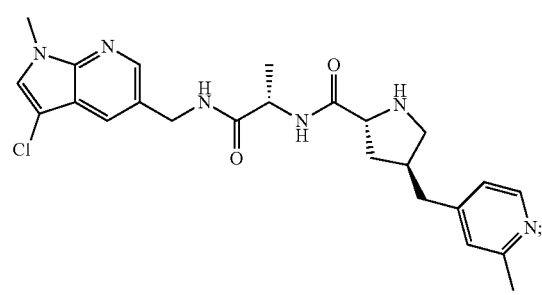
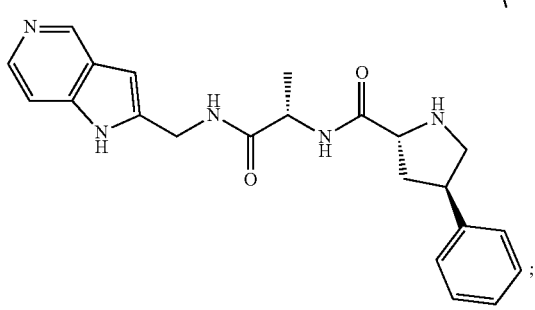

1121
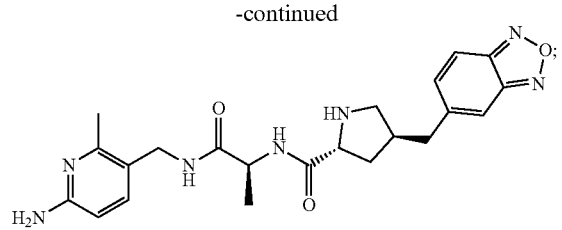
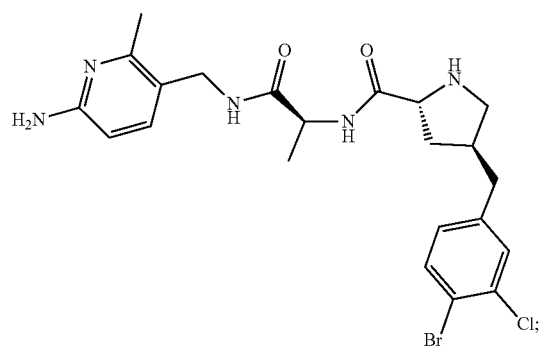
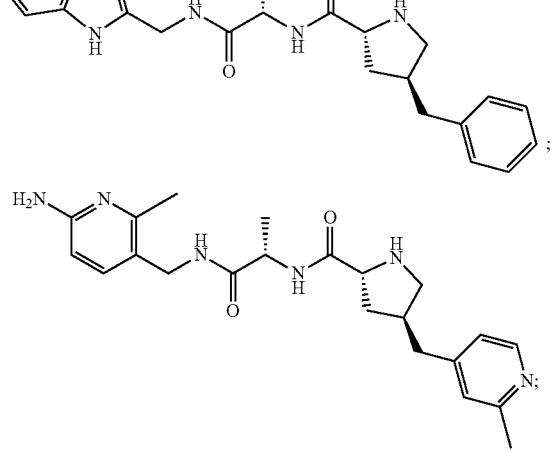
1122
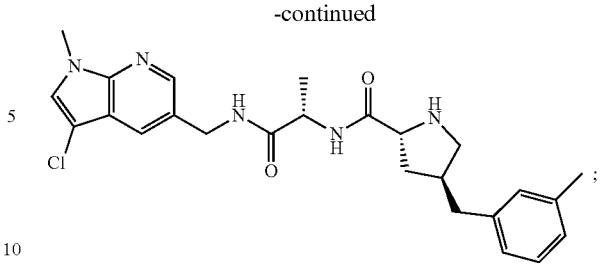
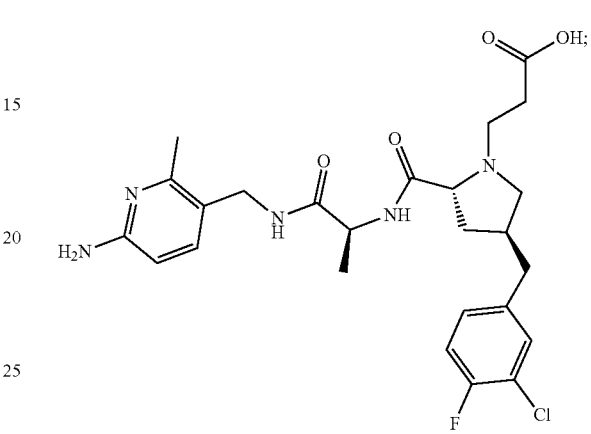
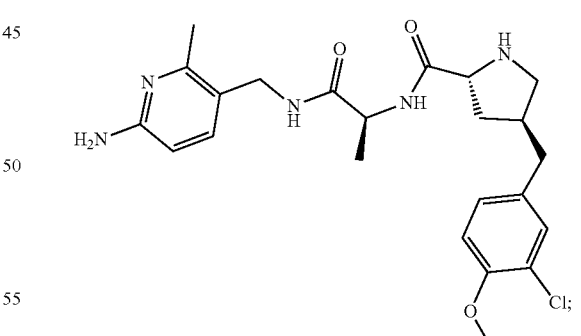
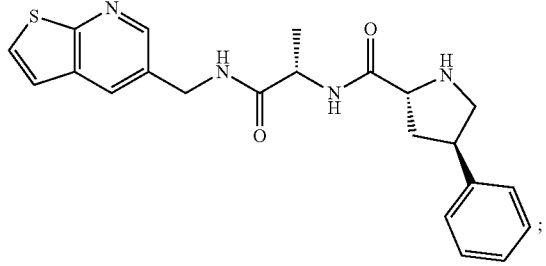
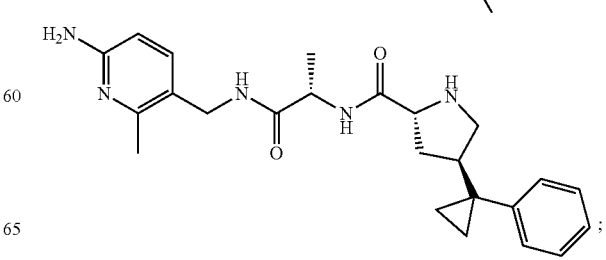

1123
-continued
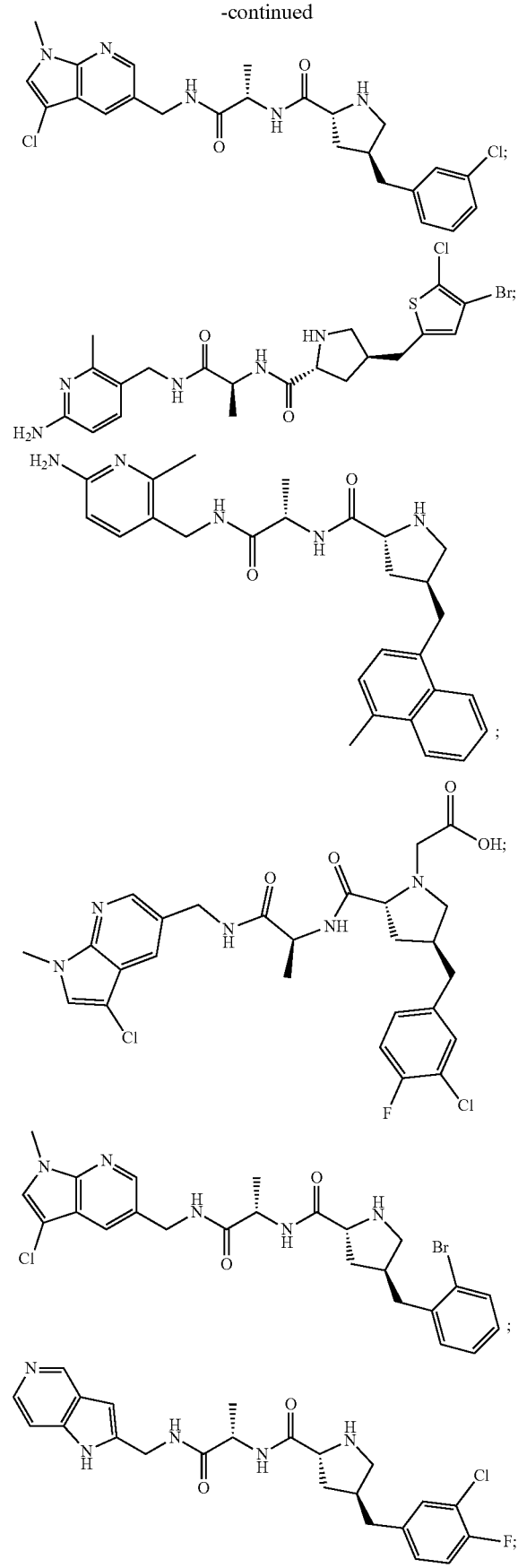
1124
-continued
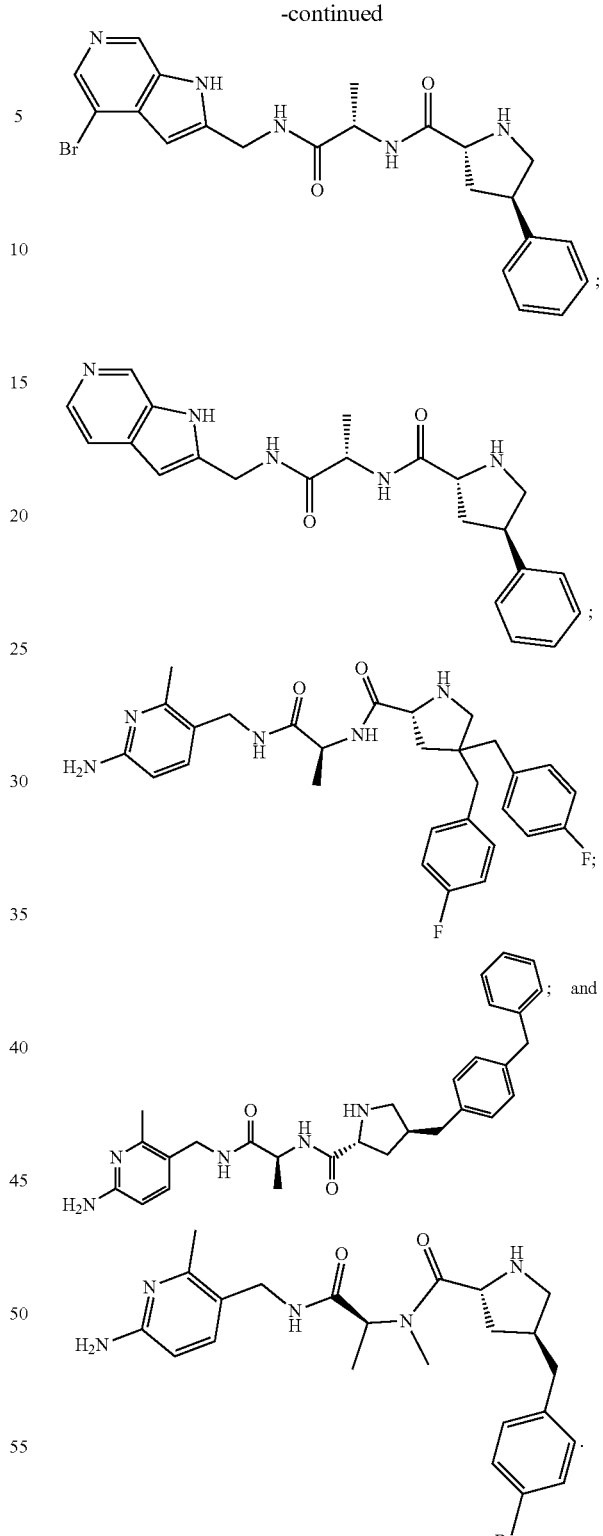
17. A pharmaceutical composition comprising a compound of claim 1, or a stereoisomer, tautomer, or pharmaceutically acceptable salt thereof, and a pharmaceutically acceptable carrier or excipient.
18. A method for inhibiting MASP-2 in a subject in need thereof, comprising administering to the subject a compound of claim 1, or a stereoisomer, tautomer, or pharmaceutically acceptable salt thereof, in an amount effective to inhibit MASP-2.

* * * * *

SEQUENCE LISTING

```
Sequence total quantity: 1
SEQ ID NO: 1            moltype = AA  length = 686
FEATURE                 Location/Qualifiers
source                  1..686
                        mol_type = protein
                        organism = Homo sapiens
SEQUENCE: 1
MRLLTLLGLL CGSVATPLGP KWPEPVFGRL ASPGFPGEYA NDQERRWTLT APPGYRLRLY   60
FTHFDLELSH LCEYDFVKLS SGAKVLATLC GQESTDTERA PGKDTFYSLG SSLDITFRSD  120
YSNEKPFTGF EAFYAAEDID ECQVAPGEAP TCDHHCHNHL GGFYCSCRAG YVLHRNKRTC  180
SALCSGQVFT QRSGELSSPE YPRPYPKLSS CTYSISLEEG FSVILDFVES FDVETHPETL  240
CPYDFLKIQT DREEHGPFCG KTLPHRIETK SNTVTITFVT DESGDHTGWK IHYTSTAQPC  300
PYPMAPPNGH VSPVQAKYIL KDSFSIFCET GYELLQGHLP LKSFTAVCQK DGSWDRPMPA  360
CSIVDCGPPD DLPSGRVEYI TGPGVTTYKA VIQYSCEETF YTMKVNDGKY VCEADGFWTS  420
SKGEKSLPVC EPVCGLSART TGGRIYGGQK AKPGDFPWQV LILGGTTAAG ALLYDNWVLT  480
AAHAVYEQKH DASALDIRMG TLKRLSPHYT QAWSEAVFIH EGYTHDAGFD NDIALIKLNN  540
KVVINSNITP ICLPRKEAES FMRTDDIGTA SGWGLTQRGF LARNLMYVDI PIVDHQKCTA  600
AYEKPPYPRG SVTANMLCAG LESGGKDSCR GDSGGALVFL DSETERWFVG GIVSWGSMNC  660
GEAGQYGVYT KVINYIPWIE NIISDF                                      686
```